US010144734B2

(12) United States Patent
Andrews et al.

(10) Patent No.: US 10,144,734 B2
(45) Date of Patent: *Dec. 4, 2018

(54) SUBSTITUTED PYRAZOLO[1,5-A]PYRIDINE COMPOUNDS AS RET KINASE INHIBITORS

(71) Applicant: Array BioPharma, Inc., Boulder, CO (US)

(72) Inventors: Steven W. Andrews, Boulder, CO (US); Sean Aronow, Boulder, CO (US); James F. Blake, Boulder, CO (US); Barbara J. Brandhuber, Boulder, CO (US); James Collier, Boulder, CO (US); Adam Cook, Boulder, CO (US); Julia Haas, Boulder, CO (US); Yutong Jiang, Boulder, CO (US); Gabrielle R. Kolakowski, Boulder, CO (US); Elizabeth A. McFaddin, Boulder, CO (US); Megan L. McKenney, Boulder, CO (US); Oren T. McNulty, Boulder, CO (US); Andrew T. Metcalf, Boulder, CO (US); David A. Moreno, Boulder, CO (US); Ginelle A. Ramann, Boulder, CO (US); Tony P. Tang, Boudler, CO (US); Li Ren, Boulder, CO (US); Shane M. Walls, Boulder, CO (US)

(73) Assignee: Array BioPharma Inc., Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/858,929

(22) Filed: Dec. 29, 2017

(65) Prior Publication Data

US 2018/0148445 A1     May 31, 2018

Related U.S. Application Data

(63) Continuation of application No. PCT/US2017/055993, filed on Oct. 10, 2017.

(60) Provisional application No. 62/566,030, filed on Sep. 29, 2017, provisional application No. 62/531,690, filed on Jul. 12, 2017, provisional application No. 62/491,180, filed on Apr. 27, 2017, provisional application No. 62/447,849, filed on Jan. 18, 2017, provisional application No. 62/409,275, filed on Oct. 10, 2016.

(51) Int. Cl.
| | | |
|---|---|---|
| *C07D 471/04* | (2006.01) |
| *A61K 31/4162* | (2006.01) |
| *A61P 1/00* | (2006.01) |
| *A61P 35/00* | (2006.01) |

(52) U.S. Cl.
CPC ........ *C07D 471/04* (2013.01); *A61K 31/4162* (2013.01); *A61P 1/00* (2018.01); *A61P 35/00* (2018.01)

(58) Field of Classification Search
CPC .......................... C07D 471/04; A61K 31/4162
See application file for complete search history.

(56) References Cited

U.S. PATENT DOCUMENTS

| | | |
|---|---|---|
| 5,844,092 A | 12/1998 | Presta et al. |
| 5,877,016 A | 3/1999 | Presta et al. |
| 5,910,574 A | 6/1999 | Presta et al. |
| 6,025,166 A | 2/2000 | Presta et al. |
| 6,027,927 A | 2/2000 | Presta et al. |
| 6,153,189 A | 11/2000 | Presta et al. |
| 6,531,152 B1 | 3/2003 | Lerner et al. |
| 6,861,509 B1 | 3/2005 | Sanicola-Nadel et al. |
| 7,384,632 B2 | 6/2008 | Devaux et al. |

(Continued)

FOREIGN PATENT DOCUMENTS

| | | |
|---|---|---|
| CN | 105255927 A | 1/2016 |
| EP | 3037547 A1 | 6/2016 |

(Continued)

OTHER PUBLICATIONS

Albaugh et al., "Discovery of GNF-5837, a Selective TRK Inhibitor with Efficacy in Rodent Cancer Tumor Models," ACS Med Chem. Lett., Jan. 1, 2012;3(2):140-145.

(Continued)

*Primary Examiner* — Matthew P Coughlin
*Assistant Examiner* — Karen Cheng
(74) *Attorney, Agent, or Firm* — Fish & Richardson P.C.

(57) ABSTRACT

Provided herein are compounds of the Formula I:

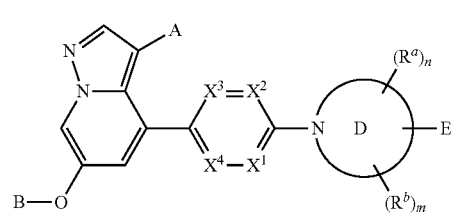

or pharmaceutically acceptable salt or solvate thereof, wherein A, B, $X^1$, $X^2$, $X^3$, $X^4$, Ring D, E, $R^a$, $R^b$, n and m have the meanings given in the specification, which are inhibitors of RET kinase and are useful in the treatment and prevention of diseases which can be treated with a RET kinase inhibitor, including RET-associated diseases and disorders.

30 Claims, No Drawings

Specification includes a Sequence Listing.

(56) References Cited

U.S. PATENT DOCUMENTS

| | | |
|---|---|---|
| 7,465,726 B2 | 12/2008 | Ahmed et al. |
| 7,504,509 B2 | 3/2009 | Ibrahim et al. |
| 7,514,446 B2 | 4/2009 | Davis-Ward et al. |
| 7,615,383 B2 | 11/2009 | Devaux et al. |
| 7,795,273 B2 | 9/2010 | Imbach et al. |
| 7,863,288 B2 | 1/2011 | Ibrahim et al. |
| 7,863,289 B2 | 1/2011 | Spevak et al. |
| 8,012,966 B2 | 9/2011 | Tang et al. |
| 8,026,247 B2 | 9/2011 | Bold et al. |
| 8,067,434 B2 | 11/2011 | Ibrahim et al. |
| 8,106,069 B2 | 1/2012 | Salom et al. |
| 8,114,989 B2 | 2/2012 | Wang et al. |
| 8,129,374 B2 | 3/2012 | Bhagwat et al. |
| 8,198,298 B2 | 6/2012 | Salom et al. |
| 8,299,057 B2 | 10/2012 | Lombardi Borgia et al. |
| 8,338,417 B2 | 12/2012 | Li et al. |
| 8,354,526 B2 | 1/2013 | Ding et al. |
| 8,399,442 B2 | 3/2013 | Berdini et al. |
| 8,450,322 B2 | 5/2013 | Andrews et al. |
| 8,461,161 B2 | 6/2013 | Burns et al. |
| 8,501,756 B2 | 8/2013 | Artman, III et al. |
| 8,513,263 B2 | 8/2013 | Haas et al. |
| 8,524,709 B2 | 9/2013 | Liang et al. |
| 8,552,002 B2 | 10/2013 | Ding et al. |
| 8,568,998 B2 | 10/2013 | Mani et al. |
| 8,629,135 B2 | 1/2014 | Gujral et al. |
| 8,637,256 B2 | 1/2014 | Ernst |
| 8,637,516 B2 | 1/2014 | Fan et al. |
| 8,642,035 B2 | 2/2014 | Luehrsen |
| 8,673,347 B2 | 3/2014 | Traversa et al. |
| 8,686,005 B2 | 4/2014 | Gregor |
| 8,691,221 B2 | 4/2014 | Pavone et al. |
| 8,741,849 B2 | 6/2014 | Panitch et al. |
| 8,754,209 B2 | 6/2014 | Sim et al. |
| 8,791,123 B2 | 7/2014 | Allen et al. |
| 8,815,901 B2 | 8/2014 | Furet et al. |
| 8,815,906 B2 | 8/2014 | Gregor et al. |
| 8,895,744 B2 | 11/2014 | Gambacorti Passerini et al. |
| 8,912,194 B2 | 12/2014 | Ciomei et al. |
| 8,912,204 B2 | 12/2014 | Ibrahim et al. |
| 8,933,084 B2 | 1/2015 | Andrews et al. |
| 8,933,230 B2 | 1/2015 | Yun et al. |
| 8,937,071 B2 | 1/2015 | Eidam et al. |
| 8,946,226 B2 | 2/2015 | Ciomei et al. |
| 9,006,256 B2 | 4/2015 | Matsui |
| 9,035,063 B2 | 5/2015 | Eidam et al. |
| 9,102,671 B2 | 8/2015 | Molteni et al. |
| 9,149,464 B2 | 10/2015 | Bakale et al. |
| 9,150,517 B2 | 10/2015 | Bakale et al. |
| 9,186,318 B2 | 11/2015 | Yun et al. |
| 9,216,172 B2 | 12/2015 | Kohno et al. |
| 9,242,977 B2 | 1/2016 | Takeuchi et al. |
| 9,260,437 B2 | 2/2016 | Ibrahim et al. |
| 9,273,051 B2 | 3/2016 | Chen et al. |
| 9,297,011 B2 | 3/2016 | Downing et al. |
| 9,321,772 B2 | 4/2016 | Dar et al. |
| 9,487,491 B2 | 11/2016 | Shimada et al. |
| 9,493,455 B2 | 11/2016 | Cheve et al. |
| 9,505,784 B2 | 11/2016 | Choi et al. |
| 9,522,910 B2 | 12/2016 | Chilov et al. |
| 9,550,772 B2 | 1/2017 | Cheve et al. |
| 9,604,980 B2 | 3/2017 | Menichincheri et al. |
| 9,669,028 B2 | 6/2017 | Vankayalapati et al. |
| 9,682,083 B2 | 6/2017 | Angiolini et al. |
| 9,738,660 B2 | 8/2017 | Yang et al. |
| 9,758,508 B2 | 9/2017 | Hong et al. |
| 9,789,100 B2 | 10/2017 | Eidam |
| 9,801,880 B2 | 10/2017 | Micklem |
| 2004/0185547 A1 | 9/2004 | Mohammadi et al. |
| 2005/0209195 A1 | 9/2005 | Menta et al. |
| 2005/0222171 A1 | 10/2005 | Bold et al. |
| 2006/0183900 A1 | 8/2006 | Huang et al. |
| 2007/0117800 A1 | 5/2007 | Arnold et al. |
| 2007/0149523 A1 | 6/2007 | Ehlert et al. |
| 2007/0265274 A1 | 11/2007 | Fagin et al. |
| 2008/0199426 A1 | 8/2008 | Sukhatme et al. |
| 2008/0234267 A1 | 9/2008 | Lackey |
| 2008/0234276 A1 | 9/2008 | Boyle et al. |
| 2008/0234284 A1 | 9/2008 | Imbach et al. |
| 2008/0262021 A1 | 10/2008 | Capraro et al. |
| 2008/0275054 A1 | 11/2008 | Holzer et al. |
| 2008/0287427 A1 | 11/2008 | Bold et al. |
| 2008/0312192 A1 | 12/2008 | Bold et al. |
| 2008/0319005 A1 | 12/2008 | Bold et al. |
| 2009/0012045 A1 | 1/2009 | Hitoshi et al. |
| 2009/0027556 A1 | 1/2009 | Bleau et al. |
| 2009/0048249 A1 | 2/2009 | Chiu et al. |
| 2009/0069360 A1 | 3/2009 | Batt et al. |
| 2009/0099167 A1 | 4/2009 | Bold et al. |
| 2009/0130229 A1 | 5/2009 | Lanzi et al. |
| 2009/0143399 A1 | 6/2009 | Hurley et al. |
| 2009/0152083 A1 | 6/2009 | Cheng et al. |
| 2009/0209496 A1 | 8/2009 | Chaplin et al. |
| 2009/0215761 A1 | 8/2009 | Whitten et al. |
| 2009/0227556 A1 | 9/2009 | Obaishi |
| 2009/0312321 A1 | 12/2009 | Ren et al. |
| 2010/0004239 A1 | 1/2010 | Tang et al. |
| 2010/0048540 A1 | 2/2010 | Boyle et al. |
| 2010/0069395 A1 | 3/2010 | Imbach et al. |
| 2010/0075916 A1 | 3/2010 | Gant et al. |
| 2010/0081675 A1 | 4/2010 | Hsieh et al. |
| 2010/0152219 A1 | 6/2010 | Block et al. |
| 2010/0173954 A1 | 7/2010 | Wilhelm et al. |
| 2010/0209488 A1 | 8/2010 | Wrasidlo et al. |
| 2010/0280012 A1 | 11/2010 | Lee |
| 2010/0297115 A1 | 11/2010 | Blaustein |
| 2010/0324065 A1 | 12/2010 | Ibrahim et al. |
| 2011/0046370 A1 | 2/2011 | Sim et al. |
| 2011/0053934 A1 | 3/2011 | Angell et al. |
| 2011/0133637 A1 | 6/2011 | Ota |
| 2011/0189167 A1 | 8/2011 | Flynn et al. |
| 2011/0195072 A1 | 8/2011 | Boulay et al. |
| 2011/0212053 A1 | 9/2011 | Qian et al. |
| 2011/0269739 A1 | 11/2011 | Kim et al. |
| 2011/0281841 A1 | 11/2011 | Lee et al. |
| 2011/0301157 A1 | 12/2011 | Bold et al. |
| 2012/0065233 A1 | 3/2012 | Gregor |
| 2012/0070410 A1 | 3/2012 | Apuy et al. |
| 2012/0225057 A1 | 9/2012 | Flynn et al. |
| 2012/0271048 A1 | 10/2012 | Sim et al. |
| 2012/0277247 A1 | 11/2012 | Menet et al. |
| 2012/0277424 A1 | 11/2012 | Sim et al. |
| 2012/0283261 A1 | 11/2012 | Bearss et al. |
| 2012/0302567 A1 | 11/2012 | Jung et al. |
| 2013/0012703 A1 | 1/2013 | Sim et al. |
| 2013/0029925 A1 | 1/2013 | Vandier et al. |
| 2013/0053370 A1 | 2/2013 | Son et al. |
| 2013/0079343 A1 | 3/2013 | Sim et al. |
| 2013/0303518 A1 | 11/2013 | Tang et al. |
| 2014/0121239 A1 | 5/2014 | Aftab |
| 2014/0137274 A1 | 5/2014 | Ishikawa |
| 2014/0272951 A1 | 9/2014 | Chakravarti et al. |
| 2014/0371219 A1 | 12/2014 | Bae et al. |
| 2015/0018336 A1 | 1/2015 | Chen et al. |
| 2015/0051222 A1 | 2/2015 | Barbugian et al. |
| 2015/0057335 A1 | 2/2015 | Kohno et al. |
| 2015/0065468 A1 | 3/2015 | Holladay et al. |
| 2015/0099721 A1 | 4/2015 | Acquaviva et al. |
| 2015/0099762 A1 | 4/2015 | Eidam et al. |
| 2015/0166564 A1 | 6/2015 | Allen et al. |
| 2015/0177246 A1 | 6/2015 | Shibata et al. |
| 2015/0238477 A1 | 8/2015 | Aftab |
| 2015/0272958 A1 | 10/2015 | Kodama et al. |
| 2015/0283132 A1 | 10/2015 | Lim et al. |
| 2015/0306086 A1 | 10/2015 | Wilcoxen |
| 2016/0000783 A1 | 1/2016 | Takeuchi et al. |
| 2016/0009709 A1 | 1/2016 | Cheve et al. |
| 2016/0046636 A1 | 2/2016 | Gray et al. |
| 2016/0137654 A1 | 5/2016 | Arrigo et al. |
| 2016/0176865 A1 | 6/2016 | Ibrahim et al. |
| 2017/0014413 A1 | 1/2017 | Downing et al. |
| 2017/0044106 A1 | 2/2017 | Aftab et al. |
| 2017/0096425 A1 | 4/2017 | Andrews et al. |
| 2017/0114032 A1 | 4/2017 | Cheng et al. |

(56) References Cited

U.S. PATENT DOCUMENTS

| | | |
|---|---|---|
| 2017/0121312 A1 | 5/2017 | Brubaker et al. |
| 2017/0226100 A1 | 8/2017 | Jiaang et al. |
| 2017/0267661 A1 | 9/2017 | Kim et al. |
| 2017/0281632 A1 | 10/2017 | Cox et al. |
| 2017/0283404 A1 | 10/2017 | Cheung et al. |
| 2017/0298074 A1 | 10/2017 | Cheung et al. |
| 2018/0009817 A1 | 1/2018 | Miyazaki et al. |
| 2018/0009818 A1 | 1/2018 | Miyazaki et al. |
| 2018/0133200 A1 | 5/2018 | Andrews et al. |
| 2018/0133207 A1 | 5/2018 | Andrews et al. |
| 2018/0133213 A1 | 5/2018 | Andrews et al. |
| 2018/0134702 A1 | 5/2018 | Andrews et al. |
| 2018/0134703 A1 | 5/2018 | Andrews et al. |

FOREIGN PATENT DOCUMENTS

| | | |
|---|---|---|
| JP | 2015109806 A | 6/2015 |
| WO | WO8705297 | 9/1987 |
| WO | WO1997044356 | 11/1997 |
| WO | WO2001016169 | 3/2001 |
| WO | WO2001062273 | 8/2001 |
| WO | WO2003020698 | 3/2003 |
| WO | WO2005044835 | 5/2005 |
| WO | WO2005051366 | 6/2005 |
| WO | WO2005062795 | 7/2005 |
| WO | WO2005070431 | 8/2005 |
| WO | WO2006089298 | 8/2006 |
| WO | WO2006123113 | 11/2006 |
| WO | WO2006130613 | 12/2006 |
| WO | WO2006131952 | 12/2006 |
| WO | WO2007002325 | 1/2007 |
| WO | WO2007002433 | 1/2007 |
| WO | WO2007022999 | 3/2007 |
| WO | WO2007054357 | 5/2007 |
| WO | WO2007057397 | 5/2007 |
| WO | WO2007057399 | 5/2007 |
| WO | WO2007087245 | 8/2007 |
| WO | WO2007109045 | 9/2007 |
| WO | WO2007110344 | 10/2007 |
| WO | WO2007136103 | 11/2007 |
| WO | WO2008031551 | 3/2008 |
| WO | WO2008079903 | 7/2008 |
| WO | WO2008079906 | 7/2008 |
| WO | WO2008079909 | 7/2008 |
| WO | WO2008080001 | 7/2008 |
| WO | WO2008080015 | 7/2008 |
| WO | WO2009007748 | 1/2009 |
| WO | WO2009012283 | 1/2009 |
| WO | WO2009013126 | 1/2009 |
| WO | WO2009014637 | 1/2009 |
| WO | WO2009017838 | 2/2009 |
| WO | WO2009023978 | 2/2009 |
| WO | WO2009042646 | 4/2009 |
| WO | WO2009053442 | 4/2009 |
| WO | WO2009071480 | 6/2009 |
| WO | WO2009092049 | 7/2009 |
| WO | WO2009118411 | 10/2009 |
| WO | WO2009143018 | 11/2009 |
| WO | WO2009143024 | 11/2009 |
| WO | WO2009152083 | 12/2009 |
| WO | WO2010031816 | 3/2010 |
| WO | WO2010033941 | 3/2010 |
| WO | WO2010048314 | 4/2010 |
| WO | WO2010058006 | 5/2010 |
| WO | WO2010111527 | 9/2010 |
| WO | WO2010145998 | 12/2010 |
| WO | WO2011006074 | 1/2011 |
| WO | WO2011022439 | 2/2011 |
| WO | WO2011045344 | 4/2011 |
| WO | WO2011092120 | 8/2011 |
| WO | WO2011133637 | 10/2011 |
| WO | WO2011146336 | 11/2011 |
| WO | WO2012034091 | 3/2012 |
| WO | WO2012034095 | 3/2012 |
| WO | WO2012047017 | 4/2012 |
| WO | WO2012053606 | 4/2012 |
| WO | WO2012101029 | 8/2012 |
| WO | WO2012101032 | 8/2012 |
| WO | WO2012109075 | 8/2012 |
| WO | WO2012113774 | 8/2012 |
| WO | WO2012116217 | 8/2012 |
| WO | WO2012139930 | 10/2012 |
| WO | WO2012143248 | 10/2012 |
| WO | WO2012152763 | 11/2012 |
| WO | WO2012158413 | 11/2012 |
| WO | WO2012171337 | 12/2012 |
| WO | WO2013014039 | 1/2013 |
| WO | WO2013016720 | 1/2013 |
| WO | WO2013036232 | 3/2013 |
| WO | WO2013042137 | 3/2013 |
| WO | WO2013050446 | 4/2013 |
| WO | WO2013050448 | 4/2013 |
| WO | WO2013074518 | 5/2013 |
| WO | WO2013102059 | 7/2013 |
| WO | WO2013174876 | 11/2013 |
| WO | WO2013183578 | 12/2013 |
| WO | WO2014011900 | 1/2014 |
| WO | WO2014019908 | 2/2014 |
| WO | WO2014072220 | 5/2014 |
| WO | WO2014075035 | 5/2014 |
| WO | WO2014078322 | 5/2014 |
| WO | WO2014078323 | 5/2014 |
| WO | WO2014078325 | 5/2014 |
| WO | WO2014078328 | 5/2014 |
| WO | WO2014078331 | 5/2014 |
| WO | WO2014078372 | 5/2014 |
| WO | WO2014078378 | 5/2014 |
| WO | WO2014078408 | 5/2014 |
| WO | WO2014078417 | 5/2014 |
| WO | WO2014078454 | 5/2014 |
| WO | WO2014083567 | 6/2014 |
| WO | WO2014086284 | 6/2014 |
| WO | WO2014141187 | 9/2014 |
| WO | WO2014160521 | 10/2014 |
| WO | WO2014160524 | 10/2014 |
| WO | WO2014184069 | 11/2014 |
| WO | WO2014194127 | 12/2014 |
| WO | WO2015017528 | 2/2015 |
| WO | WO2015017533 | 2/2015 |
| WO | WO2015057873 | 4/2015 |
| WO | WO2015058129 | 4/2015 |
| WO | WO2015061572 | 4/2015 |
| WO | WO2015079251 | 6/2015 |
| WO | WO2015108992 | 7/2015 |
| WO | WO2015112806 | 7/2015 |
| WO | WO2015124697 | 8/2015 |
| WO | WO2015161274 | 10/2015 |
| WO | WO2015161277 | 10/2015 |
| WO | WO2015175788 | 11/2015 |
| WO | WO2015191666 | 12/2015 |
| WO | WO2015191667 | 12/2015 |
| WO | WO2016011141 | 1/2016 |
| WO | WO2016011144 | 1/2016 |
| WO | WO2016011147 | 1/2016 |
| WO | WO2016022569 | 2/2016 |
| WO | WO2016027754 | 2/2016 |
| WO | WO2016037578 | 3/2016 |
| WO | WO2016038519 | 3/2016 |
| WO | WO2016038552 | 3/2016 |
| WO | WO2016075224 | 5/2016 |
| WO | WO2016077841 | 5/2016 |
| WO | WO2016081450 | 5/2016 |
| WO | WO2016096709 | 6/2016 |
| WO | WO2016127074 | 8/2016 |
| WO | WO2016137060 | 9/2016 |
| WO | WO2016141169 | 9/2016 |
| WO | WO2016168992 | 10/2016 |
| WO | WO2017009644 | 1/2017 |
| WO | WO2017011776 | 1/2017 |
| WO | WO2017013160 | 1/2017 |
| WO | WO2017026718 | 2/2017 |
| WO | WO2017027883 | 2/2017 |
| WO | WO2017043550 | 3/2017 |
| WO | WO2017049462 | 3/2017 |

(56) References Cited

FOREIGN PATENT DOCUMENTS

| WO | WO2017097697 | 6/2017 |
|---|---|---|
| WO | WO2017122815 | 7/2017 |
| WO | WO2017145050 | 8/2017 |
| WO | WO2017146116 | 8/2017 |
| WO | WO2017178844 | 10/2017 |
| WO | WO2017178845 | 10/2017 |

OTHER PUBLICATIONS

Amit M et al., "Upregulation of RET induces perineurial invasion of pancreatic adenocarcinoma." Oncogene Jun. 8, 2017; 36:3232-3239.
Andreucci et al., "Targeting the receptor tyrosine kinase RET in combination with aromatase inhibitors in ER positive breast cancer xenografts," Oncotarget, Dec. 6, 2016, 7(49):80543-80553.
Antonescu et al., "Molecular characterization of inflammatory myofibroblastic tumors with frequent ALK and ROS1 gene fusions and rare novel RET rearrangement," Am J Surg Pathol, Jul. 2015;39(7):957-967.
Aright et al., "RET tyrosine kinase signaling in development and cancer," Cytokine Growth Factor Rev, Aug.-Oct. 2005;16(4-5):441-467.
Ballerini et al., "RET fusion genes are associated with chronic myelomonocytic leukemia and enhance monocytic differentiation," Leukemia, Nov. 2012;26(11):2384-2389.
Bastien et al., Journal of Molecular Diagnostics, 18(6):1027, Abstract No. S120, 2016 Annual Meeting of the Association for Molecular Pathology, Charlotte, NC, 2016.
Behrens et al., "Gö 6976 is a potent inhibitor of neurotrophin-receptor intrinsic tyrosine kinase," J Neurochem. Mar. 1999;72(3):919-924.
Bhinge et al., "EGFR mediates activation of RET in lung adenocarcinoma with neuroendocrine differentiation characterized by ASCL1 expression," Oncotarget, Apr. 18, 2017, 8(16):27155-27165.
Borecka et al., European Journal of Cancer, (Jul. 2016) vol. 61, No. 1, pp. S26, Abstract No. 162, Meeting Info: 24th Biennial Congress of the European Association for Cancer Research, EACR 2016. Manchester, United Kingdom.
Borrello et al., "RET inhibition: implications in cancer therapy," Expert Opin. Ther. Targets, Apr. 2013, 17(4):403-419.
Boulay et al., "The Ret receptor tyrosine kinase pathway functionally interacts with the ERalpha pathway in breast cancer," Cancer Res., May 15, 2008;68(10):3743-3751.
Brodeur, "Neuroblastoma: biological insights into a clinical enigma," Nat Rev Cancer., Mar. 2003, 3(3):203-216.
Butler Tjaden et al., "The developmental etiology and pathogenesis of Hirschsprung disease," Transl. Res., Jul. 2013;162(1):1-15.
Calero et al., "Sunitinib suppress neuroblastoma growth through degradation of MYCN and inhibition of angiogenesis," PLoS One. Apr. 23, 2014;9(4):e95628.
Camilleri, "Peripheral mechanisms in irritable bowel syndrome," N Engl J Med, Oct. 25, 2012, 367(17):1626-1635.
Camoratto et al., "CEP-751 inhibits TRK receptor tyrosine kinase activity in vitro exhibits anti-tumor activity," Int J Cancer. Aug. 7, 1997;72(4):673-679.
Camós et al., "Gene expression profiling of acute myeloid leukemia with translocation t(8;16)(p11;p13) and MYST3-CREBBP rearrangement reveals a distinctive signature with a specific pattern of HOX gene expression," Cancer Res., Jul. 15, 2006;66(14):6947-6954.
Cancer Genome Atlas Network, "Comprehensive molecular characterization of human colon and rectal cancer," Nature, Jul. 18, 2012;487(7407):330-337.
Carlomagno et al., "Identification of tyrosine 806 as a molecular determinant of RET kinase sensitivity to ZD6474," Endocr. Rel. Cancer, Mar. 2009;16(1):233-241.
Carpinelli et al., "PHA-739358, a potent inhibitor of Aurora kinases with a selective target inhibition profile relevant to cancer," Mol Cancer Ther., Dec. 2007;6(12 Pt 1):3158-68.
Cecchirini et al., "Somatic in frame deletions not involving juxtamembranous cysteine residues strongly activate the RET proto-oncogene," Oncogene, May 29, 1997;14(21):2609-2612.
Ceolin et al., "Effect of 3'UTR RET Variants on RET mRNA Secondary Structure and Disease Presentation in Medullary Thyroid Carcinoma," PLoS One, Feb. 1, 2016;11(2):e0147840. doi: 10.1371/journal.pone.0147840. eCollection 2016.
Chang et al., "EGF Induced RET Inhibitor Resistance in CCDC6-RET Lung Cancer Cells," Yonsei Med J, Jan. 2017, 58(1):9-18.
Choi et al., "(R)-2-Phenylpyrrolidine Substituted Imidazopyridazines: A New Class of Potent and Selective Pan-TRK Inhibitors," ACS Med Chem Lett., Mar. 16, 2015;6(5):562-567.
Corsello et al., Endocrine Reviews, (Jun. 2014) vol. 35, No. 3, Suppl. S, pp. SUN-0322, Meeting Info.: 96th Annual Meeting and Expo of the Endocrine-Society, Chicago, IL, USA, Jun. 21-24, 2014.
Cranston et al., "RET is constitutively activated by novel tandem mutations that alter the active site resulting in multiple endocrine neoplasia type 2B," Cancer Res., Oct. 15, 2006;66(20):10179-10187.
Croucher et al., "TrkB inhibition by GNF-4256 slows growth and enhances chemotherapeutic efficacy in neuroblastoma xenografts," Cancer Chemother Pharmacol., Jan. 2015;75(1):131-141.
Davila et al., "Comprehensive genomic profiling of a rare thyroid follicular dendritic cell sarcoma," Rare Tumors, 2017, 9(2):6834.
Dawson et al., "Altered expression of RET proto-oncogene product in prostatic intraepithelial neoplasia and prostate cancer," J Natl Cancer Inst, Apr. 1, 1998;90(7):519-523.
De Almeida et al., Endocrine Reviews, 2016, vol. 37, No. 2, Supp. Supplement 1. Abstract No. SUN-068; 93th Annual Meeting and Expo of the Endocrine Society, ENDO 2016. Boston, MA, US. Apr. 1, 2016-Apr. 4, 2016.
De Groot et al., "RET as a diagnostic and therapeutic target in sporadic and hereditary endocrine tumors," Endocrine Rev, Aug. 2006;27(5):535-560.
Demeure et al., "Whole-genome Sequencing of an Aggressive BRAF Wild-type Papillary Thyroid Cancer Identified EML4—ALK Translocation as a Therapeutic Target," World J. Surg., Jun. 2014, 38(6):1296-305.
Dinér er al., "Preparation of 3-substituted-l-isopropyl-1H-pyrazolo[3,4-d]pyrimidin-4-amines as RET kinase inhibitors," J. Med. Chem., May 24, 2012, 55(10):4872-4876.
Ding et al., "Artemin, a member of the glial cell line-derived neurotrophic factor family of ligands, is HER2-regulated and mediates acquired trastuzumab resistance by promoting cancer stem cell-like behavior in mammary carcinoma cells," J Biol Chem, Jun. 6, 2014, 289(23):16057-71.
Dogan et al., Laboratory Investigation, (Feb. 2017) vol. 97, Supp. 1, pp. 323A. Abstract No. 1298, Meeting Info: 106th Annual Meeting of the United States and Canadian Academy of Pathology, USCAP 2017. San Antonio, TX, United States.
Dogan et al., "Genomic Profiling of the Two Closely Related "cousins" Acinic Cell Carcinoma and Mammary Analog Secretory Carcinoma of Salivary Glands Reveals Novel NVOA4-RET Fusion in Mammary Analog Secretory Carcinoma," Modern Pathology, vol. 30, Supp. [2], pp. 323A-323A. MA 1298, 2017.
Drilon et al., "Phase II study of cabozantinib for patients with advanced RET-rearranged lung cancers," Journal of Clinical Oncology, May 20, 2015, 33(15S):8007-8007 [Abstract Only], 6 pages.
Esseghir et al., "A role for glial cell derived neurotrophic factor induced expression by inflammatory cytokines and RET/GFR alpha 1 receptor up-regulation in breast cancer," Cancer Res, Dec. 15, 2007;67(24):11732-11741.
Fang et al., "Detection of a novel RET gene fusion in a non-small cell lung cancer patient using AMP chemistry." Journal of Thoracic Oncology, Feb. 1, 2016,11(2):S21-S22.
Flavin et al., "RET protein expression in papillary renal cell carcinoma," Urol. Oncol., Nov.-Dec. 2012;30(6):900-905.
Fugazzola et al., "Molecular and biochemical analysis of RET/PTC4, a novel oncogenic rearrangement between RET and ELE1 genes, in a post-Chernobyl papillary thyroid cancer," Oncogene, Sep. 1996, 13(5): 1093-7.

(56) References Cited

OTHER PUBLICATIONS

Futami et al., "A novel somatic point mutation of the RET Proto-oncogene in tumor tissues of small cell lung cancer patients," Jpn. J. Cancer Res., Dec. 1995, 86(12):1127-1130.
Gao et al., "Neurotrophic Factor Artemin Promotes Invasiveness and Neurotrophic Function of Pancreatic Adenocarcinoma In Vivo and In Vitro," Pancreas, Jan. 2015, 44(1):134-143.
Gattei et al., "Expression of the RET receptor tyrosine kinase and GDNFR-alpha in normal and leukemic human hematopoietic cells and stromal cells of the bone marrow microenvironment," Blood, Apr. 15, 1997;89(8):2925-2937.
Gattei, et al., "Differential expression of the RET gene in human acute myeloid leukemia," Ann. Hematol, Nov. 1998, 77(5):207-210.
Gattelli et al., "Ret inhibition decreases growth and metastatic potential of estrogen receptor positive breast cancer cells," EMBO Mol. Med., Sep. 2013;5(9):1335-1350.
Gazizova et al., Endocrine Reviews, (Jun. 2014) vol. 35, No. 3, Suppl. S, pp. SAT-0304, Meeting Info.: 96th Annual Meeting and Expo of the Endocrine-Society, Chicago, IL, USA, Jun. 21-24, 2014.
Gil et al., "Paracrine regulation of pancreatic cancer cell invasion by peripheral nerves," J. Natl. Cancer Inst., Jan. 20, 2010;102(2):107-118.
Gozgit et al., "RET fusions identified in colorectal cancer PDX models are sensitive to the potent RET inhibitor ponatinib," AACR Annual Meeting, Apr. 7, 2014, Presentation Abstract, [Abstract Only], 1 page.
Greco et al., "Molecular pathology of differentiated thyroid cancer," J. Nucl. Med. Mol. Imaging, Oct. 2009, 53:440-454.
Greene & Wuts, eds., "Protecting Groups in Organic Synthesis", 2nd ed. New York; John Wiley & Sons, Inc., 1991, Chapter One, 20 pages.
Grey et al., "The RET E616Q Variant is a Gain of Function Mutation Present in a Family with Features of Multiple Endocrine Neoplasia 2A," Endocrine Pathology, Mar. 2017, 28(1):41-48.
Grieco et al.., "PTC is a novel rearranged form of the ret proto-oncogene and is frequently detected in vivo in human thyroid papillary carcinomas," Cell, Feb. 23, 1990, 60(4):557-563.
Grubbs et al., "RET fusion as a novel driver of medullary thyroid carcinoma," J. Clin. Endocrinol. Metab., Mar. 2015;100(3):788-793.
Gura et al., "Systems for identifying new drugs are often faulty," Science, 1997, 278:1041-1042.
Halkova et al., "A novel RET/PTC variant detected in a pediatric patient with papillary thyroid cancer without ionization history," Human Pathology, Dec. 2015, 46(12):1962-1969.
Hezam et al., "Artemin promotes oncogenicity, metastasis and drug resistance in cancer cells," Rev Neurosci, Jan. 26, 2018, 29(1):93-98.
Hirshfield et al., Cancer Research, (Feb. 2017) vol. 77, No. 4, Supp. 1. Abstract No. P3-07-02. Meeting Info: 39th Annual CTRC-AACR San Antonio Breast Cancer Symposium. San Antonio, TX, United States. Dec. 6, 2016-Dec. 10, 2016.
Hoffman et al., "Activation of colonic mucosal 5-HT(4) receptors accelerates propulsive motility and inhibits visceral hypersensitivity," Gastroenterology, Apr. 2012;142(4):844-854.
Hofstra et al., "No mutations found by RET mutation scanning in sporadic and hereditary neuroblastoma," Hum Genet., Mar. 1996, 97(3):362-364.
Huang et al., "Preclinical Modeling of KIF5B—RET Fusion Lung Adenocarcinoma," Mol. Cancer Ther., Oct. 2016, 15(10):2521-2529.
Ibrahimpasic et al., "Genomic Alterations in Fatal Forms of Non-Anaplastic Thyroid Cancer: Identification of MED12 and RBM10 as Novel Thyroid Cancer Genes Associated with Tumor Virulence," Clin. Cancer Res., Oct. 2017, 23(19):5970-5980.
International Search Report and Written Opinion in International Application No. PCT/US2017/055993, dated Jan. 30, 2018, 11 pages.

Ito et al., "Expression of glial cell line-derived neurotrophic factor family members and their receptors in pancreatic cancers," Surgery, Oct. 2005, 138(4):788-794.
Iwahashi et al., "Expression of glial cell line-derived neurotrophic factor correlates with perineural invasion of bile duct carcinoma," Cancer, Jan. 1, 2002, 94(1):167-174.
Iyama et al., "Identification of Three Novel Fusion Oncogenes, SQSTM1/NTRK3, AFAP1L2/RET, and PPFIBP2/RET, in Thyroid Cancers of Young Patients in Fukushima ," Thyroid, Jun. 2017, 27(6):811-818.
Iyer et al, "AZ64 inhibits TrkB and enhances the efficacy of chemotherapy and local radiation in neuroblastoma xenografts," Cancer Chemother Pharmacol., Sep. 2012;70(3):477-486.
Johnson et al., Relationships between drug activity in NCI preclinical in vitro and in vivo models and early clinical trials, British Journal of Cancer, 84(10):1424-1431, 2001.
Joung et al., "Diffuse sclerosing variant of papillary thyroid carcinoma: major genetic alterations and prognostic implications," Histopathology, Jul. 2016, 69(1):45-53.
Jovanovic et al., "Novel RET mutations in macedonian patients with medullary thyroid carcinoma: genotype-phenotype correlations," Pril (Makedon Akad Nauk Umet Odd Med Nauki), 2015;36(1):93-107.
Ju et al., "A transforming KIF5B and RET gene fusion in lung adenocarcinoma revealed from whole-genome and transcriptome sequencing," Genome Res., Mar. 2012;22(3):436-445.
Kaneta et al., Abstract B173: Preclinical characterization and antitumor efficacy of DS-5010, a highly potent and selective RET inhibitor, Mol Cancer Ther Jan. 1, 2018 (17) (1 Supplement) B173; DOI:10.1158/1535-7163.TARG-17-B173.
Karachialiou et al ., "Real-time liquid biopsies become a reality in cancer treatment," Ann. Transl. Med , Mar. 2015, 3(3):36.
Karrasch et al., "How to Assess the Clinical Relevance of Novel RET Missense Variants in the Absence of Functional Studies?" Eur. Thyroid J., Mar. 2016;5(1):73-77.
Kato et al., "Repair by Src kinase of function-impaired RET with multiple endocrine neoplasia type 2A mutation with substitutions of tyrosines in the COOH-terminal kinase domain for phenylalanine," Cancer Res., Apr. 15, 2002, 62(8):2414-2422.
Kato et al., "RET Aberrations in Diverse Cancels: Next-Generation Sequencing of 4,871 Patients," Clin. Cancer Res., Apr. 15, 2017, 23(8):1988-1997.
Keszthelyi et al., "Revisiting concepts of visceral nociception in irritable bowel syndrome," Eur. J. Pain, Nov. 2012;16(10):1444-1454.
Kheiroddin et al., "RET Gene Analysis in Patients with Medullary Thyroid Carcinoma," Clin. Lab., Jan. 2016, 62(5):871-876.
Kim et al., "A New Germline Ala641Thr Variant in the Transmembrane Domain of the RET Gene Associated With Medullary Thyroid Cancer," Acto Endocrinologica-Bucharest, Apr. 2015, 11(2):189-194.
Kim et al., "Mammaglobin-A is a target for breast cancer vaccination," Oncoimmunology. Feb. 26, 2016;5(2):e1069940. eCollection Feb. 2016.
Kloosterman et al., "A systematic analysis of oncogenic gene fusions in primary colon cancer," Cancer Res., Jul. 15, 2017, 77(14):3814-3822.
Klugbauer et al., "A novel type of RET rearrangement (PTC8) in childhood papillary thyroid carcinomas and characterization of the involved gene (RFG8)," Cancer Res., Dec. 15, 2000;60(24):7028-32.
Kohlmann, et al., "Next-Generation Sequencing Technology Reveals a Characteristic Pattern of Molecular Mutations in 72.8% of Chronic Myelomonocytic Leukemia by Detecting Frequent Alterations in TET2, CBL, RAS, and RUNX1," J. Clin. Oncol. Aug. 20, 2010, 28(24):3858-3865.
Kohno et al., "KIF5B-RET fusions in lung adenocarcinoma," Nature Med., Feb. 12, 2012;18(3):375-377.
Kooistra et al., "KLIFS: A structural kinaseligand interaction database," Nucleic Acids Res., Jan. 2016, 44(D1)D365-D371.

(56) References Cited

OTHER PUBLICATIONS

Kraft et al, Cancer Research, 2017, vol. 77, No. 13, Supp. Supplement 1. Abstract No. 4882; American Association for Cancer Research Annual Meeting 2017. Washington, DC, United States. Apr. 1, 2017-Apr. 5, 2017.
Krampitz et al., "RET gene mutations (genotype and phenotype) of multiple endocrine neoplasia type 2 and familial medullary thyroid carcinoma," Cancer, Jul. 1, 2014;120(13):1920-1931.
Kubler et al. "Self-adjuvanted mRNA vaccination in advanced prostate cancer patients: a first-in-man phase I/IIa study," J Immunother Cancer. Jun. 16, 2015, 3:26, 14 pages.
Latteyer et al., "A 6-Base Pair in Frame Germline Deletion in Exon 7 of RET Leads to Increased RET Phosphorylation, ERK Activation, and MEN2A," J. Clin Endocrinol. Metab., Mar. 2016;101(3):1016-1022.
Le Rolle et al., "Identification and characterization of RET fusions in advanced colorectal cancer," Oncotarget, Oct. 6, 2015;6(30):28929-28937.
Lecht et al., "Angiostatic effects of K252a, a Trk inhibitor, in murine brain capillary endothelial cells," Mol Cell Biochem. Jun. 2010;339(1-2):201-213.
Lee et al., "Identification of a novel partner gene, KIAA1217, fused to RET: Functional characterization and inhibitor sensitivity of two isoforms in lung adenocarcinoma," Oncotarget, May 2, 2016, 7(24):36101-36114.
Lee et al., "Whole-exome sequencing identified mutational profiles of high-grade colon adenomas," Oncotarget, Jan. 2017, 8(4): 6579-6588.
Li et al., "Trk inhibitor attenuates the BDNF/TrkB-induced protection of neuroblastoma cells from etoposide in vitro and in vivo," Cancer Biol Ther., 2015;16(3):477-483.
Lipson et al., "Identification of new ALK and RET gene fusions from colorectal and lung cancer biopsies," Nature Med., Feb. 12, 2012;18(3):382-384.
Liu et al., "Oncogenic RET receptors display different autophosphmylation sites and substrate binding specificities," J Biol. Chem., J Biol Chem. Mar. 8, 1996;271(10):5309-5312.
Lopez-Delisle et al., "Activated ALK signals through the ERK-ETV5-RET pathway to drive neuroblastoma oncogenesis," Oncogene, Jan. 11, 2018, doi: 10.1038/s41388-017-0039-5. [Epub ahead of print].
Louis et al., "The 2016 World Health Organization Classification of Tumors of the Central Nervous System: a summary," Acta Neuropathol, Jun. 2016, 131(6):803-820.
Lu et al., "Targeted next generation sequencing identifies somatic mutations and gene fusions in papillary thyroid carcinoma," Oncotarget, Jul. 2017, 8(28):45784-45792.
Luo et al., "RET is a potential tumor suppressor gene in colorectal cancer," Oncogene, Apr. 18, 2013;32(16):2037-2047.
Mamedova et at, "Abstract #6: Construction of Baculovirial Vectors for RET Kinase Domain Mutants," Summer Undergraduate Research Programs (SURP) Student Abstracts, University of Oklahoma Health Sciences Center, 2016, p. 28 [Abstract Only].
Matsubara et al., "Identification of CCDC6-RET fusion in the human lung adenocarcinoma cell line, LC-2/ad," Journal of Thoracic Oncology, Dec. 2012;7(12):1872-1876.
McCarthy et al., "Tropomyosin receptor kinase inhibitors: a patent update 2009-2013," Expert. Opin. Ther. Pat., Jul. 2014;24(7):731-744.
Mendiola et al., "Preparation, Use, and Safety of O-Mesitylenesulfonylhydroxylamine," Org. Process Res. Dev., Jan. 2009, 13(2):263-267.
Montagnoli et al., "Anti-proliferative effects of GW441756, a novel inhibitor of NGFreceptor tyrosine kinase a (TRKA), in human sarcoma," Italian Journal of Anatomy and Embryology, Nov. 11, 2010, 115(1/2):117.
Morandi et al., "GDNF-RET signaling in ER-positive breast cancers is a key determinant of response and resistance to aromatase inhibitors," Cancer Res., Jun. 15, 2013;73(12):3783-3795.
Morgensztern et al., Journal of Thoracic Oncology, (Jan. 2017) vol. 12, No. 1, Supp. 1, pp. S717-S718, Abstract No. PI.07-035, Meeting Info: 17th World Conference of the International Association for the Study of Lung Cancer, IASLC 2016. Vienna, Austria. Dec. 4, 2016.
Mulligan et al., "Investigation of the genes for RET and its ligand complex, GDNF/GFR alpha-I, in small cell lung carcinoma," Genes Chromosomes Cancer, Apr. 1998, 21(4):326-332.
Mulligan, "RET revisited: expanding the oncogenic portfolio," Nature Reviews Cancer, Mar. 2014, 14(3):173-186.
Narayanan et al., "Discovery and preclinical characterization of novel small molecule TRK and ROS1 tyrosine kinase inhibitors for the treatment of cancer and inflammation," PLoS One. Dec. 26, 2013;8(12):e83380.
Narita et al., "Functional RET G691S polymorphism in cutaneous malignant melanoma," Oncogene, Aug. 27, 2009;28(34):3058-3068.
Nelson-Taylor et al., "Resistance to RET-Inhibition in RET-Rearranged NSCLC is Mediated by Reactivation of RAS/MAPK Signaling," Mol. Cancer Ther., Aug. 2017, 16(8):1623-1633.
Ott et al., "An immunogenic personal neoantigen vaccine for patients with melanoma," Nature. Jul. 13, 2017, 547(7662):217-221.
Pearce et al., Failure modes in anticancer drug discovery and development, Cancer Drug Design and Discovery Edited by Stephen Neidle, Chapter 18, pp. 424-435 (2008).
Petersen and Bogenmann, "The RET and TRKA pathways collaborate to regulate neuroblastoma differentiation," Oncogene, Jan. 8, 2004;23(1):213-225.
Pirker et al., "Alectinib in RET-rearranged non-small cell lung cancer—Another progress in precision medicine?" Transl. Lung Cancer Res., Dec. 2015;4(6):797-800.
Plaza-Menacho et al., "Targeting the receptor tyrosine kinase RET sensitizes breast cancer cells to tamoxifen treatment and reveals a role for RET in endocrine resistance," Oncogene, Aug. 19, 2010;29(33):4648-4657.
Plenker et al., "Drugging the catalytically inactive state of RET kinase in RET-rearranged tumors," Sci Transl Med, Jun. 14, 2017, 9(394). pii: eaah6144. doi: 10.1126/scitranslmed.aah6144.
Plosker, "Sipuleucel-T: in metastatic castration-resistant prostate cancer," Drugs. Jan. 1, 2011;71(1):101-108.
Postow et al., "Immune Checkpoint Blockade in Cancer Therapy," Journal of Clinical Oncology, Jun. 10, 2015;33(17):1974-1982.
Qi, et al., "RET mutation p.S891A in a Chinese family with familial medullary thyroid carcinoma and associated cutaneous amyloidosis binding OSMR variant p.G513D," Oncotarget, Oct. 20, 2015;6(32):33993-4003.
Rausch et al., "mRNA vaccine CV9103 and CV9104 for the treatment of prostate cancer," Human Vaccin immunother, 2014;10(11):3146-3152.
Reeser et al., "Validation of a Targeted RNA Sequencing Assay for Kinase Fusion Detection in Solid Tumors," J Mol. Diagn., Sep. 2017, 19(5):682-696.
Reungwetwattana et al., "Targeted therapies in development for non-small cell lung cancer," J Carcinog., Dec. 31, 2013;12:22.
Roblin et al., "Topical TrkA Kinase Inhibitor CT327 is an Effective, Novel Therapy for the Treatment of Pruritus due to Psoriasis: Results from Experimental Studies, and Efficacy and Safety of CT327 in a Phase 2b Clinical Trial in Patients with Psoriasis," Acta Derm Venereol, May 2015;95(5):542-548.
Romei and Elisei, "RET/PTC Translocations and Clinico-Pathological Features in Human Papillary Thyroid Carcinoma," Front Endocrinol (Lausanne), Apr. 11, 2012, 3:54.
Romei et al., European Thyroid Journal (Aug. 2016) vol. 5, Supp. Supplement 1, pp. 75; 39th Annual Meeting of the European Thyroid Association, ETA 2016. Copenhagen, Denmark. Sep. 3, 2016-Sep. 6, 2016.
Rosenzweig et al., "A case of advanced infantile myofibromatosis harboring a novel MYH10-RET fusion," Pediatr Blood Cancer, Jul. 2017;64(7). doi: 10.1002/pbc.26377. Epub Dec. 28, 2016.
Sabari et al., "Targeting RET-rearranged lung cancers with multikinase inhibitors," Oncoscience, Mar. 2017, 4(3-4):23-24.

(56) References Cited

OTHER PUBLICATIONS

Sahin et al., "Personalized RNA mutanome vaccines mobilize poly-specific therapeutic immunity against cancer," Nature, Jul. 13, 2017, 547(7662):222-226.
Saito et al., "Gene aberrations for precision medicine against lung adenocarcinoma," Cancer Science, Jun. 2016;107(6):713-720.
Santoro et al., "Development of thyroid papillary carcinomas secondary to tissue-specific expression of the RET/PTC1 oncogene in transgenic mice," Oncogene, Apr. 18, 1996, 12(8):1821-1826.
Scollo et al., "A novel RET gene mutation in a patient with apparently sporadic pheochromocytoma," Endocr. J., 2016;63(1):87-91.
Silva et al., "Identification and characterization of two novel germline RET variants associated with medullary thyroid carcinoma," Endrocrine, Jun. 2015, 49(2):366-372.
Simone, Oncology: Introduction, Cecil Textbook of Medicine, 20th Edition, vol. 1, pp. 1004-101 O, 1995.
Sjoblom et al., "The consensus coding sequences of human breast and colorectal cancers," Science, Oct. 13, 2006;314(5797):268-274.
Skalova et al., "Molecular Profiling of Mammary Analog Secretory Carcinoma Revealed a Subset of Tumors Harboring a Novel ETV6-RET Translocation: Report of 10 Cases," Am. J Surg. Pathol., Feb. 2018, 42(2):234-246.
Song et al., "Potent antitumor activity of cabozantinib, a c-MET and VEGFR2 inhibitor, in a colorectal cancer patient-derived tumor explant model," International Journal of Cancer, Apr. 15, 2015;136(8):1967-1975.
Sromek et al., "Analysis of Newly Identified and Rare Synonymous Genetic Variants in the RET Gene in Patients with Medullary Thyroid Carcinoma in Polish Population," Endocr Pathol., Sep. 2017, 28(3):198-206.
Su et al., "RET/PTC Rearrangements Are Associated with Elevated Postoperative TSH Levels and Multifocal Lesions in Papillary Thyroid Cancer without Concomitant Thyroid Benign Disease," PLoS One, Nov. 1, 2016, 11(11):e0165596.
Takeuchi et al., "RET, ROS1 and ALK fusions in lung cancer," Nature Med., Feb. 12, 2012;18(3):378-381.
Tang et al., "Coexistent genetic alterations involving ALK, RET, ROS1 or MET in 15 cases of lung adenocarcinoma," Mod Pathol., Sep. 15, 2017, doi: 10.1038/modpathol.2017.109. [Epub ahead of print].
Taraviras et al., "Signalling by the RET receptor tyrosine kinase and its role in the development of the mammalian enteric nervous system," Development, Jun. 1999;126(12):2785-2797.
Thress et al., "Identification and preclinical characterization of AZ-23, a novel, selective, and orally bioavailable inhibitor of the Trk kinase pathway," Mol. Cancer Ther., Jul. 2009;8(7):1818-1827.
Van Linden et al., "KLIFS: a knowledge based structural database to navigate kinase-ligand interaction space," J Med Chem., Jan. 23, 2014, 57(2):249-277.
Vanden et al., Annals of Oncology, 2016, vol. 27, Supp. Supplement 6. Abstract No. 427PD; 4pt European Society for Medical Oncology Congress, ESMP 2016. Copenhagen, Denmark. Oct. 7, 2016-Oct. 11, 2016.
Velcheti et al., "FRMD4A/RET: A Novel RET Oncogenic Fusion Variant in Non-Small Cell Lung Carcinoma," J Thorac Oncol., Feb. 2017, 12(2):e15-e16.
Wang et al., "Identification of 4-aminopyrazolylpyrimidines as potent inhibitors of Trk kinases," J Med Chem. Aug. 14, 2008;51(15):4672-4684.
Wang et al., "Trk kinase inhibitors as new treatments for cancer and pain," Expert Opin. Ther. Pat., Mar. 2009;19(3):305-319.
Wells and Santoro, "Targeting the RET pathway in thyroid cancer," Clin Cancer Res., Dec. 1, 2009;15(23):7119-7123.
Wells et al., "Revised American Thyroid Association guidelines for the management of medullary thyroid carcinoma," Thyroid, Jun. 2015;25(6):567-610.
Wood et al, "The genomic landscapes of human breast and colorectal cancers," Science, Nov. 16, 2007, 318(5853):1108-1113.
Yoon et al., "A Pyrazolo[3,4-d]pyrimidin-4-amine Derivative Containing an Isoxazole Moiety is a Selective and Potent Inhibitor of RET Gatekeeper Mutants," J. Med. Chem., Jan. 14, 2016, 59(1):358-373.
Zage et al.,"The selective Trk inhibitor AZ623 inhibits brain-derived neurotrophic factor-mediated neuroblastoma cell proliferation and signaling and is synergistic with topotecan," Cancer, Mar. 15, 2011;117(6):1321-1391. doi: 10.1002/cncr.25674. Epub Oct. 19, 2010.
Zeng et al. "The relationship between overexpression of glial cell-derived neurotrophic factor and its RET receptor with progression and prognosis of human pancreatic cancer," J. Int. Med. Res., Jul.-Aug. 2008;36(4):656-664.
Zhang et al., Laboratory Investigation, (Feb. 2017) vol. 97, Supp. 1, pp. 209A. Abstract No. 840, Meeting Info: 106th Annual Meeting of the United States and Canadian Academy of Pathology, USCAP 2017. San Antonio, TX, United States.
U.S. Appl. No. 15/211,702, filed Jul. 15, 2016, Steven W. Andrews.
U.S. Appl. No. 15/858,658, filed Dec. 29, 2017, Steven W. Andrews.
U.S. Appl. No. 15/860,781, filed Jan. 3, 2018, Steven W. Andrews.
U.S. Appl. No. 15/860,849, filed Jan. 3, 2018, Steven W. Andrews.
U.S. Appl. No. 15/858,240, filed Dec. 29, 2017, Steven W. Andrews.
U.S. Appl. No. 15/860,808, filed Jan. 3, 2018, Steven W. Andrews.
U.S. Appl. No. 15/860,852, filed Jan. 3, 2018, Steven W. Andrews.
U.S. Appl. No. 15/860,894, filed Jan. 3, 2018, Steven W. Andrews.
U.S. Appl. No. 15/861,244, filed Jan. 3, 2018, Steven W. Andrews.

SUBSTITUTED PYRAZOLO[1,5-A]PYRIDINE COMPOUNDS AS RET KINASE INHIBITORS

CROSS-REFERENCE TO RELATED APPLICATIONS

This application is a continuation of International Application No. PCT/US2017/055993, filed Oct. 10, 2017, which claims priority to U.S. Provisional Application Ser. No. 62/566,030, filed Sep. 29, 2017; 62/531,690, filed Jul. 12, 2017; 62/491,180, filed Apr. 27, 2017; 62/447,849, filed Jan. 18, 2017; and 62/406,275, filed Oct. 10, 2016, each of which is incorporated by reference in its entirety herein.

BACKGROUND

The present disclosure relates to novel compounds which exhibit Rearranged during Transfection (RET) kinase inhibition, pharmaceutical compositions comprising the compounds, processes for making the compounds, and the use of the compounds in therapy. More particularly, it relates to substituted pyrazolo[1,5-a]pyridine compounds useful in the treatment and prevention of diseases which can be treated with a RET kinase inhibitor, including RET-associated diseases and disorders.

RET is a single-pass transmembrane receptor belonging to the tyrosine kinase superfamily that is required for normal development, maturation and maintenance of several tissues and cell types (Mulligan, L. M., *Nature Reviews Cancer*, 2014, 14, 173-186). The extracellular portion of the RET kinase contains four calcium-dependent cadherin-like repeats involved in ligand binding and a juxtamembrane cysteine-rich region necessary for the correct folding of the RET extracellular domain, while the cytoplasmic portion of the receptor includes two tyrosine kinase subdomains.

RET signaling is mediated by the binding of a group of soluble proteins of the glial cell line-derived neurotrophic factor (GDNF) family ligands (GFLs), which also includes neurturin (NTRN), artemin (ARTN) and persephin (PSPN) (Arighi et al., *Cytokine Growth Factor Rev.*, 2005, 16, 441-67). Unlike other receptor tyrosine kinases, RET does not directly bind to GFLs and requires an additional co-receptor: that is, one of four GDNF family receptor-α (GFRα) family members, which are tethered to the cell surface by a glycosylphosphatidylinositol linkage. GFLs and GFRα family members form binary complexes that in turn bind to RET and recruit it into cholesterol-rich membrane subdomains, which are known as lipid rafts, where RET signaling occurs.

Upon binding of the ligand-co-receptor complex, RET dimerization and autophosphorylation on intracellular tyrosine residues recruits adaptor and signaling proteins to stimulate multiple downstream pathways. Adaptor protein binding to these docking sites leads to activation of Ras-MAPK and PI3K-Akt/mTOR signaling pathways or to recruitment of the CBL family of ubiquitin ligases that functions in RET downregulation of the RET-mediated functions.

Aberrant RET expression and/or activity have been demonstrated in different cancers and in gastrointestinal disorders such as irritable bowel syndrome (IBS).

SUMMARY OF THE INVENTION

It has now been found that substituted pyrazolo[1,5-a]pyridine compounds are inhibitors of RET kinase, and are useful for treating diseases such as proliferative diseases such as cancers.

Accordingly, provided herein is a compound of the Formula I:

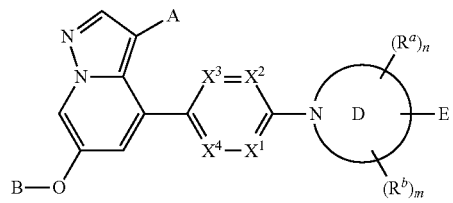

or pharmaceutically acceptable salt or solvate thereof, wherein A, B, $X^1$, $X^2$, $X^3$, $X^4$, Ring D, E, $R^a$, $R^b$, n and m are as defined herein.

Also provided herein is a pharmaceutical composition comprising a compound of Formula I or a pharmaceutically acceptable salt or solvate thereof, in admixture with a pharmaceutically acceptable diluent or carrier.

Also provided herein is a method of inhibiting cell proliferation, in vitro or in vivo, the method comprising contacting a cell with an effective amount of a compound of Formula I or a pharmaceutically acceptable salt or solvate thereof, or a pharmaceutical composition thereof as defined herein.

Also provided herein is a method of treating a RET-associated disease or disorder in a patient in need of such treatment, the method comprising administering to the patient a therapeutically effective amount of a compound of Formula I or a pharmaceutically acceptable salt or solvate thereof, or a pharmaceutical composition thereof as defined herein.

Also provided herein is a method of treating cancer and/or inhibiting metastasis associated with a particular cancer in a patient in need of such treatment, the method comprising administering to the patient a therapeutically effective amount of a compound of Formula I or a pharmaceutically acceptable salt or solvate thereof or a pharmaceutical composition thereof as defined herein.

Also provided herein is a method of treating irritable bowel syndrome (IBS) and/or pain associated with IBS in a patient in need of such treatment, the method comprising administering to the patient a therapeutically effective amount of a compound of Formula I or a pharmaceutically acceptable salt or solvate thereof or a pharmaceutical composition thereof as defined herein.

Also provided is a method of providing supportive care to a cancer patient, including preventing or minimizing gastrointestinal disorders, such as diarrhea, associated with treatment, including chemotherapeutic treatment, the method comprising administering to the patient a therapeutically effective amount of a compound of Formula I or a pharmaceutically acceptable salt or solvate thereof or a pharmaceutical composition thereof as defined herein.

Also provided herein is a compound of Formula I or a pharmaceutically acceptable salt or solvate thereof, or a pharmaceutical composition thereof as defined herein for use in therapy.

Also provided herein is a compound of Formula I or a pharmaceutically acceptable salt or solvate thereof or a pharmaceutical composition thereof as defined herein for use in the treatment of cancer and/or inhibiting metastasis associated with a particular cancer.

Also provided herein is a compound of Formula I or a pharmaceutically acceptable salt or solvate thereof or a pharmaceutical composition thereof as defined herein for use in the treatment of irritable bowel syndrome (IBS) or pain associated with IBS.

Also provided is a compound of Formula I or a pharmaceutically acceptable salt or solvate thereof or a pharmaceutical composition thereof as defined herein for use providing supportive care to a cancer patient, including preventing or minimizing gastrointestinal disorders, such as diarrhea, associated with treatment, including chemotherapeutic treatment.

Also provided herein is a compound of Formula I or a pharmaceutically acceptable salt or solvate thereof for use in the inhibition of RET kinase activity.

Also provided herein is a compound of Formula I or a pharmaceutically acceptable salt or solvate thereof or a pharmaceutical composition thereof as defined herein, for use in the treatment of a RET-associated disease or disorder.

Also provided herein is the use of a compound of Formula I or a pharmaceutically acceptable salt or solvate thereof, as defined herein in the manufacture of a medicament for the treatment of cancer and/or inhibiting metastasis associated with a particular cancer.

Also provided herein is the use of a compound of Formula I or a pharmaceutically acceptable salt or solvate thereof, as defined herein in the manufacture of a medicament for the treatment of irritable bowel syndrome (IBS) or pain associated with IBS.

Also provided herein is the use of a compound of Formula I or a pharmaceutically acceptable salt or solvate thereof, as defined herein in the manufacture of a medicament for providing supportive care to a cancer patient, including preventing or minimizing gastrointestinal disorders, such as diarrhea, associated with treatment, including chemotherapeutic treatment.

Also provided herein is a use of a compound of Formula I or a pharmaceutically acceptable salt or solvate thereof, as defined herein in the manufacture of a medicament for the inhibition of RET kinase activity.

Also provided herein is the use of a compound of Formula I or a pharmaceutically acceptable salt or solvate thereof, as defined herein, in the manufacture of a medicament for the treatment of a RET-associated disease or disorder.

Also provided herein is a method for treating cancer in a patient in need thereof, the method comprising (a) determining if the cancer is associated with a dysregulation of a RET gene, a RET kinase, or expression or activity or level of any of the same (e.g., a RET-associated cancer); and (b) if the cancer is determined to be associated with a dysregulation of a RET gene, a RET kinase, or expression or activity or level of any of the same (e.g., a RET-associated cancer), administering to the patient a therapeutically effective amount of a compound of Formula I or a pharmaceutically acceptable salt or solvate thereof, or a pharmaceutical composition thereof.

Also provided herein is a pharmaceutical combination for treating cancer (e.g., a RET-associated cancer, such as a RET-associated cancer having one or more RET inhibitor resistance mutations) in a patient in need thereof, which comprises (a) a compound of Formula I or a pharmaceutically acceptable salt or solvate thereof, (b) an additional therapeutic agent, and (c) optionally at least one pharmaceutically acceptable carrier, wherein the compound of Formula I or the pharmaceutically acceptable salt or solvate thereof and the additional therapeutic are formulated as separate compositions or dosages for simultaneous, separate or sequential use for the treatment of cancer, wherein the amounts of the compound of Formula I or a pharmaceutically acceptable salt or solvate thereof and of the additional therapeutic agent are together effective in treating the cancer. Also provided is a pharmaceutical composition comprising such a combination. Also provided herein is the use of such a combination for the preparation of a medicament for the treatment of cancer. Also provided herein is a commercial package or product comprising such a combination as a combined preparation for simultaneous, separate or sequential use; and to a method of treatment of cancer a patient in need thereof.

Also provided herein is a method for reversing or preventing acquired resistance to an anticancer drug, comprising administering a therapeutically effective amount of a compound of Formula I or a pharmaceutically acceptable salt or solvate thereof, to a patient at risk for developing or having acquired resistance to an anticancer drug. In some embodiments, the patient is administered a dose of the anticancer drug (e.g., at substantially the same time as a dose of a compound of Formula I or a pharmaceutically acceptable salt or solvate thereof is administered to the patient).

Also provided herein is a method of delaying and/or preventing development of cancer resistant to an anticancer drug in an individual, comprising administering to the individual an effective amount of a compound of Formula I or a pharmaceutically acceptable salt or solvate thereof, before, during, or after administration of an effective amount of the anticancer drug.

Also provided herein is a method of treating an individual with cancer who has an increased likelihood of developing resistance to an anticancer drug, comprising administering to the individual (a) an effective amount of a compound of Formula I before, during, or after administration of (b) an effective amount of the anticancer drug.

Also provided are methods of treating an individual with a RET-associated cancer that has one or more RET inhibitor resistance mutations that increase resistance of the cancer to a first RET inhibitor (e.g., a substitution at amino acid position 804, e.g., V804M, V804L, or V804E, and/or one or more RET inhibitor resistance mutations listed in Tables 3 and 4), that include administering a compound of Formula I or a pharmaceutically acceptable salt or solvate thereof, before, during, or after administration of another anticancer drug (e.g., a second RET kinase inhibitor).

Also provided are methods of treating an individual with a RET-associated cancer that include administering a compound of Formula I or a pharmaceutically acceptable salt or solvate thereof, before, during, or after administration of another anticancer drug (e.g., a first RET kinase inhibitor).

Also provided herein is a method for treating irritable bowel syndrome (IBS) in a patient in need thereof, the method comprising (a) determining if the IBS is associated with a dysregulation of a RET gene, a RET kinase, or expression or activity or level of any of the same; and (b) if the IBS is determined to be associated with a dysregulation of a RET gene, a RET kinase, or expression or activity or level of any of the same, administering to the patient a therapeutically effective amount of a compound of Formula I or a pharmaceutically acceptable salt or solvate thereof, or a pharmaceutical composition thereof.

Also provided herein is a pharmaceutical combination for treating irritable bowel syndrome (IBS) in a patient in need thereof, which comprises administering (a) a compound of General Formula I or a pharmaceutically acceptable salt or solvate thereof, (b) an additional therapeutic agent, and (c) optionally at least one pharmaceutically acceptable carrier, for simultaneous, separate or sequential use for the treatment of IBS, wherein the amounts of the compound of Formula I or a pharmaceutically acceptable salt or solvate thereof and of the additional therapeutic agent are together effective in treating the IBS. Also provided herein is a pharmaceutical composition comprising such a combination. Also provided herein is the use of such a combination for the preparation of a medicament for the treatment of the IBS. Also provided herein is a commercial package or product comprising such a combination as a combined preparation for simultaneous, separate or sequential use; and to a method of treatment of the IBS a patient in need thereof.

Also provided herein is a process for preparing a compound of Formula I or a pharmaceutically acceptable salt or solvate thereof.

Also provided herein is a compound of Formula I or a pharmaceutically acceptable salt or solvate thereof obtained by a process of preparing the compound as defined herein.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION OF THE INVENTION

Provided herein is a compound of Formula I:

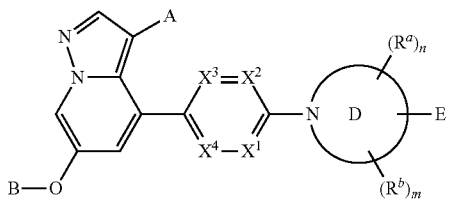

I and pharmaceutically acceptable salts and solvates thereof, wherein:

$X^1$, $X^2$, $X^3$ and $X^4$ are independently CH, CCH$_3$, CF or N, wherein zero, one or two of $X^1$, $X^2$, $X^3$ and $X^4$ is N;

A is H, CN, Cl, methyl, ethyl or cyclopropyl;

B is:
(a) hydrogen,
(b) C1-C6 alkyl optionally substituted with 1-3 fluoros,
(c) hydroxyC2-C6 alkyl- wherein the alkyl portion is optionally substituted with a C3-C6 cycloalkylidene ring,
(d) dihydroxyC3-C6 alkyl- wherein the alkyl portion is optionally substituted with a C3-C6 cycloalkylidene ring,
(e) (C1-C6 alkoxy)C1-C6 alkyl- optionally substituted with 1-3 fluoros,
(f) $(R^1R^2N)$C1-C6 alkyl- where $R^1$ and $R^2$ are independently selected from H, C1-C6 alkyl (optionally substituted with 1-3 fluoros), (C1-C6 alkoxy)C1-C6 alkyl-, (C1-C6 alkyl)C(=O)— and (C1-C6 alkoxy)C(=O)—;
(g) hetAr$^1$C1-C3 alkyl-, where hetAr$^1$ is a 5-6 membered heteroaryl ring having 1-3 ring heteroatoms independently selected from N, O and S and is optionally substituted with one or more independently selected C1-C6 alkyl substituents;
(h) (C3-C6 cycloalkyl)C1-C3 alkyl-, wherein said cycloalkyl is optionally substituted with OH,
(i) (hetCyc$^a$)C1-C3 alkyl-,
(j) hetCyc$^a$,
(k) $(R^1R^2N)$C(=O)C1-C6 alkyl-, where $R^1$ and $R^2$ are independently selected from H and C1-C6 alkyl;
(l) $(R^1R^2N)$C(=O)—, where $R^1$ and $R^2$ are independently selected from H and C1-C6 alkyl, or
(m) hetCyc$^a$C(=O)C1-C6 alkyl-;

hetCyc$^a$ is a 4-6 membered heterocyclic ring having 1-2 ring heteroatoms independently selected from N and O and optionally substituted with one or more substituents independently selected from OH, C1-C6 alkyl (optionally substituted with 1-3 fluoros), hydroxyC1-C6 alkyl, halogen, (C1-C6 alkyl)C(=O)—, C1-C6 alkoxy, oxo and (C1-C6 alkoxy)C(=O)—;

Ring D is (i) a saturated monocyclic 4-7 membered heterocyclic ring having one ring heteroatom which is nitrogen, (ii) a saturated 7-8 membered bridged heterocyclic ring having one ring heteroatom which is nitrogen, or (iii) a saturated 7-11 membered heterospirocyclic ring system having one ring heteroatom which is nitrogen;

each $R^a$ is independently C1-C6 alkyl (optionally substituted with 1-3 fluoros), hydroxyC1-C6 alkyl or (C1-C6 alkoxy)C1-C6 alkyl-;

$R^b$ is (a) hydroxy, (b) cyclopropyl, (c) hetCyc$^b$CH$_2$—, (d) $R^iR^jNC(=O)CH_2OCH_2$— where $R^i$ and $R^j$ are independently H or C1-C6 alkyl, (e) $R^cR^dN$—, (f) $R^cR^dNCH_2$—, (g) C1-C6 alkoxy-, (h) (C1-C4 alkyl)-C(=O)NH— wherein said alkyl portion is optionally substituted with hetCyc$^b$, hetAr$^a$, C1-C6 alkoxy- or R'R"N—, or said alkyl portion is optionally substituted with two substituents independently selected from R'R"N— and OH, where each R' and R" is independently hydrogen or C1-C6 alkyl, (i) (R'R"N)C1-C6 alkoxy(CH$_2$)$_n$— where n is 0 or 1 and R' and R" are independently hydrogen or C1-C6 alkyl, (j) hetCyc$^b$(C1-C3 alkyl)OCH$_2$—, (k) hetCyc$^b$C(=O)NH— or (l) hetAr$^a$C(=O)NH—;

hetCyc$^b$ is a 4-6 membered heterocyclic ring, a 7-8 membered bridged heterocyclic ring, or a 7-10 membered heterospirocyclic ring, each ring having 1-2 ring heteroatoms independently selected from N and O, wherein hetCyc$^b$ is optionally substituted with one or more substituents independently selected from OH, fluoro, C1-C6 alkyl (optionally substituted with 1-3 fluoros), hydroxyC1-C6 alkyl- (optionally substituted with 1-3 fluoros), (C1-C6 alkoxy)C1-C6 alkyl-, (C1-C6 alkoxy)C(=O)—, C1-C6 alkoxy, and R'R"N— where R' and R" are independently hydrogen or C1-C6 alkyl;

hetAr$^a$ is a 5-6 membered heteroaryl ring having 1-3 ring heteroatoms independently selected from N, O and S wherein hetAr$^a$ is optionally substituted with one or more substituents independently selected from the group consisting of halogen, CN, C1-C6 alkyl (optionally substituted with 1-3 fluoros), and C1-C6 alkoxy (optionally substituted with 1-3 fluoros), $R^c$ is hydrogen or C1-C6 alkyl;

$R^d$ is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C(=O)—, (C1-C6 alkyl)C(=O)—, $(R^kR^l N)$C1-C6 alkyl- where $R^k$ and $R^l$ are independently H or C1-C6 alkyl, R'''R''NC(=O)C1-C6 alkyl- where R''' and R'' are independently H or C1-C6 alkyl, PhCH$_2$— wherein the phenyl is optionally substituted with one or more substituents independently selected from the group consisting of halogen, CN, C1-C6 alkyl (optionally substituted with 1-3 fluoros), C1-C6 alkoxy (optionally substituted with 1-3 fluoros), (C1-C6 alkoxy)C1-C6 alkyl- (optionally substituted with 1-3 fluoros), C3-C6 cycloalkyl, hydroxyC1-C6 alkyl, (C1-C6 alkyl)SO$_2$—, R$^e$R$^f$N— and (R$^e$R$^f$N)C1-C6 alkyl- where each R$^e$ and R$^f$ is independently H or C1-C6 alkyl, (C1-C6 alkoxy)C1-C6 alkyl-, or hetCyc$^c$ where hetCyc$^c$ is a 4-6 membered heterocyclic ring having a ring heteroatom selected from N and O and optionally substituted with C1-C6 alkyl;

n is 0, 1, 2, 3, 4, 5 or 6;

m is 0 or 1;

E is:
(a) hydrogen,
(b) hydroxy,
(c) C1-C6 alkyl optionally substituted with 1-3 fluoros,
(d) Ar$^1$C1-C6 alkyl- wherein said alkyl portion is optionally substituted with 1-3 fluoros,
(e) hetAr$^2$C1-C6 alkyl-,
(f) (C1-C6 alkoxy)C1-C6 alkoxy-,
(g) Ar$^1$O—,
(h) hetAr$^2$—O—,
(i) Ar$^1$NR$^g$— where R$^g$ is H or C1-C6 alkyl,
(j) hetAr$^2$NR$^g$— where R$^g$ is H or C1-C6 alkyl,
(k) R$^3$C(=O)NR$^g$— where R$^g$ is H or C1-C6 alkyl;
(l) Ar$^1$C(=O)NR$^g$— where R$^g$ is H or C1-C6 alkyl,
(m) hetAr$^2$C(=O)NR$^g$(CH$_2$)$_p$— where p is 0 or 1 and R$^g$ is H or C1-C6 alkyl,
(n) R$^4$R$^5$NC(=O)—,
(o) Ar$^1$NR$^g$C(=O)—, where R$^g$ is H or C1-C6 alkyl,
(p) hetAr$^2$NR$^g$C(=O)—, where R$^g$ is H or C1-C6 alkyl,
(q) Ar$^1$(C1-C6 alkyl)C(=O)— wherein said alkyl portion is optionally substituted with OH, hydroxy(C1-C6 alkyl), C1-C6 alkoxy or NH$_2$,
(r) hetCyc$^5$C(=O)—,
(s) R$^4$R$^5$NC(=O)NR$^g$— where R$^g$ is H or C1-C6 alkyl, or
(t) (C1-C6 alkyl)SO$_2$—;
(u) Ar$^1$(C1-C6 alkyl)C(=O)NR$^g$— where R$^g$ is H or C1-C6 alkyl,
(v) hetAr$^4$C(=O)NR$^g$— where R$^g$ is H or C1-C6 alkyl,
(w) hetAr$^2$—S(=O)—,
(x) (C3-C6 cycloalkyl)CH$_2$SO$_2$—,
(y) Ar$^1$(C1-C6 alkyl)SO$_2$—,
(z) hetAr$^2$SO$_2$—,
(aa) Ar$^1$,
(bb) hetAr$^2$,
(cc) hetCyc$^5$,
(dd) C1-C6 alkoxy,
(ee) Ar$^1$(C1-C6 alkyl)-O—,
(ff) hetAr$^2$(C1-C6 alkyl)-O—,
(gg) hetAr$^2$—O—C1-C6 alkyl-,
(hh) Ar$^1$(C1-C6 alkyl)NR$^g$— where R$^g$ is H or C1-C6 alkyl,
(ii) hetAr$^2$—S—,
(jj) Ar$^2$SO$_2$NR$^g$(CH$_2$)$_p$— where p is 0 or 1 and R$^g$ is H or C1-C6 alkyl,
(kk) (C1-C6 alkoxy)C(=O)—,
(ll) (C1-C6 alkyl)NR$^g$C(=O)O— where R$^g$ is H or C1-C6 alkyl,
(mm) (C1-C6 alkyl)NR$^g$SO$_2$— where R$^g$ is H or C1-C6 alkyl,
(nn) hetCyc$^5$C(=O)NR$^g$— where R$^g$ is H or C1-C6 alkyl, (oo) Q-NR$^h$(C1-C3 alkyl)C(=O)NR$^g$— where R$^g$ and R$^h$ are independently H or C1-C6 alkyl and Q is H, C1-C6 alkyl or (C1-C6 alkyl)OC(=O)—,
(pp)

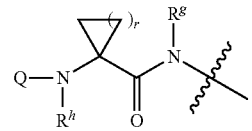

where R$^g$ and R$^h$ are independently H or C1-C6 alkyl, Q is H, C1-C6 alkyl or (C1-C6 alkyl)OC(=O)— and r is 1, 2, 3 or 4,
(qq)

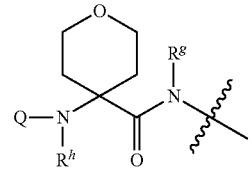

where R$^g$ and R$^h$ are independently H or C1-C6 alkyl and Q is H, C1-C6 alkyl or (C1-C6 alkyl)OC(=O)—,
(rr)

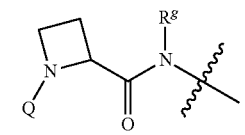

where R$^g$ is H or C1-C6 alkyl and Q is H, C1-C6 alkyl or (C1-C6 alkyl)OC(=O)—, or
(ss) R$^g$R$^h$N— where R$^g$ and R$^h$ are independently H or C1-C6 alkyl,
(tt) (C3-C6 cycloalkyl)C(=O)NR$^g$— where the cycloalkyl is optionally and independently substituted with one or more halogens,
(uu) (C1-C6 alkyl)C(=O)NR$^g$CH$_2$— where R$^g$ is H or C1-C6 alkyl, or
(vv) C1-C6 alkyl)SO$_2$NR$^g$— where R$^g$ is H or C1-C6 alkyl;

Ar$^1$ is phenyl optionally substituted with one or more substituents independently selected from the group consisting of halogen, CN, C1-C6 alkyl (optionally substituted with 1-3 fluoros), C1-C6 alkoxy (optionally substituted with 1-3 fluoros), (C1-C6 alkoxy)C1-C6 alkyl- (optionally substituted with 1-3 fluoros), C3-C6 cycloalkyl, hydroxyC1-C6 alkyl, (C1-C6 alkyl)SO$_2$—, R$^e$R$^f$N— and (R$^e$R$^f$N)C1-C6 alkyl- where each R$^e$ and R$^f$ is independently H or C1-C6 alkyl;

hetAr$^2$ is a 5-6 membered heteroaryl ring having 1-3 ring heteroatoms independently selected from N, O and S, or a 9-10 membered bicyclic heteroaryl having 1-2 ring nitrogen atoms, wherein hetAr$^2$ is optionally substituted with one or more substituents independently selected from the group consisting of halogen, CN, C1-C6 alkyl (optionally substituted with 1-3 fluoros), C1-C6 alkoxy (optionally substituted with 1-3 fluoros), (C1-C6 alkoxy)C1-C6 alkyl- (optionally substituted with 1-3 fluoros) and hydroxyC1-C6 alkoxy-;

hetCyc⁵ is a 4-6 membered saturated heterocyclic ring having 1-2 ring heteroatoms independently selected from N, O and S wherein said heterocyclic ring is optionally substituted with one or more substituents independently selected from C1-C6 alkoxy and oxo;

R³ is C1-C6 alkyl (optionally substituted with 1-3 fluoros), hydroxyC1-C6 alkyl-, C1-C6 alkoxy, C3-C6 cycloalkyl, (C3-C6 cycloalkyl)CH₂—, (C3-C6 cycloalkyl)O—, (C3-C6 cycloalkyl)CH₂O—, hetCyc⁷O—, Ph-O—, or (C1-C6 alkoxy)C1-C6 alkyl-; wherein each of said C3-C6 cycloalkyl moieties is optionally substituted with C1-C6 alkyl (optionally substituted with 1-3 fluoros), C1-C6 alkoxy, OH or R'R"N— where R' and R" are independently hydrogen or C1-C6 alkyl;

R⁴ is H or C1-C6 alkyl;

R⁵ is Ar², hetAr³, Ar²CH₂—, hetCyc⁶-CH₂—, hydroxyC1-C6 alkyl-, (C3-C6 cycloalkyl)CH₂—, or C1-C6 alkyl optionally substituted with 1-3 fluoros;

Ar² is phenyl optionally substituted with one or more substituents independently selected from the group consisting of halogen, CN, C1-C6 alkyl (optionally substituted with 1-3 fluoros), C1-C6 alkoxy (optionally substituted with 1-3 fluoros), (C1-C6 alkoxy)C1-C6 alkyl- (optionally substituted with 1-3 fluoros), C3-C6 cycloalkyl, and R$^g$R$^h$N— where R$^g$ and R$^h$ are independently H or C1-C6 alkyl, or Ar² is phenyl fused to a 6 membered heterocyclic ring having a ring nitrogen atom and optionally substituted with C1-C6 alkyl;

hetAr³ is a 5-6 membered heteroaryl ring having 1-3 ring heteroatoms independently selected from N, O and S and optionally substituted with one or more substituents independently selected from the group consisting of halogen, CN, C1-C6 alkyl (optionally substituted with 1-3 fluoros), C1-C6 alkoxy (optionally substituted with 1-3 fluoros), and (C1-C6 alkoxy)C1-C6 alkyl- (optionally substituted with 1-3 fluoros);

hetAr⁴ is pyridin-4(1H)-onyl or pyridin-2(1H)-onyl optionally substituted with one or more substituents independently selected from C1-C6 alkyl and halogen;

hetCyc⁶ is a 5-7 membered heterocyclic ring having 1-3 ring heteroatoms independently selected from N, O and S; and hetCyc⁷ is a 5-7 membered heterocyclic ring having 1-3 ring heteroatoms independently selected from N, O and S.

For complex chemical names employed herein, a substituent group is typically named before the group to which it attaches. For example, methoxyethyl comprises an ethyl backbone with a methoxy substituent.

The term "halogen" means —F (sometimes referred to herein as "fluoro" or "fluoros"), —Cl, —Br and —I.

The terms "C1-C3 alkyl", "C3-C6 alkyl", "C1-C6 alkyl", and "C2-C6 alkyl" as used herein refer to saturated linear or branched-chain monovalent hydrocarbon radicals of one to three, three to six, one to six, or two to six carbon atoms, respectively. Examples include, but are not limited to, methyl, ethyl, 1-propyl, isopropyl, 1-butyl, isobutyl, sec-butyl, tert-butyl, 2-methyl-2-propyl, pentyl, neopentyl, and hexyl.

The term "C1-C6 alkyl optionally substituted with 1-3 fluoros" as used herein refers to a C1-C6 alkyl radical as defined herein, wherein one to three hydrogen atoms is replaced with one to three fluoro atoms, respectively. Examples include, but are not limited to, fluoromethyl, difluoromethyl, trifluoromethyl, 2-fluoroethyl, 2,2-difluoroethyl, 2,2,2- and trifluoroethyl.

The term "C1-C6 alkoxy" as used herein refer to saturated linear or branched-chain monovalent alkoxy radicals of one to six carbon atoms, wherein the radical is on the oxygen atom. Examples include methoxy, ethoxy, propoxy, isopropoxy, butoxy and tert-butoxy.

The term "(C1-C6 alkoxy)C1-C6 alkyl" as used herein refers to saturated linear or branched-chain monovalent radicals of one to six carbon atoms, wherein one of the carbon atoms is substituted with a C1-C6 alkoxy group as defined herein. Examples include methoxymethyl (CH₃OCH₂—) and methoxyethyl (CH₃OCH₂CH₂—).

The term "(C1-C6 alkoxy)C1-C6 alkoxy" as used herein refers to a C1-C6 alkoxy radical as defined herein, wherein one of the carbon atoms is substituted with a C1-C6 alkoxy group as defined herein. Examples include methoxymethoxy (CH₃OCH₂O—) and ethoxymethoxy (CH₃CH₂O—CH₂O—).

The terms "hydroxyC1-C6 alkyl" and "hydroxyC2-C6 alkyl", as used herein refers to saturated linear or branched-chain monovalent alkyl radicals of one to six or two to six carbon atoms, respectively, wherein one of the carbon atoms is substituted with a hydroxy group.

The term "dihydroxyC3-C6 alkyl" as used herein refers to a C3-C6 alkyl radical as defined herein, wherein two hydrogen atoms are replaced with a hydroxy group, provided the hydroxy groups are not on the same carbon.

The term "(R¹R²N)C1-C6 alkyl" as used herein refers to a C1-C6 alkyl radical as defined herein, wherein one of the carbon atoms is substituted with a R¹R²N— group, wherein R¹ and R² are as defined herein.

The term "hetAr¹C1-C6 alkyl" as used herein refers to a C1-C6 alkyl radical as defined herein, wherein one of the carbon atoms is substituted with a hetAr¹ group, wherein hetAr¹ is as defined herein.

The term "C3-C6 cycloalkyl" as used herein refers to cyclopropyl, cyclobutyl, cyclopentyl or cyclohexyl.

The term "C3-C6 cycloalkylidene ring" as used herein refers to a divalent C3-C6 cycloalkane ring derived from a saturated 3-6 membered hydrocarbon ring by removal of two hydrogen atoms from the same carbon atom, such as for example, cyclopropylidene, cyclobutylidene, cyclopentylidene, and cyclohexylidene. It can be represented in illustrative fashion by the following structure in which n is 1, 2 or 3:

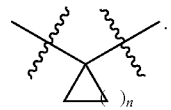

The term "(C3-C6 cycloalkyl)C1-C3 alkyl" as used herein refers to a C1-C3 alkyl radical as defined herein, wherein one of the carbon atoms is substituted with a C3-C6 cycloalkyl ring. An example is cyclobutylmethyl.

The term "(hetCyc$^a$)C1-C3 alkyl" as used herein refers to a C1-C3 alkyl radical as defined herein, wherein one of the carbon atoms is substituted with a hetCyc$^a$ group, wherein hetCyc$^a$ is as defined herein.

The term "Ar¹C1-C6 alkyl" as used herein refers to a C1-C6 alkyl radical as defined herein, wherein one of the carbon atoms is substituted with an Ar¹ group, wherein Ar¹ is as defined herein.

The terms "hetAr²C1-C6 alkyl" as used herein refers to a C1-C6 alkyl radical as defined herein, wherein one of the carbon atoms is substituted with a hetAr² group, wherein hetAr² is as defined herein.

The term "oxo" as used herein means an oxygen that is double bonded to a carbon atom, i.e., =O. For example, in one embodiment when referring to hetCyc$^a$, a 4-6 membered heterocyclic ring having 1-2 ring heteroatoms independently selected from N and O and substituted with an oxo may be, for example, a pyrrolidinyl ring substituted with oxo (e.g., a pyrrolidinonyl ring), which may be represented by the structure:

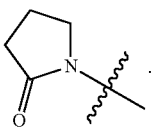 [SMILES: *N1CCCC1=O]

The term "spirocyclic ring" as used herein refers to a group having two rings joined by a spirocyclic linkage through a common single carbon atom, wherein each ring is a 4-7-membered ring (including the common carbon atom).

The term "heterospirocyclic" as used herein refers to a group having two rings joined by a spirocyclic linkage through a carbon atom, wherein each ring has 4 to 6 ring atoms (with one ring carbon atom being common to both rings), and wherein one of the ring atoms is a nitrogen atom.

The term "compound," as used herein is meant to include all stereoisomers, geometric isomers, tautomers, and isotopes of the structures depicted. Compounds herein identified by name or structure as one particular tautomeric form are intended to include other tautomeric forms unless otherwise specified.

The term "tautomer" as used herein refers to compounds whose structures differ markedly in arrangement of atoms, but which exist in easy and rapid equilibrium, and it is to be understood that compounds provided herein may be depicted as different tautomers, and when compounds have tautomeric forms, all tautomeric forms are intended to be within the scope of the invention, and the naming of the compounds does not exclude any tautomer.

It will be appreciated that certain compounds provided herein may contain one or more centers of asymmetry and may therefore be prepared and isolated in a mixture of isomers such as a racemic mixture, or in an enantiomerically pure form.

In certain embodiments of Formula I, $X^1$, $X^2$, $X^3$ and $X^4$ are independently CH or CF. In certain embodiments, each of $X^1$, $X^2$, $X^3$ and $X^4$ is CH.

In certain embodiments of Formula I, $X^1$, $X^2$, $X^3$ and $X^4$ are independently CH, CF or N, wherein one of $X^1$, $X^2$, $X^3$ and $X^4$ is N and the remainder are independently CH or CF. In certain embodiments of Formula I, $X^1$ is N, and $X^2$, $X^3$ and $X^4$ are independently CH or CF. In certain embodiments, $X^1$ is N, and $X^2$, $X^3$ and $X^4$ are CH.

In certain embodiments of Formula I, $X^1$, $X^2$, $X^3$ and $X^4$ are independently CH, CF or N, wherein two of $X^1$, $X^2$, $X^3$ and $X^4$ are N. In certain embodiments of Formula I, $X^1$ and $X^3$ are N and $X^2$ and $X^4$ are independently CH or CF. In one embodiment, $X^1$ and $X^3$ are N and $X^2$ and $X^4$ are CH.

In certain embodiments of Formula I, A is H.
In certain embodiments of Formula I, A is Cl.
In certain embodiments of Formula I, A is CN.
In certain embodiments of Formula I, A is methyl.
In certain embodiments of Formula I, A is ethyl.
In certain embodiments of Formula I, A is cyclopropyl.
In certain embodiments of Formula I, B is hydrogen.

In certain embodiments of Formula I, B is C1-C6 alkyl optionally substituted with 1-3 fluoros. Non-limiting examples include methyl, ethyl, propyl, isopropyl, isobutyl, sec-butyl, 2-ethylbutyl, neopentyl, difluoromethyl, 2,2-difluoroethyl, and 2,2,2-trifluoroethyl. In certain embodiments, B is methyl or ethyl.

In certain embodiments of Formula I, B is hydroxyC2-C6 alkyl wherein the alkyl portion is optionally substituted with a C3-C6 cycloalkylidene ring. In certain embodiments, the alkyl portion is unsubstituted. Non-limiting examples include the structures:

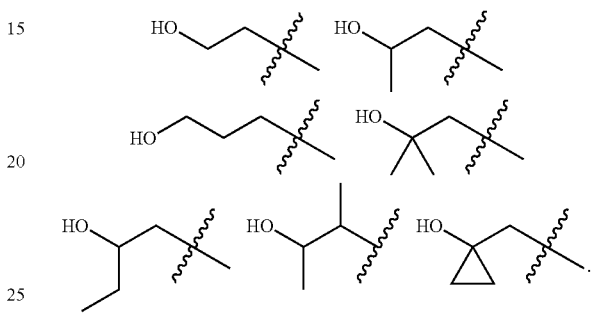

In certain embodiments of Formula I, B is dihydroxyC3-C6 alkyl- wherein the alkyl portion is optionally substituted with a C3-C6 cycloalkylidene ring. A non-limiting example includes 2,3-dihydroxypropyl.

In certain embodiments of Formula I, B is (C1-C6 alkoxy)C1-C6 alkyl- optionally substituted with 1-3 fluoros. In certain embodiments of Formula I, B is (C1-C6 alkoxy)C2-C6 alkyl- optionally substituted with 1-3 fluoros. Non-limiting examples include the structures:

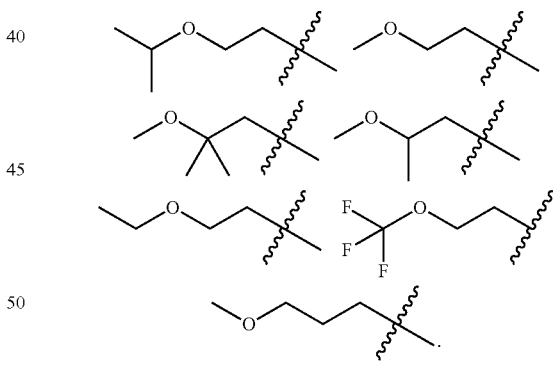

In certain embodiments of Formula I, B is ($R^1R^2N$)C1-C6 alkyl-, where $R^1$ and $R^2$ are independently H, C1-C6 alkyl (optionally substituted with 1-3 fluoros), (C1-C6 alkoxy)C1-C6 alkyl-, (C1-C6 alkyl)C(=O)— and (C1-C6 alkoxy)C(=O)—. Non-limiting examples of ($R^1R^2N$)C1-C6 alkyl- include the structures:

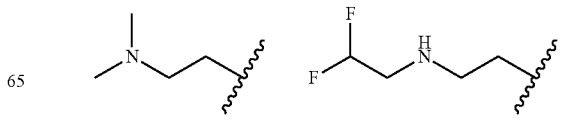

-continued

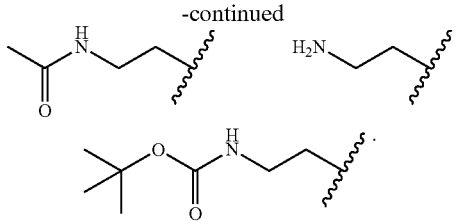

In certain embodiments of Formula I, B is hetAr¹C1-C3 alkyl-, where hetAr¹ is a 5-6 membered heteroaryl ring having 1-3 ring heteroatoms independently selected from N, O and S and is optionally substituted with one or more independently selected C1-C6 alkyl substituents. In certain embodiments, hetAr¹ is a 5-6 membered heteroaryl ring having 1-3 ring heteroatoms independently selected from N and O and is optionally substituted with C1-C6 alkyl. Non-limiting examples of hetAr¹C1-C3 alkyl- include the structures:

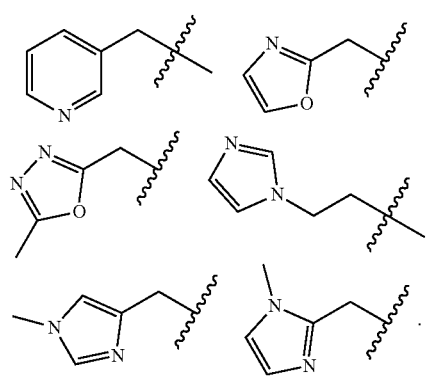

In certain embodiments of Formula I, B is (C3-C6 cycloalkyl)C1-C3 alkyl- wherein said cycloalkyl is optionally substituted with OH. A non-limiting example is cyclobutylmethyl.

In certain embodiments of Formula I, B is (hetCyc$^a$)C1-C3 alkyl-, where hetCyc$^a$ is as defined for Formula I. In certain embodiments of Formula I, B is (hetCyc$^a$)C1-C3 alkyl-, where hetCyc$^a$ is a 4-6 membered heterocyclic ring having 1-2 ring heteroatoms independently selected from N and O and is optionally substituted with one or more substituents independently selected from OH, C1-C6 alkyl (optionally substituted with 1-3 fluoros), hydroxyC1-C6 alkyl-, halogen, (C1-C6 alkyl)C(=O)—, C1-C6 alkoxy, oxo and (C1-C6 alkoxy)C(=O)—. Non-limiting examples include the structures:

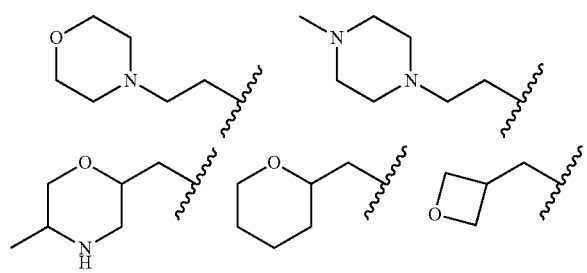

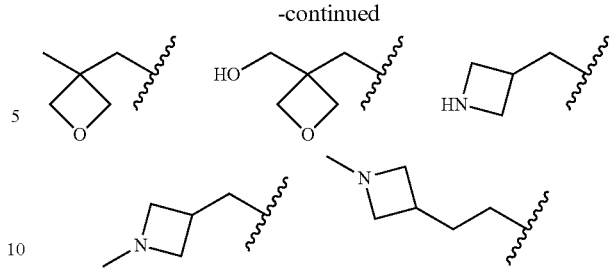

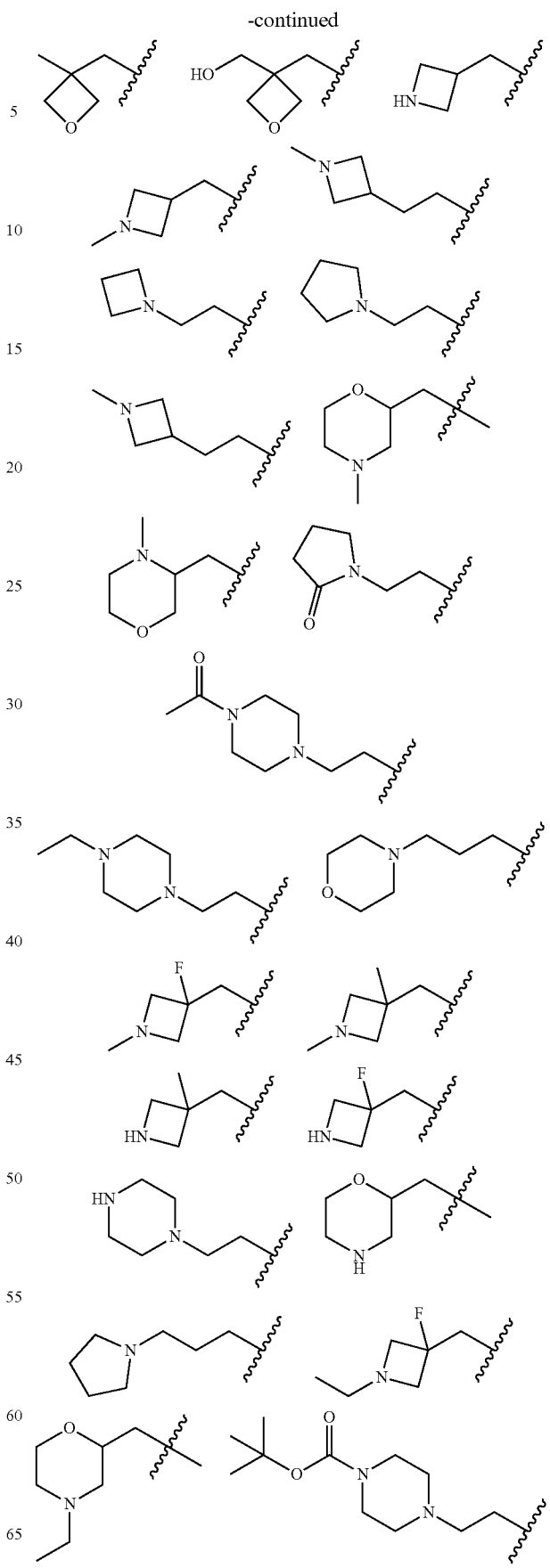

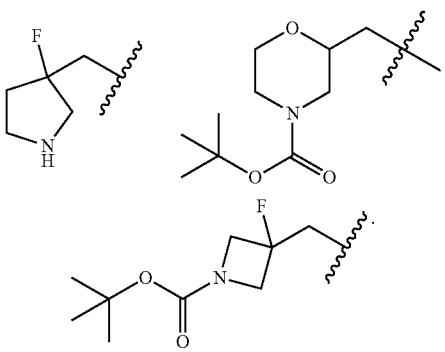

In certain embodiments of Formula I, B is hetCyc$^a$, where hetCyc$^2$ is as defined for Formula I. In certain embodiments, hetCyc$^a$ is a 4-6 membered heterocyclic ring having 1-2 ring heteroatoms independently selected from N and O and is optionally substituted with OH, C1-C6 alkyl (optionally substituted with 1-3 fluoros) or hydroxyC1-C6 alkyl-. Non-limiting examples include the structures:

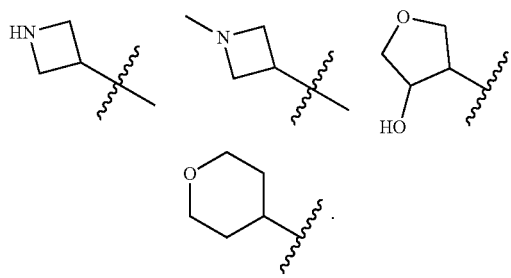

In certain embodiments of Formula I, B is (R$^1$R$^2$N)C(=O)C1-C6 alkyl- where R$^1$ and R$^2$ are independently selected from H and C1-C6 alkyl. Non-limiting examples include the structures:

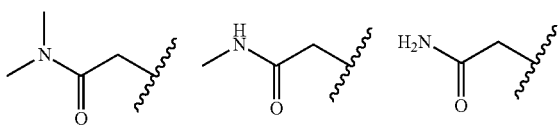

In certain embodiments of Formula I, B is (R$^1$R$^2$N)C(=O)—, where R$^1$ and R$^2$ are independently selected from H and C1-C6 alkyl. Non-limiting examples include the structure:

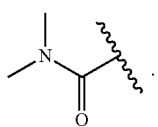

In certain embodiments of Formula I, B is hetCyc$^a$C(=O)C1-C6 alkyl- where hetCyc$^a$ is as defined for Formula I. A non-limiting example includes the structure:

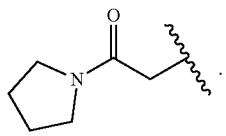 [SMILES: *CC(=O)N1CCCC1]

In certain embodiments of Formula I, B is (b) C1-C6 alkyl optionally substituted with 1-3 fluoros or (c) hydroxyC2-C6 alkyl- wherein the alkyl portion is optionally substituted with a C3-C6 cycloalkylidene ring. In certain embodiments of Formula I, B is (b) C1-C6 alkyl optionally substituted with 1-3 fluoros or (c) hydroxyC2-C6 alkyl-.

Referring now to Ring D of Formula I,

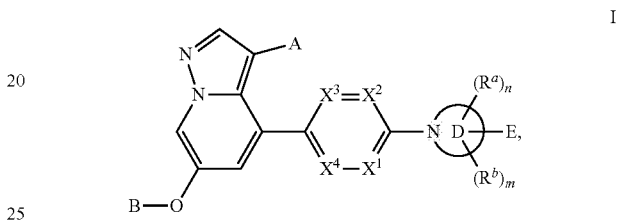

I

Ring D is (i) a saturated monocyclic 4-7 membered heterocyclic ring having one ring heteroatom which is nitrogen, (ii) a saturated 7-8 membered bridged heterocyclic ring having one ring heteroatom which is nitrogen, or (iii) a saturated 7-11 membered heterospirocyclic ring system having one ring heteroatom which is nitrogen, wherein the E group may be bonded to any ring carbon atom of Ring D, each R$^a$ may be bonded to any ring carbon atom of Ring D, and R$^b$ may be bonded to any ring carbon of Ring D, provided that the ring carbon atom bonded to the E group is optionally substituted with only one of R$^a$ or R$^b$.

In one embodiment, Ring D is a saturated monocyclic 4-7 membered heterocyclic ring having one ring heteroatom which is nitrogen. The phrase "having one ring heteroatom which is nitrogen" when Ring D is a saturated monocyclic 4-7 membered heterocyclic ring means that said ring nitrogen atom is the nitrogen atom shown in Ring D of Formula I. Nonlimiting examples include the structures:

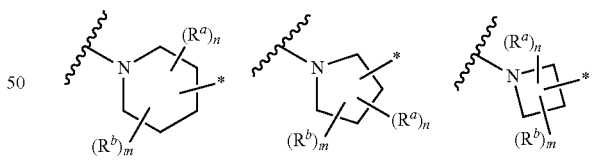

wherein the wavy line indicates the point of attachment of Ring D to the ring comprising X$^1$, X$^2$, X$^3$ and X$^4$, the asterisk indicates the point of attachment of Ring D to the E group, and R$^a$, n, R$^b$ and m are as defined for Formula I. In one embodiment, n is 0, 1, 2, 3 or 4. In one embodiment, n is 0, 1 or 2. In one embodiment, n is 0. In one embodiment, n is 1. In one embodiment, n is 2. In one embodiment, m is 0 or 1. In one embodiment, m is 0. In one embodiment, m is 1. In one embodiment, n is 0 and m is 0 or 1. In one embodiment, n is 0 or 1 and m is 0.

In one embodiment of Formula I, Ring D is a saturated monocyclic 4-6 membered heterocyclic ring having one ring heteroatom which is nitrogen selected from the structures

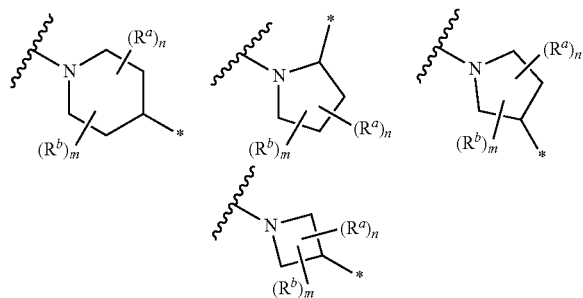

wherein the wavy line indicates the point of attachment of Ring D to the ring comprising $X^1$, $X^2$, $X^3$ and $X^4$, the asterisk indicates the point of attachment of Ring D to the E group, and $R^a$, n, $R^b$ and m are as defined for Formula I. In one embodiment, n is 0, 1, 2, 3 or 4. In one embodiment, n is 0, 1 or 2. In one embodiment, n is zero. In one embodiment, n is one. In one embodiment, n is two. In one embodiment, m is 0 or 1. In one embodiment, m is 0. In one embodiment, m is 1.

In certain embodiments of Formula I, Ring D is a saturated monocyclic 5-6 membered heterocyclic ring having one ring heteroatom which is nitrogen having the structure:

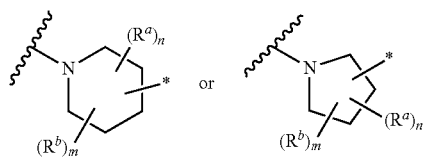

wherein the wavy line indicates the point of attachment of Ring D to the ring comprising $X^1$, $X^2$, $X^3$ and $X^4$, the asterisk indicates the point of attachment of Ring D to the E group, and $R^a$, n, $R^b$ and m are as defined for Formula I. In one embodiment, each $R^a$ is independently selected from C1-C6 alkyl (optionally substituted with 1-3 fluoros), hydroxyC1-C6 alkyl or (C1-C6 alkoxy)C1-C6 alkyl-. In one embodiment, n is 0, 1, 2, 3 or 4. In one embodiment, n is 0. In one embodiment, n is 1. In one embodiment, n is 2. In one embodiment, $R^b$ is (a) hydroxy, (b) cyclopropyl, (c) hetCyc$^b$CH$_2$— (d) $R^iR^j$NC(=O)CH$_2$OCH$_2$— where $R^i$ and $R^j$ are independently H or C1-C6 alkyl, (e) $R^cR^dN$—, (f) $R^cR^d$NCH$_2$—, (g) C1-C6 alkoxy-, (h) (C1-C4 alkyl)-C(=O)NH— wherein said alkyl portion is optionally substituted with hetCyc$^b$, hetAr$^a$, C1-C6 alkoxy- or R'R"N—, or said alkyl portion is optionally substituted with two substituents independently selected from R'R"N— and OH, where each R' and R" is independently hydrogen or C1-C6 alkyl, (i) (R'R"N)C1-C6 alkoxy(CH$_2$)$_n$— where n is 0 or 1 and R' and R" are independently hydrogen or C1-C6 alkyl, (j) hetCyc$^b$(C1-C3 alkyl)OCH$_2$—, (k) hetCyc$^b$C(=O)NH— or (l) hetAr$^a$C(=O)NH—; $R^c$ is hydrogen or C1-C6 alkyl; hetCyc$^b$ is as defined for Formula I; $R^d$ is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C(=O)—, (C1-C6 alkyl)C(=O)—, ($R^kR^l$N)C1-C6 alkyl- where $R^k$ and $R^l$ are independently H or C1-C6 alkyl, $R^mR^n$NC(=O)C1-C6 alkyl- where $R^m$ and $R^n$ are independently H or C1-C6 alkyl, PhCH$_2$—, (C1-C6 alkoxy)C1-C6 alkyl-, or hetCyc$^c$ where hetCyc$^c$ is a 4-6 membered heterocyclic ring having a ring heteroatom selected from N and O and optionally substituted with C1-C6 alkyl. In one embodiment, m is 0 or 1. In one embodiment, m is 0. In one embodiment, m is 1.

In certain embodiments of Formula I, Ring D is a saturated monocyclic 4-6 membered heterocyclic ring having one ring heteroatom which is nitrogen selected from the structures:

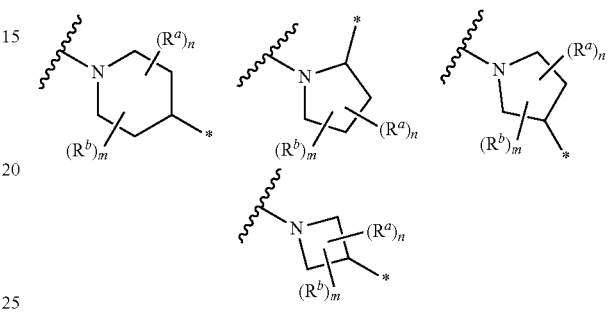

wherein the wavy line indicates the point of attachment of Ring D to the ring comprising $X^1$, $X^2$, $X^3$ and $X^4$, the asterisk indicates the point of attachment of Ring D to the E group, and $R^a$, n, $R^b$ and m are as defined for Formula I. In one embodiment, each $R^a$ is independently selected from C1-C6 alkyl (optionally substituted with 1-3 fluoros) or (C1-C6 alkoxy)C1-C6 alkyl-. In one embodiment, n is 0, 1, 2, 3 or 4. In one embodiment, n is 0, 1 or 2. In one embodiment, n is 0. In one embodiment, n is one. In one embodiment, $R^b$ is (a) hydroxy, (c) hetCyc$^b$CH$_2$—, (d) $R^iR^j$NC(=O)CH$_2$OCH$_2$— where $R^i$ and $R^j$ are independently H or C1-C6 alkyl, (e) $R^cR^dN$—, (f) $R^cR^d$NCH$_2$—, (g) C1-C6 alkoxy-, (h) (C1-C4 alkyl)-C(=O)NH— wherein said alkyl portion is optionally substituted with hetCyc$^b$, hetAr$^a$, C1-C6 alkoxy- or R'R"N—, or said alkyl portion is optionally substituted with two substituents independently selected from R'R"N— and OH, where each R' and R" is independently hydrogen or C1-C6 alkyl, (i) (R'R"N)C1-C6 alkoxy(CH$_2$)$_n$— where n is 0 or 1 and R' and R" are independently hydrogen or C1-C6 alkyl, (j) hetCyc$^b$(C1-C3 alkyl)OCH$_2$—, (k) hetCyc$^b$C(=O)NH— or (l) hetAr$^a$C(=O)NH—; hetCyc$^b$ is as defined for Formula I; $R^c$ is hydrogen or C1-C6 alkyl; $R^d$ is hydrogen, C1-C6 alkyl (optionally substituted with 1-3 fluoros), (C1-C6 alkoxy)C(=O)—, hydroxyC1-C6 alkyl (optionally substituted with 1-3 fluoros), (C1-C6 alkyl)C(=O)—, ($R^kR^l$N)C1-C6 alkyl- where $R^k$ and $R^l$ are independently H or C1-C6 alkyl, $R^mR^n$NC(=O)C1-C6 alkyl- where $R^m$ and $R^n$ are independently H or C1-C6 alkyl, PhCH$_2$—, (C1-C6 alkoxy)C1-C6 alkyl-, or hetCyc$^c$ where hetCyc$^c$ is a 4-6 membered heterocyclic ring having a ring heteroatom selected from N and O and optionally substituted with C1-C6 alkyl. In one embodiment, m is 0 or 1. In one embodiment, m is 0. In one embodiment, m is 1. In one embodiment, n is 0 or 1 and m is 0 or 1. Non-limiting examples when Ring D is an optionally substituted saturated 4-7 membered heterocyclic ring include the structures:

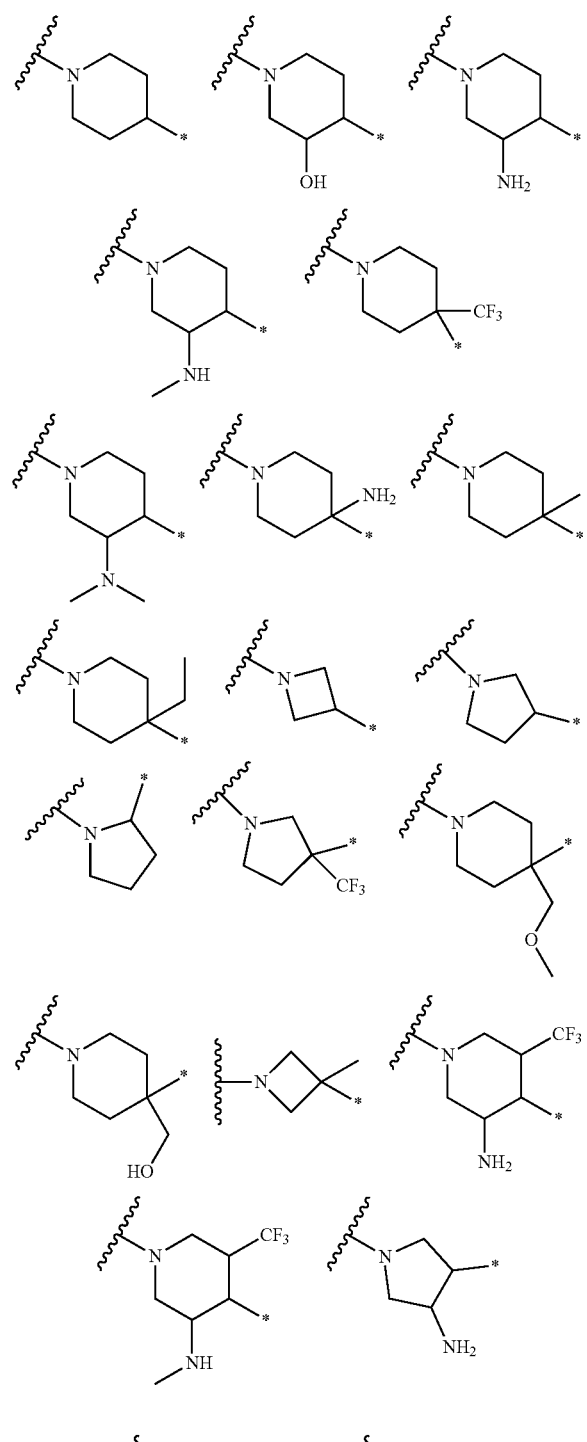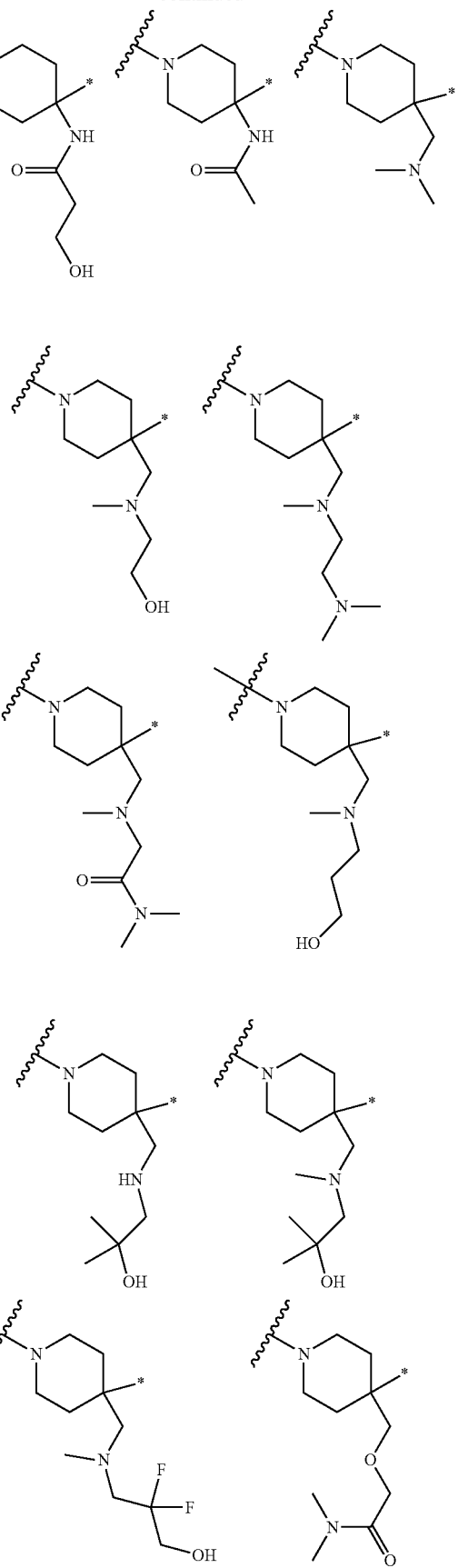

-continued
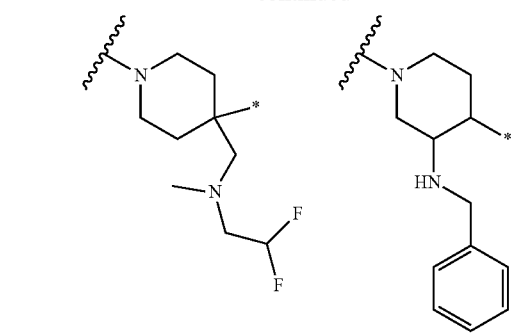
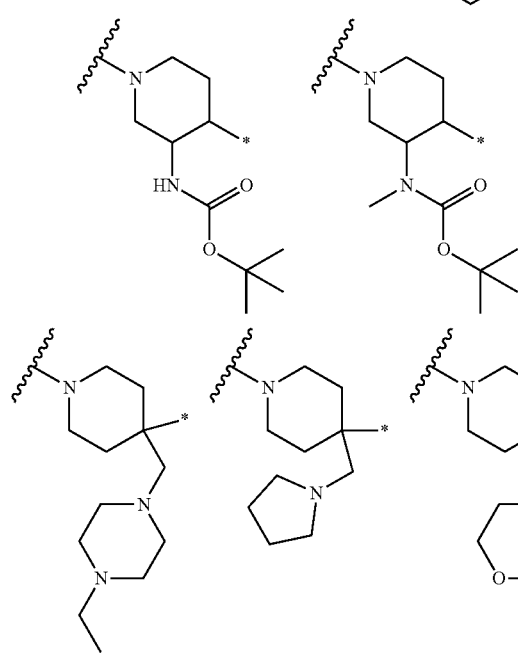
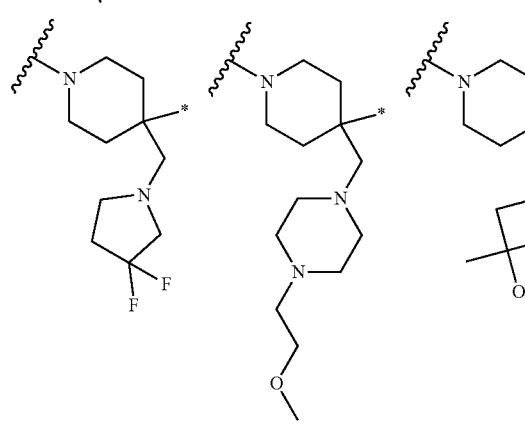
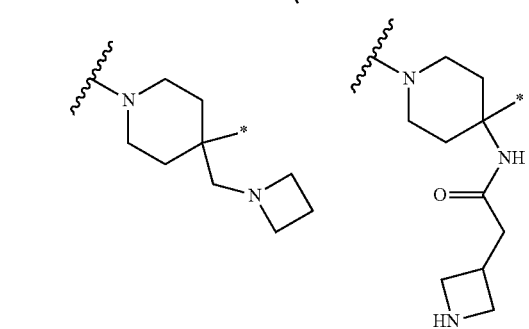
-continued
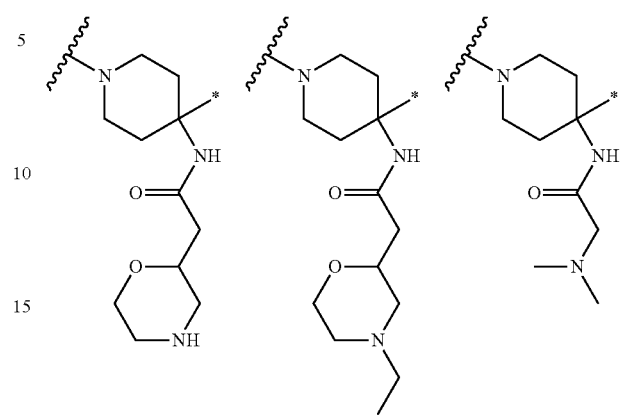
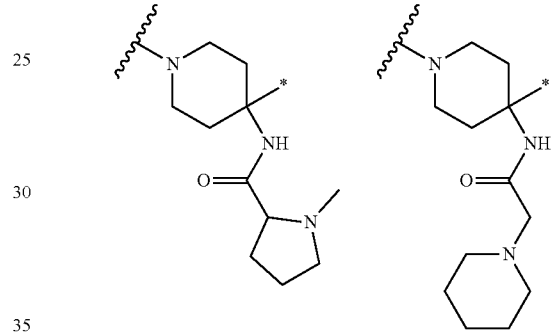
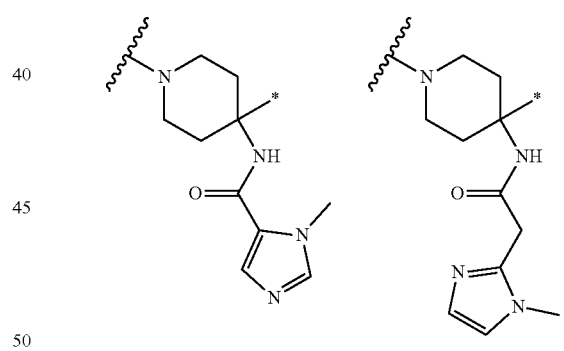
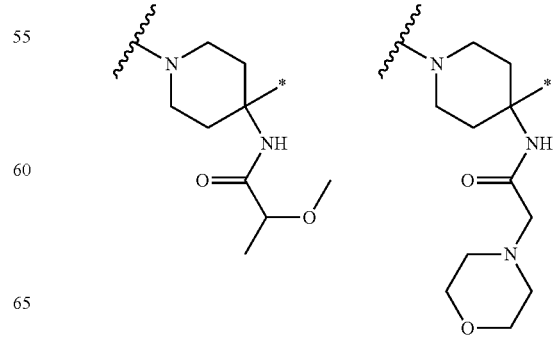

-continued
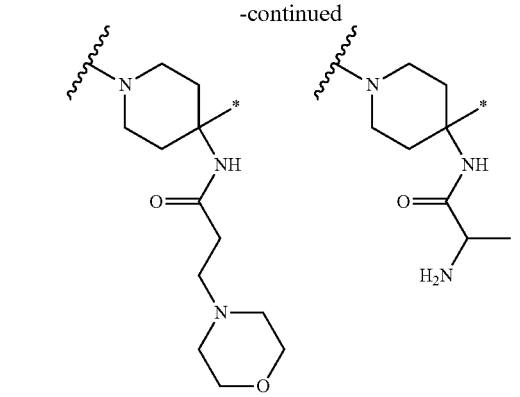
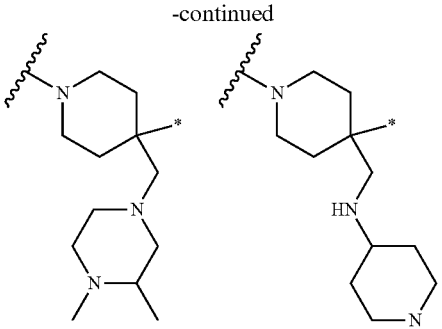
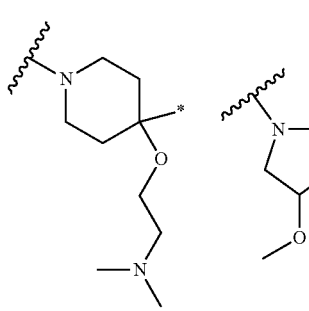
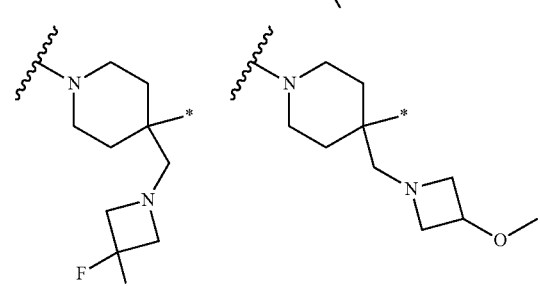
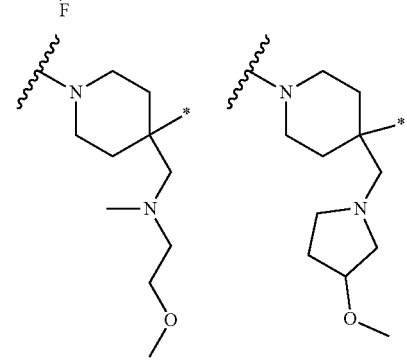
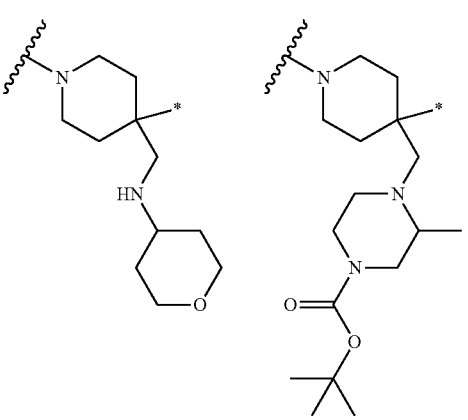

-continued

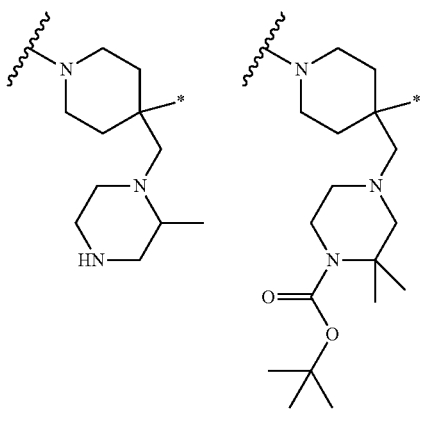
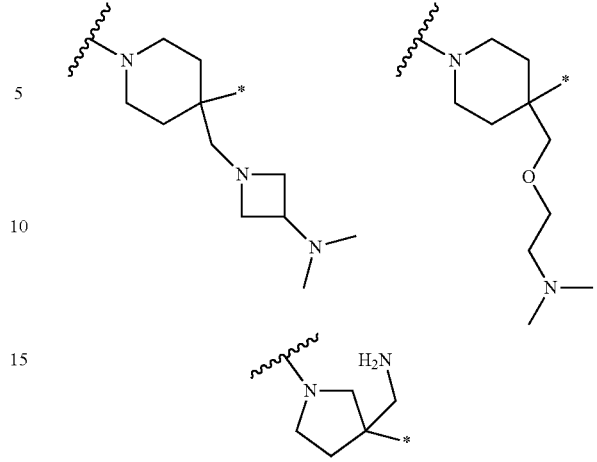

wherein the wavy line indicates the point of attachment of Ring D to the ring comprising $X^1$, $X^2$, $X^3$ and $X^4$, and asterisk indicates the point of attachment to the E group.

In one embodiment, Ring D is a saturated monocyclic 6 membered heterocyclic ring having one ring heteroatom which is nitrogen which may be represented by the structure:

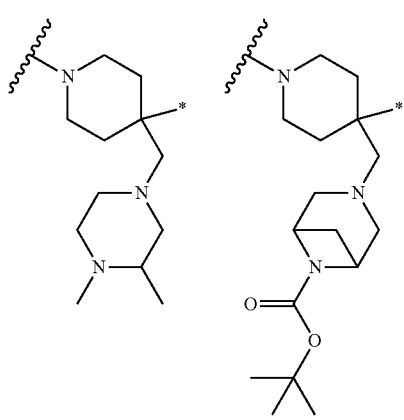

where n and m are zero, that is, Ring D may be represented by the structure:

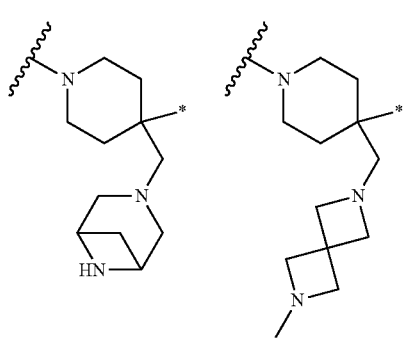
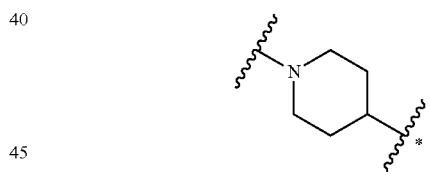

wherein the wavy line indicates the point of attachment of Ring D to the ring comprising $X^1$, $X^2$, $X^3$ and $X^4$, and the asterisk indicates the point of attachment to the E group.

In one embodiment, Ring D is a saturated 4-7 membered heterocyclic ring having one ring heteroatom which is nitrogen; E is (a) hydrogen, (b) hydroxy, (c) C1-C6 alkyl optionally substituted with 1-3 fluoros, (d) $Ar^1$C1-C6 alkyl wherein said alkyl portion is optionally substituted with 1-3 fluoros, (e) $hetAr^2$C1-C6 alkyl, (f) (C1-C6 alkoxy)C1-C6 alkoxy-, (g) $Ar^1$O—, (h) $hetAr^2$O—, (i) $Ar^1NR^g$— where $R^g$ is H or C1-C6 alkyl, (j) $hetAr^2NR^g$— where $R^g$ is H or C1-C6 alkyl, (k) $R^3$C(=O)$NR^g$— where $R^g$ is H or C1-C6 alkyl, (l) $Ar^1$C(=O)$NR^g$— where $R^g$ is H or C1-C6 alkyl, (m) $hetAr^2$C(=O)$NR^g$(CH$_2$)$_p$— where p is 0 or 1, (n) $R^4R^5$NC(=O)—, (o) $Ar^1NR^g$C(=O)—, where $R^g$ is H or C1-C6 alkyl, (p) $hetAr^2NR^g$C(=O)—, where $R^g$ is H or C1-C6 alkyl, (r) $hetCyc^5$C(=O)—, (s) $R^4R^5$NC(=O)$NR^g$— where $R^g$ is H or C1-C6 alkyl, (t) C1-C6 alkyl)SO$_2$—, (u) $Ar^1$(C1-C6 alkyl)C(=O)$NR^g$— where $R^g$ is H or C1-C6 alkyl, (v) $hetAr^4$C(=O)$NR^g$— where $R^g$ is H or

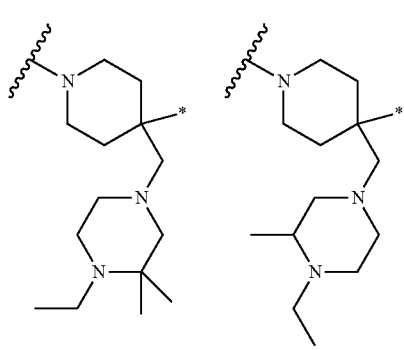

C1-C6 alkyl, (w) hetAr²—S(=O)—, (x) (C3-C6 cycloalkyl)CH₂SO₂—, (y) Ar¹(C1-C6 alkyl)SO₂—, (z) hetAr²SO₂—, (aa) Ar¹, (bb) hetAr², (cc) hetCyc⁵, (dd) C1-C6 alkoxy, (ee) Ar¹(C1-C6 alkyl)-O—, (ff) hetAr²(C1-C6 alkyl)-O—, (gg) hetAr²—O—C1-C6 alkyl-, (hh) Ar¹(C1-C6 alkyl)NR^g— where R^g is H or C1-C6 alkyl, (ii) hetAr²—S—, (jj) Ar²SO₂NR^g(CH₂)_p— where p is 0 or 1 and R^g is H or C1-C6 alkyl, (kk) (C1-C6 alkoxy)C(=O)—, (ll) (C1-C6 alkyl)NR^gC(=O)O— where R^g is H or C1-C6 alkyl, (mm) (C1-C6 alkyl)NR^gSO₂— where R^g is H or C1-C6 alkyl, (nn) hetCyc⁵C(=O)NR^g—, (oo) Q-NR^h(C1-C3 alkyl)C(=O)NR^g— where R^g and R^h are independently H or C1-C6 alkyl and Q is H, C1-C6 alkyl or (C1-C6 alkyl)OC(=O)—, (pp)

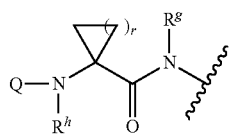

where R^g and R^h are independently H or C1-C6 alkyl, Q is H, C1-C6 alkyl or (C1-C6 alkyl)OC(=O)— and r is 1, 2, 3 or 4, (qq)

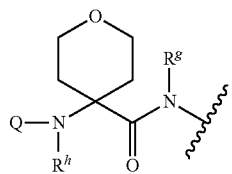

where R^g and R^h are independently H or C1-C6 alkyl and Q is H, C1-C6 alkyl or (C1-C6 alkyl)OC(=O)—, (rr)

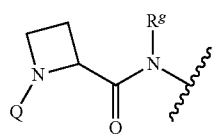

where R^g is H or C1-C6 alkyl and Q is H, C1-C6 alkyl or (C1-C6 alkyl)OC(=O)—, (ss) R^gR^hN— where R^g and R^h are independently H or C1-C6 alkyl, (tt) (C3-C6 cycloalkyl)C(=O)NR^g— where the cycloalkyl is optionally and independently substituted with one or more halogens, (uu) (C1-C6 alkyl)C(=O)NR^gCH₂— where R^g is H or C1-C6 alkyls, or (vv) C1-C6 alkyl)SO₂NR^g— where R^g is H or C1-C6 alkyl; each R^a is independently C1-C6 alkyl (optionally substituted with 1-3 fluoros), hydroxyC1-C6 alkyl or (C1-C6 alkoxy)C1-C6 alkyl-; R^b is (a) hydroxy, (b) cyclopropyl, (c) hetCyc^bCH₂-, (d) R^iR^jNC(=O)CH₂OCH₂— where R^i and R^j are independently H or C1-C6 alkyl, (e) R^cR^dN—, (f) R^cR^dNCH₂—, (g) C1-C6 alkoxy-, (h) (C1-C4 alkyl)-C(=O)NH— wherein said alkyl portion is optionally substituted with hetCyc^b, hetAr^a, C1-C6 alkoxy- or R'R"N—, or said alkyl portion is optionally substituted with two substituents independently selected from R'R"N— and OH, where each R' and R" is independently hydrogen or C1-C6 alkyl, (i) (R'R"N)C1-C6 alkoxy(CH₂)_n— where n is 0 or 1 and R' and R" are independently hydrogen or C1-C6 alkyl, (j) hetCyc^b(C1-C3 alkyl)OCH₂—, (k) hetCyc^bC(=O) NH— or (l) hetAr^aC(=O)NH—; R^c is hydrogen or C1-C6 alkyl; R^d is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C(=O)—, (C1-C6 alkyl)C(=O)—, (R^kR^lN)C1-C6 alkyl- where R^k and R^l are independently H or C1-C6 alkyl, R^mR^nNC(=O)C1-C6 alkyl- where R^m and R^n are independently H or C1-C6 alkyl, PhCH₂—, (C1-C6 alkoxy)C1-C6 alkyl-, or hetCyc^c where hetCyc^c is a 4-6 membered heterocyclic ring having a ring heteroatom selected from N and O and optionally substituted with C1-C6 alkyl; n is 0, 1, 2, 3, 4, 5 or 6; m is 0 or 1; and Ar¹, hetAr², hetAr^a, hetCyc^b, hetCyc⁵, R^g, R³, R⁴, and R⁵ are as defined for Formula I. In one embodiment, each R^a is independently selected from a C1-C6 substituent (optionally substituted with 1-3 fluoros). In one embodiment, R^b is (a) hydroxy, (c) hetCyc^bCH₂—, (d) R^iR^jNC(=O)CH₂OCH₂— where R^i and R^j are independently H or C1-C6 alkyl, (e) R^cR^dN—, (f) R^cR^dNCH₂—, (h) (C1-C4 alkyl)-C(=O)NH— wherein said alkyl portion is optionally substituted with hetCyc^b, hetAr^a, C1-C6 alkoxy- or R'R"N—, or said alkyl portion is optionally substituted with two substituents independently selected from R'R"N— and OH, where each R' and R" is independently hydrogen or C1-C6 alkyl, or (k) hetCyc^bC(=O)NH—; R^c is hydrogen or C1-C6 alkyl; R^d is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C(=O)—, (C1-C6 alkyl)C(=O)—, (R^kR^lN)C1-C6 alkyl- where R^k and R^l are independently H or C1-C6 alkyl, R^mR^nNC(=O)C1-C6 alkyl- where R^m and R^n are independently H or C1-C6 alkyl, PhCH₂—, (C1-C6 alkoxy)C1-C6 alkyl-, or hetCyc^c where hetCyc^c is a 4-6 membered heterocyclic ring having a ring heteroatom selected from N and O and optionally substituted with C1-C6 alkyl; hetCyc^b and hetAr^a are as defined for Formula I, n is 0, 1 or 2; and m is 0 or 1. In one embodiment, R^b is (a) OH, (c) hetCyc^bCH₂— wherein hetCyc^b is a 4-6 membered heterocyclic ring having 1-2 ring heteroatoms independently selected from N and O, wherein hetCyc^b is optionally substituted with C1-C6 alkyl (optionally substituted with 1-3 fluoros), (e) R^cR^dN— or (f) R^cR^dNCH₂—; R^c is hydrogen or C1-C6 alkyl; and R^d is hydrogen or C1-C6 alkyl (optionally substituted with 1-3 fluoros).

In one embodiment, Ring D is a saturated monocyclic 6-membered heterocyclic ring having one ring heteroatom which is nitrogen which may be represented by the structure:

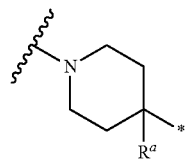

wherein the wavy line indicates the point of attachment of Ring D to the ring comprising X¹, X², X³ and X⁴, and the asterisk indicates the point of attachment to the E group, and R^a is C1-C6 alkyl (optionally substituted with 1-3 fluoros), hydroxyC1-C6 alkyl or (C1-C6 alkoxy)C1-C6 alkyl-. In one embodiment, R^a is C1-C6 alkyl.

In one embodiment, Ring D is a saturated monocyclic 6-membered heterocyclic ring having one ring heteroatom which is nitrogen which may be represented by the structures:

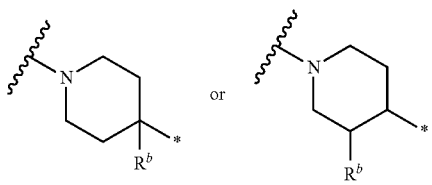

wherein the wavy line indicates the point of attachment of Ring D to the ring comprising $X^1$, $X^2$, $X^3$ and $X^4$, and the asterisk indicates the point of attachment to the E group, and $R^b$ is (a) hydroxy, (b) cyclopropyl, (c) hetCyc$^b$CH$_2$—, (d) R'R$^j$NC(═O)CH$_2$OCH$_2$— where $R^i$ and $R^j$ are independently H or C1-C6 alkyl, (e) $R^cR^dN$—, (f) $R^cR^d$NCH$_2$—, (g) C1-C6 alkoxy-, (h) (C1-C4 alkyl)-C(═O)NH— wherein said alkyl portion is optionally substituted with hetCyc$^b$, hetAr$^a$, C1-C6 alkoxy- or R'R"N—, or said alkyl portion is optionally substituted with two substituents independently selected from R'R"N— and OH, where each R' and R" is independently hydrogen or C1-C6 alkyl, (i) (R'R"N)C1-C6 alkoxy(CH$_2$)$_n$— where n is 0 or 1 and R' and R" are independently hydrogen or C1-C6 alkyl, (j) hetCyc$^b$(C1-C3 alkyl)OCH$_2$—, (k) hetCyc$^b$C(═O)NH— or (l) hetAr$^a$C(═O)NH—; $R^c$ is hydrogen or C1-C6 alkyl; $R^d$ is hydrogen, C1-C6 alkyl (optionally substituted with 1-3 fluoros), (C1-C6 alkoxy)C(═O)—, hydroxyC1-C6 alkyl (optionally substituted with 1-3 fluoros), (hydroxyC1-C6 alkyl)C(═O)—, (C1-C6 alkyl)C(═O)—, (R$^k$R$^l$N)C1-C6 alkyl- where $R^k$ and $R^l$ are independently H or C1-C6 alkyl, R$^m$R"NC(═O)C1-C6 alkyl- where $R^m$ and $R^n$ are independently H or C1-C6 alkyl, PhCH$_2$—, (C1-C6 alkoxy)C1-C6 alkyl-, or hetCyc$^c$ where hetCyc$^c$ is a 4-6 membered heterocyclic ring having a ring heteroatom selected from N and O and optionally substituted with C1-C6 alkyl. In one embodiment, $R^b$ is (a) OH, (c) hetCyc$^b$CH$_2$—, (e) $R^cR^dN$— or (f) $R^cR^d$NCH$_2$—; $R^c$ is hydrogen or C1-C6 alkyl; $R^d$ is hydrogen or C1-C6 alkyl (optionally substituted with 1-3 fluoros); and hetCyc$^b$ is as defined for Formula I. In one embodiment, $R^b$ is (c) hetCyc$^b$CH$_2$—, (e) $R^cR^dN$— or (f) $R^cR^d$NCH$_2$—; $R^c$ is hydrogen or C1-C6 alkyl; $R^d$ is hydrogen or C1-C6 alkyl (optionally substituted with 1-3 fluoros); and hetCyc$^b$ is as defined for Formula I.

In one embodiment, Ring D is a saturated 4-7 membered heterocyclic ring having one ring heteroatom which is nitrogen; E is (d) Ar$^1$C1-C6 alkyl- wherein said alkyl portion is optionally substituted with 1-3 fluoros, (e) hetAr$^2$C1-C6 alkyl-, (g) Ar$^1$O—, (h) hetAr$^2$O—, (k) R$^3$C(═O)NR$^g$ where R$^g$ is H or C1-C6 alkyl, (l) Ar$^1$C(═O)NR$^g$— where R$^g$ is H or C1-C6 alkyl, (m) hetAr$^2$C(═O)NR$^g$(CH$_2$)$_p$— where p is 0 or 1, or (n) R$^4$R$^5$NC(═O)— where n is 0, 1, 2, 3, 4, 5 or 6; m is 0 or 1; and Ar$^1$, hetAr$^2$, R$^g$, R$^3$, R$^4$, and R$^5$ are as defined for Formula I. In one embodiment, each $R^a$ is independently selected from a C1-C6 substituent, $R^b$ is OH or $R^cR^dN$— where $R^c$ is hydrogen or C1-C6 alkyl and $R^d$ is hydrogen, C1-C6 alkyl or (C1-C6 alkoxy)C(═O)—; n is 0, 1 or 2; and m is 0 or 1.

In one embodiment, Ring D is a saturated 4-7 membered heterocyclic ring having one ring heteroatom which is nitrogen; E is hydrogen; each $R^a$ is independently C1-C6 alkyl (optionally substituted with 1-3 fluoros), hydroxyC1-C6 alkyl or (C1-C6 alkoxy)C1-C6 alkyl-; $R^b$ is (a) hydroxy, (b) cyclopropyl, (c) hetCyc$^b$CH$_2$— where hetCyc$^b$ is a 4-6 membered heterocyclic ring having 1-2 ring heteroatoms independently selected from N and O, (d) R'R$^j$NC(═O)CH$_2$OCH$_2$— where $R^i$ and $R^j$ are independently H or C1-C6 alkyl, (e) $R^cR^dN$—, (f) $R^cR^d$NCH$_2$—, (g) C1-C6 alkoxy-, (h) (C1-C4 alkyl)-C(═O)NH— wherein said alkyl portion is optionally substituted with hetCyc$^b$, hetAr$^a$, C1-C6 alkoxy- or R'R"N—, or said alkyl portion is optionally substituted with two substituents independently selected from R'R"N— and OH, where each R' and R" is independently hydrogen or C1-C6 alkyl, (i) (R'R"N)C1-C6 alkoxy(CH$_2$)$_n$— where n is 0 or 1 and R' and R" are independently hydrogen or C1-C6 alkyl, or (j) hetCyc$^b$(C1-C3 alkyl)OCH$_2$—; hetCyc$^b$ is as defined for Formula I; $R^c$ is hydrogen or C1-C6 alkyl; $R^d$ is hydrogen, C1-C6 alkyl (optionally substituted with 1-3 fluoros), (C1-C6 alkoxy)C(═O)—, hydroxyC1-C6 alkyl (optionally substituted with 1-3 fluoros), (hydroxyC1-C6 alkyl)C(═O)—, (C1-C6 alkyl)C(═O)—, (R$^k$R$^l$N)C1-C6 alkyl- where $R^k$ and $R^l$ are independently H or C1-C6 alkyl, R$^m$R"NC(═O)C1-C6 alkyl- where $R^m$ and $R^n$ are independently H or C1-C6 alkyl, PhCH$_2$—, (C1-C6 alkoxy)C1-C6 alkyl-, or hetCyc$^c$ where hetCyc$^c$ is a 4-6 membered heterocyclic ring having a ring heteroatom selected from N and O and optionally substituted with C1-C6 alkyl; n is 0, 1, 2, 3, 4, 5 or 6; and m is 0 or 1. In one embodiment, Ring D is a saturated 6 membered heterocyclic ring having one ring heteroatom. In one embodiment, Ring D is a saturated 5 membered heterocyclic ring having one ring heteroatom. In one embodiment, $R^b$ is OH or $R^cR^dN$— where $R^c$ is hydrogen or C1-C6 alkyl and $R^d$ is hydrogen, C1-C6 alkyl, (C1-C6 alkoxy)C(═O)— or PhCH$_2$—. In one embodiment, n is 0, 1 or 2 and m is 0 or 1. In one embodiment, n is 0 and m is 0 or 1. Non-limiting examples include the structures:

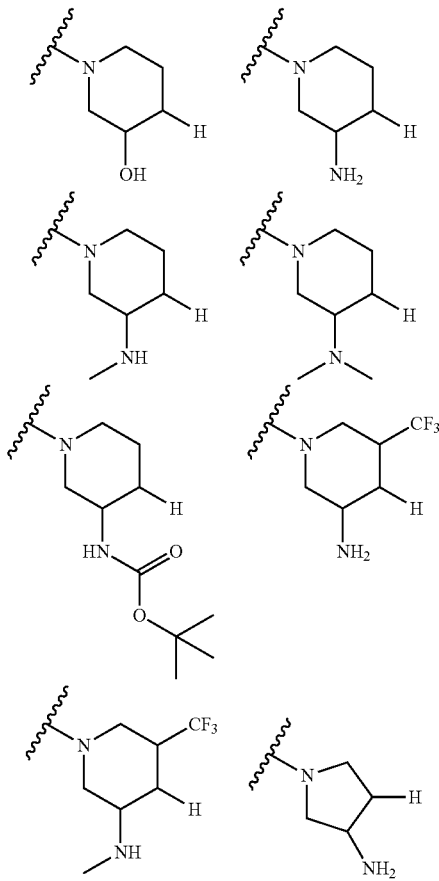

-continued

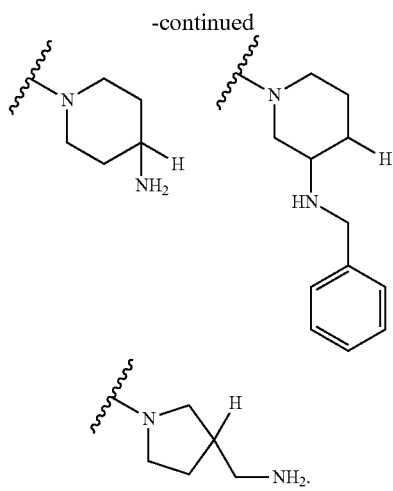

In one embodiment, Ring D is a saturated 4-7 membered heterocyclic ring having one ring heteroatom which is nitrogen; each $R^a$ is independently C1-C6 alkyl (optionally substituted with 1-3 fluoros), hydroxyC1-C6 alkyl or (C1-C6 alkoxy)C1-C6 alkyl-; $R^b$ is (a) hydroxy, (b) cyclopropyl, (c) hetCyc$^b$CH$_2$—, (d) R$^i$R$^j$NC(═O)CH$_2$OCH$_2$— where R$^i$ and R$^j$ are independently H or C1-C6 alkyl, (e) R$^c$R$^d$N—, (f) R$^c$R$^d$NCH$_2$—, (g) C1-C6 alkoxy-, (h) (C1-C4 alkyl)-C(═O)NH— wherein said alkyl portion is optionally substituted with hetCyc$^b$, hetAr$^a$, C1-C6 alkoxy- or R'R"N—, or said alkyl portion is optionally substituted with two substituents independently selected from R'R"N— and OH, where each R' and R" is independently hydrogen or C1-C6 alkyl, (i) (R'R"N)C1-C6 alkoxy(CH$_2$)$_n$— where n is 0 or 1 and R' and R" are independently hydrogen or C1-C6 alkyl, or (j) hetCyc$^b$(C1-C3 alkyl)OCH$_2$—; hetCyc$^b$ is as defined for Formula I; $R^c$ is hydrogen or C1-C6 alkyl; $R^d$ is hydrogen, C1-C6 alkyl (optionally substituted with 1-3 fluoros), (C1-C6 alkoxy)C(═O)—, hydroxyC1-C6 alkyl (optionally substituted with 1-3 fluoros), (hydroxyC1-C6 alkyl)C(═O)—, (C1-C6 alkyl)C(═O)—, (R$^k$R$^l$N)C1-C6 alkyl- where R$^k$ and R$^l$ are independently H or C1-C6 alkyl, R$^m$R$^n$NC(═O)C1-C6 alkyl- where R$^m$ and R$^n$ are independently H or C1-C6 alkyl, PhCH$_2$—, (C1-C6 alkoxy)C1-C6 alkyl-, or hetCyc$^c$ where hetCyc$^c$ is a 4-6 membered heterocyclic ring having a ring heteroatom selected from N and O and optionally substituted with C1-C6 alkyl; n is 0, 1, 2, 3, 4, 5 or 6; m is 0 or 1; and E is hydroxy. In one embodiment, n is 0, 1 or 2 and m is 0 or 1. In one embodiment, Ring D is a saturated 6 membered heterocyclic ring having one ring heteroatom which is nitrogen. In one embodiment, $R^b$ is R$^c$R$^d$N— where R$^c$ is hydrogen or C1-C6 alkyl and R$^d$ is hydrogen, C1-C6 alkyl or (C1-C6 alkoxy)C(═O)—. In one embodiment, n is 0, 1 or 2 and m is 0 or 1. In one embodiment, n is 0 and m is 0 or 1. A non-limiting example includes the structure:

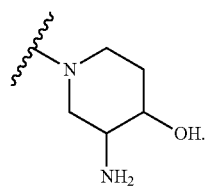 [SMILES: *N1CCC(O)C(N)C1]

In one embodiment, Ring D is a saturated 4-7 membered heterocyclic ring having one ring heteroatom which is nitrogen; each $R^a$ is independently C1-C6 alkyl (optionally substituted with 1-3 fluoros), hydroxyC1-C6 alkyl or (C1-C6 alkoxy)C1-C6 alkyl-; $R^b$ is (a) hydroxy, (b) cyclopropyl, (c) hetCyc$^b$CH$_2$—, (d) R$^i$R$^j$NC(═O)CH$_2$OCH$_2$— where R$^i$ and R$^j$ are independently H or C1-C6 alkyl, (e) R$^c$R$^d$N—, (f) R$^c$R$^d$NCH$_2$—, (g) C1-C6 alkoxy-, (h) (C1-C4 alkyl)-C(═O)NH— wherein said alkyl portion is optionally substituted with hetCyc$^b$, hetAr$^a$, C1-C6 alkoxy- or R'R"N—, or said alkyl portion is optionally substituted with two substituents independently selected from R'R"N— and OH, where each R' and R" is independently hydrogen or C1-C6 alkyl, (i) (R'R"N)C1-C6 alkoxy(CH$_2$)$_n$— where n is 0 or 1 and R' and R" are independently hydrogen or C1-C6 alkyl, or (j) hetCyc$^b$(C1-C3 alkyl)OCH$_2$—; hetCyc$^b$ is as defined for Formula I; $R^c$ is hydrogen or C1-C6 alkyl; $R^d$ is hydrogen, C1-C6 alkyl (optionally substituted with 1-3 fluoros), (C1-C6 alkoxy)C(═O)—, hydroxyC1-C6 alkyl (optionally substituted with 1-3 fluoros), (hydroxyC1-C6 alkyl)C(═O)—, (C1-C6 alkyl)C(═O)—, (R$^k$R$^l$N)C1-C6 alkyl- where R$^k$ and R$^l$ are independently H or C1-C6 alkyl, R$^m$R$^n$NC(═O)C1-C6 alkyl- where R$^m$ and R$^n$ are independently H or C1-C6 alkyl, PhCH$_2$—, (C1-C6 alkoxy)C1-C6 alkyl-, or hetCyc$^c$ where hetCyc$^c$ is a 4-6 membered heterocyclic ring having a ring heteroatom selected from N and O and optionally substituted with C1-C6 alkyl; n is 0, 1, 2, 3, 4, 5 or 6; m is 0 or 1; and E is C1-C6 alkyl optionally substituted with 1-3 fluoros. In one embodiment, Ring D is a saturated 6 membered heterocyclic ring having one ring heteroatom which is nitrogen. In one embodiment, $R^b$ is OH or R$^c$R$^d$N— where R$^c$ is hydrogen or C1-C6 alkyl and R$^d$ is hydrogen, C1-C6 alkyl or (C1-C6 alkoxy)C(═O)—. In one embodiment, n is 0, 1 or 2 and m is 0 or 1. In one embodiment, n is 0 and m is 0 or 1. Non-limiting examples include the structures:

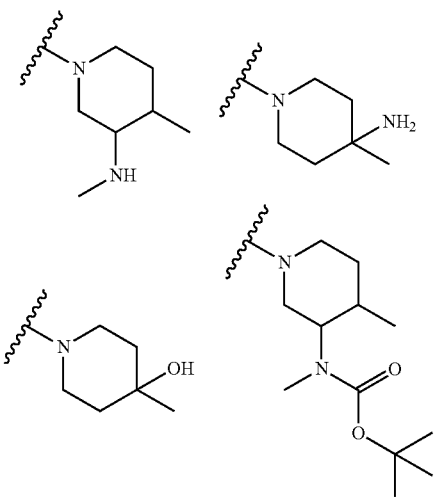

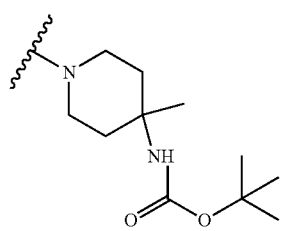

In one embodiment, Ring D is a saturated 4-7 membered heterocyclic ring having one ring heteroatom which is nitrogen, R$^a$, R$^b$, n, and m are as defined for Formula I, and E is Ar$^1$C1-C6 alkyl wherein said alkyl portion is optionally substituted with 1-3 fluoros and where Ar$^1$ is as defined for Formula I. In one embodiment, Ring D is a saturated 4-7 membered heterocyclic ring having one ring heteroatom which is nitrogen; each R$^a$ is independently C1-C6 alkyl (optionally substituted with 1-3 fluoros), hydroxyC1-C6 alkyl or (C1-C6 alkoxy)C1-C6 alkyl-; R$^b$ is (a) hydroxy, (b) cyclopropyl, (c) hetCyc$^b$CH$_2$—, (d) R$^i$R$^j$NC(=O)CH$_2$OCH$_2$— where R$^i$ and R$^j$ are independently H or C1-C6 alkyl, (e) R$^c$R$^d$N—, (f) R$^c$R$^d$NCH$_2$—, (g) C1-C6 alkoxy-, (h) (C1-C4 alkyl)-C(=O)NH— wherein said alkyl portion is optionally substituted with hetCyc$^b$, hetAr$^a$, C1-C6 alkoxy- or R'R"N—, or said alkyl portion is optionally substituted with two substituents independently selected from R'R"N— and OH, where each R' and R" is independently hydrogen or C1-C6 alkyl, (i) (R'R"N)C1-C6 alkoxy (CH$_2$)$_n$— where n is 0 or 1 and R' and R" are independently hydrogen or C1-C6 alkyl, (j) hetCyc$^b$(C1-C3 alkyl)OCH$_2$— or (k) hetCyc$^b$C(=O)NH—; hetCyc$^b$ is as defined for Formula I; R$^c$ is hydrogen or C1-C6 alkyl; R$^d$ is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C(=O)—, (C1-C6 alkyl)C(=O)—, (R$^k$R$^l$N)C1-C6 alkyl- where R$^k$ and R$^l$ are independently H or C1-C6 alkyl, R$^m$R$^n$NC(=O)C1-C6 alkyl- where R$^m$ and R$^n$ are independently H or C1-C6 alkyl, PhCH$_2$—, (C1-C6 alkoxy)C1-C6 alkyl-, or hetCyc$^c$ where hetCyc$^c$ is a 4-6 membered heterocyclic ring having a ring heteroatom selected from N and O and optionally substituted with C1-C6 alkyl; n is 0, 1, 2, 3, 4, 5 or 6; m is 0 or 1; and E is Ar$^1$C1-C6 alkyl, wherein said alkyl portion is optionally substituted with 1-3 fluoros and where Ar$^1$ is as defined for Formula I. In one embodiment, Ring D is a saturated 6 membered heterocyclic ring having one ring heteroatom which is nitrogen. In one embodiment, R$^b$ is OH. In one embodiment, n is 0, 1 or 2 and m is 0 or 1. In one embodiment, n is 0 and m is 0 or 1. Non-limiting examples include the structures:

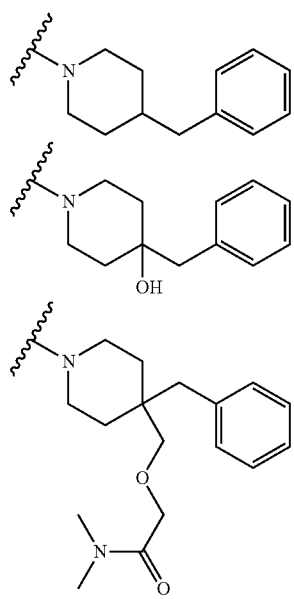

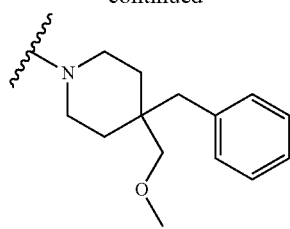

-continued

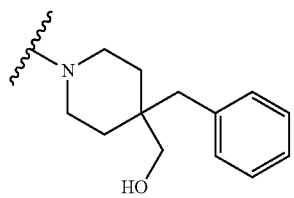

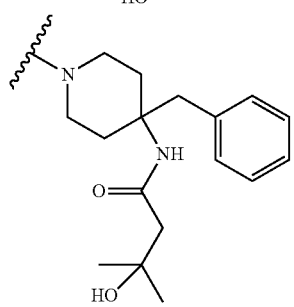

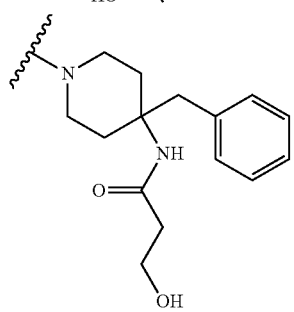

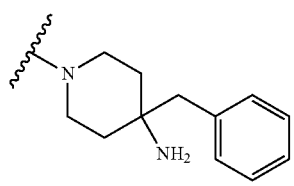

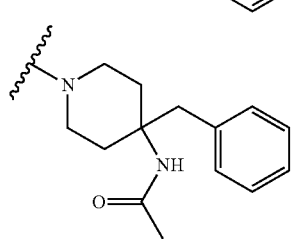

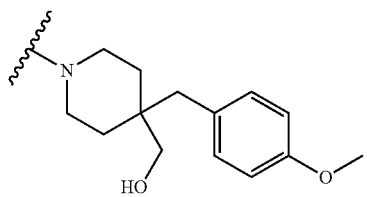

35
-continued
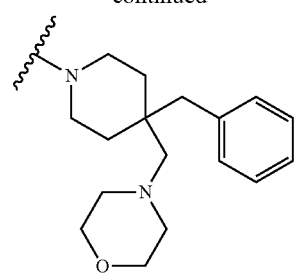
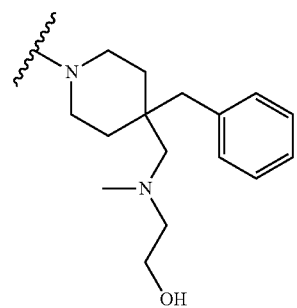
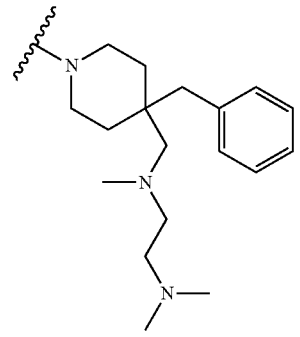
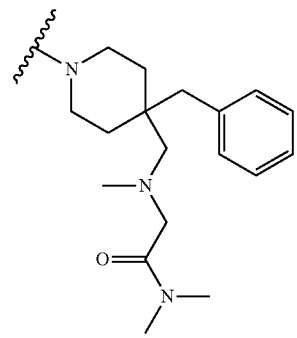
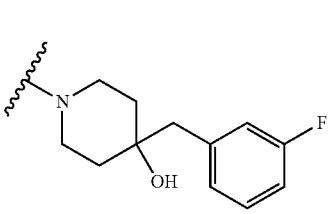
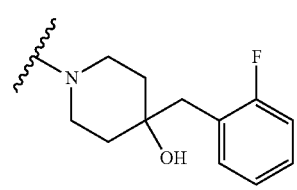
36
-continued
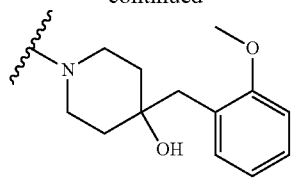
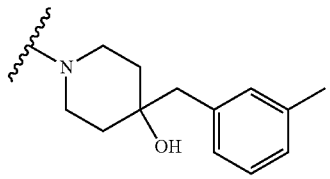
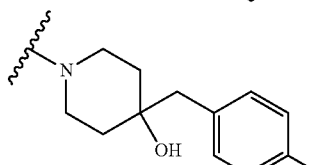
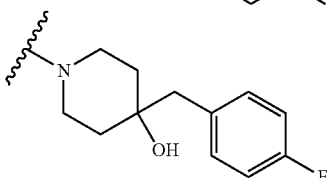
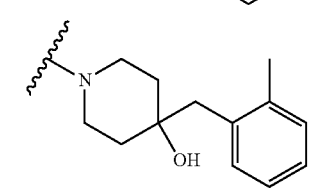
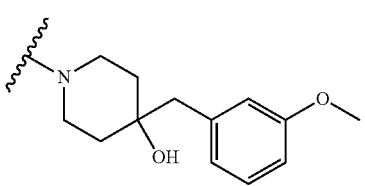
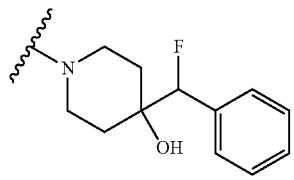
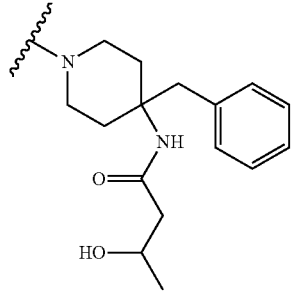

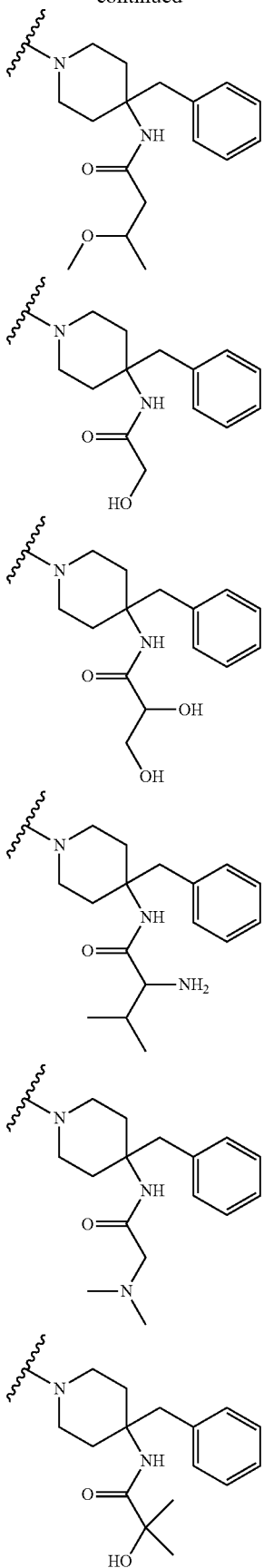
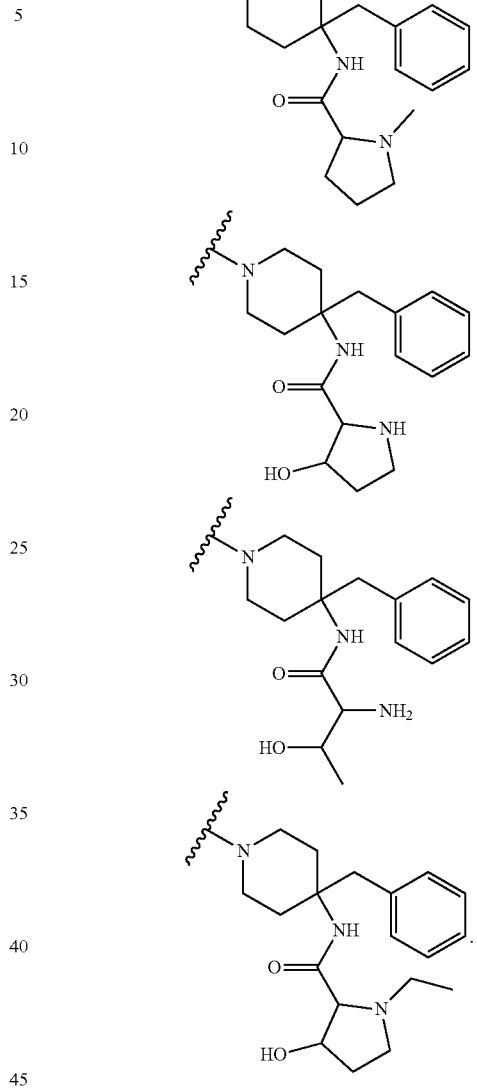

In one embodiment, Ring D is a saturated 4-7 membered heterocyclic ring having one ring heteroatom which is nitrogen; each $R^a$ is independently C1-C6 alkyl (optionally substituted with 1-3 fluoros), hydroxyC1-C6 alkyl or (C1-C6 alkoxy)C1-C6 alkyl-; $R^b$ is (a) hydroxy, (b) cyclopropyl, (c) hetCyc$^b$CH$_2$—, (d) R$^i$R$^j$NC(=O)CH$_2$OCH$_2$— where R$^i$ and R$^j$ are independently H or C1-C6 alkyl, (e) R$^c$R$^d$N—, (f) R$^c$R$^d$NCH$_2$—, (g) C1-C6 alkoxy-, (h) (C1-C4 alkyl)-C(=O)NH— wherein said alkyl portion is optionally substituted with hetCyc$^b$, hetAr$^a$, C1-C6 alkoxy- or R'R"N—, or said alkyl portion is optionally substituted with two substituents independently selected from R'R"N— and OH, where each R' and R" is independently hydrogen or C1-C6 alkyl, (i) (R'R"N)C1-C6 alkoxy(CH$_2$)$_n$— where n is 0 or 1 and R' and R" are independently hydrogen or C1-C6 alkyl, (j) hetCyc$^b$(C1-C3 alkyl)OCH$_2$—, (k) hetCyc$^b$C(=O)NH— or (l) hetAr$^a$C(=O)NH—; hetAr$^a$ and hetCyc$^b$ are as defined for Formula I; $R^c$ is hydrogen or C1-C6 alkyl; $R^d$ is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C(=O)—, (C1-C6 alkyl)C(=O)—, (R^kR^lN)C1-C6 alkyl- where R^k and R^l are independently H or C1-C6 alkyl, R'''R''NC(=O)C1-C6 alkyl- where R''' and R'' are independently H or C1-C6 alkyl, PhCH$_2$—, (C1-C6 alkoxy)C1-C6 alkyl-, or hetCyc^c where hetCyc^c is a 4-6 membered heterocyclic ring having a ring heteroatom selected from N and O and optionally substituted with C1-C6 alkyl; n is 0, 1, 2, 3, 4, 5 or 6; m is 0 or 1; and E is hetAr^1C1-C6 alkyl, where hetAr^1 is as defined for Formula I. In one embodiment, hetAr^2 is a 5-6 membered heteroaryl ring having 1-2 ring nitrogen atoms and optionally substituted with one or more substituents independently selected from the group consisting of halogen, C1-C6 alkyl (optionally substituted with 1-3 fluoros), and C1-C6 alkoxy (optionally substituted with 1-3 fluoros). In one embodiment, Ring D is a saturated 6 membered heterocyclic ring having one ring heteroatom which is nitrogen. In one embodiment, n is 0 or 1 and m is 0 or 1. In one embodiment, n is 0 and m is 0. In one embodiment, n is 0 and m is 1. In one embodiment, R^b is (a) hydroxy, (e) R^cR^dN—, (h) (C1-C4 alkyl)-C(=O)NH— wherein said alkyl portion is optionally substituted with hetCyc^b, hetAr^a, C1-C6 alkoxy- or R'R''N—, or said alkyl portion is optionally substituted with two substituents independently selected from R'R''N— and OH, where each R' and R'' is independently hydrogen or C1-C6 alkyl, (k) hetCyc^bC(=O)NH— or (l) hetAr^aC(=O)NH—. Non-limiting examples include the structures:

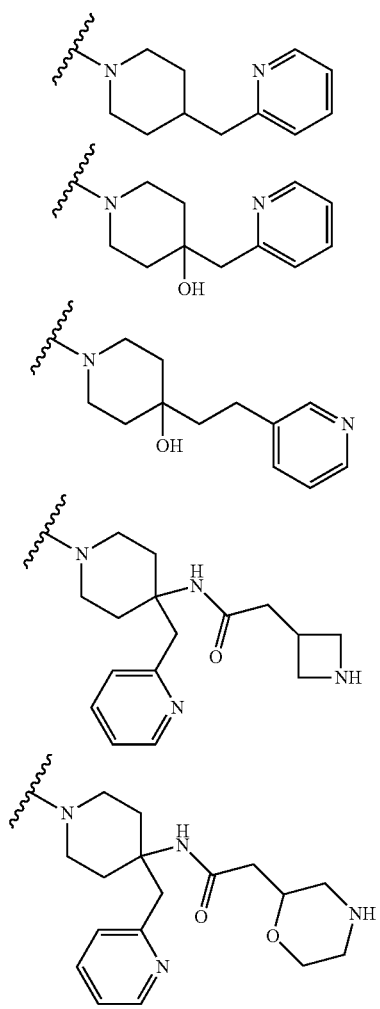

-continued

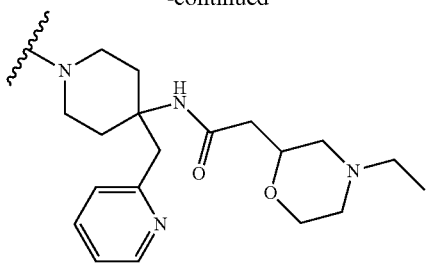

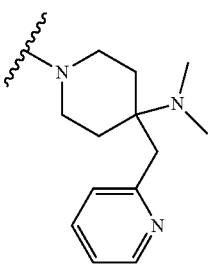
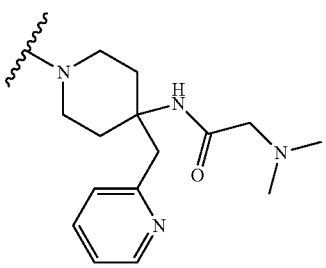

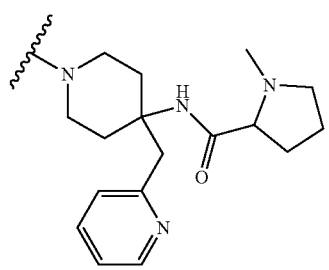

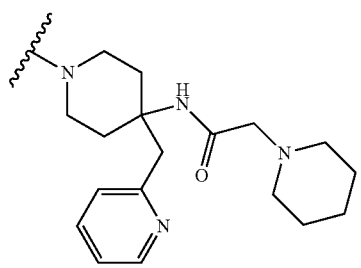

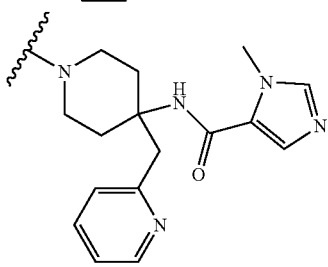

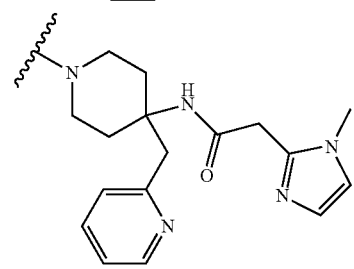

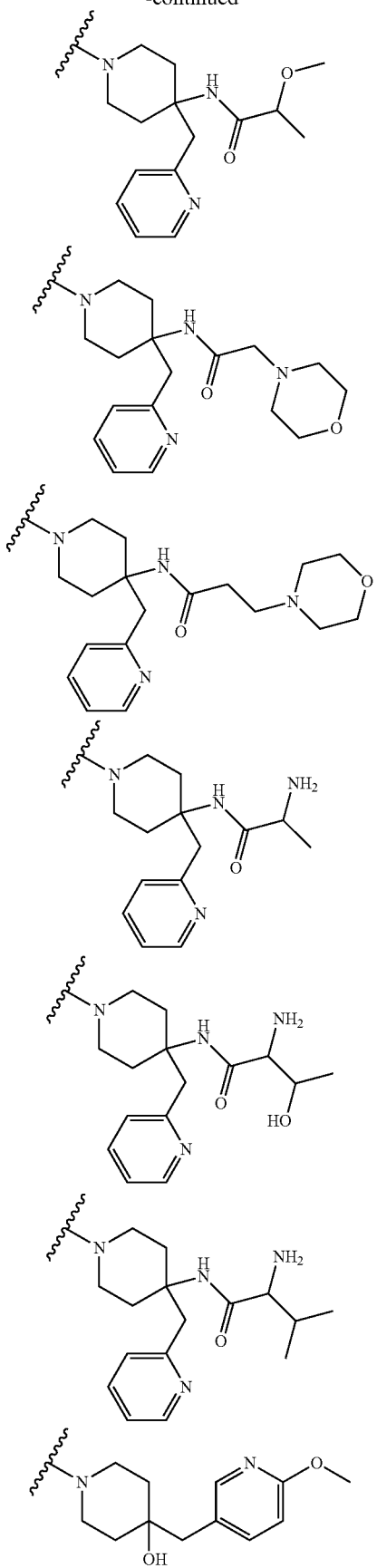
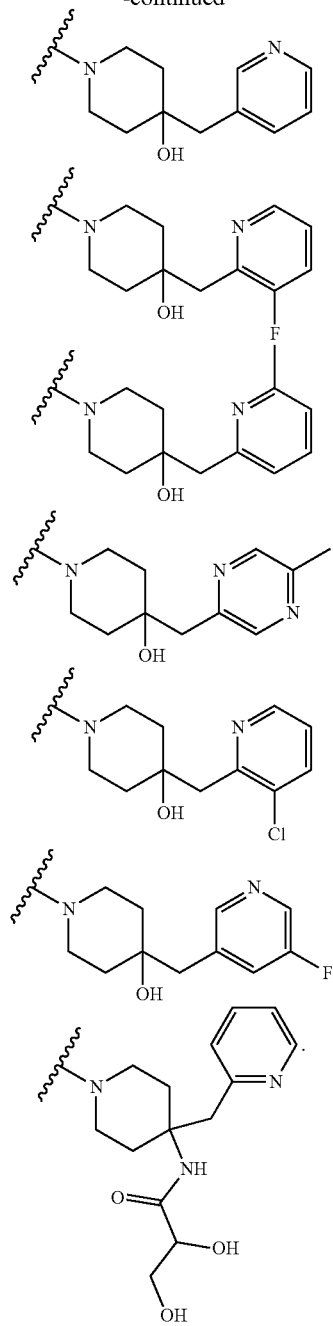

In one embodiment, Ring D is a saturated 4-7 membered heterocyclic ring having one ring heteroatom which is nitrogen; each $R^a$ is independently C1-C6 alkyl (optionally substituted with 1-3 fluoros), hydroxyC1-C6 alkyl or (C1-C6 alkoxy)C1-C6 alkyl-; $R^b$ is (a) hydroxy, (b) cyclopropyl, (c) hetCyc$^b$CH$_2$—, (d) R$^i$R$^j$NC(=O)CH$_2$OCH$_2$— where R$^i$ and R$^j$ are independently H or C1-C6 alkyl, (e) R$^c$R$^d$N—, (f) R$^c$R$^d$NCH$_2$—, (g) C1-C6 alkoxy-, (h) (C1-C4 alkyl)-C(=O)NH— wherein said alkyl portion is optionally substituted with hetCyc$^b$, hetAr$^a$, C1-C6 alkoxy- or R'R"N—, or said alkyl portion is optionally substituted with two substituents independently selected from R'R"N— and OH, where each R' and R" is independently hydrogen or C1-C6 alkyl, (i) (R'R"N)C1-C6 alkoxy(CH$_2$)$_n$— where n is 0 or 1 and R' and R" are independently hydrogen or C1-C6 alkyl, or (j) hetCyc$^b$(C1-C3 alkyl)OCH$_2$—; hetCyc$^b$ is as defined for Formula I; R$^c$ is hydrogen or C1-C6 alkyl; R$^d$ is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C(=O)—, (C1-C6 alkyl)C(=O)—, (R$^k$R$^l$N)C1-C6 alkyl- where R$^k$ and R$^l$ are independently H or C1-C6 alkyl, R$^m$R$^n$NC(=O)C1-C6 alkyl- where R$^m$ and R$^n$ are independently H or C1-C6 alkyl, PhCH$_2$—, (C1-C6 alkoxy)C1-C6 alkyl-, or hetCyc$^c$ where hetCyc$^c$ is a 4-6 membered heterocyclic ring having a ring heteroatom selected from N and O and optionally substituted with C1-C6 alkyl; n is 0, 1, 2, 3, 4, 5 or 6; m is 0 or 1; and E is (C1-C6 alkoxy)C1-C6 alkoxy-. In one embodiment, n is 0 or 1 and m is 0 or 1. In one embodiment, n is 0 and m is 0. In one embodiment, n is 0 and m is 1. In one embodiment, R$^b$ is R$^c$R$^d$N—. Non-limiting examples include the structures:

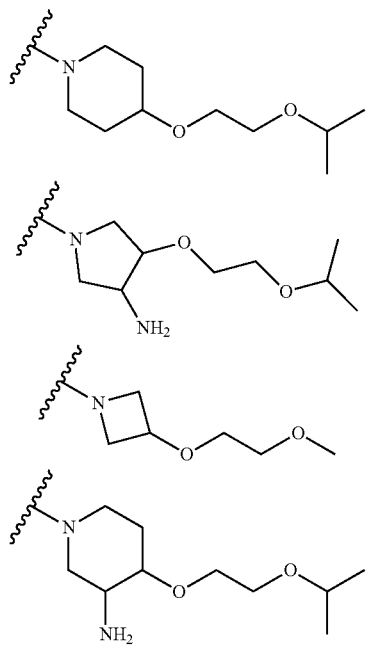

In one embodiment, Ring D is a saturated 4-7 membered heterocyclic ring having one ring heteroatom which is nitrogen; each R$^a$ is independently C1-C6 alkyl (optionally substituted with 1-3 fluoros), hydroxyC1-C6 alkyl or (C1-C6 alkoxy)C1-C6 alkyl-; R$^b$ is (a) hydroxy, (b) cyclopropyl, (c) hetCyc$^b$CH$_2$—, (d) R$^i$R$^j$NC(=O)CH$_2$OCH$_2$— where R$^i$ and R$^j$ are independently H or C1-C6 alkyl, (e) R$^c$R$^d$N—, (f) R$^c$R$^d$NCH$_2$—, (g) C1-C6 alkoxy-, (h) (C1-C4 alkyl)-C(=O)NH— wherein said alkyl portion is optionally substituted with hetCyc$^b$, hetAr$^a$, C1-C6 alkoxy- or R'R"N—, or said alkyl portion is optionally substituted with two substituents independently selected from R'R"N— and OH, where each R' and R" is independently hydrogen or C1-C6 alkyl, (i) (R'R"N)C1-C6 alkoxy(CH$_2$)$_n$— where n is 0 or 1 and R' and R" are independently hydrogen or C1-C6 alkyl, or (j) hetCyc$^b$(C1-C3 alkyl)OCH$_2$—; hetCyc$^b$ is as defined for Formula I; R$^c$ is hydrogen or C1-C6 alkyl; R$^d$ is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C(=O)—, (C1-C6 alkyl)C(=O)—, (R$^k$R$^l$N)C1-C6 alkyl- where R$^k$ and R$^l$ are independently H or C1-C6 alkyl, R$^m$R$^n$NC(=O)C1-C6 alkyl- where R$^m$ and R$^n$ are independently H or C1-C6 alkyl, PhCH$_2$—, (C1-C6 alkoxy)C1-C6 alkyl-, or hetCyc$^c$ where hetCyc$^c$ is a 4-6 membered heterocyclic ring having a ring heteroatom selected from N and O and optionally substituted with C1-C6 alkyl; n is 0, 1, 2, 3, 4, 5 or 6; m is 0 or 1; and E is Ar$^1$O—, where Ar$^1$ is as defined for Formula I. In one embodiment, Ar$^1$ is unsubstituted or substituted with one or more substituents independently selected from halogen, CN and C1-C6 alkyl (optionally substituted with 1-3 fluoros). In one embodiment, Ring D is a saturated 4 or 6 membered heterocyclic ring having one ring heteroatom which is nitrogen. In one embodiment, n is 0, 1 or 2 and m is 0 or 1. In one embodiment, n is 0 and m is 0. Non-limiting examples include the structures:

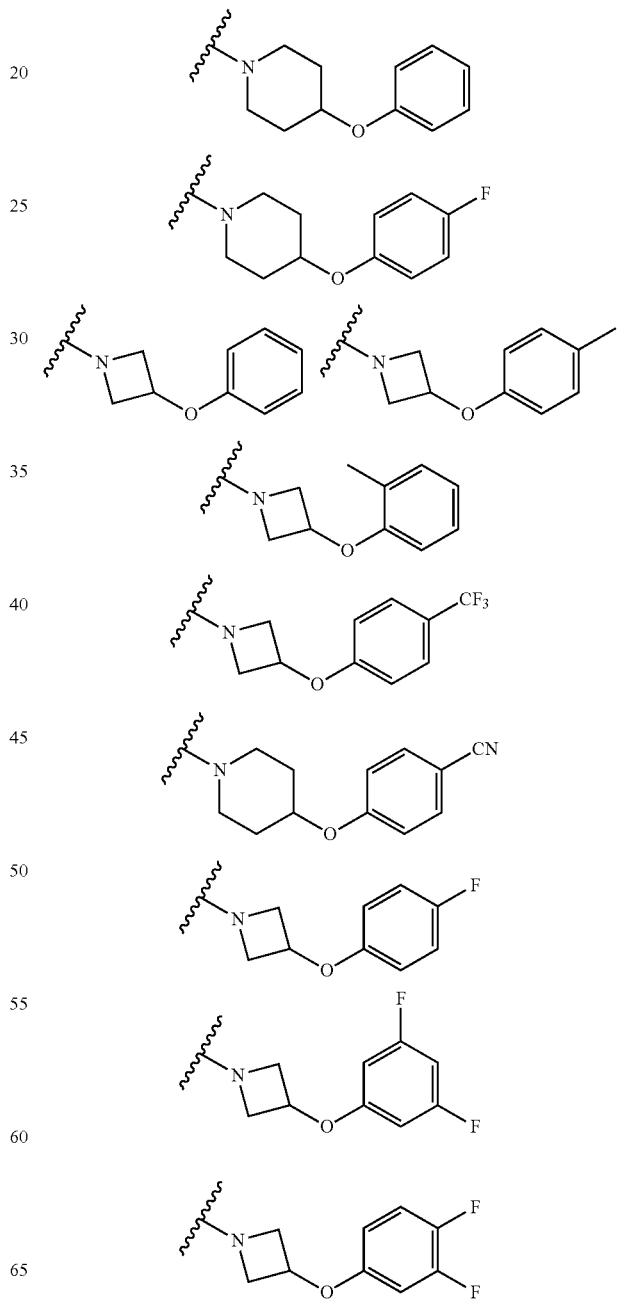

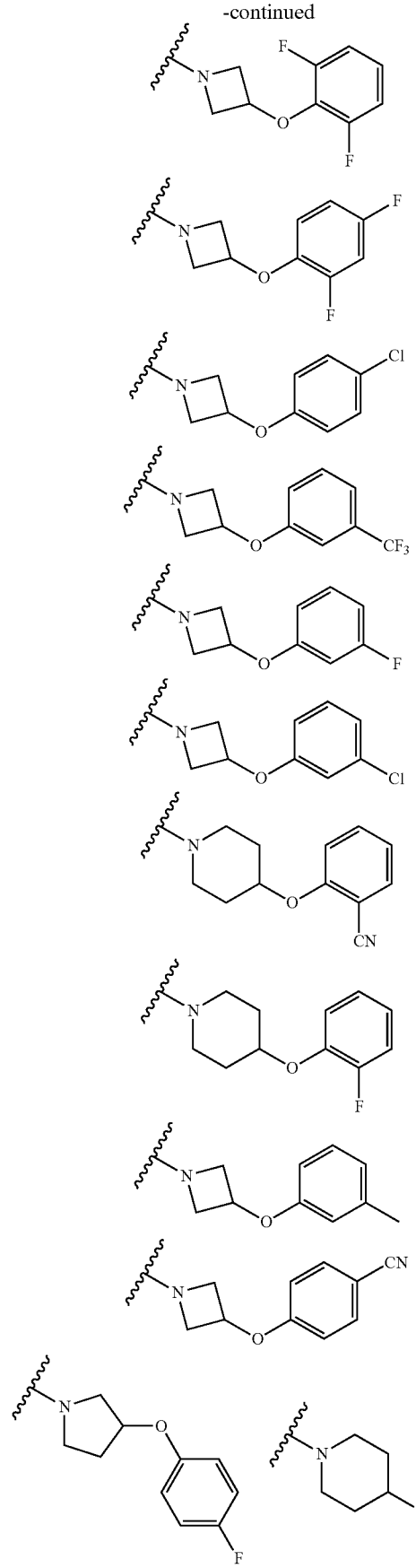

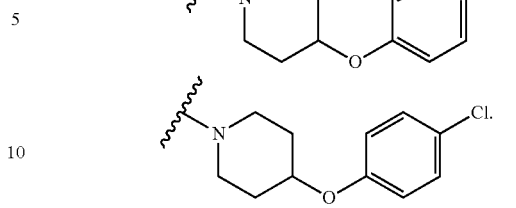

In one embodiment, Ring D is a saturated 4-7 membered heterocyclic ring having one ring heteroatom which is nitrogen; each $R^a$ is independently C1-C6 alkyl (optionally substituted with 1-3 fluoros), hydroxyC1-C6 alkyl or (C1-C6 alkoxy)C1-C6 alkyl-; $R^b$ is (a) hydroxy, (b) cyclopropyl, (c) hetCyc$^b$CH$_2$—, (d) R$^i$R$^j$NC(=O)CH$_2$OCH$_2$— where R$^i$ and R$^j$ are independently H or C1-C6 alkyl, (e) R$^c$R$^d$N—, (f) R$^c$R$^d$NCH$_2$—, (g) C1-C6 alkoxy-, (h) (C1-C4 alkyl)-C(=O)NH— wherein said alkyl portion is optionally substituted with hetCyc$^b$, hetAr$^a$, C1-C6 alkoxy- or R'R"N—, or said alkyl portion is optionally substituted with two substituents independently selected from R'R"N— and OH, where each R' and R" is independently hydrogen or C1-C6 alkyl, (i) (R'R"N)C1-C6 alkoxy(CH$_2$)$_n$— where n is 0 or 1 and R' and R" are independently hydrogen or C1-C6 alkyl, or (j) hetCyc$^b$(C1-C3 alkyl)OCH$_2$—; hetCyc$^b$ is as defined for Formula I; R$^c$ is hydrogen or C1-C6 alkyl; R$^d$ is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C(=O)—, (C1-C6 alkyl)C(=O)—, (R$^k$R$^l$N)C1-C6 alkyl- where R$^k$ and R$^l$ are independently H or C1-C6 alkyl, R$^m$R"NC(=O)C1-C6 alkyl- where R$^m$ and R" are independently H or C1-C6 alkyl, PhCH$_2$—, (C1-C6 alkoxy)C1-C6 alkyl-, or hetCyc$^e$ where hetCyc$^e$ is a 4-6 membered heterocyclic ring having a ring heteroatom selected from N and O and optionally substituted with C1-C6 alkyl; n is 0, 1, 2, 3, 4, 5 or 6; m is 0 or 1; and E is hetAr$^2$O—, where hetAr$^2$ is as defined for Formula I. In one embodiment, hetAr$^2$ is a 5-6-membered heteroaryl ring having 1-2 ring heteroatoms independently selected from N and O and is optionally substituted with one or more substituents independently selected from the group consisting of halogen, C1-C6 alkoxy (optionally substituted with 1-3 fluoros), C1-C6 alkyl (optionally substituted with 1-3 fluoros) and hydroxyC1-C6 alkoxy. In one embodiment, Ring D is a saturated 4-6 membered heterocyclic ring having one ring heteroatom which is nitrogen. In one embodiment, Ring D is a saturated 5-6 membered heterocyclic ring having one ring heteroatom which is nitrogen. In one embodiment, n is 0 or 1 and m is 0 or 1. In one embodiment, n is 0 and m is 0. In one embodiment, n is 0 and m is 1. In one embodiment, $R^a$ is C1-C6 alkyl. In one embodiment, $R^b$ is R$^c$R$^d$N—. Non-limiting examples include the structures:

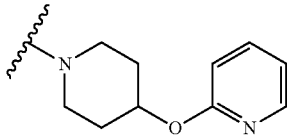

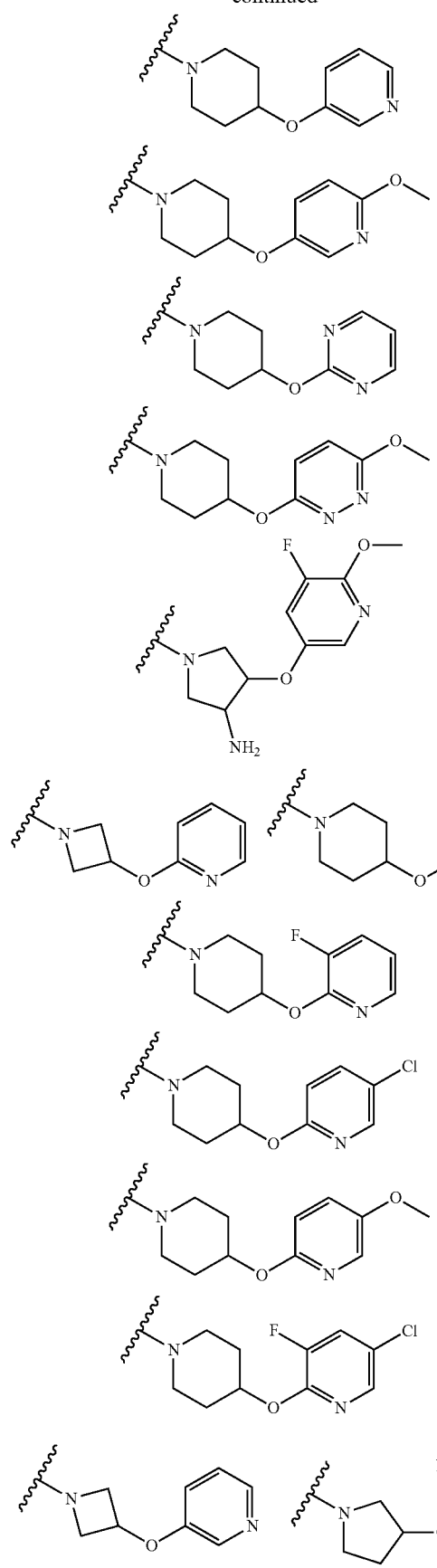
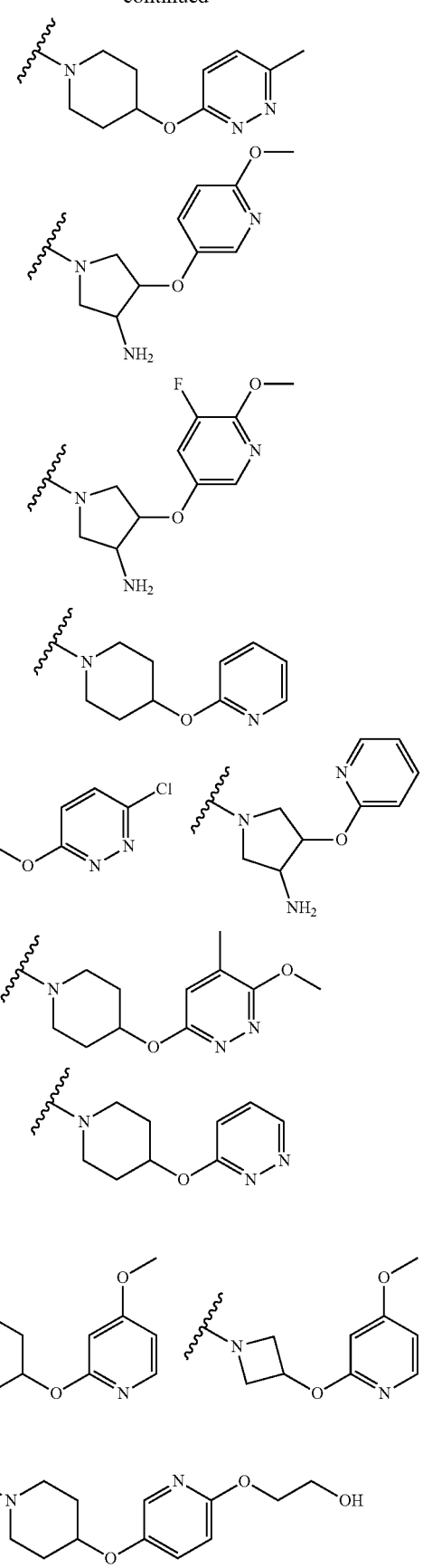

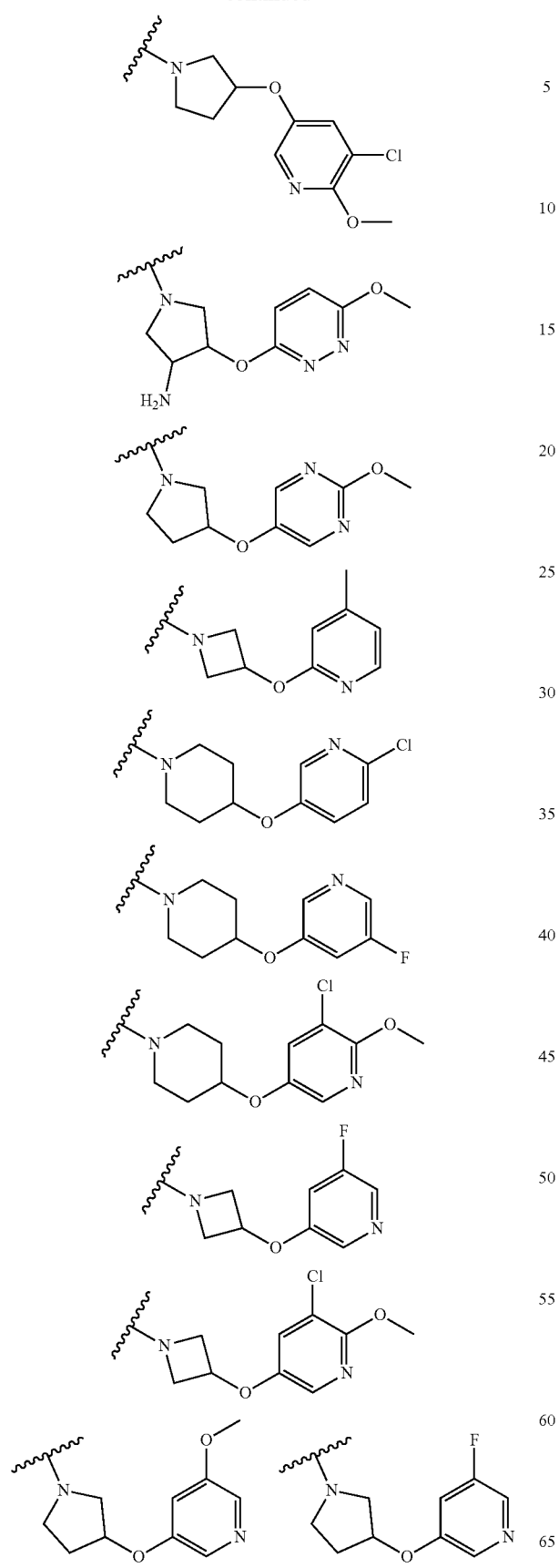
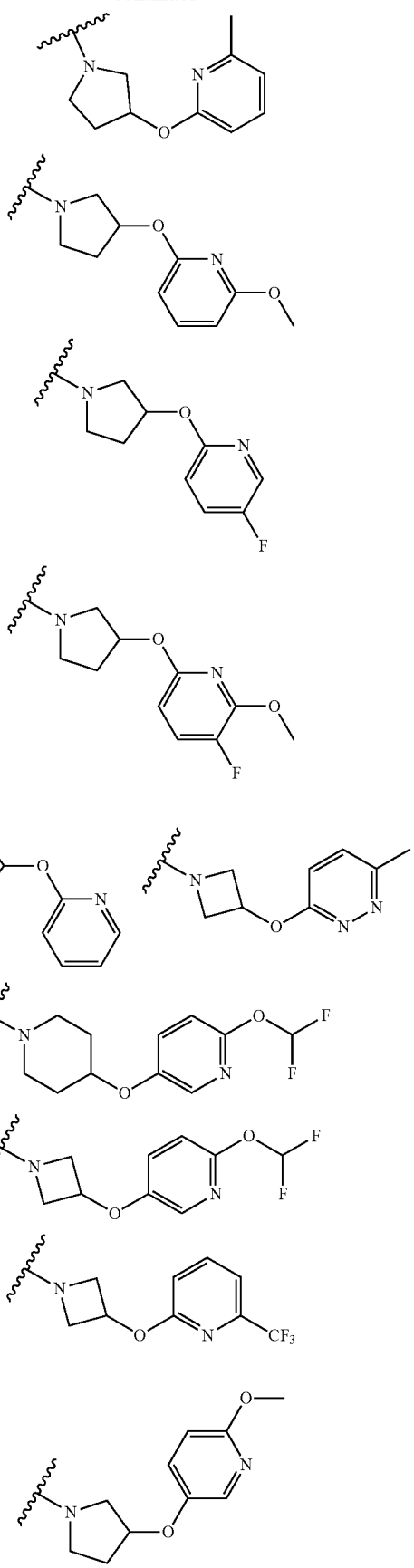

-continued
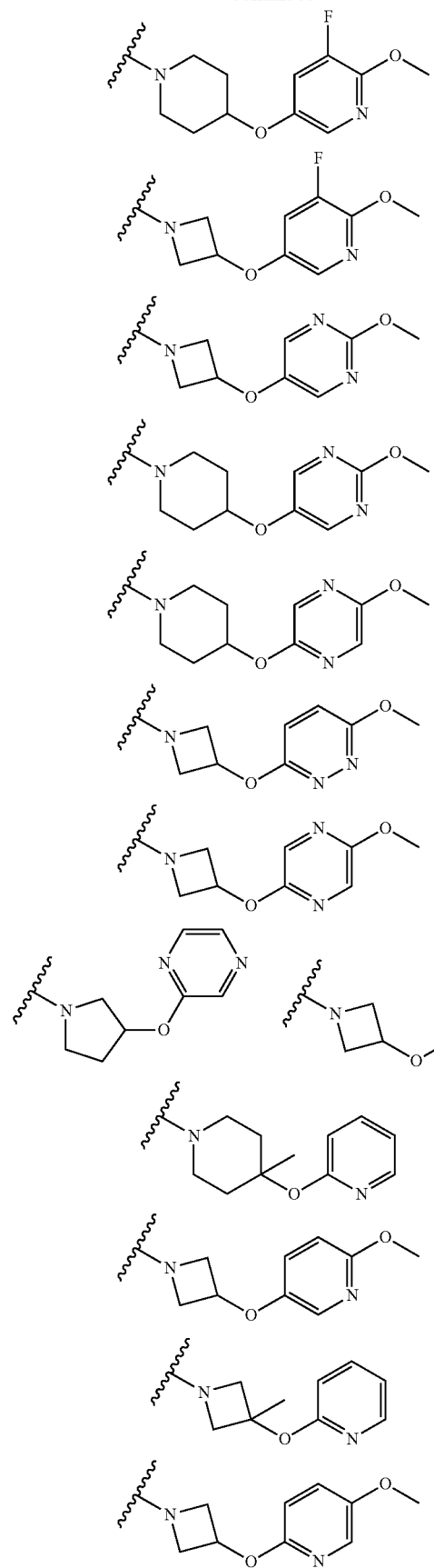
-continued
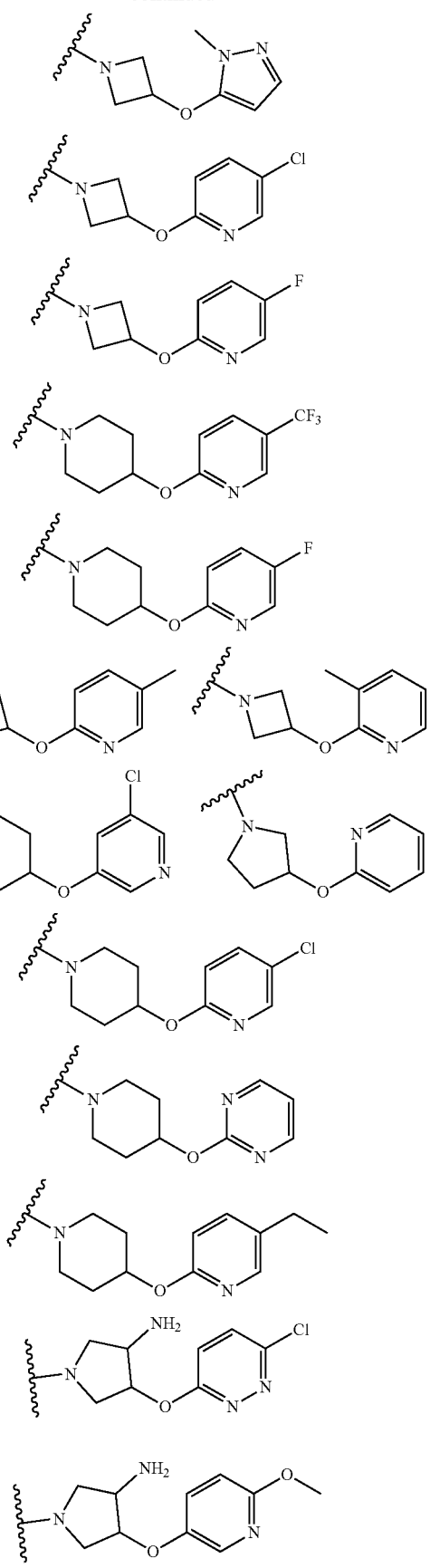

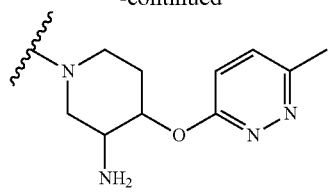

In one embodiment, Ring D is a saturated 4-7 membered heterocyclic ring having one ring heteroatom which is nitrogen; each $R^a$ is independently C1-C6 alkyl (optionally substituted with 1-3 fluoros), hydroxyC1-C6 alkyl or (C1-C6 alkoxy)C1-C6 alkyl-; $R^b$ is (a) hydroxy, (b) cyclopropyl, (c) hetCyc$^b$CH$_2$—, (d) R$^i$R$^j$NC(=O)CH$_2$OCH$_2$— where R$^i$ and R$^j$ are independently H or C1-C6 alkyl, (e) R$^c$R$^d$N—, (f) R$^c$R$^d$NCH$_2$—, (g) C1-C6 alkoxy-, (h) (C1-C4 alkyl)-C(=O)NH— wherein said alkyl portion is optionally substituted with hetCyc$^b$, hetAr$^a$, C1-C6 alkoxy- or R'R"N—, or said alkyl portion is optionally substituted with two substituents independently selected from R'R"N— and OH, where each R' and R" is independently hydrogen or C1-C6 alkyl, (i) (R'R"N)C1-C6 alkoxy(CH$_2$)$_n$— where n is 0 or 1 and R' and R" are independently hydrogen or C1-C6 alkyl, or (j) hetCyc$^b$(C1-C3 alkyl)OCH$_2$—; hetCyc$^b$ is as defined for Formula I; $R^c$ is hydrogen or C1-C6 alkyl; $R^d$ is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C(=O)—, (C1-C6 alkyl)C(=O)—, (R$^k$R$^l$N)C1-C6 alkyl- where R$^k$ and R$^l$ are independently H or C1-C6 alkyl, R$^m$R$^n$NC(=O)C1-C6 alkyl- where R$^m$ and R$^n$ are independently H or C1-C6 alkyl, PhCH$_2$—, (C1-C6 alkoxy)C1-C6 alkyl-, or hetCyc$^c$ where hetCyc$^c$ is a 4-6 membered heterocyclic ring having a ring heteroatom selected from N and O and optionally substituted with C1-C6 alkyl; n is 0, 1, 2, 3, 4, 5 or 6; m is 0 or 1; and E is Ar$^1$NR$^g$—, where Ar$^1$ is as defined for Formula I and R$^g$ is H or C1-C6 alkyl. In one embodiment, Ar$^1$ is optionally substituted with one or more halogens. In one embodiment, Ring D is a saturated 6 membered heterocyclic ring having one ring heteroatom which is nitrogen. In one embodiment, n is 0, 1 or 2 and m is 0 or 1. In one embodiment, n is 0 and m is 0. A non-limiting example includes the structure:

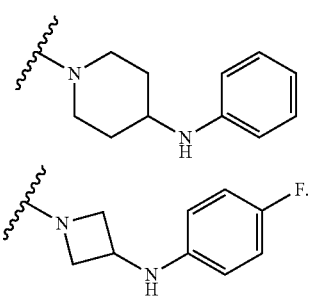

In one embodiment, Ring D is a saturated 4-7 membered heterocyclic ring having one ring heteroatom which is nitrogen; each $R^a$ is independently C1-C6 alkyl (optionally substituted with 1-3 fluoros), hydroxyC1-C6 alkyl or (C1-C6 alkoxy)C1-C6 alkyl-; $R^b$ is (a) hydroxy, (b) cyclopropyl, (c) hetCyc$^b$CH$_2$—, (d) R$^i$R$^j$NC(=O)CH$_2$OCH$_2$— where R$^i$ and R$^j$ are independently H or C1-C6 alkyl, (e) R$^c$R$^d$N—, (f) R$^c$R$^d$NCH$_2$—, (g) C1-C6 alkoxy-, (h) (C1-C4 alkyl)-C(=O)NH— wherein said alkyl portion is optionally substituted with hetCyc$^b$, hetAr$^a$, C1-C6 alkoxy- or R'R"N—, or said alkyl portion is optionally substituted with two substituents independently selected from R'R"N— and OH, where each R' and R" is independently hydrogen or C1-C6 alkyl, (i) (R'R"N)C1-C6 alkoxy(CH$_2$)$_n$— where n is 0 or 1 and R' and R" are independently hydrogen or C1-C6 alkyl, or (j) hetCyc$^b$(C1-C3 alkyl)OCH$_2$—; hetCyc$^b$ is as defined for Formula I; $R^c$ is hydrogen or C1-C6 alkyl; $R^d$ is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C(=O)—, (C1-C6 alkyl)C(=O)—, (R$^k$R$^l$N)C1-C6 alkyl- where R$^k$ and R$^l$ are independently H or C1-C6 alkyl, R$^m$R$^n$NC(=O)C1-C6 alkyl- where R$^m$ and R$^n$ are independently H or C1-C6 alkyl, PhCH$_2$—, (C1-C6 alkoxy)C1-C6 alkyl-, or hetCyc$^c$ where hetCyc$^c$ is a 4-6 membered heterocyclic ring having a ring heteroatom selected from N and O and optionally substituted with C1-C6 alkyl; n is 0, 1, 2, 3, 4, 5 or 6; m is 0 or 1; and E is hetAr$^2$NR$^g$— where hetAr$^2$ is a defined for Formula I and R$^g$ is H or C1-C6 alkyl. In one embodiment, hetAr$^2$ is a pyridyl ring optionally substituted with one or more substituents independently selected from C1-C6 alkyl and halogen. In one embodiment, n is 0, 1 or 2 and m is 0 or 1. In one embodiment, $R^a$ is C1-C6 alkyl. In one embodiment, n is 0 and m is 0. Non-limiting examples include the structures:

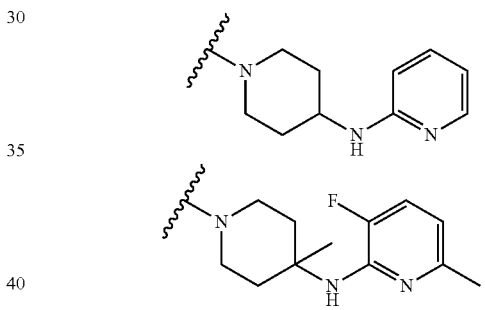

In one embodiment, Ring D is a saturated 4-7 membered heterocyclic ring having one ring heteroatom which is nitrogen; each $R^a$ is independently C1-C6 alkyl (optionally substituted with 1-3 fluoros), hydroxyC1-C6 alkyl or (C1-C6 alkoxy)C1-C6 alkyl-; $R^b$ is (a) hydroxy, (b) cyclopropyl, (c) hetCyc$^b$CH$_2$—, (d) R$^i$R$^j$NC(=O)CH$_2$OCH$_2$— where R$^i$ and R$^j$ are independently H or C1-C6 alkyl, (e) R$^c$R$^d$N—, (f) R$^c$R$^d$NCH$_2$—, (g) C1-C6 alkoxy-, (h) (C1-C4 alkyl)-C(=O)NH— wherein said alkyl portion is optionally substituted with hetCyc$^b$, hetAr$^a$, C1-C6 alkoxy- or R'R"N—, or said alkyl portion is optionally substituted with two substituents independently selected from R'R"N— and OH, where each R' and R" is independently hydrogen or C1-C6 alkyl, (i) (R'R"N)C1-C6 alkoxy(CH$_2$)$_n$— where n is 0 or 1 and R' and R" are independently hydrogen or C1-C6 alkyl, or (j) hetCyc$^b$(C1-C3 alkyl)OCH$_2$—; hetCyc$^b$ is as defined for Formula I; $R^c$ is hydrogen or C1-C6 alkyl; $R^d$ is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C(=O)—, (C1-C6 alkyl)C(=O)—, (R$^k$R$^l$N)C1-C6 alkyl- where R$^k$ and R$^l$ are independently H or C1-C6 alkyl, R$^m$R$^n$NC(=O)C1-C6 alkyl- where R$^m$ and R$^n$ are independently H or C1-C6 alkyl, PhCH$_2$—, (C1-C6 alkoxy)C1-C6 alkyl-, or hetCyc$^c$ where hetCyc$^c$ is a 4-6 membered heterocyclic ring having a ring heteroatom selected from N and O and optionally substituted with C1-C6 alkyl; n is 0, 1, 2, 3, 4, 5 or 6; m is 0 or 1; and E is $R^3C(=O)NR^g$— where $R^3$ and $R^g$ are as defined for Formula I. In one embodiment, $R^g$ is hydrogen. In one embodiment, Ring D is a saturated 6 membered heterocyclic ring having one ring heteroatom which is nitrogen. In one embodiment, n is 0, 1 or 2 and m is 0 or 1. In one embodiment, n is 0 or 1 and m is 0. In one embodiment, m is 1 and n is 0. In one embodiment, $R^a$ is C1-C6 alkyl (optionally substituted with 1-3 fluoros). In one embodiment, $R^b$ is hydroxy, hetCyc$^b$CH$_2$—, R$^c$R$^d$N—, R$^c$R$^d$NCH$_2$—, C1-C6 alkoxy, (R'R"N)C1-C6 alkoxy (CH$_2$)$_n$— where n is 0 or 1 and R' and R" are independently hydrogen or C1-C6 alkyl, or hetCyc$^b$(C1-C3 alkyl)OCH$_2$—, where hetCyc$^b$, R$^c$ and R$^d$ are as defined for Formula I. In one embodiment, $R^b$ is hetCyc$^b$CH$_2$— where hetCyc$^b$ is a 4-6 membered heterocyclic ring having 1-2 ring heteroatoms independently selected from N and O, wherein hetCyc$^b$ is optionally substituted with one or more substituents independently selected from OH, C1-C6 alkyl (optionally substituted with 1-3 fluoros), and R'R"N— where R' and R" are independently hydrogen or C1-C6 alkyl. In one embodiment, $R^b$ is R$^c$R$^d$N— or R$^c$R$^d$NCH$_2$— where R$^c$ is hydrogen or C1-C6 alkyl and R$^d$ is hydrogen or C1-C6 alkyl (optionally substituted with 1-3 fluoros). Non-limiting examples include the structures:

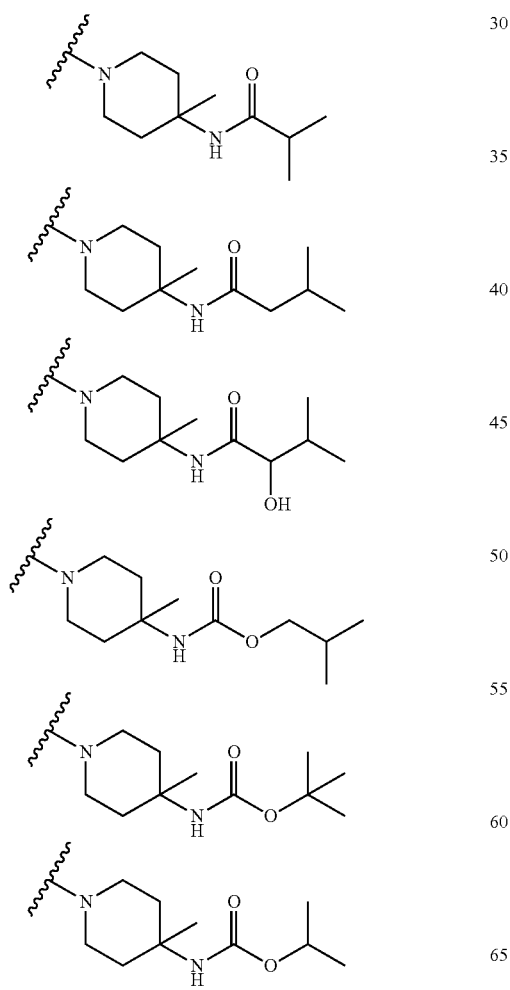

-continued

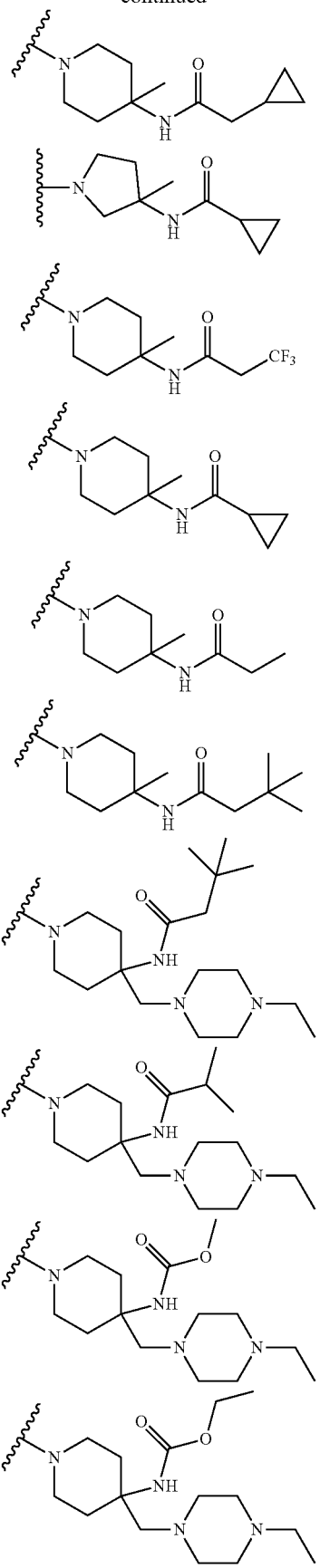

-continued
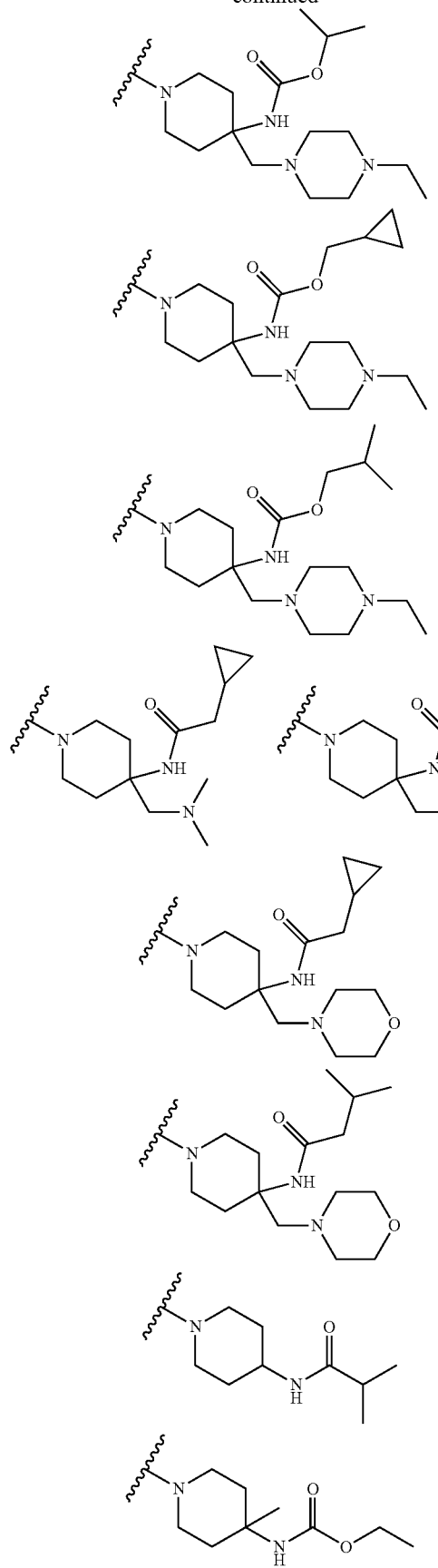
-continued
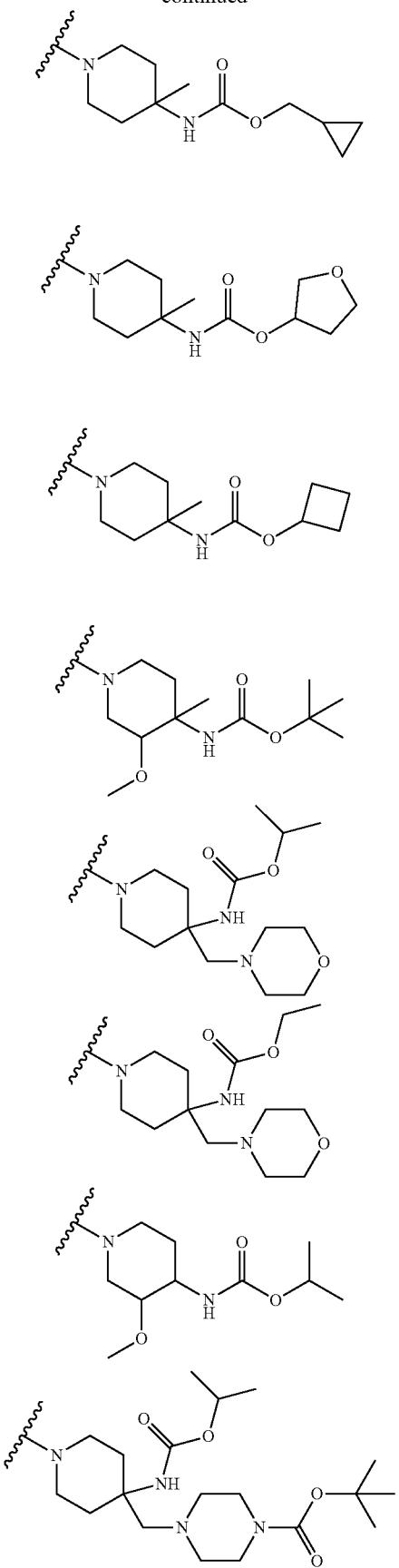

-continued
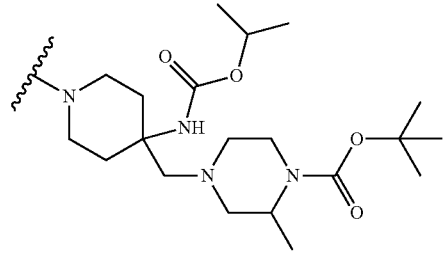
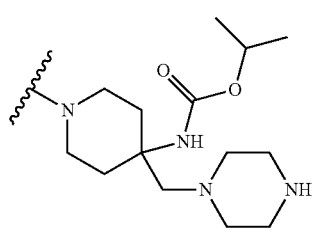
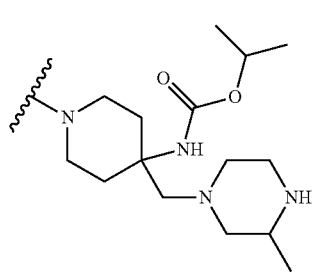
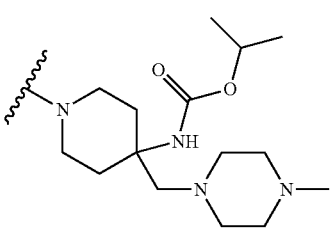
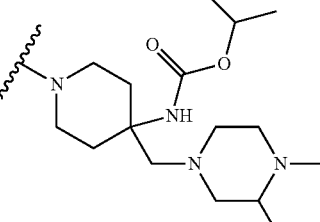
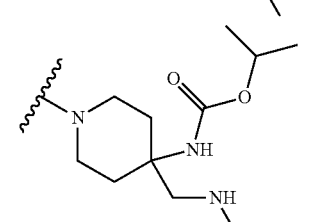
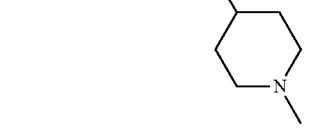
-continued
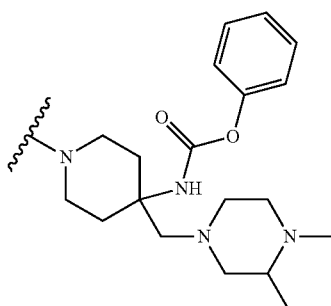
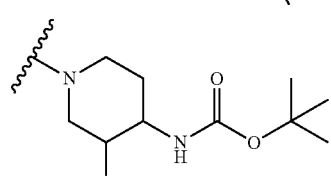
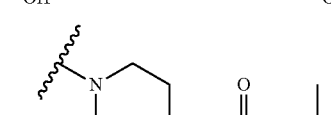
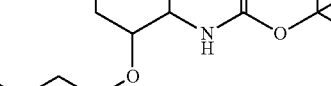
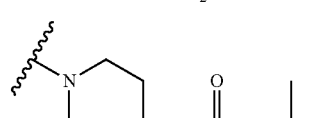
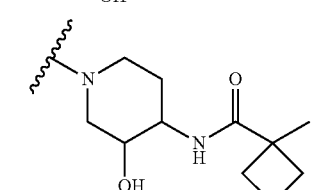
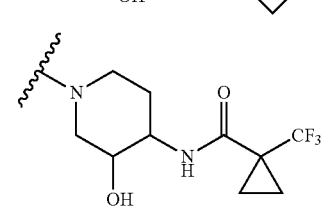

-continued
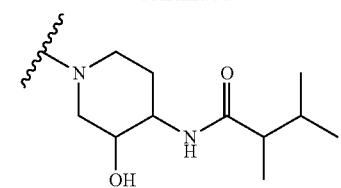
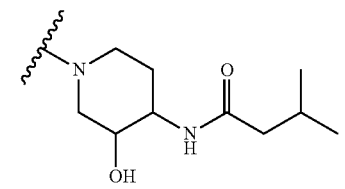
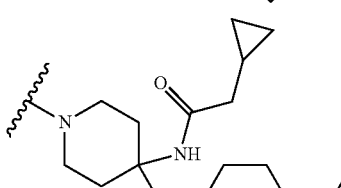
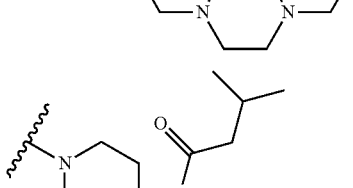
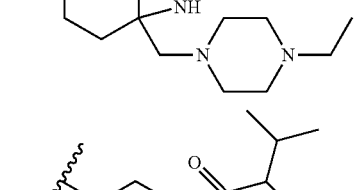
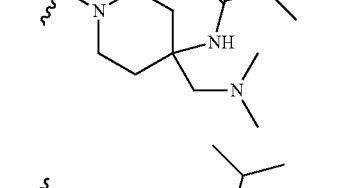
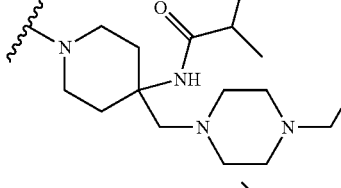
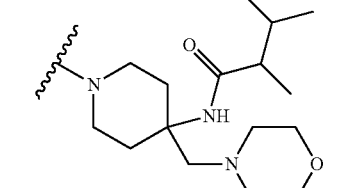
-continued
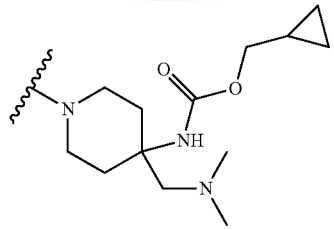
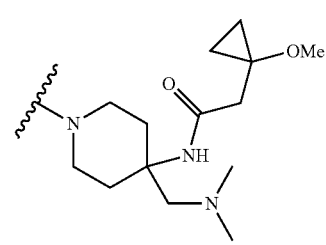
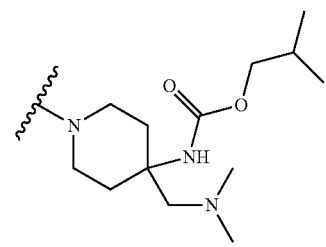
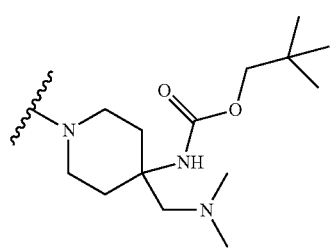
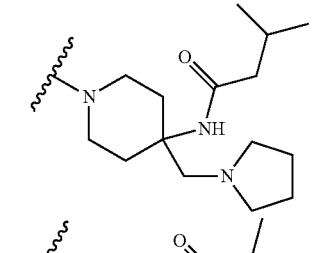
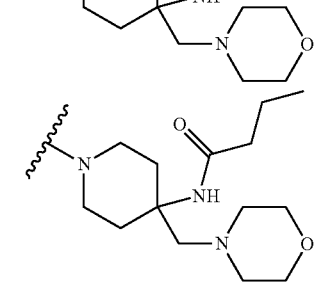

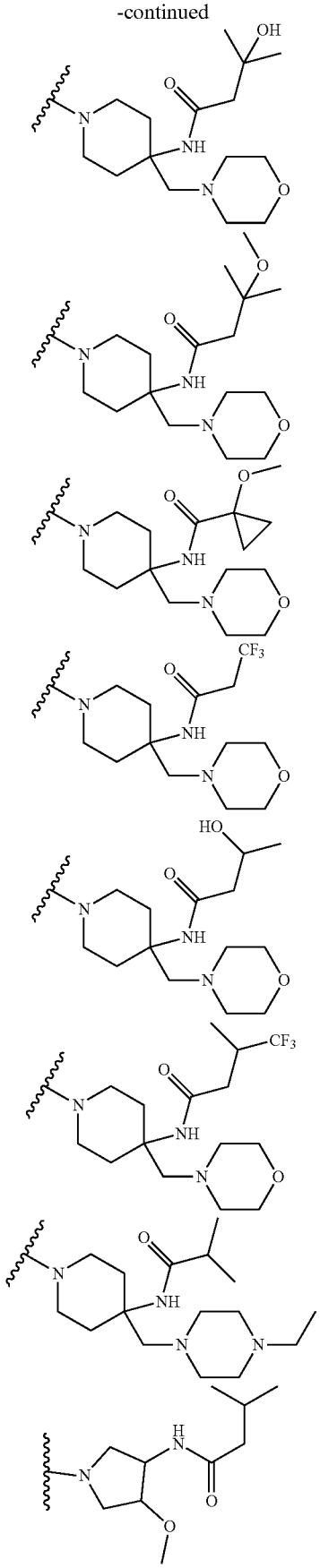
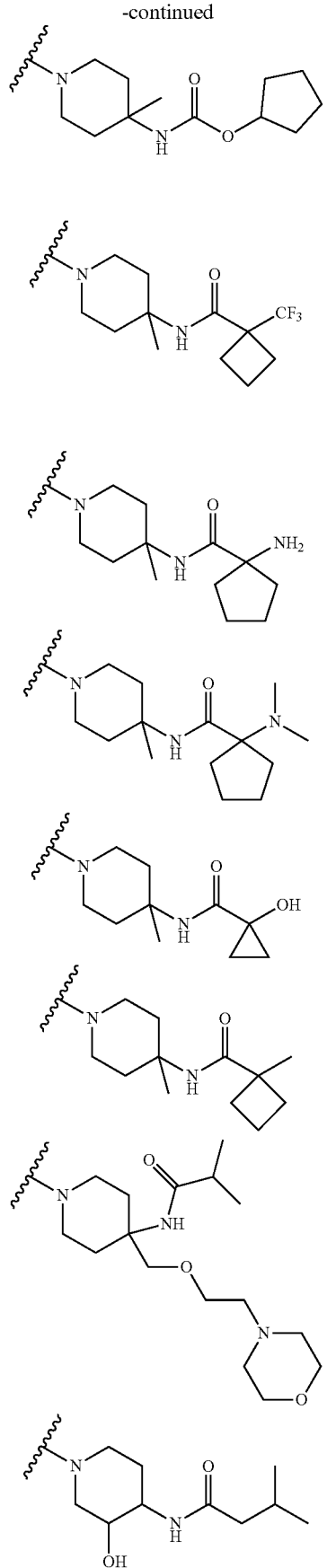

-continued

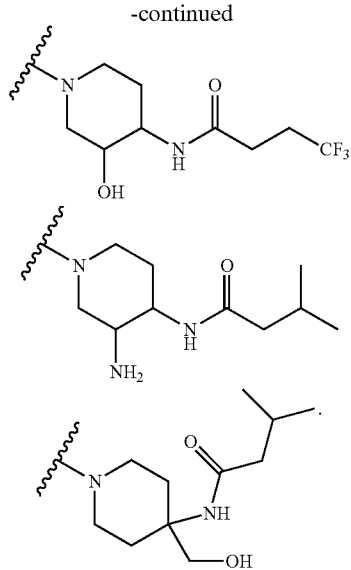

In one embodiment, Ring D is a saturated 4-7 membered heterocyclic ring having one ring heteroatom which is nitrogen; each $R^a$ is independently C1-C6 alkyl (optionally substituted with 1-3 fluoros), hydroxyC1-C6 alkyl or (C1-C6 alkoxy)C1-C6 alkyl-; $R^b$ is (a) hydroxy, (b) cyclopropyl, (c) hetCyc$^b$CH$_2$—, (d) R$^i$R$^j$NC(=O)CH$_2$OCH$_2$— where R$^i$ and R$^j$ are independently H or C1-C6 alkyl, (e) R$^c$R$^d$N—, (f) R$^c$R$^d$NCH$_2$—, (g) C1-C6 alkoxy-, (h) (C1-C4 alkyl)-C(=O)NH— wherein said alkyl portion is optionally substituted with hetCyc$^b$, hetAr$^a$, C1-C6 alkoxy- or R'R"N—, or said alkyl portion is optionally substituted with two substituents independently selected from R'R"N— and OH, where each R' and R" is independently hydrogen or C1-C6 alkyl, (i) (R'R"N)C1-C6 alkoxy(CH$_2$)$_n$— where n is 0 or 1 and R' and R" are independently hydrogen or C1-C6 alkyl, or (j) hetCyc$^b$(C1-C3 alkyl)OCH$_2$—; hetCyc$^b$ is as defined for Formula I; $R^c$ is hydrogen or C1-C6 alkyl; $R^d$ is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C(=O)—, (C1-C6 alkyl)C(=O)—, (R$^k$R$^l$N)C1-C6 alkyl- where R$^k$ and R$^l$ are independently H or C1-C6 alkyl, R$^m$R$^n$NC(=O)C1-C6 alkyl- where R$^m$ and R$^n$ are independently H or C1-C6 alkyl, PhCH$_2$—, (C1-C6 alkoxy)C1-C6 alkyl-, or hetCyc$^c$ where hetCyc$^c$ is a 4-6 membered heterocyclic ring having a ring heteroatom selected from N and O and optionally substituted with C1-C6 alkyl; n is 0, 1, 2, 3, 4, 5 or 6; m is 0 or 1; and E is Ar$^1$C(=O)NR$^g$— where Ar$^1$ is as defined for Formula I. In one embodiment, Ar$^1$ is unsubstituted or substituted with one or more substituents independently selected from halogen, CN, C1-C6 alkyl (optionally substituted with 1-3 fluoros), C1-C6 alkoxy (optionally substituted with 1-3 fluoros), C3-C6 cycloalkyl, hydroxyC1-C6 alkyl, (C1-C6 alkyl)SO$_2$—, and (R$^e$R$^f$N)C1-C6 alkyl- where each R$^e$ and R$^f$ is independently H or C1-C6 alkyl. In one embodiment, Ring D is a saturated 5-6 membered heterocyclic ring having one ring heteroatom which is nitrogen. In one embodiment, n is 0, 1 or 2 and m is 0 or 1. In one embodiment, n is 0 or 1 and m is 0. In one embodiment, n is 1 and m is 0. In one embodiment, n is 0 and m is 1. In one embodiment, $R^a$ is C1-C6 alkyl (optionally substituted with 1-3 fluoros) or hydroxyC1-C6 alkyl. In one embodiment, $R^b$ is C1-C6 alkoxy, hetCyc$^b$CH$_2$— or R$^c$R$^d$NCH$_2$—, where hetCyc$^b$, R$^c$ and R$^d$ are as defined for Formula I. In one embodiment, $R^b$ is hetCyc$^b$CH$_2$— where hetCyc$^b$ is a 4-6 membered heterocyclic ring having 1-2 ring heteroatoms independently selected from N and O, wherein hetCyc$^b$ is optionally substituted with one or more substituents independently selected from OH, fluoro, C1-C6 alkyl (optionally substituted with 1-3 fluoros) and (C1-C6 alkoxy) C1-C6 alkyl-. In one embodiment, $R^b$ is R$^c$R$^d$NCH$_2$— where R$^c$ is H or C1-C6 alkyl and R$^d$ is C1-C6 alkyl (optionally substituted with 1-3 fluoros), hydroxyC1-C6 alkyl (optionally substituted with 1-3 fluoros). In one embodiment, $R^b$ is hydroxyl. Non-limiting examples include the structures:

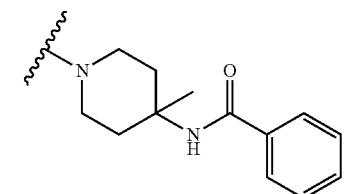
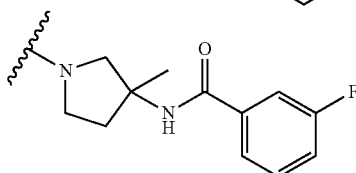
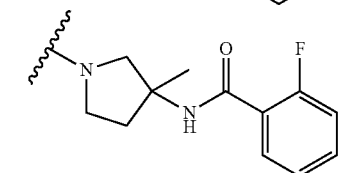
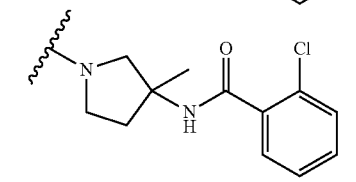
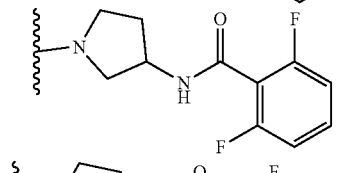
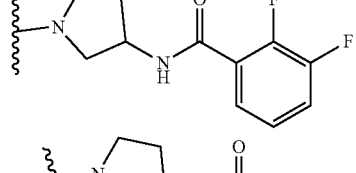
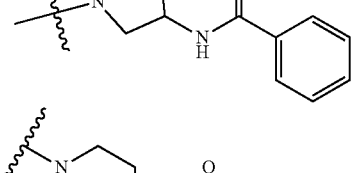
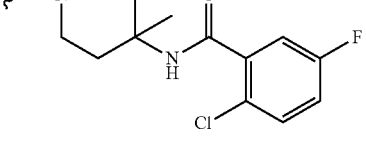

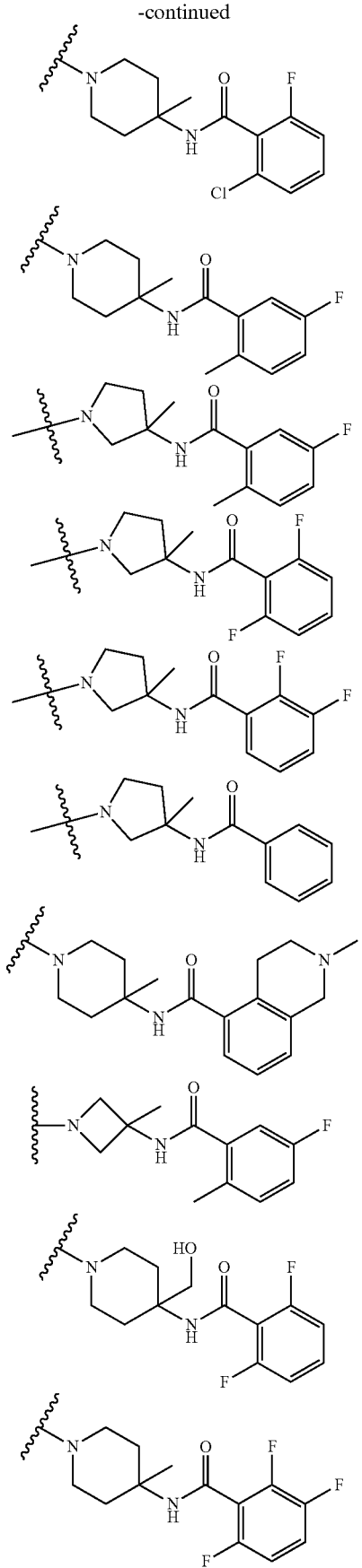
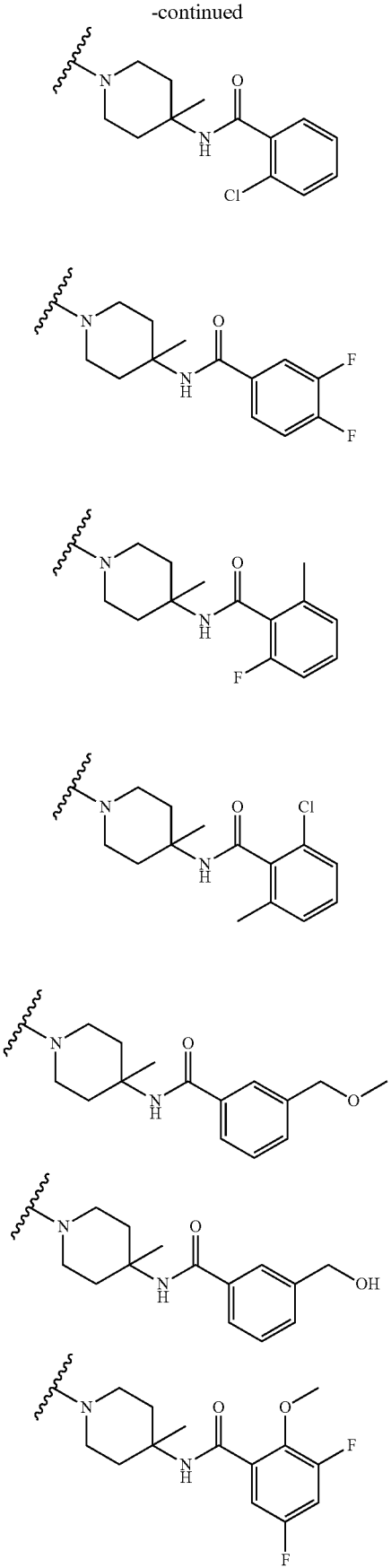

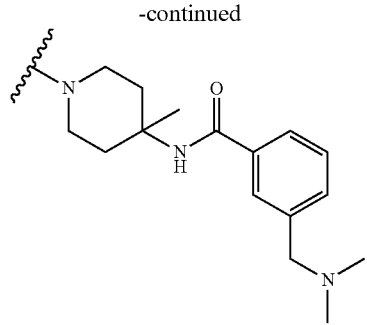
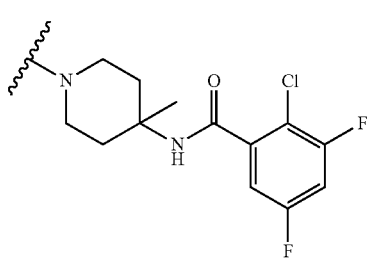
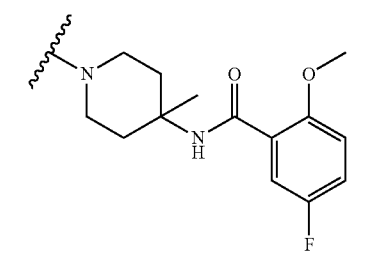
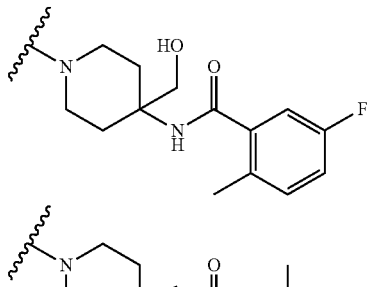
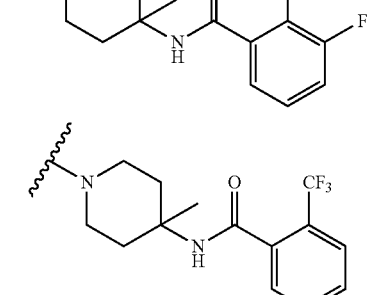
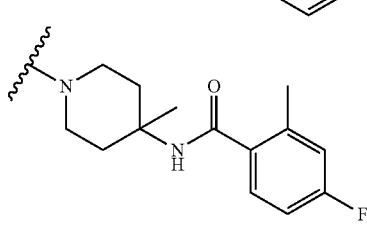
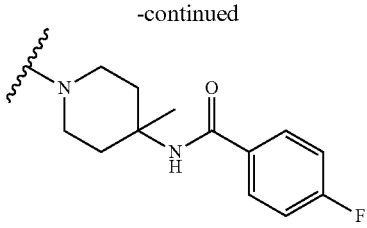
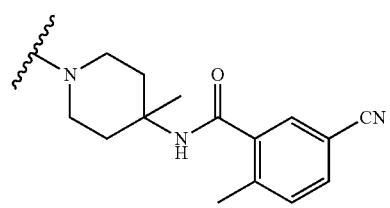
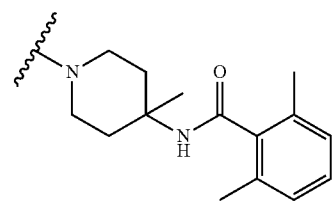
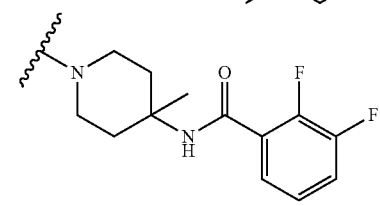
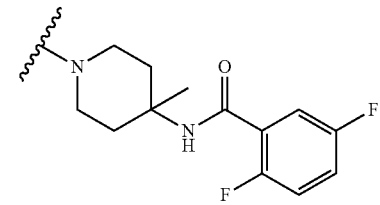
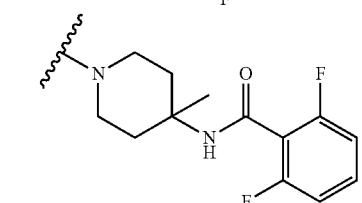
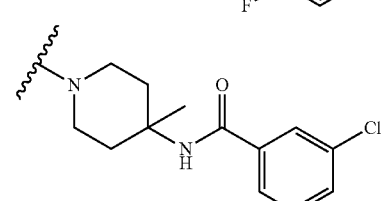
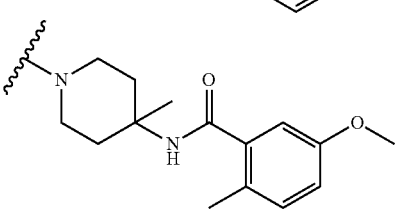

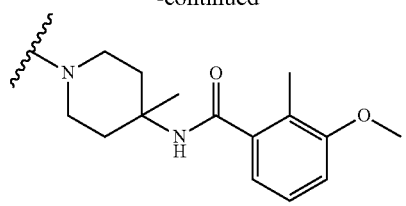
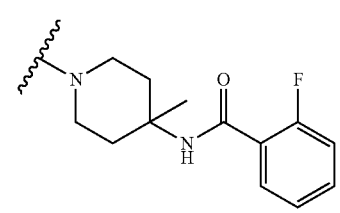
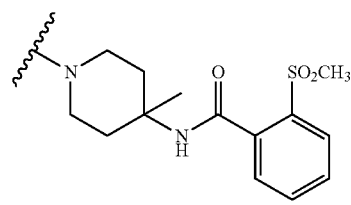
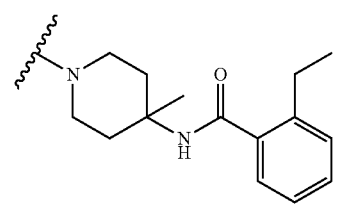
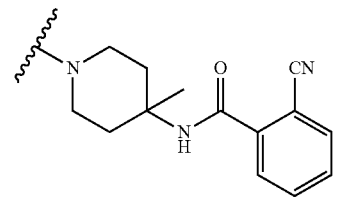
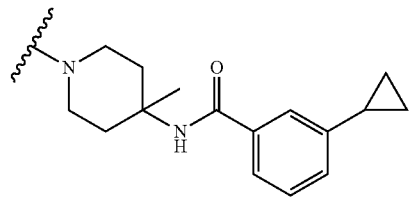
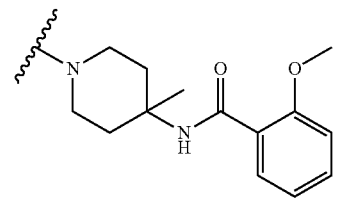
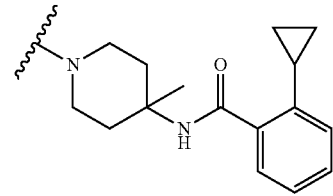
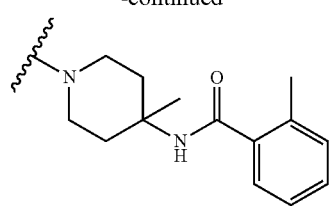
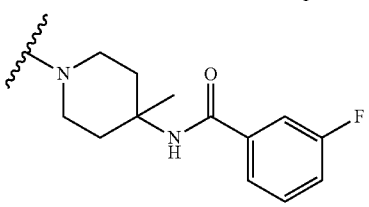
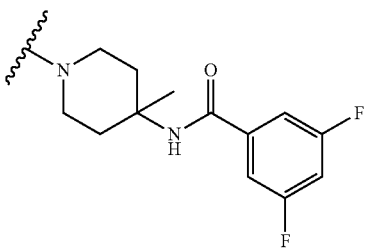
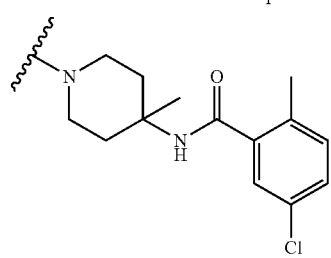
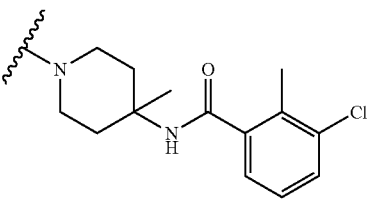
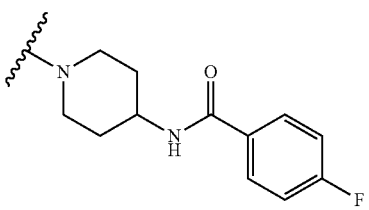
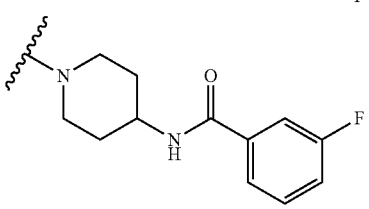
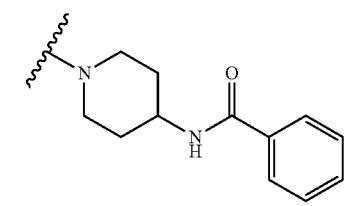

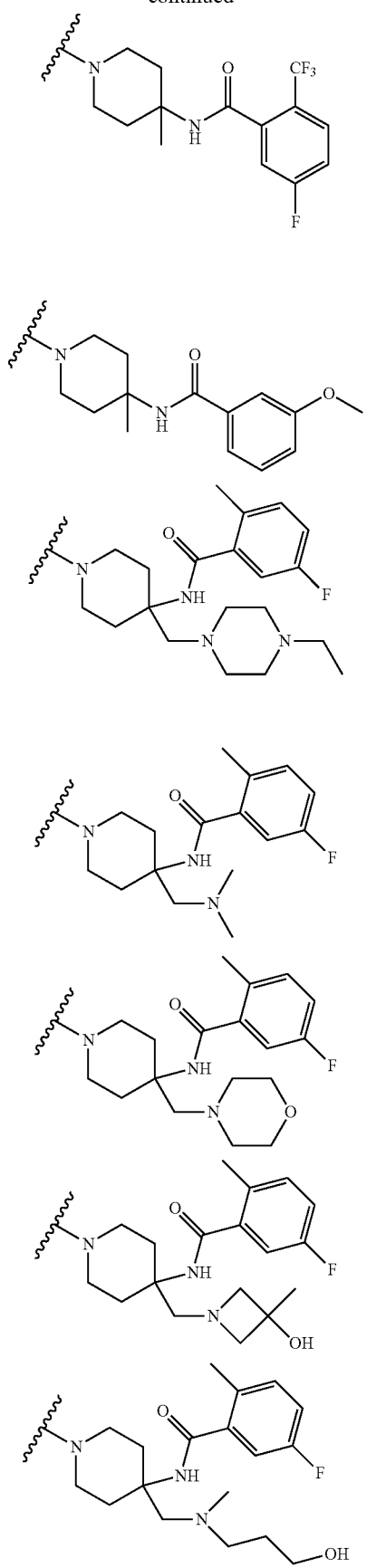
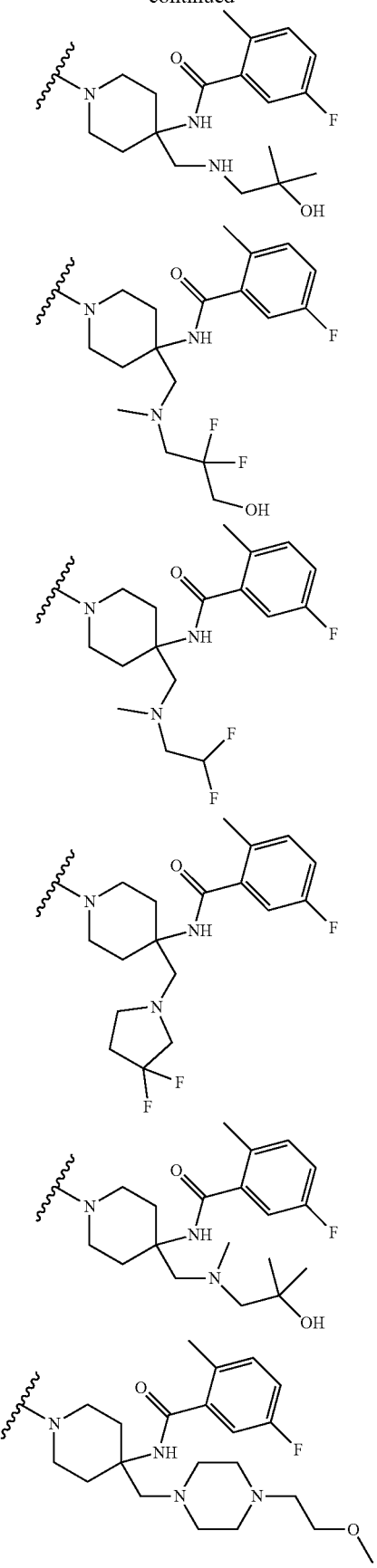

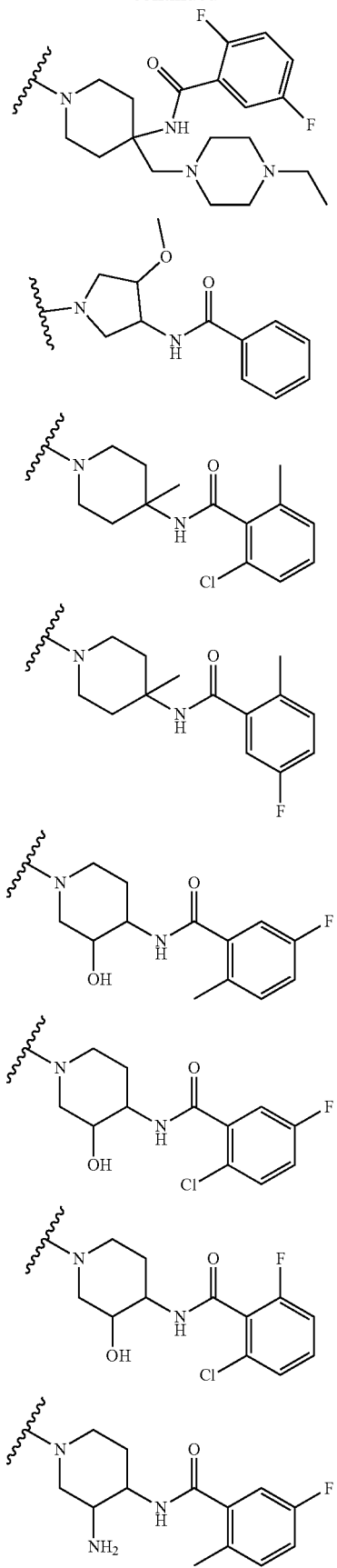

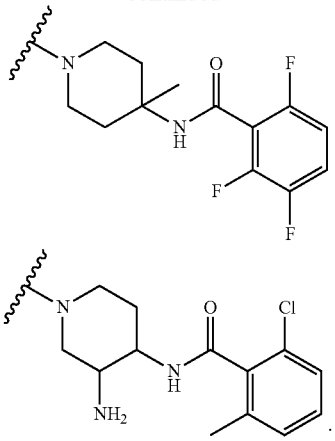

In one embodiment, Ring D is a saturated 4-7 membered heterocyclic ring having one ring heteroatom which is nitrogen; each $R^a$ is independently C1-C6 alkyl (optionally substituted with 1-3 fluoros), hydroxyC1-C6 alkyl or (C1-C6 alkoxy)C1-C6 alkyl-; $R^b$ is (a) hydroxy, (b) cyclopropyl, (c) hetCyc$^b$CH$_2$—, (d) R$^i$R$^j$NC(=O)CH$_2$OCH$_2$— where R$^i$ and R$^j$ are independently H or C1-C6 alkyl, (e) R$^c$R$^d$N—, (f) R$^c$R$^d$NCH$_2$—, (g) C1-C6 alkoxy-, (h) (C1-C4 alkyl)-C(=O)NH— wherein said alkyl portion is optionally substituted with hetCyc$^b$, hetAr$^a$, C1-C6 alkoxy- or R'R"N—, or said alkyl portion is optionally substituted with two substituents independently selected from R'R"N— and OH, where each R' and R" is independently hydrogen or C1-C6 alkyl, (i) (R'R"N)C1-C6 alkoxy(CH$_2$)$_n$— where n is 0 or 1 and R' and R" are independently hydrogen or C1-C6 alkyl, or (j) hetCyc$^b$(C1-C3 alkyl)OCH$_2$—; hetCyc$^b$ is as defined for Formula I; R$^c$ is hydrogen or C1-C6 alkyl; R$^d$ is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C(=O)—, (C1-C6 alkyl)C(=O)—, (R$^k$R$^l$N)C1-C6 alkyl- where R$^k$ and R$^l$ are independently H or C1-C6 alkyl, R$^m$R$^n$NC(=O)C1-C6 alkyl- where R$^m$ and R$^n$ are independently H or C1-C6 alkyl, PhCH$_2$—, (C1-C6 alkoxy)C1-C6 alkyl-, or hetCyc$^e$ where hetCyc$^e$ is a 4-6 membered heterocyclic ring having a ring heteroatom selected from N and O and optionally substituted with C1-C6 alkyl; n is 0, 1, 2, 3, 4, 5 or 6; m is 0 or 1; and E is hetAr$^2$C(=O)NR$^g$(CH$_2$)$_p$— where p is 0 or 1, and hetAr$^2$ and R$^g$ are as defined for Formula I. In one embodiment, hetAr$^2$ is a 5-6-membered heteroaryl ring having 1-2 ring heteroatoms independently selected from N and O and is optionally substituted with one or more substituents independently selected from the group consisting of halogen, C1-C6 alkyl (optionally substituted with 1-3 fluoros) and C1-C6 alkoxy (optionally substituted with 1-3 fluoros). In one embodiment, Ring D is a saturated 6 membered heterocyclic ring having one ring heteroatom which is nitrogen. In one embodiment, n is 0, 1 or 2 and m is 0 or 1. In one embodiment, n is 0 or 1 and m is 0. In one embodiment, $R^a$ is C1-C6 alkyl (optionally substituted with 1-3 fluoros) or hydroxyC1-C6 alkyl. In one embodiment, $R^b$ is hydroxy, hetCyc$^b$CH$_2$—, R$^c$R$^d$NCH$_2$—, C1-C6 alkoxy, or hetCyc$^b$(C1-C3 alkyl)OCH$_2$—, where hetCyc$^b$, R$^c$ and R$^d$ are as defined for Formula I. In one embodiment, R$^b$ is hetCyc$^b$CH$_2$— where hetCyc$^b$ is a 4-6 membered heterocyclic ring having 1-2 ring heteroatoms independently selected from N and O, wherein hetCyc$^b$ is optionally substituted with one or more substituents independently selected from C1-C6 alkyl (optionally substituted with 1-3 fluoros). In one embodiment, $R^b$ is $R^cR^dNCH_2-$ where $R^c$ is H or C1-C6 alkyl and $R^d$ is C1-C6 alkyl (optionally substituted with 1-3 fluoros). Non-limiting examples include the structures:
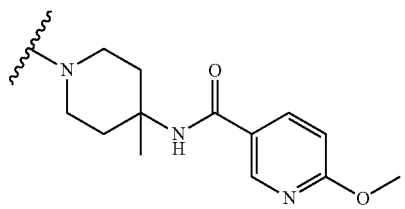
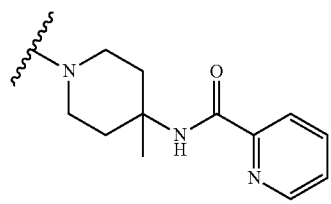
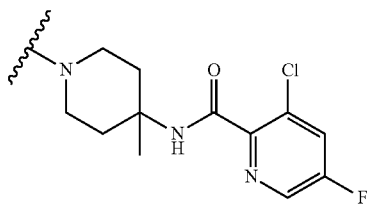
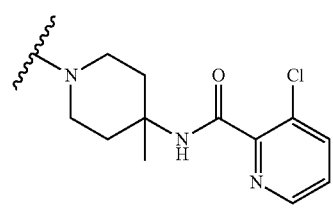
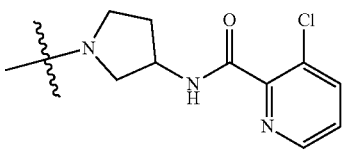
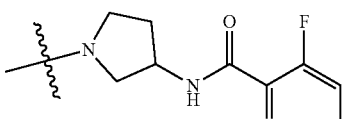
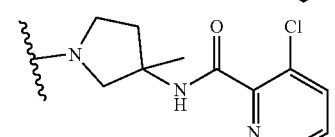
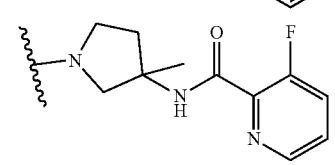
-continued
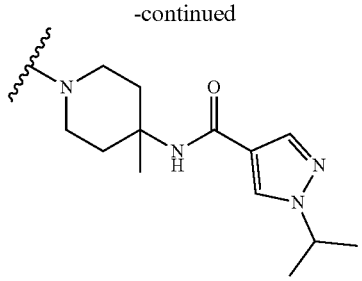
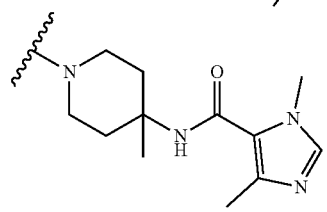
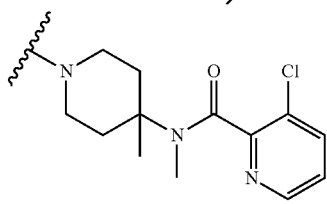
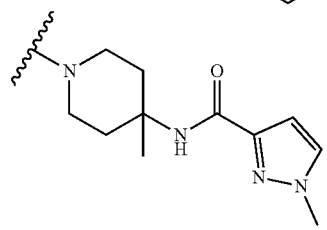
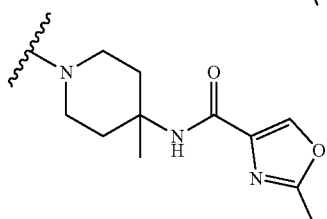
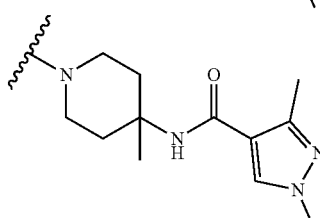
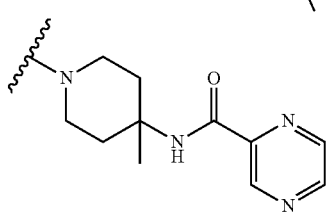
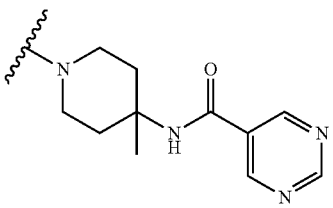

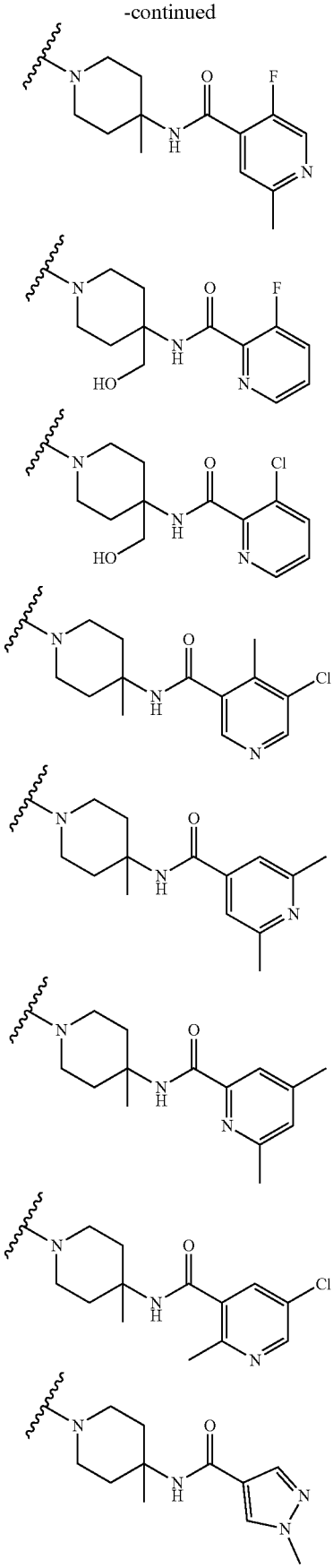
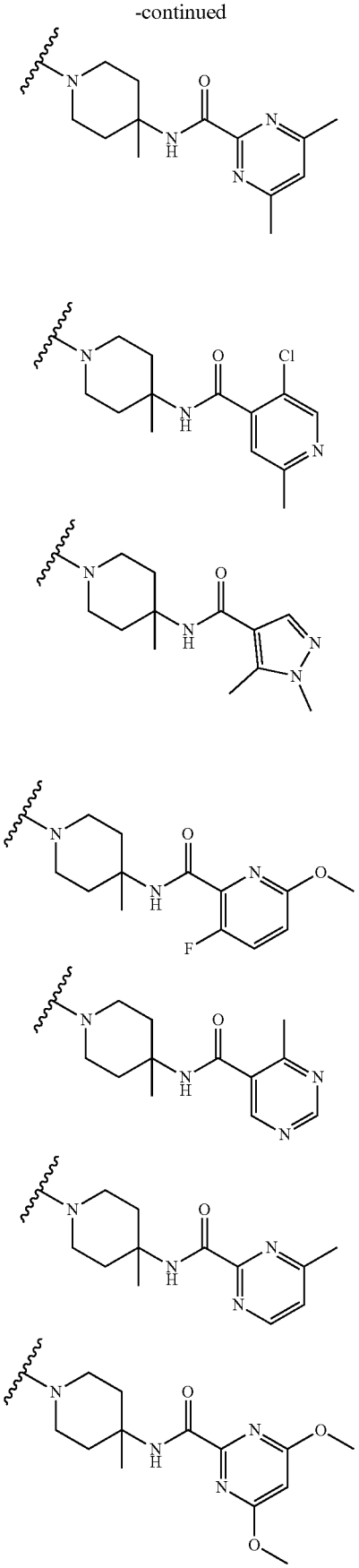

-continued
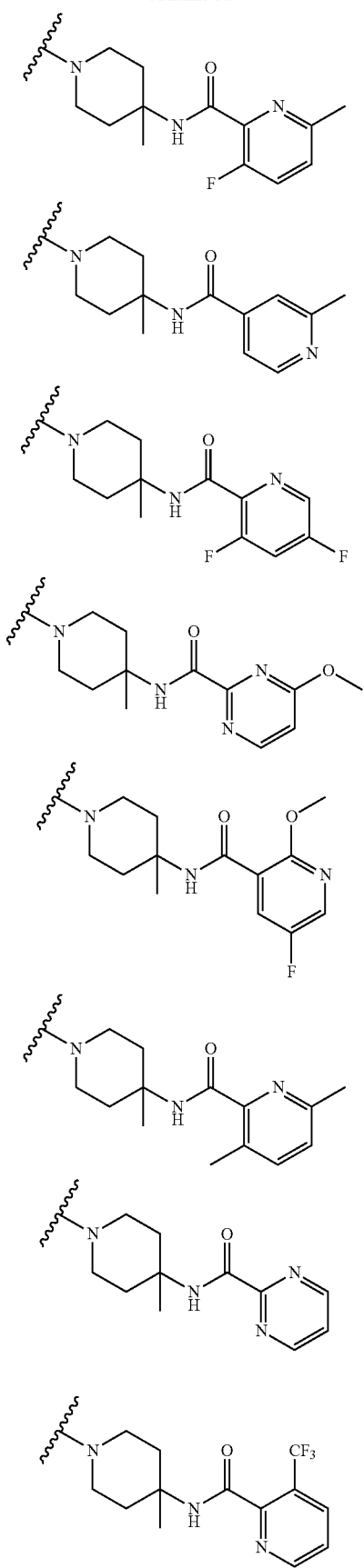
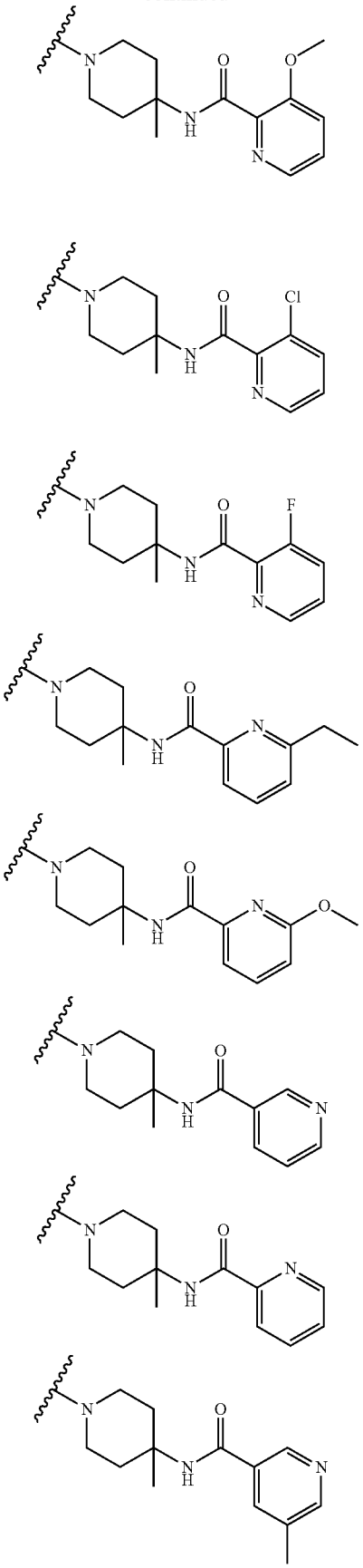

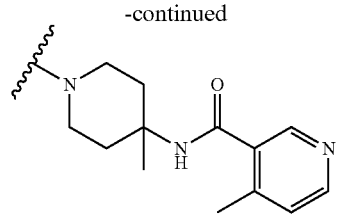
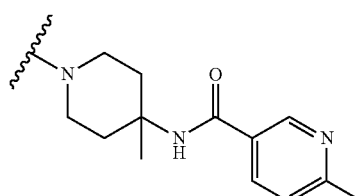
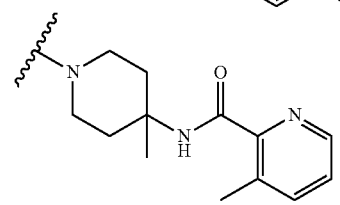
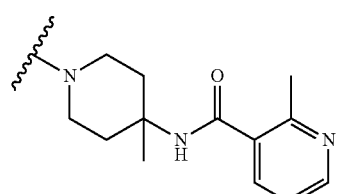
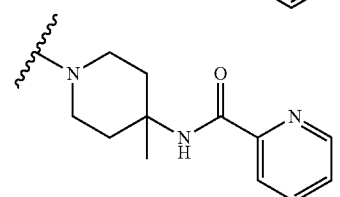
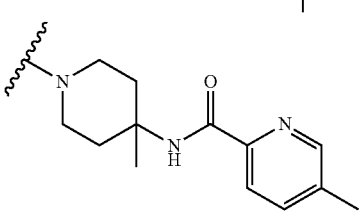
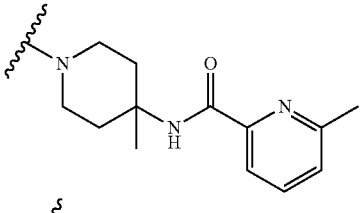
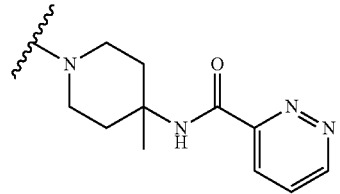
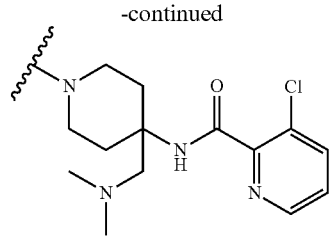
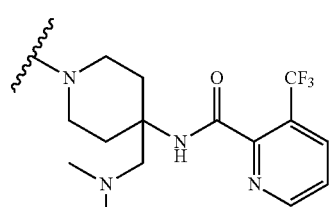
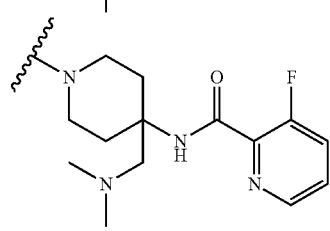
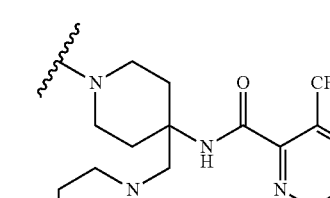
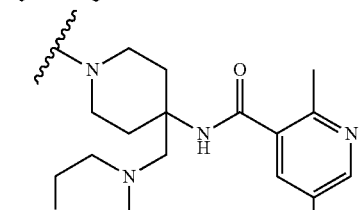
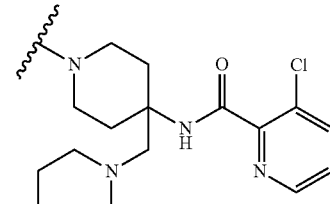
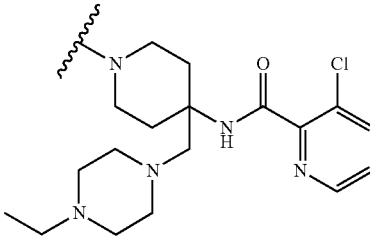

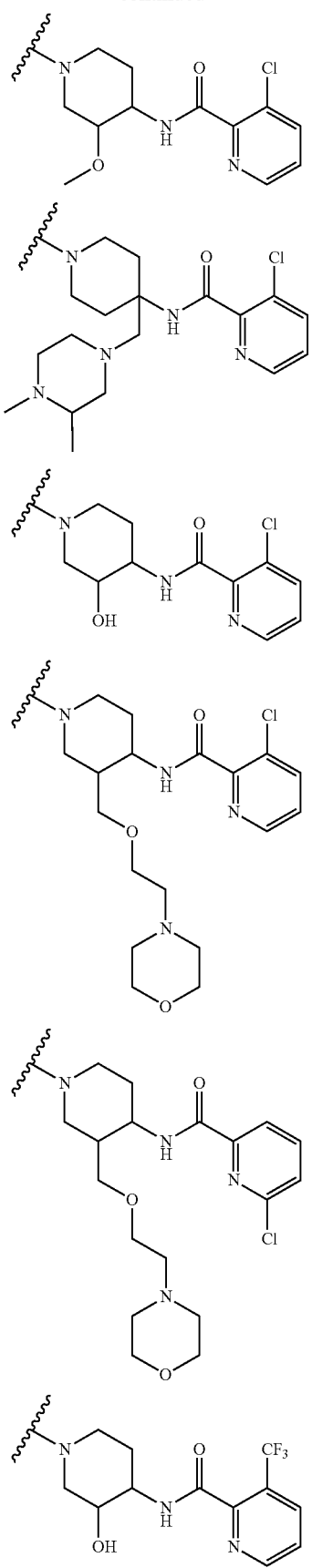
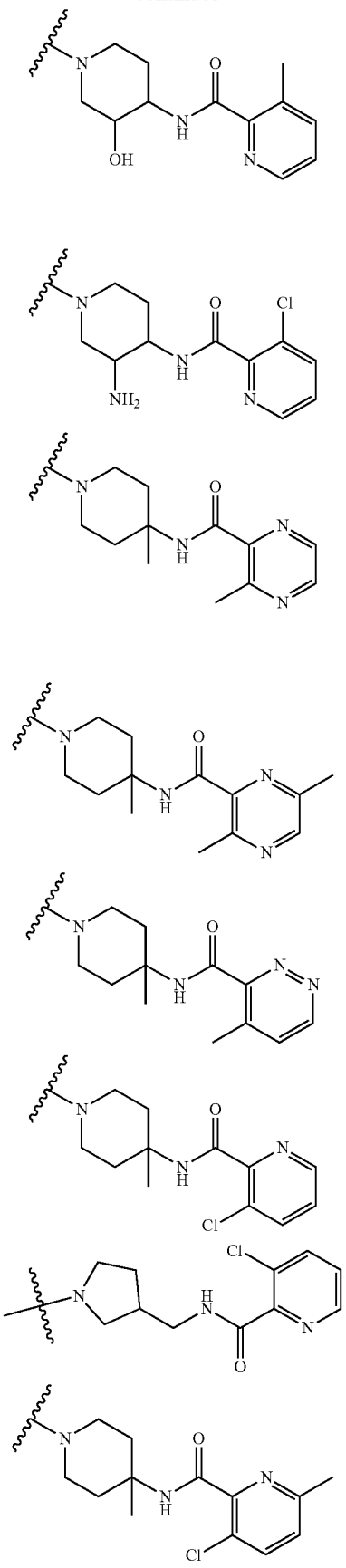

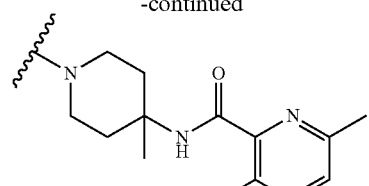

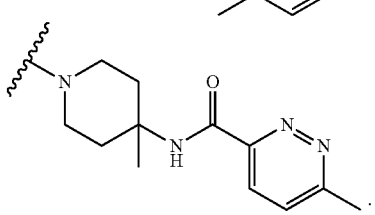

In one embodiment, Ring D is a saturated 4-7 membered heterocyclic ring having one ring heteroatom which is nitrogen; each $R^a$ is independently C1-C6 alkyl (optionally substituted with 1-3 fluoros), hydroxyC1-C6 alkyl or (C1-C6 alkoxy)C1-C6 alkyl-; $R^b$ is (a) hydroxy, (b) cyclopropyl, (c) hetCyc$^b$CH$_2$—, (d) R$^i$R$^j$NC(=O)CH$_2$OCH$_2$— where R$^i$ and R$^j$ are independently H or C1-C6 alkyl, (e) R$^c$R$^d$N—, (f) R$^c$R$^d$NCH$_2$—, (g) C1-C6 alkoxy-, (h) (C1-C4 alkyl)-C(=O)NH— wherein said alkyl portion is optionally substituted with hetCyc$^b$, hetAr$^a$, C1-C6 alkoxy- or R'R"N—, or said alkyl portion is optionally substituted with two substituents independently selected from R'R"N— and OH, where each R' and R" is independently hydrogen or C1-C6 alkyl, (i) (R'R"N)C1-C6 alkoxy(CH$_2$)$_n$— where n is 0 or 1 and R' and R" are independently hydrogen or C1-C6 alkyl, or (j) hetCyc$^b$(C1-C3 alkyl)OCH$_2$—; hetCyc$^b$ is as defined for Formula I; $R^c$ is hydrogen or C1-C6 alkyl; $R^d$ is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C(=O)—, (C1-C6 alkyl)C(=O)—, (R$^k$R$^l$N)C1-C6 alkyl- where R$^k$ and R$^l$ are independently H or C1-C6 alkyl, R$^m$R"NC(=O)C1-C6 alkyl- where R$^m$ and R" are independently H or C1-C6 alkyl, PhCH$_2$—, (C1-C6 alkoxy)C1-C6 alkyl-, or hetCyc$^c$ where hetCyc$^c$ is a 4-6 membered heterocyclic ring having a ring heteroatom selected from N and O and optionally substituted with C1-C6 alkyl; n is 0, 1, 2, 3, 4, 5 or 6; m is 0 or 1; and E is R$^4$R$^5$NC(=O)— where R$^4$ and R$^5$ are as defined for Formula I. In one embodiment, Ring D is a saturated 6 membered heterocyclic ring having one ring heteroatom which is nitrogen. In one embodiment, n is 0, 1 or 2 and m is 0 or 1. In one embodiment, n is 0 or 1 and m is 0. In one embodiment, $R^a$ is C1-C6 alkyl (optionally substituted with 1-3 fluoros) or hydroxyC1-C6 alkyl. In one embodiment, $R^b$ is hetCyc$^b$CH$_2$—, R$^c$R$^d$NCH$_2$—, or hetCyc$^b$(C1-C3 alkyl)OCH$_2$—, where hetCyc$^b$, $R^c$ and $R^d$ are as defined for Formula I. In one embodiment, $R^b$ is hetCyc$^b$CH$_2$— where hetCyc$^b$ is a 4-6 membered heterocyclic ring, a 7-8 membered bridged heterocyclic ring, or a 7-10 membered heterospirocyclic ring, each ring having 1-2 ring heteroatoms independently selected from N and O, wherein hetCyc$^b$ is optionally substituted with one or more substituents independently selected from fluoro, C1-C6 alkyl (optionally substituted with 1-3 fluoros), C1-C6 alkoxy, (C1-C6 alkoxy)C(=O)—, and R'R"N— where R' and R" are independently hydrogen or C1-C6 alkyl. In one embodiment, $R^b$ is R$^c$R$^d$NCH$_2$— where $R^c$ is H or C1-C6 alkyl and $R^d$ is C1-C6 alkyl (optionally substituted with 1-3 fluoros). Non-limiting examples includes the structures:

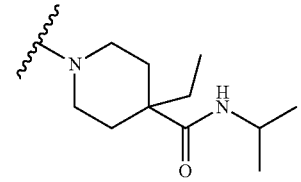

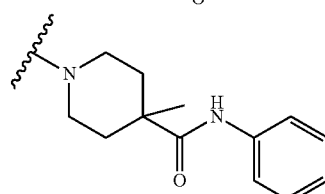

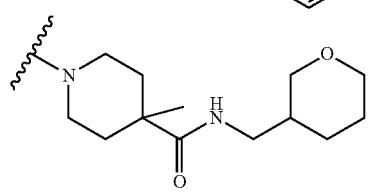

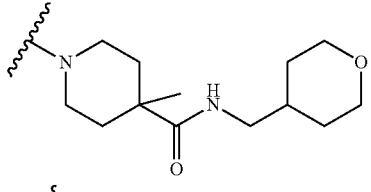

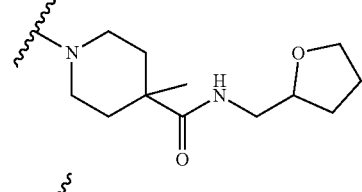

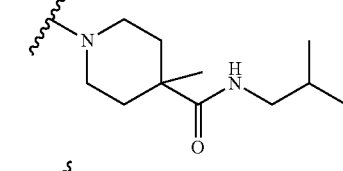

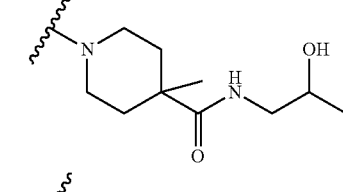

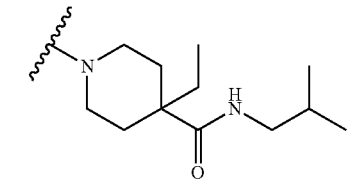

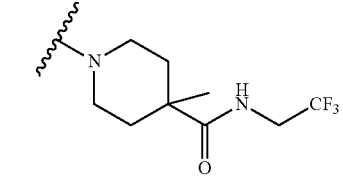

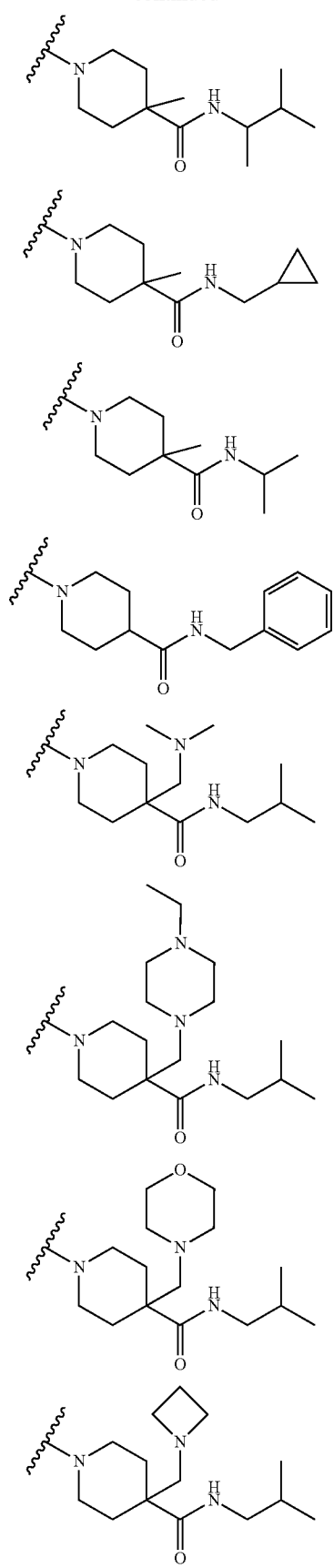
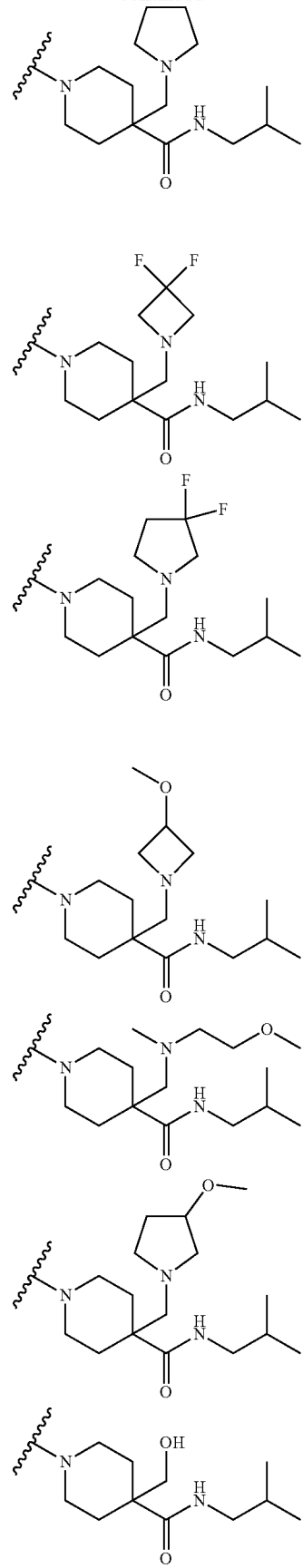

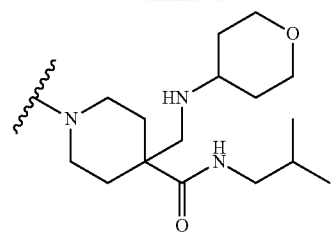
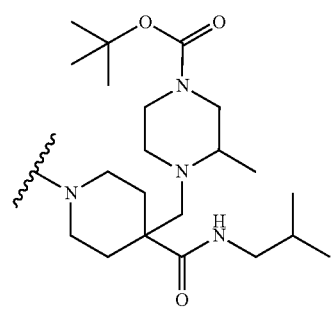
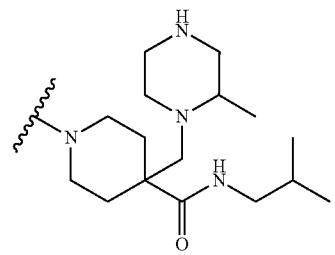
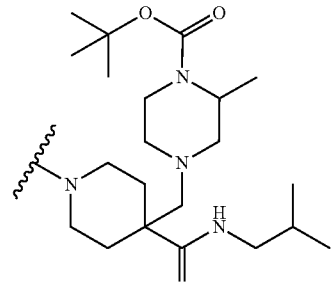
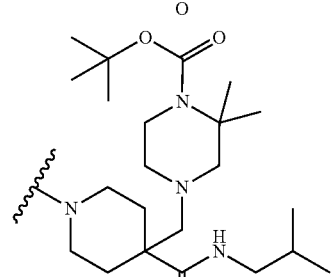
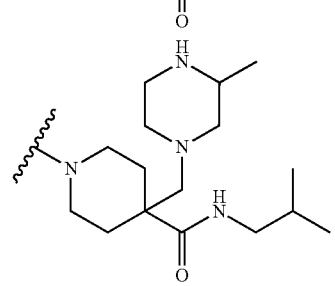
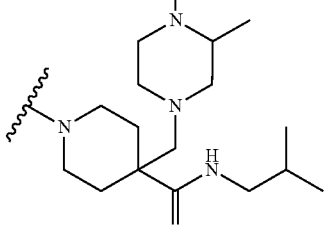
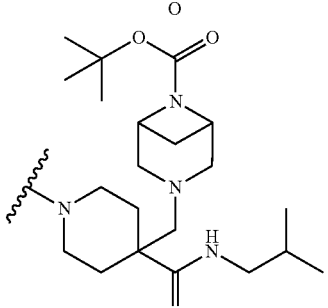
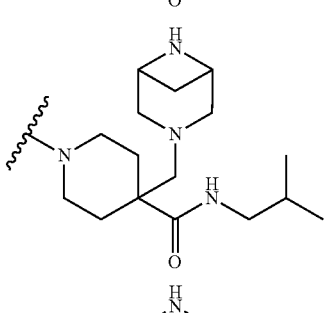
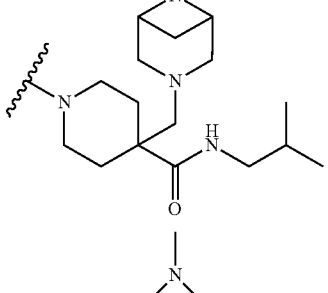
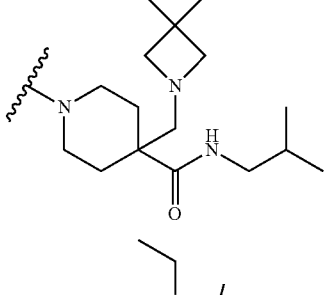
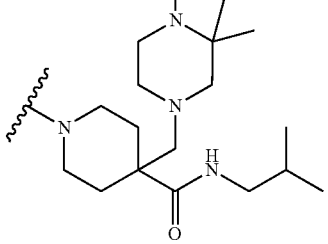

-continued

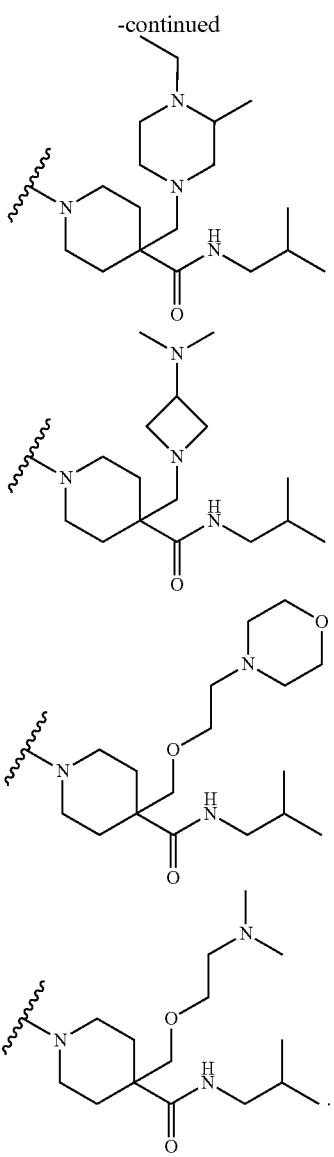

In one embodiment, Ring D is a saturated 4-7 membered heterocyclic ring having one ring heteroatom which is nitrogen; each $R^a$ is independently C1-C6 alkyl (optionally substituted with 1-3 fluoros), hydroxyC1-C6 alkyl or (C1-C6 alkoxy)C1-C6 alkyl-; $R^b$ is (a) hydroxy, (b) cyclopropyl, (c) hetCyc$^b$CH$_2$—, (d) R$^i$R$^j$NC(=O)CH$_2$OCH$_2$— where R$^i$ and R$^j$ are independently H or C1-C6 alkyl, (e) R$^c$R$^d$N—, (f) R$^c$R$^d$NCH$_2$—, (g) C1-C6 alkoxy-, (h) (C1-C4 alkyl)-C(=O)NH— wherein said alkyl portion is optionally substituted with hetCyc$^b$, hetAr$^a$, C1-C6 alkoxy- or R'R"N—, or said alkyl portion is optionally substituted with two substituents independently selected from R'R"N— and OH, where each R' and R" is independently hydrogen or C1-C6 alkyl, (i) (R'R"N)C1-C6 alkoxy(CH$_2$)$_n$— where n is 0 or 1 and R' and R" are independently hydrogen or C1-C6 alkyl, or (j) hetCyc$^b$(C1-C3 alkyl)OCH$_2$—; hetCyc$^b$ is as defined for Formula I; $R^c$ is hydrogen or C1-C6 alkyl; $R^d$ is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C(=O)—, (C1-C6 alkyl)C(=O)—, (R$^k$R$^l$N)C1-C6 alkyl- where R$^k$ and R$^l$ are independently H or C1-C6 alkyl, R'''R''''NC(=O)C1-C6 alkyl- where R''' and R'''' are independently H or C1-C6 alkyl, PhCH$_2$—, (C1-C6 alkoxy)C1-C6 alkyl-, or hetCyc$^c$ where hetCyc$^c$ is a 4-6 membered heterocyclic ring having a ring heteroatom selected from N and O and optionally substituted with C1-C6 alkyl; n is 0, 1, 2, 3, 4, 5 or 6; m is 0 or 1; and E is Ar$^1$NR$^g$C(=O)— where Ar$^1$ and R$^g$ are as defined for Formula I. In one embodiment, Ar$^1$ is unsubstituted or substituted with one or more halogens. In one embodiment, m is 0. In one embodiment n is 0 or 1. In one embodiment, $R^a$ is C1-C6 alkyl (optionally substituted with 1-3 fluoros). Non-limiting examples include the structures:

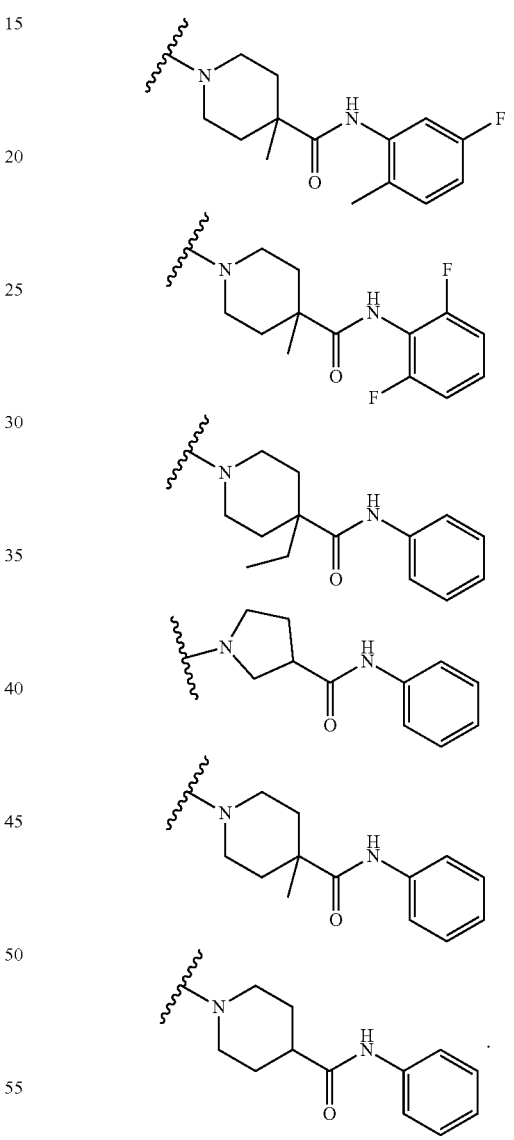

In one embodiment, Ring D is a saturated 4-7 membered heterocyclic ring having one ring heteroatom which is nitrogen; each $R^a$ is independently C1-C6 alkyl (optionally substituted with 1-3 fluoros), hydroxyC1-C6 alkyl or (C1-C6 alkoxy)C1-C6 alkyl-; $R^b$ is (a) hydroxy, (b) cyclopropyl, (c) hetCyc$^b$CH$_2$—, (d) R$^i$R$^j$NC(=O)CH$_2$OCH$_2$— where R$^i$ and R$^j$ are independently H or C1-C6 alkyl, (e) R$^c$R$^d$N—, (f) R$^c$R$^d$NCH$_2$—, (g) C1-C6 alkoxy-, (h) (C1-C4 alkyl)-C(=O)NH— wherein said alkyl portion is optionally substituted with hetCyc$^b$, hetAr$^a$, C1-C6 alkoxy- or R'R''N—, or said alkyl portion is optionally substituted with two substituents independently selected from R'R''N— and OH, where each R' and R'' is independently hydrogen or C1-C6 alkyl, (i) (R'R''N)C1-C6 alkoxy(CH$_2$)$_n$— where n is 0 or 1 and R' and R'' are independently hydrogen or C1-C6 alkyl, or (j) hetCyc$^b$(C1-C3 alkyl)OCH$_2$—; hetCyc$^b$ is as defined for Formula I; R$^c$ is hydrogen or C1-C6 alkyl; R$^d$ is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C(=O)—, (C1-C6 alkyl)C(=O)—, (R$^k$R$^l$N)C1-C6 alkyl- where R$^k$ and R$^l$ are independently H or C1-C6 alkyl, R'''R''NC(=O)C1-C6 alkyl- where R''' and R'' are independently H or C1-C6 alkyl, PhCH$_2$—, (C1-C6 alkoxy)C1-C6 alkyl-, or hetCyc$^c$ where hetCyc$^c$ is a 4-6 membered heterocyclic ring having a ring heteroatom selected from N and O and optionally substituted with C1-C6 alkyl; n is 0, 1, 2, 3, 4, 5 or 6; m is 0 or 1; and E is hetAr$^2$NR$^g$C(=O)— where hetAr$^2$ and R$^g$ are as defined for Formula I. In one embodiment, hetAr$^1$ is a 5-6 membered heteroaryl having 1-2 ring nitrogen atoms and optionally substituted with one or more substituents independently selected from C1-C6 alkyl (optionally substituted with 1-3 fluoros) and C1-C6 alkoxy (optionally substituted with 1-3 fluoros). In one embodiment, m is 0. In one embodiment n is 0 or 1. In one embodiment, R$^a$ is C1-C6 alkyl (optionally substituted with 1-3 fluoros). Non-limiting examples include the structures:

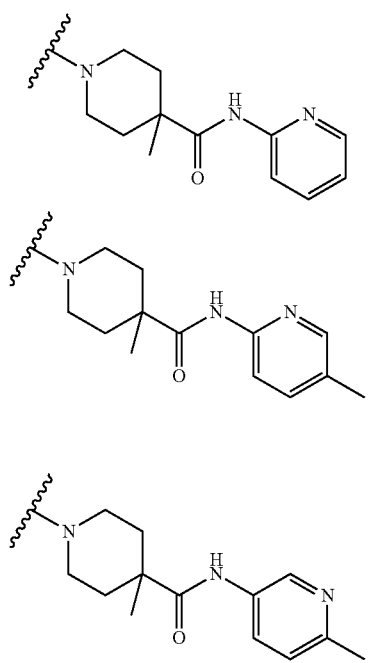

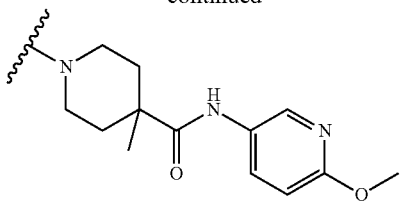

In one embodiment, Ring D is a saturated 4-7 membered heterocyclic ring having one ring heteroatom which is nitrogen; each R$^a$ is independently C1-C6 alkyl (optionally substituted with 1-3 fluoros), hydroxyC1-C6 alkyl or (C1-C6 alkoxy)C1-C6 alkyl-; R$^b$ is (a) hydroxy, (b) cyclopropyl, (c) hetCyc$^b$CH$_2$—, (d) R$^i$R$^j$NC(=O)CH$_2$OCH$_2$— where R$^i$ and R$^j$ are independently H or C1-C6 alkyl, (e) R$^c$R$^d$N—, (f) R$^c$R$^d$NCH$_2$—, (g) C1-C6 alkoxy-, (h) (C1-C4 alkyl)-C(=O)NH— wherein said alkyl portion is optionally substituted with hetCyc$^b$, hetAr$^a$, C1-C6 alkoxy- or R'R''N—, or said alkyl portion is optionally substituted with two substituents independently selected from R'R''N— and OH, where each R' and R'' is independently hydrogen or C1-C6 alkyl, (i) (R'R''N)C1-C6 alkoxy(CH$_2$)$_n$— where n is 0 or 1 and R' and R'' are independently hydrogen or C1-C6 alkyl, or (j) hetCyc$^b$(C1-C3 alkyl)OCH$_2$—; hetCyc$^b$ is as defined for Formula I; R$^c$ is hydrogen or C1-C6 alkyl; R$^d$ is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C(=O)—, (C1-C6 alkyl)C(=O)—, (R$^k$R$^l$N)C1-C6 alkyl- where R$^k$ and R$^l$ are independently H or C1-C6 alkyl, R'''R''NC(=O)C1-C6 alkyl- where R''' and R'' are independently H or C1-C6 alkyl, PhCH$_2$—, (C1-C6 alkoxy)C1-C6 alkyl-, or hetCyc$^c$ where hetCyc$^c$ is a 4-6 membered heterocyclic ring having a ring heteroatom selected from N and O and optionally substituted with C1-C6 alkyl; n is 0, 1, 2, 3, 4, 5 or 6; m is 0 or 1; and E is hetCyc$^5$C(=O)— where hetCyc$^5$ is as defined for Formula I. In one embodiment, m is 0. In one embodiment n is 0 or 1. In one embodiment, R$^a$ is C1-C6 alkyl (optionally substituted with 1-3 fluoros). A non-limiting example is the structure:

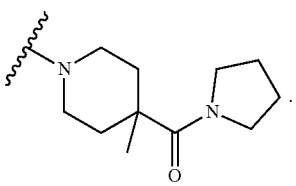 [SMILES: *N1CCC(C)(C(=O)N2CCCC2)CC1]

In one embodiment, Ring D is a saturated 4-7 membered heterocyclic ring having one ring heteroatom which is nitrogen; each R$^a$ is independently C1-C6 alkyl (optionally substituted with 1-3 fluoros), hydroxyC1-C6 alkyl or (C1-C6 alkoxy)C1-C6 alkyl-; R$^b$ is (a) hydroxy, (b) cyclopropyl, (c) hetCyc$^b$CH$_2$—, (d) R$^i$R$^j$NC(=O)CH$_2$OCH$_2$— where R$^i$ and R$^j$ are independently H or C1-C6 alkyl, (e) R$^c$R$^d$N—, (f) R$^c$R$^d$NCH$_2$—, (g) C1-C6 alkoxy-, (h) (C1-C4 alkyl)-C(=O)NH— wherein said alkyl portion is optionally substituted with hetCyc$^b$, hetAr$^a$, C1-C6 alkoxy- or R'R''N—, or said alkyl portion is optionally substituted with two substituents independently selected from R'R''N— and OH, where each R' and R'' is independently hydrogen or C1-C6 alkyl, (i) (R'R''N)C1-C6 alkoxy(CH$_2$)$_n$— where n is 0 or 1 and R' and R" are independently hydrogen or C1-C6 alkyl, or (j) hetCyc$^b$(C1-C3 alkyl)OCH$_2$—; hetCyc$^b$ is as defined for Formula I; R$^c$ is hydrogen or C1-C6 alkyl; R$^d$ is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C(=O)—, (C1-C6 alkyl)C(=O)—, (R$^k$R$^l$N)C1-C6 alkyl- where R$^k$ and R$^l$ are independently H or C1-C6 alkyl, R$^m$R$^n$NC(=O)C1-C6 alkyl- where R$^m$ and R$^n$ are independently H or C1-C6 alkyl, PhCH$_2$—, (C1-C6 alkoxy)C1-C6 alkyl-, or hetCyc$^c$ where hetCyc$^c$ is a 4-6 membered heterocyclic ring having a ring heteroatom selected from N and O and optionally substituted with C1-C6 alkyl; n is 0, 1, 2, 3, 4, 5 or 6; m is 0 or 1; and E is R$^4$R$^5$NC(=O)NR— where R$^4$, R$^5$ and R$^g$ are as defined for Formula I. In one embodiment, R$^4$ and R$^5$ are independently hydrogen or C1-C6 alkyl. In one embodiment, Ring D is a saturated 6 membered heterocyclic ring having one ring heteroatom which is nitrogen. In one embodiment, n is 0, 1 or 2 and m is 0 or 1. In one embodiment, n is 0 or 1 and m is 0. In one embodiment, R$^a$ is C1-C6 alkyl (optionally substituted with 1-3 fluoros). In one embodiment, n is 0 and m is 1. In one embodiment, R$^b$ is hetCyc$^b$CH$_2$— where hetCyc$^b$ is a 4-6 membered heterocyclic ring having 1-2 ring heteroatoms independently selected from N and O, wherein hetCyc$^b$ is optionally substituted with C1-C6 alkyl (optionally substituted with 1-3 fluoros). In one embodiment, R$^b$ is R$^c$R$^d$NCH$_2$— where R$^c$ is H or C1-C6 alkyl and R$^d$ is C1-C6 alkyl (optionally substituted with 1-3 fluoros). Non-limiting examples include the structures:

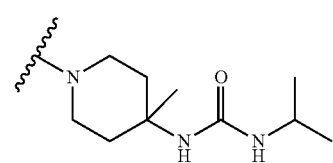

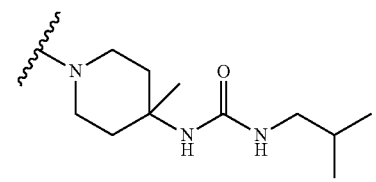

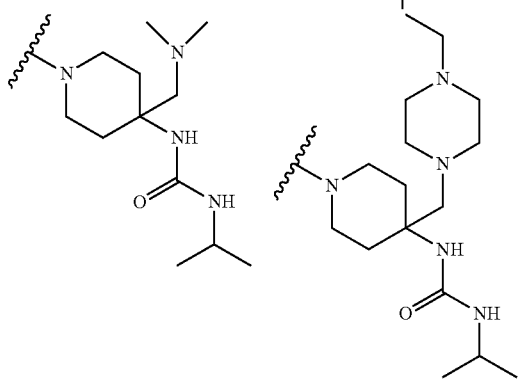

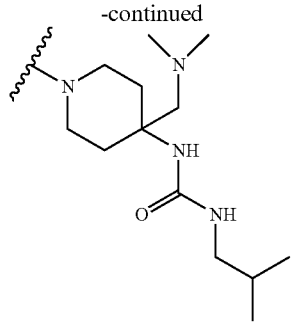

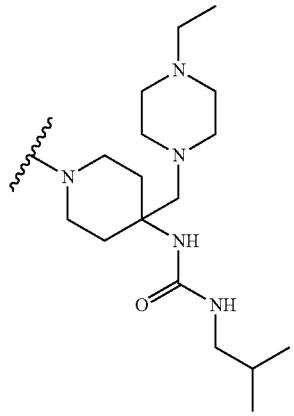

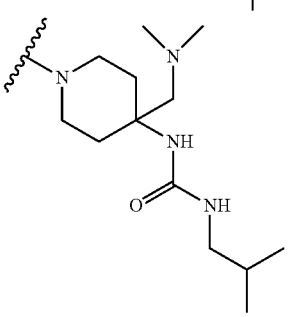

In one embodiment, Ring D is a saturated 4-7 membered heterocyclic ring having one ring heteroatom which is nitrogen; each R$^a$ is independently C1-C6 alkyl (optionally substituted with 1-3 fluoros), hydroxyC1-C6 alkyl or (C1-C6 alkoxy)C1-C6 alkyl-; R$^b$ is (a) hydroxy, (b) cyclopropyl, (c) hetCyc$^b$CH$_2$—, (d) R$^i$R$^j$NC(=O)CH$_2$OCH$_2$— where R$^i$ and R$^j$ are independently H or C1-C6 alkyl, (e) R$^c$R$^d$N—, (f) R$^c$R$^d$NCH$_2$—, (g) C1-C6 alkoxy-, (h) (C1-C4 alkyl)-C(=O)NH— wherein said alkyl portion is optionally substituted with hetCyc$^b$, hetAr$^a$, C1-C6 alkoxy- or R'R"N—, or said alkyl portion is optionally substituted with two substituents independently selected from R'R"N— and OH, where each R' and R" is independently hydrogen or C1-C6 alkyl, (i) (R'R"N)C1-C6 alkoxy(CH$_2$)$_n$— where n is 0 or 1 and R' and R" are independently hydrogen or C1-C6 alkyl, or (j) hetCyc$^b$(C1-C3 alkyl)OCH$_2$—; hetCyc$^b$ is as defined for Formula I; R$^c$ is hydrogen or C1-C6 alkyl; R$^d$ is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C(=O)—, (C1-C6 alkyl)C(=O)—, (R$^k$R$^l$N)C1-C6 alkyl- where R$^k$ and R$^l$ are independently H or C1-C6 alkyl, R$^m$R$^n$NC(=O)C1-C6 alkyl- where R$^m$ and R$^n$ are independently H or C1-C6 alkyl, PhCH$_2$—, (C1-C6 alkoxy)C1-C6 alkyl-, or hetCyc$^c$ where hetCyc$^c$ is a 4-6 membered heterocyclic ring having a ring heteroatom selected from N and O and optionally substituted with C1-C6 alkyl; n is 0, 1, 2, 3, 4, 5 or 6; m is 0 or 1; and E is (C1-C6 alkyl)SO$_2$—. In one embodiment, Ring D is a saturated 6 membered heterocyclic ring having one ring heteroatom which is nitrogen. In one embodiment, n is 0, 1 or 2 and m is 0 or 1. In one embodiment, n is 0 or 1 and m is 0. In one embodiment, R$^a$ is C1-C6 alkyl (optionally substituted with 1-3 fluoros). Non-limiting examples include the structures:

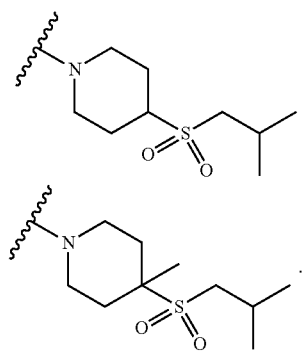

In one embodiment, Ring D is a saturated 4-7 membered heterocyclic ring having one ring heteroatom which is nitrogen; each R$^a$ is independently C1-C6 alkyl (optionally substituted with 1-3 fluoros), hydroxyC1-C6 alkyl or (C1-C6 alkoxy)C1-C6 alkyl-; R$^b$ is (a) hydroxy, (b) cyclopropyl, (c) hetCyc$^b$CH$_2$—, (d) R$^i$R$^j$NC(=O)CH$_2$OCH$_2$— where R$^i$ and R$^j$ are independently H or C1-C6 alkyl, (e) R$^c$R$^d$N—, (f) R$^c$R$^d$NCH$_2$—, (g) C1-C6 alkoxy-, (h) (C1-C4 alkyl)-C(=O)NH— wherein said alkyl portion is optionally substituted with hetCyc$^b$, hetAr$^a$, C1-C6 alkoxy- or R'R"N—, or said alkyl portion is optionally substituted with two substituents independently selected from R'R"N— and OH, where each R' and R" is independently hydrogen or C1-C6 alkyl, (i) (R'R"N)C1-C6 alkoxy(CH$_2$)$_n$— where n is 0 or 1 and R' and R" are independently hydrogen or C1-C6 alkyl, or (j) hetCyc$^b$(C1-C3 alkyl)OCH$_2$—; hetCyc$^b$ is as defined for Formula I; R$^c$ is hydrogen or C1-C6 alkyl; R$^d$ is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C(=O)—, (C1-C6 alkyl)C(=O)—, (R$^k$R$^l$N)C1-C6 alkyl- where R$^k$ and R$^l$ are independently H or C1-C6 alkyl, R$^m$R$^n$NC(=O)C1-C6 alkyl- where R$^m$ and R$^n$ are independently H or C1-C6 alkyl, PhCH$_2$—, (C1-C6 alkoxy)C1-C6 alkyl-, or hetCyc$^c$ where hetCyc$^c$ is a 4-6 membered heterocyclic ring having a ring heteroatom selected from N and O and optionally substituted with C1-C6 alkyl; n is 0, 1, 2, 3, 4, 5 or 6; m is 0 or 1; and E is Ar$^1$(C1-C6 alkyl)C(=O)NR$^g$— where Ar$^1$ and R$^g$ are as defined for Formula I. In one embodiment, Ar$^1$ is unsubstituted or substituted with one or more halogens. In one embodiment, n is 0 or 1 and m is 0. In one embodiment, R$^a$ is C1-C6 alkyl (optionally substituted with 1-3 fluoros). Non-limiting examples include the structures:

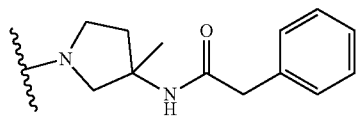

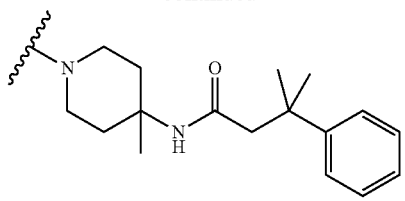

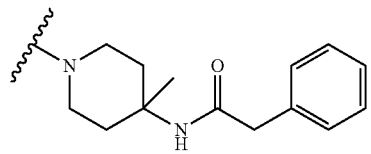

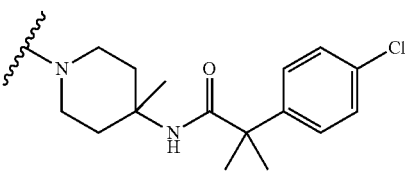

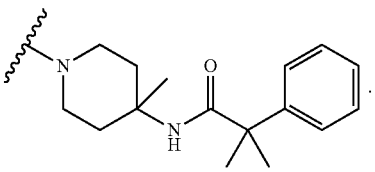

In one embodiment, Ring D is a saturated 4-7 membered heterocyclic ring having one ring heteroatom which is nitrogen; each R$^a$ is independently C1-C6 alkyl (optionally substituted with 1-3 fluoros), hydroxyC1-C6 alkyl or (C1-C6 alkoxy)C1-C6 alkyl-; R$^b$ is (a) hydroxy, (b) cyclopropyl, (c) hetCyc$^b$CH$_2$—, (d) R$^i$R$^j$NC(=O)CH$_2$OCH$_2$— where R$^i$ and R$^j$ are independently H or C1-C6 alkyl, (e) R$^c$R$^d$N—, (f) R$^c$R$^d$NCH$_2$—, (g) C1-C6 alkoxy-, (h) (C1-C4 alkyl)-C(=O)NH— wherein said alkyl portion is optionally substituted with hetCyc$^b$, hetAr$^a$, C1-C6 alkoxy- or R'R"N—, or said alkyl portion is optionally substituted with two substituents independently selected from R'R"N— and OH, where each R' and R" is independently hydrogen or C1-C6 alkyl, (i) (R'R"N)C1-C6 alkoxy(CH$_2$)$_n$— where n is 0 or 1 and R' and R" are independently hydrogen or C1-C6 alkyl, or (j) hetCyc$^b$(C1-C3 alkyl)OCH$_2$—; hetCyc$^b$ is as defined for Formula I; R$^c$ is hydrogen or C1-C6 alkyl; R$^d$ is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C(=O)—, (C1-C6 alkyl)C(=O)—, (R$^k$R$^l$N)C1-C6 alkyl- where R$^k$ and R$^l$ are independently H or C1-C6 alkyl, R$^m$R$^n$NC(=O)C1-C6 alkyl- where R$^m$ and R$^n$ are independently H or C1-C6 alkyl, PhCH$_2$—, (C1-C6 alkoxy)C1-C6 alkyl-, or hetCyc$^c$ where hetCyc$^c$ is a 4-6 membered heterocyclic ring having a ring heteroatom selected from N and O and optionally substituted with C1-C6 alkyl; n is 0, 1, 2, 3, 4, 5 or 6; m is 0 or 1; and E is hetAr$^4$C(=O)NR$^g$— where hetAr$^4$ and R$^g$ are as defined for Formula I. In one embodiment, n is 0 or 1 and m is 0. In one embodiment, R$^a$ is C1-C6 alkyl. Non-limiting examples include the structures:

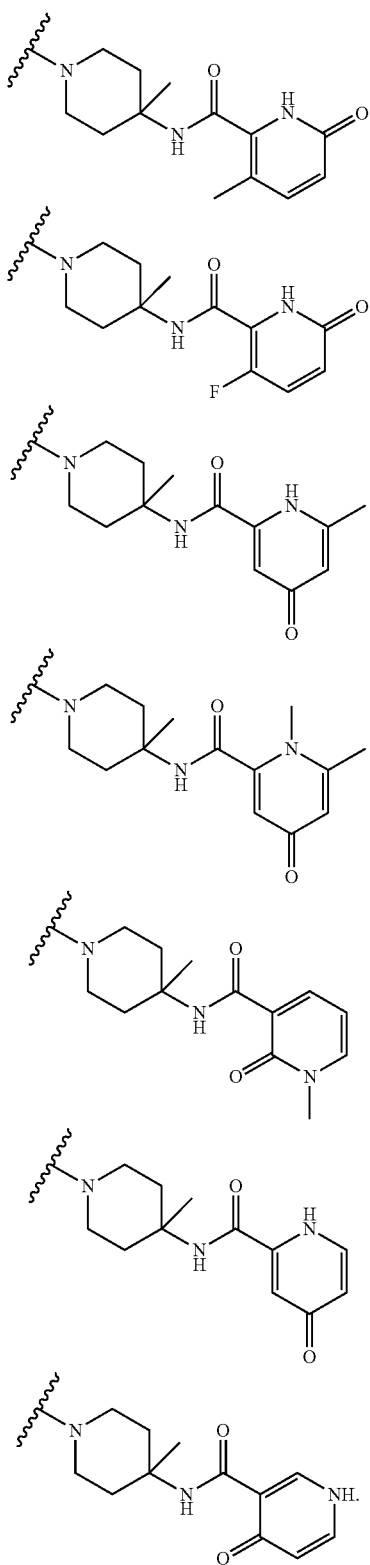

and $R^j$ are independently H or C1-C6 alkyl, (e) $R^cR^dN$—, (f) $R^cR^dNCH_2$—, (g) C1-C6 alkoxy-, (h) (C1-C4 alkyl)-C(=O)NH— wherein said alkyl portion is optionally substituted with hetCyc$^b$, hetAr$^a$, C1-C6 alkoxy- or R'R"N—, or said alkyl portion is optionally substituted with two substituents independently selected from R'R"N— and OH, where each R' and R" is independently hydrogen or C1-C6 alkyl, (i) (R'R"N)C1-C6 alkoxy(CH$_2$)$_n$— where n is 0 or 1 and R' and R" are independently hydrogen or C1-C6 alkyl, or (j) hetCyc$^b$(C1-C3 alkyl)OCH$_2$—; hetCyc$^b$ is as defined for Formula I; R is hydrogen or C1-C6 alkyl; $R^d$ is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C(=O)—, (C1-C6 alkyl)C(=O)—, ($R^kR^lN$)C1-C6 alkyl- where $R^k$ and $R^l$ are independently H or C1-C6 alkyl, $R^mR^nNC(=O)$C1-C6 alkyl- where $R^m$ and $R^n$ are independently H or C1-C6 alkyl, PhCH$_2$—, (C1-C6 alkoxy)C1-C6 alkyl-, or hetCyc$^c$ where hetCyc$^c$ is a 4-6 membered heterocyclic ring having a ring heteroatom selected from N and O and optionally substituted with C1-C6 alkyl; n is 0, 1, 2, 3, 4, 5 or 6; m is 0 or 1; and E is hetAr$^2$—S(=O)— where hetAr$^2$ is as defined for Formula I. In one embodiment, hetAr$^2$ is a 5-6-membered heteroaryl ring. In one embodiment, hetAr$^2$ is unsubstituted. In one embodiment, n is 0. In one embodiment, m is 0. A non-limiting example includes the structure:

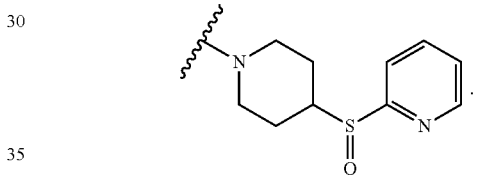

In one embodiment, Ring D is a saturated 4-7 membered heterocyclic ring having one ring heteroatom which is nitrogen; each $R^a$ is independently C1-C6 alkyl (optionally substituted with 1-3 fluoros), hydroxyC1-C6 alkyl or (C1-C6 alkoxy)C1-C6 alkyl-; $R^b$ is (a) hydroxy, (b) cyclopropyl, (c) hetCyc$^b$CH$_2$—, (d) $R^iR^jNC(=O)CH_2OCH_2$— where $R^i$ and $R^j$ are independently H or C1-C6 alkyl, (e) $R^cR^dN$—, (f) $R^cR^dNCH_2$—, (g) C1-C6 alkoxy-, (h) (C1-C4 alkyl)-C(=O)NH— wherein said alkyl portion is optionally substituted with hetCyc$^b$, hetAr$^a$, C1-C6 alkoxy- or R'R"N—, or said alkyl portion is optionally substituted with two substituents independently selected from R'R"N— and OH, where each R' and R" is independently hydrogen or C1-C6 alkyl, (i) (R'R"N)C1-C6 alkoxy(CH$_2$)$_n$— where n is 0 or 1 and R' and R" are independently hydrogen or C1-C6 alkyl, or (j) hetCyc$^b$(C1-C3 alkyl)OCH$_2$—; hetCyc$^b$ is as defined for Formula I; $R^c$ is hydrogen or C1-C6 alkyl; $R^d$ is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C(=O)—, (C1-C6 alkyl)C(=O)—, ($R^kR^lN$)C1-C6 alkyl- where $R^k$ and $R^l$ are independently H or C1-C6 alkyl, $R^mR^nNC(=O)$C1-C6 alkyl- where $R^m$ and $R^n$ are independently H or C1-C6 alkyl, PhCH$_2$—, (C1-C6 alkoxy)C1-C6 alkyl-, or hetCyc$^c$ where hetCyc$^c$ is a 4-6 membered heterocyclic ring having a ring heteroatom selected from N and O and optionally substituted with C1-C6 alkyl; n is 0, 1, 2, 3, 4, 5 or 6; m is 0 or 1; and E is (C3-C6 cycloalkyl)CH$_2$SO$_2$—. In one embodiment, n is 0. In one embodiment, m is 0. A non-limiting example includes the structure:

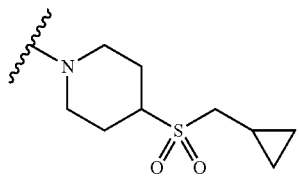

In one embodiment, Ring D is a saturated 4-7 membered heterocyclic ring having one ring heteroatom which is nitrogen; each $R^a$ is independently C1-C6 alkyl (optionally substituted with 1-3 fluoros), hydroxyC1-C6 alkyl or (C1-C6 alkoxy)C1-C6 alkyl-; $R^b$ is (a) hydroxy, (b) cyclopropyl, (c) hetCyc$^b$CH$_2$—, (d) R$^i$R$^j$NC(=O)CH$_2$OCH$_2$— where R$^i$ and R$^j$ are independently H or C1-C6 alkyl, (e) R$^c$R$^d$N—, (f) R$^c$R$^d$NCH$_2$—, (g) C1-C6 alkoxy-, (h) (C1-C4 alkyl)-C(=O)NH— wherein said alkyl portion is optionally substituted with hetCyc$^b$, hetAr$^a$, C1-C6 alkoxy- or R'R"N—, or said alkyl portion is optionally substituted with two substituents independently selected from R'R"N— and OH, where each R' and R" is independently hydrogen or C1-C6 alkyl, (i) (R'R"N)C1-C6 alkoxy(CH$_2$)$_n$— where n is 0 or 1 and R' and R" are independently hydrogen or C1-C6 alkyl, or (j) hetCyc$^b$(C1-C3 alkyl)OCH$_2$—; hetCyc$^b$ is as defined for Formula I; $R^c$ is hydrogen or C1-C6 alkyl; $R^d$ is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C(=O)—, (C1-C6 alkyl)C(=O)—, (R$^k$R$^l$N)C1-C6 alkyl- where R$^k$ and R$^l$ are independently H or C1-C6 alkyl, R$^m$R$^n$NC(=O)C1-C6 alkyl- where R$^m$ and R$^n$ are independently H or C1-C6 alkyl, PhCH$_2$—, (C1-C6 alkoxy)C1-C6 alkyl-, or hetCyc$^c$ where hetCyc$^c$ is a 4-6 membered heterocyclic ring having a ring heteroatom selected from N and O and optionally substituted with C1-C6 alkyl; n is 0, 1, 2, 3, 4, 5 or 6; m is 0 or 1; and E is Ar$^1$(C1-C6 alkyl)SO$_2$— where Ar$^1$ is as defined for Formula I. In one embodiment, Ar$^1$ is unsubstituted. In one embodiment, n is 0. In one embodiment, m is 0. A non-limiting example includes the structure:

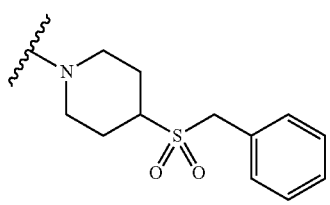

In one embodiment, Ring D is a saturated 4-7 membered heterocyclic ring having one ring heteroatom which is nitrogen; each $R^a$ is independently C1-C6 alkyl (optionally substituted with 1-3 fluoros), hydroxyC1-C6 alkyl or (C1-C6 alkoxy)C1-C6 alkyl-; $R^b$ is (a) hydroxy, (b) cyclopropyl, (c) hetCyc$^b$CH$_2$—, (d) R$^i$R$^j$NC(=O)CH$_2$OCH$_2$— where R$^i$ and R$^j$ are independently H or C1-C6 alkyl, (e) R$^c$R$^d$N—, (f) R$^c$R$^d$NCH$_2$—, (g) C1-C6 alkoxy-, (h) (C1-C4 alkyl)-C(=O)NH— wherein said alkyl portion is optionally substituted with hetCyc$^b$, hetAr$^a$, C1-C6 alkoxy- or R'R"N—, or said alkyl portion is optionally substituted with two substituents independently selected from R'R"N— and OH, where each R' and R" is independently hydrogen or C1-C6 alkyl, (i) (R'R"N)C1-C6 alkoxy(CH$_2$)$_n$— where n is 0 or 1 and R' and R" are independently hydrogen or C1-C6 alkyl, or (j) hetCyc$^b$(C1-C3 alkyl)OCH$_2$—; hetCyc$^b$ is as defined for Formula I; $R^c$ is hydrogen or C1-C6 alkyl; $R^d$ is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C(=O)—, (C1-C6 alkyl)C(=O)—, (R$^k$R$^l$N)C1-C6 alkyl- where R$^k$ and R$^l$ are independently H or C1-C6 alkyl, R$^m$R$^n$NC(=O)C1-C6 alkyl- where R$^m$ and R$^n$ are independently H or C1-C6 alkyl, PhCH$_2$—, (C1-C6 alkoxy)C1-C6 alkyl-, or hetCyc$^c$ where hetCyc$^c$ is a 4-6 membered heterocyclic ring having a ring heteroatom selected from N and O and optionally substituted with C1-C6 alkyl; n is 0, 1, 2, 3, 4, 5 or 6; m is 0 or 1; and E is hetAr$^2$SO$_2$— where hetAr$^2$ is as defined for Formula I. In one embodiment, hetAr$^2$ is a 5-6-membered heteroaryl ring. In one embodiment, hetAr$^2$ is unsubstituted. In one embodiment, n is 0. In one embodiment, m is 0. A non-limiting example includes the structure:

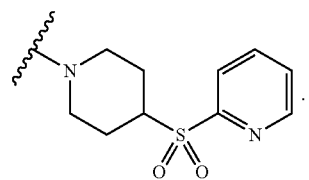 [SMILES: *N1CCC(S(=O)(=O)c2ccccn2)CC1]

In one embodiment, Ring D is a saturated 4-7 membered heterocyclic ring having one ring heteroatom which is nitrogen; each $R^a$ is independently C1-C6 alkyl (optionally substituted with 1-3 fluoros), hydroxyC1-C6 alkyl or (C1-C6 alkoxy)C1-C6 alkyl-; $R^b$ is (a) hydroxy, (b) cyclopropyl, (c) hetCyc$^b$CH$_2$—, (d) R$^i$R$^j$NC(=O)CH$_2$OCH$_2$— where R$^i$ and R$^j$ are independently H or C1-C6 alkyl, (e) R$^c$R$^d$N—, (f) R$^c$R$^d$NCH$_2$—, (g) C1-C6 alkoxy-, (h) (C1-C4 alkyl)-C(=O)NH— wherein said alkyl portion is optionally substituted with hetCyc$^b$, hetAr$^a$, C1-C6 alkoxy- or R'R"N—, or said alkyl portion is optionally substituted with two substituents independently selected from R'R"N— and OH, where each R' and R" is independently hydrogen or C1-C6 alkyl, (i) (R'R"N)C1-C6 alkoxy(CH$_2$)$_n$— where n is 0 or 1 and R' and R" are independently hydrogen or C1-C6 alkyl, or (j) hetCyc$^b$(C1-C3 alkyl)OCH$_2$—; hetCyc$^b$ is as defined for Formula I; $R^c$ is hydrogen or C1-C6 alkyl; $R^d$ is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C(=O)—, (C1-C6 alkyl)C(=O)—, (R$^k$R$^l$N)C1-C6 alkyl- where R$^k$ and R$^l$ are independently H or C1-C6 alkyl, R$^m$R$^n$NC(=O)C1-C6 alkyl- where R$^m$ and R$^n$ are independently H or C1-C6 alkyl, PhCH$_2$—, (C1-C6 alkoxy)C1-C6 alkyl-, or hetCyc$^c$ where hetCyc$^c$ is a 4-6 membered heterocyclic ring having a ring heteroatom selected from N and O and optionally substituted with C1-C6 alkyl; n is 0, 1, 2, 3, 4, 5 or 6; m is 0 or 1; and E is Ar$^1$ where Ar$^1$ is as defined for Formula I. In one embodiment, Ar$^1$ is unsubstituted. In one embodiment, n is 0. In one embodiment, m is 0 or 1. In one embodiment, $R^b$ is OH. A non-limiting example includes the structure:

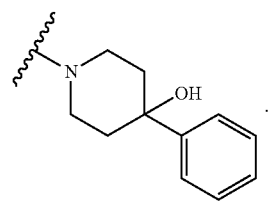 [SMILES: *N1CCC(O)(c2ccccc2)CC1]

In one embodiment, Ring D is a saturated 4-7 membered heterocyclic ring having one ring heteroatom which is nitrogen; each $R^a$ is independently C1-C6 alkyl (optionally substituted with 1-3 fluoros), hydroxyC1-C6 alkyl or (C1-C6 alkoxy)C1-C6 alkyl-; $R^b$ is (a) hydroxy, (b) cyclopropyl, (c) hetCyc$^b$CH$_2$—, (d) R$^i$R$^j$NC(=O)CH$_2$OCH$_2$— where R$^i$ and R$^j$ are independently H or C1-C6 alkyl, (e) R$^c$R$^d$N—, (f) R$^c$R$^d$NCH$_2$—, (g) C1-C6 alkoxy-, (h) (C1-C4 alkyl)-C(=O)NH— wherein said alkyl portion is optionally substituted with hetCyc$^b$, hetAr$^a$, C1-C6 alkoxy- or R'R"N—, or said alkyl portion is optionally substituted with two substituents independently selected from R'R"N— and OH, where each R' and R" is independently hydrogen or C1-C6 alkyl, (i) (R'R"N)C1-C6 alkoxy(CH$_2$)$_n$— where n is 0 or 1 and R' and R" are independently hydrogen or C1-C6 alkyl, or (j) hetCyc$^b$(C1-C3 alkyl)OCH$_2$—; hetCyc$^b$ is as defined for Formula I; $R^c$ is hydrogen or C1-C6 alkyl; $R^d$ is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C(=O)—, (C1-C6 alkyl)C(=O)—, (R$^k$R$^l$N)C1-C6 alkyl- where R$^k$ and R$^l$ are independently H or C1-C6 alkyl, R$^m$R$^n$NC(=O)C1-C6 alkyl- where R$^m$ and R$^n$ are independently H or C1-C6 alkyl, PhCH$_2$—, (C1-C6 alkoxy)C1-C6 alkyl-, or hetCyc$^c$ where hetCyc$^c$ is a 4-6 membered heterocyclic ring having a ring heteroatom selected from N and O and optionally substituted with C1-C6 alkyl; n is 0, 1, 2, 3, 4, 5 or 6; m is 0 or 1; and E is hetAr$^2$ where hetAr$^2$ is as defined for Formula I. In one embodiment, hetAr$^2$ is unsubstituted or substituted with C1-C6 alkyl (optionally substituted with 1-3 fluoros). In one embodiment, n is 0. In one embodiment, m is 0 or 1. In one embodiment, $R^b$ is OH. Non-limiting examples include the structures:

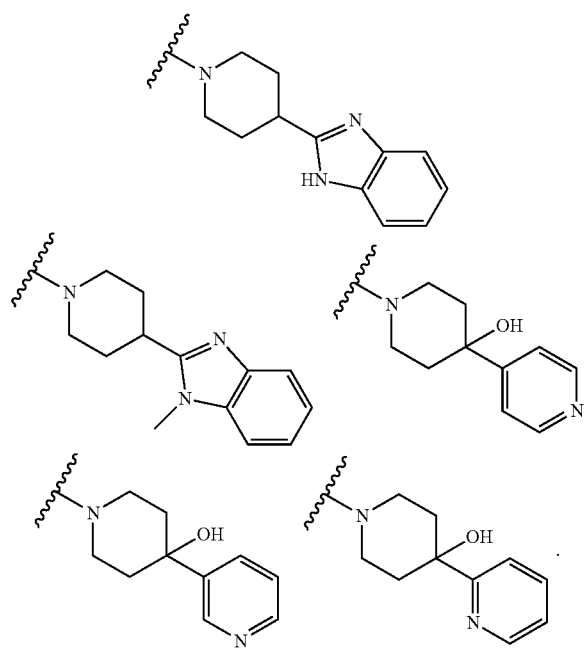

In one embodiment, Ring D is a saturated 4-7 membered heterocyclic ring having one ring heteroatom which is nitrogen; each $R^a$ is independently C1-C6 alkyl (optionally substituted with 1-3 fluoros), hydroxyC1-C6 alkyl or (C1-C6 alkoxy)C1-C6 alkyl-; $R^b$ is (a) hydroxy, (b) cyclopropyl, (c) hetCyc$^b$CH$_2$—, (d) R$^i$R$^j$NC(=O)CH$_2$OCH$_2$— where R$^i$ and R$^j$ are independently H or C1-C6 alkyl, (e) R$^c$R$^d$N—, (f) R$^c$R$^d$NCH$_2$—, (g) C1-C6 alkoxy-, (h) (C1-C4 alkyl)-C(=O)NH— wherein said alkyl portion is optionally substituted with hetCyc$^b$, hetAr$^a$, C1-C6 alkoxy- or R'R"N—, or said alkyl portion is optionally substituted with two substituents independently selected from R'R"N— and OH, where each R' and R" is independently hydrogen or C1-C6 alkyl, (i) (R'R"N)C1-C6 alkoxy(CH$_2$)$_n$— where n is 0 or 1 and R' and R" are independently hydrogen or C1-C6 alkyl, or (j) hetCyc$^b$(C1-C3 alkyl)OCH$_2$—; hetCyc$^b$ is as defined for Formula I; $R^c$ is hydrogen or C1-C6 alkyl; $R^d$ is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C(=O)—, (C1-C6 alkyl)C(=O)—, (R$^k$R$^l$N)C1-C6 alkyl- where R$^k$ and R$^l$ are independently H or C1-C6 alkyl, R$^m$R$^n$NC(=O)C1-C6 alkyl- where R$^m$ and R$^n$ are independently H or C1-C6 alkyl, PhCH$_2$—, (C1-C6 alkoxy)C1-C6 alkyl-, or hetCyc$^c$ where hetCyc$^c$ is a 4-6 membered heterocyclic ring having a ring heteroatom selected from N and O and optionally substituted with C1-C6 alkyl; n is 0, 1, 2, 3, 4, 5 or 6; m is 0 or 1; and E is hetCyc$^5$ where hetCyc$^5$ is as defined for Formula I. In one embodiment, m is 0. In one embodiment, n is 0 or 1. In one embodiment, $R^a$ is C1-C6 alkyl (optionally substituted with 1-3 fluoros). Non-limiting examples include the structures:

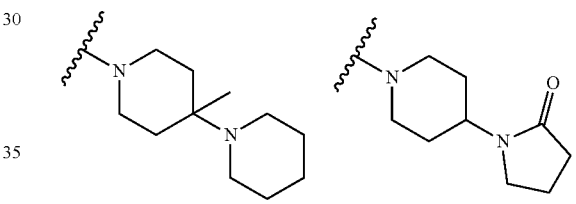

In one embodiment, Ring D is a saturated 4-7 membered heterocyclic ring having one ring heteroatom which is nitrogen; each $R^a$ is independently C1-C6 alkyl (optionally substituted with 1-3 fluoros), hydroxyC1-C6 alkyl or (C1-C6 alkoxy)C1-C6 alkyl-; $R^b$ is (a) hydroxy, (b) cyclopropyl, (c) hetCyc$^b$CH$_2$—, (d) R$^i$R$^j$NC(=O)CH$_2$OCH$_2$— where R$^i$ and R$^j$ are independently H or C1-C6 alkyl, (e) R$^c$R$^d$N—, (f) R$^c$R$^d$NCH$_2$—, (g) C1-C6 alkoxy-, (h) (C1-C4 alkyl)-C(=O)NH— wherein said alkyl portion is optionally substituted with hetCyc$^b$, hetAr$^a$, C1-C6 alkoxy- or R'R"N—, or said alkyl portion is optionally substituted with two substituents independently selected from R'R"N— and OH, where each R' and R" is independently hydrogen or C1-C6 alkyl, (i) (R'R"N)C1-C6 alkoxy(CH$_2$)$_n$— where n is 0 or 1 and R' and R" are independently hydrogen or C1-C6 alkyl, or (j) hetCyc$^b$(C1-C3 alkyl)OCH$_2$—; hetCyc$^b$ is as defined for Formula I; $R^c$ is hydrogen or C1-C6 alkyl; $R^d$ is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C(=O)—, (C1-C6 alkyl)C(=O)—, (R$^k$R$^l$N)C1-C6 alkyl- where R$^k$ and R$^l$ are independently H or C1-C6 alkyl, R$^m$R$^n$NC(=O)C1-C6 alkyl- where R$^m$ and R$^n$ are independently H or C1-C6 alkyl, PhCH$_2$—, (C1-C6 alkoxy)C1-C6 alkyl-, or hetCyc$^c$ where hetCyc$^c$ is a 4-6 membered heterocyclic ring having a ring heteroatom selected from N and O and optionally substituted with C1-C6 alkyl; n is 0, 1, 2, 3, 4, 5 or 6; m is 0 or 1; and E is C1-C6 alkoxy. In one embodiment, n is 0. In one embodiment, m is 0 or 1. In one embodiment, $R^b$ is $R^cR^dN$— where $R^c$ is H and $R^d$ is H. Non-limiting examples include the structures:

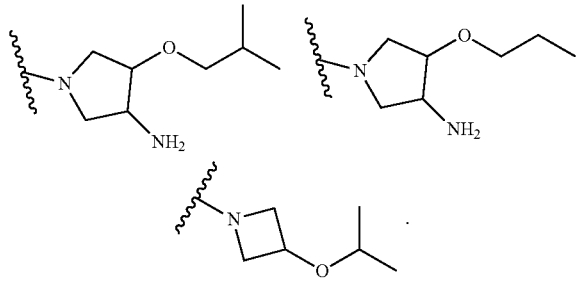

In one embodiment, Ring D is a saturated 4-7 membered heterocyclic ring having one ring heteroatom which is nitrogen; each $R^a$ is independently C1-C6 alkyl (optionally substituted with 1-3 fluoros), hydroxyC1-C6 alkyl or (C1-C6 alkoxy)C1-C6 alkyl-; $R^b$ is (a) hydroxy, (b) cyclopropyl, (c) hetCyc$^b$CH$_2$—, (d) R$^i$R$^j$NC(=O)CH$_2$OCH$_2$— where R$^i$ and R$^j$ are independently H or C1-C6 alkyl, (e) R$^c$R$^d$N—, (f) R$^c$R$^d$NCH$_2$—, (g) C1-C6 alkoxy-, (h) (C1-C4 alkyl)-C(=O)NH— wherein said alkyl portion is optionally substituted with hetCyc$^b$, hetAr$^a$, C1-C6 alkoxy- or R'R"N—, or said alkyl portion is optionally substituted with two substituents independently selected from R'R"N— and OH, where each R' and R" is independently hydrogen or C1-C6 alkyl, (i) (R'R"N)C1-C6 alkoxy(CH$_2$)$_n$— where n is 0 or 1 and R' and R" are independently hydrogen or C1-C6 alkyl, or (j) hetCyc$^b$(C1-C3 alkyl)OCH$_2$—; hetCyc$^b$ is as defined for Formula I; R is hydrogen or C1-C6 alkyl; $R^d$ is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C(=O)—, (C1-C6 alkyl)C(=O)—, (R$^k$R$^l$N)C1-C6 alkyl- where R$^k$ and R$^l$ are independently H or C1-C6 alkyl, R$^m$R$^n$NC(=O)C1-C6 alkyl- where R$^m$ and R$^n$ are independently H or C1-C6 alkyl, PhCH$_2$—, (C1-C6 alkoxy)C1-C6 alkyl-, or hetCyc$^c$ where hetCyc$^c$ is a 4-6 membered heterocyclic ring having a ring heteroatom selected from N and O and optionally substituted with C1-C6 alkyl; n is 0, 1, 2, 3, 4, 5 or 6; m is 0 or 1; and E is Ar$^1$(C1-C6 alkyl)-O— where Ar$^1$ is as defined for Formula I. In one embodiment, Ar$^1$ is unsubstituted. In one embodiment, n is 0. In one embodiment, m is 0. Non-limiting examples include the structures:

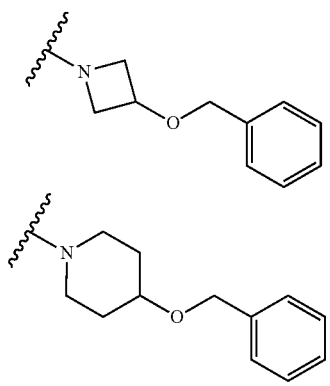

In one embodiment, Ring D is a saturated 4-7 membered heterocyclic ring having one ring heteroatom which is nitrogen; each $R^a$ is independently C1-C6 alkyl (optionally substituted with 1-3 fluoros), hydroxyC1-C6 alkyl or (C1-C6 alkoxy)C1-C6 alkyl-; $R^b$ is (a) hydroxy, (b) cyclopropyl, (c) hetCyc$^b$CH$_2$—, (g) C1-C6 alkoxy-, (h) (C1-C4 alkyl)-C(=O)NH— wherein said alkyl portion is optionally substituted with hetCyc$^b$, hetAr$^a$, C1-C6 alkoxy- or R'R"N—, or said alkyl portion is optionally substituted with two substituents independently selected from R'R"N— and OH, where each R' and R" is independently hydrogen or C1-C6 alkyl, (i) (R'R"N)C1-C6 alkoxy(CH$_2$)$_n$— where n is 0 or 1 and R' and R" are independently hydrogen or C1-C6 alkyl, or (j) hetCyc$^b$(C1-C3 alkyl)OCH$_2$—; hetCyc$^b$ is as defined for Formula I; (d) R$^i$R$^j$NC(=O)CH$_2$OCH$_2$— where R$^i$ and R$^j$ are independently H or C1-C6 alkyl, (e) R$^c$R$^d$N—, or (f) R$^c$R$^d$NCH$_2$—; R$^c$ is hydrogen or C1-C6 alkyl; $R^d$ is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C(=O)—, (C1-C6 alkyl)C(=O)—, (R$^k$R$^l$N)C1-C6 alkyl- where R$^k$ and R$^l$ are independently H or C1-C6 alkyl, R$^m$R$^n$NC(=O)C1-C6 alkyl- where R$^m$ and R$^n$ are independently H or C1-C6 alkyl, PhCH$_2$—, (C1-C6 alkoxy)C1-C6 alkyl-, or hetCyc$^c$ where hetCyc$^c$ is a 4-6 membered heterocyclic ring having a ring heteroatom selected from N and O and optionally substituted with C1-C6 alkyl; n is 0, 1, 2, 3, 4, 5 or 6; m is 0 or 1; and E is hetAr$^2$(C1-C6 alkyl)-O— where hetAr$^2$ is as defined for Formula I. In one embodiment, hetAr$^2$ is a 5-6-membered heteroaryl ring. In one embodiment, hetAr$^2$ is unsubstituted. In one embodiment, n is 0. In one embodiment, m is 0. Non-limiting examples include the structures:

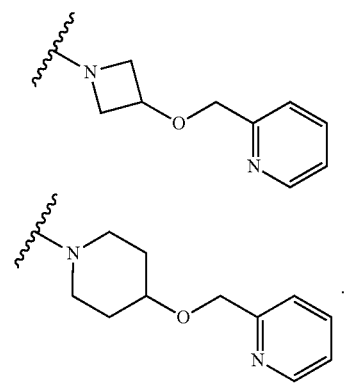

In one embodiment, Ring D is a saturated 4-7 membered heterocyclic ring having one ring heteroatom which is nitrogen; each $R^a$ is independently C1-C6 alkyl (optionally substituted with 1-3 fluoros), hydroxyC1-C6 alkyl or (C1-C6 alkoxy)C1-C6 alkyl-; $R^b$ is (a) hydroxy, (b) cyclopropyl, (c) hetCyc$^b$CH$_2$—, (d) R$^i$R$^j$NC(=O)CH$_2$OCH$_2$— where R$^i$ and R$^j$ are independently H or C1-C6 alkyl, (e) R$^c$R$^d$N—, (f) R$^c$R$^d$NCH$_2$—, (g) C1-C6 alkoxy-, (h) (C1-C4 alkyl)-C(=O)NH— wherein said alkyl portion is optionally substituted with hetCyc$^b$, hetAr$^a$, C1-C6 alkoxy- or R'R"N—, or said alkyl portion is optionally substituted with two substituents independently selected from R'R"N— and OH, where each R' and R" is independently hydrogen or C1-C6 alkyl, (i) (R'R"N)C1-C6 alkoxy(CH$_2$)$_n$— where n is 0 or 1 and R' and R" are independently hydrogen or C1-C6 alkyl, or (j) hetCyc$^b$(C1-C3 alkyl)OCH$_2$—; hetCyc$^b$ is as defined for Formula I; R$^c$ is hydrogen or C1-C6 alkyl; $R^d$ is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C (=O)—, (C1-C6 alkyl)C(=O)—, ($R^kR^lN$)C1-C6 alkyl- where $R^k$ and $R^l$ are independently H or C1-C6 alkyl, $R^mR^nNC$(=O)C1-C6 alkyl- where $R^m$ and $R^n$ are independently H or C1-C6 alkyl, PhCH$_2$—, (C1-C6 alkoxy)C1-C6 alkyl-, or hetCyc$^c$ where hetCyc$^c$ is a 4-6 membered heterocyclic ring having a ring heteroatom selected from N and O and optionally substituted with C1-C6 alkyl; n is 0, 1, 2, 3, 4, 5 or 6; m is 0 or 1; and E is hetAr$^2$—O—C1-C6 alkyl- where hetAr$^2$ is as defined for Formula I. In one embodiment, hetAr$^2$ is a 5-6-membered heteroaryl ring. In one embodiment, hetAr$^2$ is unsubstituted. In one embodiment, n is 0. In one embodiment, m is 0. Non-limiting examples include the structures:

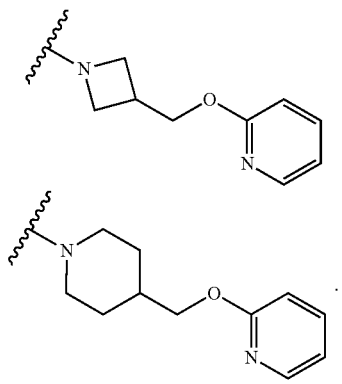

In one embodiment, Ring D is a saturated 4-7 membered heterocyclic ring having one ring heteroatom which is nitrogen; each $R^a$ is independently C1-C6 alkyl (optionally substituted with 1-3 fluoros), hydroxyC1-C6 alkyl or (C1-C6 alkoxy)C1-C6 alkyl-; $R^b$ is (a) hydroxy, (b) cyclopropyl, (c) hetCyc$^b$CH$_2$—, (d) R$^i$R$^j$NC(=O)CH$_2$OCH$_2$— where R$^i$ and R$^j$ are independently H or C1-C6 alkyl, (e) R$^c$R$^d$N—, (f) R$^c$R$^d$NCH$_2$—, (g) C1-C6 alkoxy-, (h) (C1-C4 alkyl)-C(=O)NH— wherein said alkyl portion is optionally substituted with hetCyc$^b$, hetAr$^a$, C1-C6 alkoxy- or R'R"N—, or said alkyl portion is optionally substituted with two substituents independently selected from R'R"N— and OH, where each R' and R" is independently hydrogen or C1-C6 alkyl, (i) (R'R"N)C1-C6 alkoxy(CH$_2$)$_n$— where n is 0 or 1 and R' and R" are independently hydrogen or C1-C6 alkyl, or (j) hetCyc$^b$(C1-C3 alkyl)OCH$_2$—; hetCyc$^b$ is as defined for Formula I; R$^c$ is hydrogen or C1-C6 alkyl; R$^d$ is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C (=O)—, (C1-C6 alkyl)C(=O)—, ($R^kR^lN$)C1-C6 alkyl- where $R^k$ and $R^l$ are independently H or C1-C6 alkyl, $R^mR^nNC$(=O)C1-C6 alkyl- where $R^m$ and $R^n$ are independently H or C1-C6 alkyl, PhCH$_2$—, (C1-C6 alkoxy)C1-C6 alkyl-, or hetCyc$^c$ where hetCyc$^c$ is a 4-6 membered heterocyclic ring having a ring heteroatom selected from N and O and optionally substituted with C1-C6 alkyl; n is 0, 1, 2, 3, 4, 5 or 6; m is 0 or 1; and E is Ar$^1$(C1-C6 alkyl)NR$^g$— where Ar$^1$ and R$^g$ are as defined for Formula I. In one embodiment, Ar$^1$ is unsubstituted or substituted with one or more halogens. In one embodiment, m is 0. In one embodiment, n is 0 or 1. In one embodiment, R$^1$ is C1-C6 alkyl (optionally substituted with 1-3 fluoros). Non-limiting examples include the structures:

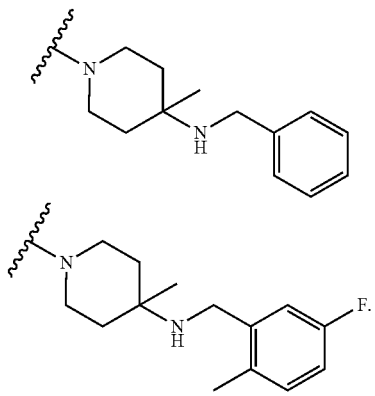

In one embodiment, Ring D is a saturated 4-7 membered heterocyclic ring having one ring heteroatom which is nitrogen; each $R^a$ is independently C1-C6 alkyl (optionally substituted with 1-3 fluoros), hydroxyC1-C6 alkyl or (C1-C6 alkoxy)C1-C6 alkyl-; $R^b$ is (a) hydroxy, (b) cyclopropyl, (c) hetCyc$^b$CH$_2$—, (d) R$^i$R$^j$NC(=O)CH$_2$OCH$_2$— where R$^i$ and R$^j$ are independently H or C1-C6 alkyl, (e) R$^c$R$^d$N—, (f) R$^c$R$^d$NCH$_2$—, (g) C1-C6 alkoxy-, (h) (C1-C4 alkyl)-C(=O)NH— wherein said alkyl portion is optionally substituted with hetCyc$^b$, hetAr$^a$, C1-C6 alkoxy- or R'R"N—, or said alkyl portion is optionally substituted with two substituents independently selected from R'R"N— and OH, where each R' and R" is independently hydrogen or C1-C6 alkyl, (i) (R'R"N)C1-C6 alkoxy(CH$_2$)$_n$— where n is 0 or 1 and R' and R" are independently hydrogen or C1-C6 alkyl, or (j) hetCyc$^b$(C1-C3 alkyl)OCH$_2$—; hetCyc$^b$ is as defined for Formula I; R$^c$ is hydrogen or C1-C6 alkyl; R$^d$ is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C (=O)—, (C1-C6 alkyl)C(=O)—, ($R^kR^lN$)C1-C6 alkyl- where $R^k$ and $R^l$ are independently H or C1-C6 alkyl, $R^mR^nNC$(=O)C1-C6 alkyl- where $R^m$ and $R^n$ are independently H or C1-C6 alkyl, PhCH$_2$—, (C1-C6 alkoxy)C1-C6 alkyl-, or hetCyc$^c$ where hetCyc$^c$ is a 4-6 membered heterocyclic ring having a ring heteroatom selected from N and O and optionally substituted with C1-C6 alkyl; n is 0, 1, 2, 3, 4, 5 or 6; m is 0 or 1; and E is hetAr$^2$—S— where hetAr$^2$ is as defined for Formula I. In one embodiment, hetAr$^2$ is a 5-6-membered heteroaryl ring. In one embodiment, hetAr$^2$ is unsubstituted. In one embodiment, n is 0. In one embodiment, m is 0. A non-limiting example is the structure:

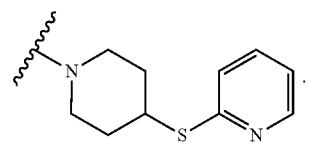 [SMILES: *N1CCC(Sc2ccccn2)CC1]

In one embodiment, Ring D is a saturated 4-7 membered heterocyclic ring having one ring heteroatom which is nitrogen; each $R^a$ is independently C1-C6 alkyl (optionally substituted with 1-3 fluoros), hydroxyC1-C6 alkyl or (C1-C6 alkoxy)C1-C6 alkyl-; $R^b$ is (a) hydroxy, (b) cyclopropyl, (c) hetCyc$^b$CH$_2$—, (d) R$^i$R$^j$NC(=O)CH$_2$OCH$_2$— where R$^i$ and R$^j$ are independently H or C1-C6 alkyl, (e) R$^c$R$^d$N—, (f) R$^c$R$^d$NCH$_2$—, (g) C1-C6 alkoxy-, (h) (C1-C4 alkyl)-C(=O)NH— wherein said alkyl portion is optionally substituted with hetCyc$^b$, hetAr$^a$, C1-C6 alkoxy- or R'R"N—, or said alkyl portion is optionally substituted with two substituents independently selected from R'R"N— and OH, where each R' and R" is independently hydrogen or C1-C6 alkyl, (i) (R'R"N)C1-C6 alkoxy(CH$_2$)$_n$— where n is 0 or 1 and R' and R" are independently hydrogen or C1-C6 alkyl, or (j) hetCyc$^b$(C1-C3 alkyl)OCH$_2$—; hetCyc$^b$ is as defined for Formula I; R$^c$ is hydrogen or C1-C6 alkyl; R$^d$ is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C(=O)—, (C1-C6 alkyl)C(=O)—, (R$^k$R$^l$N)C1-C6 alkyl- where R$^k$ and R$^l$ are independently H or C1-C6 alkyl, R$^m$R$^n$NC(=O)C1-C6 alkyl- where R$^m$ and R$^n$ are independently H or C1-C6 alkyl, PhCH$_2$—, (C1-C6 alkoxy)C1-C6 alkyl-, or hetCyc$^c$ where hetCyc$^c$ is a 4-6 membered heterocyclic ring having a ring heteroatom selected from N and O and optionally substituted with C1-C6 alkyl; n is 0, 1, 2, 3, 4, 5 or 6; m is 0 or 1; and E is Ar$^2$SO$_2$NR(CH$_2$)$_p$— where p is 0 or 1, R$^g$ is H or C1-C6 alkyl, and Ar$^2$ is as defined for Formula I. In one embodiment, p is 0. In one embodiment, p is 1. In one embodiment, Ar$^2$ is phenyl optionally substituted with one or more substituents independently selected from the group consisting of halogen, CN, C1-C6 alkyl (optionally substituted with 1-3 fluoros), C1-C6 alkoxy (optionally substituted with 1-3 fluoros), (C1-C6 alkoxy)C1-C6 alkyl- (optionally substituted with 1-3 fluoros), C3-C6 cycloalkyl, and R$^g$R$^h$N— where R$^g$ and R$^h$ are independently H or C1-C6 alkyl. In one embodiment, Ar$^2$ is phenyl optionally substituted with one or more independently selected C1-C6 alkyl (optionally substituted with 1-3 fluoros) substituents. In one embodiment, m is 0 or 1. In one embodiment, n is 0. Non-limiting examples include the structures:

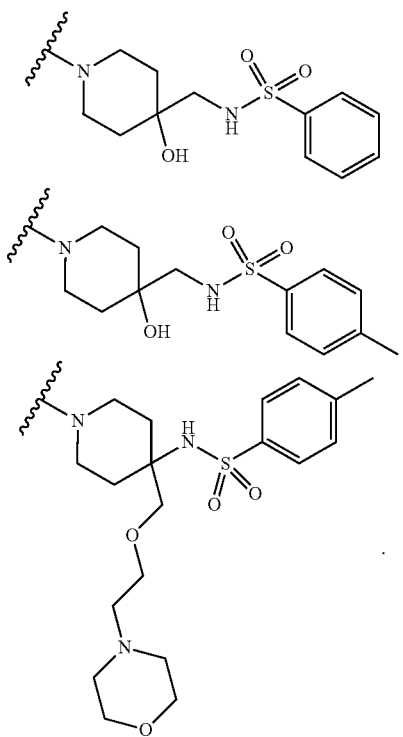

In one embodiment, Ring D is a saturated 4-7 membered heterocyclic ring having one ring heteroatom which is nitrogen; each R$^a$ is independently C1-C6 alkyl (optionally substituted with 1-3 fluoros), hydroxyC1-C6 alkyl or (C1-C6 alkoxy)C1-C6 alkyl-; R$^b$ is (a) hydroxy, (b) cyclopropyl, (c) hetCyc$^b$CH$_2$—, (d) R$^i$R$^j$NC(=O)CH$_2$OCH$_2$— where R$^i$ and R$^j$ are independently H or C1-C6 alkyl, (e) R$^c$R$^d$N—, (f) R$^c$R$^d$NCH$_2$—, (g) C1-C6 alkoxy-, (h) (C1-C4 alkyl)-C(=O)NH— wherein said alkyl portion is optionally substituted with hetCyc$^b$, hetAr$^a$, C1-C6 alkoxy- or R'R"N—, or said alkyl portion is optionally substituted with two substituents independently selected from R'R"N— and OH, where each R' and R" is independently hydrogen or C1-C6 alkyl, (i) (R'R"N)C1-C6 alkoxy(CH$_2$)$_n$— where n is 0 or 1 and R' and R" are independently hydrogen or C1-C6 alkyl, or (j) hetCyc$^b$(C1-C3 alkyl)OCH$_2$—; hetCyc$^b$ is as defined for Formula I; R$^c$ is hydrogen or C1-C6 alkyl; R$^d$ is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C(=O)—, (C1-C6 alkyl)C(=O)—, (R$^k$R$^l$N)C1-C6 alkyl- where R$^k$ and R$^l$ are independently H or C1-C6 alkyl, R$^m$R$^n$NC(=O)C1-C6 alkyl- where R$^m$ and R$^n$ are independently H or C1-C6 alkyl, PhCH$_2$—, (C1-C6 alkoxy)C1-C6 alkyl-, or hetCyc$^c$ where hetCyc$^c$ is a 4-6 membered heterocyclic ring having a ring heteroatom selected from N and O and optionally substituted with C1-C6 alkyl; n is 0, 1, 2, 3, 4, 5 or 6; m is 0 or 1; and E is (C1-C6 alkoxy)C(=O)—. In one embodiment, m is 0. In one embodiment, n is 0 or 1. In one embodiment, R$^a$ is hydroxyC1-C6 alkyl. Non-limiting examples include the structures:

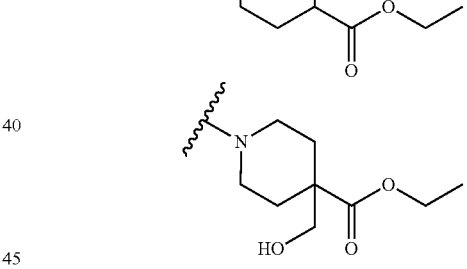

In one embodiment, Ring D is a saturated 4-7 membered heterocyclic ring having one ring heteroatom which is nitrogen; each R$^a$ is independently C1-C6 alkyl (optionally substituted with 1-3 fluoros), hydroxyC1-C6 alkyl or (C1-C6 alkoxy)C1-C6 alkyl-; R$^b$ is (a) hydroxy, (b) cyclopropyl, (c) hetCyc$^b$CH$_2$—, (d) R$^i$R$^j$NC(=O)CH$_2$OCH$_2$— where R$^i$ and R$^j$ are independently H or C1-C6 alkyl, (e) R$^c$R$^d$N—, (f) R$^c$R$^d$NCH$_2$—, (g) C1-C6 alkoxy-, (h) (C1-C4 alkyl)-C(=O)NH— wherein said alkyl portion is optionally substituted with hetCyc$^b$, hetAr$^a$, C1-C6 alkoxy- or R'R"N—, or said alkyl portion is optionally substituted with two substituents independently selected from R'R"N— and OH, where each R' and R" is independently hydrogen or C1-C6 alkyl, (i) (R'R"N)C1-C6 alkoxy(CH$_2$)$_n$— where n is 0 or 1 and R' and R" are independently hydrogen or C1-C6 alkyl, or (j) hetCyc$^b$(C1-C3 alkyl)OCH$_2$—; hetCyc$^b$ is as defined for Formula I; R$^c$ is hydrogen or C1-C6 alkyl; R$^d$ is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C(=O)—, (C1-C6 alkyl)C(=O)—, (R$^k$R$^l$N)C1-C6 alkyl-where $R^k$ and $R^l$ are independently H or C1-C6 alkyl, $R^m R^n NC(=O)$C1-C6 alkyl- where $R^m$ and $R^n$ are independently H or C1-C6 alkyl, $PhCH_2$—, (C1-C6 alkoxy)C1-C6 alkyl-, or hetCyc$^c$ where hetCyc$^c$ is a 4-6 membered heterocyclic ring having a ring heteroatom selected from N and O and optionally substituted with C1-C6 alkyl; n is 0, 1, 2, 3, 4, 5 or 6; m is 0 or 1; and E is (C1-C6 alkyl)NR$^g$C(=O)O— where R$^g$ is H or C1-C6 alkyl. In one embodiment, m is 0. In one embodiment, n is 0 or 1. In one embodiment, R$^a$ is C1-C6 alkyl (optionally substituted with 1-3 fluoros). Non-limiting examples include the structures:

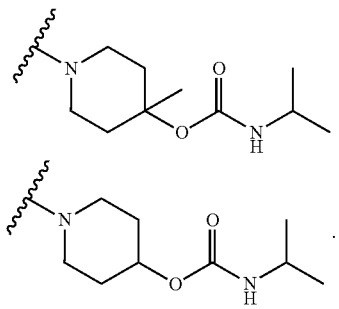

In one embodiment, Ring D is a saturated 4-7 membered heterocyclic ring having one ring heteroatom which is nitrogen; each R$^a$ is independently C1-C6 alkyl (optionally substituted with 1-3 fluoros), hydroxyC1-C6 alkyl or (C1-C6 alkoxy)C1-C6 alkyl-; R$^b$ is (a) hydroxy, (b) cyclopropyl, (c) hetCyc$^b$CH$_2$—, (d) R$^i$R$^j$NC(=O)CH$_2$OCH$_2$— where R$^i$ and R$^j$ are independently H or C1-C6 alkyl, (e) R$^c$R$^d$N—, (f) R$^c$R$^d$NCH$_2$—, (g) C1-C6 alkoxy-, (h) (C1-C4 alkyl)-C(=O)NH— wherein said alkyl portion is optionally substituted with hetCyc$^b$, hetAr$^a$, C1-C6 alkoxy- or R'R"N—, or said alkyl portion is optionally substituted with two substituents independently selected from R'R"N— and OH, where each R' and R" is independently hydrogen or C1-C6 alkyl, (i) (R'R"N)C1-C6 alkoxy(CH$_2$)$_n$— where n is 0 or 1 and R' and R" are independently hydrogen or C1-C6 alkyl, or (j) hetCyc$^b$(C1-C3 alkyl)OCH$_2$—; hetCyc$^b$ is as defined for Formula I; R$^c$ is hydrogen or C1-C6 alkyl; R$^d$ is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C(=O)—, (C1-C6 alkyl)C(=O)—, (R$^k$R$^l$N)C1-C6 alkyl- where R$^k$ and R$^l$ are independently H or C1-C6 alkyl, $R^m R^n NC(=O)$C1-C6 alkyl- where $R^m$ and $R^n$ are independently H or C1-C6 alkyl, PhCH$_2$—, (C1-C6 alkoxy)C1-C6 alkyl-, or hetCyc$^c$ where hetCyc$^c$ is a 4-6 membered heterocyclic ring having a ring heteroatom selected from N and O and optionally substituted with C1-C6 alkyl; n is 0, 1, 2, 3, 4, 5 or 6; m is 0 or 1; and E is (C1-C6 alkyl)NR$^g$SO$_2$— where R$^g$ is H or C1-C6 alkyl. In one embodiment, m is 0. In one embodiment, n is 0. A non-limiting example is the structure:

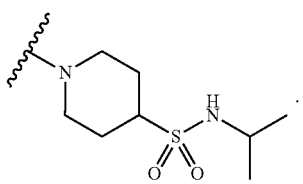 [SMILES: *N1CCC(S(=O)(=O)NC(C)C)CC1]

In one embodiment, Ring D is a saturated 4-7 membered heterocyclic ring having one ring heteroatom which is nitrogen; each R$^a$ is independently C1-C6 alkyl (optionally substituted with 1-3 fluoros), hydroxyC1-C6 alkyl or (C1-C6 alkoxy)C1-C6 alkyl-; R$^b$ is (a) hydroxy, (b) cyclopropyl, (c) hetCyc$^b$CH$_2$—, (d) R$^i$R$^j$NC(=O)CH$_2$OCH$_2$— where R$^i$ and R$^j$ are independently H or C1-C6 alkyl, (e) R$^c$R$^d$N—, (f) R$^c$R$^d$NCH$_2$—, (g) C1-C6 alkoxy-, (h) (C1-C4 alkyl)-C(=O)NH— wherein said alkyl portion is optionally substituted with hetCyc$^b$, hetAr$^a$, C1-C6 alkoxy- or R'R"N—, or said alkyl portion is optionally substituted with two substituents independently selected from R'R"N— and OH, where each R' and R" is independently hydrogen or C1-C6 alkyl, (i) (R'R"N)C1-C6 alkoxy(CH$_2$)$_n$— where n is 0 or 1 and R' and R" are independently hydrogen or C1-C6 alkyl, or (j) hetCyc$^b$(C1-C3 alkyl)OCH$_2$—; hetCyc$^b$ is as defined for Formula I; R$^c$ is hydrogen or C1-C6 alkyl; R$^d$ is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C(=O)—, (C1-C6 alkyl)C(=O)—, (R$^k$R$^l$N)C1-C6 alkyl- where R$^k$ and R$^l$ are independently H or C1-C6 alkyl, $R^m R^n NC(=O)$C1-C6 alkyl- where $R^m$ and $R^n$ are independently H or C1-C6 alkyl, PhCH$_2$—, (C1-C6 alkoxy)C1-C6 alkyl-, or hetCyc$^c$ where hetCyc$^c$ is a 4-6 membered heterocyclic ring having a ring heteroatom selected from N and O and optionally substituted with C1-C6 alkyl; n is 0, 1, 2, 3, 4, 5 or 6; m is 0 or 1; and E is hetCyc$^5$C(=O)NR$^g$— where R$^g$ is H or C1-C6 alkyl and hetCyc$^5$ is as defined for Formula I. In one embodiment, hetCyc$^5$ is a 5-6 membered heterocyclic ring having a ring nitrogen atom. In one embodiment, m is 0 or 1. In one embodiment, n is 0. In one embodiment, R$^b$ is R$^c$R$^d$NCH$_2$— where R$^c$ and R$^d$ are as defined for Formula I. In one embodiment, R$^c$ and R$^d$ are hydrogen or C1-C6 alkyl. Non-liming examples include the structures:

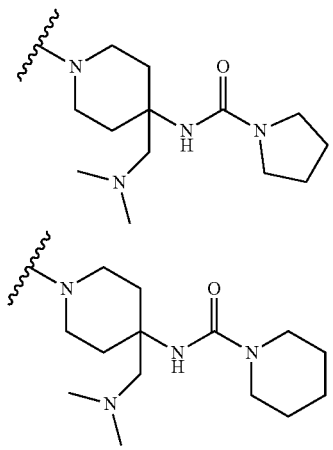

In one embodiment, Ring D is a saturated 4-7 membered heterocyclic ring having one ring heteroatom which is nitrogen; each R$^a$ is independently C1-C6 alkyl (optionally substituted with 1-3 fluoros), hydroxyC1-C6 alkyl or (C1-C6 alkoxy)C1-C6 alkyl-; R$^b$ is (a) hydroxy, (b) cyclopropyl, (c) hetCyc$^b$CH$_2$—, (d) R$^i$R$^j$NC(=O)CH$_2$OCH$_2$— where R$^i$ and R$^j$ are independently H or C1-C6 alkyl, (e) R$^c$R$^d$N—, (f) R$^c$R$^d$NCH$_2$—, (g) C1-C6 alkoxy-, (h) (C1-C4 alkyl)-C(=O)NH— wherein said alkyl portion is optionally substituted with hetCyc$^b$, hetAr$^a$, C1-C6 alkoxy- or R'R"N—, or said alkyl portion is optionally substituted with two substituents independently selected from R'R"N— and OH, where each R' and R" is independently hydrogen or C1-C6 alkyl, (i) (R'R"N)C1-C6 alkoxy(CH$_2$)$_n$— where n is 0 or 1 and R' and R" are independently hydrogen or C1-C6 alkyl, or (j) hetCyc$^b$(C1-C3 alkyl)OCH$_2$—; hetCyc$^b$ is as defined for Formula I; R$^c$ is hydrogen or C1-C6 alkyl; R$^d$ is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C(=O)—, (C1-C6 alkyl)C(=O)—, (R$^k$R$^l$N)C1-C6 alkyl- where R$^k$ and R$^l$ are independently H or C1-C6 alkyl, R$^m$R"NC(=O)C1-C6 alkyl- where R$^m$ and R$^n$ are independently H or C1-C6 alkyl, PhCH$_2$—, (C1-C6 alkoxy)C1-C6 alkyl-, or hetCyc$^c$ where hetCyc$^c$ is a 4-6 membered heterocyclic ring having a ring heteroatom selected from N and O and optionally substituted with C1-C6 alkyl; n is 0, 1, 2, 3, 4, 5 or 6; m is 0 or 1; and E is Q-NR$^h$(C1-C3 alkyl)C(=O)NR$^g$— where R$^g$ and R$^h$ are independently H or C1-C6 alkyl and Q is H, C1-C6 alkyl or (C1-C6 alkyl)OC(=O)—. In one embodiment, m is 0. In one embodiment, n is 0 or 1. In one embodiment, R$^a$ is C1-C6 alkyl (optionally substituted with 1-3 fluoros). Non-limiting examples include the structures:

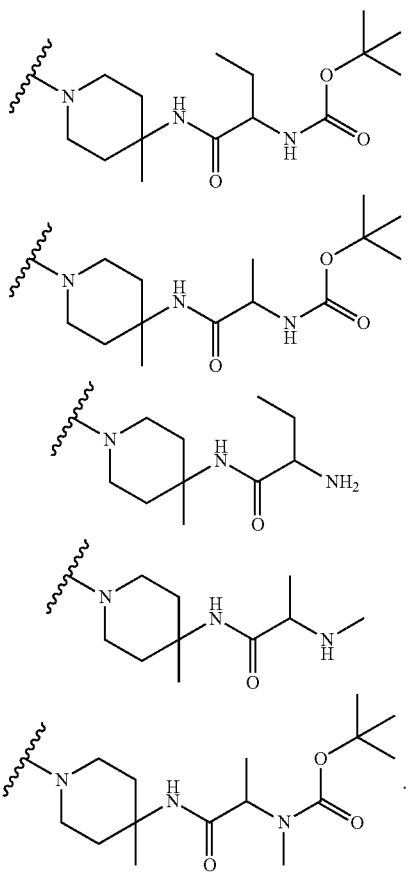

In one embodiment, Ring D is a saturated 4-7 membered heterocyclic ring having one ring heteroatom which is nitrogen; each R$^a$ is independently C1-C6 alkyl (optionally substituted with 1-3 fluoros), hydroxyC1-C6 alkyl or (C1-C6 alkoxy)C1-C6 alkyl-; R$^b$ is (a) hydroxy, (b) cyclopropyl, (c) hetCyc$^b$CH$_2$—, (d) R$^i$R$^j$NC(=O)CH$_2$OCH$_2$— where R$^i$ and R$^j$ are independently H or C1-C6 alkyl, (e) R$^c$R$^d$N—, (f) R$^c$R$^d$NCH$_2$—, (g) C1-C6 alkoxy-, (h) (C1-C4 alkyl)-C(=O)NH— wherein said alkyl portion is optionally substituted with hetCyc$^b$, hetAr$^a$, C1-C6 alkoxy- or R'R"N—, or said alkyl portion is optionally substituted with two substituents independently selected from R'R"N— and OH, where each R' and R" is independently hydrogen or C1-C6 alkyl, (i) (R'R"N)C1-C6 alkoxy(CH$_2$)$_n$— where n is 0 or 1 and R' and R" are independently hydrogen or C1-C6 alkyl, or (j) hetCyc$^b$(C1-C3 alkyl)OCH$_2$—; hetCyc$^b$ is as defined for Formula I; R$^c$ is hydrogen or C1-C6 alkyl; R$^d$ is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C(=O)—, (C1-C6 alkyl)C(=O)—, (R$^k$R$^l$N)C1-C6 alkyl- where R$^k$ and R$^l$ are independently H or C1-C6 alkyl, R$^m$R"NC(=O)C1-C6 alkyl- where R$^m$ and R$^n$ are independently H or C1-C6 alkyl, PhCH$_2$—, (C1-C6 alkoxy)C1-C6 alkyl-, or hetCyc$^c$ where hetCyc$^c$ is a 4-6 membered heterocyclic ring having a ring heteroatom selected from N and O and optionally substituted with C1-C6 alkyl; n is 0, 1, 2, 3, 4, 5 or 6; m is 0 or 1; and E is (pp)

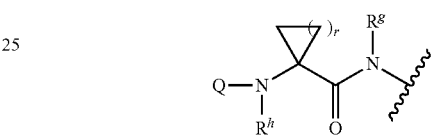

where R$^g$ and R$^h$ are independently H or C1-C6 alkyl, Q is H, C1-C6 alkyl or (C1-C6 alkyl)OC(=O)— and r is 1, 2, 3 or 4. In one embodiment, m is 0. In one embodiment, n is 0 or 1. In one embodiment, R$^a$ is C1-C6 alkyl (optionally substituted with 1-3 fluoros). Non-limiting examples include the structures:

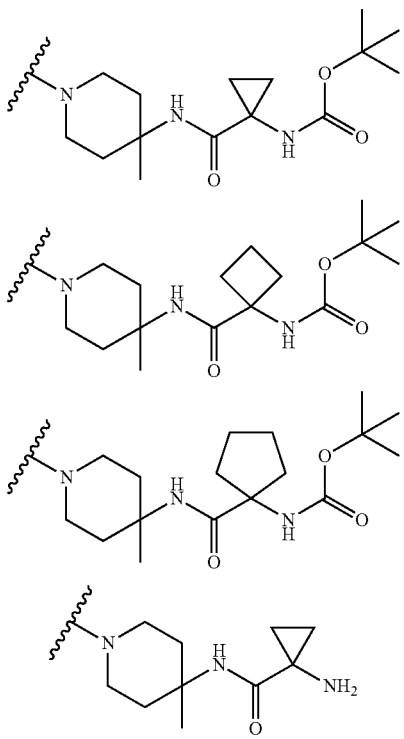

117
-continued

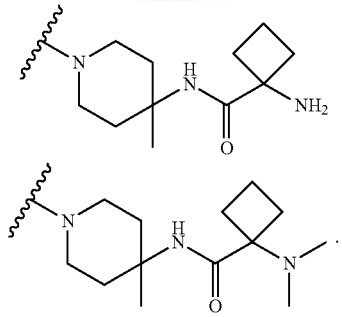

118
-continued

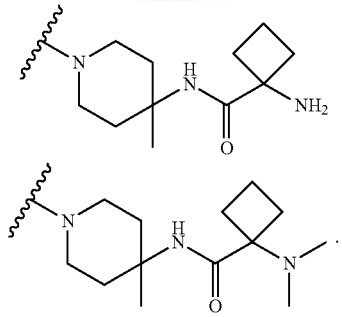

In one embodiment, Ring D is a saturated 4-7 membered heterocyclic ring having one ring heteroatom which is nitrogen; each $R^a$ is independently C1-C6 alkyl (optionally substituted with 1-3 fluoros), hydroxyC1-C6 alkyl or (C1-C6 alkoxy)C1-C6 alkyl-; $R^b$ is (a) hydroxy, (b) cyclopropyl, (c) hetCyc$^b$CH$_2$—, (d) R$^i$R$^j$NC(=O)CH$_2$OCH$_2$— where R$^i$ and R$^j$ are independently H or C1-C6 alkyl, (e) R$^c$R$^d$N—, (f) R$^c$R$^d$NCH$_2$—, (g) C1-C6 alkoxy-, (h) (C1-C4 alkyl)-C(=O)NH— wherein said alkyl portion is optionally substituted with hetCyc$^b$, hetAr$^a$, C1-C6 alkoxy- or R'R"N—, or said alkyl portion is optionally substituted with two substituents independently selected from R'R"N— and OH, where each R' and R" is independently hydrogen or C1-C6 alkyl, (i) (R'R"N)C1-C6 alkoxy(CH$_2$)$_n$— where n is 0 or 1 and R' and R" are independently hydrogen or C1-C6 alkyl, or (j) hetCyc$^b$(C1-C3 alkyl)OCH$_2$—; hetCyc$^b$ is as defined for Formula I; $R^c$ is hydrogen or C1-C6 alkyl; $R^d$ is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C(=O)—, (C1-C6 alkyl)C(=O)—, (R$^k$R$^l$N)C1-C6 alkyl- where R$^k$ and R$^l$ are independently H or C1-C6 alkyl, R$^m$R$^n$NC(=O)C1-C6 alkyl- where R$^m$ and R$^n$ are independently H or C1-C6 alkyl, PhCH$_2$—, (C1-C6 alkoxy)C1-C6 alkyl-, or hetCyc$^c$ where hetCyc$^c$ is a 4-6 membered heterocyclic ring having a ring heteroatom selected from N and O and optionally substituted with C1-C6 alkyl; n is 0, 1, 2, 3, 4, 5 or 6; m is 0 or 1; and E is

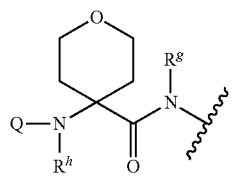

where $R^g$ and $R^h$ are independently H or C1-C6 alkyl and Q is H, C1-C6 alkyl or (C1-C6 alkyl)OC(=O)—. In one embodiment, m is 0. In one embodiment, n is 0 or 1. In one embodiment, $R^a$ is C1-C6 alkyl (optionally substituted with 1-3 fluoros). Non-limiting examples include the structures:

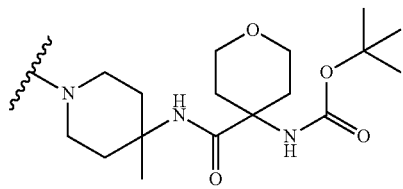

In one embodiment, Ring D is a saturated 4-7 membered heterocyclic ring having one ring heteroatom which is nitrogen; each $R^a$ is independently C1-C6 alkyl (optionally substituted with 1-3 fluoros), hydroxyC1-C6 alkyl or (C1-C6 alkoxy)C1-C6 alkyl-; $R^b$ is (a) hydroxy, (b) cyclopropyl, (c) hetCyc$^b$CH$_2$—, (d) R$^i$R$^j$NC(=O)CH$_2$OCH$_2$— where R$^i$ and R$^j$ are independently H or C1-C6 alkyl, (e) R$^c$R$^d$N—, (f) R$^c$R$^d$NCH$_2$—, (g) C1-C6 alkoxy-, (h) (C1-C4 alkyl)-C(=O)NH— wherein said alkyl portion is optionally substituted with hetCyc$^b$, hetAr$^a$, C1-C6 alkoxy- or R'R"N—, or said alkyl portion is optionally substituted with two substituents independently selected from R'R"N— and OH, where each R' and R" is independently hydrogen or C1-C6 alkyl, (i) (R'R"N)C1-C6 alkoxy(CH$_2$)$_n$— where n is 0 or 1 and R' and R" are independently hydrogen or C1-C6 alkyl, or (j) hetCyc$^b$(C1-C3 alkyl)OCH$_2$—; hetCyc$^b$ is as defined for Formula I; $R^c$ is hydrogen or C1-C6 alkyl; $R^d$ is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C(=O)—, (C1-C6 alkyl)C(=O)—, (R$^k$R$^l$N)C1-C6 alkyl- where R$^k$ and R$^l$ are independently H or C1-C6 alkyl, R$^m$R$^n$NC(=O)C1-C6 alkyl- where R$^m$ and R$^n$ are independently H or C1-C6 alkyl, PhCH$_2$—, (C1-C6 alkoxy)C1-C6 alkyl-, or hetCyc$^c$ where hetCyc$^c$ is a 4-6 membered heterocyclic ring having a ring heteroatom selected from N and O and optionally substituted with C1-C6 alkyl; n is 0, 1, 2, 3, 4, 5 or 6; m is 0 or 1; and E is

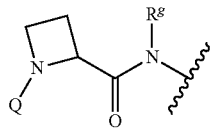

where $R^g$ is H or C1-C6 alkyl and Q is H, C1-C6 alkyl or (C1-C6 alkyl)OC(=O)—. In one embodiment, m is 0. In one embodiment, n is 0 or 1. In one embodiment, $R^a$ is C1-C6 alkyl (optionally substituted with 1-3 fluoros). Non-limiting examples include the structures:

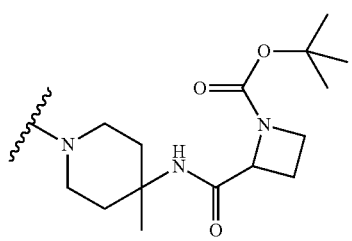

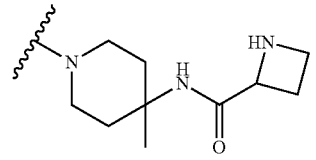

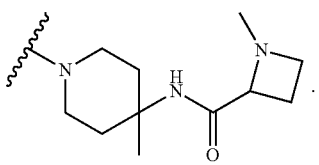

In one embodiment, Ring D is a saturated 4-7 membered heterocyclic ring having one ring heteroatom which is nitrogen; each $R^a$ is independently C1-C6 alkyl (optionally substituted with 1-3 fluoros), hydroxyC1-C6 alkyl or (C1-C6 alkoxy)C1-C6 alkyl-; $R^b$ is (a) hydroxy, (b) cyclopropyl, (c) hetCyc$^b$CH$_2$—, (d) R$^i$R$^j$NC(=O)CH$_2$OCH$_2$— where R$^i$ and R$^j$ are independently H or C1-C6 alkyl, (e) R$^c$R$^d$N—, (f) R$^c$R$^d$NCH$_2$—, (g) C1-C6 alkoxy-, (h) (C1-C4 alkyl)-C(=O)NH— wherein said alkyl portion is optionally substituted with hetCyc$^b$, hetAr$^a$, C1-C6 alkoxy- or R'R''N—, or said alkyl portion is optionally substituted with two substituents independently selected from R'R''N— and OH, where each R' and R'' is independently hydrogen or C1-C6 alkyl, (i) (R'R''N)C1-C6 alkoxy(CH$_2$)$_n$— where n is 0 or 1 and R' and R'' are independently hydrogen or C1-C6 alkyl, or (j) hetCyc$^b$(C1-C3 alkyl)OCH$_2$—; hetCyc$^b$ is as defined for Formula I; R$^c$ is hydrogen or C1-C6 alkyl; R$^d$ is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C(=O)—, (C1-C6 alkyl)C(=O)—, (R$^k$R$^l$N)C1-C6 alkyl- where R$^k$ and R$^l$ are independently H or C1-C6 alkyl, R$^m$R$^n$NC(=O)C1-C6 alkyl- where R$^m$ and R$^n$ are independently H or C1-C6 alkyl, PhCH$_2$—, (C1-C6 alkoxy)C1-C6 alkyl-, or hetCyc$^c$ where hetCyc$^c$ is a 4-6 membered heterocyclic ring having a ring heteroatom selected from N and O and optionally substituted with C1-C6 alkyl; n is 0, 1, 2, 3, 4, 5 or 6; m is 0 or 1; and E is R$^g$R$^h$N— where R$^g$ and R$^h$ are independently H or C1-C6 alkyl. In one embodiment, n is 0 or 1. In one embodiment, m is 0 or 1. In one embodiment, R$^b$ is hydroxy, C1-C6 alkoxy- or hetCyc$^b$(C1-C3 alkyl)OCH$_2$—, where hetCyc$^b$ is as defined for Formula I. In one embodiment, hetCyc$^b$ is a 5-6 membered heteroaryl ring having 1-2 ring heteroatoms independently selected from N and O. Non-limiting examples include the structures:

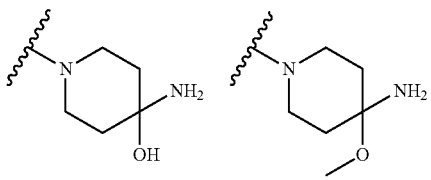

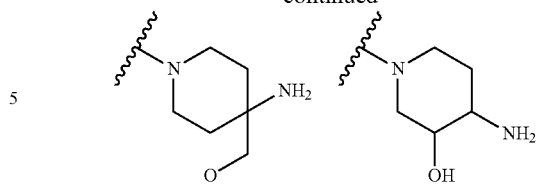

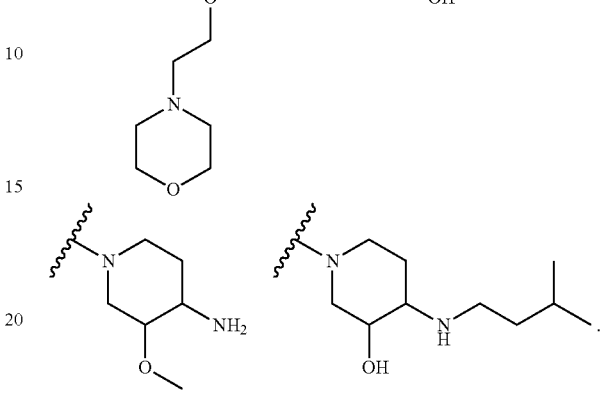

In one embodiment, Ring D is a saturated 4-7 membered heterocyclic ring having one ring heteroatom which is nitrogen; each $R^a$ is independently C1-C6 alkyl (optionally substituted with 1-3 fluoros), hydroxyC1-C6 alkyl or (C1-C6 alkoxy)C1-C6 alkyl-; $R^b$ is (a) hydroxy, (b) cyclopropyl, (c) hetCyc$^b$CH$_2$—, (d) R$^i$R$^j$NC(=O)CH$_2$OCH$_2$— where R$^i$ and R$^j$ are independently H or C1-C6 alkyl, (e) R$^c$R$^d$N—, (f) R$^c$R$^d$NCH$_2$—, (g) C1-C6 alkoxy-, (h) (C1-C4 alkyl)-C(=O)NH— wherein said alkyl portion is optionally substituted with hetCyc$^b$, hetAr$^a$, C1-C6 alkoxy- or R'R''N—, or said alkyl portion is optionally substituted with two substituents independently selected from R'R''N— and OH, where each R' and R'' is independently hydrogen or C1-C6 alkyl, (i) (R'R''N)C1-C6 alkoxy(CH$_2$)$_n$— where n is 0 or 1 and R' and R'' are independently hydrogen or C1-C6 alkyl, or (j) hetCyc$^b$(C1-C3 alkyl)OCH$_2$—; hetCyc$^b$ is as defined for Formula I; R$^c$ is hydrogen or C1-C6 alkyl; R$^d$ is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C(=O)—, (C1-C6 alkyl)C(=O)—, (R$^k$R$^l$N)C1-C6 alkyl- where R$^k$ and R$^l$ are independently H or C1-C6 alkyl, R$^m$R$^n$NC(=O)C1-C6 alkyl- where R$^m$ and R$^n$ are independently H or C1-C6 alkyl, PhCH$_2$—, (C1-C6 alkoxy)C1-C6 alkyl-, or hetCyc$^c$ where hetCyc$^c$ is a 4-6 membered heterocyclic ring having a ring heteroatom selected from N and O and optionally substituted with C1-C6 alkyl; n is 0, 1, 2, 3, 4, 5 or 6; m is 0 or 1; and E is (C3-C6 cycloalkyl)C(=O)NR$^g$— where the cycloalkyl is optionally and independently substituted with one or more halogens. A non-limiting example includes the structure:

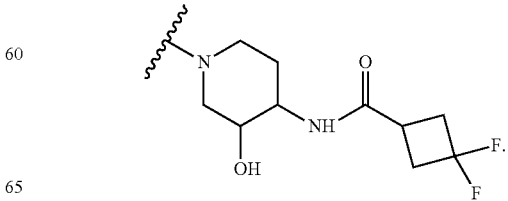

In one embodiment, Ring D is a saturated 4-7 membered heterocyclic ring having one ring heteroatom which is nitrogen; each $R^a$ is independently C1-C6 alkyl (optionally substituted with 1-3 fluoros), hydroxyC1-C6 alkyl or (C1-C6 alkoxy)C1-C6 alkyl-; $R^b$ is (a) hydroxy, (b) cyclopropyl, (c) hetCyc$^b$CH$_2$—, (d) R$^i$R$^j$NC(=O)CH$_2$OCH$_2$— where R$^i$ and R$^j$ are independently H or C1-C6 alkyl, (e) R$^c$R$^d$N—, (f) R$^c$R$^d$NCH$_2$—, (g) C1-C6 alkoxy-, (h) (C1-C4 alkyl)-C(=O)NH— wherein said alkyl portion is optionally substituted with hetCyc$^b$, hetAr$^a$, C1-C6 alkoxy- or R'R"N—, or said alkyl portion is optionally substituted with two substituents independently selected from R'R"N— and OH, where each R' and R" is independently hydrogen or C1-C6 alkyl, (i) (R'R"N)C1-C6 alkoxy(CH$_2$)$_n$— where n is 0 or 1 and R' and R" are independently hydrogen or C1-C6 alkyl, or (j) hetCyc$^b$(C1-C3 alkyl)OCH$_2$—; hetCyc$^b$ is as defined for Formula I; $R^c$ is hydrogen or C1-C6 alkyl; $R^d$ is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C(=O)—, (C1-C6 alkyl)C(=O)—, (R$^k$R$^l$N)C1-C6 alkyl- where $R^k$ and $R^l$ are independently H or C1-C6 alkyl, R'''R''NC(=O)C1-C6 alkyl- where R''' and R'' are independently H or C1-C6 alkyl, PhCH$_2$—, (C1-C6 alkoxy)C1-C6 alkyl-, or hetCyc$^c$ where hetCyc$^c$ is a 4-6 membered heterocyclic ring having a ring heteroatom selected from N and O and optionally substituted with C1-C6 alkyl; n is 0, 1, 2, 3, 4, 5 or 6; m is 0 or 1; and E is (C1-C6 alkyl)C(=O)NR$^g$CH$_2$— where $R^g$ is H or C1-C6 alkyl. A non-limiting example includes the structure:

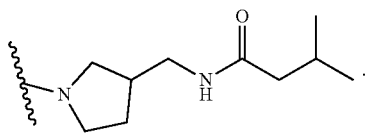 [SMILES: *N1CCC(CNC(=O)CC(C)C)C1]

In one embodiment, Ring D is a saturated 4-7 membered heterocyclic ring having one ring heteroatom which is nitrogen; each $R^a$ is independently C1-C6 alkyl (optionally substituted with 1-3 fluoros), hydroxyC1-C6 alkyl or (C1-C6 alkoxy)C1-C6 alkyl-; $R^b$ is (a) hydroxy, (b) cyclopropyl, (c) hetCyc$^b$CH$_2$—, (d) R$^i$R$^j$NC(=O)CH$_2$OCH$_2$— where R$^i$ and R$^j$ are independently H or C1-C6 alkyl, (e) R$^c$R$^d$N—, (f) R$^c$R$^d$NCH$_2$—, (g) C1-C6 alkoxy-, (h) (C1-C4 alkyl)-C(=O)NH— wherein said alkyl portion is optionally substituted with hetCyc$^b$, hetAr$^a$, C1-C6 alkoxy- or R'R"N—, or said alkyl portion is optionally substituted with two substituents independently selected from R'R"N— and OH, where each R' and R" is independently hydrogen or C1-C6 alkyl, (i) (R'R"N)C1-C6 alkoxy(CH$_2$)$_n$— where n is 0 or 1 and R' and R" are independently hydrogen or C1-C6 alkyl, or (j) hetCyc$^b$(C1-C3 alkyl)OCH$_2$—; hetCyc$^b$ is as defined for Formula I; $R^c$ is hydrogen or C1-C6 alkyl; $R^d$ is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C(=O)—, (C1-C6 alkyl)C(=O)—, (R$^k$R$^l$N)C1-C6 alkyl- where $R^k$ and $R^l$ are independently H or C1-C6 alkyl, R'''R''NC(=O)C1-C6 alkyl- where R''' and R'' are independently H or C1-C6 alkyl, PhCH$_2$—, (C1-C6 alkoxy)C1-C6 alkyl-, or hetCyc$^c$ where hetCyc$^c$ is a 4-6 membered heterocyclic ring having a ring heteroatom selected from N and O and optionally substituted with C1-C6 alkyl; n is 0, 1, 2, 3, 4, 5 or 6; m is 0 or 1; and E is C1-C6 alkyl)SO$_2$NR$^g$— where $R^g$ is H or C1-C6 alkyl. A non-limiting example includes the structure:

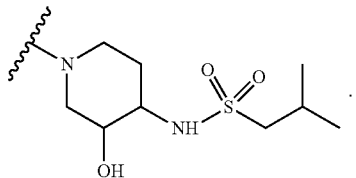 [SMILES: *N1CCC(NS(=O)(=O)CC(C)C)C(O)C1]

In one embodiment, Ring D is a saturated 7-8 membered bridged heterocyclic ring having one ring heteroatom which is nitrogen. The phrase "having one ring heteroatom which is nitrogen" when Ring D is a saturated 7-8 membered bridged heterocyclic ring means that the one ring nitrogen atom is the nitrogen atom shown in Ring D of Formula I. Non-limiting examples include rings such as

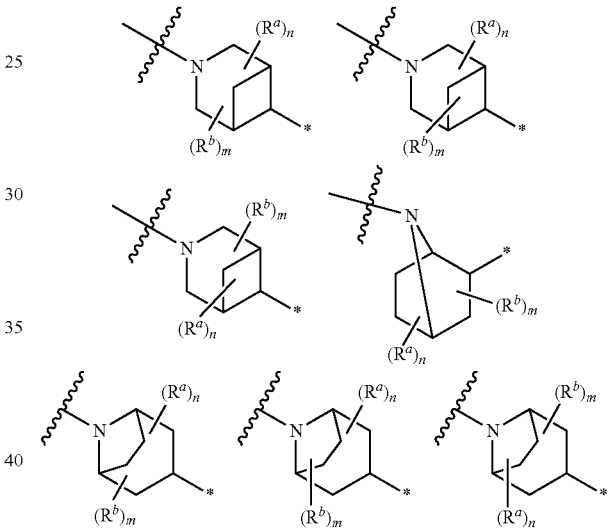

wherein the wavy line indicates the point of attachment of Ring D to the ring comprising $X^1$, $X^2$, $X^3$ and $X^4$, the asterisk indicates the point of attachment of Ring D to the E group, and $R^a$, n, $R^b$ and m are as defined for Formula I. In one embodiment, n is 0 or 1. In one embodiment, n is 0. In one embodiment, n is 1. In one embodiment, m is 0 or 1. In one embodiment, m is 0. In one embodiment, m is 1. In one embodiment, n is 0 and m is 0 or 1.

In one embodiment, Ring D is a saturated 7 membered bridged heterocyclic ring having one ring heteroatom which is nitrogen. Non-limiting examples include structures:

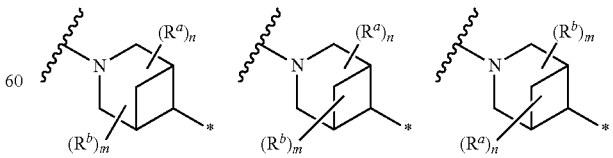

wherein the wavy line indicates the point of attachment of Ring D to the ring comprising $X^1$, $X^2$, $X^3$ and $X^4$, the asterisk indicates the point of attachment of Ring D to the E group, and $R^a$, n, $R^b$ and m are as defined for Formula I. In one embodiment, n is 0 or 1 and m is 0 or 1. In one embodiment, n is 0 and m is 0 or 1. In one embodiment, $R^b$ is $R^cR^dN$— where $R^c$ is H or C1-C6 alkyl and $R^d$ is H or C1-C6 alkyl. In one embodiment, $R^b$ is $R^cR^dN$— where $R^c$ and $R^d$ are H.

In one embodiment, Ring D is a saturated 7 membered bridged heterocyclic ring having one ring heteroatom which is nitrogen having the structure

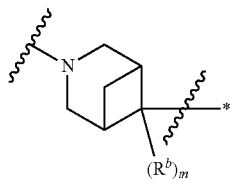

wherein the wavy line indicates the point of attachment of Ring D to the ring comprising $X^1$, $X^2$, $X^3$ and $X^4$, the asterisk indicates the point of attachment of Ring D to the E group, and $R^b$ and m are as defined for Formula I. In one embodiment, m is 0. In one embodiment, m is 1. In one embodiment, $R^b$ is $R^cR^dN$— where $R^c$ is H or C1-C6 alkyl and $R^d$ is H or C1-C6 alkyl. In one embodiment, $R^b$ is $R^cR^dN$— where $R^c$ and $R^d$ are H. Non-limiting examples include the structures:

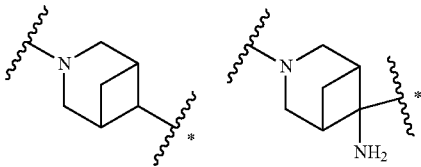 [SMILES: *C1C2CC1CN(*)C2 ; *N1CC2CC(C1)C2(*)N]

where the wavy line indicates the point of attachment of Ring D to the ring comprising $X^1$, $X^2$, $X^3$ and $X^4$, the asterisk indicates the point of attachment to the E group.

In one embodiment, Ring D is a saturated 7-8 membered bridged heterocyclic ring having one ring heteroatom which is nitrogen, and E is selected from (a) hydrogen, (b) hydroxy, (f) (C1-C6 alkoxy)C1-C6 alkoxy, (h) hetAr$^2$O—, (j) hetAr$^2$NR$^g$— where R$^g$ is H or C1-C6 alkyl, (n) R$^4$R$^5$NC(=O)—, (o) Ar$^1$NR$^g$C(=O)—, where R$^g$ is H or C1-C6 alkyl, and (p) hetAr$^2$NR$^g$C(=O)—, where R$^g$ is H or C1-C6 alkyl, where Ar$^1$, hetAr$^2$, R$^4$ and R$^5$ are as defined for Formula I.

In one embodiment, Ring D is a saturated 7-8 membered bridged heterocyclic ring having one ring heteroatom which is nitrogen, each $R^a$ is independently C1-C6 alkyl (optionally substituted with 1-3 fluoros), hydroxyC1-C6 alkyl or (C1-C6 alkoxy)C1-C6 alkyl-; $R^b$ is (a) hydroxy, (b) cyclopropyl, (c) hetCyc$^b$CH$_2$—, (d) R$^i$R$^j$NC(=O)CH$_2$OCH$_2$— where R$^i$ and R$^j$ are independently H or C1-C6 alkyl, (e) R$^c$R$^d$N—, (f) R$^c$R$^d$NCH$_2$—, (g) C1-C6 alkoxy-, (h) (C1-C4 alkyl)-C(=O)NH— wherein said alkyl portion is optionally substituted with hetCyc$^b$, hetAr$^a$, C1-C6 alkoxy- or R'R''N—, or said alkyl portion is optionally substituted with two substituents independently selected from R'R''N— and OH, where each R' and R'' is independently hydrogen or C1-C6 alkyl, (i) (R'R''N)C1-C6 alkoxy(CH$_2$)$_n$— where n is 0 or 1 and R' and R'' are independently hydrogen or C1-C6 alkyl, or (j) hetCyc$^b$(C1-C3 alkyl)OCH$_2$—; hetCyc$^b$ is as defined for Formula I; R$^c$ is hydrogen or C1-C6 alkyl; R$^d$ is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C(=O)—, (C1-C6 alkyl)C(=O)—, (R$^k$R$^l$N)C1-C6 alkyl- where R$^k$ and R$^l$ are independently H or C1-C6 alkyl, R$^m$R$^n$NC(=O)C1-C6 alkyl- where R$^m$ and R$^n$ are independently H or C1-C6 alkyl, PhCH$_2$—, (C1-C6 alkoxy)C1-C6 alkyl-, or hetCyc$^c$ where hetCyc$^c$ is a 4-6 membered heterocyclic ring having a ring heteroatom selected from N and O and optionally substituted with C1-C6 alkyl; n is 0, 1 2, 3, 4, 5 or 6; m is 0 or 1; and E is hydrogen. In one embodiment, Ring D is a saturated 7 membered bridged heterocyclic ring having one ring heteroatom which is nitrogen. In one embodiment, n is 0, 1 or 2 and m is 0 or 1. In one embodiment, n is 0 and m is 0 or 1. In one embodiment, $R^b$ is $R^cR^dN$— where $R^c$ is hydrogen or C1-C6 alkyl and $R^d$ is hydrogen, C1-C6 alkyl or (C1-C6 alkoxy)C(=O)—. A non-limiting example includes the structure:

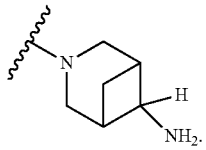

In one embodiment, Ring D is a saturated 7-8 membered bridged heterocyclic ring having one ring heteroatom which is nitrogen; each $R^a$ is independently C1-C6 alkyl (optionally substituted with 1-3 fluoros), hydroxyC1-C6 alkyl or (C1-C6 alkoxy)C1-C6 alkyl-; $R^b$ is (a) hydroxy, (b) cyclopropyl, (c) hetCyc$^b$CH$_2$—, (d) R$^i$R$^j$NC(=O)CH$_2$OCH$_2$— where R$^i$ and R$^j$ are independently H or C1-C6 alkyl, (e) R$^c$R$^d$N—, (f) R$^c$R$^d$NCH$_2$—, (g) C1-C6 alkoxy-, (h) (C1-C4 alkyl)-C(=O)NH— wherein said alkyl portion is optionally substituted with hetCyc$^b$, hetAr$^a$, C1-C6 alkoxy- or R'R''N—, or said alkyl portion is optionally substituted with two substituents independently selected from R'R''N— and OH, where each R' and R'' is independently hydrogen or C1-C6 alkyl, (i) (R'R''N)C1-C6 alkoxy(CH$_2$)$_n$— where n is 0 or 1 and R' and R'' are independently hydrogen or C1-C6 alkyl, or (j) hetCyc$^b$(C1-C3 alkyl)OCH$_2$—; hetCyc$^b$ is as defined for Formula I; R$^c$ is hydrogen or C1-C6 alkyl; R$^d$ is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C(=O)—, (C1-C6 alkyl)C(=O)—, (R$^k$R$^l$N)C1-C6 alkyl- where R$^k$ and R$^l$ are independently H or C1-C6 alkyl, R$^m$R$^n$NC(=O)C1-C6 alkyl- where R$^m$ and R$^n$ are independently H or C1-C6 alkyl, PhCH$_2$—, (C1-C6 alkoxy)C1-C6 alkyl-, or hetCyc$^c$ where hetCyc$^c$ is a 4-6 membered heterocyclic ring having a ring heteroatom selected from N and O and optionally substituted with C1-C6 alkyl; n is 0, 1, 2, 3, 4, 5 or 6; m is 0 or 1; and E is hydroxy. In one embodiment, Ring D is a saturated 7 membered bridged heterocyclic ring having one ring heteroatom which is nitrogen. In one embodiment, n is 0, 1 or 2 and m is 0 or 1. In one embodiment, n is 0 and m is 0. A non-limiting example includes the structure:

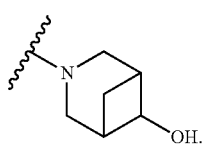 [SMILES: *N1CC2CC(C1)C2O]

In one embodiment, Ring D is a saturated 7-8 membered bridged heterocyclic ring having one ring heteroatom which is nitrogen; each $R^a$ is independently C1-C6 alkyl (optionally substituted with 1-3 fluoros), hydroxyC1-C6 alkyl or (C1-C6 alkoxy)C1-C6 alkyl-; $R^b$ is (a) hydroxy, (b) cyclopropyl, (c) hetCyc$^b$CH$_2$—, (d) R$^i$R$^j$NC(=O)CH$_2$OCH$_2$— where R$^i$ and R$^j$ are independently H or C1-C6 alkyl, (e) R$^c$R$^d$N—, (f) R$^c$R$^d$NCH$_2$—, (g) C1-C6 alkoxy-, (h) (C1-C4 alkyl)-C(=O)NH— wherein said alkyl portion is optionally substituted with hetCyc$^b$, hetAr$^a$, C1-C6 alkoxy- or R'R"N—, or said alkyl portion is optionally substituted with two substituents independently selected from R'R"N— and OH, where each R' and R" is independently hydrogen or C1-C6 alkyl, (i) (R'R"N)C1-C6 alkoxy(CH$_2$)$_n$— where n is 0 or 1 and R' and R" are independently hydrogen or C1-C6 alkyl, or (j) hetCyc$^b$(C1-C3 alkyl)OCH$_2$—; hetCyc$^b$ is as defined for Formula I; $R^c$ is hydrogen or C1-C6 alkyl; $R^d$ is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C(=O)—, (C1-C6 alkyl)C(=O)—, (R$^k$R$^l$N)C1-C6 alkyl- where R$^k$ and R$^l$ are independently H or C1-C6 alkyl, R$^m$R"NC(=O)C1-C6 alkyl- where R$^m$ and R" are independently H or C1-C6 alkyl, PhCH$_2$—, (C1-C6 alkoxy)C1-C6 alkyl-, or hetCyc$^c$ where hetCyc$^c$ is a 4-6 membered heterocyclic ring having a ring heteroatom selected from N and O and optionally substituted with C1-C6 alkyl; n is 0, 1, 2, 3, 4, 5 or 6; m is 0 or 1; and E is (C1-C6 alkoxy)C1-C6 alkoxy. In one embodiment, Ring D is a saturated 7 membered bridged heterocyclic ring having one ring heteroatom which is nitrogen. In one embodiment, n is 0, 1 or 2 and m is 0 or 1. In one embodiment, n is 0 and m is 0. A non-limiting example includes the structure:

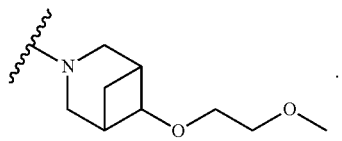 [SMILES: *N1CC2CC(C1)C2OCCOC]

In one embodiment, Ring D is a saturated 7-8 membered bridged heterocyclic ring having one ring heteroatom which is nitrogen; each $R^a$ is independently C1-C6 alkyl (optionally substituted with 1-3 fluoros), hydroxyC1-C6 alkyl or (C1-C6 alkoxy)C1-C6 alkyl-; $R^b$ is (a) hydroxy, (b) cyclopropyl, (c) hetCyc$^b$CH$_2$—, (d) R$^i$R$^j$NC(=O)CH$_2$OCH$_2$— where R$^1$ and R are independently H or C1-C6 alkyl, (e) R$^c$R$^d$N—, (f) R$^c$R$^d$NCH$_2$—, (g) C1-C6 alkoxy-, (h) (C1-C4 alkyl)-C(=O)NH— wherein said alkyl portion is optionally substituted with hetCyc$^b$, hetAr$^a$, C1-C6 alkoxy- or R'R"N—, or said alkyl portion is optionally substituted with two substituents independently selected from R'R"N— and OH, where each R' and R" is independently hydrogen or C1-C6 alkyl, (i) (R'R"N)C1-C6 alkoxy(CH$_2$)$_n$— where n is 0 or 1 and R' and R" are independently hydrogen or C1-C6 alkyl, or (j) hetCyc$^b$(C1-C3 alkyl)OCH$_2$—; hetCyc$^b$ is as defined for Formula I; $R^c$ is hydrogen or C1-C6 alkyl; $R^d$ is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C(=O)—, (C1-C6 alkyl)C(=O)—, (R$^k$R$^l$N)C1-C6 alkyl- where R$^k$ and R$^l$ are independently H or C1-C6 alkyl, R$^m$R"NC(=O)C1-C6 alkyl- where R$^m$ and R" are independently H or C1-C6 alkyl, PhCH$_2$—, (C1-C6 alkoxy)C1-C6 alkyl-, or hetCyc$^c$ where hetCyc$^c$ is a 4-6 membered heterocyclic ring having a ring heteroatom selected from N and O and optionally substituted with C1-C6 alkyl; n is 0, 1, 2, 3, 4, 5 or 6; m is 0 or 1; and E is hetAr$^2$O— where hetAr$^2$ is as defined for Formula I. In one embodiment hetAr$^2$ is a 5-6 membered heteroaryl ring having 1-2 ring nitrogen atoms optionally substituted with one or more substituents independently selected from C1-C6 alkoxy and halogen. In one embodiment, hetAr$^2$ is unsubstituted. In one embodiment, Ring D is a saturated 7 membered bridged heterocyclic ring having one ring heteroatom which is nitrogen. In one embodiment, n is 0, 1 or 2 and m is 0 or 1. In one embodiment, n is 0 or 1 and m is 0. In one embodiment, n is 0 and m is 0. Non-limiting examples include the structures:

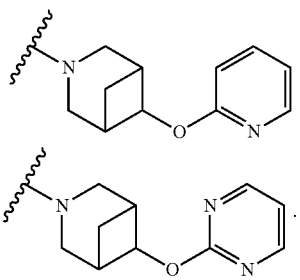

In one embodiment, Ring D is a saturated 7-8 membered bridged heterocyclic ring having one ring heteroatom which is nitrogen; each $R^a$ is independently C1-C6 alkyl (optionally substituted with 1-3 fluoros), hydroxyC1-C6 alkyl or (C1-C6 alkoxy)C1-C6 alkyl-; $R^b$ is (a) hydroxy, (b) cyclopropyl, (c) hetCyc$^b$CH$_2$—, (d) R$^i$R$^j$NC(=O)CH$_2$OCH$_2$— where R$^i$ and R$^j$ are independently H or C1-C6 alkyl, (e) R$^c$R$^d$N—, (f) R$^c$R$^d$NCH$_2$—, (g) C1-C6 alkoxy-, (h) (C1-C4 alkyl)-C(=O)NH— wherein said alkyl portion is optionally substituted with hetCyc$^b$, hetAr$^a$, C1-C6 alkoxy- or R'R"N—, or said alkyl portion is optionally substituted with two substituents independently selected from R'R"N— and OH, where each R' and R" is independently hydrogen or C1-C6 alkyl, (i) (R'R"N)C1-C6 alkoxy(CH$_2$)$_n$— where n is 0 or 1 and R' and R" are independently hydrogen or C1-C6 alkyl, or (j) hetCyc$^b$(C1-C3 alkyl)OCH$_2$—; hetCyc$^b$ is as defined for Formula I; $R^c$ is hydrogen or C1-C6 alkyl; $R^d$ is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C(=O)—, (C1-C6 alkyl)C(=O)—, (R$^k$R$^l$N)C1-C6 alkyl- where R$^k$ and R$^l$ are independently H or C1-C6 alkyl, R$^m$R"NC(=O)C1-C6 alkyl- where R$^m$ and R" are independently H or C1-C6 alkyl, PhCH$_2$—, (C1-C6 alkoxy)C1-C6 alkyl-, or hetCyc$^c$ where hetCyc$^c$ is a 4-6 membered heterocyclic ring having a ring heteroatom selected from N and O and optionally substituted with C1-C6 alkyl; n is 0, 1, 2, 3, 4, 5 or 6; m is 0 or 1; and E is hetAr$^2$NH— where hetAr$^2$ is as defined for Formula I. In one embodiment hetAr$^2$ is a 5-6 membered heteroaryl ring having 1-2 ring nitrogen atoms and optionally substituted with one or more substituents independently selected from C1-C6 alkoxy, halogen and C1-C6 alkoxy (optionally substituted with 1-3 fluoros). In one embodiment, Ring D is a saturated 7 membered bridged heterocyclic ring having one ring heteroatom which is nitrogen. In one embodiment, n is 0, 1 or 2 and m is 0 or 1. In one embodiment, n is 0 and m is 0. Non-limiting examples include the structures:

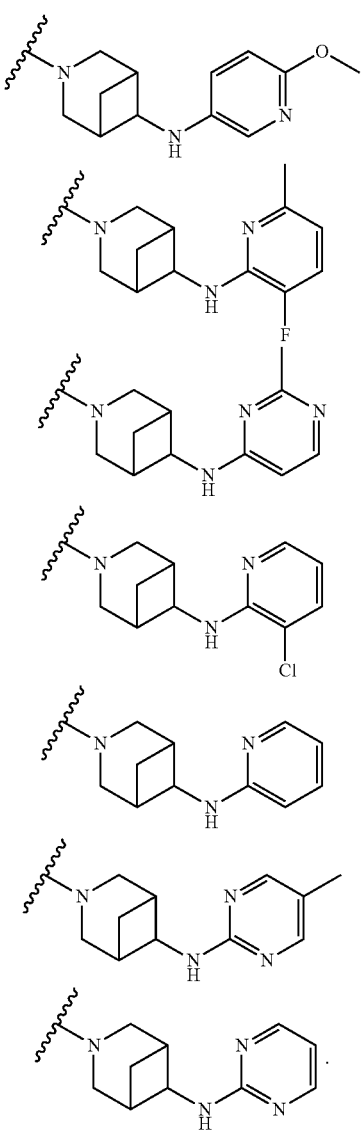

In one embodiment, Ring D is a saturated 7-8 membered bridged heterocyclic ring having one ring heteroatom which is nitrogen; each $R^a$ is independently C1-C6 alkyl (optionally substituted with 1-3 fluoros), hydroxyC1-C6 alkyl or (C1-C6 alkoxy)C1-C6 alkyl-; $R^b$ is (a) hydroxy, (b) cyclopropyl, (c) hetCyc$^b$CH$_2$—, (d) R$^i$R$^j$NC(=O)CH$_2$OCH$_2$— where R$^i$ and R$^j$ are independently H or C1-C6 alkyl, (e) R$^c$R$^d$N—, (f) R$^c$R$^d$NCH$_2$—, (g) C1-C6 alkoxy-, (h) (C1-C4 alkyl)-C(=O)NH— wherein said alkyl portion is optionally substituted with hetCyc$^b$, hetAr$^a$, C1-C6 alkoxy- or R'R"N—, or said alkyl portion is optionally substituted with two substituents independently selected from R'R"N— and OH, where each R' and R" is independently hydrogen or C1-C6 alkyl, (i) (R'R"N)C1-C6 alkoxy(CH$_2$)$_n$— where n is 0 or 1 and R' and R" are independently hydrogen or C1-C6 alkyl, or (j) hetCyc$^b$(C1-C3 alkyl)OCH$_2$—; hetCyc$^b$ is as defined for Formula I; $R^c$ is hydrogen or C1-C6 alkyl; $R^d$ is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C(=O)—, (C1-C6 alkyl)C(=O)—, (R$^k$R$^l$N)C1-C6 alkyl- where R$^k$ and R$^l$ are independently H or C1-C6 alkyl, R$^m$R$^n$NC(=O)C1-C6 alkyl- where R$^m$ and R$^n$ are independently H or C1-C6 alkyl, PhCH$_2$—, (C1-C6 alkoxy)C1-C6 alkyl-, or hetCyc$^c$ where hetCyc$^c$ is a 4-6 membered heterocyclic ring having a ring heteroatom selected from N and O and optionally substituted with C1-C6 alkyl; n is 0, 1, 2, 3, 4, 5 or 6; m is 0 or 1; and E is $R^3$C(=O)NR$^g$— where $R^3$ and $R^g$ are as defined for Formula I. In one embodiment, n is 0 and m is 0. A non-limiting example includes the structure:

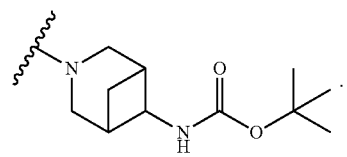 [SMILES: *N1CC2CC(C1)C2NC(=O)OC(C)(C)C]

In one embodiment, Ring D is a saturated 7-8 membered bridged heterocyclic ring having one ring heteroatom which is nitrogen; each $R^a$ is independently C1-C6 alkyl (optionally substituted with 1-3 fluoros), hydroxyC1-C6 alkyl or (C1-C6 alkoxy)C1-C6 alkyl-; $R^b$ is (a) hydroxy, (b) cyclopropyl, (c) hetCyc$^b$CH$_2$—, (d) R$^i$R$^j$NC(=O)CH$_2$OCH$_2$— where R$^i$ and R$^j$ are independently H or C1-C6 alkyl, (e) R$^c$R$^d$N—, (f) R$^c$R$^d$NCH$_2$—, (g) C1-C6 alkoxy-, (h) (C1-C4 alkyl)-C(=O)NH— wherein said alkyl portion is optionally substituted with hetCyc$^b$, hetAr$^a$, C1-C6 alkoxy- or R'R"N—, or said alkyl portion is optionally substituted with two substituents independently selected from R'R"N— and OH, where each R' and R" is independently hydrogen or C1-C6 alkyl, (i) (R'R"N)C1-C6 alkoxy(CH$_2$)$_n$— where n is 0 or 1 and R' and R" are independently hydrogen or C1-C6 alkyl, or (j) hetCyc$^b$(C1-C3 alkyl)OCH$_2$—; hetCyc$^b$ is as defined for Formula I; $R^c$ is hydrogen or C1-C6 alkyl; $R^d$ is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C(=O)—, (C1-C6 alkyl)C(=O)—, (R$^k$R$^l$N)C1-C6 alkyl- where R$^k$ and R$^l$ are independently H or C1-C6 alkyl, R$^m$R$^n$NC(=O)C1-C6 alkyl- where R$^m$ and R$^n$ are independently H or C1-C6 alkyl, PhCH$_2$—, (C1-C6 alkoxy)C1-C6 alkyl-, or hetCyc$^c$ where hetCyc$^c$ is a 4-6 membered heterocyclic ring having a ring heteroatom selected from N and O and optionally substituted with C1-C6 alkyl; n is 0, 1, 2, 3, 4, 5 or 6; m is 0 or 1; and E is Ar$^1$C(=O)NH— where Ar$^1$ is as defined for Formula I. In one embodiment, Ar$^1$ is unsubstituted. In one embodiment, n is 0 and m is 0. A non-limiting example includes the structure:

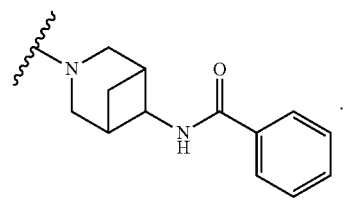 [SMILES: *N1CC2CC(C1)C2NC(=O)c1ccccc1]

In one embodiment, Ring D is a saturated 7-8 membered bridged heterocyclic ring having one ring heteroatom which is nitrogen; each $R^a$ is independently C1-C6 alkyl (optionally substituted with 1-3 fluoros), hydroxyC1-C6 alkyl or (C1-C6 alkoxy)C1-C6 alkyl-; $R^b$ is (a) hydroxy, (b) cyclopropyl, (c) hetCyc$^b$CH$_2$—, (d) R$^i$R$^j$NC(=O)CH$_2$OCH$_2$— where R$^i$ and R$^j$ are independently H or C1-C6 alkyl, (e)

R$^c$R$^d$N—, (f) R$^c$R$^d$NCH$_2$—, (g) C1-C6 alkoxy-, (h) (C1-C4 alkyl)-C(=O)NH— wherein said alkyl portion is optionally substituted with hetCyc$^b$, hetAr$^a$, C1-C6 alkoxy- or R'R"N—, or said alkyl portion is optionally substituted with two substituents independently selected from R'R"N— and OH, where each R' and R" is independently hydrogen or C1-C6 alkyl, (i) (R'R"N)C1-C6 alkoxy(CH$_2$)$_n$— where n is 0 or 1 and R' and R" are independently hydrogen or C1-C6 alkyl, or (j) hetCyc$^b$(C1-C3 alkyl)OCH$_2$—; hetCyc$^b$ is as defined for Formula I; R$^c$ is hydrogen or C1-C6 alkyl; R$^d$ is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C(=O)—, (C1-C6 alkyl)C(=O)—, (R$^k$R$^l$N)C1-C6 alkyl- where R$^k$ and R$^l$ are independently H or C1-C6 alkyl, R$^m$R"NC(=O)C1-C6 alkyl- where R$^m$ and R" are independently H or C1-C6 alkyl, PhCH$_2$—, (C1-C6 alkoxy)C1-C6 alkyl-, or hetCyc$^c$ where hetCyc$^c$ is a 4-6 membered heterocyclic ring having a ring heteroatom selected from N and O and optionally substituted with C1-C6 alkyl; n is 0, 1, 2, 3, 4, 5 or 6; m is 0 or 1; and E is hetAr$^2$C(=O)NR'— where hetAr$^2$ and R' are as defined for Formula I. In one embodiment, hetAr$^2$ is unsubstituted. In one embodiment, n is 0 and m is 0. A non-limiting example includes the structure:

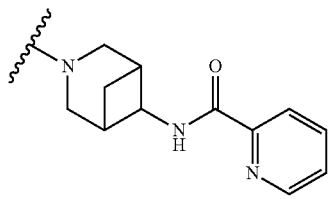

In one embodiment, Ring D is a saturated 7-8 membered bridged heterocyclic ring having one ring heteroatom which is nitrogen; each R$^a$ is independently C1-C6 alkyl (optionally substituted with 1-3 fluoros), hydroxyC1-C6 alkyl or (C1-C6 alkoxy)C1-C6 alkyl-; R$^b$ is (a) hydroxy, (b) cyclopropyl, (c) hetCyc$^b$CH$_2$—, (d) R$^i$R$^j$NC(=O)CH$_2$OCH$_2$— where R$^i$ and R$^j$ are independently H or C1-C6 alkyl, (e) R$^c$R$^d$N—, (f) R$^c$R$^d$NCH$_2$—, (g) C1-C6 alkoxy-, (h) (C1-C4 alkyl)-C(=O)NH— wherein said alkyl portion is optionally substituted with hetCyc$^b$, hetAr$^a$, C1-C6 alkoxy- or R'R"N—, or said alkyl portion is optionally substituted with two substituents independently selected from R'R"N— and OH, where each R' and R" is independently hydrogen or C1-C6 alkyl, (i) (R'R"N)C1-C6 alkoxy(CH$_2$)$_n$— where n is 0 or 1 and R' and R" are independently hydrogen or C1-C6 alkyl, or (j) hetCyc$^b$(C1-C3 alkyl)OCH$_2$—; hetCyc$^b$ is as defined for Formula I; R$^c$ is hydrogen or C1-C6 alkyl; R$^d$ is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C(=O)—, (C1-C6 alkyl)C(=O)—, (R$^k$R$^l$N)C1-C6 alkyl- where R$^k$ and R$^l$ are independently H or C1-C6 alkyl, R$^m$R"NC(=O)C1-C6 alkyl- where R$^m$ and R" are independently H or C1-C6 alkyl, PhCH$_2$—, (C1-C6 alkoxy)C1-C6 alkyl-, or hetCyc$^c$ where hetCyc$^c$ is a 4-6 membered heterocyclic ring having a ring heteroatom selected from N and O and optionally substituted with C1-C6 alkyl; n is 0, 1, 2, 3, 4, 5 or 6; m is 0 or 1; and E is R$^4$R$^5$NC(=O)— where R$^4$ and R$^5$ are as defined for Formula I. In one embodiment, Ring D is a saturated 7 membered bridged heterocyclic ring having one ring heteroatom which is nitrogen. In one embodiment, n is 0, 1 or 2 and m is 0 or 1. In one embodiment, n is 0 and m is 0. Non-limiting examples includes the structures:

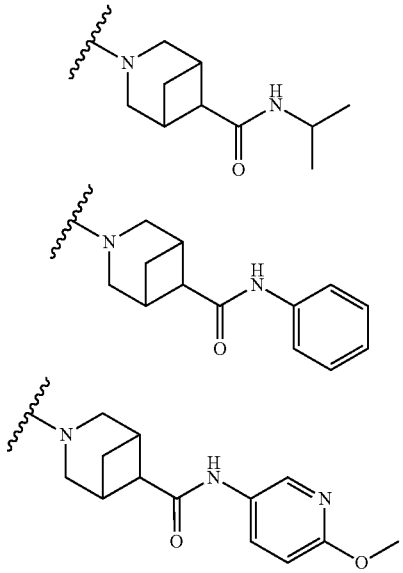

In one embodiment, Ring D is a saturated 7-8 membered bridged heterocyclic ring having one ring heteroatom which is nitrogen; each R$^a$ is independently C1-C6 alkyl (optionally substituted with 1-3 fluoros), hydroxyC1-C6 alkyl or (C1-C6 alkoxy)C1-C6 alkyl-; R$^b$ is (a) hydroxy, (b) cyclopropyl, (c) hetCyc$^b$CH$_2$—, (d) R$^i$R$^j$NC(=O)CH$_2$OCH$_2$— where R$^i$ and R$^j$ are independently H or C1-C6 alkyl, (e) R$^c$R$^d$N—, (f) R$^c$R$^d$NCH$_2$—, (g) C1-C6 alkoxy-, (h) (C1-C4 alkyl)-C(=O)NH— wherein said alkyl portion is optionally substituted with hetCyc$^b$, hetAr$^a$, C1-C6 alkoxy- or R'R"N—, or said alkyl portion is optionally substituted with two substituents independently selected from R'R"N— and OH, where each R' and R" is independently hydrogen or C1-C6 alkyl, (i) (R'R"N)C1-C6 alkoxy(CH$_2$)$_n$— where n is 0 or 1 and R' and R" are independently hydrogen or C1-C6 alkyl, or (j) hetCyc$^b$(C1-C3 alkyl)OCH$_2$—; hetCyc$^b$ is as defined for Formula I; R$^c$ is hydrogen or C1-C6 alkyl; R$^d$ is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C(=O)—, (C1-C6 alkyl)C(=O)—, (R$^k$R$^l$N)C1-C6 alkyl- where R$^k$ and R$^l$ are independently H or C1-C6 alkyl, R$^m$R"NC(=O)C1-C6 alkyl- where R$^m$ and R" are independently H or C1-C6 alkyl, PhCH$_2$—, (C1-C6 alkoxy)C1-C6 alkyl-, or hetCyc$^c$ where hetCyc$^c$ is a 4-6 membered heterocyclic ring having a ring heteroatom selected from N and O and optionally substituted with C1-C6 alkyl; n is 0, 1, 2, 3, 4, 5 or 6; m is 0 or 1; and E is Ar$^1$NR$^g$C(=O)—, where Ar$^1$ and R$^g$ areas defined for Formula I. In one embodiment, Ar$^1$ is substituted with one or more substituents independently selected from halogen, CN and C1-C6 alkyl (optionally substituted with 1-3 fluoros). In one embodiment, Ar$^1$ is unsubstituted. In one embodiment, Ring D is a saturated 7 membered bridged heterocyclic ring having one ring heteroatom which is nitrogen. In one embodiment, n is 0, 1 or 2 and m is 0 or 1. In one embodiment, n is 0 and m is 0. A non-limiting example includes the structure:

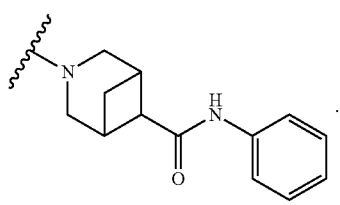 [SMILES: *N1CC2CC(C1)C2C(=O)Nc1ccccc1]

In one embodiment, Ring D is a saturated 7-8 membered bridged heterocyclic ring having one ring heteroatom which is nitrogen; each $R^a$ is independently C1-C6 alkyl (optionally substituted with 1-3 fluoros), hydroxyC1-C6 alkyl or (C1-C6 alkoxy)C1-C6 alkyl-; $R^b$ is (a) hydroxy, (b) cyclopropyl, (c) hetCyc$^b$CH$_2$—, (d) R$^i$R$^j$NC(=O)CH$_2$OCH$_2$— where R$^i$ and R$^j$ are independently H or C1-C6 alkyl, (e) R$^c$R$^d$N—, (f) R$^c$R$^d$NCH$_2$—, (g) C1-C6 alkoxy-, (h) (C1-C4 alkyl)-C(=O)NH— wherein said alkyl portion is optionally substituted with hetCyc$^b$, hetAr$^a$, C1-C6 alkoxy- or R'R"N—, or said alkyl portion is optionally substituted with two substituents independently selected from R'R"N— and OH, where each R' and R" is independently hydrogen or C1-C6 alkyl, (i) (R'R"N)C1-C6 alkoxy(CH$_2$)$_n$— where n is 0 or 1 and R' and R" are independently hydrogen or C1-C6 alkyl, or (j) hetCyc$^b$(C1-C3 alkyl)OCH$_2$—; hetCyc$^b$ is as defined for Formula I; R$^c$ is hydrogen or C1-C6 alkyl; R$^d$ is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C(=O)—, (C1-C6 alkyl)C(=O)—, (R$^k$R$^l$N)C1-C6 alkyl- where R$^k$ and R$^l$ are independently H or C1-C6 alkyl, R$^m$R$^n$NC(=O)C1-C6 alkyl- where R$^m$ and R$^n$ are independently H or C1-C6 alkyl, PhCH$_2$—, (C1-C6 alkoxy)C1-C6 alkyl-, or hetCyc$^c$ where hetCyc$^c$ is a 4-6 membered heterocyclic ring having a ring heteroatom selected from N and O and optionally substituted with C1-C6 alkyl; n is 0, 1, 2, 3, 4, 5 or 6; m is 0 or 1; and E is hetAr$^2$NR$^g$C(=O)— where hetAr$^2$ and R$^g$ are as defined for Formula I. In one embodiment hetAr$^2$ is a 5-6 membered heteroaryl ring having 1-2 ring nitrogen atoms and optionally substituted with one or more substituents independently selected from halogen and C1-C6 alkoxy. In one embodiment, Ring D is a saturated 7 membered bridged heterocyclic ring having one ring heteroatom which is nitrogen. In one embodiment, n is 0, 1 or 2 and m is 0 or 1. In one embodiment, n is 0 and m is 0. A non-limiting example includes the structure:

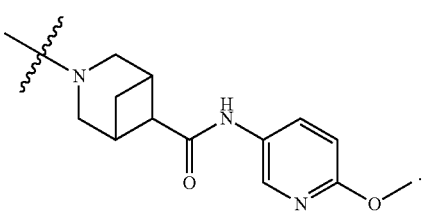 [SMILES: *N1CC2CC(C1)C2C(=O)Nc1ccc(OC)nc1]

In one embodiment, Ring D is a saturated 7-11 membered heterospirocyclic ring system having one ring heteroatom which is nitrogen; each $R^a$ is independently C1-C6 alkyl (optionally substituted with 1-3 fluoros), hydroxyC1-C6 alkyl or (C1-C6 alkoxy)C1-C6 alkyl-; $R^b$ is (a) hydroxy, (b) cyclopropyl, (c) hetCyc$^b$CH$_2$—, (d) R$^i$R$^j$NC(=O)CH$_2$OCH$_2$— where R$^i$ and R$^j$ are independently H or C1-C6 alkyl, (e) R$^c$R$^d$N—, (f) R$^c$R$^d$NCH$_2$—, (g) C1-C6 alkoxy-, (h) (C1-C4 alkyl)-C(=O)NH— wherein said alkyl portion is optionally substituted with hetCyc$^b$, hetAr$^a$, C1-C6 alkoxy- or R'R"N—, or said alkyl portion is optionally substituted with two substituents independently selected from R'R"N— and OH, where each R' and R" is independently hydrogen or C1-C6 alkyl, (i) (R'R"N)C1-C6 alkoxy(CH$_2$)$_n$— where n is 0 or 1 and R' and R" are independently hydrogen or C1-C6 alkyl, or (j) hetCyc$^b$(C1-C3 alkyl)OCH$_2$—; hetCyc$^b$ is as defined for Formula I; R$^c$ is hydrogen or C1-C6 alkyl; R$^d$ is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C(=O)—, (C1-C6 alkyl)C(=O)—, (R$^k$R$^l$N)C1-C6 alkyl- where R$^k$ and R$^l$ are independently H or C1-C6 alkyl, R$^m$R$^n$NC(=O)C1-C6 alkyl- where R$^m$ and R$^n$ are independently H or C1-C6 alkyl, PhCH$_2$—, (C1-C6 alkoxy)C1-C6 alkyl-, or hetCyc$^c$ where hetCyc$^c$ is a 4-6 membered heterocyclic ring having a ring heteroatom selected from N and O and optionally substituted with C1-C6 alkyl; n is 0, 1, 2, 3, 4, 5 or 6; m is 0 or 1. The phrase "having one ring heteroatom which is nitrogen" when Ring D is a saturated 7-11 membered heterospirocyclic ring system means that said one ring nitrogen is the ring nitrogen atom shown in Ring D of Formula I. In one embodiment, Ring D is a saturated 9 membered heterospirocyclic ring system having one ring heteroatom which is nitrogen. In one embodiment, Ring D is a 7-azaspiro[3.5]nonanyl ring, e.g., a 7-azaspiro[3.5]nonan-2-yl ring. Nonlimiting examples include the structures:

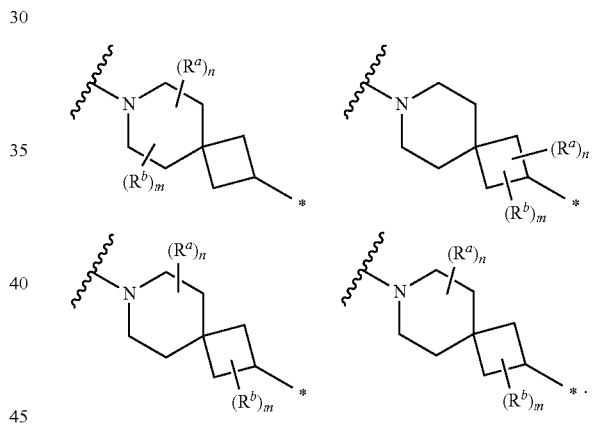

wherein the wavy line indicates the point of attachment of Ring D to the ring comprising $X^1$, $X^2$, $X^3$ and $X^4$, the asterisk indicates the point of attachment of Ring D to the E group, and $R^a$, n, $R^b$ and m are as defined for Formula I. In one embodiment, n is 0, 1 or 2 and m is 0 or 1. In one embodiment, n is 0 or 1. In one embodiment, n is 0. In one embodiment, n is 1. In one embodiment, m is 0 or 1. In one embodiment, m is 0. In one embodiment, m is 1. In one embodiment, n is 0 and m is 0.

In one embodiment, Ring D is a saturated 7-11 membered heterospirocyclic ring system having one ring heteroatom which is nitrogen; each $R^a$ is independently C1-C6 alkyl (optionally substituted with 1-3 fluoros), hydroxyC1-C6 alkyl or (C1-C6 alkoxy)C1-C6 alkyl-; $R^b$ is (a) hydroxy, (b) cyclopropyl, (c) hetCyc$^b$CH$_2$—, (d) R$^i$R$^j$NC(=O)CH$_2$OCH$_2$— where R$^i$ and R$^j$ are independently H or C1-C6 alkyl, (e) R$^c$R$^d$N—, (f) R$^c$R$^d$NCH$_2$—, (g) C1-C6 alkoxy-, (h) (C1-C4 alkyl)-C(=O)NH— wherein said alkyl portion is optionally substituted with hetCyc$^b$, hetAr$^a$, C1-C6 alkoxy- or R'R"N—, or said alkyl portion is optionally substituted with two substituents independently selected from R'R"N— and OH, where each R' and R" is independently hydrogen or C1-C6 alkyl, (i) (R'R"N)C1-C6 alkoxy(CH₂)ₙ— where n is 0 or 1 and R' and R" are independently hydrogen or C1-C6 alkyl, or (j) hetCyc$^b$(C1-C3 alkyl)OCH₂—; hetCyc$^b$ is as defined for Formula I; R$^c$ is hydrogen or C1-C6 alkyl; R$^d$ is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C(=O)—, (C1-C6 alkyl)C(=O)—, (R$^k$R$^l$N)C1-C6 alkyl- where R$^k$ and R$^l$ are independently H or C1-C6 alkyl, R'''R"NC(=O)C1-C6 alkyl- where R''' and R" are independently H or C1-C6 alkyl, PhCH₂—, (C1-C6 alkoxy)C1-C6 alkyl-, or hetCyc$^c$ where hetCyc$^c$ is a 4-6 membered heterocyclic ring having a ring heteroatom selected from N and O and optionally substituted with C1-C6 alkyl; n is 0, 1, 2, 3, 4, 5 or 6; m is 0 or 1; and E is hydrogen. In one embodiment, Ring D is a 7-azaspiro[3.5]nonanyl ring, e.g., a 7-azaspiro[3.5]nonan-2-yl ring. In one embodiment, n is 0 and m is 0 or 1. In one embodiment, R$^b$ is R$^c$R$^d$N— where R$^c$ is hydrogen or C1-C6 alkyl and R$^d$ is hydrogen, C1-C6 alkyl or (C1-C6 alkoxy)C(=O)—. Non-limiting examples include the structures:

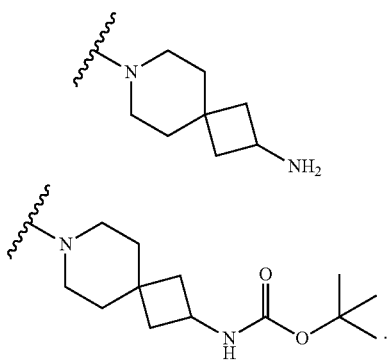

In one embodiment, Formula I includes compounds of Formula I-A, wherein:

X$^1$, X$^2$, X$^3$ and X$^4$ are independently CH, CF or N, wherein zero, one or two of X$^1$, X$^2$, X$^3$ and X$^4$ is N;

A is H, CN, Cl, methyl, ethyl or cyclopropyl;

B is
(a) hydrogen,
(b) C1-C6 alkyl optionally substituted with 1-3 fluoros,
(c) hydroxyC2-C6 alkyl- wherein the alkyl portion is optionally substituted with a C3-C6 cycloalkylidene ring,
(d) dihydroxyC3-C6 alkyl- wherein the alkyl portion is optionally substituted with a C3-C6 cycloalkylidene ring,
(e) (C1-C6 alkoxy)C1-C6 alkyl- optionally substituted with 1-3 fluoros,
(f) (R$^1$R$^2$N)C1-C6 alkyl- where R$^1$ and R$^2$ are independently selected from H, C1-C6 alkyl (optionally substituted with 1-3 fluoros), (C1-C6 alkoxy)C1-C6 alkyl-, (C1-C6 alkyl)C(=O)— and (C1-C6 alkoxy)C(=O)—;
(g) hetAr$^1$C1-C3 alkyl-, where hetAr$^1$ is a 5-6 membered heteroaryl ring having 1-3 ring heteroatoms independently selected from N, O and S and is optionally substituted with one or more independently selected C1-C6 alkyl groups;
(h) (C3-C6 cycloalkyl)C1-C3 alkyl-,
(i) (hetCyc$^a$)C1-C3 alkyl-,
(j) hetCyc$^a$,
(k) (R$^1$R$^2$N)C(=O)C1-C6 alkyl- where R$^1$ and R$^2$ are independently selected from H and C1-C6 alkyl,
(l) (R$^1$R$^2$N)C(=O)—, where R$^1$ and R$^2$ are independently selected from H and C1-C6 alkyl, or
(m) hetCyc$^a$C(=O)C1-C6 alkyl-;

hetCyc$^a$ is a 4-6 membered heterocyclic ring having 1-2 ring heteroatoms independently selected from N and O and optionally substituted with one or more substituents independently selected from OH, C1-C6 alkyl (optionally substituted with 1-3 fluoros), hydroxyC1-C6 alkyl, halogen, (C1-C6 alkyl)C(=O)—, C1-C6 alkoxy, oxo and (C1-C6 alkoxy)C(=O)—;

Ring D is a saturated 4-7 membered heterocyclic ring having one ring heteroatom which is nitrogen;

each R$^a$ is independently C1-C6 alkyl (optionally substituted with 1-3 fluoros), hydroxyC1-C6 alkyl or (C1-C6 alkoxy)C1-C6 alkyl-;

R$^b$ is (a) hydroxy, (b) cyclopropyl, (c) hetCyc$^b$CH₂—, (d) R$^i$R$^j$NC(=O)CH₂OCH₂— where R$^i$ and R$^j$ are independently H or C1-C6 alkyl, (e) R$^c$R$^d$N—, (f) R$^c$R$^d$NCH₂—, (g) C1-C6 alkoxy-, (h) (C1-C4 alkyl)-C(=O)NH— wherein said alkyl portion is optionally substituted with hetCyc$^b$, hetAr$^a$, C1-C6 alkoxy- or R'R"N—, or said alkyl portion is optionally substituted with two substituents independently selected from R'R"N— and OH, where each R' and R" is independently hydrogen or C1-C6 alkyl, (i) (R'R"N)C1-C6 alkoxy(CH₂)ₙ— where n is 0 or 1 and R' and R" are independently hydrogen or C1-C6 alkyl, (j) hetCyc$^b$(C1-C3 alkyl)OCH₂—, (k) hetCyc$^b$C(=O)NH— or (l) hetAr$^a$C(=O)NH—;

hetCyc$^b$ is a 4-6 membered heterocyclic ring, a 7-8 membered bridged heterocyclic ring, or a 7-10 membered heterospirocyclic ring, each ring having 1-2 ring heteroatoms independently selected from N and O, wherein hetCyc$^b$ is optionally substituted with one or more substituents independently selected from OH, fluoro, C1-C6 alkyl (optionally substituted with 1-3 fluoros), hydroxyC1-C6 alkyl- (optionally substituted with 1-3 fluoros), (C1-C6 alkoxy)C1-C6 alkyl-, (C1-C6 alkoxy)C(=O)—, C1-C6 alkoxy, and R'R"N— where R' and R" are independently hydrogen or C1-C6 alkyl;

hetAr$^a$ is a 5-6 membered heteroaryl ring having 1-3 ring heteroatoms independently selected from N, O and S herein hetAr$^a$ is optionally substituted with one or more substituents independently selected from the group consisting of halogen, CN, C1-C6 alkyl (optionally substituted with 1-3 fluoros), and C1-C6 alkoxy (optionally substituted with 1-3 fluoros);

R$^c$ is hydrogen or C1-C6 alkyl;

R$^d$ is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C(=O)—, (C1-C6 alkyl)C(=O)—, (R$^k$R$^l$N)C1-C6 alkyl- where R$^k$ and R$^l$ are independently H or C1-C6 alkyl, R'''R"NC(=O)C1-C6 alkyl- where R''' and R" are independently H or C1-C6 alkyl, PhCH₂—, (C1-C6 alkoxy)C1-C6 alkyl-, or hetCyc$^c$ where hetCyc$^c$ is a 4-6 membered heterocyclic ring having a ring heteroatom selected from N and O and optionally substituted with C1-C6 alkyl;

n is 0, 1, 2, 3, 4, 5 or 6;

m is 0 or 1;

E is
(a) hydrogen,
(b) hydroxy,
(c) C1-C6 alkyl optionally substituted with 1-3 fluoros,
(d) Ar$^1$C1-C6 alkyl- wherein said alkyl portion is optionally substituted with 1-3 fluoros,
(e) hetAr$^2$C1-C6 alkyl-,
(f) (C1-C6 alkoxy)C1-C6 alkoxy-, (g) Ar¹O—,
(h) hetAr²O—,
(i) Ar¹NR^g— where R^g is H or C1-C6 alkyl,
(j) hetAr²NR^g— where R^g is H or C1-C6 alkyl,
(k) R³C(=O)NR^g— where R^g is H or C1-C6 alkyl,
(l) Ar¹C(=O)NR^g— where R^g is H or C1-C6 alkyl,
(m) hetAr²C(=O)NR^g(CH_2)_p— where p is 0 or 1 and R^g is H or C1-C6 alkyl,
(n) R⁴R⁵NC(=O)—,
(o) Ar¹NR^gC(=O)—, where R^g is H or C1-C6 alkyl,
(p) hetAr²NR^gC(=O)—, where R^g is H or C1-C6 alkyl,
(r) hetCyc⁵C(=O)—,
(s) R⁴R⁵NC(=O)NR^g— where R^g is H or C1-C6 alkyl,
(t) (C1-C6 alkyl)SO_2—;
(u) Ar¹(C1-C6 alkyl)C(=O)NR^g— where R^g is H or C1-C6 alkyl,
(v) hetAr⁴C(=O)NR^g— where R^g is H or C1-C6 alkyl,
(w) hetAr²—S(=O)—,
(x) (C3-C6 cycloalkyl)CH_2SO_2—,
(y) Ar¹(C1-C6 alkyl)SO_2—,
(z) hetAr²SO_2—,
(aa) Ar¹,
(bb) hetAr²,
(cc) hetCyc⁵,
(dd) C1-C6 alkoxy,
(ee) Ar¹(C1-C6 alkyl)-O—,
(ff) hetAr²(C1-C6 alkyl)-O—,
(gg) hetAr²—O—C1-C6 alkyl-,
(hh) Ar¹(C1-C6 alkyl)NR^g— where R^g is H or C1-C6 alkyl, or
(ii) hetAr²—S—,
(jj) Ar²SO_2NR^g(CH_2)_p— where p is 0 or 1 and R^g is H or C1-C6 alkyl,
(kk) (C1-C6 alkoxy)C(=O)—,
(ll) (C1-C6 alkyl)NR^gC(=O)O— where R^g is H or C1-C6 alkyl,
(mm) (C1-C6 alkyl)NR^gSO_2— where R^g is H or C1-C6 alkyl,
(nn) hetCyc⁵C(=O)NR^g— where R^g is H or C1-C6 alkyl,
(oo) Q-NR^h(C1-C3 alkyl)C(=O)NR^g— where R^g and R^h are independently H or C1-C6 alkyl and Q is H, C1-C6 alkyl or (C1-C6 alkyl)OC(=O)—,
(pp)

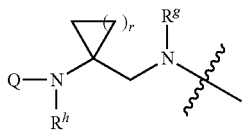

where R^g and R^h are independently H or C1-C6 alkyl, Q is H, C1-C6 alkyl or (C1-C6 alkyl)OC(=O)— and r is 1, 2, 3 or 4,
(qq)

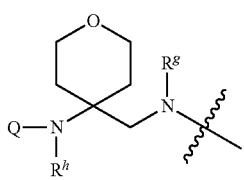

where R^g and R^h are independently H or C1-C6 alkyl and Q is H, C1-C6 alkyl or (C1-C6 alkyl)OC(=O)—, (rr)

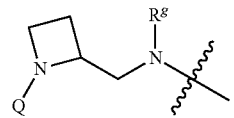

where R^g is H or C1-C6 alkyl and Q is H, C1-C6 alkyl or (C1-C6 alkyl)OC(=O)—, or
(ss) R^gR^hN— where R^g and R^h are independently H or C1-C6 alkyl,
(tt) (C3-C6 cycloalkyl)C(=O)NR^g— where the cycloalkyl is optionally and independently substituted with one or more halogens,
(uu) (C1-C6 alkyl)C(=O)NR^gCH_2— where R^g is H or C1-C6 alkyl, or
(vv) C1-C6 alkyl)SO_2NR^g— where R^g is H or C1-C6 alkyl;

Ar¹ is phenyl optionally substituted with one or more substituents independently selected from the group consisting of halogen, CN, C1-C6 alkyl (optionally substituted with 1-3 fluoros), C1-C6 alkoxy (optionally substituted with 1-3 fluoros), (C1-C6 alkoxy)C1-C6 alkyl- (optionally substituted with 1-3 fluoros), C3-C6 cycloalkyl, hydroxyC1-C6 alkyl, (C1-C6 alkyl)SO_2—, R^eR^fN— and (R^eR^fN)C1-C6 alkyl- where each R^e and R^f is independently H or C1-C6 alkyl;

hetAr² is a 5-6 membered heteroaryl ring having 1-3 ring heteroatoms independently selected from N, O and S, or a 9-10 membered bicyclic heteroaryl having 1-2 ring nitrogen atoms, wherein hetAr² is optionally substituted with one or more substituents independently selected from the group consisting of halogen, CN, C1-C6 alkyl (optionally substituted with 1-3 fluoros), C1-C6 alkoxy (optionally substituted with 1-3 fluoros), (C1-C6 alkoxy)C1-C6 alkyl- (optionally substituted with 1-3 fluoros) and hydroxyC1-C6 alkoxy-;

hetCyc⁵ is a 4-6 membered saturated heterocyclic ring having 1-2 ring heteroatoms independently selected from N, O and S wherein said heterocyclic ring is optionally substituted with one or more substituents independently selected from C1-C6 alkoxy and oxo;

R³ is C1-C6 alkyl (optionally substituted with 1-3 fluoros), hydroxyC1-C6 alkyl-, C1-C6 alkoxy, C3-C6 cycloalkyl, (C3-C6 cycloalkyl)CH_2—, (C3-C6 cycloalkyl)O—, (C3-C6 cycloalkyl)CH_2O—, hetCyc⁷O—, Ph-O—, or (C1-C6 alkoxy)C1-C6 alkyl-; wherein each of said C3-C6 cycloalkyl moieties is optionally substituted with C1-C6 alkyl (optionally substituted with 1-3 fluoros), C1-C6 alkoxy, OH or R'R''N— where R' and R'' are independently hydrogen or C1-C6 alkyl;

R⁴ is H or C1-C6 alkyl;

R⁵ is Ar², hetAr³, Ar²CH_2—, hetCyc⁶-CH_2—, hydroxyC1-C6 alkyl-, (C3-C6 cycloalkyl)CH_2—, or C1-C6 alkyl optionally substituted with 1-3 fluoros;

Ar² is phenyl optionally substituted with one or more substituents independently selected from the group consisting of halogen, CN, C1-C6 alkyl (optionally substituted with 1-3 fluoros), C1-C6 alkoxy (optionally substituted with 1-3 fluoros), (C1-C6 alkoxy)C1-C6 alkyl- (optionally substituted with 1-3 fluoros), C3-C6 cycloalkyl, and R^gR^hN— where R^g and R^h are independently H or C1-C6 alkyl, or Ar² is phenyl fused to a 6 membered heterocyclic ring having a ring nitrogen atom and optionally substituted with C1-C6 alkyl;

hetAr³ is a 5-6 membered heteroaryl ring having 1-3 ring heteroatoms independently selected from N, O and S and optionally substituted with one or more substituents independently selected from the group consisting of halogen, CN, C1-C6 alkyl (optionally substituted with 1-3 fluoros), C1-C6 alkoxy (optionally substituted with 1-3 fluoros), and (C1-C6 alkoxy)C1-C6 alkyl- (optionally substituted with 1-3 fluoros);

hetAr⁴ is pyridin-4(1H)-onyl or pyridin-2(1H)-onyl optionally substituted with one or more substituents independently selected from C1-C6 alkyl and halogen;

hetCyc⁶ is a 5-7 membered heterocyclic ring having 1-3 ring heteroatoms independently selected from N, O and S; and hetCyc⁷ is a 5-7 membered heterocyclic ring having 1-3 ring heteroatoms independently selected from N, O and S.

In one embodiment of Formula I-A, X¹ is N; X², X³ and X⁴ are CH.

In one embodiment of Formula I-A, A is CN.

In one embodiment of Formula I-A, X¹ is N; X², X³ and X⁴ are CH; and A is CN.

In one embodiment of Formula I-A, B is C1-C6 alkyl optionally substituted with 1-3 fluoros, or hydroxyC2-C6 alkyl- wherein the alkyl portion is optionally substituted with a C3-C6 cycloalkylidene ring. In one embodiment of Formula I-A, B is C1-C6 alkyl or hydroxyC2-C6 alkyl-.

In one embodiment of Formula I-A, X¹ is N; X², X³ and X⁴ are CH; A is CN; and B is C1-C6 alkyl optionally substituted with 1-3 fluoros, or hydroxyC2-C6 alkyl- wherein the alkyl portion is optionally substituted with a C3-C6 cycloalkylidene ring. In one embodiment, B is C1-C6 alkyl or hydroxyC2-C6 alkyl-.

In one embodiment of Formula I-A, X¹ is N; X², X³ and X⁴ are CH; A is CN; and B is C1-C6 alkyl optionally substituted with 1-3 fluoros. In one embodiment, B is C1-C6 alkyl.

In one embodiment of Formula I-A, X¹ is N; X², X³ and X⁴ are CH; A is CN; and B is hydroxyC2-C6 alkyl- optionally substituted with a C3-C6 cycloalkylidene ring. In one embodiment, B is hydroxyC2-C6 alkyl-.

In one embodiment of Formula I-A, Ring D is:

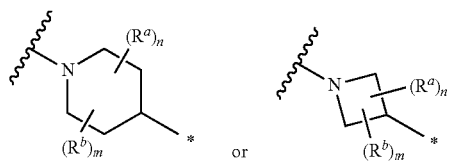

wherein the wavy line indicates the point of attachment of Ring D to the ring comprising X¹, X², X³ and X⁴, the asterisk indicates the point of attachment of Ring D to the E group, and $R^a$, n, $R^b$ and m are as defined for Formula I-A. In one embodiment, n is 0, 1, 2, 3 or 4. In one embodiment, n is 0. In one embodiment, n is 0 or 1 and m is 0 or 1. In one embodiment, n is 0 and m is 1. In one embodiment, $R^b$ is hydroxy, or $R^cR^dN$— where R is hydrogen or C1-C6 alkyl and $R^d$ is hydrogen or C1-C6 alkyl.

In one embodiment of Formula I-A, Ring D is:

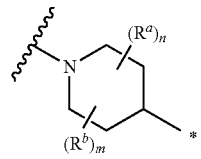

wherein the wavy line indicates the point of attachment of Ring D to the ring comprising X¹, X², X³ and X⁴, the asterisk indicates the point of attachment of Ring D to the E group, and $R^a$, n, $R^b$ and m are as defined for Formula I-A. In one embodiment, n is 0, 1, 2, 3 or 4. In one embodiment, n is 0. In one embodiment, n is 0 or 1 and m is 0 or 1. In one embodiment, n is 0 and m is 1. In one embodiment, $R^b$ is hydroxy, or $R^cR^dN$— where $R^c$ is hydrogen or C1-C6 alkyl and $R^d$ is hydrogen or C1-C6 alkyl.

In one embodiment of Formula I-A, Ring D is:

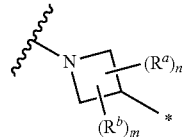

wherein the wavy line indicates the point of attachment of Ring D to the ring comprising X¹, X², X³ and X⁴, the asterisk indicates the point of attachment of Ring D to the E group, and $R^a$, n, $R^b$ and m are as defined for Formula I-A. In one embodiment, n is 0, 1, 2, 3 or 4. In one embodiment, n is 0. In one embodiment, n is 0 or 1 and m is 0 or 1. In one embodiment, n is 0 and m is 1. In one embodiment, $R^b$ is hydroxy, or $R^cR^dN$— where $R^c$ is hydrogen or C1-C6 alkyl and $R^d$ is hydrogen or C1-C6 alkyl.

In one embodiment of Formula I-A, E is (d) Ar¹C1-C6 alkyl- wherein said alkyl portion is optionally substituted with 1-3 fluoros, (e) hetAr²C1-C6 alkyl-, (g) Ar¹O—, (h) hetAr²O—, (i) Ar¹NR$^g$— where R$^g$ is H or C1-C6 alkyl, (l) Ar¹C(=O)NR$^g$— where R$^g$ is H or C1-C6 alkyl, or (m) hetAr²C(=O)NR(CH₂)$_p$—, where p is 0 or 1 and Ar¹, hetAr² and R$^g$ are as defined for Formula I-A.

In one embodiment of Formula I-A, X¹ is N; X², X³ and X⁴ are CH; A is CN; B is C1-C6 alkyl optionally substituted with 1-3 fluoros or hydroxyC2-C6 alkyl- optionally substituted with a C3-C6 cycloalkylidene ring; and Ring D is:

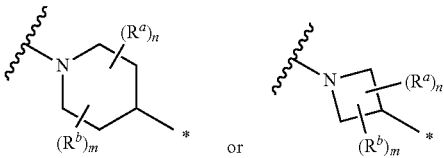

wherein the wavy line indicates the point of attachment of Ring D to the ring comprising X¹, X², X³ and X⁴, the asterisk indicates the point of attachment of Ring D to the E group, and $R^a$, n, $R^b$ and m are as defined for Formula I-A.

In one embodiment of Formula I-A, X¹ is N; X², X³ and X⁴ are CH; A is CN; B is C1-C6 alkyl optionally substituted with 1-3 fluoros or hydroxyC2-C6 alkyl- optionally substituted with a C3-C6 cycloalkylidene ring; and Ring D is:

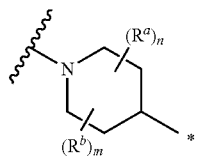

wherein the wavy line indicates the point of attachment of Ring D to the ring comprising $X^1$, $X^2$, $X^3$ and $X^4$, the asterisk indicates the point of attachment of Ring D to the E group, and $R^a$, n, $R^b$ and m are as defined for Formula I-A.

In one embodiment of Formula I-A, $X^1$ is N; $X^2$, $X^3$ and $X^4$ are CH; A is CN; B is C1-C6 alkyl optionally substituted with 1-3 fluoros or hydroxyC2-C6 alkyl- optionally substituted with a C3-C6 cycloalkylidene ring; and Ring D is:

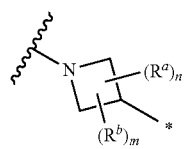

wherein the wavy line indicates the point of attachment of Ring D to the ring comprising $X^1$, $X^2$, $X^3$ and $X^4$, the asterisk indicates the point of attachment of Ring D to the E group, and $R^a$, n, $R^b$ and m are as defined for Formula I-A.

In one embodiment of Formula I-A, $X^1$ is N; $X^2$, $X^3$ and $X^4$ are CH; A is CN; B is C1-C6 alkyl optionally substituted with 1-3 fluoros; and Ring D is

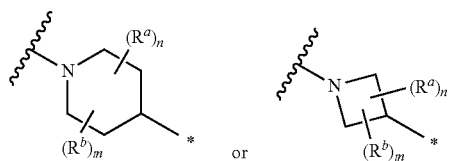

wherein the wavy line indicates the point of attachment of Ring D to the ring comprising $X^1$, $X^2$, $X^3$ and $X^4$, the asterisk indicates the point of attachment of Ring D to the E group, and $R^a$, n, $R^b$ and m are as defined for Formula I-A.

In one embodiment of Formula I-A, $X^1$ is N; $X^2$, $X^3$ and $X^4$ are CH; A is CN; B is C1-C6 alkyl optionally substituted with 1-3 fluoros; and Ring D is

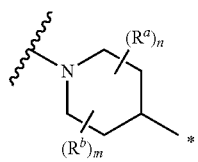

wherein the wavy line indicates the point of attachment of Ring D to the ring comprising $X^1$, $X^2$, $X^3$ and $X^4$, the asterisk indicates the point of attachment of Ring D to the E group, and $R^a$, n, $R^b$ and m are as defined for Formula I-A.

In one embodiment of Formula I-A, $X^1$ is N; $X^2$, $X^3$ and $X^4$ are CH; A is CN; B is C1-C6 alkyl optionally substituted with 1-3 fluoros; and Ring D is

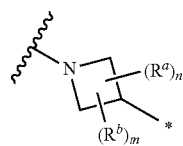

wherein the wavy line indicates the point of attachment of Ring D to the ring comprising $X^1$, $X^2$, $X^3$ and $X^4$, the asterisk indicates the point of attachment of Ring D to the E group, and $R^a$, n, $R^b$ and m are as defined for Formula I-A.

In one embodiment of Formula I-A, $X^1$ is N; $X^2$, $X^3$ and $X^4$ are CH; A is CN; B is hydroxyC2-C6 alkyl- optionally substituted with a C3-C6 cycloalkylidene ring; and Ring D is a piperidin-4-yl ring having the structure:

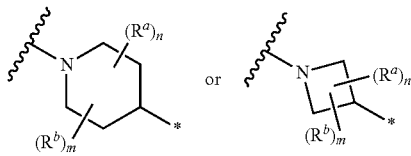

wherein the wavy line indicates the point of attachment of Ring D to the ring comprising $X^1$, $X^2$, $X^3$ and $X^4$, the asterisk indicates the point of attachment of Ring D to the E group, and $R^a$, n, $R^b$ and m are as defined for Formula I-A.

In one embodiment of Formula I-A, $X^1$ is N; $X^2$, $X^3$ and $X^4$ are CH; A is CN; B is hydroxyC2-C6 alkyl- optionally substituted with a C3-C6 cycloalkylidene ring; and Ring D is a piperidin-4-yl ring having the structure:

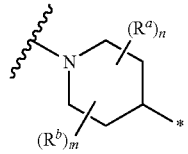

wherein the wavy line indicates the point of attachment of Ring D to the ring comprising $X^1$, $X^2$, $X^3$ and $X^4$, the asterisk indicates the point of attachment of Ring D to the E group, and $R^a$, n, $R^b$ and m are as defined for Formula I-A.

In one embodiment of Formula I-A, $X^1$ is N; $X^2$, $X^3$ and $X^4$ are CH; A is CN; B is hydroxyC2-C6 alkyl- optionally substituted with a C3-C6 cycloalkylidene ring; and Ring D is a piperidin-4-yl ring having the structure:

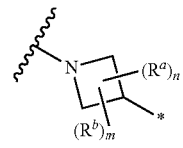

wherein the wavy line indicates the point of attachment of Ring D to the ring comprising $X^1$, $X^2$, $X^3$ and $X^4$, the asterisk indicates the point of attachment of Ring D to the E group, and $R^a$, n, $R^b$ and m are as defined for Formula I-A.

In one embodiment of Formula I-A, $X^1$ is N; $X^2$, $X^3$ and $X^4$ are CH; A is CN; B is C1-C6 alkyl optionally substituted with 1-3 fluoros or hydroxyC2-C6 alkyl- optionally substituted with a C3-C6 cycloalkylidene ring; Ring D is a piperidin-4-yl ring having the structure:

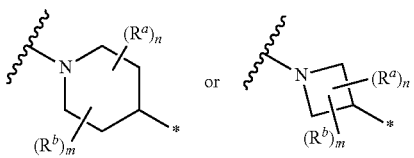

wherein the wavy line indicates the point of attachment of Ring D to the ring comprising $X^1$, $X^2$, $X^3$ and $X^4$, the asterisk indicates the point of attachment of Ring D to the E group, and $R^a$, n, $R^b$ and m are as defined for Formula I-A; and E is (d) $Ar^1$C1-C6 alkyl- wherein said alkyl portion is optionally substituted with 1-3 fluoros, (e) $hetAr^2$C1-C6 alkyl-, (g) $Ar^1$O—, (h) $hetAr^2$O—, (l) $Ar^1$C(=O)$NR^g$— where $R^g$ is H or C1-C6 alkyl, or (m) $hetAr^2$C(=O)NR$(CH_2)_p$—, where p is 0 or 1 and $Ar^1$, $hetAr^2$ and $R^g$ are as defined for Formula I-A.

In one embodiment of Formula I-A, $X^1$ is N; $X^2$, $X^3$ and $X^4$ are CH; A is CN; B is C1-C6 alkyl optionally substituted with 1-3 fluoros or hydroxyC2-C6 alkyl- optionally substituted with a C3-C6 cycloalkylidene ring; Ring D is a piperidin-4-yl ring having the structure:

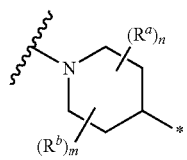

wherein the wavy line indicates the point of attachment of Ring D to the ring comprising $X^1$, $X^2$, $X^3$ and $X^4$, the asterisk indicates the point of attachment of Ring D to the E group, and $R^a$, n, $R^b$ and m are as defined for Formula I-A; and E is (d) $Ar^1$C1-C6 alkyl- wherein said alkyl portion is optionally substituted with 1-3 fluoros, (e) $hetAr^2$C1-C6 alkyl-, (g) $Ar^1$O—, (h) $hetAr^2$O—, (l) $Ar^1$C(=O)$NR^g$— where $R^g$ is H or C1-C6 alkyl, or (m) $hetAr^2$C(=O)NR$(CH_2)_p$—, where p is 0 or 1 and $Ar^1$, $hetAr^2$ and $R^g$ are as defined for Formula I-A.

In one embodiment of Formula I-A, $X^1$ is N; $X^2$, $X^3$ and $X^4$ are CH; A is CN; B is C1-C6 alkyl optionally substituted with 1-3 fluoros or hydroxyC2-C6 alkyl- optionally substituted with a C3-C6 cycloalkylidene ring; Ring D is a piperidin-4-yl ring having the structure:

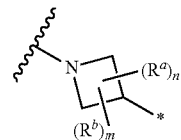

wherein the wavy line indicates the point of attachment of Ring D to the ring comprising $X^1$, $X^2$, $X^3$ and $X^4$, the asterisk indicates the point of attachment of Ring D to the E group, and $R^a$, n, $R^b$ and m are as defined for Formula I-A; and E is (d) $Ar^1$C1-C6 alkyl- wherein said alkyl portion is optionally substituted with 1-3 fluoros, (e) $hetAr^2$C1-C6 alkyl-, (g) $Ar^1$O—, (h) $hetAr^2$O—, (l) $Ar^1$C(=O)$NR^g$— where $R^g$ is H or C1-C6 alkyl, or (m) $hetAr^2$C(=O)NR$(CH_2)_p$—, where p is 0 or 1 and $Ar^1$, $hetAr^2$ and $R^g$ are as defined for Formula I-A.

In one embodiment of Formula I-A, E is (d) $Ar^1$C1-C6 alkyl- wherein said alkyl portion is optionally substituted with 1-3 fluoros, (e) $hetAr^2$C1-C6 alkyl-, (g) $Ar^1$O—, (h) $hetAr^2$O—, (l) $Ar^1$C(=O)$NR^g$— where $R^g$ is H or C1-C6 alkyl, or (m) $hetAr^2$C(=O)$NR^g(CH_2)_p$—, where p is 0 or 1 and $Ar^1$, $hetAr^2$ and $R^g$ are as defined for Formula I-A.

In one embodiment of Formula I-A, $X^1$ is N; $X^2$, $X^3$ and $X^4$ are CH; A is CN; B is C1-C6 alkyl optionally substituted with 1-3 fluoros; Ring D is

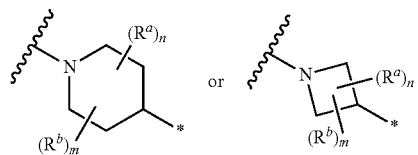

wherein the wavy line indicates the point of attachment of Ring D to the ring comprising $X^1$, $X^2$, $X^3$ and $X^4$, the asterisk indicates the point of attachment of Ring D to the E group, and $R^a$, n, $R^b$ and m are as defined for Formula I-A; and E is (d) $Ar^1$C1-C6 alkyl- wherein said alkyl portion is optionally substituted with 1-3 fluoros, (e) $hetAr^2$C1-C6 alkyl-, (g) $Ar^1$O—, (h) $hetAr^2$O—, (i) $Ar^1$NR$^g$— where $R^g$ is H or C1-C6 alkyl, (l) $Ar^1$C(=O)$NR^g$— where $R^g$ is H or C1-C6 alkyl, or (m) $hetAr^2$C(=O)$NR^g(CH_2)_p$—, where p is 0 or 1 and $Ar^1$, $hetAr^2$ and $R^g$ are as defined for Formula I-A.

In one embodiment of Formula I-A, $X^1$ is N; $X^2$, $X^3$ and $X^4$ are CH; A is CN; B is C1-C6 alkyl optionally substituted with 1-3 fluoros; Ring D is

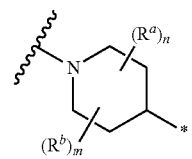

wherein the wavy line indicates the point of attachment of Ring D to the ring comprising $X^1$, $X^2$, $X^3$ and $X^4$, the asterisk indicates the point of attachment of Ring D to the E group, and $R^a$, n, $R^b$ and m are as defined for Formula I-A; and E is (d) $Ar^1$C1-C6 alkyl- wherein said alkyl portion is optionally substituted with 1-3 fluoros, (e) $hetAr^2$C1-C6 alkyl-, (g) $Ar^1$O—, (h) $hetAr^2$O—, (l) $Ar^1$C(=O)$NR^g$— where $R^g$ is H or C1-C6 alkyl, or (m) $hetAr^2$C(=O)NR$(CH_2)_p$—, where p is 0 or 1 and $Ar^1$, $hetAr^2$ and $R^g$ are as defined for Formula I-A.

In one embodiment of Formula I-A, $X^1$ is N; $X^2$, $X^3$ and $X^4$ are CH; A is CN; B is C1-C6 alkyl optionally substituted with 1-3 fluoros; Ring D is

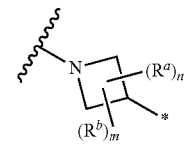

wherein the wavy line indicates the point of attachment of Ring D to the ring comprising $X^1$, $X^2$, $X^3$ and $X^4$, the asterisk indicates the point of attachment of Ring D to the E group, and $R^a$, n, $R^b$ and m are as defined for Formula I-A; and E is (d) $Ar^1$C1-C6 alkyl- wherein said alkyl portion is optionally substituted with 1-3 fluoros, (e) hetAr$^2$C1-C6 alkyl-, (g) $Ar^1$O—, (h) hetAr$^2$O—, (l) $Ar^1$C(=O)NR$^g$— where R$^g$ is H or C1-C6 alkyl, or (m) hetAr$^2$C(=O)NR (CH$_2$)$_p$—, where p is 0 or 1 and $Ar^1$, hetAr$^2$ and R$^g$ are as defined for Formula I-A.

In one embodiment of Formula I-A, $X^1$ is N; $X^2$, $X^3$ and $X^4$ are CH; A is CN; B is hydroxyC2-C6 alkyl- wherein the alkyl portion is optionally substituted with a C3-C6 cycloalkylidene ring; Ring D is

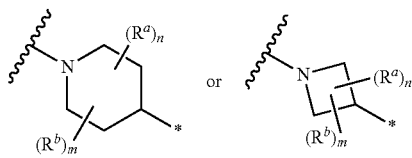

wherein the wavy line indicates the point of attachment of Ring D to the ring comprising $X^1$, $X^2$, $X^3$ and $X^4$, the asterisk indicates the point of attachment of Ring D to the E group, and $R^a$, n, $R^b$ and m are as defined for Formula I-A; and E is (d) $Ar^1$C1-C6 alkyl- wherein said alkyl portion is optionally substituted with 1-3 fluoros, (e) hetAr$^2$C1-C6 alkyl-, (g) $Ar^1$O—, (h) hetAr$^2$O—, (l) $Ar^1$C(=O)NR$^g$— where R$^g$ is H or C1-C6 alkyl, or (m) hetAr$^2$C(=O)NR (CH$_2$)$_p$—, where p is 0 or 1 and $Ar^1$, hetAr$^2$ and R$^g$ are as defined for Formula I-A.

In one embodiment of Formula I-A, $X^1$ is N; $X^2$, $X^3$ and $X^4$ are CH; A is CN; B is hydroxyC2-C6 alkyl- wherein the alkyl portion is optionally substituted with a C3-C6 cycloalkylidene ring; Ring D is

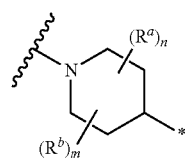

wherein the wavy line indicates the point of attachment of Ring D to the ring comprising $X^1$, $X^2$, $X^3$ and $X^4$, the asterisk indicates the point of attachment of Ring D to the E group, and $R^a$, n, $R^b$ and m are as defined for Formula I-A; and E is (d) $Ar^1$C1-C6 alkyl- wherein said alkyl portion is optionally substituted with 1-3 fluoros, (e) hetAr$^2$C1-C6 alkyl-, (g) $Ar^1$O—, (h) hetAr$^2$O—, (l) $Ar^1$C(=O)NR$^g$— where R$^g$ is H or C1-C6 alkyl, or (m) hetAr$^2$C(=O)NR (CH$_2$)$_p$—, where p is 0 or 1 and $Ar^1$, hetAr$^2$ and R$^g$ are as defined for Formula I-A.

In one embodiment of Formula I-A, $X^1$ is N; $X^2$, $X^3$ and $X^4$ are CH; A is CN; B is hydroxyC2-C6 alkyl- wherein the alkyl portion is optionally substituted with a C3-C6 cycloalkylidene ring; Ring D is

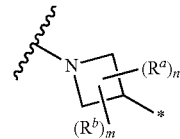

wherein the wavy line indicates the point of attachment of Ring D to the ring comprising $X^1$, $X^2$, $X^3$ and $X^4$, the asterisk indicates the point of attachment of Ring D to the E group, and $R^a$, n, $R^b$ and m are as defined for Formula I-A; and E is (d) $Ar^1$C1-C6 alkyl- wherein said alkyl portion is optionally substituted with 1-3 fluoros, (e) hetAr$^2$C1-C6 alkyl-, (g) $Ar^1$O—, (h) hetAr$^2$O—, (l) $Ar^1$C(=O)NR$^g$— where R$^g$ is H or C1-C6 alkyl, or (m) hetAr$^2$C(=O)NR (CH$_2$)$_p$—, where p is 0 or 1 and $Ar^1$, hetAr$^2$ and R$^g$ are as defined for Formula I-A.

In one embodiment, Formula I includes compounds of Formula I-B, wherein:

$X^1$, $X^2$, $X^3$ and $X^4$ are independently CH, CF or N, wherein zero, one or two of $X^1$, $X^2$, $X^3$ and $X^4$ is N;

A is H, CN, Cl, methyl, ethyl or cyclopropyl;

B is
(a) hydrogen,
(b) C1-C6 alkyl optionally substituted with 1-3 fluoros,
(c) hydroxyC2-C6 alkyl- wherein the alkyl portion is optionally substituted with a C3-C6 cycloalkylidene ring,
(d) dihydroxyC3-C6 alkyl- wherein the alkyl portion is optionally substituted with a C3-C6 cycloalkylidene ring,
(e) (C1-C6 alkoxy)C1-C6 alkyl- optionally substituted with 1-3 fluoros,
(f) ($R^1R^2$N)C1-C6 alkyl- where $R^1$ and $R^2$ are independently selected from H, C1-C6 alkyl (optionally substituted with 1-3 fluoros), (C1-C6 alkoxy)C1-C6 alkyl- and (C1-C6 alkoxy)C(=O)—;
(g) hetAr$^1$C1-C3 alkyl-, where hetAr$^1$ is a 5-6 membered heteroaryl ring having 1-3 ring heteroatoms independently selected from N, O and S and is optionally substituted with one or more independently selected C1-C6 alkyl groups;
(h) (C3-C6 cycloalkyl)C1-C3 alkyl-,
(i) (hetCyc$^a$)C1-C3 alkyl-, or
(j) hetCyc$^a$;

hetCyc$^a$ is a 4-6 membered heterocyclic ring having 1-2 ring heteroatoms independently selected from N and O and optionally substituted with one or more substituents independently selected from OH, C1-C6 alkyl (optionally substituted with 1-3 fluoros), and hydroxyC1-C6 alkyl;

Ring D is a saturated 7-8 membered bridged heterocyclic ring having one ring heteroatom which is nitrogen;

each $R^a$ is independently C1-C6 alkyl (optionally substituted with 1-3 fluoros) or hydroxyC1-C6 alkyl;

$R^b$ is hydroxy, cyclopropyl, or $R^cR^d$N— where $R^c$ is hydrogen or C1-C6 alkyl and $R^d$ is hydrogen, C1-C6 alkyl or (C1-C6 alkoxy)C(=O)—;

n is 0, 1, 2, 3, 4, 5 or 6;
m is 0 or 1;
E is
(a) hydrogen,
(b) hydroxy,
(f) (C1-C6 alkoxy)C1-C6 alkoxy,
(h) hetAr$^2$O—,
(j) hetAr$^2$NR$^g$— where R$^g$ is H or C1-C6 alkyl,
(n) $R^4R^5$NC(=O)—,
(o) $Ar^1$NR$^g$C(=O)—, where R$^g$ is H or C1-C6 alkyl, or
(p) hetAr$^2$NR$^g$C(=O)—, where R$^g$ is H or C1-C6 alkyl;

Ar¹ is phenyl optionally substituted with one or more substituents independently selected from the group consisting of halogen, CN, C1-C6 alkyl (optionally substituted with 1-3 fluoros), C1-C6 alkoxy (optionally substituted with 1-3 fluoros), (C1-C6 alkoxy)C1-C6 alkyl- (optionally substituted with 1-3 fluoros), C3-C6 cycloalkyl, and $R^eR^fN$— where $R^e$ and $R^f$ are independently H or C1-C6 alkyl;

hetAr² is a 5-6 membered heteroaryl ring having 1-3 ring heteroatoms independently selected from N, O and S, or a 9-10 membered bicyclic heteroaryl having 1-2 ring nitrogen atoms, wherein hetAr² is optionally substituted with one or more substituents independently selected from the group consisting of halogen, CN, C1-C6 alkyl (optionally substituted with 1-3 fluoros), C1-C6 alkoxy (optionally substituted with 1-3 fluoros), and (C1-C6 alkoxy)C1-C6 alkyl- (optionally substituted with 1-3 fluoros);

$R^4$ is H or C1-C6 alkyl;

$R^5$ is Ar², hetAr³ or C1-C6 alkyl optionally substituted with 1-3 fluoros;

Ar² is phenyl optionally substituted with one or more substituents independently selected from the group consisting of halogen, CN, C1-C6 alkyl (optionally substituted with 1-3 fluoros), C1-C6 alkoxy (optionally substituted with 1-3 fluoros), (C1-C6 alkoxy)C1-C6 alkyl- (optionally substituted with 1-3 fluoros), C3-C6 cycloalkyl, and $R^gR^hN$— where $R^g$ and $R^h$ are independently H or C1-C6 alkyl; and hetAr³ is a 5-6 membered heteroaryl ring having 1-3 ring heteroatoms independently selected from N, O and S and optionally substituted with one or more substituents independently selected from the group consisting of halogen, CN, C1-C6 alkyl (optionally substituted with 1-3 fluoros), C1-C6 alkoxy (optionally substituted with 1-3 fluoros), and (C1-C6 alkoxy)C1-C6 alkyl- (optionally substituted with 1-3 fluoros).

In one embodiment of Formula I-B, $X^1$ is N; $X^2$, $X^3$ and $X^4$ are CH.

In one embodiment of Formula I-B, A is CN.

In one embodiment of Formula I-B, $X^1$ is N; $X^2$, $X^3$ and $X^4$ are CH; and A is CN.

In one embodiment of Formula I-B, B is C1-C6 alkyl optionally substituted with 1-3 fluoros, or hydroxyC2-C6 alkyl- wherein the alkyl portion is optionally substituted with a C3-C6 cycloalkylidene ring. In one embodiment of Formula I-B, B is C1-C6 alkyl or hydroxyC2-C6 alkyl-.

In one embodiment of Formula I-B, $X^1$ is N; $X^2$, $X^3$ and $X^4$ are CH; A is CN; and B is C1-C6 alkyl optionally substituted with 1-3 fluoros, or hydroxyC2-C6 alkyl- wherein the alkyl portion is optionally substituted with a C3-C6 cycloalkylidene ring. In one embodiment, B is C1-C6 alkyl or hydroxyC2-C6 alkyl-.

In one embodiment of Formula I-B, $X^1$ is N; $X^2$, $X^3$ and $X^4$ are CH; A is CN; and B is C1-C6 alkyl optionally substituted with 1-3 fluoros. In one embodiment, B is C1-C6 alkyl.

In one embodiment of Formula I-B, $X^1$ is N; $X^2$, $X^3$ and $X^4$ are CH; A is CN; and hydroxyC2-C6 alkyl- wherein the alkyl portion is optionally substituted with a C3-C6 cycloalkylidene ring. In one embodiment, B is hydroxyC2-C6 alkyl-.

In one embodiment of Formula I-B, Ring D is

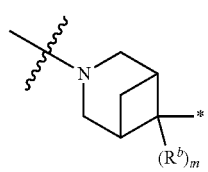

wherein the wavy line indicates the point of attachment of Ring D to the ring comprising $X^1$, $X^2$, $X^3$ and $X^4$, the asterisk indicates the point of attachment of Ring D to the E group, and $R^b$ and m are as defined for Formula I-B. In one embodiment, n is 0, 1, 2, 3 or 4. In one embodiment, n is 0. In one embodiment, n is 0 or 1 and m is 0 or 1. In one embodiment, n is 0 and m is 1. In one embodiment, $R^b$ is $R^cR^dN$— where $R^c$ is H or C1-C6 alkyl and $R^d$ is H or C1-C6 alkyl. In one embodiment, $R^b$ is $R^cR^dN$— where $R^c$ and $R^d$ are H.

In one embodiment of Formula I-B, E is $R^4R^5NC(=O)$—, where $R^4$ and $R^5$ are as defined for Formula I-B.

In one embodiment of Formula I-B, $X^1$ is N; $X^2$, $X^3$ and $X^4$ are CH; A is CN; B is C1-C6 alkyl optionally substituted with 1-3 fluoros, or hydroxyC2-C6 alkyl- wherein the alkyl portion is optionally substituted with a C3-C6 cycloalkylidene ring; and Ring D is

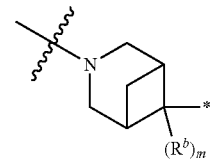

wherein the wavy line indicates the point of attachment of Ring D to the ring comprising $X^1$, $X^2$, $X^3$ and $X^4$, the asterisk indicates the point of attachment of Ring D to the E group, and $R^b$ and m are as defined for Formula I-B. In one embodiment, m is 0. In one embodiment, m is 1. In one embodiment, $R^b$ is $R^cR^dN$— where $R^c$ is H or C1-C6 alkyl and $R^d$ is H or C1-C6 alkyl. In one embodiment, $R^b$ is $R^cR^dN$— where $R^c$ and $R^d$ are H.

In one embodiment of Formula I-B, $X^1$ is N; $X^2$, $X^3$ and $X^4$ are CH; A is CN; B is C1-C6 alkyl optionally substituted with 1-3 fluoros or hydroxyC2-C6 alkyl- optionally substituted with a C3-C6 cycloalkylidene ring; Ring D is

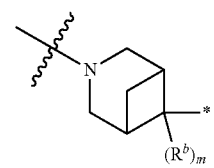

wherein the wavy line indicates the point of attachment of Ring D to the ring comprising $X^1$, $X^2$, $X^3$ and $X^4$, the asterisk indicates the point of attachment of Ring D to the E group, and $R^a$, n, $R^b$ and m are as defined for Formula I-A; and E is (n) $R^4R^5NC(=O)$—, where $R^4$ and $R^5$ are as defined for Formula I-B.

In one embodiment of Formula I-B, $X^1$ is N; $X^2$, $X^3$ and $X^4$ are CH; A is CN; B is C1-C6 alkyl optionally substituted with 1-3 fluoros or hydroxyC2-C6 alkyl- optionally substituted with a C3-C6 cycloalkylidene ring; Ring D is

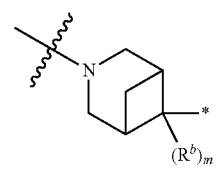

wherein the wavy line indicates the point of attachment of Ring D to the ring comprising $X^1$, $X^2$, $X^3$ and $X^4$, the asterisk indicates the point of attachment of Ring D to the E group; E is (h) hetAr²O—, (j) hetAr²NR$^g$— where R$^g$ is H or C1-C6 alkyl, (o) Ar¹NR$^g$C(=O)—, where R$^g$ is H or C1-C6 alkyl, or (p) hetAr²NR$^g$C(=O)—, where R$^g$ is H or C1-C6 alkyl; and R$^b$ and m are as defined for Formula I-B. In one embodiment, m is 0. In one embodiment, m is 1. In one embodiment, R$^b$ is R$^c$R$^d$N— where R$^c$ is H or C1-C6 alkyl and R$^d$ is H or C1-C6 alkyl. In one embodiment, R$^b$ is R$^c$R$^d$N— where R$^c$ and R$^d$ are H.

In one embodiment of Formula I-B, $X^1$ is N; $X^2$, $X^3$ and $X^4$ are CH; A is CN; B C1-C6 alkyl optionally substituted with 1-3 fluoros; Ring D is

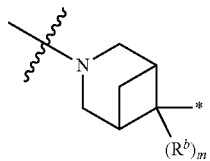

wherein the wavy line indicates the point of attachment of Ring D to the ring comprising $X^1$, $X^2$, $X^3$ and $X^4$, the asterisk indicates the point of attachment of Ring D to the E group; E is (h) hetAr²O—, (j) hetAr²NR$^g$— where R$^g$ is H or C1-C6 alkyl, (o) Ar¹NR$^g$C(=O)—, where R$^g$ is H or C1-C6 alkyl, or (p) hetAr²NR$^g$C(=O)—, where R$^g$ is H or C1-C6 alkyl; and R$^b$ and m are as defined for Formula I-B. In one embodiment, m is 0. In one embodiment, m is 1. In one embodiment, R$^b$ is R$^c$R$^d$N— where R$^c$ is H or C1-C6 alkyl and R$^d$ is H or C1-C6 alkyl. In one embodiment, R$^b$ is R$^c$R$^d$N— where R$^c$ and R$^d$ are H.

In one embodiment of Formula I-B, $X^1$ is N; $X^2$, $X^3$ and $X^4$ are CH; A is CN; B hydroxyC1-C6 alkyl wherein the alkyl portion is optionally substituted with a C3-C6 cycloalkylidene ring; and Ring D is

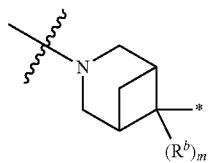

wherein the wavy line indicates the point of attachment of Ring D to the ring comprising $X^1$, $X^2$, $X^3$ and $X^4$, the asterisk indicates the point of attachment of Ring D to the E group; E is (h) hetAr²O—, (j) hetAr²NR$^g$— where R$^g$ is H or C1-C6 alkyl, (o) Ar¹NR$^g$C(=O)—, where R$^g$ is H or C1-C6 alkyl, or (p) hetAr²NR$^g$C(=O)—, where R$^g$ is H or C1-C6 alkyl; and R$^b$ and m are as defined for Formula I-B. In one embodiment, m is 0. In one embodiment, m is 1. In one embodiment, R$^b$ is R$^c$R$^d$N— where R$^c$ is H or C1-C6 alkyl and R$^d$ is H or C1-C6 alkyl. In one embodiment, R$^b$ is R$^c$R$^d$N— where R$^c$ and R$^d$ are H.

In one embodiment, Formula I includes compounds of Formula I-C,

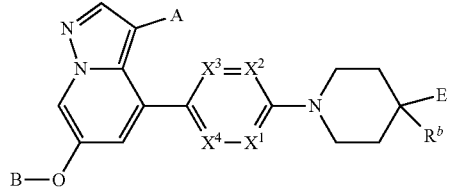

wherein:
$X^1$, $X^2$, $X^3$ and $X^4$ are independently CH, CF or N, wherein zero, one or two of $X^1$, $X^2$, $X^3$ and $X^4$ is N;
A is H, CN, Cl, methyl, ethyl or cyclopropyl;
B is
(a) hydrogen,
(b) C1-C6 alkyl optionally substituted with 1-3 fluoros,
(c) hydroxyC2-C6 alkyl- wherein the alkyl portion is optionally substituted with a C3-C6 cycloalkylidene ring,
(d) dihydroxyC3-C6 alkyl- wherein the alkyl portion is optionally substituted with a C3-C6 cycloalkylidene ring,
(e) (C1-C6 alkoxy)C1-C6 alkyl- optionally substituted with 1-3 fluoros,
(f) (R¹R²N)C1-C6 alkyl- where R¹ and R² are independently selected from H, C1-C6 alkyl (optionally substituted with 1-3 fluoros), (C1-C6 alkoxy)C1-C6 alkyl-, (C1-C6 alkyl)C(=O)— and (C1-C6 alkoxy)C(=O)—;
(g) hetAr¹C1-C3 alkyl-, where hetAr¹ is a 5-6 membered heteroaryl ring having 1-3 ring heteroatoms independently selected from N, O and S and is optionally substituted with one or more independently selected C1-C6 alkyl groups;
(h) (C3-C6 cycloalkyl)C1-C3 alkyl-,
(i) (hetCyc$^a$)C1-C3 alkyl-,
(j) hetCyc$^a$,
(k) (R¹R²N)C(=O)C1-C6 alkyl- where R¹ and R² are independently selected from H and C1-C6 alkyl, or
(l) (R¹R²N)C(=O)—, where R¹ and R² are independently selected from H and C1-C6 alkyl;
hetCyc$^a$ is a 4-6 membered heterocyclic ring having 1-2 ring heteroatoms independently selected from N and O and optionally substituted with one or more substituents independently selected from OH, C1-C6 alkyl (optionally substituted with 1-3 fluoros), hydroxyC1-C6 alkyl, halogen, (C1-C6 alkyl)C(=O)—, C1-C6 alkoxy, oxo and (C1-C6 alkoxy)C(=O)—;
R$^b$ is (a) hydroxy, (b) cyclopropyl, (c) hetCyc$^b$CH₂—, (d) R$^i$R$^j$NC(=O)CH₂OCH₂— where R$^i$ and R$^j$ are independently H or C1-C6 alkyl, (e) R$^c$R$^d$N—, (f) R$^c$R$^d$NCH₂—, (g) C1-C6 alkoxy-, (h) (C1-C4 alkyl)-C(=O)NH— wherein said alkyl portion is optionally substituted with hetCyc$^b$, hetAr$^a$, C1-C6 alkoxy- or R'R"N—, or said alkyl portion is optionally substituted with two substituents independently selected from R'R"N— and OH, where each R' and R" is independently hydrogen or C1-C6 alkyl, (i) (R'R"N)C1-C6 alkoxy(CH₂)$_n$— where n is 0 or 1 and R' and R" are independently hydrogen or C1-C6 alkyl, (j) hetCyc$^b$(C1-C3 alkyl)OCH₂—, (k) hetCyc$^b$C(=O)NH— or (l) hetAr$^a$C(=O)NH—;
hetCyc$^b$ is a 4-6 membered heterocyclic ring, a 7-8 membered bridged heterocyclic ring, or a 7-10 membered heterospirocyclic ring, each ring having 1-2 ring heteroatoms independently selected from N and O, wherein hetCyc$^b$ is optionally substituted with one or more substituents independently selected from OH, fluoro, C1-C6 alkyl (optionally substituted with 1-3 fluoros), hydroxyC1-C6 alkyl- (optionally substituted with 1-3 fluoros), (C1-C6 alkoxy)

C1-C6 alkyl-, (C1-C6 alkoxy)C(=O)—, C1-C6 alkoxy, and R'R"N— where R' and R" are independently hydrogen or C1-C6 alkyl;

hetAr$^a$ is a 5-6 membered heteroaryl ring having 1-3 ring heteroatoms independently selected from N, O and S herein hetAr$^a$ is optionally substituted with one or more substituents independently selected from the group consisting of halogen, CN, C1-C6 alkyl (optionally substituted with 1-3 fluoros), and C1-C6 alkoxy (optionally substituted with 1-3 fluoros);

R$^c$ is hydrogen or C1-C6 alkyl;

R$^d$ is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C(=O)—, (C1-C6 alkyl)C(=O)—, (R$^k$R$^l$N)C1-C6 alkyl- where R$^k$ and R$^l$ are independently H or C1-C6 alkyl, R$^m$R$^n$NC(=O)C1-C6 alkyl- where R$^m$ and R$^n$ are independently H or C1-C6 alkyl, PhCH$_2$—, (C1-C6 alkoxy)C1-C6 alkyl-, or hetCyc$^c$ where hetCyc$^c$ is a 4-6 membered heterocyclic ring having a ring heteroatom selected from N and O and optionally substituted with C1-C6 alkyl;

E is
(a) hydrogen,
(b) hydroxy,
(c) C1-C6 alkyl optionally substituted with 1-3 fluoros,
(d) Ar$^1$C1-C6 alkyl- wherein said alkyl portion is optionally substituted with 1-3 fluoros,
(e) hetAr$^2$C1-C6 alkyl-,
(f) (C1-C6 alkoxy)C1-C6 alkoxy-,
(g) Ar$^1$O—,
(h) hetAr$^2$O—,
(i) Ar$^1$NR$^g$— where R$^g$ is H or C1-C6 alkyl,
(j) hetAr$^2$NR$^g$— where R$^g$ is H or C1-C6 alkyl,
(k) R$^3$C(=O)NR$^g$— where R$^g$ is H or C1-C6 alkyl,
(l) Ar$^1$C(=O)NR$^g$— where R$^g$ is H or C1-C6 alkyl,
(m) hetAr$^2$C(=O)NR$^g$(CH$_2$)$_p$— where p is 0 or 1 and R$^g$ is H or C1-C6 alkyl,
(n) R$^4$R$^5$NC(=O)—,
(o) Ar$^1$NR$^g$C(=O)—, where R$^g$ is H or C1-C6 alkyl,
(p) hetAr$^2$NR$^g$C(=O)—, where R$^g$ is H or C1-C6 alkyl,
(r) hetCyc$^5$C(=O)—,
(s) R$^4$R$^5$NC(=O)NR$^g$— where R$^g$ is H or C1-C6 alkyl,
(t) (C1-C6 alkyl)SO$_2$—;
(u) Ar$^1$(C1-C6 alkyl)C(=O)NR$^g$— where R$^g$ is H or C1-C6 alkyl,
(v) hetAr$^4$C(=O)NR$^g$— where R$^g$ is H or C1-C6 alkyl,
(w) hetAr$^2$—S(=O)—,
(x) (C3-C6 cycloalkyl)CH$_2$SO$_2$—,
(y) Ar$^1$(C1-C6 alkyl)SO$_2$—,
(z) hetAr$^2$SO$_2$—,
(aa) Ar$^1$,
(bb) hetAr$^2$,
(cc) hetCyc$^5$,
(dd) C1-C6 alkoxy,
(ee) Ar$^1$(C1-C6 alkyl)-O—,
(ff) hetAr$^2$(C1-C6 alkyl)-O—,
(gg) hetAr$^2$—O—C1-C6 alkyl-,
(hh) Ar$^1$(C1-C6 alkyl)NR$^g$— where R$^g$ is H or C1-C6 alkyl-,
(ii) hetAr$^2$—S—,
(jj) Ar$^2$SO$_2$NR$^g$(CH$_2$)$_p$— where p is 0 or 1 and R$^g$ is H or C1-C6 alkyl,
(kk) (C1-C6 alkoxy)C(=O)—,
(ll) (C1-C6 alkyl)NR$^g$C(=O)O— where R$^g$ is H or C1-C6 alkyl,
(mm) (C1-C6 alkyl)NR$^g$SO$_2$— where R$^g$ is H or C1-C6 alkyl, (oo) Q-NR$^h$(C1-C3 alkyl)C(=O)NR$^g$— where R$^g$ and R$^h$ are independently H or C1-C6 alkyl and Q is H, C1-C6 alkyl or (C1-C6 alkyl)OC(=O)—,
(pp)

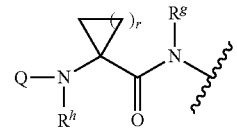

where R$^g$ and R$^h$ are independently H or C1-C6 alkyl, Q is H, C1-C6 alkyl or (C1-C6 alkyl)OC(=O)— and r is 1, 2, 3 or 4,
(qq)

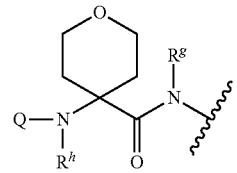

where R$^g$ and R$^h$ are independently H or C1-C6 alkyl and Q is H, C1-C6 alkyl or (C1-C6 alkyl)OC(=O)—,
(rr)

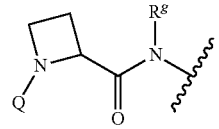

where R$^g$ is H or C1-C6 alkyl and Q is H, C1-C6 alkyl or (C1-C6 alkyl)OC(=O)—, or
(ss) R$^g$R$^h$N— where R$^g$ and R$^h$ are independently H or C1-C6 alkyl;

Ar$^1$ is phenyl optionally substituted with one or more substituents independently selected from the group consisting of halogen, CN, C1-C6 alkyl (optionally substituted with 1-3 fluoros), C1-C6 alkoxy (optionally substituted with 1-3 fluoros), (C1-C6 alkoxy)C1-C6 alkyl- (optionally substituted with 1-3 fluoros), C3-C6 cycloalkyl, hydroxyC1-C6 alkyl, (C1-C6 alkyl)SO$_2$—, R$^e$R$^f$N— and (R$^e$R$^f$N)C1-C6 alkyl- where each R$^e$ and R$^f$ is independently H or C1-C6 alkyl;

hetAr$^2$ is a 5-6 membered heteroaryl ring having 1-3 ring heteroatoms independently selected from N, O and S, or a 9-10 membered bicyclic heteroaryl having 1-2 ring nitrogen atoms, wherein hetAr$^2$ is optionally substituted with one or more substituents independently selected from the group consisting of halogen, CN, C1-C6 alkyl (optionally substituted with 1-3 fluoros), C1-C6 alkoxy (optionally substituted with 1-3 fluoros), (C1-C6 alkoxy)C1-C6 alkyl- (optionally substituted with 1-3 fluoros) and hydroxyC1-C6 alkoxy-;

hetCyc$^5$ is a 4-6 membered saturated heterocyclic ring having 1-2 ring heteroatoms independently selected from N, O and S wherein said heterocyclic ring is optionally substituted with one or more substituents independently selected from C1-C6 alkoxy and oxo;

R$^3$ is C1-C6 alkyl (optionally substituted with 1-3 fluoros), hydroxyC1-C6 alkyl-, C1-C6 alkoxy, C3-C6 cycloalkyl, (C3-C6 cycloalkyl)CH$_2$—, (C3-C6 cycloalkyl)O—, (C3-C6 cycloalkyl)CH$_2$O—, hetCyc$^7$O—, Ph-O—, or (C1-C6 alkoxy)C1-C6 alkyl-; wherein each of said C3-C6 cycloalkyl moieties is optionally substituted with C1-C6 alkyl (optionally substituted with 1-3 fluoros), C1-C6 alkoxy, OH or R'R"N— where R' and R" are independently hydrogen or C1-C6 alkyl;

R$^4$ is H or C1-C6 alkyl;

R$^5$ is Ar$^2$, hetAr$^3$, Ar$^2$CH$_2$—, hetCyc$^6$-CH$_2$—, hydroxyC1-C6 alkyl-, (C3-C6 cycloalkyl)CH$_2$—, or C1-C6 alkyl optionally substituted with 1-3 fluoros;

Ar$^2$ is phenyl optionally substituted with one or more substituents independently selected from the group consisting of halogen, CN, C1-C6 alkyl (optionally substituted with 1-3 fluoros), C1-C6 alkoxy (optionally substituted with 1-3 fluoros), (C1-C6 alkoxy)C1-C6 alkyl- (optionally substituted with 1-3 fluoros), C3-C6 cycloalkyl, and R$^g$R$^h$N— where R$^g$ and R$^h$ are independently H or C1-C6 alkyl, or Ar$^2$ is phenyl fused to a 6 membered heterocyclic ring having a ring nitrogen atom and optionally substituted with C1-C6 alkyl;

hetAr$^3$ is a 5-6 membered heteroaryl ring having 1-3 ring heteroatoms independently selected from N, O and S and optionally substituted with one or more substituents independently selected from the group consisting of halogen, CN, C1-C6 alkyl (optionally substituted with 1-3 fluoros), C1-C6 alkoxy (optionally substituted with 1-3 fluoros), and (C1-C6 alkoxy)C1-C6 alkyl- (optionally substituted with 1-3 fluoros);

hetAr$^4$ is pyridin-4(1H)-onyl or pyridin-2(1H)-onyl optionally substituted with one or more substituents independently selected from C1-C6 alkyl and halogen;

hetCyc$^6$ is a 5-7 membered heterocyclic ring having 1-3 ring heteroatoms independently selected from N, O and S; and hetCyc$^7$ is a 5-7 membered heterocyclic ring having 1-3 ring heteroatoms independently selected from N, O and S.

In one embodiment of Formula I-C, X$^1$ is N; and X$^2$, X$^3$ and X$^4$ are CH.

In one embodiment of Formula I-C, A is CN.

In one embodiment of Formula I-C, X$^1$ is N; X$^2$, X$^3$ and X$^4$ are CH; and A is CN.

In one embodiment of Formula I-C, B is C1-C6 alkyl optionally substituted with 1-3 fluoros, or hydroxyC2-C6 alkyl- wherein the alkyl portion is optionally substituted with a C3-C6 cycloalkylidene ring. In one embodiment of Formula I-C, B is C1-C6 alkyl or hydroxyC2-C6 alkyl-.

In one embodiment of Formula I-C, X$^1$ is N; X$^2$, X$^3$ and X$^4$ are CH; A is CN; and B is C1-C6 alkyl optionally substituted with 1-3 fluoros, or hydroxyC2-C6 alkyl- wherein the alkyl portion is optionally substituted with a C3-C6 cycloalkylidene ring. In one embodiment, B is C1-C6 alkyl or hydroxyC2-C6 alkyl-.

In one embodiment of Formula I-C, X$^1$ is N; X$^2$, X$^3$ and X$^4$ are CH; A is CN; and B is C1-C6 alkyl optionally substituted with 1-3 fluoros. In one embodiment, B is C1-C6 alkyl.

In one embodiment of Formula I-C, X$^1$ is N; X$^2$, X$^3$ and X$^4$ are CH; A is CN; and B is hydroxyC2-C6 alkyl- optionally substituted with a C3-C6 cycloalkylidene ring. In one embodiment, B is hydroxyC2-C6 alkyl-.

In one embodiment of Formula I-C, E is (d) Ar$^1$C1-C6 alkyl- wherein said alkyl portion is optionally substituted with 1-3 fluoros, (e) hetAr$^2$C1-C6 alkyl-, (g) Ar$^1$O—, (h) hetAr$^2$O—, (i) Ar$^1$NR$^g$— where R$^g$ is H or C1-C6 alkyl, (k) R$^3$C(=O)NR$^g$— where R$^g$ is H or C1-C6 alkyl, (l) Ar$^1$C(=O)NR$^g$— where R$^g$ is H or C1-C6 alkyl, or (m) hetAr$^2$C(=O)NR(CH$_2$)$_p$—, where p is 0 or 1 and R$^3$, R, Ar$^1$ and hetAr$^2$ are as defined for Formula I-C.

In one embodiment of Formula I-C, A is CN; B is C1-C6 alkyl optionally substituted with 1-3 fluoros; and E is (d) Ar$^1$C1-C6 alkyl- wherein said alkyl portion is optionally substituted with 1-3 fluoros, (e) hetAr$^2$C1-C6 alkyl-, (g) Ar$^1$O—, (h) hetAr$^2$O—, (i) Ar$^1$NR$^g$— where R$^g$ is H or C1-C6 alkyl, (k) R$^3$C(=O)NR$^g$— where R$^g$ is H or C1-C6 alkyl, (l) Ar$^1$C(=O)NR$^g$— where R$^g$ is H or C1-C6 alkyl, or (m) hetAr$^2$C(=O)NR$^g$(CH$_2$)$_p$—, where p is 0 or 1 and R$^3$, R$^g$, Ar$^1$ and hetAr$^2$ are as defined for Formula I-C.

In one embodiment of Formula I-C, A is CN; B is hydroxyC2-C6 alkyl- optionally substituted with a C3-C6 cycloalkylidene ring; and E is (d) Ar$^1$C1-C6 alkyl- wherein said alkyl portion is optionally substituted with 1-3 fluoros, (e) hetAr$^2$C1-C6 alkyl-, (g) Ar$^1$O—, (h) hetAr$^2$O—, (i) Ar$^1$NR$^g$— where R$^g$ is H or C1-C6 alkyl, (k) R$^3$C(=O)NR$^g$— where R$^g$ is H or C1-C6 alkyl, (l) Ar$^1$C(=O)NR$^g$— where R$^g$ is H or C1-C6 alkyl, or (m) hetAr$^2$C(=O)NR$^g$(CH$_2$)$_p$—, where p is 0 or 1 and Ar$^1$, hetAr$^2$ and R$^g$ are as defined for Formula I-C.

In one embodiment of Formula I-C, R$^b$ is (c) hetCyc$^b$CH$_2$— where hetCyc$^b$ is a 4-6 membered heterocyclic ring having 1-2 ring heteroatoms independently selected from N and O, wherein hetCyc$^b$ is optionally substituted with one or more substituents independently selected from OH, fluoro, C1-C6 alkyl (optionally substituted with 1-3 fluoros), hydroxyC1-C6 alkyl- (optionally substituted with 1-3 fluoros), and (C1-C6 alkoxy)C1-C6 alkyl-, (e) R$^c$R$^d$N—, or (f) R$^c$R$^d$NCH$_2$—; R$^c$ is hydrogen or C1-C6 alkyl; and R$^d$ is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C(=O)—, (C1-C6 alkyl)C(=O)—, (R$^k$R$^l$N)C1-C6 alkyl- where R$^k$ and R$^l$ are independently H or C1-C6 alkyl, R$^m$R$^n$NC(=O)C1-C6 alkyl- where R$^m$ and R$^n$ are independently H or C1-C6 alkyl, PhCH$_2$—, (C1-C6 alkoxy)C1-C6 alkyl-, or hetCyc$^c$ where hetCyc$^c$ is a 4-6 membered heterocyclic ring having a ring heteroatom selected from N and O and optionally substituted with C1-C6 alkyl.

In one embodiment of Formula I-C, R$^b$ is hetCyc$^b$CH$_2$— where hetCyc$^b$ is a 4-6 membered heterocyclic ring having 1-2 ring heteroatoms independently selected from N and O, wherein hetCyc$^b$ is optionally substituted with one or more substituents independently selected from OH, fluoro, C1-C6 alkyl (optionally substituted with 1-3 fluoros), hydroxyC1-C6 alkyl- (optionally substituted with 1-3 fluoros), and (C1-C6 alkoxy)C1-C6 alkyl-.

In one embodiment of Formula I-C, R$^b$ is R$^c$R$^d$N—; R$^c$ is hydrogen or C1-C6 alkyl; and R$^d$ is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C(=O)—, (C1-C6 alkyl)C(=O)—, (R$^k$R$^l$N)C1-C6 alkyl- where R$^k$ and R$^l$ are independently H or C1-C6 alkyl, R$^m$R$^n$NC(=O)C1-C6 alkyl- where R$^m$ and R$^n$ are independently H or C1-C6 alkyl, PhCH$_2$—, (C1-C6 alkoxy)C1-C6 alkyl-, or hetCyc$^c$ where hetCyc$^c$ is a 4-6 membered heterocyclic ring having a ring heteroatom selected from N and O and optionally substituted with C1-C6 alkyl.

In one embodiment of Formula I-C, R$^b$ is R$^c$R$^d$NCH$_2$—; R$^c$ is hydrogen or C1-C6 alkyl; and R$^d$ is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C(=O)—, (C1-C6 alkyl)C(=O)—, (R$^k$R$^l$N)C1-C6 alkyl- where R$^k$ and R$^l$ are independently H or C1-C6 alkyl, R$^m$R$^n$NC(=O)C1-

C6 alkyl- where R'" and R" are independently H or C1-C6 alkyl, PhCH$_2$—, (C1-C6 alkoxy)C1-C6 alkyl-, or hetCyc$^c$ where hetCyc$^c$ is a 4-6 membered heterocyclic ring having a ring heteroatom selected from N and O and optionally substituted with C1-C6 alkyl.

In one embodiment of Formula I-C, A is CN, B is hydroxyC2-C6 alkyl- optionally substituted with a C3-C6 cycloalkylidene ring; E is (d) Ar$^1$C1-C6 alkyl- wherein said alkyl portion is optionally substituted with 1-3 fluoros, (e) hetAr$^2$C1-C6 alkyl-, (g) Ar$^1$O—, (h) hetAr$^2$O—, (i) Ar$^1$NR$^g$— where R$^g$ is H or C1-C6 alkyl, (k) R$^3$C(=O)NR$^g$— where R$^g$ is H or C1-C6 alkyl, (l) Ar$^1$C(=O)NR$^g$— where R$^g$ is H or C1-C6 alkyl, or (m) hetAr$^2$C(=O)NR$^g$(CH$_2$)$_p$—, where p is 0 or 1 and R$^3$, R$^g$, Ar$^1$ and hetAr$^2$ are as defined for Formula I-C; and R$^b$ is (c) hetCyc$^b$CH$_2$— where hetCyc$^b$ is a 4-6 membered heterocyclic ring having 1-2 ring heteroatoms independently selected from N and O, wherein hetCyc$^b$ is optionally substituted with one or more substituents independently selected from OH, fluoro, C1-C6 alkyl (optionally substituted with 1-3 fluoros), hydroxyC1-C6 alkyl- (optionally substituted with 1-3 fluoros), and (C1-C6 alkoxy)C1-C6 alkyl-.

In one embodiment of Formula I-C, A is CN, B is hydroxyC2-C6 alkyl- optionally substituted with a C3-C6 cycloalkylidene ring; E is (d) Ar$^1$C1-C6 alkyl- wherein said alkyl portion is optionally substituted with 1-3 fluoros, (e) hetAr$^2$C1-C6 alkyl-, (g) Ar$^1$O—, (h) hetAr$^2$O—, (i) Ar$^1$NR$^g$— where R$^g$ is H or C1-C6 alkyl, (k) R$^3$C(=O)NR$^g$— where R$^g$ is H or C1-C6 alkyl, (l) Ar$^1$C(=O)NR$^g$— where R$^g$ is H or C1-C6 alkyl, or (m) hetAr$^2$C(=O)NR$^g$(CH$_2$)$_p$—, where p is 0 or 1 and R$^3$, R, Ar$^1$ and hetAr$^2$ are as defined for Formula I-C; R$^b$ is (e) R$^c$R$^d$N—; R$^c$ is hydrogen or C1-C6 alkyl; and R$^d$ is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C(=O)—, (C1-C6 alkyl)C(=O)—, (R$^k$R$^l$N)C1-C6 alkyl- where R$^k$ and R$^l$ are independently H or C1-C6 alkyl, R'''R''NC(=O)C1-C6 alkyl- where R'" and R" are independently H or C1-C6 alkyl, PhCH$_2$—, (C1-C6 alkoxy)C1-C6 alkyl-, or hetCyc$^c$ where hetCyc$^c$ is a 4-6 membered heterocyclic ring having a ring heteroatom selected from N and O and optionally substituted with C1-C6 alkyl.

In one embodiment of Formula I-C, A is CN, B is hydroxyC2-C6 alkyl- optionally substituted with a C3-C6 cycloalkylidene ring; E is (d) Ar$^1$C1-C6 alkyl- wherein said alkyl portion is optionally substituted with 1-3 fluoros, (e) hetAr$^2$C1-C6 alkyl-, (g) Ar$^1$O—, (h) hetAr$^2$O—, (i) Ar$^1$NR$^g$— where R$^g$ is H or C1-C6 alkyl, (k) R$^3$C(=O)NR$^g$— where R$^g$ is H or C1-C6 alkyl, (l) Ar$^1$C(=O)NR$^g$— where R$^g$ is H or C1-C6 alkyl, or (m) hetAr$^2$C(=O)NR$^g$(CH$_2$)$_p$—, where p is 0 or 1 and R$^3$, R, Ar$^1$ and hetAr$^2$ are as defined for Formula I-C; R$^b$ is (f) R$^c$R$^d$NCH$_2$—; R$^c$ is hydrogen or C1-C6 alkyl; and R$^d$ is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C(=O)—, (C1-C6 alkyl)C(=O)—, (R$^k$R$^l$N)C1-C6 alkyl- where R$^k$ and R$^l$ are independently H or C1-C6 alkyl, R'''R''NC(=O)C1-C6 alkyl- where R'" and R" are independently H or C1-C6 alkyl, PhCH$_2$—, (C1-C6 alkoxy)C1-C6 alkyl-, or hetCyc$^c$ where hetCyc$^c$ is a 4-6 membered heterocyclic ring having a ring heteroatom selected from N and O and optionally substituted with C1-C6 alkyl.

In one embodiment of Formula I-C, A is CN; B is C1-C6 alkyl optionally substituted with 1-3 fluoros; E is (d) Ar$^1$C1-C6 alkyl- wherein said alkyl portion is optionally substituted with 1-3 fluoros, (e) hetAr$^2$C1-C6 alkyl-, (g) Ar$^1$O—, (h) hetAr$^2$O—, (i) Ar$^1$NR$^g$— where R$^g$ is H or C1-C6 alkyl, (k) R$^3$C(=O)NR$^g$— where R$^g$ is H or C1-C6 alkyl, (l) Ar$^1$C(=O)NR$^g$— where R$^g$ is H or C1-C6 alkyl, or (m) hetAr$^2$C(=O)NR$^g$(CH$_2$)$_p$—, where p is 0 or 1 and R$^3$, R$^g$, Ar$^1$ and hetAr$^2$ are as defined for Formula I-C; and R$^b$ is (c) hetCyc$^b$CH$_2$— where hetCyc$^b$ is a 4-6 membered heterocyclic ring having 1-2 ring heteroatoms independently selected from N and O, wherein hetCyc$^b$ is optionally substituted with one or more substituents independently selected from OH, fluoro, C1-C6 alkyl (optionally substituted with 1-3 fluoros), hydroxyC1-C6 alkyl- (optionally substituted with 1-3 fluoros), and (C1-C6 alkoxy)C1-C6 alkyl-.

In one embodiment of Formula I-C, A is CN; B is C1-C6 alkyl optionally substituted with 1-3 fluoros; E is (d) Ar$^1$C1-C6 alkyl- wherein said alkyl portion is optionally substituted with 1-3 fluoros, (e) hetAr$^2$C1-C6 alkyl-, (g) Ar$^1$O—, (h) hetAr$^2$O—, (i) Ar$^1$NR$^g$— where R$^g$ is H or C1-C6 alkyl, (k) R$^3$C(=O)NR$^g$— where R$^g$ is H or C1-C6 alkyl, (l) Ar$^1$C(=O)NR$^g$— where R$^g$ is H or C1-C6 alkyl, or (m) hetAr$^2$C(=O)NR$^g$(CH$_2$)$_p$—, where p is 0 or 1 and R$^3$, R$^g$, Ar$^1$ and hetAr$^2$ are as defined for Formula I-C; R$^b$ is (e) R$^c$R$^d$N—; R$^c$ is hydrogen or C1-C6 alkyl; and R$^d$ is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C(=O)—, (C1-C6 alkyl)C(=O)—, (R$^k$R$^l$N)C1-C6 alkyl- where R$^k$ and R$^l$ are independently H or C1-C6 alkyl, R'''R''NC(=O)C1-C6 alkyl- where R'" and R" are independently H or C1-C6 alkyl, PhCH$_2$—, (C1-C6 alkoxy)C1-C6 alkyl-, or hetCyc$^c$ where hetCyc$^c$ is a 4-6 membered heterocyclic ring having a ring heteroatom selected from N and O and optionally substituted with C1-C6 alkyl.

In one embodiment of Formula I-C, A is CN; B is C1-C6 alkyl optionally substituted with 1-3 fluoros; E is (d) Ar$^1$C1-C6 alkyl- wherein said alkyl portion is optionally substituted with 1-3 fluoros, (e) hetAr$^2$C1-C6 alkyl-, (g) Ar$^1$O—, (h) hetAr$^2$O—, (i) Ar$^1$NR$^g$— where R$^g$ is H or C1-C6 alkyl, (k) R$^3$C(=O)NR$^g$— where R$^g$ is H or C1-C6 alkyl, (l) Ar$^1$C(=O)NR$^g$— where R$^g$ is H or C1-C6 alkyl, or (m) hetAr$^2$C(=O)NR$^g$(CH$_2$)$_p$—, where p is 0 or 1 and R$^3$, R$^g$, Ar$^1$ and hetAr$^2$ are as defined for Formula I-C; R$^b$ is (f) R$^c$R$^d$NCH$_2$—; R is hydrogen or C1-C6 alkyl; and R$^d$ is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C(=O)—, (C1-C6 alkyl)C(=O)—, (R$^k$R$^l$N)C1-C6 alkyl- where R$^k$ and R$^l$ are independently H or C1-C6 alkyl, R'''R''NC(=O)C1-C6 alkyl- where R'" and R" are independently H or C1-C6 alkyl, PhCH$_2$—, (C1-C6 alkoxy)C1-C6 alkyl-, or hetCyc$^c$ where hetCyc$^c$ is a 4-6 membered heterocyclic ring having a ring heteroatom selected from N and O and optionally substituted with C1-C6 alkyl.

In one embodiment of Formula I-C, X$^1$ is N; X$^2$, X$^3$ and X$^4$ are CH; A is CN; B is hydroxyC2-C6 alkyl- optionally substituted with a C3-C6 cycloalkylidene ring; E is (d) Ar$^1$C1-C6 alkyl- wherein said alkyl portion is optionally substituted with 1-3 fluoros, (e) hetAr$^2$C1-C6 alkyl-, (g) Ar$^1$O—, (h) hetAr$^2$O—, (i) Ar$^1$NR$^g$— where R$^g$ is H or C1-C6 alkyl, (k) R$^3$C(=O)NR$^g$— where R$^g$ is H or C1-C6 alkyl, (l) Ar$^1$C(=O)NR$^g$— where R$^g$ is H or C1-C6 alkyl, or (m) hetAr$^2$C(=O)NR$^g$(CH$_2$)$_p$—, where p is 0 or 1 and R$^3$, R, Ar$^1$ and hetAr$^2$ are as defined for Formula I-C; and R$^b$ is (c) hetCyc$^b$CH$_2$— where hetCyc$^b$ is a 4-6 membered heterocyclic ring having 1-2 ring heteroatoms independently selected from N and O, wherein hetCyc$^b$ is optionally substituted with one or more substituents independently selected from OH, fluoro, C1-C6 alkyl (optionally substituted with 1-3 fluoros), hydroxyC1-C6 alkyl- (optionally substituted with 1-3 fluoros), and (C1-C6 alkoxy)C1-C6 alkyl-.

In one embodiment of Formula I-C, $X^1$ is N; $X^2$, $X^3$ and $X^4$ are CH; A is CN; B is hydroxyC2-C6 alkyl- optionally substituted with a C3-C6 cycloalkylidene ring; E is (d) $Ar^1$C1-C6 alkyl- wherein said alkyl portion is optionally substituted with 1-3 fluoros, (e) $hetAr^2$C1-C6 alkyl-, (g) $Ar^1$O—, (h) $hetAr^2$O—, (i) $Ar^1NR^g$— where $R^g$ is H or C1-C6 alkyl, (k) $R^3C(\!=\!O)NR^g$— where $R^g$ is H or C1-C6 alkyl, (l) $Ar^1C(\!=\!O)NR^g$— where $R^g$ is H or C1-C6 alkyl, or (m) $hetAr^2C(\!=\!O)NR^g(CH_2)_p$—, where p is 0 or 1 and $R^3$, $R^g$, $Ar^1$ and $hetAr^2$ are as defined for Formula I-C; $R^b$ is (e) $R^cR^dN$—; $R^c$ is hydrogen or C1-C6 alkyl; and $R^d$ is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C(=O)—, (C1-C6 alkyl)C(=O)—, $(R^kR^lN)$C1-C6 alkyl- where $R^k$ and $R^l$ are independently H or C1-C6 alkyl, $R'''R''NC(\!=\!O)$C1-C6 alkyl- where $R'''$ and $R''$ are independently H or C1-C6 alkyl, $PhCH_2$—, (C1-C6 alkoxy)C1-C6 alkyl-, or $hetCyc^c$ where $hetCyc^c$ is a 4-6 membered heterocyclic ring having a ring heteroatom selected from N and O and optionally substituted with C1-C6 alkyl.

In one embodiment of Formula I-C, $X^1$ is N; $X^2$, $X^3$ and $X^4$ are CH; A is CN; B is hydroxyC2-C6 alkyl- optionally substituted with a C3-C6 cycloalkylidene ring; E is (d) $Ar^1$C1-C6 alkyl- wherein said alkyl portion is optionally substituted with 1-3 fluoros, (e) $hetAr^2$C1-C6 alkyl-, (g) $Ar^1$O—, (h) $hetAr^2$O—, (i) $Ar^1NR^g$— where $R^g$ is H or C1-C6 alkyl, (k) $R^3C(\!=\!O)NR^g$— where $R^g$ is H or C1-C6 alkyl, (l) $Ar^1C(\!=\!O)NR^g$— where $R^g$ is H or C1-C6 alkyl, or (m) $hetAr^2C(\!=\!O)NR^g(CH_2)_p$—, where p is 0 or 1 and $R^3$, $R^g$, $Ar^1$ and $hetAr^2$ are as defined for Formula I-C; $R^b$ is (f) $R^cR^dNCH_2$—; $R^c$ is hydrogen or C1-C6 alkyl; and $R^d$ is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C(=O)—, (C1-C6 alkyl)C(=O)—, $(R^kR^lN)$C1-C6 alkyl- where $R^k$ and $R^l$ are independently H or C1-C6 alkyl, $R'''R''NC(\!=\!O)$C1-C6 alkyl- where $R'''$ and $R''$ are independently H or C1-C6 alkyl, $PhCH_2$—, (C1-C6 alkoxy)C1-C6 alkyl-, or $hetCyc^c$ where $hetCyc^c$ is a 4-6 membered heterocyclic ring having a ring heteroatom selected from N and O and optionally substituted with C1-C6 alkyl.

In one embodiment of Formula I-C, $X^1$ is N; $X^2$, $X^3$ and $X^4$ are CH; A is CN; B is C1-C6 alkyl optionally substituted with 1-3 fluoros; E is (d) $Ar^1$C1-C6 alkyl- wherein said alkyl portion is optionally substituted with 1-3 fluoros, (e) $hetAr^2$C1-C6 alkyl-, (g) $Ar^1$O—, (h) $hetAr^2$O—, (i) $Ar^1NR^g$— where $R^g$ is H or C1-C6 alkyl, (k) $R^3C(\!=\!O)NR^g$— where $R^g$ is H or C1-C6 alkyl, (l) $Ar^1C(\!=\!O)NR^g$— where $R^g$ is H or C1-C6 alkyl, or (m) $hetAr^2C(\!=\!O)NR^g(CH_2)_p$—, where p is 0 or 1 and $R^3$, $R^g$, $Ar^1$ and $hetAr^2$ are as defined for Formula I-C; and $R^b$ is (c) $hetCyc^bCH_2$— where $hetCyc^b$ is a 4-6 membered heterocyclic ring having 1-2 ring heteroatoms independently selected from N and O, wherein $hetCyc^b$ is optionally substituted with one or more substituents independently selected from OH, fluoro, C1-C6 alkyl (optionally substituted with 1-3 fluoros), hydroxyC1-C6 alkyl- (optionally substituted with 1-3 fluoros), and (C1-C6 alkoxy)C1-C6 alkyl-.

In one embodiment of Formula I-C, $X^1$ is N; $X^2$, $X^3$ and $X^4$ are CH; A is CN; B is C1-C6 alkyl optionally substituted with 1-3 fluoros; E is (d) $Ar^1$C1-C6 alkyl- wherein said alkyl portion is optionally substituted with 1-3 fluoros, (e) $hetAr^2$C1-C6 alkyl-, (g) $Ar^1$O—, (h) $hetAr^2$O—, (i) $Ar^1NR^g$— where $R^g$ is H or C1-C6 alkyl, (k) $R^3C(\!=\!O)NR^g$— where $R^g$ is H or C1-C6 alkyl, (l) $Ar^1C(\!=\!O)NR^g$— where $R^g$ is H or C1-C6 alkyl, or (m) $hetAr^2C(\!=\!O)NR^g(CH_2)_p$—, where p is 0 or 1 and $R^3$, $R^g$, $Ar^1$ and $hetAr^2$ are as defined for Formula I-C; $R^b$ is (e) $R^cR^dN$—; $R^c$ is hydrogen or C1-C6 alkyl; and $R^d$ is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C(=O)—, (C1-C6 alkyl)C(=O)—, $(R^kR^lN)$C1-C6 alkyl- where $R^k$ and $R^l$ are independently H or C1-C6 alkyl, $R'''R''NC(\!=\!O)$C1-C6 alkyl- where $R'''$ and $R''$ are independently H or C1-C6 alkyl, $PhCH_2$—, (C1-C6 alkoxy)C1-C6 alkyl-, or $hetCyc^c$ where $hetCyc^c$ is a 4-6 membered heterocyclic ring having a ring heteroatom selected from N and O and optionally substituted with C1-C6 alkyl.

In one embodiment of Formula I-C, $X^1$ is N; $X^2$, $X^3$ and $X^4$ are CH; A is CN; B is C1-C6 alkyl optionally substituted with 1-3 fluoros; E is (d) $Ar^1$C1-C6 alkyl- wherein said alkyl portion is optionally substituted with 1-3 fluoros, (e) $hetAr^2$C1-C6 alkyl-, (g) $Ar^1$O—, (h) $hetAr^2$O—, (i) $Ar^1NR^g$— where $R^g$ is H or C1-C6 alkyl, (k) $R^3C(\!=\!O)NR^g$— where $R^g$ is H or C1-C6 alkyl, (l) $Ar^1C(\!=\!O)NR^g$— where $R^g$ is H or C1-C6 alkyl, or (m) $hetAr^2C(\!=\!O)NR^g(CH_2)_p$—, where p is 0 or 1 and $R^3$, R, $Ar^1$ and $hetAr^2$ are as defined for Formula I-C; $R^b$ is (f) $R^cR^dNCH_2$—; R is hydrogen or C1-C6 alkyl; and $R^d$ is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C(=O)—, (C1-C6 alkyl)C(=O)—, $(R^kR^lN)$C1-C6 alkyl- where $R^k$ and $R^l$ are independently H or C1-C6 alkyl, $R'''R''NC(\!=\!O)$C1-C6 alkyl- where $R'''$ and $R''$ are independently H or C1-C6 alkyl, $PhCH_2$—, (C1-C6 alkoxy)C1-C6 alkyl-, or $hetCyc^c$ where $hetCyc^c$ is a 4-6 membered heterocyclic ring having a ring heteroatom selected from N and O and optionally substituted with C1-C6 alkyl.

In one embodiment, Formula I includes compounds of Formula I-D, wherein:

$X^1$ and $X^3$ are N, and $X^2$ and $X^4$ are CH or CF; and A, B, E, $R^a$, $R^b$, m and n are as defined for Formula I.

In one embodiment of Formula I-D, A is CN.

In one embodiment of Formula I-D, B is (c) hydroxyC2-C6 alkyl- wherein the alkyl portion is optionally substituted with a C3-C6 cycloalkylidene ring, (f) $(R^1R^2N)$C1-C6 alkyl- where $R^1$ and $R^2$ are independently selected from H, C1-C6 alkyl (optionally substituted with 1-3 fluoros), (C1-C6 alkoxy)C1-C6 alkyl-, (C1-C6 alkyl)C(=O)— and (C1-C6 alkoxy)C(=O)—, (g) $hetAr^1$C1-C3 alkyl-, where $hetAr^1$ is a 5-6 membered heteroaryl ring having 1-3 ring heteroatoms independently selected from N, O and S and is optionally substituted with one or more independently selected C1-C6 alkyl substituents, or (i) $(hetCyc^a)$C1-C3 alkyl-; and $hetCyc^a$ is a 4-6 membered heterocyclic ring having 1-2 ring heteroatoms independently selected from N and O and optionally substituted with one or more substituents independently selected from OH, C1-C6 alkyl (optionally substituted with 1-3 fluoros), hydroxyC1-C6 alkyl, halogen, (C1-C6 alkyl)C(=O)—, C1-C6 alkoxy, oxo and (C1-C6 alkoxy)C(=O)—.

In one embodiment of Formula I-D, A is CN; B is (c) hydroxyC2-C6 alkyl- wherein the alkyl portion is optionally substituted with a C3-C6 cycloalkylidene ring, (f) $(R^1R^2N)$C1-C6 alkyl- where $R^1$ and $R^2$ are independently selected from H, C1-C6 alkyl (optionally substituted with 1-3 fluoros), (C1-C6 alkoxy)C1-C6 alkyl-, (C1-C6 alkyl)C(=O)— and (C1-C6 alkoxy)C(=O)—, (g) hetAr¹C1-C3 alkyl-, where hetAr¹ is a 5-6 membered heteroaryl ring having 1-3 ring heteroatoms independently selected from N, O and S and is optionally substituted with one or more independently selected C1-C6 alkyl substituents, or (i) (hetCyc$^a$)C1-C3 alkyl-; and hetCyc$^a$ is a 4-6 membered heterocyclic ring having 1-2 ring heteroatoms independently selected from N and O and optionally substituted with one or more substituents independently selected from OH, C1-C6 alkyl (optionally substituted with 1-3 fluoros), hydroxyC1-C6 alkyl, halogen, (C1-C6 alkyl)C(=O)—, C1-C6 alkoxy, oxo and (C1-C6 alkoxy)C(=O)—.

In one embodiment of Formula I-D, E is (l) Ar¹C(=O)NR$^g$— where R$^g$ is H or C1-C6 alkyl, or (m) hetAr²C(=O)NR$^g$(CH$_2$)$_p$— where p is 0 or 1 and R$^g$ is H or C1-C6 alkyl.

In one embodiment of Formula I-D, A is CN; B is (c) hydroxyC2-C6 alkyl- wherein the alkyl portion is optionally substituted with a C3-C6 cycloalkylidene ring, (f) (R¹R²N)C1-C6 alkyl- where R¹ and R² are independently selected from H, C1-C6 alkyl (optionally substituted with 1-3 fluoros), (C1-C6 alkoxy)C1-C6 alkyl-, (C1-C6 alkyl)C(=O)— and (C1-C6 alkoxy)C(=O)—, (g) hetAr¹C1-C3 alkyl-, where hetAr¹ is a 5-6 membered heteroaryl ring having 1-3 ring heteroatoms independently selected from N, O and S and is optionally substituted with one or more independently selected C1-C6 alkyl substituents, or (i) (hetCyc$^a$)C1-C3 alkyl-; hetCyc$^a$ is a 4-6 membered heterocyclic ring having 1-2 ring heteroatoms independently selected from N and O and optionally substituted with one or more substituents independently selected from OH, C1-C6 alkyl (optionally substituted with 1-3 fluoros), hydroxyC1-C6 alkyl, halogen, (C1-C6 alkyl)C(=O)—, C1-C6 alkoxy, oxo and (C1-C6 alkoxy)C(=O)—; and E is (l) Ar¹C(=O)NR$^g$— where R$^g$ is H or C1-C6 alkyl, or (m) hetAr²C(=O)NR$^g$(CH$_2$)$_p$— where p is 0 or 1 and R$^g$ is H or C1-C6 alkyl.

In one embodiment of Formula I-D, m is 1; and n is 0 or 1.

In one embodiment of Formula I-D, m is 1; and n is 0.

In one embodiment of Formula I-D, m is 1; n is 0; and R$^b$ is hydroxy.

In one embodiment of Formula I-D, m is 0; and n is 0 or 1.

In one embodiment of Formula I-D, m is 0; n is 0 or 1; and R$^a$ is C1-C6 alkyl optionally substituted with 1-3 fluoros.

In one embodiment of Formula I-D, A is CN; B is (c) hydroxyC2-C6 alkyl- wherein the alkyl portion is optionally substituted with a C3-C6 cycloalkylidene ring, (f) (R¹R²N)C1-C6 alkyl- where R¹ and R² are independently selected from H, C1-C6 alkyl (optionally substituted with 1-3 fluoros), (C1-C6 alkoxy)C1-C6 alkyl-, (C1-C6 alkyl)C(=O)— and (C1-C6 alkoxy)C(=O)—, (g) hetAr¹C1-C3 alkyl-, where hetAr¹ is a 5-6 membered heteroaryl ring having 1-3 ring heteroatoms independently selected from N, O and S and is optionally substituted with one or more independently selected C1-C6 alkyl substituents, or (i) (hetCyc$^a$)C1-C3 alkyl-; hetCyc$^a$ is a 4-6 membered heterocyclic ring having 1-2 ring heteroatoms independently selected from N and O and optionally substituted with one or more substituents independently selected from OH, C1-C6 alkyl (optionally substituted with 1-3 fluoros), hydroxyC1-C6 alkyl, halogen, (C1-C6 alkyl)C(=O)—, C1-C6 alkoxy, oxo and (C1-C6 alkoxy)C(=O)—; E is (l) Ar¹C(=O)NR$^g$— where R$^g$ is H or C1-C6 alkyl, or (m) hetAr²C(=O)NR$^g$(CH$_2$)$_p$— where p is 0 or 1 and R$^g$ is H or C1-C6 alkyl; m is 0 or 1; n is 0 or 1; R$^a$ is C1-C6 alkyl optionally substituted with 1-3 fluoros; and R$^b$ is hydroxy. In one embodiment, m is 1, n is 0, and R$^b$ is hydroxy. In one embodiment, m is 0, n is 1, and R$^b$ is C1-C6 alkyl optionally substituted with 1-3 fluoros.

In one embodiment of Formula I-D, Ring D is

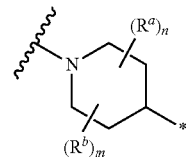

wherein the wavy line indicates the point of attachment of Ring D to the ring comprising X¹, X², X³ and X⁴, the asterisk indicates the point of attachment of Ring D to the E group.

In one embodiment of Formula I-D, A is CN; B is (c) hydroxyC2-C6 alkyl- wherein the alkyl portion is optionally substituted with a C3-C6 cycloalkylidene ring, (f) (R¹R²N)C1-C6 alkyl- where R¹ and R² are independently selected from H, C1-C6 alkyl (optionally substituted with 1-3 fluoros), (C1-C6 alkoxy)C1-C6 alkyl-, (C1-C6 alkyl)C(=O)— and (C1-C6 alkoxy)C(=O)—, (g) hetAr¹C1-C3 alkyl-, where hetAr¹ is a 5-6 membered heteroaryl ring having 1-3 ring heteroatoms independently selected from N, O and S and is optionally substituted with one or more independently selected C1-C6 alkyl substituents, or (i) (hetCyc$^a$)C1-C3 alkyl-; hetCyc$^a$ is a 4-6 membered heterocyclic ring having 1-2 ring heteroatoms independently selected from N and O and optionally substituted with one or more substituents independently selected from OH, C1-C6 alkyl (optionally substituted with 1-3 fluoros), hydroxyC1-C6 alkyl, halogen, (C1-C6 alkyl)C(=O)—, C1-C6 alkoxy, oxo and (C1-C6 alkoxy)C(=O)—; E is (l) Ar¹C(=O)NR$^g$— where R$^g$ is H or C1-C6 alkyl, or (m) hetAr²C(=O)NR$^g$(CH$_2$)$_p$— where p is 0 or 1 and R$^g$ is H or C1-C6 alkyl; m is 0 or 1; n is 0 or 1; R$^a$ is C1-C6 alkyl optionally substituted with 1-3 fluoros; and Ring D is

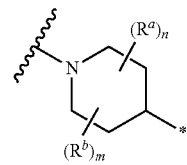

wherein the wavy line indicates the point of attachment of Ring D to the ring comprising X¹, X², X³ and X⁴, the asterisk indicates the point of attachment of Ring D to the E group. In one embodiment, m is 1, n is 0, and R$^b$ is hydroxy. In one embodiment, m is 0, n is 1, and R$^b$ is C1-C6 alkyl optionally substituted with 1-3 fluoros.

In one embodiment, compounds of Formula I include compounds of Formula I-E:

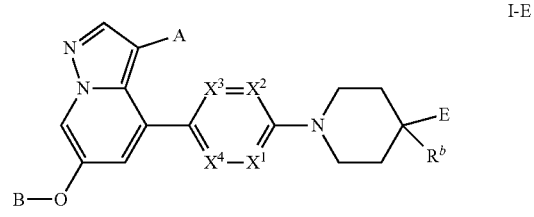

I-E where E is (k) $R^3C(=O)NR^g$— where $R^g$ is H or C1-C6 alkyl; $R^b$ is (c) hetCyc$^b$CH$_2$—; and $R^3$, A, B, $X^1$, $X^2$, $X^3$ and $X^4$ are as defined for Formula I.

In one embodiment of Formula I-E, $X^1$ is N; and $X^2$, $X^3$ and $X^4$ are CH.

In one embodiment of Formula I-E, A is CN.

In one embodiment of Formula I-E, $X^1$ is N; $X^2$, $X^3$ and $X^4$ are CH; and A is CN.

In one embodiment of Formula I-E, B is C1-C6 alkyl optionally substituted with 1-3 fluoros.

In one embodiment of Formula I-E, $X^1$ is N; $X^2$, $X^3$ and $X^4$ are CH; A is CN; and B is C1-C6 alkyl optionally substituted with 1-3 fluoros.

In one embodiment, compounds of Formula I include compounds of Formula I-F

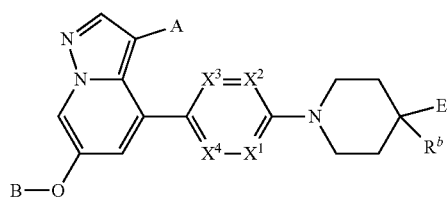

I-F where E is (d) Ar$^1$C1-C6 alkyl- wherein said alkyl portion is optionally substituted with 1-3 fluoros or (e) hetAr$^2$C1-C6 alkyl-; $R^b$ is (a) hydroxy, (d) R$^i$R$^j$NC(=O)CH$_2$OCH$_2$— where R$^i$ and R$^j$ are independently H or C1-C6 alkyl, or (e) R$^c$R$^d$N—; and $X^1$, $X^1$, $X^3$, $X^4$, A, B, Ar$^1$, hetAr$^2$, R$^c$ and R$^d$ are as defined for Formula I.

In one embodiment of Formula I-F, $X^1$ is N; and $X^2$, $X^3$ and $X^4$ are CH. In one embodiment, E is (d) Ar$^1$C1-C6 alkyl- wherein said alkyl portion is optionally substituted with 1-3 fluoros. In one embodiment, E is (e) hetAr$^2$C1-C6 alkyl-.

In one embodiment of Formula I-F, A is CN. In one embodiment, E is (d) Ar$^1$C1-C6 alkyl- wherein said alkyl portion is optionally substituted with 1-3 fluoros. In one embodiment, E is (e) hetAr$^2$C1-C6 alkyl-.

In one embodiment of Formula I-F, B is C1-C6 alkyl optionally substituted with 1-3 fluoros, or hydroxyC2-C6 alkyl- wherein the alkyl portion is optionally substituted with a C3-C6 cycloalkylidene ring. In one embodiment of Formula I-F, B is C1-C6 alkyl or hydroxyC2-C6 alkyl-. In one embodiment, E is (d) Ar$^1$C1-C6 alkyl- wherein said alkyl portion is optionally substituted with 1-3 fluoros. In one embodiment, E is (e) hetAr$^2$C1-C6 alkyl-.

In one embodiment of Formula I-F, $X^1$ is N; $X^2$, $X^3$ and $X^4$ are CH; A is CN; and B is C1-C6 alkyl optionally substituted with 1-3 fluoros, or hydroxyC2-C6 alkyl- wherein the alkyl portion is optionally substituted with a C3-C6 cycloalkylidene ring. In one embodiment, B is C1-C6 alkyl or hydroxyC2-C6 alkyl-. In one embodiment, E is (d) Ar$^1$C1-C6 alkyl- wherein said alkyl portion is optionally substituted with 1-3 fluoros. In one embodiment, E is (e) hetAr$^2$C1-C6 alkyl-.

In one embodiment of Formula I-F, $X^1$ is N; $X^2$, $X^3$ and $X^4$ are CH; A is CN; B is C1-C6 alkyl optionally substituted with 1-3 fluoros, or hydroxyC2-C6 alkyl- wherein the alkyl portion is optionally substituted with a C3-C6 cycloalkylidene ring; and $R^b$ is (a) hydroxy. In one embodiment, E is (d) Ar$^1$C1-C6 alkyl- wherein said alkyl portion is optionally substituted with 1-3 fluoros. In one embodiment, E is (e) hetAr$^2$C1-C6 alkyl-.

In one embodiment of Formula I-F, $X^1$ is N; $X^2$, $X^3$ and $X^4$ are CH; A is CN; B is C1-C6 alkyl optionally substituted with 1-3 fluoros, or hydroxyC2-C6 alkyl- wherein the alkyl portion is optionally substituted with a C3-C6 cycloalkylidene ring; and $R^b$ is (d) R$^i$R$^j$NC(=O)CH$_2$OCH$_2$— where R$^i$ and R$^j$ are independently H or C1-C6 alkyl. In one embodiment, E is (d) Ar$^1$C1-C6 alkyl- wherein said alkyl portion is optionally substituted with 1-3 fluoros. In one embodiment, E is (e) hetAr$^2$C1-C6 alkyl-.

In one embodiment of Formula I-F, $X^1$ is N; $X^2$, $X^3$ and $X^4$ are CH; A is CN; B is C1-C6 alkyl optionally substituted with 1-3 fluoros, or hydroxyC2-C6 alkyl- wherein the alkyl portion is optionally substituted with a C3-C6 cycloalkylidene ring; and $R^b$ is (e) R$^c$R$^d$N— where R$^c$ and R$^d$ are as defined for Formula I. In one embodiment, E is (d) Ar$^1$C1-C6 alkyl- wherein said alkyl portion is optionally substituted with 1-3 fluoros. In one embodiment, E is (e) hetAr$^2$C1-C6 alkyl-.

In one embodiment of Formula I-F, $X^1$ is N; $X^2$, $X^3$ and $X^4$ are CH; A is CN; B is C1-C6 alkyl optionally substituted with 1-3 fluoros, or hydroxyC2-C6 alkyl- wherein the alkyl portion is optionally substituted with a C3-C6 cycloalkylidene ring; and $R^b$ is (e) R$^c$R$^d$N— where R$^c$ and R$^d$ are as defined for Formula I. In one embodiment, E is (d) Ar$^1$C1-C6 alkyl- wherein said alkyl portion is optionally substituted with 1-3 fluoros. In one embodiment, E is (e) hetAr$^2$C1-C6 alkyl-.

In one embodiment, compounds of Formula I include compounds of Formula I-G

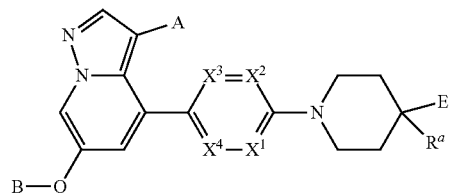

I-G where E is (l) Ar$^1$C(=O)NR$^g$— where R$^g$ is H or C1-C6 alkyl or (m) hetAr$^2$C(=O)NR$^g$(CH$_2$)$_p$— where p is 0 or 1 and R$^g$ is H or C1-C6 alkyl; R$^a$ is C1-C6 alkyl optionally substituted with 1-3 fluoros; and Ar$^1$, hetAr$^2$, $X^1$, $X^1$, $X^3$, $X^4$, A and B are as defined for Formula I.

In one embodiment of Formula I-G, $X^1$ is N; and $X^2$, $X^3$ and $X^4$ are CH.

In one embodiment of Formula I-G, A is CN.

In one embodiment of Formula I-G, B is (b) C1-C6 alkyl optionally substituted with 1-3 fluoros, (c) hydroxyC2-C6 alkyl- wherein the alkyl portion is optionally substituted with a C3-C6 cycloalkylidene ring, (f) (R$^1$R$^2$N)C1-C6 alkyl- where R$^1$ and R$^2$ are independently selected from H, C1-C6 alkyl (optionally substituted with 1-3 fluoros), (C1-C6 alkoxy)C1-C6 alkyl-, (C1-C6 alkyl)C(=O)— and (C1-C6 alkoxy)C(=O)—, (g) hetAr$^1$C1-C3 alkyl-, where hetAr$^1$ is a 5-6 membered heteroaryl ring having 1-3 ring heteroatoms independently selected from N, O and S and is optionally substituted with one or more independently selected C1-C6 alkyl substituents, or (i) (hetCyc$^a$)C1-C3 alkyl-, where hetCyc$^a$ is as defined for Formula I.

In one embodiment of Formula I-G, $X^1$ is N; $X^2$, $X^3$ and $X^4$ are CH; A is CN; and B is C1-C6 alkyl optionally substituted with 1-3 fluoros. In one embodiment, B is C1-C6 alkyl.

In one embodiment of Formula I-G, $X^1$ is N; $X^2$, $X^3$ and $X^4$ are CH; A is CN; and B is hydroxyC2-C6 alkyl- optionally substituted with a C3-C6 cycloalkylidene ring. In one embodiment, B is hydroxyC2-C6 alkyl-.

In one embodiment of Formula I-G, $X^1$ is N; $X^2$, $X^3$ and $X^4$ are CH; A is CN; and B is $(R^1R^2N)$C1-C6 alkyl- where $R^1$ and $R^2$ are independently selected from H, C1-C6 alkyl (optionally substituted with 1-3 fluoros), (C1-C6 alkoxy)C1-C6 alkyl-, (C1-C6 alkyl)C(=O)— and (C1-C6 alkoxy)C(=O)—.

In one embodiment of Formula I-G, $X^1$ is N; $X^2$, $X^3$ and $X^4$ are CH; A is CN; and B is hetAr$^1$C1-C3 alkyl-, where hetAr$^1$ is a 5-6 membered heteroaryl ring having 1-3 ring heteroatoms independently selected from N, O and S and is optionally substituted with one or more independently selected C1-C6 alkyl substituents.

In one embodiment of Formula I-G, $X^1$ is N; $X^2$, $X^3$ and $X^4$ are CH; A is CN; and B is (hetCyc$^a$)C1-C3 alkyl-, where hetCyc$^a$ is as defined for Formula I.

In one embodiment, compounds of Formula I include compounds of Formula I-H

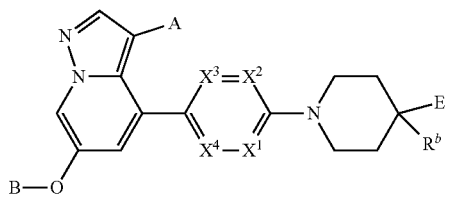

I-H where E is (l) Ar$^1$C(=O)NR$^g$— where R$^g$ is H or C1-C6 alkyl or (m) hetAr$^2$C(=O)NR$^g$(CH$_2$)$_p$— where p is 0 or 1 and R$^g$ is H or C1-C6 alkyl; R$^b$ is (a) hydroxy, (c) hetCyc$^b$CH$_2$—, (f) R$^c$R$^d$NCH$_2$—, (g) C1-C6 alkoxy-, or (j) hetCyc$^b$(C1-C3 alkyl)OCH$_2$—; and Ar$^1$, hetAr$^2$, $X^1$, $X^1$, $X^3$, $X^4$, A, B, hetCyc$^b$, R$^c$ and R$^d$ are as defined for Formula I.

In one embodiment of Formula I-H, $X^1$ is N; and $X^2$, $X^3$ and $X^4$ are CH.

In one embodiment of Formula I-H, A is CN.

In one embodiment of Formula I-H, B is (b) C1-C6 alkyl optionally substituted with 1-3 fluoros. In one embodiment, B is C1-C6 alkyl.

In one embodiment of Formula I-H, $X^1$ is N; $X^2$, $X^3$ and $X^4$ are CH; A is CN; and B is C1-C6 alkyl optionally substituted with 1-3 fluoros. In one embodiment, B is C1-C6 alkyl.

In one embodiment of Formula I-H, $X^1$ is N; $X^2$, $X^3$ and $X^4$ are CH; A is CN; B is C1-C6 alkyl optionally substituted with 1-3 fluoros; and R$^b$ is (a) hydroxy.

In one embodiment of Formula I-H, $X^1$ is N; $X^2$, $X^3$ and $X^4$ are CH; A is CN; B is C1-C6 alkyl optionally substituted with 1-3 fluoros; and R$^b$ is (c) hetCyc$^b$CH$_2$—.

In one embodiment of Formula I-H, $X^1$ is N; $X^2$, $X^3$ and $X^4$ are CH; A is CN; B is C1-C6 alkyl optionally substituted with 1-3 fluoros; and R$^b$ is (f) R$^c$R$^d$NCH$_2$—.

In one embodiment of Formula I-H, $X^1$ is N; $X^2$, $X^3$ and $X^4$ are CH; A is CN; B is C1-C6 alkyl optionally substituted with 1-3 fluoros; and R$^b$ is (g) C1-C6 alkoxy-.

In one embodiment of Formula I-H, $X^1$ is N; $X^2$, $X^3$ and $X^4$ are CH; A is CN; B is C1-C6 alkyl optionally substituted with 1-3 fluoros; and R$^b$ is (j) hetCyc$^b$(C1-C3 alkyl)OCH$_2$—.

In one embodiment, compounds of Formula I include compounds of Formula I-I

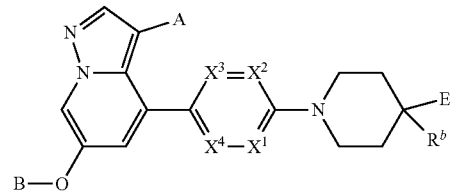

I-I where E is (n) R$^4$R$^5$NC(=O)—; R$^b$ is (c) hetCyc$^b$CH$_2$—, (f) R$^c$R$^d$NCH$_2$— or (j) hetCyc$^b$(C1-C3 alkyl)OCH$_2$—; and $X^1$, $X^1$, $X^3$, $X^4$, A, B, hetCyc$^b$, R$^c$, R$^d$, R$^4$ and R$^5$ are as defined for Formula I.

In one embodiment of Formula I-I, $X^1$ is N; and $X^2$, $X^3$ and $X^4$ are CH.

In one embodiment of Formula I-I, A is CN.

In one embodiment of Formula I-I, B is (b) C1-C6 alkyl optionally substituted with 1-3 fluoros. In one embodiment, B is C1-C6 alkyl.

In one embodiment of Formula I-I, $X^1$ is N; $X^2$, $X^3$ and $X^4$ are CH; A is CN; and B is C1-C6 alkyl optionally substituted with 1-3 fluoros. In one embodiment, B is C1-C6 alkyl.

In one embodiment of Formula I-H, $X^1$ is N; $X^2$, $X^3$ and $X^4$ are CH; A is CN; B is C1-C6 alkyl optionally substituted with 1-3 fluoros; and R$^b$ is (c) hetCyc$^b$CH$_2$—.

In one embodiment of Formula I-H, $X^1$ is N; $X^2$, $X^3$ and $X^4$ are CH; A is CN; B is C1-C6 alkyl optionally substituted with 1-3 fluoros; and R$^b$ is (f) R$^c$R$^d$NCH$_2$—.

In one embodiment of Formula I-H, $X^1$ is N; $X^2$, $X^3$ and $X^4$ are CH; A is CN; B is C1-C6 alkyl optionally substituted with 1-3 fluoros; and R$^b$ is (j) hetCyc$^b$(C1-C3 alkyl)OCH$_2$—.

In one embodiment, compounds of Formula I include compounds of Formula I-I

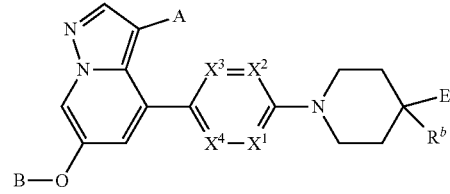

I-I where E is (n) R$^4$R$^5$NC(=O)—; R$^b$ is (c) hetCyc$^b$CH$_2$—, (f) R$^c$R$^d$NCH$_2$—, or (j) hetCyc$^b$(C1-C3 alkyl)OCH$_2$—; and $X^1$, $X^1$, $X^3$, $X^4$, A, B, R$^4$, R$^5$, hetCyc$^b$, R$^c$ and R$^d$ are as defined for Formula I.

In one embodiment of Formula I-I, $X^1$ is N; and $X^2$, $X^3$ and $X^4$ are CH.

In one embodiment of Formula I-I, A is CN.

In one embodiment of Formula I-I, B is (b) C1-C6 alkyl optionally substituted with 1-3 fluoros or (i) (hetCyc$^a$)C1-C3 alkyl-.

In one embodiment of Formula I-I, $X^1$ is N; $X^2$, $X^3$ and $X^4$ are CH; A is CN; and B is (b) C1-C6 alkyl optionally substituted with 1-3 fluoros.

In one embodiment of Formula I-I, $X^1$ is N; $X^2$, $X^3$ and $X^4$ are CH; A is CN; and B is (i) (hetCyc$^a$)C1-C3 alkyl-.

In one embodiment of Formula I-I, $X^1$ is N; $X^2$, $X^3$ and $X^4$ are CH; A is CN; B is (b) C1-C6 alkyl optionally substituted with 1-3 fluoros or (i) (hetCyc$^a$)C1-C3 alkyl-; and R$^b$ is (c) hetCyc$^b$CH$_2$—.

In one embodiment of Formula I-I, $X^1$ is N; $X^2$, $X^3$ and $X^4$ are CH; A is CN; B is (b) C1-C6 alkyl optionally substituted with 1-3 fluoros or (i) (hetCyc$^a$)C1-C3 alkyl-; and $R^b$ is (f) $R^cR^dNCH_2$—.

In one embodiment of Formula I-I, $X^1$ is N; $X^2$, $X^3$ and $X^4$ are CH; A is CN; B is (b) C1-C6 alkyl optionally substituted with 1-3 fluoros or (i) (hetCyc$^a$)C1-C3 alkyl-; and $R^b$ is (j) hetCyc$^b$(C1-C3 alkyl)OCH$_2$—.

In one embodiment, compounds of Formula I include compounds of Formula I-J

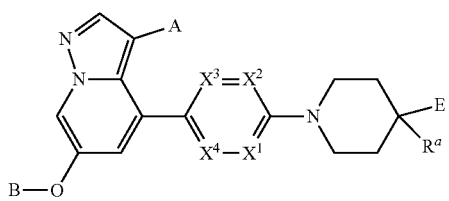

I-J where E is (n) $R^4R^5NC(=O)$—; $R^a$ is C1-C6 alkyl optionally substituted with 1-3 fluoros; and $X^1$, $X^1$, $X^3$, $X^4$, A, B, $R^4$ and $R^5$ are as defined for Formula I.

In one embodiment of Formula I-J, $X^1$ is N; and $X^2$, $X^3$ and $X^4$ are CH.

In one embodiment of Formula I-J, A is CN.

In one embodiment of Formula I-J, $X^1$ is N; $X^2$, $X^3$ and $X^4$ are CH; and A is CN.

In one embodiment of Formula I-J, B is (b) C1-C6 alkyl optionally substituted with 1-3 fluoros. In one embodiment, B is (b) C1-C6 alkyl.

In one embodiment of Formula I-J, B is (c) hydroxyC2-C6 alkyl- wherein the alkyl portion is optionally substituted with a C3-C6 cycloalkylidene ring. In one embodiment of Formula I-J, B is (c) hydroxyC2-C6 alkyl- In one embodiment of Formula I-J, $X^1$ is N; $X^2$, $X^3$ and $X^4$ are CH; A is CN; and B is (b) C1-C6 alkyl optionally substituted with 1-3 fluoros. In one embodiment, B is (b) C1-C6 alkyl.

In one embodiment of Formula I-J, $X^1$ is N; $X^2$, $X^3$ and $X^4$ are CH; A is CN; and B is (c) hydroxyC2-C6 alkyl- wherein the alkyl portion is optionally substituted with a C3-C6 cycloalkylidene ring. In one embodiment of Formula I-J, B is (c) hydroxyC2-C6 alkyl-.

In one embodiment, compounds of Formula I include compounds of Formula I-K where E is (l) Ar$^1$C(=O)NR$^g$— where R$^g$ is H or C1-C6 alkyl or (m) hetAr$^2$C(=O)NR$^g$(CH$_2$)$_p$— where p is 0 or 1 and R$^g$ is H or C1-C6 alkyl; Ring D is

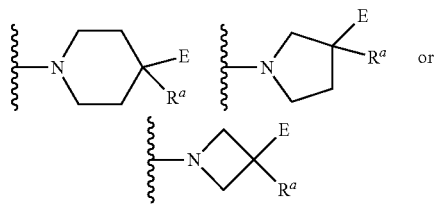

where the wavy line indicates the point of attachment of Ring D to the ring comprising $X^1$, $X^2$, $X^3$ and $X^4$; $R^a$ is C1-C6 alkyl optionally substituted with 1-3 fluoros; and $X^1$, $X^2$, $X^3$, $X^4$, A, B, Ar$^1$ and hetAr$^2$ are as defined for Formula I.

In one embodiment of Formula I-K, $X^1$ is N; and $X^2$, $X^3$ and $X^4$ are CH.

In one embodiment of Formula I-K, A is CN.

In one embodiment of Formula I-K, $X^1$ is N; $X^2$, $X^3$ and $X^4$ are CH; and A is CN.

In one embodiment of Formula I-K, B is (a) hydrogen, (b) C1-C6 alkyl optionally substituted with 1-3 fluoros, (c) hydroxyC2-C6 alkyl- wherein the alkyl portion is optionally substituted with a C3-C6 cycloalkylidene ring, (f) (R$^1$R$^2$N)C1-C6 alkyl- where R$^1$ and R$^2$ are independently selected from H, C1-C6 alkyl (optionally substituted with 1-3 fluoros), (C1-C6 alkoxy)C1-C6 alkyl- and (C1-C6 alkoxy)C(=O)—, (g) hetAr$^1$C1-C3 alkyl-, where hetAr$^1$ is a 5-6 membered heteroaryl ring having 1-3 ring heteroatoms independently selected from N, O and S and is optionally substituted with one or more independently selected C1-C6 alkyl substituents, or (i) (hetCyc$^a$)C1-C3 alkyl-, where hetCyc$^a$ is as defined for Formula I.

In one embodiment of Formula I-K, $X^1$ is N; $X^2$, $X^3$ and $X^4$ are CH; A is CN; and B is (a) hydrogen.

In one embodiment of Formula I-K, $X^1$ is N; $X^2$, $X^3$ and $X^4$ are CH; A is CN; and B is (b) C1-C6 alkyl optionally substituted with 1-3 fluoros.

In one embodiment of Formula I-K, $X^1$ is N; $X^2$, $X^3$ and $X^4$ are CH; A is CN; and B is (c) hydroxyC2-C6 alkyl- wherein the alkyl portion is optionally substituted with a C3-C6 cycloalkylidene ring.

In one embodiment of Formula I-K, $X^1$ is N; $X^2$, $X^3$ and $X^4$ are CH; A is CN; and B is (f) (R$^1$R$^2$N)C1-C6 alkyl- where R$^1$ and R$^2$ are independently selected from H, C1-C6 alkyl (optionally substituted with 1-3 fluoros), (C1-C6 alkoxy)C1-C6 alkyl- and (C1-C6 alkoxy)C(=O)—.

In one embodiment of Formula I-K, $X^1$ is N; $X^2$, $X^3$ and $X^4$ are CH; A is CN; and B is (g) hetAr$^1$C1-C3 alkyl-, where hetAr$^1$ is a 5-6 membered heteroaryl ring having 1-3 ring heteroatoms independently selected from N, O and S and is optionally substituted with one or more independently selected C1-C6 alkyl substituents.

In one embodiment of Formula I-K, $X^1$ is N; $X^2$, $X^3$ and $X^4$ are CH; A is CN; and B is (i) (hetCyc$^a$)C1-C3 alkyl-, where hetCyc$^a$ is as defined for Formula I.

In one embodiment, compounds of Formula I include compounds of Formula I-L where E is (g) Ar$^1$O— or (h) hetAr$^2$—O—; Ring D is

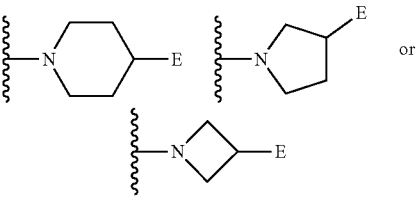

where the wavy line indicates the point of attachment of Ring D to the ring comprising $X^1$, $X^2$, $X^3$ and $X^4$; and $X^1$, $X^1$, $X^3$, $X^4$, A, B, Ar$^1$ and hetAr$^2$ are as defined for Formula I.

In one embodiment of Formula I-L, $X^1$ is N; and $X^2$, $X^3$ and $X^4$ are CH.

In one embodiment of Formula I-L, A is CN.

In one embodiment of Formula I-L, $X^1$ is N; $X^2$, $X^3$ and $X^4$ are CH; and A is CN.

In one embodiment of Formula I-L, B is (b) C1-C6 alkyl optionally substituted with 1-3 fluoros, (c) hydroxyC2-C6 alkyl- wherein the alkyl portion is optionally substituted with a C3-C6 cycloalkylidene ring, (i) (hetCyc$^a$)C1-C3 alkyl- or (k) (R$^1$R$^2$N)C(=O)C1-C6 alkyl- where R$^1$ and R$^2$ are independently selected from H and C1-C6 alkyl.

In one embodiment of Formula I-L, X$^1$ is N; X$^2$, X$^3$ X$^4$ are CH; and A is CN; and B is (b) C1-C6 alkyl optionally substituted with 1-3 fluoros.

In one embodiment of Formula I-L, X$^1$ is N; X$^2$, X$^3$ X$^4$ are CH; and A is CN; and B is (c) hydroxyC2-C6 alkyl- wherein the alkyl portion is optionally substituted with a C3-C6 cycloalkylidene ring.

In one embodiment of Formula I-L, X$^1$ is N; X$^2$, X$^3$ X$^4$ are CH; and A is CN; and B is (i) (hetCyc$^a$)C1-C3 alkyl- or (k) (R$^1$R$^2$N)C(=O)C1-C6 alkyl- where R$^1$ and R$^2$ are independently selected from H and C1-C6 alkyl.

In one embodiment, compounds of Formula I include compounds of Formula I-M

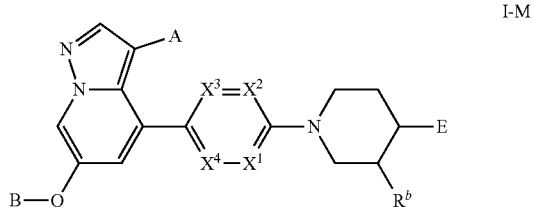

I-M where E is (k) R$^3$C(=O)NR$^g$ where R$^g$ is H or C1-C6 alkyl; R$^b$ is (a) hydroxy; and X$^1$, X$^2$, X$^3$, X$^4$, R$^3$, A and B, are as defined for Formula I.

In one embodiment of Formula I-M, X$^1$ is N; and X$^2$, X$^3$ and X$^4$ are CH.

In one embodiment of Formula I-M, A is CN.

In one embodiment of Formula I-M, X$^1$ is N; X$^2$, X$^3$ and X$^4$ are CH; and A is CN.

In one embodiment of Formula I-M, B is (b) C1-C6 alkyl optionally substituted with 1-3 fluoros. In one embodiment, B is (b) C1-C6 alkyl.

In one embodiment of Formula I-M, X$^1$ is N; X$^2$, X$^3$ and X$^4$ are CH; A is CN; and B is (b) C1-C6 alkyl optionally substituted with 1-3 fluoros. In one embodiment, B is (b) C1-C6 alkyl.

In one embodiment of Formula I-M, R$^3$ is C1-C6 alkyl (optionally substituted with 1-3 fluoros), C1-C6 alkoxy, or C3-C6 cycloalkyl, wherein said C3-C6 cycloalkyl is optionally substituted with C1-C6 alkyl (optionally substituted with 1-3 fluoros), C1-C6 alkoxy, OH, or R'R"N— where R' and R" are independently hydrogen or C1-C6 alkyl.

The compounds of Formula I include pharmaceutically acceptable salts thereof. In addition, the compounds of Formula I also include other salts of such compounds which are not necessarily pharmaceutically acceptable salts, and which may be useful as intermediates for preparing and/or purifying compounds of Formula I and/or for separating enantiomers of compounds of Formula I. Non-limiting examples of pharmaceutically acceptable salts of compounds of Formula I include monohydrochloride, dihydrochloride, trifluoroacetic acid, and di-trifluoroacetic acid salts. In one embodiment, compounds of Formula I include trifluoroacetic acid and dihydrochloride salts.

It will further be appreciated that the compounds of Formula I or their salts may be isolated in the form of solvates, and accordingly that any such solvate is included within the scope of the present invention. For example, compounds of Formula I and salts thereof can exist in unsolvated as well as solvated forms with pharmaceutically acceptable solvents such as water, ethanol, and the like.

In one embodiment, the compounds of Formula I include the compounds of Examples 1-819 and stereoisomers and pharmaceutically acceptable salts and solvates thereof. In one embodiment, the compounds of Examples 1-819 are in the free base form. In one embodiment, the compounds of Examples 1-819 are dihydrochloride or trifluoroacetic acid salts.

The term "pharmaceutically acceptable" indicates that the compound, or salt or composition thereof is compatible chemically and/or toxicologically with the other ingredients comprising a formulation and/or the patient being treated therewith.

Compounds provided herein may also contain unnatural proportions of atomic isotopes at one or more of the atoms that constitute such compounds. That is, an atom, in particular when mentioned in relation to a compound according to Formula I, comprises all isotopes and isotopic mixtures of that atom, either naturally occurring or synthetically produced, either with natural abundance or in an isotopically enriched form. For example, when hydrogen is mentioned, it is understood to refer to $^1$H, $^2$H, $^3$H or mixtures thereof; when carbon is mentioned, it is understood to refer to $^{11}$C, $^{12}$C, $^{13}$C, $^{14}$C or mixtures thereof; when nitrogen is mentioned, it is understood to refer to $^{13}$N, $^{14}$N, $^{15}$N or mixtures thereof; when oxygen is mentioned, it is understood to refer to $^{14}$O, $^{15}$O, $^{16}$O, $^{17}$O, $^{18}$O or mixtures thereof; and when fluoro is mentioned, it is understood to refer to $^{18}$F, $^{19}$F or mixtures thereof. The compounds provided herein therefore also comprise compounds with one or more isotopes of one or more atoms, and mixtures thereof, including radioactive compounds, wherein one or more non-radioactive atoms has been replaced by one of its radioactive enriched isotopes. Radiolabeled compounds are useful as therapeutic agents, e.g., cancer therapeutic agents, research reagents, e.g., assay reagents, and diagnostic agents, e.g., in vivo imaging agents. All isotopic variations of the compounds provided herein, whether radioactive or not, are intended to be encompassed within the scope of the present invention.

For illustrative purposes, Schemes 1-6 show general methods for preparing the compounds provided herein as well as key intermediates. For a more detailed description of the individual reaction steps, see the Examples section below. Those skilled in the art will appreciate that other synthetic routes may be used to synthesize the inventive compounds. Although specific starting materials and reagents are depicted in the Schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

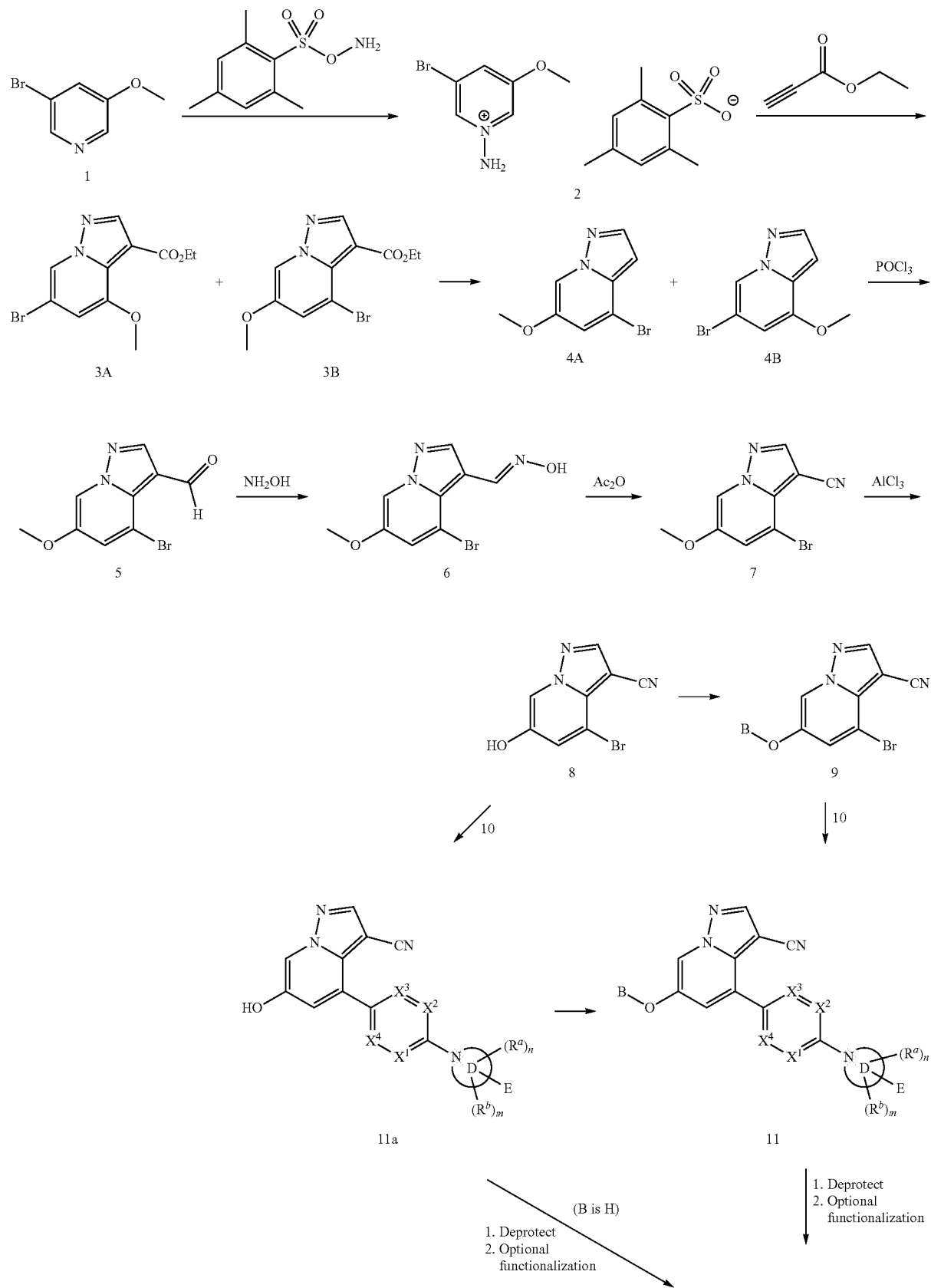
SCHEME 1

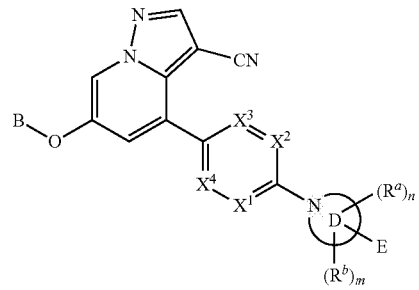

12

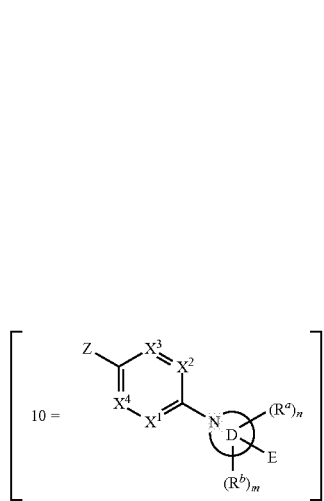

10 =

Scheme 1 shows a general scheme for the synthesis of compound X where A is CN, and B, $X^1$, $X^2$, $X^3$, $X^4$, Ring D, $R^a$, $R^b$, n, m and E are as defined for Formula I.

Compound 2 is obtained by treating 3-bromo-5-methoxypyridine (compound 1), which is commercially available, with O-(mesitylsulfonyl)hydroxylamine. The O-mesitylsulfonylhydroxylamine may be prepared as described in Mendiola, J., et al., Org. Process Res. Dev. 2009, 13(2), 263-267. Compound 2 may be reacted with ethyl propiolate to provide a mixture of compounds 3A and 3B, which typically are obtained in a ratio of approximately 2:1 to 9:1, respectively. The mixture of compounds 3A and 3B may be treated with 48% HBr at elevated temperatures, followed by recrystallization or chromatography purifications, to isolate compound 4A as the minor isomer and compound 4B as the major isomer. After isolation, compound 4A may be treated with POCl₃ to provide compound 5. The formyl group may be converted to an oxime group using NH₂OH to provide compound 6. The oxime group may be converted to a nitrile group using acetic anhydride to provide compound 7. The methoxy group of compound 7 may be converted to a hydroxy group by treating compound 7 with aluminum trichloride to provide compound 8.

When group B is hydrogen, compound 12 may be prepared by coupling compound 8 with the corresponding boronic ester compound 10 (where Ring D, E, $X^1$, $X^2$, $X^3$ and $X^4$ are as defined for Formula I; Z is —B(OR$^x$)(OR$^y$) and R$^z$ and R$^y$ are H or (1-6C)alkyl, or R$^x$ and R$^y$ together with the atoms to which they are connected form a 5-6 membered ring optionally substituted with 1-4 substituents selected from (C1-C3 alkyl)) to provide compound 11a using appropriate palladium-catalyzed cross-coupling reaction conditions, e.g., Suzuki coupling reaction conditions (for example, a palladium catalyst and optionally a ligand in the presence of an inorganic base, for example, Pd(PPh₃)₄ and Na₂CO₃ in dioxane at elevated temperatures), wherein if Ring D of compound 10 is substituted with an R$^b$ substituent that is R$^c$R$^d$N— wherein one or both of R$^c$ and R$^d$ is hydrogen, the nitrogen atom of R$^b$ may be protected with an appropriate amino protecting group prior to coupling. The amino protecting group if present on a substituent of Ring D of compound 11a may be removed under standard conditions (for example, a Boc group may be removed by treating compound 11a to acidic conditions, e.g., HCl) to provide compound 12 where B is hydrogen. Alternatively, the E group may be functionalized (i.e., reacted or treated with an appropriate reagent) under standard conditions such as described below to provide compound 12 where B is hydrogen and E is as defined for Formula I except that E is not hydrogen.

Alternatively, when group B is as defined for Formula I other than hydrogen, Compound 11a may be reacted with a reagent such as C1-C6 alkyl-OH, (C1-C6 alkoxy)C1-C6 alkyl-OH optionally substituted with 1-3 fluoros, hetAr¹C1-C3 alkyl-OH, (C3-C6 cycloalkyl)C1-C3 alkyl-OH, (hetCyc$^a$)C1-C3 alkyl-OH, hetCyc$^a$OH or hetCyc$^a$C(=O)C1-C6 alkyl-OH, where hetAr¹ and hetCyc$^a$ are as defined for Formula I, under Mitsunobu reaction conditions (PPh₃ and diisopropyl azodicarboxylate) to provide compound 11. Compound 12 may then be prepared from compound 11 as described above.

Alternatively, when group B is as defined for Formula I other than hydrogen, compound 9 may be prepared by reacting compound 8 with a reagent such as C1-C6 alkyl-X optionally substituted with 1-3 fluoros, hydroxyC2-C6 alkyl-X wherein the alkyl portion is optionally substituted with a C3-C6 cycloalkylidene ring, dihydroxyC3-C6 alkyl-X wherein the alkyl portion is optionally substituted with a C3-C6 cycloalkylidene ring, (C1-C6 alkoxy)C1-C6 alkyl-X optionally substituted with 1-3 fluoros, (R¹R²N)C1-C6 alkyl-X, hetAr¹C1-C3 alkyl-X, (C3-C6 cycloalkyl)C1-C3 alkyl-X, (hetCyc$^a$)C1-C3 alkyl-X, hetCyc$^a$-X, or hetCyc$^a$C(=O)C1-C6 alkyl-X, where R¹, R², hetAr¹, and hetCyc$^a$ are as defined for Formula I and X is a leaving atom or group (such as a halide or triflate), wherein each of said reagents is optionally substituted with a protecting group (e.g., a t-butyldimethylsilyl group if the B group has one or two additional hydroxy groups), in the presence of a base (for example, an alkali metal carbonate, such as potassium carbonate). For example, when B is C1-C6 alkyl optionally substituted with 1-3 fluoros, compound may be prepared by reacting compound 8 with a C1-C6 alkyl-X, where X is a halogen such as Br or Cl, or a leaving group such as triflate. Compound 11 may then be prepared by coupling compound 9 with the corresponding boronic ester compound 10 using appropriate palladium-catalyzed cross-coupling reaction conditions, e.g., Suzuki coupling reaction conditions (for example, a palladium catalyst and optionally a ligand in the presence of an inorganic base, for example, Pd(PPh$_3$)$_4$ and Na$_2$CO$_3$ in dioxane at elevated temperatures), wherein if Ring D of compound 10 is substituted with an R$^b$ substituent that is R$^c$R$^d$N— wherein one or both of R$^c$ and R$^d$ is hydrogen, the nitrogen atom of R$^b$ may be protected with an appropriate amino protecting group prior to coupling. Compound 12 may then be prepared from compound 11 as described above.

SCHEME 2

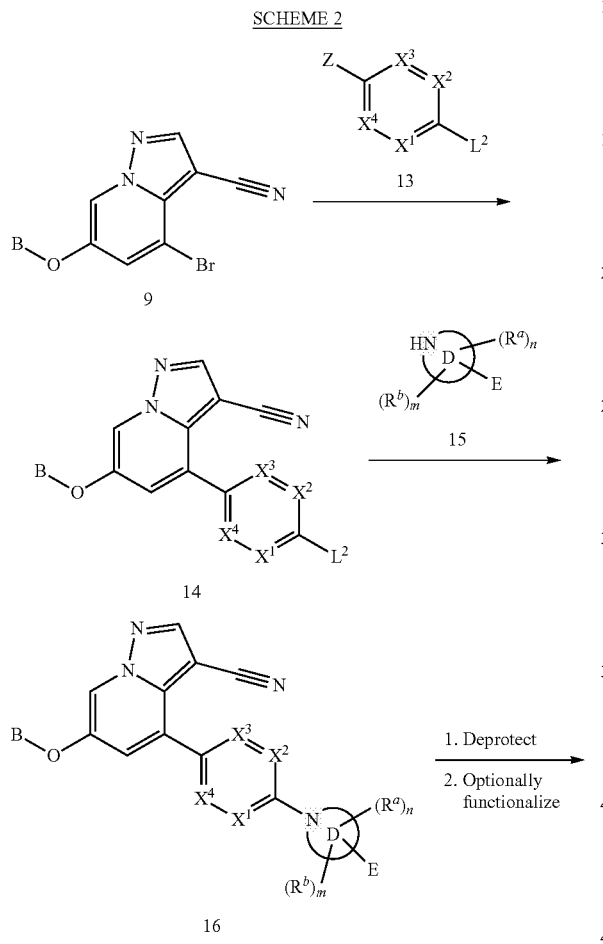

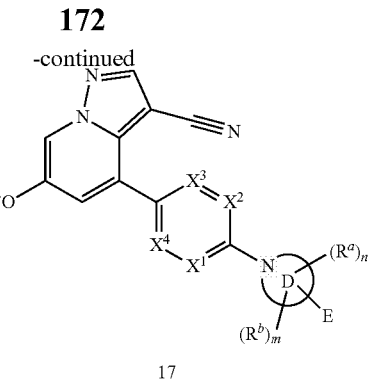

Scheme 2 shows another general scheme for the synthesis of compound 17 where A is CN, and B, X$^1$, X$^2$, X$^3$, X$^4$, Ring D, R$^a$, R$^b$, n, m and E are as defined for Formula I.

Compound 9 (prepared, e.g., as described in Scheme 1) in which B is as defined for Formula I, may be coupled with compound 13 (where X$^1$, X$^2$, X$^3$ and X$^4$ are as defined for Formula I; L$^2$ is a leaving group such as a triflate or halide); Z is —B(OR$^x$)(OR$^y$) and R$^z$ and R$^y$ are H or (1-6C)alkyl, or R$^x$ and R$^y$ together with the atoms to which they are connected form a 5-6 membered ring optionally substituted with 1-4 substituents selected from (C1-C3 alkyl)), using appropriate palladium-catalyzed cross-coupling reaction conditions, e.g., Suzuki coupling reaction conditions (for example, a palladium catalyst and optionally a ligand in the presence of an inorganic base, for example, Pd(PPh$_3$)$_4$ and Na$_2$CO$_3$ in dioxane at elevated temperatures) to provide compound 14. Compound 16 may be prepared by coupling compound 14 with compound 15 under appropriate S$_N$Ar conditions (for example, optionally in the presence of a base such as K$_2$CO$_3$ and at elevated temperature), wherein if Ring D of compound 15 is substituted with an R$^b$ substituent that is R$^c$R$^d$N— wherein one or both of R$^c$ and R$^d$ is hydrogen, the nitrogen atom of R$^b$ may be protected with an appropriate amino protecting group prior to coupling. The amino protecting group if present may then be removed under standard conditions (for example, a Boc group may be removed by treating compound 1 to acidic conditions, e.g., HCl) to provide compound 17 where E is H.

Alternatively, the E group may be functionalized (i.e., reacted or treated with an appropriate reagent) under standard conditions such as described below to provide compound 17 where E is as defined for Formula I except that E is not H.

SCHEME 3

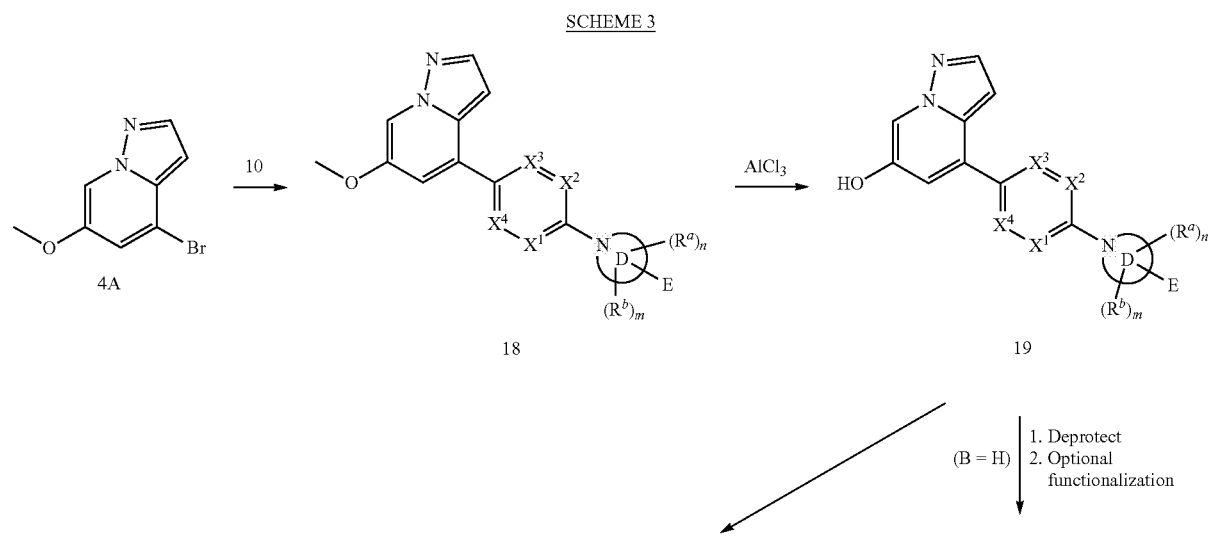

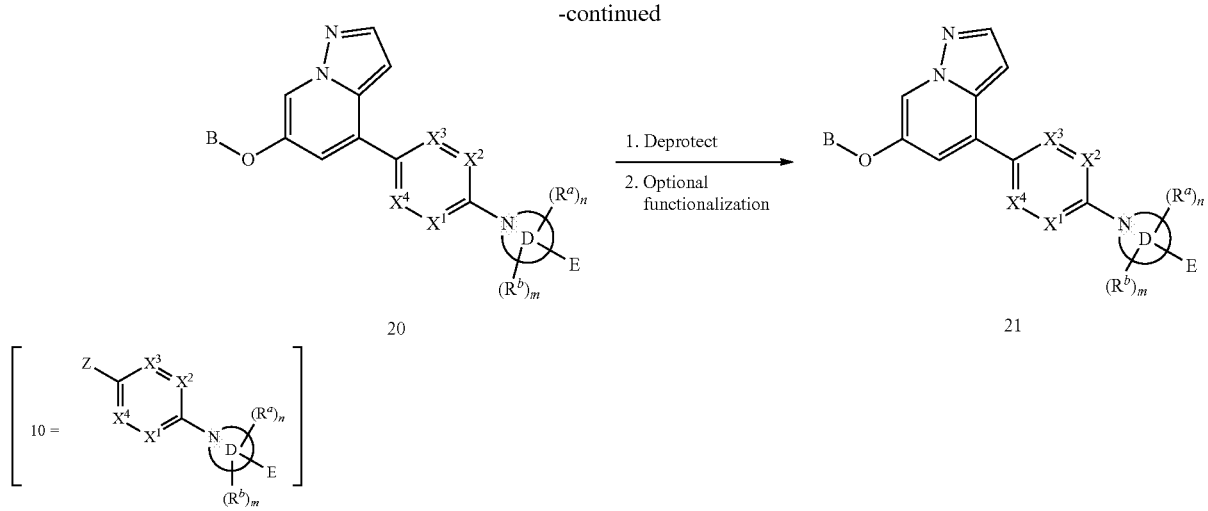

Scheme 3 shows a general scheme for the synthesis of Compound 21 where A is H, and B, $X^1$, $X^2$, $X^3$, $X^4$, Ring D, $R^a$, $R^b$, n, m and E are as defined for Formula I.

Compound 18 may be prepared by coupling compound 4A (prepared e.g., as described in Scheme 1) with the corresponding boronic ester compound 10 (where Ring D, $X^1$, $X^2$, $X^3$ and $X^4$ are as defined for Formula I; Z is —B(OR$^x$)(OR$^y$) and R$^z$ and R$^y$ are H or (1-6C)alkyl, or R$^x$ and R$^y$ together with the atoms to which they are connected form a 5-6 membered ring optionally substituted with 1-4 substituents selected from (C1-C3 alkyl)) using appropriate palladium-catalyzed cross-coupling reaction conditions, e.g., Suzuki coupling reaction conditions (for example, a palladium catalyst and optionally a ligand in the presence of an inorganic base, for example, Pd(PPh$_3$)$_4$ and Na$_2$CO$_3$ in dioxane at elevated temperatures), wherein if Ring D of compound 10 is substituted with an $R^b$ substituent that is $R^c R^d N$— wherein one or both of $R^c$ and $R^d$ is hydrogen, the nitrogen atom of $R^b$ may be protected with an appropriate amino protecting group prior to coupling. Compound 19 may be prepared by treating compound 18 with aluminum trichloride.

When B is as defined for Formula I other than hydrogen, compound 20 may be prepared by reacting compound 19 with a reagent such as C1-C6 alkyl-X optionally substituted with 1-3 fluoros, hydroxyC2-C6 alkyl-X wherein the alkyl portion is optionally substituted with a C3-C6 cycloalkylidene ring, dihydroxyC3-C6 alkyl-X wherein the alkyl portion is optionally substituted with a C3-C6 cycloalkylidene ring, (C1-C6 alkoxy)C1-C6 alkyl-X optionally substituted with 1-3 fluoros, ($R^1R^2N$)C1-C6 alkyl-X, hetAr$^1$C1-C3 alkyl-X, (C3-C6 cycloalkyl)C1-C3 alkyl-X, (hetCyc$^a$)C1-C3 alkyl-X, hetCyc$^a$-X or hetCyc$^a$C(=O)C1-C6 alkyl-X, where $R^1$, $R^2$, hetAr$^1$, and hetCyc$^a$ are as defined for Formula I and X is a leaving atom or group (such as a halide or triflate), wherein each of said reagents is optionally substituted with a protecting group (e.g., a t-butyldimethylsilyl group if B has one or two additional hydroxy groups). For example, when B is C1-C6 alkyl optionally substituted with 1-3 fluoros, compound may be prepared by reacting compound 19 with C1-C6 alkyl-X, where X is a halogen such as Br or Cl, or a leaving group such as triflate. Compound 21 may then be prepared from compound 20. If Ring D comprises a substituent having an amino protecting group, the amino protecting group may be removed under standard conditions (for example, a Boc group may be removed by treating compound 20 to acidic conditions, e.g., HCl) to provide compound 21 where E is H.

Alternatively, the E group of compound 20 may be functionalized (i.e., reacted or treated with an appropriate reagent) under standard conditions such as described below to provide compound 21 where E is as defined for Formula I except that E is not H.

Alternatively, when group B is hydrogen, compound 21 may be prepared from compound 19 according to the deprotection and optional functionalization steps described herein.

SCHEME 4

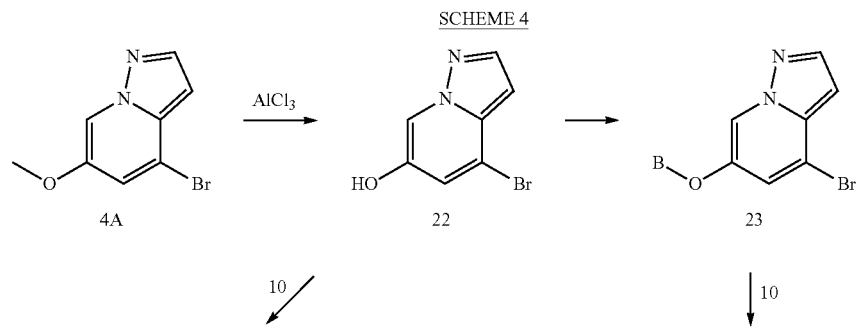

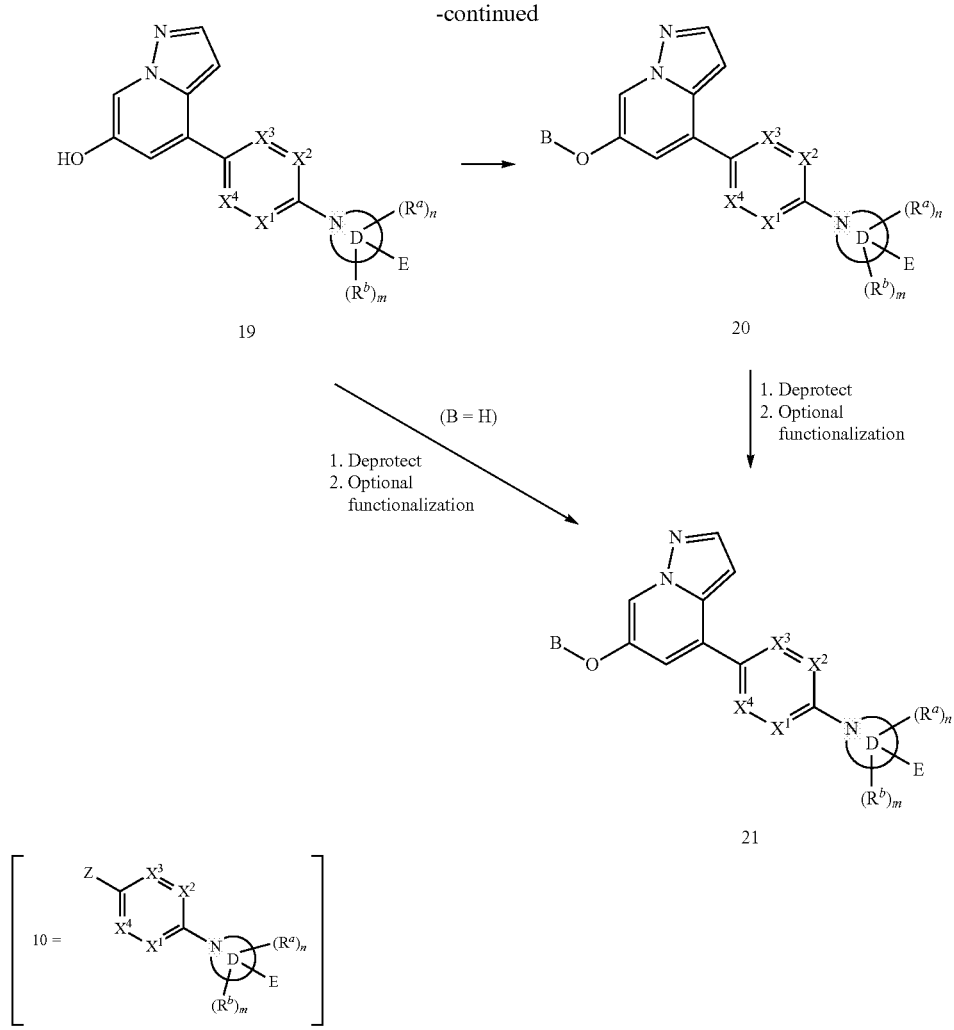

Scheme 4 shows an alternative general scheme for the synthesis of Compound 21 where A is H, and B, $X^1$, $X^2$, $X^3$, $X^4$, Ring D, $R^a$, $R^b$, n, m and E are as defined for Formula I.

Compound 22 may be prepared by treating compound 4A (prepared e.g., as described in Scheme 1) with aluminum trichloride.

When group B is hydrogen, compound 19 may be prepared by coupling compound 22 with the corresponding boronic ester compound 10 (where Ring D, $X^1$, $X^2$, $X^3$ and $X^4$ are as defined for Formula I; Z is —B(OR$^x$)(OR$^y$) and R$^z$ and R$^y$ are H or (1-6C)alkyl, or R$^x$ and R$^y$ together with the atoms to which they are connected form a 5-6 membered ring optionally substituted with 1-4 substituents selected from (C1-C3 alkyl)) using appropriate palladium-catalyzed cross-coupling reaction conditions, e.g., Suzuki coupling reaction conditions (for example, a palladium catalyst and optionally a ligand in the presence of an inorganic base, for example, Pd(PPh$_3$)$_4$ and Na$_2$CO$_3$ in dioxane at elevated temperatures), wherein if Ring D of compound 10 is substituted with an $R^b$ substituent that is R$^c$R$^d$N— wherein one or both of R$^c$ and R$^d$ is hydrogen, the nitrogen atom of R$^b$ may be protected with an appropriate amino protecting group prior to coupling. Compound 21 may be prepared from compound 19 according to the process described for Scheme 3.

Alternatively, when group B is as defined for Formula I other than hydrogen, compound 23 may be prepared by reacting compound 22 with a reagent such as C1-C6 alkyl-X optionally substituted with 1-3 fluoros, hydroxyC2-C6 alkyl-X wherein the alkyl portion is optionally substituted with a C3-C6 cycloalkylidene ring, dihydroxyC3-C6 alkyl-X wherein the alkyl portion is optionally substituted with a C3-C6 cycloalkylidene ring, (C1-C6 alkoxy)C1-C6 alkyl-X optionally substituted with 1-3 fluoros, (R$^1$R$^2$N)C1-C6 alkyl-X, hetAr$^1$C1-C3 alkyl-X, (C3-C6 cycloalkyl)C1-C3 alkyl-X, (hetCyc$^a$)C1-C3 alkyl-X, hetCyc$^a$-X or hetCyc$^a$C(=O)C1-C6 alkyl-X, where R$^1$, R$^2$, hetAr$^1$, and hetCyc$^a$ are as defined for Formula I and X is a leaving atom or group (such as a halide or triflate), wherein each of said reagents is optionally substituted with a protecting group (e.g., a t-butyldimethylsilyl group if B has one or two additional hydroxy groups). For example, when B is C1-C6 alkyl optionally substituted with 1-3 fluoros, compound may be prepared by reacting compound 22 with C1-C6 alkyl-X, where X is a halogen such as Br or Cl, or a leaving group such as triflate. Compound 20 may be prepared by coupling compound 23 with compound 10 as described in Scheme 3. Compound 21 may be prepared from compound 20 according to the process described for Scheme 3.

Alternatively, when group B is as defined for Formula I other than hydrogen, compound 20 may be prepared by reacting compound 19 with a group such as (C1-C6 alkyl) OH, an appropriately substituted (C1-C3 alkyl)OH, an appropriately substituted (C1-C6 alkyl)OH, or hetCyc$^a$OH (i.e., where hetCyc$^a$ a 4-6 membered heterocyclic ring having 1-2 ring heteroatoms independently selected from N and O and is optionally substituted with OH, C1-C6 alkyl (optionally substituted with 1-3 fluoros) or hydroxyC1-C6 alkyl) under Mitsunobu reaction conditions (PPh$_3$ and diisopropyl azodicarboxylate). Compound 21 may be prepared from compound 20 according to the process described for Scheme 3.

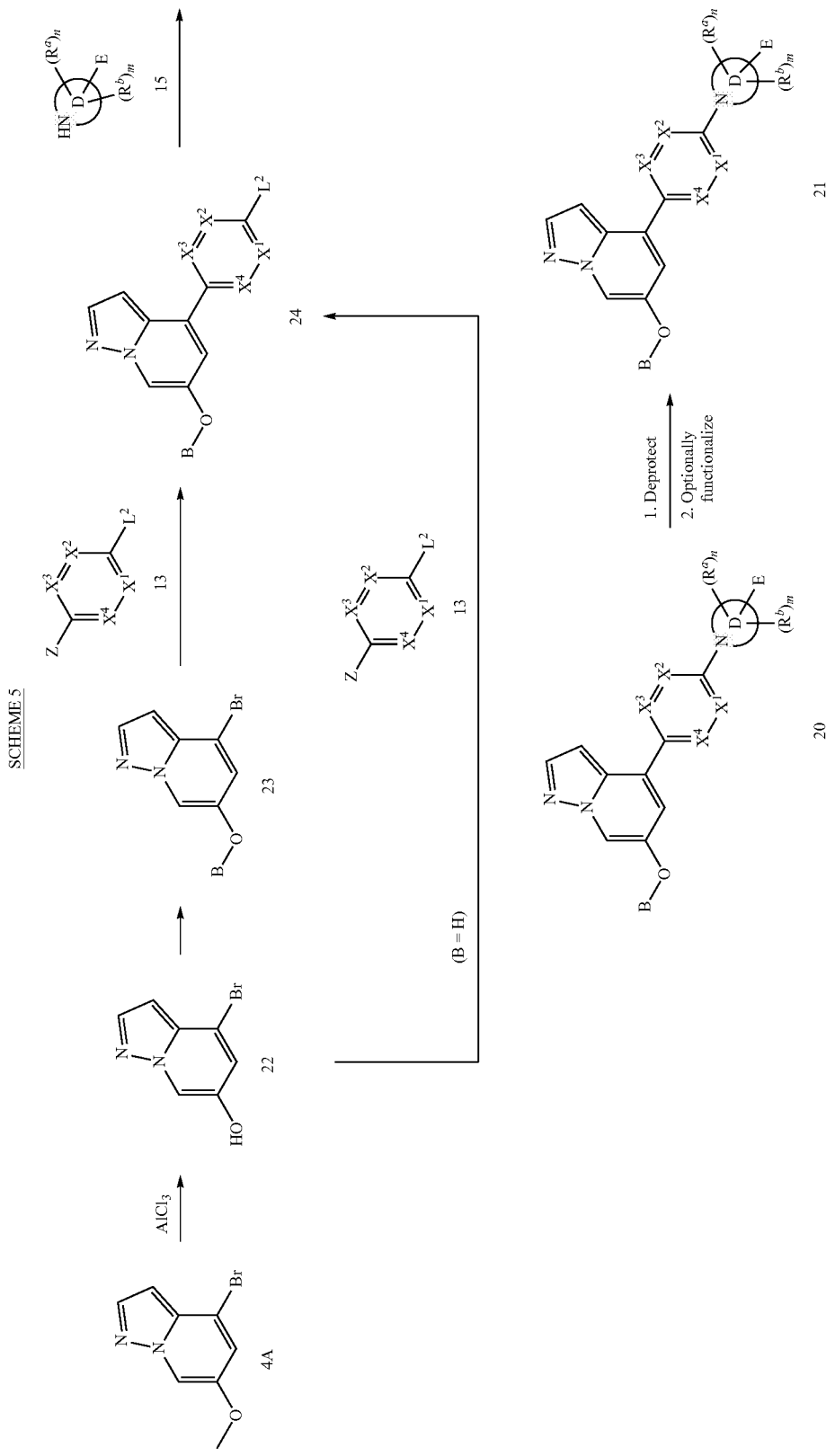

Scheme 5 shows an alternative general scheme for the synthesis of Compound 21 where A is H, and B, $X^1$, $X^2$, $X^3$, $X^4$, Ring D, $R^a$, $R^b$, n, m and E are as defined for Formula I.

Compound 22 may be prepared by treating compound 4A (prepared e.g., as described in Scheme 1) with aluminum trichloride.

When group B is as defined for Formula I other than hydrogen, compound 23 may be prepared by reacting compound 22 with a reagent such as C1-C6 alkyl-X optionally substituted with 1-3 fluoros, hydroxyC2-C6 alkyl-X wherein the alkyl portion is optionally substituted with a C3-C6 cycloalkylidene ring, dihydroxyC3-C6 alkyl-X wherein the alkyl portion is optionally substituted with a C3-C6 cycloalkylidene ring, (C1-C6 alkoxy)C1-C6 alkyl-X optionally substituted with 1-3 fluoros, $(R^1R^2N)$C1-C6 alkyl-X, hetAr$^1$C1-C3 alkyl-X, (C3-C6 cycloalkyl)C1-C3 alkyl-X, (hetCyc$^a$)C1-C3 alkyl-X, hetCyc$^a$-X or hetCyc$^a$C(=O)C1-C6 alkyl-X, where $R^1$, $R^2$, hetAr$^1$, and hetCyc$^a$ are as defined for Formula I and X is a leaving atom or group (such as a halide or triflate), wherein each of said reagents is optionally substituted with a protecting group (e.g., a t-butyldimethylsilyl group if B has one or two additional hydroxy groups). For example, when B is C1-C6 alkyl optionally substituted with 1-3 fluoros, compound may be prepared by reacting compound 22 with C1-C6 alkyl-X, where X is a halogen such as Br or Cl, or a leaving group such as triflate.

Compound 24 may be prepared by reacting compound 23 with compound 13 (where $X^1$, $X^2$, $X^3$ and $X^4$ are as defined for Formula I; $L^2$ is a leaving group such as a triflate or halide); Z is —B(OR$^x$)(OR$^y$) and $R^z$ and $R^y$ are H or (1-6C)alkyl, or $R^x$ and $R^y$ together with the atoms to which they are connected form a 5-6 membered ring optionally substituted with 1-4 substituents selected from (C1-C3 alkyl)) using appropriate palladium-catalyzed cross-coupling reaction conditions, e.g., Suzuki coupling reaction conditions (for example, a palladium catalyst and optionally a ligand in the presence of an inorganic base, for example, Pd(PPh$_3$)$_4$ and Na$_2$CO$_3$ in dioxane at elevated temperatures).

When group B is hydrogen, compound 24 may be prepared by reacting compound 22 directly with compound 13 as described above.

Compound 20 may be prepared by coupling compound 24 with compound 15 where Ring D and E are as defined for Formula I under appropriate S$_N$Ar conditions (for example, optionally in the presence of a base such as K$_2$CO$_3$ and at elevated temperature). If Ring D of compound 15 comprises a substituent having a primary or secondary ring nitrogen atom, the nitrogen atom is protected with an appropriate amino protecting group prior to coupling, and then the amino protecting group may be removed subsequent to coupling as described above.

Compound 21 may be prepared from compound 20 according to the process described for Scheme 3.

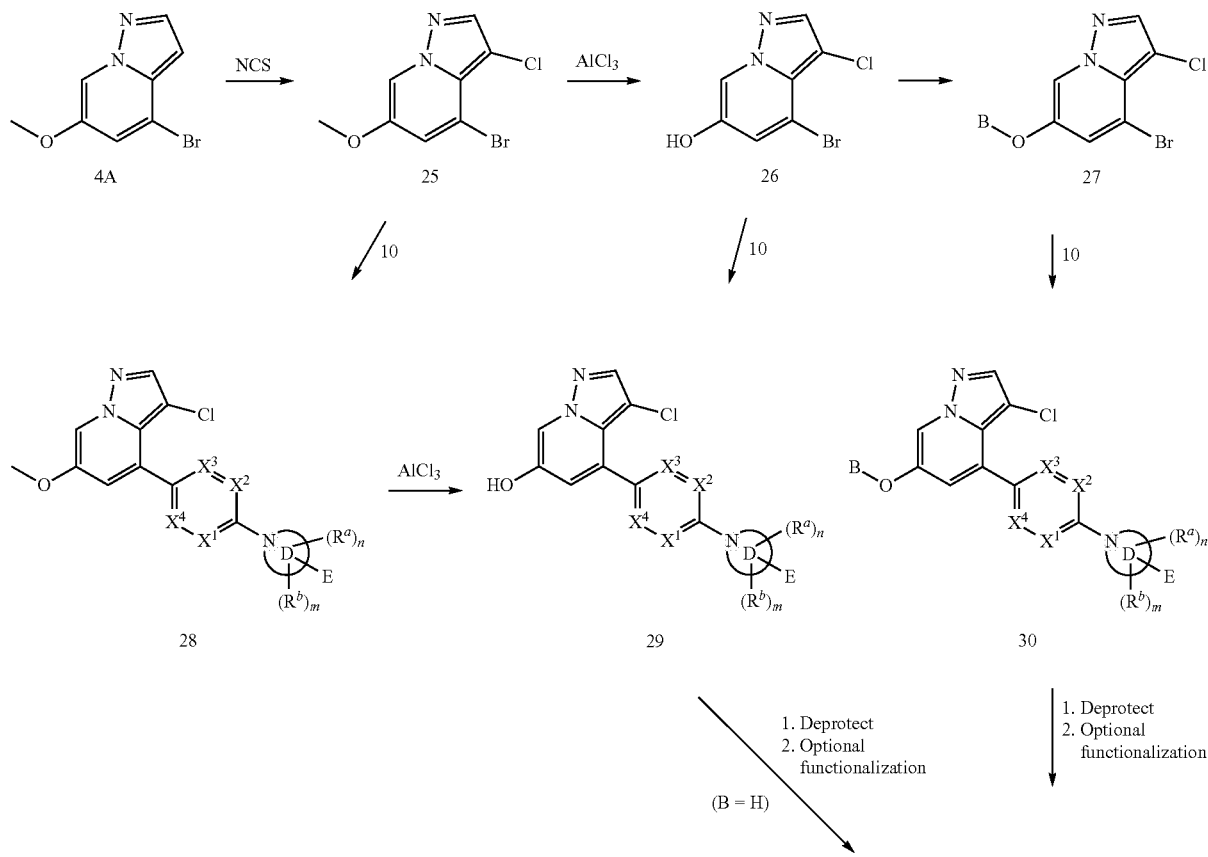

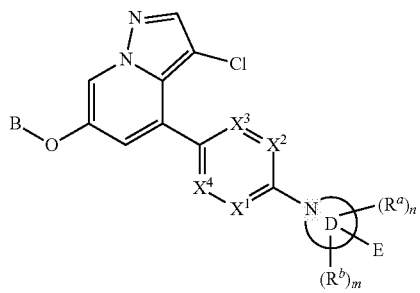

31

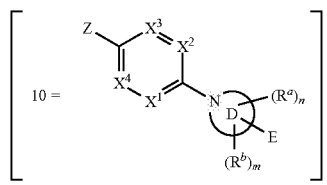

Scheme 6 shows a general scheme for the synthesis of Compound 31 where A is Cl, and B, $X^1$, $X^2$, $X^3$, $X^4$, Ring D, $R^a$, $R^b$, n, m and E are as defined for Formula I.

Compound 25 may be prepared by treating compound 4A (prepared e.g., as described in Scheme 1) with aluminum trichloride.

Compound 26 may be prepared by treating compound 25 with aluminum trichloride.

When group B is as defined for Formula I other than hydrogen, compound 27 may be prepared by reacting compound 26 with a reagent such as C1-C6 alkyl-X optionally substituted with 1-3 fluoros, hydroxyC2-C6 alkyl-X wherein the alkyl portion is optionally substituted with a C3-C6 cycloalkylidene ring, dihydroxyC3-C6 alkyl-X wherein the alkyl portion is optionally substituted with a C3-C6 cycloalkylidene ring, (C1-C6 alkoxy)C1-C6 alkyl-X optionally substituted with 1-3 fluoros, ($R^1R^2N$)C1-C6 alkyl-X, hetAr$^1$C1-C3 alkyl-X, (C3-C6 cycloalkyl)C1-C3 alkyl-X, (hetCyc$^a$)C1-C3 alkyl-X, hetCyc$^a$-X or hetCyc$^a$C(=O)C1-C6 alkyl-X, where $R^1$, $R^2$, hetAr$^1$, and hetCyc$^a$ are as defined for Formula I and X is a leaving atom or group (such as a halide or triflate), wherein each of said reagents is optionally substituted with a protecting group (e.g., a t-butyldimethylsilyl group if B has one or two additional hydroxy groups). For example, when B is C1-C6 alkyl optionally substituted with 1-3 fluoros, compound may be prepared by reacting compound 26 with C1-C6 alkyl-X, where X is a halogen such as Br or Cl, or a leaving group such as triflate.

Compounds 28 (when group B is methyl), 29 (when group B is hydrogen) and 30 (when group B is other than hydrogen) may be prepared by coupling compounds 25, 26 and 27, respectively, with the corresponding boronic ester compound 10 (where Ring D, E, $X^1$, $X^2$, $X^3$ and $X^4$ are as defined for Formula I; Z is —B(OR$^x$)(OR$^y$) and $R^z$ and $R^y$ are H or (1-6C)alkyl, or $R^x$ and $R^y$ together with the atoms to which they are connected form a 5-6 membered ring optionally substituted with 1-4 substituents selected from (C1-C3 alkyl)) using appropriate palladium-catalyzed cross-coupling reaction conditions, e.g., Suzuki coupling reaction conditions (for example, a palladium catalyst and optionally a ligand in the presence of an inorganic base, for example, Pd(PPh$_3$)$_4$ and Na$_2$CO$_3$ in dioxane at elevated temperatures), wherein if Ring D of is substituted with an $R^b$ substituent that is $R^cR^dN$— wherein one or both of $R^c$ and $R^d$ is hydrogen, the nitrogen atom of $R^b$ may be protected with an appropriate amino protecting group prior to coupling. The amino protecting group if present on a substituent of Ring D of compound 29 or 30 may be removed under standard conditions (for example, a Boc group may be removed by treating compound 1 to acidic conditions, e.g., HCl) to provide compound 31 where E is H.

Alternatively, the E group may be functionalized (i.e., reacted or treated with an appropriate reagent) under standard conditions such as described below to provide compound 31 where E is as defined for Formula I except that E is not H.

The E group of compounds 11, 11a, 16, 19, 20, 29 and 30 described in Schemes 1-6 may be functionalized (i.e., reacted or treated with an appropriate reagent) to introduce an E group, where E is any of the E groups defined for Formula I with the exception of hydrogen, using standard chemistry well known to persons skilled in the art. As used herein, the term "functionalized" refers to a process step in the E group of a compound of general Formula I is reacted or treated with an appropriate reagent to provide a compound of Formula I where E is as defined for Formula I except that E is other than hydrogen.

For example, an amide derivative (e.g., where E is Ar$^1$C(=O)NR$^g$—, hetAr$^2$C(=O)NR$^g$(CH$_2$)$_p$— p is 0 or 1, or $R^4R^5NC$(=O)NR$^g$—, may be obtained by reacting compound 11 wherein E is —NH$_2$ with an carboxylic acid derivative such as an acid chloride using conventional amide bond formation conditions, for example in the presence of a base (e.g., an amine base such as DIEA) in an appropriate solvent (such as DCM) to provide a functionalized compound 12. Alternative, compound 11 wherein E is —NH$_2$ may be reacted with an carboxylic acid using conventional amide bond formation conditions, for example by treating the carboxylic acid with an activating agent (e.g., HATU) followed by addition of compound 11 in the presence of a base ((e.g., an amine base such as DIEA) in an appropriate solvent (such as DMA) to provide a functionalized compound 12. The same chemistry may be utilized with compounds 11a, 16, 19, 20, 29 and 30 to prepare functionalized compounds 12, 17, 21 and 31.

As another example, a urea derivative, (e.g., where E is $R^4R^5NHC$(=O)NR$^g$—) may be prepared reacting a compound 11 where E is —NH$_2$ with a compound having the formula R$^4$R$^5$N=C(=O) where R$^4$ and R$^5$ are as defined for Formula I in the presence of an appropriate base (e.g., DIEA) to provide a functionalized compound 12. The same chemistry may be utilized with compounds 11a, 16, 19, 20, 29 and 30 to prepare functionalized compounds 12, 17, 21 and 31.

As another example, an alkoxy, aryloxy or heteroaryloxy derivative (e.g., where E is (C1-C6 alkoxy)C1-C6 alkoxy, Ar$^1$O— or hetAr$^2$O—), may be prepared by reacting a compound 11 where E is hydroxy with a compound having the formula (C1-C6 alkoxy)C1-C6 alkyl-X, Ar$^1$—X or hetAr$^2$—X, where X is a halogen, in the presence of an inorganic base (e.g., an alkali metal hydride, such as sodium hydride or potassium hydride) in an appropriate solvent (e.g., an aprotic solvent such as DMA). The same chemistry may be utilized with compounds 11a, 16, 19, 20, 29 and 30 to prepare functionalized compounds 12, 17, 21 and 31.

The term "amino protecting group" as used herein refers to a derivative of the groups commonly employed to block or protect an amino group while reactions are carried out on other functional groups on the compound. Examples of suitable protecting groups for use in any of the processes described herein include carbamates, amides, alkyl and aryl groups, imines, as well as many N-heteroatom derivatives which can be removed to regenerate the desired amine group. Non-limiting examples of amino protecting groups are acetyl, trifluoroacetyl, t-butyloxycarbonyl ("Boc"), benzyloxycarbonyl ("CBz") and 9-fluorenylmethyleneoxycarbonyl ("Fmoc"). Further examples of these groups, and other protecting groups, are found in T. W. Greene, et al. *Greene's Protective Groups in Organic Synthesis*. New York: Wiley Interscience, 2006.

Accordingly, further provided herein is a process for preparing of a compound of Formula I or a pharmaceutically acceptable salt thereof as defined herein which comprises:

(a) for a compound of Formula I where E is H, A is CN, and B, X$^1$, X$^2$, X$^3$, X$^4$, Ring D, R$^a$, R$^b$, m and n are as defined for Formula I, coupling a corresponding compound 9 having the formula

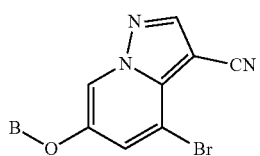

where B is as defined for Formula I, with a corresponding boronate ester having the formula 10

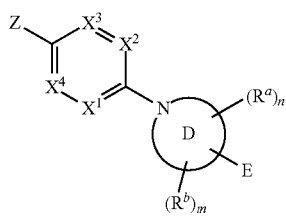

where Z is —B(OR$^x$)(OR$^y$) and R$^x$ and R$^y$ are H or (1-6C)alkyl, or R$^x$ and R$^y$ together with the atoms to which they are connected form a 5-6 membered ring optionally substituted with 1-4 substituents selected from (C1-C3 alkyl), and Ring D, E, X$^1$, X$^2$, X$^3$, X$^4$, R$^a$, R$^b$, m and n are as defined for Formula I, wherein if Ring D is substituted with an R$^b$ substituent that is R$^c$R$^d$N— wherein one or both of R$^c$ and R$^d$ is hydrogen, the nitrogen atom of R$^b$ may be protected with an amino protecting group prior to coupling, in the presence of a palladium catalyst and optionally a ligand and in the presence of a base, optionally followed by removal of the amino protecting group if present; or (b) for a compound of Formula I where A, B, X$^1$, X$^2$, X$^3$, X$^4$, Ring D, R$^a$, R$^b$, m, n, and E are as defined for Formula I with the exception that E is not hydrogen, functionalizing a corresponding compound of the formula

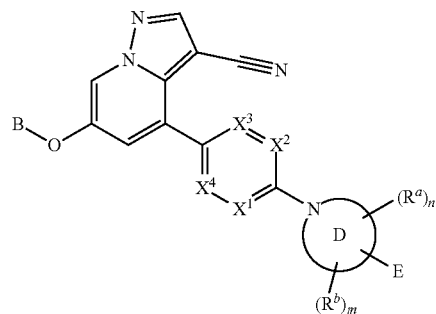

wherein Ring D, B, X$^1$, X$^2$, X$^3$, X$^4$, R$^a$, R$^b$, m and n are as defined for Formula I and E$^1$ is —NH$_2$ or OH; or (c) for a compound of Formula I where A is CN and B, X$^1$, X$^2$, X$^3$, X$^4$, Ring D, R$^a$, R$^b$, m, n, and E are as defined for Formula I, reacting a corresponding compound of the formula 14

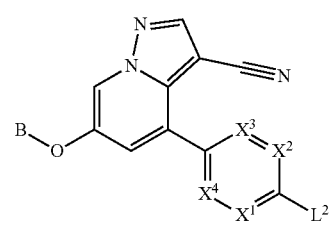

wherein Ring D, B, X$^1$, X$^2$, X$^3$, and X$^4$ are as defined for Formula I and L$^2$ is a leaving group such as a halogen or triflate, with a compound of the formula 15

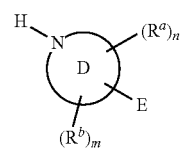

wherein Ring D, R$^a$, R$^b$, m, n, and E are as defined for Formula I and wherein if Ring D is substituted with an R$^b$ substituent that is R$^c$R$^d$N— wherein one or both of R$^c$ and R$^d$ is hydrogen, the nitrogen atom of R$^b$ may be protected with an appropriate amino protecting group prior to coupling, in the presence of a base, optionally followed by removal of the amino protecting group if present; or (d) for a compound of Formula I where E is H, A is CN, and B, $X^1$, $X^2$, $X^3$, $X^4$, and Ring D are as defined for Formula I, coupling a corresponding compound of formula 14

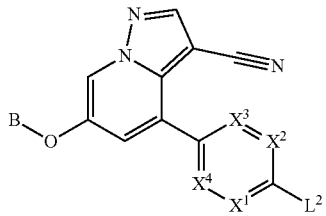

14 where $L^2$ is a leaving group and B, $X^1$, $X^2$, $X^3$, and $X^4$ are as defined for Formula I, with a compound of formula 15

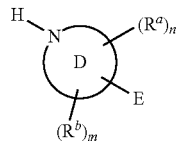

15 where Ring D, $R^a$, $R^b$, m and n are as defined for Formula I and E is hydrogen, wherein if Ring D is substituted with an $R^b$ substituent that is $R^cR^dN$— wherein one or both of $R^c$ and $R^d$ is hydrogen, the nitrogen atom of $R^b$ may be protected with an appropriate amino protecting group prior to coupling, in the presence of a base, optionally followed by removal of the amino protecting group if present; or (e) for a compound of Formula I where A is H, B is H, and $X^1$, $X^2$, $X^3$, $X^4$, Ring D and E are as defined for Formula I, treating a corresponding compound of formula 18

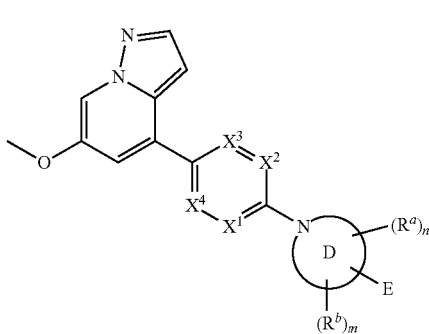

18 where A is H, B is H, and $X^1$, $X^2$, $X^3$, $X^4$, Ring D, $R^a$, $R^b$, m, n, and E are as defined for Formula I wherein if Ring D is substituted with an $R^b$ substituent that is $R^cR^dN$— wherein one or both of $R^c$ and $R^d$ is hydrogen, the nitrogen atom of $R^b$ may be protected with an amino protecting group, with aluminum trichloride to provide compound 19

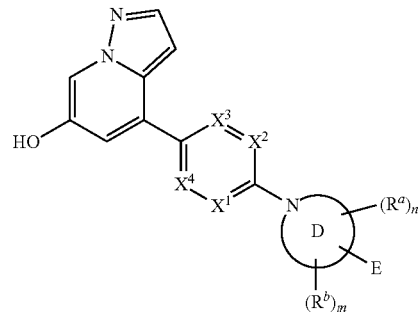

19 optionally followed by removal of the amino protecting group if present; or (f) for a compound of Formula I where A is H, and B, $X^1$, $X^2$, $X^3$, $X^4$, Ring D, $R^a$, $R^b$, m, n, and E are as defined for Formula I, (i) treating a corresponding compound of formula 18

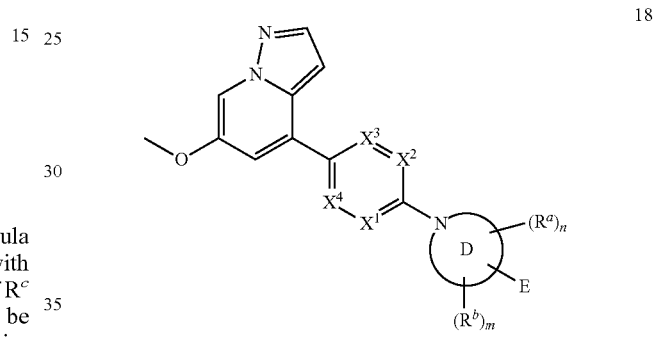

18 where A is H, and $X^1$, $X^2$, $X^3$, $X^4$, Ring D, $R^a$, $R^b$, m, n, and E are as defined for Formula I, wherein if Ring D is substituted with an $R^b$ substituent that is $R^cR^dN$— wherein one or both of $R^c$ and $R^d$ is hydrogen, the nitrogen atom of $R^b$ may be protected with an appropriate amino protecting group, with aluminum trichloride to provide compound 19

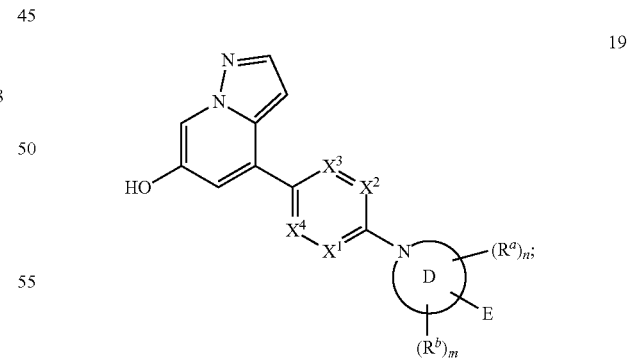

19

(ii) reacting compound 19 with C1-C6 alkyl-X optionally substituted with 1-3 fluoros, hydroxyC2-C6 alkyl-X wherein the alkyl portion is optionally substituted with a C3-C6 cycloalkylidene ring, dihydroxyC3-C6 alkyl-X wherein the alkyl portion is optionally substituted with a C3-C6 cycloalkylidene ring, (C1-C6 alkoxy)C1-C6 alkyl-X optionally substituted with 1-3 fluoros, $(R^1R^2N)$C1-C6 alkyl-X, hetAr$^1$C1-C3 alkyl-X, (C3-C6 cycloalkyl)C1-C3 alkyl-X, (hetCyc$^a$)C1-C3 alkyl-X, hetCyc$^a$-X or hetCyc$^a$C(=O)C1-C6 alkyl-X, where R$^1$, R$^2$, hetAr$^1$, and hetCyc$^a$ are as defined for Formula I and X is a leaving atom or group, optionally followed by removal of the amino protecting group if present; or (g) for a compound of Formula I where A is H or Cl, B is H, and X$^1$, X$^2$, X$^3$, X$^4$, Ring D, R$^a$, R$^b$, m, n, and E are as defined for Formula I, coupling a compound of formula

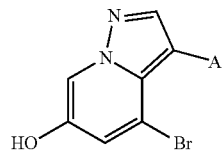

where A is H or Cl with a boronate ester having formula 10

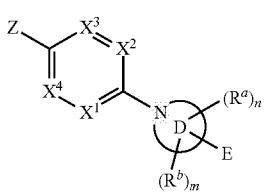

where Z is —B(OR$^x$)(OR$^y$) and R$^x$ and R$^y$ are H or (1-6C)alkyl, or R$^x$ and R$^y$ together with the atoms to which they are connected form a 5-6 membered ring optionally substituted with 1-4 substituents selected from (C1-C3 alkyl), and Ring D, E, X$^1$, X$^2$, X$^3$, X$^4$, R$^a$, R$^b$, m and n are as defined for Formula I, wherein if Ring D is substituted with an R$^b$ substituent that is R$^c$R$^d$N— wherein one or both of R$^c$ and R$^d$ is hydrogen, the nitrogen atom of R$^b$ may be protected with an amino protecting group prior to said coupling, in the presence of a palladium catalyst and optionally a ligand and in the presence of a base, optionally followed by removal of the amino protecting group if present; or (h) for a compound of Formula I where A is H or Cl, and B, X$^1$, X$^2$, X$^3$, X$^4$, Ring D, R$^a$, R$^b$, m, n, and E are as defined for Formula I, coupling a compound of the formula

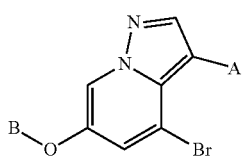

where A is H or Cl, with a corresponding boronate ester compound of formula 10

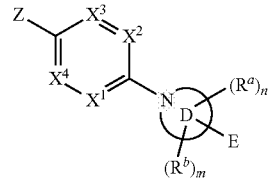

where Z is —B(OR$^x$)(OR$^y$) and R$^x$ and R$^y$ are H or (1-6C)alkyl, or R$^x$ and R$^y$ together with the atoms to which they are connected form a 5-6 membered ring optionally substituted with 1-4 substituents selected from (C1-C3 alkyl), and Ring D, E, X$^1$, X$^2$, X$^3$, X$^4$, R$^a$, R$^b$, m and n are as defined for Formula I, wherein if Ring D is substituted with an R$^b$ substituent that is R$^c$R$^d$N— wherein one or both of R$^c$ and R$^d$ is hydrogen, the nitrogen atom of R$^b$ may be protected with an amino protecting group prior to said coupling, in the presence of a palladium catalyst and optionally a ligand and in the presence of a base, and optionally followed by removal of the amino protecting group if present; or (i) for a compound of Formula I where A is H, and B, X$^1$, X$^2$, X$^3$, X$^4$, Ring D, R$^a$, R$^b$, m, n, and E are as defined for Formula I, coupling a compound of formula 24

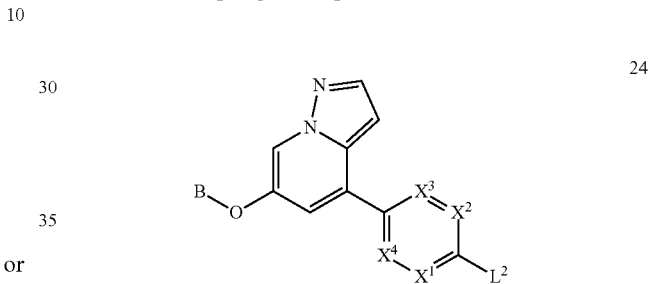

where B, X$^1$, X$^2$, X$^3$ and X$^4$, are as defined for Formula I and L$^2$ is a leaving group or atom, with a corresponding compound of formula 15

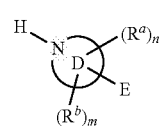

where Ring D, R$^a$, R$^b$, m, n, and E are as defined for Formula I wherein if Ring D is substituted with an R$^b$ substituent that is R$^c$R$^d$N— wherein one or both of R$^c$ and R$^d$ is hydrogen, the nitrogen atom of R$^b$ may be protected with an amino protecting group, optionally followed by removal of the amino protecting group if present; and removing any additional protecting groups if present and optionally forming a pharmaceutically acceptable salt thereof.

The term "amino protecting group" as used herein refers to a derivative of the groups commonly employed to block or protect an amino group while reactions are carried out on other functional groups on the compound. Examples of suitable protecting groups for use in any of the processes described herein include carbamates, amides, alkyl and aryl groups, imines, as well as many N-heteroatom derivatives which can be removed to regenerate the desired amine group. Non-limiting examples of amino protecting groups are acetyl, trifluoroacetyl, t-butyloxycarbonyl ("Boc"), benzyloxycarbonyl ("CBz") and 9-fluorenylmethyleneoxycarbonyl ("Fmoc"). Further examples of these groups, and other protecting groups, are found in T. W. Greene, et al., Greene's Protective Groups in Organic Synthesis. New York: Wiley Interscience, 2006.

Hydroxy groups may be protected with any convenient hydroxy protecting group, for example as described in T. W. Greene, et al., Greene's Protective Groups in Organic Synthesis. New York: Wiley Interscience, 2006. Examples include benzyl, trityl, silyl ethers, and the like.

Nitrogen atoms in compounds described in any of the above methods may be protected with any convenient nitrogen protecting group, for example as described in Greene & Wuts, eds., "Protecting Groups in Organic Synthesis", $2^{nd}$ ed. New York; John Wiley & Sons, Inc., 1991. Examples of nitrogen protecting groups include acyl and alkoxycarbonyl groups, such as t-butoxycarbonyl (BOC), phenoxycarbonyl, and [2-(trimethylsilyl)ethoxy]methyl (SEM).

The ability of test compounds to act as RET inhibitors may be demonstrated by the assay described in Example A. $IC_{50}$ values are shown in Table 5.

In some embodiments, the compounds provided herein exhibit potent and selective RET inhibition. For example, the compounds provided herein exhibit nanomolar potency against wild type RET and select RET mutants, including the KIF5B-RET fusion and V804M gatekeeper mutation, with minimal activity against related kinases.

In some embodiments, the compounds of Formula I or a pharmaceutically acceptable salt or solvate thereof, selectively target a RET kinase. For example, a compound of Formula I or a pharmaceutically acceptable salt or solvate thereof, can selectively target a RET kinase over another kinase or non-kinase target.

In some embodiments, a compound of Formula I or a pharmaceutically acceptable salt or solvate thereof, exhibits at least a 30-fold selectivity for a RET kinase over another kinase. For example, a compound of Formula I or a pharmaceutically acceptable salt or solvate thereof, exhibits at least a 40-fold selectivity; at least a 50-fold selectivity; at least a 60-fold selectivity; at least a 70-fold selectivity; at least a 80-fold selectivity; at least a 90-fold selectivity; at least 100-fold selectivity; at least 200-fold selectivity; at least 300-fold selectivity; at least 400-fold selectivity; at least 500-fold selectivity; at least 600-fold selectivity; at least 700-fold selectivity; at least 800-fold selectivity; at least 900-fold selectivity; or at least 1000-fold selectivity for a RET kinase over another kinase. In some embodiments, selectivity for a RET kinase over another kinase is measured in a cellular assay (e.g., a cellular assay as provided herein).

In some embodiments, the compounds provided herein can exhibit selectivity for a RET kinase over a KDR kinase (e.g., VEGFR2). In some embodiments, the selectivity for a RET kinase over a KDR kinase is observed without loss of gatekeeper mutant potency. In some embodiments, the selectivity over a KDR kinase is at least 10-fold (e.g., at least a 40-fold selectivity; at least a 50-fold selectivity; at least a 60-fold selectivity; at least a 70-fold selectivity; at least a 80-fold selectivity; at least a 90-fold selectivity; at least 100-fold selectivity; at least 150-fold selectivity; at least 200-fold selectivity; at least 250-fold selectivity; at least 300-fold selectivity; at least 350-fold selectivity; or at least 400-fold selectivity) as compared to the inhibition of KIF5B-RET (i.e. the compounds were more potent against KIF5B-RET than KDR). In some embodiments, the selectivity for a RET kinase over a KDR kinase is about 30-fold.

In some embodiments, the selectivity for a RET kinase over a KDR kinase is at least 100-fold. In some embodiments, the selectivity for a RET kinase over a KDR kinase is at least 150-fold. In some embodiments, the selectivity for a RET kinase over a KDR kinase is at least 400-fold. Without being bound by any theory, potent KDR kinase inhibition is believed to be a common feature among multikinase inhibitors (MKIs) that target RET and may be the source of the dose-limiting toxicities observed with such compounds.

In some embodiments, inhibition of V804M was similar to that observed for wild-type RET. For example, inhibition of V804M was within about 2-fold (e.g., about 5-fold, about 7-fold, about 10-fold) of inhibition of wild-type RET (i.e. the compounds were similarly potent against wild-type RET and V804M). In some embodiments, selectivity for a wild-type or V804M RET kinase over another kinase is measured in an enzyme assay (e.g., an enzyme assay as provided herein). In some embodiments, the compounds provided herein exhibit selective cytotoxicity to RET-mutant cells.

In some embodiments, the compounds provided herein exhibit brain and/or central nervous system (CNS) penetrance. Such compounds are capable of crossing the blood brain barrier and inhibiting a RET kinase in the brain and/or other CNS structures. In some embodiments, the compounds provided herein are capable of crossing the blood brain barrier in a therapeutically effective amount. For example, treatment of a patient with cancer (e.g., a RET-associated cancer such as a RET-associated brain or CNS cancer) can include administration (e.g., oral administration) of the compound to the patient. In some such embodiments, the compounds provided herein are useful for treating a primary brain tumor or metastatic brain tumor.

In some embodiments, the compounds of Formula I or a pharmaceutically acceptable salt or solvate thereof, exhibit one or more of high GI absorption, low clearance, and low potential for drug-drug interactions.

Compounds of Formula I are useful for treating diseases and disorders which can be treated with a RET kinase inhibitor, such as RET-associated diseases and disorders, e.g., proliferative disorders such as cancers, including hematological cancers and solid tumors, and gastrointestinal disorders such as IBS.

As used herein, terms "treat" or "treatment" refer to therapeutic or palliative measures. Beneficial or desired clinical results include, but are not limited to, alleviation, in whole or in part, of symptoms associated with a disease or disorder or condition, diminishment of the extent of disease, stabilized (i.e., not worsening) state of disease, delay or slowing of disease progression, amelioration or palliation of the disease state (e.g., one or more symptoms of the disease), and remission (whether partial or total), whether detectable or undetectable. "Treatment" can also mean prolonging survival as compared to expected survival if not receiving treatment.

As used herein, the terms "subject," "individual," or "patient," are used interchangeably, refers to any animal, including mammals such as mice, rats, other rodents, rabbits, dogs, cats, swine, cattle, sheep, horses, primates, and humans. In some embodiments, the patient is a human. In some embodiments, the subject has experienced and/or exhibited at least one symptom of the disease or disorder to be treated and/or prevented. In some embodiments, the subject has been identified or diagnosed as having a cancer with a dysregulation of a RET gene, a RET protein, or expression or activity, or level of any of the same (a RET-associated cancer) (e.g., as determined using a regulatory agency-approved, e.g., FDA-approved, assay or kit). In some embodiments, the subject has a tumor that is positive for a dysregulation of a RET gene, a RET protein, or expression or activity, or level of any of the same (e.g., as determined using a regulatory agency-approved assay or kit). The subject can be a subject with a tumor(s) that is positive for a dysregulation of a RET gene, a RET protein, or expression or activity, or level of any of the same (e.g., identified as positive using a regulatory agency-approved, e.g., FDA-approved, assay or kit). The subject can be a subject whose tumors have a dysregulation of a RET gene, a RET protein, or expression or activity, or a level of the same (e.g., where the tumor is identified as such using a regulatory agency-approved, e.g., FDA-approved, kit or assay). In some embodiments, the subject is suspected of having a RET-associated cancer. In some embodiments, the subject has a clinical record indicating that the subject has a tumor that has a dysregulation of a RET gene, a RET protein, or expression or activity, or level of any of the same (and optionally the clinical record indicates that the subject should be treated with any of the compositions provided herein). In some embodiments, the patient is a pediatric patient.

The term "pediatric patient" as used herein refers to a patient under the age of 21 years at the time of diagnosis or treatment. The term "pediatric" can be further be divided into various subpopulations including: neonates (from birth through the first month of life); infants (1 month up to two years of age); children (two years of age up to 12 years of age); and adolescents (12 years of age through 21 years of age (up to, but not including, the twenty-second birthday)). Berhman R E, Kliegman R, Arvin A M, Nelson W E. *Nelson Textbook of Pediatrics,* 15th Ed. Philadelphia: W.B. Saunders Company, 1996; Rudolph A M, et al. *Rudolph's Pediatrics,* 21st Ed. New York: McGraw-Hill, 2002; and Avery M D, First L R. *Pediatric Medicine,* 2nd Ed. Baltimore: Williams & Wilkins; 1994. In some embodiments, a pediatric patient is from birth through the first 28 days of life, from 29 days of age to less than two years of age, from two years of age to less than 12 years of age, or 12 years of age through 21 years of age (up to, but not including, the twenty-second birthday). In some embodiments, a pediatric patient is from birth through the first 28 days of life, from 29 days of age to less than 1 year of age, from one month of age to less than four months of age, from three months of age to less than seven months of age, from six months of age to less than 1 year of age, from 1 year of age to less than 2 years of age, from 2 years of age to less than 3 years of age, from 2 years of age to less than seven years of age, from 3 years of age to less than 5 years of age, from 5 years of age to less than 10 years of age, from 6 years of age to less than 13 years of age, from 10 years of age to less than 15 years of age, or from 15 years of age to less than 22 years of age.

In certain embodiments, compounds of Formula I are useful for preventing diseases and disorders as defined herein (for example, autoimmune diseases, inflammatory diseases, and cancer). The term "preventing" as used herein means the prevention of the onset, recurrence or spread, in whole or in part, of the disease or condition as described herein, or a symptom thereof.

The term "RET-associated disease or disorder" as used herein refers to diseases or disorders associated with or having a dysregulation of a RET gene, a RET kinase (also called herein RET kinase protein), or the expression or activity or level of any (e.g., one or more) of the same (e.g., any of the types of dysregulation of a RET gene, a RET kinase, a RET kinase domain, or the expression or activity or level of any of the same described herein). Non-limiting examples of a RET-associated disease or disorder include, for example, cancer and gastrointestinal disorders such as irritable bowel syndrome (IBS).

The term "RET-associated cancer" as used herein refers to cancers associated with or having a dysregulation of a RET gene, a RET kinase (also called herein RET kinase protein), or expression or activity, or level of any of the same. Non-limiting examples of a RET-associated cancer are described herein.

The phrase "dysregulation of a RET gene, a RET kinase, or the expression or activity or level of any of the same" refers to a genetic mutation (e.g., a RET gene translocation that results in the expression of a fusion protein, a deletion in a RET gene that results in the expression of a RET protein that includes a deletion of at least one amino acid as compared to the wild-type RET protein, a mutation in a RET gene that results in the expression of a RET protein with one or more point mutations, or an alternative spliced version of a RET mRNA that results in a RET protein having a deletion of at least one amino acid in the RET protein as compared to the wild-type RET protein) or a RET gene amplification that results in overexpression of a RET protein or an autocrine activity resulting from the overexpression of a RET gene in a cell that results in a pathogenic increase in the activity of a kinase domain of a RET protein (e.g., a constitutively active kinase domain of a RET protein) in a cell. As another example, a dysregulation of a RET gene, a RET protein, or expression or activity, or level of any of the same, can be a mutation in a RET gene that encodes a RET protein that is constitutively active or has increased activity as compared to a protein encoded by a RET gene that does not include the mutation. For example, a dysregulation of a RET gene, a RET protein, or expression or activity, or level of any of the same, can be the result of a gene or chromosome translocation which results in the expression of a fusion protein that contains a first portion of RET that includes a functional kinase domain, and a second portion of a partner protein (i.e., that is not RET). In some examples, dysregulation of a RET gene, a RET protein, or expression or activity or level of any of the same can be a result of a gene translocation of one RET gene with another non-RET gene. Non-limiting examples of fusion proteins are described in Table 1. Non-limiting examples of RET kinase protein point mutations/insertions/deletions are described in Table 2. Additional examples of RET kinase protein mutations (e.g., point mutations) are RET inhibitor resistance mutations. Non-limiting examples of RET inhibitor resistance mutations are described in Tables 3 and 4.

The term "wildtype" or "wild-type" describes a nucleic acid (e.g., a RET gene or a RET mRNA) or protein (e.g., a RET protein) that is found in a subject that does not have a RET-associated disease, e.g., a RET-associated cancer (and optionally also does not have an increased risk of developing a RET-associated disease and/or is not suspected of having a RET-associated disease), or is found in a cell or tissue from a subject that does not have a RET-associated disease, e.g., a RET-associated cancer (and optionally also does not have an increased risk of developing a RET-associated disease and/or is not suspected of having a RET-associated disease).

The term "regulatory agency" refers to a country's agency for the approval of the medical use of pharmaceutical agents with the country. For example, a non-limiting example of a regulatory agency is the U.S. Food and Drug Administration (FDA).

Provided herein is a method of treating cancer (e.g., a RET-associated cancer) in a patient in need of such treatment, the method comprising administering to the patient a therapeutically effective amount of a compound of Formula I or a pharmaceutically acceptable salt or solvate thereof or a pharmaceutical composition thereof. For example, provided herein are methods for treating a RET-associated cancer in a patient in need of such treatment, the method comprising a) detecting a dysregulation of a RET gene, a RET kinase, or the expression or activity or level of any of the same in a sample from the patient; and b) administering a therapeutically effective amount of a compound of Formula I or a pharmaceutically acceptable salt or solvate thereof. In some embodiments, the dysregulation of a RET gene, a RET kinase, or the expression or activity or level of any of the same includes one or more fusion proteins. Non-limiting examples of RET gene fusion proteins are described in Table 1. In some embodiments, the fusion protein is KIF5B-RET. In some embodiments, the dysregulation of a RET gene, a RET kinase, or the expression or activity or level of any of the same includes one or more RET kinase protein point mutations/insertions. Non-limiting examples of RET kinase protein point mutations/insertions/deletions are described in Table 2. In some embodiments, the RET kinase protein point mutations/insertions/deletions are selected from the group consisting of M918T, M918V, C634W, V804L, and V804M. In some embodiments, a compound of Formula I is selected from i) Example No. 1-20; ii) Example No. 21-40; iii) Example No. 41-49; iv) Example No. 50-70; v) Example No. 71-89; vi) Example No. 90-109; vii) Example No. 110-129; viii) Example No. 130-149; ix) Example No. 150-169; x) Example No. 170-189; xi) Example No. 190-209; xii) Example No. 210-229; xiii) Example No. 230-249; xiv) Example No. 250-259; xv) Example No. 270-289; xvi) Example No. 290-309; xvii) Example No. 310-329; xviii) Example No. 330-349; xix) Example No. 350-369; xx) Example No. 370-384; xxi) Example No. 385-394; xxii) Example No. 395-407; xxiii) Example No. 408-427; xxiii) Example No. 428-447; xxiv) Example No. 448-467; or xxvi) Example No. 468-488; xxvii) Example No. 489-509; xxviii) Example No. 510-530; xxvix) Example No. 531-551; xxx) Example No. 552-572; xxxi) Example No. 573-593; xxxii) Example No. 594-614; xxxiii) Example No. 615-635; xxxiv) Example No. 636-686; xxxv) Example No. 687-707; xxxvi) Example No. 708-728; xxxvii) Example No. 729-749; xxxviii) Example No. 750-770; xxxix) Example No. 771-791; xl) Example No. 792-812; xli) Example No. 813-819.

In some embodiments of any of the methods or uses described herein, the cancer (e.g., RET-associated cancer) is a hematological cancer. In some embodiments of any of the methods or uses described herein, the cancer (e.g., RET-associated cancer) is a solid tumor. In some embodiments of any of the methods or uses described herein, the cancer (e.g., RET-associated cancer) is lung cancer (e.g., small cell lung carcinoma or non-small cell lung carcinoma), papillary thyroid cancer, medullary thyroid cancer, differentiated thyroid cancer, recurrent thyroid cancer, refractory differentiated thyroid cancer, lung adenocarcinoma, bronchioles lung cell carcinoma, multiple endocrine neoplasia type 2A or 2B (MEN2A or MEN2B, respectively), pheochromocytoma, parathyroid hyperplasia, breast cancer, colorectal cancer (e.g., metastatic colorectal cancer), papillary renal cell carcinoma, ganglioneuromatosis of the gastroenteric mucosa, inflammatory myofibroblastic tumor, or cervical cancer. In some embodiments of any of the methods or uses described herein, the cancer (e.g., RET-associated cancer) is selected from the group of: acute lymphoblastic leukemia (ALL), acute myeloid leukemia (AML), cancer in adolescents, adrenocortical carcinoma, anal cancer, appendix cancer, astrocytoma, atypical teratoid/rhabdoid tumor, basal cell carcinoma, bile duct cancer, bladder cancer, bone cancer, brain stem glioma, brain tumor, breast cancer, bronchial tumor, Burkitt lymphoma, carcinoid tumor, unknown primary carcinoma, cardiac tumors, cervical cancer, childhood cancers, chordoma, chronic lymphocytic leukemia (CLL), chronic myelogenous leukemia (CML), chronic myeloproliferative neoplasms, colon cancer, colorectal cancer, craniopharyngioma, cutaneous T-cell lymphoma, bile duct cancer, ductal carcinoma in situ, embryonal tumors, endometrial cancer, ependymoma, esophageal cancer, esthesioneuroblastoma, Ewing sarcoma, extracranial germ cell tumor, extragonadal germ cell tumor, extrahepatic bile duct cancer, eye cancer, fallopian tube cancer, fibrous histiocytoma of bone, gallbladder cancer, gastric cancer, gastrointestinal carcinoid tumor, gastrointestinal stromal tumors (GIST), germ cell tumor, gestational trophoblastic disease, glioma, hairy cell tumor, hairy cell leukemia, head and neck cancer, heart cancer, hepatocellular cancer, histiocytosis, Hodgkin's lymphoma, hypopharyngeal cancer, intraocular melanoma, islet cell tumors, pancreatic neuroendocrine tumors, Kaposi sarcoma, kidney cancer, Langerhans cell histiocytosis, laryngeal cancer, leukemia, lip and oral cavity cancer, liver cancer, lung cancer, lymphoma, macroglobulinemia, malignant fibrous histiocytoma of bone, osteocarcinoma, melanoma, Merkel cell carcinoma, mesothelioma, metastatic squamous neck cancer, midline tract carcinoma, mouth cancer, multiple endocrine neoplasia syndromes, multiple myeloma, mycosis fungoides, myelodysplastic syndromes, myelodysplastic/myeloproliferative neoplasms, myelogenous leukemia, myeloid leukemia, multiple myeloma, myeloproliferative neoplasms, nasal cavity and paranasal sinus cancer, nasopharyngeal cancer, neuroblastoma, non-Hodgkin's lymphoma, non-small cell lung cancer, oral cancer, oral cavity cancer, lip cancer, oropharyngeal cancer, osteosarcoma, ovarian cancer, pancreatic cancer, papillomatosis, paraganglioma, paranasal sinus and nasal cavity cancer, parathyroid cancer, penile cancer, pharyngeal cancer, pheochromosytoma, pituitary cancer, plasma cell neoplasm, pleuropulmonary blastoma, pregnancy and breast cancer, primary central nervous system lymphoma, primary peritoneal cancer, prostate cancer, rectal cancer, renal cell cancer, retinoblastoma, rhabdomyosarcoma, salivary gland cancer, sarcoma, Sezary syndrome, skin cancer, small cell lung cancer, small intestine cancer, soft tissue sarcoma, squamous cell carcinoma, squamous neck cancer, stomach cancer, T-cell lymphoma, testicular cancer, throat cancer, thymoma and thymic carcinoma, thyroid cancer, transitional cell cancer of the renal pelvis and ureter, unknown primary carcinoma, urethral cancer, uterine cancer, uterine sarcoma, vaginal cancer, vulvar cancer, and Wilms' tumor.

In some embodiments, a hematological cancer (e.g., hematological cancers that are RET-associated cancers) is selected from the group consisting of leukemias, lymphomas (non-Hodgkin's lymphoma), Hodgkin's disease (also called Hodgkin's lymphoma), and myeloma, for instance, acute lymphocytic leukemia (ALL), acute myeloid leukemia (AML), acute promyelocytic leukemia (APL), chronic lymphocytic leukemia (CLL), chronic myeloid leukemia (CML), chronic myelomonocytic leukemia (CMML), chronic neutrophilic leukemia (CNL), acute undifferentiated leukemia (AUL), anaplastic large-cell lymphoma (ALCL), prolymphocytic leukemia (PML), juvenile myelomonocytic leukemia (JMML), adult T-cell ALL, AML with trilineage myelodysplasia (AML/TMDS), mixed lineage leukemia (MLL), myelodysplastic syndromes (MDSs), myeloproliferative disorders (MPD), and multiple myeloma (MM). Additional examples of hematological cancers include myeloproliferative disorders (MPD) such as polycythemia vera (PV), essential thrombocytopenia (ET) and idiopathic primary myelofibrosis (IMF/IPF/PMF). In one embodiment, the hematological cancer (e.g., the hematological cancer that is a RET-associated cancer) is AML or CMML.

In some embodiments, the cancer (e.g., the RET-associated cancer) is a solid tumor. Examples of solid tumors (e.g., solid tumors that are RET-associated cancers) include, for example, thyroid cancer (e.g., papillary thyroid carcinoma, medullary thyroid carcinoma), lung cancer (e.g., lung adenocarcinoma, small-cell lung carcinoma), pancreatic cancer, pancreatic ductal carcinoma, breast cancer, colon cancer, colorectal cancer, prostate cancer, renal cell carcinoma, head and neck tumors, neuroblastoma, and melanoma. See, for example, Nature Reviews Cancer, 2014, 14, 173-186.

In some embodiments, the cancer is selected from the group consisting of lung cancer, papillary thyroid cancer, medullary thyroid cancer, differentiated thyroid cancer, recurrent thyroid cancer, refractory differentiated thyroid cancer, multiple endocrine neoplasia type 2A or 2B (MEN2A or MEN2B, respectively), pheochromocytoma, parathyroid hyperplasia, breast cancer, colorectal cancer, papillary renal cell carcinoma, ganglioneuromatosis of the gastroenteric mucosa, and cervical cancer.

In some embodiments, the patient is a human.

Compounds of Formula I and pharmaceutically acceptable salts and solvates thereof are also useful for treating a RET-associated cancer.

Accordingly, also provided herein is a method for treating a patient diagnosed with or identified as having a RET-associated cancer, e.g., any of the exemplary RET-associated cancers disclosed herein, comprising administering to the patient a therapeutically effective amount of a compound of Formula I or a pharmaceutically acceptable salt or solvate thereof, or a pharmaceutical composition thereof as defined herein.

Dysregulation of a RET kinase, a RET gene, or the expression or activity or level of any (e.g., one or more) of the same can contribute to tumorigenesis. For example, a dysregulation of a RET kinase, a RET gene, or expression or activity or level of any of the same can be a translocation, overexpression, activation, amplification, or mutation of a RET kinase, a RET gene, or a RET kinase domain. Translocation can include translocations involving the RET kinase domain, mutations can include mutations involving the RET ligand-binding site, and amplification can be of a RET gene. Other dysregulations can include RET mRNA splice variants and RET autocrine/paracrine signaling, which can also contribute to tumorigenesis.

In some embodiments, the dysregulation of a RET gene, a RET kinase, or expression or activity or level of any of the same, includes overexpression of wild-type RET kinase (e.g., leading to autocrine activation). In some embodiments, the dysregulation of a RET gene, a RET kinase protein, or expression or activity or level of any of the same, includes overexpression, activation, amplification, or mutation in a chromosomal segment comprising the RET gene or a portion thereof, including, for example, the kinase domain portion, or a portion capable of exhibiting kinase activity.

In some embodiments, the dysregulation of a RET gene, a RET kinase protein, or expression or activity or level of any of the same, includes one or more chromosome translocations or inversions resulting in a RET gene fusion. In some embodiments, the dysregulation of a RET gene, a RET kinase protein, or expression or activity or level of any of the same, is a result of genetic translocations in which the expressed protein is a fusion protein containing residues from a non-RET partner protein, and includes a minimum of a functional RET kinase domain.

Non-limiting examples of RET fusion proteins are shown in Table 1.

TABLE 1

Exemplary RET Fusion Partners and Cancers

| Fusion Partner | Non-limiting Exemplary RET-Associated Cancer(s) |
| --- | --- |
| BCR | Chronic Myelomonocytic Leukemia (CMML) |
| CLIP1 | Adenocarcinoma |
| KIF5B | NSCLC, Ovarian Cancer, Spitzoid Neoplasms; Lung Adenocarcinoma[3, 4, 14, 28]; Adenosquamous Carcinomas[15] |
| CCDC6 (also called PTC1, D10S170, or H4) | NSCLC, Colon Cancer, Papillary Thyroid Cancer; Adenocarcinomas; Lung Adenocarcinoma; Metastatic Colorectal Cancer[5]; Adenosquamous Carcinomas[15], Breast Cancer[30] |
| PTC1ex9 (a novel CCDC6 rearrangement) | Metastatic papillary thyroid cancer[2] |
| NCOA4 (also called PTC3, ELE1, and RFG) | Papillary Thyroid Cancer[21], NSCLC, Colon Cancer, Salivary Gland Cancer, Metastatic Colorectal Cancer[5]; Lung Adenocarcinoma[15]; Adenosquamous Carcinomas[15] Diffuse Sclerosing Variant of Papillary Thyroid Cancer[16], Breast Cancer[30], Acinic Cell Carcinoma[32], Mammary Analog Secretory Carcinoma[33] |
| TRIM33 (also called PTC7 and RFG7) | NSCLC, Papillary Thyroid Cancer |
| ERC1 (also called ELKS) | Papillary Thyroid Cancer, Breast Cancer |
| FGFR1OP | CMML, Primary Myelofibrosis with secondary Acute Myeloid Leukemia |
| MBD1(also known as PCM1) | Papillary Thyroid Cancer |
| RAB61P2 | Papillary Thyroid Cancer |
| PRKAR1A (also called PTC2) | Papillary Thyroid Cancer |
| TRIM24 (also called PTC6) | Papillary Thyroid Cancer |
| KTN1 (also called PTC8) | Papillary Thyroid Cancer |
| GOLGA5 (also called PTC5) | Papillary Thyroid Cancer, Spitzoid Neoplasms |
| HOOK3 | Papillary Thyroid Cancer |
| KIAA1468 (also called PTC9 and RFG9) | Papillary Thyroid Cancer, Lung Adenocarcinoma[8, 12] |
| TRIM27 (also called RFP) | Papillary Thyroid Cancer |
| AKAP13 | Papillary Thyroid Cancer |
| FKBP15 | Papillary Thyroid Cancer |
| SPECC1L | Papillary Thyroid Cancer; Thyroid Gland Carcinoma |
| TBL1XR1 | Papillary Thyroid Cancer; Thyroid Gland Carcinoma |

TABLE 1-continued

Exemplary RET Fusion Partners and Cancers

| Fusion Partner | Non-limiting Exemplary RET-Associated Cancer(s) |
|---|---|
| CEP55 | Diffuse Gastric Cancer[7] |
| CUX1 | Lung Adenocarcinoma |
| ACBD5 | Papillary Thyroid Carcinoma |
| MYH13 | Medullary Thyroid Carcinoma[1] |
| Uncharacterized | Inflammatory Myofibroblastic Tumor[6] |
| PIBF1 | Bronchiolus Lung Cell Carcinoma[9] |
| KIAA1217 (also called SKT) | Papillary Thyroid Cancerm[10, 13] Lung Adenocarcinoma[14] NSCLC[14] |
| MPRIP | NSCLC[11] |
| HRH4-RET | Thyroid cancer and/or paillary thyroid carcinoma[17] |
| Ria-RET | Thyroid cancer and/or papillary thyroid carcinoma[17] |
| RFG8 | Papillary thyroid carcinoma[18] |
| FOXP4 | Lung adenocarcinoma[19] |
| MYH10 | Infantile myofibromatosis[20] |
| HTIF1 | Various[22] |
| TIF1G | Various[22] |
| H4L | Various[22] |
| PTC4 (a novel NCO4/ELE1 rearrangement) | Papillary thyroid cancer[23] |
| FRMD4A | NSCLC[24] |
| SQSTM1 | Papillary thyroid carcinoma[25] |
| AFAP1L2 | Papillary thyroid carcinoma[25] |
| AFAP1 | NSCLC[31] |
| PPFIBP2 | Papillary thyroid carcinoma[25] |
| EML4 | Papillary thyroid cancer[26] |
| PARD3 | NSCLC[27] |
| UVELD | Papillary thyroid cancer[29] |
| RASGEF1A | Breast cancer[30] |
| TEL | In vitro[34] |
| RUFY1 | Colorectal Cancer[35] |
| OLFM4 | Small-Bowel Cancer[36] |
| UEVLD | Papillary Thyroid Carcinoma[37] |
| DLG5 | Non-Anaplastic Thyroid (NAT) Cancer[38] |
| RRBP1 | Colon Cancer[39] |

[1]Grubbs et al., *J. Clin. Endocrinol. Metab.* 100: 788-793, 2015.
[2]Halkova et al., *Human Pathology* 46: 1962-1969, 2015.
[3]U.S. Pat. No. 9,297,011
[4]U.S. Pat. No. 9,216,172
[5]Le Rolle et al., *Oncotarget*. 6(30): 28929-37, 2015.
[6]Antonescu et al., *Am J Surg Pathol.* 39(7): 957-67, 2015.
[7]U.S. Patent Application Publication No. 2015/0177246.
[8]U.S. Patent Application Publication No. 2015/0057335.
[9]Japanese Patent Application Publication No. 2015/109806A.
[10]Chinese Patent Application Publication No. 105255927A.
[11]Fang, et al. *Journal of Thoracic Oncology* 11.2 (2016): S21-S22.
[12]European Patent Application Publication No. EP3037547A1.
[13]Lee et al., *Oncotarget*. DOI: 10.18632/oncotarget.9137, e-published ahead of printing, 2016.
[14]Saito et al., *Cancer Science* 107: 713-720, 2016.
[15]Pirker et al., *Transl. Lung Cancer Res.* 4(6): 797-800, 2015.
[16]Joung et al., *Histopathology* 69(1): 45-53, 2016.
[17]PCT Patent Application Publication No. WO 2016/141169.
[18]Klugbauer et al., *Cancer Res.*, 60(24): 7028-32, 2000.
[19]Bastien et al., *Journal of Molecular Diagnostics*, 18(6): 1027, Abstract Number: S120, 2016 Annual Meeting of the Association for Molecular Pathology, Charlotte, NC, 2016.
[20]Rosenzweig et al., *Pediatr Blood Cancer*, doi: 10.1002/pbc.26377, 2016.
[21]Su et al., *PLoS One*, 11(111): e0165596, 2016.
[22]U.S. Pat. No. 9,487,491.
[23]Fugazzola et al., *Oncogene*, 13(5): 1093-7, 1996.
[24]Velcheti et al., *J Thorac Oncol.*, 12(2): e15-e16. doi: 10.1016/j.jtho.2016.11.274, 2017.
[25]Iyama et al., *Thyroid*, doi: 10.1089/thy.2016.0673, 2017.
[26]Demeure et al., *World J Surg.*. 38(6): 1296-305. doi: 10.1007/s00268-014-2485-3, 2014.
[27]Sabari et al., *Oncoscience*, Advance Publications, www.impactjournals.com/oncoscience/files/papers/1/345/345.pdf, 2017.
[28]U.S. Patent Application Publication No. 2017/0014413.
[29]Lu et al., *Oncotarget*, doi: 10.18632/oncotarget.17412, [Epub ahead of print], 2017.
[30]Hirshfield et al., *Cancer Research*, (February 2017) Vol. 77, No. 4, Supp. 1. Abstract Number: P3-07-02. Meeting Info: 39th Annual CTRC-AACR San Antonio Breast Cancer Symposium. San Antonio, TX, United States. 6 Dec. 2016-10 Dec. 2016.
[31]Morgensztern et al., *Journal of Thoracic Oncology*, (January 2017) Vol. 12, No. 1, Supp. 1, pp. S717-S718, Abstract Number: P1.07-035, Meeting Info: 17th World Conference of the International Association for the Study of Lung Cancer, IASLC 2016. Vienna, Austria. 4 Dec. 2016.
[32]Dogan et al., *Laboratory Investigation*, (February 2017) Vol. 97, Supp. 1, pp. 323A. Abstract Number: 1298, Meeting Info: 106th Annual Meeting of the United States and Canadian Academy of Pathology, USCAP 2017. San Antonio, TX, United States.
[33]Dogan et al., MODERN PATHOLOGY, Vol. 30, Supp. [2], pp. 323A-323A. MA 1298, 2017.
[34]PCT Patent Application Publication No. WO 2017/146116.
[35]PCT Patent Application Publication No. WO 2017/122815.
[36]Reeser et al., *J. Mol. Diagn.*, 19(5): 682-696, doi: 10.1016/j.jmoldx.2017.05.006, 2017.
[37]Lu et al., *Oncotarget*, 8(28): 45784-45792, doi: 10.18632/oncotarget.17412, 2017.
[38]Ibrahimpasic et al., *Clin. Cancer Res.*, doi: 10.1158/1078-0432.CCR-17-1183, 2017.
[39]Kloosterman et al., *Cancer Res.*, 77(14): 3814-3822. doi: 10.1158/0008-5472.CAN-16-3563, 2017.

In some embodiments, the dysregulation of a RET gene, a RET kinase, or expression or activity or level of any of the same, includes one or more deletions (e.g., deletion of an amino acid at position 4), insertions, or point mutation(s) in a RET kinase. In some embodiments, the dysregulation of a RET gene, a RET kinase, or expression or activity or level of any of the same, includes a deletion of one or more residues from the RET kinase, resulting in constitutive activity of the RET kinase domain.

In some embodiments, the dysregulation of a RET gene, a RET kinase, or expression or activity or level of any of the same, includes at least one point mutation in a RET gene that results in the production of a RET kinase that has one or more amino acid substitutions, insertions, or deletions as compared to the wild-type RET kinase (see, for example, the point mutations listed in Table 2).

TABLE 2

Activating RET Kinase Protein Point Mutations/Insertions/Deletions
Exemplary RET Point Mutations Amino acid position 2
Amino acid position 3
Amino acid position 4
Amino acid position 5
Amino acid position 6
Amino acid position 7
Amino acid position 8
Amino acid position 11
Amino acid position 12
Amino acid position 13
Amino acid position 20
Amino acid position 32 (e.g., S32L)
Amino acid position 34 (e.g., D34S)
Amino acid position 40 (e.g., L40P)
Amino acid position 56 (e.g., L56M)[30]
Amino acid position 64 (e.g., P64L)
Amino acid position 67 (e.g., R67H)
Amino acid position 114 (e.g., R114H)
Amino acid position 136 (e.g., glutamic acid to stop codon)
Amino acid position 145 (e.g., V145G)
Amino acid position 180 (e.g., arginine to stop codon)
Amino acid position 200
Amino acid position 292 (e.g., V292M)

TABLE 2-continued

Activating RET Kinase Protein Point Mutations/Insertions/Deletions
Exemplary RET Point Mutations Amino acid position 294
Amino acid position 321 (e.g., G321R)
Amino acid position 330 (e.g., R330Q)
Amino acid position 338 (e.g., T338I)
Amino acid position 360 (e.g., R360W)
Amino acid position 373 (e.g., alanine to frameshift)
Amino acid position 393 (e.g., F393L)
Amino acid position 423 (e.g., G423R)[27]
Amino acid position 432
Amino acid position 446 (e.g., G446R)[28]
Δ Amino acid residues 505-506 (6-Base Pair In-Frame Germline Deletion in Exon 7)[3]
Amino acid position 510 (e.g., A510V)
Amino acid position 511 (e.g., E511K)
Amino acid position 513 (e.g., G513D)[7*]
Amino acid position 515 (e.g., C515S, C515W[4])
Amino acid position 525 (e.g., R525W)[7*]
Amino acid position 531 (e.g., C531R, or 9 base pair duplication[2])
Amino acid position 532 (e.g., duplication)[2]
Amino acid position 533 (e.g., G533C, G533S)
Amino acid position 550 (e.g., G550E)
Amino acid position 591 (e.g., V591I)
Amino acid position 593 (e.g., G593E)
Amino acid position 595 (e.g., E595D and E595A)[18]
Amino acid position 600 (e.g., R600Q)
Amino acid position 602 (e.g., I602V)[6]
Amino acid position 603 (e.g., K603Q, K603E[2])
Amino acid position 606 (e.g., Y606C)
Amino acid position 609 (e.g., C609Y, C609S, C609G, C609R, C609F, C609W, C690C[32])
Amino acid position 611 (e.g., C611R, C611S, C611G, C611Y, C611F, C611W)
Amino acid position 616 (e.g., E616Q)[23]
Amino acid position 618 (e.g., C618S, C618Y, C618R, C618Y, C618G, C618F, C618W)
Amino acid position 619 (e.g., F619F)
Amino acid position 620 (e.g., C620S, C620W, C620R, C620G, C620L, C620Y, C620F)
Amino acid position 623 (e.g., E623K)
Amino acid position 624 (e.g., D624N)
Amino acid position 630 (e.g., C630A, C630R, C630S, C630Y, C630F, C630W)
Amino acid position 631 (e.g., D631N, D631Y, D631A, D631G, D631V, D631E,)
Amino acid position 632 (e.g., E632K, E632G[5, 11])
Δ Amino acid residues 632-633 (6-Base Pair In-Frame Germline Deletion in Exon 11)[9]
Amino acid position 633 (e.g., 9 base pair duplication[2])
Amino acid position 634 (e.g., C634W, C634Y, C634S, C634R, C634F, C634G, C634L, C634A, or C634T, or an insertion ELCR[2], or a 12 base pair duplication[2]) (e.g., causing MTC)
Amino acid position 635 (e.g., R635G)
Amino acid position 636 (e.g., T636P[2], T636M[4])
Amino acid position 640 (e.g., A640G)
Amino acid position 641 (e.g., A641S, A641T[8])
Amino acid position 648 (e.g., V648I)
Amino acid position 649 (e.g., S649L)[28]
Amino acid position 664 (e.g., A664D)
Amino acid position 665 (e.g., H665Q)
Amino acid position 666 (e.g., K666E, K666M, K666N, K666R)
Amino acid position 675 (T675T, silent nucleotide change)[18]
Amino acid position 686 (e.g., S686N)
Amino acid position 689 (e.g., S689T)[18]
Amino acid position 691 (e.g., G691S)
Amino acid position 694 (e.g., R694Q)
Amino acid position 700 (e.g., M700L)
Amino acid position 706 (e.g., V706M, V706A)
Amino acid position 713 splice variant (e.g., E713K)[6]
Amino acid position 732 (e.g., E732K)[20]
Amino acid position 736 (e.g., G736R)[6]
Amino acid position 748 (e.g., G748C)
Amino acid position 750 (e.g., A750P)
Amino acid position 765 (e.g., S765P)
Amino acid position 766 (e.g., P766S, P766M[6])
Amino acid position 768 (e.g., E768Q, E768D)
Amino acid position 769 (e.g., L769L)
Amino acid position 770 (e.g., R770Q)
Amino acid position 771 (e.g., D771N)
Amino acid position 777 (e.g., N777S)
Amino acid position 778 (e.g., V778I)
Amino acid position 781 (e.g., Q781R)
Amino acid position 788 (e.g., I788I[32])
Amino acid position 790 (e.g., L790F)
Amino acid position 791 (e.g., Y791F, Y791N[24])
Amino acid position 802
Amino acid position 804 (e.g., V804L[15, 16], V804M[15, 16], V804E[12]) (e.g., causing MTC)
Amino acid position 805 (e.g., E805K)
Amino acid position 804/805 (e.g., V804M/E805K)[17]
Amino acid position 806 (e.g., Y806F, Y806S[12], Y806G, Y806C[2, 12, 14], Y806E[14], Y806H[12], Y806N[12], Y806Y[32])
Amino acid position 810 (e.g., G810R[12], G810S[12], G810A[13])
Amino acid position 818 (e.g., E818K)
Amino acid position 819 (e.g., S819I)
Amino acid position 823 (e.g., G823E)
Amino acid position 826 (e.g., Y826M, Y826S)[10]
Amino acid position 833 (e.g., R833C)
Amino acid position 836 (e.g., S836S)[19]
Amino acid position 841 (e.g., P841L, P841P)
Amino acid position 843 (e.g., E843D)
Amino acid position 844 (e.g., R844W, R844Q, R844L)
Amino acid position 848 (e.g., M848T)
Amino acid position 852 (e.g., I852M)
Amino acid position 865 (e.g., L865V)[12]
Amino acid position 870 (e.g., L870F)[12]
Amino acid position 873 (e.g., R873W)
Amino acid position 876 (e.g., A876V)
Amino acid position 881 (e.g., L881V)
Amino acid position 882
Amino acid position 883 (e.g., A883F, A883S, A883T)
Amino acid position 884 (e.g., E884K)
Amino acid position 886 (e.g., R886W)
Amino acid position 891 (e.g., S891A, S891S[32])
Amino acid position 897 (e.g., R897Q)
Amino acid position 898 (e.g., D898V)
Amino acid position 900 (e.g., Y900F)[22]
Amino acid position 901 (e.g., E901K)
Amino acid position 904 (e.g., S904F, S904S, S904C[2])
Amino acid position 905 (e.g., Y905F)[22]
Amino acid position 907 (e.g., K907E, K907M)
Amino acid position 908 (e.g., R908K)
Amino acid position 911 (e.g., G911D)
Amino acid position 912 (e.g., R912P, R912Q)
Amino acid position 918 (e.g., M918T[2], M918V, M918L[6]) (e.g., causing MTC)
Amino acid position 919 (e.g., A919V)
Amino acid position 921 (e.g., E921K)
Amino acid position 922 (e.g., S922P, S922Y)
Amino acid position 930 (e.g., T930M)
Amino acid position 961 (e.g., F961L)
Amino acid position 972 (e.g., R972G)
Amino acid position 981 (e.g., Y981F)[22]
Amino acid position 982 (e.g., R982C)
Amino acid position 1009 (e.g., M1009V)
Amino acid position 1015 (e.g., Y1015F)[22]
Amino acid position 1017 (e.g., D1017N)
Amino acid position 1041 (e.g., V1041G)
Amino acid position 1064 (e.g., M1064T)
Amino acid position 1096 (e.g., Y1096F)[21]
RET + 3[1]
(In-Frame Deletion in Exons 6 and 11)[25]
(3bp In-Frame Deletion in Exon 15)[26]
Nucleotide position 2136 + 2 (e.g., 2136 + 2T > G)[29]
(del632-636 ins6)[31]

TABLE 2-continued

Activating RET Kinase Protein Point Mutations/Insertions/Deletions
Exemplary RET Point Mutations Amino acid positions 791 and 852 (e.g., Y791F + I852M)[31]
Amino acid positions 634 and 852 (e.g., C634R + I852M)[31]

[1] U.S. Patent Application Publication No. 2014/0272951.
[2] Krampitz et al., Cancer 120: 1920-1931, 2014.
[3] Latteyer, et al., J. Clin. Endocrinol. Metab. 101(3): 1016-22, 2016.
[4] Silva, et al. Endocrine 49.2: 366-372, 2015.
[5] Scollo, et al., Endocr. J. 63(1): 87-91, 2016.
[6] Jovanovic, et al., Prilozi 36(1): 93-107, 2015.
[7] Qi, et al., Oncotarget. 6(32): 33993-4003, 2015. * R525W and G513D appear to act in combination with S891A to enchance oncogenic activity.
[8] Kim, et al. ACTA ENDOCRINOLOGICA-BUCHAREST 11.2, 189-194, 2015.
[9] Cecchirini, et al. Oncogene, 14, 2609-2612, 1997.
[10] Karrasch, et al. Eur. Thyroid J., 5(1): 73-7, 2016.
[11] Scollo et al., Endocr. J. 63: 87-91, 2016.
[12] PCT Patent Application Publication No. WO 2016/127074.
[13] Huang et al., Mol. Cancer Ther., 2016 Aug. 5. pii: molcanther.0258.2016. [Epub ahead of print].
[14] Carlomagno, et al., Endocr. Rel. Cancer 16(1): 233-41, 2009.
[15] Yoon et al., J. Med. Chem. 59(1): 358-73, 2016.
[16] U.S. Pat. No. 8,629,135.
[17] Cranston, et al., Cancer Res. 66(20): 10179-87, 2006.
[18] Kheiroddin et al., Clin. Lab. 62(5): 871-6, 2016.
[19] Ceolin et al., PLoS One. 11(2): e0147840, doi: 10.1371/journal.pone.0147840, 2016.
[20] Nadezda et al., Summer Undergraduate Research Programs (SURP) Student Abstracts, University of Oklahoma Health Sciences Center, 2016.
[21] Liu et al., J. Biol. Chem., 271(10): 5309-12, 1995.
[22] Kato et al., Cancer Res., 62: 2414-22, 2002.
[23] Grey et al., Endocrine Pathology, doi: 10.1007/s12022-016-9451-6, 2016.
[24] De Almeida et al., Endocrine Reviews, 2016, Vol. 37, No. 2, Supp. Supplement 1. Abstract Number: SUN-068; 98th Annual Meeting and Expo of the Endocrine Society, ENDO 2016. Boston, MA, US. 1 Apr. 2016-4 Apr. 2016.
[25] Vanden et al., Annals of Oncology, 2016, Vol. 27, Supp. Supplement 6. Abstract Number: 427PD; 41st European Society for Medical Oncology Congress, ESMP 2016. Copenhagen, Denmark. 7 Oct. 2016-11 Oct. 2016.
[26] Romei et al., European Thyroid Journal (August 2016) Vol. 5, Supp. Supplement 1, pp. 75; 39th Annual Meeting of the European Thyroid Association, ETA 2016. Copenhagen, Denmark. 3 Sep. 2016-6 Sep. 2016.
[27] Lee et al., Oncotarget, 8(4): 6579-6588, doi: 10.18632/oncotarget.14172, 2017.
[28] Zhang et al., Laboratory Investigation, (February 2017) Vol. 97, Supp. 1, pp. 209A. Abstract Number: 840, Meeting Info: 106th Annual Meeting of the United States and Canadian Academy of Pathology, USCAP 2017. San Antonio, TX, United States.
[29] Borecka et al., European Journal of Cancer, (July 2016) Vol. 61, No. 1, pp. S26, Abstract Number: 162, Meeting Info: 24th Biennial Congress of the European Association for Cancer Research, EACR 2016. Manchester, United Kingdom.
[30] Corsello et al., Endocrine Reviews, (JUN 2014) Vol. 35, No. 3, Suppl. S, pp. SUN-0322, Meeting Info.: 96th Annual Meeting and Expo of the Endocrine-Society, Chicago, IL, USA, Jun. 21-24, 2014.
[31] Gazizova et al., Endocrine Reviews, (JUN 2014) Vol. 35, No. 3, Suppl. S, pp. SAT-0304, Meeting Info.: 96th Annual Meeting and Expo of the Endocrine-Society, Chicago, IL, USA, Jun. 21-24, 2014.
[32] Sromek et al., Endocr Pathol., doi: 10.1007/s12022-017-9487-2, 2017.

In some embodiments, the dysregulation of a RET gene, a RET kinase, or expression or activity or level of any of the same, includes at least one point mutation in a RET gene that results in the production of a RET kinase that has one or more amino acid substitutions, insertions, or deletions as compared to the wild-type RET kinase (see, for example, the point mutations listed in Table 2a).

Exemplary Activating RET Kinase Protein Point Mutations/Insertions/Deletions

Exemplary RET Point Mutations

Amino acid position 20
Amino acid position 32 (e.g., S32L)
Amino acid position 34 (e.g., D34S)
Amino acid position 40 (e.g., L40P)
Amino acid position 64 (e.g., P64L)
Amino acid position 67 (e.g., R67H)
Amino acid position 114 (e.g., R114H)
Amino acid position 145 (e.g., V145G)
Amino acid position 200
Amino acid position 292 (e.g., V292M)
Amino acid position 294
Amino acid position 321 (e.g., G321R)
Amino acid position 330 (e.g., R330Q)

Exemplary RET Point Mutations

Amino acid position 338 (e.g., T338I)
Amino acid position 360 (e.g., R360W)
Amino acid position 393 (e.g., F393L)
Amino acid position 432
Δ Amino acid residues 505-506 (6-Base Pair In-Frame Germline Deletion in Exon 7)
Amino acid position 510 (e.g., A510V)
Amino acid position 511 (e.g., E511K)
Amino acid position 513 (e.g., G513D)
Amino acid position 515 (e.g., C515S, C515W[4])
Amino acid position 525 (e.g., R525W)
Amino acid position 531 (e.g., C531R, or 9 base pair duplication)
Amino acid position 532 (e.g., duplication)
Amino acid position 533 (e.g., G533C, G533S)
Amino acid position 550 (e.g., G550E)
Amino acid position 591 (e.g., V591I)
Amino acid position 593 (e.g., G593E)
Amino acid position 595 (e.g., E595D and E595A)
Amino acid position 600 (e.g., R600Q)
Amino acid position 602 (e.g., I602V)
Amino acid position 603 (e.g., K603Q, K603E)
Amino acid position 606 (e.g., Y606C)
Amino acid position 609 (e.g., C609Y, C609S, C609G, C609R, C609F, C609W)
Amino acid position 611 (e.g., C611R, C611S, C611G, C611Y, C611F, C611W)
Amino acid position 616 (e.g., E616Q)
Amino acid position 618 (e.g., C618S, C618Y, C618R, C618G, C618F, C618W)
Amino acid position 620 (e.g., C620S, C620W, C620R, C620G, C620L, C620Y, C620F)
Amino acid position 623 (e.g., E623K)
Amino acid position 624 (e.g., D624N)
Amino acid position 630 (e.g., C630A, C630R, C630S, C630Y, C630F, C630W)
Amino acid position 631 (e.g., D631N, D631Y, D631A, D631G, D631V, D631E,)
Amino acid position 632 (e.g., E632K, E632G)
Δ Amino acid residues 632-633 (6-Base Pair In-Frame Germline Deletion in Exon 11)
Amino acid position 633 (e.g., 9 base pair duplication)
Amino acid position 634 (e.g., C634W, C634Y, C634S, C634R, C634F, C634G, C634L, C634A, or C634T, or an insertion ELCR, or a 12 base pair duplication) (e.g., causing MTC)
Amino acid position 635 (e.g., R635G)
Amino acid position 636 (e.g., T636P, T636M)
Amino acid position 640 (e.g., A640G)
Amino acid position 641 (e.g., A641S, A641T)
Amino acid position 648 (e.g., V648I)
Amino acid position 649 (e.g., S649L)
Amino acid position 664 (e.g., A664D)
Amino acid position 665 (e.g., H665Q)
Amino acid position 666 (e.g., K666E, K666M, K666N, K666R)
Amino acid position 686 (e.g., S686N)
Amino acid position 689 (e.g., S689T)
Amino acid position 691 (e.g., G691S)
Amino acid position 694 (e.g., R694Q)
Amino acid position 700 (e.g., M700L)
Amino acid position 706 (e.g., V706M, V706A)
Amino acid position 713 splice variant (e.g., E713K)
Amino acid position 732 (e.g., E732K)
Amino acid position 736 (e.g., G736R)
Amino acid position 748 (e.g., G748C)
Amino acid position 750 (e.g., A750P)
Amino acid position 765 (e.g., S765P)
Amino acid position 766 (e.g., P766S, P766M)
Amino acid position 768 (e.g., E768Q, E768D)
Amino acid position 769 (e.g., L769L)
Amino acid position 770 (e.g., R770Q)
Amino acid position 771 (e.g., D771N)
Amino acid position 777 (e.g., N777S)
Amino acid position 778 (e.g., V778I)
Amino acid position 781 (e.g., Q781R)
Amino acid position 790 (e.g., L790F)

| Exemplary RET Point Mutations |
|---|
| Amino acid position 791 (e.g., Y791F, Y791N) |
| Amino acid position 802 |
| Amino acid position 804 (e.g., V804L, V804M, V804E) (e.g., causing MTC) |
| Amino acid position 805 (e.g., E805K) |
| Amino acid position 804/805 (e.g., V804M/E805K) |
| Amino acid position 806 (e.g., Y806F, Y806S, Y806G, Y806C, Y806E, Y806H, Y806N) |
| Amino acid position 810 (e.g., G810R, G810S, G810A) |
| Amino acid position 818 (e.g., E818K) |
| Amino acid position 819 (e.g., S819I) |
| Amino acid position 823 (e.g., G823E) |
| Amino acid position 826 (e.g., Y826M, Y826S) |
| Amino acid position 833 (e.g., R833C) |
| Amino acid position 836 (e.g., S836S) |
| Amino acid position 841 (e.g., P841L, P841P) |
| Amino acid position 843 (e.g., E843D) |
| Amino acid position 844 (e.g., R844W, R844Q, R844L) |
| Amino acid position 848 (e.g., M848T) |
| Amino acid position 852 (e.g., I852M) |
| Amino acid position 865 (e.g., L865V) |
| Amino acid position 870 (e.g., L870F) |
| Amino acid position 873 (e.g., R873W) |
| Amino acid position 876 (e.g., A876V) |
| Amino acid position 881 (e.g., L881V) |
| Amino acid position 882 |
| Amino acid position 883 (e.g., A883F, A883S, A883T) |
| Amino acid position 884 (e.g., E884K) |
| Amino acid position 886 (e.g., R886W) |
| Amino acid position 891 (e.g., S891A) |
| Amino acid position 897 (e.g., R897Q) |
| Amino acid position 898 (e.g., D898V) |
| Amino acid position 900 (e.g., Y900F) |
| Amino acid position 901 (e.g., E901K) |
| Amino acid position 904 (e.g., S904F, S904S, S904C) |
| Amino acid position 907 (e.g., K907E, K907M) |
| Amino acid position 908 (e.g., R908K) |
| Amino acid position 911 (e.g., G911D) |
| Amino acid position 912 (e.g., R912P, R912Q) |
| Amino acid position 918 (e.g., M918T, M918V, M918L) (e.g., causing MTC) |
| Amino acid position 919 (e.g., A919V) |
| Amino acid position 921 (e.g., E921K) |
| Amino acid position 922 (e.g., S922P, S922Y) |
| Amino acid position 930 (e.g., T930M) |
| Amino acid position 961 (e.g., F961L) |
| Amino acid position 972 (e.g., R972G) |
| Amino acid position 982 (e.g., R982C) |
| Amino acid position 1009 (e.g., M1009V) |
| Amino acid position 1015 (e.g., Y1015F) |
| Amino acid position 1017 (e.g., D1017N) |
| Amino acid position 1041 (e.g., V1041G) |
| Amino acid position 1064 (e.g., M1064T) |
| Amino acid position 1096 (e.g., Y1096F) |
| RET + 3 |
| (In-Frame Deletion in Exons 6 and 11) |
| (3bp In-Frame Deletion in Exon 15) |

In some embodiments, the dysregulation of a RET gene, a RET kinase, or expression or activity or level of any of the same, includes a splice variation in a RET mRNA which results in an expressed protein that is an alternatively spliced variant of RET having at least one residue deleted (as compared to the wild-type RET kinase) resulting in a constitutive activity of a RET kinase domain.

A "RET kinase inhibitor" as defined herein includes any compound exhibiting RET inhibition activity. In some embodiments, a RET kinase inhibitor is selective for a RET kinase. Exemplary RET kinase inhibitors can exhibit inhibition activity ($IC_{50}$) against a RET kinase of less than about 1000 nM, less than about 500 nM, less than about 200 nM, less than about 100 nM, less than about 50 nM, less than about 25 nM, less than about 10 nM, or less than about 1 nM as measured in an assay as described herein. In some embodiments, a RET kinase inhibitor can exhibit inhibition activity ($IC_{50}$) against a RET kinase of less than about 25 nM, less than about 10 nM, less than about 5 nM, or less than about 1 nM as measured in an assay as provided herein.

As used herein, a "first RET kinase inhibitor" or "first RET inhibitor" is a RET kinase inhibitor as defined herein, but which does not include a compound of Formula I or a pharmaceutically acceptable salt or solvate thereof as defined herein. As used herein, a "second RET kinase inhibitor" or a "second RET inhibitor" is a RET kinase inhibitor as defined herein, but which does not include a compound of Formula I or a pharmaceutically acceptable salt or solvate thereof as defined herein. When both a first and a second RET inhibitor are present in a method provided herein, the first and second RET kinase inhibitor are different.

In some embodiments, the dysregulation of a RET gene, a RET kinase, or expression or activity or level of any of the same, includes at least one point mutation in a RET gene that results in the production of a RET kinase that has one or more amino acid substitutions or insertions or deletions in a RET gene that results in the production of a RET kinase that has one or more amino acids inserted or removed, as compared to the wild-type RET kinase. In some cases, the resulting RET kinase is more resistant to inhibition of its phosphotransferase activity by one or more first RET kinase inhibitor(s), as compared to a wildtype RET kinase or a RET kinase not including the same mutation. Such mutations, optionally, do not decrease the sensitivity of the cancer cell or tumor having the RET kinase to treatment with a compound of Formula I or a pharmaceutically acceptable salt or solvate thereof (e.g., as compared to a cancer cell or a tumor that does not include the particular RET inhibitor resistance mutation). In such embodiments, a RET inhibitor resistance mutation can result in a RET kinase that has one or more of an increased $V_{max}$, a decreased $K_m$ for ATP, and an increased $K_D$ for a first RET kinase inhibitor, when in the presence of a first RET kinase inhibitor, as compared to a wildtype RET kinase or a RET kinase not having the same mutation in the presence of the same first RET kinase inhibitor.

In other embodiments, the dysregulation of a RET gene, a RET kinase, or expression or activity or level of any of the same, includes at least one point mutation in a RET gene that results in the production of a RET kinase that has one or more amino acid substitutions as compared to the wild-type RET kinase, and which has increased resistance to a compound of Formula I or a pharmaceutically acceptable salt or solvate thereof, as compared to a wildtype RET kinase or a RET kinase not including the same mutation. In such embodiments, a RET inhibitor resistance mutation can result in a RET kinase that has one or more of an increased $V_{max}$, a decreased $K_m$, and a decreased $K_D$ in the presence of a compound of Formula I or a pharmaceutically acceptable salt or solvate thereof, as compared to a wildtype RET kinase or a RET kinase not having the same mutation in the presence of the same compound of Formula I or a pharmaceutically acceptable salt or solvate thereof.

Examples of RET inhibitor resistance mutations can, e.g., include point mutations, insertions, or deletions in and near the ATP binding site in the tertiary structure of RET kinase, including but not limited to the gatekeeper residue, P-loop residues, residues in or near the DFG motif, and ATP cleft solvent front amino acid residues. Additional examples of these types of mutations include changes in residues that may affect enzyme activity and/or drug binding including but are not limited to residues in the activation loop, residues near or interacting with the activation loop, residues contributing to active or inactive enzyme conformations, changes including mutations, deletions, and insertions in the loop proceeding the C-helix and in the C-helix. Specific residues or residue regions that may be changed (and are RET inhibitor resistance mutations) include but are not limited to those listed in Table 3 based on the human wildtype RET protein sequence (e.g., SEQ ID NO: 1). Additional examples of RET inhibitor resistance mutation positions are shown in Table 4. Changes to these residues may include single or multiple amino acid changes, insertions within or flanking the sequences, and deletions within or flanking the sequences.

Exemplary Sequence of Mature Human RET Protein (SEQ ID NO: 1)

```
MAKATSGAAG LRLLLLLLLP LLGKVALGLY FSRDAYWEKL
YVDQAAGTPL LYVHALRDAP EEVPSFRLGQ HLYGTYRTRL
HENNWICIQE DTGLLYLNRS LDHSSWEKLS VRNRGFPLLT
VYLKVFLSPT SLREGECQWP GCARVYFSFF NTSFPACSSL
KPRELCFPET RPSFRIRENR PPGTFHQFRL LPVQFLCPNI
SVAYRLLEGE GLPFRCAPDS LEVSTRWALD REQREKYELV
AVCTVHAGAR EEVVMVPFPV TVYDEDDSAP TFPAGVDTAS
AVVEFKRKED TVVATLRVFD ADVVPASGEL VRRYTSTLLP
GDTWAQQTFR VEHWPNETSV QANGSFVRAT VHDYRLVLNR
NLSISENRTM QLAVLVNDSD FQGPGAGVLL LHFNVSVLPV
SLHLPSTYSL SVSRRARRFA QIGKVCVENC QAFSGINVQY
KLHSSGANCS TLGVVTSAED TSGILFVNDT KALRRPKCAE
LHYMVVATDQ QTSRQAQAQL LVTVEGSYVA EEAGCPLSCA
VSKRRLECEE CGGLGSPTGR CEWRQGDGKG ITRNFSTCSP
STKTCPDGHC DVVETQDINI CPQDCLRGSI VGGHEPGEPR
GIKAGYGTCN CFPEEEKCFC EPEDIQDPLC DELCRTVIAA
AVLFSFIVSV LLSAFCIHCY HKFAHKPPIS SAEMTFRRPA
QAFPVSYSSS GARRPSLDSM ENQVSVDAFK ILEDPKWEFP
RKNLVLGKTL GEGEFGKVVK ATAFHLKGRA GYTTVAVKML
KENASPSELR DLLSEFNVLK QVNHPHVIKL YGACSQDGPL
LLIVEYAKYG SLRGFLRESR KVGPGYLGSG GSRNSSSLDH
PDERALTMGD LISFAWQISQ GMQYLAEMKL VHRDLAARNI
LVAEGRKMKI SDFGLSRDVY EEDSYVKRSQ GRIPVKWMAI
ESLFDHIYTT QSDVWSFGVL LWEIVTLGGN PYPGIPPERL
FNLLKTGHRM ERPDNCSEEM YRLMLQCWKQ EPDKRPVFAD
ISKDLEKMMV KRRDYLDLAA STPSDSLIYD DGLSEEETPL
VDCNNAPLPR ALPSTWIENK LYGMSDPNWP GESPVPLTRA
DGTNTGFPRY PNDSVYANWM LSPSAAKLMD TFDS
```

In some embodiments, compounds of Formula I and pharmaceutically acceptable salts and solvates are useful in treating patients that develop cancers with RET inhibitor resistance mutations (e.g., that result in an increased resistance to a first RET inhibitor, e.g., a substitution at amino acid position 804, e.g., V804M, V804L, or V804E, and/or one or more RET inhibitor resistance mutations listed in Tables 3 and 4) by either dosing in combination or as a follow-up therapy to existing drug treatments (e.g., other RET kinase inhibitors; e.g., first and/or second RET kinase inhibitors). Exemplary first and second RET kinase inhibitors are described herein. In some embodiments, a first or second RET kinase inhibitor can be selected from the group consisting of cabozantinib, vandetanib, alectinib, sorafenib, lenvatinib, ponatinib, dovitinib, sunitinib, foretinib, BLU667, and BLU6864.

In some embodiments, compounds of Formula I or pharmaceutically acceptable salts and solvates thereof are useful for treating a cancer that has been identified as having one or more RET inhibitor resistance mutations (that result in an increased resistance to a first or second RET inhibitor, e.g., a substitution at amino acid position 804, e.g., V804M, V804L, or V804E). Non-limiting examples of RET inhibitor resistance mutations are listed in Tables 3 and 4.

TABLE 3

RET Inhibitor Resistance Mutations
Exemplary RET Resistance Mutations

Amino acid position 732 (e.g., E732K)[7]
Amino acid position 788 (e.g., I788N)[8]
Amino acid position 804 (e.g., V804M[1,2], V804L[1,2], V804E[6])
Amino acid position 804/805 (e.g., V804M/E805K)[3]
Amino acid position 806 (e.g., Y806C[4,6], Y806E[4], Y806S[6], Y806H[6], Y806N[6])
Amino acid position 810 (e.g., G810A[5], G810R[6], G810S[6])
Amino acid position 865 (e.g., L865V[6])
Amino acid position 870 (e.g., L870F[6])

[1]Yoon et al., *J. Med. Chem.* 59(1): 358-73, 2016.
[2]U.S. Pat. No. 8,629,135.
[3]Cranston, et al., *Cancer Res.* 66(20): 10179-87, 2006.
[4]Carlomagno, et al., *Endocr. Rel. Cancer* 16(1): 233-41, 2009.
[5]Huang et al., Mol. Cancer Ther., 2016 Aug. 5. pii: molcanther.0258.2016. [Epub ahead of print].
[6]PCT Patent Application Publication No. WO 2016/127074.
[7]Nadezda et al., Summer Undergraduate Research Programs (SURP) Student Abstracts, University of Oklahoma Health Sciences Center, 2016.
[8]Plenker et al., *Sci. Transl. Med.*, 9(394), doi: 10.1126/scitranslmed.aah6144, 2017.

TABLE 4

Additional Exemplary Amino Acid Positions of RET Inhibitor Resistance Mutations

| RET Amino Acid and Position | Exemplary Mutation | Mechanistic Resistance Rationale |
|---|---|---|
| L730 | P | Steric hindrance and/or active conformational effect |
| G731 | V | Steric hindrance and/or active conformational effect |
| E732 | K | Steric hindrance and/or active conformational effect |
| G733 | V | Steric hindrance and/or active conformational effect |
| E734 | K | Steric hindrance and/or active conformational effect |
| L760 | M | Active conformational effect |
| K761 | E | Active conformational effect |
| E762 | K | Active conformational effect |
| N763 | D | Active conformational effect |
| A764 | V | Active conformational effect |
| S765 | N | Active conformational effect |
| P766 | A | Active conformational effect |
| S767 | C | Active conformational effect |
| E768 | K | Active conformational effect |
| L779 | M | Steric hindrance and/or active conformational effect |

TABLE 4-continued

Additional Exemplary Amino Acid Positions of RET Inhibitor Resistance Mutations

| RET Amino Acid and Position | Exemplary Mutation | Mechanistic Resistance Rationale |
| --- | --- | --- |
| I788 | M | Steric hindrance and/or active conformational effect |
| M868 | R | Steric hindrance and/or active conformational effect |
| K869 | E | Steric hindrance and/or active conformational effect |
| L870 | Q | Steric hindrance and/or active conformational effect |
| V871 | M | Steric hindrance and/or active conformational effect |
| H872 | R | Steric hindrance and/or active conformational effect |
| R873 | P | Steric hindrance and/or active conformational effect |
| D874 | Y | Steric hindrance and/or active conformational effect |
| L881 | R | Steric hindrance and/or active conformational effect |
| L895 | M | Active conformational effect |
| S896 | N | Active conformational effect |
| R897 | C | Active conformational effect |
| D898 | Y | Active conformational effect |
| V899 | G | Active conformational effect |
| Y900 | D | Active conformational effect |
| E901 | K | Active conformational effect |
| E902 | K | Active conformational effect |
| D903 | Y | Active conformational effect |
| S904 | C | Active conformational effect |
| Y905 | D | Active conformational effect |
| V906 | M | Active conformational effect |
| K907 | E | Active conformational effect |
| R908 | P | Active conformational effect |
| S909 | C | Active conformational effect |
| Q910 | R | Active conformational effect |
| G911 | C | Active conformational effect |
| R912 | P | Active conformational effect |

The oncogenic role of RET was firstly described in papillary thyroid carcinoma (PTC) (Grieco et al., Cell, 1990, 60, 557-63), which arises from follicular thyroid cells and is the most common thyroid malignancy. Approximately 20-30% of PTC harbor somatic chromosomal rearrangements (translocations or inversions) linking the promoter and the 5' portions of constitutively expressed, unrelated genes to the RET tyrosine kinase domain (Greco et al., Q. J Nucl. Med. Mol. Imaging, 2009, 53, 440-54), therefore driving its ectopic expression in thyroid cells. To date, a variety of fusion partners have been identified, all providing a protein/protein interaction domain that induces ligand-independent RET dimerization and constitutive kinase activity (see, e.g., Table 1). The role of RET-PTC rearrangements in the pathogenesis of PTC has been confirmed in transgenic mice (Santoro et al., Oncogene, 1996, 12, 1821-6). Recently, a 10.6 Mb pericentric inversion in chromosome 10, where RET gene maps, has been identified in about 2% of lung adenocarcinoma patients, generating different variants of the chimeric gene KIF5B-RET (Ju et al., Genome Res., 2012, 22, 436-45; Kohno et al., 2012, Nature Med., 18, 375-7; Takeuchi et al., Nature Med., 2012, 18, 378-81; Lipson et al., 2012, Nature Med., 18, 382-4). The fusion transcripts are highly expressed and all the resulting chimeric proteins contain the N-terminal portion of the coiled-coil region of KIF5B, which mediates homodimerization, and the entire RET kinase domain. None of RET positive patients harbor other known oncogenic alterations (such as EGFR or K-Ras mutation, ALK translocation), supporting the possibility that KIF5B-RET fusion could be a driver mutation of lung adenocarcinoma. The oncogenic potential of KIF5B-RET has been confirmed by transfecting the fusion gene into cultured cell lines: similarly to what has been observed with RET-PTC fusion proteins, KIF5B-RET is constitutively phosphorylated and induces NIH-3T3 transformation and IL-3 independent growth of BA-F3 cells. However, other RET fusion proteins have been identified in lung adenocarcinoma patients, such as the CCDC6-RET fusion protein, which has been found to play a key role in the proliferation of the human lung adenocarcinoma cell line LC-2/ad (Journal of Thoracic Oncology, 2012, 7(12):1872-1876). RET inhibitors have been shown to be useful in treating lung cancers involving RET rearrangements (Drilon, A. E. et al. J Clin Oncol 33, 2015 (suppl; abstr 8007)). RET fusion proteins have also been identified in patients having colorectal cancer (Song Eun-Kee, et al. International Journal of Cancer, 2015, 136: 1967-1975).

Besides rearrangements of the RET sequence, gain of function point mutations of RET proto-oncogene are also driving oncogenic events, as shown in medullary thyroid carcinoma (MTC), which arises from parafollicular calcitonin-producing cells (de Groot, et al., Endocrine Rev., 2006, 27, 535-60; Wells and Santoro, Clin. Cancer Res., 2009, 15, 7119-7122). Around 25% of MTC are associated with multiple endocrine neoplasia type 2 (MEN2), a group of inherited cancer syndromes affecting neuroendocrine organs caused by germline activating point mutations of RET. In MEN2 subtypes (MEN2A, MEN2B and Familial MTC/FMTC) RET gene mutations have a strong phenotype-genotype correlation defining different MTC aggressiveness and clinical manifestations of the disease. In MEN2A syndrome mutations involve one of the six cysteine residues (mainly C634) located in the cysteine-rich extracellular region, leading to ligand-independent homodimerization and constitutive RET activation. Patients develop MTC at a young age (onset at 5-25 years) and may also develop pheochromocytoma (50%) and hyperparathyroidism. MEN2B is mainly caused by M918T mutation, which is located in the kinase domain. This mutation constitutively activates RET in its monomeric state and alters substrate recognition by the kinase. MEN2B syndrome is characterized by an early onset (<1 year) and very aggressive form of MTC, pheochromocytoma (50% of patients) and ganglioneuromas. In FMTC the only disease manifestation is MTC, usually occurring at an adult age. Many different mutations have been detected, spanning the entire RET gene. The remaining 75% of MTC cases are sporadic and about 50% of them harbor RET somatic mutations: the most frequent mutation is M918T that, as in MEN2B, is associated with the most aggressive phenotype. Somatic point mutations of RET have also been described in other tumors such as colorectal cancer (Wood et al., Science, 2007, 318, 1108-13) and small cell lung carcinoma (Jpn. J. Cancer Res., 1995, 86, 1127-30).

RET signaling components have been found to be expressed in primary breast tumors and to functionally interact with estrogen receptor-α pathway in breast tumor cell lines (Boulay et al., Cancer Res. 2008, 68, 3743-51; Plaza-Menacho et al., Oncogene, 2010, 29, 4648-57), while RET expression and activation by GDNF family ligands could play an important role in perineural invasion by different types of cancer cells (Ito et al., Surgery, 2005, 138, 788-94; Gil et al., J. Natl. Cancer Inst., 2010, 102, 107-18; Iwahashi et al., Cancer, 2002, 94, 167-74).

RET is also expressed in 30-70% of invasive breast cancers, with expression being relatively more frequent in estrogen receptor-positive tumors (Plaza-Menacho, I., et al.,

*Oncogene*, 2010, 29, 4648-4657; Esseghir, S., et al., *Cancer Res.*, 2007, 67, 11732-11741; Morandi, A., et al., *Cancer Res.*, 2013, 73, 3783-3795; Gattelli, A., *EMBO Mol. Med.*, 2013, 5, 1335-1350).

The identification of RET rearrangements has been reported in a subset of (patient-derived xenograft) PDX established from colorectal cancer. Although the frequency of such events in colorectal cancer patients remains to be defined, these data suggest a role of RET as a target in this indication (Gozgit et al., AACRz Annual Meeting 2014). Studies have shown that the RET promoter is frequently methylated in colorectal cancers, and heterozygous missense mutations, which are predicted to reduce RET expression, are identified in 5-10% of cases, which suggests that RET might have some features of a tumor suppressor in sporadic colon cancers (Luo, Y., et al., *Oncogene*, 2013, 32, 2037-2047; Sjoblom, T., et al., *Science*, 2006, 268-274; Cancer Genome Atlas Network, *Nature*, 2012, 487, 330-337).

An increasing number of tumor types are now being shown to express substantial levels of wild-type RET kinase that could have implications for tumor progression and spread. RET is expressed in 50-65% of pancreatic ductal carcinomas, and expression is more frequent in metastatic and higher grade tumors (Ito, Y, et al., *Surgery*, 2005, 138, 788-794; Zeng, Q., et al., *J. Int. Med. Res.* 2008, 36, 656-664).

In neoplasms of hematopoietic lineages, RET is expressed in acute myeloid leukemia (AML) with monocytic differentiation, as well as in CMML (Gattei, V. et al., *Blood*, 1997, 89, 2925-2937; Gattei, V., et al., *Ann. Hematol*, 1998, 77, 207-210; Camos, M., *Cancer Res.* 2006, 66, 6947-6954). Recent studies have identified rare chromosomal rearrangements that involve RET in patients with chronic myelomonocytic leukemia (CMML). CMML is frequently associated with rearrangements of several tyrosine kinases, which result in the expression of chimeric cytosolic oncoproteins that lead to activation of RAS pathways (Kohlmann, A., et al., *J. Clin. Oncol.* 2010, 28, 2858-2865). In the case of RET, gene fusions that link RET with BCR (BCR-RET) or with fibroblast growth factor receptor 1 oncogene partner (FGFR1OP-RET) were transforming in early hematopoietic progenitor cells and could shift maturation of these cells towards monocytic paths, probably through the initiation of RET-mediated RAS signaling (Ballerini, P., et al., *Leukemia*, 2012, 26, 2384-2389).

RET expression has also been shown to occur in several other tumor types, including prostate cancer, small-cell lung carcinoma, melanoma, renal cell carcinoma, and head and neck tumors (Narita, N., et al., *Oncogene*, 2009, 28, 3058-3068; Mulligan, L. M., et al., *Genes Chromosomes Cancer*, 1998, 21, 326-332; Flavin, R., et al., *Urol. Oncol.*, 2012, 30, 900-905; Dawson, D. M., *J Natl Cancer Inst*, 1998, 90, 519-523).

In neuroblastoma, RET expression and activation by GFLs has roles in tumor cell differentiation, potentially collaborating with other neurotrophic factor receptors to down regulate N-Myc, the expression of which is a marker of poor prognosis (Hofstra, R. M., W., et al., *Hum. Genet.* 1996, 97, 362-364; Petersen, S. and Bogenmann, E., *Oncogene*, 2004, 23, 213-225; Brodeur, G. M., *Nature Ref Cancer*, 2003, 3, 203-216).

Multitargeted inhibitors which cross react with RET are known (Borrello, M. G., et al., *Expert Opin. Ther. Targets*, 2013, 17(4), 403-419; International Patent Application Nos. WO 2014/141187, WO 2014/184069, and WO 2015/079251).

Accordingly, provided herein are methods for treating a patient diagnosed with (or identified as having) a cancer that include administering to the patient a therapeutically effective amount of a compound of Formula I or a pharmaceutically acceptable salt or solvate thereof. Also provided herein are methods for treating a patient identified or diagnosed as having a RET-associated cancer that include administering to the patient a therapeutically effective amount of a compound of Formula I or a pharmaceutically acceptable salt or solvate thereof or a pharmaceutical composition thereof. In some embodiments, the patient that has been identified or diagnosed as having a RET-associated cancer through the use of a regulatory agency-approved, e.g., FDA-approved test or assay for identifying dysregulation of a RET gene, a RET kinase, or expression or activity or level of any of the same, in a patient or a biopsy sample from the patient or by performing any of the non-limiting examples of assays described herein. In some embodiments, the test or assay is provided as a kit. In some embodiments, the cancer is a RET-associated cancer. For example, the RET-associated cancer can be a cancer that includes one or more RET inhibitor resistance mutations.

Also provided are methods for treating cancer in a patient in need thereof, the method comprising: (a) determining if the cancer in the patient is a RET-associated cancer; and (b) if the cancer is determined to be a RET-associated cancer, administering to the patient a therapeutically effective amount of a compound of Formula I or a pharmaceutically acceptable salt or solvate thereof or a pharmaceutical composition thereof. Some embodiments of these methods further include administering to the subject another anticancer agent (e.g., a second RET inhibitor, a second compound of Formula I or a pharmaceutically acceptable salt or solvate thereof, or immunotherapy). In some embodiments, the subject was previously treated with a first RET inhibitor or previously treated with another anticancer treatment, e.g., resection of the tumor or radiation therapy. In some embodiments, the patient is determined to have a RET-associated cancer through the use of a regulatory agency-approved, e.g., FDA-approved test or assay for identifying dysregulation of a RET gene, a RET kinase, or expression or activity or level of any of the same, in a patient or a biopsy sample from the patient or by performing any of the non-limiting examples of assays described herein. In some embodiments, the test or assay is provided as a kit. In some embodiments, the cancer is a RET-associated cancer. For example, the RET-associated cancer can be a cancer that includes one or more RET inhibitor resistance mutations.

Also provided are methods of treating a patient that include performing an assay on a sample obtained from the patient to determine whether the patient has a dysregulation of a RET gene, a RET kinase, or expression or activity or level of any of the same, and administering (e.g., specifically or selectively administering) a therapeutically effective amount of a compound of Formula I or a pharmaceutically acceptable salt or solvate thereof or a pharmaceutical composition thereof to the patient determined to have a dysregulation of a RET gene, a RET kinase, or expression or activity or level of any of the same. Some embodiments of these methods further include administering to the subject another anticancer agent (e.g., a second RET inhibitor, a second compound of Formula I or a pharmaceutically acceptable salt or solvate thereof, or immunotherapy). In some embodiments of these methods, the subject was previously treated with a first RET inhibitor or previously treated with another anticancer treatment, e.g., resection of a tumor or radiation therapy. In some embodiments, the patient is a patient suspected of having a RET-associated cancer, a patient presenting with one or more symptoms of a RET-associated cancer, or a patient having an elevated risk of developing a RET-associated cancer. In some embodiments, the assay utilizes next generation sequencing, pyrosequencing, immunohistochemistry, or break apart FISH analysis. In some embodiments, the assay is a regulatory agency-approved assay, e.g., FDA-approved kit. Additional, non-limiting assays that may be used in these methods are described herein. Additional assays are also known in the art. In some embodiments, the dysregulation of a RET gene, a RET kinase, or expression or activity or level of any of the same includes one or more RET inhibitor resistance mutations.

Also provided is a compound of Formula I or a pharmaceutically acceptable salt or solvate thereof or a pharmaceutical composition thereof for use in treating a RET-associated cancer in a patient identified or diagnosed as having a RET-associated cancer through a step of performing an assay (e.g., an in vitro assay) on a sample obtained from the patient to determine whether the patient has a dysregulation of a RET gene, a RET kinase, or expression or activity or level of any of the same, where the presence of a dysregulation of a RET gene, a RET kinase, or expression or activity or level of any of the same, identifies that the patient has a RET-associated cancer. Also provided is the use of a compound of Formula I or a pharmaceutically acceptable salt or solvate thereof for the manufacture of a medicament for treating a RET-associated cancer in a patient identified or diagnosed as having a RET-associated cancer through a step of performing an assay on a sample obtained from the patient to determine whether the patient has a dysregulation of a RET gene, a RET kinase, or expression or activity or level of any of the same where the presence of dysregulation of a RET gene, a RET kinase, or expression or activity or level of any of the same, identifies that the patient has a RET-associated cancer. Some embodiments of any of the methods or uses described herein further include recording in the patient's clinical record (e.g., a computer readable medium) that the patient is determined to have a dysregulation of a RET gene, a RET kinase, or expression or activity or level of any of the same, through the performance of the assay, should be administered a compound of Formula I or a pharmaceutically acceptable salt or solvate thereof or a pharmaceutical composition thereof. In some embodiments, the assay utilizes next generation sequencing, pyrosequencing, immunohistochemistry, or break apart FISH analysis. In some embodiments, the assay is a regulatory agency-approved assay, e.g., FDA-approved kit. In some embodiments, the dysregulation of a RET gene, a RET kinase, or expression or activity or level of any of the same includes one or more RET inhibitor resistance mutations.

Also provided is a compound of Formula I or a pharmaceutically acceptable salt or solvate thereof, for use in the treatment of a cancer in a patient in need thereof or a patient identified or diagnosed as having a RET-associated cancer. Also provided is the use of a compound of Formula I or a pharmaceutically acceptable salt or solvate thereof for the manufacture of a medicament for treating a cancer in a patient identified or diagnosed as having a RET-associated cancer. In some embodiments, the cancer is a RET-associated cancer, for example, a RET-associated cancer having one or more RET inhibitor resistance mutations. In some embodiments, a patient is identified or diagnosed as having a RET-associated cancer through the use of a regulatory agency-approved, e.g., FDA-approved, kit for identifying dysregulation of a RET gene, a RET kinase, or expression or activity or level of any of the same, in a patient or a biopsy sample from the sample. As provided herein, a RET-associated cancer includes those described herein and known in the art.

In some embodiments of any of the methods or uses described herein, the patient has been identified or diagnosed as having a cancer with a dysregulation of a RET gene, a RET kinase, or expression or activity or level of any of the same. In some embodiments of any of the methods or uses described herein, the patient has a tumor that is positive for a dysregulation of a RET gene, a RET kinase, or expression or activity or level of any of the same. In some embodiments of any of the methods or uses described herein, the patient can be a patient with a tumor(s) that is positive for a dysregulation of a RET gene, a RET kinase, or expression or activity or level of any of the same. In some embodiments of any of the methods or uses described herein, the patient can be a patient whose tumors have a dysregulation of a RET gene, a RET kinase, or expression or activity or level of any of the same. In some embodiments of any of the methods or uses described herein, the patient is suspected of having a RET-associated cancer (e.g., a cancer having one or more RET inhibitor resistance mutations). In some embodiments, provided herein are methods for treating a RET-associated cancer in a patient in need of such treatment, the method comprising a) detecting a dysregulation of a RET gene, a RET kinase, or the expression or activity or level of any of the same in a sample from the patient; and b) administering a therapeutically effective amount of a compound of Formula I or a pharmaceutically acceptable salt or solvate thereof. In some embodiments, the dysregulation of a RET gene, a RET kinase, or the expression or activity or level of any of the same includes one or more fusion proteins. Non-limiting examples of RET gene fusion proteins are described in Table 1. In some embodiments, the fusion protein is KIF5B-RET. In some embodiments, the dysregulation of a RET gene, a RET kinase, or the expression or activity or level of any of the same includes one or more RET kinase protein point mutations/insertions/deletions. Non-limiting examples of RET kinase protein point mutations/insertions/deletions are described in Table 2. In some embodiments, the RET kinase protein point mutations/insertions/deletions are selected from the group consisting of M918T, M918V, C634W, V804L, and V804M. In some embodiments, the dysregulation of a RET gene, a RET kinase, or the expression or activity or level of any of the same includes one or more RET inhibitor resistance mutations. Non-limiting examples of RET inhibitor resistance mutations are described in Tables 3 and 4. In some embodiments, the RET inhibitor resistance mutation is V804M. In some embodiments, the cancer with a dysregulation of a RET gene, a RET kinase, or expression or activity or level of any of the same is determined using a regulatory agency-approved, e.g., FDA-approved, assay or kit. In some embodiments, the tumor that is positive for a dysregulation of a RET gene, a RET kinase, or expression or activity or level of any of the same is a tumor positive for one or more RET inhibitor resistance mutations. In some embodiments, the tumor with a dysregulation of a RET gene, a RET kinase, or expression or activity or level of any of the same is determined using a regulatory agency-approved, e.g., FDA-approved, assay or kit.

In some embodiments of any of the methods or uses described herein, the patient has a clinical record indicating that the patient has a tumor that has a dysregulation of a RET gene, a RET kinase, or expression or activity or level of any of the same (e.g., a tumor having one or more RET inhibitor resistance mutations). In some embodiments, the clinical record indicates that the patient should be treated with one or more of the compounds of Formula I or a pharmaceutically acceptable salts or solvates thereof or compositions provided herein. In some embodiments, the cancer with a dysregulation of a RET gene, a RET kinase, or expression or activity or level of any of the same is a cancer having one or more RET inhibitor resistance mutations. In some embodiments, the cancer with a dysregulation of a RET gene, a RET kinase, or expression or activity or level of any of the same is determined using a regulatory agency-approved, e.g., FDA-approved, assay or kit. In some embodiments, the tumor that is positive for a dysregulation of a RET gene, a RET kinase, or expression or activity or level of any of the same is a tumor positive for one or more RET inhibitor resistance mutations. In some embodiments, the tumor with a dysregulation of a RET gene, a RET kinase, or expression or activity or level of any of the same is determined using a regulatory agency-approved, e.g., FDA-approved, assay or kit.

Also provided are methods of treating a patient that include administering a therapeutically effective amount of a compound of Formula I or a pharmaceutically acceptable salt or solvate thereof to a patient having a clinical record that indicates that the patient has a dysregulation of a RET gene, a RET kinase, or expression or activity or level of any of the same. Also provided is the use of a compound of Formula I or a pharmaceutically acceptable salt or solvate thereof for the manufacture of a medicament for treating a RET-associated cancer in a patient having a clinical record that indicates that the patient has a dysregulation of a RET gene, a RET kinase, or expression or activity or level of any of the same. Some embodiments of these methods and uses can further include: a step of performing an on a sample obtained from the patient to determine whether the patient has a dysregulation of a RET gene, a RET kinase, or expression or activity or level of any of the same, and recording the information in a patient's clinical file (e.g., a computer readable medium) that the patient has been identified to have a dysregulation of a RET gene, a RET kinase, or expression or activity or level of any of the same. In some embodiments, the assay is an in vitro assay. For example, an assay that utilizes next generation sequencing, immunohistochemistry, or break apart FISH analysis. In some embodiments, the assay is a regulatory agency-approved, e.g., FDA-approved, kit. In some embodiments, the dysregulation of a RET gene, RET kinase, or expression or activity or level of any of the same includes one or more RET inhibitor resistance mutations.

Also provided herein is a method of treating a subject. The method includes performing an assay on a sample obtained from the subject to determine whether the subject has a dysregulation of a RET gene, a RET protein, or expression or level of any of the same. The method also includes administering to a subject determined to have a dysregulation of a RET gene, a RET protein, or expression or activity, or level of any of the same a therapeutically effective amount of a compound of Formula I or a pharmaceutically acceptable salt or solvate thereof. In some embodiments, the dysregulation in a RET gene, a RET kinase protein, or expression or activity of the same is a gene or chromosome translocation that results in the expression of a RET fusion protein (e.g., any of the RET fusion proteins described herein). In some embodiments, the RET fusion can be selected from a KIF5B-RET fusion and a CCDC6-RET fusion. In some embodiments, the dysregulation in a RET gene, a RET kinase protein, or expression or activity or level of any of the same is one or more point mutation in the RET gene (e.g., any of the one or more of the RET point mutations described herein). The one or more point mutations in a RET gene can result, e.g., in the translation of a RET protein having one or more of the following amino acid substitutions: M918T, M918V, C634W, V804L, and V804M. In some embodiments, the dysregulation in a RET gene, a RET kinase protein, or expression or activity or level of any of the same is one or more RET inhibitor resistance mutations (e.g., any combination of the one or more RET inhibitor resistance mutations described herein). Some embodiments of these methods further include administering to the subject another anticancer agent (e.g., a second RET inhibitor a second compound of Formula I or a pharmaceutically acceptable salt or solvate thereof, or immunotherapy).

In some embodiments, the compounds provided herein exhibit brain and/or central nervous system (CNS) penetrance. Such compounds are capable of crossing the blood brain barrier and inhibiting a RET kinase in the brain and/or other CNS structures. In some embodiments, the compounds provided herein are capable of crossing the blood brain barrier in a therapeutically effective amount. For example, treatment of a patient with cancer (e.g., a RET-associated cancer such as a RET-associated brain or CNS cancer) can include administration (e.g., oral administration) of the compound to the patient. In some such embodiments, the compounds provided herein are useful for treating a primary brain tumor or metastatic brain tumor. For example, the compounds can be used in the treatment of one or more of gliomas such as glioblastoma (also known as glioblastoma multiforme), astrocytomas, oligodendrogliomas, ependymomas, and mixed gliomas, meningiomas, medulloblastomas, gangliogliomas, schwannomas (neurilemmomas), and craniopharyngiomas (see, for example, the tumors listed in Louis, D. N. et al. *Acta Neuropathol* 131(6), 803-820 (June 2016)). In some embodiments, the brain tumor is a primary brain tumor. In some embodiments, the patient has previously been treated with another anticancer agent, e.g., another RET inhibitor (e.g., a compound that is not a compound of General Formula I) or a multi-kinase inhibitor. In some embodiments, the brain tumor is a metastatic brain tumor. In some embodiments, the patient has previously been treated with another anticancer agent, e.g., another RET inhibitor (e.g., a compound that is not a compound of General Formula I) or a multi-kinase inhibitor.

Also provided are methods (e.g., in vitro methods) of selecting a treatment for a patient identified or diagnosed as having a RET-associated cancer. Some embodiments can further include administering the selected treatment to the patient identified or diagnosed as having a RET-associated cancer. For example, the selected treatment can include administration of a therapeutically effective amount of a compound of Formula I or a pharmaceutically acceptable salt or solvate thereof. Some embodiments can further include a step of performing an assay on a sample obtained from the patient to determine whether the patient has a dysregulation of a RET gene, a RET kinase, or expression or activity or level of any of the same, and identifying and diagnosing a patient determined to have a dysregulation of a RET gene, a RET kinase, or expression or activity or level of any of the same, as having a RET-associated cancer. In some embodiments, the cancer is a RET-associated cancer having one or more RET inhibitor resistance mutations. In some embodiments, the patient has been identified or diagnosed as having a RET-associated cancer through the use of a regulatory agency-approved, e.g., FDA-approved, kit for identifying dysregulation of a RET gene, a RET kinase, or expression or activity or level of any of the same, in a patient or a biopsy sample from the patient. In some embodiments, the RET-associated cancers is a cancer described herein or known in the art. In some embodiments, the assay is an in vitro assay. For example, an assay that utilizes the next generation sequencing, immunohistochemistry, or break apart FISH analysis. In some embodiments, the assay is a regulatory agency-approved, e.g., FDA-approved, kit.

Also provided herein are methods of selecting a treatment for a patient, wherein the methods include a step of performing an assay on a sample obtained from the patient to determine whether the patient has a dysregulation of a RET gene, a RET kinase, or expression or activity or level of any of the same (e.g., one or more RET inhibitor resistance mutations), and identifying or diagnosing a patient determined to have a dysregulation of a RET gene, a RET kinase, or expression or activity or level of any of the same, as having a RET-associated cancer. Some embodiments further include administering the selected treatment to the patient identified or diagnosed as having a RET-associated cancer. For example, the selected treatment can include administration of a therapeutically effective amount of a compound of Formula I or a pharmaceutically acceptable salt or solvate thereof to the patient identified or diagnosed as having a RET-associated cancer. In some embodiments, the assay is an in vitro assay. For example, an assay that utilizes the next generation sequencing, immunohistochemistry, or break apart FISH analysis. In some embodiments, the assay is a regulatory agency-approved, e.g., FDA-approved, kit.

Also provided are methods of selecting a patient for treatment, wherein the methods include selecting, identifying, or diagnosing a patient having a RET-associated cancer, and selecting the patient for treatment including administration of a therapeutically-effective amount of a compound of Formula I or a pharmaceutically acceptable salt or solvate thereof. In some embodiments, identifying or diagnosing a patient as having a RET-associated cancer can include a step of performing an assay on a sample obtained from the patient to determine whether the patient has a dysregulation of a RET gene, a RET kinase, or expression or activity or level of any of the same, and identifying or diagnosing a patient determined to have a dysregulation of a RET gene, a RET kinase, or expression or activity or level of any of the same, as having a RET-associated cancer. In some embodiments, the method of selecting a treatment can be used as a part of a clinical study that includes administration of various treatments of a RET-associated cancer. In some embodiments, a RET-associated cancer is a cancer having one or more RET inhibitor resistance mutations. In some embodiments, the assay is an in vitro assay. For example, an assay that utilizes the next generation sequencing, immunohistochemistry, or break apart FISH analysis. In some embodiments, the assay is a regulatory agency-approved, e.g., FDA-approved, kit. In some embodiments, the dysregulation of the RET gene, the RET kinase, or expression or activity or level of any of the same includes one or more RET inhibitor resistance mutations.

In some embodiments of any of the methods or uses described herein, an assay used to determine whether the patient has a dysregulation of a RET gene, or a RET kinase, or expression or activity or level of any of the same, using a sample from a patient can include, for example, next generation sequencing, immunohistochemistry, fluorescence microscopy, break apart FISH analysis, Southern blotting, Western blotting, FACS analysis, Northern blotting, and PCR-based amplification (e.g., RT-PCR and quantitative real-time RT-PCR). As is well-known in the art, the assays are typically performed, e.g., with at least one labelled nucleic acid probe or at least one labelled antibody or antigen-binding fragment thereof. Assays can utilize other detection methods known in the art for detecting dysregulation of a RET gene, a RET kinase, or expression or activity or levels of any of the same (see, e.g., the references cited herein). In some embodiments, the dysregulation of the RET gene, the RET kinase, or expression or activity or level of any of the same includes one or more RET inhibitor resistance mutations. In some embodiments, the sample is a biological sample or a biopsy sample (e.g., a paraffin-embedded biopsy sample) from the patient. In some embodiments, the patient is a patient suspected of having a RET-associated cancer, a patient having one or more symptoms of a RET-associated cancer, and/or a patient that has an increased risk of developing a RET-associated cancer)

In the field of medical oncology it is normal practice to use a combination of different forms of treatment to treat each patient with cancer. In medical oncology the other component(s) of such conjoint treatment or therapy in addition to compositions provided herein may be, for example, surgery, radiotherapy, and chemotherapeutic agents, such as kinase inhibitors, signal transduction inhibitors and/or monoclonal antibodies. Compounds of Formula I therefore may also be useful as adjuvants to cancer treatment, that is, they can be used in combination with one or more additional therapies or therapeutic agents, for example a chemotherapeutic agent that works by the same or by a different mechanism of action.

In some embodiments of any the methods described herein, the compound of Formula I (or a pharmaceutically acceptable salt or solvate thereof) is administered in combination with a therapeutically effective amount of at least one additional therapeutic agent selected from one or more additional therapies or therapeutic (e.g., chemotherapeutic) agents.

Non-limiting examples of additional therapeutic agents include: other RET-targeted therapeutic agents (i.e. a first or second RET kinase inhibitor), receptor tyrosine kinase-targeted therapeutic agents, signal transduction pathway inhibitors, checkpoint inhibitors, modulators of the apoptosis pathway (e.g. obataclax); cytotoxic chemotherapeutics, angiogenesis-targeted therapies, immune-targeted agents, including immunotherapy, and radiotherapy.

In some embodiments, the other RET-targeted therapeutic is a multikinase inhibitor exhibiting RET inhibition activity. In some embodiments, the other RET-targeted therapeutic inhibitor is selective for a RET kinase. Exemplary RET kinase inhibitors can exhibit inhibition activity ($IC_{50}$) against a RET kinase of less than about 1000 nM, less than about 500 nM, less than about 200 nM, less than about 100 nM, less than about 50 nM, less than about 25 nM, less than about 10 nM, or less than about 1 nM as measured in an assay as described herein. In some embodiments, a RET kinase inhibitors can exhibit inhibition activity ($IC_{50}$) against a RET kinase of less than about 25 nM, less than about 10 nM, less than about 5 nM, or less than about 1 nM as measured in an assay as provided herein.

Non-limiting examples of RET-targeted therapeutic agents include alectinib, apatinib, cabozantinib (XL-184), dovitinib, lenvatinib, motesanib, nintedanib, ponatinib, regorafenib, sitravatinib (MGCD516), sunitinib, sorafenib, vatalanib, vandetanib, AUY-922 (5-(2,4-Dihydroxy-5-iso-propyl-phenyl)-N-ethyl-4-[4-(morpholinomethyl)phenyl] isoxazole-3-carboxamide), BLU6864, BLU-667, DCC-2157, GSK3179106, NVP-AST487 (1-[4-[(4-ethylpiperazin-1-yl)methyl]-3-(trifluoromethyl)phenyl]-3-

[4-[6-(methylamino)pyrimidin-4-yl]oxy)phenyl]urea), PZ-1, RPI-1 (1,3-dihydro-5,6-dimethoxy-3-[(4-hydroxyphenyl)methylene]-H-indol-2-one), RXDX-105 (1-(3-((6,7-dimethoxyquinazolin-4-yl)oxy)phenyl)-3-(5-(1,1,1-trifluoro-2-methylpropan-2-yl)isoxazol-3-yl)urea), SPP86 (1-Isopropyl-3-(phenylethynyl)-1H-pyrazolo[3,4-d]pyrimidin-4-amine), and TG101209 (N-(1,1-dimethylethyl)-3-[[5-methyl-2-[[4-(4-methyl-1-piperazinyl)phenyl]amino]-4-pyrimidinyl]amino]-benzenesulfonamide).

Additional examples of other RET kinase inhibitors include those described in U.S. Pat. Nos. 9,150,517 and 9,149,464, and International Publication No. WO 2014075035, all of which are hereby incorporated by reference. For example, in some embodiments the other RET inhibitor is a compound of formula I:

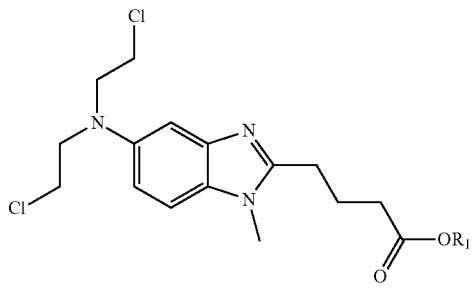

wherein $R_1$ is $C_6$-$C_{24}$alkyl or polyethylene glycol; or a pharmaceutically acceptable salt form thereof. In some embodiments, the other RET inhibitor is 4-{5-[bis-(chloroethyl)-amino]-1-methyl-1H-benzimidazol-2-yl}butyric acid dodecyl ester.

Additional examples of other RET kinase inhibitors include those described in International Publication No. WO 2016127074, which is hereby incorporated by reference. For example, in some embodiments, the other RET inhibitor is a compound of Formula (I) or a pharmaceutically acceptable salt thereof, wherein:

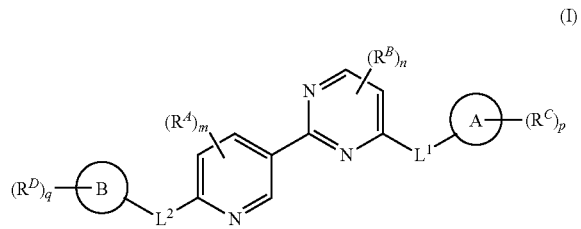

wherein Rings A and B are each independently selected from aryl, heteroaryl, cycloalkyl and heterocyclyl;

each $L^1$ and $L^2$ is independently selected from a bond, —(C1-C6 alkylene)-, —(C2-C6alkenylene)-, —(C2-C6 alkynylene)-, —(C1-C6 haloalkylene)-, —(C1-C6 heteroalkylene)-, —C(O)—, —O—, —S—, —S(O), —S(O)$_2$—, —N(R$^1$)—, —O—(C1-C6 alkylene)-, —(C1-C6 alkylene)-O—, —N(R$^1$)—C(O)—, —C(O)N(R$^1$)—, —(C1-C6 alkylene)-N(R$^1$)—, —N(R$^1$)—(C1-C6 alkylene)-, —N(R)—C(O)—(C1-C6 alkylene)-, —(C1-C6 alkylene)-N(R$^1$)—C(O)—, —C(O)—N(R$^1$)—(C1-C6 alkylene)-, —(C1-C6 alkylene)-C(O)—N(R$^1$)—, —N(R$^1$)—S(O)$_2$—, —S(O)$_2$—N(R$^1$)—, —N(R$^1$)—S(O)$_2$—(C1-C6 alkylene)-, and —S(O)$_2$—N(R$^1$)—(C1-C6 alkylene)-; wherein each alkylene, alkenylene, alkynylene, haloalkylene, and heteroalkylene is independently substituted with 0-5 occurrences of R';

each $R^A$ and $R^B$ is independently selected from C1-C6 alkyl, C1-C6 alkoxy, halo, C1-C6 haloalkyl, C1-C6 hydroxyalkyl, C1-C6 heteroalkyl, and —N(R$^1$)(R$^1$); wherein each alkyl, alkoxy, haloalkyl, hydroxyalkyl, and hydroxyalkyl is independently substituted with 0-5 occurrences of R$^a$;

each $R^C$ and $R^D$ is independently selected from C1-C6 alkyl, C2-C6 alkenyl, C2-C6 alkynyl, C1-C6 alkoxy, halo, C1-C6 heteroalkyl, C1-C6 haloalkyl, C1-C6 haloalkoxy, C1-C6 hydroxyalkyl, cycloalkyl, aryl, heteroaryl, aryloxy, aralkyl, heterocyclyl, heterocyclylalkyl, nitro, cyano, —C(O)R$^1$, —OC(O)R$^1$, —C(O)OR$^1$, —(C1-C6 alkylene)-C(O)R$^1$, —SR$^1$, —S(O)$_2$R$^1$, —S(O)$_2$—N(R$^1$)(R$^1$), —(C1-C6 alkylene)-S(O)$_2$R$^1$, —(C1-C6 alkylene)-S(O)$_2$—N(R$^1$)(R), —N(R$^1$)(R$^1$)—C(O)—N(R$^1$)(R$^1$)—N(R$^1$)—C(O)R$^1$, —N(R$^1$)—C(O)OR$^1$, —(C1-C6 alkylene)-N(R$^1$)—C(O)R$^1$, —N(R$^1$)S(O)$_2$R$^1$, and —P(O)(R$^1$)(R$^1$); wherein each of alkyl, alkenyl, alkynyl, alkoxy, heteroalkyl, haloalkyl, haloalkoxy, hydroxyalkyl, cycloalkyl, aryl, heteroaryl, aryloxy, aralkyl, heterocyclyl, and heterocyclylalkyl is independently substituted with 0-5 occurrences of R$^a$; or 2 $R^C$ or 2 $R^D$ together with the carbon atom(s) to which they are attached form a cycloalkyl or heterocyclyl ring independently substituted with 0-5 occurrences of R$^a$;

each $R^1$ is independently selected from hydrogen, hydroxyl, halo, thiol, C1-C6 alkyl, C1-C6 thioalkyl, C1-C6 alkoxy, C1-C6 haloalkyl, C1-C6 hydroxyalkyl, C1-C6 heteroalkyl, cycloalkyl, cycloalkylalkyl, heteroarylalkyl, heterocyclyl, and heterocyclylalkyl, wherein each of alkyl, thioalkyl, alkoxy, haloalkyl, hydroxyalkyl, heteroalkyl, cycloalkyl, cycloalkylalkyl, heteroarylalkyl, heterocyclyl, and heterocyclylalkyl is independently substituted with 0-5 occurrences of R$^b$, or 2 $R^1$ together with the atom(s) to which they are attached form a cycloalkyl or heterocyclyl ring independently substituted with 0-5 occurrences of R$^b$;

each $R^a$ and $R^b$ is independently C1-C6 alkyl, halo, hydroxyl, C1-C6 haloalkyl, C1-C6 heteroalkyl, C1-C6 hydroxyalkyl, C1-C6 alkoxy, cycloalkyl, heterocyclyl, or cyano, wherein each of alkyl, haloalkyl, heteroalkyl, hydroxyalkyl, alkoxy, cycloalkyl and heterocyclyl is independently substituted with 0-5 occurrences of R';

each R' is C1-C6 alkyl, C1-C6 heteroalkyl, halo, hydroxyl, C1-C6 haloalkyl, C1-C6 hydroxyalkyl, cycloalkyl or cyano; or 2 R', together with the atom(s) to which they are attached form a cycloalkyl or heterocyclyl ring;

m is 0, 1, 2, or 3;

n is 0, 1, or 2; and p and q are each independently 0, 1, 2, 3, or 4. For example, a RET inhibitor can be selected from the group consisting of:

221 222
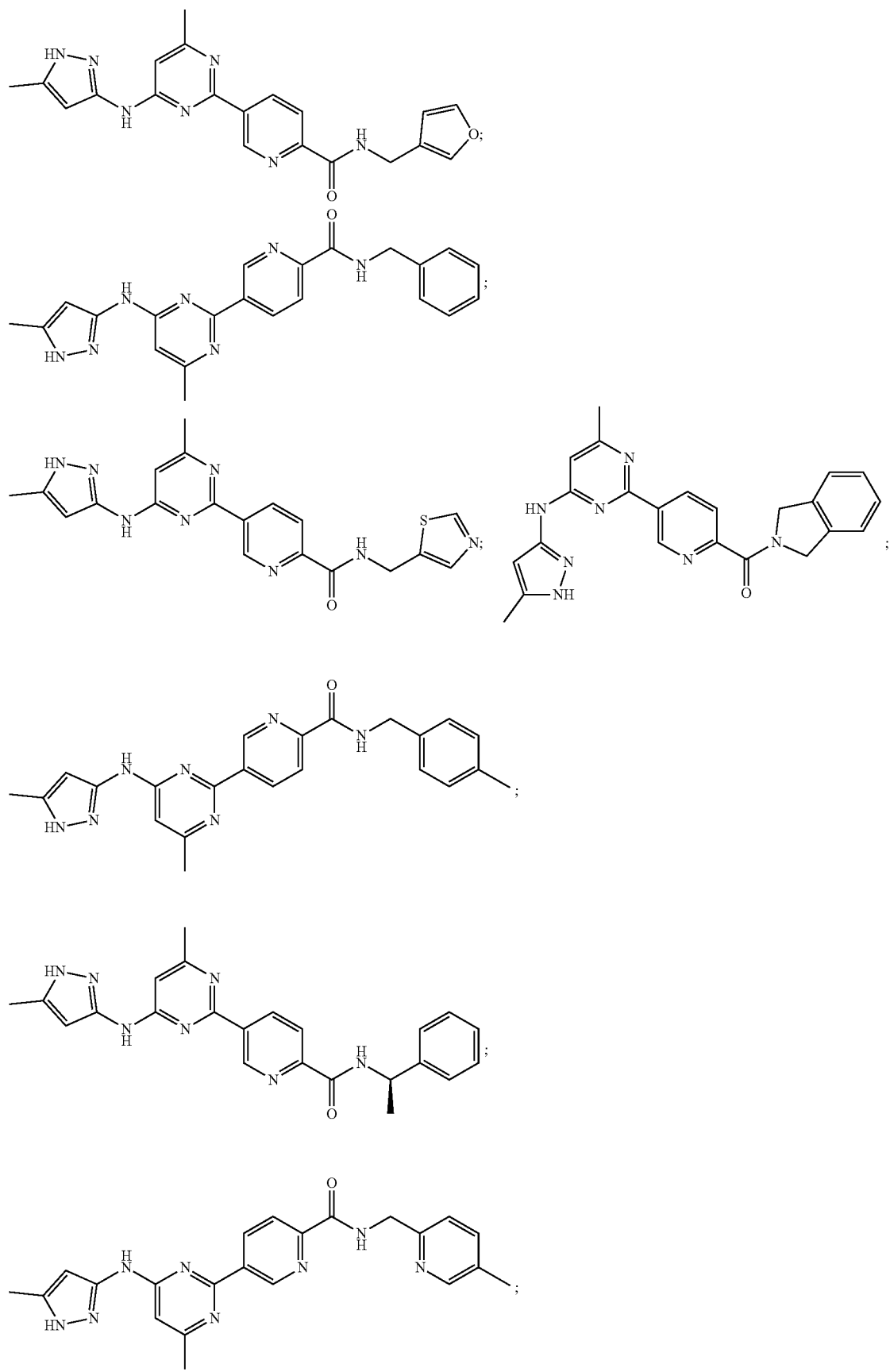

-continued
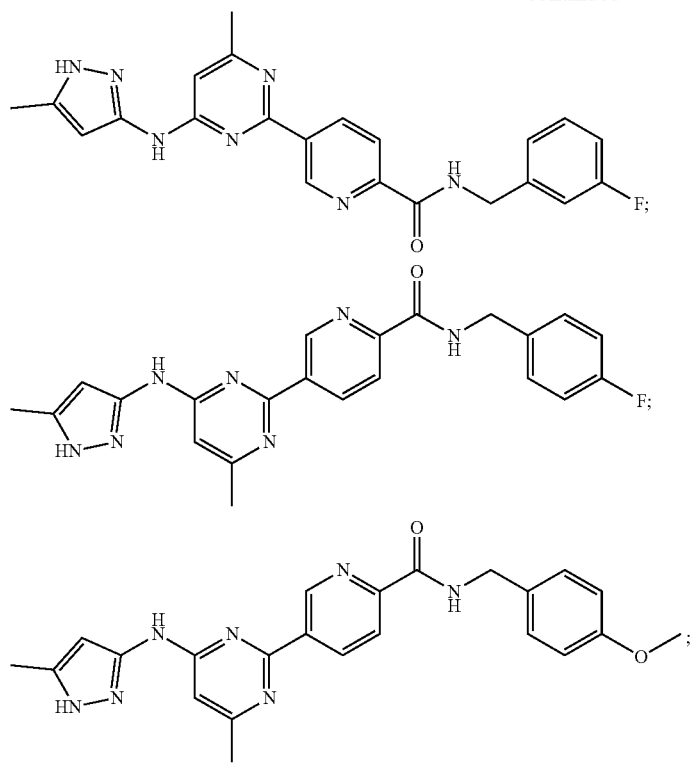
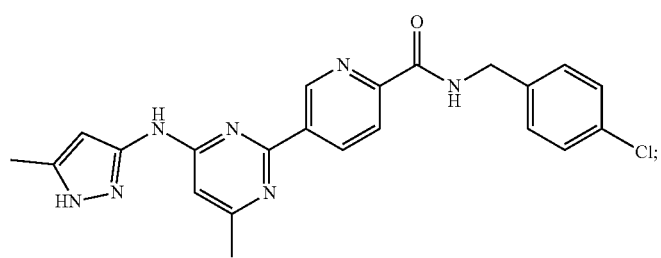
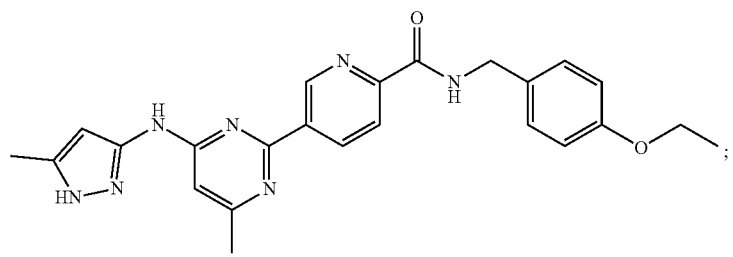
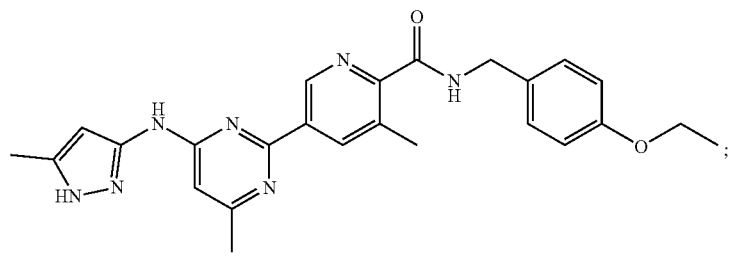

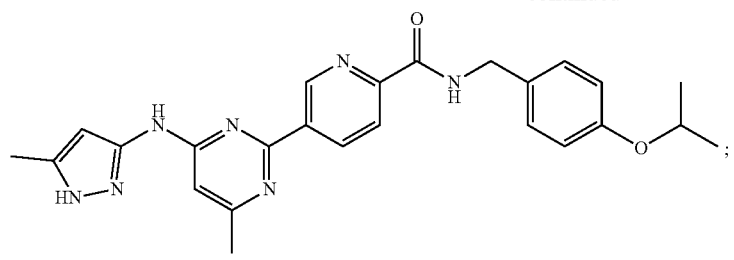
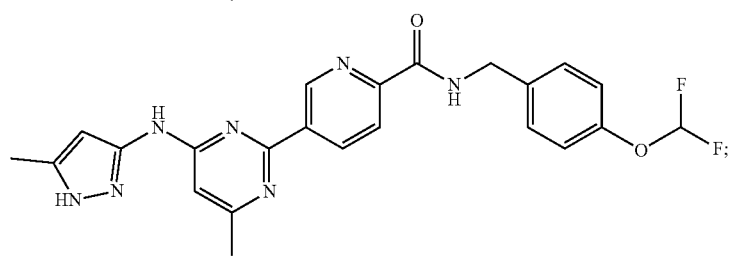
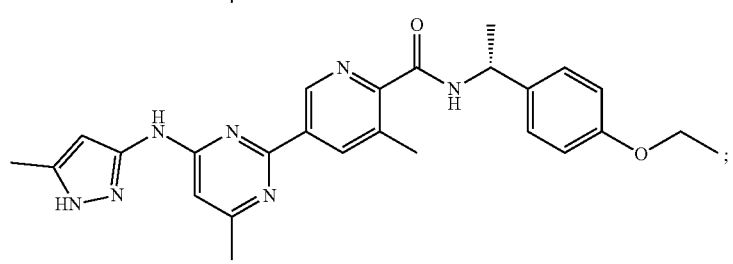
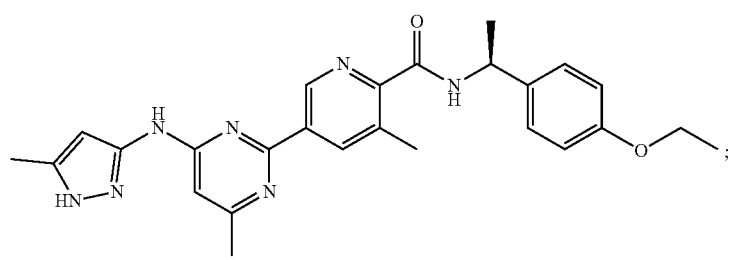
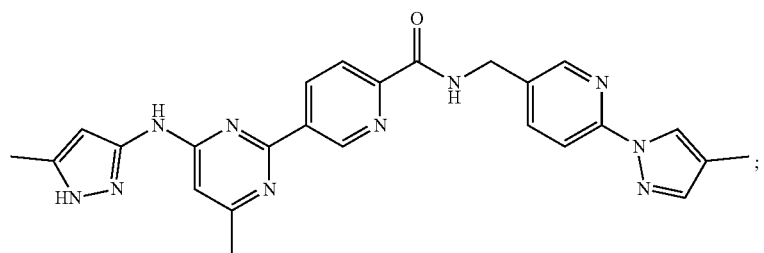
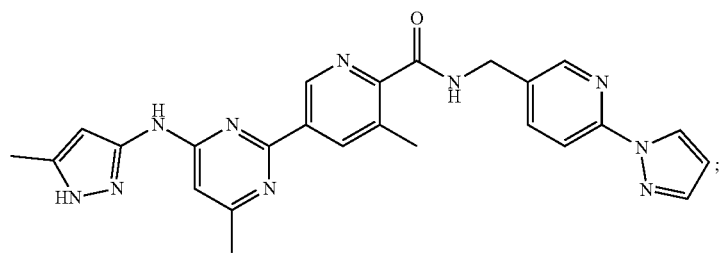

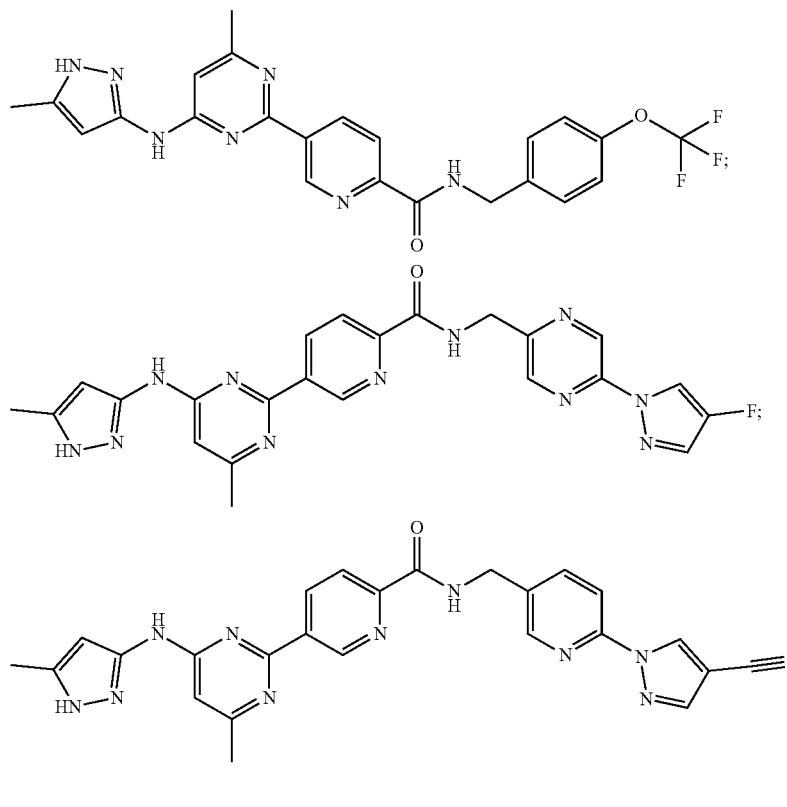
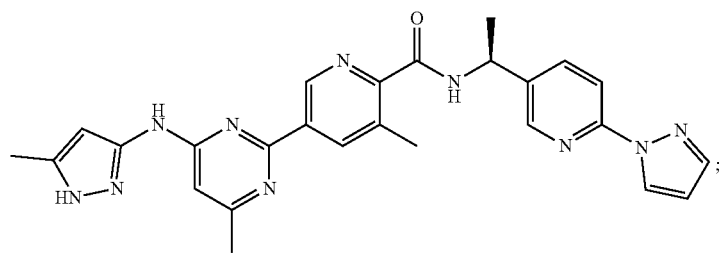
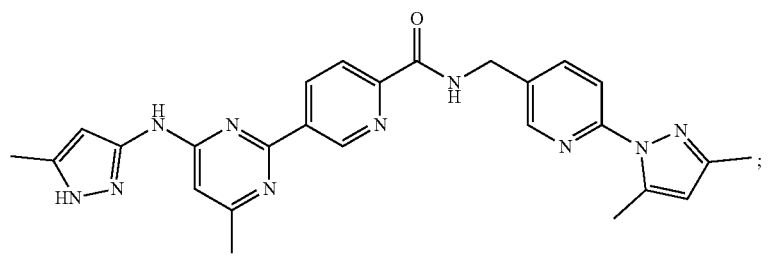
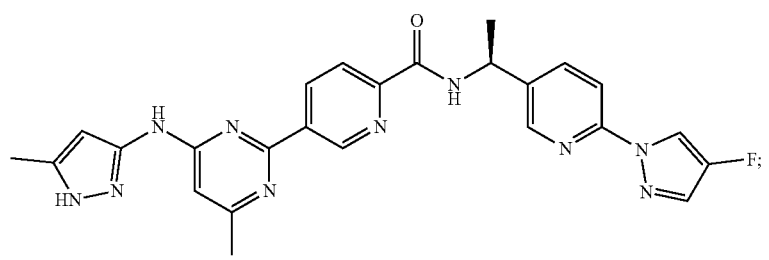

-continued
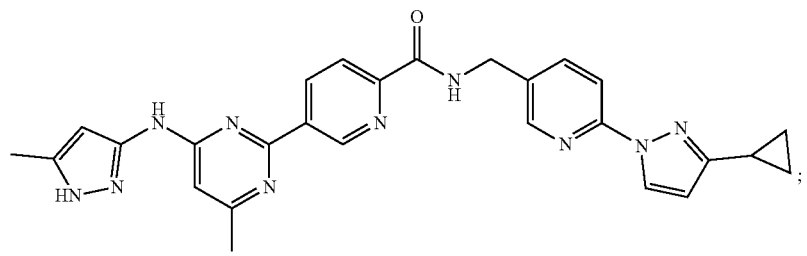
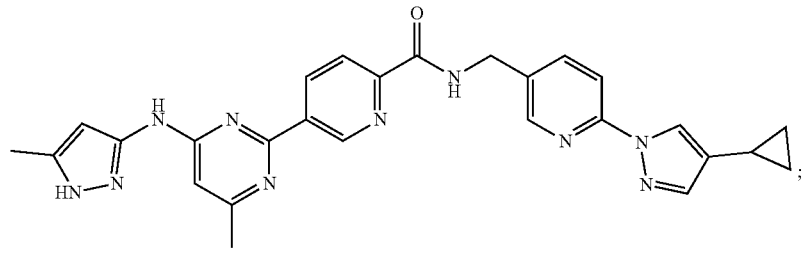
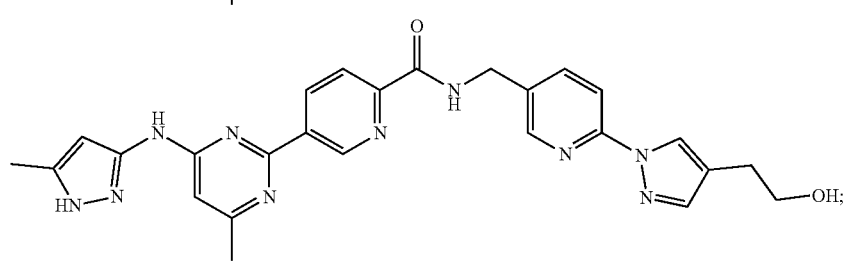
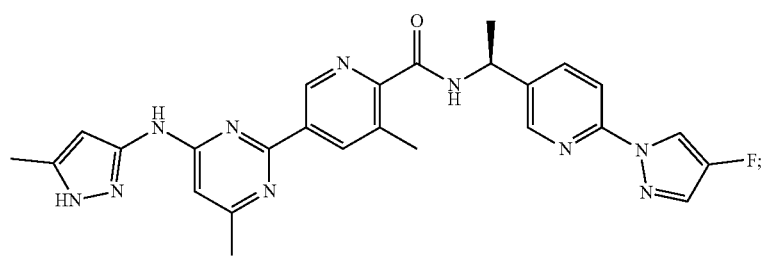
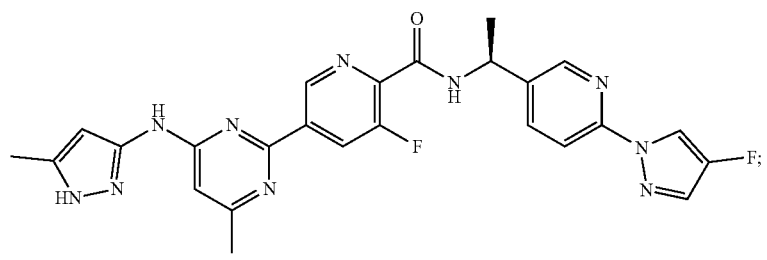
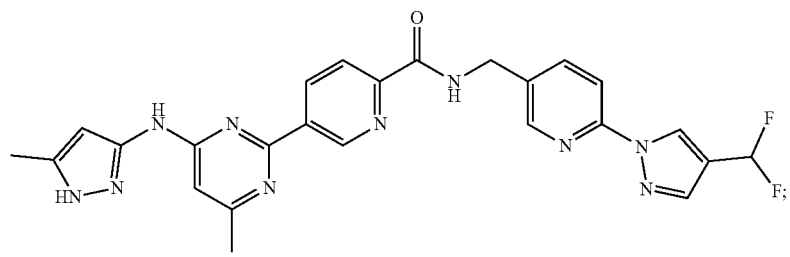

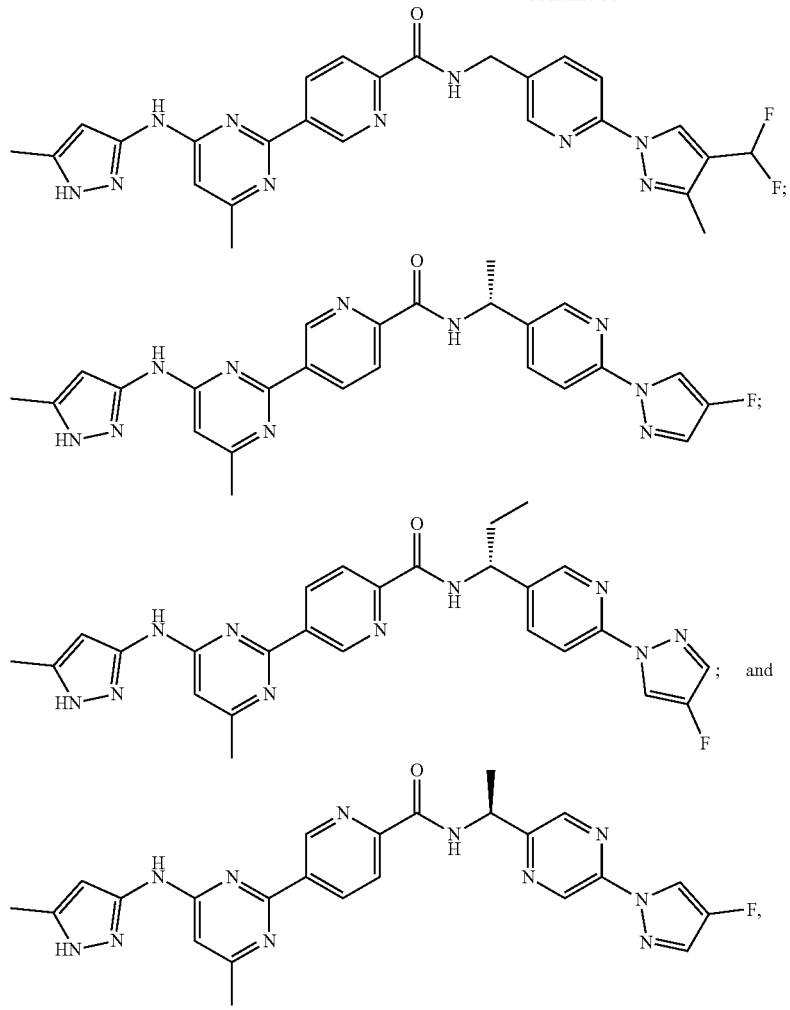

or a pharmaceutically acceptable salt thereof.

In some embodiments, a RET inhibitor is selected from the group consisting of: ABT-348 (N-[4-[4-Amino-7-[1-(2-hydroxyethyl)-1H-pyrazol-4-yl]thieno[3,2-c]pyridin-3-yl]phenyl]-N'-(3-fluorophenyl)urea); AD-57, which has the structure:

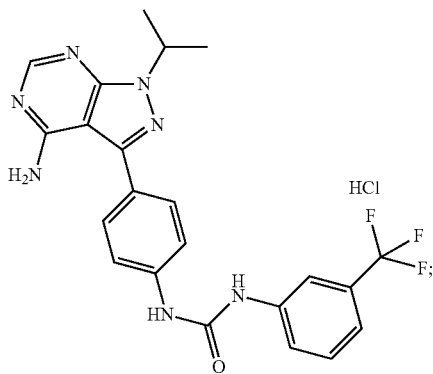 [SMILES: CC(C)n1nc(-c2ccc(NC(=O)Nc3cccc(C(F)(F)F)c3)cc2)c2c(N)ncnc21 ; Cl]

AD-80 (1-(4-(4-amino-1-isopropyl-1H-pyrazolo[3,4-d]pyrimidin-3-yl)phenyl)-3-(2-fluoro-5-(trifluoromethyl)phenyl)urea); ALW-II-41-27 (N-(5-(((4-((4-ethylpiperazin-1-yl)methyl)-3-(trifluoromethyl)phenyl)carbamoyl)-2-methylphenyl)-5-(thiophen-2-yl)nicotinamide); Amuvatinib (MP470) (N-(benzo[d][1,3]dioxol-5-ylmethyl)-4-(benzofuro[3,2-d]pyrimidin-4-yl)piperazine-1-carbothioamide); BPR1J373 (a derivative of 5-phenylthiazol-2-ylamine-pyriminide); CLM3; doramapimod (BIRB-796) (1-(3-(tert-butyl)-1-(p-tolyl)-1H-pyrazol-5-yl)-3-(4-(2-morpholinoethoxy)naphthalen-1-yl)urea); DS-5010; famitinib (5-[2-(diethyl amino)ethyl]-2-[(Z)-(5-fluoro-2-oxo-1H-indol-3-ylidene)methyl]-3-methyl-6,7-dihydro-1H-pyrrolo[3,2-c]pyridin-4-one); fedratinib (SAR 302503, TG101348) (N-(tert-butyl)-3-((5-methyl-2-((4-(2-(pyrrolidin-1-yl)ethoxy)phenyl)amino)pyrimidin-4-yl)amino)benzenesulfonamide); GSK3179106; GSK3352589; HG-6-63-01 ((E)-3-(2-(4-chloro-1H-pyrrolo[2,3-b]pyridin-5-yl)vinyl)-N-(4-((4-ethylpiperazin-1-yl)methyl)-3-(trifluoromethyl)phenyl)-4-methylbenzamide); NVP-BBT594 (5-((6-acetamidopyrimidin-4-yl)oxy)-N-(4-((4-methylpiperazin-1-yl)methyl)-3-(trifluoromethyl)phenyl)indoline-1-carboxamide); PP2 (4-amino-5-(4-chlorophenyl)-7-(dimethylethyl)pyrazolo[3,4-d]pyrimidine); PP242 (2-(4-amino-1-isopropyl-1H-pyrazolo[3,4-d]pyrimidin-3-yl)-1H-indol-5-ol); quizartinib (AC220) (1-(5-(tert-butyl)isoxazol-3-yl)-3-(4-(7-(2-morpholinoethoxy)benzo[d]imidazo[2,1-b]

thiazol-2-yl)phenyl)urea); semaxanib (SU5416, VEGFR2 Kinase Inhibitor III) ((Z)-3-((3,5-dimethyl-1H-pyrrol-2-yl)methylene)indolin-2-one); SU4984 (3-[4-(1-formylpiperazin-4-yl)benzylidenyl]-2-indolinone); Withaferin A ((4β,5β,6β,22R)-4,27-Dihydroxy-5,6:22,26-diepoxyergosta-2,24-diene-1,26-dione); XL-999 ((Z)-5-((1-ethylpiperidin-4-yl)amino)-3-((3-fluorophenyl)(5-methyl-1H-imidazol-2-yl)methylene)indolin-2-one); XMD 15-44 (N-(4-((4-ethylpiperazin-1-yl)methyl)-3-(trifluoromethyl)phenyl)-4-methyl-3-(pyridin-3-ylethynyl)benzamide); Y078-DM1 (antibody drug conjugate composed of a RET antibody (Y078) linked to a derivative of the cytotoxic agent maytansine); and Y078-DM1 (antibody drug conjugate composed of a RET antibody (Y078) linked to a derivative of the cytotoxic agent maytansine).

Further examples of RET inhibitors include: N-(2-fluoro-5-trifluoromethylphenyl)-N'-{4'-[(2"-benzamido)pyridin-4"-ylamino]phenyl}urea; 1-isopropyl-3-(phenylethynyl)-1H-pyrazolo[3,4-d]pyrimidin-4-amine; 3-((6,7-dimethoxyquinazolin-4-yl)amino)-4-fluoro-2-methylphenol; N-(5-(tert-butyl)isoxazol-3-yl)-2-(4-(imidazo[1,2-a]pyridin-6-yl)phenyl)acetamide; N-(5-(tert-butyl)isoxazol-3-yl)-2-(3-(imidazo[1,2-b]pyridazin-6-yloxy)phenyl)acetamide; 2-amino-6-{[2-(4-chlorophenyl)-2-oxoethyl]sulfanyl}-4-(3-thienyl)pyridine-3,5-dicarbonitrile; and 3-arylureidobenzylidene-indolin-2-ones.

Yet other therapeutic agents include RET inhibitors such as those described, for example, in U.S. Pat. Nos. 7,504,509; 8,012,966; 8,299,057; 8,399,442; 8,067,434; 8,629,135; 8,895,744; 8,937,071; 9,006,256; and 9,035,063; U.S. Publication Nos. 2015/0272958; 2015/0238477; 2014/0121239; 20160176865; 2011/0053934; 2011/0301157; 2010/0324065; 2009/0227556; 2009/0130229; 2009/0099167; 2005/0209195; International Publication Nos. WO 2017/043550; WO 2017/026718; WO 2016/037578; WO 2016/038519; WO 2016/038552; WO 2014/184069; WO 2014/072220; WO 2012/053606; WO 2009/017838; WO 2008/031551; WO 2007/136103; WO 2007/087245; WO 2007/057399; WO 2005/051366; WO 2005/062795; and WO 2005/044835; and J. Med. Chem. 2012, 55 (10), 4872-4876, all of which are hereby incorporated by reference in their entireties.

Non-limiting examples of receptor tyrosine kinase (e.g., Trk) targeted therapeutic agents, include afatinib, cabozantinib, cetuximab, crizotinib, dabrafenib, entrectinib, erlotinib, gefitinib, imatinib, lapatinib, lestaurtinib, nilotinib, pazopanib, panitumumab, pertuzumab, sunitinib, trastuzumab, 1-((3S,4R)-4-(3-fluorophenyl)-1-(2-methoxyethyl)pyrrolidin-3-yl)-3-(4-methyl-3-(2-methylpyrimidin-5-yl)-1-phenyl-1H-pyrazol-5-yl)urea, AG 879, AR-772, AR-786, AR-256, AR-618, AZ-23, AZ623, DS-6051, Gö 6976, GNF-5837, GTx-186, GW 441756, LOXO-101, MGCD516, PLX7486, RXDX101, TPX-0005, and TSR-011. Additional Trk targeted therapeutic agents include those described in U.S. Pat. Nos. 8,450,322; 8,513,263; 8,933,084; 8,791,123; 8,946,226; 8,450,322; 8,299,057; and 8,912,194; U.S. Publication No. 2016/0137654; 2015/0166564; 2015/0051222; 2015/0283132; and 2015/0306086; International Publication No. WO 2010/033941; WO 2010/048314; WO 2016/077841; WO 2011/146336; WO 2011/006074; WO 2010/033941; WO 2012/158413; WO 2014078454; WO 2014078417; WO 2014078408; WO 2014078378; WO 2014078372; WO 2014078331; WO 2014078328; WO 2014078325; WO 2014078323; WO 2014078322; WO 2015175788; WO 2009/013126; WO 2013/174876; WO 2015/124697; WO 2010/058006; WO 2015/017533; WO 2015/112806; WO 2013/183578; and WO 2013/074518, all of which are hereby incorporated by reference in their entireties.

Further examples of Trk inhibitors can be found in U.S. Pat. No. 8,637,516, International Publication No. WO 2012/034091, U.S. Pat. No. 9,102,671, International Publication No. WO 2012/116217, U.S. Publication No. 2010/0297115, International Publication No. WO 2009/053442, U.S. Pat. No. 8,642,035, International Publication No. WO 2009092049, U.S. Pat. No. 8,691,221, International Publication No. WO2006131952, all of which are incorporated by reference in their entireties herein. Exemplary Trk inhibitors include GNF-4256, described in *Cancer Chemother. Pharmacol.* 75(1):131-141, 2015; and GNF-5837 (N-[3-[[2,3-dihydro-2-oxo-3-(1H-pyrrol-2-ylmethylene)-1H-indol-6-yl]amino]-4-methylphenyl]-N'-[2-fluoro-5-(trifluoromethyl)phenyl]-urea), described in *ACS Med. Chem. Lett.* 3(2):140-145, 2012, each of which is incorporated by reference in its entirety herein.

Additional examples of Trk inhibitors include those disclosed in U.S. Publication No. 2010/0152219, U.S. Pat. No. 8,114,989, and International Publication No. WO 2006/123113, all of which are incorporated by reference in their entireties herein. Exemplary Trk inhibitors include AZ623, described in *Cancer* 117(6):1321-1391, 2011; AZD6918, described in *Cancer Biol. Ther.* 16(3):477-483, 2015; AZ64, described in *Cancer Chemother. Pharmacol.* 70:477-486, 2012; AZ-23 ((S)-5-Chloro-N2-(1-(5-fluoropyridin-2-yl)ethyl)-N4-(5-isopropoxy-1H-pyrazol-3-yl)pyrimidine-2,4-diamine), described in *Mol. Cancer Ther.* 8:1818-1827, 2009; and AZD7451; each of which is incorporated by reference in its entirety.

A Trk inhibitor can include those described in U.S. Pat. Nos. 7,615,383; 7,384,632; 6,153,189; 6,027,927; 6,025,166; 5,910,574; 5,877,016; and 5,844,092, each of which is incorporated by reference in its entirety.

Further examples of Trk inhibitors include CEP-751, described in *Int. J. Cancer* 72:672-679, 1997; CT327, described in *Acta Derm. Venereol.* 95:542-548, 2015; compounds described in International Publication No. WO 2012/034095; compounds described in U.S. Pat. No. 8,673,347 and International Publication No. WO 2007/022999; compounds described in U.S. Pat. No. 8,338,417; compounds described in International Publication No. WO 2016/027754; compounds described in U.S. Pat. No. 9,242,977; compounds described in U.S. Publication No. 2016/0000783; sunitinib (N-(2-diethylaminoethyl)-5-[(Z)-(5-fluoro-2-oxo-1H-indol-3-ylidene)methyl]-2,4-dimethyl-1H-pyrrole-3-carboxamide), as described in *PLoS One* 9:e95628, 2014; compounds described in International Publication No. WO 2011/133637; compounds described in U.S. Pat. No. 8,637,256; compounds described in *Expert. Opin. Ther. Pat.* 24(7):731-744, 2014; compounds described in *Expert Opin. Ther. Pat.* 19(3):305-319, 2009; (R)-2-phenylpyrrolidine substituted imidazopyridazines, e.g., GNF-8625, (R)-1-(6-(6-(2-(3-fluorophenyl)pyrrolidin-1-yl)imidazo[1,2-b]pyridazin-3-yl)-[2,4'-bipyridin]-2'-yl)piperidin-4-ol as described in ACS Med. Chem. Lett. 6(5):562-567, 2015; GTx-186 and others, as described in *PLoS One* 8(12):e83380, 2013; K252a ((9S-(9α, 10β,12α))-2,3,9,10,11,12-hexahydro-10-hydroxy-10-(methoxycarbonyl)-9-methyl-9,12-epoxy-1H-diindolo[1,2,3-fg:3',2',1'-kl]pyrrolo[3,4-i][1,6]benzodiazocin-1-one), as described in *Mol. Cell Biochem.* 339(1-2):201-213, 2010; 4-aminopyrazolylpyrimidines, e.g., AZ-23 (((S)-5-chloro-N2-(1-(5-fluoropyridin-2-yl)ethyl)-N4-(5-isopropoxy-1H-pyrazol-3-yl)pyrimidine-2,4-diamine)), as described in *J. Med. Chem.* 51(15):

4672-4684, 2008; PHA-739358 (danusertib), as described in *Mol. Cancer Ther.* 6:3158, 2007; Gö 6976 (5,6,7,13-tetrahydro-13-methyl-5-oxo-12H-indolo[2,3-a]pyrrolo[3,4-c]carbazole-12-propanenitrile), as described in *J. Neurochem.* 72:919-924, 1999; GW441756 ((3Z)-3-[(1-methylindol-3-yl)methylidene]-1H-pyrrolo[3,2-b]pyridin-2-one), as described in *IJAE* 115:117, 2010; milciclib (PHA-848125AC), described in *J. Carcinog.* 12:22, 2013; AG-879 ((2E)-3-[3,5-Bis(1,1-dimethylethyl)-4-hydroxyphenyl]-2-cyano-2-propenethioamide); altiratinib (N-(4-((2-(cyclopropanecarboxamido)pyridin-4-yl)oxy)-2,5-difluorophenyl)-N-(4-fluorophenyl)cyclopropane-1,1-dicarboxamide); cabozantinib (N-(4-((6,7-Dimethoxyquinolin-4-yl)oxy)phenyl)-N'-(4-fluorophenyl)cyclopropane-1,1-dicarboxamide); lestaurtinib ((5 S,6S,8R)-6-Hydroxy-6-(hydroxymethyl)-5-methyl-7,8,14,15-tetrahydro-5H-16-oxa-4b,8a, 14-triaza-5,8-methanodibenzo[b,h]cycloocta[jkl]cyclopenta[e]-as-indacen-13(6H)-one); dovatinib (4-amino-5-fluoro-3-[6-(4-methylpiperazin-1-yl)-1H-benzimidazol-2-yl]quinolin-2 (1H)-one mono 2-hydroxypropanoate hydrate); sitravatinib (N-(3-fluoro-4-((2-(5-(((2-methoxyethyl)amino)methyl)pyridin-2-yl)thieno[3,2-b]pyridin-7-yl)oxy)phenyl)-N-(4-fluorophenyl)cyclopropane-1,1-dicarboxamide); ONO-5390556; regorafenib (4-[4-({[4-Chloro-3-(trifluoromethyl)phenyl]carbamoyl}amino)-3-fluorophenoxy]-N-methylpyridine-2-carboxamide hydrate); and VSR-902A; all of the references above are incorporated by reference in their entireties herein.

The ability of a Trk inhibitor to act as a TrkA, TrkB, and/or Trk C inhibitor may be tested using the assays described in Examples A and B in U.S. Pat. No. 8,513,263, which is incorporated herein by reference.

In some embodiments, signal transduction pathway inhibitors include Ras-Raf-MEK-ERK pathway inhibitors (e.g., binimetinib, selumetinib, encorafinib, sorafenib, trametinib, and vemurafenib), PI3K-Akt-mTOR-S6K pathway inhibitors (e.g. everolimus, rapamycin, perifosine, temsirolimus), and other kinase inhibitors, such as baricitinib, brigatinib, capmatinib, danusertib, ibrutinib, milciclib, quercetin, regorafenib, ruxolitinib, semaxanib, AP32788, BLU285, BLU554, INCB39110, INCB40093, INCB50465, INCB52793, INCB54828, MGCD265, NMS-088, NMS-1286937, PF 477736 ((R)-amino-N-[5,6-dihydro-2-(1-methyl-1H-pyrazol-4-yl)-6-oxo-1Hpyrrolo[4,3,2-ef][2,3]benzodiazepin-8-yl]-cyclohexaneacetamide), PLX3397, PLX7486, PLX8394, PLX9486, PRN1008, PRN1371, RXDX103, RXDX106, RXDX108, and TG101209 (N-tert-butyl-3-(5-methyl-2-(4-(4-methylpiperazin-1-yl)phenylamino)pyrimidin-4-ylamino)benzenesulfonamide).

Non-limiting examples of checkpoint inhibitors include ipilimumab, tremelimumab, nivolumab, pidilizumab, MPDL3208A, MEDI4736, MSB0010718C, BMS-936559, BMS-956559, BMS-935559 (MDX-1105), AMP-224, and pembrolizumab.

In some embodiments, cytotoxic chemotherapeutics are selected from arsenic trioxide, bleomycin, cabazitaxel, capecitabine, carboplatin, cisplatin, cyclophosphamide, cytarabine, dacarbazine, daunorubicin, docetaxel, doxorubicin, etoposide, fluorouracil, gemcitabine, irinotecan, lomustine, methotrexate, mitomycin C, oxaliplatin, paclitaxel, pemetrexed, temozolomide, and vincristine.

Non-limiting examples of angiogenesis-targeted therapies include aflibercept and bevacizumab.

The term "immunotherapy" refers to an agent that modulates the immune system. In some embodiments, an immunotherapy can increase the expression and/or activity of a regulator of the immune system. In some embodiments, an immunotherapy can decrease the expression and/or activity of a regulator of the immune system. In some embodiments, an immunotherapy can recruit and/or enhance the activity of an immune cell.

In some embodiments, the immunotherapy is a cellular immunotherapy (e.g., adoptive T-cell therapy, dendritic cell therapy, natural killer cell therapy). In some embodiments, the cellular immunotherapy is sipuleucel-T (APC8015; Provenge™; Plosker (2011) Drugs 71(1): 101-108). In some embodiments, the cellular immunotherapy includes cells that express a chimeric antigen receptor (CAR). In some embodiments, the cellular immunotherapy is a CAR-T cell therapy. In some embodiments, the CAR-T cell therapy is tisagenlecleucel (Kymriah™).

In some embodiments, the immunotherapy is an antibody therapy (e.g., a monoclonal antibody, a conjugated antibody). In some embodiments, the antibody therapy is bevacizumab (Mvasti™, Avastin®), trastuzumab (Herceptin®), avelumab (Bavencio®), rituximab (MabThera™, Rituxan®), edrecolomab (Panorex), daratumuab (Darzalex®), olaratumab (Lartruvo™), ofatumumab (Arzerra®), alemtuzumab (Campath®), cetuximab (Erbitux®), oregovomab, pembrolizumab (Keytruda®), dinutiximab (Unituxin®), obinutuzumab (Gazyva®), tremelimumab (CP-675,206), ramucirumab (Cyramza®), ublituximab (TG-1101), panitumumab (Vectibix®), elotuzumab (Empliciti™), avelumab (Bavencio®), necitumumab (Portrazza™), cirmtuzumab (UC-961), ibritumomab (Zevalin®), isatuximab (SAR650984), nimotuzumab, fresolimumab (GC1008), lirilumab (INN), mogamulizumab (Poteligeo®), ficlatuzumab (AV-299), denosumab (Xgeva®), ganitumab, urelumab, pidilizumab or amatuximab.

In some embodiments, the immunotherapy is an antibody-drug conjugate. In some embodiments, the antibody-drug conjugate is gemtuzumab ozogamicin (Mylotarg™), inotuzumab ozogamicin (Besponsa®), brentuximab vedotin (Adcetris®), ado-trastuzumab emtansine (TDM-1; Kadcyla®), mirvetuximab soravtansine (IMGN853) or anetumab ravtansine In some embodiments, the immunotherapy includes blinatumomab (AMG103; Blincyto®) or midostaurin (Rydapt).

In some embodiments, the immunotherapy includes a toxin. In some embodiments, the immunotherapy is denileukin diftitox (Ontak®).

In some embodiments, the immunotherapy is a cytokine therapy. In some embodiments, the cytokine therapy is an interleukin 2 (IL-2) therapy, an interferon alpha (IFNα) therapy, a granulocyte colony stimulating factor (G-CSF) therapy, an interleukin 12 (IL-12) therapy, an interleukin 15 (IL-15) therapy, an interleukin 7 (IL-7) therapy or an erythropoietin-alpha (EPO) therapy. In some embodiments, the IL-2 therapy is aldesleukin (Proleukin®). In some embodiments, the IFNα therapy is IntronA® (Roferon-A®). In some embodiments, the G-CSF therapy is filgrastim (Neupogen®).

In some embodiments, the immunotherapy is an immune checkpoint inhibitor. In some embodiments, the immunotherapy includes one or more immune checkpoint inhibitors. In some embodiments, the immune checkpoint inhibitor is a CTLA-4 inhibitor, a PD-1 inhibitor or a PD-L1 inhibitor. In some embodiments, the CTLA-4 inhibitor is ipilimumab (Yervoy®) or tremelimumab (CP-675,206). In some embodiments, the PD-1 inhibitor is pembrolizumab (Keytruda®) or nivolumab (Opdivo®). In some embodiments, the PD-L1 inhibitor is atezolizumab (Tecentriq®), avelumab (Bavencio®) or durvalumab (Imfinzi™).

In some embodiments, the immunotherapy is mRNA-based immunotherapy. In some embodiments, the mRNA-based immunotherapy is CV9104 (see, e.g., Rausch et al. (2014) Human Vaccin Immunother 10(11): 3146-52; and Kubler et al. (2015) J. Immunother Cancer 3:26).

In some embodiments, the immunotherapy is *bacillus* Calmette-Guerin (BCG) therapy.

In some embodiments, the immunotherapy is an oncolytic virus therapy. In some embodiments, the oncolytic virus therapy is talimogene alherparepvec (T-VEC; Imlygic®).

In some embodiments, the immunotherapy is a cancer vaccine. In some embodiments, the cancer vaccine is a human papillomavirus (HPV) vaccine. In some embodiments, the HPV vaccine is Gardasil®, Gardasil9® or Cervarix®. In some embodiments, the cancer vaccine is a hepatitis B virus (HBV) vaccine. In some embodiments, the HBV vaccine is Engerix-B®, Recombivax HB® or GI-13020 (Tarmogen®). In some embodiments, the cancer vaccine is Twinrix® or Pediarix®. In some embodiments, the cancer vaccine is BiovaxID®, Oncophage®, GVAX, ADXS11-001, ALVAC-CEA, PROSTVAC®, Rindopepimut®, CimaVax-EGF, lapuleucel-T (APC8024; Neuvenge™), GRNVAC1, GRNVAC2, GRN-1201, hepcortespenlisimut-L (Hepko-V5), DCVAX®, SCIB1, BMT CTN 1401, PrCa VBIR, PANVAC, ProstAtak®, DPX-Survivac, or viagenpumatucel-L (HS-110).

In some embodiments, the immunotherapy is a peptide vaccine. In some embodiments, the peptide vaccine is nelipepimut-S(E75) (NeuVax™), IMA901, or SurVaxM (SVN53-67). In some embodiments, the cancer vaccine is an immunogenic personal neoantigen vaccine (see, e.g., Ott et al. (2017) Nature 547: 217-221; Sahin et al. (2017) Nature 547: 222-226). In some embodiments, the cancer vaccine is RGSH4K, or NEO-PV-01. In some embodiments, the cancer vaccine is a DNA-based vaccine. In some embodiments, the DNA-based vaccine is a mammaglobin-A DNA vaccine (see, e.g., Kim et al. (2016) OncoImmunology 5(2): e1069940).

In some embodiments, immune-targeted agents are selected from aldesleukin, interferon alfa-2b, ipilimumab, lambrolizumab, nivolumab, prednisone, and sipuleucel-T.

Non-limiting examples of radiotherapy include radioiodide therapy, external-beam radiation, and radium 223 therapy.

Additional kinase inhibitors include those described in, for example, U.S. Pat. Nos. 7,514,446; 7,863,289; 8,026,247; 8,501,756; 8,552,002; 8,815,901; 8,912,204; 9,260,437; 9,273,051; U.S. Publication No. US 2015/0018336; International Publication No. WO 2007/002325; WO 2007/002433; WO 2008/080001; WO 2008/079906; WO 2008/079903; WO 2008/079909; WO 2008/080015; WO 2009/007748; WO 2009/012283; WO 2009/143018; WO 2009/143024; WO 2009/014637; 2009/152083; WO 2010/111527; WO 2012/109075; WO 2014/194127; WO 2015/112806; WO 2007/110344; WO 2009/071480; WO 2009/118411; WO 2010/031816; WO 2010/145998; WO 2011/092120; WO 2012/101032; WO 2012/139930; WO 2012/143248; WO 2012/152763; WO 2013/014039; WO 2013/102059; WO 2013/050448; WO 2013/050446; WO 2014/019908; WO 2014/072220; WO 2014/184069; and WO 2016/075224 all of which are hereby incorporated by reference in their entireties.

Further examples of kinase inhibitors include those described in, for example, WO 2016/081450; WO 2016/022569; WO 2016/011141; WO 2016/011144; WO 2016/011147; WO 2015/191667; WO 2012/101029; WO 2012/113774; WO 2015/191666; WO 2015/161277; WO 2015/161274; WO 2015/108992; WO 2015/061572; WO 2015/058129; WO 2015/057873; WO 2015/017528; WO/2015/017533; WO 2014/160521; and WO 2014/011900, each of which is hereby incorporated by reference in its entirety.

Accordingly, also provided herein is a method of treating cancer, comprising administering to a patient in need thereof a pharmaceutical combination for treating cancer which comprises (a) a compound of Formula I or a pharmaceutically acceptable salt or solvate thereof, (b) an additional therapeutic agent, and (c) optionally at least one pharmaceutically acceptable carrier for simultaneous, separate or sequential use for the treatment of cancer, wherein the amounts of the compound of Formula I or a pharmaceutically acceptable salt or solvate thereof and the additional therapeutic agent are together effective in treating the cancer.

In some embodiments, the additional therapeutic agent(s) includes any one of the above listed therapies or therapeutic agents which are standards of care in cancers wherein the cancer has a dysregulation of a RET gene, a RET protein, or expression or activity, or level of any of the same.

These additional therapeutic agents may be administered with one or more doses of the compound of Formula I, or a pharmaceutically acceptable salt or solvate thereof, or pharmaceutical composition thereof, as part of the same or separate dosage forms, via the same or different routes of administration, and/or on the same or different administration schedules according to standard pharmaceutical practice known to one skilled in the art.

Also provided herein is (i) a pharmaceutical combination for treating a cancer in a patient in need thereof, which comprises (a) a compound of Formula I or a pharmaceutically acceptable salt or solvate thereof, (b) at least one additional therapeutic agent (e.g., any of the exemplary additional therapeutic agents described herein or known in the art), and (c) optionally at least one pharmaceutically acceptable carrier for simultaneous, separate or sequential use for the treatment of cancer, wherein the amounts of the compound of Formula I or pharmaceutically acceptable salt or solvate thereof and of the additional therapeutic agent are together effective in treating the cancer; (ii) a pharmaceutical composition comprising such a combination; (iii) the use of such a combination for the preparation of a medicament for the treatment of cancer; and (iv) a commercial package or product comprising such a combination as a combined preparation for simultaneous, separate or sequential use; and to a method of treatment of cancer in a patient in need thereof. In one embodiment the patient is a human. In some embodiments, the cancer is a RET-associated cancer. For example, a RET-associated cancer having one or more RET inhibitor resistance mutations.

The term "pharmaceutical combination", as used herein, refers to a pharmaceutical therapy resulting from the mixing or combining of more than one active ingredient and includes both fixed and non-fixed combinations of the active ingredients. The term "fixed combination" means that a compound of Formula I or a pharmaceutically acceptable salt or solvate thereof and at least one additional therapeutic agent (e.g., a chemotherapeutic agent), are both administered to a patient simultaneously in the form of a single composition or dosage. The term "non-fixed combination" means that a compound of Formula I or a pharmaceutically acceptable salt or solvate thereof and at least one additional therapeutic agent (e.g., chemotherapeutic agent) are formulated as separate compositions or dosages such that they may be administered to a patient in need thereof simultaneously, concurrently or sequentially with variable intervening time limits, wherein such administration provides effective levels of the two or more compounds in the body of the patient. These also apply to cocktail therapies, e.g. the administration of three or more active ingredients Accordingly, also provided herein is a method of treating a cancer, comprising administering to a patient in need thereof a pharmaceutical combination for treating cancer which comprises (a) a compound of Formula I or pharmaceutically acceptable salt or solvate thereof, (b) an additional therapeutic agent, and (c) optionally at least one pharmaceutically acceptable carrier for simultaneous, separate or sequential use for the treatment of cancer, wherein the amounts of the compound of Formula I or pharmaceutically acceptable salt or solvate thereof and the additional therapeutic agent are together effective in treating the cancer. In one embodiment, the compound of Formula I or pharmaceutically acceptable salt or solvate thereof, and the additional therapeutic agent are administered simultaneously as separate dosages. In one embodiment, the compound of Formula I or pharmaceutically acceptable salt or solvate thereof, and the additional therapeutic agent are administered as separate dosages sequentially in any order, in jointly therapeutically effective amounts, e.g. in daily or intermittently dosages. In one embodiment, the compound of Formula I or pharmaceutically acceptable salt or solvate thereof, and the additional therapeutic agent are administered simultaneously as a combined dosage. In some embodiments, the cancer is a RET-associated cancer. For example, a RET-associated cancer having one or more RET inhibitor resistance mutations.

Also provided herein is a method of treating a disease or disorder mediated by RET in a patient in need of such treatment, the method comprising administering to the patient a therapeutically effective amount of a compound of Formula I or a pharmaceutically acceptable salt or solvate thereof or a pharmaceutical composition thereof. In some embodiments, the disease or disorder mediated by RET is a dysregulation of RET gene, a RET kinase, or expression or activity or level of any of the same. For example the dysregulation of a RET gene, a RET kinase, or expression or activity or level of any of the same includes one or more RET inhibitor resistance mutations. A disease or disorder mediated by RET can include any disease, disorder or condition that is directly or indirectly linked to expression or activity of RET, including overexpression and/or abnormal activity levels. In one embodiment, the disease is cancer (e.g., a RET-associated cancer). In one embodiment, the cancer is any of the cancers or RET-associated cancers described herein.

Although the genetic basis of tumorigenesis may vary between different cancer types, the cellular and molecular mechanisms required for metastasis appear to be similar for all solid tumor types. During a metastatic cascade, the cancer cells lose growth inhibitory responses, undergo alterations in adhesiveness and produce enzymes that can degrade extracellular matrix components. This leads to detachment of tumor cells from the original tumor, infiltration into the circulation through newly formed vasculature, migration and extravasation of the tumor cells at favorable distant sites where they may form colonies. A number of genes have been identified as being promoters or suppressors of metastasis. For example, overexpression of glial cell-derived neurotrophic factor (GDNF) and its RET receptor tyrosine kinase have been correlated with cancer proliferation and metastasis. See, e.g., Zeng, Q. et al. *J. Int. Med. Res.* (2008) 36(4): 656-64.

Accordingly, also provided herein are methods for inhibiting, preventing, aiding in the prevention, or decreasing the symptoms of metastasis of a cancer in a patient in need thereof, the method comprising administering to the patient a therapeutically effective amount of a compound of Formula I or a pharmaceutically acceptable salt or solvate thereof or a pharmaceutical composition thereof. Such methods can be used in the treatment of one or more of the cancers described herein. See, e.g., US Publication No. 2013/0029925; International Publication No. WO 2014/083567; and U.S. Pat. No. 8,568,998. In some embodiments, the cancer is a RET-associated cancer. In some embodiments, the compound of Formula I or a pharmaceutically acceptable salt or solvate thereof is used in combination with an additional therapy or another therapeutic agent, including a chemotherapeutic agent, such as a kinase inhibitor. For example, a first or second RET kinase inhibitor.

The term "metastasis" is an art known term and means the formation of an additional tumor (e.g., a solid tumor) at a site distant from a primary tumor in a subject or patient, where the additional tumor includes the same or similar cancer cells as the primary tumor.

Also provided are methods of decreasing the risk of developing a metastasis or an additional metastasis in a patient having a RET-associated cancer that include: selecting, identifying, or diagnosing a patient as having a RET-associated cancer, and administering a therapeutically effective amount of a compound of Formula I or a pharmaceutically acceptable salt or solvate thereof to the patient selected, identified, or diagnosed as having a RET-associated cancer. Also provided are methods of decreasing the risk of developing a metastasis or an additional metastasis in a patient having a RET-associated cancer that includes administering a therapeutically effective amount of a compound of Formula I or a pharmaceutically acceptable salt or solvent thereof to a patient having a RET-associated cancer. The decrease in the risk of developing a metastasis or an additional metastasis in a patient having a RET-associated cancer can be compared to the risk of developing a metastasis or an additional metastasis in the patient prior to treatment, or as compared to a patient or a population of patients having a similar or the same RET-associated cancer that has received no treatment or a different treatment. In some embodiments, the RET-associated cancer is a RET-associated cancer having one or more RET inhibitor resistance mutations.

The phrase "risk of developing a metastasis" means the risk that a subject or patient having a primary tumor will develop an additional tumor (e.g., a solid tumor) at a site distant from a primary tumor in a subject or patient over a set period of time, where the additional tumor includes the same or similar cancer cells as the primary tumor. Methods for reducing the risk of developing a metastasis in a subject or patient having a cancer are described herein.

The phrase "risk of developing additional metastases" means the risk that a subject or patient having a primary tumor and one or more additional tumors at sites distant from the primary tumor (where the one or more additional tumors include the same or similar cancer cells as the primary tumor) will develop one or more further tumors distant from the primary tumor, where the further tumors include the same or similar cancer cells as the primary tumor. Methods for reducing the risk of developing additional metastasis are described herein.

As used herein, a "first RET kinase inhibitor" or "first RET inhibitor" is a RET kinase inhibitor as defined herein, but which does not include a compound of Formula I or a pharmaceutically acceptable salt or solvate thereof as defined herein. As used herein, a "second RET kinase inhibitor" or a "second RET inhibitor" is a RET kinase inhibitor as defined herein, but which does not include a compound of Formula I or a pharmaceutically acceptable salt or solvate thereof as defined herein. When both a first and a second RET inhibitor are present in a method provided herein, the first and second RET kinase inhibitor are different.

In some embodiments, the presence of one or more RET inhibitor resistance mutations in a tumor causes the tumor to be more resistant to treatment with a first RET inhibitor. Methods useful when a RET inhibitor resistance mutation causes the tumor to be more resistant to treatment with a first RET inhibitor are described below. For example, provided herein are methods of treating a subject having a cancer that include: identifying a subject having a cancer cell that has one or more RET inhibitor resistance mutations; and administering to the identified subject a compound of Formula I or a pharmaceutically acceptable salt or solvate thereof. In some embodiments, the compound of Formula I or a pharmaceutically acceptable salt or solvate thereof is administered in combination with the first RET inhibitor. Also provided are methods of treating a subject identified as having a cancer cell that has one or more RET inhibitor resistance mutations that include administering to the subject a compound of Formula I or a pharmaceutically acceptable salt or solvate thereof. In some embodiments, the compound of Formula I or a pharmaceutically acceptable salt or solvate thereof is administered in combination with the first RET inhibitor. In some embodiments, the one or more RET inhibitor resistance mutations confer increased resistance to a cancer cell or tumor to treatment with the first RET inhibitor. In some embodiments, the one or more RET inhibitor resistance mutations include one or more RET inhibitor resistance mutations listed in Tables 3 and 4. For example, the one or more RET inhibitor resistance mutations can include a substitution at amino acid position 804, e.g., V804M, V804L, or V804E.

For example, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of a first RET inhibitor, wherein the first RET inhibitor is selected from the group consisting of cabozantinib, vandetanib, alectinib, sorafenib, lenvatinib, ponatinib, dovitinib, sunitinib, foretinib, BLU667, and BLU6864. In some embodiments, the methods further comprise (after (b)) (c) determining whether a cancer cell in a sample obtained from the subject has at least one RET inhibitor resistance mutation; and (d) administering a compound of Formula I, or a pharmaceutically acceptable salt of solvate thereof as a monotherapy or in conjunction with another anticancer agent to the subject if the subject has a cancer cell that has at least one RET inhibitor resistance mutation; or (e) administering additional doses of the first RET inhibitor of step (b) to the subject if the subject has a cancer cell that does not have a RET inhibitor resistance mutation. In some embodiments, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of a first RET inhibitor, wherein the first RET inhibitor is selected from the group consisting of cabozantinib, vandetanib, alectinib, sorafenib, lenvatinib, ponatinib, dovitinib, sunitinib, foretinib, BLU667, and BLU6864. In some embodiments, the methods further comprise (after (b)) (c) determining whether a cancer cell in a sample obtained from the subject has at least one RET inhibitor resistance mutation; and (d) administering a compound of Formula I selected from i) Example No. 1-20; ii) Example No. 21-40; iii) Example No. 41-49; iv) Example No. 50-70; v) Example No. 71-89; vi) Example No. 90-109; vii) Example No. 110-129; viii) Example No. 130-149; ix) Example No. 150-169; x) Example No. 170-189; xi) Example No. 190-209; xii) Example No. 210-229; xiii) Example No. 230-249; xiv) Example No. 250-259; xv) Example No. 270-289; xvi) Example No. 290-309; xvii) Example No. 310-329; xviii) Example No. 330-349; xix) Example No. 350-369; xx) Example No. 370-384; xxi) Example No. 385-394; xxii) Example No. 395-407; xxiii) Example No. 408-427; xxiii) Example No. 428-447; xxiv) Example No. 448-467; or xxvi) Example No. 468-488; xxvii) Example No. 489-509; xxviii) Example No. 510-530; xxvix) Example No. 531-551; xxx) Example No. 552-572; xxxi) Example No. 573-593; xxxii) Example No. 594-614; xxxiii) Example No. 615-635; xxxiv) Example No. 636-686; xxxv) Example No. 687-707; xxxvi) Example No. 708-728; xxxvii) Example No. 729-749; xxxviii) Example No. 750-770; xxxix) Example No. 771-791; xl) Example No. 792-812; xli) Example No. 813-819, or a pharmaceutically acceptable salt of solvate thereof as a monotherapy or in conjunction with another anticancer agent to the subject if the subject has a cancer cell that has at least one RET inhibitor resistance mutation; or (e) administering additional doses of the first RET inhibitor of step (b) to the subject if the subject has a cancer cell that does not have a RET inhibitor resistance mutation. In some embodiments, provided herein are methods for treating a RET-associated cancer in a subject in need of such treatment, the method comprising (a) detecting one or more fusion proteins of Table 1 and/or one or more RET kinase protein point mutations/insertions/deletions of Table 2 in a sample from the subject; and (b) administering to the subject a therapeutically effective amount of a first RET inhibitor, wherein the first RET inhibitor is selected from the group consisting of cabozantinib, vandetanib, alectinib, sorafenib, lenvatinib, ponatinib, dovitinib, sunitinib, foretinib, BLU667, and BLU6864. In some embodiments, the methods further comprise (after (b)) (c) determining whether a cancer cell in a sample obtained from the subject has at least one RET inhibitor resistance mutation of Tables 3 or 4; and (d) administering a compound of Formula I selected from i) Example No. 1-20; ii) Example No. 21-40; iii) Example No. 41-49; iv) Example No. 50-70; v) Example No. 71-89; vi) Example No. 90-109; vii) Example No. 110-129; viii) Example No. 130-149; ix) Example No. 150-169; x) Example No. 170-189; xi) Example No. 190-209; xii) Example No. 210-229; xiii) Example No. 230-249; xiv) Example No. 250-259; xv) Example No. 270-289; xvi) Example No. 290-309; xvii) Example No. 310-329; xviii) Example No. 330-349; xix) Example No. 350-369; xx) Example No. 370-384; xxi) Example No. 385-394; xxii) Example No. 395-407; xxiii) Example No. 408-427; xxiii) Example No. 428-447; xxiv) Example No. 448-467; or xxvi) Example No. 468-488; xxvii) Example No. 489-509; xxviii) Example No. 510-530; xxvix) Example No. 531-551; xxx) Example No. 552-572; xxxi) Example No. 573-593; xxxii) Example No. 594-614; xxxiii) Example No. 615-635; xxxiv) Example No. 636-686; xxxv) Example No. 687-707; xxxvi) Example No. 708-728; xxxvii) Example No. 729-749;

xxxviii) Example No. 750-770; xxxix) Example No. 771-791; xl) Example No. 792-812; xli) Example No. 813-819, or a pharmaceutically acceptable salt of solvate thereof as a monotherapy or in conjunction with another anticancer agent to the subject if the subject has a cancer cell that has at least one RET inhibitor resistance mutation; or (e) administering additional doses of the first RET inhibitor of step (b) to the subject if the subject has a cancer cell that does not have a RET inhibitor resistance mutation. In some embodiments, provided herein are methods for treating a RET-associated cancer in a subject in need of such treatment, the method comprising (a) detecting the fusion protein KIF5B-RET in a sample from the subject; and (b) administering to the subject a therapeutically effective amount of a first RET inhibitor, wherein the first RET inhibitor is selected from the group consisting of cabozantinib, vandetanib, alectinib, sorafenib, lenvatinib, ponatinib, dovitinib, sunitinib, foretinib, BLU667, and BLU6864. In some embodiments, the methods further comprise (after (b)) (c) determining whether a cancer cell in a sample obtained from the subject has the RET inhibitor resistance mutation V804M; and (d) administering a compound of Formula I or a pharmaceutically acceptable salt or solvate thereof selected from the group consisting of a compound of Formula I selected from i) Example No. 1-20; ii) Example No. 21-40; iii) Example No. 41-49; iv) Example No. 50-70; v) Example No. 71-89; vi) Example No. 90-109; vii) Example No. 110-129; viii) Example No. 130-149; ix) Example No. 150-169; x) Example No. 170-189; xi) Example No. 190-209; xii) Example No. 210-229; xiii) Example No. 230-249; xiv) Example No. 250-259; xv) Example No. 270-289; xvi) Example No. 290-309; xvii) Example No. 310-329; xviii) Example No. 330-349; xix) Example No. 350-369; xx) Example No. 370-384; xxi) Example No. 385-394; xxii) Example No. 395-407; xxiii) Example No. 408-427; xxiii) Example No. 428-447; xxiv) Example No. 448-467; or xxvi) Example No. 468-488; xxvii) Example No. 489-509; xxviii) Example No. 510-530; xxvix) Example No. 531-551; xxx) Example No. 552-572; xxxi) Example No. 573-593; xxxii) Example No. 594-614; xxxiii) Example No. 615-635; xxxiv) Example No. 636-686; xxxv) Example No. 687-707; xxxvi) Example No. 708-728; xxxvii) Example No. 729-749; xxxviii) Example No. 750-770; xxxix) Example No. 771-791; xl) Example No. 792-812; xli) Example No. 813-819, or a pharmaceutically acceptable salt of solvate thereof as a monotherapy or in conjunction with another anticancer agent to the subject if the subject has a cancer cell that has at least one RET inhibitor resistance mutation; or (e) administering additional doses of the first RET inhibitor of step (b) to the subject if the subject has a cancer cell that does not have a RET inhibitor resistance mutation.

As another example, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of a compound of Formula I, or a pharmaceutically acceptable salt of solvate thereof. In some embodiments, the methods further comprise (after (b)) (c) determining whether a cancer cell in a sample obtained from the subject has at least one RET inhibitor resistance mutation; and (d) administering a second RET inhibitor, wherein the second RET inhibitor is selected from the group consisting of cabozantinib, vandetanib, alectinib, sorafenib, lenvatinib, ponatinib, dovitinib, sunitinib, foretinib, BLU667, and BLU6864, as a monotherapy or in conjunction with another anticancer agent to the subject if the subject has a cancer cell that has at least one RET inhibitor resistance mutation; or (e) administering additional doses of the compound of Formula I or a pharmaceutically acceptable salt or solvate thereof of step (b) to the subject if the subject has a cancer cell that does not have a RET inhibitor resistance mutation. In some embodiments, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of a compound of Formula I selected from i) Example No. 1-20; ii) Example No. 21-40; iii) Example No. 41-49; iv) Example No. 50-70; v) Example No. 71-89; vi) Example No. 90-109; vii) Example No. 110-129; viii) Example No. 130-149; ix) Example No. 150-169; x) Example No. 170-189; xi) Example No. 190-209; xii) Example No. 210-229; xiii) Example No. 230-249; xiv) Example No. 250-259; xv) Example No. 270-289; xvi) Example No. 290-309; xvii) Example No. 310-329; xviii) Example No. 330-349; xix) Example No. 350-369; xx) Example No. 370-384; xxi) Example No. 385-394; xxii) Example No. 395-407; xxiii) Example No. 408-427; xxiii) Example No. 428-447; xxiv) Example No. 448-467; or xxvi) Example No. 468-488; xxvii) Example No. 489-509; xxviii) Example No. 510-530; xxvix) Example No. 531-551; xxx) Example No. 552-572; xxxi) Example No. 573-593; xxxii) Example No. 594-614; xxxiii) Example No. 615-635; xxxiv) Example No. 636-686; xxxv) Example No. 687-707; xxxvi) Example No. 708-728; xxxvii) Example No. 729-749; xxxviii) Example No. 750-770; xxxix) Example No. 771-791; xl) Example No. 792-812; xli) Example No. 813-819, or a pharmaceutically acceptable salt of solvate thereof. In some embodiments, the methods further comprise (after (b)) (c) determining whether a cancer cell in a sample obtained from the subject has at least one RET inhibitor resistance mutation; and (d) administering a second RET inhibitor, wherein the second RET inhibitor is selected from the group consisting of cabozantinib, vandetanib, alectinib, sorafenib, lenvatinib, ponatinib, dovitinib, sunitinib, foretinib, BLU667, and BLU6864, as a monotherapy or in conjunction with another anticancer agent to the subject if the subject has a cancer cell that has at least one RET inhibitor resistance mutation; or (e) administering additional doses of the compound of Formula I or a pharmaceutically acceptable salt or solvate thereof of step (b) to the subject if the subject has a cancer cell that does not have a RET inhibitor resistance mutation. In some embodiments, provided herein are methods for treating a RET-associated cancer in a subject in need of such treatment, the method comprising (a) detecting one or more fusion proteins of Table 1 and/or one or more RET kinase protein point mutations/insertions/deletions of Table 2 in a sample from the subject; and (b) administering to the subject a therapeutically effective amount of a compound of Formula I selected from i) Example No. 1-20; ii) Example No. 21-40; iii) Example No. 41-49; iv) Example No. 50-70; v) Example No. 71-89; vi) Example No. 90-109; vii) Example No. 110-129; viii) Example No. 130-149; ix) Example No. 150-169; x) Example No. 170-189; xi) Example No. 190-209; xii) Example No. 210-229; xiii) Example No. 230-249; xiv) Example No. 250-259; xv) Example No. 270-289; xvi) Example No. 290-309; xvii) Example No. 310-329; xviii) Example No. 330-349; xix) Example No. 350-369; xx) Example No. 370-384; xxi) Example No. 385-394; xxii) Example No. 395-407; xxiii) Example No. 408-427; xxiii) Example No. 428-447; xxiv)

Example No. 448-467; or xxvi) Example No. 468-488; xxvii) Example No. 489-509; xxviii) Example No. 510-530; xxix) Example No. 531-551; xxx) Example No. 552-572; xxxi) Example No. 573-593; xxxii) Example No. 594-614; xxxiii) Example No. 615-635; xxxiv) Example No. 636-686; xxxv) Example No. 687-707; xxxvi) Example No. 708-728; xxxvii) Example No. 729-749; xxxviii) Example No. 750-770; xxxix) Example No. 771-791; xl) Example No. 792-812; xli) Example No. 813-819, or a pharmaceutically acceptable salt of solvate thereof. In some embodiments, the methods further comprise (after (b)) (c) determining whether a cancer cell in a sample obtained from the subject has at least one RET inhibitor resistance mutation of Tables 3 or 4; and (d) administering a second RET inhibitor, wherein the second RET inhibitor is selected from the group consisting of cabozantinib, vandetanib, alectinib, sorafenib, lenvatinib, ponatinib, dovitinib, sunitinib, foretinib, BLU667, and BLU6864, as a monotherapy or in conjunction with another anticancer agent to the subject if the subject has a cancer cell that has at least one RET inhibitor resistance mutation; or (e) administering additional doses of the compound of Formula I or a pharmaceutically acceptable salt or solvate thereof of step (b) to the subject if the subject has a cancer cell that does not have a RET inhibitor resistance mutation. In some embodiments, provided herein are methods for treating a RET-associated cancer in a subject in need of such treatment, the method comprising (a) detecting the fusion protein KIF5B-RET in a sample from the subject; and (b) administering to the subject a therapeutically effective amount of a compound of Formula I selected from i) Example No. 1-20; ii) Example No. 21-40; iii) Example No. 41-49; iv) Example No. 50-70; v) Example No. 71-89; vi) Example No. 90-109; vii) Example No. 110-129; viii) Example No. 130-149; ix) Example No. 150-169; x) Example No. 170-189; xi) Example No. 190-209; xii) Example No. 210-229; xiii) Example No. 230-249; xiv) Example No. 250-259; xv) Example No. 270-289; xvi) Example No. 290-309; xvii) Example No. 310-329; xviii) Example No. 330-349; xix) Example No. 350-369; xx) Example No. 370-384; xxi) Example No. 385-394; xxii) Example No. 395-407; xxiii) Example No. 408-427; xxiii) Example No. 428-447; xxiv) Example No. 448-467; or xxvi) Example No. 468-488; xxvii) Example No. 489-509; xxviii) Example No. 510-530; xxix) Example No. 531-551; xxx) Example No. 552-572; xxxi) Example No. 573-593; xxxii) Example No. 594-614; xxxiii) Example No. 615-635; xxxiv) Example No. 636-686; xxxv) Example No. 687-707; xxxvi) Example No. 708-728; xxxvii) Example No. 729-749; xxxviii) Example No. 750-770; xxxix) Example No. 771-791; xl) Example No. 792-812; xli) Example No. 813-819, or a pharmaceutically acceptable salt of solvate thereof. In some embodiments, the methods further comprise (after (b)) (c) determining whether a cancer cell in a sample obtained from the subject has the RET inhibitor resistance mutation V804M; and (d) administering a second RET inhibitor, wherein the second RET inhibitor is selected from the group consisting of cabozantinib, vandetanib, alectinib, sorafenib, lenvatinib, ponatinib, dovitinib, sunitinib, foretinib, BLU667, and BLU6864, as a monotherapy or in conjunction with another anticancer agent to the subject if the subject has a cancer cell that has at least one RET inhibitor resistance mutation; or (e) administering additional doses of the compound of Formula I or a pharmaceutically acceptable salt or solvate thereof of step (b) to the subject if the subject has a cancer cell that does not have a RET inhibitor resistance mutation.

Also, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of a compound of Formula I or a pharmaceutically acceptable salt or solvate thereof. In some embodiments, the methods further comprise (after (b)) (c) determining whether a cancer cell in a sample obtained from the subject has at least one RET inhibitor resistance mutation; and (d) administering additional doses of the compound of Formula I or a pharmaceutically acceptable salt or solvate thereof of step (b) to the subject as a monotherapy or in conjunction with another anticancer agent (e.g., a second RET inhibitor, a second compound of Formula I or a pharmaceutically acceptable salt thereof, or immunotherapy) or anticancer therapy (e.g., surgery or radiation) if the subject has a cancer cell that has at least one RET inhibitor resistance mutation. In some embodiments, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of a compound of Formula I selected from i) Example No. 1-20; ii) Example No. 21-40; iii) Example No. 41-49; iv) Example No. 50-70; v) Example No. 71-89; vi) Example No. 90-109; vii) Example No. 110-129; viii) Example No. 130-149; ix) Example No. 150-169; x) Example No. 170-189; xi) Example No. 190-209; xii) Example No. 210-229; xiii) Example No. 230-249; xiv) Example No. 250-259; xv) Example No. 270-289; xvi) Example No. 290-309; xvii) Example No. 310-329; xviii) Example No. 330-349; xix) Example No. 350-369; xx) Example No. 370-384; xxi) Example No. 385-394; xxii) Example No. 395-407; xxiii) Example No. 408-427; xxiii) Example No. 428-447; xxiv) Example No. 448-467; or xxvi) Example No. 468-488; xxvii) Example No. 489-509; xxviii) Example No. 510-530; xxvix) Example No. 531-551; xxx) Example No. 552-572; xxxi) Example No. 573-593; xxxii) Example No. 594-614; xxxiii) Example No. 615-635; xxxiv) Example No. 636-686; xxxv) Example No. 687-707; xxxvi) Example No. 708-728; xxxvii) Example No. 729-749; xxxviii) Example No. 750-770; xxxix) Example No. 771-791; xl) Example No. 792-812; xli) Example No. 813-819, or a pharmaceutically acceptable salt of solvate thereof. In some embodiments, the methods further comprise (after (b)) (c) determining whether a cancer cell in a sample obtained from the subject has at least one RET inhibitor resistance mutation; and (d) administering additional doses of the compound of Formula I or a pharmaceutically acceptable salt or solvate thereof of step (b) to the subject as a monotherapy or in conjunction with another anticancer agent (e.g., a second RET inhibitor, a second compound of Formula I or a pharmaceutically acceptable salt thereof, or immunotherapy) or anticancer therapy (e.g., surgery or radiation) if the subject has a cancer cell that has at least one RET inhibitor resistance mutation. In some embodiments, provided herein are methods for treating a RET-associated cancer in a subject in need of such treatment, the method comprising (a) detecting one or more fusion proteins of Table 1 and/or one or more RET kinase protein point mutations/insertions/deletions of Table 2 in a sample from the subject; and (b) administering to the subject a therapeutically effective amount of a compound of Formula I or a pharmaceutically acceptable salt or solvate thereof selected from the group consisting of a compound of Formula I selected from i) Example No. 1-20; ii) Example No. 21-40;

iii) Example No. 41-49; iv) Example No. 50-70; v) Example No. 71-89; vi) Example No. 90-109; vii) Example No. 110-129; viii) Example No. 130-149; ix) Example No. 150-169; x) Example No. 170-189; xi) Example No. 190-209; xii) Example No. 210-229; xiii) Example No. 230-249; xiv) Example No. 250-259; xv) Example No. 270-289; xvi) Example No. 290-309; xvii) Example No. 310-329; xviii) Example No. 330-349; xix) Example No. 350-369; xx) Example No. 370-384; xxi) Example No. 385-394; xxii) Example No. 395-407; xxiii) Example No. 408-427; xxiii) Example No. 428-447; xxiv) Example No. 448-467; or xxvi) Example No. 468-488; xxvii) Example No. 489-509; xxviii) Example No. 510-530; xxvix) Example No. 531-551; xxx) Example No. 552-572; xxxi) Example No. 573-593; xxxii) Example No. 594-614; xxxiii) Example No. 615-635; xxxiv) Example No. 636-686; xxxv) Example No. 687-707; xxxvi) Example No. 708-728; xxxvii) Example No. 729-749; xxxviii) Example No. 750-770; xxxix) Example No. 771-791; xl) Example No. 792-812; xli) Example No. 813-819, or a pharmaceutically acceptable salt of solvate thereof. In some embodiments, the methods further comprise (after (b)) (c) determining whether a cancer cell in a sample obtained from the subject has at least one RET inhibitor resistance mutation of Tables 3 or 4; and (d) administering additional doses of the compound of Formula I or a pharmaceutically acceptable salt or solvate thereof of step (b) to the subject as a monotherapy or in conjunction with another anticancer agent (e.g., a second RET inhibitor, a second compound of Formula I or a pharmaceutically acceptable salt thereof, or immunotherapy) or anticancer therapy (e.g., surgery or radiation) if the subject has a cancer cell that has at least one RET inhibitor resistance mutation. In some embodiments, a second RET inhibitor selected from the group consisting of cabozantinib, vandetanib, alectinib, sorafenib, lenvatinib, ponatinib, dovitinib, sunitinib, foretinib, BLU667, and BLU6864 is administered in step (d). In some embodiments, provided herein are methods for treating a RET-associated cancer in a subject in need of such treatment, the method comprising (a) detecting the fusion protein KIF5B-RET in a sample from the subject; and (b) administering to the subject a therapeutically effective amount of a compound of Formula I selected from i) Example No. 1-20; ii) Example No. 21-40; iii) Example No. 41-49; iv) Example No. 50-70; v) Example No. 71-89; vi) Example No. 90-109; vii) Example No. 110-129; viii) Example No. 130-149; ix) Example No. 150-169; x) Example No. 170-189; xi) Example No. 190-209; xii) Example No. 210-229; xiii) Example No. 230-249; xiv) Example No. 250-259; xv) Example No. 270-289; xvi) Example No. 290-309; xvii) Example No. 310-329; xviii) Example No. 330-349; xix) Example No. 350-369; xx) Example No. 370-384; xxi) Example No. 385-394; xxii) Example No. 395-407; xxiii) Example No. 408-427; xxiii) Example No. 428-447; xxiv) Example No. 448-467; or xxvi) Example No. 468-488; xxvii) Example No. 489-509; xxviii) Example No. 510-530; xxvix) Example No. 531-551; xxx) Example No. 552-572; xxxi) Example No. 573-593; xxxii) Example No. 594-614; xxxiii) Example No. 615-635; xxxiv) Example No. 636-686; xxxv) Example No. 687-707; xxxvi) Example No. 708-728; xxxvii) Example No. 729-749; xxxviii) Example No. 750-770; xxxix) Example No. 771-791; xl) Example No. 792-812; xli) Example No. 813-819, or a pharmaceutically acceptable salt of solvate thereof. In some embodiments, the methods further comprise (after (b)) (c) determining whether a cancer cell in a sample obtained from the subject has the RET inhibitor resistance mutation V804M; and (d) administering additional doses of the compound of Formula I or a pharmaceutically acceptable salt or solvate thereof of step (b) to the subject as a monotherapy or in conjunction with another anticancer agent (e.g., a second RET inhibitor, a second compound of Formula I or a pharmaceutically acceptable salt thereof, or immunotherapy) or anticancer therapy (e.g., surgery or radiation) if the subject has a cancer cell that has at least one RET inhibitor resistance mutation. In some embodiments, a second RET inhibitor selected from the group consisting of cabozantinib, vandetanib, alectinib, sorafenib, lenvatinib, ponatinib, dovitinib, sunitinib, foretinib, BLU667, and BLU6864 is administered in step (d).

Also provided are methods of selecting a treatment for a subject having a cancer that include: identifying a subject having a cancer cell that has one or more RET inhibitor resistance mutations; and selecting a treatment that includes administration of a compound of Formula I or a pharmaceutically acceptable salt or solvate thereof. In some embodiments, the one or more RET inhibitor resistance mutations confer increased resistance to a cancer cell or tumor to treatment with a first RET inhibitor. In some embodiments, the compound of Formula I or a pharmaceutically acceptable salt or solvate thereof is administered in combination with the first RET inhibitor. Also provided are methods of selecting a treatment for a subject having a cancer that include: selecting a treatment that includes administration of a compound of Formula I or a pharmaceutically acceptable salt or solvate thereof for a subject identified as having a cancer cell that has one or more RET inhibitor resistance mutations. Also provided are methods of selecting a subject having a cancer for a treatment that does not include a first RET inhibitor as a monotherapy that include: identifying a subject having a cancer cell that has one or more RET inhibitor resistance mutations; and selecting the identified subject for a treatment that includes a compound of Formula I or a pharmaceutically acceptable salt or solvate thereof. Also provided are methods of selecting a subject having a cancer for a treatment that does not include a first RET inhibitor as a monotherapy that include: selecting a subject identified as having a cancer cell that has one or more RET inhibitor resistance mutations for a treatment that includes administration of a compound of Formula I or a pharmaceutically acceptable salt or solvate thereof. In some embodiments, the one or more RET inhibitor resistance mutations include one or more RET inhibitor resistance mutations listed in Tables 3 and 4. In some embodiments, the one or more RET inhibitor resistance mutations can include a substitution at amino acid position 804, e.g., V804M, V804L, or V804E.

Also provided are methods of determining the likelihood that a subject having a cancer (e.g., a RET-associated cancer) will have a positive response to treatment with a first RET inhibitor as a monotherapy that include: determining whether a cancer cell in a sample obtained from the subject has one or more RET inhibitor resistance mutations; and determining that a subject having a cancer cell that has one or more RET inhibitor resistance mutations has a decreased likelihood of having a positive response (i.e. an increased likelihood of having a negative response) to treatment with a first RET inhibitor as a monotherapy. Also provided are methods of determining the likelihood that a subject having a cancer (e.g., a RET-associated cancer) will have a positive response to treatment with a first RET inhibitor as a monotherapy that include: determining whether a cancer cell in a sample obtained from the subject has one or more RET inhibitor resistance mutations; and determining that a subject not having a cancer cell that has one or more RET inhibitor resistance mutations has an increased likelihood of having a positive response to treatment with a first RET inhibitor as a monotherapy as compared to a subject having a cancer cell that has one or more RET inhibitor resistance mutations. Also provided are methods of predicting the efficacy of treatment with a first RET inhibitor as a monotherapy in a subject having cancer that include: determining whether a cancer cell in a sample obtained from the subject has one or more RET inhibitor resistance mutations; and determining that treatment with a first RET inhibitor as a monotherapy is less likely to be effective in a subject having a cancer cell in a sample obtained from the subject that has one or more RET inhibitor resistance mutations. Also provided are methods of predicting the efficacy of treatment with a first RET inhibitor as a monotherapy in a subject having cancer that include: determining that treatment with a first RET inhibitor as a monotherapy is less likely to be effective in a subject having a cancer cell in a sample obtained from the subject that has one or more RET inhibitor resistance mutations. In some embodiments, the one or more RET inhibitor resistance mutations confer increased resistance to a cancer cell or tumor to treatment with the first RET inhibitor. In some embodiments, the one or more RET inhibitor resistance mutations include one or more RET inhibitor resistance mutations listed in Tables 3 and 4. For example, the one or more RET inhibitor resistance mutations can include a substitution at amino acid position 804, e.g., V804M, V804L, or V804E.

Also provided are methods of treating a subject having a cancer that include: (a) administering one or more doses of a first RET inhibitor to the subject for a period of time; (b) after (a), determining whether a cancer cell in a sample obtained from the subject has at least one RET inhibitor resistance mutation; and (c) administering a compound of Formula I or a pharmaceutically acceptable salt or solvate thereof as a monotherapy or in conjunction with another anticancer agent to the subject if the subject has a cancer cell that has at least one RET inhibitor resistance mutation; or (d) administering additional doses of the first RET inhibitor of step (a) to the subject if the subject has a cancer cell that does not have a RET inhibitor resistance mutation. In some embodiments, where the subject is administered additional doses of the first RET inhibitor of step (a), the subject can also be administered another anticancer agent (e.g., a second RET inhibitor or a compound of Formula I or a pharmaceutically acceptable salt or solvate thereof, or immunotherapy). In some embodiments, the additional anticancer agent is any anticancer agent known in the art. For example, the additional anticancer agent is another RET inhibitor (e.g., a second RET inhibitor). In some embodiments, the additional anticancer agent is an immunotherapy. In some embodiments of step (c), another RET inhibitor can be the first RET inhibitor administered in step (a). In some embodiments, the one or more RET inhibitor resistance mutations confer increased resistance to a cancer cell or tumor to treatment with the first RET inhibitor. In some embodiments, the one or more RET inhibitor resistance mutations include one or more RET inhibitor resistance mutations listed in Tables 3 and 4. For example, the one or more RET inhibitor resistance mutations can include a substitution at amino acid position 804, e.g., V804M, V804L, or V804E.

Also provided are methods of treating a subject having a cancer that include: (a) administering one or more doses of a first RET inhibitor to the subject for a period of time; (b) after (a), determining whether a cancer cell in a sample obtained from the subject has at least one RET inhibitor resistance mutation; and (c) administering a second RET inhibitor as a monotherapy or in conjunction with another anticancer agent to the subject if the subject has a cancer cell that has at least one RET inhibitor resistance mutation; or (d) administering additional doses of the first RET inhibitor step (a) to the subject if the subject has a cancer cell that does not have a RET inhibitor resistance mutation. In some embodiments, where the subject is administered additional doses of the first RET inhibitor of step (a), the subject can also be administered another anticancer agent. In some embodiments, the one or more RET inhibitor resistance mutations confer increased resistance to a cancer cell or tumor to treatment with the first RET inhibitor. In some embodiments, the one or more RET inhibitor resistance mutations include one or more RET inhibitor resistance mutations listed in Tables 3 and 4. For example, the one or more RET inhibitor resistance mutations can include a substitution at amino acid position 804, e.g., V804M, V804L, or V804E. In some embodiments, the additional anticancer agent is any anticancer agent known in the art. For example, the additional anticancer agent is another RET inhibitor (e.g., a compound of Formula I or a pharmaceutically acceptable salt or solvate thereof). In some embodiments, the additional anticancer agent is an immunotherapy.

Also provided are methods of treating a subject having a cancer (e.g., a RET-associated cancer) that include: (a) determining whether a cancer cell in a sample obtained from a subject having a cancer and previously administered one or more doses of a first RET inhibitor, has one or more RET inhibitor resistance mutations; and (b) administering a compound of Formula I or a pharmaceutically acceptable salt or solvate thereof as a monotherapy or in conjunction with another anticancer agent to the subject if the subject has a cancer cell that has at least one RET inhibitor resistance mutation; or (c) administering additional doses of the first RET inhibitor previously administered to the subject if the subject has cancer cell that does not have a RET inhibitor resistance mutation. In some embodiments, where the subject is administered additional doses of the first RET inhibitor previously administered to the subject, the subject can also be administered another anticancer agent (e.g., a compound of Formula I or a pharmaceutically acceptable salt or solvate thereof, or immunotherapy). In some embodiments, the one or more RET inhibitor resistance mutations confer increased resistance to a cancer cell or tumor to treatment with the first RET inhibitor. In some embodiments, the one or more RET inhibitor resistance mutations include one or more RET inhibitor resistance mutations listed in Tables 3 and 4. For example, the one or more RET inhibitor resistance mutations can include a substitution at amino acid position 804, e.g., V804M, V804L, or V804E. In some embodiments, the additional anticancer agent is any anticancer agent known in the art. For example, the additional anticancer agent is another RET inhibitor (e.g., a second RET inhibitor). In some embodiments, the additional anticancer agent is an immunotherapy. In some embodiments of step (b), another anticancer agent can be the first RET inhibitor administered in step (a).

Also provided are methods of treating a subject having a cancer that include: (a) determining whether a cancer cell in a sample obtained from a subject having a cancer and previously administered one or more doses of a first RET inhibitor has one or more RET inhibitor resistance mutations; and (b) administering a second RET inhibitor as a monotherapy or in conjunction with another anticancer agent to the subject if the subject has a cancer cell that has at least one RET inhibitor resistance mutation; or (c) administering additional doses of the first RET inhibitor previously administered to the subject if the subject has a cancer cell that does not have a RET inhibitor resistance mutation. In some embodiments, where the subject is administered additional doses of the first RET inhibitor previously administered to the subject, the subject can also be administered another anticancer agent. In some embodiments, the one or more RET inhibitor resistance mutations confer increased resistance to a cancer cell or tumor to treatment with the first RET inhibitor. In some embodiments, the one or more RET inhibitor resistance mutations include one or more RET inhibitor resistance mutations listed in Tables 3 and 4. For example, the one or more RET inhibitor resistance mutations can include a substitution at amino acid position 804, e.g., V804M, V804L, or V804E. In some embodiments, the additional anticancer agent is any anticancer agent known in the art. For example, the additional anticancer agent is another RET inhibitor (e.g., a compound of Formula I or a pharmaceutically acceptable salt or solvate thereof). In some embodiments, the additional anticancer agent is an immunotherapy. In some embodiments of (b), another anticancer agent can be the first RET inhibitor administered in step (a).

Also provided are methods of selecting a treatment for a subject having a cancer that include (a) administering one or more doses of a first RET inhibitor to the subject for a period of time; (b) after (a), determining whether a cancer cell in a sample obtained from the subject has at least one RET inhibitor resistance mutation; and (c) selecting a compound of Formula I or a pharmaceutically acceptable salt or solvate thereof as a monotherapy or in conjunction with another anticancer agent for the subject if the subject has a cancer cell that has one or more RET inhibitor resistance mutations; or (d) selecting additional doses of the first RET inhibitor of step (a) for the subject if the subject has a cancer cell that does not have a RET inhibitor resistance mutation. In some embodiments, when additional doses of the first RET inhibitor of step (a) are selected for the subject, the method can further include selecting doses of another anticancer agent for the subject. In some embodiments, the one or more RET inhibitor resistance mutations confer increased resistance to a cancer cell or tumor to treatment with the first RET inhibitor. In some embodiments, the one or more RET inhibitor resistance mutations include one or more RET inhibitor resistance mutations listed in Tables 3 and 4. For example, the one or more RET inhibitor resistance mutations can include a substitution at amino acid position 804, e.g., V804M, V804L, or V804E. In some embodiments, the additional anticancer agent is any anticancer agent known in the art. For example, the additional anticancer agent is another RET inhibitor (e.g., a second RET inhibitor). In some embodiments, the additional anticancer agent is an immunotherapy. In some embodiments of step (c), another RET inhibitor can be the first RET inhibitor administered in step (a).

Also provided are methods of selecting a treatment for a subject having a cancer that include (a) administering one or more doses of a first RET inhibitor to the subject for a period of time; (b) after (a), determining whether a cancer cell in a sample obtained from the subject has at least one RET inhibitor resistance mutation; and (c) selecting a second RET inhibitor as a monotherapy or in conjunction with another anticancer agent if the subject has a cancer cell that has one or more RET inhibitor resistance mutations; or (d) selecting additional doses of the first RET inhibitor of step (a) for the subject if the subject has a cancer cell that does not have a RET inhibitor resistance mutation. In some embodiments, when additional doses of the first RET inhibitor of step (a) are selected for the subject, the method can further include selecting doses of another anticancer agent for the subject. In some embodiments, the one or more RET inhibitor resistance mutations confer increased resistance to a cancer cell or tumor to treatment with the first RET inhibitor. In some embodiments, the one or more RET inhibitor resistance mutations include one or more RET inhibitor resistance mutations listed in Tables 3 and 4. For example, the one or more RET inhibitor resistance mutations can include a substitution at amino acid position 804, e.g., V804M, V804L, or V804E. In some embodiments, the additional anticancer agent is any anticancer agent known in the art. For example, the additional anticancer agent is another RET inhibitor (e.g., a compound of Formula I or a pharmaceutically acceptable salt or solvate thereof). In some embodiments, the additional anticancer agent is an immunotherapy. In some embodiments, another RET can be the first RET inhibitor administered in step (a).

Also provided are methods of selecting a treatment for a subject having a cancer that include (a) determining whether a cancer cell in a sample obtained from a subject having a cancer and previously administered one or more doses of a first RET inhibitor has one or more RET inhibitor resistance mutations; (b) selecting a compound of Formula I or a pharmaceutically acceptable salt or solvate thereof as a monotherapy or in conjunction with another anticancer agent for the subject if the subject has a cancer cell that has at least one RET inhibitor resistance mutation; or (c) selecting additional doses of the first RET inhibitor previously administered to the subject if the subject has a cancer cell that does not have a RET inhibitor resistance mutation. In some embodiments, when additional doses of the first RET inhibitor previously administered to the subject are selected for the subject, the method can further include selecting doses of another anticancer agent (e.g., a compound of Formula I or a pharmaceutically acceptable salt or solvate thereof, or immunotherapy) for the subject. In some embodiments, the one or more RET inhibitor resistance mutations confer increased resistance to a cancer cell or tumor to treatment with the first RET inhibitor. In some embodiments, the one or more RET inhibitor resistance mutations include one or more RET inhibitor resistance mutations listed in Tables 3 and 4. For example, the one or more RET inhibitor resistance mutations can include a substitution at amino acid position 804, e.g., V804M, V804L, or V804E. In some embodiments, the additional anticancer agent is any anticancer agent known in the art. For example, the additional anticancer agent is another RET inhibitor (e.g., a second RET inhibitor). In some embodiments, the additional anticancer agent is an immunotherapy. In some embodiments of step (c), another RET inhibitor can be the first RET inhibitor administered in step (a).

Also provided are methods of selecting a treatment for a subject having a cancer that include (a) determining whether a cancer cell in a sample obtained from a subject having a cancer and previously administered one or more doses of a first RET inhibitor has one or more RET inhibitor resistance mutations; (b) selecting a second RET inhibitor as a monotherapy or in conjunction with another anticancer agent for the subject if the subject has a cancer cell that has at least one RET inhibitor resistance mutation; or (c) selecting additional doses of the first RET inhibitor previously administered to the subject if the subject has a cancer cell that does not have a RET inhibitor resistance mutation. In some embodiments, when additional doses of the first RET inhibitor previously administered to the subject are selected for the subject, the method can further include selecting doses of another anticancer agent (e.g., a compound of Formula I or a pharmaceutically acceptable salt or solvate thereof, or immunotherapy) for the subject. In some embodiments, the one or more RET inhibitor resistance mutations confer increased resistance to a cancer cell or tumor to treatment with the first RET inhibitor. In some embodiments, the one or more RET inhibitor resistance mutations include one or more RET inhibitor resistance mutations listed in Tables 3 and 4. For example, the one or more RET inhibitor resistance mutations can include a substitution at amino acid position 804, e.g., V804M, V804L, or V804E. In some embodiments, the additional anticancer agent is any anticancer agent known in the art. For example, the additional anticancer agent is another RET inhibitor (e.g., a compound of Formula I or a pharmaceutically acceptable salt or solvate thereof). In some embodiments, the additional anticancer agent is an immunotherapy. In some embodiments, another RET can be the first RET inhibitor administered in step (a).

Also provided are methods of determining a subject's risk for developing a cancer that has some resistance to a first RET inhibitor that include: determining whether a cell in a sample obtained from the subject has one or more RET inhibitor resistance mutations; and identifying a subject having a cell that has one or more RET inhibitor resistance mutations, as having an increased likelihood of developing a cancer that has some resistance to the first RET inhibitor. Also provided are methods of determining a subject's risk for developing a cancer that has some resistance to a first RET inhibitor that include: identifying a subject having a cell that has one or more RET inhibitor resistance mutations, as having an increased likelihood of developing a cancer that has some resistance to the first RET inhibitor. Also provided are methods of determining the presence of a cancer that has some resistance to a first RET inhibitor that include: determining whether a cancer cell in a sample obtained from the subject has one or more RET inhibitor resistance mutations; and determining that the subject having a cancer cell that has one or more RET inhibitor resistance mutations has a cancer that has some resistance to the first RET inhibitor. Also provided are methods of determining the presence of a cancer that has some resistance to a first RET inhibitor in a subject that include: determining that a subject having a cancer cell that has one or more RET inhibitor resistance mutations, has a cancer that has some resistance to the first RET inhibitor. In some embodiments, the one or more RET inhibitor resistance mutations confer increased resistance to a cancer cell or tumor to treatment with the first RET inhibitor. In some embodiments, the one or more RET inhibitor resistance mutations include one or more RET inhibitor resistance mutations listed in Tables 3 and 4. For example, the one or more RET inhibitor resistance mutations can include a substitution at amino acid position 804, e.g., V804M, V804L, or V804E.

In some embodiments of any of the methods described herein, a RET inhibitor resistance mutation that confers increased resistance to a cancer cell or tumor to treatment with a first RET inhibitor can be any of the RET inhibitor resistance mutations listed in Table 3 or 4 (e.g., a substitution at amino acid position 804, e.g., V804M, V804L, or V804E).

In some embodiments, the presence of one or more RET inhibitor resistance mutations in a tumor causes the tumor to be more resistant to treatment with a compound of Formula I or a pharmaceutically acceptable salt or solvate thereof. Methods useful when a RET inhibitor resistance mutation causes the tumor to be more resistant to treatment with a compound of Formula I or a pharmaceutically acceptable salt or solvate thereof are described below. For example, provided herein are methods of treating a subject having a cancer that include: identifying a subject having a cancer cell that has one or more RET inhibitor resistance mutations; and administering to the identified subject a treatment that does not include a compound of Formula I or a pharmaceutically acceptable salt or solvate thereof as a monotherapy (e.g., a second RET kinase inhibitor). Also provided are methods of treating a subject identified as having a cancer cell that has one or more RET inhibitor resistance mutations that include administering to the subject a treatment that does not include a compound of Formula I or a pharmaceutically acceptable salt or solvate thereof as a monotherapy (e.g., a second RET kinase inhibitor). In some embodiments, the one or more RET inhibitor resistance mutations confer increased resistance to a cancer cell or tumor to treatment with a compound of Formula I or a pharmaceutically acceptable salt or solvate thereof.

Also provided are methods of selecting a treatment for a subject having a cancer that include: identifying a subject having a cancer cell that has one or more RET inhibitor resistance mutations; and selecting a treatment that does not include a compound of Formula I or a pharmaceutically acceptable salt or solvate thereof as a monotherapy for the identified subject (e.g., a second RET kinase inhibitor). Also provided are methods of selecting a treatment for a subject having a cancer that include: selecting a treatment that does not include a compound of Formula I or a pharmaceutically acceptable salt or solvate thereof as a monotherapy (e.g., a second RET kinase inhibitor) for a subject identified as having a cancer cell that has one or more RET inhibitor resistance mutations. Also provided are methods of selecting a subject having a cancer for a treatment that does not include a compound of Formula I or a pharmaceutically acceptable salt or solvate thereof as a monotherapy (e.g., a second RET kinase inhibitor) that include: identifying a subject having a cancer cell that has one or more RET inhibitor resistance mutations; and selecting the identified subject for a treatment that does not include a compound of Formula I or a pharmaceutically acceptable salt or solvate thereof as a monotherapy (e.g., a second RET kinase inhibitor). Also provided are methods of selecting a subject having a cancer for a treatment that does not include a compound of Formula I or a pharmaceutically acceptable salt or solvate thereof as a monotherapy (e.g., a second RET kinase inhibitor) that include: selecting a subject identified as having a cancer cell that has one or more RET inhibitor resistance mutations for a treatment that does not include a compound of Formula I or a pharmaceutically acceptable salt or solvate thereof as a monotherapy. In some embodiments, the one or more RET inhibitor resistance mutations confer increased resistance to a cancer cell or tumor to treatment with a compound of Formula I or a pharmaceutically acceptable salt or solvate thereof.

Also provided are methods of determining the likelihood that a subject having a cancer will have a positive response to treatment with a compound of Formula I or a pharmaceutically acceptable salt or solvate thereof as a monotherapy that include: determining whether a cancer cell in a sample obtained from the subject has one or more RET inhibitor resistance mutations; and determining that the subject having the cancer cell that has one or more RET inhibitor resistance mutations has a decreased likelihood of having a positive response to treatment with a compound of Formula I or a pharmaceutically acceptable salt or solvate thereof as a monotherapy. Also provided are methods of determining the likelihood that a subject having cancer will have a positive response to treatment with a compound of Formula I or a pharmaceutically acceptable salt or solvate thereof as a monotherapy that include: determining that a subject having a cancer cell that has one or more RET inhibitor resistance mutations has a decreased likelihood of having a positive response to treatment with a compound of Formula I or a pharmaceutically acceptable salt or solvate thereof as a monotherapy. Also provided are methods of predicting the efficacy of treatment with a compound of Formula I or a pharmaceutically acceptable salt or solvate thereof as a monotherapy in a subject having cancer that include: determining whether a cancer cell in a sample obtained from the subject has one or more RET inhibitor resistance mutations; and determining that treatment with a compound of Formula I or a pharmaceutically acceptable salt or solvate thereof as a monotherapy is less likely to be effective in a subject having a cancer cell in a sample obtained from the subject that has one or more RET inhibitor resistance mutations. Also provided are methods of predicting the efficacy of treatment with a compound of Formula I or a pharmaceutically acceptable salt or solvate thereof as a monotherapy in a subject having cancer that include: determining that treatment with a compound of Formula I or a pharmaceutically acceptable salt or solvate thereof as a monotherapy is less likely to be effective in a subject having a cancer cell in a sample obtained from the subject that has one or more RET inhibitor resistance mutations. In some embodiments, the one or more RET inhibitor resistance mutations confer increased resistance to a cancer cell or tumor to treatment with a compound of Formula I or a pharmaceutically acceptable salt or solvate thereof.

Also provided are methods of treating a subject having a cancer that include: (a) administering one or more doses of a compound of Formula I or a pharmaceutically acceptable salt or solvate thereof for a period of time; (b) after (a), determining whether a cancer cell in a sample obtained from the subject has one or more RET inhibitor resistance mutations; and (c) administering a second RET inhibitor or a second compound of Formula I or a pharmaceutically acceptable salt or solvate thereof as a monotherapy or in conjunction with another anticancer agent to a subject having a cancer cell that has one or more RET inhibitor resistance mutations; or (d) administering additional doses of the compound of Formula I or a pharmaceutically acceptable salt or solvate thereof of step (a) to a subject having a cancer cell that does not have a RET inhibitor resistance mutation. In some embodiments, where the subject is administered additional doses of the compound of Formula I or a pharmaceutically acceptable salt or solvate thereof of step (a), the subject can also be administered another anticancer agent or a second compound of Formula I or a pharmaceutically acceptable salt or solvate thereof. In some embodiments, the one or more RET inhibitor resistance mutations confer increased resistance to a cancer cell or tumor to treatment with a compound of Formula I or a pharmaceutically acceptable salt or solvate thereof. In some embodiments, the additional anticancer agent is any anticancer agent known in the art. For example, the additional anticancer agent is another RET inhibitor (e.g., a second RET inhibitor). In some embodiments, the additional anticancer agent is an immunotherapy. In some embodiments, another RET can be the compound of Formula I or a pharmaceutically acceptable salt or solvate thereof administered in step (a).

Also provided are methods of treating a subject having a cancer that include: (a) determining whether a cancer cell in a sample obtained from a subject having a cancer and previously administered one or more doses of a compound of Formula I or a pharmaceutically acceptable salt or solvate thereof, has one or more RET inhibitor resistance mutations; (b) administering a second RET inhibitor or a second compound of Formula I or a pharmaceutically acceptable salt or solvate thereof as a monotherapy or in conjunction with another anticancer agent to a subject having a cancer cell that has one or more RET inhibitor resistance mutations; or (c) administering additional doses of the compound of Formula I or a pharmaceutically acceptable salt or solvate thereof previously administered to a subject having a cancer cell that does not have a RET inhibitor resistance mutation. In some embodiments, where the subject is administered additional doses of the compound of Formula I or a pharmaceutically acceptable salt or solvate thereof of step (a), the subject can also be administered another anticancer agent. In some embodiments, the one or more RET inhibitor resistance mutations confer increased resistance to a cancer cell or tumor to treatment with a compound of Formula I or a pharmaceutically acceptable salt or solvate thereof. In some embodiments, the additional anticancer agent is any anticancer agent known in the art. For example, the additional anticancer agent is another RET inhibitor (e.g., a second RET inhibitor). In some embodiments, the additional anticancer agent is an immunotherapy. In some embodiments, another RET can be the compound of Formula I or a pharmaceutically acceptable salt or solvate thereof administered in step (a).

Also provided are methods of selecting a treatment for a subject having a cancer that include: (a) administering one or more doses of a compound of Formula I or a pharmaceutically acceptable salt or solvate thereof to the subject for a period of time; (b) after (a), determining whether a cancer cell in a sample obtained from the subject has one or more RET inhibitor resistance mutations; and (c) selecting a second RET inhibitor or a second compound of Formula I or a pharmaceutically acceptable salt or solvate thereof as a monotherapy or in conjunction with another anticancer agent for the subject if the subject has a cancer cell that has a RET inhibitor resistance mutation; or (d) selecting additional doses of the compound of Formula I or a pharmaceutically acceptable salt or solvate thereof of step (a) for the subject if the subject has a cancer cell that does not have a RET inhibitor resistance mutation. In some embodiments, where additional doses of a compound of Formula I or a pharmaceutically acceptable salt or solvate thereof of step (a) are selected for the subject, the method can also include further selecting another anticancer agent. In some embodiments, the one or more RET inhibitor resistance mutations confer increased resistance to a cancer cell or tumor to treatment with a compound of Formula I or a pharmaceutically acceptable salt or solvate thereof. In some embodiments, the additional anticancer agent is any anticancer agent known in the art. For example, the additional anticancer agent is another RET inhibitor (e.g., a second RET inhibitor). In some embodiments, the additional anticancer agent is an immunotherapy. In some embodiments, another RET can be the compound of Formula I or a pharmaceutically acceptable salt or solvate thereof administered in step (a).

Also provided are methods of selecting a treatment for a subject having a cancer that include: (a) determining whether a cancer cell in a sample obtained from a subject having a cancer and previously administered one or more doses of a compound of Formula I or a pharmaceutically acceptable salt or solvate thereof, has one or more RET inhibitor resistance mutations; (b) selecting a second RET inhibitor or a second compound of Formula I or a pharmaceutically acceptable salt or solvate thereof as a monotherapy or in conjunction with another anticancer agent for the subject if the subject has a cancer cell that has a RET inhibitor resistance mutation; or (c) selecting additional doses of the compound of Formula I or a pharmaceutically acceptable salt or solvate thereof previously administered to the subject if the subject has a cancer cell that does not have a RET inhibitor resistance mutation. In some embodiments, where additional doses of the compound of Formula I or a pharmaceutically acceptable salt or solvate thereof of step (a) are selected for the subject, the method can also include further selecting another anticancer agent. In some embodiments, the one or more RET inhibitor resistance mutations confer increased resistance to a cancer cell or tumor to treatment with a compound of Formula I or a pharmaceutically acceptable salt or solvate thereof. In some embodiments, the additional anticancer agent is any anticancer agent known in the art. For example, the additional anticancer agent is another RET inhibitor (e.g., a second RET inhibitor). In some embodiments, the additional anticancer agent is an immunotherapy. In some embodiments, another RET can be the compound of Formula I or a pharmaceutically acceptable salt or solvate thereof administered in step (a).

Also provided are methods of determining a subject's risk for developing a cancer that has some resistance to a compound of Formula I or a pharmaceutically acceptable salt or solvate thereof that include: determining whether a cell in a sample obtained from the subject has one or more RET inhibitor resistance mutations; and identifying the subject if the subject has a cell that has one or more RET inhibitor resistance mutations as having an increased likelihood of developing a cancer that has some resistance to a compound of Formula I or a pharmaceutically acceptable salt or solvate thereof. Also provided are methods of determining a subject's risk for developing a cancer that has some resistance to a compound of Formula I or a pharmaceutically acceptable salt or solvate thereof that include: identifying a subject having a cell that has one or more RET inhibitor resistance mutations as having an increased likelihood of developing a cancer that has some resistance to a compound of Formula I or a pharmaceutically acceptable salt or solvate thereof. Also provided are methods of determining the presence of a cancer that has some resistance to a compound of Formula I or a pharmaceutically acceptable salt or solvate thereof that includes: determining whether a cancer cell in a sample obtained from the subject has one or more RET inhibitor resistance mutations; and determining that the subject having the cancer cell that has one or more RET inhibitor resistance mutations has a cancer that has some resistance to a compound of Formula I or a pharmaceutically acceptable salt or solvate thereof. Also provided are methods of determining the presence of a cancer that has some resistance to a compound of Formula I or a pharmaceutically acceptable salt or solvate thereof in a subject that include: determining that a subject having a cancer cell that has one or more RET inhibitor resistance mutations has a cancer that has some resistance to a compound of Formula I or a pharmaceutically acceptable salt or solvate thereof. In some embodiments, the one or more RET inhibitor resistance mutations confer increased resistance to a cancer cell or tumor to treatment with a compound of Formula I or a pharmaceutically acceptable salt or solvate thereof.

In some embodiments of any of the methods described herein, a RET inhibitor resistance mutation that confers increased resistance to a cancer cell or tumor to treatment with a compound of Formula I or a pharmaceutically acceptable salt or solvate thereof, can be any of the RET inhibitor resistance mutations listed in Table 3 or 4.

Methods of determining the level of resistance of a cancer cell or a tumor to a RET inhibitor (e.g., any of the RET inhibitors described herein or known in the art) can be determined using methods known in the art. For example, the level of resistance of a cancer cell to a RET inhibitor can be assessed by determining the $IC_{50}$ of a RET inhibitor (e.g., any of the RET inhibitors described herein or known in the art) on the viability of a cancer cell. In other examples, the level of resistance of a cancer cell to a RET inhibitor can be assessed by determining the growth rate of the cancer cell in the presence of a RET inhibitor (e.g., any of the RET inhibitors described herein). In other examples, the level of resistance of a tumor to a RET inhibitor can be assessed by determining the mass or size of one or more tumors in a subject over time during treatment with a RET inhibitor (e.g., any of the RET inhibitors described herein). In other examples, the level of resistance of a cancer cell or a tumor to a RET inhibitor can be indirectly assessed by determining the activity of a RET kinase including one or more of the RET inhibitor resistance mutations (i.e., the same RET kinase expressed in a cancer cell or a tumor in a subject). The level of resistance of a cancer cell or tumor having one or more RET inhibitor resistance mutations to a RET inhibitor is relative to the level of resistance in a cancer cell or tumor that does not have a RET inhibitor resistance mutation (e.g., a cancer cell or tumor that does not have the same RET inhibitor resistance mutations, a cancer cell or a tumor that does not have any RET inhibitor resistance mutations, or a cancer cell or a tumor that expresses a wildtype RET protein). For example, the determined level of resistance of a cancer cell or a tumor having one or more RET inhibitor resistance mutations can be greater than about 1%, greater than about 2%, greater than about 3%, greater than about 4%, greater than about 5%, greater than about 6%, greater than about 7%, greater than about 8%, greater than about 9%, greater than about 10%, greater than about 11%, greater than about 12%, greater than about 13%, greater than about 14%, greater than about 15%, greater than about 20%, greater than about 25%, greater than about 30%, greater than about 35%, greater than about 40%, greater than about 45%, greater than about 50%, greater than about 60%, greater than about 70%, greater than about 80%, greater than about 90%, greater than about 100%, greater than about 110%, greater than about 120%, greater than about 130%, greater than about 140%, greater than about 150%, greater than about 160%, greater than about 170%, greater than about 180%, greater than about 190%, greater than about 200%, greater than about 210%, greater than about 220%, greater than about 230%, greater than about 240%, greater than about 250%, greater than about 260%, greater than about 270%, greater than about 280%, greater than about 290%, or greater than about 300% of the level of resistance in a cancer cell or tumor that does not have a RET inhibitor resistance mutation (e.g., a cancer cell or tumor that does not have the same RET inhibitor resistance mutations, a cancer cell or a tumor that does not have any RET inhibitor resistance mutations, or a cancer cell or a tumor that expresses a wildtype RET protein).

RET is thought to play an important role in the development and survival of afferent nociceptors in the skin and gut. RET kinase knock-out mice lack enteric neurons and have other nervous system anomalies suggesting that a functional RET kinase protein product is necessary during development (Taraviras, S. et al., *Development,* 1999, 126:2785-2797). Moreover population studies of patients with Hirschsprung's disease characterized by colonic obstruction due to lack of normal colonic enervation have a higher proportion of both familial and sporadic loss of function RET mutations (Butler Tjaden N., et al., *Transl. Res.*, 2013, 162: 1-15). Irritable bowel syndrome (IBS) is a common illness affecting 10-20% of individuals in developed countries and is characterized by abnormal bowel habits, bloating and visceral hypersensitivity (Camilleri, M., *N. Engl. J. Med.*, 2012, 367: 1626-1635). While the etiology of IBS is unknown it is thought to result from either a disorder between the brain and gastrointestinal tract, a disturbance in the gut microbiome or increased inflammation. The resulting gastrointestinal changes affect normal bowel transit resulting in either diarrhea or constipation. Furthermore in many IBS patients the sensitization of the peripheral nervous system results in visceral hypersensitivity or allodynia (Keszthelyi, D., *Eur. J. Pain*, 2012, 16: 1444-1454). See, e.g., U.S. Publication No. 2015/0099762.

Accordingly, provided herein are methods for treating a patient diagnosed with (or identified as having) an irritable bowel syndrome (IBS) including diarrhea-predominant, constipation-predominant or alternating stool pattern, functional bloating, functional constipation, functional diarrhea, unspecified functional bowel disorder, functional abdominal pain syndrome, chronic idiopathic constipation, functional esophageal disorders, functional gastroduodenal disorders, functional anorectal pain, and inflammatory bowel disease that include administering to the patient a therapeutically effective amount of a compound of Formula I or a pharmaceutically acceptable salt or solvate thereof.

Also provided herein are methods for treating a patient identified or diagnosed as having a RET-associated irritable bowel syndrome (IBS) (e.g., a patient that has been identified or diagnosed as having a RET-associated irritable bowel syndrome (IBS) through the use of a regulatory agency-approved, e.g., FDA-approved, kit for identifying dysregulation of a RET gene, a RET kinase, or expression or activity or level of any of the same, in a patient or a biopsy sample from the patient) that include administering to the patient a therapeutically effective amount of a compound of Formula I or a pharmaceutically acceptable salt or solvate thereof.

Also provided herein are methods for treating pain associated with IBS that include administering to the patient a therapeutically effective amount of a compound of Formula I or a pharmaceutically acceptable salt or solvate thereof. In some embodiments, a compound of Formula I or a pharmaceutically acceptable salt or solvate thereof is administered in combination with another therapeutic agent useful for treating one or more symptoms of IBS.

Also provided are methods for treating an irritable bowel syndrome (IBS) in a patient in need thereof, the method comprising: (a) determining if the irritable bowel syndrome (IBS) in the patient is a RET-associated IBS (e.g., using a regulatory-agency approved, e.g., FDA-approved, kit for identifying dysregulation of a RET gene, a RET kinase, or expression or activity or level of any of the same, in a patient or a biopsy sample from the patient, or by performing any of the non-limiting examples of assays described herein); and (b) if the IBS is determined to be a RET-associated IBS, administering to the patient a therapeutically effective amount of a compound of Formula I or a pharmaceutically acceptable salt or solvate thereof.

In some embodiments, the compounds of the present invention are useful for treating irritable bowel syndrome (IBS) in combination with one or more additional therapeutic agents or therapies effective in treating the irritable bowel syndrome that work by the same or a different mechanism of action. The at least one additional therapeutic agent may be administered with a compound of Formula I or a pharmaceutically acceptable salt or solvate thereof as part of the same or separate dosage forms, via the same or different routes of administration, and on the same or different administration schedules according to standard pharmaceutical practice known to one skilled in the art.

Non-limiting examples of additional therapeutics for the treatment of irritable bowel syndrome (IBS) include probiotics, fiber supplements (e.g., *psyllium*, methylcellulose), anti-diarrheal medications (e.g., loperamide), bile acid binders (e.g., cholestyramine, colestipol, colesevelam), anticholinergic and antispasmodic medications (e.g., hyoscyamine, dicyclomine), antidepressant medications (e.g., tricyclic antidepressant such as imipramine or notriptyline or a selective serotonin reuptake inhibitor (S SRI) such as fluoxetine or paroxetine), antibiotics (e.g., rifaximin), alosetron, and lubiprostone.

Accordingly, also provided herein are methods of treating irritable bowel syndrome (IBS), comprising administering to a patient in need thereof a pharmaceutical combination for treating IBS which comprises (a) a compound of Formula I or pharmaceutically acceptable salt or solvate thereof, (b) an additional therapeutic agent, and (c) optionally at least one pharmaceutically acceptable carrier for simultaneous, separate or sequential use for the treatment of IBS, wherein the amounts of the compound of Formula I or pharmaceutically acceptable salt or solvate thereof and the additional therapeutic agent are together effective in treating the IBS. In one embodiment, the compound of Formula I or pharmaceutically acceptable salt or solvate thereof, and the additional therapeutic agent are administered simultaneously as separate dosages. In one embodiment, the compound of Formula I or pharmaceutically acceptable salt or solvate thereof, and the additional therapeutic agent are administered as separate dosages sequentially in any order, in jointly therapeutically effective amounts, e.g. in daily or intermittently dosages. In one embodiment, compound of Formula I or pharmaceutically acceptable salt or solvate thereof, and the additional therapeutic agent are administered simultaneously as a combined dosage.

Also provided herein is (i) a pharmaceutical combination for treating irritable bowel syndrome in a patient in need thereof, which comprises (a) a compound of Formula I or a pharmaceutically acceptable salt or solvate thereof, (b) at least one additional therapeutic agent (e.g., any of the exemplary additional therapeutic agents described herein for treating irritable bowel syndrome or known in the art), and (c) optionally at least one pharmaceutically acceptable carrier for simultaneous, separate or sequential use for the treatment of irritable bowel syndrome, wherein the amounts of the compound of Formula I or pharmaceutically acceptable salt or solvate thereof and of the additional therapeutic agent are together effective in treating the irritable bowel syndrome; (ii) a pharmaceutical composition comprising such a combination; (iii) the use of such a combination for the preparation of a medicament for the treatment of irritable bowel syndrome; and (iv) a commercial package or product comprising such a combination as a combined preparation for simultaneous, separate or sequential use; and to a method of treatment of irritable bowel syndrome in a patient in need thereof. In one embodiment the patient is a human.

The term "pharmaceutical combination", as used herein, refers to a pharmaceutical therapy resulting from the mixing or combining of more than one active ingredient and includes both fixed and non-fixed combinations of the active ingredients. The term "fixed combination" means that a compound of Formula I or a pharmaceutically acceptable salt or solvate thereof and at least one additional therapeutic agent (e.g., an agent effective in treating irritable bowel syndrome), are both administered to a patient simultaneously in the form of a single composition or dosage. The term "non-fixed combination" means that a compound of Formula I or a pharmaceutically acceptable salt or solvate thereof and at least one additional therapeutic agent (e.g., an agent effective in treating irritable bowel syndrome) are formulated as separate compositions or dosages, such that they may be administered to a patient in need thereof simultaneously, concurrently or sequentially with variable intervening time limits, wherein such administration provides effective levels of the two or more compounds in the body of the patient. In one embodiment, the compound of Formula I and the additional therapeutic agent are formulated as separate unit dosage forms, wherein the separate dosages forms are suitable for either sequential or simultaneous administration. These also apply to cocktail therapies, e.g. the administration of three or more active ingredients.

In some embodiments, a compound provided herein can be used as an agent for supportive care for a patient undergoing cancer treatment. For example, a compound of Formula I or a pharmaceutically acceptable salt or solvate thereof, can be useful to reduce one or more symptoms associated with treatment with one or more cancer therapies such as diarrheal or constipations complications and/or abdominal pain. See, for example, U.S. Publication No. 2015/0099762 and Hoffman, J. M. et al. *Gastroenterology* (2012) 142:844-854. Accordingly, a compound, or a pharmaceutically acceptable salt thereof, or composition provided herein can be administered to a patient to address one or more complications associated with cancer treatment (e.g., gastrointestinal complications such as diarrhea, constipation, or abdominal pain).

In some embodiments, a therapeutically effective amount of a compound of Formula I or a pharmaceutically acceptable salt or solvate thereof, can be administered to a patient undergoing cancer treatment (e.g., a patient experiencing an adverse event associated with cancer treatment such as an immune-related adverse event or a gastrointestinal complication including diarrhea, constipation, and abdominal pain). For example, a compound provided herein, or a pharmaceutically acceptable salt thereof, can be used in the treatment of colitis or IBS associated with administration of a checkpoint inhibitor; see, e.g., Postow, M. A. et al. *Journal of Clinical Oncology* (2015) 33: 1974-1982. In some such embodiments, a compound provided herein, or a pharmaceutically acceptable salt thereof, can be formulated to exhibit low bioavailability and/or be targeted for delivery in the gastrointestinal tract. See, for example, U.S. Pat. No. 6,531,152.

Also provided is a method for inhibiting RET kinase activity in a cell, comprising contacting the cell with a compound of Formula I. In one embodiment, the contacting is in vitro. In one embodiment, the contacting is in vivo. In one embodiment, the contacting is in vivo, wherein the method comprises administering an effective amount of a compound of Formula I or a pharmaceutically acceptable salt or solvate thereof to a subject having a cell having RET kinase activity. In some embodiments, the cell is a cancer cell. In one embodiment, the cancer cell is any cancer as described herein. In some embodiments, the cancer cell is a RET-associated cancer cell. In some embodiments, the cell is a gastrointestinal cell.

Also provided is a method for inhibiting RET kinase activity in a mammalian cell, comprising contacting the cell with a compound of Formula I. In one embodiment, the contacting is in vitro. In one embodiment, the contacting is in vivo. In one embodiment, the contacting is in vivo, wherein the method comprises administering an effective amount of a compound of Formula I or a pharmaceutically acceptable salt or solvate thereof to a mammal having a cell having RET kinase activity. In some embodiments, the mammalian cell is a mammalian cancer cell. In one embodiment, the mammalian cancer cell is any cancer as described herein. In some embodiments, the mammalian cancer cell is a RET-associated cancer cell. In some embodiments, the mammalian cell is a gastrointestinal cell.

As used herein, the term "contacting" refers to the bringing together of indicated moieties in an in vitro system or an in vivo system. For example, "contacting" a RET kinase with a compound provided herein includes the administration of a compound provided herein to an individual or patient, such as a human, having a RET kinase, as well as, for example, introducing a compound provided herein into a sample containing a cellular or purified preparation containing the RET kinase.

Also provided herein is a method of inhibiting cell proliferation, in vitro or in vivo, the method comprising contacting a cell with an effective amount of a compound of Formula I or a pharmaceutically acceptable salt or solvate thereof, or a pharmaceutical composition thereof as defined herein The phrase "effective amount" means an amount of compound that, when administered to a patient in need of such treatment, is sufficient to (i) treat a RET kinase-associated disease or disorder, (ii) attenuate, ameliorate, or eliminate one or more symptoms of the particular disease, condition, or disorder, or (iii) delay the onset of one or more symptoms of the particular disease, condition, or disorder described herein. The amount of a compound of Formula I that will correspond to such an amount will vary depending upon factors such as the particular compound, disease condition and its severity, the identity (e.g., weight) of the patient in need of treatment, but can nevertheless be routinely determined by one skilled in the art.

When employed as pharmaceuticals, the compounds of Formula I can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Oral administration can include a dosage form formulated for once-daily or twice-daily (BID) administration. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable Also provided herein are pharmaceutical compositions which contain, as the active ingredient, a compound of Formula I or a pharmaceutically acceptable salt or solvate thereof, in combination with one or more pharmaceutically acceptable carriers (excipients). In some embodiments, the composition is suitable for topical administration. In making the compositions provided herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders. In one embodiment, the composition is formulated for oral administration. In one embodiment, the composition is formulated as a tablet or capsule.

The compositions comprising a compound of Formula I or a pharmaceutically acceptable salt or solvate thereof can be formulated in a unit dosage form, each dosage containing from about 5 to about 1,000 mg (1 g), more usually about 100 mg to about 500 mg, of the active ingredient. The term "unit dosage form" refers to physically discrete units suitable as unitary dosages for human subjects and other patients, each unit containing a predetermined quantity of active material (i.e., a compound for Formula I as provided herein) calculated to produce the desired therapeutic effect, in association with a suitable pharmaceutical excipient.

In some embodiments, the compositions provided herein contain from about 5 mg to about 50 mg of the active ingredient. One having ordinary skill in the art will appreciate that this embodies compounds or compositions containing about 5 mg to about 10 mg, about 10 mg to about 15 mg, about 15 mg to about 20 mg, about 20 mg to about 25 mg, about 25 mg to about 30 mg, about 30 mg to about 35 mg, about 35 mg to about 40 mg, about 40 mg to about 45 mg, or about 45 mg to about 50 mg of the active ingredient.

In some embodiments, the compositions provided herein contain from about 50 mg to about 500 mg of the active ingredient. One having ordinary skill in the art will appreciate that this embodies compounds or compositions containing about 50 mg to about 100 mg, about 100 mg to about 150 mg, about 150 mg to about 200 mg, about 200 mg to about 250 mg, about 250 mg to about 300 mg, about 350 mg to about 400 mg, or about 450 mg to about 500 mg of the active ingredient.

In some embodiments, the compositions provided herein contain from about 500 mg to about 1,000 mg of the active ingredient. One having ordinary skill in the art will appreciate that this embodies compounds or compositions containing about 500 mg to about 550 mg, about 550 mg to about 600 mg, about 600 mg to about 650 mg, about 650 mg to about 700 mg, about 700 mg to about 750 mg, about 750 mg to about 800 mg, about 800 mg to about 850 mg, about 850 mg to about 900 mg, about 900 mg to about 950 mg, or about 950 mg to about 1,000 mg of the active ingredient.

In some embodiments, the compounds provided herein can be administered in an amount ranging from about 1 mg/kg to about 100 mg/kg. In some embodiments, the compound provided herein can be administered in an amount of about 1 mg/kg to about 20 mg/kg, about 5 mg/kg to about 50 mg/kg, about 10 mg/kg to about 40 mg/kg, about 15 mg/kg to about 45 mg/kg, about 20 mg/kg to about 60 mg/kg, or about 40 mg/kg to about 70 mg/kg. For example, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, or about 100 mg/kg. In some embodiments, such administration can be once-daily or twice-daily (BID) administration.

The active compound may be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

Provided herein are pharmaceutical kits useful, for example, in the treatment of RET-associated diseases or disorders, such as cancer or irritable bowel syndrome (IBS), which include one or more containers containing a pharmaceutical composition comprising a therapeutically effective amount of a compound provided herein. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trials including first-in-human, dose ranging and efficacy trials, in healthy patients and/or those suffering from a given disorder, may be completed according to methods well known in the clinical and medical arts.

EXAMPLES

The following examples illustrate the invention.

BIOLOGICAL EXAMPLES

Example A

RET Enzyme Assay

Compounds of Formula I were screened for their ability to inhibit wildtype and V804M mutant RET kinase using CisBio's HTRF® KinEASE™-TK assay technology. Briefly, N-terminal GST tagged recombinant human RET cytoplasmic domain (aa 658-end) from Eurofins (0.25 nM RET; Catalog No. 14-570M) or N-terminal GST tagged recombinant human V804M mutant RET cytoplasmic domain (aa 658-end) from Millipore (0.25 nM enzyme; Catalog No. 14-760) was incubated with 250 nM TK-substrate biotin (CisBio, part of Catalog No. 62TK0PEC) and 1 mM ATP along with test compound in a buffer consisting of 25 mM HEPES pH 7.4, 10 mM $MgCl_2$, 0.01% Triton X-100, and 2% DMSO in a volume of 8 μL. Compounds were typically prepared in a threefold serial dilution in DMSO and added to the assay to give the appropriate final concentration. After a 30-minute incubation at 22° C., the reaction was quenched by adding 8 μL of quench solution containing 31.25 nM Sa-XL665 and 1×TK-ab-Cryptate in HTRF detection buffer (all from CisBio, part of Cat. No. 62TK0PEC). After a 1 hour incubation at 22° C., the extent of reaction was determined using a PerkinElmer EnVision multimode plate reader via HTRF dual wavelength detection, and the percent of control (POC) was calculated using a ratiometric emission factor. 100 POC was determined using no test compounds and 0 POC was determined using pre-quenched control reactions. The POC values were fit to a 4 parameter logistic curve, and the $IC_{50}$ is defined as the concentration of inhibitor at which the POC equals 50 for the fitted curve. The $IC_{50}$ values for the compounds tested in this assay are provided in Table 5.

Example B

RET Cell Assay

The cellular potency of a compound inhibiting RET kinase was determined in HEK-293 cells expressing a Kif5b-RET fusion protein. Briefly, HEK-293 cells expressing a Kif5b-RET fusion protein were plated at 50K cells/well in 96 well poly-D-Lysine coated plates the day prior to the assay. The cells were incubated for 1 hour with test compound in DMEM (Dulbecco's Modified Eagle Medium) at a final DMSO concentration of 0.5%. Compounds were typically prepared in a three fold serial dilution in DMSO and added to the assay to give the appropriate final concentration. After 1 hour the media was removed, the cells were fixed with 3.8% formaldehyde for 20 min, washed with PBS, and permeabilized for 10 min with 100% methanol. The plates were then washed with PBS-0.05% Tween20, and blocked with LI-COR Blocking solution (LI-COR catalog #927-40000) for 1 hour. Plates were washed with PBS-0.05% Tween20, then incubated with anti-phospho-RET (Tyr1062) (Santa Cruz catalog #sc-20252-R) antibody and anti-GAPDH (Millipore catalog # MAB374) antibody for 2 hours. The plates were washed with PBS-0.05% Tween20, and incubated with anti-rabbit 680 (Molecular Probes catalog No. A21109) and anti-mouse 800 (LI-COR catalog No. 926-32210) secondary antibodies for 1 hour. All antibodies were diluted in LI-COR Block containing 0.05% Tween. The plates were washed with PBS-0.05% Tween20, 100 µL PBS was added to each well, and the plates were read on a LI-COR Aerius fluorescent plate reader. The phospho-RET signal was normalized to the GAPDH signal. 100 POC (percent of control) was determined using no test compounds and 0 POC was determined using 1 µM of a control inhibitor. The POC values were fit to a 4 parameter logistic curve. The $IC_{50}$ value is the point where the curve crosses 50 POC. The $IC_{50}$ values for the compounds tested in this assay are provided in Table 5.

Example C

RET G810R Mutant Assay

The potency of a compound inhibiting G81 OR mutant RET kinase was determined using CisBio's HTRF Kinease-TK assay technology. The assays contained G81OR mutant RET produced at Array Biopharma, Inc. (1 nM enzyme— p1982 Lot. No. 160713. The kinase was incubated with 250 nM TK-substrate biotin (CisBio, part of Catalog #62TK0PEC) and 1 mM ATP along with test compound in a buffer consisting of 25 mM HEPES, pH 7.4, 10 mM $MgCl_2$, 0.01% Triton X-100, and 2% DMSO in a volume of 8 µL. Compounds were typically prepared as a three-fold serial dilution in DMSO and added to the assay to give the appropriate final concentration. After a 60-min incubation at 22° C., the reaction was quenched by adding 8 µL of quench solution containing 31.25 nM Sa-XL665 and 1×TK-Ab-Cryptate in HTRF detection buffer (all from CisBio, part of cat #62TK0PEC). After a 1-h incubation at 22° C., the extent of reaction was determined using a PerkinElmer EnVision multimode plate reader via HTRF dual wavelength detection, and the percent of control (POC) was calculated using a ratiometric emission factor. One hundred POC was determined using no test compounds, and 0 POC was determined using pre-quenched control reactions. A 4-parameter logistic curve was fit to the POC values as a function of the concentration of compound, and the $IC_{50}$ value was the point where the best-fit curve crossed 50 POC.

TABLE 5

$IC_{50}$'s of compounds tested in the assay of Examples A, B and C

| Ex. # | RET Enzyme (wild type) $IC_{50}$ (nM) | RET enzyme (V804M) $IC_{50}$ (nM) | KIF5B-RET pTYR1062 Cell $IC_{50}$ (nM) | RET Enzyme (G810R) IC50 (nM) |
|---|---|---|---|---|
| 1 | 91.5 | 758.2 | 205.6 | 1026 |
| 2 | 1891.7 | 3930.6 | N/A | N/A |
| 3 | 82.9 | 587.7 | 143 | N/A |
| 4 | 231.4 | 1969.1 | N/A | N/A |
| 5 | 457.3 | 3808.5 | N/A | 3669 |
| 6 | 1518.4 | N/A | N/A | N/A |
| 7 | 105.5 | 1107.7 | 364 | N/A |
| 8 | 41.5 | 285.3 | 146.2 | N/A |
| 9 | 18.8 | 24.6 | 9.8 | 128 |
| 10 | 61.2 | 264.4 | 163.8 | N/A |
| 11 | 93.6 | 511.3 | 722.8 | N/A |
| 12 | 34.8 | 328.3 | 212.8 | N/A |
| 13 | 23.1 | 127.2 | 54.8 | N/A |
| 14 | 199.1 | 817.4 | N/A | N/A |
| 15 | 264.6 | 1038.8 | N/A | N/A |
| 16 | 69.9 | 199.1 | 61.1 | N/A |
| 17 | 165.4 | 1874.7 | N/A | N/A |
| 18 | 54.7 | 632.3 | 366.1 | N/A |
| 19 | 24.6 | 120.1 | 20.6 | N/A |
| 20 | 336.9 | 1571.7 | N/A | N/A |
| 21 | 15.5 | 70.6 | 25.5 | N/A |
| 22 | 16.6 | 138.1 | 38 | N/A |
| 23 | 15.6 | 83.9 | 43.3 | N/A |
| 24 | 49 | 355 | 310 | N/A |
| 25 | 38.1 | 207.5 | 330 | N/A |
| 26 | 40.6 | 183.2 | 165.6 | N/A |
| 27 | 15.3 | 50.4 | 8.3 | 636 |
| 28 | 158 | 1020.9 | N/A | N/A |
| 29 | 15.5 | 54.6 | 8.4 | 613 |
| 30 | 49.6 | 236.4 | 41.1 | N/A |
| 31 | 75.8 | 316.4 | 137.9 | N/A |
| 32 | 90.2 | 502.2 | 97.8 | N/A |
| 33 | 44.5 | 215.2 | 20.8 | N/A |
| 34 | 64.9 | 402.2 | 72.2 | N/A |
| 35 | 8.4 | 17.3 | 2.7 | 133 |
| 36 | 8 | 20.2 | 6.3 | N/A |
| 37 | 16 | 39.3 | 4.7 | N/A |
| 38 | 13.3 | 22 | 3.6 | N/A |
| 39 | 17.2 | 54.3 | 12.7 | 550 |
| 40 | 18.5 | 70 | 16.8 | 632 |
| 41 | 80.2 | 248.9 | 48 | N/A |
| 42 | 6.7 | 13.6 | 1.5 | N/A |
| 43 | 12.2 | 21 | 5.4 | N/A |
| 44 | 20.7 | 108.2 | 31.6 | 195 |
| 45 | 6.3 | 20.9 | 2.9 | 37 |
| 46 | 14.5 | 44.5 | 11.2 | N/A |
| 47 | 13.7 | 34.8 | 4.2 | 64 |
| 48 | 10 | 17.3 | 2.5 | N/A |
| 49 | 29.6 | 169 | 34.6 | 1375 |
| 50 | 67.8 | 585.6 | 135.5 | N/A |
| 51 | 112.7 | 442.8 | N/A | N/A |
| 52 | 20.1 | 49.7 | 2 | N/A |
| 53 | 14.4 | 27.9 | 1.3 | N/A |
| 54 | 10.8 | 21.1 | 1.2 | N/A |
| 55 | 22.9 | 70.7 | 3.4 | N/A |
| 56 | 13.9 | 35.9 | 1.2 | N/A |
| 57 | 14.8 | 94.5 | 12.5 | N/A |
| 58 | 68.6 | 692.1 | 153.1 | N/A |

TABLE 5-continued

IC$_{50}$'s of compounds tested in the assay of Examples A, B and C

| Ex. # | RET Enzyme (wild type) IC$_{50}$ (nM) | RET enzyme (V804M) IC$_{50}$ (nM) | KIF5B-RET pTYR1062 Cell IC$_{50}$ (nM) | RET Enzyme (G810R) IC50 (nM) |
|---|---|---|---|---|
| 59 | 74.3 | 401.5 | 170.7 | N/A |
| 60 | 50.5 | 194.2 | 93 | N/A |
| 61 | 22.4 | 97.5 | 17.8 | N/A |
| 62 | 13.4 | 31.9 | 1.7 | 92 |
| 63 | 66.5 | 511.9 | 150.1 | N/A |
| 64 | 19.2 | 69 | 10 | 628 |
| 65 | 9.1 | 45.7 | 6.1 | N/A |
| 66 | 9.1 | 27.5 | 1.5 | N/A |
| 67 | 21.6 | 49.9 | 11.4 | N/A |
| 68 | 19 | 64.8 | 13.3 | N/A |
| 69 | 14.9 | 49.7 | 11.7 | N/A |
| 70 | 16.4 | 46.4 | 10.1 | N/A |
| 71 | 74.6 | 586.8 | 80 | N/A |
| 72 | 14.7 | 46.2 | 2 | N/A |
| 73 | 16.3 | 49.1 | 1.9 | N/A |
| 74 | 11.5 | 57.4 | 10.3 | N/A |
| 75 | 24.6 | 50.2 | 4.7 | N/A |
| 76 | 23.9 | 77.6 | 54.9 | N/A |
| 77 | 16.5 | 33.3 | 3 | N/A |
| 78 | 25 | 34.5 | 2 | 280 |
| 79 | 43.3 | 105.7 | 6.3 | 755 |
| 80 | 13.9 | 25.9 | 2 | N/A |
| 81 | 11.2 | 27 | 2.6 | N/A |
| 82 | 61.3 | 250.6 | 58.5 | N/A |
| 83 | 34.2 | 79.6 | 6.8 | 1711 |
| 84 | 25.5 | 128.8 | 45.6 | N/A |
| 85 | 39.8 | 150.8 | 91.3 | N/A |
| 86 | 16.7 | 72.5 | 20 | N/A |
| 87 | 5.3 | 30.7 | 9.7 | 463 |
| 88 | 26.2 | 71 | 4.2 | N/A |
| 89 | 26.9 | 282.8 | 38.7 | N/A |
| 90 | 29.3 | 153.9 | 30.8 | N/A |
| 91 | 13.3 | 52.7 | 7.9 | N/A |
| 92 | 11.3 | 40.3 | 6.4 | N/A |
| 93 | 9.4 | 19 | 1.8 | N/A |
| 94 | 16.8 | 28.8 | 3.7 | N/A |
| 95 | 79.9 | 478.5 | 1667 | N/A |
| 96 | 48.9 | 311.9 | 689.8 | N/A |
| 97 | 137.5 | 602.4 | N/A | N/A |
| 98 | 208.9 | 1549.4 | N/A | N/A |
| 99 | 21.1 | 100.7 | 265.2 | N/A |
| 100 | 38 | 100.5 | 10.6 | N/A |
| 101 | 12.8 | 29.7 | 1.2 | N/A |
| 102 | 11.8 | 27.5 | 1 | N/A |
| 103 | 61.8 | 323.2 | 57.7 | N/A |
| 104 | 10.7 | 20.4 | 3.1 | N/A |
| 105 | 11.2 | 25 | 1.2 | 96 |
| 106 | 24.7 | 90.3 | 12.2 | N/A |
| 107 | 12.4 | 51.6 | 9.4 | N/A |
| 108 | 12.6 | 73.9 | 5.6 | N/A |
| 109 | 18.3 | 65.2 | 30 | N/A |
| 110 | 22.6 | 42.8 | 44.4 | N/A |
| 111 | 25.3 | 255.8 | 40 | N/A |
| 112 | 40.4 | 243.5 | 48.5 | N/A |
| 113 | 70.5 | 237.4 | 168.4 | N/A |
| 114 | 65.6 | 106.8 | 37.4 | N/A |
| 115 | 155.9 | 321.8 | N/A | N/A |
| 116 | 86.9 | 578 | 136.1 | N/A |
| 117 | 46.2 | 160 | 39.1 | N/A |
| 118 | 49.8 | 352.6 | 51 | N/A |
| 119 | 69.9 | 119.7 | 34.9 | N/A |
| 120 | 177.4 | 846.1 | N/A | N/A |
| 121 | 276.1 | 1622.5 | N/A | N/A |
| 122 | 124.3 | 580.7 | N/A | N/A |
| 123 | 51.1 | 123.4 | 73.6 | N/A |
| 124 | 31.3 | 104.4 | 8.9 | N/A |
| 125 | 24.1 | 134.3 | 32.7 | N/A |
| 126 | 222.4 | 1516.6 | N/A | N/A |
| 127 | 43.2 | 191.1 | 26.5 | N/A |
| 128 | 94.8 | 584.7 | 113.7 | N/A |
| 129 | 21.7 | 37.8 | 3.2 | N/A |
| 130 | 21 | 40.5 | 3.5 | N/A |
| 131 | 21 | 40.7 | 3.5 | N/A |
| 132 | 24.8 | 68.4 | 7.6 | N/A |
| 133 | 16 | 31.1 | 2.4 | N/A |
| 134 | 34.5 | 187.9 | 68.2 | N/A |
| 135 | 22.1 | 151.2 | 41.8 | N/A |
| 136 | 31.9 | 196.3 | 130.5 | N/A |
| 137 | 30.3 | 242.4 | 226.8 | N/A |
| 138 | 164.5 | 1108.6 | N/A | N/A |
| 139 | 12.4 | 22.8 | 1.4 | N/A |
| 140 | 7.9 | 47 | 9.2 | N/A |
| 141 | 48.1 | 346.6 | 115.6 | N/A |
| 142 | 56 | 405.5 | 169.2 | N/A |
| 143 | 50.1 | 310.5 | 377.3 | N/A |
| 144 | 9.8 | 22.2 | 1.1 | N/A |
| 145 | 32.3 | 118.3 | 9.1 | N/A |
| 146 | 19.1 | 47.6 | 1.6 | N/A |
| 147 | 18.5 | 44.7 | 5.6 | N/A |
| 148 | 102.7 | 1153.6 | N/A | N/A |
| 149 | 131.8 | 1076.2 | N/A | N/A |
| 150 | 133.2 | 1117.3 | N/A | N/A |
| 151 | 39.5 | 129.6 | 77.2 | N/A |
| 152 | 49.9 | 163.6 | 106 | N/A |
| 153 | 230.6 | 2403.5 | N/A | N/A |
| 154 | 142.6 | 962.4 | N/A | N/A |
| 155 | 21.3 | 97.2 | 44.1 | N/A |
| 156 | 28.4 | 108 | 31 | N/A |
| 157 | 21.3 | 47.2 | 10.2 | N/A |
| 158 | 1716.6 | 10000 | N/A | N/A |
| 159 | 25.3 | 181.2 | 49.7 | N/A |
| 160 | 91 | 512.3 | 294.2 | N/A |
| 161 | 8.7 | 19.2 | 6.1 | N/A |
| 162 | 17.4 | 45.7 | 9.8 | N/A |
| 163 | 28.8 | 104.4 | 34.9 | N/A |
| 164 | 358.2 | 4281.1 | N/A | N/A |
| 165 | 14.6 | 60.1 | 37.6 | N/A |
| 166 | 1023.9 | 10000 | N/A | N/A |
| 167 | 16.7 | 39.3 | 9.2 | N/A |
| 168 | 5.8 | 14.6 | 5.2 | N/A |
| 169 | 8.2 | 35.3 | 13.7 | N/A |
| 170 | 44.3 | 260.8 | 162.6 | N/A |
| 171 | 29.3 | 134.2 | 89.7 | N/A |
| 172 | 338.7 | 3403.3 | N/A | N/A |
| 173 | 1976.5 | 10000 | N/A | N/A |
| 174 | 9.8 | 17.8 | 3.2 | N/A |
| 175 | 75.8 | 417.4 | 272.4 | N/A |
| 176 | 26.4 | 77.5 | 18.4 | N/A |
| 177 | 20.9 | 46 | 13.3 | N/A |
| 178 | 73.2 | 429.1 | 354.2 | N/A |
| 179 | 27.1 | 139 | 59.6 | N/A |
| 180 | 68.6 | 328.6 | 362.8 | N/A |
| 181 | 83.6 | 478 | 78.6 | N/A |
| 182 | 191.5 | 1299.6 | N/A | N/A |
| 183 | 15.4 | 41.2 | 23.4 | N/A |
| 184 | 40 | 379.3 | 271 | N/A |
| 185 | 10.4 | 93.9 | 50 | N/A |
| 186 | 15.5 | 68.9 | 25.4 | N/A |
| 187 | 5 | 15.2 | 8.3 | N/A |
| 188 | 13.7 | 75.5 | 44.6 | N/A |
| 189 | 9.2 | 35 | 36.7 | N/A |
| 190 | 22.4 | 201.9 | 39.1 | N/A |
| 191 | 93.7 | 1197.3 | 968.7 | N/A |
| 192 | 12.9 | 50.5 | 27.3 | N/A |
| 193 | 21.1 | 73.8 | 26.2 | N/A |
| 194 | 70.3 | 585.5 | 165.6 | N/A |
| 195 | 124.6 | 1864.5 | N/A | N/A |
| 196 | 16 | 200.5 | 29.5 | N/A |
| 197 | 45.3 | 316.2 | 179.3 | N/A |
| 198 | 18.3 | 126.7 | 61.7 | N/A |
| 199 | 14.7 | 107.5 | 40.3 | N/A |
| 200 | 554.4 | 4088.7 | N/A | N/A |
| 201 | 10.5 | 22.7 | 4.5 | 165 |
| 202 | 11.6 | 26.5 | 18.9 | 181 |
| 203 | 9.2 | 68.3 | 23.3 | N/A |
| 204 | 82.3 | 813.1 | N/A | 495 |
| 205 | 10.7 | 62.1 | 6.5 | 275 |
| 206 | 13.8 | 91.1 | 44.2 | N/A |

TABLE 5-continued $IC_{50}$'s of compounds tested in the assay of Examples A, B and C

| Ex. # | RET Enzyme (wild type) $IC_{50}$ (nM) | RET enzyme (V804M) $IC_{50}$ (nM) | KIF5B-RET pTYR1062 Cell $IC_{50}$ (nM) | RET Enzyme (G810R) IC50 (nM) |
|---|---|---|---|---|
| 207 | 18 | 92.7 | 27 | 496 |
| 208 | 20 | 87.2 | 23.9 | N/A |
| 209 | 11 | 141.8 | 36.3 | N/A |
| 210 | 19.7 | 272.8 | 94.7 | 1600 |
| 211 | 84 | 767.9 | 445.1 | 8099 |
| 212 | 19.2 | 69.4 | 12 | 286 |
| 213 | 16.3 | 137.4 | 34.3 | N/A |
| 214 | 21.4 | 38.4 | 14.2 | N/A |
| 215 | 30.2 | 272 | 110.6 | N/A |
| 216 | 195.9 | 1574.7 | N/A | N/A |
| 217 | 7.9 | 45.3 | 15.5 | N/A |
| 218 | 25.3 | 222 | 69.5 | N/A |
| 219 | 17.3 | 109.2 | 43.9 | N/A |
| 220 | 33 | 229.7 | 57.2 | N/A |
| 221 | 10.9 | 49.9 | 16.3 | N/A |
| 222 | 22.2 | 59.5 | 6.3 | N/A |
| 223 | 193.6 | 1614.9 | N/A | N/A |
| 224 | 14.4 | 84.5 | 14.5 | N/A |
| 225 | 39.1 | 316.7 | 141.6 | N/A |
| 226 | 16.9 | 152.4 | 20.9 | N/A |
| 227 | 18 | 140.5 | 26.5 | N/A |
| 228 | 33.5 | 411.4 | 64.8 | N/A |
| 229 | 10.3 | 213.5 | 140.45 | N/A |
| 230 | 251.3 | 3206.5 | N/A | N/A |
| 231 | 12.8 | 56.9 | 7.6 | N/A |
| 232 | 22.1 | 122.9 | 127.3 | N/A |
| 233 | 10.5 | 44 | 5.3 | N/A |
| 234 | 15.1 | 49.8 | 5.2 | N/A |
| 235 | 26.9 | 155 | 32.1 | N/A |
| 236 | 30.3 | 132.7 | 22.4 | N/A |
| 237 | 23.9 | 74.7 | 12.6 | 1169 |
| 238 | 99 | 573.7 | 260.9 | N/A |
| 239 | 11.9 | 33.8 | 4.6 | 253 |
| 240 | 15.4 | 51 | 4.5 | 245 |
| 241 | 21.7 | 131 | 18.1 | 834 |
| 242 | 13.2 | 96.2 | 18.9 | 284 |
| 243 | 10.6 | 69.3 | 9.4 | 303 |
| 244 | 19.9 | 91.1 | 20.9 | 353 |
| 245 | 36.1 | 218.5 | 56.3 | 1675 |
| 246 | 38.5 | 299.6 | 85 | 3494 |
| 247 | 55.2 | 306 | 145.4 | N/A |
| 248 | 11.3 | 55.2 | 25.4 | N/A |
| 249 | 46.4 | 181.6 | 27.5 | N/A |
| 250 | 76.5 | 508.2 | 98.8 | N/A |
| 251 | 8.4 | 31.7 | 16.7 | N/A |
| 252 | 8 | 16.8 | 5.4 | N/A |
| 253 | 25.3 | 61.3 | 38.8 | N/A |
| 254 | 120.1 | 298.9 | N/A | N/A |
| 255 | 30.7 | 69.1 | 12.4 | N/A |
| 256 | 24.5 | 86.8 | 51.2 | N/A |
| 257 | 20.3 | 88.7 | 30.6 | N/A |
| 258 | 12.3 | 19.2 | 1.2 | N/A |
| 259 | 16.8 | 39.1 | 10.8 | N/A |
| 260 | 131.7 | 534.8 | N/A | N/A |
| 261 | 24.6 | 154.7 | 86.9 | N/A |
| 262 | 49.4 | 337.2 | 88.8 | N/A |
| 263 | 90.8 | 888.2 | 318.9 | N/A |
| 264 | 30.4 | 118.7 | 26.8 | N/A |
| 265 | 7.6 | 19.3 | 10.8 | N/A |
| 266 | 29.4 | 182.5 | 32.5 | N/A |
| 267 | 18.1 | 67.1 | 15.9 | N/A |
| 268 | 23.3 | 128.6 | 23.1 | N/A |
| 269 | 18.8 | 70.2 | 4.9 | N/A |
| 270 | 16.9 | 44.8 | 10.5 | N/A |
| 271 | 44.9 | 137.3 | 8.6 | N/A |
| 272 | 17.9 | 55.2 | 14.7 | N/A |
| 273 | 21.3 | 41.6 | 7.9 | N/A |
| 274 | 16.5 | 64.2 | 20.2 | N/A |
| 275 | 39.9 | 460.1 | 124.3 | N/A |
| 276 | 640.7 | 4408.8 | N/A | N/A |
| 277 | 29.8 | 242.6 | 74.9 | 779 |
| 278 | 22.7 | 186.3 | 108.5 | 858 |
| 279 | 33.4 | 147.7 | 20.2 | N/A |
| 280 | 226.2 | 620.7 | N/A | N/A |
| 281 | 23 | 140.8 | 65.3 | N/A |
| 282 | 36.1 | 144.6 | 31.6 | 2304 |
| 283 | 17.1 | 83.7 | 18.1 | 1077 |
| 284 | 76.6 | 693.1 | 141.6 | 5741 |
| 285 | 103.4 | 961.7 | N/A | 10000 |
| 286 | 29.8 | 93.8 | 14.1 | 864 |
| 287 | 17.3 | 77.8 | 9.1 | N/A |
| 288 | 16.1 | 80 | 7.7 | N/A |
| 289 | 18 | 119.4 | 52.4 | N/A |
| 290 | 17.3 | 158.3 | 80.5 | N/A |
| 291 | 95.4 | 895.5 | 956.6 | N/A |
| 292 | 14.7 | 122.6 | 36.4 | N/A |
| 293 | 106.2 | 904.7 | N/A | N/A |
| 294 | 15.1 | 244.4 | 111.3 | N/A |
| 295 | 29 | 81.4 | 19.7 | N/A |
| 296 | 50.8 | 247.6 | 110.8 | N/A |
| 297 | 121 | 737.2 | N/A | N/A |
| 298 | 94.9 | 606.4 | 251.1 | N/A |
| 299 | 6.8 | 14.9 | 5.6 | N/A |
| 300 | 14.8 | 57.4 | 13.3 | N/A |
| 301 | 6.1 | 32.6 | 4.7 | 52 |
| 302 | 11.8 | 26.7 | 13.7 | 74 |
| 303 | 14.1 | 28.7 | 4.6 | 73 |
| 304 | 22.1 | 68.3 | 10.3 | 136 |
| 305 | 10.7 | 47.2 | 5.8 | 75 |
| 306 | 23.3 | 95.2 | 4.3 | 239 |
| 307 | 25.5 | 39.8 | 395.1 | N/A |
| 308 | 11.3 | 28.8 | 14.5 | 329 |
| 309 | 7.6 | 18.1 | 18 | N/A |
| 310 | 14.7 | 30.8 | 3.2 | 67 |
| 311 | 8.3 | 15.4 | 3.7 | 28 |
| 312 | 7.7 | 35.3 | 10 | 43 |
| 313 | 52.1 | 230.2 | 107.6 | N/A |
| 314 | 14.2 | 30.7 | 13.9 | 66 |
| 315 | 16.5 | 50.2 | 12 | 164 |
| 316 | 18.8 | 47.5 | 9.4 | 165 |
| 317 | 25.9 | 69.7 | 6.6 | 104 |
| 318 | 6.6 | 15.8 | 3.5 | 32 |
| 319 | 17.8 | 85.6 | 9.3 | 160 |
| 320 | 20.6 | 59.3 | 3.7 | N/A |
| 321 | 9.8 | 37.3 | 14.3 | 65 |
| 322 | 13.7 | 27.4 | 8.9 | 73 |
| 323 | 16.1 | 30.5 | 3.6 | 69 |
| 324 | 8.7 | 22 | 1.4 | 30 |
| 325 | 17.1 | 70.9 | 23.4 | 255 |
| 326 | 103.9 | 661.8 | 203.1 | N/A |
| 327 | 13.2 | 22.8 | 11.7 | N/A |
| 328 | 14.9 | 109.7 | 19.4 | N/A |
| 329 | 112 | 751 | 225.8 | N/A |
| 330 | 165.9 | 745.5 | N/A | N/A |
| 331 | 18.9 | 137.3 | 34.5 | N/A |
| 332 | 11 | 48.3 | 29.8 | N/A |
| 333 | 963.6 | 6081 | N/A | N/A |
| 334 | 6.6 | 28.5 | 18.1 | 79 |
| 335 | 68.7 | 221.2 | 172.9 | 163 |
| 336 | 16.6 | 88.9 | 30.8 | 241 |
| 337 | 391.6 | 1085.9 | N/A | 1000 |
| 338 | 11 | 33.7 | 15 | 52 |
| 339 | 726.9 | 2657.9 | N/A | 5804 |
| 340 | 12.9 | 33.5 | 2.2 | 92 |
| 341 | 7.6 | 12 | 4.4 | 21 |
| 342 | 12.4 | 32 | 7.6 | 58 |
| 343 | 15.1 | 50.4 | 20 | 80 |
| 344 | 27.1 | 233.5 | 58.7 | 168 |
| 345 | 717 | 3887.4 | N/A | 3617 |
| 346 | 135 | 1472.2 | N/A | N/A |
| 347 | 189.6 | 1812.1 | N/A | N/A |
| 348 | 31.1 | 135.4 | 71.8 | N/A |
| 349 | 101.1 | 627.6 | 131 | N/A |
| 350 | 21.7 | 185.6 | 43.4 | N/A |
| 351 | 133.5 | 1286.4 | N/A | N/A |
| 352 | 89.6 | 1553.9 | 229.9 | N/A |
| 353 | 87.6 | 647.4 | 148.9 | N/A |
| 354 | 53 | 542.9 | 137.6 | N/A |

TABLE 5-continued

IC$_{50}$'s of compounds tested in the assay of Examples A, B and C

| Ex. # | RET Enzyme (wild type) IC$_{50}$ (nM) | RET enzyme (V804M) IC$_{50}$ (nM) | KIF5B-RET pTYR1062 Cell IC$_{50}$ (nM) | RET Enzyme (G810R) IC50 (nM) |
|---|---|---|---|---|
| 355 | 210 | 2822.4 | N/A | N/A |
| 356 | 159.5 | 2217.3 | N/A | N/A |
| 357 | 194.6 | 1446.7 | N/A | N/A |
| 358 | 7.6 | 41.3 | 7.6 | 38 |
| 359 | 10.9 | 56.9 | 7 | 123 |
| 360 | 88.9 | 833.3 | 277.9 | N/A |
| 361 | 11.7 | 74.4 | 9.2 | 90 |
| 362 | 4.4 | 16.9 | 4.7 | 19 |
| 363 | 5.5 | 22.7 | 3.3 | 35 |
| 364 | 104.8 | 972.1 | N/A | N/A |
| 365 | 347.5 | 3719.7 | N/A | N/A |
| 366 | 451.4 | 2866.2 | N/A | N/A |
| 367 | 37.1 | 89.4 | 41 | N/A |
| 368 | 22.6 | 69.6 | 5.5 | 159 |
| 369 | 34.3 | 55.4 | 5.2 | 92 |
| 370 | 19.6 | 111.5 | 24.6 | N/A |
| 371 | 4.2 | 19.7 | 23.6 | 24 |
| 372 | 18.3 | 55 | 18.6 | 109 |
| 373 | 29.7 | 233.8 | 116.5 | N/A |
| 374 | 9.8 | 58.5 | 23.9 | 43 |
| 375 | 155.4 | 749.7 | N/A | 1073 |
| 376 | 93 | 428.3 | 168.4 | 1069 |
| 377 | 57.7 | 314.8 | 39.4 | 754 |
| 378 | N/A | N/A | N/A | N/A |
| 379 | 8.8 | 21.8 | 4.8 | 54 |
| 380 | 7.1 | 14.7 | 6.3 | 41 |
| 381 | 10.3 | 24.7 | 15.1 | N/A |
| 382 | 20.5 | 62.9 | 8.8 | N/A |
| 383 | 21.5 | 43.4 | 18.3 | 62 |
| 384 | 5.7 | 14 | 2.6 | 22 |
| 385 | 5.8 | 26.4 | 4.7 | 37 |
| 386 | 9.7 | 101.9 | 9.8 | 67 |
| 387 | 52.7 | 497 | 429.3 | 327 |
| 388 | 22 | 71 | 18.6 | 75 |
| 389 | 13.4 | 26 | 1.3 | 124 |
| 390 | 11.1 | 37.2 | 4.3 | 63 |
| 391 | 6.7 | 10.6 | 2 | 21 |
| 392 | 48.9 | 212.5 | 54.2 | 458 |
| 393 | 6.4 | 52.8 | 9.3 | 58 |
| 394 | 7.5 | 31 | 3.5 | 39 |
| 395 | 26.4 | 102.8 | 146.9 | 146 |
| 396 | 26.5 | 87.5 | 115.8 | 114 |
| 397 | 17.5 | 40.2 | 16.8 | 86 |
| 398 | 230.7 | 2422.2 | N/A | 8419 |
| 399 | 26.1 | 56.9 | 4.1 | 319 |
| 400 | 13.7 | 36.6 | 8.2 | 189 |
| 401 | 19 | 33.6 | 2.9 | 109 |
| 402 | 11.7 | 18.5 | 3.2 | 71 |
| 403 | 22.3 | 37.1 | 2.1 | 182 |
| 404 | 12.2 | 31.2 | 20.7 | 94 |
| 405 | 8 | 28.2 | 12.7 | N/A |
| 406 | 12.2 | 54.9 | 19.1 | 73 |
| 407 | 14 | 47.5 | 19.7 | 42 |
| 408 | 30.2 | 239.8 | 72.6 | N/A |
| 409 | 8.9 | 12.7 | 3.3 | N/A |
| 410 | 8.7 | 14.3 | 3.9 | N/A |
| 411 | 150.2 | 1078.2 | N/A | N/A |
| 412 | 17.3 | 89.7 | 13.6 | N/A |
| 413 | 637 | 3424.7 | N/A | 5467 |
| 414 | 15.8 | 50.1 | 16.5 | 145 |
| 415 | 6.9 | 24 | 5.6 | N/A |
| 416 | 8.6 | 38.6 | 8.6 | N/A |
| 417 | 32 | 58 | 204.9 | 89 |
| 418 | 340.2 | 473.3 | N/A | N/A |
| 419 | 106.5 | 176.3 | N/A | N/A |
| 420 | 147.4 | 227.9 | N/A | N/A |
| 421 | 25.7 | 61.9 | 70.1 | 159 |
| 422 | 16.5 | 30.7 | 28.9 | 116 |
| 423 | 23.6 | 54.1 | 38.2 | 144 |
| 424 | 42.2 | 32.4 | 137.4 | 273 |
| 425 | 31.2 | 70.3 | 74 | 195 |
| 426 | 238.4 | 457 | N/A | N/A |
| 427 | 41.8 | 72.8 | 152.3 | 1122 |
| 428 | 47.5 | 104.2 | 141.5 | N/A |
| 429 | 56.2 | 222.5 | 745.3 | 4107 |
| 430 | 334.7 | 542 | N/A | N/A |
| 431 | 38.2 | 102 | 47.8 | 854 |
| 432 | 32.2 | 81.2 | 9.5 | 239 |
| 433 | 20.2 | 48.5 | 2.7 | 90 |
| 434 | 6.2 | 45.2 | 7.7 | 32 |
| 435 | 12.4 | 35.2 | 2.7 | 57 |
| 436 | 19.3 | 96.2 | 8.7 | 182 |
| 437 | 21.8 | 87.2 | 9.4 | 95 |
| 438 | 14.9 | 92.8 | 28.2 | 68 |
| 439 | 22 | 142.6 | 16.3 | 118 |
| 440 | 13.2 | 30 | 5 | N/A |
| 441 | 12.4 | 49.9 | 13.8 | 231 |
| 442 | 15 | 56.2 | 6.9 | 70 |
| 443 | 12.6 | 47.7 | 6.5 | 111 |
| 444 | 15.2 | 60.4 | 12.7 | N/A |
| 445 | 19.6 | 161.3 | 17.2 | 89 |
| 446 | 26.2 | 94.8 | 52.8 | 241 |
| 447 | 24.8 | 163 | 98.3 | N/A |
| 448 | 22.9 | 161.9 | 80.1 | N/A |
| 449 | 85.4 | 1111.1 | 417.2 | N/A |
| 450 | 20.8 | 180.6 | 38 | 137 |
| 451 | 15.5 | 84.5 | 18.3 | 86 |
| 452 | 9.8 | 71.2 | 22.3 | 109 |
| 453 | 21.4 | 158.4 | 24.8 | 245 |
| 454 | 20.7 | 189.5 | 64.3 | 195 |
| 455 | 25.8 | 83.8 | 16.6 | 231 |
| 456 | 17.7 | 42.9 | 11.9 | 75 |
| 457 | 74.8 | 395 | 238.5 | 470 |
| 458 | 35.6 | 239.4 | 82.4 | 414 |
| 459 | 12.7 | 70 | 461.8 | 297 |
| 460 | 12.3 | 87.4 | 22.9 | 401 |
| 461 | 45.9 | 357.6 | 65.6 | 725 |
| 462 | 22.9 | 93 | 63.2 | 283 |
| 463 | 34.6 | 190.7 | 36.4 | 454 |
| 464 | 39.5 | 211.9 | 32.7 | 312 |
| 465 | 28.6 | 121.4 | 21.7 | 383 |
| 466 | 41.7 | 203.7 | 55.7 | N/A |
| 467 | 383.8 | 2091.3 | N/A | N/A |
| 468 | 20.1 | 83.1 | 17.6 | N/A |
| 469 | 42.9 | 208.2 | 139.2 | N/A |
| 470 | 12.5 | 95.1 | 29.6 | N/A |
| 471 | 44.7 | 391.4 | 88.2 | N/A |
| 472 | 22 | 171 | 47.3 | N/A |
| 473 | 19.8 | 68.1 | 11 | 195 |
| 474 | 12.8 | 141.4 | 43.5 | N/A |
| 475 | 10.1 | 69.9 | 25.6 | N/A |
| 476 | 9.3 | 62.8 | 19.5 | N/A |
| 477 | 19.4 | 173.3 | 34.7 | N/A |
| 478 | 59.9 | 613.7 | 116.5 | N/A |
| 479 | 728.3 | 2778.9 | N/A | N/A |
| 480 | 317.3 | 1708 | N/A | 1739 |
| 481 | 16.6 | 88.9 | 30.8 | N/A |
| 482 | 47 | N/A | N/A | 10000 |
| 483 | 127 | 508 | N/A | N/A |
| 484 | 590.6 | 3508.1 | N/A | N/A |
| 485 | 3.7 | 30.7 | 32.3 | N/A |
| 486 | 397.9 | 2303.6 | N/A | N/A |
| 487 | 5.5 | 35.1 | 88 | 78 |
| 488 | 8.4 | 73 | 23.9 | N/A |
| 489 | 20.5 | 484.2 | 73.9 | 104 |
| 490 | 913.7 | 10000 | N/A | 10000 |
| 491 | 65.1 | 358 | N/A | 269 |
| 492 | 20.1 | 80.5 | 30.6 | 55 |
| 493 | 12.8 | 166.2 | 17.2 | 79 |
| 494 | 55.2 | 307.3 | N/A | 276 |
| 495 | 40.4 | 358.1 | 57.6 | 176 |
| 496 | 118.7 | 588.3 | N/A | 422 |
| 497 | 110.2 | 573.8 | N/A | 896 |
| 498 | 71.9 | 216.1 | 171.4 | 194 |
| 499 | 322.1 | 446.8 | N/A | 3336 |
| 500 | 108.6 | 2197.9 | N/A | 1205 |
| 501 | 276 | 3898.7 | N/A | 5553 |
| 502 | 78.1 | 1145.1 | 142.1 | 1034 |

TABLE 5-continued

IC$_{50}$'s of compounds tested in the assay of Examples A, B and C

| Ex. # | RET Enzyme (wild type) IC$_{50}$ (nM) | RET enzyme (V804M) IC$_{50}$ (nM) | KIF5B-RET pTYR1062 Cell IC$_{50}$ (nM) | RET Enzyme (G810R) IC50 (nM) |
|---|---|---|---|---|
| 503 | 103.7 | 718.4 | N/A | 970 |
| 504 | 10.2 | 64.8 | 9.5 | 47 |
| 505 | 250.4 | 3282.6 | N/A | 1670 |
| 506 | 432.1 | 6553.4 | N/A | 2012 |
| 507 | 49.4 | 528.9 | 1223 | 399 |
| 508 | 45.1 | 211.1 | 110.1 | 292 |
| 509 | 12.8 | 195.8 | 38.7 | 82 |
| 510 | 523.6 | 6442.1 | N/A | 10000 |
| 511 | 598 | 10000 | N/A | 1111 |
| 512 | 65.7 | 719.4 | 235.1 | 1093 |
| 513 | 13.9 | 185.6 | 29 | 106 |
| 514 | 26.1 | 101.1 | 35.7 | 207 |
| 515 | 141.8 | 1027.2 | N/A | 2392 |
| 516 | 114.8 | 720.7 | N/A | 944 |
| 517 | 265.9 | 10000 | N/A | 10000 |
| 518 | 478 | 1164.2 | N/A | 4570 |
| 519 | 10.2 | 35.1 | 7.8 | 42 |
| 520 | 8.2 | 31.1 | 5.6 | 22 |
| 521 | 59.6 | 402.5 | N/A | 723 |
| 522 | 12.2 | 98.4 | 9.6 | 56 |
| 523 | 11.2 | 39.3 | 7.4 | 63 |
| 524 | 25 | 154.3 | 28 | 111 |
| 525 | 20.4 | 207.4 | 35.2 | 133 |
| 526 | 24.6 | 123.5 | 22.7 | 94 |
| 527 | 24.4 | 443.8 | 104.2 | 261 |
| 528 | 6.4 | 14.7 | 3 | 18 |
| 529 | 115.8 | 1111.9 | N/A | 698 |
| 530 | 534.8 | 10000 | N/A | 10000 |
| 531 | 26.9 | 159.1 | 34.4 | 158 |
| 532 | 98.9 | 471.6 | 454.3 | 841 |
| 533 | 454.3 | 6705.6 | N/A | 6786 |
| 534 | 107.5 | 2683.6 | N/A | 3297 |
| 535 | 173 | 1520.5 | N/A | 1050 |
| 536 | 403.9 | 1511.9 | N/A | 2854 |
| 537 | 317.9 | 1394.1 | N/A | 3052 |
| 538 | 620.6 | 4423.4 | N/A | 5231 |
| 539 | 434.8 | 2716.5 | N/A | 5008 |
| 540 | 329.1 | 2134.6 | N/A | 4435 |
| 541 | 10.6 | 89.4 | 5 | 106 |
| 542 | 28.8 | 179.5 | 33.5 | 209 |
| 543 | 7.8 | 91.9 | 10 | 80 |
| 544 | 21.7 | 343 | 25.2 | 278 |
| 545 | 90.6 | N/A | N/A | 836 |
| 546 | 29.8 | 243.3 | 157.7 | 274 |
| 547 | 68.6 | 762.1 | 388 | 1382 |
| 548 | 33.5 | 441.1 | 320.4 | 395 |
| 549 | 50.7 | 688.6 | 481 | 1088 |
| 550 | 45.2 | 724.2 | 218.7 | 1219 |
| 551 | 60.5 | 1990.8 | 130.9 | 666 |
| 552 | 44.6 | 311.3 | 75.3 | 394 |
| 553 | 138.2 | 732.8 | N/A | 1775 |
| 554 | 255.7 | 6537.2 | N/A | 1442 |
| 555 | 19.9 | 189.4 | 35 | 258 |
| 556 | 12.5 | 22.8 | 41.8 | 114 |
| 557 | 29.1 | 266.5 | 45.2 | 420 |
| 558 | 27.7 | 192.5 | 34.2 | 345 |
| 559 | 55.3 | 508.7 | 100.1 | 693 |
| 560 | 23.9 | 166.7 | 35.6 | 280 |
| 561 | 361.7 | 2985.3 | N/A | 7429 |
| 562 | 37.6 | 195.9 | 25.2 | 176 |
| 563 | 41.7 | 176.5 | 51.6 | 211 |
| 564 | 11.1 | 17.9 | 3.1 | 39 |
| 565 | 13.7 | 116.3 | 23.3 | 168 |
| 566 | 10.1 | 147.2 | 51.7 | 124 |
| 567 | 7.8 | 140.2 | 37.9 | 66 |
| 568 | 35.5 | 216.6 | 141.4 | 331 |
| 569 | 20.8 | 59.9 | 9.9 | 40 |
| 570 | 7.2 | 28.9 | 6.5 | 44 |
| 571 | 8.9 | 55.3 | 5.3 | 48 |
| 572 | 11.2 | 67.6 | 36.7 | 116 |
| 573 | 15.2 | 94.1 | 48.3 | 155 |
| 574 | 28.5 | 212.1 | 65.8 | 119 |
| 575 | 33.2 | 165.7 | 219.1 | 144 |
| 576 | 439.5 | 3690.9 | N/A | 1217 |
| 577 | 203.6 | 1673.1 | N/A | 602 |
| 578 | 9.8 | 43.7 | 7.6 | 51 |
| 579 | 9.8 | 27.4 | 4.1 | 32 |
| 580 | 8 | 25.3 | 7.4 | 55 |
| 581 | 8.4 | 21.4 | 3.3 | 35 |
| 582 | 18.2 | 32.9 | 11.4 | 62 |
| 583 | 46.3 | 308.9 | 109 | 642 |
| 584 | 13.7 | 110.7 | 23.3 | 226 |
| 585 | 32.3 | 304.7 | 33.4 | 289 |
| 586 | 25.7 | 158.9 | 10.9 | 251 |
| 587 | 30.8 | 96.9 | 13.2 | 95 |
| 588 | 58.8 | 513.1 | 91.4 | 467 |
| 589 | 57.4 | 716 | 136.5 | 677 |
| 590 | 92.3 | 443.3 | 122.6 | 431 |
| 591 | 122.8 | 2320.8 | N/A | 2022 |
| 592 | 25 | 270.7 | 54.2 | 280 |
| 593 | 31.9 | 245.7 | 42.2 | 309 |
| 594 | 30.5 | 85.6 | 8.45 | 71 |
| 595 | 45.5 | 348.4 | 55.6 | N/A |
| 597 | 6 | 13.6 | 2.2 | 25 |
| 598 | 10.9 | 59.1 | 10.2 | 48 |
| 599 | 17 | 35.8 | 4.8 | 94 |
| 600 | 14 | 79.4 | 17.7 | 113 |
| 601 | 17 | 67.7 | 11 | 97 |
| 602 | 7.6 | 49 | 7.2 | 61 |
| 603 | 17.2 | 68 | 10 | 158 |
| 604 | 18.2 | 43.4 | 5.9 | 129 |
| 605 | 784.1 | 3987.4 | N/A | 6980 |
| 606 | 15.1 | 119.6 | 51.7 | 226 |
| 607 | 21.1 | 69.4 | 23.3 | 320 |
| 608 | 22.9 | 130.6 | 488.2 | 193 |
| 609 | 190.9 | 983.7 | N/A | 1113 |
| 610 | 27.1 | 195.1 | 142.4 | 296 |
| 611 | 36 | 150.3 | 34.9 | 457 |
| 612 | 13.9 | 139.4 | 225.6 | 258 |
| 613 | 10 | 27.2 | 3.2 | 48 |
| 614 | 19.3 | 49.8 | 9.5 | 76 |
| 615 | 9.6 | 24 | 8.9 | 62 |
| 616 | 23.6 | 67.9 | 10.9 | N/A |
| 617 | 44.9 | 118.6 | 15 | N/A |
| 618 | 15.1 | 148.5 | 39.4 | 319 |
| 619 | 14.3 | 77.4 | 13.1 | 286 |
| 620 | 15.8 | N/A | 19 | 333 |
| 621 | 16.4 | 83 | 22.6 | 260 |
| 622 | 23 | 196.5 | 104.8 | 582 |
| 623 | 31.3 | 139.5 | 20.7 | 363 |
| 624 | 30.3 | 280.2 | 34.8 | 414 |
| 625 | 105.1 | 718.3 | N/A | 3513 |
| 626 | 20.4 | 112.7 | 1071.8 | 415 |
| 627 | 41 | 254.4 | 1667 | 917 |
| 628 | 18.3 | 272.7 | 79 | 259 |
| 629 | 13.7 | 125.9 | 43.4 | 293 |
| 630 | 16.8 | 87.5 | 80.6 | 270 |
| 631 | 29 | 244.9 | 23.6 | 312 |
| 632 | 38.9 | 98.9 | 107.8 | 507 |
| 633 | 14.5 | 124.1 | 45.1 | 165 |
| 634 | 30.1 | 251.1 | 71.4 | 272 |
| 635 | 17.5 | 94.8 | 222.9 | 228 |
| 636 | 30.7 | 158.7 | 100.8 | 315 |
| 637 | 263.6 | 1952 | N/A | 2112 |
| 638 | 21.4 | 237.6 | 22.4 | 213 |
| 639 | 105.1 | 442.8 | N/A | 1131 |
| 640 | 47.3 | 166.4 | 801.5 | 508 |
| 641 | 13.3 | 88.7 | 6.9 | 86 |
| 642 | 27.1 | 255.4 | 19.6 | 930 |
| 643 | 32.4 | 183.4 | 17.6 | 223 |
| 644 | 25.1 | 203.8 | 19.7 | 185 |
| 645 | 12.4 | 86 | 10.6 | 89 |
| 646 | 30.9 | 207.8 | 23.5 | 159 |
| 647 | 34.9 | 361.6 | 50.5 | 279 |
| 648 | 72 | 575.9 | 125.7 | 888 |
| 649 | 112 | 793.4 | N/A | 1029 |
| 650 | 149.6 | 1088.8 | N/A | 1017 |
| 651 | 6.5 | 53.9 | 48.9 | 78 |

TABLE 5-continued

IC$_{50}$'s of compounds tested in the assay of Examples A, B and C

| Ex. # | RET Enzyme (wild type) IC$_{50}$ (nM) | RET enzyme (V804M) IC$_{50}$ (nM) | KIF5B-RET pTYR1062 Cell IC$_{50}$ (nM) | RET Enzyme (G810R) IC50 (nM) |
|---|---|---|---|---|
| 652 | 14.9 | 181.6 | 177.5 | 190 |
| 653 | 12.3 | 39.5 | 228.7 | 108 |
| 654 | 10.2 | 90.6 | 10.5 | 114 |
| 655 | 27.5 | 79.7 | 19.8 | 149 |
| 656 | 6.3 | 35 | 4.3 | 54 |
| 657 | 15.5 | 86.5 | 17.7 | 91 |
| 658 | 19.4 | 159.3 | 161.1 | 191 |
| 659 | 14.7 | 133.3 | 14.6 | 267 |
| 660 | 16.2 | 106.9 | 9.1 | 168 |
| 661 | 36.2 | 142.4 | 48.9 | 274 |
| 662 | 9.8 | 42.4 | 10.4 | 46 |
| 663 | 492.1 | 5103.1 | N/A | 10000 |
| 664 | 3959.5 | 10000 | N/A | 10000 |
| 665 | 729.5 | 3613.2 | N/A | 10000 |
| 666 | 29.6 | 41.9 | 27.2 | 72 |
| 667 | 174.9 | 493.3 | N/A | 994 |
| 668 | 45.6 | 133.5 | 66.1 | 604 |
| 669 | 22 | 59.1 | 28.8 | 402 |
| 670 | 18.4 | 67 | 17.5 | 194 |
| 671 | 20.7 | 75.1 | 23.1 | 159 |
| 672 | 13 | 52.3 | 23.9 | 148 |
| 673 | 11.1 | 65.5 | 21.4 | 157 |
| 674 | 39.3 | 105.4 | 3.2 | 279 |
| 675 | 30.2 | 91 | 2.4 | 249 |
| 676 | 12.9 | 30.1 | 8 | 141 |
| 677 | 13.5 | 26.8 | 5 | 61 |
| 678 | 17.9 | 38.4 | 2.3 | 55 |
| 679 | 18 | 33.3 | 2.3 | 135 |
| 680 | 5.2 | 28.9 | 12 | 88 |
| 681 | 42.9 | 226.1 | 25.2 | 311 |
| 682 | 24.9 | 53.3 | 4.9 | 106 |
| 683 | 16.5 | 90.2 | 11.5 | 196 |
| 684 | 15.2 | 40.9 | 4.3 | 122 |
| 685 | 19.6 | 53.2 | 7.7 | 498 |
| 686 | 11 | 40.7 | 8.6 | 174 |
| 687 | 14.8 | 45.4 | 13.2 | 81 |
| 688 | 5 | 11.5 | 5.4 | 109 |
| 689 | 12.7 | 50.4 | 9 | 165 |
| 690 | 3.7 | 12.6 | 3.7 | 42 |
| 691 | 21.9 | 31.5 | 3 | 85 |
| 692 | 9.3 | 38.9 | 7.8 | 128 |
| 693 | 6 | 63.3 | 14.1 | 183 |
| 694 | 27.7 | 74.2 | 4.8 | 161 |
| 695 | 21.8 | 82.1 | 28.6 | 204 |
| 696 | 42.4 | 61 | 11.7 | 277 |
| 697 | 34.7 | 93 | 8.4 | 382 |
| 698 | 6.1 | 16 | 81.5 | 114 |
| 699 | 16 | 26.5 | 8.8 | 153 |
| 700 | 78.7 | 88.5 | N/A | 357 |
| 701 | 6.1 | 21.3 | 25.1 | 162 |
| 702 | 10.7 | 48.3 | 10.5 | 130 |
| 703 | 7.2 | 26.3 | 14.7 | 63 |
| 704 | 21.9 | 87.4 | 10.9 | 218 |
| 705 | 4.6 | 17.8 | 24.3 | 131 |
| 706 | 17 | 121.7 | 16.5 | 4540 |
| 707 | 9.1 | 36.3 | 11.6 | 59 |
| 708 | 43 | 450 | 372 | 1044 |
| 709 | 11 | 32 | 8 | 83 |
| 710 | 53 | 517 | 103 | 467 |
| 711 | 6 | 11 | 3 | 26 |
| 712 | 20 | 191 | 29 | 315 |
| 713 | 17 | 276 | 90 | 284 |
| 714 | 32 | 303 | 103 | 747 |
| 715 | 34 | 132 | 66 | 158 |
| 716 | 125 | 765 | N/A | 1151 |
| 717 | 23 | 473 | 268 | 1405 |
| 718 | 34 | 310 | 85 | 607 |
| 719 | 16 | 112 | 47 | 123 |
| 720 | 435 | 3438 | 938 | 10000 |
| 721 | 14 | 30 | 30 | 58 |
| 722 | 2 | 10 | 3 | 15 |
| 723 | 3 | 10 | 2 | 13 |
| 724 | 15 | 95 | 11 | 40 |
| 725 | 4 | 15 | 2 | 16 |
| 726 | 44 | 176 | 105 | 214 |
| 727 | 24 | 195 | 67 | 194 |
| 728 | 19 | 316 | 80 | 804 |
| 729 | 7 | 21 | 13 | 35 |
| 730 | 5 | 12 | 5 | 16 |
| 731 | 5 | 15 | 8 | 27 |
| 732 | 96 | 455 | N/A | 472 |
| 733 | 434 | 8002 | N/A | 10000 |
| 734 | 52 | 321 | 80 | 694 |
| 735 | 56 | 568 | N/A | 6169 |
| 736 | 53 | 993 | N/A | 10000 |
| 737 | 69 | 295 | 105 | 10000 |
| 738 | 40 | 304 | 18 | 10000 |
| 739 | 68 | 301 | 96 | 10000 |
| 740 | 43 | 320 | 119 | 8460 |
| 741 | 217 | 1315 | N/A | 5702 |
| 742 | 4 | 24 | 5 | 648 |
| 743 | 12 | 63 | 6 | 1119 |
| 744 | 40 | 218 | 36 | 1109 |
| 745 | 128 | 966 | N/A | 10000 |
| 746 | 28 | 97 | 15 | 1283 |
| 747 | 19 | 66 | 12 | 1490 |
| 748 | 14 | 81 | 12 | 1999 |
| 749 | 25 | 152 | 15 | 2584 |
| 750 | 42 | 212 | 23 | 4308 |
| 751 | 48 | 256 | 39 | 1530 |
| 752 | 143 | 2665 | N/A | 10000 |
| 753 | 13 | 72 | 7 | 943 |
| 754 | 7 | 73 | 16 | 543 |
| 755 | 143 | 1197 | 483 | 1305 |
| 756 | 6 | 50 | 22 | 81 |
| 757 | 19 | 537 | 41 | 2375 |
| 758 | 29 | 164 | 15 | 570 |
| 759 | 11 | 137 | 11 | 338 |
| 760 | 53 | 508 | 76 | 2594 |
| 761 | 18 | 134 | 13 | 394 |
| 762 | 12 | 116 | 11 | 239 |
| 763 | 22 | 124 | 16 | 3272 |
| 764 | 79 | 247 | 418 | 351 |
| 765 | 578 | 3799 | N/A | 10000 |
| 766 | 23 | 361 | 54 | 351 |
| 767 | 23 | 196 | 13 | 592 |
| 768 | 11 | 118 | 16 | 1984 |
| 769 | 12 | 162 | 36 | 6870 |
| 770 | 4 | 24 | 12 | 63 |
| 771 | 9 | 26 | 4 | 52 |
| 772 | 8 | 24 | 4 | 30 |
| 773 | 12 | 10000 | 9 | 10000 |
| 774 | 8 | 45 | 6 | 51 |
| 775 | 3 | 16 | 5 | 26 |
| 776 | 10 | 46 | 11 | 94 |
| 777 | 3 | 13 | 3 | 25 |
| 778 | 23 | 129 | 19 | 192 |
| 779 | 19 | 66 | 13 | 58 |
| 780 | 21 | 91 | 15 | 328 |
| 781 | 41 | 90 | 7 | 154 |
| 782 | 33 | 221 | 92 | 520 |
| 783 | 3 | 43 | 62 | 76 |
| 784 | 24 | 77 | 17 | 796 |
| 785 | 37 | 142 | 20 | 1475 |
| 786 | 48 | 179 | 13 | 965 |
| 787 | 22 | 60 | 8 | 541 |
| 788 | 23 | 93 | 9 | 983 |
| 789 | 23 | 159 | 8 | 1022 |
| 790 | 8 | 35 | 34 | 268 |
| 791 | 16 | 77 | 19 | 107 |
| 792 | 13 | 106 | 18 | 92 |
| 793 | 8 | 47 | 11 | 76 |
| 794 | 5 | 32 | 7 | 29 |
| 795 | 16 | 245 | 25 | 122 |
| 796 | 5 | 34 | 7 | 21 |
| 797 | 10 | 30 | 11 | 423 |
| 798 | 9 | 9 | 11 | 222 |
| 799 | 21 | 37 | 28 | 274 |

TABLE 5-continued

IC$_{50}$'s of compounds tested in the assay of Examples A, B and C

| Ex. # | RET Enzyme (wild type) IC$_{50}$ (nM) | RET enzyme (V804M) IC$_{50}$ (nM) | KIF5B-RET pTYR1062 Cell IC$_{50}$ (nM) | RET Enzyme (G810R) IC50 (nM) |
|---|---|---|---|---|
| 800 | 9 | 21 | 6 | 86 |
| 801 | 114 | 1078 | N/A | 1744 |
| 802 | 176 | 818 | N/A | 1214 |
| 803 | 62 | 213 | N/A | 384 |
| 804 | 71 | 266 | N/A | 368 |
| 805 | 33 | 319 | 72 | 301 |
| 806 | 33 | 180 | 59 | 276 |
| 807 | 5 | 21 | 6 | 55 |
| 808 | 6 | 27 | 5 | 51 |
| 809 | 8 | 37 | 9 | 73 |
| 810 | 19 | 78 | 13 | 128 |
| 811 | 7 | 24 | 9 | 94 |
| 812 | 16 | 83 | 26 | 158 |
| 813 | 6 | 23 | 8 | 38 |
| 814 | 8 | 24 | 9 | 64 |
| 815 | 9 | 37 | 13 | 87 |
| 816 | 13 | 39 | 24 | 83 |
| 817 | 7 | 27 | 29 | 80 |
| 818 | 38 | 253 | 60 | 431 |
| 819 | 23 | 149 | 55 | 245 |

N/A = not available

SYNTHETIC EXAMPLES

Synthesis of Synthetic Intermediates

Intermediate P1

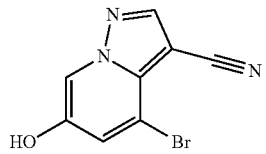 [SMILES: N#Cc1cnn2cc(O)cc(Br)c12]

4-Bromo-6-hydroxypyrazolo[1,5-a]pyridine-3-carbonitrile

Part A: Preparation of O-(mesitylsulfonyl)hydroxylamine

Step 1: Preparation of tert-butyl (mesitylsulfonyl)oxycarbamate

To a 0° C. solution of 2,4,6-trimethylbenzene-1-sulfonyl chloride (10.0 g, 45.72 mmol) and tert-butyl hydroxycarbamate (6.088 g, 45.72 mmol) in MTBE (100 mL) was added TEA (14.46 mL, 48.01 mmol) drop-wise while stirring. The resulting suspension was stirred at 0° C. for an additional 30 min and then warmed to ambient temperature. The reaction was then diluted with water (100 mL), adjusted to pH 4 with 1 N HCl$_{(aq)}$. The organic layer was dried (Na$_2$SO$_4$), filtered and concentrated to yield the title compound initially as a yellowish oil, which upon drying overnight under high vacuum became a white solid (12.89 g, 89% yield). $^1$H NMR (CDCl$_3$) δ 7.66 (br s, 1H), 6.98 (s, 2H), 2.67 (s, 6H), 2.32 (s, 3H), 1.31 (s, 9H).

Step 2: Preparation of O-(mesitylsulfonyl)hydroxylamine

To TFA (117 mL, 1521 mmol) at 0° C. was slowly added tert-butyl (mesitylsulfonyl)oxycarbamate (39.0 g, 124 mmol) over 25 min. The reaction mixture was stirred at 0° C. for 1.5 h and then quenched with the sequential addition of crushed ice and water. The resulting thick suspension was vigorously stirred at ambient temperature for 5 min. Without allowing the filter cake to run dry, the solids were collected by careful vacuum filtration followed by subsequent rinsing with water (4 L) until the filtrate reached pH 6 (Caution: explosion risk exists with dry compound at ambient temperature). The wet filter cake was taken up in DCM (150 mL) and the resulting biphasic solution was separated. The DCM layer was dried over MgSO$_4$ for 30 min and then filtered and rinsed with DCM (420 mL) to provide the title compound as a 0.22 M solution in DCM Part B: Preparation of 4-Bromo-6-hydroxypyrazolo [1,5-a]pyridine-3-carbonitrile Step 1: Preparation of 1-amino-3-bromo-5-methoxypyridin-1-ium 2,4,6-trimethylbenzenesulfonate To a solution of O-(mesitylsulfonyl)hydroxylamine (Part A, 26.6 g, 117 mmol) in DCM (570 mL) cooled to 0° C. was added 3-bromo-5-methoxypyridine (22.1 g, 117 mmol) in portions. The reaction mixture was stirred for 1 h at 0° C. then treated with additional 3-bromo-5-methoxypyridine (250 mg, 1.39 mmol) and stirred for an additional 2 h at 0° C. The reaction mixture was diluted with Et$_2$O (600 mL), stirred at 0° C. for 10 min and then vacuum filtered, rinsed with Et$_2$O (3×250 mL). Upon reduction in volume by about ⅓, the filtrate yielded additional precipitate which was collected by filtration. Both filter cakes were dried in vacuo to provide the title compound (39.3 g, 83% yield). $^1$H NMR (CDCl$_3$) δ 9.25 (br s, 1H), 8.99 (m, 1H), 8.74 (m, 1H), 7.46 (m, 1H), 6.83 (s, 2H), 3.92 (s, 3H), 2.65 (s, 6H), 2.22 (s, 3H).

Step 2: Preparation of Ethyl 6-bromo-4-methoxypyrazolo[1,5-a]pyridine-3-carboxylate and Ethyl 4-bromo-6-methoxypyrazolo[1,5-a]pyridine-3-carboxylate To a magnetically stirred white suspension of 1-amino-3-bromo-5-methoxypyridin-1-ium 2,4,6-trimethylbenzenesulfonate (33.24 g, 82.42 mmol) in DMF (82 mL) at ambient temperature was added TEA (22.98 mL, 164.8 mmol), followed by drop-wise addition of ethyl propiolate (16.71 mL, 164.8 mmol). After vigorous stirring for 2 d, the reaction was slowly quenched via portion-wise addition to rapidly stirring ice water (820 mL). The mixture was stirred at ambient temperature for 10 min and then vacuum filtered. Solids collected were rinsed with water and air-dried, yielding the title compounds as an orange solid in an isomeric ratio of about 4:1 (by $^1$H NMR) with the 6-Br isomer as the major isomer (21 g). The wet solid isomeric mixture (about 75% w/w) was directly used in Step 3 without further purification. MS (apci) m/z=298.9, 300.9 (M+H). Regioisomeric ratio was determined by MeO chemical shift in $^1$H NMR (CDCl$_3$) δ 3.98 (6-Br isomer) vs. 3.83 (4-Br isomer).

Step 3: Preparation of 6-bromo-4-methoxypyrazolo [1,5-a]pyridine (P1) and 4-bromo-6-methoxypyrazolo[1,5-a]pyridine The isomeric mixture of ethyl 6-bromo-4-methoxypyrazolo[1,5-a]pyridine-3-carboxylate and ethyl 4-bromo-4- methoxypyrazolo[1,5-a]pyridine-3-carboxylate from Step 2 (15 g, 50.1 mmol) was added to 48% HBr (114 mL) while stirring, then heated at 80° C. for 90 min followed by stirring at ambient temperature overnight. The resulting suspension was vacuum filtered and rinsed with water. The aqueous filtrate and the filter cake were treated independently. The filter cake was taken up in MTBE and vacuum filtered to remove insoluble impurities. The MTBE filtrate was dried over anhydrous $Na_2SO_4$, filtered and concentrated in vacuo to yield 6-bromo-4-methoxypyrazolo[1,5-a]pyridine as a beige solid (about 98:2 6-/4-Br; 5.08 g). MS (apci) m/z=226.9, 228.9 (M+H). $^1$H NMR (CDCl$_3$) δ 8.26 (m, 1H), 7.82 (d, 1H), 6.61 (m, 1H), 6.43 (m, 1H), 3.94 (s, 3H). Independently the original aqueous reaction mixture filtrate was extracted with EtOAc. The combined organic extracts were dried ($Na_2SO_4$), filtered and concentrated in vacuo. The crude residue was taken up in DCM (50 mL) and then filtered to remove insoluble solids. Concentration of the DCM filtrate under vacuum followed by silica chromatography (0 to 50% EtOAc/hexanes) yielded a second batch of 6-bromo-4-methoxypyrazolo[1,5-a]pyridine (Intermediate P1) as white solid (upper $R_f$ spot, 2.06 g), as well as the minor isomer title compound 4-bromo-6-methoxypyrazolo[1,5-a]pyridine (Intermediate P2) also as white solid (lower $R_f$ spot, 1.32 g). MS (apci) m/z=226.9, 228.9 (M+H). $^1$H NMR (CDCl$_3$) δ 8.02 (m, 1H), 7.85 (d, 1H), 7.17 (d, 1H), 6.55 (m, 1H), 3.80 (s, 3H).

Step 4: Preparation of 4-bromo-6-methoxypyrazolo[1,5-a]pyridine-3-carbaldehyde

A solution of 4-bromo-6-methoxypyrazolo[1,5-a]pyridine (5.0 g, 22 mmol) in DMF (220 mL) was cooled to 0° C. and then slowly treated with POCl$_3$ (6.2 mL, 66 mmol). The reaction was warmed to ambient temperature and stirred overnight. The reaction mixture was cooled to 0° C., quenched with water (220 mL), and basified with 6 M NaOH$_{(aq)}$ to pH 9-10. The reaction mixture was stirred for 1 h and then vacuum filtered. The solids were rinsed sequentially with water and MTBE. The collected solid was suspended in DCM (500 mL) and stirred in a sonicating bath for 30 min and then vacuum filtered. The filtrate was retained, while the filter cake was taken up in water (300 mL) and extracted with DCM. The organic extracts, along with the retained DCM filtrate, were combined and dried over anhydrous $Na_2SO_4$, then filtered and concentrated in vacuo to provide the title compound (4.84 g, 86% yield). MS (apci), m/z=256.9 (M+H).

Step 5: Preparation of 4-bromo-6-methoxypyrazolo[1,5-a]pyridine-3-carbaldehyde oxime To a suspension of 4-bromo-6-methoxypyrazolo[1,5-a]pyridine-3-carbaldehyde (4.84 g, 19.0 mmol) in EtOH (253 mL) at ambient temperature was added water (127 mL) and hydroxylamine hydrochloride (1.98 g, 28.5 mmol). After stirring at 50° C. overnight, the reaction mixture was cooled to ambient temperature and concentrated in vacuo. The residue was suspended in water (150 mL) and then quenched slowly with saturated NaHCO$_{3(aq)}$ (30 mL). After stirring for 1 hour at ambient temperature the suspension was vacuum filtered and the filter cake rinsed sequentially with H$_2$O (500 mL) and MTBE (100 mL) to yield the title compound as a 2:1 E/Z mixture (5.13 g, quantitative yield), which was used in the next step without further purification. MS (apci) m/z=271.9 (M+H).

Step 6: Preparation of 4-bromo-6-methoxypyrazolo[1,5-a]pyridine-3-carbonitrile

The E/Z mixture of 4-bromo-6-methoxypyrazolo[1,5-a]pyridine-3-carbaldehyde oxime (4.95 g, 18.33 mmol) in acetic anhydride (172.9 mL, 1833 mmol) was stirred at 140° C. for 25 h, and then cooled to ambient temperature. The resulting suspension was further cooled in an ice bath for 15 min and then vacuum filtered and rinsed sequentially with water and MTBE to provide the title compound (3.74 g, 81% yield). $^1$H NMR (d$^6$-DMSO) δ 8.70 (s, 1H), 8.60 (s, 1H), 7.78 (s, 1H), 3.83 (s, 3H).

Step 7: Preparation of 4-Bromo-6-hydroxypyrazolo[1,5-a]pyridine-3-carbonitrile

A slurry of 4-bromo-6-methoxypyrazolo[1,5-a]pyridine-3-carbonitrile (50.0 g, 198.4 mmol) in DCE (500 mL) was treated with AlCl$_3$ (79.34 g, 595.1 mmol). Under a N$_{2(g)}$ atmosphere, the resulting mixture was stirred 19 h at 76° C., before cooling to room temperature. Using THF (1750 mL) as a rinse solvent, the reaction mixture was poured into a mechanically stirred suspension of sodium sulfate decahydrate (10 eq, 639 g) in THF (1000 mL). After stirring overnight at ambient temperature, the resulting suspension was filtered, and the solids were rinsed with additional THF (2×250 mL). The filtrate was concentrated in vacuo, and the resulting solid was dried under high vacuum for 3 days to afford the title compound (46.18 g, 98% yield) in sufficient purity for subsequent use. $^1$H NMR (d$^6$-DMSO) δ 10.48 (s, 1H), 8.58 (s, 1H), 8.38 (d, 1H), 7.64 (3, 1H).

Intermediate P5

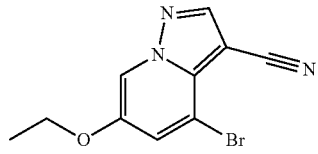

4-Bromo-6-ethoxypyrazolo[1,5-a]pyridine-3-carbonitrile

A solution of 4-bromo-6-hydroxypyrazolo[1,5-a]pyridine-3-carbonitrile (Intermediate P1; 4.0 g, 16.80 mmol) in DMA (100 mL) was treated with K$_2$CO$_{3(s)}$ (7.0 g, 51 mmol) and iodoethane (2.0 mL, 25 mmol) and then stirred for 3 hrs at 60° C. The reaction mixture was cooled to ambient temperature and then quenched with 1:1 NH$_4$OH/Water. The resulting suspension was filtered, and the solids were isolated to provide the title compound (4.35 g, 97% yield) in sufficient purity for subsequent use.

Intermediate P6

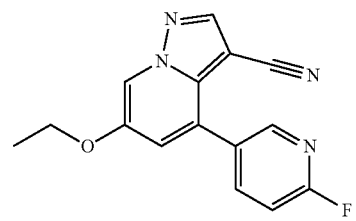 [SMILES: CCOc1cc(-c2ccc(F)nc2)c2c(C#N)cnn2c1]

6-Ethoxy-4-(6-fluoropyridin-3-yl)pyrazolo[1,5-a]pyridine-3-carbonitrile

In a pressure vessel, a solution of 4-bromo-6-ethoxypyrazolo[1,5-a]pyridine-3-carbonitrile (Intermediate P5; 500 mg, 1.88 mmol) in dioxane (9.40 mL) was treated sequentially with 2-fluoro-5-(4,4,5,5-tetramethyl-1,3,2-dioxaborolan-2-yl)pyridine (629 mg, 2.82 mmol), Pd(PPh$_3$)$_4$ (217 mg, 0.188 mmol) and 2 M Na$_2$CO$_{3(aq)}$ (4.70 mL, 9.40). The resulting mixture was sparged with Ar$_{(g)}$ and then the vessel was sealed. The mixture was stirred 8 h at 90° C., and then overnight at ambient temperature. The reaction mixture was diluted with water and extracted with EtOAc. The combined organic extracts were washed with water and brine, dried over anhydrous Na$_2$SO$_{4(s)}$, filtered and concentrated in vacuo. The crude residue was purified by silica chromatography (25-100% EtOAc in hexanes as the gradient eluent) to cleanly provide the title compound (500 mg, 94% yield). MS (apci) m/z=283.1 (M+H).

Intermediate P25

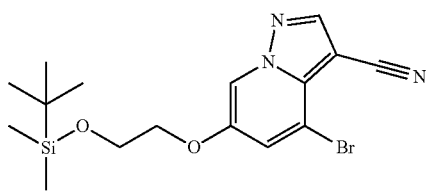 [SMILES: CC(C)(C)[Si](C)(C)OCCOc1cc(Br)c2c(C#N)cnn2c1]

4-Bromo-6-(2-((tert-butyldimethylsilyl)oxy)ethoxy)pyrazolo[1,5-a]pyridine-3-carbonitrile A mixture of (2-bromoethoxy)(tert-butyl)dimethylsilane (451 μL, 2.10 mmol), 4-bromo-6-hydroxypyrazolo[1,5-a]pyridine-3-carbonitrile (Intermediate P1; 500 mg, 2.10 mmol) and K$_2$CO$_{3(s)}$ (871 mg, 6.30 mmol) in DMF (10.5 mL) was stirred for 1 day at 50° C. After cooling to ambient temperature, the reaction mixture was diluted with EtOAc and washed with water and brine. The resulting organic extracts were directly purified by silica chromatography (0-100% EtOAc/hexanes as the gradient eluent) to cleanly provide the title compound (420 mg, 49% yield).

Intermediate P26

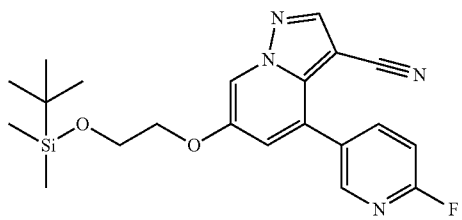 [SMILES: CC(C)(C)[Si](C)(C)OCCOc1cc(-c2ccc(F)nc2)c2c(C#N)cnn2c1]

6-(2-((tert-butyldimethylsilyl)oxy)ethoxy)-4-(6-fluoropyridin-3-yl)pyrazolo[1,5-a]pyridine-3-carbonitrile In a pressure vessel, a solution of 4-bromo-6-(2-((tert-butyldimethylsilyl)oxy)ethoxy)pyrazolo[1,5-a]pyridine-3-carbonitrile (Intermediate P25; 420 mg, 1.06 mmol) in dioxane (10.6 mL) was treated sequentially with 2-fluoro-5-(4,4,5,5-tetramethyl-1,3,2-dioxaborolan-2-yl)pyridine (355 mg, 1.59 mmol), Pd(PPh$_3$)$_4$ (61.2 mg, 0.530 mmol) and 2 M Na$_2$CO$_{3(aq)}$ (2.65 mL, 5.30). The resulting mixture was sparged with Ar$_{(g)}$ and the vessel was sealed. The mixture was stirred 8 h at 90° C., and then overnight at ambient temperature. The reaction mixture was diluted with water and extracted with EtOAc. The combined organic extracts were washed with water (10 mL) and brine (10 mL), then were dried over anhydrous Na$_2$SO$_{4(s)}$, filtered and concentrated in vacuo. The crude residue was purified by silica chromatography (using 0-15% MeOH in DCM as the gradient eluent) to afford impure title compound. The impure material was re-subjected to silica chromatography (0-50% EtOAc in Hexanes as the gradient eluent) to cleanly provide the title compound (351 mg, 80% yield). $^1$H NMR (400 MHz, DMSO-d$_6$-) δ: 8.81 (d, 1H, J=2.0 Hz), 8.61 (s, 1H), 8.48 (d, 1H, J=2.7 Hz), 8.25 (td, 1H, J=7.8, 2.7 Hz), 7.47 (d, 1H, J=1.9 Hz), 7.38 (dd, 1H, J=7.8, 2.3 Hz), 4.21 (t, 2H, J=4.3 Hz), 3.97 (t, 2H, J=4.7 Hz), 0.86 (s, 9H), 0.08 (s, 6H).

Intermediate P41

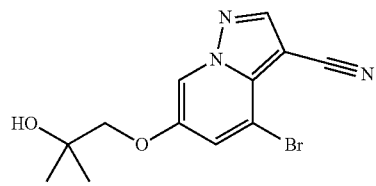 [SMILES: CC(C)(O)COc1cc(Br)c2c(C#N)cnn2c1]

4-Bromo-6-(2-hydroxy-2-methylpropoxy)pyrazolo[1,5-a]pyridine-3-carbonitrile

In a pressure vessel, a mixture of 4-bromo-6-hydroxypyrazolo[1,5-a]pyridine-3-carbonitrile (Intermediate P1; 10.0 g, 42.0 mmol) and K$_2$CO$_{3(s)}$ (17.4 g, 126 mmol) in DMF (50 mL) was treated with 2,2-dimethyloxirane (36.9 mL, 420 mmol). After sealing the vessel, the reaction mixture was stirred for 12 h at 60° C., then for 12 h at 85° C. The mixture was allowed to cool to ambient temperature. The room temperature mixture was poured into water (400 mL), then stirred for 1 hour at ambient temperature. The resultant suspension was vacuum filtered and the filter cake was rinsed with water. The solids were collected and dried in vacuo to cleanly provide the title compound (11 g, 84% yield).

Intermediate P42

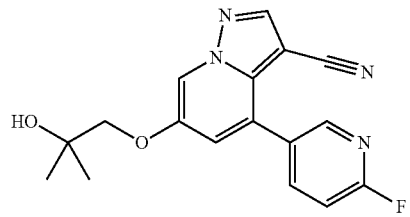 [SMILES: CC(C)(O)COc1cc(-c2ccc(F)nc2)c2c(C#N)cnn2c1]

4-(6-fluoropyridin-3-yl)-6-(2-hydroxy-2-methyl-propoxy)pyrazolo[1,5-a]pyridine-3-carbonitrile A mixture of 4-bromo-6-(2-hydroxy-2-methylpropoxy)pyrazolo[1,5-a]pyridine-3-carbonitrile (Intermediate P41; 10.0 g, 32.2 mmol), 2-fluoro-5-(4,4,5,5-tetramethyl-1,3,2-dioxaborolan-2-yl)pyridine (10.8 g, 48.4 mmol) and Pd(PPh$_3$)$_4$ (1.12 g, 0.967 mmol) in dioxane (200 mL) was treated with 2 M Na$_2$CO$_{3(aq)}$ (64.5 mL, 129 mmol). The resulting mixture was sparged with Ar$_{(g)}$, then stirred for 12 h at 85° C. under an atmosphere of N$_{2(g)}$. After cooling to ambient temperature, the resultant mixture was poured into cold water (1.5 L). The pH of the mixture was adjusted to about pH 6 with the addition of 10% citric acid. After stirring for 1 hour at ambient temperature, the resultant suspension was vacuum filtered. The solids were collected and dried in vacuo to cleanly provide the title compound (10 g, 95% yield).

Intermediate P46

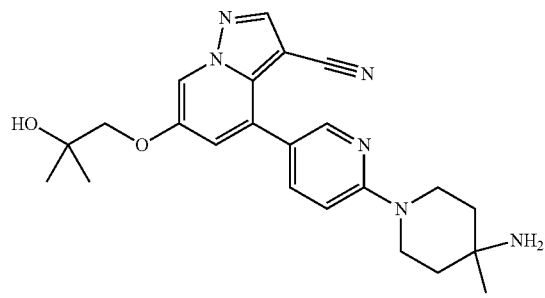 [SMILES: CC(C)(O)COc1cc(-c2ccc(N3CCC(C)(N)CC3)nc2)c2c(C#N)cnn2c1]

4-(6-(4-amino-4-methylpiperidin-1-yl)pyridin-3-yl)-6-(2-hydroxy-2-methylpropoxy)pyrazolo[1,5-a]pyridine-3-carbonitrile Step 1: Preparation of tert-butyl (1-(5-(3-cyano-6-(2-hydroxy-2-methylpropoxy)pyrazolo[1,5-a]pyridin-4-yl)pyridin-2-yl)-4-methylpiperidin-4-yl)carbamate A solution of 4-(6-fluoropyridin-3-yl)-6-(2-hydroxy-2-methylpropoxy)pyrazolo[1,5-a]pyridine-3-carbonitrile (Intermediate P42; 100 mg, 0.306 mmol) in DMA (2.04 mL) was treated sequentially with tert-butyl (4-methylpiperidin-4-yl)carbamate (98.5 mg, 0.460 mmol) and DIEA (107 µL, 0.613 mmol). The resulting mixture was sparged with Ar$_{(g)}$, then stirred overnight at 90° C. After cooling to ambient temperature, the reaction mixture was diluted with water and washed with DCM. The combined organic extracts were washed with water and brine, then dried over anhydrous Na$_2$SO$_{4(s)}$, filtered and concentrated in vacuo to afford the title compound (22.4 mg, 50% yield) in sufficient purity for step 2. MS (apci) m/z=521.3 (M+H).

Step 2: Preparation of 4-(6-(4-amino-4-methylpiperidin-1-yl)pyridin-3-yl)-6-(2-hydroxy-2-methyl-propoxy)pyrazolo[1,5-a]pyridine-3-carbonitrile A solution of tert-butyl (1-(5-(3-cyano-6-(2-hydroxy-2-methylpropoxy)pyrazolo[1,5-a]pyridin-4-yl)pyridin-2-yl)-4-methylpiperidin-4-yl)carbamate (160 mg, 0.307 mmol) in DCM (1.54 mL) was treated with TFA (1 mL, 13.8 mmol). After stirring for 30 min at ambient temperature, the mixture was treated with additional TFA (1 mL) and stirred an additional 1 hour at ambient temperature. The reaction mixture was concentrated in vacuo and the residue was purified by silica chromatography (1-9% MeOH in DCM with 0.1-0.9% NH$_4$OH as the gradient eluent) to cleanly provide the title compound (110 mg, 85% yield). MS (apci) m/z=421.2 (M+H).

Intermediate P47

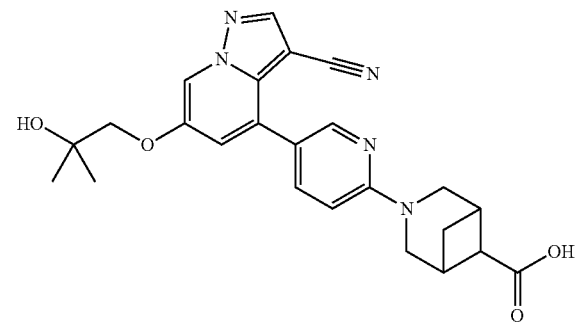 [SMILES: CC(C)(O)COc1cc(-c2ccc(N3CC4CC(C3)C4C(=O)O)nc2)c2c(C#N)cnn2c1]

3-(5-(3-cyano-6-(2-hydroxy-2-methylpropoxy)pyrazolo[1,5-a]pyridin-4-yl)pyridin-2-yl)-3-azabicyclo[3.1.1]heptane-6-carboxylic acid Step 1: Preparation of methyl 3-(5-(3-cyano-6-(2-hydroxy-2-methylpropoxy)pyrazolo[1,5-a]pyridin-4-yl)pyridin-2-yl)-3-azabicyclo[3.1.1]heptane-6-carboxylate A solution of 4-(6-fluoropyridin-3-yl)-6-(2-hydroxy-2-methylpropoxy)pyrazolo[1,5-a]pyridine-3-carbonitrile (Intermediate P42; 103.4 mg, 0.3169 mmol) in DMA (2.11 mL) was treated sequentially with methyl 3-azabicyclo[3.1.1]heptane-6-carboxylate (88.52 mg, 0.5703 mmol) and DIEA (110.7 µL, 0.6337 mmol) and then sparged with Ar$_{(g)}$ for 5 min. The mixture was stirred overnight at 90° C., then for 4 h at 100° C., before introducing TEA (0.2 mL). The mixture was stirred overnight at 100° C., then for 4 days at 90° C. After cooling to ambient temperature, the reaction mixture was diluted with water and washed with DCM. The combined organic extracts were washed with water and brine, then dried over anhydrous Na$_2$SO$_{4(s)}$, filtered and concentrated in vacuo. The crude residue was purified by silica chromatography (1-9% MeOH in DCM as the gradient eluent) to afford the title compound (134 mg, 58% yield). MS (apci) m/z=462.2 (M+H).

Step 2: Preparation of 3-(5-(3-cyano-6-(2-hydroxy-2-methylpropoxy)pyrazolo[1,5-a]pyridin-4-yl)pyridin-2-yl)-3-azabicyclo[3.1.1]heptane-6-carboxylic acid A solution of methyl 3-(5-(3-cyano-6-(2-hydroxy-2-methylpropoxy)pyrazolo[1,5-a]pyridin-4-yl)pyridin-2-yl)-3-azabicyclo[3.1.1]heptane-6-carboxylate (134 mg, 0.290 mmol) in EtOH (2.90 mL) was treated with 2 M NaOH$_{(aq)}$ (436 µL). After stirring overnight at ambient temperature, the mixture was brought to pH 4 with the addition of 2.0 N HCl$_{(aq)}$, and then the aqueous layer was returned to pH 7 with the addition of saturated NaHCO$_{3(aq)}$. The aqueous phase was extracted with DCM. The combined organic extracts were washed with brine, then dried over anhydrous Na$_2$SO$_{4(s)}$, filtered and concentrated in vacuo to afford the title compound (100 mg, 77% yield). MS (apci) m/z=448.2 (M+H).

Intermediate P48

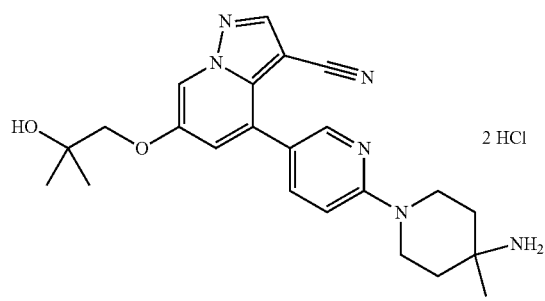 [SMILES: CC(C)(O)COc1cc(-c2ccc(N3CCC(C)(N)CC3)nc2)c2c(C#N)cnn2c1]

4-(6-(4-amino-4-methylpiperidin-1-yl)pyridin-3-yl)-6-(2-hydroxy-2-methylpropoxy)pyrazolo[1,5-a]pyridine-3-carbonitrile dihydrochloride Step 1: Preparation of tert-butyl (1-(5-(3-cyano-6-(2-hydroxy-2-methylpropoxy)pyrazolo[1,5-a]pyridin-4-yl)pyridin-2-yl)-4-methylpiperidin-4-yl)carbamate A solution of 4-(6-fluoropyridin-3-yl)-6-(2-hydroxy-2-methylpropoxy)pyrazolo[1,5-a]pyridine-3-carbonitrile (Intermediate P42; 2.535 g, 7.768 mmol) in DMSO (6.1 mL) was treated sequentially with tert-butyl (4-methylpiperidin-4-yl)carbamate (1.998 mg, 9.322 mmol) and DIEA (4.06 mL, 23.3 mmol). The resulting mixture stirred overnight at 90° C. After cooling to ambient temperature, the reaction mixture was poured into 80 mL water and diluted with 80 mL heptane and stirred for 1 hour. The suspension was filtered and the solids were rinsed with 25 mL water then 25 mL heptane. The isolated solids were dried under vacuum for 18 hours to afford the title compound (4.04 g, 99.9% yield) in sufficient purity for step 2. MS (apci) m/z=521.3 (M+H)

Step 2: Preparation of 4-(6-(4-amino-4-methylpiperidin-1-yl)pyridin-3-yl)-6-(2-hydroxy-2-methylpropoxy)pyrazolo[1,5-a]pyridine-3-carbonitrile dihydrochloride A solution of tert-butyl (1-(5-(3-cyano-6-(2-hydroxy-2-methylpropoxy)pyrazolo[1,5-a]pyridin-4-yl)pyridin-2-yl)-4-methylpiperidin-4-yl)carbamate (4.04 g, 7.76 mmol) in DCM (20 mL) was cooled to 0° C. The reaction was treated with TFA (5.98 mL) and allowed to warm to RT. After stirring for 30 min at ambient the reaction mixture was concentrated in vacuo. The residue was dissolved in MeOH (20 mL) and cooled to 0° C. and then treated with Hydrochloric acid, 5 to 6N solution in 2-propanol (15.5 mL, 77.5 mmol) and stirred for 15 min at 0° C. The reaction was diluted with 20 mL MTBE, filtered, and solids were rinsed with 20 mL 1:1 MTBE: MeOH. The isolated solids were dried under vacuum to cleanly provide the title compound (3.37 g, 88% yield). MS (apci) m/z=421.2 (M+H).

Intermediate P49

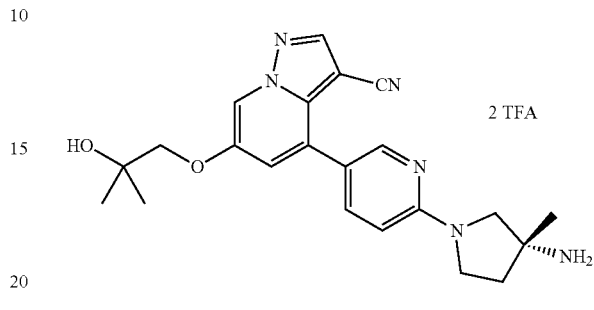

(R)-4-(6-(3-amino-3-methylpyrrolidin-1-yl)pyridin-3-yl)-6-(2-hydroxy-2-methylpropoxy)pyrazolo[1,5-a]pyridine-3-carbonitrile bis(2,2,2-trifluoroacetate)

Step 1: Preparation of tert-butyl (R)-(1-(5-(3-cyano-6-(2-hydroxy-2-methylpropoxy)pyrazolo[1,5-a]pyridin-4-yl)pyridin-2-yl)-3-methylpyrrolidin-3-yl)carbamate To a mixture of 4-(6-fluoropyridin-3-yl)-6-(2-hydroxy-2-methylpropoxy)pyrazolo[1,5-a]pyridine-3-carbonitrile (Intermediate P42; 750 mg, 2.30 mmol) and (R)-(3-Methylpyrrolidin-3-yl)-carbamic acid tert-butyl ester HCl (644 mg, 3.22 mmol) in DMSO (4.6 mL) was added DIEA (1.2 mL, 6.89 mmol). The reaction mixture was stirred 12 h at 90° C. After cooling to ambient temperature, the reaction mixture was diluted into cold water and stirred for 2 h at ambient temperature. The suspension was filtered and the solids were rinsed with water. The isolated solids were dried under vacuum for 48 h to afford the title compound (1.05 g, 90% yield) in sufficient purity for step 2. MS (apci) m/z=507.3 (M+H)

Step 2: (R)-4-(6-(3-amino-3-methylpyrrolidin-1-yl)pyridin-3-yl)-6-(2-hydroxy-2-methylpropoxy)pyrazolo[1,5-a]pyridine-3-carbonitrile bis(2,2,2-trifluoroacetate)

To a solution of (R)-(1-(5-(3-cyano-6-(2-hydroxy-2-methylpropoxy)pyrazolo[1,5-a]pyridin-4-yl)pyridin-2-yl)-3-methylpyrrolidin-3-yl)carbamate (1.05 g, 2.07 mmol) in 3 mL DCM was treated with TFA (3 mL, 39 mmol). The reaction mixture was stirred for 4 h at ambient temperature, and then concentrated in vacuo. The residue was diluted with DCM (4 mL) and toluene (1 mL) and stirred at ambient temperature for 15 min. The mixture was concentrated in vacuo and dried under vacuum for 2 days to afford the title compound with quantitative yield. MS (apci) m/z=407.3 (M+H).

Intermediate P50

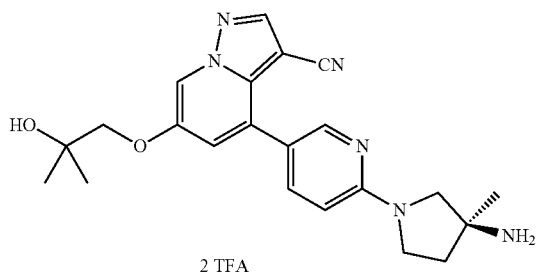 [SMILES: CC(C)(O)COc1cc(-c2ccc(N3CC[C@](C)(N)C3)nc2)c2c(C#N)cnn2c1]

2 TFA (S)-4-(6-(3-amino-3-methylpyrrolidin-1-yl)pyridin-3-yl)-6-(2-hydroxy-2-methylpropoxy)pyrazolo[1,5-a]pyridine-3-carbonitrile bis(2,2,2-trifluoroacetate)

Step 1: Preparation of tert-butyl (S)-(1-(5-(3-cyano-6-(2-hydroxy-2-methylpropoxy)pyrazolo[1,5-a]pyridin-4-yl)pyridin-2-yl)-3-methylpyrrolidin-3-yl)carbamate To a mixture of 4-(6-fluoropyridin-3-yl)-6-(2-hydroxy-2-methylpropoxy)pyrazolo[1,5-a]pyridine-3-carbonitrile (Intermediate P42; 700 mg, 2.15 mmol) and (S)-(3-Methylpyrrolidin-3-yl)-carbamic acid tert-butyl ester HCl (601 mg, 3.0 mmol) in DMSO (4.3 mL) was added DIEA (1.1 mL, 6.44 mmol). The reaction mixture was stirred 12 h at 90° C. After cooling to ambient temperature, the reaction mixture was diluted into cold water and stirred for 2 h at ambient temperature. The suspension was filtered and the solids were rinsed with water. The isolated solids were dried under vacuum for 48 h to afford the title compound (950 mg, 87% yield) in sufficient purity for step 2. MS (apci) m/z=507.3 (M+H)

Step 2: Preparation of (S)-4-(6-(3-amino-3-methylpyrrolidin-1-yl)pyridin-3-yl)-6-(2-hydroxy-2-methylpropoxy)pyrazolo[1,5-a]pyridine-3-carbonitrile bis(2,2,2-trifluoroacetate)

To a solution of tert-butyl (S)-(1-(5-(3-cyano-6-(2-hydroxy-2-methylpropoxy)pyrazolo[1,5-a]pyridin-4-yl)pyridin-2-yl)-3-methylpyrrolidin-3-yl)carbamate (950 mg, 1.88 mmol) in 3 mL DCM was treated with TFA (3 mL, 39 mmol). The reaction mixture was stirred for 4 h at ambient temperature, and then concentrated in vacuo. The residue was diluted with DCM (4 mL) and toluene (1 mL) and stirred at ambient temperature for 15 min. The mixture was concentrated in vacuo and dried under vacuum for 2 days afford the title compound with quantitative yield. MS (apci) m/z=407.2 (M+H).

Intermediate P51

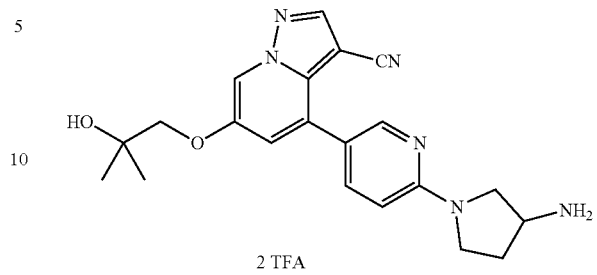

2 TFA 4-(6-(3-aminopyrrolidin-1-yl)pyridin-3-yl)-6-(2-hydroxy-2-methylpropoxy)pyrazolo[1,5-a]pyridine-3-carbonitrile bis(2,2,2-trifluoroacetate)

Step 1: Preparation of tert-butyl (1-(5-(3-cyano-6-(2-hydroxy-2-methylpropoxy)pyrazolo[1,5-a]pyridin-4-yl)pyridin-2-yl)pyrrolidin-3-yl)carbamate To a mixture of 4-(6-fluoropyridin-3-yl)-6-(2-hydroxy-2-methylpropoxy)pyrazolo[1,5-a]pyridine-3-carbonitrile (Intermediate P42; 850 mg, 2.60 mmol) and 3-(tert-butoxycarbonylamino)pyrrolidine (679 mg, 3.65 mmol) in DMSO (5.2 mL) was added DIEA (1.36 mL, 7.81 mmol). The reaction mixture was stirred 12 h at 90° C. After cooling to ambient temperature, the reaction mixture was diluted into cold water and stirred for 2 h at ambient temperature. The suspension was filtered and the solids were rinsed with water. The isolated solids were dried under vacuum for 48 h to afford the title compound (1.26 g, 98% yield) in sufficient purity for step 2. MS (apci) m/z=493.3 (M+H)

Step 2: Preparation of 4-(6-(3-aminopyrrolidin-1-yl)pyridin-3-yl)-6-(2-hydroxy-2-methylpropoxy)pyrazolo[1,5-a]pyridine-3-carbonitrile bis(2,2,2-trifluoroacetate)

To a solution of tert-butyl (1-(5-(3-cyano-6-(2-hydroxy-2-methylpropoxy)pyrazolo[1,5-a]pyridin-4-yl)pyridin-2-yl)pyrrolidin-3-yl)carbamate (950 mg, 1.88 mmol) in 3 mL DCM was treated with TFA (3 mL, 39 mmol). The reaction mixture was stirred for 4 h at ambient temperature, and then concentrated in vacuo. The residue was diluted with DCM (4 mL) and toluene (1 mL) and stirred at ambient temperature for 15 min. The mixture was concentrated in vacuo and dried under vacuum for 2 days afford the title compound with quantitative yield. MS (apci) m/z=393.2 (M+H).

Intermediate P52

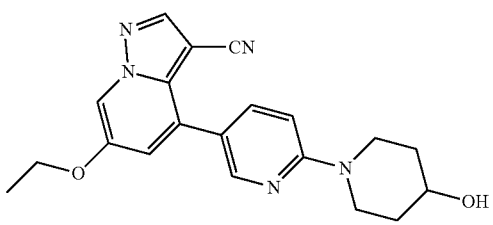 [SMILES: CCOc1cc(-c2ccc(N3CCC(O)CC3)nc2)c2c(C#N)cnn2c1]

6-ethoxy-4-(6-(4-hydroxypiperidin-1-yl)pyridin-3-yl)pyrazolo[1,5-a]pyridine-3-carbonitrile To a solution of 6-ethoxy-4-(6-fluoropyridin-3-yl)pyrazolo[1,5-a]pyridine-3-carbonitrile (Intermediate P6, 0.500 g, 1.77 mmol) in DMSO (3.5 mL) was added TEA (0.741 mL, 5.31 mmol) and piperidin-4-ol (269 mg, 2.66 mmol). The reaction mixture was stirred at 70° C. for 5 h. After cooling to ambient temperature, the reaction mixture was poured into ice water. The resultant solids were isolated by vacuum filtration to afford the title compound (501 mg, 1.38 mmol, 77.8% yield). MS (apci) m/z=364.2 (M+H).

Intermediate P53

6-(2-hydroxy-2-methylpropoxy)-4-(6-(4-(pyridin-2-ylthio)piperidin-1-yl)pyridin-3-yl)pyrazolo[1,5-a]pyridine-3-carbonitrile To a solution of 4-(6-fluoropyridin-3-yl)-6-(2-hydroxy-2-methylpropoxy)pyrazolo[1,5-a]pyridine-3-carbonitrile (Intermediate P42; 210 mg, 0.64 mmol) and 2-(piperidin-4-ylsulfanyl)pyridine (357 mg, 1.84 mmol) in DMA (1.6 mL) was added TEA (628 μL, 4.50 mmol). The reaction mixture was stirred overnight at 95° C. After cooling to ambient temperature, the reaction mixture was diluted water and extracted with EtOAc. The organic extracts were washed with water and brine. The organic extracts were dried over anhydrous $Na_2SO_{4(s)}$, filtered and concentrated in vacuo. The residue was purified by silica chromatography (10-90% EtOAc in Hexanes to afford the title compound (20 mg, 61% yield). MS (apci) m/z=501.2 (M+H).

Intermediate P55

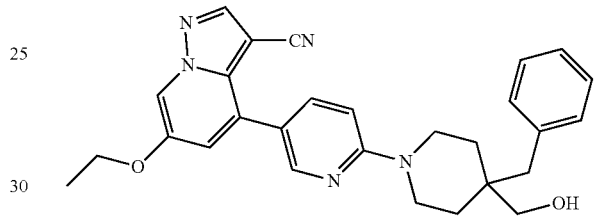

4-(6-(4-benzyl-4-hydroxypiperidin-1-yl)pyridin-3-yl)-6-ethoxypyrazolo[1,5-a]pyridine-3-carbonitrile To a solution of 6-ethoxy-4-(6-fluoropyridin-3-yl)pyrazolo[1,5-a]pyridine-3-carbonitrile (Intermediate P6, 30 mg, 0.106 mmol) in DMA (0.5 mL) was added TEA (0.044 mL, 0.319 mmol) and 4-benzylpiperidin-4-ol (40.7 mg, 0.213 mmol) The reaction mixture was stirred at 90° C. for 24 h. After cooling to ambient temperature, the reaction mixture was diluted with DCM and washed with saturated $NH_4Cl_{(aq)}$ then water. The combined aqueous washes were further extracted with DCM, and the combined organic extracts were dried over anhydrous $Na_2SO_{4(s)}$ and concentrated in vacuo. The residue was purified by silica chromatography (30-100% EtOAc in hexanes as the gradient eluent) to afford the title compound (39 mg, 0.0860 mmol, 80.9% yield). MS (apci) m/z=454.2 (M+H).

Intermediate P54

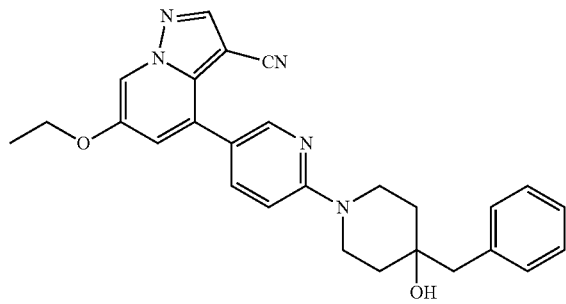 [SMILES: CCOc1cc(-c2ccc(N3CCC(O)(Cc4ccccc4)CC3)nc2)c2c(C#N)cnn2c1]

4-(6-(4-benzyl-4-(hydroxymethyl)piperidin-1-yl)pyridin-3-yl)-6-ethoxypyrazolo[1,5-a]pyridine-3-carbonitrile To a solution of 6-ethoxy-4-(6-fluoropyridin-3-yl)pyrazolo[1,5-a]pyridine-3-carbonitrile (Intermediate P6, 100.5 mg, 0.3560 mmol) in DMSO (3 ml) was added (4-benzylpiperidin-4-yl)methanol hydrochloride (151.5 mg, 0.6267 mmol) and cesium carbonate (812.0 mg, 2.492 mmol). The reaction mixture was stirred at 60° C. for 24 h. After cooling to ambient temperature, the reaction mixture was diluted with DCM and washed with water and saturated $NH_4Cl_{(aq)}$. The combined aqueous layers were extracted with DCM, and the combined organic extracts were dried over anhydrous $Na_2SO_{4(s)}$ and concentrated. The residue was purified by silica chromatography (0-100% EtOAc in hexanes as the gradient eluent) to afford the title compound (118.2 mg, 0.2528 mmol, 71.00% yield). MS (apci) m/z=468.2 (M+H).

Intermediate P56

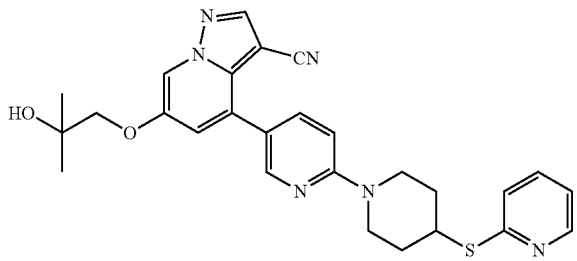 [SMILES: CC(C)(O)COc1cc(-c2ccc(N3CCC(Sc4ccccn4)CC3)nc2)c2c(C#N)cnn2c1]

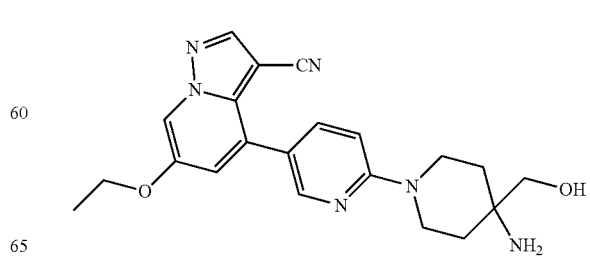

4-(6-(4-amino-4-(hydroxymethyl)piperidin-1-yl)pyridin-3-yl)-6-ethoxypyrazolo[1,5-a]pyridine-3-carbonitrile

Step 1: Preparation of methyl 4-((tert-butoxycarbonyl)amino)-1-(5-(3-cyano-6-ethoxypyrazolo[1,5-a]pyridin-4-yl)pyridin-2-yl)piperidine-4-carboxylate To a solution of 6-ethoxy-4-(6-fluoropyridin-3-yl)pyrazolo[1,5-a]pyridine-3-carbonitrile (Intermediate P6, 303.4 mg, 1.075 mmol) in DMSO (21.50 mL) was added 4-N-Boc-amino-piperidine-4-carboxylic acid methyl ester (416.5 mg, 1.612 mmol) and potassium carbonate (297.1 mg, 2.150 mmol). The reaction mixture was stirred at 110° C. for 72 h. The reaction mixture was diluted with water and extracted with EtOAc. The combined organic extracts were dried over anhydrous $MgSO_{4(s)}$ and concentrated in vacuo. The resultant crude residue was purified by silica chromatography (0-100% EtOAc in hexanes as the gradient eluent) to afford the title compound (76.7 mg, 13.7% yield) in sufficient purity for step 2. MS (apci) m/z=521.2 (M+H).

Step 2: Preparation of tert-butyl (1-(5-(3-cyano-6-ethoxypyrazolo[1,5-a]pyridin-4-yl)pyridin-2-yl)-4-(hydroxymethyl)piperidin-4-yl)carbamate To a solution of lithium borohydride (0.0120 mL, 0.365 mmol) in THF (0.912 mL) was added methyl 4-((tert-butoxycarbonyl)amino)-1-(5-(3-cyano-6-ethoxypyrazolo[1,5-a]pyridin-4-yl)pyridin-2-yl)piperidine-4-carboxylate (47.5 mg, 0.0912 mmol). The reaction mixture was stirred at rt for 2 h. The reaction mixture was concentrated in vacuo, and the residue was diluted with EtOAc and washed with brine. The organic extract was dried over anhydrous $MgSO_{4(s)}$ and concentrated in vacuo to afford the title compound as crude product (65.9 mg), which was used in the next step without further purifications. MS (apci) m/z=493.2 (M+H).

Step 3: Preparation of 4-(6-(4-amino-4-(hydroxymethyl)piperidin-1-yl)pyridin-3-yl)-6-ethoxypyrazolo[1,5-a]pyridine-3-carbonitrile A solution of tert-butyl (1-(5-(3-cyano-6-ethoxypyrazolo[1,5-a]pyridin-4-yl)pyridin-2-yl)-4-(hydroxymethyl)piperidin-4-yl)carbamate (65.9 mg, 0.134 mmol) in DCM (1 mL) was treated with TFA (0.2 mL, 2.68 mmol). The reaction mixture was stirred at rt 30 min then concentrated in vacuo. The residue was taken up in DCM and washed with saturated $Na_2CO_3$. The aqueous fraction was extracted with DCM, and the combined organic extracts were dried over anhydrous $MgSO_{4(s)}$ and concentrated in vacuo to afford the title compound (35.6 mg, 68% yield). MS (apci) m/z=393.2 (M+H).

Intermediate P57

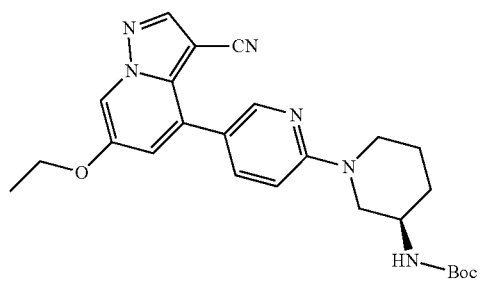 [SMILES: CCOc1cc(-c2ccc(N3CCC[C@@H](NC(=O)OC(C)(C)C)C3)nc2)c2c(C#N)cnn2c1]

tert-butyl (R)-(1-(5-(3-cyano-6-ethoxypyrazolo[1,5-a]pyridin-4-yl)pyridin-2-yl)piperidin-3-yl)carbamate To a solution of 6-ethoxy-4-(6-fluoropyridin-3-yl)pyrazolo[1,5-a]pyridine-3-carbonitrile (Intermediate P6, 0.147 g, 0.521 mmol) in DMSO (1 mL) was added tert-butyl (R)-piperidin-3-ylcarbamate (209 mg, 1.04 mmol) and potassium carbonate (216 mg, 1.56 mmol). The reaction mixture was heated to 110° C. for 72 h. After cooling to ambient temperature, the reaction mixture was diluted with DCM and quenched with saturated $NH_4Cl$ and extracted into additional DCM. The combined organic extracts were dried over anhydrous $Na_2SO_{4(s)}$ and concentrated in vacuo. The residue was purified by silica chromatography (0-100% EtOAc in hexanes as the gradient eluent) to afford the title compound (100 mg, 0.216 mmol, 41.5% yield). MS (apci) m/z=463.2 (M+H).

Intermediate P58

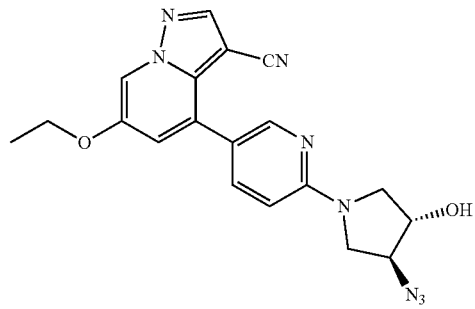 [SMILES: CCOc1cc(-c2ccc(N3C[C@H](N=[N+]=[N-])[C@@H](O)C3)nc2)c2c(C#N)cnn2c1]

4-(6-((3S,4S)-3-azido-4-hydroxypyrrolidin-1-yl)pyridin-3-yl)-6-ethoxypyrazolo[1,5-a]pyridine-3-carbonitrile

Step 1: Preparation of (3S,4S)-tert-butyl 3-azido-4-hydroxypyrrolidine-1-carboxylate A solution of tert-butyl 6-oxa-3-azabicyclo[3.1.0]hexane-3-carboxylate (15.42 g, 83.25 mmol), (R)—N,N'-Bis(3,5-Di-tert-butylsalicylidene)-1,2-cyclohexanediaminochromium(III) chloride (0.5904 g, 0.8325 mmol), potassium carbonate (13.81 g, 99.90 mmol), and azidotrimethylsilane (12.79 ml, 91.58 mmol) was sparged with nitrogen and stirred at rt for 24 h. The reaction mixture was treated with silica gel (30 g) and water (2 mL) and stirred at rt for an additional 72 h. The solution was filtered through a pad of Celite® and concentrated in vacuo. The residue was purified by silica chromatography (20-50% EtOAc in hexanes as the gradient eluent) to afford the title compound (18.5 g, 81.05 mmol, 97.36% yield) in sufficient purity for step 2.

Step 2: Preparation of (3S,4S)-4-azidopyrrolidin-3-ol dihydrochloride

A solution of tert-butyl (3S,4S)-3-azido-4-hydroxypyrrolidine-1-carboxylate (0.500 g, 2.19 mmol) in DCM (2.19 mL) was treated with 6M HCl in IPA (4.5 mL, 27 mmol). The reaction mixture was stirred at rt for 4 h, at which time the reaction mixture was concentrated in vacuo to afford the title compound (assumed theoretical yield, 0.440 g, 2.19 mmol) in sufficient purity for step 3. MS (apci) m/z=129.1 (M+H).

Step 3: Preparation of 4-(6-((3S,4S)-3-azido-4-hydroxypyrrolidin-1-yl)pyridin-3-yl)-6-ethoxypyrazolo[1,5-a]pyridine-3-carbonitrile To a solution of 6-ethoxy-4-(6-fluoropyridin-3-yl)pyrazolo[1,5-a]pyridine-3-carbonitrile (Intermediate P6, 0.300 g, 1.06 mmol) in DMSO (2 mL) was added N-ethyl-N-isopropylpropan-2-amine (3.70 mL, 21.3 mmol) and (3S,4S)-4-azidopyrrolidin-3-ol dihydrochloride (0.427 g, 2.13 mmol) The reaction mixture was stirred 100° C. for 24 h. After cooling to ambient temperature, the reaction mixture was quenched with saturated $NH_4Cl_{(aq)}$ and extracted into DCM. The combined organic extracts were dried over anhydrous $Na_2SO_{4(s)}$ and concentrated in vacuo. The residue was purified by silica chromatography (20-100% EtOAc in hexanes as the gradient eluent) to afford the title compound (0.220 g, 0.564 mmol, 53.0% yield over two steps). MS (apci) m/z=391.15

Intermediate P59

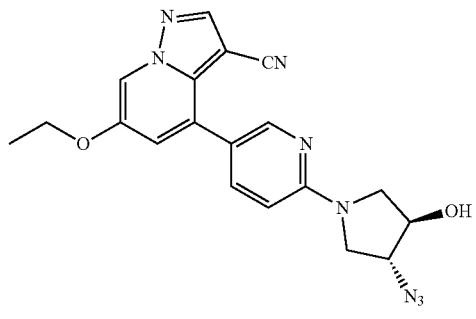 [SMILES: CCOc1cc(-c2ccc(N3C[C@@H](O)[C@H](N=[N+]=[N-])C3)nc2)c2c(C#N)cnn2c1]

4-(6-((3R,4R)-3-azido-4-hydroxypyrrolidin-1-yl)pyridin-3-yl)-6-ethoxypyrazolo[1,5-a]pyridine-3-carbonitrile Step 1: Preparation of (3R,4R)-tert-butyl 3-azido-4-hydroxypyrrolidine-1-carboxylate A solution of tert-butyl 6-oxa-3-azabicyclo[3.1.0]hexane-3-carboxylate (15.42 g, 83.25 mmol), (1 S,2S)-(−)-[1,2-Cyclohexanediamino-N,N'-bis(3,5-di-t-butylsalicylidene)] chromium (III) chloride (1.181 g, 1.665 mmol), and azidotrimethylsilane (12.79 ml, 91.58 mmol) was sparged with nitrogen and stirred at rt for 24 h. To this was added potassium carbonate (13.81 g, 99.90 mmol) in MeOH (100 mL), and the reaction mixture was stirred an additional 5 h at rt. The solution was filtered through a pad of Celite® and concentrated in vacuo. The residue was taken up in EtOAc and water. The aqueous fraction was extracted with EtOAc, and the combined organic extracts were washed successively with saturated $NaHCO_{3(aq)}$, water, and brine. They were dried over anhydrous $MgSO_{4(s)}$ and concentrated in vacuo. The residue was purified by silica chromatography (20% EtOAc in hexanes as the eluent) to afford the title compound (18.5 g, 81.05 mmol, 97.36% yield) in sufficient purity for step 2.

Step 2: Preparation of (3R,4R)-4-azidopyrrolidin-3-ol dihydrochloride

A solution of tert-butyl (3R,4R)-3-azido-4-hydroxypyrrolidine-1-carboxylate (0.500 g, 2.19 mmol) in DCM (2.19 mL) was treated with 6M HCl in IPA (4.5 mL, 27 mmol). The reaction mixture was stirred at rt for 4 h, at which time the reaction mixture was concentrated in vacuo to afford the title compound (assumed theoretical yield, 0.440 g, 2.19 mmol) in sufficient purity for step 3. MS (apci) m/z=129.1 (M+H).

Step 3: Preparation of 4-(6-((3R,4R)-3-azido-4-hydroxypyrrolidin-1-yl)pyridin-3-yl)-6-ethoxypyrazolo[1,5-a]pyridine-3-carbonitrile To a solution of 6-ethoxy-4-(6-fluoropyridin-3-yl)pyrazolo[1,5-a]pyridine-3-carbonitrile (Intermediate P6, 0.300 g, 1.06 mmol) in DMSO (2 mL) was added N-ethyl-N-isopropylpropan-2-amine (3.70 mL, 21.3 mmol) and (3R,4R)-4-azidopyrrolidin-3-ol dihydrochloride (0.427 g, 2.13 mmol) The reaction mixture was stirred 100° C. for 24 h. After cooling to ambient temperature, the reaction mixture was quenched with saturated $NH_4Cl_{(aq)}$ and extracted into DCM. The combined organic extracts were dried over anhydrous $Na_2SO_{4(s)}$ and concentrated in vacuo. The residue was purified by silica chromatography (20-100% EtOAc in hexanes as the gradient eluent) to afford the title compound (0.205 g, 0.525 mmol, 49.4% yield over two steps). MS (apci) m/z=391.2 (M+H).

Intermediate P60

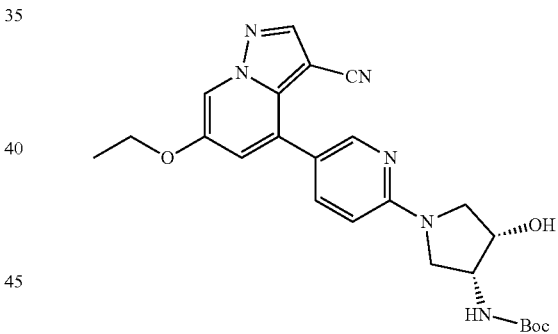

tert-butyl ((3R,4S)-1-(5-(3-cyano-6-ethoxypyrazolo[1,5-a]pyridin-4-yl)pyridin-2-yl)-4-hydroxypyrrolidin-3-yl)carbamate To a solution of 6-ethoxy-4-(6-fluoropyridin-3-yl)pyrazolo[1,5-a]pyridine-3-carbonitrile (Intermediate P6, 0.215 g, 0.762 mmol) in DMSO (1.5 mL) was added N-ethyl-N-isopropylpropan-2-amine (0.663 ml, 3.81 mmol) and tert-butyl ((3R,4S)-4-hydroxypyrrolidin-3-yl)carbamate (0.231 g, 1.14 mmol). The reaction mixture was stirred 100° C. for 24 h. After cooling to ambient temperature, the reaction mixture was quenched with saturated $NH_4Cl_{(aq)}$ and extracted into DCM. The combined organic extracts were dried over anhydrous $Na_2SO_{4(s)}$ and concentrated in vacuo. The residue was purified by silica chromatography (20-100% EtOAc in hexanes as the gradient eluent) to afford the title compound (0.347 g, 0.747 mmol, 98.1% yield). MS (apci) m/z=465.3 (M+H).

Intermediate P61

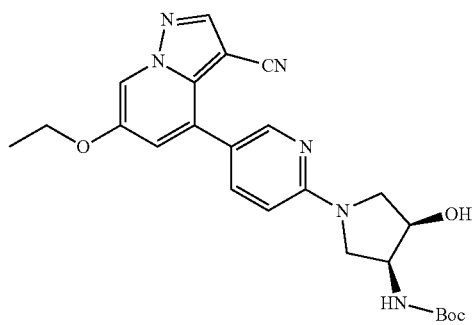 [SMILES: CCOc1cc(-c2ccc(N3C[C@@H](O)[C@@H](NC(=O)OC(C)(C)C)C3)nc2)c2c(C#N)cnn2c1]

tert-butyl ((3S,4R)-1-(5-(3-cyano-6-ethoxypyrazolo
[1,5-a]pyridin-4-yl)pyridin-2-yl)-4-hydroxypyrroli-
din-3-yl)carbamate To a solution of 6-ethoxy-4-(6-fluoropyridin-3-yl)pyrazolo[1,5-a]pyridine-3-carbonitrile (Intermediate P6, 0.215 g, 0.762 mmol) in DMSO (1.5 mL) was added N-ethyl-N-isopropylpropan-2-amine (0.663 ml, 3.81 mmol) and tert-butyl ((3S,4R)-4-hydroxypyrrolidin-3-yl)carbamate (0.231 g, 1.14 mmol). The reaction mixture was stirred 100° C. for 24 h. After cooling to ambient temperature, the reaction mixture was quenched with saturated $NH_4Cl_{(aq)}$ and extracted into DCM. The combined organic extracts were dried over anhydrous $Na_2SO_{4(s)}$ and concentrated in vacuo. The residue was purified by silica chromatography (0-100% EtOAc in hexanes as the gradient eluent) to afford the title compound (0.284 g, 0.611 mmol, 80.3% yield). MS (apci) m/z=465.2 (M+H).

Intermediate P62

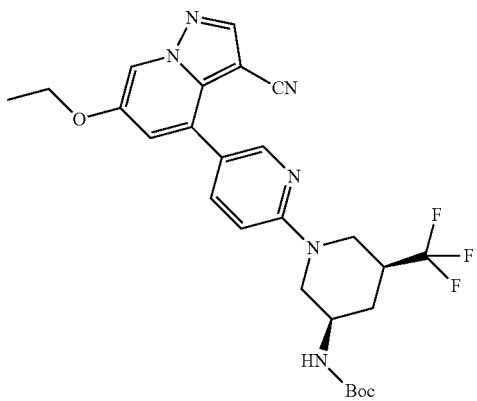 [SMILES: CCOc1cc(-c2ccc(N3C[C@H](NC(=O)OC(C)(C)C)C[C@H](C(F)(F)F)C3)nc2)c2c(C#N)cnn2c1]

tert-butyl ((3R,5S)-1-(5-(3-cyano-6-ethoxypyrazolo
[1,5-a]pyridin-4-yl)pyridin-2-yl)-5-(trifluoromethyl)
piperidin-3-yl)carbamate To a solution of 6-ethoxy-4-(6-fluoropyridin-3-yl)pyrazolo[1,5-a]pyridine-3-carbonitrile (Intermediate P6, 0.060 g, 0.21 mmol) in DMSO (0.4 mL) was added potassium carbonate (0.15 g, 1.1 mmol) and tert-butyl ((3R,5S)-5-(trifluoromethyl)piperidin-3-yl)carbamate (0.171 g, 0.638 mmol). The reaction mixture was stirred at 110° C. for 24 h. After cooling to ambient temperature, the reaction mixture was quenched with saturated $NH_4Cl_{(aq)}$ and extracted into DCM. The combined organic extracts were dried over anhydrous $Na_2SO_{4(s)}$ and concentrated in vacuo. The residue was purified by silica chromatography (0-100% EtOAc in hexanes as the gradient eluent) to afford the title compound (0.0538 g 47.7% yield) in sufficient purity for step 2. MS (apci) m/z=531.2 (M+H).

Intermediate P63

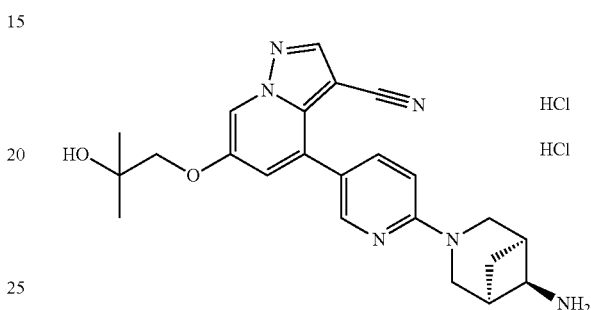

4-(6-((1R,5 S,6r)-6-amino-3-azabicyclo[3.1.1]hep-
tan-3-yl)pyridin-3-yl)-6-(2-hydroxy-2-methyl-
propoxy)pyrazolo[1,5-a]pyridine-3-carbonitrile
dihydrochloride Step 1: Preparation of tert-butyl ((1R,5S,6r)-3-(5-
(3-cyano-6-(2-hydroxy-2-methylpropoxy)pyrazolo
[1,5-a]pyridin-4-yl)pyridin-2-yl)-3-azabicyclo[3.1.1]
heptan-6-yl)carbamate To a solution of 4-(6-fluoropyridin-3-yl)-6-(2-hydroxy-2-methylpropoxy)pyrazolo[1,5-a]pyridine-3-carbonitrile (Intermediate P42; 200 mg, 0.57 mmol) and tert-butyl ((1R,5S,6r)-3-azabicyclo[3.1.1]heptan-6-yl)carbamate (169 mg, 0.80 mmol) in DMSO (0.57 mL) was added DIEA (298 µL, 1.71 mmol). Under a $N_{2(g)}$ atmosphere, reaction was stirred overnight at 90° C. After cooling to ambient temperature, the reaction mixture was diluted with water (5.7 mL). The suspension was filtered and the solids were rinsed with water (3×5 mL) then MTBE (3×5 mL). The isolated solids were dried under vacuum while the MTBE filtrate was concentrated in vacuo. The filtrate residue was purified by C18 reverse phase chromatography (5-50% ACN in water). The precipitate solids and chromatography product were combined and concentrated in vacuo to cleanly provide the title compound (292 mg, 98% yield) in sufficient purity for step 2. MS (apci) m/z=519.20 (M+H)

Step 2: Preparation of 4-(6-((1R,5S,6r)-6-amino-3-
azabicyclo[3.1.1]heptan-3-yl)pyridin-3-yl)-6-(2-
hydroxy-2-methylpropoxy)pyrazolo[1,5-a]pyridine-
3-carbonitrile dihydrochloride To a solution of tert-butyl ((1R,5S,6r)-3-(5-(3-cyano-6-(2-hydroxy-2-methylpropoxy)pyrazolo[1,5-a]pyridin-4-yl)pyridin-2-yl)-3-azabicyclo[3.1.1]heptan-6-yl)carbamate (148 mg, 0.29 mmol) in MeOH (571 µL) was added HCl (conc.) (476 µL, 5.71 mmol) dropwise. The reaction was stirred for 2 h at ambient temperature. The reaction was diluted with EtOAc (1 mL) and was stirred at ambient temperature for 10 minutes. MTBE (1 mL) was added and a suspension formed. The suspension was filtered and solids were rinsed with 10% MeOH in MTBE (3×1 mL) to cleanly provide the title compound (114 mg, 81% yield). MS (apci) m/z=419.15 (M+H).

Intermediate P64

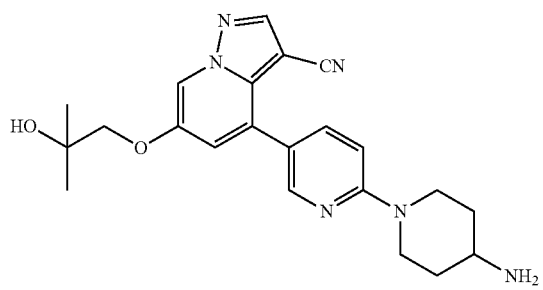 [SMILES: CC(C)(O)COc1cc(-c2ccc(N3CCC(N)CC3)nc2)c2c(C#N)cnn2c1]

4-(6-(4-aminopiperidin-1-yl)pyridin-3-yl)-6-(2-hydroxy-2-methylpropoxy)pyrazolo[1,5-a]pyridine-3-carbonitrile Step 1: Preparation of tert-butyl (1-(5-(3-cyano-6-(2-hydroxy-2-methylpropoxy)pyrazolo[1,5-a]pyridin-4-yl)pyridin-2-yl)piperidin-4-yl)carbamate To a solution of 4-(6-fluoropyridin-3-yl)-6-(2-hydroxy-2-methylpropoxy)pyrazolo[1,5-a]pyridine-3-carbonitrile (Intermediate P42; 205 mg, 0.628 mmol) and tert-butyl piperidin-4-ylcarbamate (252 mg, 1.26 mmol) in DMA (2.09 mL) was added DIEA (549 μL, 3.14 mmol). The reaction was stirred 2 h at 95° C. After cooling to ambient temperature, the reaction mixture was diluted with water and extracted with EtOAc. The organic extracts were washed with water and brine. The organic extracts were dried over anhydrous $Na_2SO_{4(s)}$, filtered and concentrated in vacuo to afford the title compound (assumed quantitative yield, 319 mg) in sufficient purity for step 2. MS (apci) m/z=507.20 (M+H)

Step 2: Preparation of 4-(6-(4-aminopiperidin-1-yl)pyridin-3-yl)-6-(2-hydroxy-2-methylpropoxy)pyrazolo[1,5-a]pyridine-3-carbonitrile To a solution of tert-butyl (1-(5-(3-cyano-6-(2-hydroxy-2-methylpropoxy)pyrazolo[1,5-a]pyridin-4-yl)pyridin-2-yl)piperidin-4-yl)carbamate (319 mg, 0.63 mmol) in DCM (3.15 mL) was added TFA (3.14 mL, 40.9 mmol). The reaction was stirred for 30 min at ambient temperature. The reaction was concentrated in vacuo. The residue was resuspended in DCM and purified using silica chromatography (1-9% MeOH in DCM with 0.1-0.9% $NH_4OH$ as the gradient eluent) to cleanly provide the title compound (37 mg, 53% yield) MS (apci) m/z=407.2 (M+H).

Intermediate P65

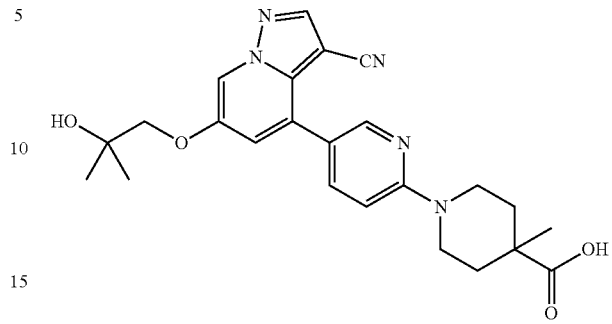

1-(5-(3-cyano-6-(2-hydroxy-2-methylpropoxy)pyrazolo[1,5-a]pyridin-4-yl)pyridin-2-yl)-4-methylpiperidine-4-carboxylic acid Step 1: Preparation of methyl 1-(5-(3-cyano-6-(2-hydroxy-2-methylpropoxy)pyrazolo[1,5-a]pyridin-4-yl)pyridin-2-yl)-4-methylpiperidine-4-carboxylate To a solution of 4-(6-fluoropyridin-3-yl)-6-(2-hydroxy-2-methylpropoxy)pyrazolo[1,5-a]pyridine-3-carbonitrile (Intermediate P42; 1.04 mg, 3.19 mmol) and 4-Methyl-piperidine-4-carboxylic acid methyl ester (1.00 mg, 6.37 mmol) in DMSO (3.2 mL) was added DIEA (1.67 mL, 9.56 mmol). The reaction was stirred 16 h at 90° C. After cooling to ambient temperature, the reaction mixture was diluted with water and extracted with EtOAc. The organic extracts were washed with water and brine. The organic extracts were dried over anhydrous $Na_2SO_{4(s)}$, filtered and concentrated in vacuo. The residue was purified using silica chromatography (30-100% Hexanes to EtOAc) to afford the title compound (1.40 g, 95% yield) in sufficient purity for step 2. MS (apci) m/z=464.2 (M+H).

Step 2: Preparation of 1-(5-(3-cyano-6-(2-hydroxy-2-methylpropoxy)pyrazolo[1,5-a]pyridin-4-yl)pyridin-2-yl)-4-methylpiperidine-4-carboxylic acid To a solution of methyl 1-(5-(3-cyano-6-(2-hydroxy-2-methylpropoxy)pyrazolo[1,5-a]pyridin-4-yl)pyridin-2-yl)-4-methylpiperidine-4-carboxylate (1.40 g, 3.02 mmol) in THF (15 mL) and MeOH (15 mL) and treated with potassium hydroxide (4.53 mL, 9.06 mmol). The reaction was stirred for 48 h at ambient temperature. The reaction was concentrated in vacuo. The residue was diluted with water and extracted with $Et_2O$. The aqueous layer was acidified to pH 5 using 4N HCl and extracted with 4:1 DCM:IPA. The combined organic extracts were washed with water. The organic extracts were dried over anhydrous $Na_2SO_{4(s)}$, filtered and concentrated in vacuo to afford the title compound (1.20 g, 88% yield) in sufficient purity for step 2. MS (apci) m/z=450.2

Intermediate P66

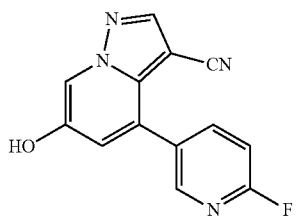 [SMILES: N#Cc1cnn2cc(O)cc(-c3ccc(F)nc3)c12]

4-(6-fluoropyridin-3-yl)-6-hydroxypyrazolo[1,5-a]pyridine-3-carbonitrile

In a pressure vessel, a solution of 4-bromo-6-hydroxypyrazolo[1,5-a]pyridine-3-carbonitrile (Intermediate P1; 15.4 g, 64.7 mmol) in dioxane (320 mL) was treated sequentially with 2-fluoro-5-(4,4,5,5-tetramethyl-1,3,2-dioxaborolan-2-yl)pyridine (15.2 g, 67.9 mmol), Pd(PPh$_3$)$_4$ (3.74 g, 3.23 mmol) and 2 M Na$_2$CO$_{3(aq)}$ (97 mL, 194 mmol). The resulting mixture was sparged with Ar$_{(g)}$ and then the vessel was sealed. The mixture was stirred 16 h at 80° C. After cooling to ambient temperature, the reaction mixture was diluted with MTBE and extracted with 1 M NaOH. The combined aqueous layers were extracted with MTBE. The combined aqueous layers were acidified to pH 4 with 4 M HCl. The suspension was filtered and washed with water to cleanly provide the title compound (14.8 g, 72% yield). MS (apci) m/z=253.1 (M−H) $^1$H NMR (400 MHz, DMSO-d$_6$) δ 8.53 (s, 1H), 8.48-8.47 (d, 1H), 8.41-8.40 (d, 1H), 8.26-8.21 (m, 1H), 7.38-7.36 (m, 1H), 7.31-7.30 (d, 1H).

Intermediate P67

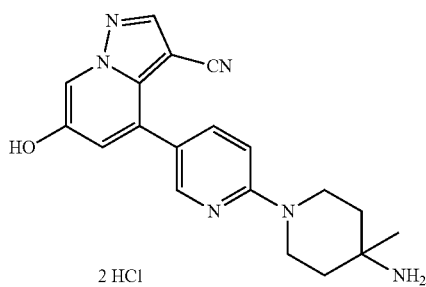 [SMILES: CC1(N)CCN(c2ccc(-c3cc(O)cn4ncc(C#N)c34)cn2)CC1]

4-(6-(4-amino-4-methylpiperidin-1-yl)pyridin-3-yl)-6-hydroxypyrazolo[1,5-a]pyridine-3-carbonitrile dihydrochloride Step 1: Preparation of tert-butyl (1-(5-(3-cyano-6-hydroxypyrazolo[1,5-a]pyridin-4-yl)pyridin-2-yl)-4-methylpiperidin-4-yl)carbamate To a solution of 4-(6-fluoropyridin-3-yl)-6-hydroxypyrazolo[1,5-a]pyridine-3-carbonitrile (Intermediate P66; 3.0 g, 9.44 mmol) and tert-butyl 4-methylpiperidin-4-ylcarbamate (2.83 mg, 13.2 mmol) in DMSO (12 mL) was added DIEA (4.93 mL, 28.3 mmol). The reaction was stirred 16 h at 90° C. After cooling to ambient temperature, the reaction mixture was diluted into water and acidified to pH 5 using a 10% citric acid solution and stirred for 15 min at ambient temperature. The suspension was filtered and the precipitate was rinsed with water. The isolated solids were dissolved in 4:1 DCM:IPA and dried over anhydrous Na$_2$SO$_{4(s)}$, filtered and concentrated in vacuo. The residue was purified using silica chromatography (5-75% EtOAc in DCM) to afford the title compound (assumed theoretical yield, 4.23 g) in sufficient purity for step 2. MS (apci) m/z=449.3 (M+H)

Step 2: Preparation of 4-(6-(4-amino-4-methylpiperidin-1-yl)pyridin-3-yl)-6-hydroxypyrazolo[1,5-a]pyridine-3-carbonitrile dihydrochloride To a solution of tert-butyl (1-(5-(3-cyano-6-hydroxypyrazolo[1,5-a]pyridin-4-yl)pyridin-2-yl)-4-methylpiperidin-4-yl)carbamate (assumed 4.23 g, 9.44 mmol) in MeOH (30 mL) was added HCl (5-6 N solution in 2-propanol, 28.3 mL, 142 mmol). The reaction was stirred for 2.5 h at ambient temperature. The reaction was diluted with MTBE (30 mL) and stirred for 30 min at ambient temperature. The suspension was filtered and washed with MTBE (50 mL) to cleanly provide the title compound (2.18 g, 55% yield over two steps) MS (apci) m/z=349.2 (M+H).

Intermediate P68

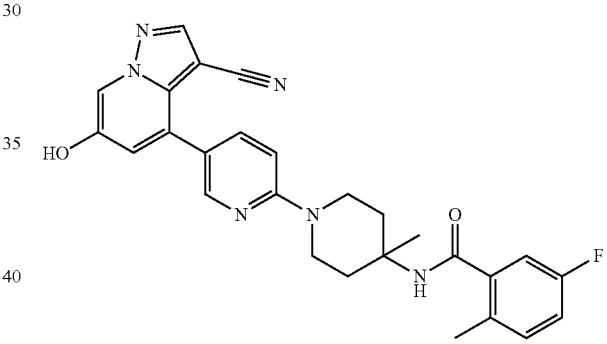

N-(1-(5-(3-cyano-6-hydroxypyrazolo[1,5-a]pyridin-4-yl)pyridin-2-yl)-4-methylpiperidin-4-yl)-5-fluoro-2-methylbenzamide To a solution of 4-(6-(4-amino-4-methylpiperidin-1-yl)pyridin-3-yl)-6-hydroxypyrazolo[1,5-a]pyridine-3-carbonitrile dihydrochloride (Intermediate P67; 503 mg, 1.19 mmol), 5-fluoro-2-methylbenzoic acid (552 mg, 3.58 mmol), and HATU (1.36 g, 3.58 mmol) in DMSO (5 mL) was added DIEA (1.7 mL, 9.55 mmol). The reaction was stirred 16 h at ambient temperature. The reaction mixture was diluted with THF (4 mL) and treated with NaOH (5.97 mL, 11.9 mmol) and stirred for 4 h at ambient temperature. The reaction was concentrated in vacuo. The residue was diluted with EtOAc and washed with water. The pH was adjusted to pH 5 with AcOH and then extracted with EtOAc. The organic extracts were washed with brine. The organic extracts were dried over anhydrous Na$_2$SO$_{4(s)}$, filtered and concentrated in vacuo. The residue was purified using silica chromatography (50-100% Hexanes to EtOAc) to afford the title compound (534 mg, 92% yield) in sufficient purity for step 2. MS (apci) m/z=485.2 (M+H).

Intermediate P69

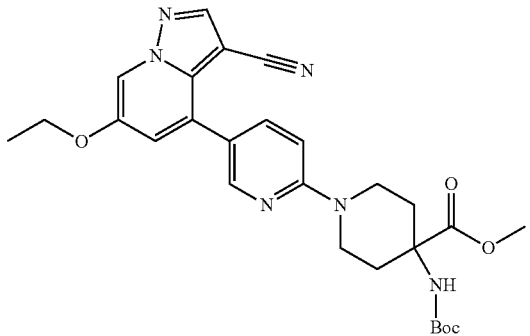 [SMILES: CCOc1cc(-c2ccc(N3CCC(NC(=O)OC(C)(C)C)(C(=O)OC)CC3)nc2)c2c(C#N)cnn2c1]

methyl 4-((tert-butoxycarbonyl)amino)-1-(5-(3-cyano-6-ethoxypyrazolo[1,5-a]pyridin-4-yl)pyridin-2-yl)piperidine-4-carboxylate To a solution of 6-ethoxy-4-(6-fluoropyridin-3-yl)pyrazolo[1,5-a]pyridine-3-carbonitrile (Intermediate P6, 0.700 g, 2.480 mmol) in DMSO (4.96 mL) was added DIEA (1.296 mL, 7.439 mmol) and methyl 4-((tert-butoxycarbonyl)amino)piperidine-4-carboxylate (0.8968 g, 3.472 mmol). The reaction mixture was stirred 90° C. for 24 h. After cooling to ambient temperature, the reaction mixture was quenched water and extracted into EtOAc. The combined organic extracts were washed with saturated NaCl$_{(aq)}$, dried over anhydrous Na$_2$SO$_{4(s)}$ and concentrated in vacuo. The residue was purified by silica chromatography (10-90% EtOAc in hexanes as the gradient eluent) to afford the title compound (1.003 g, 1.927 mmol, 77.69% yield). MS (apci) m/z=521.3 (M+H).

Intermediate P70

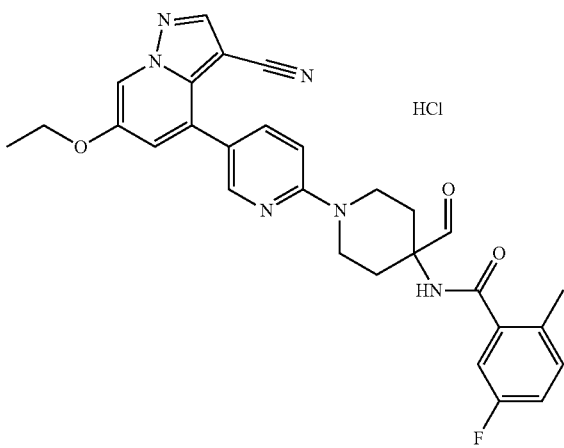 [SMILES: CCOc1cc(-c2ccc(N3CCC(C=O)(NC(=O)c4cc(F)ccc4C)CC3)nc2)c2c(C#N)cnn2c1 ; Cl]

N-(1-(5-(3-cyano-6-ethoxypyrazolo[1,5-a]pyridin-4-yl)pyridin-2-yl)-4-formylpiperidin-4-yl)-5-fluoro-2-methylbenzamide Step 1: Preparation of methyl 4-amino-1-(5-(3-cyano-6-ethoxypyrazolo[1,5-a]pyridin-4-yl)pyridin-2-yl)piperidine-4-carboxylate A solution of methyl 4-((tert-butoxycarbonyl)amino)-1-(5-(3-cyano-6-ethoxypyrazolo[1,5-a]pyridin-4-yl)pyridin-2-yl)piperidine-4-carboxylate (Intermediate P69, 0.8 g, 1.5 mmol) in DCM was treated with TFA. The reaction mixture was stirred at rt for 24 h, then concentrated in vacuo. HCl in iPrOH (6N) was added to the mixture to precipitate product. The suspension was stirred at RT for 1 h then concentrated, affording the title compound (assumed theoretical yield, 0.65 g, 1.5 mmol) in sufficient purity for step 2. MS (apci) m/z=421.25 (M+H).

Step 2: Preparation of methyl 1-(5-(3-cyano-6-ethoxypyrazolo[1,5-a]pyridin-4-yl)pyridin-2-yl)-4-(5-fluoro-2-methylbenzamido)piperidine-4-carboxylate To a solution of methyl 4-amino-1-(5-(3-cyano-6-ethoxypyrazolo[1,5-a]pyridin-4-yl)pyridin-2-yl)piperidine-4-carboxylate (0.65 g, 1.5 mmol) in DCM (31 mL) was added 5-fluoro-2-methylbenzoic acid (0.36 g, 2.3 mmol) and HATU (0.88 g, 2.3 mmol). The reaction mixture was stirred at rt for 1 h, at which time a catalytic amount of DMAP was added. The reaction mixture was stirred at 50° C. for 1 h, then cooled to RT and purified directly by silica chromatography (0-100% EtOAc in Hexanes then 1-10% MeOH in CHCl$_3$ as the gradient eluent) to afford the title compound (0.8 g, 1.4 mmol, 93% yield over two steps) in sufficient purity for step 3. MS (apci) m/z=557.2 (M+H).

Step 3: Preparation of N-(1-(5-(3-cyano-6-ethoxypyrazolo[1,5-a]pyridin-4-yl)pyridin-2-yl)-4-(hydroxymethyl)piperidin-4-yl)-5-fluoro-2-methylbenzamide To a solution of methyl 1-(5-(3-cyano-6-ethoxypyrazolo[1,5-a]pyridin-4-yl)pyridin-2-yl)-4-(5-fluoro-2-methylbenzamido)piperidine-4-carboxylate (750 mg, 1.35 mmol) in THF (26.949 mL) at 0° C. was added lithium borohydride (117 mg, 5.39 mmol). The reaction mixture was stirred at 0° C. for 1 h. The reaction mixture was diluted with EtOAc and washed with a 10% aqueous citric acid solution. The organic extract was dried and concentrated in vacuo. The residue was purified by silica chromatography (0-100% EtOAc in Hexanes then 1-10% MeOH in EtOAc as the gradient eluent) to afford the title compound (700 mg, 1.32 mmol, 98.3% yield) in sufficient purity for step 4. MS (apci) m/z=529.1 (M+H).

Step 4: Preparation of N-(1-(5-(3-cyano-6-ethoxypyrazolo[1,5-a]pyridin-4-yl)pyridin-2-yl)-4-formylpiperidin-4-yl)-5-fluoro-2-methylbenzamide To a solution of N-(1-(5-(3-cyano-6-ethoxypyrazolo[1,5-a]pyridin-4-yl)pyridin-2-yl)-4-(hydroxymethyl)piperidin-4-yl)-5-fluoro-2-methylbenzamide (100 mg, 0.189 mmol) in DCM (0.946 mL) at 0° C. was added 3-oxo-1λ5-benzo[d][1,2]iodaoxole-1,1,1 (3H)-triyl triacetate (201 mg, 0.473 mmol). The reaction mixture was warmed to rt and stirred at that temperature for 1 h, at which time additional 3-oxo- 115-benzo[d][1,2]iodaoxole-1,1,1 (3H)-triyl triacetate (201 mg, 0.473 mmol) was added. The reaction mixture was stirred at rt an additional 15 min, then quenched with EtOAc and saturated NaHCO$_{3(aq)}$. The organic extract was washed with Na$_2$S$_2$O$_{3(aq)}$, dried, and concentrated in vacuo. The residue was purified by silica chromatography (0-100% EtOAc in Hexanes then 1-10% MeOH in EtOAc as the gradient eluent) to afford the title compound (358 mg, 55.3% yield). MS (apci) m/z=527.15 (M+H).

Intermediate P71 tert-butyl (1-(5-(3-cyano-6-ethoxypyrazolo[1,5-a]pyridin-4-yl)pyridin-2-yl)-4-formylpiperidin-4-yl)carbamate

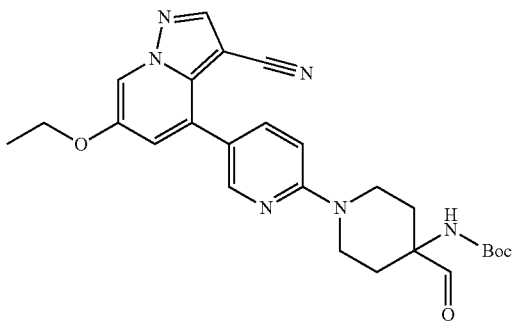 [SMILES: CCOc1cc(-c2ccc(N3CCC(C=O)(NC(=O)OC(C)(C)C)CC3)nc2)c2c(C#N)cnn2c1]

Step 1: Preparation of tert-butyl (1-(5-(3-cyano-6-ethoxypyrazolo[1,5-a]pyridin-4-yl)pyridin-2-yl)-4-(hydroxymethyl)piperidin-4-yl)carbamate To a solution of methyl 4-((tert-butoxycarbonyl)amino)-1-(5-(3-cyano-6-ethoxypyrazolo[1,5-a]pyridin-4-yl)pyridin-2-yl)piperidine-4-carboxylate (Intermediate P69, 1.00 g, 1.92 mmol) in THF (12.8 mL) at 0° C. was added lithium borohydride (0.167 g, 7.68 mmol). The reaction mixture was allowed to reach rt and stirred at this temperature for 24 h. The reaction mixture was quenched with water, and the residual solids were removed by filtration. The filtrate was extracted with EtOAc, and the combined organic extracts were washed with saturated NaCl$_{(aq)}$. The organic extracts were dried over anhydrous Na$_2$SO$_{4(s)}$ and concentrated in vacuo. The residue was purified by silica chromatography (10-90% EtOAc in hexanes as the gradient eluent) to afford the title compound (0.832 g, 1.69 mmol, 87.9% yield) in sufficient purity for step 2. MS (apci) m/z=493.3 (M+H).

Step 2: Preparation of tert-butyl (1-(5-(3-cyano-6-ethoxypyrazolo[1,5-a]pyridin-4-yl)pyridin-2-yl)-4-formylpiperidin-4-yl)carbamate To a solution of tert-butyl (1-(5-(3-cyano-6-ethoxypyrazolo[1,5-a]pyridin-4-yl)pyridin-2-yl)-4-(hydroxymethyl)piperidin-4-yl)carbamate (0.832 g, 1.69 mmol) in THF (16.9 mL) was added 3-oxo-115-benzo[d][1,2]iodaoxole-1,1,1 (3H)-triyl triacetate (0.832 g, 1.69 mmol). The reaction mixture was stirred at rt for 24 h then quenched with water. The mixture was extracted with EtOAc, and the combined organic extracts were washed with saturated NaCl$_{(aq)}$. The organic extracts were concentrated in vacuo, and the residue was purified by silica chromatography (10-90% EtOAc in hexanes as the gradient eluent) to afford the title compound (0.594 g, 1.21 mmol, 71.7% yield). MS (apci) m/z=491.2 (M+H).

Intermediate P72

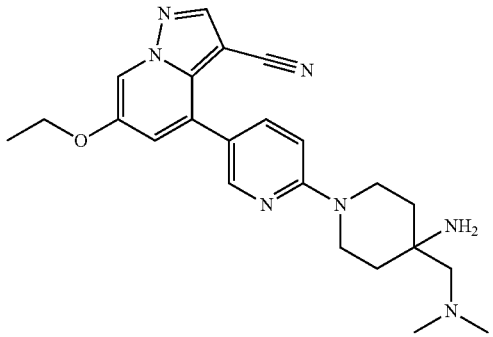 [SMILES: CCOc1cc(-c2ccc(N3CCC(N)(CN(C)C)CC3)nc2)c2c(C#N)cnn2c1]

4-(6-(4-amino-4-((dimethylamino)methyl)piperidin-1-yl)pyridin-3-yl)-6-ethoxypyrazolo[1,5-a]pyridine-3-carbonitrile Step 1: Preparation of tert-butyl (1-(5-(3-cyano-6-ethoxypyrazolo[1,5-a]pyridin-4-yl)pyridin-2-yl)-4-((dimethylamino)methyl)piperidin-4-yl)carbamate To a mixture of tert-butyl (1-(5-(3-cyano-6-ethoxypyrazolo[1,5-a]pyridin-4-yl)pyridin-2-yl)-4-formylpiperidin-4-yl)carbamate (0.594 g, 1.21 mmol) in DCM (0.077 mL) was added dimethylamine hydrochloride (0.197 g, 2.42 mmol) and DIEA (0.443 mL, 2.54 mmol). This mixture was stirred at rt for 15 min, then sodium triacetoxyborohydride (0.385 g, 1.82 mmol) was slowly added. The reaction mixture was stirred at rt for 24 h then quenched with water. The solution was extracted with EtOAc, and the combined organic extracts were washed with saturated NaCl$_{(aq)}$. The organic extracts were dried over anhydrous Na$_2$SO$_{4(s)}$ and concentrated in vacuo, and the residue was purified by silica chromatography (10-90% EtOAc in hexanes as the gradient eluent) to afford the title compound (0.181 g, 0.348 mmol, 28.8% yield) in sufficient purity for step 2. MS (apci) m/z=520.3 (M+H).

Step 2: Preparation of 4-(6-(4-amino-4-((dimethylamino)methyl)piperidin-1-yl)pyridin-3-yl)-6-ethoxypyrazolo[1,5-a]pyridine-3-carbonitrile A mixture of tert-butyl (1-(5-(3-cyano-6-ethoxypyrazolo[1,5-a]pyridin-4-yl)pyridin-2-yl)-4-((dimethylamino)methyl)piperidin-4-yl)carbamate (0.181 g, 0.348 mmol) in DCM (0.02 mL) was treated with TFA (0.0268 mL). The reaction mixture was stirred at rt. The reaction mixture was concentrated in vacuo, resuspended in DCM, and washed successively with saturated NaHCO$_{3(aq)}$ and saturated NaCl$_{(aq)}$. The organic extract was dried over anhydrous Na$_2$SO$_{4(s)}$ and concentrated in vacuo to afford the title compound (0.145 g, 0.346 mmol, 99.2% yield). MS (apci) m/z=420.3 (M+H).

Intermediate P73

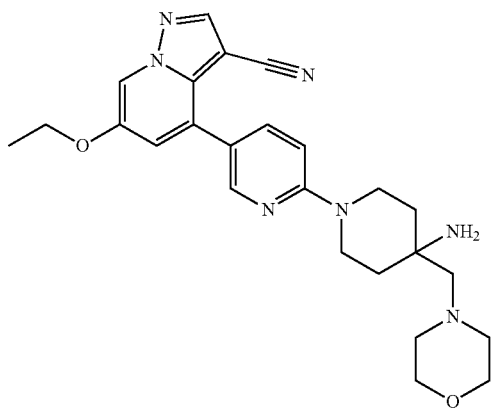 [SMILES: CCOc1cc(-c2ccc(N3CCC(N)(CN4CCOCC4)CC3)nc2)c2c(C#N)cnn2c1]

4-(6-(4-amino-4-(morpholinomethyl)piperidin-1-yl)pyridin-3-yl)-6-ethoxypyrazolo[1,5-a]pyridine-3-carbonitrile

Step 1: Preparation of tert-butyl (1-(5-(3-cyano-6-ethoxypyrazolo[1,5-a]pyridin-4-yl)pyridin-2-yl)-4-(morpholinomethyl)piperidin-4-yl)carbamate To a solution of tert-butyl (1-(5-(3-cyano-6-ethoxypyrazolo[1,5-a]pyridin-4-yl)pyridin-2-yl)-4-formylpiperidin-4-yl)carbamate (Intermediate P71, 400 mg, 0.815 mmol) in DCM (4.077 mL) was added morpholine (0.07703 mL, 0.815 mmol) and sodium triacetoxyborohydride (346 mg, 1.63 mmol). The reaction mixture was stirred at rt for 72 h. The reaction mixture was concentrated in vacuo, and the residue was purified by C-18 reverse phase chromatography (5-95% ACN in water [+0.1% TFA] as the gradient eluent). The fractions containing the desired product were diluted with 4:1 DCM/IPA and washed successively with saturated NaHCO$_{3(aq)}$ and saturated NaCl$_{(aq)}$. The organic extract was dried over anhydrous Na$_2$SO$_{4(s)}$, filtered, and concentrated in vacuo to afford the title compound (assumed theoretical yield, 458 mg, 0.815 mmol) in sufficient purity for step 2. MS (apci) m/z=562.4 (M+H).

Step 2: Preparation of 4-(6-(4-amino-4-(morpholinomethyl)piperidin-1-yl)pyridin-3-yl)-6-ethoxypyrazolo[1,5-a]pyridine-3-carbonitrile A solution of tert-butyl (1-(5-(3-cyano-6-ethoxypyrazolo[1,5-a]pyridin-4-yl)pyridin-2-yl)-4-(morpholinomethyl)piperidin-4-yl)carbamate (458 mg, 0.815 mmol) in DCM (0.815 mL) was treated with TFA (0.0628 mL, 0.815 mmol). The reaction mixture was stirred at rt for 1 h. The reaction mixture was quenched with 4:1 DCM/IPA and water. The mixture was washed successively with saturated NaHCO$_{3(aq)}$ and saturated NaCl$_{(aq)}$. The organic extract was dried over anhydrous Na$_2$SO$_{4(s)}$, filtered, and concentrated in vacuo to afford the title compound (135 mg, 0.292 mmol, 35.9% yield over two steps). MS (apci) m/z=462.3 (M+H).

Intermediate P74

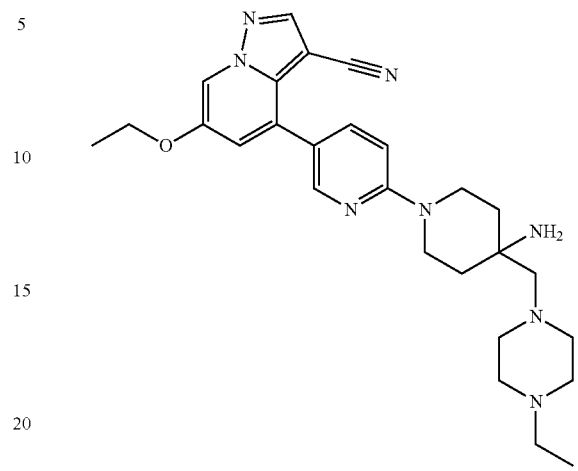

4-(6-(4-amino-4-((4-ethylpiperazin-1-yl)methyl)piperidin-1-yl)pyridin-3-yl)-6-ethoxypyrazolo[1,5-a]pyridine-3-carbonitrile A solution of tert-butyl (1-(5-(3-cyano-6-ethoxypyrazolo[1,5-a]pyridin-4-yl)pyridin-2-yl)-4-((4-ethylpiperazin-1-yl)methyl)piperidin-4-yl)carbamate (Example 379, 0.149 g, 0.253 mmol) in DCM (0.0163 mL) was treated with HCl in IPA (0.00769 mL, 0.253 mmol). The reaction mixture was stirred at rt then quenched with DCM and saturated Na$_2$CO$_{3(aq)}$. The organic extract was dried over anhydrous MgSO$_{4(s)}$, filtered, then concentrated in vacuo to afford the title compound (assumed theoretical yield, 0.124 g, 0.253 mmol). MS (apci) m/z=489.3 (M+H).

Intermediate P75

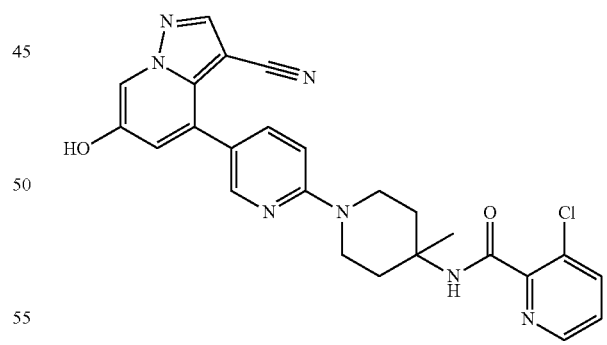

3-chloro-N-(1-(5-(3-cyano-6-hydroxypyrazolo[1,5-a]pyridin-4-yl)pyridin-2-yl)-4-methylpiperidin-4-yl)picolinamide To a solution of 4-(6-(4-amino-4-methylpiperidin-1-yl)pyridin-3-yl)-6-hydroxypyrazolo[1,5-a]pyridine-3-carbonitrile dihydrochloride (Intermediate P67; 256 mg, 0.608 mmol), 3-Chloropicolinic acid (287 mg, 1.82 mmol), and HATU (294 mg, 1.82 mmol) in DMSO (3 mL) was added DIEA (0.74 mL, 4.25 mmol). The reaction was stirred overnight at ambient temperature. The reaction mixture was diluted with EtOAc (10 mL) and washed with water (10 mL) and 4:1AcOH:water (10 mL) and then extracted with EtOAc. The organic extracts were washed with 4:1 AcOH: Water and then brine. The organic extracts were dried over anhydrous $Na_2SO_{4(s)}$, filtered and concentrated in vacuo. The residue was diluted with THF (4 mL) and 2M NaOH (6 mL). The solution was concentrated in vacuo. The residue was resuspended in DCM (2 mL) and purified by C18 reverse phase chromatography (5-95% ACN in water with 0.1% TFA as the gradient eluent) to afford the title compound as the TFA salt. The TFA salt was resuspended in DCM and passed through a Pl-HCO$_3$ resin to elute the free-based product. The organic eluents were concentrated in vacuo and recrystallized using DCM/Hexanes to afford the title compound (226 mg, 76% yield). MS (apci) m/z=488.2 (M+H).

Intermediate P76

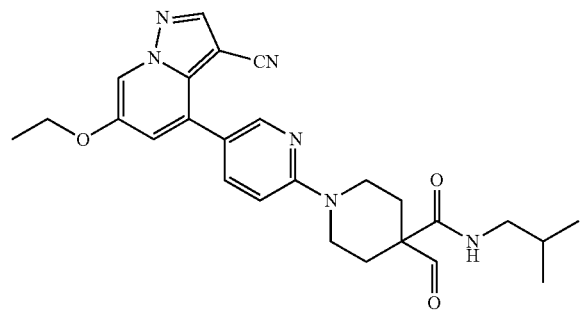 [SMILES: CCOc1cc(-c2ccc(N3CCC(C=O)(C(=O)NCC(C)C)CC3)nc2)c2c(C#N)cnn2c1]

1-(5-(3-cyano-6-ethoxypyrazolo[1,5-a]pyridin-4-yl)
pyridin-2-yl)-4-formyl-N-isobutylpiperidine-4-car-
boxamide Step 1: Preparation of methyl 1-(5-(3-cyano-6-
ethoxypyrazolo[1,5-a]pyridin-4-yl)pyridin-2-yl)-4-
(isobutylcarbamoyl)piperidine-4-carboxylate To a solution of 6-ethoxy-4-(6-fluoropyridin-3-yl)pyrazolo[1,5-a]pyridine-3-carbonitrile (Intermediate P6, 616.0 mg, 2.182 mmol) in DMSO (8.7 mL) was added methyl 4-(isobutylcarbamoyl)piperidine-4-carboxylate (1058 mg, 4.364 mmol) and DIEA (0.7602 mL, 4.364 mmol). The reaction mixture was stirred at 75° C. for 16 h. After cooling to ambient temperature, the reaction mixture was diluted with EtOAc and washed successively with water and saturated $NaCl_{(aq)}$. The organic extract was dried over anhydrous $Na_2SO_{4(s)}$, filtered, and concentrated in vacuo. The residue was purified by silica chromatography (5-95% acetone in DCM as the gradient eluent) to afford the title compound (818.0 mg, 1.621 mmol, 74% yield) in sufficient purity for step 2. MS (apci) m/z=505.3 (M+H).

Step 2: Preparation of 1-(5-(3-cyano-6-ethoxypyra-
zolo[1,5-a]pyridin-4-yl)pyridin-2-yl)-4-(hydroxym-
ethyl)-N-isobutylpiperidine-4-carboxamide To a solution of methyl 1-(5-(3-cyano-6-ethoxypyrazolo [1,5-a]pyridin-4-yl)pyridin-2-yl)-4-(isobutylcarbamoyl)piperidine-4-carboxylate (818.0 mg, 1.621 mmol) in MeOH (16 mL) was added sodium borohydride (98%, 1532 mg, 40.1 mmol). The reaction mixture was stirred at rt for 17 h. The reaction mixture was diluted with DCM and washed with water. The organic extract was dried over anhydrous $Na_2SO_{4(s)}$, filtered, and concentrated in vacuo to afford the title compound (762 mg, 1.599 mmol, 99% yield) in sufficient purity for step 3. MS (apci) m/z=477.3 (M+H).

Step 3: Preparation of 1-(5-(3-cyano-6-ethoxypyra-
zolo[1,5-a]pyridin-4-yl)pyridin-2-yl)-4-formyl-N-
isobutylpiperidine-4-carboxamide A solution of 1-(5-(3-cyano-6-ethoxypyrazolo[1,5-a]pyridin-4-yl)pyridin-2-yl)-4-(hydroxymethyl)-N-isobutylpiperidine-4-carboxamide (762.0 mg, 1.599 mmol) in DCM (16 mL) was treated with 3-oxo-1λ5-benzo[d][1,2]iodaoxole-1,1,1(3H)-triyl triacetate (813.8 mg, 1.919 mmol). The reaction mixture was stirred at rt for 16 h. The crude reaction mixture was concentrated in vacuo, and the residue was directly purified by silica chromatography (5-95% EtOAc in DCM as the gradient eluent) to afford the title compound (555.2 mg, 1.170 mmol, 73.17% yield). MS (apci) m/z=475.2 (M+H).

Intermediate P77

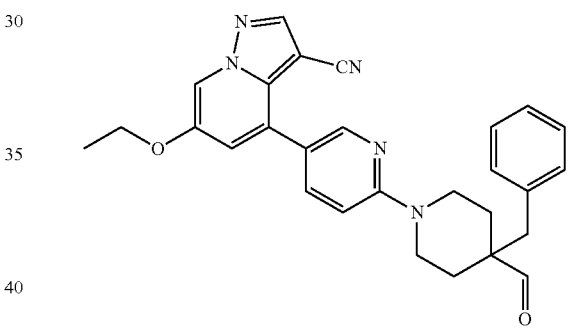

4-(6-(4-benzyl-4-formylpiperidin-1-yl)pyridin-3-yl)-
6-ethoxypyrazolo[1,5-a]pyridine-3-carbonitrile Step 1: Preparation of 4-(6-(4-benzyl-4-(hydroxym-
ethyl)piperidin-1-yl)pyridin-3-yl)-6-ethoxypyrazolo
[1,5-a]pyridine-3-carbonitrile To a solution of 6-ethoxy-4-(6-fluoropyridin-3-yl)pyrazolo[1,5-a]pyridine-3-carbonitrile (Intermediate P6, 100.5 mg, 0.3560 mmol) in DMSO (3 mL) was added (4-benzylpiperidin-4-yl)methanol hydrochloride (151.5 mg, 0.6267 mmol), and cesium carbonate (812.0 mg, 2.492 mmol). The reaction mixture was stirred at 60° C. for 24 h. After cooling to ambient temperature, the reaction mixture was diluted with DCM and washed successively with water and saturated $NH_4Cl_{(aq)}$. The aqueous fractions were extracted with DCM, and the combined organic extracts were dried over anhydrous $Na_2SO_{4(s)}$ then purified by silica chromatography (0-100% EtOAc in hexanes as the gradient eluent) to afford the title compound (118.2 mg, 0.2528 mmol, 71.00% yield) in sufficient purity for step 2. MS (apci) m/z=468.2 (M+H).

Step 2: Preparation of 4-(6-(4-benzyl-4-formylpiperidin-1-yl)pyridin-3-yl)-6-ethoxypyrazolo[1,5-a]pyridine-3-carbonitrile A solution of 4-(6-(4-benzyl-4-(hydroxymethyl)piperidin-1-yl)pyridin-3-yl)-6-ethoxypyrazolo[1,5-a]pyridine-3-carbonitrile (51.3 mg, 0.110 mmol) in DCM (1.5 mL) was treated with 3-oxo-1l5-benzo[d][1,2]iodaoxole-1,1,1(3H)-triyl triacetate (93.1 mg, 0.219 mmol). The reaction mixture was stirred at rt for 1.5 h. The reaction mixture was quenched with saturated NaHCO$_{3(aq)}$ and extracted with DCM. The combined organic extracts were dried over anhydrous Na$_2$SO$_{4(s)}$ and purified by silica chromatography (0-100% EtOAc in hexanes as the gradient eluent) to afford the title compound (46.7 mg, 0.100 mmol, 91.4% yield) in sufficient purity for step 2. MS (apci) m/z=466.3 (M+H).

Intermediate P78

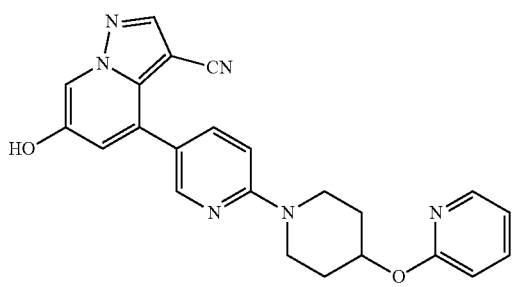 [SMILES: N#Cc1cnn2cc(O)cc(-c3ccc(N4CCC(Oc5ccccn5)CC4)nc3)c12]

6-hydroxy-4-(6-(4-(pyridin-2-yloxy)piperidin-1-yl)pyridin-3-yl)pyrazolo[1,5-a]pyridine-3-carbonitrile

Step 1: Preparation of 2-(4-(pyridin-2-yloxy)piperidin-1-yl)-5-(4,4,5,5-tetramethyl-1,3,2-dioxaborolan-2-yl)pyridine To a solution of 2-Chloropyridine-5-boronic acid, pinacol ester (1.18 g, 4.93 mmol) in DMSO (5.0 mL) was added DIEA (4.29 mL, 24.6 mmol) and 2-(piperidin-4-yloxy)pyridine dihydrochloride (1.55 g, 6.16 mmol). The reaction mixture was stirred at 90° C. for 72 h. After cooling to ambient temperature, the reaction mixture was quenched with water and extracted with EtOAc. The combined organic extracts were successively washed with water and saturated NaCl$_{(aq)}$ then dried over anhydrous Na$_2$SO$_{4(s)}$, filtered, and concentrated in vacuo to afford the title compound (1.19 g, 3.12 mmol, 63.3% yield) in sufficient purity for step 2.

Step 2: Preparation of 6-hydroxy-4-(6-(4-(pyridin-2-yloxy)piperidin-1-yl)pyridin-3-yl)pyrazolo[1,5-a]pyridine-3-carbonitrile A solution of 4-bromo-6-hydroxypyrazolo[1,5-a]pyridine-3-carbonitrile (Intermediate P1, 800.5 mg, 3.363 mmol) in 4:1 dioxane:water (30 mL) was treated with 2-(4-(pyridin-2-yloxy)piperidin-1-yl)-5-(4,4,5,5-tetramethyl-1,3,2-dioxaborolan-2-yl)pyridine (1410.406 mg, 3.699 mmol), tetrakis(triphenylphosphine)palladium (0) (388.6035 mg, 0.3363 mmol), and aqueous potassium carbonate (1394.277 mg, 10.088 mmol). The reaction mixture was sparged with argon and stirred at 90° C. for 16 h. After cooling to ambient temperature, the reaction mixture was quenched with water and adjusted to pH 7 with 4N HCl. The mixture was extracted with 4:1 DCM:IPA, and the combined organic extracts were dried over anhydrous Na$_2$SO$_{4(s)}$, filtered, and concentrated in vacuo. The residue was purified by silica chromatography (5-95% acetone in hexanes as the gradient eluent) to afford the title compound (475.3 mg, 1.152 mmol, 34.3% yield). MS (apci) m/z=413.2 (M+H).

Intermediate P79

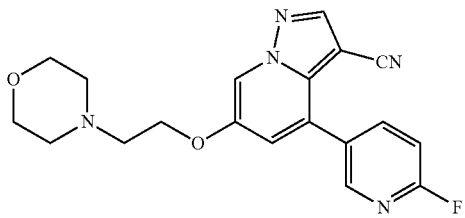 [SMILES: N#Cc1cnn2cc(OCCN3CCOCC3)cc(-c3ccc(F)nc3)c12]

4-(6-fluoropyridin-3-yl)-6-(2-morpholinoethoxy)pyrazolo[1,5-a]pyridine-3-carbonitrile

Step 1: Preparation of 4-bromo-6-(2-morpholinoethoxy)pyrazolo[1,5-a]pyridine-3-carbonitrile A solution of 4-bromo-6-hydroxypyrazolo[1,5-a]pyridine-3-carbonitrile (Intermediate P1, 1000 mg, 4.201 mmol) in DMA (21.005 L) was treated with potassium carbonate (1742 mg, 12.60 mmol) and 4-(2-chloroethyl)morpholine (1.132 mL, 8.402 mmol). The reaction mixture was stirred at 50° C. for 72 h. After cooling to ambient temperature, the reaction mixture was quenched with saturated NaCl$_{(aq)}$. The resultant precipitate was isolated by filtration to afford the title compound (1475 mg, 4.200 mmol, 99% yield) in sufficient purity for step 2. MS (apci) m/z=351 (M$^+$).

Step 2: Preparation of 4-(6-fluoropyridin-3-yl)-6-(2-morpholinoethoxy)pyrazolo[1,5-a]pyridine-3-carbonitrile A solution of 4-bromo-6-(2-morpholinoethoxy)pyrazolo[1,5-a]pyridine-3-carbonitrile (0.83 g, 1.394 mmol) in 1,4-dioxane (1000 mL) was treated with 2-Fluoro-5-(4,4,5,5-tetramethyl-1,3,2-dioxaborolan-2-yl)pyridine (373.2181 mg, 1.673 mmol), tetrakis(triphenylphosphine)palladium (0) (32.22577 mg, 0.0279 mmol), and aqueous potassium carbonate (2.092 mL, 4.183 mmol). The reaction mixture was sparged with argon and stirred at 90° C. for 16 h. After cooling to ambient temperature, the reaction mixture was diluted with MTBE and washed with 1N NaOH. The aqueous fractions were extracted with MTBE then adjusted to pH 4 with 4N HCl. Saturated NaCl$_{(aq)}$ was added and the aqueous mixture was extracted with 4:1 DCM/IPA. The combined organic extracts were dried over anhydrous Na$_2$SO$_{4(s)}$, filtered and concentrated in vacuo to afford the title compound (0.341 g, 0.928 mmol, 66.6% yield). MS (apci) m/z=368.1 (M+H).

Intermediate P80

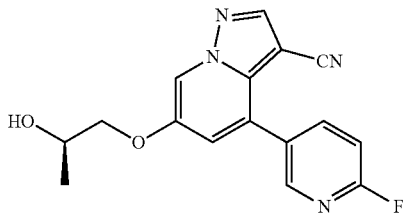 [SMILES: C[C@@H](O)COc1cc(-c2ccc(F)nc2)c2c(C#N)cnn2c1]

(R)-4-(6-fluoropyridin-3-yl)-6-(2-hydroxypropoxy)pyrazolo[1,5-a]pyridine-3-carbonitrile To a solution of 4-(6-fluoropyridin-3-yl)-6-hydroxypyrazolo[1,5-a]pyridine-3-carbonitrile (Intermediate P66, 0.2027 g, 0.78935 mmol) in THF (3.16 mL) was added aqueous sodium hydroxide (2M, 0.40257 mL, 0.80514 mmol) dropwise. The mixture was stirred at rt for 1 h, at which time (R)-2-methyloxirane (0.33181 mL, 4.7361 mmol) was added. The reaction mixture was stirred at 80° C. for 16 h. After cooling to ambient temperature, the pH was adjusted to 5 by addition of a 10% aqueous citric acid solution. The mixture was extracted with EtOAc, then the combined organic extracts were washed successively with water and saturated $NaCl_{(aq)}$ then dried over anhydrous $Na_2SO_{4(s)}$, filtered, and concentrated in vacuo. The residue was purified by silica chromatography (10-90% EtOAc in hexanes as the gradient eluent) to afford the title compound (0.084 g, 0.26897 mmol, 34.074% yield. MS (apci) m/z=313.1 (M+H).

Intermediate P81

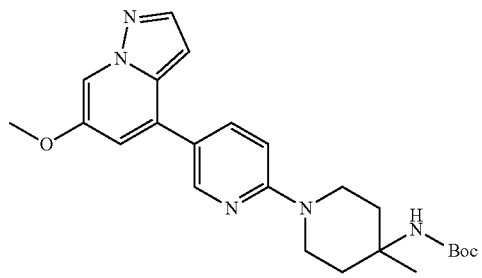 [SMILES: COc1cc(-c2ccc(N3CCC(C)(NC(=O)OC(C)(C)C)CC3)nc2)c2ccnn2c1]

tert-butyl (1-(5-(6-methoxypyrazolo[1,5-a]pyridin-4-yl)pyridin-2-yl)-4-methylpiperidin-4-yl)carbamate

Step 1: Preparation of 4-(6-fluoropyridin-3-yl)-6-methoxypyrazolo[1,5-a]pyridine To a solution of 4-bromo-6-methoxypyrazolo[1,5-a]pyridine (5.122 g, 22.56 mmol) in 1,4-dioxane (45.12 mL) was added 2-fluoro-5-(4,4,5,5-tetramethyl-1,3,2-dioxaborolan-2-yl)pyridine (6.038 g, 27.07 mmol), tetrakis(triphenylphosphine)palladium (0) (1.043 g, 0.9023 mmol), and aqueous sodium carbonate (2M, 23.69 mL, 47.37 mmol). The reaction mixture was stirred at 80° C. for 16 h. After cooling to ambient temperature, the reaction mixture was poured onto water and stirred for 4 h. The resultant precipitate was isolated by vacuum filtration then taken up in MTBE and stirred an additional 30 min. The precipitate was isolated by vacuum filtration to afford the title compound (4.616 g, 18.98 mmol, 84.13% yield) in sufficient purity for step 2. MS (apci) m/z=244.1 (M+H).

Step 2: Preparation of tert-butyl (1-(5-(6-methoxypyrazolo[1,5-a]pyridin-4-yl)pyridin-2-yl)-4-methylpiperidin-4-yl)carbamate To a solution of 4-(6-fluoropyridin-3-yl)-6-methoxypyrazolo[1,5-a]pyridine (2.25 g, 9.25 mmol) in DMSO (18.5 mL) was added tert-butyl (4-methylpiperidin-4-yl)carbamate (2.97 g, 13.9 mmol) and DIEA (4.83 mL, 27.8 mmol). The reaction mixture was stirred at 90° C. for 16 h. After cooling to ambient temperature, the reaction mixture was quenched with water and extracted with EtOAc. The combined organic extracts were washed with saturated $NaCl_{(aq)}$, dried over anhydrous $Na_2SO_{4(s)}$, and concentrated in vacuo. The residue was purified by silica chromatography (10-90% EtOAc in hexanes as the gradient eluent) to afford the title compound (3.8 g, 8.68 mmol, 93.9% yield). MS (apci) m/z=438.3 (M+H).

Intermediate P82

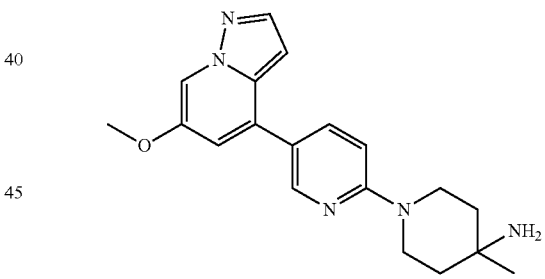

1-(5-(6-methoxypyrazolo[1,5-a]pyridin-4-yl)pyridin-2-yl)-4-methylpiperidin-4-amine A solution of tert-butyl (1-(5-(6-methoxypyrazolo[1,5-a]pyridin-4-yl)pyridin-2-yl)-4-methylpiperidin-4-yl)carbamate (Intermediate P81, 0.500 g, 1.14 mmol) in DCM (5 mL) was treated with TFA (5 mL). The reaction mixture was stirred at rt for 1 h. The reaction mixture was concentrated in vacuo, and the residue was diluted with EtOAc and washed successively with saturated $NaHCO_{3(aq)}$ and saturated $NaCl_{(aq)}$. The organic extract was dried over anhydrous $Na_2SO_{4(s)}$, and concentrated in vacuo to afford the title compound (0.38 g, 1.13 mmol, 98.5% yield). MS (apci) m/z=338.2 (M+H).

Intermediate P83

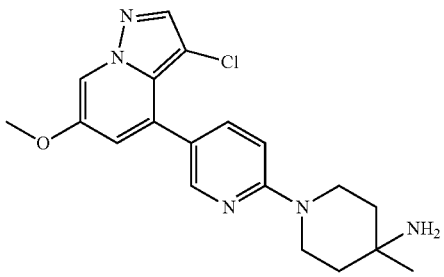 [SMILES: COc1cc(-c2ccc(N3CCC(C)(N)CC3)nc2)c2c(Cl)cnn2c1]

1-(5-(3-chloro-6-methoxypyrazolo[1,5-a]pyridin-4-yl)pyridin-2-yl)-4-methylpiperidin-4-amine

Step 1: Preparation of tert-butyl (1-(5-(3-chloro-6-methoxypyrazolo[1,5-a]pyridin-4-yl)pyridin-2-yl)-4-methylpiperidin-4-yl)carbamate To a solution of tert-butyl (1-(5-(6-methoxypyrazolo[1,5-a]pyridin-4-yl)pyridin-2-yl)-4-methylpiperidin-4-yl)carbamate (Intermediate P81, 0.800 g, 1.83 mmol) in DCM (12.2 mL) was added NCS (0.293 g, 2.19 mmol). The reaction mixture was stirred at rt for 16 h. The reaction mixture was diluted with EtOAc and washed successively with water and saturated NaCl$_{(aq)}$. The organic extract was dried over anhydrous Na$_2$SO$_{4(s)}$, and concentrated in vacuo. The residue was purified by silica chromatography (10-90% EtOAc in hexanes as the gradient eluent) to afford the title compound (0.765 g, 1.62 mmol, 88.6% yield) in sufficient purity for step 2. MS (apci) m/z=472.2 (M+H).

Step 2: Preparation of 1-(5-(3-chloro-6-methoxypyrazolo[1,5-a]pyridin-4-yl)pyridin-2-yl)-4-methylpiperidin-4-amine A solution of tert-butyl (1-(5-(3-chloro-6-methoxypyrazolo[1,5-a]pyridin-4-yl)pyridin-2-yl)-4-methylpiperidin-4-yl)carbamate (0.765 g, 1.62 mmol) in DCM (12 mL) was treated with TFA (12 mL). The reaction mixture was stirred at rt for 1 h. The reaction mixture was diluted with EtOAc and washed successively with saturated NaHCO$_{3(aq)}$ and saturated NaCl$_{(aq)}$. The organic extract was dried over anhydrous Na$_2$SO$_{4(s)}$, and concentrated in vacuo to afford the title compound (0.548 g, 1.47 mmol, 90.9% yield). MS (apci) m/z=372.2 (M+H).

Intermediate P84

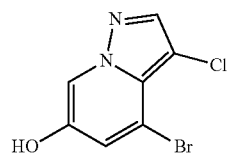 [SMILES: Oc1cc(Br)c2c(Cl)cnn2c1]

4-bromo-3-chloropyrazolo[1,5-a]pyridin-6-ol

Step 1: Preparation of 4-bromo-3-chloro-6-methoxypyrazolo[1,5-a]pyridine

To a solution of 4-bromo-6-methoxypyrazolo[1,5-a]pyridine (15 g, 66.06 mmol) in DCM (100 mL) was added NCS (8.821 g, 66.06 mmol). The reaction mixture was sonicated for 5 min then stirred at rt for 24 h. The reaction mixture was diluted with Et$_2$O, in which it was stirred for 10 min then sonicated for 2 min. The solid precipitate was isolated by vacuum filtration to afford the title compound (18.69 g, 71.47 mmol, 108.2% yield) in sufficient purity for step 2. MS (apci) m/z=263.1 (M+H).

Step 2: Preparation of 4-bromo-3-chloropyrazolo[1,5-a]pyridin-6-ol

A solution of 4-bromo-3-chloro-6-methoxypyrazolo[1,5-a]pyridine (7.59 g, 29.0 mmol) in DCE (290 mL) was sparged with N$_2$ and treated with aluminum trichloride (11.6 g, 87.1 mmol) over the course of 5 min. The reaction mixture was stirred at 76° C. for 16 h. After cooling to ambient temperature, the reaction mixture was quenched with DMA then concentrated in vacuo. The residue was taken up in water and cooled on ice for 30 min. The resultant precipitate was isolated by vacuum filtration then taken up in DMA. The solution was filtered through a plug of silica to afford the title compound as a solution in DMA (assumed quantitative yield, 7.00 g, 28.3 mmol).

Intermediate P85

1-((3-chloro-4-(6-fluoropyridin-3-yl)pyrazolo[1,5-a]pyridin-6-yl)oxy)-2-methylpropan-2-ol

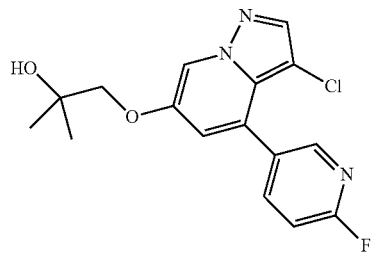 [SMILES: CC(C)(O)COc1cc(-c2ccc(F)nc2)c2c(Cl)cnn2c1]

Step 1: Preparation of 1-((4-bromo-3-chloropyrazolo[1,5-a]pyridin-6-yl)oxy)-2-methylpropan-2-ol To a solution of 4-bromo-3-chloropyrazolo[1,5-a]pyridin-6-ol (Intermediate P84, 4.2 g, 17.0 mmol) in DMA (300 mL) was added potassium carbonate (23.5 g, 170 mmol) and 2,2-dimethyloxirane (14.9 mL, 169.8 mmol). The reaction mixture was stirred at 85° C. for 2 h. After cooling to ambient temperature, the reaction mixture was quenched with 1:1 saturated NH$_4$Cl$_{(aq)}$/water. The solution was extracted with EtOAc. The combined organic extracts were dried over anhydrous Na$_2$SO$_{4(s)}$ and concentrated in vacuo to afford the title compound (2.62 g, 5.74 mmol, 33.8% yield) in sufficient purity for step 2. MS (apci) m/z=321.0 (M+H).

Step 2: Preparation of 1-((3-chloro-4-(6-fluoropyridin-3-yl)pyrazolo[1,5-a]pyridin-6-yl)oxy)-2-methylpropan-2-ol To a solution of 1-((4-bromo-3-chloropyrazolo[1,5-a]pyridin-6-yl)oxy)-2-methylpropan-2-ol (1.44 g, 4.51 mmol) in 1,4-dioxane was added 2-fluoro-5-(4,4,5,5-tetramethyl-1,3,2-dioxaborolan-2-yl)pyridine (1.51 g, 6.76 mmol), tetrakis(triphenylphosphine)palladium(O) (0.260 g, 0.225 mmol), and aqueous sodium carbonate (2M, 50 mL, 100 mmol). The reaction mixture was sparged with $N_2$ and stirred at 90° C. for 16 h. After cooling to ambient temperature, the reaction mixture was quenched with water. The solution was extracted with MTBE, and the combined organic extracts were dried over anhydrous $Na_2SO_{4(s)}$, and concentrated in vacuo. The residue was purified by silica chromatography (0-100% EtOAc in hexanes as the gradient eluent) to afford the title compound (0.37 g, 1.10 mmol, 24.5% yield). MS (apci) m/z=336.1 (M+H).

Intermediate P86

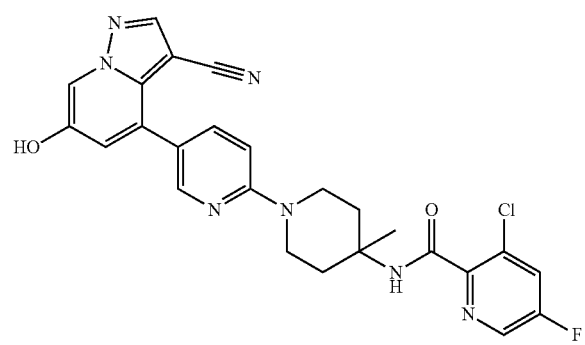 [SMILES: CC1(NC(=O)c2ncc(F)cc2Cl)CCN(c2ccc(-c3cc(O)cn4ncc(C#N)c34)cn2)CC1]

3-chloro-N-(1-(5-(3-cyano-6-hydroxypyrazolo[1,5-a]pyridin-4-yl)pyridin-2-yl)-4-methylpiperidin-4-yl)-5-fluoropicolinamide To a solution of 4-(6-(4-amino-4-methylpiperidin-1-yl)pyridin-3-yl)-6-hydroxypyrazolo[1,5-a]pyridine-3-carbonitrile dihydrochloride (Intermediate P67, 0.253 g, 0.600 mmol) in DCM (3 mL) was added 3-chloro-5-fluoropicolinic acid (0.232 g, 1.32 mmol), HATU (0.502 g, 1.32 mmol), and DIEA (0.524 mL, 3.00 mmol). The reaction mixture was stirred at rt for 30 min. The reaction mixture was diluted with DCM and washed with aqueous citric acid (adjusted to pH 5). The aqueous mixture was extracted with DCM, and the combined organic extracts were washed successively with water and saturated $NaCl_{(aq)}$ then dried over anhydrous $Na_2SO_{4(s)}$ and concentrated in vacuo. The residue was taken up in THF and 2M NaOH and stirred at rt for 5 min. The mixture was diluted with DCM, washed with aqueous citric acid (adjusted to pH 5), and extracted with 4:1 DCM/IPA. The combined organic extracts were washed with saturated $NaCl_{(aq)}$, dried over anhydrous $Na_2SO_{4(s)}$, filtered, and concentrated in vacuo. The residue was purified by C-18 reverse phase chromatography (5-95% ACN in water [+0.1% TFA] as the gradient eluent). The fractions containing the desired product were diluted with 4:1 DCM/IPA and washed successively with saturated $NaHCO_{3(aq)}$ and saturated $NaCl_{(aq)}$. The organic extract was dried over anhydrous $Na_2SO_{4(s)}$, filtered, and concentrated in vacuo to afford the title compound (0.325 g, 0.578 mmol, 96.3% yield). MS (apci) m/z=506.2 (M+H).

Intermediate P87

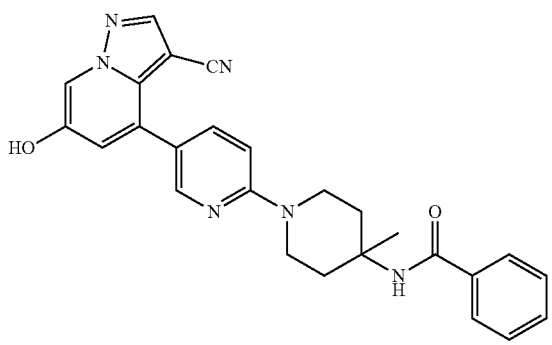 [SMILES: CC1(NC(=O)c2ccccc2)CCN(c2ccc(-c3cc(O)cn4ncc(C#N)c34)cn2)CC1]

N-(1-(5-(3-cyano-6-hydroxypyrazolo[1,5-a]pyridin-4-yl)pyridin-2-yl)-4-methylpiperidin-4-yl)benzamide To a solution of 4-(6-(4-amino-4-methylpiperidin-1-yl)pyridin-3-yl)-6-hydroxypyrazolo[1,5-a]pyridine-3-carbonitrile dihydrochloride (Intermediate P67, 255.4 mg, 0.606 mmol) in DCM (6 mL) was added benzoic acid (185.072 mg, 1.51545 mmol), HATU (576.228 mg, 1.515 mmol), and DIEA (1.056 mL, 6.06 mmol). The reaction mixture was stirred at rt for 16 h then concentrated in vacuo. The residue was taken up in THF and treated with 2M $KOH_{(aq)}$. The mixture was stirred at rt for 1 h then adjusted to pH 4 by addition of 2M HCl. The mixture was diluted with water and extracted with 4:1 DCM/IPA. The combined organic extracts were washed with water then dried over anhydrous $Na_2SO_{4(s)}$, filtered, and concentrated in vacuo. The residue was purified by C-18 reverse phase chromatography (5-95% ACN in water [+0.1% TFA] as the gradient eluent). The fractions containing the desired product were washed with saturated $NaHCO_{3(aq)}$ and extracted with 4:1 DCM/IPA. The combined organic extracts were dried over anhydrous $Na_2SO_{4(s)}$, filtered, and concentrated in vacuo to afford the title compound (172.5 mg, 0.381 mmol, 62.9% yield). MS (apci) m/z=453.2 (M+H).

Intermediate P88

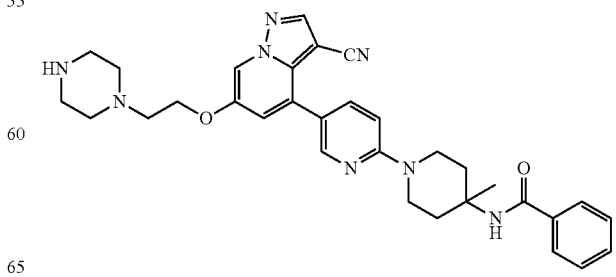

N-(1-(5-(3-cyano-6-(2-(piperazin-1-yl)ethoxy)pyrazolo[1,5-a]pyridin-4-yl)pyridin-2-yl)-4-methylpiperidin-4-yl)benzamide

Step 1: Preparation of tert-butyl 4-(2-((4-(6-(4-benzamido-4-methylpiperidin-1-yl)pyridin-3-yl)-3-cyanopyrazolo[1,5-a]pyridin-6-yl)oxy)ethyl)piperazine-1-carboxylate To a solution of N-(1-(5-(3-cyano-6-hydroxypyrazolo[1,5-a]pyridin-4-yl)pyridin-2-yl)-4-methylpiperidin-4-yl)benzamide (Intermediate P87, 157.2 mg, 0.3474 mmol) in DMA (3.5 mL) was added tert-Butyl 4-(2-chloroethyl)tetrahydro-1(2H)-pyrazinecarboxylate (172.8 mg, 0.6948 mmol) and cesium carbonate (565.9 mg, 1.737 mmol). The reaction mixture was stirred at 60° C. for 16 h. After cooling to ambient temperature, the reaction mixture was diluted with EtOAc and washed successively with water and saturated NaCl$_{(aq)}$. The combined organic extracts were dried over anhydrous Na$_2$SO$_{4(s)}$, filtered, and concentrated in vacuo to afford the title compound (assumed theoretical yield, 231 mg, 0.3474 mmol) in sufficient purity for step 2. MS (apci) m/z=665.4 (M+H).

Step 2: Preparation of N-(1-(5-(3-cyano-6-(2-(piperazin-1-yl)ethoxy)pyrazolo[1,5-a]pyridin-4-yl)pyridin-2-yl)-4-methylpiperidin-4-yl)benzamide A solution of tert-butyl 4-(2-((4-(6-(4-benzamido-4-methylpiperidin-1-yl)pyridin-3-yl)-3-cyanopyrazolo[1,5-a]pyridin-6-yl)oxy)ethyl)piperazine-1-carboxylate in DCM (1.75 mL) was treated with TFA (1.75 mL, 22.9 mmol). The reaction mixture was stirred at rt for 30 min then concentrated in vacuo. The residue was directly purified by C-18 reverse phase chromatography (5-95% ACN in water (+0.1% TFA) as the gradient eluent). The fractions containing the desired product were washed with saturated NaHCO$_{3(aq)}$ and extracted with 4:1 DCM/IPA. The combined organic extracts were dried over anhydrous Na$_2$SO$_{4(s)}$, filtered, and concentrated in vacuo to afford the title compound (111.8 mg, 0.1980 mmol, 56.99% yield over two steps). MS (apci) m/z=565.3

Intermediate P89

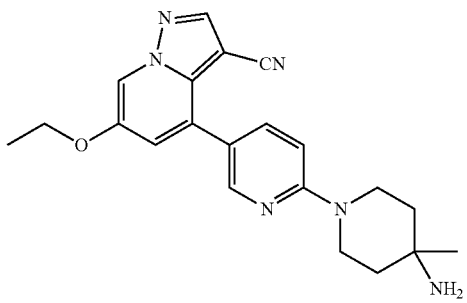 [SMILES: CCOc1cc(-c2ccc(N3CCC(C)(N)CC3)nc2)c2c(C#N)cnn2c1]

4-(6-(4-amino-4-methylpiperidin-1-yl)pyridin-3-yl)-6-ethoxypyrazolo[1,5-a]pyridine-3-carbonitrile A solution of tert-butyl (1-(5-(3-cyano-6-ethoxypyrazolo[1,5-a]pyridin-4-yl)pyridin-2-yl)-4-methylpiperidin-4-yl)carbamate (Example 469, 100 mg, 0.210 mmol) in DCM (2 mL) was treated with TFA (2 mL). The reaction mixture was stirred at rt for 1 h. The crude reaction mixture was directly purified by silica chromatography (5-50% [MeOH+2% NH$_4$OH] in DCM as the gradient eluent) to afford the title compound (20 mg, 0.0531 mmol, 25.3% yield). MS (apci) m/z=377.2 (M+H).

Intermediate P90

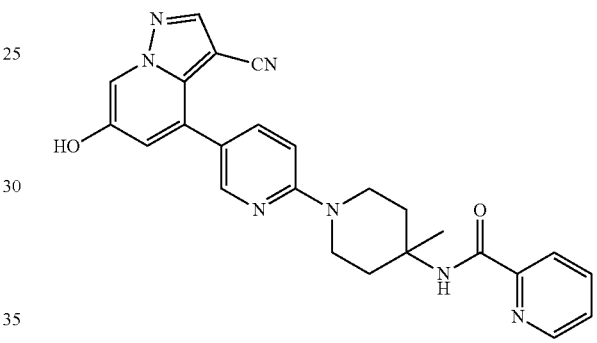

N-(1-(5-(3-cyano-6-hydroxypyrazolo[1,5-a]pyridin-4-yl)pyridin-2-yl)-4-methylpiperidin-4-yl)picolinamide To a solution of 4-(6-(4-amino-4-methylpiperidin-1-yl)pyridin-3-yl)-6-hydroxypyrazolo[1,5-a]pyridine-3-carbonitrile dihydrochloride (Intermediate P67, 1.38 g, 3.2754 mmol) in DCM (6.5507 mL) was added 2-Picolinic acid (1.0081 g, 8.1884 mmol), HATU (3.1135 g, 8.1884 mmol), and DIEA (5.7207 mL, 32.754 mmol). The reaction mixture was stirred at rt for 1 h then concentrated in vacuo. The residue was taken up in THF and 2M aqueous KOH and stirred at rt for 30 min. The mixture was adjusted to pH 4 by addition of 1M HCl and extracted with 4:1 DCM/IPA. The combined organic extracts were washed successively with water and saturated NaCl$_{(aq)}$ then dried over anhydrous Na$_2$SO$_{4(s)}$, filtered, and concentrated in vacuo. The residue was purified by C-18 reverse phase chromatography (5-95% ACN in water (+0.1% TFA) as the gradient eluent). The fractions containing the desired product were diluted with 4:1 DCM/IPA and washed successively with saturated NaHCO$_{3(aq)}$ and saturated NaCl$_{(aq)}$. The organic extract was dried over anhydrous Na$_2$SO$_{4(s)}$, filtered, and concentrated in vacuo to afford the title compound (737 mg, 1.6251 mmol, 49.616% yield). MS (apci) m/z=454.2 (M+H).

Intermediate P91

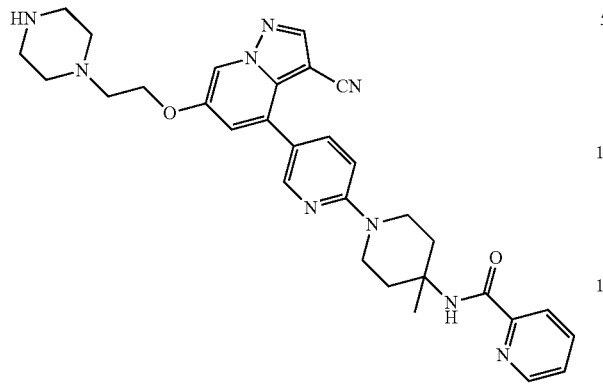

N-(1-(5-(3-cyano-6-(2-(piperazin-1-yl)ethoxy)pyrazolo[1,5-a]pyridin-4-yl)pyridin-2-yl)-4-methylpiperidin-4-yl)picolinamide

Step 1: Preparation of tert-butyl 4-(2-((3-cyano-4-(6-(4-methyl-4-(picolinamido)piperidin-1-yl)pyridin-3-yl)pyrazolo[1,5-a]pyridin-6-yl)oxy)ethyl)piperazine-1-carboxylate To a solution of N-(1-(5-(3-cyano-6-hydroxypyrazolo[1,5-a]pyridin-4-yl)pyridin-2-yl)-4-methylpiperidin-4-yl)picolinamide (Intermediate P90, 120 mg, 0.265 mmol) in DMA (2.646 mL) was added tert-Butyl 4-(2-chloroethyl)tetrahydro-1(2H)-pyrazinecarboxylate (65.8 mg, 0.265 mmol) and cesium carbonate (431 mg, 1.32 mmol). The reaction mixture was stirred at 60° C. for 48 h. After cooling to ambient temperature, the reaction mixture was diluted with 4:1 DCM/IPA and washed successively with saturated NaHCO$_{3(aq)}$ and saturated NaCl$_{(aq)}$. The organic extract was dried over anhydrous Na$_2$SO$_{4(s)}$, filtered, and concentrated in vacuo to afford the title compound (176 mg, 0.264 mmol, 99.9% yield) in sufficient purity for step 2. MS (apci) m/z=666.4 (M+H).

Step 2: Preparation of N-(1-(5-(3-cyano-6-(2-(piperazin-1-yl)ethoxy)pyrazolo[1,5-a]pyridin-4-yl)pyridin-2-yl)-4-methylpiperidin-4-yl)picolinamide A solution of tert-butyl 4-(2-((3-cyano-4-(6-(4-methyl-4-(picolinamido)piperidin-1-yl)pyridin-3-yl)pyrazolo[1,5-a]pyridin-6-yl)oxy)ethyl)piperazine-1-carboxylate (176 mg, 0.264 mmol) in DCM (2.643 mL) was treated with TFA (0.2 mL). The reaction mixture was stirred at rt for 1 h. The reaction mixture was diluted with 4:1 DCM/IPA and washed successively with saturated NaHCO$_{3(aq)}$, water, and saturated NaCl$_{(aq)}$. The organic extract was dried over anhydrous Na$_2$SO$_{4(s)}$, filtered, and concentrated in vacuo to afford the title compound (assumed theoretical yield, 150 mg, 0.264 mmol). MS (apci) m/z=566.4 (M+H).

Intermediate P92

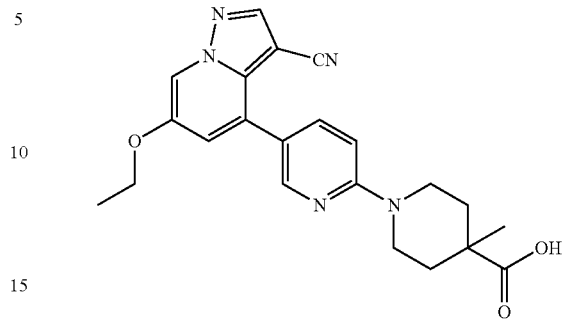

1-(5-(3-cyano-6-ethoxypyrazolo[1,5-a]pyridin-4-yl)pyridin-2-yl)-4-methylpiperidine-4-carboxylic acid

Step 1: Preparation of methyl 1-(5-(3-cyano-6-ethoxypyrazolo[1,5-a]pyridin-4-yl)pyridin-2-yl)-4-methylpiperidine-4-carboxylate To a solution of 6-ethoxy-4-(6-fluoropyridin-3-yl)pyrazolo[1,5-a]pyridine-3-carbonitrile (Intermediate P6, 0.9974 g, 3.533 mmol) in DMA (14.13 mL) was added methyl 4-methylpiperidine-4-carboxylate (1.666 g, 10.6 mmol) and TEA (2.396 mL, 17.67 mmol). The reaction mixture was stirred at 80° C. for 16 h. After cooling to ambient temperature, the reaction mixture was diluted with EtOAc and washed successively with water and brine. The aqueous fractions were extracted with 4:1 DCM/IPA. The combined organic extracts were concentrated in vacuo, and the residue was taken up in EtOAc and washed successively with water and brine. The organic extract was dried over anhydrous Na$_2$SO$_{4(s)}$, filtered, and concentrated in vacuo. The residue was purified by silica chromatography (5-95% EtOAc in hexanes as the gradient eluent) to afford the title compound (436.4 mg, 1.040 mmol, 29.44%) in sufficient purity for step 2. MS (apci) m/z=420.2 (M+H).

Step 2: Preparation of 1-(5-(3-cyano-6-ethoxypyrazolo[1,5-a]pyridin-4-yl)pyridin-2-yl)-4-methylpiperidine-4-carboxylic acid A mixture of methyl 1-(5-(3-cyano-6-ethoxypyrazolo[1,5-a]pyridin-4-yl)pyridin-2-yl)-4-methylpiperidine-4-carboxylate (776.5 mg, 1.851 mmol) in 1:1 THF/MeOH (37 mL) was treated with KOH (aq. 2M) (3.7 mL, 7.4 mmol). After stirred at rt for 80 h, the reaction mixture was diluted with 1N NaOH and washed successively with MTBE and DCM. After phase-separation, the aqueous layer was acidified to ca. pH 5 and extracted with 4:1 DCM/IPA. The combined organic extracts were dried over anhydrous Na$_2$SO$_{4(s)}$, filtered, and concentrated in vacuo to afford the title compound (470.4 mg, 1.160 mmol, 62.68% yield). MS (apci) m/z=406.2 (M+H).

Intermediate P93

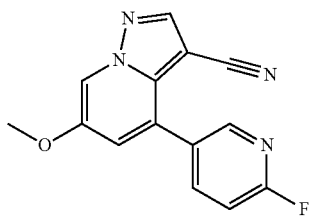 [SMILES: COc1cc(-c2ccc(F)nc2)c2c(C#N)cnn2c1]

4-(6-fluoropyridin-3-yl)-6-methoxypyrazolo[1,5-a]pyridine-3-carbonitrile

In a pressure tube, a mixture of 4-bromo-6-methoxypyrazolo[1,5-a]pyridine-3-carbonitrile (Intermediate P1, Step 6; 1.1854 g, 4.7026 mmol), 2-fluoro-5-(4,4,5,5-tetramethyl-1,3,2-dioxaborolan-2-yl)pyridine (1.2587 g, 5.6432 mmol), Pd(PPh$_3$)$_4$ (0.1087 g, 0.094 mmol) and 2 M Na$_2$CO$_{3(aq)}$ (15 mL, 30 mmol) in dioxane (15 mL) was sparged with N$_{2(g)}$. The vessel was sealed, and the sparged mixture was stirred for 4 d at 60° C. After cooling to ambient temperature, the reaction mixture was quenched with water. The resultant precipitate was filtered, washed with water, and then purified by silica chromatography (0-25% MeOH in DCM) to afford the title compound (734.6 mg, 58% yield). MS (apci), m/z=269.1 (M+H).

Intermediate P94

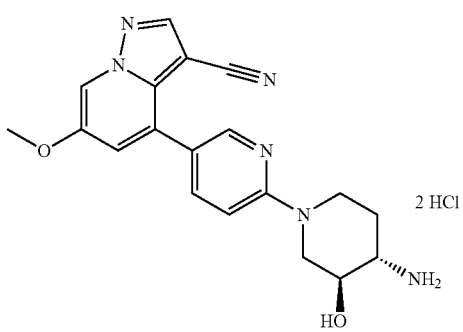 [SMILES: COc1cc(-c2ccc(N3CC[C@H](N)[C@@H](O)C3)nc2)c2c(C#N)cnn2c1]

4-(6-((3S,4S)-4-amino-3-hydroxypiperidin-1-yl)pyridin-3-yl)-6-methoxypyrazolo[1,5-a]pyridine-3-carbonitrile dihydrochloride A solution of tert-butyl ((3S,4S)-1-(5-(3-cyano-6-methoxypyrazolo[1,5-a]pyridin-4-yl)pyridin-2-yl)-3-hydroxypiperidin-4-yl)carbamate (Example 514, 274.5 mg, 0.5909 mmol) in dioxane (3 mL) was treated with 37% HCl (97 L, 1.18 mmol), then stirred overnight at ambient temperature. The resulting mixture was concentrated in vacuo to afford the title compound (258 mg, 100% yield). MS (apci) m/z=365.2 (M+H).

Intermediate P95

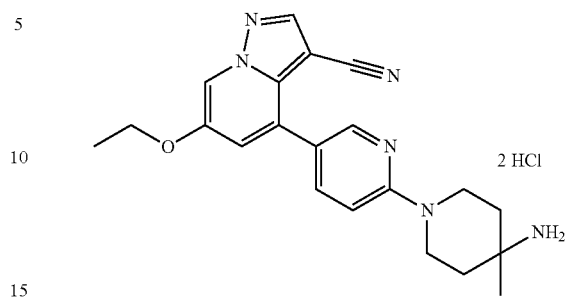

4-(6-(4-amino-4-methylpiperidin-1-yl)pyridin-3-yl)-6-ethoxypyrazolo[1,5-a]pyridine-3-carbonitrile dihydrochloride A stirring, ambient temperature, solution of tert-butyl (1-(5-(3-cyano-6-ethoxypyrazolo[1,5-a]pyridin-4-yl)pyridin-2-yl)-4-methylpiperidin-4-yl)carbamate (Example 469, 807 mg, 1.69 mmol) in MeOH (3387 μL) was treated dropwise with 12 M HCl$_{(aq)}$ (1.41 mL, 16.9 mmol). The resulting mixture was stirred overnight at ambient temperature. The resulting thick slurry was diluted with MeOH (ca. 1 mL), and vacuum filtered. The solids were rinsed with MeOH (3×1 mL) and MTBE (3×10 mL), then dried in vacuo to afford the title compound (690 mg, 91% yield). MS (apci) m/z=377.2 (M+H).

Intermediate P96

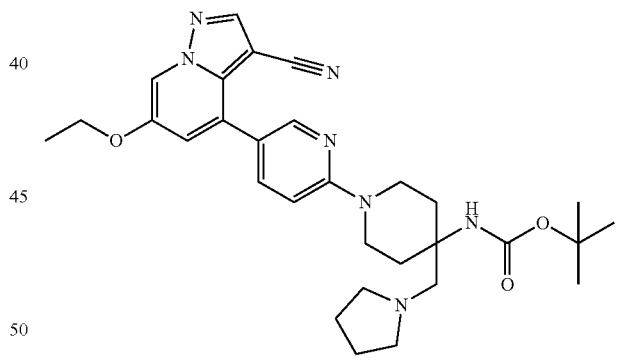

Tert-butyl (1-(5-(3-cyano-6-ethoxypyrazolo[1,5-a]pyridin-4-yl)pyridin-2-yl)-4-(pyrrolidin-1-ylmethyl)piperidin-4-yl)carbamate Tert-Butyl (1-(5-(3-cyano-6-ethoxypyrazolo[1,5-a]pyridin-4-yl)pyridin-2-yl)-4-formylpiperidin-4-yl)carbamate (Intermediate P71, 100 mg, 0.2038 mmol) was added to solution of pyrrolidine (681 μL, 0.82 mmol) and TEA (142 μL, 1.0 mmol) in DCM (1.0 mL), and the mixture was stirred for 1 h at ambient temperature. Subsequently, NaBH(AcO)$_3$ (86.4 mg, 0.41 mmol) was added, and the resulting mixture was stirred for 2.5 h at ambient temperature then concentrated in vacuo. The residue was purified by C18 reverse phase chromatography (5-95% ACN:water with 0.1% TFA).

Fractions containing the desired product were combined, diluted with 4:1 DCM:iPrOH, then sequentially extracted with saturated NaHCO$_{3(aq)}$, water and brine. The organic extracts were dried over anhydrous Na$_2$SO$_{4(s)}$, filtered, and concentrated in vacuo to cleanly afford the title compound (40 mg, 36% yield). MS (apci) m/z=546.3 (M+H).

Intermediate P97

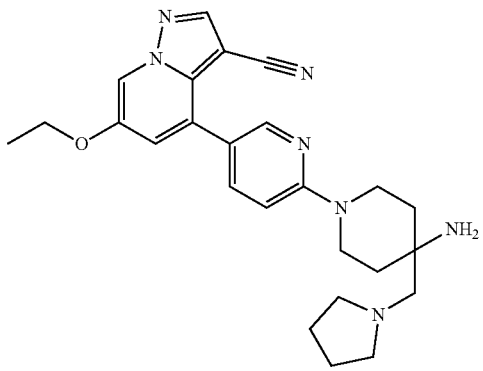 [SMILES: CCOc1cc(-c2ccc(N3CCC(N)(CN4CCCC4)CC3)nc2)c2c(C#N)cnn2c1]

4-(6-(4-amino-4-(pyrrolidin-1-ylmethyl)piperidin-1-yl)pyridin-3-yl)-6-ethoxypyrazolo[1,5-a]pyridine-3-carbonitrile A solution of tert-butyl (1-(5-(3-cyano-6-ethoxypyrazolo[1,5-a]pyridin-4-yl)pyridin-2-yl)-4-(pyrrolidin-1-ylmethyl)piperidin-4-yl)carbamate (Intermediate P96; 40 mg, 0.073 mmol) in DCE (4.7 µL) and TFA (5.6 µL, 0.073 mmol) was stirred for 90 min at ambient temperature. The resulting mixture was diluted with 4:1 DCM:iPrOH, then sequentially extracted with saturated NaHCO$_{3(aq)}$, water and brine. The organic extracts were dried over anhydrous Na$_2$SO$_{4(s)}$, filtered, and concentrated in vacuo to cleanly afford the title compound (30 mg, 92% yield). MS (apci) m/z=446.3 (M+H).

Intermediate P98

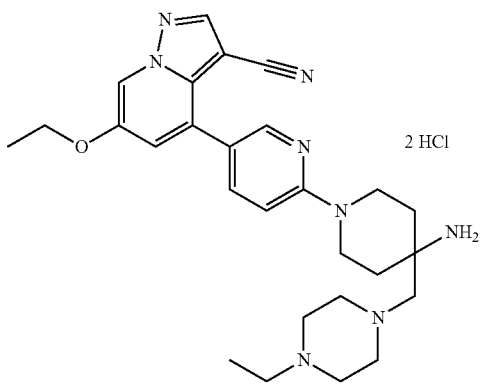 [SMILES: CCOc1cc(-c2ccc(N3CCC(N)(CN4CCN(CC)CC4)CC3)nc2)c2c(C#N)cnn2c1]

4-(6-(4-amino-4-((4-ethylpiperazin-1-yl)methyl)piperidin-1-yl)pyridin-3-yl)-6-ethoxypyrazolo[1,5-a]pyridine-3-carbonitrile dihydrochloride A solution of tert-butyl (1-(5-(3-cyano-6-ethoxypyrazolo[1,5-a]pyridin-4-yl)pyridin-2-yl)-4-((4-ethylpiperazin-1-yl)methyl)piperidin-4-yl)carbamate (Example 379, 171.2 mg, 0.2908 mmol) in dioxane (5.0 mL) was treated with 12 M HCl$_{(aq)}$ (23.88 L, 0.2908 mmol). The resulting mixture was stirred for 45 min at ambient temperature before concentrating the mixture in vacuo to cleanly afford the title compound (205.5 mg, quantitative yield). MS (apci) m/z=489.3 (M+H).

Intermediate P99

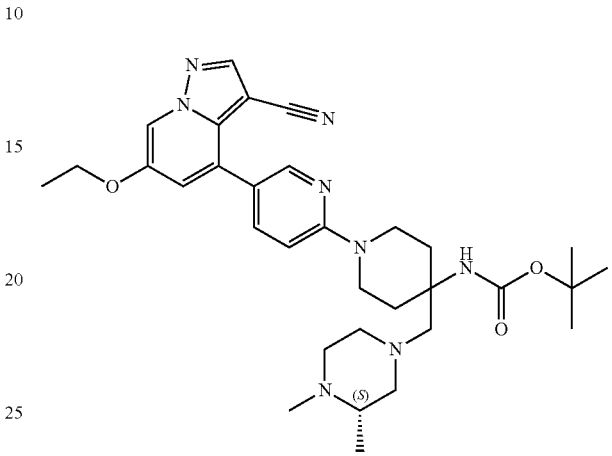

tert-butyl (S)-(1-(5-(3-cyano-6-ethoxypyrazolo[1,5-a]pyridin-4-yl)pyridin-2-yl)-4-((3,4-dimethylpiperazin-1-yl)methyl)piperidin-4-yl)carbamate A solution of tert-butyl (1-(5-(3-cyano-6-ethoxypyrazolo[1,5-a]pyridin-4-yl)pyridin-2-yl)-4-formylpiperidin-4-yl)carbamate (Intermediate P71, 278 mg, 0.567 mmol) and (S)-1,2-dimethylpiperazine (Intermediate P93; 270 mg, 2.36 mmol) in DCE (5 mL) was stirred for 30 min at ambient temperature before adding NaBH(AcO)$_3$ (480.4 mg, 2.267 mmol). The resulting mixture was stirred overnight at ambient temperature, then concentrated in vacuo. The residue was suspended in 4:1 DCM:iPrOH, and extracted sequentially with saturated NaHCO$_{3(aq)}$ (2×) and brine. The organic extracts were dried over anhydrous Na$_2$SO$_{4(s)}$, filtered and concentrated in vacuo. The residue was purified by silica chromatography (using 0-15% [MeOH with 1% NH$_4$OH] in DCM as the gradient eluent) to cleanly afford the title compound (133 mg, 40% yield). MS (apci) m/z=589.3 (M+H).

Intermediate P100

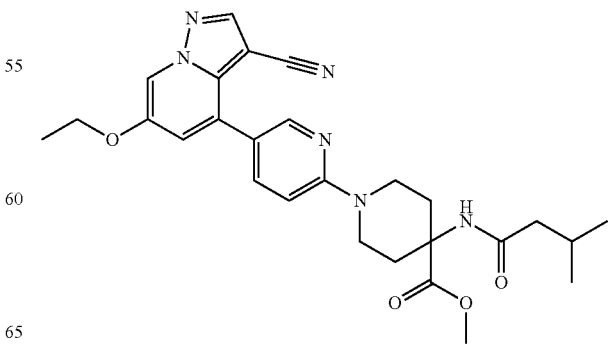

methyl 1-(5-(3-cyano-6-ethoxypyrazolo[1,5-a]pyridin-4-yl)pyridin-2-yl)-4-(3-methylbutanamido)piperidine-4-carboxylate A solution of methyl 4-amino-1-(5-(3-cyano-6-ethoxypyrazolo[1,5-a]pyridin-4-yl)pyridin-2-yl)piperidine-4-carboxylate (Step 1, Intermediate P70, 500 mg, 1.19 mmol) in DCM (5 mL) was treated with DIEA (415.4 µL, 2.378 mmol), then stirred for 10 min at 0° C. The cold solution was treated dropwise with isovaleryl chloride (174 µL, 1.43 mmol). The resulting mixture was stirred for 1 h at 0° C. The mixture was diluted with 4:1 DCM:iPrOH, and extracted with saturated NaHCO$_{3(aq)}$ (2×). After back extracting the aqueous extracts with DCM, all organic extracts were combined, dried over anhydrous Na$_2$SO$_{4(s)}$, filtered, and concentrated in vacuo to cleanly afford the title compound (943.9 mg, 79% yield). MS (apci) m/z=505.2 (M+H).

Intermediate P101

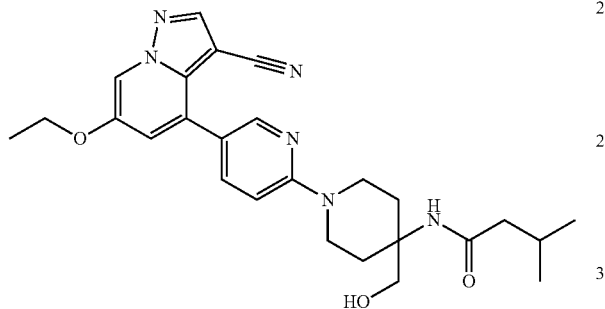

N-(1-(5-(3-cyano-6-ethoxypyrazolo[1,5-a]pyridin-4-yl)pyridin-2-yl)-4-(hydroxymethyl)piperidin-4-yl)-3-methylbutanamide A solution of methyl 1-(5-(3-cyano-6-ethoxypyrazolo[1,5-a]pyridin-4-yl)pyridin-2-yl)-4-(3-methylbutanamido)piperidine-4-carboxylate (Intermediate P93; 476.3 mg, 0.9439 mmol) in THF (5 mL) was stirred for 20 min at 0° C. The cold solution was treated with LiBH$_4$ (82.24 mg, 3.776 mmol). The resulting mixture was stirred overnight at ambient temperature, then concentrated in vacuo. The residue was dissolved in EtOAc, and extracted with brine (3×). After back extracting the aqueous extracts with EtOAc, the organic extracts were combined, dried over anhydrous Na$_2$SO$_{4(s)}$, filtered, and concentrated in vacuo. The crude product was purified by silica chromatography (using 40-100% EtOAc in Hexanes as the gradient eluent) to cleanly afford the title compound (95.7 mg, 21% yield). MS (apci) m/z=477.25 (M+H).

Intermediate P102

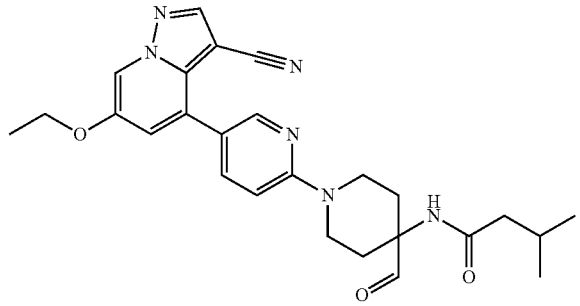 [SMILES: CCOc1cc(-c2ccc(N3CCC(C=O)(NC(=O)CC(C)C)CC3)nc2)c2c(C#N)cnn2c1]

N-(1-(5-(3-cyano-6-ethoxypyrazolo[1,5-a]pyridin-4-yl)pyridin-2-yl)-4-formylpiperidin-4-yl)-3-methylbutanamide A solution of N-(1-(5-(3-cyano-6-ethoxypyrazolo[1,5-a]pyridin-4-yl)pyridin-2-yl)-4-(hydroxymethyl)piperidin-4-yl)-3-methylbutanamide (Intermediate P101; 95.7 mg, 0.201 mmol) in DCM (2 mL) was treated with DMP (170 mg, 0.402 mmol). The resulting mixture was stirred for 1.5 h at ambient temperature. The reaction mixture was diluted with DCM, and extracted with saturated NaHCO$_{3(aq)}$. After back extracting the aqueous extracts with DCM, the organic extracts were combined, dried over anhydrous Na$_2$SO$_{4(s)}$, and filtered. The filtrate was purified directly by silica chromatography (using 20-80% EtOAc in Hexanes as the gradient eluent) to cleanly afford the title compound (41.0 mg, 43% yield). MS (apci) m/z=475.2 (M+H).

Intermediate P103

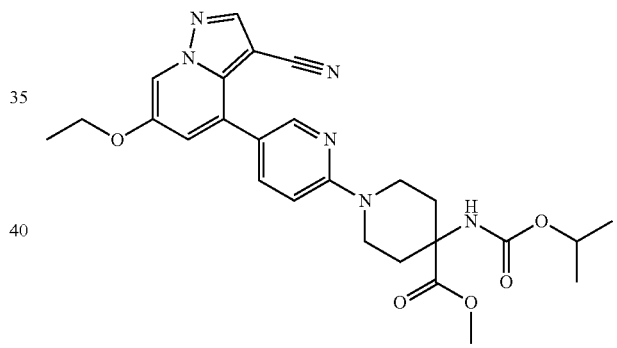

methyl 1-(5-(3-cyano-6-ethoxypyrazolo[1,5-a]pyridin-4-yl)pyridin-2-yl)-4-((isopropoxycarbonyl)amino)piperidine-4-carboxylate A solution of methyl 4-amino-1-(5-(3-cyano-6-ethoxypyrazolo[1,5-a]pyridin-4-yl)pyridin-2-yl)piperidine-4-carboxylate (step 1, Intermediate P70, 334.8 mg, 0.7962 mmol) in DCM (51.23 µL) was treated with DIEA (278.1 µL, 1.592 mmol), then stirred for 10 min at 0° C. The cold solution was treated dropwise with isopropyl carbonochloridate (955.5 µL, 0.9555 mmol). The resulting mixture was stirred for 40 min at 0° C., then overnight at ambient temperature. The mixture was purified directly by silica chromatography (using 30-70% EtOAc in Hexanes as the gradient eluent) to cleanly afford the title compound (323.5 mg, 80% yield). MS (apci) m/z=507.15 (M+H).

Intermediate P104

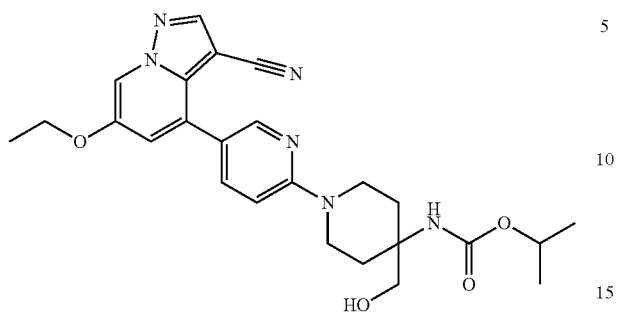

isopropyl (1-(5-(3-cyano-6-ethoxypyrazolo[1,5-a]
pyridin-4-yl)pyridin-2-yl)-4-(hydroxymethyl)piperi-
din-4-yl)carbamate A solution of methyl 1-(5-(3-cyano-6-ethoxypyrazolo[1,
5-a]pyridin-4-yl)pyridin-2-yl)-4-((isopropoxycarbonyl)
amino)piperidine-4-carboxylate (Intermediate P103; 323.5 mg, 0.6386 mmol) in THF (3 mL) was stirred for 20 min at 0° C. The cold solution was treated with LiBH$_4$ (55.64 mg, 2.554 mmol). The resulting mixture was stirred overnight at ambient temperature, then concentrated in vacuo. The residue was dissolved in DCM, and extracted with brine. The organic extracts were purified directly by silica chromatography (using 30-100% EtOAc in Hexanes as the gradient eluent) to cleanly afford the title compound (171.7 mg, 56% yield). MS (apci) m/z=479.2 (M+H).

Intermediate P105

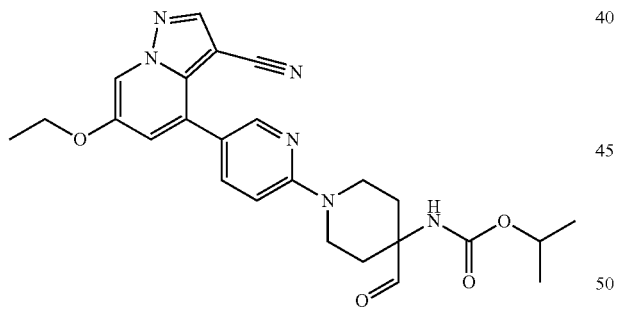

isopropyl (1-(5-(3-cyano-6-ethoxypyrazolo[1,5-a]
pyridin-4-yl)pyridin-2-yl)-4-formylpiperidin-4-yl)
carbamate A solution of isopropyl (1-(5-(3-cyano-6-ethoxypyrazolo
[1,5-a]pyridin-4-yl)pyridin-2-yl)-4-(hydroxymethyl)piperi-
din-4-yl)carbamate (Intermediate P104; 171 mg, 0.357 mmol) in DCM (1 mL) was treated with DMP (303.1 mg, 0.7147 mmol). The resulting mixture was stirred overnight at ambient temperature. The reaction mixture was diluted with DCM, and extracted sequentially with water and brine. After back extracting the aqueous extracts with DCM, the organic extracts were combined, dried over anhydrous Na$_2$SO$_{4(s)}$, and filtered. The filtrate was purified directly by silica chromatography (using 20-80% EtOAc in Hexanes as the gradient eluent) to cleanly afford the title compound (167.4 mg, 98% yield). MS (apci) m/z=477.2 (M+H).

Intermediate P106

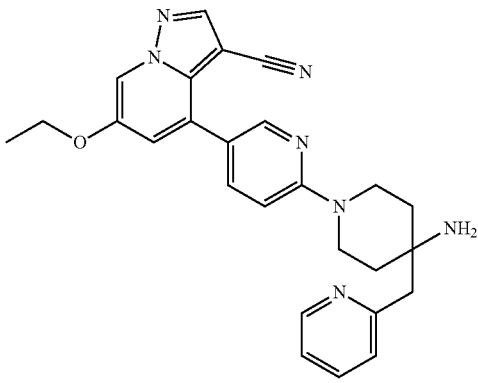 [SMILES: CCOc1cc(-c2ccc(N3CCC(N)(Cc4ccccn4)CC3)nc2)c2c(C#N)cnn2c1]

4-(6-(4-amino-4-(pyridin-2-ylmethyl)piperidin-1-yl)
pyridin-3-yl)-6-ethoxypyrazolo[1,5-a]pyridine-3-
carbonitrile A solution of 4-(pyridin-2-ylmethyl)piperidin-4-amine bis(2,2,2-trifluoroacetate) (Intermediate R41; 287.5 mg, 0.6856 mmol) in DMF (2 mL) was treated with 6-ethoxy-4-(6-fluoropyridin-3-yl)pyrazolo[1,5-a]pyridine-3-carbonitrile (Intermediate P6, 176 mg, 0.624 mmol), K$_2$CO$_{3(s)}$ (431 mg, 3.12 mmol) was stirred overnight at 70° C. The mixture was cooled to ambient temperature, diluted with water (50 mL) and extracted with DCM (3×20 mL). The organic extracts were dried over anhydrous Na$_2$SO$_{4(s)}$, filtered, and concentrated in vacuo. The crude residue was purified by silica chromatography (0-15% MeOH in DCM) to afford the title compound (73 mg, 26% yield). MS (apci) m/z=454 (M+H).

Intermediate P107

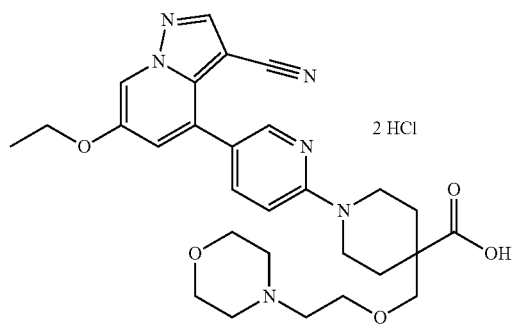 [SMILES: CCOc1cc(-c2ccc(N3CCC(COCCN4CCOCC4)(C(=O)O)CC3)nc2)c2c(C#N)cnn2c1]

1-(5-(3-cyano-6-ethoxypyrazolo[1,5-a]pyridin-4-yl)
pyridin-2-yl)-4-((2-morpholinoethoxy)methyl)piperi-
dine-4-carboxylic acid dihydrochloride A solution of 1-(5-(3-cyano-6-ethoxypyrazolo[1,5-a]pyri-
din-4-yl)pyridin-2-yl)-4-(hydroxymethyl)piperidine-4-carboxylic acid (Intermediate P156; 30 mg, 0.071 mmol) in DMF (1 mL) was treated with NaH (60 wt. % in mineral oil; 8.5 mg, 0.21 mmol). The suspension was stirred for 5 min at 50° C., then treated with 4-(2-chloroethyl)morpholine (32 mg, 0.21 mmol). The resulting mixture was stirred for 15 h at 50° C. before introducing additional NaH (2 equivalents) and 4-(2-chloroethyl)morpholine (3 equivalents). The mixture was stirred for 4 h at 70° C. After cooling to ambient temperature, the mixture was concentrated in vacuo, and diluted with MeOH (2 mL). The methanolic mixture was treated with 2 M NaOH$_{(aq)}$ (2 mL), and stirred for 15 h at 50° C. After cooling to ambient temperature, the reaction mixture was concentrated in vacuo, and purified by C18 reverse phase chromatography (5-95% acetonitrile/water). Fractions containing the desired product were combined, concentrated in vacuo, and then treated with 4 M HCl in dioxane. The HCl mixture was concentrated in vacuo to afford the title compound (25 mg, 58% yield). MS (apci) m/z=535.2 (M+H).

Intermediate P108

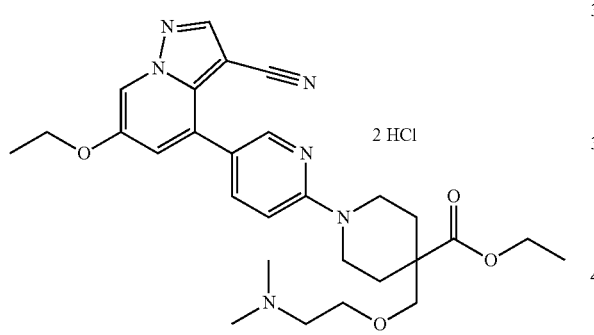

Ethyl 1-(5-(3-cyano-6-ethoxypyrazolo[1,5-a]pyridin-4-yl)pyridin-2-yl)-4-((2-(dimethylamino)ethoxy)methyl)piperidine-4-carboxylate dihydrochloride A solution of ethyl 1-(5-(3-cyano-6-ethoxypyrazolo[1,5-a]pyridin-4-yl)pyridin-2-yl)-4-(hydroxymethyl)piperidine-4-carboxylate (Example 701; 30 mg, 0.067 mmol) in DMF (1 mL) was treated with NaH (60 wt. % in mineral oil; 21 mg, 0.53 mmol). The suspension was stirred for 5 min at 50° C., then treated with 2-chloro-N,N-dimethylethane-1-amine hydrochloride (38 mg, 0.27 mmol). The resulting mixture was stirred for 1 h at ambient temperature then for 15 h at 50° C. After cooling to ambient temperature, the mixture was diluted with water and extracted with DCM. The organic extracts were purified by C18 reverse phase chromatography (5-95% ACN:water with 0.1% TFA). Fractions containing the desired product were combined, passed through a basic resin (Stratospheres Pl-HCO$_3$) rinsing with 1 M HCl$_{(aq)}$, then concentrated in vacuo to afford the title compound (6 mg, 17% yield). MS (apci) m/z=521.3 (M+H).

Intermediate P109

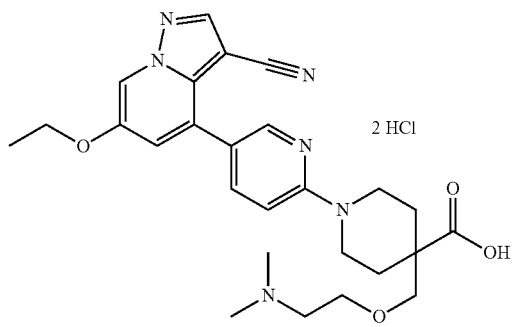 [SMILES: CCOc1cc(-c2ccc(N3CCC(COCCN(C)C)(C(=O)O)CC3)nc2)c2c(C#N)cnn2c1]

1-(5-(3-cyano-6-ethoxypyrazolo[1,5-a]pyridin-4-yl)pyridin-2-yl)-4-((2-(dimethylamino)ethoxy)methyl)piperidine-4-carboxylic acid dihydrochloride A mixture of ethyl 1-(5-(3-cyano-6-ethoxypyrazolo[1,5-a]pyridin-4-yl)pyridin-2-yl)-4-((2-(dimethylamino)ethoxy)methyl)piperidine-4-carboxylate dihydrochloride (8 mg, 0.02 mmol), 2 M NaOH$_{(aq)}$ (1 mL) and EtOH (1 mL) was stirred for 60 h at ambient temperature. After concentrating the mixture in vacuo, the residue was purified by C18 reverse phase chromatography (5-95% ACN:water with 0.1% TFA). Fractions containing the desired product were combined, concentrated in vacuo and then treated with 4 M HCl in dioxane. The HCl mixture was concentrated in vacuo to afford the title compound (4 mg, 53% yield). MS (apci) m/z=493.4 (M+H).

Intermediate P110

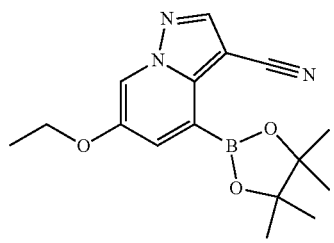 [SMILES: CCOc1cc(B2OC(C)(C)C(C)(C)O2)c2c(C#N)cnn2c1]

6-ethoxy-4-(4,4,5,5-tetramethyl-1,3,2-dioxaborolan-2-yl)pyrazolo[1,5-a]pyridine-3-carbonitrile In a pressure vessel, a solution of 4-bromo-6-ethoxypyrazolo[1,5-a]pyridine-3-carbonitrile (Intermediate P5, 1.37 g, 5.15 mmol) in dioxane (52 mL) was treated with bis(pinacolato)diboron (3.92 g, 15.4 mmol), PdCl$_2$(dppf).CH$_2$Cl$_2$ (0.420 g, 0.515 mmol), and KOAc (1.52 g, 15.4 mmol), then sparged with Ar$_{(g)}$. The vessel was sealed, and the mixture was stirred for 16 h at 90° C. After cooling to ambient temperature, the reaction mixture was diluted with EtOAc, and washed sequentially with water (2×) and brine (1×). The organic extracts were dried over anhydrous Na$_2$SO$_{4(s)}$, filtered and concentrated in vacuo. The crude residue was purified by silica chromatography (using 5-75%

Hexanes-EtOAc as the gradient eluent) to cleanly afford the title compound (1.31 g, 81% yield). MS (apci) m/z=314.2 (M+H).

Intermediate P111

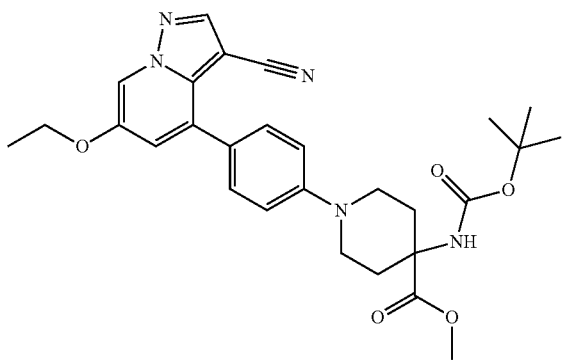 [SMILES: CCOc1cc(-c2ccc(N3CCC(NC(=O)OC(C)(C)C)(C(=O)OC)CC3)cc2)c2c(C#N)cnn2c1]

methyl 4-((tert-butoxycarbonyl)amino)-1-(4-(3-cyano-6-ethoxypyrazolo[1,5-a]pyridin-4-yl)phenyl)piperidine-4-carboxylate In a pressure vessel, a solution of methyl 1-(4-bromophenyl)-4-((tert-butoxycarbonyl)amino)piperidine-4-carboxylate (Intermediate R43; 377.4 mg, 0.9131 mmol) in dioxane (77 mL) was treated with 6-ethoxy-4-(4,4,5,5-tetramethyl-1,3,2-dioxaborolan-2-yl)pyrazolo[1,5-a]pyridine-3-carbonitrile (Intermediate P110; 314.5 mg, 1.004 mmol), Pd(PPh$_3$)$_4$ (105.5 mg, 0.09131 mmol) and K$_2$CO$_{3(s)}$ (378.6 mg, 2.739 mmol), then sparged with Ar$_{(g)}$. The vessel was sealed, and stirred for 16 h at 90° C. After cooling to ambient temperature, the reaction mixture was diluted with EtOAc, and washed sequentially with water (2×) and brine (1×). The organic extracts were dried over anhydrous Na$_2$SO$_{4(s)}$, filtered and concentrated in vacuo. The crude residue was purified by silica chromatography (using 5-95% Hexanes-EtOAc as the gradient eluent) to cleanly afford the title compound (173.0 mg, 36% yield). MS (apci) m/z=520.3 (M+H).

Intermediate P112

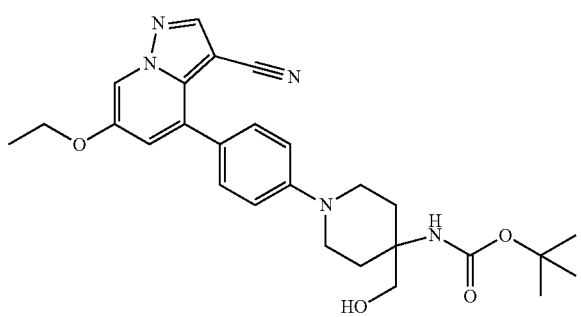 [SMILES: CCOc1cc(-c2ccc(N3CCC(CO)(NC(=O)OC(C)(C)C)CC3)cc2)c2c(C#N)cnn2c1]

tert-butyl (1-(4-(3-cyano-6-ethoxypyrazolo[1,5-a]pyridin-4-yl)phenyl)-4-(hydroxymethyl)piperidin-4-yl)carbamate A solution of methyl 4-((tert-butoxycarbonyl)amino)-1-(4-(3-cyano-6-ethoxypyrazolo[1,5-a]pyridin-4-yl)phenyl)piperidine-4-carboxylate (Intermediate P111; 173.0 mg, 0.3329 mmol) in THF (3.3 mL) was stirred at 0° C., then treated with LiBH$_4$ (36.26 mg, 1.665 mmol). The resulting mixture was stirred overnight at ambient temperature, then diluted with 10% citric acid solution, and extracted with EtOAc (2×). The combined organic extracts were washed sequentially with water (1×) and brine (1×), dried over anhydrous Na$_2$SO$_{4(s)}$, filtered, and concentrated in vacuo. The crude product was purified by silica chromatography (using 5-95% Hexanes-Acetone as the gradient eluent) to cleanly afford the title compound (64 mg, 39% yield). MS (apci) m/z=492.3 (M+H).

Intermediate P113

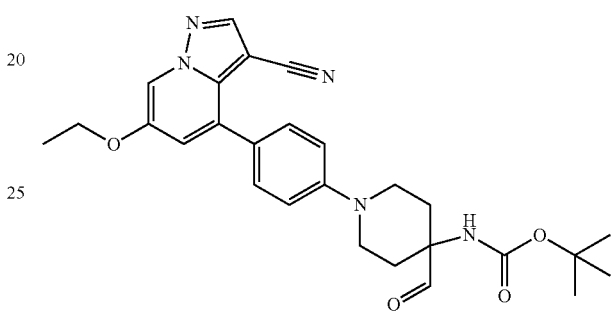

tert-butyl (1-(4-(3-cyano-6-ethoxypyrazolo[1,5-a]pyridin-4-yl)phenyl)-4-formylpiperidin-4-yl)carbamate A solution of tert-butyl (1-(4-(3-cyano-6-ethoxypyrazolo[1,5-a]pyridin-4-yl)phenyl)-4-(hydroxymethyl)piperidin-4-yl)carbamate (Intermediate P112; 64.0 mg, 0.130 mmol) in DCM (1.3 mL) was treated with DMP (66.3 mg, 0.156 mmol). The resulting mixture was stirred for 16 h at ambient temperature. The reaction mixture was concentrated in vacuo. The crude residue was purified directly by silica chromatography (using 5-95% Hexanes-EtOAc as the gradient eluent) to cleanly afford the title compound (41.8 mg, 66% yield). MS (apci) m/z=490.3 (M+H).

Intermediate P114

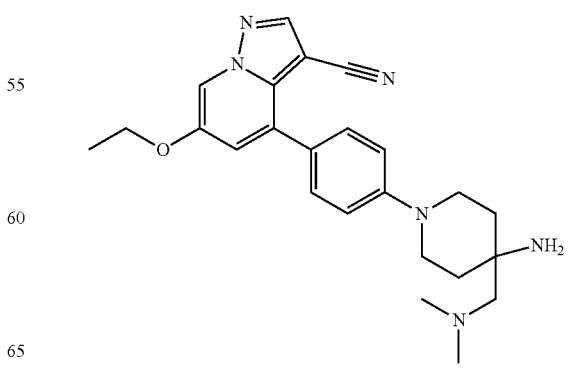

4-(4-(4-amino-4-((dimethylamino)methyl)piperidin-1-yl)phenyl)-6-ethoxypyrazolo[1,5-a]pyridine-3-carbonitrile Step 1: Preparation of tert-butyl (1-(4-(3-cyano-6-ethoxypyrazolo[1,5-a]pyridin-4-yl)phenyl)-4-((dimethylamino)methyl)piperidin-4-yl)carbamate A solution of dimethylamine hydrochloride (34.8 mg, 0.427 mmol) in DCM (1.7 mL) was treated with TEA (59.5 µL, 0.427 mmol). The mixture was stirred at for 15 minutes at ambient temperature before tert-butyl (1-(4-(3-cyano-6-ethoxypyrazolo[1,5-a]pyridin-4-yl)phenyl)-4-formylpiperidin-4-yl)carbamate (Intermediate P113; 41.8 mg, 0.0854 mmol) was added. The resulting mixture was stirred for 15 min at ambient temperature, then $NaBH(AcO)_3$ (90.5 mg, 0.427 mmol) was added. The reaction mixture was stirred for 16 h at room temperature. The mixture was diluted with 4:1 DCM:iPrOH, and washed with water. The organic extracts were washed sequentially with water (1×) and brine (1×), dried over anhydrous $Na_2SO_{4(s)}$, filtered, and concentrated in vacuo afford the title compound which was carried directly into Step 2 (0.0854 mmol, quantitative yield was assumed). MS (apci) m/z=519.3 (M+H).

Step 2: Preparation of 4-(4-(4-amino-4-((dimethylamino)methyl)piperidin-1-yl)phenyl)-6-ethoxypyrazolo[1,5-a]pyridine-3-carbonitrile Crude tert-butyl (1-(4-(3-cyano-6-ethoxypyrazolo[1,5-a]pyridin-4-yl)phenyl)-4-((dimethylamino)methyl)piperidin-4-yl)carbamate (Step 1, 0.0854 mmol) was 1:1 DCM:TFA (2.0 mL), and stirred for 30 min at ambient temperature before concentrating the mixture in vacuo. The crude residue was suspended in 4:1 DCM:iPrOH, and extracted with saturated $NaHCO_{3(aq)}$ (2×). The organic extracts were dried over anhydrous $Na_2SO_{4(s)}$, filtered and concentrated in vacuo to afford the title compound (35.7 mg, quantitative yield). MS (apci) m/z=419.3 (M+H).

Intermediate P115

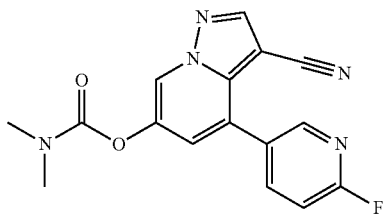 [SMILES: CN(C)C(=O)Oc1cc(-c2ccc(F)nc2)c2c(C#N)cnn2c1]

3-cyano-4-(6-fluoropyridin-3-yl)pyrazolo[1,5-a]pyridin-6-yl dimethylcarbamate

A solution of 4-(6-fluoropyridin-3-yl)-6-hydroxypyrazolo[1,5-a]pyridine-3-carbonitrile (Intermediate P66, 145.9 mg, 0.5739 mmol) and DIEA (200.5 µL, 1.148 mmol) in DCM (2.0 mL) was treated with dimethylcarbamic chloride (92.57 mg, 0.8609 mmol), then stirred overnight at ambient temperature. The reaction mixture was washed with water. The organic extracts were separated, and purified directly by silica chromatography (using 20-80% Hexanes/EtOAc as the gradient eluent) to cleanly afford the title compound (158.4 mg, 85% yield). MS (apci) m/z=326.1 (M+H).

Intermediate P116

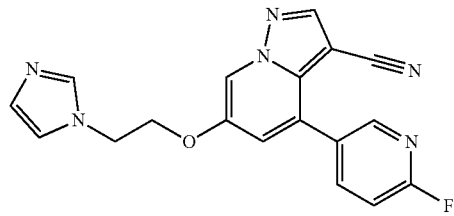 [SMILES: N#Cc1cnn2cc(OCCn3ccnc3)cc(-c3ccc(F)nc3)c12]

6-(2-(1H-imidazol-1-yl)ethoxy)-4-(6-fluoropyridin-3-yl)pyrazolo[1,5-a]pyridine-3-carbonitrile A mixture of 4-(6-fluoropyridin-3-yl)-6-hydroxypyrazolo[1,5-a]pyridine-3-carbonitrile (Intermediate P66, 100.3 mg, 0.3945 mmol), 1-(2-chloroethyl)-1H-imidazole hydrochloride (197.7 mg, 1.184 mmol) and $Cs_2CO_{3(s)}$ (1.285 g, 3.945 mmol) in DMA (2.0 mL) was stirred overnight at 60° C. After cooling to ambient temperature, the reaction mixture was diluted with water and washed sequentially with DCM (4×) and 4:1 DCM:iPrOH. The combined organic extracts were dried over anhydrous $Na_2SO_{4(s)}$, and filtered. The filtrate was purified directly by silica chromatography (using 0-25% DCM/MeOH with 1% $NH_4OH$ as the gradient eluent) to cleanly afford the title compound (158.4 mg, 85% yield). MS (apci) m/z=349.10 (M+H).

Intermediate P117

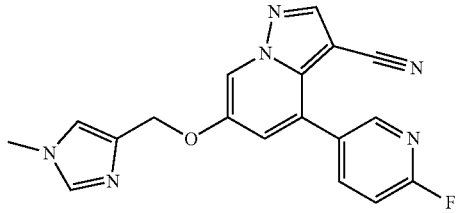 [SMILES: Cn1cnc(COc2cc(-c3ccc(F)nc3)c3c(C#N)cnn3c2)c1]

4-(6-fluoropyridin-3-yl)-6-((1-methyl-1H-imidazol-4-yl)methoxy)pyrazolo[1,5-a]pyridine-3-carbonitrile A mixture of 4-(6-fluoropyridin-3-yl)-6-hydroxypyrazolo[1,5-a]pyridine-3-carbonitrile (Intermediate P66, 103.6 mg, 0.4075 mmol), 4-(chloromethyl)-1-methyl-1H-imidazole hydrochloride (199.7 mg, 1.196 mmol) and $Cs_2CO_{3(s)}$ (1.328 g, 4.075 mmol) in DMA (2.0 mL) was stirred for 1 d at 60° C., then for an additional 1 d at 110° C. After cooling to ambient temperature, the reaction mixture was acidified with 2 M $HCl_{(aq)}$, and purified directly by C18 reverse phase chromatography (using 0-70% water/ACN with 0.1% TFA as the gradient eluent). Fractions containing the desired product were combined, partially concentrated in vacuo to remove the ACN, then partitioned between saturated $NaHCO_{3(aq)}$ and 4:1 DCM:iPrOH. The biphasic mixture was extracted with additional 4:1 DCM:iPrOH (3×). The combined organic extracts were dried over anhydrous $Na_2SO_{4(s)}$,

Intermediate P118

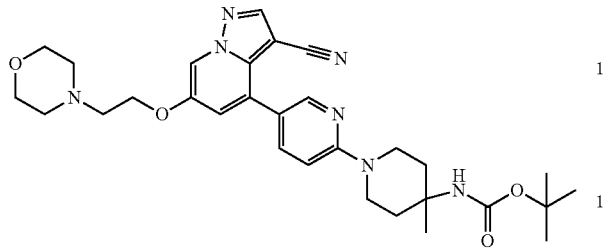

tert-butyl (1-(5-(3-cyano-6-(2-morpholinoethoxy) pyrazolo[1,5-a]pyridin-4-yl)pyridin-2-yl)-4-methyl-piperidin-4-yl)carbamate A solution of 4-(6-fluoropyridin-3-yl)-6-(2-morpholinoethoxy)pyrazolo[1,5-a]pyridine-3-carbonitrile (Intermediate P79, 485 mg, 1.32 mmol) in DMSO (2.64 mL) was treated with tert-butyl 4-methylpiperidin-4-ylcarbamate (396 mg, 1.85 mmol) and DIEA (690 μL, 3.96 mmol) was stirred overnight at 90° C. After cooling to ambient temperature, the reaction mixture was poured into water (200 mL), and acidified to pH 5 with 10% citric acid. After stirring for 15 min at ambient temperature, the aqueous suspension was vacuum filtered. The solids were purified by silica chromatography (5-95%: 10% MeOH in DCM with 1% NH$_4$OH/DCM) to afford the title compound (390 mg, 53% yield). MS (apci) m/z=562.3 (M+H).

Intermediate P119

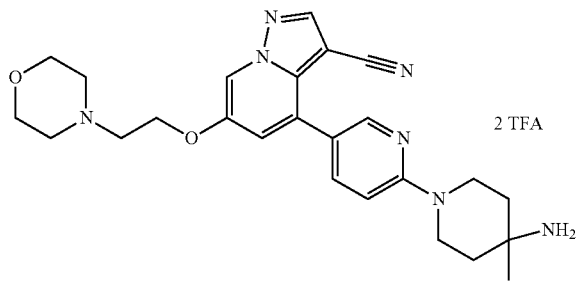 [SMILES: CC1(N)CCN(c2ccc(-c3cc(OCCN4CCOCC4)cn4ncc(C#N)c34)cn2)CC1]

4-(6-(4-amino-4-methylpiperidin-1-yl)pyridin-3-yl)-6-(2-morpholinoethoxy)pyrazolo[1,5-a]pyridine-3-carbonitrile bis(2,2,2-trifluoroacetate)

A solution of tert-butyl (1-(5-(3-cyano-6-(2-morpholinoethoxy)pyrazolo[1,5-a]pyridin-4-yl)pyridin-2-yl)-4-methylpiperidin-4-yl)carbamate (Intermediate P118; 390 mg, 0.694 mmol) was suspended in DCM (3 mL) and treated with TFA (1.0 mL). The resulting mixture was stirred for 2 h at ambient temperature before concentrating the mixture in vacuo to afford the title compound as a TFA salt (229.6 mg, 48% yield). MS: m/z=462.3 (M+H).

Intermediate P120

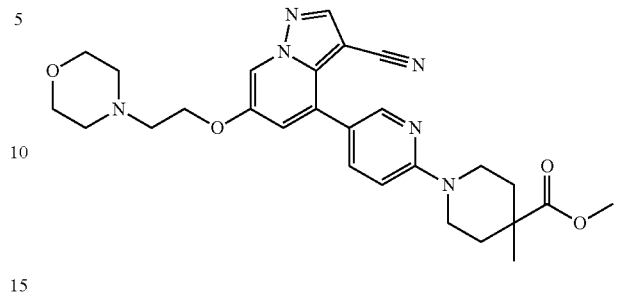

methyl 1-(5-(3-cyano-6-(2-morpholinoethoxy)pyrazolo[1,5-a]pyridin-4-yl)pyridin-2-yl)-4-methylpiperidine-4-carboxylate A solution of 4-(6-fluoropyridin-3-yl)-6-(2-morpholinoethoxy)pyrazolo[1,5-a]pyridine-3-carbonitrile (Intermediate P79, 305.6 mg, 0.8318 mmol) in DMF (3.327 mL) was treated with methyl 4-methylpiperidine-4-carboxylate (350.3 μL, 2.495 mmol) and TEA (564.2 μL, 4.159 mmol) was stirred overnight at 90° C. After cooling to ambient temperature, the reaction mixture diluted with EtOAc, and washed sequentially with water (3×) and brine (1×). After washing the aqueous extracts with 4:1 DCM:iPrOH, the DCM:iPrOH extracts were concentrated in vacuo. The residue was dissolved in EtOAc, then extracted with water (3×) and brine (1×) before combining with the original EtOAc extracts. The combined EtOAc extracts were dried over anhydrous Na$_2$SO$_{4(s)}$, filtered and concentrated in vacuo. The crude residue was purified by silica chromatography (using 5-95% Hexanes:EtOAc as the gradient eluent) to afford the title compound (354 mg, 84% yield). MS (apci) m/z=505.3 (M+H).

Intermediate P121

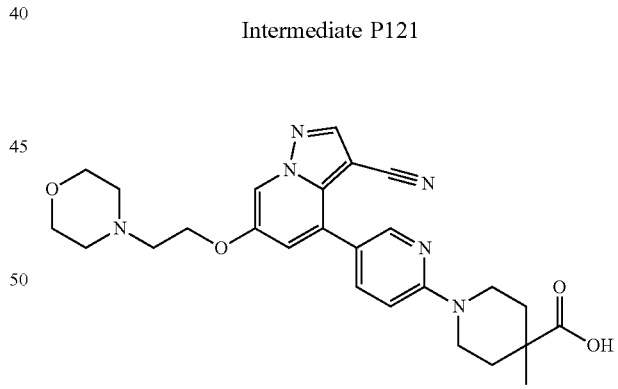

1-(5-(3-cyano-6-(2-morpholinoethoxy)pyrazolo[1,5-a]pyridin-4-yl)pyridin-2-yl)-4-methylpiperidine-4-carboxylic acid A solution of methyl 1-(5-(3-cyano-6-(2-morpholinoethoxy)pyrazolo[1,5-a]pyridin-4-yl)pyridin-2-yl)-4-methylpiperidine-4-carboxylate (Intermediate P120; 354 mg, 0.702 mmol) in 1:1 THF:MeOH (3.0 mL) was treated with 2.0 M KOH$_{(aq)}$ (3.5 mL, 7.02 mmol), then stirred for 64 h at ambient temperature. The resulting mixture was diluted with water then treated with 1.0 M NaOH$_{(aq)}$ to bring the mixture (filtered and concentrated in vacuo to afford the title compound (26.0 mg, 18% yield). MS (apci) m/z=349.10 (M+H).)

to pH 14. The mixture was extracted with 4:1 DCM:iPrOH (3×). The aqueous extracts were acidified (ca. pH 4) with the addition of 1.0 M HCl$_{(aq)}$, then extracted with 4:1 DCM:iPrOH (3×). The organic extracts from the acid extraction were combined, dried over anhydrous Na$_2$SO$_{4(s)}$, filtered, and concentrated in vacuo to afford the title compound (298 mg, 87% yield). MS (apci) m/z=505.3 (M+H).

Intermediate P122

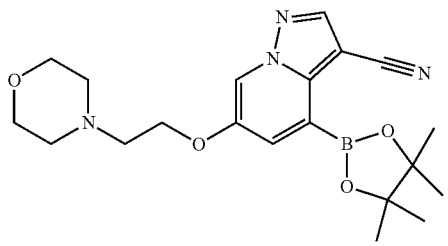 [SMILES: CC1(C)OB(c2cc(OCCN3CCOCC3)cn3ncc(C#N)c23)OC1(C)C]

6-(2-morpholinoethoxy)-4-(4,4,5,5-tetramethyl-1,3,2-dioxaborolan-2-yl)pyrazolo[1,5-a]pyridine-3-carbonitrile In a pressure vessel, a mixture of 4-bromo-6-(2-morpholinoethoxy)pyrazolo[1,5-a]pyridine-3-carbonitrile (Intermediate P79, step 1, 426 mg, 1.21 mmol), bis(pinacolato)diboron (3.08 g, 12.1 mmol), PdCl$_2$(dppf).CH$_2$Cl$_2$ (89 mg, 0.121 mmol) and KOAc (595 mg, 6.06 mmol) in dioxane (10 mL) was sparged with N$_{2(g)}$ for 1 min. The vessel was sealed, and the mixture was stirred overnight at 90° C. After cooling to ambient temperature, the reaction mixture was diluted with DCM (15 mL), and filtered through Celite®. The filtrate was concentrated in vacuo, and the residue was purified by silica chromatography (using 0-100% Hexanes/Acetone as the gradient eluent) to afford the title compound (185 mg, 38% yield). MS (apci) m/z=317 (M+H).

Intermediate P123

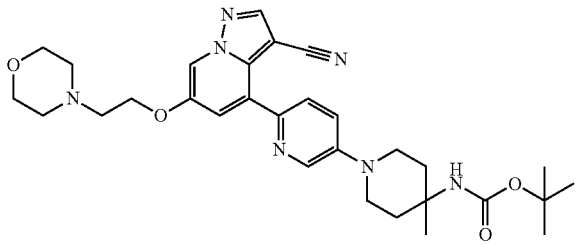 [SMILES: CC1(NC(=O)OC(C)(C)C)CCN(c2ccc(-c3cc(OCCN4CCOCC4)cn4ncc(C#N)c34)nc2)CC1]

tert-butyl (1-(6-(3-cyano-6-(2-morpholinoethoxy)pyrazolo[1,5-a]pyridin-4-yl)pyridin-3-yl)-4-methylpiperidin-4-yl)carbamate In a pressure tube, a suspension of 6-(2-morpholinoethoxy)-4-(4,4,5,5-tetramethyl-1,3,2-dioxaborolan-2-yl)pyrazolo[1,5-a]pyridine-3-carbonitrile (Intermediate P122; 24 mg, 0.061 mmol) in 3:1 dioxane:water (0.4 mL) was treated with Cs$_2$CO$_{3(s)}$ (60 mg, 0.18 mmol) and tert-butyl (1-(6-bromopyridin-3-yl)-4-methylpiperidin-4-yl)carbamate (Intermediate R45; 25 mg, 0.068 mmol), then sparged with N$_{2(g)}$ for 5 min. The resulting mixture was treated with X-phos (150.9 mg, 0.3165 mmol) and Pd$_2$(dba)$_3$ (144.9 mg, 0.1582 mmol), then sparged with N$_{2(g)}$. After sealing the vessel, the reaction mixture was stirred for 20 h at 80° C. After cooling to ambient temperature, the resulting suspension was diluted with water (25 mL) and extracted with DCM (2×25 mL). The combined organic extracts were dried over anhydrous MgSO$_{4(s)}$, filtered and concentrated in vacuo. The crude residue was purified by silica chromatography (using 0-90% Acetone/Hexanes as the gradient eluent) to cleanly afford the title compound (5.4 mg, 16% yield). MS (apci) m/z=562.3 (M+H).

Intermediate P124

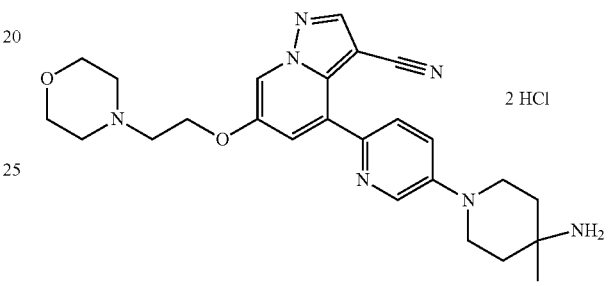

4-(5-(4-amino-4-methylpiperidin-1-yl)pyridin-2-yl)-6-(2-morpholinoethoxy)pyrazolo[1,5-a]pyridine-3-carbonitrile dihydrochloride A solution of tert-butyl (1-(6-(3-cyano-6-(2-morpholinoethoxy)pyrazolo[1,5-a]pyridin-4-yl)pyridin-3-yl)-4-methylpiperidin-4-yl)carbamate (Intermediate P123; 5.0 mg, 0.0089 mmol) in DCM (500 μL) was treated with 5-6 N HCl in iPrOH (534 μL, 2.67 mmol), and stirred for 30 min at ambient temperature. The resulting mixture was concentrated in vacuo, azeotroping with Et$_2$O, and then dried under high vacuum to afford the title compound (4.8 mg, quantitative yield). MS (apci) m/z=462.3 (M+H).

Intermediate P125

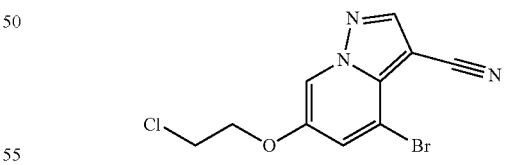

A mixture of 4-bromo-6-(2-chloroethoxy)pyrazolo[1,5-a]pyridine-3-carbonitrile

A mixture of 4-bromo-6-hydroxypyrazolo[1,5-a]pyridine-3-carbonitrile (Intermediate P1, 574 mg, 2.41 mmol) in DMF (2.41 mL) was treated sequentially with anhydrous K$_2$CO$_{3(s)}$ (1.67 g, 12.1 mmol) and 1-chloro-2-iodoethane (221 μL, 2.41 mmol), then stirred for 48 h at ambient temperature. Subsequently, additional 1-chloro-2-iodoethane (221 μL, 2.41 mmol) was introduced, and the mixture was stirred for an additional 60 h at ambient temperature. The reaction mixture was partitioned between DCM and water. The resulting emulsion was filtered, and the biphasic filtrate was separated. After back extracting the aqueous extracts with 4:1 DCM:iPrOH (3×), all organic extracts were combined, dried over anhydrous $Na_2SO_{4(s)}$, filtered and concentrated in vacuo. The crude residue was purified by silica chromatography (using 0-100% EtOAc/Hexanes as the gradient eluent) to cleanly afford the title compound (331 mg, 46% yield). $^1$H NMR (CDCl$_3$) δ 8.19 (s, 1H), 8.11 (d, 1H), 7.47 (d, 1H), 4.24 (t, 2H), 3.84 (t, 2H).

Intermediate P126

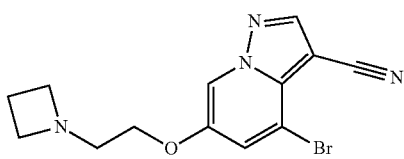 [SMILES: N#Cc1cnn2cc(OCCN3CCC3)cc(Br)c12]

6-(2-(azetidin-1-yl)ethoxy)-4-bromopyrazolo[1,5-a]pyridine-3-carbonitrile

A solution of 4-bromo-6-(2-chloroethoxy)pyrazolo[1,5-a]pyridine-3-carbonitrile (Intermediate P125; 77 mg, 0.256 mmol) in DMF (256 μL) was treated sequentially with DIEA (447 μl, 2.56 mmol) and azetidine (43.9 mg, 0.769 mmol). The resulting mixture was stirred overnight at 60° C. After cooling to ambient temperature, the reaction mixture was diluted with water, and the resultant suspension was filtered. The solids were collected, and dried under high vacuum to cleanly afford the title compound (42 mg, 51% yield). MS (apci) m/z=321 (M+H).

Intermediate P127

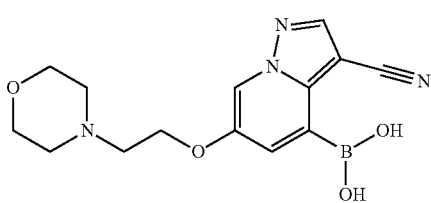 [SMILES: N#Cc1cnn2cc(OCCN3CCOCC3)cc(B(O)O)c12]

(3-cyano-6-(2-morpholinoethoxy)pyrazolo[1,5-a]pyridin-4-yl)boronic acid

In a pressure vessel, a mixture of 4-bromo-6-(2-morpholinoethoxy)pyrazolo[1,5-a]pyridine-3-carbonitrile (Intermediate P79, step 1, 200 mg, 0.3360 mmol), bis(pinacolato)diboron (1.446 g, 5.694 mmol), PdCl$_2$(dppf).CH$_2$Cl$_2$ (46.4 mg, 0.0570 mmol) and KOAc (167.7 mg, 1.709 mmol) in dioxane (3.36 mL) was sparged with Ar$_{(g)}$, for 10 min. The vessel was sealed, and the mixture was stirred overnight at 90° C. After cooling to ambient temperature, the reaction mixture was diluted with DCM, and filtered through GF/F paper. The filtrate was concentrated in vacuo, and the residue was purified by silica chromatography (using 0-20% MeOH in DCM with 2% NH$_4$OH as the gradient eluent). The purified residue was dissolved in DCM (2 mL) and triturated with Et$_2$O (5 mL). The resulting suspension was filtered, and the solids were isolated to afford the title compound (60 mg, 56% yield). MS (apci) m/z=317.1 (M+H).

Intermediate P128

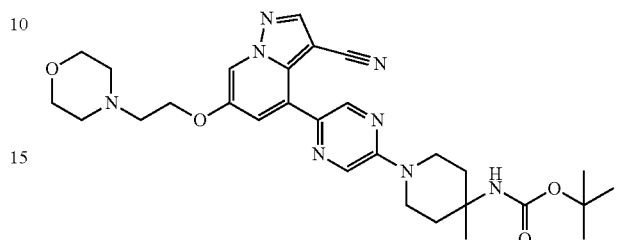

tert-butyl (1-(5-(3-cyano-6-(2-morpholinoethoxy)pyrazolo[1,5-a]pyridin-4-yl)pyrazin-2-yl)-4-methyl-piperidin-4-yl)carbamate In a pressure tube, a mixture of (3-cyano-6-(2-morpholinoethoxy)pyrazolo[1,5-a]pyridin-4-yl)boronic acid (Intermediate P127; 215 mg, 0.680 mmol), tert-butyl (1-(5-chloropyrazin-2-yl)-4-methylpiperidin-4-yl)carbamate (Intermediate R46; 37.6 mg, 0.0991 mmol), X-phos (64.8 mg, 0.136 mmol) and Pd$_2$(dba)$_3$ (31.1 mg, 0.0340 mmol) in dioxane (3.40 mL) was treated with 2 M K$_3$PO$_{4(aq)}$ (1.02 mL, 2.04 mmol). The mixture was sparged with Ar$_{(g)}$ for 10 min, and then the vessel was sealed. The reaction mixture was stirred overnight at 80° C. After cooling to ambient temperature, the reaction mixture was diluted with DCM and extracted sequentially with water and brine. The organic extracts were dried over anhydrous $Na_2SO_{4(s)}$, filtered and concentrated in vacuo. The crude residue was purified by silica chromatography (using 0-100% EtOAc/Hexanes followed by 0-10% MeOH in DCM with 0.1% NH$_4$OH as the gradient eluent) to cleanly afford the title compound (102 mg, 27% yield). MS (apci) m/z=563.3 (M+H).

Intermediate P129

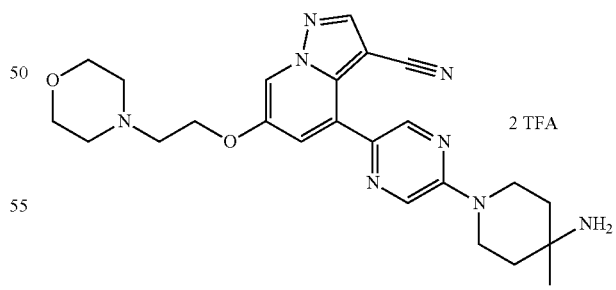

4-(5-(4-amino-4-methylpiperidin-1-yl)pyrazin-2-yl)-6-(2-morpholinoethoxy)pyrazolo[1,5-a]pyridine-3-carbonitrile bis(2,2,2-trifluoroacetate)

A solution tert-butyl (1-(5-(3-cyano-6-(2-morpholinoethoxy)pyrazolo[1,5-a]pyridin-4-yl)pyrazin-2-yl)-4-methylpiperidin-4-yl)carbamate (Intermediate P128; 102 mg, 0.181 mmol) in DCM (1 mL) and TFA (1.4 mL, 18.1 mmol) was stirred for 2.5 h at ambient temperature. The reaction mixture was concentrated in vacuo. The residue was diluted with DCM, then triturated with Et$_2$O, and concentrated in vacuo (repeat trituration 3×). The solid residue was dried under high vacuum to afford the title compound (125 mg, 100% yield). MS (apci) m/z=463.3 (M+H).

Intermediate P130

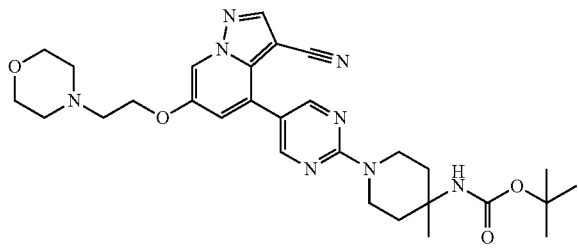 [SMILES: CC1(NC(=O)OC(C)(C)C)CCN(c2ncc(-c3cc(OCCN4CCOCC4)cn4ncc(C#N)c34)cn2)CC1]

tert-butyl (1-(5-(3-cyano-6-(2-morpholinoethoxy) pyrazolo[1,5-a]pyridin-4-yl)pyrimidin-2-yl)-4-methylpiperidin-4-yl)carbamate Step 1: Preparation of (2-(4-((tert-butoxycarbonyl) amino)-4-methylpiperidin-1-yl)pyrimidin-5-yl)boronic acid In a pressure vessel, a mixture of tert-butyl (4-methylpiperidin-4-yl)carbamate (0.23 g, 1.1 mmol), 2-fluoro-5-(4,4,5,5-tetramethyl-1,3,2-dioxaborolan-2-yl)pyrimidine (0.2 g, 0.89 mmol) and K$_2$CO$_{3(s)}$ (0.62 g, 4.5 mmol) was combined in dioxane (8.9 mL), and the vessel was sealed. The reaction mixture was stirred overnight at 60° C. After cooling to ambient temperature, the reaction mixture was directly used for the next step assuming quantitative yield. MS (apci) m/z=337.2 (M+H).

Step 2: Preparation of tert-butyl (1-(5-(3-cyano-6-(2-morpholinoethoxy)pyrazolo[1,5-a]pyridin-4-yl) pyrimidin-2-yl)-4-methylpiperidin-4-yl)carbamate In a sealed vessel, a solution of (2-(4-((tert-butoxycarbonyl)amino)-4-methylpiperidin-1-yl)pyrimidin-5-yl)boronic acid (300 mg, 0.892 mmol) and K$_2$CO$_{3(s)}$ (617 mg, 4.46 mmol) in dioxane (8.92 mL) was treated with water (0.892 mL), 4-bromo-6-(2-morpholinoethoxy)pyrazolo[1,5-a]pyridine-3-carbonitrile (Intermediate P79, step 1, 313 mg, 0.892 mmol) and Pd(PPh$_3$)$_4$ (103 mg, 0.0892 mmol), then sparged with Ar$_{(g)}$. After sealing the vessel, the reaction mixture was stirred for 16 h at 80° C. After cooling to ambient temperature, the reaction mixture was diluted with EtOAc, and washed with brine (3×). The organic extracts were dried over anhydrous Na$_2$SO$_{4(s)}$, filtered and concentrated in vacuo. The crude residue was purified by silica chromatography (using 0-20% MeOH in EtOAc as the gradient eluent) to cleanly afford the title compound (243 mg, 36% yield). MS (apci) m/z=563.4 (M+H).

Intermediate P131

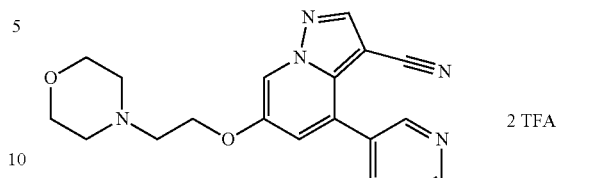

4-(2-(4-amino-4-methylpiperidin-1-yl)pyrimidin-5-yl)-6-(2-morpholinoethoxy)pyrazolo[1,5-a]pyridine-3-carbonitrile bis(2,2,2-trifluoroacetate)

A solution tert-butyl (1-(5-(3-cyano-6-(2-morpholinoethoxy)pyrazolo[1,5-a]pyridin-4-yl)pyrimidin-2-yl)-4-methylpiperidin-4-yl)carbamate (Intermediate P130; 91 mg, 0.147 mmol in DCM (2 mL) and TFA (2 mL, 26 mmol) was stirred overnight at ambient temperature, then treated with additional TFA (2 mL). The reaction mixture was stirred for 4 h at 40° C., and 60 h at ambient temperature before concentrating in vacuo. The residue was dried under high vacuum for 3 h to afford the title compound (101.52 mg, quantitative yield). MS (apci) m/z=463.3 (M+H).

Intermediate P132

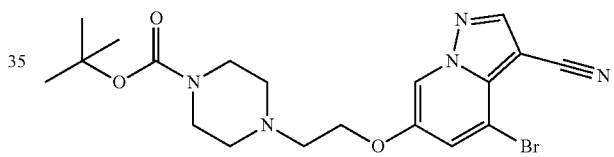

tert-butyl 4-(2-((4-bromo-3-cyanopyrazolo[1,5-a] pyridin-6-yl)oxy)ethyl)piperazine-1-carboxylate A mixture of 4-bromo-6-hydroxypyrazolo[1,5-a]pyridine-3-carbonitrile (Intermediate P1, 200 mg, 0.840 mmol) in DMA (4.20 mL) was treated sequentially with K$_2$CO$_{3(s)}$ (348 mg, 12.1 mmol) and tert-butyl 4-(2-bromoethyl)piperazine-1-carboxylate (493 mg, 1.68 mmol), then stirred for 3 h at 60° C. After cooling to ambient temperature, the mixture was diluted with brine. The resulting suspension was filtered, and the solids were rinsed with water (5×). The solids the were collected, dissolved in DCM and concentrated in vacuo to cleanly afford the title compound (239 mg, 63% yield). MS (apci) m/z=452.0 (M+H).

The compounds in Table bbb were prepared using a similar procedure to that used for the synthesis of tert-butyl 4-(2-((4-bromo-3-cyanopyrazolo[1,5-a]pyridin-6-yl)oxy) ethyl)piperazine-1-carboxylate (Intermediate P132) replacing tert-butyl 4-(2-bromoethyl)piperazine-1-carboxylate with (1.0-2.0 equivalents) of the appropriate alkyl halide (or alkyl halide salt). Reactions were conducted between 50-60° C., and monitored for completion by LCMS, and reaction durations were adjusted accordingly. Where noted (*) an additional work up step was required, involving an aqueous work up of the filtrate (or the reaction mixture) using DCM, water and brine, followed by a chromatographic purification of the organics from the extraction using an appropriate gradient eluent.

TABLE bbb

| Intermediate # | Structure | Chemical Name | Analytical |
|---|---|---|---|
| P133 | 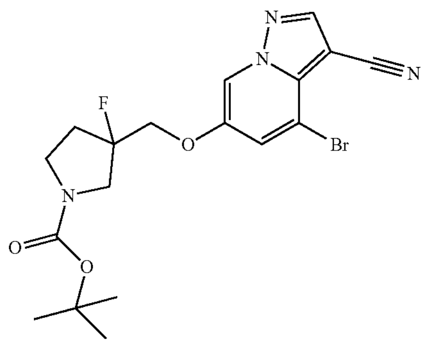 [SMILES: CC(C)(C)OC(=O)N1CCC(F)(COc2cc(Br)c3c(C#N)cnn3c2)C1] | tert-butyl 3-(((4-bromo-3-cyanopyrazolo[1,5-a]pyridin-6-yl)oxy)methyl)-3-fluoropyrrolidine-1-carboxylate | $^1$H NMR (CDCl$_3$) δ 8.20 (s, 1H), 8.14 (d, 1H), 7.49 (br m, 1H), 4.19 m, 2H), 3.46-3.82 (m, 6H), 2.28 (m, 1H), 2.09 (m, 1H) 1.46 (s, 12H). |
| P134 | 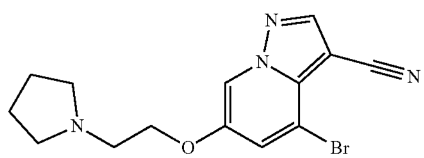 [SMILES: N#Cc1cnn2cc(OCCN3CCCC3)cc(Br)c12] | 4-bromo-6-(2-(pyrrolidin-1-yl)ethoxy)pyrazolo[1,5-a]pyridine-3-carbonitrile | MS (apci) m/z 337 (M + 2, with Br pattern) |
| P135* | 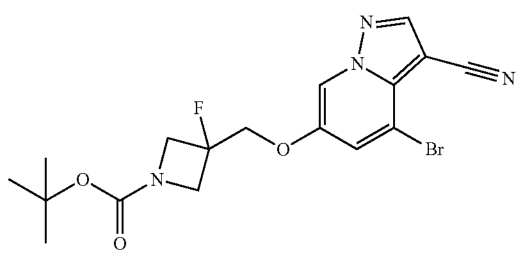 [SMILES: CC(C)(C)OC(=O)N1CC(F)(COc2cc(Br)c3c(C#N)cnn3c2)C1] | tert-butyl 3-(((4-bromo-3-cyanopyrazolo[1,5-a]pyridin-6-yl)oxy)methyl)-3-fluoroazetidine-1-carboxylate | $^1$H NMR (CDCl$_3$) δ 8.83 (d, 1H), 8.67 (s, 1H), 7.91 (d, 1H), 4.49-4.55 (d, 2H), 3.91-4.15 (m, 4H), 1.39 (s, 9H) |
| P136* | 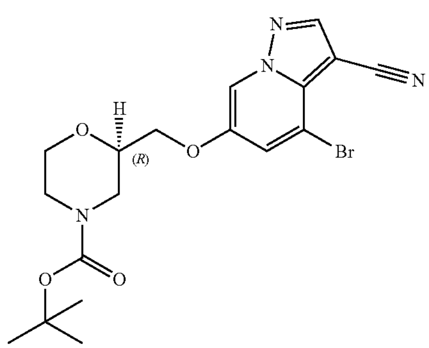 | tert-butyl (R)-2-(((4-bromo-3-cyanopyrazolo[1,5-a]pyridin-6-yl)oxy)methyl)morpholine-4-carboxylate | $^1$H NMR (CDCl$_3$) 8.21 (s, 1H), 8.17 (d, 1H), 7.50 (d, 1H), 3.78-4.42 (m, 9H), 1.48 (s, 9H) |
| P137* | 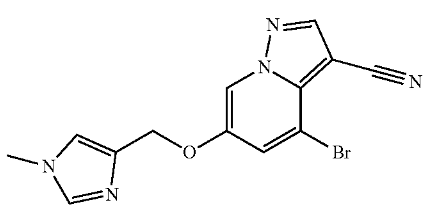 [SMILES: Cn1cnc(COc2cc(Br)c3c(C#N)cnn3c2)c1] | 4-bromo-6-((1-methyl-1H-imidazol-4-yl)methoxy)pyrazolo[1,5-a]pyridine-3-carbonitrile | MS (apci) m/z 334 (M + 2, with Br pattern) |

TABLE bbb-continued

| Intermediate # | Structure | Chemical Name | Analytical |
|---|---|---|---|
| P138* | 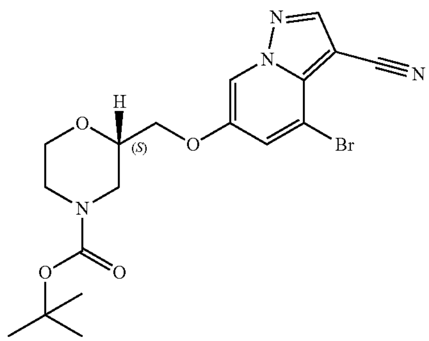 | tert-butyl (S)-2-(((4-bromo-3-cyanopyrazolo[1,5-a]pyridin-6-yl)oxy)methyl)morpholine-4-carboxylate | ¹H NMR (CDCl₃) 8.23 (d, 1H), 8.21 (s, 1H), 7.51 (d, 1H), 3.52-4.14 (m, 9H), 1.48 (s, 9H) |
| P139* | 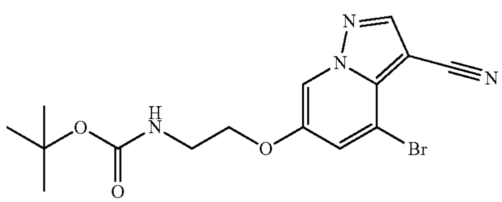 [SMILES: CC(C)(C)OC(=O)NCCOc1cc(Br)c2c(C#N)cnn2c1] | tert-butyl (2-((4-bromo-3-cyanopyrazolo[1,5-a]pyridin-6-yl)oxy)ethyl)carbamate | ¹H NMR (CDCl₃) δ 8.19 (s, 1H), 8.10 (d, 1H), 7.43 (d, 1H), 4.91 (s, 1H), 4.03 (t, 2H), 3.56 (t, 2H), 1.44 (s, 9H) |

Intermediate P140

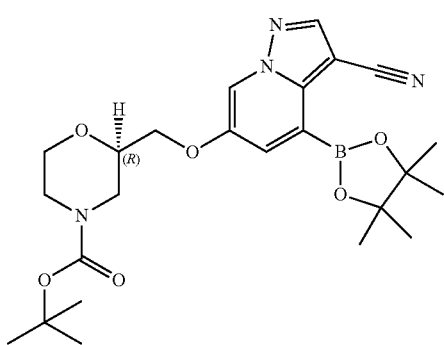

tert-butyl (R)-2-(((3-cyano-4-(4,4,5,5-tetramethyl-1,3,2-dioxaborolan-2-yl)pyrazolo[1,5-a]pyridin-6-yl)oxy)methyl)morpholine-4-carboxylate In a pressure vessel, a mixture of tert-butyl (R)-2-(((4-bromo-3-cyanopyrazolo[1,5-a]pyridin-6-yl)oxy)methyl)morpholine-4-carboxylate (Intermediate P136; 367 mg, 0.839 mmol), bis(pinacolato)diboron (2.131 g, 8.39 mmol), PdCl₂(dppf).CH₂Cl₂ (68.4 mg, 0.0839 mmol) and KOAc (412 mg, 4.20 mmol) in dioxane (8.393 mL) was sparged with Ar$_{(g)}$, for 10 min. The vessel was sealed, and the mixture was stirred overnight at 80° C. After cooling to ambient temperature, the reaction mixture was diluted with EtOAc, and filtered through GF/F paper. The filtrate was concentrated in vacuo, and the residue was triturated with pentane. The pentane suspension was filtered, and the solids were isolated to afford the title compound (304 mg, 75% yield). ¹HNMR (CDCl₃) δ 8.19 (s, 1H), 7.70 (s, 1H), 7.25 (s, 1H), 3.80-4.12 (m, 6H), 3.52-3.75 (m, 3H), 1.57 (s, 9H), 1.49 (s, 12H).

The compounds in Table ccc were prepared using a similar procedure to that used for the synthesis of tert-butyl (R)-2-(((3-cyano-4-(4,4,5,5-tetramethyl-1,3,2-dioxaborolan-2-yl)pyrazolo[1,5-a]pyridin-6-yl)oxy)methyl)morpholine-4-carboxylate (Intermediate P140) replacing tert-butyl (R)-2-(((4-bromo-3-cyanopyrazolo[1,5-a]pyridin-6-yl)oxy)methyl)morpholine-4-carboxylate (Intermediate P136) with the appropriate 4-bromo-6-alkoxypyrazolo[1,5-a]pyridine-3-carbonitrile from Table bbb (or the synthetic intermediate referenced therein). Reactions were monitored for completion by LCMS, and reaction durations were adjusted accordingly. Work ups were conducted with either DCM or EtOAc, and where noted (*) either a second trituration from pentane or a chromatographic purification using an appropriate gradient eluent (in place of the trituration) was required.

TABLE ccc

| Intermediate # | Structure | Chemical Name | Analytical |
|---|---|---|---|
| P141* | 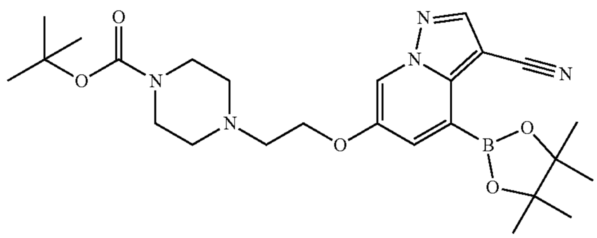 | tert-butyl 4-(2-((3-cyano-4-(4,4,5,5-tetramethyl-1,3,2-dioxaborolan-2-yl)pyrazolo[1,5-a]pyridin-6-yl)oxy)ethyl)piperazine-1-carboxylate | MS (apci) m/z 416.2 (M-Pinacol) ¹H NMR (CDCl₃) δ 8.19 (s, 1H), 8.16 (d, 1H), 7.65 (d, 1H), 4.10 (t, 2H), 3.45 (t, 4H), 2.83 (t, 2H), 2.51 (t, 4H) 1.45 (s, 9H), 1.41 (s, 12H). |
| P142 | 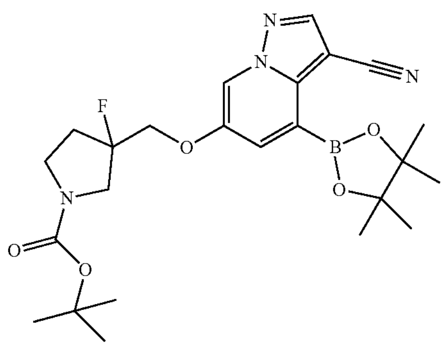 [SMILES: CC(C)(C)OC(=O)N1CCC(F)(COc2cc(B3OC(C)(C)C(C)(C)O3)c3c(C#N)cnn3c2)C1] | tert-butyl 3-(((3-cyano-4-(4,4,5,5-tetramethyl-1,3,2-dioxaborolan-2-yl)pyrazolo[1,5-a]pyridin-6-yl)oxy)methyl)-3-fluoropyrrolidine-1-carboxylate | ¹H NMR (CDCl₃) δ 8.20 (m, 2H), 7.67 (s, 1H), 4.17 (m, 2H), 3.49-3.84 (m, 5H), 2.00-2.35 (m, 3H), 1.45 (s, 9H), 1.42 (s, 12H). |
| P143* | 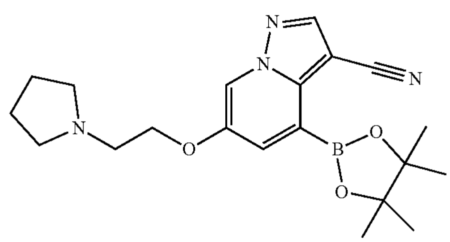 | 6-(2-(pyrrolidin-1-yl)ethoxy)-4-(4,4,5,5-tetramethyl-1,3,2-dioxaborolan-2-yl)pyrazolo[1,5-a]pyridine-3-carbonitrile | MS (apci) m/z 301.1 (M-Pinacol) |
| P144 | 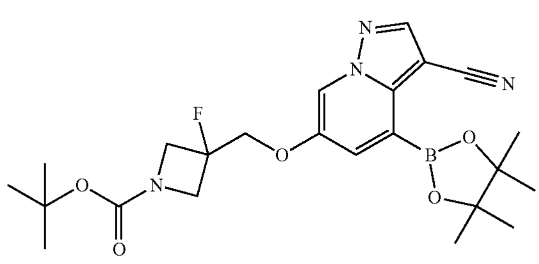 [SMILES: CC(C)(C)OC(=O)N1CC(F)(COc2cc(B3OC(C)(C)C(C)(C)O3)c3c(C#N)cnn3c2)C1] | tert-butyl 3-(((3-cyano-4-(4,4,5,5-tetramethyl-1,3,2-dioxaborolan-2-yl)pyrazolo[1,5-a]pyridin-6-yl)oxy)methyl)-3-fluoroazetidine-1-carboxylate | ¹H NMR (CDCl₃) δ 8.21 (d, 1H), 8.19 (s, 1H), 7.69 (d, 1H), 4.11-4.39 (m, 6H), 1.45 (s, 9H), 1.41 (s, 12H) |
| P145 | 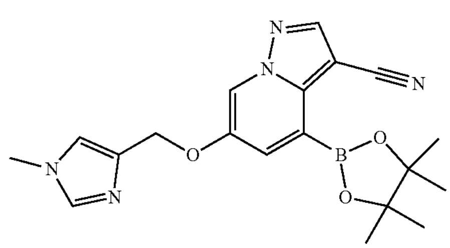 | 6-((1-methyl-1H-imidazol-4-yl)methoxy)-4-(4,4,5,5-tetramethyl-1,3,2-dioxaborolan-2-yl)pyrazolo[1,5-a]pyridine-3-carbonitrile | ¹H NMR (CDCl₃) δ 8.36 (s, 1H), 8.18 (d, 1H), 7.45 (d, 1H), 7.01 (d, 1H), 6.97 (s, 1H), 5.05 (s, 2H), 3.71 (s, 3H), 1.26 (s, 12H) |

TABLE ccc-continued

| Intermediate # | Structure | Chemical Name | Analytical |
|---|---|---|---|
| P146 | 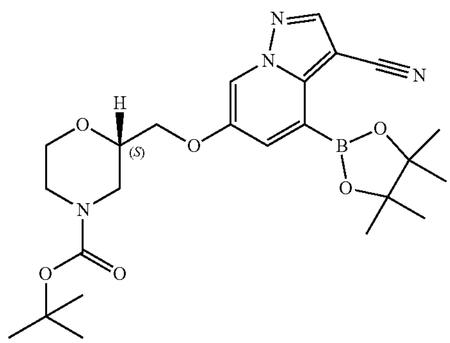 | tert-butyl (S)-2-(((3-cyano-4-(4,4,5,5-tetramethyl-1,3,2-dioxaborolan-2-yl)pyrazolo[1,5-a]pyridin-6-yl)oxy)methyl)morpholine-4-carboxylate | ¹H NMR (CDCl₃) δ 8.20 (d, 1H), 7.69 (s, 1H), 7.26 (d, 1H), 3.54-4.25 (m, 9H), 1.48 (s, 9H), 1.42 (s, 12H) |
| P147 | 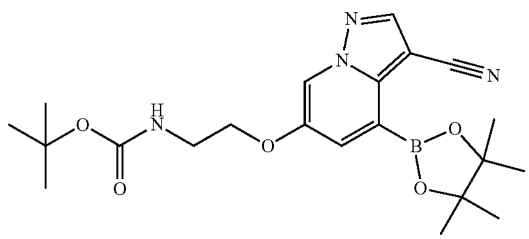 | tert-butyl (2-((3-cyano-4-(4,4,5,5-tetramethyl-1,3,2-dioxaborolan-2-yl)pyrazolo[1,5-a]pyridin-6-yl)oxy)ethyl)carbamate | MS (apci) m/z 347.1 (M-pinacol) |

Intermediate P148

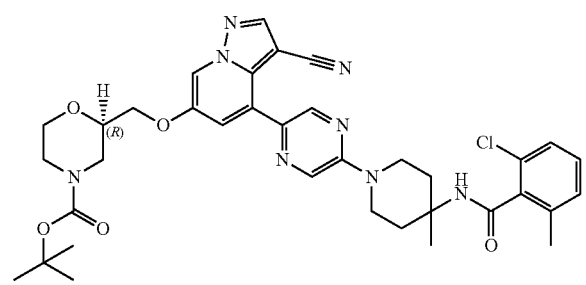

Tert-butyl (R)-2-(((4-(5-(4-(2-chloro-6-methylbenzamido)-4-methylpiperidin-1-yl)pyrazin-2-yl)-3-cyanopyrazolo[1,5-a]pyridin-6-yl)oxy)methyl)morpholine-4-carboxylate In a pressure tube, a mixture of tert-butyl (R)-2-(((3-cyano-4-(4,4,5,5-tetramethyl-1,3,2-dioxaborolan-2-yl)pyrazolo[1,5-a]pyridin-6-yl)oxy)methyl)morpholine-4-carboxylate (Intermediate P140; 96 mg, 0.198 mmol), 2-chloro-N-(1-(5-chloropyrazin-2-yl)-4-methylpiperidin-4-yl)-6-methylbenzamide (Intermediate R48; 37.6 mg, 0.0991 mmol), 2 M K₃PO₄(aq) (149 µL, 0.297 mmol), X-phos (9.45 mg, 0.0198 mmol) and Pd₂(dba)₃ (4.54 mg, 0.00495 mmol) in dioxane (1.0 mL) was sparged with Ar(g) for 10 min, and then the vessel was sealed. The reaction mixture was stirred overnight at 80° C. After cooling to ambient temperature, the reaction mixture was diluted with DCM, and extracted sequentially with water (3×) and brine (1×). The organic extracts were concentrated in vacuo, and purified by silica chromatography (using 0-100% EtOAc/Hexanes as the gradient eluent) to cleanly afford the title compound (40.3 mg, 58% yield). MS (apci) m/z=701.2 (M+H).

The compounds in Table ddd were prepared using a similar procedure to that used for the synthesis of tert-butyl (R)-2-(((4-(5-(4-(2-chloro-6-methylbenzamido)-4-methylpiperidin-1-yl)pyrazin-2-yl)-3-cyanopyrazolo[1,5-a]pyridin-6-yl)oxy)methyl)morpholine-4-carboxylate (Intermediate P148) replacing of tert-butyl (R)-2-(((3-cyano-4-(4,4,5,5-tetramethyl-1,3,2-dioxaborolan-2-yl)pyrazolo[1,5-a]pyridin-6-yl)oxy)methyl)morpholine-4-carboxylate (Intermediate P140) with the appropriate boronate ester from Table ccc (or the synthetic intermediate referenced therein). Reactions were monitored for completion by LCMS, and reaction durations were adjusted accordingly. The title compounds were isolated following a chromatographic purification using an appropriate eluent.

TABLE ddd

| Intermediate # | Structure | Chemical Name | MS (apci) m/z |
|---|---|---|---|
| P149 | 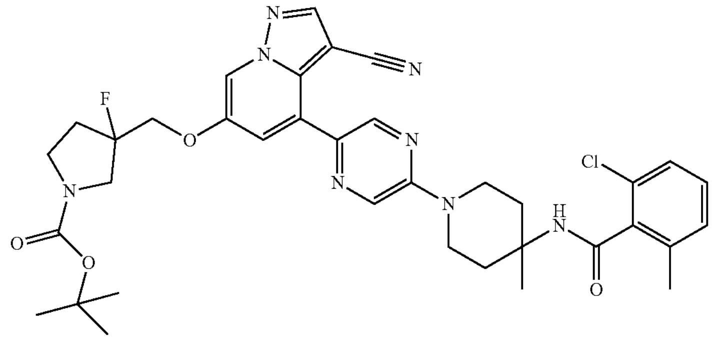 [SMILES: Cc1cccc(Cl)c1C(=O)NC1(C)CCN(c2cnc(-c3cc(OCC4(F)CCN(C(=O)OC(C)(C)C)C4)cn4ncc(C#N)c34)cn2)CC1] | tert-butyl 3-(((4-(5-(4-(2-chloro-6-methylbenzamido)-4-methylpiperidin-1-yl)pyrazin-2-yl)-3-cyanopyrazolo[1,5-a]pyridin-6-yl)oxy)methyl)-3-fluoropyrrolidine-1-carboxylate | 703.2 (M + H) |
| P150 | 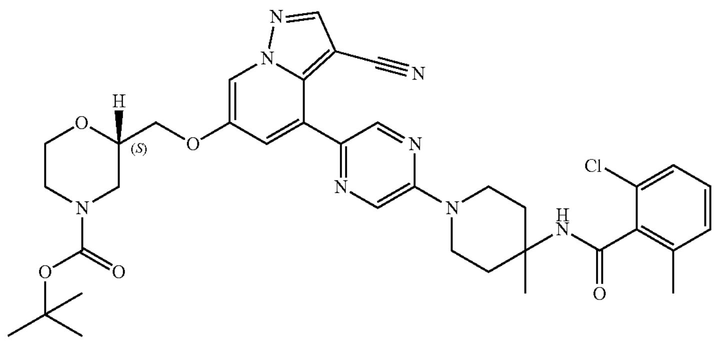 | tert-butyl (S)-2-(((4-(5-(4-(2-chloro-6-methylbenzamido)-4-methylpiperidin-1-yl)pyrazin-2-yl)-3-cyanopyrazolo[1,5-a]pyridin-6-yl)oxy)methyl)morpholine-4-carboxylate | 701.2 (M + H) |
| P151 | 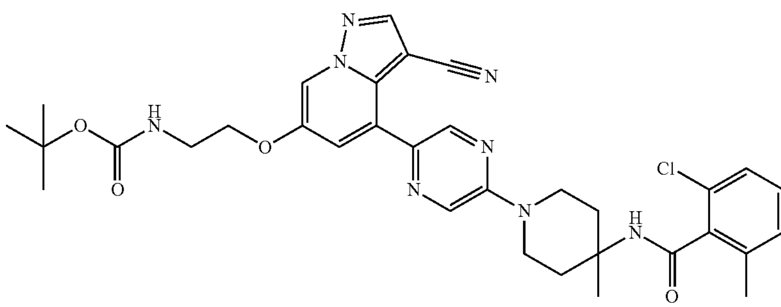 [SMILES: Cc1cccc(Cl)c1C(=O)NC1(C)CCN(c2cnc(-c3cc(OCCNC(=O)OC(C)(C)C)cn4ncc(C#N)c34)cn2)CC1] | tert-butyl (2-((4-(5-(4-(2-chloro-6-methylbenzamido)-4-methylpiperidin-1-yl)pyrazin-2-yl)-3-cyanopyrazolo[1,5-a]pyridin-6-yl)oxy)ethyl)carbamate | 645.2 (M + H) |

Intermediate P152

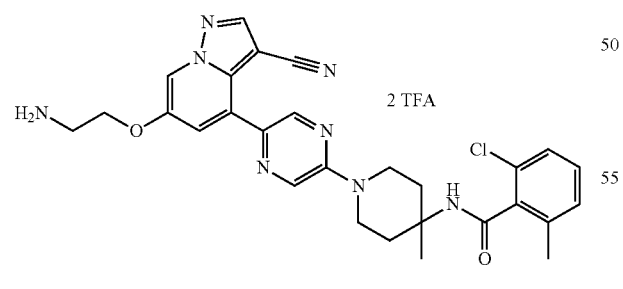

N-(1-(5-(6-(2-aminoethoxy)-3-cyanopyrazolo[1,5-a]pyridin-4-yl)pyrazin-2-yl)-4-methylpiperidin-4-yl)-2-chloro-6-methylbenzamide bis(2,2,2-trifluoroacetate)

A solution tert-butyl (2-((4-(5-(4-(2-chloro-6-methylbenzamido)-4-methylpiperidin-1-yl)pyrazin-2-yl)-3-cyanopyrazolo[1,5-a]pyridin-6-yl)oxy)ethyl)carbamate (Intermediate P151; 134 mg, 0.208 mmol) in DCM (1 mL) and TFA (0.5 mL, 6.53 mmol) was stirred overnight at ambient temperature. The reaction mixture was concentrated in vacuo to afford the title compound (161 mg, quantitative yield). MS (apci) m/z=545.2 (M+H).

Intermediate P153

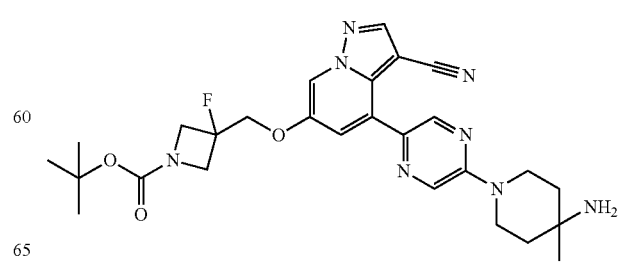

Tert-butyl 3-(((4-(5-(4-amino-4-methylpiperidin-1-yl)pyrazin-2-yl)-3-cyanopyrazolo[1,5-a]pyridin-6-yl)oxy)methyl)-3-fluoroazetidine-1-carboxylate In a pressure tube, a mixture of tert-butyl 3-(((3-cyano-4-(4,4,5,5-tetramethyl-1,3,2-dioxaborolan-2-yl)pyrazolo[1,5-a]pyridin-6-yl)oxy)methyl)-3-fluoroazetidine-1-carboxylate (Intermediate P144; 155 mg, 0.328 mmol), 1-(5-chloropyrazin-2-yl)-4-methylpiperidin-4-amine bis(2,2,2-trifluoroacetate) (Intermediate R47; 149 mg, 0.328 mmol), was treated with 2 M $K_3PO_{4(aq)}$ (492 µL, 0.984 mmol), X-phos (31.3 mg, 0.0656 mmol) and $Pd_2(dba)_3$ (15.0 mg, 0.0164 mmol) in dioxane (1.64 mL) was sparged with $Ar_{(g)}$ for 3 min, and then the vessel was sealed. The reaction mixture was stirred for 4 h at 80° C. After cooling to ambient temperature, the reaction mixture was purified directly, first by silica chromatography (using 0-30% MeOH in DCM as the gradient eluent) then by C18 reverse phase chromatography (using 5-95% ACN in water with 0.1% TFA as the gradient eluent) to afford the TFA salt of the title compound. The TFA salt was diluted with DCM, then extracted with saturated $NaHCO_{3(aq)}$. The organic extracts were dried over anhydrous $Na_2SO_{4(s)}$, filtered, and concentrated in vacuo to cleanly afford the title compound (27 mg, 15% yield). MS (apci) m/z=473.2 (M+H).

Intermediate P154

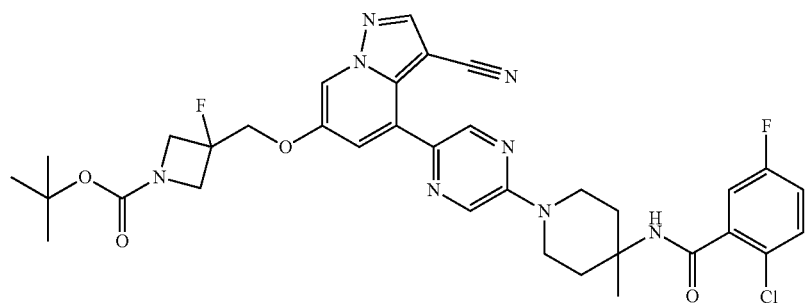 [SMILES: CC1(NC(=O)c2cc(F)ccc2Cl)CCN(c2cnc(-c3cc(OCC4(F)CN(C(=O)OC(C)(C)C)C4)cn4ncc(C#N)c34)cn2)CC1]

Tert-butyl 3-(((4-(5-(4-(2-chloro-5-fluorobenzamido)-4-methylpiperidin-1-yl)pyrazin-2-yl)-3-cyanopyrazolo[1,5-a]pyridin-6-yl)oxy)methyl)-3-fluoroazetidine-1-carboxylate A solution of 2-chloro-5-fluorobenzoic acid (5.9 mg, 0.034 mmol), tert-butyl 3-(((4-(5-(4-amino-4-methylpiperidin-1-yl)pyrazin-2-yl)-3-cyanopyrazolo[15-a]pyridin-6-yl)oxy)methyl)-3-fluoroazetidine-1-carboxylate (Intermediate P153; 6 mg, 0.011 mmol), DIEA (20 µL, 0.11 mmol) and HATU (8.5 mg, 0.022 mmol) in DCM (112 µL) was stirred overnight at ambient temperature. The resulting mixture was purified directly by silica chromatography (using 0-100% EtOAc in Hexanes as the gradient eluent) to cleanly provide the title compound (3 mg, 39% yield). MS (apci) m/z=693.2 (M+H).

Intermediate P155

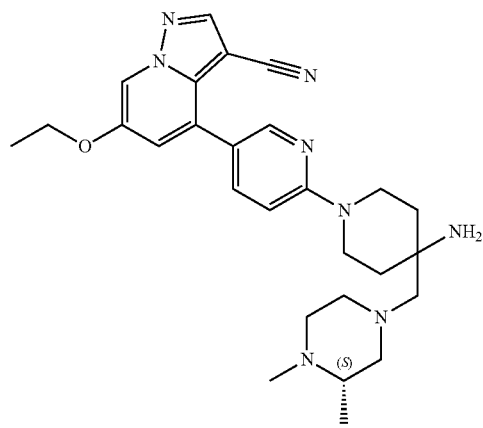

(S)-4-(6-(4-amino-4-((3,4-dimethylpiperazin-1-yl)methyl)piperidin-1-yl)pyridin-3-yl)-6-ethoxypyrazolo[1,5-a]pyridine-3-carbonitrile A solution of tert-butyl (S)-(1-(5-(3-cyano-6-ethoxypyrazolo[1,5-a]pyridin-4-yl)pyridin-2-yl)-4-((3,4-dimethylpiperazin-1-yl)methyl)piperidin-4-yl)carbamate (Intermediate P99; 133.0 mg, 0.2259 mmol) in dioxane (5.0 mL) was treated with 12 M $HCl_{(aq)}$ (37.1 µL, 0.452 mmol). The resulting mixture was stirred for 4 d at ambient temperature before concentrating the mixture in vacuo. The residue was dissolved in 4:1 DCM:iPrOH, and extracted with saturated $NaHCO_{3(aq)}$ (2×). The aqueous extracts were washed with additional 4:1 DCM:iPrOH (3×). The combined organic extracts were dried over anhydrous $Na_2SO_{4(s)}$, filtered and concentrated in vacuo to cleanly afford the title compound (70.1 mg, 64% yield). MS (apci) m/z=489.3 (M+H).

Intermediate P156

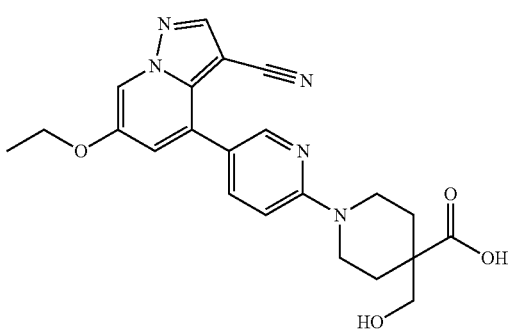 [SMILES: CCOc1cc(-c2ccc(N3CCC(CO)(C(=O)O)CC3)nc2)c2c(C#N)cnn2c1]

Intermediate P156 was isolated as a side product in the preparation of ethyl 1-(5-(3-cyano-6-ethoxy-pyrazolo[1,5-a]pyridin-4-yl)pyridin-2-yl)-4-(hydroxymethyl)piperidine-4-carboxylate (Example 701)

Intermediate P157

2-chloro-N-(1-(5-(3-cyano-6-((3-fluoroazetidin-3-yl)methoxy)pyrazolo[1,5-a]pyridin-4-yl)pyrazin-2-yl)-4-methylpiperidin-4-yl)-5-fluorobenzamide bis(2,2,2-trifluoroacetate)

A solution tert-butyl 3-(((4-(5-(4-(2-chloro-5-fluorobenzamido)-4-methylpiperidin-1-yl)pyrazin-2-yl)-3-cyanopyrazolo[1,5-a]pyridin-6-yl)oxy)methyl)-3-fluoroazetidine-1-carboxylate (Intermediate P154; 19 mg, 0.027 mmol) in DCM (2 mL) and TFA (2 mL, 13 mmol) was stirred for 2 h at ambient temperature. The reaction mixture was concentrated in vacuo to afford the title compound (16 mg, 73% yield). MS (apci) m/z=593.2 (M+H).

Intermediate P158

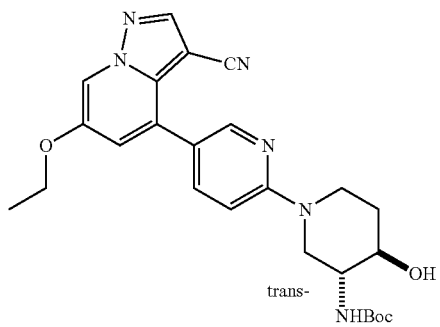 [SMILES: CCOc1cc(-c2ccc(N3CC[C@@H](O)[C@H](NC(=O)OC(C)(C)C)C3)nc2)c2c(C#N)cnn2c1]

tert-butyl ((3r,4r)-1-(5-(3-cyano-6-ethoxypyrazolo[1,5-a]pyridin-4-yl)pyridin-2-yl)-4-hydroxypiperidin-3-yl)carbamate A mixture of 6-ethoxy-4-(6-fluoropyridin-3-yl)pyrazolo[1,5-a]pyridine-3-carbonitrile (Intermediate P6, 0.204 g, 0.723 mmol), tert-butyl ((3r,4r)-4-hydroxypiperidin-3-yl)carbamate (0.313 g, 1.45 mmol) and DIEA (0.378 ml, 2.17 mmol) in DMSO (1.81 mL) was heated at 90° C. overnight. After cooling to RT, the reaction mixture was partitioned between EtOAc and water. After phase-separation, the aqueous layer was extracted with EtOAc. The organic extracts were combined, washed with brine, dried with $Na_2SO_4$ and concentrated to yield the title product (0.33 g, 0.69 mmol, 95% yield). MS (apci) m/z=479.2 (M+H).

Intermediate P159

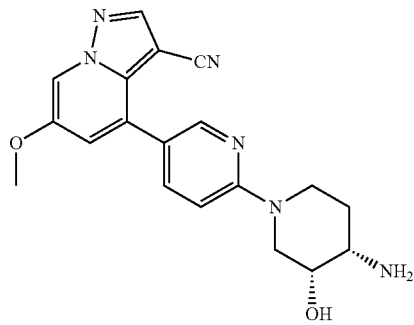 [SMILES: COc1cc(-c2ccc(N3CC[C@H](N)[C@H](O)C3)nc2)c2c(C#N)cnn2c1]

4-(6-((3R,4S)-4-amino-3-hydroxypiperidin-1-yl)pyridin-3-yl)-6-methoxypyrazolo[1,5-a]pyridine-3-carbonitrile Step 1: Preparation of tert-butyl ((3R,4S)-1-(5-(3-cyano-6-methoxypyrazolo[1,5-a]pyridin-4-yl)pyridin-2-yl)-3-hydroxypiperidin-4-yl)carbamate A mixture of 4-(6-fluoropyridin-3-yl)-6-methoxypyrazolo[1,5-a]pyridine-3-carbonitrile (Intermediate P93, 0.206 g, 0.768 mmol), tert-butyl ((3R,4S)-3-hydroxypiperidin-4-yl)carbamate (0.216 g, 0.998 mmol) and DIEA (0.669 mL, 3.84 mmol) in DMSO (1.92 mL) was heated to 90° C. overnight. The reaction mixture was worked up with EtOAc and water. The organic layers were washed with brine, dried with $Na_2SO_4$, filtered and concentrated. The crude material was purified by silica chromatography (1-10% MeOH in DCM) to yield the title product (0.223 g, 62.5% yield). MS (apci) m/z=465.2 (M+H).

Step 2: Preparation of 4-(6-((3R,4S)-4-amino-3-hydroxypiperidin-1-yl)pyridin-3-yl)-6-methoxypyrazolo[1,5-a]pyridine-3-carbonitrile Tert-butyl ((3R,4S)-1-(5-(3-cyano-6-methoxypyrazolo[1,5-a]pyridin-4-yl)pyridin-2-yl)-3-hydroxypiperidin-4-yl)carbamate (0.223 g, 0.480 mmol) was taken up in DCM and TFA (1 mL each) and stirred for 1 h. The mixture was concentrated, taken up in DCM and stirred with MP-carbonate for 20 min. The mixture was filtered and concentrated to give the title product (0.055 g, 31.4% yield). MS (apci) m/z=365.1 (M+H).

Intermediate P160

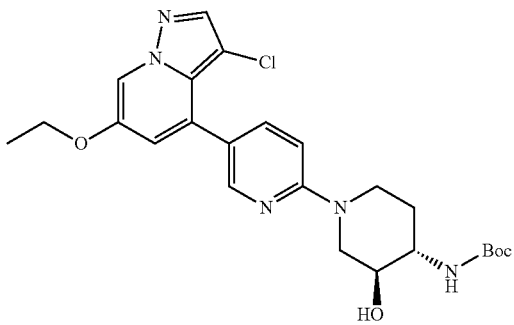 [SMILES: CCOc1cc(-c2ccc(N3CC[C@H](NC(=O)OC(C)(C)C)[C@@H](O)C3)nc2)c2c(Cl)cnn2c1]

tert-butyl ((3S,4S)-1-(5-(3-chloro-6-ethoxypyrazolo [1,5-a]pyridin-4-yl)pyridin-2-yl)-3-hydroxypiperidin-4-yl)carbamate A solution of 3-chloro-6-ethoxy-4-(6-fluoropyridin-3-yl) pyrazolo[1,5-a]pyridine (Example 425, Step 2; 93.1 mg, 0.319 mmol) and tert-butyl ((3S,4S)-3-hydroxypiperidin-4-yl)carbamate (104 mg, 0.479 mmol) in DMSO (2 mL) was treated with DIEA (0.279 mL, 1.60 mmol) and stirred at 115° C. overnight. After cooling to RT, the reaction mixture was diluted with water and filtered, yielding the title compound (112 mg, 72% yield). MS (apci) m/z=488.2 (M+H).

Intermediate P161

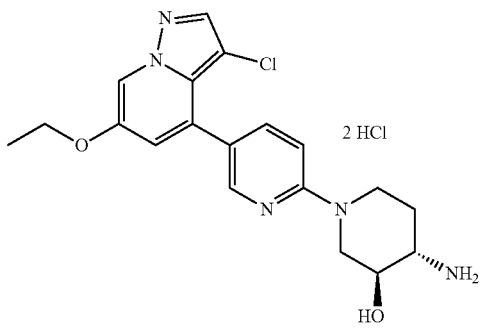 [SMILES: CCOc1cc(-c2ccc(N3CC[C@H](N)[C@@H](O)C3)nc2)c2c(Cl)cnn2c1]

(3S,4S)-4-amino-1-(5-(3-chloro-6-ethoxypyrazolo[1, 5-a]pyridin-4-yl)pyridin-2-yl)piperidin-3-ol dihydrochloride A solution of tert-butyl ((3S,4S)-1-(5-(3-chloro-6-ethoxy-pyrazolo[1,5-a]pyridin-4-yl)pyridin-2-yl)-3-hydroxypiperidin-4-yl)carbamate (Intermediate P160, 110 mg, 0.225 mmol) in 1,4-dioxane (2 mL, 0.225 mmol) was treated with HCl (0.0370 mL, 0.451 mmol) and stirred at RT overnight. Removal of solvent under vacuum yielded the title compound as solid assuming quantitative yield. MS (apci) m/z=388.2 (M+H).

Intermediate P162

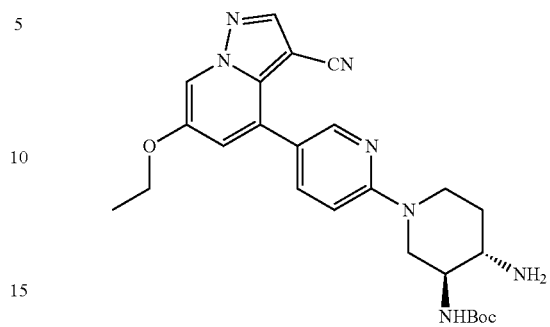

tert-butyl ((3S,4S)-4-amino-1-(5-(3-cyano-6-ethoxy-pyrazolo[1,5-a]pyridin-4-yl)pyridin-2-yl)piperidin-3-yl)carbamate Step 1: Preparation of tert-butyl ((3S,4R)-1-(5-(3-cyano-6-ethoxypyrazolo[1,5-a]pyridin-4-yl)pyridin-2-yl)-4-hydroxypiperidin-3-yl)carbamate A mixture of 6-ethoxy-4-(6-fluoropyridin-3-yl)pyrazolo [1,5-a]pyridine-3-carbonitrile (Intermediate P6, 0.270 g, 0.957 mmol), tert-butyl ((3S,4R)-4-hydroxypiperidin-3-yl) carbamate (0.414 g, 1.91 mmol) and Hunig's base (0.500 ml, 2.87 mmol) in DMSO (2.39 mL) was heated to 90° C. overnight. The reaction mixture was worked up with EtOAc and water. The organic layers were washed with brine, dried with $Na_2SO_4$, filtered and concentrated to yield the title compound (0.291 g, 63.6% yield). MS (apci) m/z=479.2 (M+H).

Step 2: Preparation of (3S,4R)-3-((tert-butoxycarbonyl)amino)-1-(5-(3-cyano-6-ethoxypyrazolo[1,5-a] pyridin-4-yl)pyridin-2-yl)piperidin-4-yl methanesulfonate A mixture of tert-butyl ((3S,4R)-1-(5-(3-cyano-6-ethoxy-pyrazolo[1,5-a]pyridin-4-yl)pyridin-2-yl)-4-hydroxypiperidin-3-yl)carbamate (0.291 g, 0.608 mmol), methanesulfonyl chloride (0.0471 ml, 0.608 mmol) and Hunig's base (0.159 ml, 0.912 mmol) in DCM (6.08 mL) was stirred at RT overnight. The mixture was the worked up with DCM and water. The organic layers were washed with brine, dried with $Na_2SO_4$, filtered and concentrated to yield the title compound (0.293 g, 86.6% yield). MS (apci) m/z=557.2 (M+H).

Step 3: Preparation of tert-butyl ((3S,4S)-4-azido-1-(5-(3-cyano-6-ethoxypyrazolo[1,5-a]pyridin-4-yl) pyridin-2-yl)piperidin-3-yl)carbamate (3S,4R)-3-((tert-butoxycarbonyl)amino)-1-(5-(3-cyano-6-ethoxypyrazolo[1,5-a]pyridin-4-yl)pyridin-2-yl)piperidin-4-yl methanesulfonate (0.293 g, 0.526 mmol) and $NaN_3$ (0.0513 g, 0.790 mmol) in DMF (2.11 mL) was heated to 90° C. overnight. The mixture was worked up with DCM and water. The organic layers were washed with brine, dried with $Na_2SO_4$, filtered and concentrated. The crude material was purified by silica chromatography (1-10% MeOH in DCM) to yield the title compound (0.177 g, 66.8% yield). MS (apci) m/z=504.2 (M+H).

Step 4: Preparation of tert-butyl ((3S,4S)-4-amino-1-(5-(3-cyano-6-ethoxypyrazolo[1,5-a]pyridin-4-yl)pyridin-2-yl)piperidin-3-yl)carbamate Tert-butyl ((3S,4 S)-4-azido-1-(5-(3-cyano-6-ethoxypyrazolo[1,5-a]pyridin-4-yl)pyridin-2-yl)piperidin-3-yl)carbamate (0.177 g, 0.351 mmol) and Pd/C (0.00748 g, 0.0703 mmol) in MeOH (3.51 mL) was stirred under $H_2$ balloon overnight. This was the filtered and concentrated to give the title compound (0.152 g, 90.6% yield). MS (apci) m/z=478.2 (M+H).

Intermediate P163

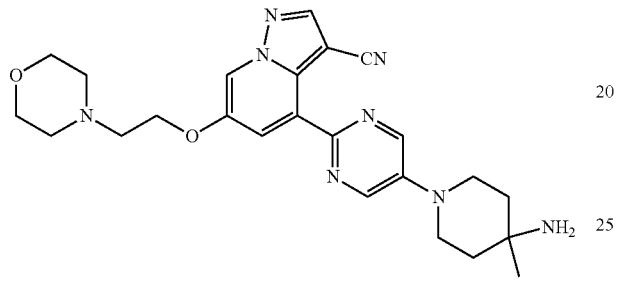

4-(5-(4-amino-4-methylpiperidin-1-yl)pyrimidin-2-yl)-6-(2-morpholinoethoxy)pyrazolo[1,5-a]pyridine-3-carbonitrile

Step 1: Preparation of 4-(5-bromopyrimidin-2-yl)-6-(2-morpholinoethoxy)pyrazolo[1,5-a]pyridine-3-carbonitrile To a mixture of (3-cyano-6-(2-morpholinoethoxy)pyrazolo[1,5-a]pyridin-4-yl)boronic acid (Intermediate P127, 86 mg, 0.27 mmol) and 5-bromo-2-iodopyrimidine (78 mg, 0.27 mmol) in dioxane (2 mL) and water (0.8 mL) was added XPhos (26 mg, 0.054 mmol), $Pd_2(dba)_3$ (12 mg, 0.014 mmol) and 2M $K_3PO_4$ (0.4 mL, 0.8 mmol). The reaction was heated to 60° C. for 3 hours. After cooling to RT, the reaction was partitioned between DCM and water (15 mL each), followed by extracting the aqueous with DCM (2×15 mL). The organic extracts were combined and concentrated. The crude material was purified by silica chromatography (0 to 100% acetone in hexanes) to yield the title compound (48 mg, 41%). MS (apci) m/z=429.1, 431.1 (M+H).

Step 2: Preparation of tert-butyl (1-(2-(3-cyano-6-(2-morpholinoethoxy)pyrazolo[1,5-a]pyridin-4-yl)pyrimidin-5-yl)-4-methylpiperidin-4-yl)carbamate A mixture of 4-(5-bromopyrimidin-2-yl)-6-(2-morpholinoethoxy)pyrazolo[1,5-a]pyridine-3-carbonitrile (48 mg, 0.11 mmol), tert-butyl (4-methylpiperidin-4-yl)carbamate (36 mg, 0.17 mmol), $Cs_2CO_3$ (73 mg, 0.22 mmol), XPHOS (11 mg, 0.022 mmol) and $Pd_2dba_3$ (10 mg, 0.011 mmol) in dioxane (1 mL) was heated at 90° C. overnight. The reaction mixture was diluted with water (25 mL) and extracted with DCM (2×25 mL). The combined organic extracts were filtered through a Celite® pad and concentrated under reduced pressure. The crude material was purified by silica chromatography (10-100% acetone in hexanes) to yield the title compound (22 mg, 35%). MS (apci) m/z=563.3 (M+H).

Step 3: Preparation of 4-(5-(4-amino-4-methylpiperidin-1-yl)pyrimidin-2-yl)-6-(2-morpholinoethoxy)pyrazolo[1,5-a]pyridine-3-carbonitrile A mixture of tert-butyl (1-(2-(3-cyano-6-(2-morpholinoethoxy)pyrazolo[1,5-a]pyridin-4-yl)pyrimidin-5-yl)-4-methylpiperidin-4-yl)carbamate (22 mg, 0.04 mmol) in 1:1 DCM:TFA was stirred at RT for 1 h and then concentrated. The crude material was taken up in minimal amount of MeOH and passed thru a P1-HCO$_3$ resin plug. Removal of solvent under reduced pressure yielded the title compound with quantitative yield. MS (apci) m/z=463.2 (M+H).

Intermediate P164

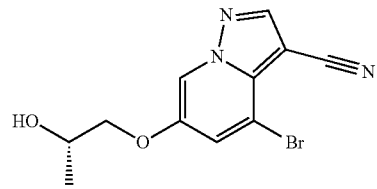 [SMILES: C[C@H](O)COc1cc(Br)c2c(C#N)cnn2c1]

(S)-4-bromo-6-(2-hydroxypropoxy)pyrazolo[1,5-a]pyridine-3-carbonitrile

A mixture of 4-bromo-6-hydroxypyrazolo[1,5-a]pyridine-3-carbonitrile (Intermediate P1; 500 mg, 2.10 mmol) in DMF (4 mL) was treated sequentially with $K_2CO_{3(s)}$ (1451 mg, 10.5 mmol) and (S)-2-methyloxirane (1830 mg, 31.5 mmol). The reaction mixture was stirred for 3 d at 50° C. in a sealed vessel. After cooling to ambient temperature, the reaction mixture was diluted with water (50 mL) and extracted with DCM (2×50 mL). The combined organic extracts were washed with brine (50 mL). The resultant emulsion was filtered through a coarse glass frit, and the biphasic filtrate was separated. The organic extracts were washed again with brine (50 mL), then dried over anhydrous $MgSO_{4(s)}$, filtered and concentrated in vacuo. The crude residue was purified by silica chromatography (using 0-90% EtOAc/Hexanes as the gradient eluent) to cleanly provide the title compound (357 mg, 57% yield). $^1$H NMR (400 MHz, CDCl$_3$) δ 8.21 (s, 1H), 8.14 (d, 1H), 7.49 (d, 1H), 4.25 (m, 1H), 3.96 (dd, 1H), 3.86 (dd, 1H), 1.33 (d, 3H).

Intermediate P165

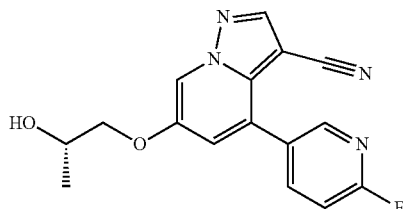

(S)-4-(6-fluoropyridin-3-yl)-6-(2-hydroxypropoxy)pyrazolo[1,5-a]pyridine-3-carbonitrile In a pressure tube, a solution of (S)-4-bromo-6-(2-hydroxypropoxy)pyrazolo[1,5-a]pyridine-3-carbonitrile (Intermediate P164; 357 mg, 1.21 mmol) in dioxane (6 mL) was treated with 2-fluoro-5-(4,4,5,5-tetramethyl-1,3,2-dioxaborolan-2-yl)pyridine (323 mg, 1.45 mmol), and 2 M Na$_2$CO$_{3(aq)}$ (1808 μL, 3.62 mmol) was sparged with N$_{2(g)}$ for 5 min. The resulting mixture was treated with Pd(PPh$_3$)$_4$ (34.8 mg, 0.0301 mmol) then sparged again with N$_{2(g)}$ for 5 min, before sealing the vessel. The reaction mixture was stirred for 22 h at 80° C. After cooling to ambient temperature, the reaction mixture was diluted with water (25 mL) and stirred for 1 h. The resulting suspension was vacuum filtered and the solids were collected to cleanly provide the title compound (191 mg, 51% yield). MS (apci) m/z=313.1 (M+H).

Intermediate P166

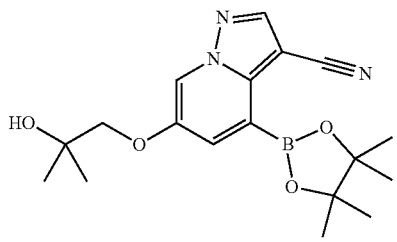 [SMILES: CC(C)(O)COc1cc(B2OC(C)(C)C(C)(C)O2)c2c(C#N)cnn2c1]

6-(2-hydroxy-2-methylpropoxy)-4-(4,4,5,5-tetramethyl-1,3,2-dioxaborolan-2-yl)pyrazolo[1,5-a]pyridine-3-carbonitrile In a pressure vessel, a mixture of 4-bromo-6-(2-hydroxy-2-methylpropoxy)pyrazolo[1,5-a]pyridine-3-carbonitrile (Intermediate P41; 2.0 g, 6.4 mmol), bis(pinacolato)diboron (2.5 g, 9.7 mmol), PdCl$_2$(dppf).CH$_2$Cl$_2$ (0.53 g, 0.64 mmol), and KOAc (1.9 g, 19 mmol) in dioxane (15 mL) was sparged with Ar$_{(g)}$ for 10 min. The vessel was sealed and the mixture was stirred overnight at 90° C. After cooling to room temperature, the reaction mixture was diluted with EtOAc (100 mL). The resulting suspension was filtered, and the filter cake was washed with EtOAc. The filtrate was concentrated in vacuo, and the residue was purified by silica chromatography (25% EtOAc in Hexanes as the eluent) to afford the title compound (2.2 g, 91% yield). $^1$H-NMR (400 MHz, CDCl$_3$) δ: 8.19 (s, 1H), 8.17 (d, J=2.3 Hz, 1H), 7.66 (d, J=2.3 Hz, 1H), 3.80 (s, 2H), 1.41 (s, 12H), 1.35 (s, 6H).

Intermediate P167

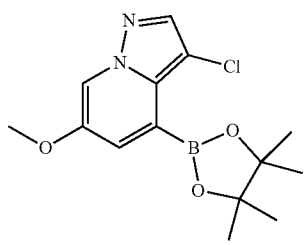

3-chloro-6-methoxy-4-(4,4,5,5-tetramethyl-1,3,2-dioxaborolan-2-yl)pyrazolo[1,5-a]pyridine A mixture of 4-bromo-3-chloro-6-methoxypyrazolo[1,5-a]pyridine (Intermediate P84, Step 1; 152 mg, 0.581 mmol), PdCl$_2$(dppf).CH$_2$Cl$_2$ (23.7 mg, 0.029 mmol), KOAc (285 mg, 2.91 mmol) and bis(pinacolato)diboron (443 mg, 1.74 mmol) in dioxane (5.8 mL) was sparged with Ar$_{(g)}$. The reaction vessel was sealed, and the mixture was stirred for 2 h 15 min at 90° C. After cooling to ambient temperature, the reaction mixture was filtered through Celite®. The filtrate was concentrated in vacuo to afford the title compound (102 mg, 57%). MS (apci) m/z=309.1 (M+H).

Intermediate P168

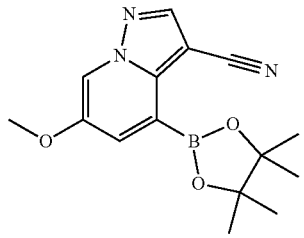

6-methoxy-4-(4,4,5,5-tetramethyl-1,3,2-dioxaborolan-2-yl)pyrazolo[1,5-a]pyridine-3-carbonitrile A mixture of 4-bromo-6-methoxypyrazolo[1,5-a]pyridine-3-carbonitrile (Intermediate P1, Step 6; 150 mg, 0.6 mmol), PdCl$_2$(dppf) (17 mg, 0.02 mmol), KOAc (165 mg, 1.7 mmol) and 4,4,4',4',5,5,5',5'-octamethyl-2,2'-bi(1,3,2-dioxaborolane) (267 mg, 1.05 mmol) in dioxane (4 mL) was sparged with argon, then heated to 90° C. for 3 h. After cooling to RT, the reaction was filtered through Celite® and concentrated. The crude material was purified by silica chromatography (0-10% MeOH/DCM) to afford the title product (126 mg, 70%).

Intermediate P169

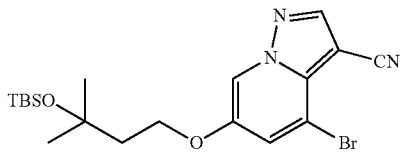 [SMILES: CC(C)(CCOc1cc(Br)c2c(C#N)cnn2c1)O[Si](C)(C)C(C)(C)C]

4-bromo-6-(3-((tert-butyldimethylsilyl)oxy)-3-methylbutoxy)pyrazolo[1,5-a]pyridine-3-carbonitrile To a solution of 4-bromo-6-hydroxypyrazolo[1,5-a]pyridine-3-carbonitrile (Intermediate P1; 194 mg, 0.815 mmol) in DMA (4.0 mL, 0.815 mmol) was added K$_2$CO$_3$ (338 mg, 2.44 mmol) then ((4-bromo-2-methylbutan-2-yl)oxy)(tert-butyl)dimethylsilane (459 mg, 1.63 mmol). The reaction was sealed and heated at 60° C. overnight. After cooling to RT, the reaction was diluted with brine and filtered, rinsed with water. The solid obtained was dissolved in minimal amount of DCM, followed by addition of Et$_2$O to induce precipitation. After stirred for 2 h, the suspension was filtered to afford the title product (250 mg, 70%). 1H-NMR (400 MHz, CDCl$_3$) δ: 8.19 (s, 1H), 8.09 (br d, 1H), 7.42 (br d, 1H), 4.13 (t, 2H), 1.97 (t, 2H), 1.31 (s, 6H), 0.86 (s, 9H), 0.10 (s, 6H).

Intermediate P170

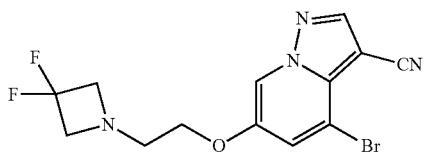 [SMILES: N#Cc1cnn2cc(OCCN3CC(F)(F)C3)cc(Br)c12]

4-bromo-6-(2-(3,3-difluoroazetidin-1-yl)ethoxy)
pyrazolo[1,5-a]pyridine-3-carbonitrile To a mixture of 4-bromo-6-(2-chloroethoxy)pyrazolo[1,5-a]pyridine-3-carbonitrile (Intermediate P125; 50 mg, 0.17 mmol) in DMF (0.33 mL) were added DIEA (291 µl, 1.7 mmol), followed by 3,3-difluoroazetidine (46 mg, 0.50 mmol). The reaction was stirred at 60° C. for 4 d, after which additional 3,3-difluoroazetidine (46 mg, 0.50 mmol) was added and heating resumed for another 16 h to reach completion. The reaction was diluted with water and filtered to afford the title product, which was directly used without further purifications (31 mg, 37%). MS (apci) m/z=357, 359 (M+H).

Intermediate P171

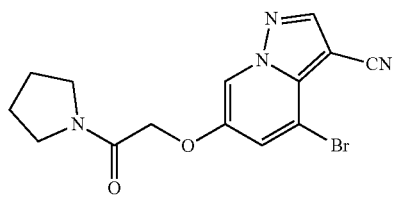 [SMILES: N#Cc1cnn2cc(OCC(=O)N3CCCC3)cc(Br)c12]

4-bromo-6-(2-oxo-2-(pyrrolidin-1-yl)ethoxy)pyrazolo[1,5-a]pyridine-3-carbonitrile To a solution of 4-bromo-6-hydroxypyrazolo[1,5-a]pyridine-3-carbonitrile (Intermediate P1; 100 mg, 0.420 mmol) in DMA (2 mL) were added $K_2CO_3$ (87.1 mg, 0.63 mmol) then 2-chloro-1-(pyrrolidin-1-yl)ethan-1-one (74.4 mg, 0.504 mmol). The reaction was heated at 50° C. overnight, then poured into water (10 mL) and stirred for 1 h before it was filtered and rinsed with water (5 mL), yielding the title product as beige solid (127 mg, 86%). $^1$HNMR (CDCl$_3$) δ 8.20 (s, 1H), 8.19 (d, 1H), 7.50 (d, 1H), 4.66 (s, 2H), 3.54 (t, 2H), 3.47 (t, 2H), 2.04 (m, 2H), 1.90 (m, 2H).

Intermediate P172

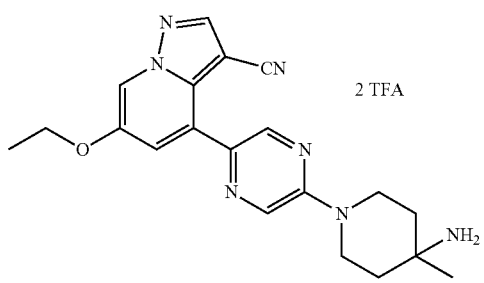 [SMILES: CCOc1cc(-c2cnc(N3CCC(C)(N)CC3)cn2)c2c(C#N)cnn2c1]

4-(5-(4-amino-4-methylpiperidin-1-yl)pyrazin-2-yl)-6-ethoxypyrazolo[1,5-a]pyridine-3-carbonitrile bis(2,2,2-trifluoroacetate)

Step 1: Preparation of tert-butyl (1-(5-(3-cyano-6-ethoxypyrazolo[1,5-a]pyridin-4-yl)pyrazin-2-yl)-4-methylpiperidin-4-yl)carbamate A mixture of 6-ethoxy-4-(4,4,5,5-tetramethyl-1,3,2-dioxaborolan-2-yl)pyrazolo[1,5-a]pyridine-3-carbonitrile (Intermediate P110; 500 mg, 1.60 mmol), tert-butyl (1-(5-chloropyrazin-2-yl)-4-methylpiperidin-4-yl)carbamate (Intermediate R46; 521.8 mg, 1.60 mmol), $K_3PO_4$ (2 M aq, 2.4 mL, 4.79 mmol), dicyclohexyl(2',4',6'-triisopropyl-[1,1'-biphenyl]-2-yl)phosphane (152.2 mg, 0.32 mmol) and Pd$_2$(dba)$_3$ (73.10 mg, 0.080 mmol) in 1,4-dioxane (8.0 mL) was degassed with argon for 3 min, then sealed and heated to 80° C. overnight. After an aqueous workup the crude material was purified using silica chromatography (0-100% EtOAc in hexanes) to afford the title product (338.5 mg, 44%). MS (apci) m/z=478.2 (M+H).

Step 2: Preparation of 4-(5-(4-amino-4-methylpiperidin-1-yl)pyrazin-2-yl)-6-ethoxypyrazolo[1,5-a]pyridine-3-carbonitrile bis(2,2,2-trifluoroacetate)

To a solution of tert-butyl (1-(5-(3-cyano-6-ethoxypyrazolo[1,5-a]pyridin-4-yl)pyrazin-2-yl)-4-methylpiperidin-4-yl)carbamate (338.5 mg, 0.71 mmol) in DCM (2 mL) was added 2,2,2-trifluoroacetic acid (2 mL). After stirred at RT for 1 h, the reaction was diluted with Et$_2$O (20 mL) and filtered to afford the title product (342 mg, 80%). MS (apci) m/z=378.1 (M+H).

Intermediate P173

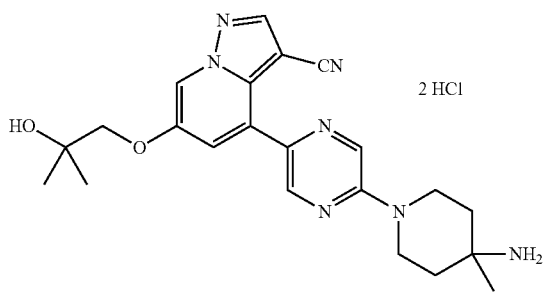 [SMILES: CC(C)(O)COc1cc(-c2cnc(N3CCC(C)(N)CC3)cn2)c2c(C#N)cnn2c1]

4-(5-(4-amino-4-methylpiperidin-1-yl)pyrazin-2-yl)-6-(2-hydroxy-2-methylpropoxy)pyrazolo[1,5-a]pyridine-3-carbonitrile dihydrochloride The title product was prepared according to the procedure described in Intermediate P172, replacing 6-ethoxy-4-(4,4,5,5-tetramethyl-1,3,2-dioxaborolan-2-yl)pyrazolo[1,5-a]pyridine-3-carbonitrile with 6-(2-hydroxy-2-methylpropoxy)-4-(4,4,5,5-tetramethyl-1,3,2-dioxaborolan-2-yl)pyrazolo[1,5-a]pyridine-3-carbonitrile (Intermediate P166) in Step 1. MS (apci) m/z=422.3 (M+H).

Intermediate P174

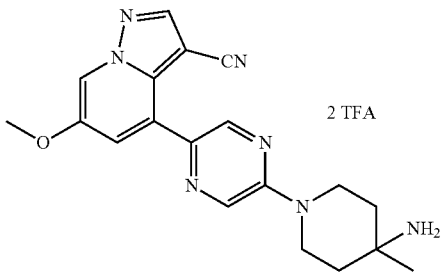 [SMILES: COc1cc(-c2cnc(N3CCC(C)(N)CC3)cn2)c2c(C#N)cnn2c1]

4-(5-(4-amino-4-methylpiperidin-1-yl)pyrazin-2-yl)-6-methoxypyrazolo[1,5-a]pyridine-3-carbonitrile bis(2,2,2-trifluoroacetate)

Step 1: Preparation of tert-butyl (4-methyl-1-(5-(4,4,5,5-tetramethyl-1,3,2-dioxaborolan-2-yl)pyrazin-2-yl)piperidin-4-yl)carbamate In a pressure vessel were combined tert-butyl (1-(5-chloropyrazin-2-yl)-4-methylpiperidin-4-yl)carbamate (Intermediate R46; 26 mg, 0.080 mmol), 4,4,4',4',5,5,5',5'-octamethyl-2,2'-bi(1,3,2-dioxaborolane) (202 mg, 0.80 mmol), PdCl$_2$(dppf)-DCM (6.5 mg, 0.0080 mmol), KOAc (39 mg, 0.40 mmol) and dioxane (796 µl). The reaction mixture was sparged with argon for 10 min before it was sealed and heated to 90° C. overnight. After cooling to RT, the reaction was partitioned between DCM and water, extracting the aqueous with DCM (3×) after phase-separation. The combined organic extracts were washed with brine, then dried (Na$_2$SO$_4$), filtered and concentrated. The crude material was used directly in the next step assuming quantitative yield

Step 2: Preparation of tert-butyl (1-(5-(3-cyano-6-methoxypyrazolo[1,5-a]pyridin-4-yl)pyrazin-2-yl)-4-methylpiperidin-4-yl)carbamate A mixture of 4-bromo-6-methoxypyrazolo[1,5-a]pyridine-3-carbonitrile (Intermediate P1, Step 6; 300 mg, 1.19 mmol), tert-butyl (4-methyl-1-(5-(4,4,5,5-tetramethyl-1,3,2-dioxaborolan-2-yl)pyrazin-2-yl)piperidin-4-yl)carbamate (1158 mg, 1.19 mmol), Pd(Ph$_3$P)$_4$ (138 mg, 0.119 mmol) and Na$_2$CO$_3$ (2 M aq, 3.6 mL, 7.14 mmol) in dioxane (6.0 mL) was sparged with argon for 10 min then heated to 80° C. overnight. After cooling to ambient temperature, the reaction was diluted with water (10 mL) and extracted with 4:1 DCM:IPA (5×10 mL). The combined organic extractions was passed through a Phase Separator frit, and the filtrate was concentrated then purified by silica gel chromatography (0-10% MeOH in DCM) to afford the title product as solid (173 mg, 31%). MS (apci) m/z=464.2 (M+H).

Step 3: Preparation of 4-(5-(4-amino-4-methylpiperidin-1-yl)pyrazin-2-yl)-6-methoxypyrazolo[1,5-a]pyridine-3-carbonitrile bis(2,2,2-trifluoroacetate)

To a solution of tert-butyl (1-(5-(3-cyano-6-methoxypyrazolo[1,5-a]pyridin-4-yl)pyrazin-2-yl)-4-methylpiperidin-4-yl)carbamate (173 mg, 0.336 mmol) in DCM (2 mL) was added TFA (2 mL). After stirred at RT for 30 min, the reaction was diluted with Et$_2$O (20 mL) and filtered to yield the title product (163 mg, 78%). MS (apci) m/z=364.2 (M+H).

Intermediate P175

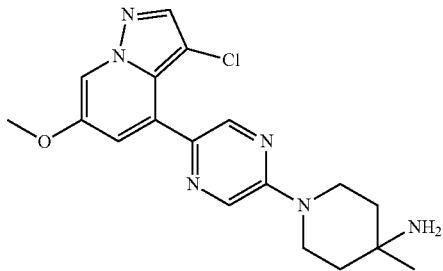 [SMILES: COc1cc(-c2cnc(N3CCC(C)(N)CC3)cn2)c2c(Cl)cnn2c1]

1-(5-(3-chloro-6-methoxypyrazolo[1,5-a]pyridin-4-yl)pyrazin-2-yl)-4-methylpiperidin-4-amine A mixture of 3-chloro-6-methoxy-4-(4,4,5,5-tetramethyl-1,3,2-dioxaborolan-2-yl)pyrazolo[1,5-a]pyridine (P167 55 mg, 0.18 mmol), 1-(5-chloropyrazin-2-yl)-4-methylpiperidin-4-amine (R47, 40 mg, 0.18 mmol), dicyclohexyl(2',4',6'-triisopropyl-[1,1'-biphenyl]-2-yl)phosphane (17 mg, 0.036 mmol)), and Pd$_2$(dba)$_3$ (8.2 mg, 0.0089 mmol) in 1,4-dioxane (891 µL) and K$_3$PO$_4$ (2 M aq, 267 µL) was sparged with argon before sealed and heated to 80° C. overnight. After cooling to RT, the reaction was diluted with DCM, washed with water and brine, then dried (Na$_2$SO$_4$), filtered and concentrated. The residue was purified using silica chromatography (0-20% MeOH in DCM with 0.2% NH$_4$OH) to afford the title compound (29 mg, 44%). LCMS m/z=373.1 (M+H).

Intermediate P176

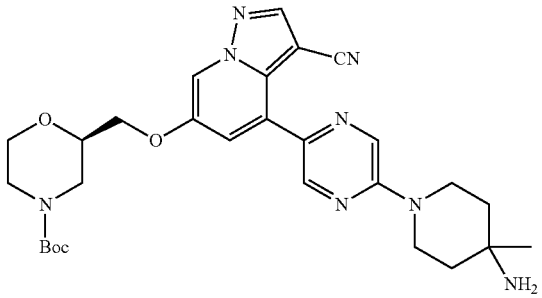 [SMILES: CC1(N)CCN(c2cnc(-c3cc(OC[C@H]4CN(C(=O)OC(C)(C)C)CCO4)cn4ncc(C#N)c34)cn2)CC1]

tert-butyl (R)-2-(((4-(5-(4-amino-4-methylpiperidin-1-yl)pyrazin-2-yl)-3-cyanopyrazolo[1,5-a]pyridin-6-yl)oxy)methyl)morpholine-4-carboxylate The title compound (36 mg, 16%) was prepared by a similar method as described in Intermediate P175, replacing 3-chloro-6-methoxy-4-(4,4,5,5-tetramethyl-1,3,2-dioxaborolan-2-yl)pyrazolo[1,5-a]pyridine with tert-butyl (R)-2-(((3-cyano-4-(4,4,5,5-tetramethyl-1,3,2-dioxaborolan-2-yl)pyrazolo[1,5-a]pyridin-6-yl)oxy)methyl)morpholine-4-carboxylate (Intermediate P140). LCMS m/z=549.3 (M+H).

Intermediate P177

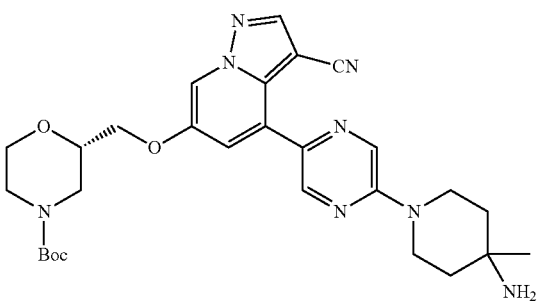 [SMILES: CC1(N)CCN(c2cnc(-c3cc(OC[C@@H]4CN(C(=O)OC(C)(C)C)CCO4)cn4ncc(C#N)c34)cn2)CC1]

tert-butyl (S)-2-(((4-(5-(4-amino-4-methylpiperidin-1-yl)pyrazin-2-yl)-3-cyanopyrazolo[1,5-a]pyridin-6-yl)oxy)methyl)morpholine-4-carboxylate The title compound (36 mg, 16%) was prepared by a similar method as described in Intermediate P175, replacing 3-chloro-6-methoxy-4-(4,4,5,5-tetramethyl-1,3,2-dioxaborolan-2-yl)pyrazolo[1,5-a]pyridine with tert-butyl (S)-2-(((3-cyano-4-(4,4,5,5-tetramethyl-1,3,2-dioxaborolan-2-yl)pyrazolo[1,5-a]pyridin-6-yl)oxy)methyl)morpholine-4-carboxylate (Intermediate P146). LCMS m/z=549.3 (M+H).

Intermediate R3

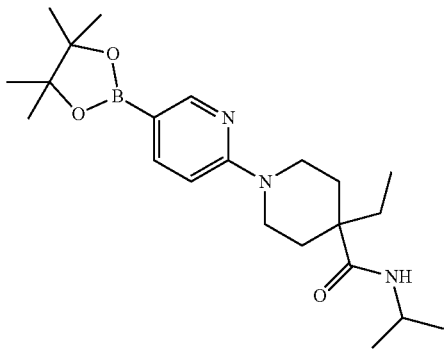 [SMILES: CCC1(C(=O)NC(C)C)CCN(c2ccc(B3OC(C)(C)C(C)(C)O3)cn2)CC1]

4-Ethyl-N-isopropyl-1-(5-(4,4,5,5-tetramethyl-1,3,2-dioxaborolan-2-yl)pyridin-2-yl)piperidine-4-carboxamide

Step 1: Preparation of 1-(5-boronopyridin-2-yl)-4-ethylpiperidine-4-carboxylic acid A solution of 2-fluoro-5-(4,4,5,5-tetramethyl-1,3,2-dioxaborolan-2-yl)pyridine (2.0 g, 9.0 mmol) in DMSO (18 mL) was treated with 4-ethylpiperidine-4-carboxylic acid (4.7 g, 30 mmol) and $K_2CO_{3(s)}$ (5.0 g, 36 mmol). The resulting mixture was stirred overnight at 80° C. After cooling to ambient temperature, the reaction mixture was diluted with water, and extracted with 20% MeOH/DCM. The combined organic extracts were dried over anhydrous $Na_2SO_{4(s)}$, filtered, and concentrated in vacuo to afford the title compound (4.2 g, quantitative yield). The material was carried forward without further purification. MS (apci) m/z=320.2 (M+H).

Step 2: Preparation of 4-Ethyl-N-isopropyl-1-(5-(4,4,5,5-tetramethyl-1,3,2-dioxaborolan-2-yl)pyridin-2-yl)piperidine-4-carboxamide A solution of 1-(5-boronopyridin-2-yl)-4-ethylpiperidine-4-carboxylic acid (2.45 g, 8.81 mmol) in DMA (35 mL) was treated sequentially with DIEA (8.44 mL, 48.5 mmol), propan-2-amine (2.25 mL, 26.4 mmol), and HATU (8.37 g, 22.0 mmol), then stirred overnight at ambient temperature. The resulting mixture was diluted with water, and extracted with 20% MeOH/DCM. The combined organic extracts were dried over anhydrous $Na_2SO_{4(s)}$, filtered, and concentrated in vacuo. The crude residue was purified by C18 reverse phase chromatography (0-80% ACN/water as the gradient eluent) to cleanly provide the title compound (1.0 g, 36% yield). MS (apci) m/z=411.2 (M+H).

Intermediate R8

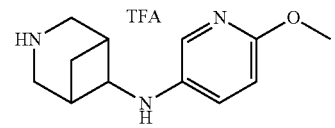

N-(6-methoxypyridin-3-yl)-3-azabicyclo[3.1.1]heptan-6-amine (TFA salt)

Step 1: Preparation of tert-butyl 6-((6-methoxypyridin-3-yl)amino)-3-azabicyclo[3.1.1]heptane-3-carboxylate Under an atmosphere of $N_{2(g)}$, a solution of tert-butyl 6-oxo-3-azabicyclo[3.1.1]heptane-3-carboxylate (40 mg, 0.19 mmol) and 6-methoxypyridin-3-amine (33 mg, 0.27 mmol) in 1:1 MeOH:DCE (1.5 mL) was treated with decaborane (6.9 mg, 0.057 mmol). After stirring overnight at ambient temperature, the reaction mixture was quenched with water. The resulting biphasic mixture was extracted with DCM. The combined organic extracts were dried over anhydrous $Na_2SO_{4(s)}$, filtered, and concentrated in vacuo. The crude residue was purified by silica chromatography (40-100% EtOAc/Hexanes as the gradient eluent) to afford the title compound (56 mg, 93% yield). MS (apci) m/z=320.2 (M+H).

Step 2: Preparation of N-(6-methoxypyridin-3-yl)-3-azabicyclo[3.1.1]heptan-6-amine (TFA salt)

A solution of tert-butyl 6-((6-methoxypyridin-3-yl)amino)-3-azabicyclo[3.1.1]heptane-3-carboxylate (56 mg, 0.175 mmol) in DCM (500 μL) was treated with trifluroacetic acid (TFA) (0.40 mL, 5.26 mmol and stirred overnight at ambient temperature. The reaction mixture was concentrated in vacuo and purified by C18 reverse phase chromatography (5-95% water-ACN with 0.01% TFA as the gradient eluent) to cleanly provide the title compound as TFA salt. (25 mg, 65% yield). MS (apci) m/z=220.1 (M+H).

Intermediate R13

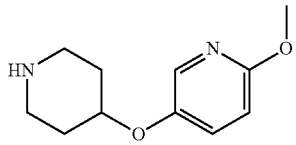

(2-methoxy-5-(piperidin-4-yloxy)pyridine

Step 1: Preparation of tert-butyl 4-((6-methoxypyridin-3-yl)oxy)piperidine-1-carboxylate A solution of 6-methoxypyridin-3-ol (100 mg, 0.799 mmol) and tert-butyl 4-hydroxypiperidine-1-carboxylate (161 mg, 0.799 mmol) in THF was treated with PPh$_3$ (231 mg, 0879 mmol), then sparged with Ar$_{(g)}$ for 5 min. While stirring at ambient temperature, the mixture was treated slowly with DIAD (186 μL, 0.959 mmol). The resulting reaction mixture was stirred for 9 h at ambient temperature, then overnight at 70° C. before introducing additional DIAD (186 μL, 0.959 mmol). The reaction mixture was stirred for 4 h at 70° C. and then allowed to cool to ambient temperature. After concentrating the reaction mixture in vacuo, the residue was suspended in DCM and washed with saturated Na$_2$CO$_{3(aq)}$, water and brine. The combined organic extracts were dried over anhydrous Na$_2$SO$_{4(s)}$, filtered and concentrated in vacuo to afford the title compound (246 mg, quantitative yield). MS (apci) m/z=309.15 (M+H).

Step 2: Preparation of 2-methoxy-5-(piperidin-4-yloxy)pyridine

A solution of tert-butyl 4-((6-methoxypyridin-3-yl)oxy)piperidine-1-carboxylate (246 mg, 0.80 mmol) in DCM (4.0 mL) was treated with TFA (4.0 mL, 0.80 mmol), then stirred for 5 min at ambient temperature before introducing additional TFA (1 mL). After stirring for 45 min at ambient temperature, the reaction mixture was concentrated in vacuo. The crude residue was purified by silica chromatography (1-9% MeOH in DCM with 0.1-0.9% NH$_4$OH as the gradient eluent) to cleanly provide the title compound (127.5 mg, 77% yield). MS (apci) m/z=209.1 (M+H).

Intermediate R14

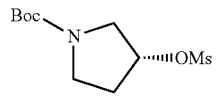

Tert-butyl (R)-3-((methylsulfonyl)oxy)pyrrolidine-1-carboxylate

A solution of N-tert-Butoxycarbonyl-(R)-(−)-3-pyrrolidinol (2.0 g, 10.7 mmol) in DCM (28 mL) was treated with TEA (2.9 mL, 21.4 mmol). The solution was cooled to 0° C. for 30 minutes. Then methanesulfonyl chloride (868 μL, 11.2 mmol) was added. The reaction was stirred at 0° C. for 30 minutes. The reaction was diluted with DCM and washed with saturated NaHCO$_{3(aq)}$. The organic extracts were dried over anhydrous Na$_2$SO$_{4(s)}$, filtered and concentrated in vacuo. The residue was purified by silica chromatography (5-95% EtOAc in Hexanes as the gradient eluent) to afford the title compound (2.83 g, 100% yield). $^1$H NMR (400 MHz, DMSO-d6) δ 5.24 (s, 1H), 3.55-3.38 (m, 3H), 3.31-3.27 (m, 1H), 3.23 (s, 3H), 2.18-2.08 (m, 2H), 1.40 (s, 9H).

Intermediate R15

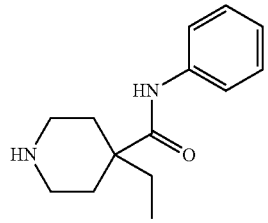 [SMILES: CCC1(C(=O)Nc2ccccc2)CCNCC1]

4-ethyl-N-phenylpiperidine-4-carboxamide

Step 1: Preparation of tert-butyl 4-ethyl-4-(phenylcarbamoyl)piperidine-1-carboxylate A solution of 1-(tert-butoxycarbonyl)-4-ethylpiperidine-4-carboxylic acid (269.5 mg, 1.047 mmol) and HATU (477.9 mg, 1.257 mmol) in DMF (3.9 mL) was treated with DIEA (3.649 mL, 2.095 mmol) and aniline (0.1051 mL, 1.152 mmol). The reaction mixture was stirred at 60° C. for 60 h. The reaction mixture was diluted with EtOAc and washed successively with water and saturated NaCl$_{(aq)}$. The combined organic extracts were dried over anhydrous Na$_2$SO$_{4(s)}$ and concentrated in vacuo. The residue was purified by silica chromatography (0-100% EtOAc in hexanes as the gradient eluent) to afford the title compound (assumed theoretical yield, 348.1 mg, 1.047 mmol) in sufficient purity for step 2. MS (apci) m/z=233.2 (M+H-Boc).

Step 2: Preparation of 4-ethyl-N-phenylpiperidine-4-carboxamide

A solution tert-butyl 4-ethyl-4-(phenylcarbamoyl)piperidine-1-carboxylate (348.1 mg, 1.047 mmol) in DCM (2 mL) was treated with TFA (2 mL) and stirred at rt for 1 h. The reaction mixture was concentrated in vacuo. The residue was diluted with saturated NaHCO$_{3(aq)}$ and extracted with 4:1 DCM/IPA. The combined organic extracts were dried over anhydrous Na$_2$SO$_{4(s)}$ and concentrated in vacuo to afford the title compound (162.4 mg, 0.6990 mmol, 66.7% yield over two steps). MS (apci) m/z=233.1 (M+H).

Intermediate R16

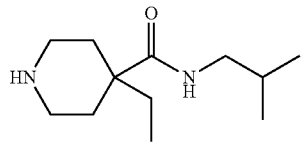

4-ethyl-N-isobutylpiperidine-4-carboxamide

Step 1: Preparation of tert-butyl 4-ethyl-4-(isobutylcarbamoyl)piperidine-1-carboxylate A solution of 1-(tert-butoxycarbonyl)-4-ethylpiperidine-4-carboxylic acid (260.3 mg, 1.012 mmol) and HATU (461.5 mg, 1.214 mmol) in DMF (3.9 mL) was treated with DIEA (3.524 mL, 2.023 mmol) and 2-methylpropan-1-amine (81.38 mg, 1.113 mmol). The reaction mixture was stirred at 60° C. for 60 h. The reaction mixture was diluted with EtOAc and washed successively with water and saturated NaCl$_{(aq)}$. The combined organic extracts were dried over anhydrous Na$_2$SO$_{4(s)}$ and concentrated in vacuo. The residue was purified by silica chromatography (1-95% EtOAc in hexanes as the gradient eluent) to afford the title compound (assumed theoretical yield, 216 mg, 1.012 mmol) in sufficient purity for step 2. MS (apci) m/z=213.2 (M+H-Boc).

Step 2: Preparation of 4-ethyl-N-isobutylpiperidine-4-carboxamide

A solution tert-butyl 4-ethyl-4-(isobutylcarbamoyl)piperidine-1-carboxylate (216 mg, 1.012 mmol) in DCM (1 mL) was treated with TFA (1 mL) and stirred at rt for 16 h. The reaction mixture was concentrated in vacuo. The residue was diluted with saturated NaHCO$_{3(aq)}$ and extracted with 4:1 DCM/IPA. The combined organic extracts were dried over anhydrous Na$_2$SO$_{4(s)}$ and concentrated in vacuo to afford the title compound (100.8 mg, 0.3988 mmol, 39% yield over two steps). MS (apci) m/z=213.2 (M+H).

Intermediate R17

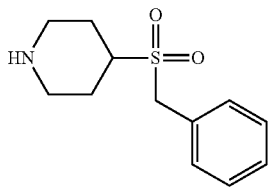 [SMILES: O=S(=O)(Cc1ccccc1)C1CCNCC1]

4-(benzylsulfonyl)piperidine

Step 1: Preparation of tert-butyl 4-(benzylthio)piperidine-1-carboxylate

A solution of tert-butyl 4-mercaptopiperidine-1-carboxylate (211.2 mg, 0.9718 mmol) and benzyl bromide (199.5 mg, 1.166 mmol) in DMF (3.9 mL) was treated with potassium carbonate (537.2 mg, 3.887 mmol). The reaction mixture was stirred at 70° C. for 60 h. After cooling to ambient temperature, the reaction mixture was diluted with EtOAc and washed successively with water and saturated NaCl$_{(aq)}$. The combined organic extracts were concentrated in vacuo, and the residue was purified by silica chromatography (1-50% EtOAc in hexanes as the gradient eluent) to afford the title compound (290.1 mg, 0.9436 mmol, 97% yield) in sufficient purity for step 2. MS (apci) m/z=208.1 (M+H-Boc).

Step 2: Preparation of tert-butyl 4-(benzylsulfonyl)piperidine-1-carboxylate To a solution of tert-butyl 4-(benzylthio)piperidine-1-carboxylate (290.1 mg, 0.9436 mmol) in DCM (9.5 mL) was added 3-chlorobenzoperoxoic acid (488.5 mg, 2.831 mmol). The reaction mixture was stirred at 0° C. and gradually warmed to rt, then stirred at rt for 16 h. The reaction mixture was concentrated in vacuo, and the residue was purified by silica chromatography (0-95% EtOAc in hexanes as the gradient eluent) to afford the title compound (assumed theoretical yield, 320.3 mg, 0.9436 mmol) in sufficient purity for step 3. MS (apci) m/z=240.1 (M+H-Boc).

Step 3: Preparation of 4-(benzylsulfonyl)piperidine

A solution of tert-butyl 4-(benzylsulfonyl)piperidine-1-carboxylate (320.3 mg, 0.9436 mmol) in DCM (2 mL) was treated with TFA (2 mL, 26 mmol). The reaction mixture was stirred at rt for 15 min. The reaction mixture was washed with saturated NaHCO$_{3(aq)}$ then extracted with 4:1 DCM/IPA. The combined organic extracts were concentrated in vacuo to afford the title compound (138.0 mg, 0.5766 mmol, 61.1% yield over two steps). MS (apci) m/z=240.1 (M+H).

Intermediate R18

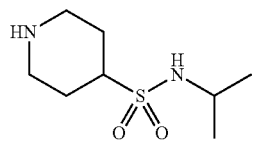

N-isopropylpiperidine-4-sulfonamide

Step 1: Preparation of tert-butyl 4-(N-isopropylsulfamoyl)piperidine-1-carboxylate A mixture of tert-butyl 4-(chlorosulfonyl)piperidine-1-carboxylate (1.0137 g, 3.5723 mmol) in DCM (2 mL) was treated with pyridine (722 µL, 8.93 mmol) and propan-2-amine (460 µL, 5.36 mmol), then stirred overnight at ambient temperature. The resulting mixture was washed with water (4×). The organic extracts were dried over anhydrous Na$_2$SO$_{4(s)}$, filtered, and concentrated in vacuo to afford the title compound in sufficient purity to carry into step 2 (1.09 g, quantitative yield). MS (apci) m/z=207.2 [(M-Boc)+H].

Step 2: Preparation of N-isopropylpiperidine-4-sulfonamide

Crude tert-butyl 4-(N-isopropylsulfamoyl)piperidine-1-carboxylate (1.09 g, 3.56 mmol) was suspended in DCM (5 mL) and treated with TFA (2.5 mL, 32 mmol). The resulting mixture was stirred for 3 h at ambient temperature before concentrating the mixture in vacuo. The crude residue was suspended in 4:1 DCM:iPrOH, and extracted with saturated NaHCO$_{3(aq)}$. The organic extracts were dried over anhydrous Na$_2$SO$_{4(s)}$, filtered and concentrated in vacuo to afford the title compound (734 mg, quantitative yield). MS (apci) m/z=207.2 (M+H).

Intermediate R19

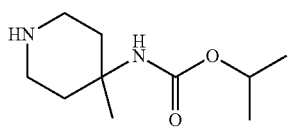

isopropyl (4-methylpiperidin-4-yl)carbamate

Step 1: Preparation of tert-butyl 4-((isopropoxycarbonyl)amino)-4-methylpiperidine-1-carboxylate A mixture of tert-butyl 4-amino-4-methylpiperidine-1-carboxylate (546.5 mg, 2.550 mmol) and DIEA (1113 µL, 6.375 mmol) in DCM (164.1 µL) was cooled to 0° C., then treated dropwise (over 10 min) with isopropyl carbonochloridate (3825 µL, 3.825 mmol). After being allowed to gradually warm to ambient temperature, the mixture was stirred overnight at ambient temperature. The mixture was concentrated in vacuo, and the crude residue was purified by silica chromatography (using 0-100% Hexanes/EtOAc as the gradient eluent) to cleanly afford the title compound (746.6 mg, 97% yield). MS (apci) m/z=201.2 (M+H).

Step 2: Part A: Preparation of isopropyl (4-methylpiperidin-4-yl)carbamate

A mixture of tert-butyl 4-((isopropoxycarbonyl)amino)-4-methylpiperidine-1-carboxylate (315.0 mg, 1.049 mmol) in DCM (4 mL) was treated dropwise with TFA (2.5 mL, 32 mmol). The resulting mixture was stirred for 1 h at ambient temperature before concentrating the mixture in vacuo. The crude residue was suspended in DCM, treated with saturated NaHCO$_{3(aq)}$, and then the biphasic mixture was extracted with 4:1 DCM:iPrOH. The aqueous phase was set aside for Step 2: Part B. The combined organic extracts were dried over anhydrous Na$_2$SO$_{4(s)}$, filtered and concentrated in vacuo to afford the title compound (96.0 mg, 46% yield). MS (apci) m/z=201.2 (M+H).

Step 2: Part B: Preparation of isopropyl (4-methylpiperidin-4-yl)carbamate hydrochloride

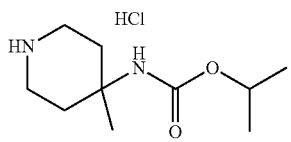

Additional title compound, in the form of the HCl salt, was extracted from the aqueous phase by adjusting the pH of the aqueous extracts to pH 2 with the addition of 2M HCl$_{(aq)}$. The acidified aqueous extracts were concentrated in vacuo, reducing the volume by half. Trituration of this mixture with dioxane afforded a precipitate, which was collected by filtration. Subsequent, air drying of the solids provided the HCl salt of the title compound (182.7 mg, quantitative yield based on expected recovery). MS (apci) m/z=201.2 (M+H):

Intermediate R20

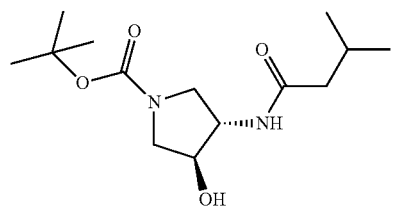 [SMILES: CC(C)CC(=O)N[C@H]1CN(C(=O)OC(C)(C)C)C[C@@H]1O]

tert-butyl (3S,4S)-3-hydroxy-4-(3-methylbutanamido)pyrrolidine-1-carboxylate

A solution of tert-butyl (3S,4S)-3-amino-4-hydroxypyrrolidine-1-carboxylate (355.5 mg, 1.758 mmol) in DCM (2 mL) was treated with DIEA (921.0 µL, 5.273 mmol) then stirred for 30 min at 0° C. The 0° C. mixture was treated dropwise with isovaleryl chloride (235.7 µL, 1.933 mmol). The resulting mixture was stirred for 20 min, over which time the temperature was allowed to gradually reach ambient temperature. The reaction mixture was diluted with DCM, and washed with saturated NaHCO$_{3(aq)}$. The organic extracts were directly purified by silica chromatography (using 20-100% EtOAc in Hexanes as the gradient eluent) to cleanly provide the title compound (487.2 mg, 97% yield). MS (apci) m/z=187.2 ([M-boc]+H).

Intermediate R21

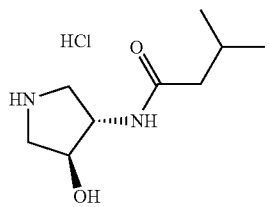

N-((3S,4S)-4-hydroxypyrrolidin-3-yl)-3-methylbutanamide hydrochloride

A solution of tert-butyl (3S,4S)-3-hydroxy-4-(3-methylbutanamido)pyrrolidine-1-carboxylate (Intermediate R20; 487.2 mg, 1.701 mmol) in dioxane (2.0 mL) was treated with 12 M HCl$_{(aq)}$ (139.7 µL, 1.701 mmol). The resulting mixture was stirred for 2 h at ambient temperature before concentrating the mixture in vacuo to afford the title compound (378 mg, 100% yield). MS (apci) m/z=187.2 (M+H-Boc).

Intermediate R22

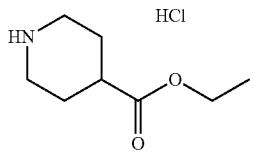

ethyl piperidine-4-carboxylate hydrochloride

A solution of 1-(tert-butyl) 4-ethyl piperidine-1,4-dicarboxylate (321.9 mg, 1.251 mmol) in DCM (2.0 mL) was treated with TFA (2.0 mL, 25.96 mmol). The resulting mixture was stirred overnight at ambient temperature before concentrating the mixture in vacuo. The crude residue was suspended in dioxane, and treated with 12 M HCl$_{(aq)}$. The resulting mixture was concentrated in vacuo to afford the title compound (240 mg, 99% yield).

Intermediate R23

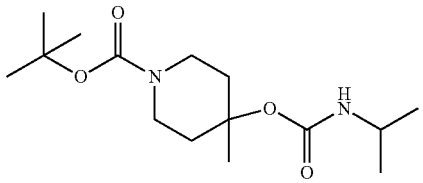 [SMILES: CC(C)NC(=O)OC1(C)CCN(C(=O)OC(C)(C)C)CC1]

tert-butyl 4-((isopropylcarbamoyl)oxy)-4-methylpiperidine-1-carboxylate

A solution of 2-isocyanatopropane (50.5 mg, 0.593 mmol) in DCM (2 mL) and 12 M HCl$_{(aq)}$ (2.44 µL, 0.0297 mmol) was stirred 5 min at ambient temperature, then added to tert-butyl 4-hydroxy-4-methylpiperidine-1-carboxylate (172.1 mg, 0.7994 mmol). The reaction mixture was stirred overnight at ambient temperature before introducing additional 2-isocyanatopropane (50.5 mg, 0.593 mmol) and 12 M HCl$_{(aq)}$ (2.44 µL, 0.0297 mmol). The resulting mixture was stirred for 3 h at ambient temperature before another equivalent of 2-isocyanatopropane (50.5 mg, 0.593 mmol) was introduced. After stirring overnight at ambient temperature, the reaction mixture was concentrated in vacuo. The crude residue was purified directly by silica chromatography (using 0-100% Hexanes/EtOAc as the gradient eluent) to cleanly provide the title compound (180 mg, quantitative yield). MS (apci) m/z=201.2 (M+H).

Intermediate R24

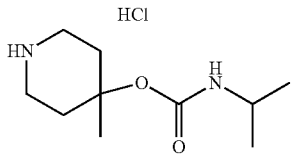

4-methylpiperidin-4-yl isopropylcarbamate hydrochloride

A solution of to tert-butyl 4-((isopropylcarbamoyl)oxy)-4-methylpiperidine-1-carboxylate (Intermediate R23; 60 mg, 0.20 mmol) in DCM (1.0 mL) was treated with TFA (1.0 mL, 13.0 mmol). The resulting mixture was stirred for 30 min at ambient temperature before concentrating the mixture in vacuo. The crude residue was suspended in dioxane (1 mL), and treated with two drops of conc. HCl$_{(aq)}$. The resulting mixture was concentrated in vacuo to afford the title compound (50 mg, quantitative yield). MS (apci) m/z=201.2 (M+H).

Intermediate R25

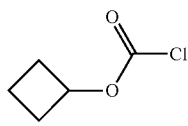

Cyclobutyl Carbonochloridate

The title compound (93.3 mg, 0.693 mmol, quantitative yield is assumed) was prepared and worked up using a similar procedure to that described for (S)-tetrahydrofuran-3-yl carbonochloridate (Intermediate R54), replacing (S)-tetrahydrofuran-3-ol (100 mg, 1.13 mmol) with cyclobutanol (54.3 µl, 0.693 mmol).

Intermediate R26

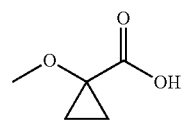

1-methoxycyclopropane-1-carboxylic acid

Step 1: Preparation of methyl 1-methoxycyclopropane-1-carboxylate

A solution of 1-hydroxy-1-cyclopropanecarboxylic acid (1.02 g, 9.99 mmol) in DMF (33 mL) was treated sequentially with iodomethane (1.56 mL, 25.0 mmol) and NaH (60 wt. % in mineral oil; 1.00 g, 25.0 mmol), then stirred for 16 h at ambient temperature. The resulting mixture was diluted with water, and then extracted with Et$_2$O (2×). The combined organic extracts were washed sequentially with water (3×) and brine (1×), and then dried over anhydrous Na$_2$SO$_{4(s)}$, filtered, and concentrated in vacuo to afford the title compound in sufficient purity to carry into step 2 (1.30 g, quantitative yield).

Step 2: Preparation of 1-methoxycyclopropane-1-carboxylic acid

A solution of crude methyl 1-methoxycyclopropane-1-carboxylate (Step 1; 1.30, 9.99 mmol, assumed) in 1:1 THF:MeOH (60 mL) was treated with 2.0 M KOH$_{(aq)}$. (14.99 mL, 29.97 mmol), then stirred for 60 h at ambient temperature. The resulting mixture was diluted with Et$_2$O, and extracted with 1.0 M NaOH$_{(aq)}$ (2×). The combined aqueous extracts were acidified to pH~2 with the addition of 4.0 M HCl$_{(aq)}$, then extracted with DCM (2×). The combined DCM extracts were dried over anhydrous Na$_2$SO$_{4(s)}$, filtered, and concentrated in vacuo to afford the title compound (240 mg, 99% yield). $^1$H NMR (400 MHz, DMSO-d$_6$) δ 12.56 (s, 1H), 3.29 (s, 3H), 1.14-1.04 (m, 4H).

Intermediate R27

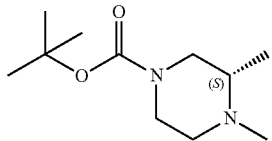

tert-butyl (S)-3,4-dimethylpiperazine-1-carboxylate

A solution of tert-butyl (S)-3-methylpiperazine-1-carboxylate (4.9980 g, 24.955 mmol) in DCM (10 mL) was treated with formaldehyde (37 wt % in water with 5-15% MeOH stabilizer; 2.79 mL, 37.4 mmol), and stirred for 2.5 h at ambient temperature. The reaction mixture was treated with NaBH(AcO)$_3$ (7.9334 mg, 37.432 mmol), and stirred overnight at room temperature. The reaction mixture was concentrated in vacuo. The residue was diluted with 4:1 DCM:iPrOH, and filtered. The filtrate was extracted sequentially with saturated NaHCO$_{3(aq)}$ (2×) and water. The organic extracts were dried over anhydrous Na$_2$SO$_{4(s)}$, filtered, and concentrated in vacuo to cleanly afford the title compound (3.9335 g, 74% yield). MS (apci) m/z=215.2 (M+H).

Intermediate R28

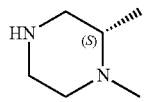

(S)-1,2-dimethylpiperazine

A solution of tert-butyl (S)-3,4-dimethylpiperazine-1-carboxylate (Intermediate R27; 3.9335 g, 18.354 mmol) in DCM (2.0 mL) was treated with TFA (1.5 mL, 19.5 mmol). The resulting mixture was stirred overnight at ambient temperature before concentrating the mixture in vacuo. The residue was diluted with 4:1 DCM:iPrOH, and extracted with saturated NaHCO$_{3(aq)}$. The aqueous extracts were back extracted with 4:1 DCM:iPrOH. The combined organic extracts were dried over anhydrous Na$_2$SO$_{4(s)}$, filtered, and concentrated in vacuo to cleanly afford the title compound (2.0 g, 95% yield). MS (apci) m/z=115.3 (M+H).

Intermediate R29

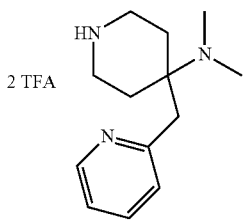 [SMILES: CN(C)C1(Cc2ccccn2)CCNCC1]

N,N-dimethyl-4-(pyridin-2-ylmethyl)piperidin-4-amine bis(2,2,2-trifluoroacetate)

Step 1: Preparation of tert-butyl 4-(dimethylamino)-4-(pyridin-2-ylmethyl)piperidine-1-carboxylate A solution of tert-Butyl 4-amino-4-(pyridin-2-ylmethyl)piperidine-1-carboxylate (50.2 mg, 0.172 mmol) in DCM (1.15 mL) was treated with formaldehyde (37 wt. % in water with 5-15% MeOH stabilizer; 64.7 μl, 0.861 mmol) and NaBH(AcO)$_3$ (365 mg, 1.72 mmol), and stirred for 1 h at ambient temperature. The reaction mixture was diluted with water and the biphasic mixture was extracted with DCM (3×). The combined organic extracts were washed with brine. After back extracting all aqueous extracts once again with DCM, all DCM extracts were combined and concentrated in vacuo. The crude residue was purified by silica chromatography (50-100% EtOAc/Hexanes followed by 0-10% MeOH in EtOAc) to cleanly afford the title compound (55 mg, 100% yield). MS (apci) m/z=320.2 (M+H).

Step 2: Preparation of N,N-dimethyl-4-(pyridin-2-ylmethyl)piperidin-4-amine bis(2,2,2-trifluoroacetate)

A mixture of tert-butyl 4-(dimethylamino)-4-(pyridin-2-ylmethyl)piperidine-1-carboxylate (55 mg, 0.172 mmol) in DCM (2 mL) was treated with TFA (1 mL, 6.51 mmol). The resulting mixture was stirred overnight at ambient temperature before concentrating the mixture in vacuo to afford the title compound (77.0 mg, quantitative yield). MS (apci) m/z=220.1 (M+H).

Intermediate R30

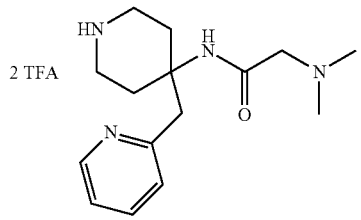 [SMILES: CN(C)CC(=O)NC1(Cc2ccccn2)CCNCC1]

2-(dimethylamino)-N-(4-(pyridin-2-ylmethyl)piperidin-4-yl)acetamide bis(2,2,2-trifluoroacetate)

Step 1: Preparation of tert-butyl 4-(2-(dimethylamino)acetamido)-4-(pyridin-2-ylmethyl)piperidine-1-carboxylate A solution of 1 tert-butyl 4-amino-4-(pyridin-2-ylmethyl)piperidine-1-carboxylate (50 mg, 0.172 mmol) in DCM (1144 μL) was treated sequentially with HATU (78.3 mg, 0.206 mmol), DIEA (59.8 μL, 0.343 mmol) and N,N-dimethylglycine (19.5 mg, 0.189 mmol). The resulting mixture was stirred overnight at ambient temperature, and then purified directly by C18 reverse phase chromatography (using 5-95% ACN/water with 0.1% TFA as the gradient eluent) to afford the title compound as the TFA salt. The TFA salt was suspended in MeOH (5 mL), eluted through a basic resin (Stratospheres P1-HCO3) to cleanly afford the title compound (50 mg, 77% yield). MS (apci) m/z=377.2 (M+H).

Step 2: Preparation of 2-(dimethylamino)-N-(4-(pyridin-2-ylmethyl)piperidin-4-yl)acetamide bis(2,2,2-trifluoroacetate)

A mixture of tert-butyl 4-(2-(dimethylamino)acetamido)-4-(pyridin-2-ylmethyl)piperidine-1-carboxylate (50 mg, 0.13 mmol) in DCM (1 mL) was treated with TFA (1 mL, 13.07 mmol). The resulting mixture was stirred for 1 h at ambient temperature to afford the title compound (50 mg, 75% yield). MS (apci) m/z=277.2 (M+H).

The compounds in Table aaa were prepared using a similar 2 step procedure to that used for the synthesis of 2-(dimethylamino)-N-(4-(pyridin-2-ylmethyl)piperidin-4-yl)acetamide bis(2,2,2-trifluoroacetate) (Intermediate R30) replacing N,N-dimethylglycine in step 1 with (1.0-1.1 equivalents) of the appropriate carboxylic acid.

TABLE aaa

| Int # | Structure | Chemical Name | MS (apci) m/z |
|---|---|---|---|
| R31 | 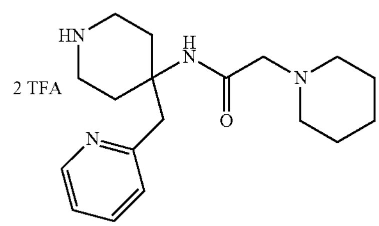 | 2-(piperidin-1-yl)-N-(4-(pyridin-2-ylmethyl)piperidin-4-yl)acetamide bis(2,2,2-trifluoroacetate) | 317.3 (M + H) |
| R32 | 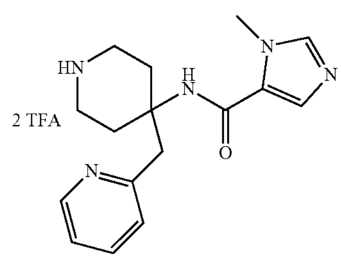 | 1-methyl-N-(4-(pyridin-2-ylmethyl)piperidin-4-yl)-1H-imidazole-5-carboxamide bis(2,2,2-trifluoroacetate) | 300.2 (M + H) |
| R33 | 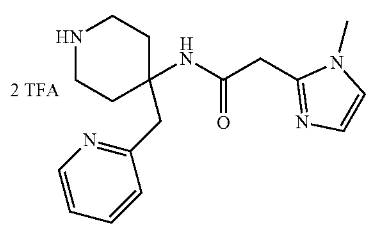 | 2-(1-methyl-1H-imidazol-2-yl)-N-(4-(pyridin-2-ylmethyl)piperidin-4-yl)acetamide bis(2,2,2-trifluoroacetate) | 314.3 (M + H) |
| R34 | 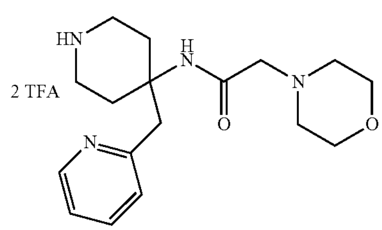 | 2-morpholino-N-(4-(pyridin-2-ylmethyl)piperidin-4-yl)acetamide bis(2,2,2-trifluoroacetate) | 319.2 (M + H) |
| R35 | 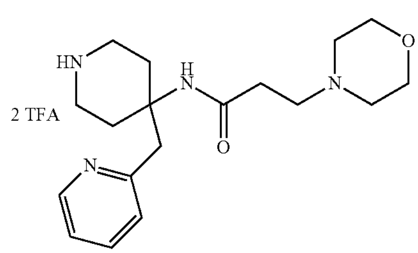 | 3-morpholino-N-(4-(pyridin-2-ylmethyl)piperidin-4-yl)propanamide bis(2,2,2-trifluoroacetate) | 333.2 (M + H) |

TABLE aaa-continued

| Int # | Structure | Chemical Name | MS (apci) m/z |
|---|---|---|---|
| R36 | 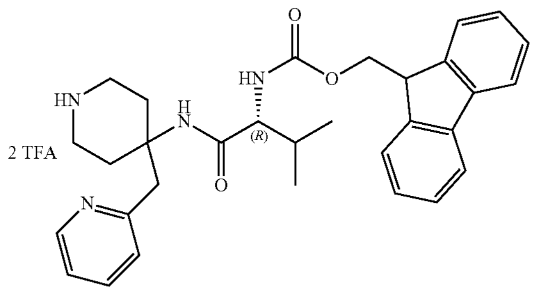 | (9H-fluoren-9-yl)methyl (R)-(3-methyl-1-oxo-1-((4-(pyridin-2-ylmethyl)piperidin-4-yl)amino)butan-2-yl)carbamate bis(2,2,2-trifluoroacetate) | 513.2 (M + H) |
| R37 | 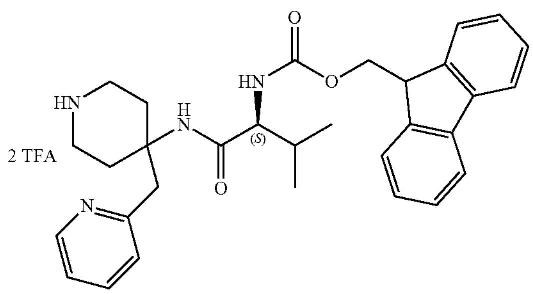 | (9H-fluoren-9-yl)methyl (S)-(3-methyl-1-oxo-1-((4-(pyridin-2-ylmethyl)piperidin-4-yl)amino)butan-2-yl)carbamate bis(2,2,2-trifluoroacetate) | 513.2 (M + H) |

Intermediate R38

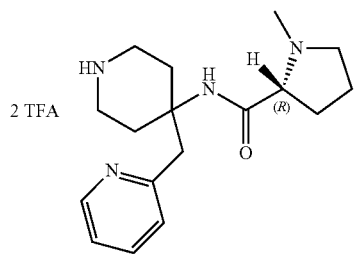

(R)-1-methyl-N-(4-(pyridin-2-ylmethyl)piperidin-4-yl)pyrrolidine-2-carboxamide bis(2,2,2-trifluoroacetate)

Step 1: Preparation of tert-butyl (R)-4-(1-methylpyrrolidine-2-carboxamido)-4-(pyridin-2-ylmethyl)piperidine-1-carboxylate A solution of 1 tert-butyl 4-amino-4-(pyridin-2-ylmethyl) piperidine-1-carboxylate (50 mg, 0.172 mmol) in DCM (1144 μL) was treated sequentially with HATU (78.3 mg, 0.206 mmol), DIEA (59.8 μL, 0.343 mmol) and N-methyl-D-proline hydrochloride (28.4 mg, 0.172 mmol). The resulting mixture was stirred overnight at ambient temperature, and then purified directly by C18 reverse phase chromatography (using 5-95% ACN/water with 0.1% TFA as the gradient eluent) to afford the title compound as the TFA salt. The TFA salt was suspended in MeOH (5 mL), eluted through a basic resin (Stratospheres P1-HCO3) to cleanly afford the title compound (55 mg, 80% yield). MS (apci) m/z=408.3 (M+H).

Step 2: Preparation of (R)-1-methyl-N-(4-(pyridin-2-ylmethyl)piperidin-4-yl)pyrrolidine-2-carboxamide bis(2,2,2-trifluoroacetate)

A mixture of tert-butyl (R)-4-(1-methylpyrrolidine-2-carboxamido)-4-(pyridin-2-ylmethyl)piperidine-1-carboxylate (55 mg, 0.14 mmol) in DCM (1 mL) was treated with TFA (1 mL, 13.07 mmol). The resulting mixture was stirred for 1 h at ambient temperature before concentrating the mixture in vacuo to afford the title compound (55 mg, 76% yield). MS (apci) m/z=303.2 (M+H).

Intermediate R39

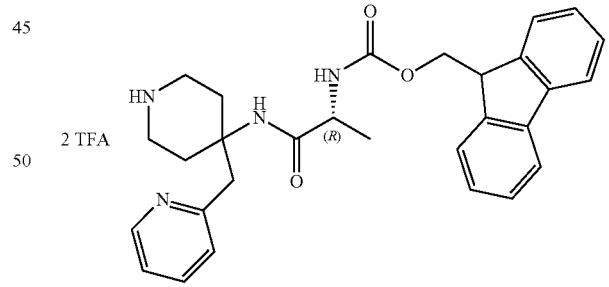

(9H-fluoren-9-yl)methyl (R)-(1-oxo-1-((4-(pyridin-2-ylmethyl)piperidin-4-yl)amino)propan-2-yl)carbamate bis(2,2,2-trifluoroacetate)

Step 1: Preparation of tert-butyl (R)-4-(2-((((9H-fluoren-9-yl)methoxy)carbonyl)amino)propanamido)-4-(pyridin-2-ylmethyl)piperidine-1-carboxylate A solution of 1 tert-butyl 4-amino-4-(pyridin-2-ylmethyl) piperidine-1-carboxylate (51.3 mg, 0.176 mmol) in DCM (880 µL) was treated sequentially with HATU (80.3 mg, 0.211 mmol), DIEA (61.3 µL, 0.352 mmol) and (((9H-fluoren-9-yl)methoxy)carbonyl)-D-alanine (58.0 mg, 0.176 mmol), then stirred at ambient temperature for 2 d. The reaction mixture was washed with water, then dried over Na$_2$SO$_{4(s)}$, filtered, and concentrated. The crude was purified by silica chromatography (0-100% EtOAc/hexanes followed by 0-10% MeOH/EtOAc) to cleanly afford the title compound (107 mg, quantitative yield). MS (apci) m/z=585.2 (M+H).

Step 2: Preparation of (9H-fluoren-9-yl)methyl (R)-(1-oxo-1-((4-(pyridin-2-ylmethyl)piperidin-4-yl)amino)propan-2-yl)carbamate bis(2,2,2-trifluoroacetate)

A mixture of tert-butyl (R)-4-(2-((((9H-fluoren-9-yl)methoxy)carbonyl)amino)propanamido)-4-(pyridin-2-ylmethyl)piperidine-1-carboxylate (55 mg, 0.14 mmol) in DCM (1 mL) was treated with TFA (0.5 mL, 6.53 mmol). The resulting mixture was stirred for 1 h at ambient temperature before concentrating the mixture in vacuo to afford the title compound (130 mg, 100% yield). MS (apci) m/z=485.2 (M+H).

Intermediate R40

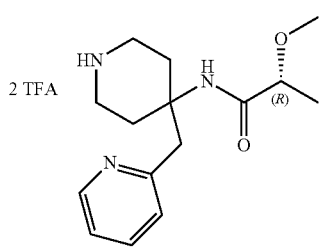

(R)-2-methoxy-N-(4-(pyridin-2-ylmethyl)piperidin-4-yl)propanamide bis(2,2,2-trifluoroacetate Step 1: Preparation of tert-butyl (R)-4-(2-methoxypropanamido)-4-(pyridin-2-ylmethyl)piperidine-1-carboxylate A solution of 1 tert-butyl 4-amino-4-(pyridin-2-ylmethyl)piperidine-1-carboxylate (51.3 mg, 0.176 mmol) in DCM (880 µL) was treated sequentially with HATU (80.3 mg, 0.211 mmol), DIEA (61.3 µL, 0.352 mmol) and (R)-(+)-2-methoxypropionic acid (18.9 µL, 0.176 mmol). The resulting mixture was stirred overnight at ambient temperature. The reaction mixture was purified directly by silica chromatography (using a stepped gradient of 0-100% EtOAc/Hex followed by 0-10% MeOH/EtOAc) to cleanly afford the title compound (0.176 mmol, quantitative yield was assumed), which was carried directly into step 2. MS (apci) m/z=378.2 (M+H).

Step 2: Preparation of (R)-2-methoxy-N-(4-(pyridin-2-ylmethyl)piperidin-4-yl)propanamide bis(2,2,2-trifluoroacetate A mixture of tert-butyl (R)-4-(2-methoxypropanamido)-4-(pyridin-2-ylmethyl)piperidine-1-carboxylate (Step 1; 0.176 mmol) in DCM (1 mL) was treated with TFA (1 mL, 13.07 mmol). The mixture was stirred for 1 h at ambient temperature before concentrating the mixture in vacuo to afford the title compound (123 mg, quantitative yield). MS (apci) m/z=278.2 (M+H).

Intermediate R41

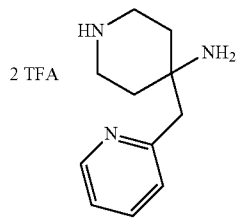 [SMILES: NC1(Cc2ccccn2)CCNCC1]

4-(pyridin-2-ylmethyl)piperidin-4-amine bis(2,2,2-trifluoroacetate)

A mixture of 1 tert-butyl 4-amino-4-(pyridin-2-ylmethyl)piperidine-1-carboxylate (200 mg, 0.686 mmol) in DCM (0.25 mL) was treated with TFA (0.25 mL, 3.27 mmol). The resulting mixture was stirred for 1.75 h at ambient temperature before concentrating the mixture in vacuo to afford the title compound (287 mg, 100% yield). MS (apci) m/z=192.2 (M+H)

Intermediate R42

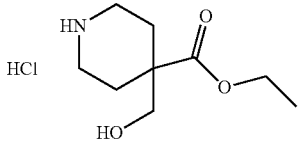

ethyl 4-(hydroxymethyl)piperidine-4-carboxylate hydrochloride

Step 1: Preparation of 1-(tert-butyl) 4-ethyl 4-(hydroxymethyl)piperidine-1,4-dicarboxylate A solution of 1-tert-butyl 4-ethyl piperidine-1,4-dicarboxylate (6.86 g, 26.6 mmol) in THF (30 mL) was cooled to −40° C. The cold solution was treated slowly with LiHMDS (53.3 mL, 53.3 mmol) and stirred at −40 OC for 1 h. Subsequently, paraformaldehyde (3.20 g, 106.6 mmol) was added, and the reaction mixture was warmed to ambient temperature, then stirred for 14 h. The reaction was quenched with water and saturated NaHCO$_{3(aq)}$, then extracted with DCM (3×). The combined organic layers were washed with brine, then dried over anhydrous Na$_2$SO$_{4(s)}$, filtered, and concentrated in vacuo. to afford the title compound (10.6 g, quantitative yield). The portion of the crude residue (1 g) was purified directly by silica chromatography (using 9:1 to 1:1 Hexanes:EtOAc as the gradient eluent) to cleanly afford the title compound, which was carried directly into step 2. MS (apci) m/z=188.1 (M+H-Boc).

Step 2: Preparation of ethyl 4-(hydroxymethyl)piperidine-4-carboxylate hydrochloride A solution of 1-(tert-butyl) 4-ethyl 4-(hydroxymethyl) piperidine-1,4-dicarboxylate (250 mg, 0.870 mmol) in MeOH (1740 µL) was treated dropwise with 12 M HCl$_{(aq)}$ (725 µL, 8.70 mmol), then stirred overnight at ambient temperature. The reaction mixture was diluted with MeOH, and concentrated in vacuo. The resultant residue was triturated with EtOAc (5 mL) and ACN (5 mL), then concentrated in vacuo to cleanly afford the title compound (195 mg, 100% yield).

Intermediate R43

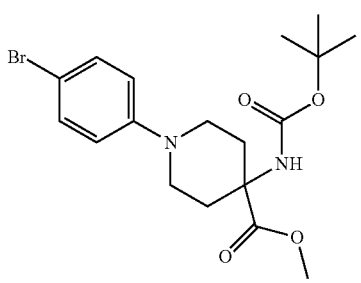 [SMILES: COC(=O)C1(NC(=O)OC(C)(C)C)CCN(c2ccc(Br)cc2)CC1]

methyl 1-(4-bromophenyl)-4-((tert-butoxycarbonyl)amino)piperidine-4-carboxylate

In a pressure vessel, a solution of methyl 4-((tert-butoxycarbonyl)amino)piperidine-4-carboxylate (1.99 g, 7.70 mmol) in dioxane (77 mL) was treated with 1,4-dibromobenzene (5.45 g, 23.1 mmol), Pd$_2$(dba)$_3$ (0.705 g, 0.770 mmol), (+)-BINAP (0.959 g, 1.54 mmol) and Cs$_2$CO$_{3(s)}$ (7.53 g, 23.1 mmol), then sparged with Ar$_{(g)}$. The vessel was sealed, and stirred for 16 h at 90° C. After cooling to ambient temperature, the reaction mixture was diluted with EtOAc, and washed with water (2×) and brine (1×). The organic extracts were dried over anhydrous Na$_2$SO$_{4(s)}$, filtered and concentrated in vacuo. The crude residue was purified by silica chromatography (using 5-75% Hexanes-EtOAc as the gradient eluent) to cleanly afford the title compound (377.4 mg, 81% yield). MS (apci) m/z=415.2 (M+2 with Br pattern).

Intermediate R44

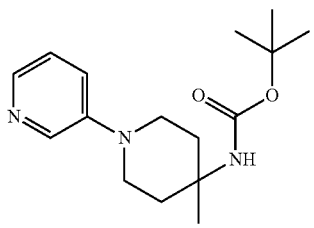 [SMILES: CC1(NC(=O)OC(C)(C)C)CCN(c2cccnc2)CC1]

tert-butyl (4-methyl-1-(pyridin-3-yl)piperidin-4-yl)carbamate

In a pressure tube, a suspension of 3-bromopyridine (304.9 µL, 3.165 mmol), tert-butyl (4-methylpiperidin-4-yl)carbamate (678.2 mg, 3.165 mmol), and Cs$_2$CO$_{3(s)}$ (2.062 g, 6.329 mmol) in dioxane (15 mL) was sparged with N$_{2(g)}$ for 5 min then treated with X-phos (150.9 mg, 0.3165 mmol) and Pd$_2$(dba)$_3$ (144.9 mg, 0.1582 mmol). The resulting mixture was sparged with N$_{2(g)}$. After sealing the vessel, the reaction mixture was stirred for 60 h at 90° C. After cooling to ambient temperature, the resulting suspension was diluted with water (25 mL) and extracted with DCM (2×25 mL). The combined organic extracts were dried over anhydrous MgSO$_{4(s)}$, filtered and concentrated in vacuo. The crude residue was purified by silica chromatography (0-50% acetone/hexanes) to afford the title compound (639.9 mg, 81% yield). MS (apci) m/z=292.2 (M+H).

Intermediate R45

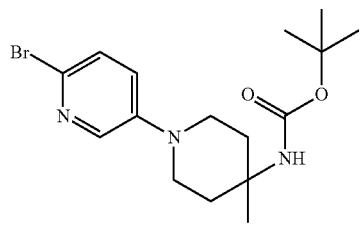 [SMILES: CC1(NC(=O)OC(C)(C)C)CCN(c2cnc(Cl)cn2)CC1]

tert-butyl (1-(6-bromopyridin-3-yl)-4-methylpiperidin-4-yl)carbamate

A solution of tert-butyl (4-methyl-1-(pyridin-3-yl)piperidin-4-yl)carbamate (Intermediate R44; 50 mg, 0.172 mmol) in DCM (0.5 mL) was cooled to 0° C., then treated with NBS (30.5 mg, 0.172 mmol). The resulting mixture was stirred for 1 h at 0° C., and then diluted with water. The biphasic mixture was extracted with DCM (2×1 mL). The combined organic extracts were partially concentrated then purified directly by silica chromatography (0-90% acetone/hexanes) to afford the title compound (50.2 mg, 79% yield). MS (apci) m/z=372.2 (M+H).

Intermediate R46

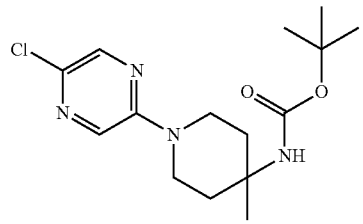

tert-butyl (1-(5-chloropyrazin-2-yl)-4-methylpiperidin-4-yl)carbamate

In a sealed vessel, a mixture of tert-butyl (4-methylpiperidin-4-yl)carbamate (1.44 g, 6.71 mmol), 2,5-dichloropyrazine (1.00 g, 6.71 mmol) and $K_2CO_{3(s)}$ (4.64 g, 33.6 mmol) in dioxane (67.1 mL) was stirred for 60 h at 60° C. After cooling to ambient temperature, the resulting suspension was diluted with EtOAc, filtered through Celite® then concentrated in vacuo. The crude residue was purified by silica chromatography (0-100% EtOAc in hexanes) to afford the title compound (657 mg, 30% yield). MS (apci) m/z=327.1 (M+H).

Intermediate R47

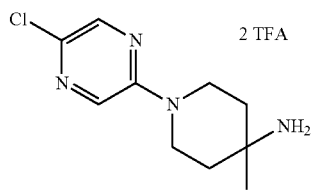

1-(5-chloropyrazin-2-yl)-4-methylpiperidin-4-amine bis(2,2,2-trifluoroacetate)

A mixture of tert-butyl (1-(5-chloropyrazin-2-yl)-4-methylpiperidin-4-yl)carbamate (Intermediate R46; 500 mg, 1.53 mmol) in DCM (0.5 mL) was treated with TFA (0.25 mL, 3.27 mmol). The resulting mixture was stirred for 2 h at ambient temperature before concentrating the mixture in vacuo to afford the title compound (696 mg, quantitative yield). MS (apci) m/z=227.1 (M+H).

Intermediate R48

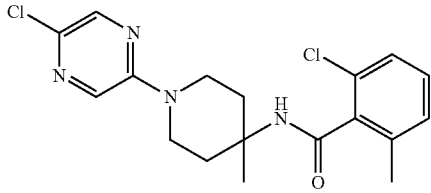 [SMILES: Cc1cccc(Cl)c1C(=O)NC1(C)CCN(c2cnc(Cl)cn2)CC1]

2-chloro-N-(1-(5-chloropyrazin-2-yl)-4-methylpiperidin-4-yl)-6-methylbenzamide

A solution of 1-(5-chloropyrazin-2-yl)-4-methylpiperidin-4-amine bis(2,2,2-trifluoroacetate) (Intermediate R47; 596 mg, 1.31 mmol) in DCM (26 mL) was treated sequentially with 2-chloro-6-methylbenzoic acid (1.345 g, 7.89 mmol), HATU (1.999 g, 5.26 mmol) and DIEA (4.6 mL 26.3 mmol). The resulting mixture was stirred overnight at ambient temperature, before concentrating the mixture in vacuo. The crude residue was purified by silica chromatography (0-60% EtOAc in hexanes) to afford the title compound (360 mg, 72% yield). MS (apci) m/z=379 (M+H).

Intermediate R49

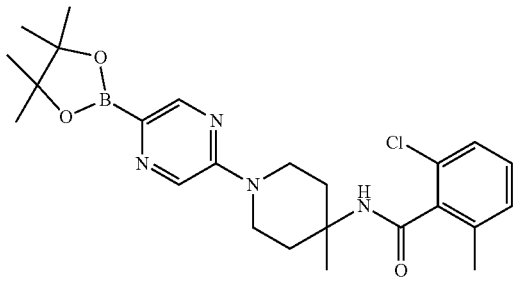 [SMILES: Cc1cccc(Cl)c1C(=O)NC1(C)CCN(c2cnc(B3OC(C)(C)C(C)(C)O3)cn2)CC1]

2-chloro-6-methyl-N-(4-methyl-1-(5-(4,4,5,5-tetramethyl-1,3,2-dioxaborolan-2-yl)pyrazin-2-yl)piperidin-4-yl)benzamide In a pressure vessel, a mixture of 2-chloro-N-(1-(5-chloropyrazin-2-yl)-4-methylpiperidin-4-yl)-6-methylbenzamide (Intermediate R48; 730 mg, 1.92 mmol), bis(pinacolato)diboron (4.888 g, 19.2 mmol), KOAc (944 mg, 9.62 mmol) and $PdCl_2(dppf) \cdot CH_2Cl_2$ (157 mg, 0.192 mmol), in dioxane (19.25 mL) was sparged with $Ar_{(g)}$. The vessel was sealed, and the mixture was stirred overnight at 80° C. After cooling to ambient temperature, the reaction mixture was diluted with DCM, and filtered through a GF/F filter. The filtrate was concentrated in vacuo, and the residue was triturated with pentane (50 mL). The resulting suspension was sonicated for 4 min, and then filtered. The solids were collected to afford the title compound (980 mg, 54% yield). MS (apci) m/z=389.1 (M+H).

Intermediate R50

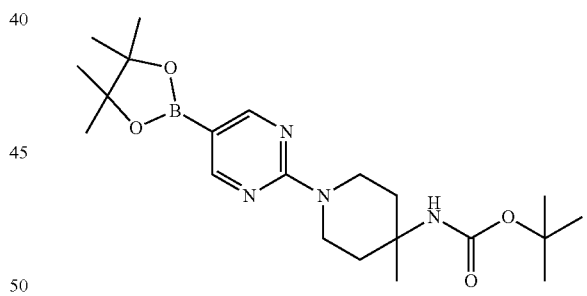

tert-butyl (4-methyl-1-(5-(4,4,5,5-tetramethyl-1,3,2-dioxaborolan-2-yl)pyrimidin-2-yl)piperidin-4-yl)carbamate In a pressure vessel, a mixture of tert-butyl (4-methylpiperidin-4-yl)carbamate (0.23 g, 1.1 mmol), 2-fluoro-5-(4,4,5,5-tetramethyl-1,3,2-dioxaborolan-2-yl)pyrimidine (0.2 g, 0.89 mmol) and $K_2CO_{3(s)}$ (944 mg, 9.62 mmol) was combined in dioxane (8.9 mL). The vessel was sealed, and the reaction mixture was stirred overnight at 60° C. After cooling to ambient temperature, the reaction mixture was preserved as a suspension (i.e. without further work up, purification or isolation) containing the title compound (assumed 370 mg, quantitative yield. MS (apci) m/z=419.3 (M+H).

Intermediate R51

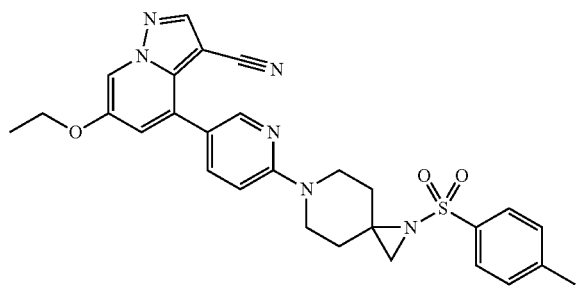 [SMILES: CCOc1cc(-c2ccc(N3CCC4(CC3)CN4S(=O)(=O)c3ccc(C)cc3)nc2)c2c(C#N)cnn2c1]

6-ethoxy-4-(6-(1-tosyl-1,6-diazaspiro[2.5]octan-6-yl)pyridin-3-yl)pyrazolo[1,5-a]pyridine-3-carbonitrile A mixture of 4-(6-(4-amino-4-(hydroxymethyl)piperidin-1-yl)pyridin-3-yl)-6-ethoxypyrazolo[1,5-a]pyridine-3-carbonitrile (Intermediate P56, 78.5 mg, 0.200 mmol), TsCl (114 mg, 0.600 mmol), DMAP (4.89 mg, 0.0400 mmol) and TEA (139 µL, 1.00 mmol) in DCM (3 mL) was stirred for 1.5 h at ambient temperature, before introducing additional TsCl (38 mg, 0.20 mmol). After stirring for an additional 15 h at ambient temperature, the resulting mixture was purified directly by silica chromatography (using 0-50% EtOAc in Hexanes as the gradient eluent) to afford the title compound (55 mg, 52% yield). MS (apci) m/z=529.2 (M+H), 551.2 (M+Na).

Intermediate R52

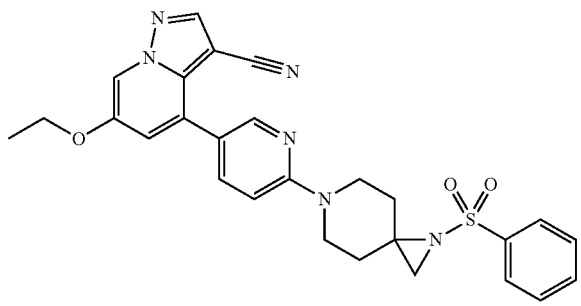 [SMILES: CCOc1cc(-c2ccc(N3CCC4(CC3)CN4S(=O)(=O)c3ccccc3)nc2)c2c(C#N)cnn2c1]

6-ethoxy-4-(6-(1-(phenylsulfonyl)-1,6-diazaspiro[2.5]octan-6-yl)pyridin-3-yl)pyrazolo[1,5-a]pyridine-3-carbonitrile A suspension of 4-(6-(4-amino-4-(hydroxymethyl)piperidin-1-yl)pyridin-3-yl)-6-ethoxypyrazolo[1,5-a]pyridine-3-carbonitrile (Intermediate P56, 40 mg, 0.10 mmol), and TEA (57 µL, 0.41 mmol) in DCM (2 mL) was treated sequentially with benzenesulfonyl chloride (33 µL, 0.25 mmol) and DMAP (1.2 mg, 0.01 mmol). The resulting mixture was stirred for 22 h at ambient temperature. The reaction mixture was purified directly by silica chromatography (0-70% EtOAc in hexanes) to afford the title compound (26 mg, 50% yield). MS (apci) m/z=515.2 (M+H), 537.1 (M+Na).

Intermediate R53

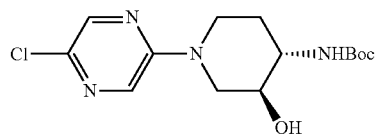 [SMILES: CC(C)(C)OC(=O)N[C@H]1CCN(c2cnc(Cl)cn2)C[C@@H]1O]

Tert-butyl ((3S,4S)-1-(5-chloropyrazin-2-yl)-3-hydroxypiperidin-4-yl)carbamate

A solution of 2,5-dichloropyrazine (217 mg, 1.46 mmol), tert-butyl ((3S,4S)-3-hydroxypiperidin-4-yl)carbamate (300 mg, 1.387 mmol) and $K_2CO_3$ (575 mg, 2.25 mmol) in DMSO (2.3 mL) was stirred at 90° C. for 12 h, then at room temperature overnight. The reaction was diluted with water (15 mL) and extracted with DCM (3×15 mL). The combined organic extracts was washed with brine (15 mL), dried over anhydrous $Na_2SO_{4(s)}$, filtered, and concentrated in vacuo. The crude was purified by silica chromatography (0-15% MeOH/DCM) followed by reverse phase chromatography (0 to 98% MeCN/water). The fractions containing product were combined, concentrated to remove most ACN, diluted with sat. $NaHCO_3$ (15 mL) and extracted with DCM (3×15 mL). The combined organic extracts was washed with brine (15 mL) and dried over anhydrous $Na_2SO_{4(s)}$, filtered, and concentrated in vacuo to afford the title compound (180.7 mg, 40% yield). MS (apci) m/z=329.2 (M+H).

Intermediate R54

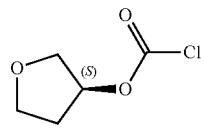

(S)-tetrahydrofuran-3-yl carbonochloridate

A solution of triphosgene (111 mg, 0.375 mmol) in DCM (284 µL) was stirred at 0° C., while sequentially adding dropwise (S)-tetrahydrofuran-3-ol (100 mg, 1.13 mmol) and a solution of pyridine (91.8 µL, 1.13 mmol) in DCM (0.15 mL). The resulting mixture was stirred for 1.5 h at 0° C., then for an additional 0.5 h at ambient temperature. The resulting mixture was filtered to remove pyridinium solids. The filtrate containing the title compound in DCM was collected and used as is in subsequent steps assuming quantitative yield.

Intermediate R55

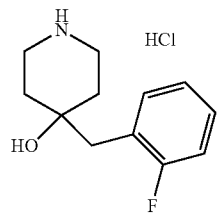 [SMILES: OC1(Cc2ccccc2F)CCNCC1 ; Cl]

4-(2-fluorobenzyl)piperidin-4-ol hydrochloride

Step 1: Preparation of tert-butyl 4-(2-fluorobenzyl)-4-hydroxypiperidine-1-carboxylate To a solution of (2-fluorobenzyl)magnesium chloride (0.5 M in Et$_2$O, 2.4 mL, 1.227 mmol) cooled to −78° C. was added tert-butyl 4-oxopiperidine-1-carboxylate (203.7 mg, 1.022 mmol) portionwise. The reaction mixture was allowed to gradually warm up to RT and stirred overnight. After removal of solvent under reduced pressure, the residue was taken up in DCM and washed with water and brine. The organic layer was concentrated and the crude material was treated with silica chromatography (0-70% EtOAc in hexanes) to yield the title compound as colorless oil (143.9 mg, 45.5%). MS (apci) m/z=210.2 (M+H-Boc).

Step 2: Preparation of 4-(2-fluorobenzyl)piperidin-4-ol hydrochloride

A solution of tert-butyl 4-(2-fluorobenzyl)-4-hydroxypiperidine-1-carboxylate (143.9 mg, 0.4651 mmol) in 1,4-dioxane (0.5 mL) was treated with conc. HCl (0.038 mL, 0.46 mmol) and stirred at RT for 1 h. Removal of solvent under reduced pressure gave the title product as colorless oil (114 mg, 99% yield). MS (apci) m/z=210.1 (M+H).

Intermediate R56

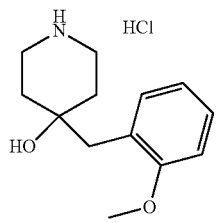

4-(2-methoxybenzyl)piperidin-4-ol hydrochloride

Step 1: Preparation of tert-butyl 4-hydroxy-4-(2-methoxybenzyl)piperidine-1-carboxylate To a solution of (2-methoxybenzyl)magnesium chloride (0.25 M in 2-methyltetrahydrofuran, 4.8 mL, 1.2 mmol) cooled to −78° C. was added tert-butyl 4-oxopiperidine-1-carboxylate (207.0 mg, 1.04 mmol) portionwise. The reaction was stirred at −78° C. for 2 h before it was quenched with sat. NH$_4$Cl (aq.). After phase-separation, the aqueous was extracted with EtOAc (3×). The organic extracts were combined, dried over Na$_2$SO$_4$, filtered and concentrated. The residue was purified by silica chromatography (0-70% EtOAc in hexanes) to afford the title compound as a colorless oil (64.1 mg, 19%). MS (apci) m/z=222.2 (M+H-Boc).

Step 2: Preparation of 4-(2-methoxybenzyl)piperidin-4-ol hydrochloride

The title product (51 mg, 99%) was prepared according to the procedure described for the preparation of Intermediate R55, Step 2. MS (apci) m/z=222.2 (M+H).

Intermediate R57

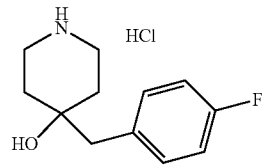

4-(4-fluorobenzyl)piperidin-4-ol hydrochloride

Step 1: Preparation of tert-butyl 4-(4-fluorobenzyl)-4-hydroxypiperidine-1-carboxylate To a solution of (4-fluorobenzyl)magnesium chloride (0.5 M in 2-methyltetrahydrofuran, 7.5 mL, 3.75 mmol) cooled to 0° C. was added tert-butyl 4-oxopiperidine-1-carboxylate (496.4 mg, 2.49 mmol) portionwise. The mixture was stirred at 0° C. for 30 min before it was quenched with sat. NH$_4$Cl$_{(aq)}$. After phase-separation, the aqueous was extracted with EtOAc (3×). The organic extracts were combined, dried over Na$_2$SO$_4$, filtered and concentrated. The residue was purified by silica chromatography (0-70% EtOAc in hexanes) to afford the title compound as a colorless oil (950.5 mg, 73%). MS (apci) m/z=210.2 (M+H-Boc).

Step 2: Preparation of 4-(2-methoxybenzyl)piperidin-4-ol hydrochloride

The title product (51 mg, 99%) was prepared according to the procedure described for the preparation of Intermediate R55, Step 2. MS (apci) m/z=210.1 (M+H).

Intermediate R58

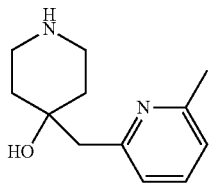

4-((6-methylpyridin-2-yl)methyl)piperidin-4-ol

Step 1: Preparation of tert-butyl 4-hydroxy-4-((6-methylpyridin-2-yl)methyl)piperidine-1-carboxylate To a flask that was dried under vacuum with heat was added 2,6-dimethylpyridine (0.06 mL, 0.5 mmol) and dry THF (1.1 mL) under argon. After cooling to −78° C., n-BuLi (2.5 M in THF, 0.17 mL, 0.43 mmol) was introduced. The reaction was allowed to warm up to 0° C., then cooled to −78° C. again, and 1-benzylpiperidin-4-one (66 mg, 0.33 mmol) was added. The reaction was allowed to slowly warm up to RT and stirred for 3 h before it was partitioned between DCM and water. After phase-separation and extracting the aqueous with DCM (2×), the organic extracts were combined, dried (Na$_2$SO$_4$), filtered and concentrated. The crude was purified by silica chromatography (0-20% MeOH in DCM) to afford the title compound (73 mg, 71%). MS (apci) m/z=307.2 (M+H).

Step 2: Preparation of 4-((6-methylpyridin-2-yl)methyl)piperidin-4-ol

A mixture of tert-butyl 4-hydroxy-4-((6-methylpyridin-2-yl)methyl)piperidine-1-carboxylate (73 mg, 0.24 mmol) in DCM (3 mL) and TFA (2 mL) was stirred at RT for 2 h before it was concentrated. The residue was taken up in minimal amount of MeOH and passed thru a P1-HCO₃ resin plug. Removal of solvent under reduced pressure yielded the title compound with quantitative yield. MS (apci) m/z=207.1 (M+H).

Intermediate R59

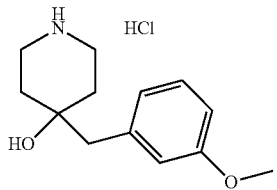 [SMILES: Cl ; COc1cccc(CC2(O)CCNCC2)c1]

4-(3-methoxybenzyl)piperidin-4-ol hydrochloride

Step 1: Preparation of tert-butyl 4-hydroxy-4-(3-methoxybenzyl)piperidine-1-carboxylate To a solution of (3-methoxybenzyl)magnesium chloride (0.25 M in 2-methyltetrahydrofuran, 15 mL, 3.75 mmol) cooled to 0° C. was added tert-butyl 4-oxopiperidine-1-carboxylate (678 mg, 3.40 mmol) portionwise. The reaction mixture was allowed to slowly warm up to RT and stirred overnight before quenched with sat. NH₄Cl (aq.). After phase-separation, the aqueous was extracted with EtOAc (3×). The organic extracts were combined, dried over Na₂SO₄, filtered and concentrated. The residue was purified by silica chromatography (0-70% EtOAc in hexanes) to afford the title compound as a colorless oil (1.09 g). MS (apci) m/z=222.2 (M+H-Boc).

Step 2: Preparation of 4-(3-methoxybenzyl)piperidin-4-ol hydrochloride

The title product was prepared according to the procedure described for the preparation of Intermediate R55, Step 2. MS (apci) m/z=222.1 (M+H).
RE23649-093

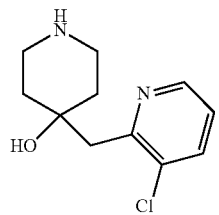

4-((3-chloropyridin-2-yl)methyl)piperidin-4-ol

Step 1: Preparation of tert-butyl 4-((3-chloropyridin-2-yl)methyl)-4-hydroxypiperidine-1-carboxylate A solution of 3-chloro-2-methylpyridine (64.2 mg, 0.50 mmol) in THF (1 mL) was sparged with N₂ and cooled to −78° C. before n-butyllithium (2.5 M THF, 0.16 mL, 0.41 mmol) was added dropwise. After stirred at −78° C. for 45 min, the mixture was warmed to RT and stirred for 2 h before cooled again to −78° C. A solution of tert-butyl 4-oxopiperidine-1-carboxylate (74.2 mg, 0.37 mmol) in THF (1.5 mL) was added dropwise. After stirring for 2 hr at −78° C., the mixture was warmed to rt and stirred for 2 d. The reaction was then partitioned between EtOAc and sat. NH₄Cl$_{(aq)}$. After phase-separation, the aqueous was extracted with EtOAc (3×). The organic extracts were combined, dried over Na₂SO₄, filtered and concentrated. The residue was purified by silica chromatography (10-90% EtOAc in hexanes) to afford the title compound as a colorless oil (103.5 mg, 85%). MS (apci) m/z=227.1 (M+H-Boc).

Step 2: Preparation of 4-((3-chloropyridin-2-yl)methyl)piperidin-4-ol

A solution of tert-butyl 4-((3-chloropyridin-2-yl)methyl)-4-hydroxypiperidine-1-carboxylate (103.5 mg, 0.32 mmol) in DCM (1.5 mL) was treated with TFA (1.5 mL) and stirred at RT overnight. After removal of solvent under reduced pressure, the residue was treated with NaHCO₃ (sat.) and extracted with 4:1 DCM/IPA (4×). The combined organic extracts were passed through a phase-separator frit and concentrated to afford the title product as a colorless oil (71.1 mg, 99%). MS (apci) m/z=227.1 (M+H).

Intermediate R61

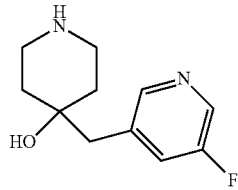 [SMILES: OC1(Cc2cncc(F)c2)CCNCC1]

4-((5-fluoropyridin-3-yl)methyl)piperidin-4-ol

Step 1: Preparation of tert-butyl 4-((5-fluoropyridin-3-yl)methyl)-4-hydroxypiperidine-1-carboxylate A solution of 3-fluoro-5-methylpyridine (279 mg, 2.51 mmol) in THF (1.5 mL) was sparged with N₂ and cooled to −78° C. before butyllithium (2.5 M THF, 0.79 mL, 1.99 mmol) was added dropwise. After 5 min stirring, a solution of tert-butyl 4-oxopiperidine-1-carboxylate (359.7 mg, 1.805 mmol) in THF (1.5 mL) was added dropwise, and stirring continued for another 5 min. The reaction was then quenched with sat. NH₄Cl$_{(aq)}$ and filtered. After phase-separation, the organic layer was washed with water, dried (Na₂SO₄), filtered and concentrated. The crude material was purified by silica chromatography (10-90% EtOAc in hexanes) to afford the title product as a colorless oil (104.9 mg, 18.7%). MS (apci) m/z=211.1 (M+H-Boc).

Step 2: Preparation of 4-((5-fluoropyridin-3-yl)methyl)piperidin-4-ol

The title product was prepared according to the procedure described for the preparation of Intermediate R60, Step 2. MS (apci) m/z=211.2 (M+H).

The compounds in Table R1 were prepared using similar methods as described for the preparation of Intermediate R56 (Method A), Intermediate R57 (Method B), Intermediate R60 (Method C), Intermediate R55 (Method D) or Intermediate R58 (Method E), using the appropriate reagent and chromatography conditions for Step 1.

TABLE R1

| Intermediate | Method | Structure | Chemical Name | LCMS m/z |
|---|---|---|---|---|
| R62 | A | 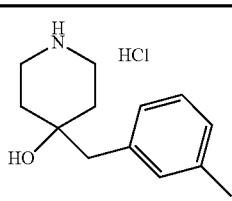 | 4-(3-methylbenzyl)piperidin-4-ol hydrochloride | 206.2 (M + H) |
| R63 | A | 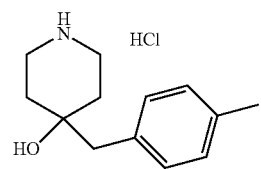 | 4-(4-methylbenzyl)piperidin-4-ol hydrochloride | 206.3 (M + H) |
| R64 | B | 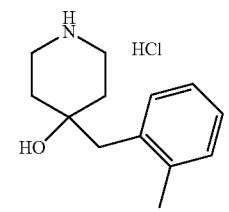 | 4-(2-methylbenzyl)piperidin-4-ol hydrochloride | 206.2 (M + H) |
| R65 | C | 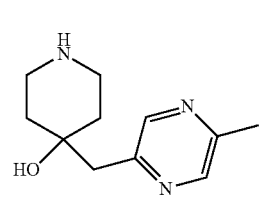 | 4-((5-methylpyrazin-2-yl)methyl)piperidin-4-ol | 208.2 (M + H) |
| R66 | C | 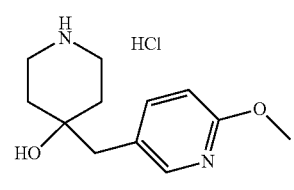 | 4-((6-methoxypyridin-3-yl)methyl)piperidin-4-ol hydrochloride | 223.1 (M + H) |
| R67 | D | 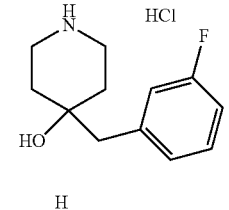 | 4-(3-fluorobenzyl)piperidin-4-ol hydrochloride | 210.2 (M + H) |
| R68 | E | 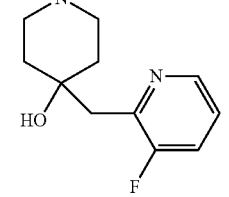 | 4-((3-fluoropyridin-2-yl)methyl)piperidin-4-ol | 211.2 (M + H) |

Intermediate R69

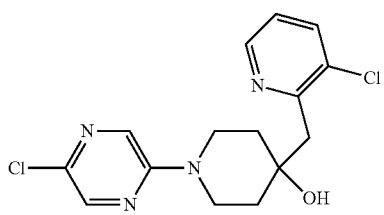 [SMILES: OC1(Cc2ncccc2Cl)CCN(c2cnc(Cl)cn2)CC1]

1-(5-chloropyrazin-2-yl)-4-((3-chloropyridin-2-yl)methyl)piperidin-4-ol

A solution of 4-((3-chloropyridin-2-yl)methyl)piperidin-4-ol (R60, 222.0 mg, 0.98 mmol) and 2,5-dichloropyrazine (145.9 mg, 0.98 mmol) in DMSO (2 mL) was treated with DIEA (0.86 mL, 4.90 mmol) and stirred at 100° C. overnight. After cooling to RT the reaction was diluted with H$_2$O and extracted with 4:1 DCM/IPA (3×). The organic extracts were combined and concentrated. The crude residue was purified by silica chromatography (20-80% EtOAc in hexanes) to afford the title product as a colorless oil (206.7 mg, 62% yield). MS (apci) m/z=339.1 (M+H).

Intermediate R70

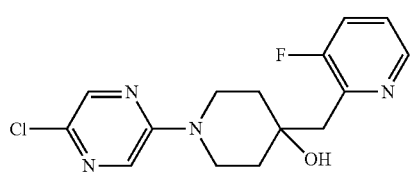 [SMILES: OC1(Cc2ncccc2F)CCN(c2cnc(Cl)cn2)CC1]

1-(5-chloropyrazin-2-yl)-4-((3-fluoropyridin-2-yl)methyl)piperidin-4-ol

The title product (460 mg, 59%) was prepared according to the procedure described for the preparation of Intermediate R69, replacing 4-((3-chloropyridin-2-yl)methyl)piperidin-4-ol with 4-((3-fluoropyridin-2-yl)methyl)piperidin-4-ol (Intermediate R68). MS (apci) m/z=323.1 (M+H).

Intermediate R71

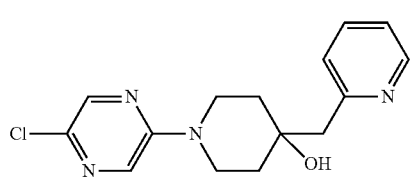 [SMILES: OC1(Cc2ccccn2)CCN(c2cnc(Cl)cn2)CC1]

1-(5-chloropyrazin-2-yl)-4-(pyridin-2-ylmethyl)piperidin-4-ol

The title product (550 mg, 96%) was prepared according to the procedure described for the preparation of Intermediate R69, replacing 4-((3-chloropyridin-2-yl)methyl)piperidin-4-ol with 4-(pyridin-2-ylmethyl)piperidin-4-ol dihydrochloride. MS (apci) m/z=305.1 (M+H).

Intermediate R72

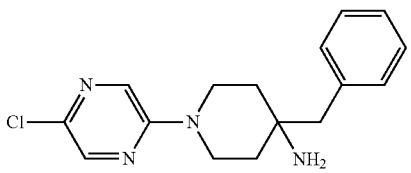 [SMILES: NC1(Cc2ccccc2)CCN(c2cnc(Cl)cn2)CC1]

4-benzyl-1-(5-chloropyrazin-2-yl)piperidin-4-amine

Step 1: Preparation of 4-benzylpiperidin-4-amine bis(2,2,2-trifluoroacetate)

A mixture of tert-butyl 4-amino-4-benzylpiperidine-1-carboxylate (210 mg, 0.723 mmol) in DCM (2 mL) and TFA (1 mL) was stirred at RT for ~3 h before it was concentrated to yield the title compound assuming quantitative yield. MS (apci) m/z=191.2 (M+H).

Step 2: Preparation of 4-benzyl-1-(5-chloropyrazin-2-yl)piperidin-4-amine

To a solution of 2,5-dichloropyrazine (0.1316 mL, 0.7243 mmol) in DMSO (10 mL) were added K$_2$CO$_3$ (300.3 mg, 2.173 mmol) followed by 4-benzylpiperidin-4-amine bis(2,2,2-trifluoroacetate) (303 mg, 0.72 mmol). The reaction was sealed and heated at 75° C. overnight. After cooling to RT, the reaction was diluted with EtOAc (10 mL) and water (20 mL). After phase-separation, the aqueous was extracted with EtOAc (2×). The combined organic extracts were concentrated and used directly in the next step. MS (apci) m/z=303.1 (M+H).

SYNTHETIC EXAMPLES

Example 1

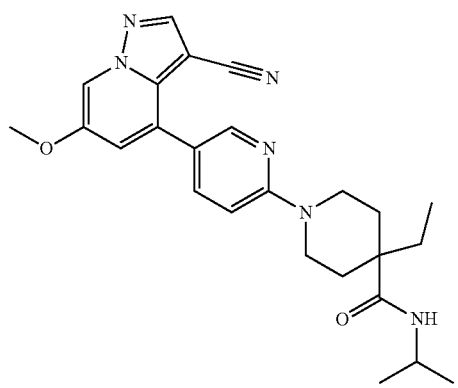 [SMILES: CCC1(C(=O)NC(C)C)CCN(c2ccc(-c3cc(OC)cn4ncc(C#N)c34)cn2)CC1]

1-(5-(3-Cyano-6-methoxypyrazolo[1,5-a]pyridin-4-yl)pyridin-2-yl)-4-ethyl-N-isopropylpiperidine-4-carboxamide A stirred solution of 4-bromo-6-methoxypyrazolo[1,5-a]pyridine-3-carbonitrile (Intermediate P1, Step 6 of Part B; 20 mg, 0.0793 mmol) in dioxane (33.7 mL) was treated with (6-(4-ethyl-4-(isopropylcarbamoyl)piperidin-1-yl)pyridin-3-yl)boronic acid (Intermediate R3; 38.0 mg, 0.119 mmol) and 2 M $K_2CO_{3(aq)}$ (79.3 µL, 0.159 mmol). The mixture was purged with $N_{2(g)}$ for 5 min, then treated with X-Phos (7.56 mg, 0.0159 mmol) and $Pd_2(dba)_3$ (3.63 mg, 0.00397 mmol), and purged again with $N_{2(g)}$ for an additional 5 min. The resulting reaction mixture was stirred overnight at 80° C. After cooling to ambient temperature, the reaction mixture was diluted with water and the biphasic mixture was extracted with EtOAc. The combined organic extracts were dried over anhydrous $Na_2SO_{4(s)}$, filtered, and concentrated in vacuo. Purification of the crude residue by silica chromatography (0-10% MeOH/DCM in EtOAc as the gradient eluent) cleanly provided the title compound (29.2 mg, 82% yield). MS (apci) m/z=447.2 (M+H).

Example 2

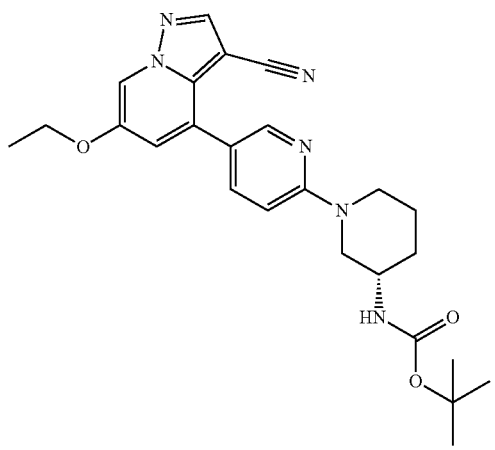 [SMILES: CCOc1cc(-c2ccc(N3CCC[C@H](NC(=O)OC(C)(C)C)C3)nc2)c2c(C#N)cnn2c1]

tert-butyl (S)-(1-(5-(3-cyano-6-ethoxypyrazolo[1,5-a]pyridin-4-yl)pyridin-2-yl)piperidin-3-yl)carbamate A suspension of 6-ethoxy-4-(6-fluoropyridin-3-yl)pyrazolo[1,5-a]pyridine-3-carbonitrile (Intermediate P6; 0.086 g, 0.30 mmol) in DMSO (709 µL) was treated with tert-butyl (S)-piperidin-3-ylcarbamate (180 mg, 0.91 mmol) and $K_2CO_{3(s)}$ (170 mg, 1.2 mmol) was stirred overnight at 110° C. The reaction mixture was cooled to ambient temperature, and then diluted with DCM. The pH of the resulting mixture was adjusted to about pH 7 with the addition of saturated $NH_4Cl_{(aq)}$. The biphasic mixture was extracted with DCM, and the combined organic extracts were dried over anhydrous $Na_2SO_{4(s)}$, filtered, and concentrated in vacuo. The crude residue was purified by silica chromatography (0-15% MeOH/EtOAc as the gradient eluent) to afford the title compound (94 mg, 67% yield). MS (apci) m/z=463.3 (M+H).

Example 3

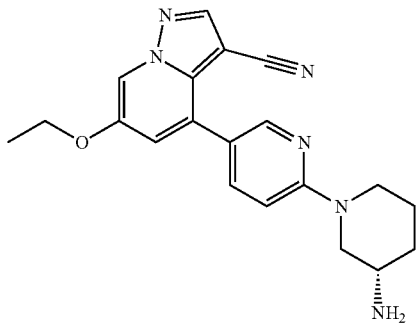 [SMILES: CCOc1cc(-c2ccc(N3CCC[C@H](N)C3)nc2)c2c(C#N)cnn2c1]

(S)-4-(6-(3-aminopiperidin-1-yl)pyridin-3-yl)-6-ethoxypyrazolo[1,5-a]pyridine-3-carbonitrile A solution of tert-butyl (S)-(1-(5-(3-cyano-6-ethoxypyrazolo[1,5-a]pyridin-4-yl)pyridin-2-yl)piperidin-3-yl)carbamate (Example 2; 10 mg, 0.0216 mmol) in DCM (500 µL) was treated with TFA (49.7 µL, 0.6486 mmol) and stirred overnight at ambient temperature. The reaction mixture was diluted with DCM and directly purified by C18 reverse phase chromatography (20-80% ACN/Water with 0.1% formic acid as the gradient eluent) to afford the title compound (5.7 mg, 73% yield). MS (apci) m/z=363.2 (M+H).

Example 4

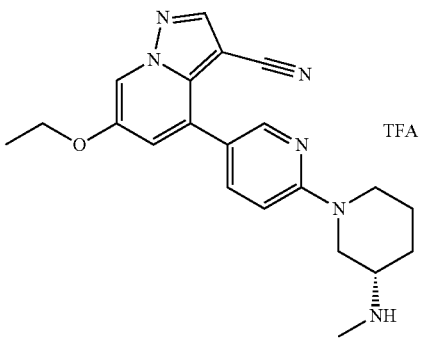 [SMILES: CCOc1cc(-c2ccc(N3CCC[C@H](NC)C3)nc2)c2c(C#N)cnn2c1]

(S)-6-ethoxy-4-(6-(3-(methylamino)piperidin-1-yl)pyridin-3-yl)pyrazolo[1,5-a]pyridine-3-carbonitrile (TFA salt)

Step 1: Preparation of tert-butyl (S)-(1-(5-(3-cyano-6-ethoxypyrazolo[1,5-a]pyridin-4-yl)pyridin-2-yl)piperidin-3-yl)(methyl)carbamate 2,2,2-trifluoroacetate A solution of tert-butyl (S)-(1-(5-(3-cyano-6-ethoxypyrazolo[1,5-a]pyridin-4-yl)pyridin-2-yl)piperidin-3-yl)carbamate (Example 2; 0.026 g, 0.0562 mmol) in DMA (250 µL) was treated with TEA (94 µL, 0.675 mmol) and a solution of iodomethane (1 drop, approximately 3.5 µL, 0562 mmol) in DMA (250 µL). The reaction mixture was stirred 2 h at ambient temperature before introducing additional concentrated iodomethane (2 drops, approximately 7 μL, 1.1 mmol). The reaction mixture was allowed to stir overnight at 0° C. Due to insufficient reaction progression, the reaction mixture was treated with NaH (60% in mineral oil; 3 mg, 0.125 mmol). The resulting mixture was allowed to stir 6 h at ambient temperature, and then additional concentrated iodomethane (4 drops, approximately 14 μL, 2.25 mmol) was added. The reaction mixture was stirred overnight at ambient temperature, and then quenched with water in DCM. The resulting biphasic mixture was extracted with DCM, and the combined organic extracts were dried over anhydrous $Na_2SO_{4(s)}$, filtered, and concentrated in vacuo. The residue was purified by C18 reverse phase chromatography (5-95% ACN in water with 0.01% TFA as the gradient eluent) to afford the title compound as the TFA Salt (13.7 mg, 51% yield). MS (apci) m/z=477.3 (M+H).

Step 2: Preparation of (S)-6-ethoxy-4-(6-(3-(methylamino)piperidin-1-yl)pyridin-3-yl)pyrazolo[1,5-a]pyridine-3-carbonitrile A solution of tert-butyl (S)-(1-(5-(3-cyano-6-ethoxypyrazolo[1,5-a]pyridin-4-yl)pyridin-2-yl)piperidin-3-yl)(methyl)carbamate 2,2,2-trifluoroacetate (step 1, 13.7 mg, 0.0288 mmol) in DCM (500 μL) was treated with TFA (22.0 μL, 0.288 mmol) was stirred for 5 h at ambient temperature. The reaction mixture was diluted with MeOH (1 mL) and purified directly by C18 reverse phase chromatography (5-95% ACN in water with 0.01% TFA as the gradient eluent) to afford the title compound (9.7 mg, 90% yield). MS (apci) m/z=377.2 (M+H).

Example 5

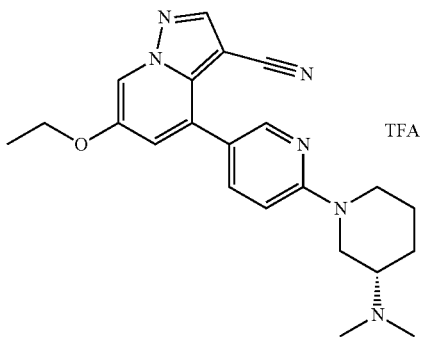 [SMILES: CCOc1cc(-c2ccc(N3CCC[C@H](N(C)C)C3)nc2)c2c(C#N)cnn2c1]

(S)-4-(6-(3-(dimethylamino)piperidin-1-yl)pyridin-3-yl)-6-ethoxypyrazolo[1,5-a]pyridine-3-carbonitrile (TFA salt)

A solution of tert-butyl (S)-(1-(5-(3-cyano-6-ethoxypyrazolo[1,5-a]pyridin-4-yl)pyridin-2-yl)piperidin-3-yl)carbamate (Example 2; 20 mg, 0.0432 mmol) and formaldehyde (130 μL, 0.140 mmol) in formic acid (326 μL) was stirred 4 h at ambient temperature and then an additional 2 h at 90° C. Due to insufficient reaction progression, the reaction mixture was treated with NaH (60% in mineral oil; 3 mg, 0.125 mmol). The resulting mixture was quenched with saturated NH₄Cl(a). The resulting biphasic mixture was concentrated in vacuo. The residue was purified by C18 reverse phase chromatography (5-95% ACN in water with 0.01% TFA as the gradient eluent) to afford the title compound (5.5 mg, 33% yield). MS (apci) m/z=391.2 (M+H).

Example 6

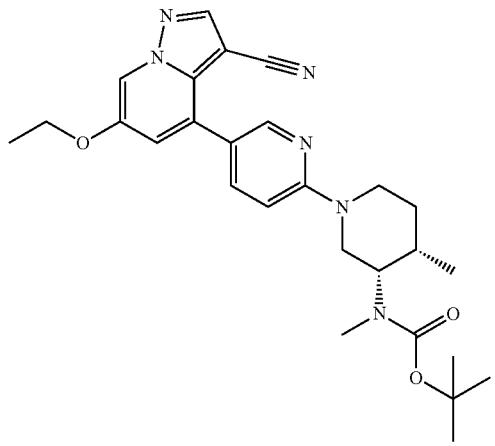 [SMILES: CCOc1cc(-c2ccc(N3CC[C@H](C)[C@H](N(C)C(=O)OC(C)(C)C)C3)nc2)c2c(C#N)cnn2c1]

tert-butyl ((3S,4S)-1-(5-(3-cyano-6-ethoxypyrazolo [1,5-a]pyridin-4-yl)pyridin-2-yl)-4-methylpiperidin-3-yl)(methyl)carbamate A suspension of 6-ethoxy-4-(6-fluoropyridin-3-yl)pyrazolo[1,5-a]pyridine-3-carbonitrile (Intermediate P6; 0.060 g, 0.21 mmol) in DMSO (1.0 mL) was treated with tert-butyl methyl((3S,4S)-4-methylpiperidin-3-yl)carbamate (97 mg, 0.43 mmol) and $K_2CO_{3(s)}$ (120 mg, 0.85 mmol) was stirred for 10 h at 90° C. The reaction mixture was cooled to ambient temperature and then quenched with the addition of a 1:1 mixture of water and saturated $NH_4Cl_{(aq)}$. The resulting mixture was extracted with DCM. The combined organic extracts were dried over anhydrous $Na_2SO_{4(s)}$, filtered, and concentrated in vacuo. The crude residue was purified by C18 reverse phase chromatography (20-90% ACN/water as the gradient eluent) to afford the title compound (63 mg, 60% yield). MS (apci) m/z=491.3 (M+H).

Example 7

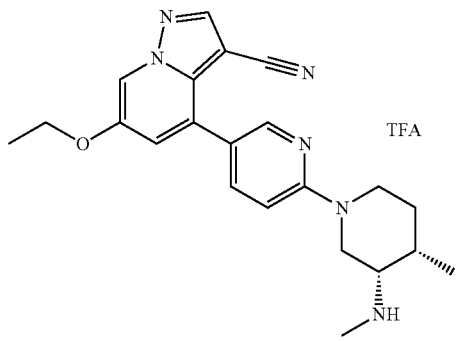 [SMILES: CCOc1cc(-c2ccc(N3CC[C@H](C)[C@H](NC)C3)nc2)c2c(C#N)cnn2c1]

6-Ethoxy-4-(6-((3S,4S)-4-methyl-3-(methylamino) piperidin-1-yl)pyridin-3-yl)pyrazolo[1,5-a]pyridine-3-carbonitrile (TFA salt)

A suspension of tert-butyl ((3S,4S)-1-(5-(3-cyano-6-ethoxypyrazolo[1,5-a]pyridin-4-yl)pyridin-2-yl)-4-methylpiperidin-3-yl)(methyl)carbamate (Example 6; 63 mg, 0.13 mmol) in DCM (0.5 mL) was treated with TFA (98.3 µL, 1.284 mmol). The reaction mixture was stirred for 5 h at ambient temperature, and then concentrated in vacuo. The crude residue was purified by C18 reverse phase chromatography (5-95% ACN in water with 0.01% TFA as the gradient eluent) to afford the title compound as TFA salt (41.1 mg, 82% yield). MS (apci) m/z=391.2 (M+H).

Example 8

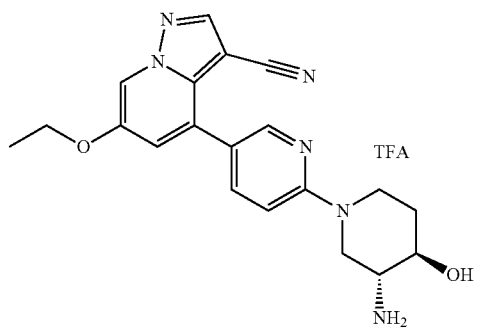 [SMILES: CCOc1cc(-c2ccc(N3CC[C@@H](O)[C@H](N)C3)nc2)c2c(C#N)cnn2c1]

4-(6-((3R,4R)-3-amino-4-hydroxypiperidin-1-yl) pyridin-3-yl)-6-ethoxypyrazolo[1,5-a]pyridine-3-carbonitrile 2,2,2-trifluoroacetate A suspension of 6-ethoxy-4-(6-fluoropyridin-3-yl)pyrazolo[1,5-a]pyridine-3-carbonitrile Intermediate P6; 87 mg, 0.31 mmol) in DMSO (3.0 mL) was treated with tert-butyl ((3R,4R)-4-hydroxypiperidin-3-yl)carbamate (200 mg, 0.92 mmol) and $K_2CO_{3(s)}$ (170 mg, 1.2 mmol) was stirred overnight at 110° C. After cooling to ambient temperature, the reaction mixture was diluted with DCM, and the pH of the mixture was adjusted to about pH 7 with the addition of saturated $NH_4Cl_{(aq)}$. The resulting biphasic mixture was extracted with DCM. The combined organic extracts were dried over anhydrous $Na_2SO_{4(s)}$, filtered, and concentrated in vacuo. The crude residue was purified by C18 reverse phase chromatography (10-85% ACN in water with 0.01% TFA as the gradient eluent) to provide a 2:1 mixture of the title compound plus the Boc protected title compound. The mixture was next purified by C18 reverse phase chromatography (5-95% ACN in water with 0.1 w/w % TFA) to afford the title compound as the TFA salt (15 mg, 13% yield). MS (apci) m/z=379.1 (M+H).

Example 9

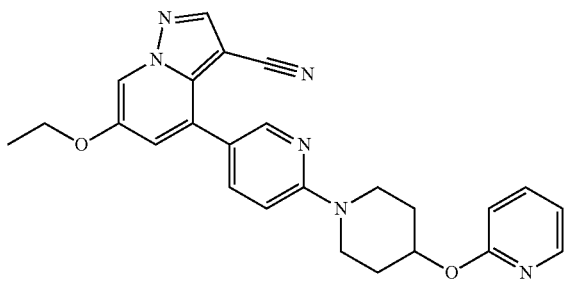 [SMILES: CCOc1cc(-c2ccc(N3CCC(Oc4ccccn4)CC3)nc2)c2c(C#N)cnn2c1]

6-ethoxy-4-(6-(4-(pyridin-2-yloxy)piperidin-1-yl) pyridin-3-yl)pyrazolo[1,5-a]pyridine-3-carbonitrile A suspension of 6-ethoxy-4-(6-fluoropyridin-3-yl)pyrazolo[1,5-a]pyridine-3-carbonitrile (Intermediate P6; 30 mg, 0.11 mmol), 2-(piperidin-4-yloxy)pyridine (28.4 mg, 0.159 mmol), and TEA (44 µL, 0.319 mmol) in DMA (500 µL) was stirred overnight at 90° C. After cooling to ambient temperature, the reaction mixture was diluted with DCM and quenched with water. The resulting biphasic mixture was extracted with DCM. The combined organic extracts were dried over anhydrous $Na_2SO_{4(s)}$, filtered, and concentrated in vacuo. The crude residue was purified by silica chromatography (40-100% EtOAc/Hexanes as the gradient eluent) to afford the title compound (23.6 mg, 50% yield). MS (apci) m/z=441.2 (M+H).

Example 10

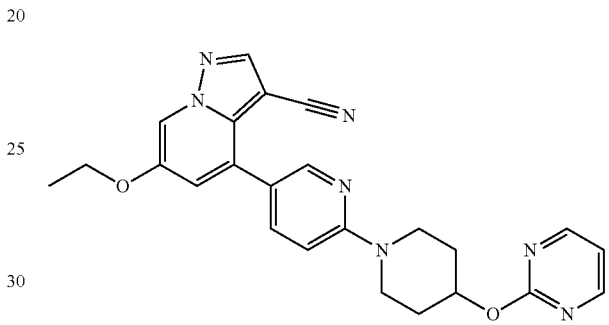

6-ethoxy-4-(6-(4-(pyrimidin-2-yloxy)piperidin-1-yl) pyridin-3-yl)pyrazolo[1,5-a]pyridine-3-carbonitrile The title compound (18.6 mg, 40% yield) was prepared and purified using a similar procedure to that described for Example 9, replacing 2-(piperidin-4-yloxy)pyridine with 2-(piperidin-4-yloxy)pyrimidine. MS (apci) m/z=442.3 (M+H).

Example 11

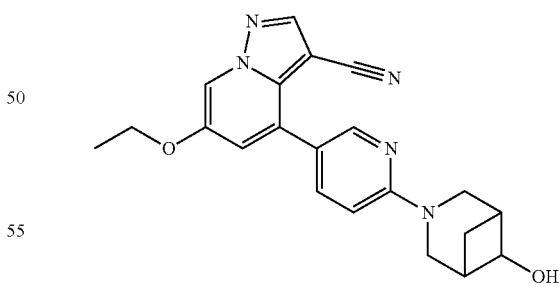

6-ethoxy-4-(6-(6-hydroxy-3-azabicyclo[3.1.1]heptan-3-yl)pyridin-3-yl)pyrazolo[1,5-a]pyridine-3-carbonitrile The title compound was prepared, quenched and worked up using similar procedures to those described for Example 6, replacing tert-butyl ((3R,4R)-4-hydroxypiperidin-3-yl)carbamate with 3-azabicyclo[3.1.1]heptan-6-ol. The crude residue was suspended in 19:1 Et$_2$O:MeOH, and the resultant suspension was filtered to cleanly provide the title compound (73.2 mg, 61% yield). MS (apci) m/z=376.2 (M+H).

Example 12

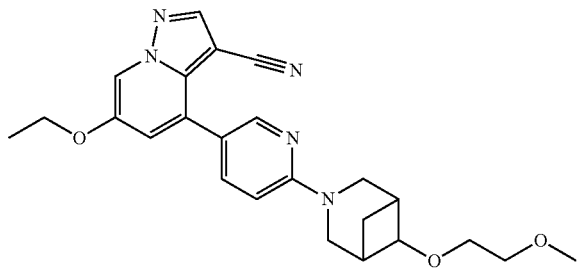 [SMILES: CCOc1cc(-c2ccc(N3CC4CC(C3)C4OCCOC)nc2)c2c(C#N)cnn2c1]

6-ethoxy-4-(6-(6-(2-methoxyethoxy)-3-azabicyclo [3.1.1]heptan-3-yl)pyridin-3-yl)pyrazolo[1,5-a]pyridine-3-carbonitrile A cold (0° C.) suspension of 6-ethoxy-4-(6-(6-hydroxy-3-azabicyclo[3.1.1]heptan-3-yl)pyridin-3-yl)pyrazolo[1,5-a]pyridine-3-carbonitrile (Example 11; 15 mg, 0.040 mmol) in DMA (500 μL) was treated with NaH (3 mg, 0.12 mmol). The resulting mixture was allowed to warm to ambient temperature, before introducing 1-bromo-2-methoxyethane (56 mg, 0.40 mmol). After stirring for 1 hour at 90° C., the reaction mixture was cooled to ambient temperature and quenched with water. The resulting mixture was diluted with additional water and brine, and was extracted with DCM. The combined organic extracts were dried over anhydrous Na$_2$SO$_{4(s)}$, filtered, and concentrated in vacuo. The residue was purified by silica chromatography (0-15% MeOH/EtOAc as the gradient eluent) to afford the title compound (7.7 mg, 44% yield). MS (apci) m/z=434.2 (M+H).

Example 13

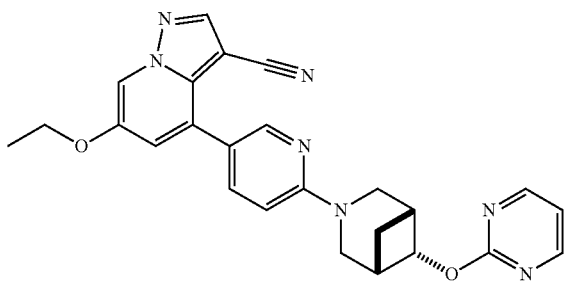

6-ethoxy-4-(6-((rel-1R,5 S,6R)-6-(pyrimidin-2-yloxy)-3-azabicyclo[3.1.1]heptan-3-yl)pyridin-3-yl) pyrazolo[1,5-a]pyridine-3-carbonitrile A cold (0° C.) suspension of 6-ethoxy-4-(6-(6-hydroxy-3-azabicyclo[3.1.1]heptan-3-yl)pyridin-3-yl)pyrazolo[1,5-a]pyridine-3-carbonitrile (Example 11; 20 mg, 0.0533 mmol) in DMSO (500 μL) was treated with NaH (2.6 mg, 0.107 mmol) The resulting mixture was allowed to warm to ambient temperature, and 2-chloropyrimidine (18.3 mg, 0.160 mmol) was added. After stirring for 0.5 h at 50° C., the reaction mixture was cooled to ambient temperature and quenched dropwise with water. The resulting mixture was diluted with additional water and brine and then extracted with DCM. The combined organic extracts were dried over anhydrous Na$_2$SO$_{4(s)}$, filtered, and concentrated in vacuo. The residue was purified by silica chromatography (0-15% MeOH/EtOAc as the gradient eluent) to afford the title compound (13.9 mg, 58% yield). MS (apci) m/z=454.2 (M+H).

Example 14

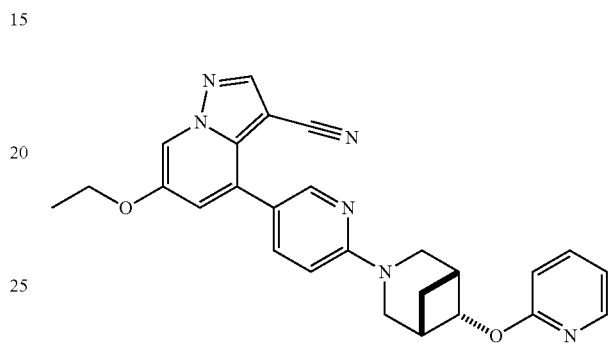

6-ethoxy-4-(6-((rel-1R,5 S,6R)-6-(pyridin-2-yloxy)-3-azabicyclo[3.1.1]heptan-3-yl)pyridin-3-yl)pyrazolo[1,5-a]pyridine-3-carbonitrile The title compound was prepared using a similar method to that described for Example 13, replacing 2-chloropyrimidine with 2-chloropyridine. Purification by silica chromatography (40-100% EtOAc/hexanes as the gradient eluent) cleanly provided the title compound (11.3 mg, 47% yield). (MS (apci) m/z=453.2 (M+H).

Example 15

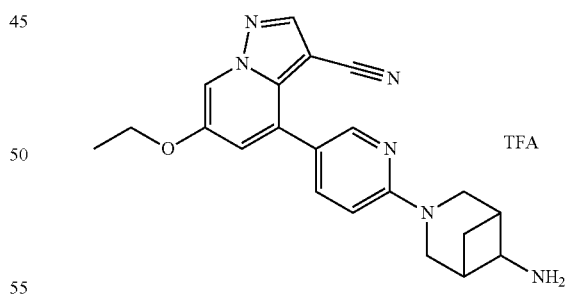

(4-(6-(6-amino-3-azabicyclo[3.1.1]heptan-3-yl)pyridin-3-yl)-6-ethoxypyrazolo[1,5-a]pyridine-3-carbonitrile (TFA salt)

Step 1: Preparation of tert-butyl (3-(5-(3-cyano-6-ethoxypyrazolo[1,5-a]pyridin-4-yl)pyridin-2-yl)-3-azabicyclo[3.1.1]heptan-6-yl)carbamate A suspension of 6-ethoxy-4-(6-fluoropyridin-3-yl)pyrazolo[1,5-a]pyridine-3-carbonitrile (Intermediate P6; 0.065 g, 0.23 mmol), tert-butyl (3-azabicyclo[3.1.1]heptan-6-yl) carbamate (98 mg, 0.46 mmol) and K₂CO₃(s) (130 mg, 0.92 mmol) in DMSO (500 μL) was stirred overnight at 90° C. The reaction mixture was diluted with DCM, and quenched with water. The resulting biphasic mixture was diluted with additional water and brine, and then extracted with DCM. The combined organic extracts were dried over anhydrous Na₂SO₄(s), filtered, and concentrated in vacuo. The residue was purified by silica chromatography (40-100% EtOAc/hexanes as the gradient eluent) to afford the title compound (7.3 mg, 67% yield). MS (apci) m/z=475.2 (M+H).

Step 2: Preparation of 4-(6-(6-amino-3-azabicyclo [3.1.1]heptan-3-yl)pyridin-3-yl)-6-ethoxypyrazolo[1, 5-a]pyridine-3-carbonitrile 2,2,2-trifluoroacetate A solution of tert-butyl (3-(5-(3-cyano-6-ethoxypyrazolo [1,5-a]pyridin-4-yl)pyridin-2-yl)-3-azabicyclo[3.1.1]heptan-6-yl)carbamate (90 mg, 0.1896 mmol) in DCM (1.25 mL) was treated with TFA (581 μL, 7.59 mmol) and stirred overnight at ambient temperature. The reaction mixture was concentrated in vacuo, and the residue was purified by C18 reverse phase chromatography (5-95% ACN in water with 0.01% TFA as the gradient eluent) to afford the title compound as TFA salt (8.72 mg,). MS (apci) m/z=375.2 (M+H).

Example 16

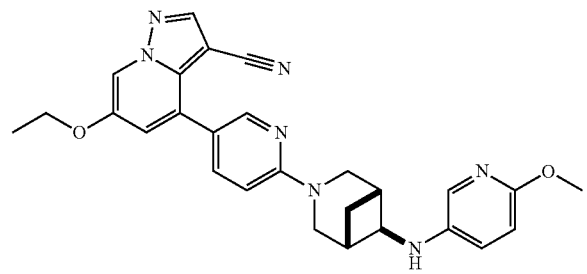

6-ethoxy-4-(6-((rel-1R,5 S,6S)-6-((6-methoxypyridin-3-yl)amino)-3-azabicyclo[3.1.1]heptan-3-yl) pyridin-3-yl)pyrazolo[1,5-a]pyridine-3-carbonitrile A suspension of 6-ethoxy-4-(6-fluoropyridin-3-yl)pyrazolo[1,5-a]pyridine-3-carbonitrile (Intermediate P6; 64.4 mg, 0.228 mmol), N-(6-methoxypyridin-3-yl)-3-azabicyclo [3.1.1]heptan-6-amine 2,2,2-trifluoroacetate (Intermediate R8; 25 mg, 0.114 mmol) in DMSO (500 μL) was treated with K₂CO₃(s) (63.0 mg, 0.456 mmol) and stirred overnight at 90° C. After cooling to ambient temperature, the reaction mixture was diluted with DCM and quenched with water. The resulting biphasic mixture was extracted with DCM. The combined organic extracts were dried over anhydrous Na₂SO₄(s), filtered, and concentrated in vacuo. The crude residue was purified by silica chromatography (40-100% EtOAc/hexanes as the gradient eluent) to afford the title compound (10.2 mg, 19% yield). MS (apci) m/z=482.3 (M+H).

Example 17

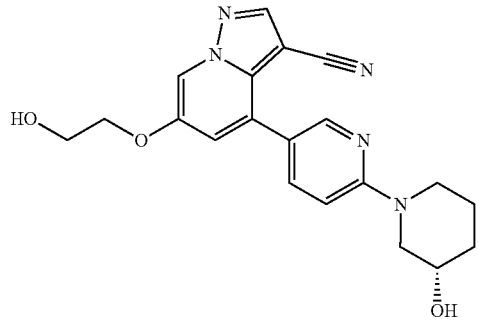 [SMILES: N#Cc1cnn2cc(OCCO)cc(-c3ccc(N4CCC[C@H](O)C4)nc3)c12]

(S)-6-(2-hydroxyethoxy)-4-(6-(3-hydroxypiperidin-1-yl)pyridin-3-yl)pyrazolo[1,5-a]pyridine-3-carbonitrile A solution of 6-(2-((tert-butyldimethylsilyl)oxy)ethoxy)-4-(6-fluoropyridin-3-yl)pyrazolo[1,5-a]pyridine-3-carbonitrile (Intermediate P26; 30 mg, 0.073 mmol) in DMSO (1.5 mL) was treated with (S)-3-hydroxypiperidine hydrochloride (0.050 g, 0.36 mmol) and K₂CO₃(s) (40 mg, 0.29 mmol) and stirred 2 h at 110° C. After cooling to ambient temperature, the reaction mixture was quenched with water. The resultant suspension was filtered, and the isolated solids were purified by silica chromatography (0-20% MeOH in DCM as the gradient eluent) to afford the title compound (7.5 mg, 27% yield). MS (apci) m/z=380.1 (M+H).

Example 18

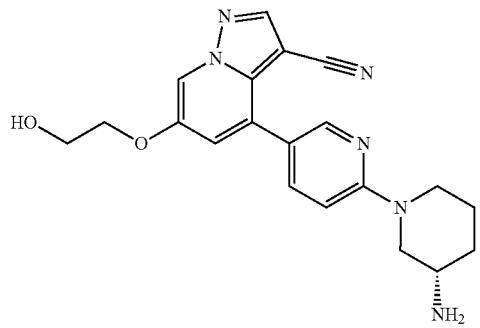 [SMILES: N#Cc1cnn2cc(OCCO)cc(-c3ccc(N4CCC[C@H](N)C4)nc3)c12]

(S)-4-(6-(3-aminopiperidin-1-yl)pyridin-3-yl)-6-(2-hydroxyethoxy)pyrazolo[1,5-a]pyridine-3-carbonitrile A solution of 6-(2-((tert-butyldimethylsilyl)oxy)ethoxy)-4-(6-fluoropyridin-3-yl)pyrazolo[1,5-a]pyridine-3-carbonitrile (Intermediate P26; 60 mg, 0.15 mmol) in DMSO (2.9 mL) was treated with (S)-3-(tert-butoxycarbonylamino)piperidine (0.12 g, 0.58 mmol) and K₂CO₃(s) (80 mg, 0.58 mmol) and stirred for 1 hour at 110° C. After cooling to ambient temperature, the reaction mixture was neutralized with the addition 1 M HCl(aq). The resultant suspension was extracted with DCM, and the organic extracts were dried over anhydrous Na₂SO₄(s), filtered and concentrated in vacuo. The residue was purified by silica chromatography (0-10% MeOH in DCM as the gradient eluent) to afford the Boc-protected title compound. The Boc-protected material was dissolved in DCM (3 mL) then treated with 4 N HCl in dioxanes (3 mL). After stirring overnight at ambient temperature, the reaction mixture was concentrated in vacuo. The residue was purified by silica chromatography (0-100% [20% MeOH, 2% NH$_4$OH, 78% DCM] in DCM as the gradient eluent) to cleanly provide the title compound (20 mg, 35% yield). MS (apci) m/z=379.2 (M+H).

Example 19

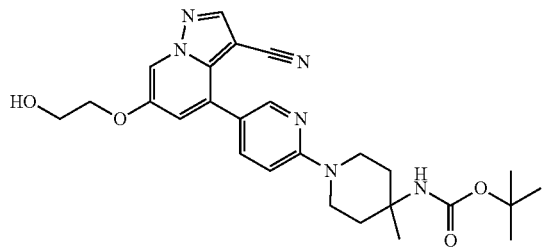 [SMILES: CC1(NC(=O)OC(C)(C)C)CCN(c2ccc(-c3cc(OCCO)cn4ncc(C#N)c34)cn2)CC1]

tert-butyl (1-(5-(3-cyano-6-(2-hydroxyethoxy)pyrazolo[1,5-a]pyridin-4-yl)pyridin-2-yl)-4-methylpiperidin-4-yl)carbamate A solution of 6-(2-((tert-butyldimethylsilyl)oxy)ethoxy)-4-(6-fluoropyridin-3-yl)pyrazolo[1,5-a]pyridine-3-carbonitrile (Intermediate P26; 111 mg, 0.269 mmol) and tert-butyl N-(4-methyl-4-piperidyl)carbamate (173 mg, 0.807 mmol) in DMSO (2.5 mL) was stirred for 1 hour at 110° C. After cooling to ambient temperature, the reaction mixture was quenched with water. The resultant suspension was filtered, and the solids were collected to cleanly provide the title compound (65 mg, 49% yield). MS (apci) m/z=493.2 (M+H).

Example 20

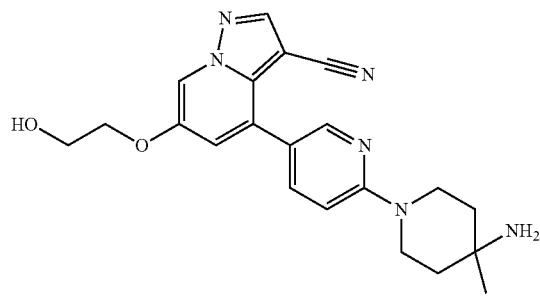 [SMILES: CC1(N)CCN(c2ccc(-c3cc(OCCO)cn4ncc(C#N)c34)cn2)CC1]

4-(6-(4-amino-4-methylpiperidin-1-yl)pyridin-3-yl)-6-(2-hydroxyethoxy)pyrazolo[1,5-a]pyridine-3-carbonitrile A solution of tert-butyl (1-(5-(3-cyano-6-(2-hydroxyethoxy)pyrazolo[1,5-a]pyridin-4-yl)pyridin-2-yl)-4-methylpiperidin-4-yl)carbamate (Example 19; 45 mg, 0.091 mmol) in DCM (2 mL) was treated with 4 N HCl in dioxanes (3 mL, 12 mmol) and stirred for 2 h at ambient temperature. The resultant mixture was concentrated in vacuo to afford the title compound as the HCl salt. The salt was dissolved in MeOH, filtered through an Agilent PL-HCO$_3$ MP SPE filter (to neutralize the HCl salt), and concentrated in vacuo to cleanly provide the title compound (30 mg, 84% yield). MS (apci) m/z=393.2 (M+H).

Example 21

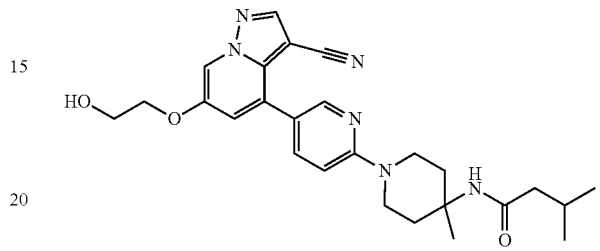

N-(1-(5-(3-cyano-6-(2-hydroxyethoxy)pyrazolo[1,5-a]pyridin-4-yl)pyridin-2-yl)-4-methylpiperidin-4-yl)-3-methylbutanamide A solution of 4-(6-(4-amino-4-methylpiperidin-1-yl)pyridin-3-yl)-6-(2-hydroxyethoxy)pyrazolo[1,5-a]pyridine-3-carbonitrile (Example 20; 15 mg, 0.038 mmol) in DCM (191 µL) was treated sequentially with DIEA (20 µL, 0.11 mmol) and isovaleryl chloride (5.1 µL, 0.042 mmol) and stirred overnight at ambient temperature. The reaction mixture was concentrated in vacuo, and the residue was purified by silica chromatography (0-20% MeOH in DCM as the gradient eluent) to cleanly provide the title compound (4.8 mg, 26% yield). MS (apci) m/z=477.2 (M+H).

Example 22

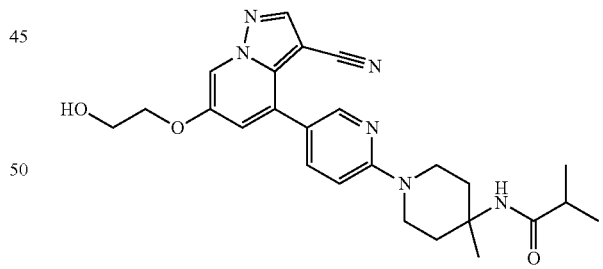

N-(1-(5-(3-cyano-6-(2-hydroxyethoxy)pyrazolo[1,5-a]pyridin-4-yl)pyridin-2-yl)-4-methylpiperidin-4-yl)isobutyramide The title compound was prepared using a similar procedure to that described for Example 21, replacing isovaleryl chloride with isobutyryl chloride and using 5 equivalents of DIE. Following purification by silica chromatography (0-20% MeOH in DCM as the gradient eluent), the title compound was cleanly isolated (3.8 mg, 21% yield). MS (apci) m/z=463.2 (M+H).

Example 23

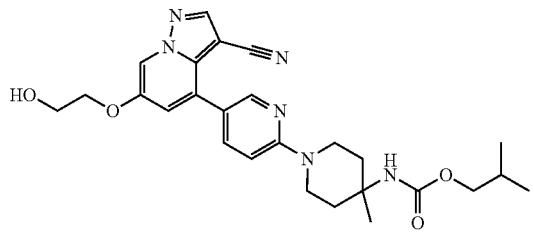 [SMILES: CC(C)COC(=O)NC1(C)CCN(c2ccc(-c3cc(OCCO)cn4ncc(C#N)c34)cn2)CC1]

Isobutyl (1-(5-(3-cyano-6-(2-hydroxyethoxy)pyra-zolo[1,5-a]pyridin-4-yl)pyridin-2-yl)-4-methylpip-eridin-4-yl)carbamate The title compound was prepared using a similar procedure to that described for Example 21, replacing isovaleryl chloride with isobutyl chloroformate (1 equivalent). Following purification by silica chromatography (0-20% MeOH in DCM as the gradient eluent), the title compound was cleanly isolated (6.6 mg, 35% yield). MS (apci) m/z=493.2 (M+H).

Example 24

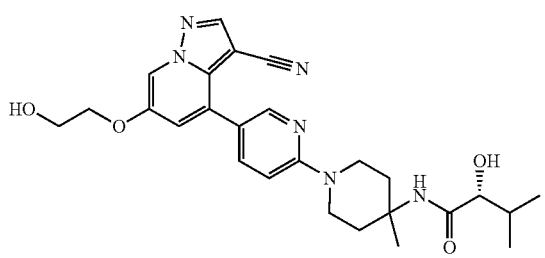 [SMILES: CC(C)[C@@H](O)C(=O)NC1(C)CCN(c2ccc(-c3cc(OCCO)cn4ncc(C#N)c34)cn2)CC1]

(R)—N-(1-(5-(3-cyano-6-(2-hydroxyethoxy)pyra-zolo[1,5-a]pyridin-4-yl)pyridin-2-yl)-4-methylpip-eridin-4-yl)-2-hydroxy-3-methylbutanamide A solution of 4-(6-(4-amino-4-methylpiperidin-1-yl)pyridin-3-yl)-6-(2-hydroxyethoxy)pyrazolo[1,5-a]pyridine-3-carbonitrile (Example 20; 15 mg, 0.038 mmol) in DCM (764 µL) was treated (R)-2-hydroxy-3-methylbutanoic acid (5.42 mg, 0.0459), HATU (17.4 mg, 0.0459 mmol) and DIEA (26.6 µL, 0.153 mmol), and stirred overnight at ambient temperature. The mixture was concentrated in vacuo, and then purified by silica chromatography (0-20% MeOH in DCM as the gradient eluent) to afford the title compound contaminated with DIEA. The impure residue was partitioned between MTBE and saturated $NH_4Cl_{(aq)}$. The combined organic extracts were concentrated in vacuo to cleanly provide the title compound (1.6 mg, 9% yield). MS (apci) m/z=493.2 (M+H).

Example 25

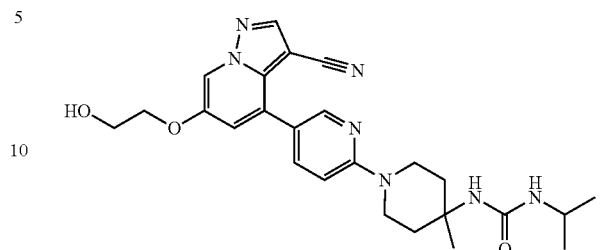

1-(1-(5-(3-Cyano-6-(2-hydroxyethoxy)pyrazolo[1,5-a]pyridin-4-yl)pyridin-2-yl)-4-methylpiperidin-4-yl)-3-isopropylurea A solution of 4-(6-(4-amino-4-methylpiperidin-1-yl)pyridin-3-yl)-6-(2-hydroxyethoxy)pyrazolo[1,5-a]pyridine-3-carbonitrile (Example 20; 15 mg, 0.038 mmol) in anhydrous DMA (191 µL) was treated sequentially with DIEA (20.0 µL, 0.115 mmol) and isopropyl isocyanate (3.78 µL, 0.0382 mmol). After stirring overnight at ambient temperature, the reaction mixture was purified directly by C18 reverse phase chromatography (5-95% ACN in water with 0.1% TFA as the gradient eluent) to cleanly provide the title compound as a TFA salt. The salt was dissolved in MeOH, filtered through an Agilent PL-HCO3 MP SPE tube to neutralize, and the filtrate was concentrated in vacuo to cleanly provide the title compound (4.15 mg, 23% yield). MS (apci) m/z=478.2 (M+H).

Example 26

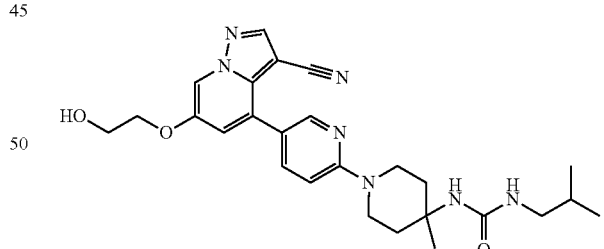

1-(1-(5-(3-Cyano-6-(2-hydroxyethoxy)pyrazolo[1,5-a]pyridin-4-yl)pyridin-2-yl)-4-methylpiperidin-4-yl)-3-isobutylurea The title compound (2.0, 11% yield) was prepared, purified and neutralized using a similar procedure to that described for Example 25, replacing isopropyl isocyanate with 1-isocyanato-2-methylpropane. MS (apci) m/z=492.3 (M+H).

Example 27

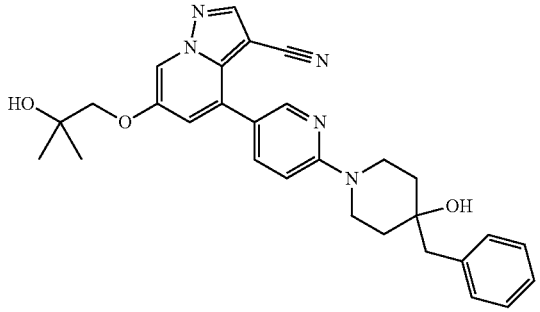 [SMILES: CC(C)(O)COc1cc(-c2ccc(N3CCC(O)(Cc4ccccc4)CC3)nc2)c2c(C#N)cnn2c1]

4-(6-(4-benzyl-4-hydroxypiperidin-1-yl)pyridin-3-yl)-6-(2-hydroxy-2-methylpropoxy)pyrazolo[1,5-a]pyridine-3-carbonitrile A mixture of 4-(6-fluoropyridin-3-yl)-6-(2-hydroxy-2-methylpropoxy)pyrazolo[1,5-a]pyridine-3-carbonitrile (Intermediate P42; 29.3 mg, 0.0898 mmol), 4-benzylpiperidin-4-ol (25.8 mg, 0.135 mmol) and TEA (37.5 µL, 0.269 mmol) in DMA (599 µL) was stirred overnight at 90° C. After cooling to ambient temperature, the reaction mixture was diluted with water and washed with DCM. The organic extracts were washed with brine, then dried over anhydrous $Na_2SO_{4(s)}$, filtered and concentrated in vacuo. The residue was purified by C18 reverse phase chromatography (5-95% water:ACN with 0.1% TFA as the gradient eluent) to afford the title compound as the TFA salt. The TFA salt was dissolved in DCM and washed with saturated $Na_2CO_{3(aq)}$. The organic extracts were washed with brine, then dried over anhydrous $Na_2SO_{4(s)}$, filtered and concentrated in vacuo to cleanly provide the title compound (22.4 mg, 50% yield). MS (apci) m/z=498.2 (M+H).

Example 28

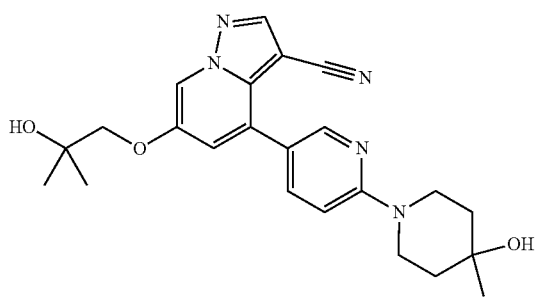 [SMILES: CC(C)(O)COc1cc(-c2ccc(N3CCC(C)(O)CC3)nc2)c2c(C#N)cnn2c1]

6-(2-hydroxy-2-methylpropoxy)-4-(6-(4-hydroxy-4-methylpiperidin-1-yl)pyridin-3-yl)pyrazolo[1,5-a]pyridine-3-carbonitrile The title compound (10.8 mg, 28% yield) was prepared and purified using a similar procedure to that described for Example 27, replacing 4-benzylpiperidin-4-ol with 4-methylpiperidin-4-ol. MS (apci) m/z=422.1 (M+H).

Example 29

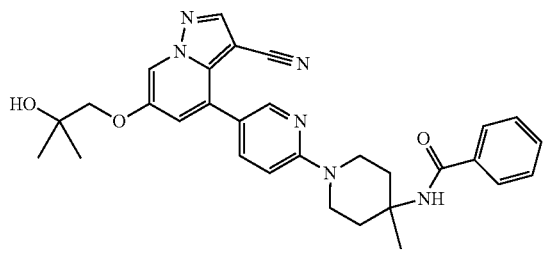 [SMILES: CC(C)(O)COc1cc(-c2ccc(N3CCC(C)(NC(=O)c4ccccc4)CC3)nc2)c2c(C#N)cnn2c1]

N-(1-(5-(3-cyano-6-(2-hydroxy-2-methylpropoxy)pyrazolo[1,5-a]pyridin-4-yl)pyridin-2-yl)-4-methylpiperidin-4-yl)benzamide A mixture of 4-(6-(4-amino-4-methylpiperidin-1-yl)pyridin-3-yl)-6-(2-hydroxy-2-methylpropoxy)pyrazolo[1,5-a]pyridine-3-carbonitrile (Intermediate P46; 36 mg, 0.0856 mmol), benzoic acid (20.9 mg, 0.171 mmol) and HATU (35.8 mg, 0.0942 mmol) in DCM (856 µL) was treated with DIEA (74.8 µL, 0.428 mmol) and then stirred for 2 h at ambient temperature. The reaction mixture was concentrated in vacuo. The residue was suspended in 60:40 ACN:water containing 2% TFA, then filtered through a syringe filter. The filtrate was purified directly by C18 reverse phase chromatography (5-95% ACN in water with 0.1% TFA as the gradient eluent) to afford the title compound as the TFA salt. The TFA salt was treated with saturated $NaHCO_{3(aq)}$ and extracted with DCM. The combined organic extracts were washed with brine, then dried over anhydrous $Na_2SO_{4(s)}$, filtered and concentrated in vacuo to afford the title compound (33.2 mg, 74% yield). MS (apci) m/z=525.25 (M+H).

The compounds in Table N were prepared using a similar method to that described for the synthesis of Example 29, replacing benzoic acid with the appropriate carboxylic acid. Reactions were monitored for completion by LCMS, and reaction durations were adjusted accordingly. Title compounds were cleanly isolated following chromatographic purification using an appropriate gradient eluent (and if necessary converted to the free base).

TABLE N

| Ex # | Structure | Chemical Name | MS (apci) m/z |
|---|---|---|---|
| 30 | 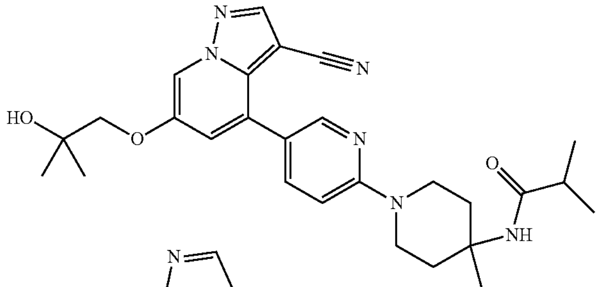 [SMILES: CC(C)C(=O)NC1(C)CCN(c2ccc(-c3cc(OCC(C)(C)O)cn4ncc(C#N)c34)cn2)CC1] | N-(1-(5-(3-cyano-6-(2-hydroxy-2-methylpropoxy)pyrazolo[1,5-a]pyridin-4-yl)pyridin-2-yl)-4-methylpiperidin-4-yl)isobutyramide | 491.3 (M + H) |
| 31 | 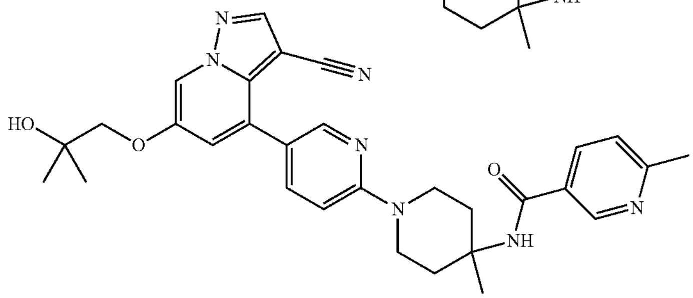 | N-(1-(5-(3-cyano-6-(2-hydroxy-2-methylpropoxy)pyrazolo[1,5-a]pyridin-4-yl)pyridin-2-yl)-4-methylpiperidin-4-yl)-6-methoxynicotinamide | 556.3 (M + H) |

Example 32

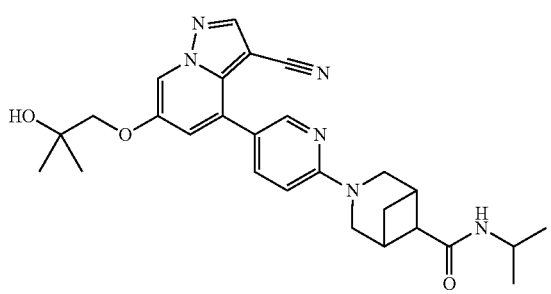 [SMILES: CC(C)NC(=O)C1C2CC1CN(c1ccc(-c3cc(OCC(C)(C)O)cn4ncc(C#N)c34)cn1)C2]

3-(5-(3-cyano-6-(2-hydroxy-2-methylpropoxy)pyrazolo[1,5-a]pyridin-4-yl)pyridin-2-yl)-N-isopropyl-3-azabicyclo[3.1.1]heptane-6-carboxamide A mixture of 3-(5-(3-cyano-6-(2-hydroxy-2-methylpropoxy)pyrazolo[1,5-a]pyridin-4-yl)pyridin-2-yl)-3-azabicyclo[3.1.1]heptane-6-carboxylic acid (Intermediate P47; 32 mg, 0.072 mmol), propan-2-amine (11.7 µL, 0.143 mmol) and HATU (29.9 mg, 0.358 mmol) in DCM (715 µL) was treated with DIEA (62.4 µL, 0.358 mmol) and then stirred overnight at ambient temperature. The reaction mixture was concentrated in vacuo. The residue was purified by silica chromatography (1-6% MeOH in DCM as the gradient eluent) to afford the title compound (8.3 mg, 24% yield). MS (apci) m/z=489.3 (M+H).

The compounds in Table O were prepared using a similar method to that described for the synthesis of Example 32, replacing propan-2-amine with the appropriate amine. Reactions were monitored for completion by LCMS, and reaction durations were adjusted accordingly. Title compounds were cleanly isolated following chromatographic purification using an appropriate gradient eluent.

TABLE O

| Ex # | Structure | Chemical Name | MS (apci) m/z |
|---|---|---|---|
| 33 | 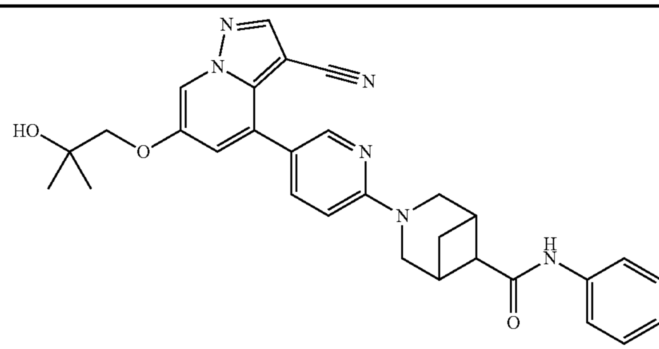 | 3-(5-(3-cyano-6-(2-hydroxy-2-methylpropoxy)pyrazolo[1,5-a]pyridin-4-yl)pyridin-2-yl)-N-phenyl-3-azabicyclo[3.1.1]heptane-6-carboxamide | 523.2 (M + H) |

TABLE O-continued

| Ex # | Structure | Chemical Name | MS (apci) m/z |
|---|---|---|---|
| 34 | 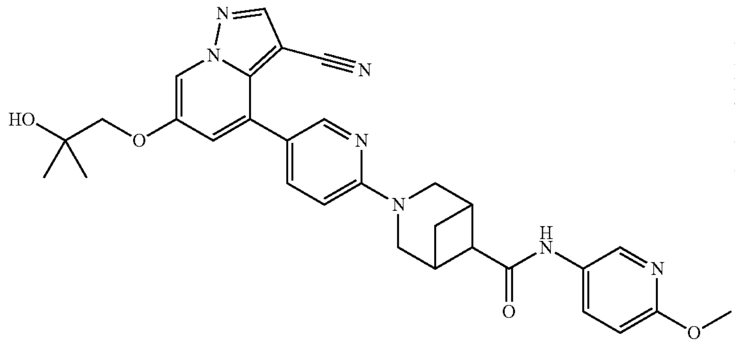 [SMILES: COc1ccc(NC(=O)C2C3CC2CN(c2ccc(-c4cc(OCC(C)(C)O)cn5ncc(C#N)c45)cn2)C3)cn1] | 3-(5-(3-cyano-6-(2-hydroxy-2-methylpropoxy)pyrazolo[1,5-a]pyridin-4-yl)pyridin-2-yl)-N-(6-methoxypyridin-3-yl)-3-azabicyclo[3.1.1]heptane-6-carboxamide | 554.25 (M + H) |

Example 35

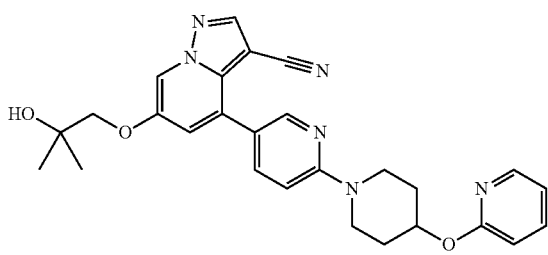 [SMILES: CC(C)(O)COc1cc(-c2ccc(N3CCC(Oc4ccccn4)CC3)nc2)c2c(C#N)cnn2c1]

6-(2-hydroxy-2-methylpropoxy)-4-(6-(4-(pyridin-2-yloxy)piperidin-1-yl)pyridin-3-yl)pyrazolo[1,5-a]pyridine-3-carbonitrile A mixture of 4-(6-fluoropyridin-3-yl)-6-(2-hydroxy-2-methylpropoxy)pyrazolo[1,5-a]pyridine-3-carbonitrile (Intermediate P42; 29.7 mg, 0.0910 mmol), 2-(piperidin-4-yloxy)pyridine (24.3 mg, 0.137 mmol) and TEA (38.1 μL, 0.273 mmol) in DMA (607 μL) was stirred overnight at 90° C. After cooling to ambient temperature, the reaction mixture was diluted with water and washed with DCM. The organic extracts were washed with brine, then dried over anhydrous $Na_2SO_{4(s)}$, filtered and concentrated in vacuo. The residue was purified by C18 reverse phase chromatography (5-95% ACN in water with 0.1% TFA as the gradient eluent) to afford the title compound as the TFA salt. The TFA salt was dissolved in DCM and washed with saturated $Na_2CO_{3(aq)}$. The organic extracts were washed with brine, then dried over anhydrous $Na_2SO_{4(s)}$, filtered and concentrated in vacuo to cleanly provide the title compound (12.1 mg, 27% yield). MS (apci) m/z=485.2 (M+H). $^1$H NMR (400 MHz, CDCl$_3$) δ: 8.34 (d, 1H), 8.20 (s, 1H), 8.15 (m, 2H), 7.71 (dd, 1H), 7.58 (m, 1H), 7.15 (d, 1H), 6.86 (m, 1H), 6.81 (d, 1H), 6.74 (d, 1H), 5.35 (m, 1H), 4.06 (m, 2H), 3.86 (s, 2H), 3.55 (m, 2H), 2.15 (m, 2H), 1.88 (m, 2H), 1.40 (s, 6H).

The compounds in Table P were prepared using a similar method to that described for the synthesis of Example 35, replacing 2-(piperidin-4-yloxy)pyridine with the appropriate piperidine. Reactions were monitored for completion by LCMS, and reaction durations were adjusted accordingly.

TABLE P

| Ex # | Structure | Chemical Name | MS (apci) m/z |
|---|---|---|---|
| 36 | 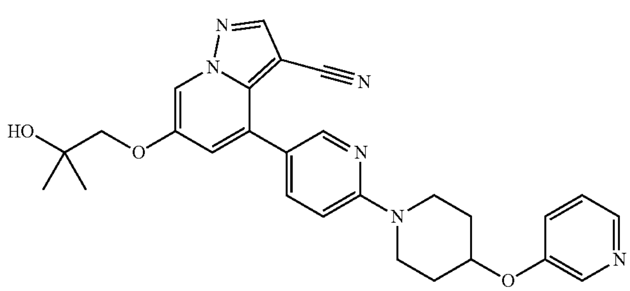 [SMILES: CC(C)(O)COc1cc(-c2ccc(N3CCC(Oc4cccnc4)CC3)nc2)c2c(C#N)cnn2c1] | 6-(2-hydroxy-2-methylpropoxy)-4-(6-(4-(pyridin-3-yloxy)piperidin-1-yl)pyridin-3-yl)pyrazolo[1,5-a]pyridine-3-carbonitrile | 485.2 (M + H) |

TABLE P-continued

| Ex # | Structure | Chemical Name | MS (apci) m/z |
|---|---|---|---|
| 37 | 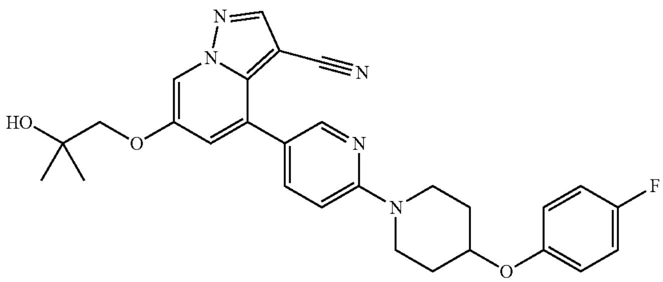 [SMILES: CC(C)(O)COc1cc(-c2ccc(N3CCC(Oc4ccc(F)cc4)CC3)nc2)c2c(C#N)cnn2c1] | 4-(6-(4-(4-fluorophenoxy)piperidin-1-yl)pyridin-3-yl)-6-(2-hydroxy-2-methylpropoxy)pyrazolo[1,5-a]pyridine-3-carbonitrile | 502.2 (M + H) |
| 38 | 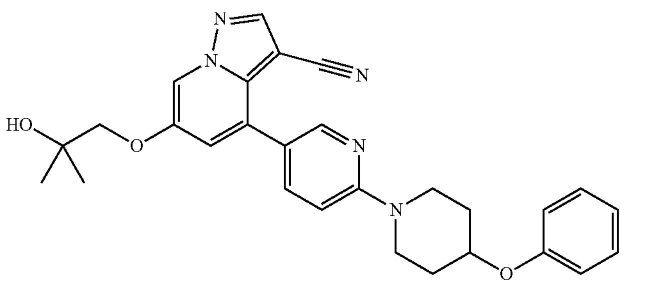 [SMILES: CC(C)(O)COc1cc(-c2ccc(N3CCC(Oc4ccccc4)CC3)nc2)c2c(C#N)cnn2c1] | 6-(2-hydroxy-2-methylpropoxy)-4-(6-(4-phenoxypiperidin-1-yl)pyridin-3-yl)pyrazolo[1,5-a]pyridine-3-carbonitrile | 484.2 (M + H) |
| 39 | 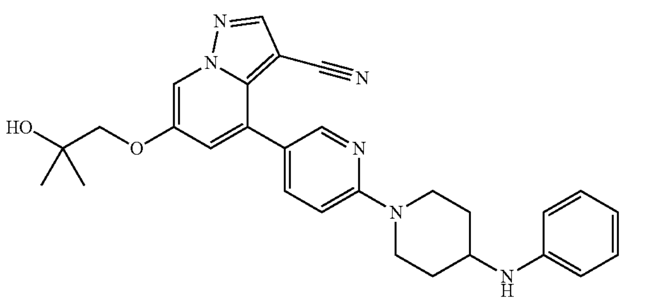 [SMILES: CC(C)(O)COc1cc(-c2ccc(N3CCC(Nc4ccccc4)CC3)nc2)c2c(C#N)cnn2c1] | 6-(2-hydroxy-2-methylpropoxy)-4-(6-(4-phenylamino)piperidin-1-yl)pyridin-3-yl)pyrazolo[1,5-a]pyridine-3-carbonitrile | 483.2 (M + H) |
| 40 | 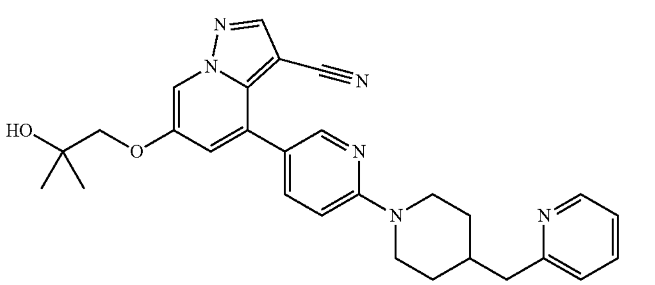 [SMILES: CC(C)(O)COc1cc(-c2ccc(N3CCC(Cc4ccccn4)CC3)nc2)c2c(C#N)cnn2c1] | 6-(2-hydroxy-2-methylpropoxy)-4-(6-(4-(pyridin-2-ylmethyl)piperidin-1-yl)pyridin-3-yl)pyrazolo[1,5-a]pyridine-3-carbonitrile | 483.2 (M + H) |
| 41 | 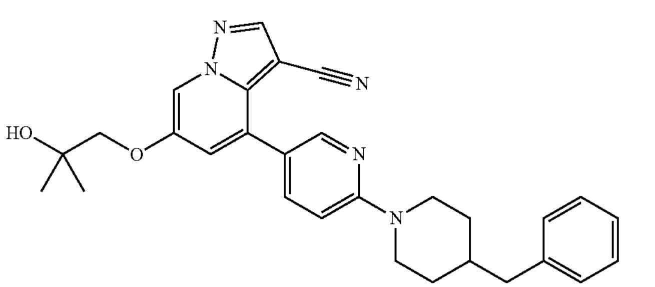 [SMILES: CC(C)(O)COc1cc(-c2ccc(N3CCC(Cc4ccccc4)CC3)nc2)c2c(C#N)cnn2c1] | 4-(6-(4-benzylpiperidin-1-yl)pyridin-3-yl)-6-(2-hydroxy-2-methylpropoxy)pyrazolo[1,5-a]pyridine-3-carbonitrile | 482.2 (M + H) |

Example 42

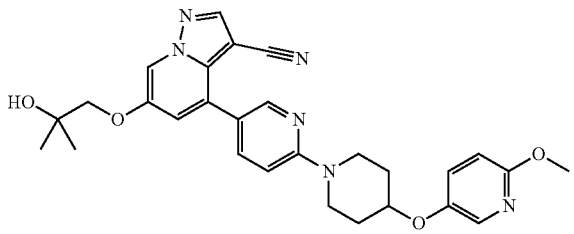 [SMILES: COc1ccc(OC2CCN(c3ccc(-c4cc(OCC(C)(C)O)cn5ncc(C#N)c45)cn3)CC2)cn1]

6-(2-hydroxy-2-methylpropoxy)-4-(6-(4-((6-methoxypyridin-3-yl)oxy)piperidin-1-yl)pyridin-3-yl)pyrazolo[1,5-a]pyridine-3-carbonitrile A solution of 2-methoxy-5-(piperidin-4-yloxy)pyridine (Intermediate R13; 66.1 mg, 0.317 mmol) in DMA (794 µL) was treated with 4-(6-fluoropyridin-3-yl)-6-(2-hydroxy-2-methylpropoxy)pyrazolo[1,5-a]pyridine-3-carbonitrile (Intermediate P42; 51.8 mg, 0.159 mmol), and TEA (43.4 µL, 0.317 mmol). The resulting mixture was sparged with $Ar_{(g)}$ then stirred overnight at 110° C. After cooling to ambient temperature, the reaction mixture was diluted with DCM and washed with saturated $NaHCO_{3(aq)}$, and brine. The combined organic extracts were dried over anhydrous $Na_2SO_{4(s)}$, filtered and concentrated in vacuo. The residue was purified by C18 reverse phase chromatography (5-95% ACN in water with 0.1% TFA as the gradient eluent) to afford the title compound as the TFA salt. The TFA salt was dissolved in DCM and washed with saturated $NaHCO_{3(aq)}$. The aqueous extracts were back extracted with DCM. The combined organic extracts were washed with brine, and subsequently dried over anhydrous $Na_2SO_{4(s)}$, filtered and concentrated in vacuo to cleanly provide the title compound (41 mg, 50% yield). MS (apci) m/z=515.2 (M+H).

Example 43

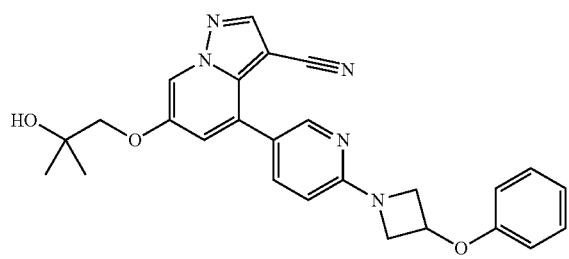 [SMILES: CC(C)(O)COc1cc(-c2ccc(N3CC(Oc4ccccc4)C3)nc2)c2c(C#N)cnn2c1]

6-(2-hydroxy-2-methylpropoxy)-4-(6-(3-phenoxyazetidin-1-yl)pyridin-3-yl)pyrazolo[1,5-a]pyridine-3-carbonitrile A mixture of 4-(6-fluoropyridin-3-yl)-6-(2-hydroxy-2-methylpropoxy)pyrazolo[1,5-a]pyridine-3-carbonitrile (Intermediate P42; 42.7 mg, 0.131 mmol), 3-phenoxyazetidine (23.4 mg, 0.157 mmol) and TEA (54.7 µL, 0.393 mmol) in DMA (872 µL) was stirred overnight at 90° C. After cooling to ambient temperature, the reaction mixture was diluted with water and washed with DCM. The organic extracts were washed with brine and dried over anhydrous $Na_2SO_4$ $(s)$, filtered and concentrated in vacuo. The residue was purified by C18 reverse phase chromatography (5-95% ACN in water with 0.1% TFA as the gradient eluent) to afford the title compound as the TFA salt. The TFA salt was dissolved in DCM and washed with saturated $Na_2CO_{3(aq)}$. The combined organic extracts were washed with brine, then dried over anhydrous $Na_2SO_{4(s)}$, filtered and concentrated in vacuo to cleanly provide the title compound (14.1 mg, 24% yield). MS (apci) m/z=456.2 (M+H).

Example 44

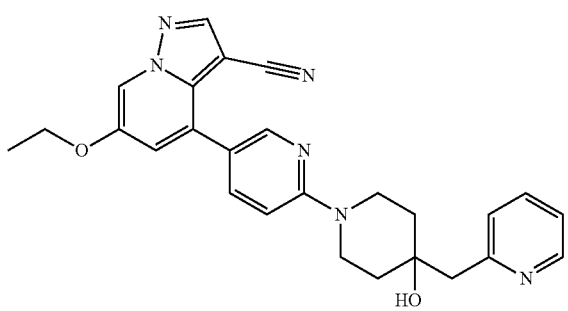 [SMILES: CCOc1cc(-c2ccc(N3CCC(O)(Cc4ccccn4)CC3)nc2)c2c(C#N)cnn2c1]

6-ethoxy-4-(6-(4-hydroxy-4-(pyridin-2-ylmethyl)piperidin-1-yl)pyridin-3-yl)pyrazolo[1,5-a]pyridine-3-carbonitrile 6-ethoxy-4-(6-fluoropyridin-3-yl)pyrazolo[1,5-a]pyridine-3-carbonitrile (Intermediate P6, 0.030 g, 0.11 mmol), triethylamine (0.044 mL, 0.32 mmol) and 4-(pyridin-2-ylmethyl)piperidin-4-ol (0.041 g, 0.21 mmol) were combined in DMA (0.5 mL) and stirred at 90° C. for 5 h. The reaction mixture was diluted with DCM (5 mL), sat. $NH_4Cl$ (aq., 5 mL) and water (20 mL). After phase-separation, the aqueous layer was extracted with DCM. The combined organic extracts were dried ($Na_2SO_4$), filtered, concentrated and purified by silica chromatography (30-100% EtOAc/hexanes) to provide the title product as solid (0.022 g, 46% yield). $^1$H NMR (400 MHz, $CDCl_3$) δ 8.5 (dq, 1H), 8.3 (d, 1H), 8.15 (s, 1H), 8.05 (d, 1H), 7.65 (qd, 2H), 7.15 (qd, 1H), 7.1 (d, 1H), 7.05 (d, 1H), 6.75 (d, 1H), 6.05 (br s, 1H), 4.1 (q, 2H), 3.45 (m, 2H), 2.9 (s, 2H), 1.6 (m, 4H), 1.5 (t, 3H). LCMS (apci) m/z=455.2 (M+H).

Example 45

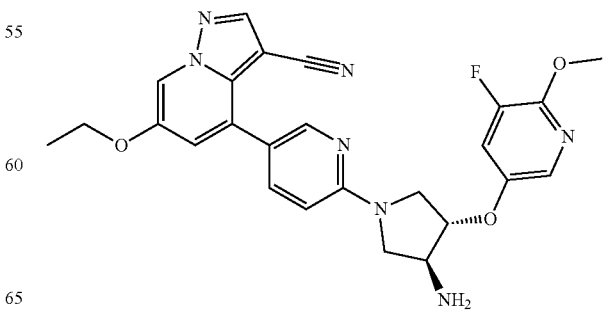

4-(6-((3S,4S)-3-amino-4-((5-fluoro-6-methoxypyridin-3-yl)oxy)pyrrolidin-1-yl)pyridin-3-yl)-6-ethoxypyrazolo[1,5-a]pyridine-3-carbonitrile Step 1: Preparation of tert-butyl ((3S,4R)-1-(5-(3-cyano-6-ethoxypyrazolo[1,5-a]pyridin-4-yl)pyridin-2-yl)-4-hydroxypyrrolidin-3-yl)carbamate 6-ethoxy-4-(6-fluoropyridin-3-yl)pyrazolo[1,5-a]pyridine-3-carbonitrile (Intermediate P6, 0.22 g, 0.76 mmol), N-ethyl-N-isopropylpropan-2-amine (0.66 mL, 3.81 mmol), and tert-butyl ((3S,4R)-4-hydroxypyrrolidin-3-yl)carbamate (0.23 g, 1.14 mmol) were combined in DMSO (1.5 mL) and stirred at 100° C. for 60 h. The reaction mixture was diluted with sat. $NH_4Cl$ and extracted into DCM. The combined organic extracts were dried ($Na_2SO_4$), filtered, concentrated in vacuo and purified by silica chromatography (0-100% EtOAc/hexanes) to provide the product as solid (0.28 g, 80% yield).

Step 2: Preparation of 4-(6-((3S,4S)-3-amino-4-((5-fluoro-6-methoxypyridin-3-yl)oxy)pyrrolidin-1-yl)pyridin-3-yl)-6-ethoxypyrazolo[1,5-a]pyridine-3-carbonitrile A mixture of tert-butyl ((3S,4R)-1-(5-(3-cyano-6-ethoxypyrazolo[1,5-a]pyridin-4-yl)pyridin-2-yl)-4-hydroxypyrrolidin-3-yl)carbamate (0.030 g, 0.07 mmol), 5-fluoro-6-methoxypyridin-3-ol (0.037 g, 0.26 mmol), and triphenylphosphine (0.068 g, 0.26 mmol) was combined in 1:1 DCM/THF (0.7 mL). The reaction vessel was sparged with argon, and diisopropyl (E)-diazene-1,2-dicarboxylate (0.035 mL, 0.26 mmol) was added. The reaction was stirred at room temperature for 48 h. The reaction mixture was diluted with DCM and $H_2O$, filtered through phase separating paper, and extracted into DCM. The combined organic extracts were dried ($Na_2SO_4$), filtered, concentrated in vacuo and purified by silica chromatography (0-100% EtOAc/hexanes). The fractions containing the Boc-protected title compound were concentrated, and the residue was diluted with 6 mL 1:1 DCM/5N HCl in isopropyl alcohol. This mixture was stirred at room temperature 24 h. The combined organic extracts were washed with 2M NaOH and purified by reverse phase chromatography (0-80% ACN/Water [0.1% Formic Acid]) to provide the title compound (2.2 mg, 7.0% yield). $^1H$ NMR (400 MHz, $CD_3OD$) δ 8.4 (d, 1H), 8.3 (s, 1H), 8.25 (dd, 1H), 7.75 (dd, 1H), 7.7 (d, 1H), 7.3 (dd, 1H), 7.2 (d, 1H), 6.7 (dd, 1H), 4.1 (m, 2H), 3.95 (s, 3H), 3.9 (m, 2H), 3.7 (dd, 1H), 3.6 (dd, 1H), 3.3 (s, 2H), 1.45 (t, 3H). LCMS (apci) m/z=490.1 (M+H).

Example 46

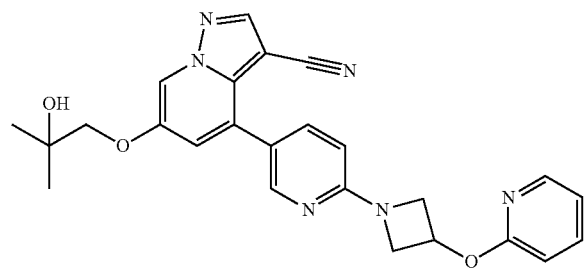 [SMILES: CC(C)(O)COc1cc(-c2ccc(N3CC(Oc4ccccn4)C3)nc2)c2c(C#N)cnn2c1]

6-(2-hydroxy-2-methylpropoxy)-4-(6-(3-(pyridin-2-yloxy)azetidin-1-yl)pyridin-3-yl)pyrazolo[1,5-a]pyridine-3-carbonitrile A mixture of 4-(6-fluoropyridin-3-yl)-6-(2-hydroxy-2-methylpropoxy)pyrazolo[1,5-a]pyridine-3-carbonitrile (0.040 g, 0.12 mmol) (Intermediate P42), 2-(azetidin-3-yloxy)pyridine dihydrochloride (0.055 g, 0.24 mmol) and triethylamine (0.10 mL, 0.74 mmol) in DMA (0.82 mL) was heated in a sealed vial to 90° C. overnight. After cooling to ambient temperature, the reaction was partitioned between DCM and water (10 mL each). After phase-separation, the aqueous was extracted with DCM (2×10 mL). The combined organic extracts was washed with brine, dried ($Na_2SO_4$), filtered and concentrated. The crude was purified by preparative HPLC (5-95% ACN in water with 0.1% TFA) to yield the title product as a TFA salt, which was then converted to the free base by partitioning in DCM and $Na_2CO_3$ (sat. aq). The combined organic extracts were washed with brine, dried ($Na_2SO_4$), filtered and concentrated to yield the title product (4.7 mg, 8.4% yield). $^1H$ NMR ($CDCl_3$) δ 8.31 (dd, 1H), 8.19 (s, 1H), 8.14 (m, 2H), 7.68 (dd, 1H), 7.61 (m, 1H), 7.13 (d, 1H), 6.91 (m, 1H), 6.80 (m, 1H), 6.44 (dd, 1H), 5.57 (m, 1H), 4.55 (m, 2H), 4.15 (m, 2H), 3.86 (s, 2H), 1.39 (s, 6H). LCMS (apci) m/z=457.2 (M+H).

Example 47

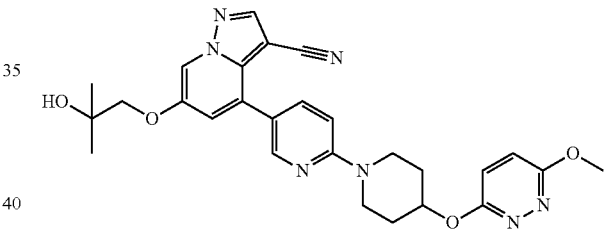

6-(2-hydroxy-2-methylpropoxy)-4-(6-(4-((6-methoxypyridazin-3-yl)oxy)piperidin-1-yl)pyridin-3-yl)pyrazolo[1,5-a]pyridine-3-carbonitrile A mixture of 4-(6-fluoropyridin-3-yl)-6-(2-hydroxy-2-methylpropoxy)pyrazolo[1,5-a]pyridine-3-carbonitrile (0.031 g, 0.095 mmol) (Intermediate P42), 3-methoxy-6-(piperidin-4-yloxy)pyridazine dihydrochloride (0.090 g, 0.32 mmol), triethylamine (0.10 mL, 0.76 mmol) in DMA (0.32 mL) was heated in a sealed vial to 95° C. overnight. After cooling to ambient temperature, the reaction mixture was diluted with DCM (10 mL) and sequentially washed with sat. $NaHCO_3$ (15 mL), water (2×15 mL) and brine (15 mL), then dried ($Na_2SO_4$), filtered and concentrated. The crude material was purified by C18 reverse phase chromatography (5-95% ACN in water with 0.01% TFA) and the combined product fractions was concentrated and converted to the free base with sat. $NaHCO_3$ (15 mL). The aqueous layer was extracted with DCM (3×15 mL). The combined organic extracts were washed with brine (15 mL), dried ($Na_2SO_4$), filtered and concentrated to afford the title compound as a white solid (22.5 mg, 46% yield). $^1H$ NMR ($CDCl_3$) δ 8.32 (dd, 1H), 8.19 (s, 1H), 8.13 (d, 1H), 7.68 (dd, 1H), 7.13 (d, 1H), 6.92 (m, 2H), 6.80 (m, 1H), 5.42 (m, 1H), 4.10 (m, 2H), 4.04 (s, 3H), 3.84 (s, 2H), 3.46 (m, 2H), 2.22 (m, 2H), 1.88 (m, 2H), 1.39 (s, 6H). LCMS (apci) m/z=516.2 (M+H).

Example 48

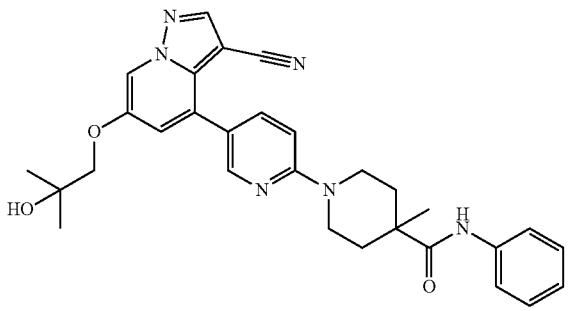 [SMILES: CC(C)(O)COc1cc(-c2ccc(N3CCC(C)(C(=O)Nc4ccccc4)CC3)nc2)c2c(C#N)cnn2c1]

1-(5-(3-cyano-6-(2-hydroxy-2-methylpropoxy)pyrazolo[1,5-a]pyridin-4-yl)pyridin-2-yl)-4-methyl-N-phenylpiperidine-4-carboxamide A solution of 4-(6-fluoropyridin-3-yl)-6-(2-hydroxy-2-methylpropoxy)pyrazolo[1,5-a]pyridine-3-carbonitrile (25 mg, 0.077 mmol) (Intermediate P42), 4-methyl-N-phenylpiperidine-4-carboxamide (66.9 mg, 0.31 mmol) and triethylamine (104 μL, 0.77 mmol) in DMA (0.4 mL) was heated in a sealed vessel at 80° C. for 32 h. The reaction was then cooled to room temperature, diluted with EtOAc and washed with water and brine. The combined organic extracts were dried over $Na_2SO_4$, filtered, and concentrated in vacuo. The crude material was purified by preparative HPLC (5 to 95% ACN in water with 0.1% TFA) to provide the title product as a TFA salt, which was converted to the free base by partitioning between 20% IPA in DCM and $NaHCO_3$ (sat. aq). After phase-separation, the aqueous layer was extracted with DCM. The combined organic extracts were dried ($Na_2SO_4$), filtered, and concentrated under vacuum to afford the title product as white solid (23.7 mg, 56% yield). LCMS (apci) m/z=525.2 (M+H). $^1$H NMR (400 MHz, $d_6$-DMSO) δ 9.38 (s, 1H), 8.66-8.65 (d, 1H), 8.57 (s, 1H), 8.33-8.32 (d, 1H), 7.77-7.74 (dd, 1H), 7.66-7.64 (m, 2H), 7.32-7.28 (m, 3H), 7.07-7.03 (m, 1H), 6.98-6.96 (d, 1H), 4.70 (s, 1H), 3.95-3.87 (m, 4H), 3.42-3.36 (m, 2H), 2.23-2.19 (m, 2H), 1.58-1.52 (m, 2H), 1.30 (s, 3H), 1.22 (s, 6H).

Example 49

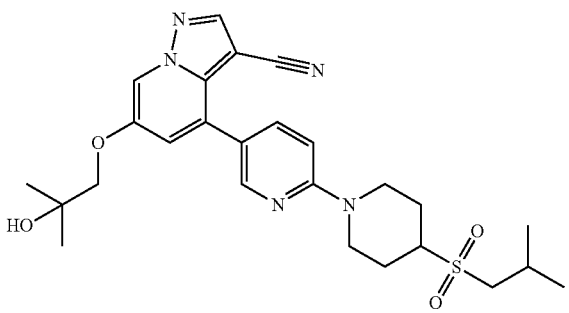 [SMILES: CC(C)CS(=O)(=O)C1CCN(c2ccc(-c3cc(OCC(C)(C)O)cn4ncc(C#N)c34)cn2)CC1]

6-(2-hydroxy-2-methylpropoxy)-4-(6-(4-(isobutylsulfonyl)piperidin-1-yl)pyridin-3-yl)pyrazolo[1,5-a]pyridine-3-carbonitrile 4-(6-fluoropyridin-3-yl)-6-(2-hydroxy-2-methylpropoxy)pyrazolo[1,5-a]pyridine-3-carbonitrile (27.2 mg, 0.083 mmol) (Intermediate P42) and 4-(isobutyl sulfonyl)piperidine (51.3 mg, 0.25 mmol) were dissolved in DMA (0.5 mL, 0.15 M) at room temperature. The reaction mixture was treated with triethylamine (56 μL, 0.42 mmol), sealed, and heated at 80° C. for 36 h. The reaction mixture was then cooled to room temperature, diluted with ethyl acetate and washed with water and brine. The combined organic extracts were dried over $Na_2SO_4$, filtered, and concentrated in vacuo. The crude material was purified by preparative HPLC (5 to 95% ACN in water with 0.1% TFA) to provide the product as a TFA salt, which was converted to the free base by partitioning between 20% IPA in DCM and $NaHCO_3$ (sat. aq). After phase separation, the aqueous layer was extracted with DCM. The combined organic extracts were dried ($Na_2SO_4$), filtered, and concentrated under vacuum to afford the title product as a white solid (20 mg, 47% yield). LCMS (apci) m/z=512.2 (M+H). $^1$H-NMR (400 MHz, $d_6$-DMSO) δ 8.67-8.66 (d, 1H), 8.57 (s, 1H), 8.35-8.34 (d, 1H), 7.81-7.78 (dd, 1H), 7.32-7.31 (d, 1H), 7.03-7.01 (d, 1H), 4.70 (s, 1H), 4.57-4.54 (m, 2H), 3.87 (s, 2H), 3.46-3.36 (m, 1H), 3.01-2.93 (m, 4H), 2.29-2.19 (m, 1H), 2.10-2.06 (m, 2H), 1.64-1.53 (m, 2H), 1.22 (s, 6H), 1.07-1.03 (m, 7H).

Example 50

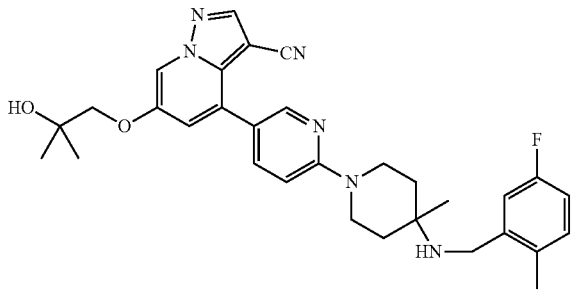 [SMILES: Cc1ccc(F)cc1CNC1(C)CCN(c2ccc(-c3cc(OCC(C)(C)O)cn4ncc(C#N)c34)cn2)CC1]

4-(6-(4-(((5-fluoro-2-methylbenzyl)amino)-4-methylpiperidin-1-yl)pyridin-3-yl)-6-(2-hydroxy-2-methylpropoxy)pyrazolo[1,5-a]pyridine-3-carbonitrile To a solution of 4-(6-(4-amino-4-methylpiperidin-1-yl)pyridin-3-yl)-6-(2-hydroxy-2-methylpropoxy)pyrazolo[1,5-a]pyridine-3-carbonitrile (Intermediate P46; 50 mg, 0.119 mmol) in DCM (1 mL) was added DIEA (73 μL, 0.416 mmol). The solution stirred for 10 min at ambient temperature. 5-Fluoro-2-methylbenzaldehyde (29 μL, 0.238 mmol) was added, followed by NaBH(AcO)$_3$ (76 mg, 0.357 mmol) The resulting reaction mixture was allowed to stir 12 h at ambient temperature. The reaction was diluted with DCM and washed with saturated NaHCO$_{3(aq)}$. The combined organic extracts were dried over anhydrous Na$_2$SO$_{4(s)}$, filtered and concentrated in vacuo. The residue was purified by silica chromatography (1-10% MeOH in DCM with 0.1-1% NH$_4$OH as the gradient eluent) to cleanly provide the title compound (25 mg, 39% yield). MS (apci) m/z=543.3 (M+H)

Example 51

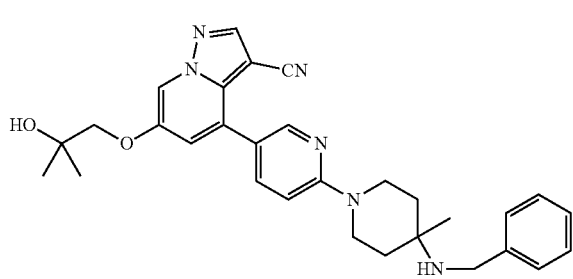 [SMILES: CC(C)(O)COc1cc(-c2ccc(N3CCC(C)(NCc4ccccc4)CC3)nc2)c2c(C#N)cnn2c1]

4-(6-(4-(benzylamino)-4-methylpiperidin-1-yl)pyridin-3-yl)-6-(2-hydroxy-2-methylpropoxy)pyrazolo[1,5-a]pyridine-3-carbonitrile To a solution of 4-(6-(4-amino-4-methylpiperidin-1-yl)pyridin-3-yl)-6-(2-hydroxy-2-methylpropoxy)pyrazolo[1,5-a]pyridine-3-carbonitrile (Intermediate P46; 50 mg, 0.119 mmol) in DCM (1 mL) was added DIEA (73 L, 0.416 mmol). The solution stirred for 10 min at ambient temperature. Then benzaldehyde (25 mg, 0.238 mmol) was added, followed by NaBH(AcO)$_3$ (76 mg, 0.357 mmol) The resulting reaction mixture was allowed to stir 12 h at ambient temperature. The reaction was diluted with DCM and washed with saturated NaHCO$_{3(aq)}$. The combined organic extracts were dried over anhydrous Na$_2$SO$_{4(s)}$, filtered and concentrated in vacuo. The residue was purified by silica chromatography (1-10% MeOH in DCM with 0.1-1% NH$_4$OH as the gradient eluent) to cleanly provide the title compound (27 mg, 45% yield) MS (apci) m/z=511.3 (M+H)

Example 52

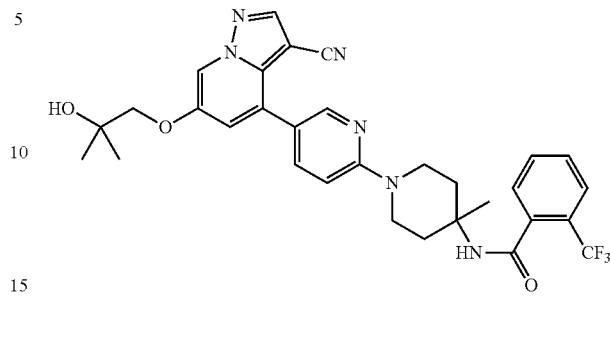

N-(1-(5-(3-cyano-6-(2-hydroxy-2-methylpropoxy)pyrazolo[1,5-a]pyridin-4-yl)pyridin-2-yl)-4-methylpiperidin-4-yl)-2-(trifluoromethyl)benzamide A mixture of 4-(6-(4-amino-4-methylpiperidin-1-yl)pyridin-3-yl)-6-(2-hydroxy-2-methylpropoxy)pyrazolo[1,5-a]pyridine-3-carbonitrile (Intermediate P46; 50 mg, 0.12 mmol), HATU (50 mg, 0.13 mmol), and 2-(trifluoromethyl)benzoic acid (25 mg, 0.13 mmol) in DMSO (1 mL) was treated with DIEA (83 μL, 0.48 mmol) and then stirred for 18 h at ambient temperature. The reaction mixture was concentrated in vacuo. The reaction mixture was diluted with EtOAc and washed with water. The organic extracts then dried over anhydrous MgSO$_{4(s)}$, filtered and concentrated in vacuo. The residue was purified by silica chromatography (1-10% MeOH in DCM with 0.1-1% NH$_4$OH as the gradient eluent) to cleanly provide the title compound (37 mg, 53% yield) MS (apci) m/z=593.3 (M+H).

The compounds in Table Q were prepared using a similar method to that described for the synthesis of Example 52, replacing 2-(trifluoromethyl)benzoic acid with the appropriate carboxylic acid. Reactions were monitored for completion by LCMS, and reaction durations were adjusted accordingly. Title compounds were cleanly isolated following chromatographic purification using an appropriate gradient eluent (and if necessary converted to the free base).

TABLE Q

| Ex. # | Structure | Chemical Name | LCMS m/z |
|---|---|---|---|
| 53 | 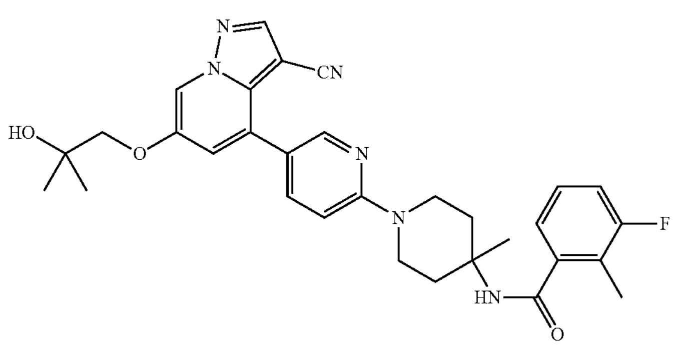 [SMILES: Cc1c(F)cccc1C(=O)NC1(C)CCN(c2ccc(-c3cc(OCC(C)(C)O)cn4ncc(C#N)c34)cn2)CC1] | N-(1-(5-(3-cyano-6-(2-hydroxy-2-methylpropoxy)pyrazolo[1,5-a]pyridin-4-yl)pyridin-2-yl)-4-methylpiperidin-4-yl)-3-fluoro-2-methylbenzamide | 557.3 (M + H) |

TABLE Q-continued

| Ex. # | Structure | Chemical Name | LCMS m/z |
|---|---|---|---|
| 54 | 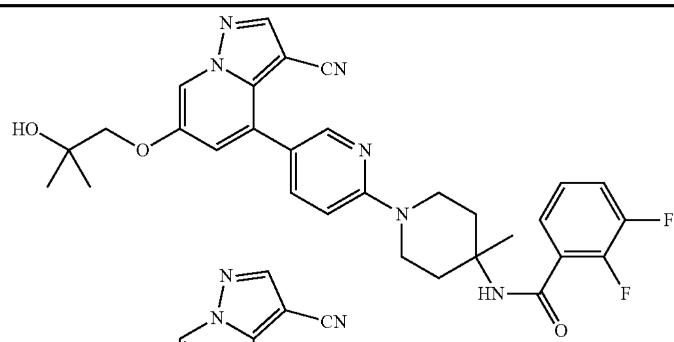 | N-(1-(5-(3-cyano-6-(2-hydroxy-2-methylpropoxy)pyrazolo[1,5-a]pyridin-4-yl)pyridin-2-yl)-4-methylpiperidin-4-yl)-2,3-difluorobenzamide | 561.3 (M + H) |
| 55 | 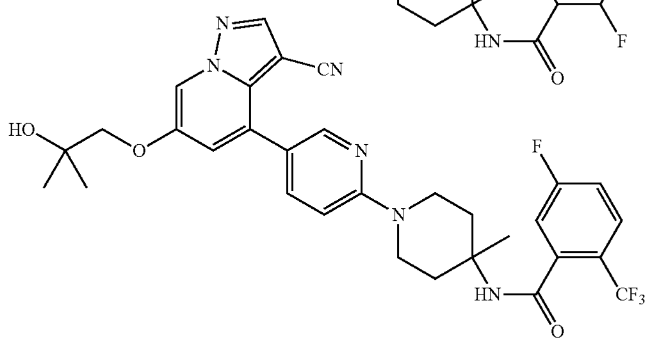 | N-(1-(5-(3-cyano-6-(2-hydroxy-2-methylpropoxy)pyrazolo[1,5-a]pyridin-4-yl)pyridin-2-yl)-4-methylpiperidin-4-yl)-5-fluoro-2-(trifluoromethyl)benzamide | 611.3 (M + H) |

Example 56

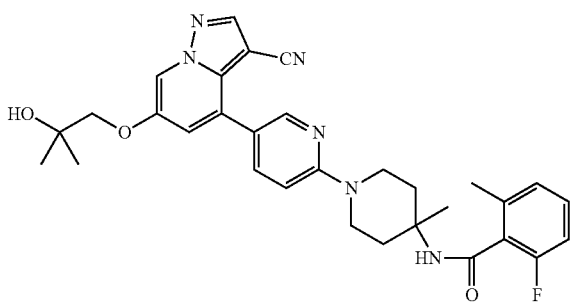 [SMILES: Cc1cccc(F)c1C(=O)NC1(C)CCN(c2ccc(-c3cc(OCC(C)(C)O)cn4ncc(C#N)c34)cn2)CC1]

N-(1-(5-(3-cyano-6-(2-hydroxy-2-methylpropoxy)pyrazolo[1,5-a]pyridin-4-yl)pyridin-2-yl)-4-methylpiperidin-4-yl)-2-fluoro-6-methylbenzamide A mixture of 4-(6-(4-amino-4-methylpiperidin-1-yl)pyridin-3-yl)-6-(2-hydroxy-2-methylpropoxy)pyrazolo[1,5-a]pyridine-3-carbonitrile (Intermediate P46; 50 mg, 0.12 mmol), HATU (90 mg, 0.24 mmol), and 2-Fluoro-6-methylbenzoic acid (37 mg, 0.24 mmol) in DMSO (1 mL) was treated with DIEA (93 µL, 0.54 mmol) and then stirred for 18 h at ambient temperature. The reaction mixture was concentrated in vacuo. The reaction mixture was diluted with EtOAc and washed with water. The organic extracts were dried over anhydrous $MgSO_{4(s)}$, filtered and concentrated in vacuo. The residue was purified by silica chromatography (1-10% MeOH in DCM with 0.1-1% $NH_4OH$ as the gradient eluent) to cleanly provide the title compound (35 mg, 53% yield) MS (apci) m/z=557.3 (M+H).

The compounds in Table R were prepared using a similar method to that described for the synthesis of Example 56, replacing 2-Fluoro-6-methylbenzoic acid with the appropriate carboxylic acid. Reactions were monitored for completion by LCMS, and reaction durations were adjusted accordingly. Title compounds were cleanly isolated following chromatographic purification using an appropriate gradient eluent (and if necessary converted to the free base).

TABLE R

| Ex. # | Structure | Chemical Name | LCMS m/z |
|---|---|---|---|
| 57 | 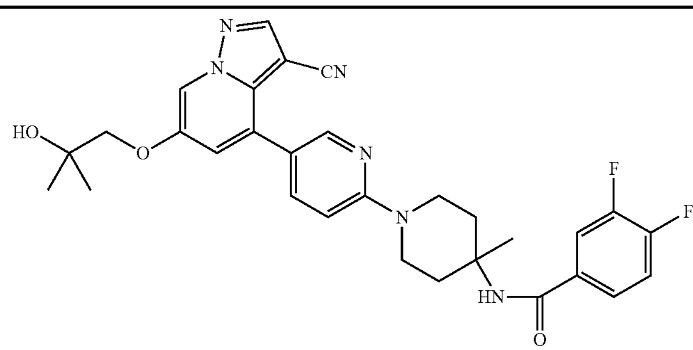 | N-(1-(5-(3-cyano-6-(2-hydroxy-2-methylpropoxy)pyrazolo[1,5-a]pyridin-4-yl)pyridin-2-yl)-4-methylpiperidin-4-yl)-3,4-difluorobenzamide | 561.3 (M + H) |

TABLE R-continued

| Ex. # | Structure | Chemical Name | LCMS m/z |
|---|---|---|---|
| 58 | 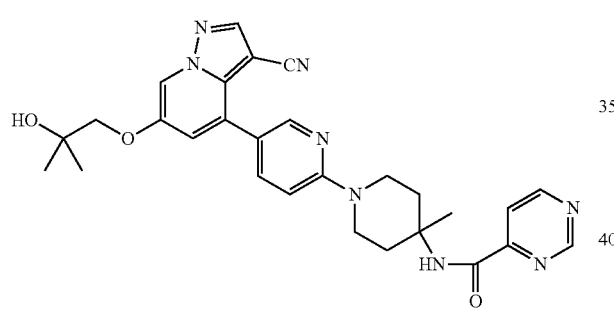 | N-(1-(5-(3-cyano-6-(2-hydroxy-2-methylpropoxy)pyrazolo[1,5-a]pyridin-4-yl)pyridin-2-yl)-4-methylpiperidin-4-yl)-2,6-dimethylisonicotinamide | 554.3 (M + H) |

Example 59

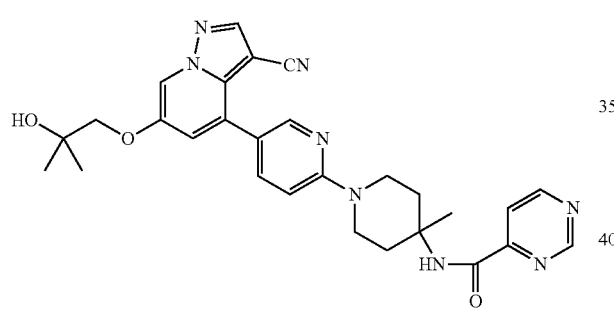

N-(1-(5-(3-cyano-6-(2-hydroxy-2-methylpropoxy)pyrazolo[1,5-a]pyridin-4-yl)pyridin-2-yl)-4-methylpiperidin-4-yl)pyrimidine-4-carboxamide A mixture of 4-(6-(4-amino-4-methylpiperidin-1-yl)pyridin-3-yl)-6-(2-hydroxy-2-methylpropoxy)pyrazolo[1,5-a]pyridine-3-carbonitrile (Intermediate P46; 43 mg, 0.10 mmol), HATU (77.8 mg, 0.21 mmol), and pyrimidine-4-carboxylic acid (12.7 mg, 0.10 mmol) in DMSO (600 μL) was treated with DIEA (80 μL, 0.46 mmol) and then stirred for 18 h at ambient temperature. The reaction mixture was diluted with EtOAc and washed with water. The organic extracts then dried over anhydrous $MgSO_{4(s)}$, filtered and concentrated in vacuo. The residue was purified by silica chromatography (1-10% MeOH in DCM with 0.1-1% $NH_4OH$ as the gradient eluent) to cleanly provide the title compound (35 mg, 53% yield). MS (apci) m/z=527.3 (M+H).

Example 60

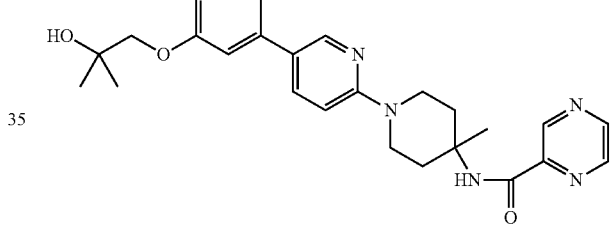

N-(1-(5-(3-cyano-6-(2-hydroxy-2-methylpropoxy)pyrazolo[1,5-a]pyridin-4-yl)pyridin-2-yl)-4-methylpiperidin-4-yl)-3,4-difluorobenzamide The compound was prepared using a similar method to that described for the synthesis of Example 59, replacing pyrimidine-4-carboxylic acid with pyrazine-2-carboxylic acid. MS (apci) m/z=527.2 (M+H).

Example 61

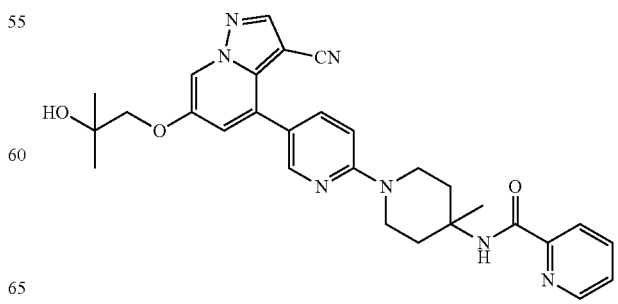

N-(1-(5-(3-cyano-6-(2-hydroxy-2-methylpropoxy)pyrazolo[1,5-a]pyridin-4-yl)pyridin-2-yl)-4-methyl-piperidin-4-yl)picolinamide A mixture of 4-(6-(4-amino-4-methylpiperidin-1-yl)pyridin-3-yl)-6-(2-hydroxy-2-methylpropoxy)pyrazolo[1,5-a]pyridine-3-carbonitrile (Intermediate P46; 35 mg, 0.08 mmol), HATU (34.8 mg, 0.09 mmol), and picolinic acid (22.6 mg, 0.18 mmol) in DCM (832 µL) was treated with DIEA (47 µL, 0.35 mmol) and then stirred for 18 h at ambient temperature. The reaction mixture was concentrated in vacuo. The residue was suspended in 60:40 ACN:water containing 2% TFA. The solution was purified directly by C18 reverse phase chromatography (5-95% ACN in water with 0.1% TFA as the gradient eluent) to afford the title compound as the TFA salt. The TFA salt was treated with saturated NaHCO$_{3(aq)}$ and extracted with DCM. The combined organic extracts were washed with brine, then dried over anhydrous Na$_2$SO$_{4(s)}$, filtered and concentrated in vacuo to afford the title compound (43.7 mg, 49.3% yield). MS (apci) m/z=526.20 (M+H). $^1$H NMR (400 MHz, CDCl$_3$) δ 8.54 (m, 1H), 8.33 (d, 1H), 8.19 (s, 1H), 8.18 (dt, 1H), 8.16 (s, br, 1H), 8.14 (d, 1H), 7.85 (td, 1H). 7.70 (dd, 1H), 7.43 (m, 1H), 7.13 (d, 1H), 6.80 (d, 1H), 4.08 (m, 2H), 3.85 (s, 2H), 3.37 (m, 2H), 2.42 (m, 2H), 1.82 (m, 2H), 1.59 (s, 3H), 1.39 (s, 6H)

Example 62

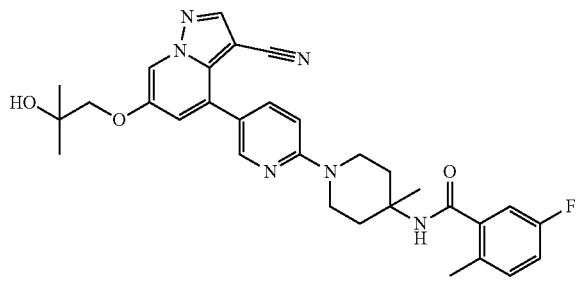 [SMILES: Cc1ccc(F)cc1C(=O)NC1(C)CCN(c2ccc(-c3cc(OCC(C)(C)O)cn4ncc(C#N)c34)cn2)CC1]

N-(1-(5-(3-cyano-6-(2-hydroxy-2-methylpropoxy)pyrazolo[1,5-a]pyridin-4-yl)pyridin-2-yl)-4-methyl-piperidin-4-yl)-5-fluoro-2-methylbenzamide A mixture of 4-(6-(4-amino-4-methylpiperidin-1-yl)pyridin-3-yl)-6-(2-hydroxy-2-methylpropoxy)pyrazolo[1,5-a]pyridine-3-carbonitrile (Intermediate P46; 15.8 mg, 0.038 mmol), HATU (15.7 mg, 0.041 mmol), and 5-Fluoro-2-methylbenzoic acid (11.6 mg, 0.075 mmol) in DCM (1.07 mL) was treated with DIEA (33 µL, 0.19 mmol) and then stirred for 18 h at ambient temperature. The reaction mixture was concentrated in vacuo. The residue was suspended in 60:40 ACN:water containing 2% TFA. The solution was purified directly by C18 reverse phase chromatography (5-95% ACN in water with 0.1% TFA as the gradient eluent) to afford the title compound as the TFA salt. The TFA salt was treated with saturated NaHCO$_{3(aq)}$ and extracted with DCM. The combined organic extracts were washed with brine, then dried over anhydrous Na$_2$SO$_{4(s)}$, filtered and concentrated in vacuo to afford the title compound (11.2 mg, 53.6% yield). MS (apci) m/z=557.3 (M+H). $^1$H NMR (400 MHz, CDCl$_3$) δ 8.34 (d, 1H), 8.20 (s, 1H), 8.15 (d, 1H), 7.71 (dd, 1H), 7.17 (dd, 1H). 7.14 (d, 1H), 7.06 (dd, 1H), 7.00 (td, 1H), 6.81 (d, 1H), 5.50 (s, br, 1H), 4.01 (m, 2H), 3.86 (s, 2H), 3.41 (m, 2H), 2.41 (s, 3H), 2.30 (m, 2H), 1.84 (m, 2H), 1.61 (s, 3H), 1.39 (s, 6H)

The compounds in Table S were prepared using a similar method to that described for the synthesis of Example 62, replacing 5-Fluoro-2-methylbenzoic acid with the appropriate carboxylic acid. Reactions were monitored for completion by LCMS, and reaction durations were adjusted accordingly. Title compounds were cleanly isolated following chromatographic purification using an appropriate gradient eluent (and if necessary converted to the free base).

TABLE S

| Ex. # | Structure | Chemical Name | LCMS m/z |
|---|---|---|---|
| 63 | 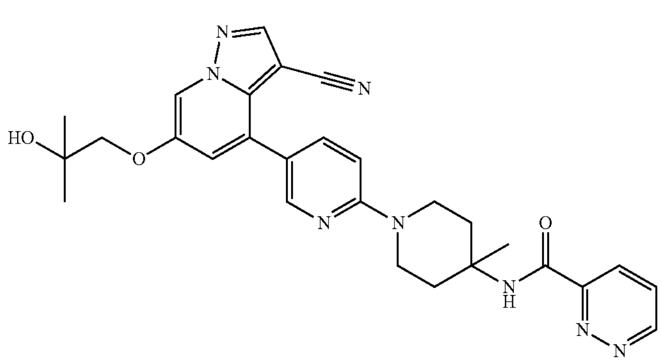 [SMILES: CC(C)(O)COc1cc(-c2ccc(N3CCC(C)(NC(=O)c4cccnn4)CC3)nc2)c2c(C#N)cnn2c1] | N-(1-(5-(3-cyano-6-(2-hydroxy-2-methylpropoxy)pyrazolo[1,5-a]pyridin-4-yl)pyridin-2-yl)-4-methylpiperidin-4-yl)pyridazine-3-carboxamide | 527.20 (M + H) |

TABLE S-continued

| Ex. # | Structure | Chemical Name | LCMS m/z |
|---|---|---|---|
| 64 | 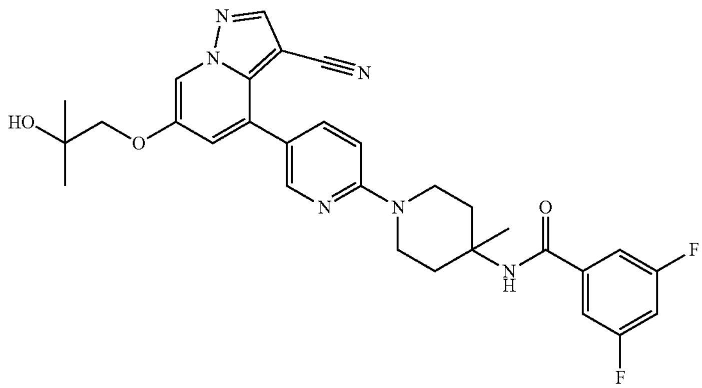 [SMILES: CC(C)(O)COc1cc(-c2ccc(N3CCC(C)(NC(=O)c4cc(F)cc(F)c4)CC3)nc2)c2c(C#N)cnn2c1] | N-(1-(5-(3-cyano-6-(2-hydroxy-2-methylpropoxy)pyrazolo[1,5-a]pyridin-4-yl)pyridin-2-yl)-4-methylpiperidin-4-yl)-3,5-difluorobenzamide | 561.2 (M + H) |
| 65 | 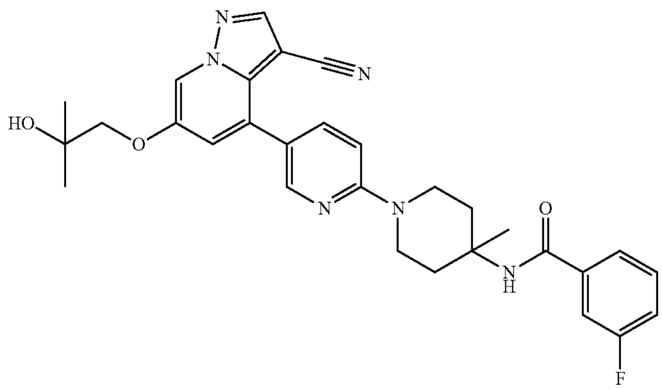 [SMILES: CC(C)(O)COc1cc(-c2ccc(N3CCC(C)(NC(=O)c4cccc(F)c4)CC3)nc2)c2c(C#N)cnn2c1] | N-(1-(5-(3-cyano-6-(2-hydroxy-2-methylpropoxy)pyrazolo[1,5-a]pyridin-4-yl)pyridin-2-yl)-4-methylpiperidin-4-yl)-3-fluorobenzamide | 543.2 (M + H) |
| 66 | 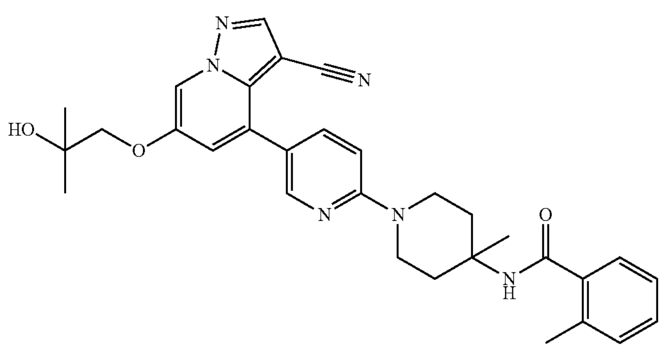 [SMILES: Cc1ccccc1C(=O)NC1(C)CCN(c2ccc(-c3cc(OCC(C)(C)O)cn4ncc(C#N)c34)cn2)CC1] | N-(1-(5-(3-cyano-6-(2-hydroxy-2-methylpropoxy)pyrazolo[1,5-a]pyridin-4-yl)pyridin-2-yl)-4-methylpiperidin-4-yl)-2-methylbenzamide | 539.3 (M + H) |
| 67 | 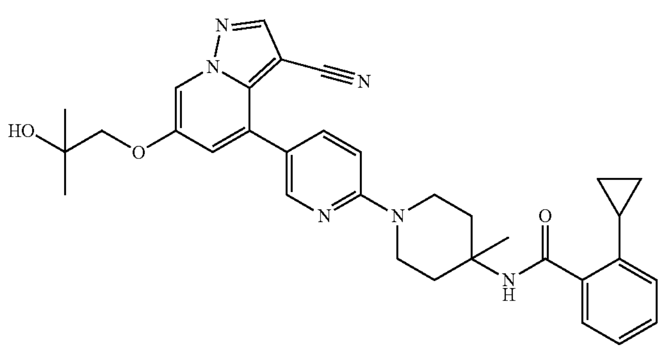 [SMILES: CC(C)(O)COc1cc(-c2ccc(N3CCC(C)(NC(=O)c4ccccc4C4CC4)CC3)nc2)c2c(C#N)cnn2c1] | N-(1-(5-(3-cyano-6-(2-hydroxy-2-methylpropoxy)pyrazolo[1,5-a]pyridin-4-yl)pyridin-2-yl)-4-methylpiperidin-4-yl)-2-cyclopropylbenzamide | 565.3 (M + H) |

TABLE S-continued

| Ex. # | Structure | Chemical Name | LCMS m/z |
|---|---|---|---|
| 68 | 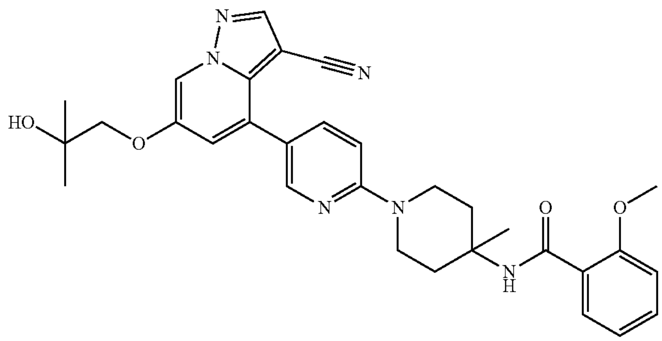 [SMILES: COc1ccccc1C(=O)NC1(C)CCN(c2ccc(-c3cc(OCC(C)(C)O)cn4ncc(C#N)c34)cn2)CC1] | N-(1-(5-(3-cyano-6-(2-hydroxy-2-methylpropoxy)pyrazolo[1,5-a]pyridin-4-yl)pyridin-2-yl)-4-methylpiperidin-4-yl)-2-methoxybenzamide | 555.3 (M + H) |
| 69 | 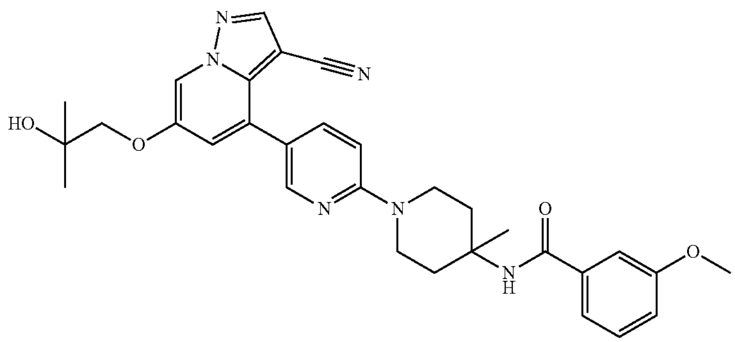 [SMILES: COc1cccc(C(=O)NC2(C)CCN(c3ccc(-c4cc(OCC(C)(C)O)cn5ncc(C#N)c45)cn3)CC2)c1] | N-(1-(5-(3-cyano-6-(2-hydroxy-2-methylpropoxy)pyrazolo[1,5-a]pyridin-4-yl)pyridin-2-yl)-4-methylpiperidin-4-yl)-3-methoxybenzamide | 555.3 (M + H) |
| 70 | 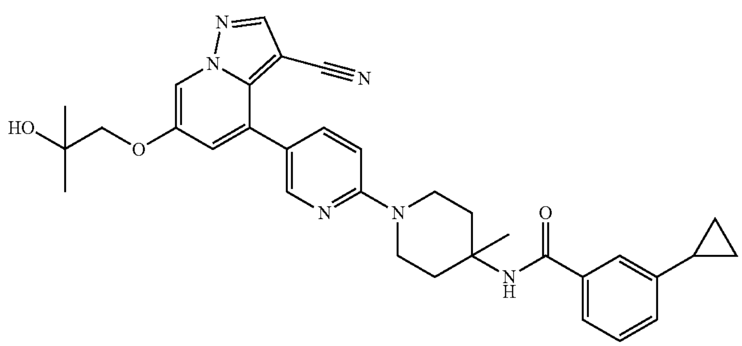 [SMILES: CC(C)(O)COc1cc(-c2ccc(N3CCC(C)(NC(=O)c4cccc(C5CC5)c4)CC3)nc2)c2c(C#N)cnn2c1] | N-(1-(5-(3-cyano-6-(2-hydroxy-2-methylpropoxy)pyrazolo[1,5-a]pyridin-4-yl)pyridin-2-yl)-4-methylpiperidin-4-yl)-3-cyclopropylbenzamide | 565.3 (M + H) |
| 71 | 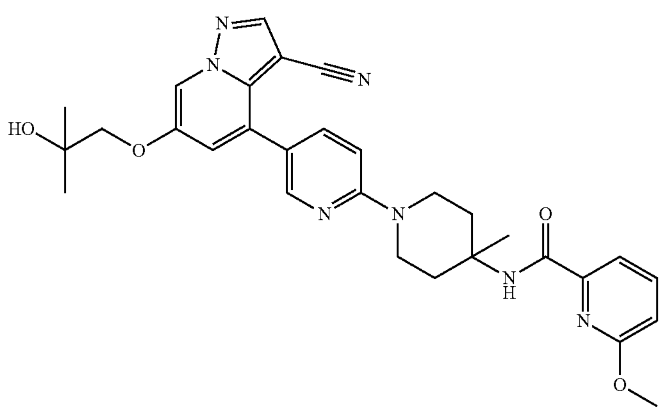 [SMILES: COc1cccc(C(=O)NC2(C)CCN(c3ccc(-c4cc(OCC(C)(C)O)cn5ncc(C#N)c45)cn3)CC2)n1] | N-(1-(5-(3-cyano-6-(2-hydroxy-2-methylpropoxy)pyrazolo[1,5-a]pyridin-4-yl)pyridin-2-yl)-4-methylpiperidin-4-yl)-6-methoxypicolinamide | 556.3 (M + H) |

TABLE S-continued

| Ex. # | Structure | Chemical Name | LCMS m/z |
|---|---|---|---|
| 72 | 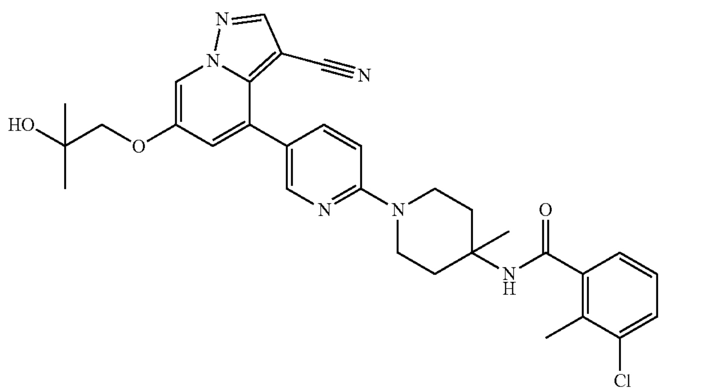 [SMILES: Cc1c(Cl)cccc1C(=O)NC1(C)CCN(c2ccc(-c3cc(OCC(C)(C)O)cn4ncc(C#N)c34)cn2)CC1] | 3-chloro-N-(1-(5-(3-cyano-6-(2-hydroxy-2-methylpropoxy)pyrazolo[1,5-a]pyridin-4-yl)pyridin-2-yl)-4-methylpiperidin-4-yl)-2-methylbenzamide | 573.3 (M + H) |
| 73 | 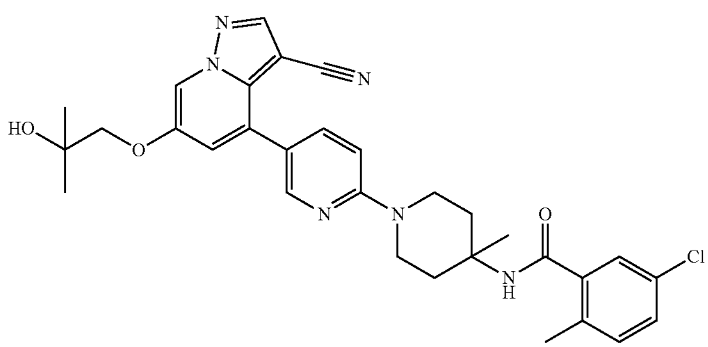 [SMILES: Cc1ccc(Cl)cc1C(=O)NC1(C)CCN(c2ccc(-c3cc(OCC(C)(C)O)cn4ncc(C#N)c34)cn2)CC1] | 5-chloro-N-(1-(5-(3-cyano-6-(2-hydroxy-2-methylpropoxy)pyrazolo[1,5-a]pyridin-4-yl)pyridin-2-yl)-4-methylpiperidin-4-yl)-2-methylbenzamide | 573.3 (M + H) |
| 74 | 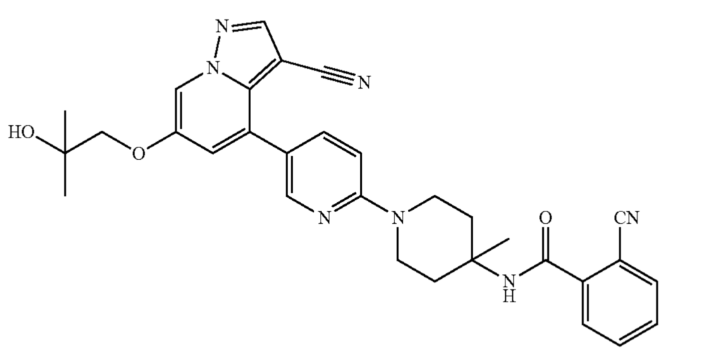 [SMILES: CC(C)(O)COc1cc(-c2ccc(N3CCC(C)(NC(=O)c4ccccc4C#N)CC3)nc2)c2c(C#N)cnn2c1] | 2-cyano-N-(1-(5-(3-cyano-6-(2-hydroxy-2-methylpropoxy)pyrazolo[1,5-a]pyridin-4-yl)pyridin-2-yl)-4-methylpiperidin-4-yl)-benzamide | 550.3 (M + H) |
| 75 | 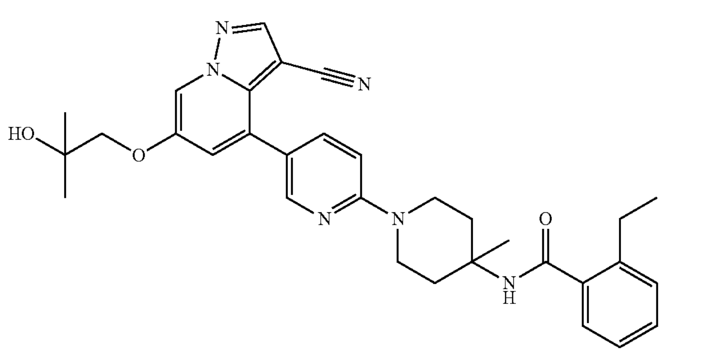 [SMILES: CCc1ccccc1C(=O)NC1(C)CCN(c2ccc(-c3cc(OCC(C)(C)O)cn4ncc(C#N)c34)cn2)CC1] | N-(1-(5-(3-cyano-6-(2-hydroxy-2-methylpropoxy)pyrazolo[1,5-a]pyridin-4-yl)pyridin-2-yl)-4-methylpiperidin-4-yl)-2-ethylbenzamide | 553.3 (M + H) |

TABLE S-continued

| Ex. # | Structure | Chemical Name | LCMS m/z |
|---|---|---|---|
| 76 | 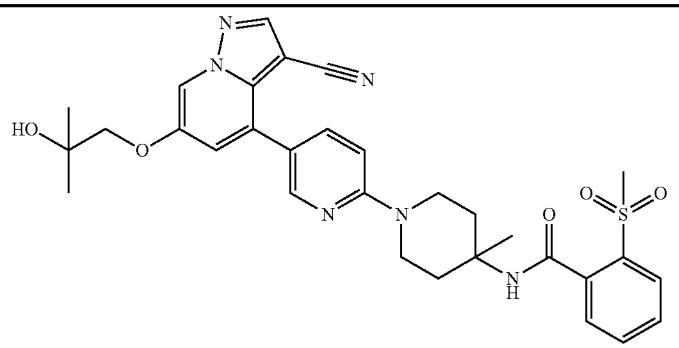 | N-(1-(5-(3-cyano-6-(2-hydroxy-2-methylpropoxy)pyrazolo[1,5-a]pyridin-4-yl)pyridin-2-yl)-4-methylpiperidin-4-yl)-2-(methylsulfonyl)benzamide | 603.3 (M + H) |
| 77 | 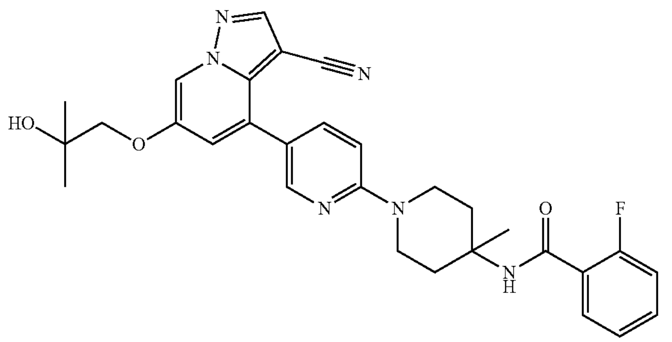 [SMILES: CC(C)(O)COc1cc(-c2ccc(N3CCC(C)(NC(=O)c4ccccc4F)CC3)nc2)c2c(C#N)cnn2c1] | N-(1-(5-(3-cyano-6-(2-hydroxy-2-methylpropoxy)pyrazolo[1,5-a]pyridin-4-yl)pyridin-2-yl)-4-methylpiperidin-4-yl)-2-fluorobenzamide | 543.3 (M + H) |

Example 78

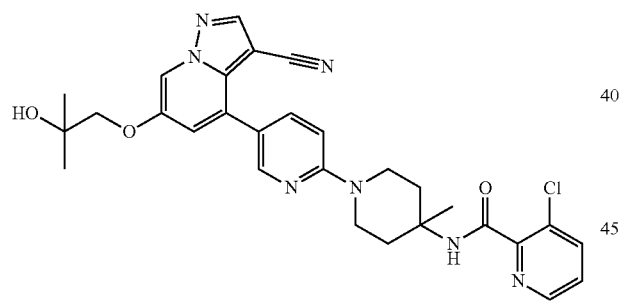

3-chloro-N-(1-(5-(3-cyano-6-(2-hydroxy-2-methylpropoxy)pyrazolo[1,5-a]pyridin-4-yl)pyridin-2-yl)-4-methylpiperidin-4-yl)picolinamide A mixture of 4-(6-(4-amino-4-methylpiperidin-1-yl)pyridin-3-yl)-6-(2-hydroxy-2-methylpropoxy)pyrazolo[1,5-a]pyridine-3-carbonitrile (Intermediate P46; 50 mg, 0.12 mmol), HATU (50 mg, 0.13 mmol), and 3-chloropicolinic acid (37 mg, 0.24 mmol) in DMSO (1.2 mL, 0.1 M) was treated with DIEA (100 μL, 0.59 mmol) and then stirred for 1 h at ambient temperature. The reaction mixture was diluted with EtOAc and washed with water. The organic extracts were washed with brine, then dried over anhydrous Na$_2$SO$_{4(s)}$, filtered and concentrated in vacuo. The residue was suspended in 60:40 ACN:water containing 2% TFA. The solution was purified directly by C18 reverse phase chromatography (5-95% ACN in water with 0.1% TFA as the gradient eluent) to afford the title compound as the TFA salt. The TFA salt was treated with saturated NaHCO$_{3(aq)}$ and extracted with DCM. The combined organic extracts were washed with brine, then dried over anhydrous Na$_2$SO$_{4(s)}$, filtered and concentrated in vacuo to afford the title compound (45 mg, 68% yield). MS (apci) m/z=560.2 (M+H). $^1$H NMR (400 MHz, CDCl$_3$) δ 8.43 (dd, 1H), 8.32 (d, 1H), 8.18 (s, 1H), 8.12 (d, 1H), 7.88 (s, br, 1H), 7.81 (dd, 1H). 7.68 (dd, 1H), 7.35 (dd, 1H), 7.11 (d, 1H), 6.78 (d, 1H), 4.06 (m, 2H), 3.85 (s, 2H), 3.36 (m, 2H), 2.38 (m, 2H), 1.79 (m, 2H), 1.60 (s, 3H), 1.38 (s, 6H).

Example 79

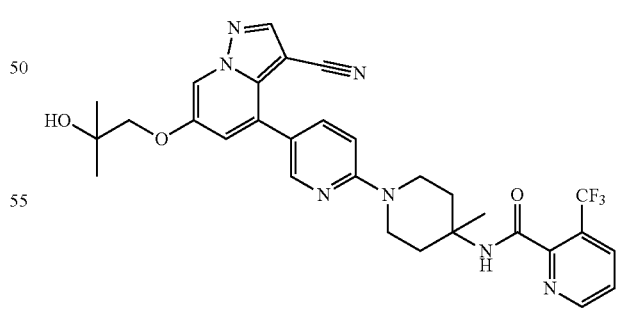

N-(1-(5-(3-cyano-6-(2-hydroxy-2-methylpropoxy)pyrazolo[1,5-a]pyridin-4-yl)pyridin-2-yl)-4-methylpiperidin-4-yl)-3-(trifluoromethyl)picolinamide A mixture of 4-(6-(4-amino-4-methylpiperidin-1-yl)pyridin-3-yl)-6-(2-hydroxy-2-methylpropoxy)pyrazolo[1,5-a]

pyridine-3-carbonitrile (Intermediate P46; 50 mg, 0.12 mmol), HATU (50 mg, 0.13 mmol), and 3-(trifluoromethyl)picolinic acid (45.4 mg, 0.24 mmol) in DMSO (1.19 mL, 0.1 M) was treated with DIEA (104 µL, 0.60 mmol) and then stirred for 18 h at ambient temperature. The reaction mixture was diluted with EtOAc and washed with water. The organic extracts were washed with brine, then dried over anhydrous Na$_2$SO$_{4(s)}$, filtered and concentrated in vacuo. The residue was suspended in 60:40 ACN:water containing 2% TFA. The solution was purified directly by C18 reverse phase chromatography (5-95% ACN in water with 0.1% TFA as the gradient eluent) to afford the title compound as the TFA salt. The TFA salt was treated with saturated NaHCO$_{3(aq)}$ and extracted with DCM. The combined organic extracts were washed with brine, then dried over anhydrous Na$_2$SO$_{4(s)}$, filtered and concentrated in vacuo to afford the title compound (46.5 mg, 66% yield). MS (apci) m/z=594.3 (M+H). $^1$H NMR (400 MHz, CDCl$_3$) δ 8.8.71 (d, 1H), 8.34 (d, 1H), 8.19 (s, 1H), 8.16 (d, 1H), 8.14 (d, 1H), 7.70 (dd, 1H). 7.56 (dd, 1H), 7.52 (s, br, 1H), 7.13 (d, 1H), 6.80 (d, 1H), 4.06 (m, 2H), 3.85 (s, 2H), 3.36 (m, 2H), 2.40 (m, 2H), 1.82 (m, 2H), 1.60 (s, 3H), 1.39 (s, 6H).

Example 80

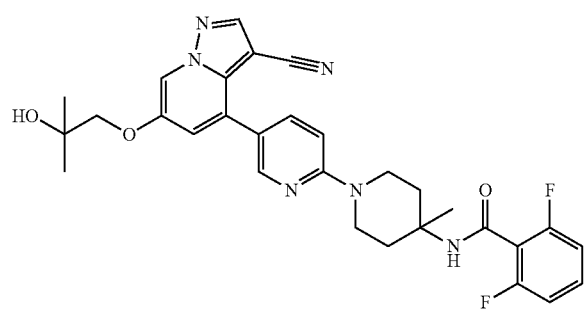 [SMILES: CC(C)(O)COc1cc(-c2ccc(N3CCC(C)(NC(=O)c4c(F)cccc4F)CC3)nc2)c2c(C#N)cnn2c1]

N-(1-(5-(3-cyano-6-(2-hydroxy-2-methylpropoxy)pyrazolo[1,5-a]pyridin-4-yl)pyridin-2-yl)-4-methyl-piperidin-4-yl)-2,6-difluorobenzamide A mixture of 4-(6-(4-amino-4-methylpiperidin-1-yl)pyridin-3-yl)-6-(2-hydroxy-2-methylpropoxy)pyrazolo[1,5-a]pyridine-3-carbonitrile (Intermediate P46; 50 mg, 0.12 mmol), HATU (50 mg, 0.13 mmol), and 2,6-difluorobenzoic acid (37.6 mg, 0.24 mmol) in DMSO (1.19 mL, 0.1 M) was treated with DIEA (104 µL, 0.60 mmol) and then stirred for 18 h at ambient temperature. The reaction mixture was diluted with EtOAc and washed with water. The organic extracts were washed with brine, then dried over anhydrous Na$_2$SO$_{4(s)}$, filtered and concentrated in vacuo. The residue was suspended in 60:40 ACN:water containing 2% TFA. The solution was purified directly by C18 reverse phase chromatography (5-95% ACN in water with 0.1% TFA as the gradient eluent) to afford the title compound as the TFA salt. The TFA salt was treated with saturated NaHCO$_{3(aq)}$ and extracted with DCM. The combined organic extracts were washed with brine, then dried over anhydrous Na$_2$SO$_{4(s)}$, filtered and concentrated in vacuo to afford the title compound (46.5 mg, 66% yield). MS (apci) m/z=561.2 (M+H).

Example 81

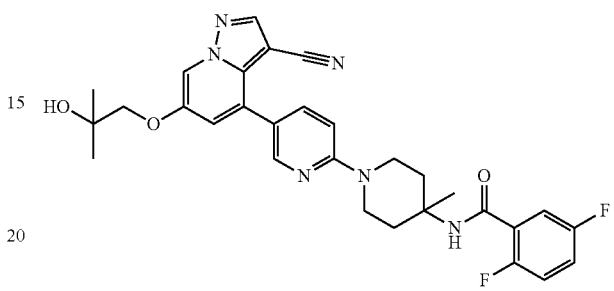

N-(1-(5-(3-cyano-6-(2-hydroxy-2-methylpropoxy)pyrazolo[1,5-a]pyridin-4-yl)pyridin-2-yl)-4-methyl-piperidin-4-yl)-2,5-difluorobenzamide A mixture of 4-(6-(4-amino-4-methylpiperidin-1-yl)pyridin-3-yl)-6-(2-hydroxy-2-methylpropoxy)pyrazolo[1,5-a]pyridine-3-carbonitrile (Intermediate P46; 67 mg, 0.16 mmol), HATU (67 mg, 0.18 mmol), and 2,5-difluorobenzoic acid (50 mg, 0.32 mmol) in DMSO (1.6 mL, 0.1 M) was treated with DIEA (0.14 mL, 0.80 mmol) and then stirred for 18 h at ambient temperature. The reaction mixture was diluted with EtOAc and washed with water. The organic extracts were washed with brine, then dried over anhydrous Na$_2$SO$_{4(s)}$, filtered and concentrated in vacuo. The residue was suspended in 60:40 ACN:water containing 2% TFA. The solution was purified directly by C18 reverse phase chromatography (5-95% ACN in water with 0.1% TFA as the gradient eluent) to afford the title compound as the TFA salt. The TFA salt was treated with saturated NaHCO$_{3(aq)}$ and extracted with DCM. The combined organic extracts were washed with brine, then dried over anhydrous Na$_2$SO$_{4(s)}$, filtered and concentrated in vacuo to afford the title compound (57 mg, 64% yield). MS (apci) m/z=561.2 (M+H). $^1$H NMR (400 MHz, CDCl$_3$) δ 8.34 (d, 1H), 8.20 (s, 1H), 8.14 (d, 1H), 7.76 (m, 1H). 7.70 (dd, 1H), 7.14 (m, 3H), 6.80 (d, 1H), 6.62 (d, 1H), 4.06 (m, 2H), 3.86 (s, 2H), 3.34 (m, 2H), 2.31 (m, 2H), 1.81 (m, 2H), 1.59 (s, 3H), 1.39 (s, 6H).

The compounds in Table T were prepared using a similar method to that described for the synthesis of Example 81, replacing 2,5-difluorobenzoic acid with the appropriate carboxylic acid. Reactions were monitored for completion by LCMS, and reaction durations were adjusted accordingly. Title compounds were cleanly isolated following chromatographic purification using an appropriate gradient eluent (and if necessary converted to the free base).

TABLE T

| Ex. # | Structure | Chemical Name | LCMS m/z |
|---|---|---|---|
| 82 | 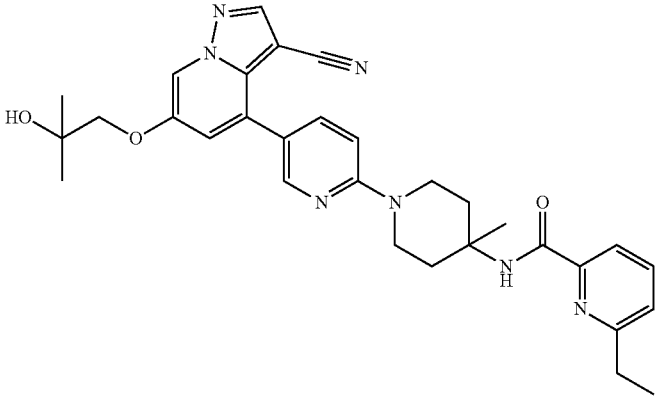 [SMILES: CCc1cccc(C(=O)NC2(C)CCN(c3ccc(-c4cc(OCC(C)(C)O)cn5ncc(C#N)c45)cn3)CC2)n1] | N-(1-(5-(3-cyano-6-(2-hydroxy-2-methylpropoxy)pyrazolo[1,5-a]pyridin-4-yl)pyridin-2-yl)-4-methylpiperidin-4-yl)-6-ethylpicolinamide | 554.3 (M + H) |
| 83 | 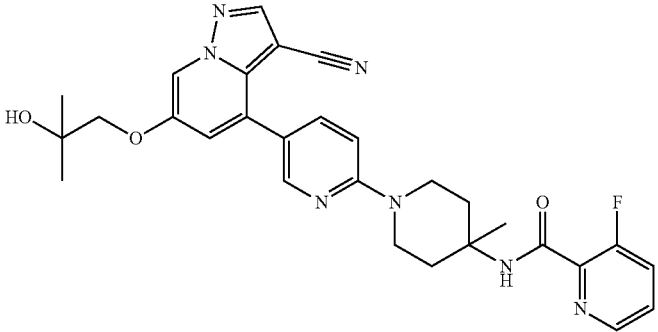 [SMILES: CC(C)(O)COc1cc(-c2ccc(N3CCC(C)(NC(=O)c4ncccc4F)CC3)nc2)c2c(C#N)cnn2c1] | N-(1-(5-(3-cyano-6-(2-hydroxy-2-methylpropoxy)pyrazolo[1,5-a]pyridin-4-yl)pyridin-2-yl)-4-methylpiperidin-4-yl)-3-fluoropicolinamide | 544.3 (M + H) |
| 84 | 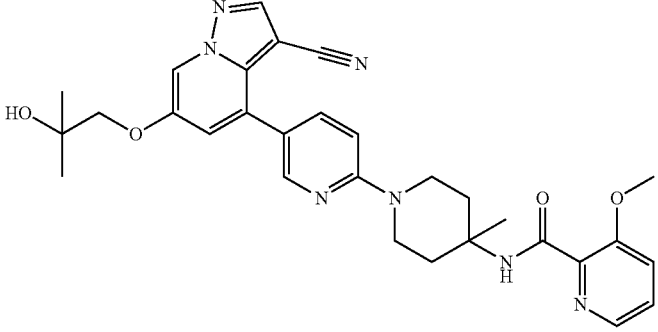 [SMILES: COc1cccnc1C(=O)NC1(C)CCN(c2ccc(-c3cc(OCC(C)(C)O)cn4ncc(C#N)c34)cn2)CC1] | N-(1-(5-(3-cyano-6-(2-hydroxy-2-methylpropoxy)pyrazolo[1,5-a]pyridin-4-yl)pyridin-2-yl)-4-methylpiperidin-4-yl)-3-methoxypicolinamide | 556.3 (M + H) |
| 85 | 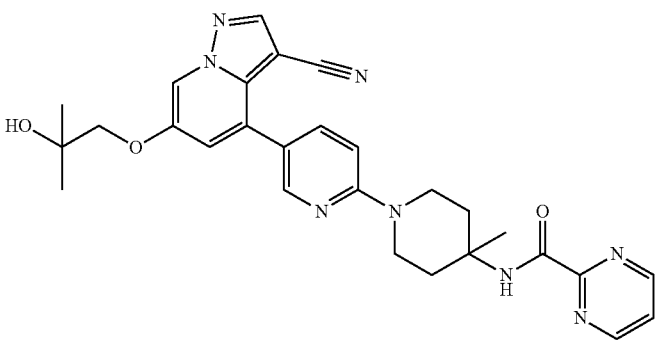 [SMILES: CC(C)(O)COc1cc(-c2ccc(N3CCC(C)(NC(=O)c4ncccn4)CC3)nc2)c2c(C#N)cnn2c1] | N-(1-(5-(3-cyano-6-(2-hydroxy-2-methylpropoxy)pyrazolo[1,5-a]pyridin-4-yl)pyridin-2-yl)-4-methylpiperidin-4-yl)pyrimidine-2-carboxamide | 527.2 (M + H) |

TABLE T-continued

| Ex. # | Structure | Chemical Name | LCMS m/z |
|---|---|---|---|
| 86 | 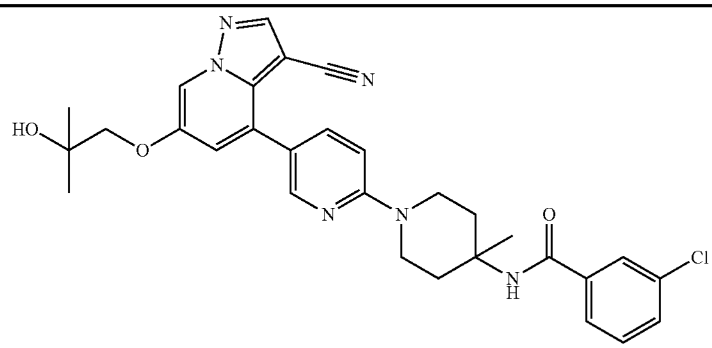 | 3-chloro-N-(1-(5-(3-cyano-6-(2-hydroxy-2-methylpropoxy)pyrazolo[1,5-a]pyridin-4-yl)pyridin-2-yl)-4-methylpiperidin-4-yl)benzamide | 559.2 (M + H) |

Example 87

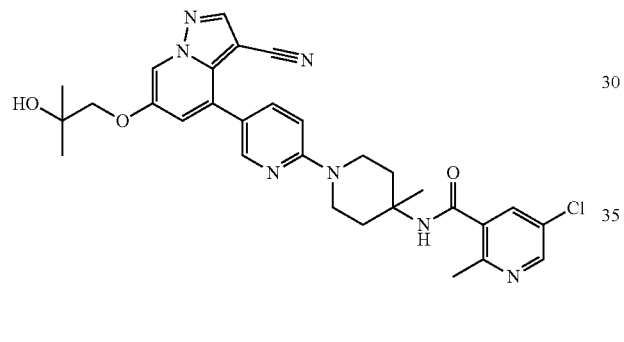

5-chloro-N-(1-(5-(3-cyano-6-(2-hydroxy-2-methyl-propoxy)pyrazolo[1,5-a]pyridin-4-yl)pyridin-2-yl)-4-methylpiperidin-4-yl)-2-methylnicotinamide A mixture of 4-(6-(4-amino-4-methylpiperidin-1-yl)pyridin-3-yl)-6-(2-hydroxy-2-methylpropoxy)pyrazolo[1,5-a]pyridine-3-carbonitrile dihydrochloride (Intermediate P48; 53 mg, 0.107 mmol), HATU (44.9 mg, 0.118 mmol), and 5-Chloro-2-methyl-3-pyridinecarboxylic acid (36.9 mg, 0.107 mmol) in DMSO (1.28 mL, 0.1 M) was treated with DIEA (0.09 mL, 0.54 mmol) and then stirred for 18 h at ambient temperature. The reaction mixture was diluted with EtOAc and washed with water. The organic extracts were washed with brine, then dried over anhydrous Na$_2$SO$_{4(s)}$, filtered and concentrated in vacuo. The residue was suspended in 60:40 ACN:water containing 2% TFA. The solution was purified directly by C18 reverse phase chromatography (5-95% ACN in water with 0.1% TFA as the gradient eluent) to afford the title compound as the TFA salt. The TFA salt was treated with saturated NaHCO$_{3(aq)}$ and extracted with DCM. The combined organic extracts were washed with brine, then dried over anhydrous Na$_2$SO$_{4(s)}$, filtered and concentrated in vacuo to afford the title compound (26.1 mg, 42% yield). MS (apci) m/z=574.2 (M+H).

Example 88

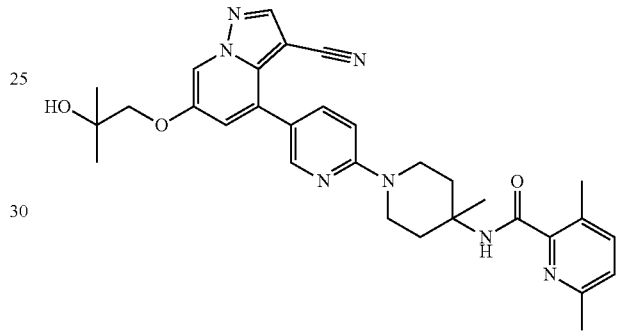

N-(1-(5-(3-cyano-6-(2-hydroxy-2-methylpropoxy)pyrazolo[1,5-a]pyridin-4-yl)pyridin-2-yl)-4-methyl-piperidin-4-yl)-3,6-dimethylpicolinamide A mixture of 4-(6-(4-amino-4-methylpiperidin-1-yl)pyridin-3-yl)-6-(2-hydroxy-2-methylpropoxy)pyrazolo[1,5-a]pyridine-3-carbonitrile dihydrochloride (Intermediate P48; 63 mg, 0.128 mmol), HATU (67 mg, 0.18 mmol), and 3,6-Dimethylpicolinic acid (38.6 mg, 0.26 mmol) in DMSO (1.28 mL, 0.1 M) was treated with DIEA (0.11 mL, 0.64 mmol) and then stirred for 18 h at ambient temperature. The reaction mixture was diluted with EtOAc and washed with water. The organic extracts were washed with brine, then dried over anhydrous Na$_2$SO$_{4(s)}$, filtered and concentrated in vacuo. The residue was suspended in 60:40 ACN:water containing 2% TFA. The solution was purified directly by C18 reverse phase chromatography (5-95% ACN in water with 0.1% TFA as the gradient eluent) to afford the title compound as the TFA salt. The TFA salt was treated with saturated NaHCO$_{3(aq)}$ and extracted with DCM. The combined organic extracts were washed with brine, then dried over anhydrous Na$_2$SO$_{4(s)}$, filtered and concentrated in vacuo to afford the title compound (57 mg, 64% yield). MS (apci) m/z=554.3 (M+H).

The compounds in Table U were prepared using a similar method to that described for the synthesis of Example 88, replacing 3,6-Dimethylpicolinic acid with the appropriate carboxylic acid. Reactions were monitored for completion by LCMS, and reaction durations were adjusted accordingly. Title compounds were cleanly isolated following chromatographic purification using an appropriate gradient eluent (and if necessary converted to the free base).

TABLE U

| Ex. # | Structure | Chemical Name | LCMS m/z |
|---|---|---|---|
| 89 | 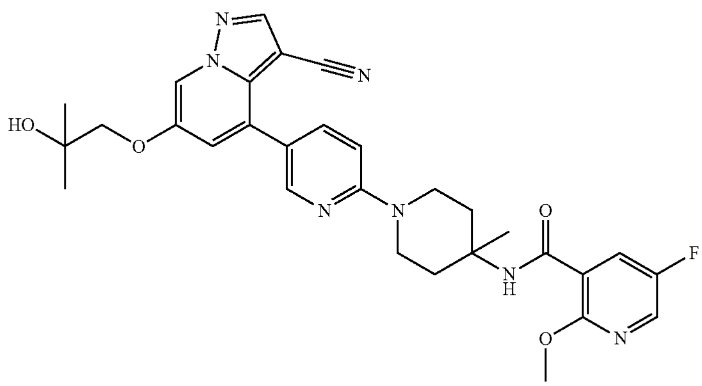 [SMILES: COc1ncc(F)cc1C(=O)NC1(C)CCN(c2ccc(-c3cc(OCC(C)(C)O)cn4ncc(C#N)c34)cn2)CC1] | N-(1-(5-(3-cyano-6-(2-hydroxy-2-methylpropoxy)pyrazolo[1,5-a]pyridin-4-yl)pyridin-2-yl)-4-methylpiperidin-4-yl)-5-fluoro-2-methoxynicotinamide | 574.3 (M + H) |
| 90 | 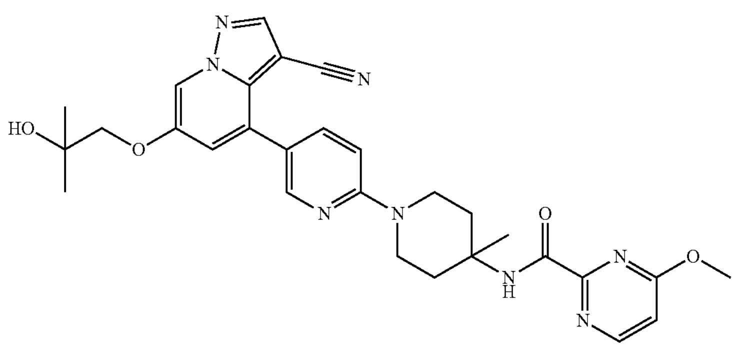 [SMILES: COc1ccnc(C(=O)NC2(C)CCN(c3ccc(-c4cc(OCC(C)(C)O)cn5ncc(C#N)c45)cn3)CC2)n1] | N-(1-(5-(3-cyano-6-(2-hydroxy-2-methylpropoxy)pyrazolo[1,5-a]pyridin-4-yl)pyridin-2-yl)-4-methylpiperidin-4-yl)-4-methoxypyrimidine-2-carboxamide | 557.3 (M + H) |
| 91 | 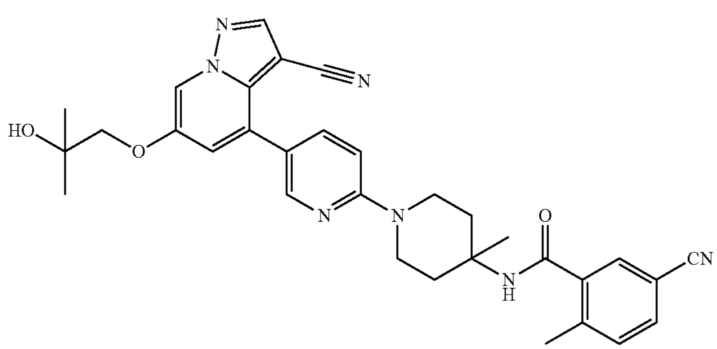 [SMILES: Cc1ccc(C#N)cc1C(=O)NC1(C)CCN(c2ccc(-c3cc(OCC(C)(C)O)cn4ncc(C#N)c34)cn2)CC1] | 5-cyano-N-(1-(5-(3-cyano-6-(2-hydroxy-2-methylpropoxy)pyrazolo[1,5-a]pyridin-4-yl)pyridin-2-yl)-4-methylpiperidin-4-yl)-2-methylbenzamide | 564.3 (M + H) |
| 92 | 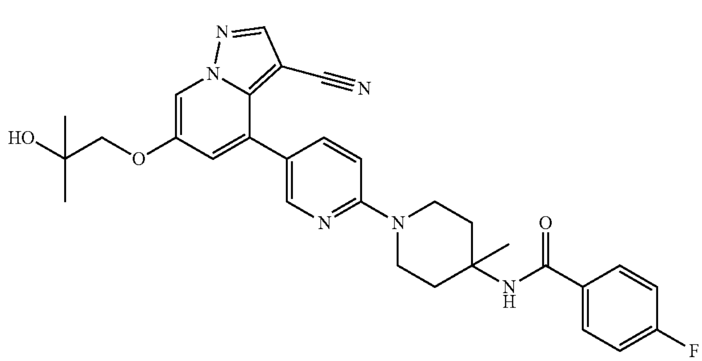 [SMILES: CC(C)(O)COc1cc(-c2ccc(N3CCC(C)(NC(=O)c4ccc(F)cc4)CC3)nc2)c2c(C#N)cnn2c1] | N-(1-(5-(3-cyano-6-(2-hydroxy-2-methylpropoxy)pyrazolo[1,5-a]pyridin-4-yl)pyridin-2-yl)-4-methylpiperidin-4-yl)-4-fluorobenzamide | 543.2 (M + H) |

TABLE U-continued

| Ex. # | Structure | Chemical Name | LCMS m/z |
|---|---|---|---|
| 93 | 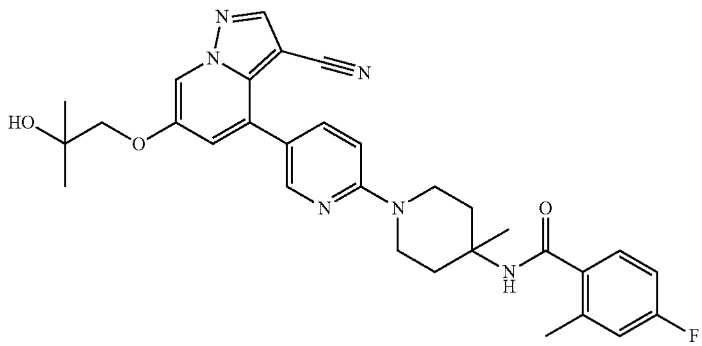 [SMILES: Cc1cc(F)ccc1C(=O)NC1(C)CCN(c2ccc(-c3cc(OCC(C)(C)O)cn4ncc(C#N)c34)cn2)CC1] | N-(1-(5-(3-cyano-6-(2-hydroxy-2-methylpropoxy)pyrazolo[1,5-a]pyridin-4-yl)pyridin-2-yl)-4-methylpiperidin-4-yl)-4-fluoro-2-methylbenzamide | 557.3 (M + H) |
| 94 | 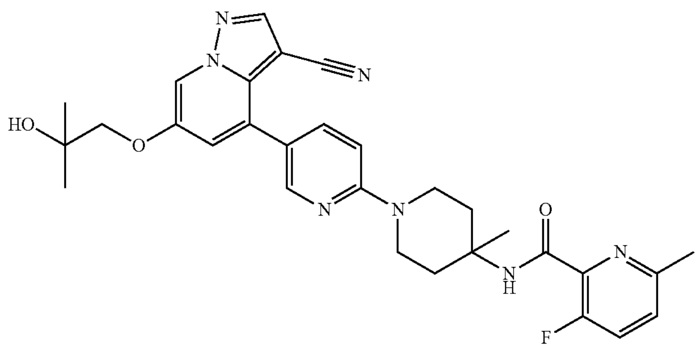 [SMILES: Cc1ccc(F)c(C(=O)NC2(C)CCN(c3ccc(-c4cc(OCC(C)(C)O)cn5ncc(C#N)c45)cn3)CC2)n1] | N-(1-(5-(3-cyano-6-(2-hydroxy-2-methylpropoxy)pyrazolo[1,5-a]pyridin-4-yl)pyridin-2-yl)-4-methylpiperidin-4-yl)-3-fluoro-6-methylpicolinamide | 558.3 (M + H) |
| 95 | 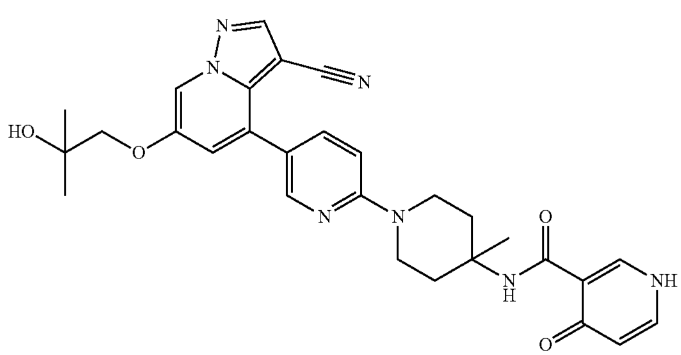 [SMILES: CC(C)(O)COc1cc(-c2ccc(N3CCC(C)(NC(=O)c4c[nH]ccc4=O)CC3)nc2)c2c(C#N)cnn2c1] | N-(1-(5-(3-cyano-6-(2-hydroxy-2-methylpropoxy)pyrazolo[1,5-a]pyridin-4-yl)pyridin-2-yl)-4-methylpiperidin-4-yl)-4-oxo-1,4-dihydropyridine-3-carboxamide | 542.3 (M + H) |
| 96 | 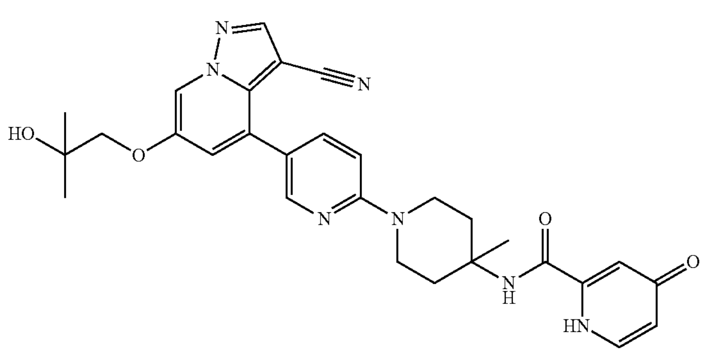 [SMILES: CC(C)(O)COc1cc(-c2ccc(N3CCC(C)(NC(=O)c4cc(=O)cc[nH]4)CC3)nc2)c2c(C#N)cnn2c1] | N-(1-(5-(3-cyano-6-(2-hydroxy-2-methylpropoxy)pyrazolo[1,5-a]pyridin-4-yl)pyridin-2-yl)-4-methylpiperidin-4-yl)-4-oxo-1,4-dihydropyridine-2-carboxamide | 542.3 (M + H) |

| Ex. # | Structure | Chemical Name | LCMS m/z |
|---|---|---|---|
| 97 | 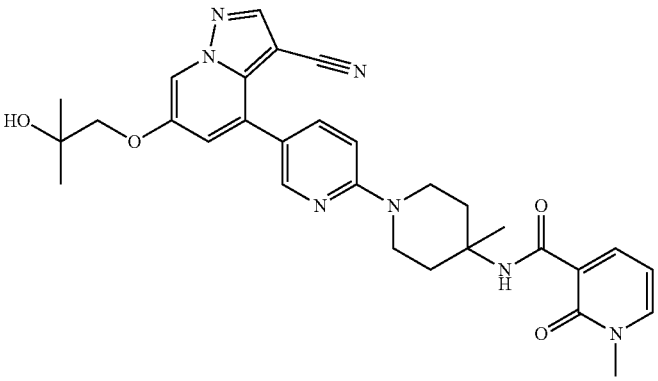 [SMILES: Cn1cccc(C(=O)NC2(C)CCN(c3ccc(-c4cc(OCC(C)(C)O)cn5ncc(C#N)c45)cn3)CC2)c1=O] | N-(1-(5-(3-cyano-6-(2-hydroxy-2-methylpropoxy)pyrazolo[1,5-a]pyridin-4-yl)pyridin-2-yl)-4-methylpiperidin-4-yl)-1-methyl-2-oxo-1,2-dihydropyridine-3-carboxamide | 556.2 (M + H) |
| 98 | 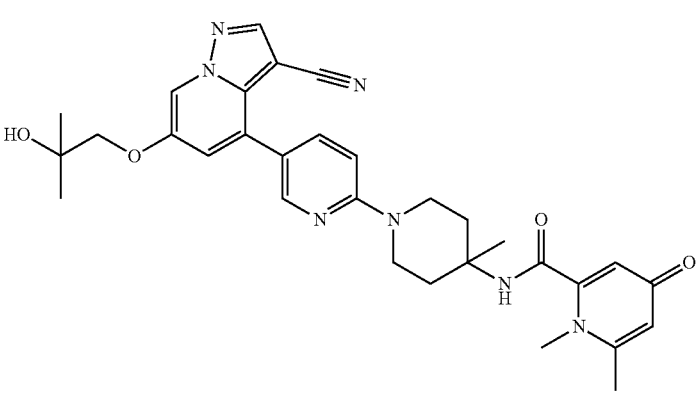 [SMILES: Cc1cc(=O)cc(C(=O)NC2(C)CCN(c3ccc(-c4cc(OCC(C)(C)O)cn5ncc(C#N)c45)cn3)CC2)n1C] | N-(1-(5-(3-cyano-6-(2-hydroxy-2-methylpropoxy)pyrazolo[1,5-a]pyridin-4-yl)pyridin-2-yl)-4-methylpiperidin-4-yl)-1,6-dimethyl-4-oxo-1,4-dihydropyridine-2-carboxamide | 570.3 (M + H) |
| 99 | 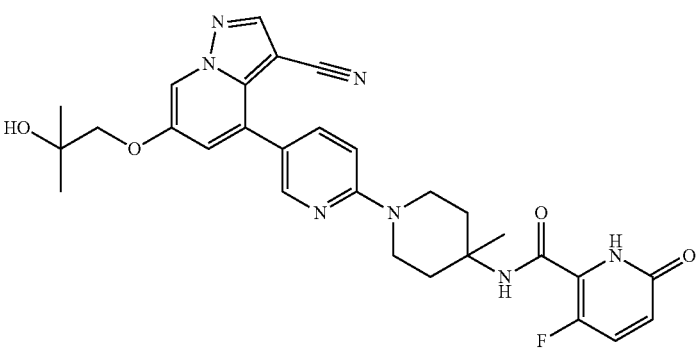 [SMILES: CC(C)(O)COc1cc(-c2ccc(N3CCC(C)(NC(=O)c4[nH]c(=O)ccc4F)CC3)nc2)c2c(C#N)cnn2c1] | N-(1-(5-(3-cyano-6-(2-hydroxy-2-methylpropoxy)pyrazolo[1,5-a]pyridin-4-yl)pyridin-2-yl)-4-methylpiperidin-4-yl)-3-fluoro-6-oxo-1,6-dihydropyridine-2-carboxamide | 560.3 (M + H) |
| 100 | 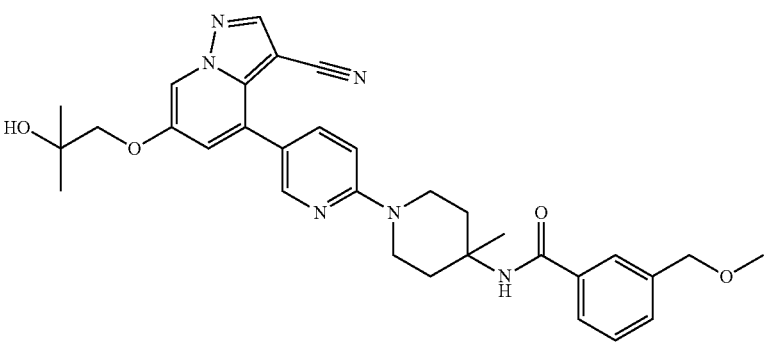 [SMILES: COCc1cccc(C(=O)NC2(C)CCN(c3ccc(-c4cc(OCC(C)(C)O)cn5ncc(C#N)c45)cn3)CC2)c1] | N-(1-(5-(3-cyano-6-(2-hydroxy-2-methylpropoxy)pyrazolo[1,5-a]pyridin-4-yl)pyridin-2-yl)-4-methylpiperidin-4-yl)-3-(methoxymethyl)benzamide | 569.3 (M + H) |

TABLE U-continued

| Ex. # | Structure | Chemical Name | LCMS m/z |
|---|---|---|---|
| 101 | 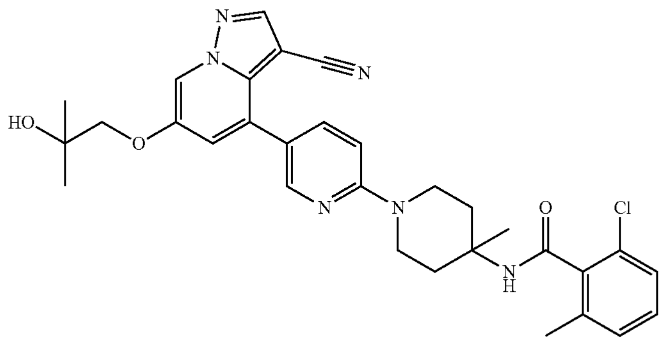 [SMILES: Cc1cccc(Cl)c1C(=O)NC1(C)CCN(c2ccc(-c3cc(OCC(C)(C)O)cn4ncc(C#N)c34)cn2)CC1] | 2-chloro-N-(1-(5-(3-cyano-6-(2-hydroxy-2-methylpropoxy)pyrazolo[1,5-a]pyridin-4-yl)pyridin-2-yl)-4-methylpiperidin-4-yl)-6-methylbenzamide | 573.2 (M + H) |
| 102 | 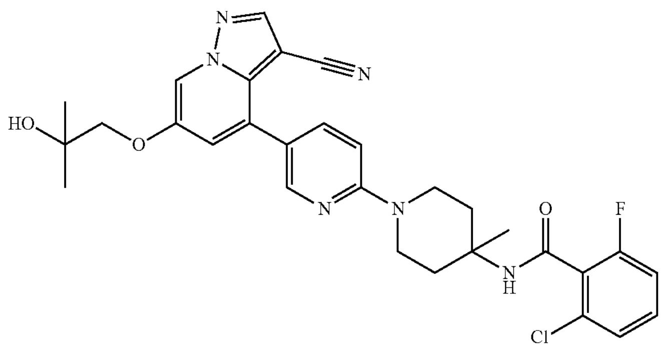 [SMILES: CC(C)(O)COc1cc(-c2ccc(N3CCC(C)(NC(=O)c4c(F)cccc4Cl)CC3)nc2)c2c(C#N)cnn2c1] | 2-chloro-N-(1-(5-(3-cyano-6-(2-hydroxy-2-methylpropoxy)pyrazolo[1,5-a]pyridin-4-yl)pyridin-2-yl)-4-methylpiperidin-4-yl)-6-fluorobenzamide | 577.2 (M + H) |
| 103 | 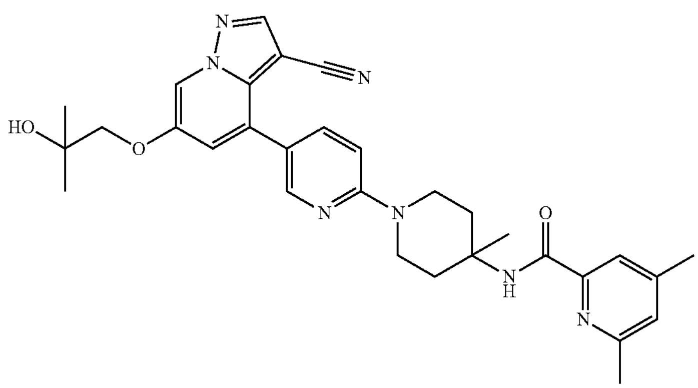 [SMILES: Cc1cc(C)nc(C(=O)NC2(C)CCN(c3ccc(-c4cc(OCC(C)(C)O)cn5ncc(C#N)c45)cn3)CC2)c1] | N-(1-(5-(3-cyano-6-(2-hydroxy-2-methylpropoxy)pyrazolo[1,5-a]pyridin-4-yl)pyridin-2-yl)-4-methylpiperidin-4-yl)-4,6-dimethylpicolinamide | 554.3 (M + H) |
| 104 | 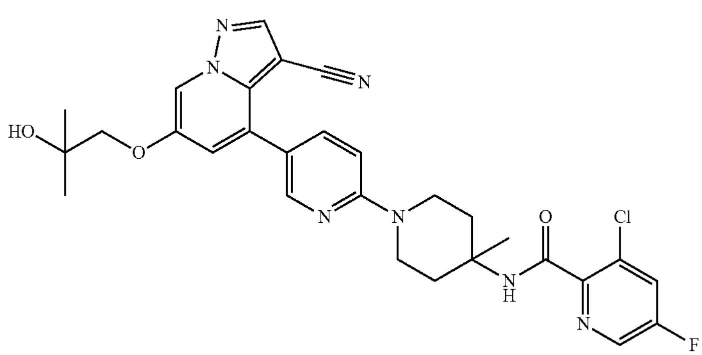 [SMILES: CC(C)(O)COc1cc(-c2ccc(N3CCC(C)(NC(=O)c4ncc(F)cc4Cl)CC3)nc2)c2c(C#N)cnn2c1] | 3-chloro-N-(1-(5-(3-cyano-6-(2-hydroxy-2-methylpropoxy)pyrazolo[1,5-a]pyridin-4-yl)pyridin-2-yl)-4-methylpiperidin-4-yl)-5-fluoropicolinamide | 578.2 (M + H) |

Example 105

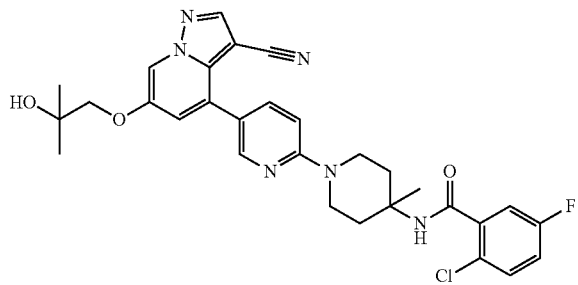 [SMILES: CC(C)(O)COc1cc(-c2ccc(N3CCC(C)(NC(=O)c4cc(F)ccc4Cl)CC3)nc2)c2c(C#N)cnn2c1]

2-chloro-N-(1-(5-(3-cyano-6-(2-hydroxy-2-methylpropoxy)pyrazolo[1,5-a]pyridin-4-yl)pyridin-2-yl)-4-methylpiperidin-4-yl)-5-fluorobenzamide A mixture of 4-(6-(4-amino-4-methylpiperidin-1-yl)pyridin-3-yl)-6-(2-hydroxy-2-methylpropoxy)pyrazolo[1,5-a]pyridine-3-carbonitrile dihydrochloride (Intermediate P48; 56 mg, 0.11 mmol), HATU (47.5 mg, 0.125 mmol), and 2-Chloro-5-fluorobenzoic acid (39.6 mg, 0.23 mmol) in DMSO (1.13 mL, 0.1 M) was treated with DIEA (0.06 mL, 0.125 mmol) and then stirred for 4 h at ambient temperature. The reaction mixture was concentrated in vacuo. The reaction mixture was diluted with EtOAc and washed with water. The organic extracts were washed with brine, then dried over anhydrous $Na_2SO_{4(s)}$, filtered and concentrated in vacuo. The residue was suspended in 60:40 ACN:water containing 2% TFA. The solution was purified directly by C18 reverse phase chromatography (5-95% ACN in water with 0.1% TFA as the gradient eluent) to afford the title compound as the TFA salt. The TFA salt was treated with saturated $NaHCO_{3(aq)}$ and extracted with DCM. The combined organic extracts were washed with brine, then dried over anhydrous $Na_2SO_{4(s)}$, filtered and concentrated in vacuo to afford the title compound (34.3 mg, 52% yield). MS (apci) m/z=577.2 (M+H).

The compounds in Table V were prepared using a similar method to that described for the synthesis of Example 105, replacing 2-Chloro-5-fluorobenzoic acid with the appropriate carboxylic acid. Reactions were monitored for completion by LCMS, and reaction durations were adjusted accordingly. Title compounds were cleanly isolated following chromatographic purification using an appropriate gradient eluent (and if necessary converted to the free base).

TABLE V

| Ex. # | Structure | Chemical Name | LCMS m/z |
|---|---|---|---|
| 106 | | N-(1-(5-(3-cyano-6-(2-hydroxy-2-methylpropoxy)pyrazolo[1,5-a]pyridin-4-yl)pyridin-2-yl)-4-methylpiperidin-4-yl)-5-fluoro-2-methoxybenzamide | 573.3 (M + H) |
| 107 | | N-(1-(5-(3-cyano-6-(2-hydroxy-2-methylpropoxy)pyrazolo[1,5-a]pyridin-4-yl)pyridin-2-yl)-4-methylpiperidin-4-yl)-3-fluoro-6-methoxypicolinamide | 574.2 (M + H) |

Example 108

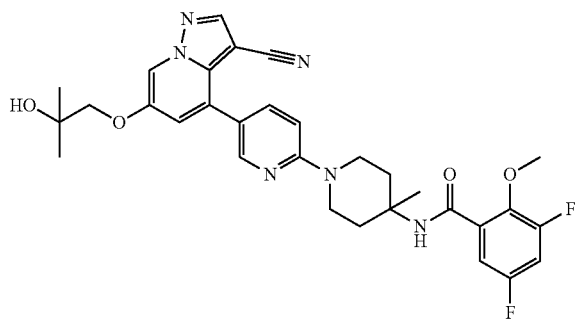 [SMILES: COc1c(F)cc(F)cc1C(=O)NC1(C)CCN(c2ccc(-c3cc(OCC(C)(C)O)cn4ncc(C#N)c34)cn2)CC1]

N-(1-(5-(3-cyano-6-(2-hydroxy-2-methylpropoxy)
pyrazolo[1,5-a]pyridin-4-yl)pyridin-2-yl)-4-methyl-
piperidin-4-yl)-3,5-difluoro-2-methoxybenzamide A mixture of 4-(6-(4-amino-4-methylpiperidin-1-yl)pyridin-3-yl)-6-(2-hydroxy-2-methylpropoxy)pyrazolo[1,5-a]pyridine-3-carbonitrile dihydrochloride (Intermediate P48; 52 mg, 0.105 mmol), HATU (44.1 mg, 0.116 mmol), 3,5-difluoro-2-methoxybenzoic acid (19.8 mg, 0.105 mmol) in DMSO (1.05 mL, 0.1 M) was treated with DIEA (0.09 mL, 0.527 mmol) and then stirred for 2 h at ambient temperature. The reaction mixture was diluted with EtOAc and washed with water. The organic extracts were washed with brine, then dried over anhydrous $Na_2SO_{4(s)}$, filtered and concentrated in vacuo. The residue was suspended in 60:40 ACN:water containing 2% TFA. The solution was purified directly by C18 reverse phase chromatography (5-95% ACN in water with 0.1% TFA as the gradient eluent) to afford the title compound as the TFA salt. The TFA salt was treated with saturated $NaHCO_{3(aq)}$ and extracted with DCM. The combined organic extracts were washed with brine, then dried over anhydrous $Na_2SO_{4(s)}$, filtered and concentrated in vacuo to afford the title compound (41.6 mg, 66.8% yield). MS (apci) m/z=591.3 (M+H).

Example 109

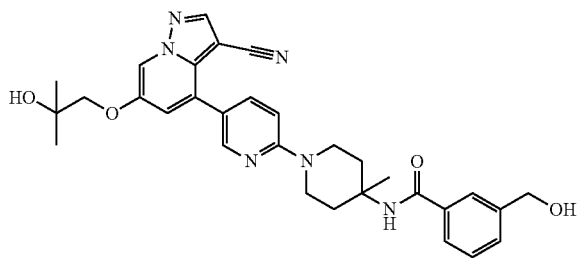 [SMILES: CC(C)(O)COc1cc(-c2ccc(N3CCC(C)(NC(=O)c4cccc(CO)c4)CC3)nc2)c2c(C#N)cnn2c1]

N-(1-(5-(3-cyano-6-(2-hydroxy-2-methylpropoxy)
pyrazolo[1,5-a]pyridin-4-yl)pyridin-2-yl)-4-methyl-
piperidin-4-yl)-3-(hydroxymethyl)benzamide Prepared using a similar method to that described for the synthesis of Example 108, replacing 3,5-difluoro-2-methoxybenzoic acid with the appropriate carboxylic acid. The reaction was monitored for completion by LCMS, and reaction duration was adjusted accordingly. The title compound was cleanly isolated following chromatographic purification using an appropriate gradient eluent (and if necessary converted to the free base). MS (apci) m/z=555.3 (M+H).

Example 110

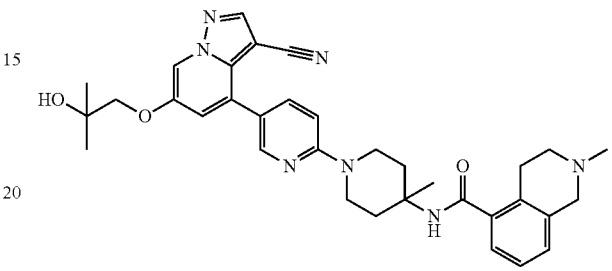

N-(1-(5-(3-cyano-6-(2-hydroxy-2-methylpropoxy)
pyrazolo[1,5-a]pyridin-4-yl)pyridin-2-yl)-4-methyl-
piperidin-4-yl)-2-methyl-1,2,3,4-tetrahydroisoquinoline-5-carboxamide Step 1: Preparation of tert-butyl 5-((1-(5-(3-cyano-6-(2-hydroxy-2-methylpropoxy)pyrazolo[1,5-a]pyridin-4-yl)pyridin-2-yl)-4-methylpiperidin-4-yl)carbamoyl)-3,4-dihydroisoquinoline-2(1H)-carboxylate A mixture of 4-(6-(4-amino-4-methylpiperidin-1-yl)pyridin-3-yl)-6-(2-hydroxy-2-methylpropoxy)pyrazolo[1,5-a]pyridine-3-carbonitrile dihydrochloride (Intermediate P48; 50 mg, 0.10 mmol), HATU (42 mg, 0.11 mmol), 2-(tert-butoxycarbonyl)-1,2,3,4-tetrahydroisoquinoline-5-carboxylic acid (56 mg, 0.20 mmol) in DMSO (1.0 mL, 0.1 M) was treated with DIEA (0.09 mL, 0.51 mmol) and then stirred for 2 h at ambient temperature. The reaction mixture was concentrated in vacuo. The reaction mixture was diluted with EtOAc and washed with water. The organic extracts were washed with brine, then dried over anhydrous $Na_2SO_{4(s)}$, filtered and concentrated in vacuo. The residue was purified by silica chromatography (0.5-9% MeOH in DCM with 0.05-0.9% $NH_4OH$ as the gradient eluent) to afford the title compound (63 mg, 91% yield) in sufficient purity for step 2. MS (apci) m/z=680.4 (M+H)

Step 2: Preparation of N-(1-(5-(3-cyano-6-(2-hydroxy-2-methylpropoxy)pyrazolo[1,5-a]pyridin-4-yl)pyridin-2-yl)-4-methylpiperidin-4-yl)-1,2,3,4-tetrahydroisoquinoline-5-carboxamide Tert-butyl 5-((1-(5-(3-cyano-6-(2-hydroxy-2-methylpropoxy)pyrazolo[1,5-a]pyridin-4-yl)pyridin-2-yl)-4-methylpiperidin-4-yl)carbamoyl)-3,4-dihydroisoquinoline-2(1H)-carboxylate (62 mg, 0.091 mmol) in DCM (0.46 mL) was treated with TFA (0.46 mL, 0.68 mmol) and stirred at ambient temperature for 15 minutes. The reaction was concentrated in vacuo and resuspended in 10 mL DCM and passed through a Pl-HCO₃ resin to free-base product. Plug was washed with 10 mL DCM. Solution was concentrated in vacuo to afford the title compound (53 mg, 100% yield) in sufficient purity for step 3. MS (apci) m/z=580.3 (M+H)

Step 3: Preparation of N-(1-(5-(3-cyano-6-(2-hydroxy-2-methylpropoxy)pyrazolo[1,5-a]pyridin-4-yl)pyridin-2-yl)-4-methylpiperidin-4-yl)-2-methyl-1,2,3,4-tetrahydroisoquinoline-5-carboxamide N-(1-(5-(3-cyano-6-(2-hydroxy-2-methylpropoxy)pyrazolo[1,5-a]pyridin-4-yl)pyridin-2-yl)-4-methylpiperidin-4-yl)-1,2,3,4-tetrahydroisoquinoline-5-carboxamide (53 mg, 0.091 mmol) in DMA (0.9 mL, 0.1M) was treated with sodium triacetoxyhydroborate (194 mg, 0.914 mmol) followed by formaldehyde (127 μL, 0.457 mmol). The reaction was stirred at ambient temperature for 30 min. The reaction mixture was diluted with EtOAc and washed with water. The organic extracts were washed with brine, then dried over anhydrous Na$_2$SO$_{4(s)}$, filtered and concentrated in vacuo. An additional aqueous extraction was performed using 20 mL 4:1 DCM:IPA, organics were dried with anhydrous Na$_2$SO$_{4(s)}$, filtered and concentrated in vacuo. The residue was suspended in 60:40 ACN:water containing 2% TFA. The solution was purified directly by C18 reverse phase chromatography (5-95% ACN in water with 0.1% TFA as the gradient eluent) to afford the title compound as the TFA salt. The TFA salt was treated with saturated NaHCO$_{3(aq)}$ and extracted with 4:1DCM:IPA. The combined organic extracts were washed with brine, then dried over anhydrous Na$_2$SO$_{4(s)}$, filtered and concentrated in vacuo to afford the title compound (41.6 mg, 66.8% yield). MS (apci) m/z=594.3 (M+H).

Example 111

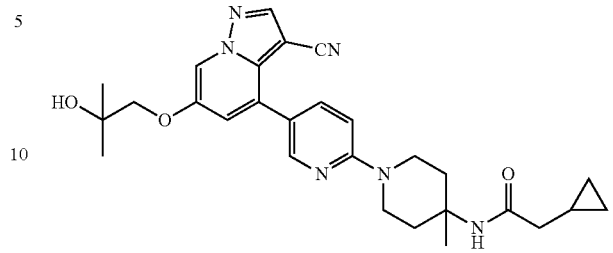

N-(1-(5-(3-cyano-6-(2-hydroxy-2-methylpropoxy)pyrazolo[1,5-a]pyridin-4-yl)pyridin-2-yl)-4-methylpiperidin-4-yl)-2-cyclopropylacetamide A mixture of 4-(6-(4-amino-4-methylpiperidin-1-yl)pyridin-3-yl)-6-(2-hydroxy-2-methylpropoxy)pyrazolo[1,5-a]pyridine-3-carbonitrile (Intermediate P46; 21 mg, 0.05 mmol), HATU (23 mg, 0.06 mmol), Cyclopropylacetic acid (5 mg, 0.05 mmol) in DCM (100 L) was treated with DIEA (35 μL, 0.2 mmol) and then stirred for 18 h at ambient temperature. The reaction mixture was diluted with DCM and washed with water. The organic extracts were washed with brine, then dried over anhydrous Na$_2$SO$_{4(s)}$, filtered and concentrated in vacuo. The residue was purified by silica chromatography (50-100% EtOAc in Hexanes then 0-20% MeOH in EtOAc as the gradient eluent) to cleanly provide the title compound (17 mg, 67.5% yield) MS (apci) m/z=503.30 (M+H).

The compounds in Table W were prepared using a similar method to that described for the synthesis of Example 111, replacing cyclopropylacetic acid with the appropriate carboxylic acid. Reactions were monitored for completion by LCMS, and reaction durations were adjusted accordingly. Title compounds were cleanly isolated following chromatographic purification using an appropriate gradient eluent (and if necessary converted to the free base).

TABLE W

| Ex. # | Structure | Chemical Name | LCMS m/z |
|---|---|---|---|
| 112 | 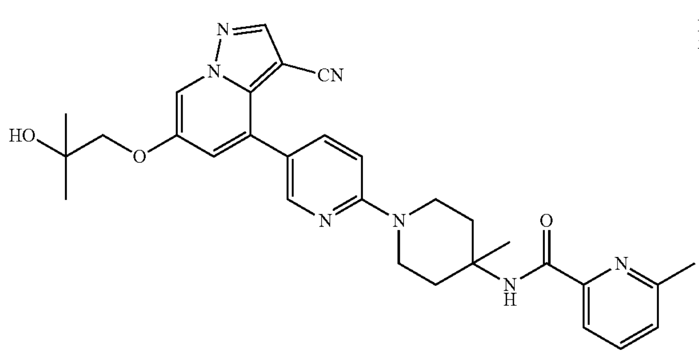 | N-(1-(5-(3-cyano-6-(2-hydroxy-2-methylpropoxy)pyrazolo[1,5-a]pyridin-4-yl)pyridin-2-yl)-4-methylpiperidin-4-yl)-6-methylpicolinamide | 540.30 (M + H) |

TABLE W-continued

| Ex. # | Structure | Chemical Name | LCMS m/z |
|---|---|---|---|
| 113 | 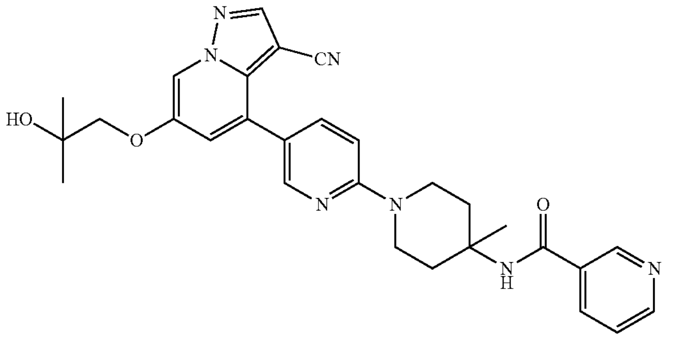 [SMILES: CC(C)(O)COc1cc(-c2ccc(N3CCC(C)(NC(=O)c4cccnc4)CC3)nc2)c2c(C#N)cnn2c1] | N-(1-(5-(3-cyano-6-(2-hydroxy-2-methylpropoxy)pyrazolo[1,5-a]pyridin-4-yl)pyridin-2-yl)-4-methylpiperidin-4-yl)nicotinamide | 526.25 (M + H) |
| 114 | 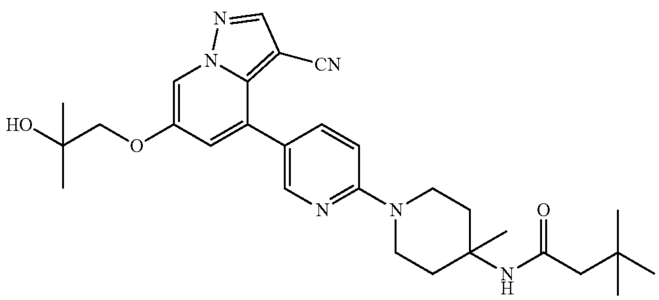 [SMILES: CC(C)(C)CC(=O)NC1(C)CCN(c2ccc(-c3cc(OCC(C)(C)O)cn4ncc(C#N)c34)cn2)CC1] | N-(1-(5-(3-cyano-6-(2-hydroxy-2-methylpropoxy)pyrazolo[1,5-a]pyridin-4-yl)pyridin-2-yl)-4-methylpiperidin-4-yl)-3,3-dimethylbutanamide | 519.30 (M + H) |
| 115 | 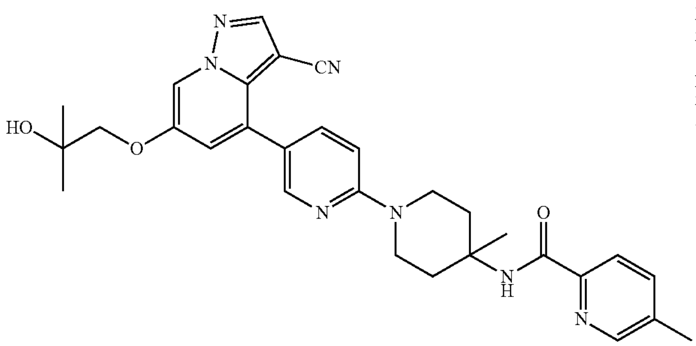 [SMILES: Cc1ccc(C(=O)NC2(C)CCN(c3ccc(-c4cc(OCC(C)(C)O)cn5ncc(C#N)c45)cn3)CC2)nc1] | N-(1-(5-(3-cyano-6-(2-hydroxy-2-methylpropoxy)pyrazolo[1,5-a]pyridin-4-yl)pyridin-2-yl)-4-methylpiperidin-4-yl)-5-methylpicolinamide | 540.30 (M + H) |

Example 116

N-(1-(5-(3-cyano-6-(2-hydroxy-2-methylpropoxy)pyrazolo[1,5-a]pyridin-4-yl)pyridin-2-yl)-4-methylpiperidin-4-yl)propionamide

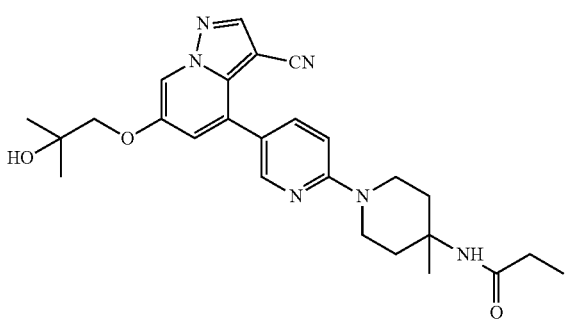 [SMILES: CCC(=O)NC1(C)CCN(c2ccc(-c3cc(OCC(C)(C)O)cn4ncc(C#N)c34)cn2)CC1]

A mixture of 4-(6-(4-amino-4-methylpiperidin-1-yl)pyridin-3-yl)-6-(2-hydroxy-2-methylpropoxy)pyrazolo[1,5-a]pyridine-3-carbonitrile (Intermediate P46; 21.3 mg, 0.051 mmol), HATU (21 mg, 0.055 mmol), propionic acid (3.4 μL, 0.046 mmol) in DCM (92 μL) was treated with DIEA (32 μL, 0.18 mmol) and then stirred for 18 h at ambient temperature. The reaction mixture was diluted with DCM and washed with water. The organic extracts were washed with brine, then dried over anhydrous $Na_2SO_{4(s)}$, filtered and concentrated in vacuo. The residue was purified by silica chromatography (50-100% EtOAc in Hexanes then 0-20% MeOH in EtOAc as the gradient eluent) to cleanly provide the title compound (17.5 mg, 79.7% yield) MS (apci) m/z=477.25 (M+H).

The compounds in Table X were prepared using a similar method to that described for the synthesis of Example 116, replacing propionic acid with the appropriate carboxylic acid. Reactions were monitored for completion by LCMS, and reaction durations were adjusted accordingly. Title compounds were cleanly isolated following chromatographic purification using an appropriate gradient eluent (and if necessary converted to the free base).

N-(1-(5-(3-cyano-6-(2-hydroxy-2-methylpropoxy)pyrazolo[1,5-a]pyridin-4-yl)pyridin-2-yl)-4-methylpiperidin-4-yl)-4-methylpicolinamide 2,2,2-trifluoroacetate A mixture of 4-(6-(4-amino-4-methylpiperidin-1-yl)pyridin-3-yl)-6-(2-hydroxy-2-methylpropoxy)pyrazolo[1,5-a]pyridine-3-carbonitrile (Intermediate P46; 20 mg, 0.048

TABLE X

| Ex. # | Structure | Chemical Name | LCMS m/z |
|---|---|---|---|
| 117 | 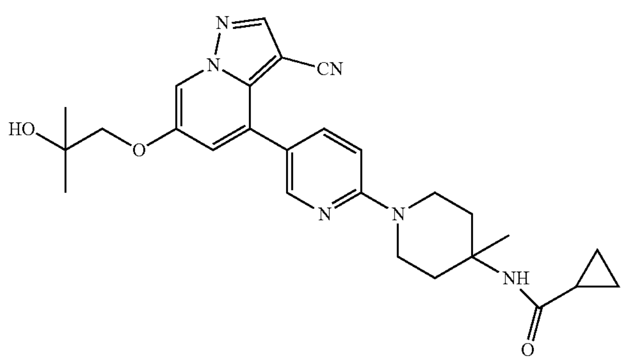 [SMILES: CC(C)(O)COc1cc(-c2ccc(N3CCC(C)(NC(=O)C4CC4)CC3)nc2)c2c(C#N)cnn2c1] | N-(1-(5-(3-cyano-6-(2-hydroxy-2-methylpropoxy)pyrazolo[1,5-a]pyridin-4-yl)pyridin-2-yl)-4-methylpiperidin-4-yl)cyclopropanecarboxamide | 489.30 (M + H) |
| 118 | 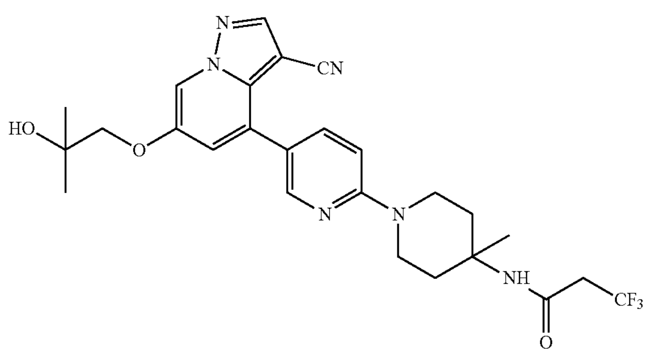 [SMILES: CC(C)(O)COc1cc(-c2ccc(N3CCC(C)(NC(=O)CC(F)(F)F)CC3)nc2)c2c(C#N)cnn2c1] | N-(1-(5-(3-cyano-6-(2-hydroxy-2-methylpropoxy)pyrazolo[1,5-a]pyridin-4-yl)pyridin-2-yl)-4-methylpiperidin-4-yl)-3,3,3-trifluoropropanamide | 531.20 (M + H) |

Example 119

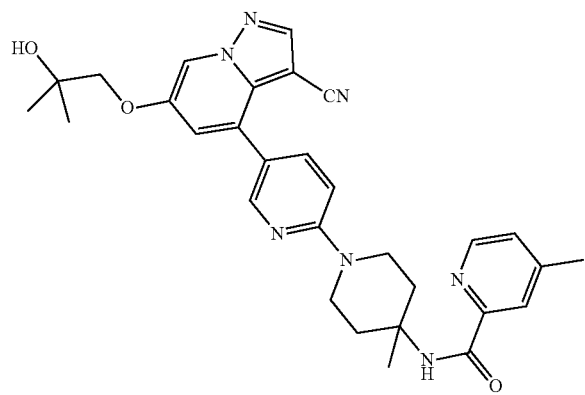 [SMILES: Cc1ccnc(C(=O)NC2(C)CCN(c3ccc(-c4cc(OCC(C)(C)O)cn5ncc(C#N)c45)cn3)CC2)c1]

mmol), HATU (54 mg, 0.14 mmol), 4-methylpicolinic acid (6.52 mg, 0.048 mmol) in DCM (238 μL) was treated with DIEA (33 μL, 0.19 mmol) and then stirred for 1 h at ambient temperature. The reaction mixture was filtered to remove solids, then the filtrate was concentrated in vacuo. The residue was purified by C18 reverse phase chromatography (5-95% ACN in water with 0.1% TFA as the gradient eluent) to afford the title compound as the TFA salt (14.2 mg, 55.3% yield). MS (apci) m/z=540.3 (M+H).

The compounds in Table Y were prepared using a similar method to that described for the synthesis of Example 119, replacing 4-methylpicolinic acid with the appropriate carboxylic acid. Reactions were monitored for completion by LCMS, and reaction durations were adjusted accordingly. Title compounds were cleanly isolated following chromatographic purification using an appropriate gradient eluent.

TABLE Y

| Ex. # | Structure | Chemical Name | LCMS m/z |
|---|---|---|---|
| 120 | 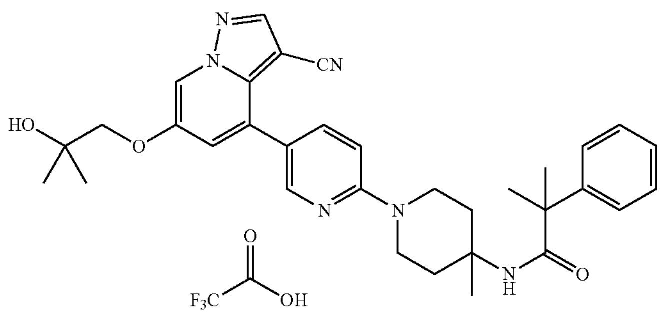 | N-(1-(5-(3-cyano-6-(2-hydroxy-2-methylpropoxy)pyrazolo[1,5-a]pyridin-4-yl)pyridin-2-yl)-4-methylpiperidin-4-yl)-2-methyl-2-phenylpropanamide 2,2,2-trifluoroacetate | 567.3 (M + H) |
| 121 | 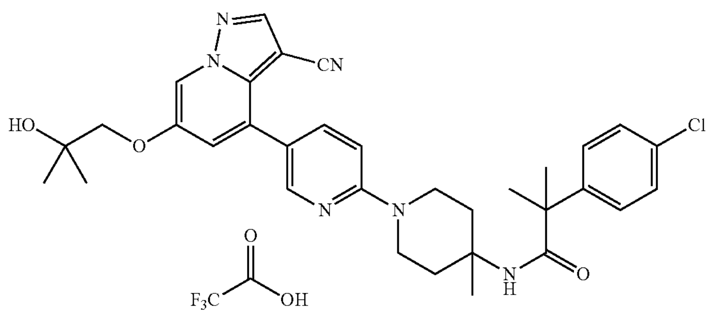 | 2-(4-chlorophenyl)-N-(1-(5-(3-cyano-6-(2-hydroxy-2-methylpropoxy)pyrazolo[1,5-a]pyridin-4-yl)pyridin-2-yl)-4-methylpiperidin-4-yl)-2-methylpropanamide 2,2,2-trifluoroacetate | 601.3 (M + H) |

Example 122

N-(1-(5-(3-cyano-6-(2-hydroxy-2-methylpropoxy)pyrazolo[1,5-a]pyridin-4-yl)pyridin-2-yl)-4-methylpiperidin-4-yl)-6-methylnicotinamide

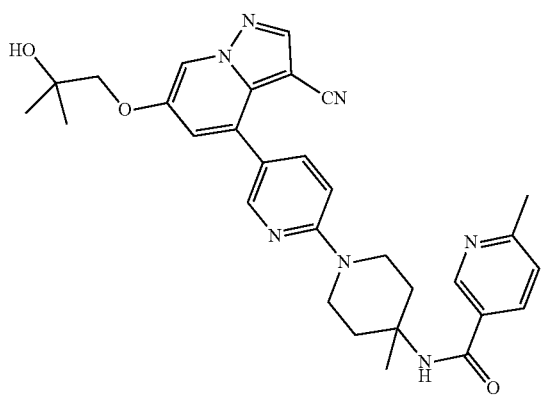 [SMILES: Cc1ccc(C(=O)NC2(C)CCN(c3ccc(-c4cc(OCC(C)(C)O)cn5ncc(C#N)c45)cn3)CC2)cn1]

A mixture of 4-(6-(4-amino-4-methylpiperidin-1-yl)pyridin-3-yl)-6-(2-hydroxy-2-methylpropoxy)pyrazolo[1,5-a]pyridine-3-carbonitrile (Intermediate P46; 20 mg, 0.048 mmol), HATU (54 mg, 0.14 mmol), 6-methylnicotinic acid (6.52 mg, 0.048 mmol) in DCM (238 μL) was treated with DIEA (33 μL, 0.19 mmol) and then stirred for 4 h at ambient temperature. The reaction was purified directly by silica chromatography (1-10% MeOH in CHCl₃ with 0.1-1% NH₄OH as the gradient eluent) to cleanly provide the title compound (10 mg, 39% yield) MS (apci) m/z=540.3 (M+H).

The compounds in Table Z were prepared using a similar method to that described for the synthesis of Example 122, replacing 6-methylnicotinic acid with the appropriate carboxylic acid. Reactions were monitored for completion by LCMS, and reaction durations were adjusted accordingly. Title compounds were cleanly isolated following chromatographic purification using an appropriate gradient eluent (and if necessary converted to the free base).

TABLE Z

| Ex. # | Structure | Chemical Name | LCMS m/z |
|---|---|---|---|
| 123 | 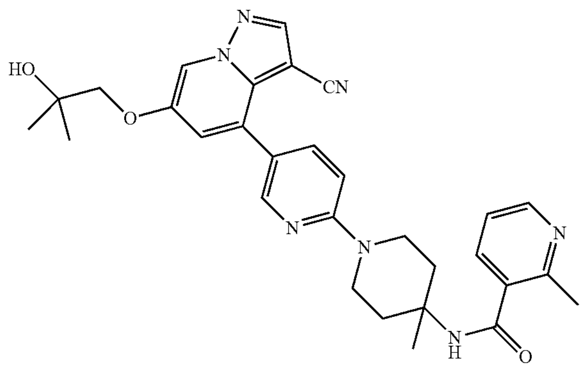 [SMILES: Cc1ncccc1C(=O)NC1(C)CCN(c2ccc(-c3cc(OCC(C)(C)O)cn4ncc(C#N)c34)cn2)CC1] | N-(1-(5-(3-cyano-6-(2-hydroxy-2-methylpropoxy)pyrazolo[1,5-a]pyridin-4-yl)pyridin-2-yl)-4-methylpiperidin-4-yl)-2-methylnicotinamide | 540.3 (M + H) |
| 124 | 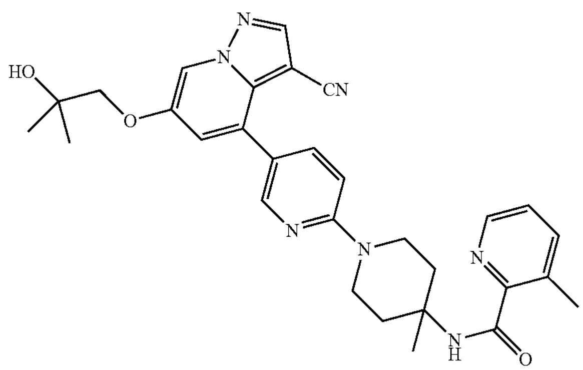 [SMILES: Cc1cccnc1C(=O)NC1(C)CCN(c2ccc(-c3cc(OCC(C)(C)O)cn4ncc(C#N)c34)cn2)CC1] | N-(1-(5-(3-cyano-6-(2-hydroxy-2-methylpropoxy)pyrazolo[1,5-a]pyridin-4-yl)pyridin-2-yl)-4-methylpiperidin-4-yl)-3-methylpicolinamide | 540.3 (M + H) |
| 125 | 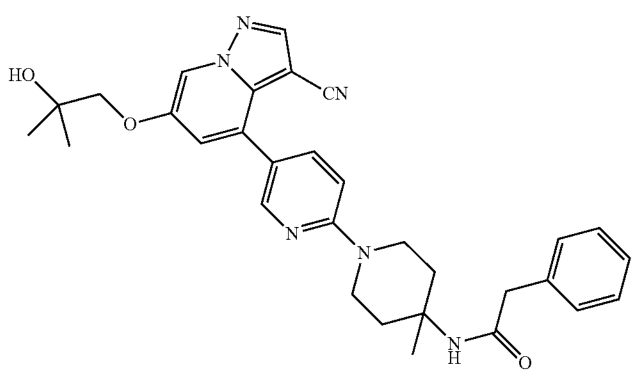 [SMILES: CC(C)(O)COc1cc(-c2ccc(N3CCC(C)(NC(=O)Cc4ccccc4)CC3)nc2)c2c(C#N)cnn2c1] | N-(1-(5-(3-cyano-6-(2-hydroxy-2-methylpropoxy)pyrazolo[1,5-a]pyridin-4-yl)pyridin-2-yl)-4-methylpiperidin-4-yl)-2-phenylacetamide | 539.3 (M + H) |
| 126 | 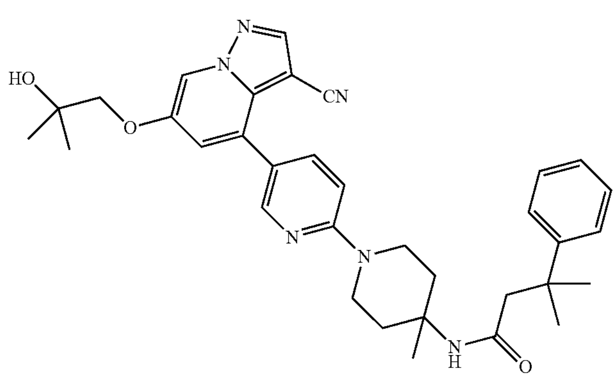 [SMILES: CC(C)(O)COc1cc(-c2ccc(N3CCC(C)(NC(=O)CC(C)(C)c4ccccc4)CC3)nc2)c2c(C#N)cnn2c1] | N-(1-(5-(3-cyano-6-(2-hydroxy-2-methylpropoxy)pyrazolo[1,5-a]pyridin-4-yl)pyridin-2-yl)-4-methylpiperidin-4-yl)-3-methyl-3-phenylbutanamide | 581.3 (M + H) |

TABLE Z-continued

| Ex. # | Structure | Chemical Name | LCMS m/z |
|---|---|---|---|
| 127 | 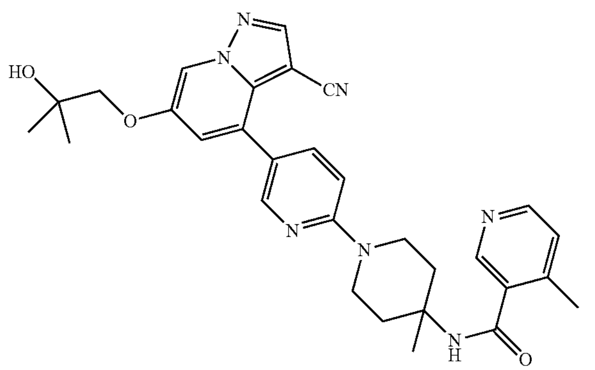 [SMILES: Cc1ccncc1C(=O)NC1(C)CCN(c2ccc(-c3cc(OCC(C)(C)O)cn4ncc(C#N)c34)cn2)CC1] | N-(1-(5-(3-cyano-6-(2-hydroxy-2-methylpropoxy)pyrazolo[1,5-a]pyridin-4-yl)pyridin-2-yl)-4-methylpiperidin-4-yl)-4-methylnicotinamide | 540.3 (M + H) |
| 128 | 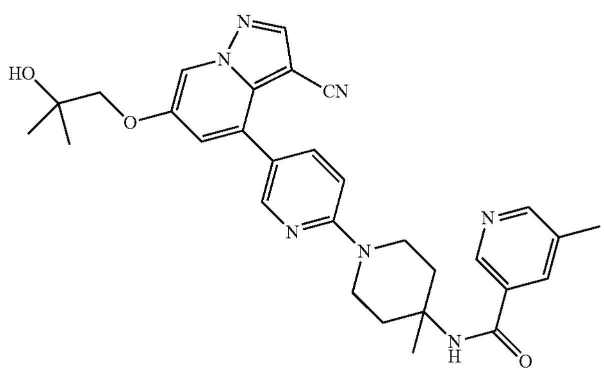 [SMILES: Cc1cncc(C(=O)NC2(C)CCN(c3ccc(-c4cc(OCC(C)(C)O)cn5ncc(C#N)c45)cn3)CC2)c1] | N-(1-(5-(3-cyano-6-(2-hydroxy-2-methylpropoxy)pyrazolo[1,5-a]pyridin-4-yl)pyridin-2-yl)-4-methylpiperidin-4-yl)-5-methylnicotinamide | 540.3 (M + H) |

Example 129

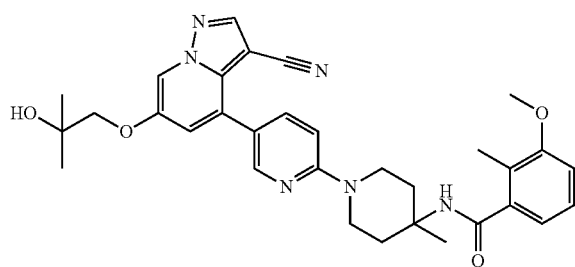 [SMILES: COc1cccc(C(=O)NC2(C)CCN(c3ccc(-c4cc(OCC(C)(C)O)cn5ncc(C#N)c45)cn3)CC2)c1C]

N-(1-(5-(3-cyano-6-(2-hydroxy-2-methylpropoxy)pyrazolo[1,5-a]pyridin-4-yl)pyridin-2-yl)-4-methylpiperidin-4-yl)-3-methoxy-2-methylbenzamide A mixture of 4-(6-(4-amino-4-methylpiperidin-1-yl)pyridin-3-yl)-6-(2-hydroxy-2-methylpropoxy)pyrazolo[1,5-a]pyridine-3-carbonitrile (Intermediate P46; 50 mg, 0.12 mmol), HATU (54 mg, 0.14 mmol), 3-methoxy-2-methylbenzoic acid (24 mg, 0.14 mmol) in DMSO (793 µL) was treated with DIEA (25 µL, 0.14 mmol) and then stirred for 18 h at ambient temperature. The reaction mixture was diluted with EtOAc and washed with water. The organic extracts were washed with brine, then dried over anhydrous $Na_2SO_{4(s)}$, filtered and concentrated in vacuo. The solution was purified directly by C18 reverse phase chromatography (5-95% ACN in water with 0.1% TFA as the gradient eluent) to afford the title compound as the TFA salt. The TFA salt was treated with saturated $NaHCO_{3(aq)}$ and extracted with DCM. The combined organic extracts were washed with brine, then dried over anhydrous $Na_2SO_{4(s)}$, filtered and concentrated in vacuo to afford the title compound (25 mg, 37% yield). MS (apci) m/z=569.3 (M+H).

The compounds in Table AA were prepared using a similar method to that described for the synthesis of Example 129, replacing 3-methoxy-2-methylbenzoic acid with the appropriate carboxylic acid. Reactions were monitored for completion by LCMS, and reaction durations were adjusted accordingly. Title compounds were cleanly isolated following chromatographic purification using an appropriate gradient eluent (and if necessary converted to the free base).

TABLE AA

| Ex. # | Structure | Chemical Name | MS (apci) m/z |
|---|---|---|---|
| 130 | 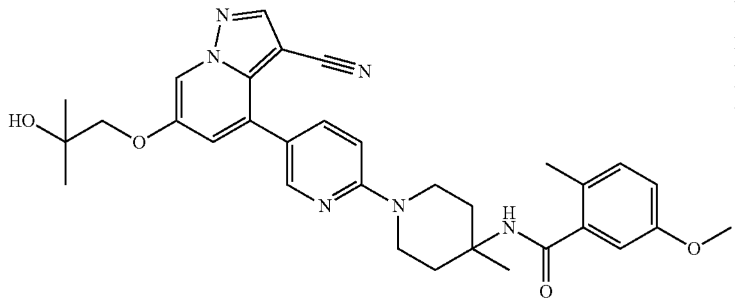 | N-(1-(5-(3-cyano-6-(2-hydroxy-2-methylpropoxy)pyrazolo[1,5-a]pyridin-4-yl)pyridin-2-yl)-4-methylpiperidin-4-yl)-5-methoxy-2-methylbenzamide | 569.3 (M + H) |
| 131 | 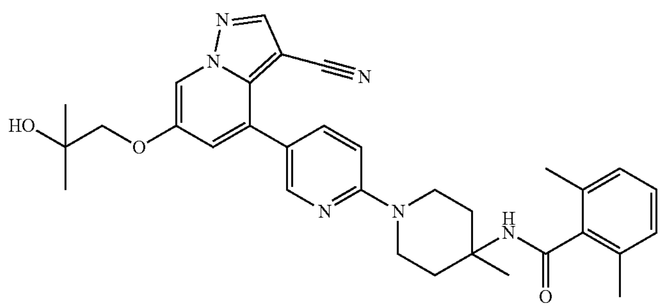 [SMILES: Cc1cccc(C)c1C(=O)NC1(C)CCN(c2ccc(-c3cc(OCC(C)(C)O)cn4ncc(C#N)c34)cn2)CC1] | N-(1-(5-(3-cyano-6-(2-hydroxy-2-methylpropoxy)pyrazolo[1,5-a]pyridin-4-yl)pyridin-2-yl)-4-methylpiperidin-4-yl)-2,6-dimethylbenzamide | 553.3 (M + H) |

Example 132

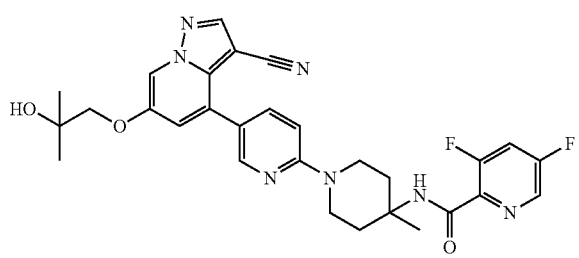 [SMILES: CC(C)(O)COc1cc(-c2ccc(N3CCC(C)(NC(=O)c4ncc(F)cc4F)CC3)nc2)c2c(C#N)cnn2c1]

N-(1-(5-(3-cyano-6-(2-hydroxy-2-methylpropoxy)pyrazolo[1,5-a]pyridin-4-yl)pyridin-2-yl)-4-methylpiperidin-4-yl)-3,5-difluoropicolinamide A mixture of 4-(6-(4-amino-4-methylpiperidin-1-yl)pyridin-3-yl)-6-(2-hydroxy-2-methylpropoxy)pyrazolo[1,5-a]pyridine-3-carbonitrile dihydrochloride (Intermediate P48; 50 mg, 0.10 mmol), HATU (59 mg, 0.16 mmol), 3,5-difluoropicolinic acid (25 mg, 0.16 mmol) in DMSO (793 µL) was treated with DIEA (73 µL, 0.42 mmol) and then stirred for 18 h at ambient temperature. The reaction mixture was diluted with EtOAc and washed with water. The organic extracts were washed with brine, then dried over anhydrous $Na_2SO_{4(s)}$, filtered and concentrated in vacuo. The solution was purified directly by C18 reverse phase chromatography (5-95% ACN in water with 0.1% TFA as the gradient eluent) to afford the title compound as the TFA salt. The TFA salt was treated with saturated $NaHCO_{3(aq)}$ and extracted with DCM. The combined organic extracts were washed with brine, then dried over anhydrous $Na_2SO_{4(s)}$, filtered and concentrated in vacuo to afford the title compound (29.7 mg, 44.5% yield). MS (apci) m/z=562.2 (M+H).

The compounds in Table BB were prepared using a similar method to that described for the synthesis of Example 132, replacing 3,5-difluoropicolinic acid with the appropriate carboxylic acid. Reactions were monitored for completion by LCMS, and reaction durations were adjusted accordingly. Title compounds were cleanly isolated following chromatographic purification using an appropriate gradient eluent (and if necessary converted to the free base).

TABLE BB

| Ex. # | Structure | Chemical Name | LCMS m/z |
|---|---|---|---|
| 133 | 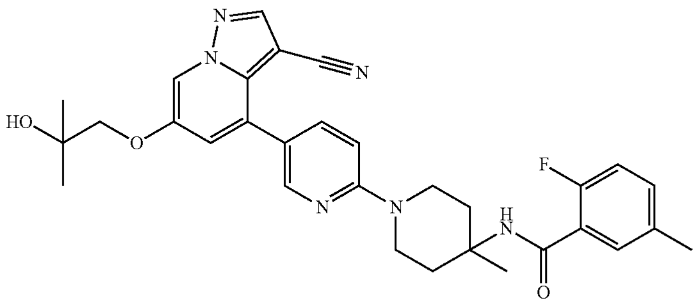 [SMILES: Cc1ccc(F)c(C(=O)NC2(C)CCN(c3ccc(-c4cc(OCC(C)(C)O)cn5ncc(C#N)c45)cn3)CC2)c1] | N-(1-(5-(3-cyano-6-(2-hydroxy-2-methylpropoxy)pyrazolo[1,5-a]pyridin-4-yl)pyridin-2-yl)-4-methylpiperidin-4-yl)-2-fluoro-5-methylbenzamide | 557.3 (M + H) |
| 134 | 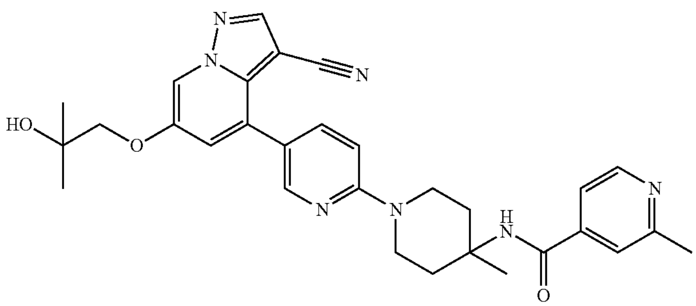 [SMILES: Cc1cc(C(=O)NC2(C)CCN(c3ccc(-c4cc(OCC(C)(C)O)cn5ncc(C#N)c45)cn3)CC2)ccn1] | N-(1-(5-(3-cyano-6-(2-hydroxy-2-methylpropoxy)pyrazolo[1,5-a]pyridin-4-yl)pyridin-2-yl)-4-methylpiperidin-4-yl)-2-methylisonicotinamide | 540.3 (M + H) |
| 135 | 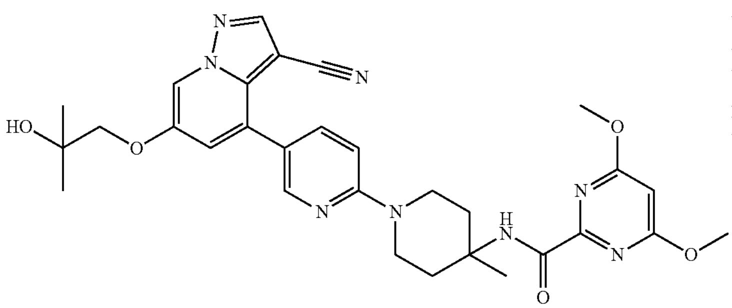 [SMILES: COc1cc(OC)nc(C(=O)NC2(C)CCN(c3ccc(-c4cc(OCC(C)(C)O)cn5ncc(C#N)c45)cn3)CC2)n1] | N-(1-(5-(3-cyano-6-(2-hydroxy-2-methylpropoxy)pyrazolo[1,5-a]pyridin-4-yl)pyridin-2-yl)-4-methylpiperidin-4-yl)-4,6-dimethoxypyrimidine-2-carboxamide | 587.3 (M + H) |
| 136 | 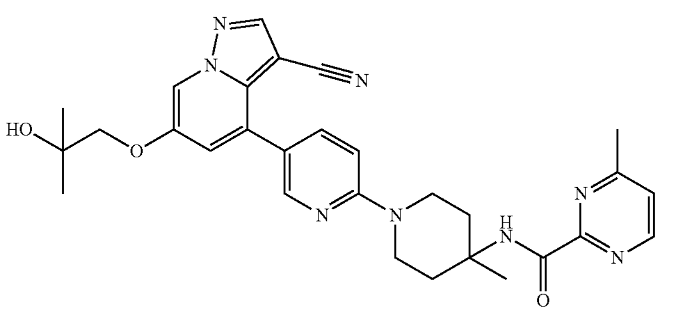 [SMILES: Cc1ccnc(C(=O)NC2(C)CCN(c3ccc(-c4cc(OCC(C)(C)O)cn5ncc(C#N)c45)cn3)CC2)n1] | N-(1-(5-(3-cyano-6-(2-hydroxy-2-methylpropoxy)pyrazolo[1,5-a]pyridin-4-yl)pyridin-2-yl)-4-methylpiperidin-4-yl)-4-methylpyrimidine-2-carboxamide | 541.3 (M + H) |
| 137 | 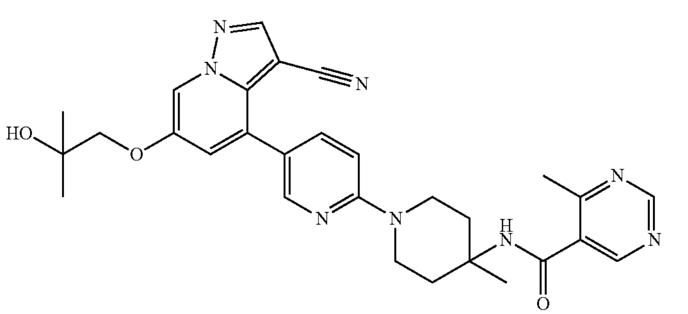 [SMILES: Cc1ncncc1C(=O)NC1(C)CCN(c2ccc(-c3cc(OCC(C)(C)O)cn4ncc(C#N)c34)cn2)CC1] | N-(1-(5-(3-cyano-6-(2-hydroxy-2-methylpropoxy)pyrazolo[1,5-a]pyridin-4-yl)pyridin-2-yl)-4-methylpiperidin-4-yl)-4-methylpyrimidine-5-carboxamide | 541.3 (M + H) |

TABLE BB-continued

| Ex. # | Chemical Name | LCMS m/z |
|---|---|---|
| 138 | N-(1-(5-(3-cyano-6-(2-hydroxy-2-methylpropoxy)pyrazolo[1,5-a]pyridin-4-yl)pyridin-2-yl)-4-methylpiperidin-4-yl)-6-methyl-4-oxo-1,4-dihydropyridine-2-carboxamide | 556.3 |
| 139 | 2-chloro-N-(1-(5-(3-cyano-6-(2-hydroxy-2-methylpropoxy)pyrazolo[1,5-a]pyridin-4-yl)pyridin-2-yl)-4-methylpiperidin-4-yl)-3,5-difluorobenzamide | 595.2 (M + H) |
| 140 | 5-chloro-N-(1-(5-(3-cyano-6-(2-hydroxy-2-methylpropoxy)pyrazolo[1,5-a]pyridin-4-yl)pyridin-2-yl)-4-methylpiperidin-4-yl)-2-methylisonicotinamide | 561.3 (M + H) |
| 141 | N-(1-(5-(3-cyano-6-(2-hydroxy-2-methylpropoxy)pyrazolo[1,5-a]pyridin-4-yl)pyridin-2-yl)-4-methylpiperidin-4-yl)-4,6-dimethylpyrimidine-2-carboxamide | 555.3 (M + H) |
| 142 | N-(1-(5-(3-cyano-6-(2-hydroxy-2-methylpropoxy)pyrazolo[1,5-a]pyridin-4-yl)pyridin-2-yl)-4-methylpiperidin-4-yl)-3-((dimethylamino)methyl)benzamide | 582.3 (M + H) |

Example 143

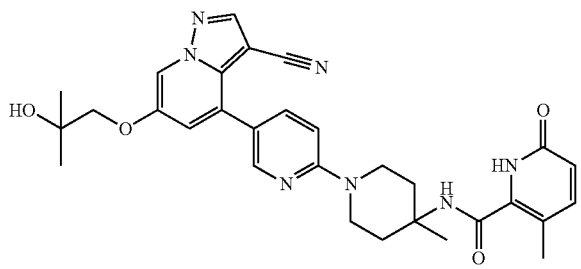 [SMILES: Cc1ccc(=O)[nH]c1C(=O)NC1(C)CCN(c2ccc(-c3cc(OCC(C)(C)O)cn4ncc(C#N)c34)cn2)CC1]

N-(1-(5-(3-cyano-6-(2-hydroxy-2-methylpropoxy)
pyrazolo[1,5-a]pyridin-4-yl)pyridin-2-yl)-4-methyl-
piperidin-4-yl)-3-methyl-6-oxo-1,6-dihydropyridine-
2-carboxamide A mixture of 4-(6-(4-amino-4-methylpiperidin-1-yl)pyridin-3-yl)-6-(2-hydroxy-2-methylpropoxy)pyrazolo[1,5-a]pyridine-3-carbonitrile dihydrochloride (Intermediate P48; 50 mg, 0.10 mmol), HATU (90 mg, 0.238 mmol), 6-hydroxy-3-methylpicolinic acid (36 mg, 0.238 mmol) in DMSO (793 µL) was treated with DIEA (93 µL, 0.535 mmol) and then stirred for 18 h at ambient temperature. The reaction mixture was diluted with EtOAc and washed with water. The organic extracts were washed with brine, then dried over anhydrous $Na_2SO_{4(s)}$, filtered and concentrated in vacuo. The solution was purified directly by C18 reverse phase chromatography (5-95% ACN in water with 0.1% TFA as the gradient eluent) to afford the title compound as the TFA salt. The TFA salt was treated with saturated $NaHCO_{3(aq)}$ and extracted with DCM. The combined organic extracts were washed with brine, then dried over anhydrous $Na_2SO_{4(s)}$, filtered and concentrated in vacuo to afford the title compound (10 mg, 15.1% yield). MS (apci) m/z=556.3 (M+H).

The compounds in Table CC were prepared using a similar method to that described for the synthesis of Example 143, replacing 6-Hydroxy-3-methylpicolinic acid with the appropriate carboxylic acid. Reactions were monitored for completion by LCMS, and reaction durations were adjusted accordingly. Title compounds were cleanly isolated following chromatographic purification using an appropriate gradient eluent (and if necessary converted to the free base).

TABLE CC

| Ex. # | Structure | Chemical Name | LCMS m/z |
|---|---|---|---|
| 144 | 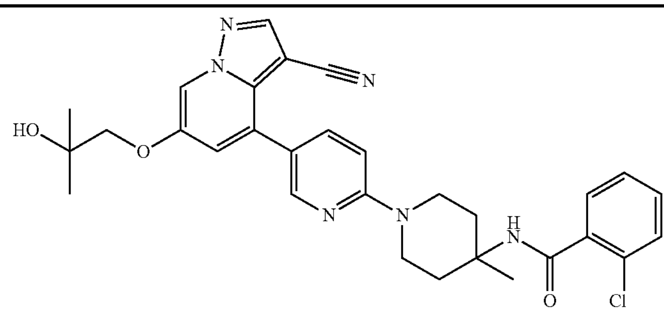 | 2-chloro-N-(1-(5-(3-cyano-6-(2-hydroxy-2-methylpropoxy)pyrazolo[1,5-a]pyridin-4-yl)pyridin-2-yl)-4-methylpiperidin-4-yl)benzamide | 559.2 (M + H) |
| 145 | 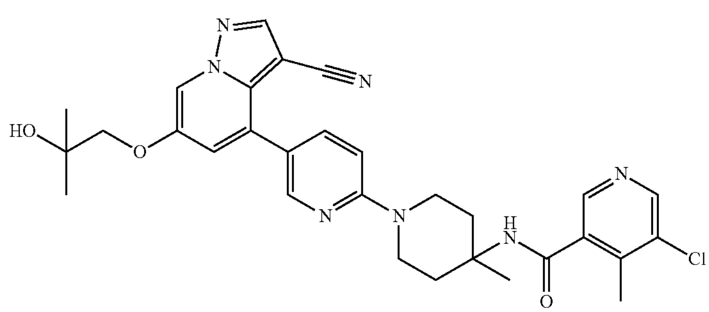 [SMILES: Cc1c(Cl)cncc1C(=O)NC1(C)CCN(c2ccc(-c3cc(OCC(C)(C)O)cn4ncc(C#N)c34)cn2)CC1] | 5-chloro-N-(1-(5-(3-cyano-6-(2-hydroxy-2-methylpropoxy)pyrazolo[1,5-a]pyridin-4-yl)pyridin-2-yl)-4-methylpiperidin-4-yl)-4-methylnicotinamide | 574.3 (M + H) |
| 146 | 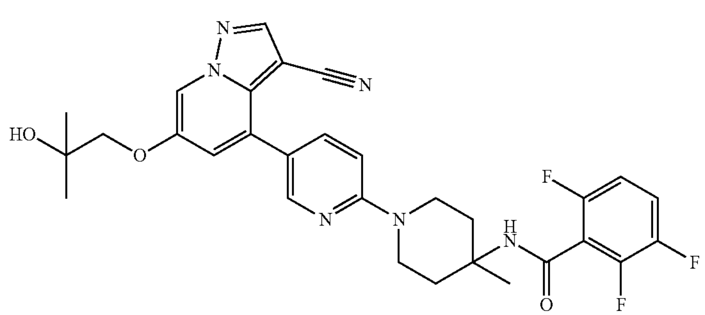 [SMILES: CC(C)(O)COc1cc(-c2ccc(N3CCC(C)(NC(=O)c4c(F)ccc(F)c4F)CC3)nc2)c2c(C#N)cnn2c1] | N-(1-(5-(3-cyano-6-(2-hydroxy-2-methylpropoxy)pyrazolo[1,5-a]pyridin-4-yl)pyridin-2-yl)-4-methylpiperidin-4-yl)-2,3,6-trifluorobenzamide | 579.3 (M + H) |

Example 147

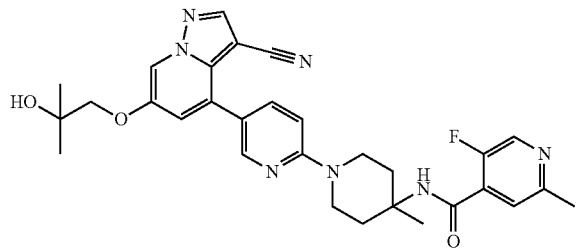 [SMILES: Cc1cc(C(=O)NC2(C)CCN(c3ccc(-c4cc(OCC(C)(C)O)cn5ncc(C#N)c45)cn3)CC2)c(F)cn1]

N-(1-(5-(3-cyano-6-(2-hydroxy-2-methylpropoxy)
pyrazolo[1,5-a]pyridin-4-yl)pyridin-2-yl)-4-methyl-
piperidin-4-yl)-5-fluoro-2-methylisonicotinamide A mixture of 4-(6-(4-amino-4-methylpiperidin-1-yl)pyridin-3-yl)-6-(2-hydroxy-2-methylpropoxy)pyrazolo[1,5-a]pyridine-3-carbonitrile dihydrochloride (Intermediate P48; 50 mg, 0.10 mmol), HATU (90 mg, 0.238 mmol), 5-Fluoro-2-methylisonicotinic acid (18 mg, 0.12 mmol) in DMSO (793 µL) was treated with DIEA (93 µL, 0.535 mmol) and then stirred for 18 h at ambient temperature. The reaction mixture was diluted with EtOAc and washed with water. The organic extracts were washed with brine, then dried over anhydrous $Na_2SO_{4(s)}$, filtered and concentrated in vacuo. The reaction was purified directly by silica chromatography (1-10% MeOH in DCM as the gradient eluent) to cleanly provide the title compound (41.9 mg, 63.2% yield) MS (apci) m/z=558.3 (M+H).

Example 148

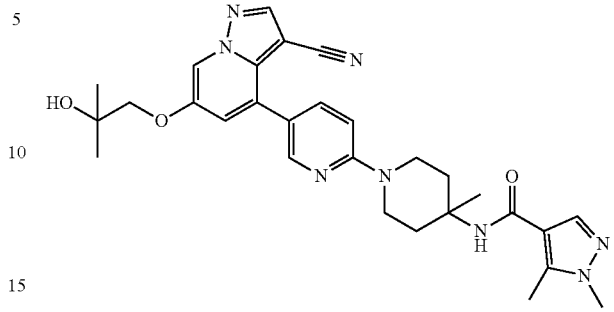

N-(1-(5-(3-cyano-6-(2-hydroxy-2-methylpropoxy)
pyrazolo[1,5-a]pyridin-4-yl)pyridin-2-yl)-4-methyl-
piperidin-4-yl)-1,5-dimethyl-1H-pyrazole-4-carbox-
amide A mixture of 4-(6-(4-amino-4-methylpiperidin-1-yl)pyridin-3-yl)-6-(2-hydroxy-2-methylpropoxy)pyrazolo[1,5-a]pyridine-3-carbonitrile dihydrochloride (Intermediate P46; 50 mg, 0.12 mmol), HATU (54 mg, 0.14 mmol), 1,5-dimethyl-1H-pyrazole-4-carboxylic acid (25 mg, 0.18 mmol) in DCM (2.4 mL) was treated with DIEA (104 µL, 0.59 mmol) and then stirred for 16 h at ambient temperature. The reaction mixture was diluted with DCM and washed with saturated $NaHCO_3$. The organic extracts were dried over anhydrous $Na_2SO_{4(s)}$, filtered and concentrated in vacuo. The reaction was purified by silica chromatography (1-10% MeOH in EtOAc as the gradient eluent) to cleanly provide the title compound (41.9 mg, 63.2% yield) MS (apci) m/z=543.20 (M+H).

The compounds in Table DD were prepared using a similar method to that described for the synthesis of Example 148, replacing 1,5-dimethyl-1H-pyrazole-4-carboxylic acid with the appropriate carboxylic acid. Reactions were monitored for completion by LCMS, and reaction durations were adjusted accordingly. Title compounds were cleanly isolated following chromatographic purification using an appropriate gradient eluent (and if necessary converted to the free base).

TABLE DD

| Ex. # | Structure | Chemical Name | LCMS m/z |
|---|---|---|---|
| 149 | 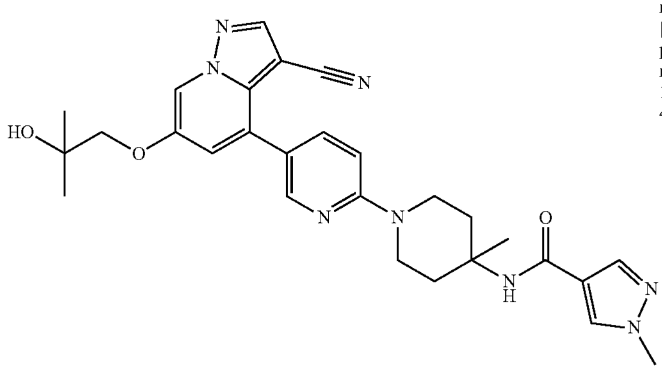 | N-(1-(5-(3-cyano-6-(2-hydroxy-2-methylpropoxy)pyrazolo[1,5-a]pyridin-4-yl)pyridin-2-yl)-4-methylpiperidin-4-yl)-1-methyl-1H-pyrazole-4-carboxamide | 528.6 (M + H) |

TABLE DD-continued

| Ex. # | Structure | Chemical Name | LCMS m/z |
|---|---|---|---|
| 150 | 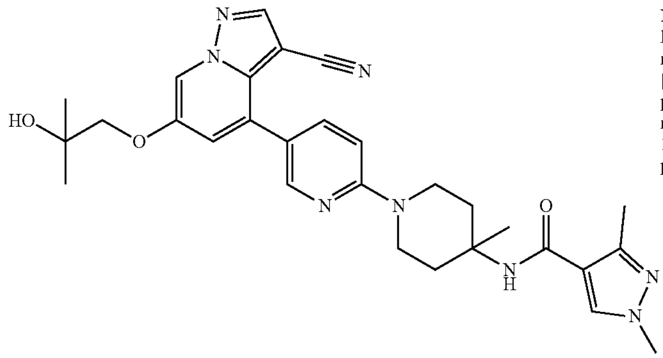 | N-(1-(5-(3-cyano-6-(2-hydroxy-2-methylpropoxy)pyrazolo[1,5-a]pyridin-4-yl)pyridin-2-yl)-4-methylpiperidin-4-yl)-1,3-dimethyl-1H-pyrazole-4-carboxamide | 543.2 (M + H) |

Example 151

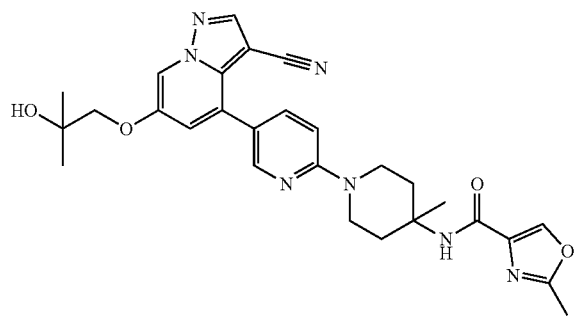 [SMILES: Cc1nc(C(=O)NC2(C)CCN(c3ccc(-c4cc(OCC(C)(C)O)cn5ncc(C#N)c45)cn3)CC2)co1]

N-(1-(5-(3-cyano-6-(2-hydroxy-2-methylpropoxy)pyrazolo[1,5-a]pyridin-4-yl)pyridin-2-yl)-4-methyl-piperidin-4-yl)-2-methyloxazole-4-carboxamide A mixture of 4-(6-(4-amino-4-methylpiperidin-1-yl)pyridin-3-yl)-6-(2-hydroxy-2-methylpropoxy)pyrazolo[1,5-a]pyridine-3-carbonitrile dihydrochloride (Intermediate P46; 50 mg, 0.12 mmol), HATU (54 mg, 0.14 mmol), 2-methyloxazole-4-carboxylic acid (18 mg, 0.14 mmol) in DCM (2.4 mL) was treated with DIEA (104 µL, 0.59 mmol) and then stirred for 20 h at ambient temperature. The reaction mixture was diluted with DCM (5 mL) and washed with 0.1M NaOH. The organic extracts were dried over anhydrous $Na_2SO_{4(s)}$, filtered and concentrated in vacuo. The residue was triturated with MTBE to cleanly provide the title compound (15 mg, 23.8% yield) MS (apci) m/z=543.20 (M+H).

The compounds in Table EE were prepared using a similar method to that described for the synthesis of Example 151, replacing 2-methyloxazole-4-carboxylic acid with the appropriate carboxylic acid. Reactions were monitored for completion by LCMS, and reaction durations were adjusted accordingly. Title compounds were cleanly isolated following the same a basic workup and trituration purification.

TABLE EE

| Ex. # | Structure | Chemical Name | LCMS m/z |
|---|---|---|---|
| 152 | 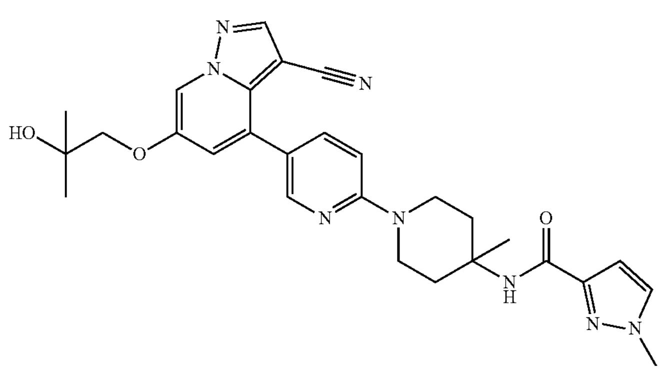 [SMILES: Cn1ccc(C(=O)NC2(C)CCN(c3ccc(-c4cc(OCC(C)(C)O)cn5ncc(C#N)c45)cn3)CC2)n1] | N-(1-(5-(3-cyano-6-(2-hydroxy-2-methylpropoxy)pyrazolo[1,5-a]pyridin-4-yl)pyridin-2-yl)-4-methylpiperidin-4-yl)-1-methyl-1H-pyrazole-3-carboxamide | 528.2 (M + H) |

TABLE EE-continued

| Ex. # | Structure | Chemical Name | LCMS m/z |
|---|---|---|---|
| 153 | 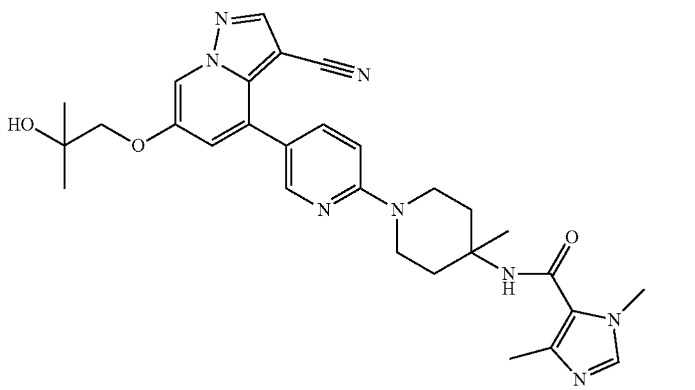 [SMILES: Cc1ncn(C)c1C(=O)NC1(C)CCN(c2ccc(-c3cc(OCC(C)(C)O)cn4ncc(C#N)c34)cn2)CC1] | N-(1-(5-(3-cyano-6-(2-hydroxy-2-methylpropoxy)pyrazolo[1,5-a]pyridin-4-yl)pyridin-2-yl)-4-methylpiperidin-4-yl)-1,4-dimethyl-1H-imidazole-5-carboxamide | 543.20 (M + H) |
| 154 | 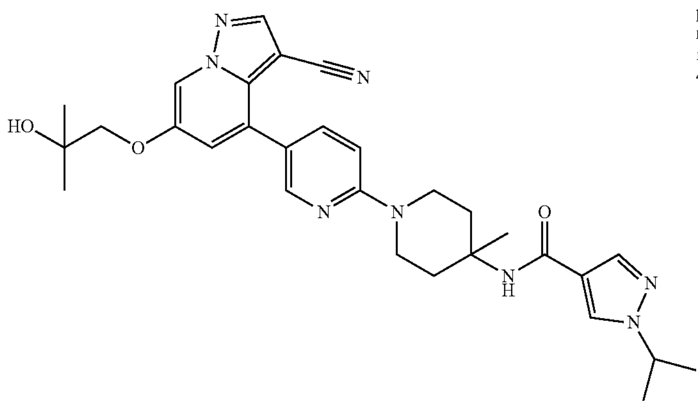 | N-(1-(5-(3-cyano-6-(2-hydroxy-2-methylpropoxy)pyrazolo[1,5-a]pyridin-4-yl)pyridin-2-yl)-4-methylpiperidin-4-yl)-1-isopropyl-1H-pyrazole-4-carboxamide | 557.20 (M + H) |

Example 155

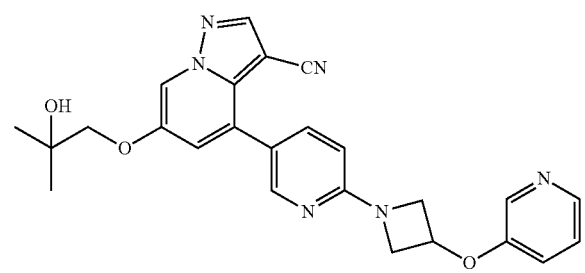 [SMILES: CC(C)(O)COc1cc(-c2ccc(N3CC(Oc4cccnc4)C3)nc2)c2c(C#N)cnn2c1]

6-(2-hydroxy-2-methylpropoxy)-4-(6-(3-(pyridin-3-yloxy)azetidin-1-yl)pyridin-3-yl)pyrazolo[1,5-a]pyridine-3-carbonitrile A mixture of 4-(6-fluoropyridin-3-yl)-6-(2-hydroxy-2-methylpropoxy)pyrazolo[1,5-a]pyridine-3-carbonitrile (Intermediate P42; 30.7 mg, 0.0941 mmol), 3-(azetidin-3-yloxy)pyridine (28.3 mg, 0.188 mmol) and TEA (78.7 µL, 0.564 mmol) in DMA (627 µL) was stirred overnight at 90° C. After cooling to ambient temperature, the reaction mixture was diluted with water and washed with DCM. The organic extracts were washed with brine and dried over anhydrous $Na_2SO_{4(s)}$, filtered and concentrated in vacuo. The residue was purified by C18 reverse phase chromatography (5-95% ACN in water with 0.1% TFA as the gradient eluent) to afford the title compound as the TFA salt. The TFA salt was dissolved in DCM and washed with saturated $Na_2CO_{3(aq)}$. The combined organic extracts were washed with brine, then dried over anhydrous $Na_2SO_{4(s)}$, filtered and concentrated in vacuo to cleanly provide the title compound (17 mg, 39.6% yield). MS (apci) m/z=457.2 (M+H).

The compounds in Table FF were prepared using a similar method to that described for the synthesis of Example 155, replacing 3-(azetidin-3-yloxy)pyridine with the appropriate azetidine nucleophile. Reactions were monitored for completion by LCMS, and reaction durations were adjusted accordingly. Title compounds were cleanly isolated following chromatographic purification using an appropriate gradient eluent (and if necessary converted to the free base).

TABLE FF

| Ex. # | Structure | Chemical Name | LCMS m/z |
|---|---|---|---|
| 156 | 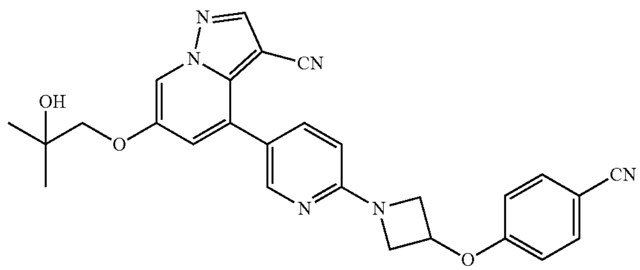 [SMILES: CC(C)(O)COc1cc(-c2ccc(N3CC(Oc4ccc(C#N)cc4)C3)nc2)c2c(C#N)cnn2c1] | 4-(6-(3-(4-cyanophenoxy)azetidin-1-yl)pyridin-3-yl)-6-(2-hydroxy-2-methylpropoxy)pyrazolo[1,5-a]pyridine-3-carbonitrile | 481.1 (M + H) |
| 157 | 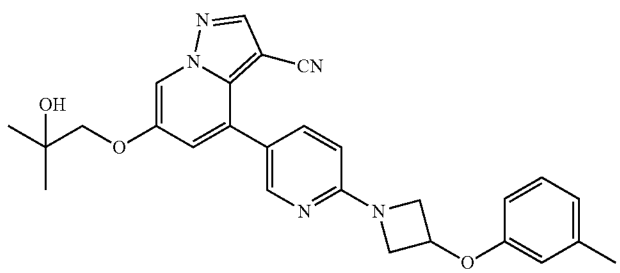 [SMILES: Cc1cccc(OC2CN(c3ccc(-c4cc(OCC(C)(C)O)cn5ncc(C#N)c45)cn3)C2)c1] | 6-(2-hydroxy-2-methylpropoxy)-4-(6-(3-(m-tolyloxy)azetidin-1-yl)pyridin-3-yl)pyrazolo[1,5-a]pyridine-3-carbonitrile | 470.2 (M + H) |
| 158 | 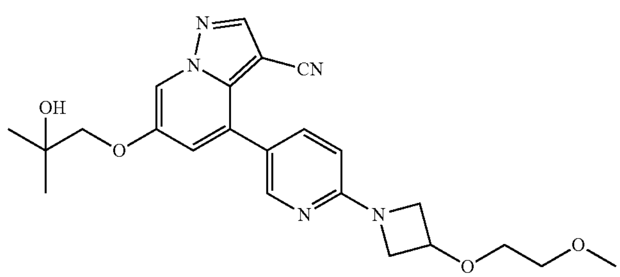 [SMILES: COCCOC1CN(c2ccc(-c3cc(OCC(C)(C)O)cn4ncc(C#N)c34)cn2)C1] | 6-(2-hydroxy-2-methylpropoxy)-4-(6-(3-(2-methoxyethoxy)azetidin-1-yl)pyridin-3-yl)pyrazolo[1,5-a]pyridine-3-carbonitrile | 438.2 (M + H) |
| 159 | 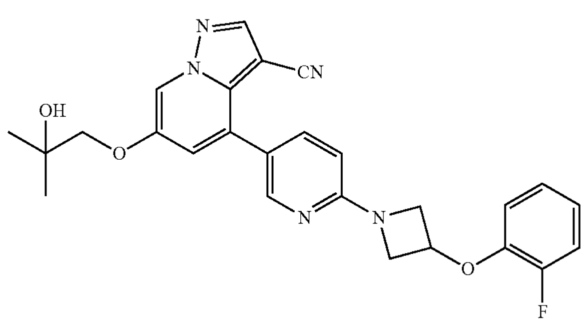 [SMILES: CC(C)(O)COc1cc(-c2ccc(N3CC(Oc4ccccc4F)C3)nc2)c2c(C#N)cnn2c1] | 4-(6-(3-(2-fluorophenoxy)azetidin-1-yl)pyridin-3-yl)-6-(2-hydroxy-2-methylpropoxy)pyrazolo1,5-a]pyridine-3-carbonitrile | 474.1 (M + H) |
| 160 | 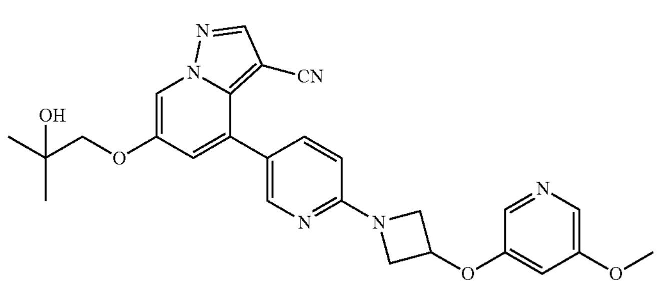 [SMILES: COc1cncc(OC2CN(c3ccc(-c4cc(OCC(C)(C)O)cn5ncc(C#N)c45)cn3)C2)c1] | 6-(2-hydroxy-2-methylpropoxy)-4-(6-(3-((5-methoxypyridin-3-yl)oxy)azetidin-1-yl)pyridin-3-yl)pyrazolo[1,5-a]pyridine-3-carbonitrile | 487.1 (M + H) |

TABLE FF-continued

| Ex. # | Structure | Chemical Name | LCMS m/z |
|---|---|---|---|
| 161 | 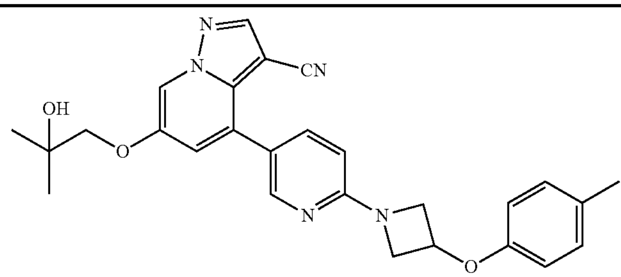 | 6-(2-hydroxy-2-methylpropoxy)-4-(6-(3-(p-tolyloxy)azetidin-1-yl)pyridin-3-yl)pyrazolo[1,5-a]pyridine-3-carbonitrile | 470.2 (M + H) |
| 162 | 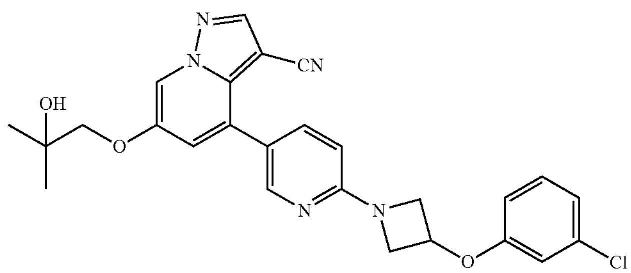 [SMILES: CC(C)(O)COc1cc(-c2ccc(N3CC(Oc4cccc(Cl)c4)C3)nc2)c2c(C#N)cnn2c1] | 4-(6-(3-(3-chlorophenoxy)azetidin-1-yl)pyridin-3-yl)-6-(2-hydroxy-2-methylpropoxy)pyrazolo[1,5-a]pyridine-3-carbonitrile | 490.1 (M + H) |

Example 163

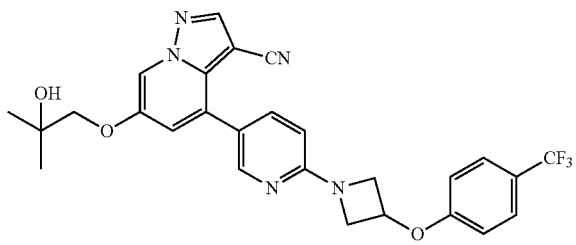 [SMILES: CC(C)(O)COc1cc(-c2ccc(N3CC(Oc4ccc(C(F)(F)F)cc4)C3)nc2)c2c(C#N)cnn2c1]

6-(2-hydroxy-2-methylpropoxy)-4-(6-(3-(4-(trifluoromethyl)phenoxy)azetidin-1-yl)pyridin-3-yl)pyrazolo[1,5-a]pyridine-3-carbonitrile A mixture of 4-(6-fluoropyridin-3-yl)-6-(2-hydroxy-2-methylpropoxy)pyrazolo[1,5-a]pyridine-3-carbonitrile (Intermediate P42; 36.4 mg, 0.112 mmol), 3-(4-(trifluoromethyl)phenoxy)azetidine hydrochloride (70.7 mg, 0.279 mmol) and TEA (93.3 μL, 0.669 mmol) in DMA (372 μL) was stirred overnight at 90° C. After cooling to ambient temperature, the reaction mixture was diluted with water and washed with DCM. The organic extracts were washed with brine and dried over anhydrous $Na_2SO_{4(s)}$, filtered and concentrated in vacuo. The residue was purified by C18 reverse phase chromatography (5-95% ACN in water with 0.1% TFA as the gradient eluent) to afford the title compound as the TFA salt. The TFA salt was dissolved in DCM and washed with saturated $Na_2CO_{3(aq)}$. The combined organic extracts were washed with brine, then dried over anhydrous $Na_2SO_{4(s)}$, filtered and concentrated in vacuo to cleanly provide the title compound (15 mg, 25.7% yield). MS (apci) m/z=524.1 (M+H).

Example 164

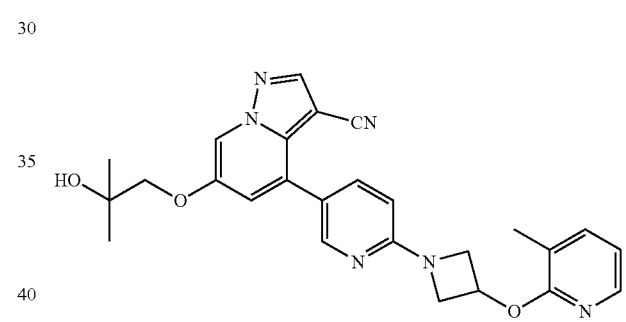

6-(2-hydroxy-2-methylpropoxy)-4-(6-(3-((3-methylpyridin-2-yl)oxy)azetidin-1-yl)pyridin-3-yl)pyrazolo[1,5-a]pyridine-3-carbonitrile A mixture of 4-(6-fluoropyridin-3-yl)-6-(2-hydroxy-2-methylpropoxy)pyrazolo[1,5-a]pyridine-3-carbonitrile (Intermediate P42; 35 mg, 0.107 mmol), 2-(azetidin-3-yloxy)-3-methylpyridine dihydrochloride (76.3 mg, 0.322 mmol) and TEA (117 μL, 0.858 mmol) in DMA (358 μL) was stirred overnight at 105° C. After cooling to ambient temperature, the reaction mixture was diluted with DCM and washed with saturated $Na_2CO_{3(aq)}$. The organic extracts were washed with water. Then the organic extracts were washed with brine and dried over anhydrous $Na_2SO_{4(s)}$, filtered and concentrated in vacuo. The residue was suspended in 60:40 ACN:water containing 2% TFA. The solution was purified directly by C18 reverse phase chromatography (5-95% ACN in water with 0.1% TFA as the gradient eluent) to afford the title compound as the TFA salt. The TFA salt was treated with saturated $NaHCO_{3(aq)}$ and extracted with DCM. The combined organic extracts were washed with brine, then dried over anhydrous $Na_2SO_{4(s)}$, filtered and concentrated in vacuo to afford the title compound (9.4 mg, 18.6% yield). MS (apci) m/z=471.10 (M+H).

The compounds in Table GG were prepared using a similar method to that described for the synthesis of Example 164, replacing 2-(azetidin-3-yloxy)-3-methylpyridine dihydrochloride with the appropriate azetidine nucleophile. Reactions were monitored for completion by LCMS, and reaction durations were adjusted accordingly. Title compounds were cleanly isolated following chromatographic purification using an appropriate gradient eluent (and if necessary converted to the free base).

TABLE GG

| Ex. # | Structure | Chemical Name | LCMS m/z |
|---|---|---|---|
| 165 | 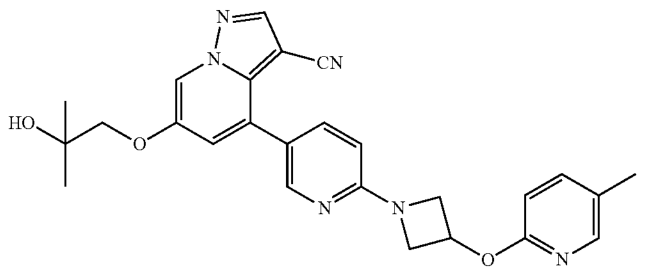 [SMILES: Cc1ccc(OC2CN(c3ccc(-c4cc(OCC(C)(C)O)cn5ncc(C#N)c45)cn3)C2)nc1] | 6-(2-hydroxy-2-methylpropoxy)-4-(6-(3-((5-methylpyridin-2-yl)oxy)azetidin-1-yl)pyridin-3-yl)pyrazolo[1,5-a]pyridine-3-carbonitrile | 471.20 (M + H) |
| 166 | 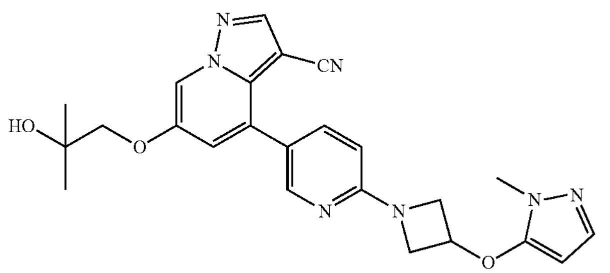 [SMILES: Cn1nccc1OC1CN(c2ccc(-c3cc(OCC(C)(C)O)cn4ncc(C#N)c34)cn2)C1] | 6-(2-hydroxy-2-methylpropoxy)-4-(6-(3-((1-methyl-1H-pyrazol-5-yl)oxy)azetidin-1-yl)pyridin-3-yl)pyrazolo[1,5-a]pyridine-3-carbonitrile | 460.20 (M + H) |
| 167 | 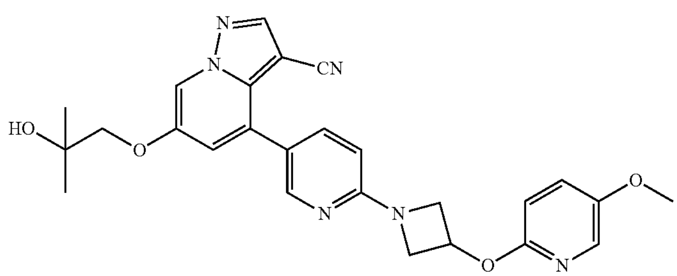 [SMILES: COc1ccc(OC2CN(c3ccc(-c4cc(OCC(C)(C)O)cn5ncc(C#N)c45)cn3)C2)nc1] | 6-(2-hydroxy-2-methylpropoxy)-4-(6-(3-((5-methoxypyridin-2-yl)oxy)azetidin-1-yl)pyridin-3-yl)pyrazolo[1,5-a]pyridine-3-carbonitrile | 487.20 (M + H) |
| 168 | 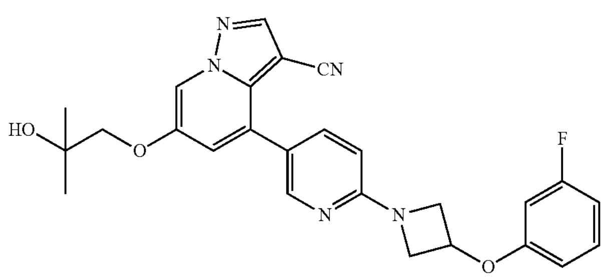 [SMILES: CC(C)(O)COc1cc(-c2ccc(N3CC(Oc4cccc(F)c4)C3)nc2)c2c(C#N)cnn2c1] | 4-(6-(3-(3-fluorophenoxy)azetidin-1-yl)pyridin-3-yl)-6-(2-hydroxy-2-methylpropoxy)pyrazolo[1,5-a]pyridine-3-carbonitrile | 474.20 (M + H) |

Example 169

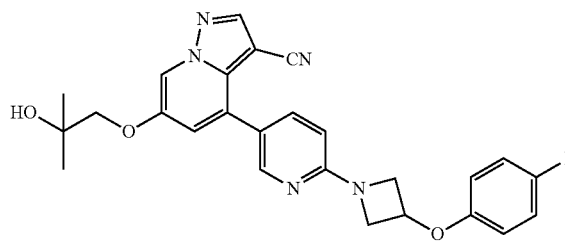

4-(6-(3-(4-fluorophenoxy)azetidin-1-yl)pyridin-3-yl)-6-(2-hydroxy-2-methylpropoxy)pyrazolo[1,5-a]pyridine-3-carbonitrile A mixture of 4-(6-fluoropyridin-3-yl)-6-(2-hydroxy-2-methylpropoxy)pyrazolo[1,5-a]pyridine-3-carbonitrile (Intermediate P42; 36.5 mg, 0.112 mmol), 3-(4-fluorophenoxy)azetidine hydrochloride (68.3 mg, 0.336 mmol) and TEA (91.8 μL, 0.671 mmol) in DMA (358 μL) was stirred overnight at 105° C. After cooling to ambient temperature, the reaction mixture was diluted with DCM and washed with water. Then the organic extracts were washed with brine and dried over anhydrous Na$_2$SO$_{4(s)}$, filtered and concentrated in vacuo. The residue was suspended in 60:40 ACN:water containing 2% TFA. The solution was purified directly by C18 reverse phase chromatography (5-95% ACN in water with 0.1% TFA as the gradient eluent) to afford the title compound as the TFA salt. The TFA salt was treated with saturated NaHCO$_{3(aq)}$ and extracted with DCM. The combined organic extracts were washed with brine, then dried over anhydrous Na$_2$SO$_{4(s)}$, filtered and concentrated in vacuo to afford the title compound (23.5 mg, 44.4% yield). MS (apci) m/z=474.20 (M+H).

Example 170

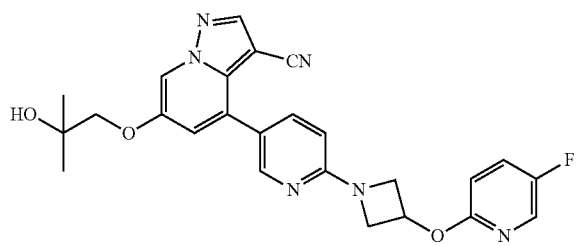 [SMILES: CC(C)(O)COc1cc(-c2ccc(N3CC(Oc4ccc(F)cn4)C3)nc2)c2c(C#N)cnn2c1]

4-(6-(3-((5-fluoropyridin-2-yl)oxy)azetidin-1-yl)pyridin-3-yl)-6-(2-hydroxy-2-methylpropoxy)pyrazolo[1,5-a]pyridine-3-carbonitrile A mixture of 4-(6-fluoropyridin-3-yl)-6-(2-hydroxy-2-methylpropoxy)pyrazolo[1,5-a]pyridine-3-carbonitrile (Intermediate P42; 35 mg, 0.107 mmol), 2-(azetidin-3-yloxy)-5-fluoropyridine dihydrochloride (51.7 mg, 0.215 mmol) and TEA (65.1 μL, 0.644 mmol) in DMA (358 μL) was stirred overnight at 105° C. After cooling to ambient temperature, the reaction mixture was diluted with DCM and washed with water. Then the organic extracts were washed with brine and dried over anhydrous Na$_2$SO$_{4(s)}$, filtered and concentrated in vacuo. The residue was suspended in 60:40 ACN:water containing 2% TFA. The solution was purified directly by C18 reverse phase chromatography (5-95% ACN in water with 0.1% TFA as the gradient eluent) to afford the title compound as the TFA salt. The TFA salt was treated with saturated NaHCO$_{3(aq)}$ and extracted with DCM. The combined organic extracts were washed with brine, then dried over anhydrous Na$_2$SO$_{4(s)}$, filtered and concentrated in vacuo to afford the title compound (8.3 mg, 16.3% yield). MS (apci) m/z=475.20 (M+H).

Example 171

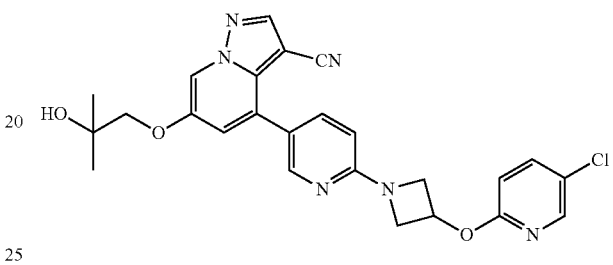

4-(6-(3-((5-chloropyridin-2-yl)oxy)azetidin-1-yl)pyridin-3-yl)-6-(2-hydroxy-2-methylpropoxy)pyrazolo[1,5-a]pyridine-3-carbonitrile A mixture of 4-(6-fluoropyridin-3-yl)-6-(2-hydroxy-2-methylpropoxy)pyrazolo[1,5-a]pyridine-3-carbonitrile (Intermediate P42; 35 mg, 0.107 mmol), 2-(azetidin-3-yloxy)-5-chloropyridine dihydrochloride (94.7 mg, 0.368 mmol) and TEA (117 μL, 0.858 mmol) in DMA (358 μL) was stirred overnight at 105° C. After cooling to ambient temperature, the reaction mixture was diluted with DCM and washed with water. Then the organic extracts were washed with brine, dried over anhydrous Na$_2$SO$_{4(s)}$, filtered and concentrated in vacuo. The residue was suspended in 60:40 ACN:water containing 2% TFA. The solution was purified directly by C18 reverse phase chromatography (5-95% ACN in water with 0.1% TFA as the gradient eluent) to afford the title compound as the TFA salt. The TFA salt was treated with saturated NaHCO$_{3(aq)}$ and extracted with DCM. The combined organic extracts were washed with brine, then dried over anhydrous Na$_2$SO$_{4(s)}$, filtered and concentrated in vacuo to afford the title compound (19.1 mg, 36.3% yield). MS (apci) m/z=491.10 (M+H).

Example 172

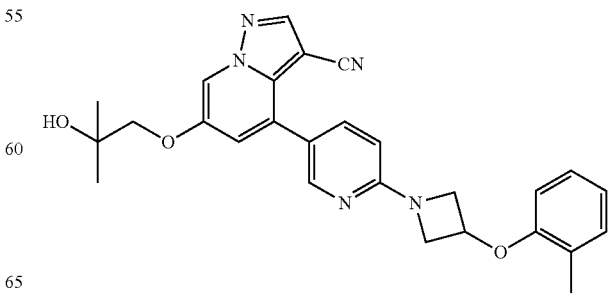

6-(2-hydroxy-2-methylpropoxy)-4-(6-(3-(o-tolyloxy)azetidin-1-yl)pyridin-3-yl)pyrazolo[1,5-a]pyridine-3-carbonitrile A mixture of 4-(6-fluoropyridin-3-yl)-6-(2-hydroxy-2-methylpropoxy)pyrazolo[1,5-a]pyridine-3-carbonitrile (Intermediate P42; 35 mg, 0.107 mmol), 3-(2-Methylphenoxy)azetidine (52.2 mg, 0.322 mmol) and TEA (44 µL, 0.322 mmol) in DMA (358 µL) was stirred overnight at 105° C. After cooling to ambient temperature, the reaction mixture was diluted with DCM and washed with water. Then the organic extracts were washed with brine and dried over anhydrous $Na_2SO_{4(s)}$, filtered and concentrated in vacuo. The reaction was purified by silica chromatography (40-90% EtOAc in Hexanes as the gradient eluent). Impurities remained and product-containing fractions were concentrated in vacuo. The residue was suspended in 60:40 ACN:water containing 2% TFA. The solution was purified directly by C18 reverse phase chromatography (5-95% ACN in water with 0.1% TFA as the gradient eluent) to afford the title compound as the TFA salt. The TFA salt was treated with saturated $NaHCO_{3(aq)}$ and extracted with DCM. The combined organic extracts were washed with brine, then dried over anhydrous $Na_2SO_{4(s)}$, filtered and concentrated in vacuo to afford the title compound (21.6 mg, 42.9% yield). MS (apci) m/z=470.20 (M+H).

Example 173

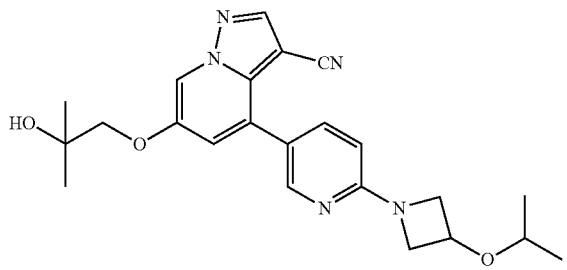 [SMILES: CC(C)OC1CN(c2ccc(-c3cc(OCC(C)(C)O)cn4ncc(C#N)c34)cn2)C1]

6-(2-hydroxy-2-methylpropoxy)-4-(6-(3-isopropoxyazetidin-1-yl)pyridin-3-yl)pyrazolo[1,5-a]pyridine-3-carbonitrile A mixture of 4-(6-fluoropyridin-3-yl)-6-(2-hydroxy-2-methylpropoxy)pyrazolo[1,5-a]pyridine-3-carbonitrile (Intermediate P42; 35 mg, 0.107 mmol), 3-(1-methylethoxy)-azetidine hydrochloride (48.8 mg, 0.322 mmol) and TEA (73 µL, 0.536 mmol) in DMA (358 µL) was stirred overnight at 90° C. After cooling to ambient temperature, the reaction mixture was diluted with DCM and washed with water. The organic extracts were washed with brine and dried over anhydrous $Na_2SO_{4(s)}$, filtered and concentrated in vacuo. The residue was suspended in 60:40 ACN:water containing 2% TFA. The solution was purified directly by C18 reverse phase chromatography (5-95% ACN in water with 0.1% TFA as the gradient eluent) to afford the title compound as the TFA salt. The TFA salt was treated with saturated $NaHCO_{3(aq)}$ and extracted with DCM. The combined organic extracts were washed with brine, then dried over anhydrous $Na_2SO_{4(s)}$, filtered and concentrated in vacuo to afford the title compound (16.8 mg, 37.2% yield). MS (apci) m/z=422.20 (M+H).

The compounds in Table HH were prepared using a similar method to that described for the synthesis of 173, replacing 3-(1-methylethoxy)-azetidine hydrochloride with the appropriate azetidine nucleophile. Reactions were monitored for completion by LCMS, and reaction durations were adjusted accordingly. Title compounds were cleanly isolated following chromatographic purification using an appropriate gradient eluent (and if necessary converted to the free base).

TABLE HH

| Ex. # | Structure | Chemical Name | LCMS m/z |
|---|---|---|---|
| 174 | 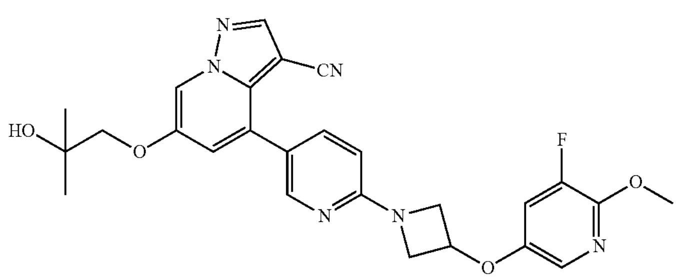 [SMILES: COc1ncc(OC2CN(c3ccc(-c4cc(OCC(C)(C)O)cn5ncc(C#N)c45)cn3)C2)cc1F] | 4-(6-(3-((5-fluoro-6-methoxypyridin-3-yl)oxy)azetidin-1-yl)pyridin-3-yl)-6-(2-hydroxy-2-methylpropoxy)pyrazolo[1,5-a]pyridine-3-carbonitrile | 505.20 (M + H) |
| 175 | 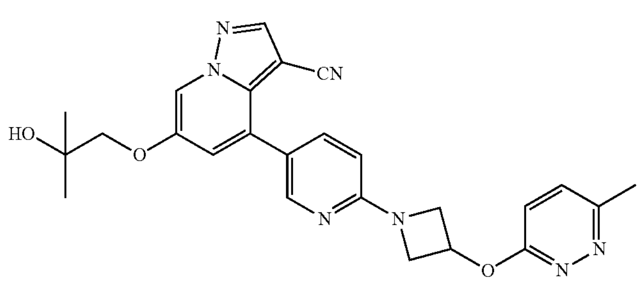 [SMILES: Cc1ccc(OC2CN(c3ccc(-c4cc(OCC(C)(C)O)cn5ncc(C#N)c45)cn3)C2)nn1] | 6-(2-hydroxy-2-methylpropoxy)-4-(6-(3-((6-methylpyridazin-3-yl)oxy)azetidin-1-yl)pyridin-3-yl)pyrazolo[1,5-a]pyridine-3-carbonitrile | 472.20 (M + H) |

Example 176

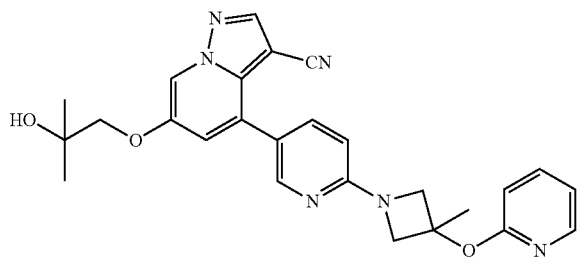 [SMILES: CC(C)(O)COc1cc(-c2ccc(N3CC(C)(Oc4ccccn4)C3)nc2)c2c(C#N)cnn2c1]

6-(2-hydroxy-2-methylpropoxy)-4-(6-(3-methyl-3-(pyridin-2-yloxy)azetidin-1-yl)pyridin-3-yl)pyrazolo[1,5-a]pyridine-3-carbonitrile A mixture of 4-(6-fluoropyridin-3-yl)-6-(2-hydroxy-2-methylpropoxy)pyrazolo[1,5-a]pyridine-3-carbonitrile (Intermediate P42; 76.1 mg, 0.233 mmol), 2-((3-methylazetidin-3-yl)oxy)pyridine (95 mg, 0.579 mmol) and TEA (159 µL, 1.17 mmol) in DMA (777 µL) was stirred overnight at 105° C. After cooling to ambient temperature, the reaction mixture was diluted with DCM and washed with water. The organic extracts were washed with brine and dried over anhydrous Na$_2$SO$_{4(s)}$, filtered and concentrated in vacuo. The residue was suspended in 60:40 ACN:water containing 2% TFA. The solution was purified directly by C18 reverse phase chromatography (5-95% ACN in water with 0.1% TFA as the gradient eluent) to afford the title compound as the TFA salt. The TFA salt was treated with saturated NaHCO$_{3(aq)}$ and extracted with DCM. The combined organic extracts were washed with brine, then dried over anhydrous Na$_2$SO$_{4(s)}$, filtered and concentrated in vacuo to afford the title compound (33 mg, 30.1% yield). MS (apci) m/z=471.20 (M+H).

Example 177

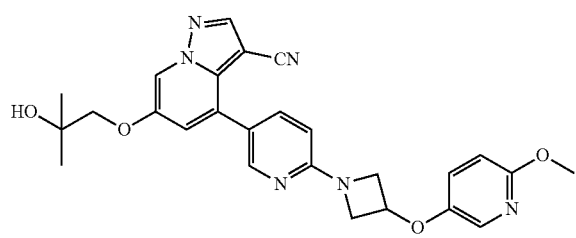 [SMILES: COc1ccc(OC2CN(c3ccc(-c4cc(OCC(C)(C)O)cn5ncc(C#N)c45)cn3)C2)cn1]

6-(2-hydroxy-2-methylpropoxy)-4-(6-(3-((6-methoxypyridin-3-yl)oxy)azetidin-1-yl)pyridin-3-yl)pyrazolo[1,5-a]pyridine-3-carbonitrile A mixture of 4-(6-fluoropyridin-3-yl)-6-(2-hydroxy-2-methylpropoxy)pyrazolo[1,5-a]pyridine-3-carbonitrile (Intermediate P42; 75.8 mg, 0.232 mmol), 5-(azetidin-3-yloxy)-2-methoxypyridine (93 mg, 0.516 mmol) and TEA (118 µL, 1.16 mmol) in DMA (774 µL) was stirred overnight at 95° C. After cooling to ambient temperature, the reaction mixture was diluted with DCM and washed with water. The organic extracts were washed with brine and dried over anhydrous Na$_2$SO$_{4(s)}$, filtered and concentrated in vacuo. The residue was suspended in 60:40 ACN:water containing 2% TFA. The solution was purified directly by C18 reverse phase chromatography (5-95% ACN in water with 0.1% TFA as the gradient eluent) to afford the title compound as the TFA salt. The TFA salt was treated with saturated NaHCO$_{3(aq)}$ and extracted with DCM. The combined organic extracts were washed with brine, then dried over anhydrous Na$_2$SO$_{4(s)}$, filtered and concentrated in vacuo to afford the title compound (65.6 mg, 58% yield). MS (apci) m/z=487.15 (M+H).

Example 178

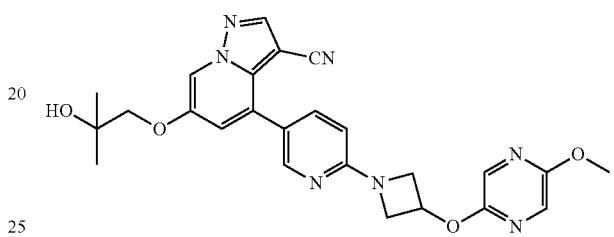

6-(2-hydroxy-2-methylpropoxy)-4-(6-(3-((5-methoxypyrazin-2-yl)oxy)azetidin-1-yl)pyridin-3-yl)pyrazolo[1,5-a]pyridine-3-carbonitrile A mixture of 4-(6-fluoropyridin-3-yl)-6-(2-hydroxy-2-methylpropoxy)pyrazolo[1,5-a]pyridine-3-carbonitrile (Intermediate P42; 32.2 mg, 0.0987 mmol), 2-(azetidin-3-yloxy)-5-methoxypyrazine (41.7 mg, 0.230 mmol) and TEA (67.5 µL, 0.493 mmol) in DMA (329 µL) was stirred overnight at 95° C. After cooling to ambient temperature, the reaction mixture was diluted with DCM and washed with water. The organic extracts were washed with brine and dried over anhydrous Na$_2$SO$_{4(s)}$, filtered and concentrated in vacuo. The residue was suspended in 60:40 ACN:water containing 2% TFA. The solution was purified directly by C18 reverse phase chromatography (5-95% ACN in water with 0.1% TFA as the gradient eluent) to afford the title compound as the TFA salt. The TFA salt was treated with saturated NaHCO$_{3(aq)}$ and extracted with DCM. The combined organic extracts were washed with brine, then dried over anhydrous Na$_2$SO$_{4(s)}$, filtered and concentrated in vacuo to afford the title compound (14.8 mg, 30.8% yield). MS (apci) m/z=488.20 (M+H).

Example 179

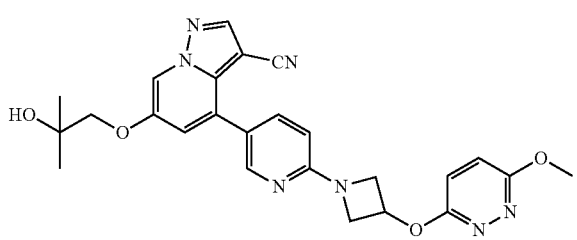 [SMILES: COc1ccc(OC2CN(c3ccc(-c4cc(OCC(C)(C)O)cn5ncc(C#N)c45)cn3)C2)nn1]

6-(2-hydroxy-2-methylpropoxy)-4-(6-(3-((6-methoxypyridazin-3-yl)oxy)azetidin-1-yl)pyridin-3-yl)pyrazolo[1,5-a]pyridine-3-carbonitrile A mixture of 4-(6-fluoropyridin-3-yl)-6-(2-hydroxy-2-methylpropoxy)pyrazolo[1,5-a]pyridine-3-carbonitrile (Intermediate P42; 32.2 mg, 0.0987 mmol), 3-(azetidin-3-yloxy)-6-methoxypyridazine (51 mg, 0.281 mmol) and TEA (67.5 µL, 0.493 mmol) in DMA (329 µL) was stirred overnight at 95° C. After cooling to ambient temperature, the reaction mixture was diluted with DCM and washed with water. The organic extracts were washed with brine and dried over anhydrous $Na_2SO_{4(s)}$, filtered and concentrated in vacuo. The residue was suspended in 60:40 ACN:water containing 2% TFA. The solution was purified directly by C18 reverse phase chromatography (5-95% ACN in water with 0.1% TFA as the gradient eluent) to afford the title compound as the TFA salt. The TFA salt was treated with saturated $NaHCO_{3(aq)}$ and extracted with DCM. The combined organic extracts were washed with brine, then dried over anhydrous $Na_2SO_{4(s)}$, filtered and concentrated in vacuo to afford the title compound (28.6 mg, 59.5% yield). MS (apci) m/z=488.20 (M+H).

Example 180

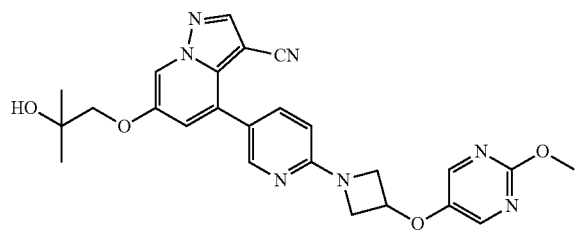 [SMILES: COc1ncc(OC2CN(c3ccc(-c4cc(OCC(C)(C)O)cn5ncc(C#N)c45)cn3)C2)cn1]

6-(2-hydroxy-2-methylpropoxy)-4-(6-(3-((2-methoxypyrimidin-5-yl)oxy)azetidin-1-yl)pyridin-3-yl)pyrazolo[1,5-a]pyridine-3-carbonitrile A mixture of 4-(6-fluoropyridin-3-yl)-6-(2-hydroxy-2-methylpropoxy)pyrazolo[1,5-a]pyridine-3-carbonitrile (Intermediate P42; 30.0 mg, 0.0919 mmol), 5-(azetidin-3-yloxy)-2-methoxypyrimidine (56 mg, 0.309 mmol) and TEA (101 µL, 0.735 mmol) in DMA (306 µL) was stirred overnight at 95° C. After cooling to ambient temperature, the reaction mixture was diluted with DCM and washed with water. The organic extracts were washed with brine and dried over anhydrous $Na_2SO_{4(s)}$, filtered and concentrated in vacuo. The residue was suspended in 60:40 ACN:water containing 2% TFA. The solution was purified directly by C18 reverse phase chromatography (5-95% ACN in water with 0.1% TFA as the gradient eluent) to afford the title compound as the TFA salt. The TFA salt was treated with saturated $NaHCO_{3(aq)}$ and extracted with DCM. The combined organic extracts were washed with brine, then dried over anhydrous $Na_2SO_{4(s)}$, filtered and concentrated in vacuo to afford the title compound (14.9 mg, 33.2% yield). MS (apci) m/z=488.20 (M+H).

Example 181

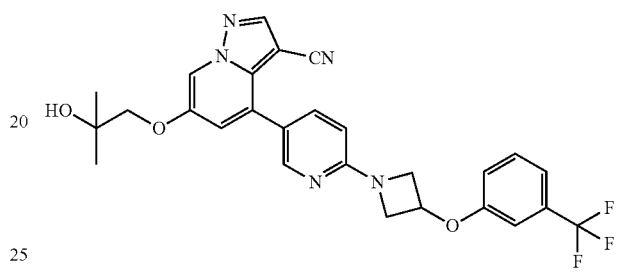

6-(2-hydroxy-2-methylpropoxy)-4-(6-(3-(3-(trifluoromethyl)phenoxy)azetidin-1-yl)pyridin-3-yl)pyrazolo[1,5-a]pyridine-3-carbonitrile A mixture of 4-(6-fluoropyridin-3-yl)-6-(2-hydroxy-2-methylpropoxy)pyrazolo[1,5-a]pyridine-3-carbonitrile (Intermediate P42; 31.9 mg, 0.0978 mmol), 3-[3-(trifluoromethyl)phenoxy]azetidine hydrochloride (74.4 mg, 0.293 mmol) and TEA (93.6 µL, 0.684 mmol) in DMA (326 µL) was stirred overnight at 105° C. After cooling to ambient temperature, the reaction mixture was diluted with DCM and washed with saturated $NaHCO_{3(aq)}$. The organic extracts were washed with water. Then the organic extracts were washed with brine and dried over anhydrous $Na_2SO_{4(s)}$, filtered and concentrated in vacuo. The residue was suspended in 60:40 ACN:water containing 2% TFA. The solution was purified directly by C18 reverse phase chromatography (5-95% ACN in water with 0.1% TFA as the gradient eluent) to afford the title compound as the TFA salt. The TFA salt was treated with saturated $NaHCO_{3(aq)}$ and extracted with DCM. The combined organic extracts were washed with brine, then dried over anhydrous $Na_2SO_{4(s)}$, filtered and concentrated in vacuo to afford the title compound (36.6 mg, 71.5% yield). MS (apci) m/z=524.10 (M+H).

The compounds in Table II were prepared using a similar method to that described for the synthesis of Example 181, replacing 3-[3-(trifluoromethyl)phenoxy]azetidine hydrochloride with the appropriate azetidine nucleophile. Reactions were monitored for completion by LCMS, and reaction durations were adjusted accordingly. Title compounds were cleanly isolated following chromatographic purification.

TABLE II

| Ex. # | Structure | Chemical Name | LCMS m/z |
|---|---|---|---|
| 182 | 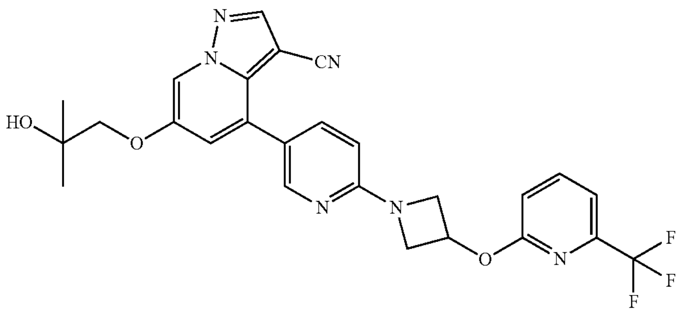 [SMILES: CC(C)(O)COc1cc(-c2ccc(N3CC(Oc4cccc(C(F)(F)F)n4)C3)nc2)c2c(C#N)cnn2c1] | 6-(2-hydroxy-2-methylpropoxy)-4-(6-(3-((6-(trifluoromethyl)pyridin-2-yl)oxy)azetidin-1-yl)pyridin-3-yl)pyrazolo[1,5-a]pyridine-3-carbonitrile | 525.10 (M + H) |
| 183 | 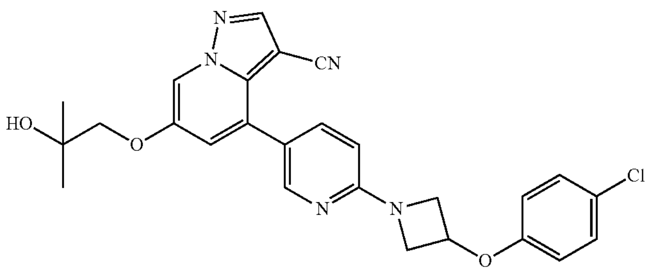 [SMILES: CC(C)(O)COc1cc(-c2ccc(N3CC(Oc4ccc(Cl)cc4)C3)nc2)c2c(C#N)cnn2c1] | 4-(6-(3-(4-chlorophenoxy)azetidin-1-yl)pyridin-3-yl)-6-(2-hydroxy-2-methylpropoxy)pyrazolo[1,5-a]pyridine-3-carbonitrile | 490.10 (M + H) |
| 184 | 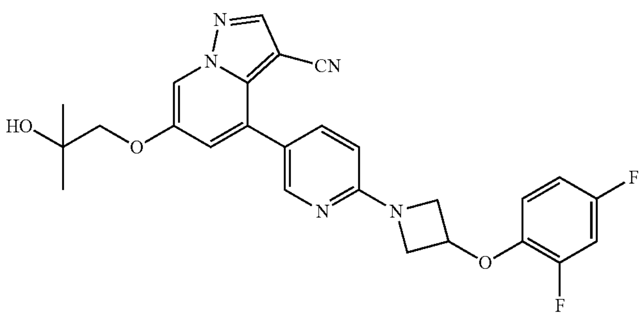 [SMILES: CC(C)(O)COc1cc(-c2ccc(N3CC(Oc4ccc(F)cc4F)C3)nc2)c2c(C#N)cnn2c1] | 4-(6-(3-(2,4-difluorophenoxy)azetidin-1-yl)pyridin-3-yl)-6-(2-hydroxy-2-methylpropoxy)pyrazolo[1,5-a]pyridine-3-carbonitrile | 492.15 (M + H) |
| 185 | 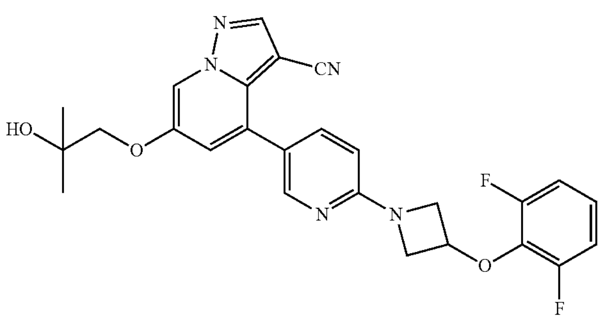 [SMILES: CC(C)(O)COc1cc(-c2ccc(N3CC(Oc4c(F)cccc4F)C3)nc2)c2c(C#N)cnn2c1] | 4-(6-(3-(2,6-difluorophenoxy)azetidin-1-yl)pyridin-3-yl)-6-(2-hydroxy-2-methylpropoxy)pyrazolo[1,5-a]pyridine-3-carbonitrile | 492.10 (M + H) |
| 186 | 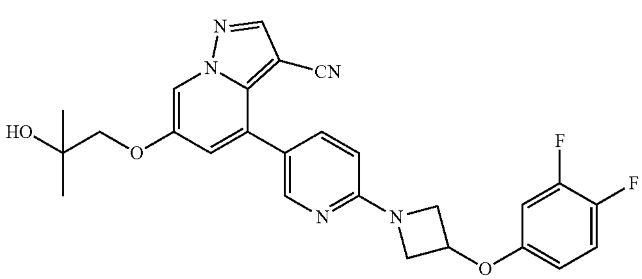 [SMILES: CC(C)(O)COc1cc(-c2ccc(N3CC(Oc4ccc(F)c(F)c4)C3)nc2)c2c(C#N)cnn2c1] | 4-(6-(3-(3,4-difluorophenoxy)azetidin-1-yl)pyridin-3-yl)-6-(2-hydroxy-2-methylpropoxy)pyrazolo[1,5-a]pyridine-3-carbonitrile | 492.10 (M + H) |

TABLE II-continued

| Ex. # | Structure | Chemical Name | LCMS m/z |
|---|---|---|---|
| 187 | 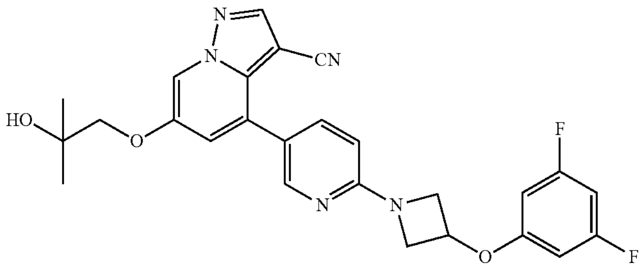 [SMILES: CC(C)(O)COc1cc(-c2ccc(N3CC(Oc4cc(F)cc(F)c4)C3)nc2)c2c(C#N)cnn2c1] | 4-(6-(3-(3,5-difluorophenoxy)azetidin-1-yl)pyridin-3-yl)-6-(2-hydroxy-2-methylpropoxy)pyrazolo[1,5-a]pyridine-3-carbonitrile | 492.15 (M + H) |
| 188 | 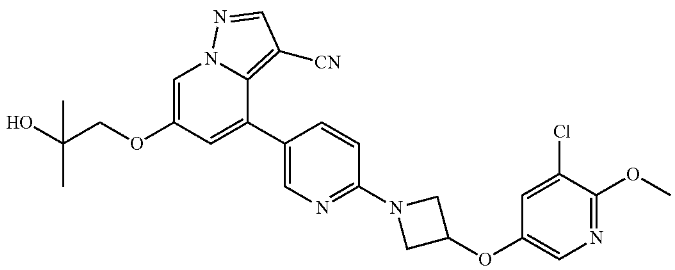 [SMILES: COc1ncc(OC2CN(c3ccc(-c4cc(OCC(C)(C)O)cn5ncc(C#N)c45)cn3)C2)cc1Cl] | 4-(6-(3-((5-chloro-6-methoxypyridin-3-yl)oxy)azetidin-1-yl)pyridin-3-yl)-6-(2-hydroxy-2-methylpropoxy)pyrazolo[1,5-a]pyridine-3-carbonitrile | 521.0 (M + H) |
| 189 | 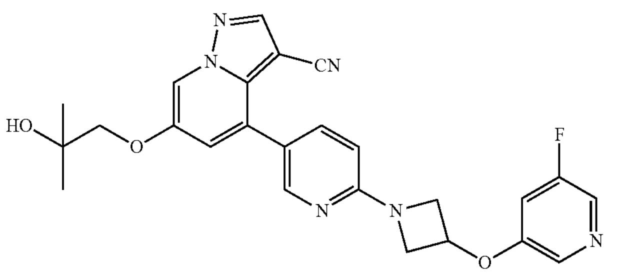 [SMILES: CC(C)(O)COc1cc(-c2ccc(N3CC(Oc4cncc(F)c4)C3)nc2)c2c(C#N)cnn2c1] | 4-(6-(3-((5-fluoropyridin-3-yl)oxy)azetidin-1-yl)pyridin-3-yl)-6-(2-hydroxy-2-methylpropoxy)pyrazolo[1,5-a]pyridine-3-carbonitrile | 475.10 (M + H) |
| 190 | 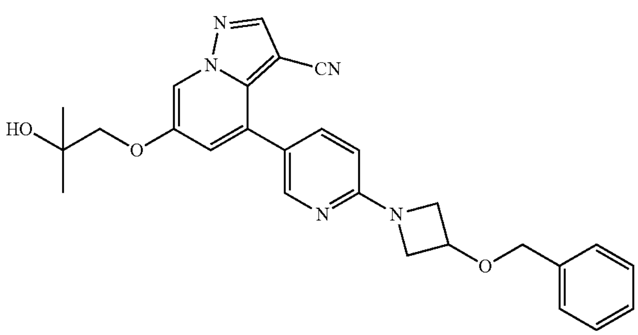 [SMILES: CC(C)(O)COc1cc(-c2ccc(N3CC(OCc4ccccc4)C3)nc2)c2c(C#N)cnn2c1] | 4-(6-(3-(benzyloxy)azetidin-1-yl)pyridin-3-yl)-6-(2-hydroxy-2-methylpropoxy)pyrazolo[1,5-a]pyridine-3-carbonitrile | 470.20 (M + H) |
| 191 | 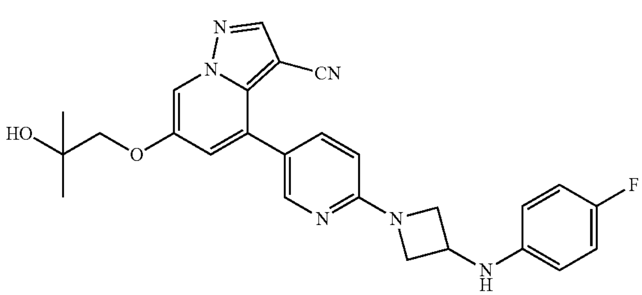 [SMILES: CC(C)(O)COc1cc(-c2ccc(N3CC(Nc4ccc(F)cc4)C3)nc2)c2c(C#N)cnn2c1] | 4-(6-(3-((4-fluorophenyl)amino)azetidin-1-yl)pyridin-3-yl)-6-(2-hydroxy-2-methylpropoxy)pyrazolo[1,5-a]pyridine-3-carbonitrile | 473.20 (M + H) |

Example 192

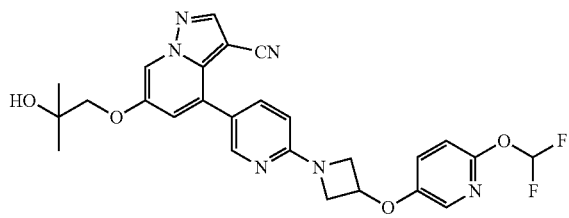 [SMILES: CC(C)(O)COc1cc(-c2ccc(N3CC(Oc4ccc(OC(F)F)nc4)C3)nc2)c2c(C#N)cnn2c1]

4-(6-(3-((6-(difluoromethoxy)pyridin-3-yl)oxy)azetidin-1-yl)pyridin-3-yl)-6-(2-hydroxy-2-methylpropoxy)pyrazolo[1,5-a]pyridine-3-carbonitrile A mixture of 4-(6-fluoropyridin-3-yl)-6-(2-hydroxy-2-methylpropoxy)pyrazolo[1,5-a]pyridine-3-carbonitrile (Intermediate P42; 30.7 mg, 0.0941 mmol), 5-(azetidin-3-yloxy)-2-(difluoromethoxy)pyridine (55 mg, 0.254 mmol) and TEA (64.3 µL, 0.470 mmol) in DMA (314 µL) was stirred overnight at 95° C. After cooling to ambient temperature, the reaction mixture was diluted with EtOAc and washed with water. Then the organic extracts were washed with brine and dried over anhydrous $Na_2SO_{4(s)}$, filtered and concentrated in vacuo. The residue was suspended in 60:40 ACN:water containing 2% TFA. The solution was purified directly by C18 reverse phase chromatography (5-95% ACN in water with 0.1% TFA as the gradient eluent) to afford the title compound as the TFA salt. The TFA salt was treated with saturated $NaHCO_{3(aq)}$ and extracted with DCM. The combined organic extracts were washed with brine, then dried over anhydrous $Na_2SO_{4(s)}$, filtered and concentrated in vacuo to afford the title compound (39.9 mg, 81.2% yield). MS (apci) m/z=523.20 (M+H).

Example 193

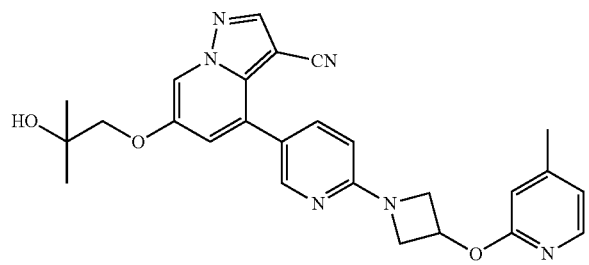 [SMILES: Cc1ccnc(OC2CN(c3ccc(-c4cc(OCC(C)(C)O)cn5ncc(C#N)c45)cn3)C2)c1]

6-(2-hydroxy-2-methylpropoxy)-4-(6-(3-((4-methylpyridin-2-yl)oxy)azetidin-1-yl)pyridin-3-yl)pyrazolo[1,5-a]pyridine-3-carbonitrile A mixture of 4-(6-fluoropyridin-3-yl)-6-(2-hydroxy-2-methylpropoxy)pyrazolo[1,5-a]pyridine-3-carbonitrile (Intermediate P42; 25.5 mg, 0.0781 mmol), 2-(azetidin-3-yloxy)-4-methylpyridine (50 mg, 0.304 mmol) and TEA (74.8 µL, 0.547 mmol) in DMA (391 µL) was stirred overnight at 95° C. After cooling to ambient temperature, the reaction mixture was diluted with water and extracted with EtOAc. The organic extracts were washed with water. Then the organic extracts were washed with brine and dried over anhydrous $Na_2SO_{4(s)}$, filtered and concentrated in vacuo. The residue was suspended in 60:40 ACN:water containing 2% TFA. The solution was purified directly by C18 reverse phase chromatography (5-95% ACN in water with 0.1% TFA as the gradient eluent) to afford the title compound as the TFA salt. The TFA salt was treated with saturated $NaHCO_{3(aq)}$ and extracted with DCM. The combined organic extracts were washed with brine, then dried over anhydrous $Na_2SO_{4(s)}$, filtered and concentrated in vacuo to afford the title compound (19.3 mg, 52.5% yield). MS (apci) m/z=471.3 (M+H).

Example 194

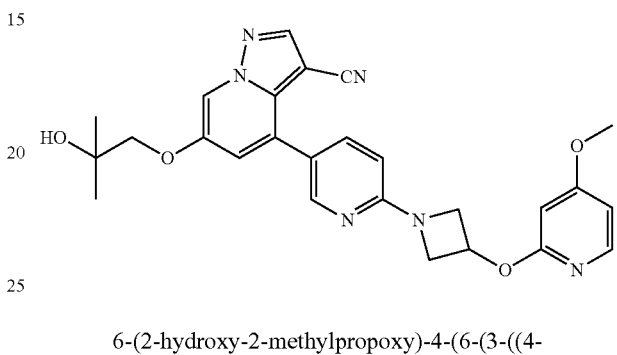

6-(2-hydroxy-2-methylpropoxy)-4-(6-(3-((4-methoxypyridin-2-yl)oxy)azetidin-1-yl)pyridin-3-yl)pyrazolo[1,5-a]pyridine-3-carbonitrile A mixture of 4-(6-fluoropyridin-3-yl)-6-(2-hydroxy-2-methylpropoxy)pyrazolo[1,5-a]pyridine-3-carbonitrile (Intermediate P42; 28 mg, 0.0858 mmol), 2-(azetidin-3-yloxy)-4-methoxypyridine (15.5 mg, 0.858 mmol) and TEA (82.1 µL, 0.601 mmol) in DMA (286 µL) was stirred overnight at 95° C. After cooling to ambient temperature, the reaction mixture was diluted with water and extracted with EtOAc. The organic extracts were washed with water. Then the organic extracts were washed with brine and dried over anhydrous $Na_2SO_{4(s)}$, filtered and concentrated in vacuo. The residue was suspended in 60:40 ACN:water containing 2% TFA. The solution was purified directly by C18 reverse phase chromatography (5-95% ACN in water with 0.1% TFA as the gradient eluent) to afford the title compound as the TFA salt. The TFA salt was treated with saturated $NaHCO_{3(aq)}$ and extracted with DCM. The combined organic extracts were washed with brine, then dried over anhydrous $Na_2SO_{4(s)}$, filtered and concentrated in vacuo to afford the title compound (16.9 mg, 40.5% yield). MS (apci) m/z=487.20 (M+H).

Example 195

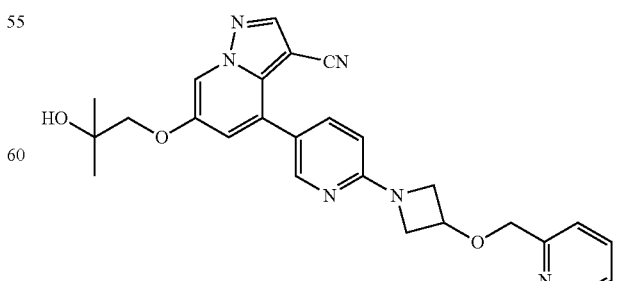

6-(2-hydroxy-2-methylpropoxy)-4-(6-(3-(pyridin-2-ylmethoxy)azetidin-1-yl)pyridin-3-yl)pyrazolo[1,5-a]pyridine-3-carbonitrile A mixture of 4-(6-fluoropyridin-3-yl)-6-(2-hydroxy-2-methylpropoxy)pyrazolo[1,5-a]pyridine-3-carbonitrile (Intermediate P42; 25 mg, 0.077 mmol), 2-((azetidin-3-yloxy)methyl)pyridine (17 mg, 0.10 mmol) and TEA (73 μL, 0.54 mmol) in DMA (260 μL) was stirred overnight at 95° C. After cooling to ambient temperature, the reaction mixture was diluted with water and extracted with EtOAc. The organic extracts were washed with water. Then the organic extracts were washed with brine and dried over anhydrous Na$_2$SO$_{4(s)}$, filtered and concentrated in vacuo. The residue was suspended in 60:40 ACN:water containing 2% TFA. The solution was purified directly by C18 reverse phase chromatography (5-95% ACN in water with 0.1% TFA as the gradient eluent) to afford the title compound as the TFA salt. The TFA salt was treated with saturated NaHCO$_{3(aq)}$ and extracted with DCM. The combined organic extracts were washed with brine, then dried over anhydrous Na$_2$SO$_{4(s)}$, filtered and concentrated in vacuo to afford the title compound (6.6 mg, 18% yield). MS (apci) m/z=471.20 (M+H).

Example 196

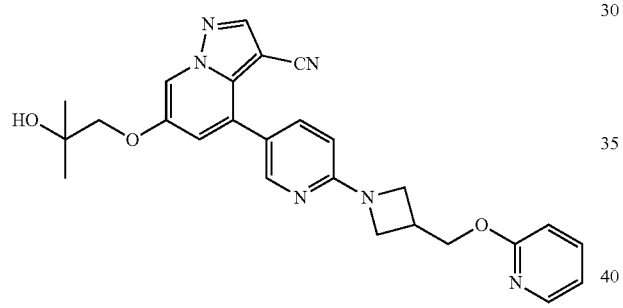

6-(2-hydroxy-2-methylpropoxy)-4-(6-(3-((pyridin-2-yloxy)methyl)azetidin-1-yl)pyridin-3-yl)pyrazolo[1,5-a]pyridine-3-carbonitrile A mixture of 4-(6-fluoropyridin-3-yl)-6-(2-hydroxy-2-methylpropoxy)pyrazolo[1,5-a]pyridine-3-carbonitrile (Intermediate P42; 26 mg, 0.0797 mmol), 2-(azetidin-3-ylmethoxy)pyridine (73.5 mg, 0.448 mmol) and TEA (76.3 μL, 0.558 mmol) in DMA (266 μL) was stirred overnight at 95° C. After cooling to ambient temperature, the reaction mixture was diluted with water and extracted with EtOAc. The organic extracts were washed with water. Then the organic extracts were washed with brine and dried over anhydrous Na$_2$SO$_{4(s)}$, filtered and concentrated in vacuo. The residue was suspended in 60:40 ACN:water containing 2% TFA. The solution was purified directly by C18 reverse phase chromatography (5-95% ACN in water with 0.1% TFA as the gradient eluent) to afford the title compound as the TFA salt. The TFA salt was treated with saturated NaHCO$_{3(aq)}$ and extracted with DCM. The combined organic extracts were washed with brine, then dried over anhydrous Na$_2$SO$_{4(s)}$, filtered and concentrated in vacuo to afford the title compound (16.6 mg, 44.3% yield). MS (apci) m/z=471.20 (M+H).

Example 197

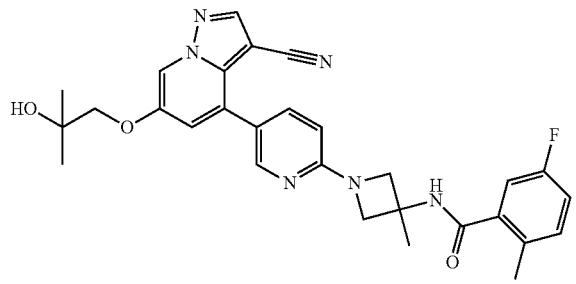 [SMILES: Cc1ccc(F)cc1C(=O)NC1(C)CN(c2ccc(-c3cc(OCC(C)(C)O)cn4ncc(C#N)c34)cn2)C1]

N-(1-(5-(3-cyano-6-(2-hydroxy-2-methylpropoxy)pyrazolo[1,5-a]pyridin-4-yl)pyridin-2-yl)-3-methylazetidin-3-yl)-5-fluoro-2-methylbenzamide Step 1: Preparation of tert-butyl (1-(5-(3-cyano-6-(2-hydroxy-2-methylpropoxy)pyrazolo[1,5-a]pyridin-4-yl)pyridin-2-yl)-3-methylazetidin-3-yl)carbamate A mixture of 4-(6-fluoropyridin-3-yl)-6-(2-hydroxy-2-methylpropoxy)pyrazolo[1,5-a]pyridine-3-carbonitrile (Intermediate P42; 753 mg, 2.307 mmol), tert-butyl (3-methylazetidin-3-yl)carbamate hydrochloride (770.9 mg, 3.461 mmol) and DIEA (1.809 mL, 10.38 mmol) in DMSO (4.615 mL) was stirred overnight at 90° C. After cooling to ambient temperature, the reaction mixture was diluted with water and extracted with EtOAc. The organic extracts were washed with brine and dried over anhydrous Na$_2$SO$_{4(s)}$, filtered and concentrated in vacuo. The residue was purified by silica chromatography (1-10% MeOH in DCM as the gradient eluent) to afford the title compound (1.089 g, 95.81% yield) in sufficient purity for step 2. MS (apci) m/z=493.3 (M+H).

Step 2: Preparation of 4-(6-(3-amino-3-methylazetidin-1-yl)pyridin-3-yl)-6-(2-hydroxy-2-methylpropoxy)pyrazolo[1,5-a]pyridine-3-carbonitrile A solution of tert-butyl (1-(5-(3-cyano-6-(2-hydroxy-2-methylpropoxy)pyrazolo[1,5-a]pyridin-4-yl)pyridin-2-yl)-3-methylazetidin-3-yl)carbamate (1.089 g, 2.211 mmol) in DCM (5.527 mL) was treated with TFA (10 mL, 130 mmol). After stirring for 1 h at ambient temperature the mixture was concentrated in vacuo and the residue diluted with EtOAc and washed with saturated NaHCO$_{3(aq)}$. The organic extracts were washed with brine and dried over anhydrous Na$_2$SO$_{4(s)}$, filtered and concentrated in vacuo to cleanly provide the title compound (800 mg, 92.2% yield) in sufficient purity for step 3. MS (apci) m/z=393.2 (M+H).

Step 3: Preparation of N-(1-(5-(3-cyano-6-(2-hydroxy-2-methylpropoxy)pyrazolo[1,5-a]pyridin-4-yl)pyridin-2-yl)-3-methylazetidin-3-yl)-5-fluoro-2-methylbenzamide A mixture of 4-(6-(3-amino-3-methylazetidin-1-yl)pyridin-3-yl)-6-(2-hydroxy-2-methylpropoxy)pyrazolo[1,5-a]pyridine-3-carbonitrile (54 mg, 0.138 mmol), HATU (57.5 mg, 0.151 mmol), 5-Fluoro-2-methylbenzoic acid (42.4 mg, 0.275 mmol) in DMSO (1.38 mL) was treated with DIEA (120 μL, 0.688 mmol) and then stirred overnight at ambient temperature. The reaction mixture was diluted with EtOAc and washed with water. The organic extracts were washed with brine, then dried over anhydrous $Na_2SO_{4(s)}$, filtered and concentrated in vacuo. The residue was purified by silica chromatography (00.5-10% MeOH in DCM with 0.05-1% $NH_4OH$ as the gradient eluent) to cleanly provide the title compound (48.2 mg, 66.3% yield) MS (apci) m/z=529.2 (M+H)

Example 198

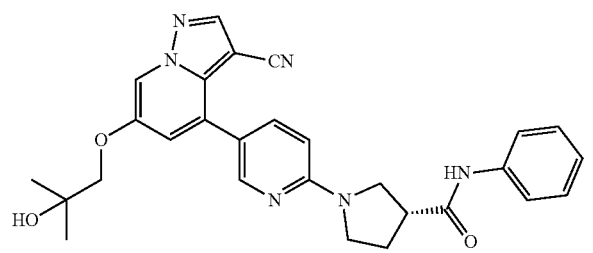 [SMILES: CC(C)(O)COc1cc(-c2ccc(N3CC[C@@H](C(=O)Nc4ccccc4)C3)nc2)c2c(C#N)cnn2c1]

(R)-1-(5-(3-cyano-6-(2-hydroxy-2-methylpropoxy) pyrazolo[1,5-a]pyridin-4-yl)pyridin-2-yl)-N-phenylpyrrolidine-3-carboxamide Step 1: Preparation of tert-butyl (R)-3-(phenylcarbamoyl)pyrrolidine-1-carboxylate A mixture of (R)-1-N-Boc-beta-proline (504.1 mg, 2.34 mmol), HATU (1.069 g, 2.810 mmol), and Aniline (239.9 mg, 2.576 mmol) in DCM (25 mL) was treated with DIEA (816 µL, 4.684 mmol) and then stirred 60 hours at ambient temperature. The reaction mixture concentrated in vacuo. The residue was purified by silica chromatography (10-60% EtOAc in Hexanes as the gradient eluent) to afford the title compound (assumed theoretical yield, 679 mg, 2.34 mmol) in sufficient purity for step 2. MS (apci) m/z=191.10 (M-Boc).

Step 2: Preparation of (R)—N-phenylpyrrolidine-3-carboxamide

Tert-butyl (R)-3-(phenylcarbamoyl)pyrrolidine-1-carboxylate (assumed 679 mg, 2.34 mmol) in 2 mL DCM was treated with TFA (2 mL, 26 mmol). The reaction mixture was stirred for 16 h at ambient temperature, and then concentrated in vacuo. The crude residue was diluted with 4:1 DCM:IPA and washed with saturated $NaHCO_{3(aq)}$. The organic extracts were dried over anhydrous $Na_2SO_{4(s)}$, filtered and concentrated in vacuo to afford the title compound (218.9 mg, 49.13% yield over two steps) in sufficient purity for step 3. MS (apci) m/z=191.10 (M+H).

Step 3: Preparation of (R)-1-(5-(3-cyano-6-(2-hydroxy-2-methylpropoxy)pyrazolo[1,5-a]pyridin-4-yl) pyridin-2-yl)-N-phenylpyrrolidine-3-carboxamide A mixture of 4-(6-fluoropyridin-3-yl)-6-(2-hydroxy-2-methylpropoxy)pyrazolo[1,5-a]pyridine-3-carbonitrile (Intermediate P42; 33.4 mg, 0.102 mmol, (R)—N-phenylpyrrolidine-3-carboxamide (58.4 mg, 0.307 mmol) and TEA (69.4 µL, 0.512 mmol) in DMA (512 µL) was stirred overnight at 80° C. After cooling to ambient temperature, the reaction mixture was diluted with EtOAc and washed with water. The organic extracts were washed with brine and the organic extracts were concentrated in vacuo. The residue was purified directly by C18 reverse phase chromatography (5-95% ACN in water with 0.1% TFA as the gradient eluent) to afford the title compound as the TFA salt. The TFA salt was treated with saturated $NaHCO_{3(aq)}$ and extracted with 4:1 DCM:IPA. The combined organic extracts were dried over anhydrous $Na_2SO_{4(s)}$, filtered and concentrated in vacuo to afford the title compound (36.8 mg, 72.4% yield). MS (apci) m/z=497.2 (M+H).

Example 199

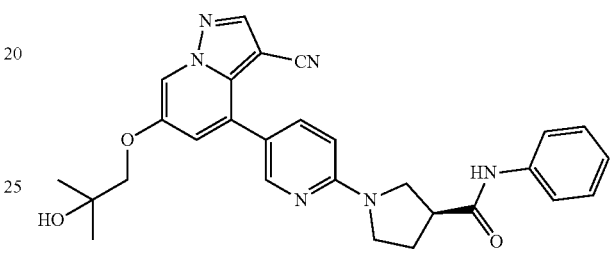

(S)-1-(5-(3-cyano-6-(2-hydroxy-2-methylpropoxy) pyrazolo[1,5-a]pyridin-4-yl)pyridin-2-yl)-N-phenylpyrrolidine-3-carboxamide Step 1: Preparation of tert-butyl (S)-3-(phenylcarbamoyl)pyrrolidine-1-carboxylate A mixture of tert-butyl (S)-3-(phenylcarbamoyl)pyrrolidine-1-carboxylate (518.6 mg, 2.409 mmol), HATU (1.008 g, 2.891 mmol), and aniline (269.3 mg, 2.891 mmol) in DCM (25 mL) was treated with DIEA (816 µL, 4.684 mmol) and then stirred 60 hours at ambient temperature. The reaction mixture concentrated in vacuo. The residue was purified by silica chromatography (10-60% EtOAc in Hexanes as the gradient eluent) to afford the title compound (assume theoretical yield, 699 mg, 2.409 mmol) in sufficient purity for step 2. MS (apci) m/z=191.10 (M-Boc).

Step 2: Preparation of (S)—N-phenylpyrrolidine-3-carboxamide

Tert-butyl (S)-3-(phenylcarbamoyl)pyrrolidine-1-carboxylate (assumed 699 mg, 2.409 mmol) in 2 mL DCM was treated with TFA (2 mL, 26 mmol). The reaction mixture was stirred for 16 h at ambient temperature, and then concentrated in vacuo. The crude residue was diluted with 4:1 DCM:IPA and washed with saturated $NaHCO_{3(aq)}$. The organic extracts were dried over anhydrous $Na_2SO_{4(s)}$, filtered and concentrated in vacuo to afford the title compound (458.4 mg, 98% yield over two steps) in sufficient purity for step 3. MS (apci) m/z=191.10 (M+H).

Step 3: Preparation of (S)-1-(5-(3-cyano-6-(2-hydroxy-2-methylpropoxy)pyrazolo[1,5-a]pyridin-4-yl) pyridin-2-yl)-N-phenylpyrrolidine-3-carboxamide A mixture of 4-(6-fluoropyridin-3-yl)-6-(2-hydroxy-2-methylpropoxy)pyrazolo[1,5-a]pyridine-3-carbonitrile (Intermediate P42; 28 mg, 0.086 mmol), (S)—N-phenylpyrrolidine-3-carboxamide (49 mg, 0.257 mmol) and TEA (58 µL, 0.429 mmol) in DMA (572 µL) was stirred overnight at 80° C. After cooling to ambient temperature, the reaction mixture was diluted with EtOAc and washed with water. The organic extracts were washed with brine and the organic extracts were concentrated in vacuo. The residue was purified directly by C18 reverse phase chromatography (5-95% ACN in water with 0.1% TFA as the gradient eluent) to afford the title compound as the TFA salt. The TFA salt was treated with saturated NaHCO$_{3(aq)}$ and extracted with 4:1 DCM:IPA. The combined organic extracts were dried over anhydrous Na$_2$SO$_{4(s)}$, filtered and concentrated in vacuo to afford the title compound (16.7 mg, 39% yield). MS (apci) m/z=497.2 (M+H).

Example 200

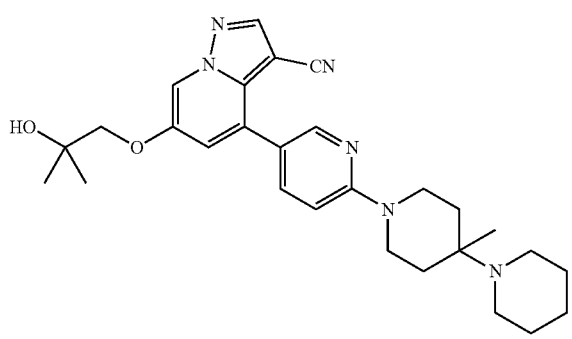 [SMILES: CC(C)(O)COc1cc(-c2ccc(N3CCC(C)(N4CCCCC4)CC3)nc2)c2c(C#N)cnn2c1]

6-(2-hydroxy-2-methylpropoxy)-4-(6-(4'-methyl-[1,4'-bipiperidin]-1'-yl)pyridin-3-yl)pyrazolo[1,5-a]pyridine-3-carbonitrile A mixture of 4-(6-fluoropyridin-3-yl)-6-(2-hydroxy-2-methylpropoxy)pyrazolo[1,5-a]pyridine-3-carbonitrile (Intermediate P42; 50 mg, 0.153 mmol), 4'-Methyl-[1,4']bipiperidinyl dihydrochloride (54.7 mg, 0.215 mmol) and DIEA (133 µL, 0.766 mmol) in DMSO (306 µL) was sparged with argon and stirred overnight at 90° C. After cooling to ambient temperature, the reaction mixture was diluted with EtOAc and washed with water. The combined organic extracts were dried over anhydrous Na$_2$SO$_{4(s)}$, filtered and concentrated in vacuo. The residue was purified directly by C18 reverse phase chromatography (5-95% ACN in water with 0.1% TFA as the gradient eluent) to afford the title compound as the TFA salt. The TFA salt was treated with saturated NaHCO$_{3(aq)}$ and extracted with EtOAc. The combined organic extracts were dried over anhydrous Na$_2$SO$_{4(s)}$, filtered and concentrated in vacuo to afford the title compound (27 mg, 36% yield). MS (apci) m/z=489.3 (M+H).

Example 201

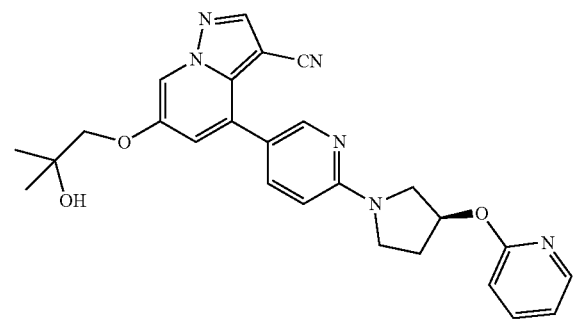 [SMILES: CC(C)(O)COc1cc(-c2ccc(N3CC[C@H](Oc4ccccn4)C3)nc2)c2c(C#N)cnn2c1]

(S)-6-(2-hydroxy-2-methylpropoxy)-4-(6-(3-(pyridin-2-yloxy)pyrrolidin-1-yl)pyridin-3-yl)pyrazolo[1,5-a]pyridine-3-carbonitrile A mixture of 4-(6-fluoropyridin-3-yl)-6-(2-hydroxy-2-methylpropoxy)pyrazolo[1,5-a]pyridine-3-carbonitrile (Intermediate P42; 394 mg, 1.208 mmol, (S)-2-(pyrrolidin-3-yloxy)-pyridine dihydrochloride (1.146 g, 4.833 mmol) and TEA (1.639 mL, 12.08 mmol) in DMA (12 mL) was stirred 16 h at 90° C. After cooling to ambient temperature, the reaction mixture was diluted with water and extracted with EtOAc. The organic extracts were washed with water. Then the organic extracts were washed with brine and dried over anhydrous Na$_2$SO$_{4(s)}$, filtered and concentrated in vacuo. The residue was purified directly by C18 reverse phase chromatography (5-95% ACN in water with 0.1% TFA as the gradient eluent) to afford the title compound as the TFA salt. The TFA salt was treated with saturated NaHCO$_{3(aq)}$ and extracted with 4:1 DCM:IPA. The combined organic extracts were dried over anhydrous Na$_2$SO$_{4(s)}$, filtered and concentrated in vacuo to afford the title compound (400 mg, 70% yield). MS (apci) m/z=471.2 (M+H). $^1$H NMR (400 MHz, DMSO) δ 8.65-8.64 (d, 1H), 8.56 (s, 1H), 8.31-8.30 (dd, 1H), 8.22-8.20 (m, 1H), 7.76-7.69 (m, 2H), 7.26-7.25 (d, 1H), 7.01-6.98 (m, 1H), 6.85-6.83 (m, 1H), 6.61-6.59 (d, 1H), 5.69-5.67 (m, 1H), 4.69 (s, 1H), 3.86-3.81 (m, 3H), 3.70-3.65 (m, 2H), 3.60-3.53 (m, 1H), 2.42-2.22 (m, 2H), 1.22 (s, 6H)

Example 202

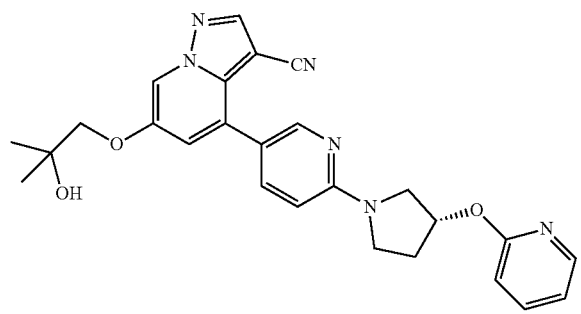 [SMILES: CC(C)(O)COc1cc(-c2ccc(N3CC[C@@H](Oc4ccccn4)C3)nc2)c2c(C#N)cnn2c1]

(R)-6-(2-hydroxy-2-methylpropoxy)-4-(6-(3-(pyridin-2-yloxy)pyrrolidin-1-yl)pyridin-3-yl)pyrazolo[1,5-a]pyridine-3-carbonitrile A solution of 4-(6-fluoropyridin-3-yl)-6-(2-hydroxy-2-methylpropoxy)pyrazolo[1,5-a]pyridine-3-carbonitrile (Intermediate P42; 25 mg, 0.077 mmol) in DMA (100 μL) was treated with TEA (27 μL, 0.192 mmol) and (R)-2-(pyrrolidin-3-yloxy)pyridine hydrochloride (15.4 mg, 0.077 mmol) and was stirred overnight at 110° C. After cooling to ambient temperature, the reaction mixture was diluted with water (10 mL) and extracted with DCM (3×10 mL) using a phase separator frit. The organic extracts were concentrated in vacuo. The residue was purified directly by C18 reverse phase chromatography (0-60% ACN in water as the gradient eluent) to cleanly provide the title compound (16 mg, 44% yield). MS (apci) m/z=471.2 (M+H).

Example 203

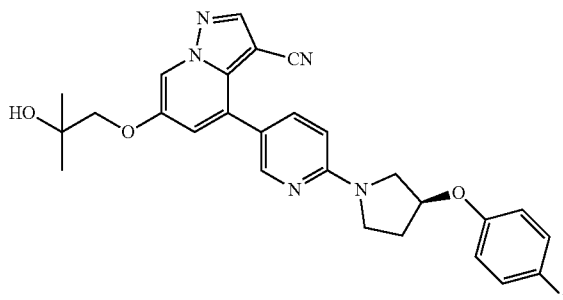

(S)-4-(6-(3-(4-fluorophenoxy)pyrrolidin-1-yl)pyridin-3-yl)-6-(2-hydroxy-2-methylpropoxy)pyrazolo[1,5-a]pyridine-3-carbonitrile A solution of 4-(6-fluoropyridin-3-yl)-6-(2-hydroxy-2-methylpropoxy)pyrazolo[1,5-a]pyridine-3-carbonitrile (Intermediate P42; 31.6 mg, 0.097 mmol) in DMA (1 mL) was treated with (S)-3-(4-fluorophenoxy)pyrrolidine hydrochloride (22.1 mg, 0.102 mmol) followed by TEA (65.7 μL, 0.484 mmol) and was stirred overnight at 90° C. Additional (S)-3-(4-fluorophenoxy)pyrrolidine hydrochloride (8.8 mg, 0.48 mmol) was added to the reaction and reaction continued to stir for an additional 16 h at 90° C. After cooling to ambient temperature, the reaction mixture was diluted with water and extracted with EtOAc. The organic extracts were washed with water. Then the organic extracts were washed with brine and dried over anhydrous $Na_2SO_{4(s)}$, filtered and concentrated in vacuo. The residue was purified by silica chromatography (5-50% Acetone in DCM as the gradient eluent). An impurity remained so product-containing fractions were concentrated in vacuo. The residue was repurified by C18 reverse phase chromatography (5-95% ACN in water with 0.1% TFA as the gradient eluent) to afford the title compound as the TFA salt. The TFA salt was treated with saturated $NaHCO_{3(aq)}$ and extracted with 4:1 DCM:IPA. The combined organic extracts were dried over anhydrous $Na_2SO_{4(s)}$, filtered and concentrated in vacuo to afford the title compound (9.8 mg, 20.8% yield). MS (apci) m/z=488.2 (M+H).

Example 204

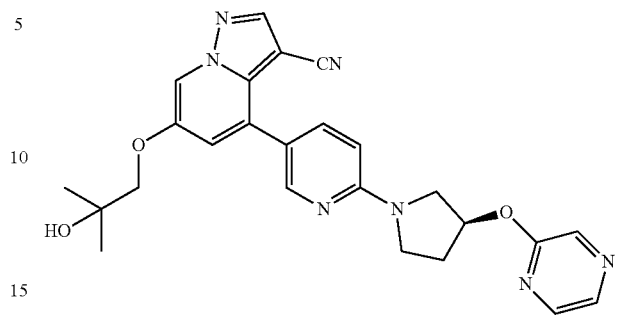

(S)-6-(2-hydroxy-2-methylpropoxy)-4-(6-(3-(pyrazin-2-yloxy)pyrrolidin-1-yl)pyridin-3-yl)pyrazolo[1,5-a]pyridine-3-carbonitrile

Step 1: Preparation of tert-butyl (S)-3-(pyrazin-2-yloxy)pyrrolidine-1-carboxylate To a solution of tert-butyl (S)-3-(phenylcarbamoyl)pyrrolidine-1-carboxylate (264.5 mg, 1.413 mmol) in DMF (7.1 mL) was added 2-chloropyrazine (192.2 mg, 1.695 mmol) followed by sodium hydride (60% w/w, 113 mg, 2.825 mmol) and then the reaction mixture was stirred for 16 hours at 80° C. After cooling to ambient temperature, the reaction mixture was diluted with water and extracted with EtOAc. The organic extracts were washed with water. Then the organic extracts were washed with brine and dried over anhydrous $Na_2SO_{4(s)}$, filtered and concentrated in vacuo. The residue was purified by silica chromatography (5-60% EtOAc in Hexanes as the gradient eluent) to afford the title compound (assume theoretical yield, 374.9 mg, 1.413 mmol) in sufficient purity for step 2. $^1$HNMR (400 MHz, DMSO-d6) δ 8.31 (s, 1H), 8.22 (s, 2H), 5.49 (s, 1H), 3.64-3.57 (m, 1H), 3.48-3.31 (m, 3H), 2.23-2.04 (m, 2H), 1.40-1.39 (d, 9H).

Step 2: Preparation of (S)-2-(pyrrolidin-3-yloxy)pyrazine

To a solution of tert-butyl (S)-3-(pyrazin-2-yloxy)pyrrolidine-1-carboxylate (assumed 374.9 mg, 1.413 mmol) in 3 mL DCM was treated with TFA (3 mL, 39 mmol). The reaction mixture was stirred for 0.5 h at ambient temperature, and then concentrated in vacuo. The crude residue was diluted with 4:1 DCM:IPA and washed with saturated $NaHCO_{3(aq)}$. The organic extracts were dried over anhydrous $Na_2SO_{4(s)}$, filtered and concentrated in vacuo to afford the title compound (72.1 mg, 31% yield over two steps) in sufficient purity for step 3. 1H NMR (400 MHz, DMSO-d6) δ 8.27 (s, 1H), 8.21 (s, 2H), 5.46-5.42 (m, 1H), 3.25-3.21 (m, 1H), 3.09-2.95 (m, 3H), 2.17-2.08 (m, 1H), 1.96-1.89 (m, 1H).

Step 3: Preparation of (S)-6-(2-hydroxy-2-methylpropoxy)-4-(6-(3-(pyrazin-2-yloxy)pyrrolidin-1-yl)pyridin-3-yl)pyrazolo[1,5-a]pyridine-3-carbonitrile To a solution of 4-(6-fluoropyridin-3-yl)-6-(2-hydroxy-2-methylpropoxy)pyrazolo[15-a]pyridine-3-carbonitrile (Intermediate P42; 30.8 mg, 0.094 mmol) in DMA (2 mL) was added TEA (64 µL, 0.472 mmol) followed by (S)-2-(pyrrolidin-3-yloxy)pyrazine (71.7 mg, 0.434 mmol). The reaction mixture was stirred overnight at 90° C. After cooling to ambient temperature, the reaction was purified directly by C18 reverse phase chromatography (5-95% ACN in water with 0.1% TFA as the gradient eluent). An impurity remained and product-containing fractions were concentrated in vacuo. The residue was repurified by silica chromatography (5-95% Acetone in DCM as the gradient eluent) to afford the title compound (36.2 mg, 81% yield). MS (apci) m/z=472.2 (M+H).

Example 205

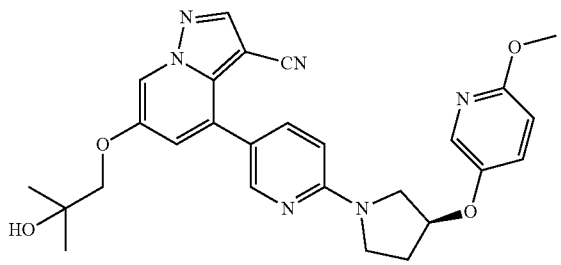 [SMILES: COc1ccc(O[C@H]2CCN(c3ccc(-c4cc(OCC(C)(C)O)cn5ncc(C#N)c45)cn3)C2)cn1]

(S)-6-(2-hydroxy-2-methylpropoxy)-4-(6-(3-((6-methoxypyridin-3-yl)oxy)pyrrolidin-1-yl)pyridin-3-yl)pyrazolo[1,5-a]pyridine-3-carbonitrile Step 1: Preparation of tert-butyl (S)-3-((6-methoxypyridin-3-yl)oxy)pyrrolidine-1-carboxylate To a solution of tert-butyl (R)-3-((methylsulfonyl)oxy)pyrrolidine-1-carboxylate (Intermediate R14; 208.7 mg, 0.787 mmol) in DMF (8 mL) was added 5-hydroxy-2-methoxylpyridine (118.1 mg, 0.944 mmol) followed by potassium carbonate (217.4 mg, 1.573 mmol) and then the reaction mixture was stirred for 16 hours at 90° C. After cooling to ambient temperature, the reaction mixture was diluted with water and extracted with EtOAc. The organic extracts were washed with water. Then the organic extracts were washed with brine and dried over anhydrous $Na_2SO_{4(s)}$, filtered and concentrated in vacuo. The residue was purified by silica chromatography (5-75% Acetone in DCM as the gradient eluent) to afford the title compound (assume theoretical yield, 231 mg, 0.787 mmol) in sufficient purity for step 2. MS (apci) m/z=295.1 (M+H).

Step 2: Preparation of (S)-2-methoxy-5-(pyrrolidin-3-yloxy)pyridine

To a solution of tert-butyl (S)-3-((6-methoxypyridin-3-yl)oxy)pyrrolidine-1-carboxylate (assumed 231 mg, 0.787 mmol) in 2 mL DCM was treated with TFA (2 mL, 26 mmol). The reaction mixture was stirred for 15 min at ambient temperature, and then concentrated in vacuo. The crude residue was diluted with 4:1 DCM:IPA and washed with saturated $NaHCO_{3(aq)}$. The organic extracts were dried over anhydrous $Na_2SO_{4(s)}$, filtered and concentrated in vacuo to afford the title compound (54.6 mg, 36% yield over two steps) in sufficient purity for step 3. MS (apci) m/z=195.1 (M+H).

Step 3: Preparation of (S)-6-(2-hydroxy-2-methylpropoxy)-4-(6-(3-((6-methoxypyridin-3-yl)oxy)pyrrolidin-1-yl)pyridin-3-yl)pyrazolo[1,5-a]pyridine-3-carbonitrile To a solution of 4-(6-fluoropyridin-3-yl)-6-(2-hydroxy-2-methylpropoxy)pyrazolo[1,5-a]pyridine-3-carbonitrile (Intermediate P42; 60.8 mg, 0.186 mmol) in DMA (2 mL) was added TEA (126 µL, 0.932 mmol) followed by (S)-2-methoxy-5-(pyrrolidin-3-yloxy)pyridine (54.3 mg, 0.279 mmol). The reaction mixture was stirred overnight at 90° C. After cooling to ambient temperature, the reaction was purified by C18 reverse phase chromatography (5-95% ACN in water with 0.1% TFA as the gradient eluent) to afford the title compound as the TFA salt. The TFA salt was treated with saturated $NaHCO_{3(aq)}$ and extracted with 4:1 DCM:IPA. The combined organic extracts were dried over anhydrous $Na_2SO_{4(s)}$, filtered and concentrated in vacuo to afford the title compound (39.5 mg, 42% yield). MS (apci) m/z=501.2 (M+H).

Example 206

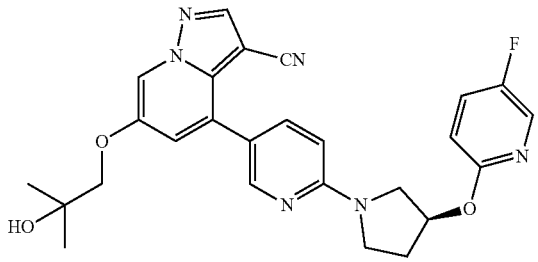 [SMILES: CC(C)(O)COc1cc(-c2ccc(N3CC[C@H](Oc4ccc(F)cn4)C3)nc2)c2c(C#N)cnn2c1]

(S)-6-(2-hydroxy-2-methylpropoxy)-4-(6-(3-((6-methoxypyridin-3-yl)oxy)pyrrolidin-1-yl)pyridin-3-yl)pyrazolo[1,5-a]pyridine-3-carbonitrile Step 1: Preparation of tert-butyl (S)-3-((5-fluoropyridin-2-yl)oxy)pyrrolidine-1-carboxylate To a solution of tert-butyl (R)-3-((methylsulfonyl)oxy)pyrrolidine-1-carboxylate (Intermediate R14; 200.8 mg, 0.757 mmol) in DMF (8 mL) was added 5-fluoro-2-hydroxypyridine (102.7 mg, 0.908 mmol) followed by potassium carbonate (209.2 mg, 1.514 mmol) and then the reaction mixture was stirred for 60 hours at 90° C. After cooling to ambient temperature, the reaction mixture was diluted with EtOAc washed with water. Then the organic extracts were washed with brine and dried over anhydrous $Na_2SO_{4(s)}$, filtered and concentrated in vacuo. The residue was purified by silica chromatography (5-75% Acetone in DCM as the gradient eluent) to afford the title compound (assume theoretical yield, 213.5 mg, 0.757 mmol) in sufficient purity for step 2. MS (apci) m/z=183.1 (M-Boc).

Step 2: Preparation of (S)-5-fluoro-2-(pyrrolidin-3-yloxy)pyridine

To a solution tert-butyl (S)-3-((5-fluoropyridin-2-yl)oxy)pyrrolidine-1-carboxylate (assumed 213.5 mg, 0.75 mmol) in 2 mL DCM was treated with TFA (2 mL, 26 mmol). The reaction mixture was stirred for 15 min at ambient temperature, and then concentrated in vacuo. The crude residue was diluted with 4:1 DCM:IPA and washed with saturated NaHCO$_{3(aq)}$. The organic extracts were dried over anhydrous Na$_2$SO$_{4(s)}$, filtered and concentrated in vacuo to afford the title compound (57.2 mg, 41% yield over two steps) in sufficient purity for step 3. MS (apci) m/z=183.1 (M+H).

Step 3: Preparation of (S)-6-(2-hydroxy-2-methylpropoxy)-4-(6-(3-((6-methoxypyridin-3-yl)oxy)pyrrolidin-1-yl)pyridin-3-yl)pyrazolo[1,5-a]pyridine-3-carbonitrile To a mixture of 4-(6-fluoropyridin-3-yl)-6-(2-hydroxy-2-methylpropoxy)pyrazolo[1,5-a]pyridine-3-carbonitrile (Intermediate P42; 30.3 mg, 0.093 mmol) and (S)-5-fluoro-2-(pyrrolidin-3-yloxy)pyridine (55.8 mg, 0.31 mmol) in DMA (2 mL) was added TEA (63 L, 0.464 mmol). The reaction mixture was stirred 16 h at 90° C. After cooling to ambient temperature, the reaction mixture was diluted with EtOAc washed with water. Then the organic extracts were washed with brine and dried over anhydrous Na$_2$SO$_{4(s)}$, filtered and concentrated in vacuo. The reaction was purified by C18 reverse phase chromatography (5-95% ACN in water with 0.1% TFA as the gradient eluent) to afford the title compound as the TFA salt. The TFA salt was treated with saturated NaHCO$_{3(aq)}$ and extracted with 4:1 DCM:IPA. The combined organic extracts were dried over anhydrous Na$_2$SO$_{4(s)}$, filtered and concentrated in vacuo to afford the title compound (29.6 mg, 65% yield). MS (apci) m/z=489.2 (M+H).

Example 207

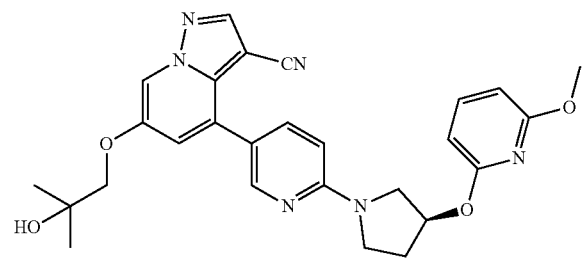 [SMILES: COc1cccc(O[C@H]2CCN(c3ccc(-c4cc(OCC(C)(C)O)cn5ncc(C#N)c45)cn3)C2)n1]

(S)-6-(2-hydroxy-2-methylpropoxy)-4-(6-(3-((6-methoxypyridin-2-yl)oxy)pyrrolidin-1-yl)pyridin-3-yl)pyrazolo[1,5-a]pyridine-3-carbonitrile Step 1: Preparation of tert-butyl (S)-3-((6-methoxypyridin-2-yl)oxy)pyrrolidine-1-carboxylate To a mixture of (S)-1-Boc-3-hydroxypyrrolidine (112.5 mg, 0.601 mmol) and 2-Chloro-6-methoxypyridine (86 μL, 0.721 mmol) in DMF (6 mL) was added sodium hydride (60% w/w, 48.1 mg, 1.20 mmol) and then the reaction mixture was stirred for 16 hours at 80° C. Additional sodium hydride (60% w/w, 48.1 mg, 1.20 mmol) was added and the reaction mixture was stirred for an additional 16 hours at 80° C. After cooling to ambient temperature, the reaction mixture was diluted with EtOAc and washed with water. Then the organic extracts were washed with brine and dried over anhydrous Na$_2$SO$_{4(s)}$, filtered and concentrated in vacuo. The residue was purified by silica chromatography (5-95% EtOAc in Hexanes as the gradient eluent) to afford the title compound as crude product that was directly used in the next step, assuming quantitative yield. MS (apci) m/z=195.1 (M-Boc).

Step 2: Preparation of (S)-2-methoxy-6-(pyrrolidin-3-yloxy)pyridine

To a solution of tert-butyl (S)-3-((6-methoxypyridin-2-yl)oxy)pyrrolidine-1-carboxylate (assumed 176.8 mg, 0.601 mmol) in 2 mL DCM was treated with TFA (2 mL). The reaction mixture was stirred for 15 min at ambient temperature, and then concentrated in vacuo. The crude residue was diluted with 4:1 DCM:IPA and washed with saturated NaHCO$_{3(aq)}$. The organic extracts were dried over anhydrous Na$_2$SO$_{4(s)}$, filtered and concentrated in vacuo to afford the title compound (81.6 mg, 70% yield over two steps) in sufficient purity for step 3. MS (apci) m/z=195.1 (M+H).

Step 3: Preparation of (S)-6-(2-hydroxy-2-methylpropoxy)-4-(6-(3-((6-methoxypyridin-2-yl)oxy)pyrrolidin-1-yl)pyridin-3-yl)pyrazolo[1,5-a]pyridine-3-carbonitrile To a mixture of 4-(6-fluoropyridin-3-yl)-6-(2-hydroxy-2-methylpropoxy)pyrazolo[1,5-a]pyridine-3-carbonitrile (Intermediate P42; 57.2 mg, 0.175 mmol) and (S)-2-methoxy-6-(pyrrolidin-3-yloxy)pyridine (71.5 mg, 0.368 mmol) in DMA (3 mL) was added TEA (64 μL, 0.472 mmol). The reaction mixture was stirred overnight at 80° C. After cooling to ambient temperature, the reaction mixture was diluted with EtOAc washed with water. Then the organic extracts were washed with brine and dried over anhydrous Na$_2$SO$_{4(s)}$, filtered and concentrated in vacuo. The reaction was purified by C18 reverse phase chromatography (5-95% ACN in water with 0.1% TFA as the gradient eluent) to afford the title compound as the TFA salt. The TFA salt was treated with saturated NaHCO$_{3(aq)}$ and extracted with 4:1 DCM:IPA. The combined organic extracts were dried over anhydrous Na$_2$SO$_{4(s)}$, filtered and concentrated in vacuo to afford the title compound (56.6 mg, 65% yield). MS (apci) m/z=501.2 (M+H).

Example 208

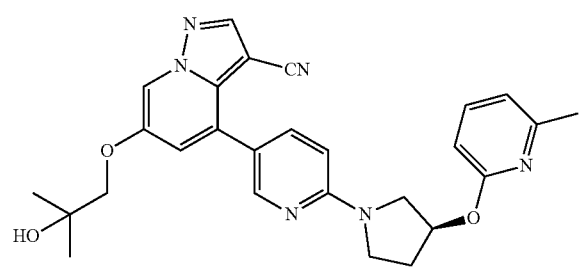 [SMILES: Cc1cccc(O[C@H]2CCN(c3ccc(-c4cc(OCC(C)(C)O)cn5ncc(C#N)c45)cn3)C2)n1]

(S)-6-(2-hydroxy-2-methylpropoxy)-4-(6-(3-((6-methylpyridin-2-yl)oxy)pyrrolidin-1-yl)pyridin-3-yl)pyrazolo[1,5-a]pyridine-3-carbonitrile Step 1: Preparation of tert-butyl (S)-3-((6-methylpyridin-2-yl)oxy)pyrrolidine-1-carboxylate To a mixture of (S)-1-Boc-3-hydroxypyrrolidine (112.5 mg, 0.601 mmol) and 2-chloro-6-methylpyridine (74 μL, 0.669 mmol) in DMF (6 mL) was added sodium hydride (60% w/w, 44.6 mg, 1.11 mmol) and then the reaction mixture was stirred for 16 hours at 80° C. Additional sodium hydride (60% w/w, 44.6 mg, 1.11 mmol) was added and the reaction mixture was stirred for an additional 16 hours at 80° C. After cooling to ambient temperature, the reaction mixture was diluted with EtOAc and washed with water. Then the organic extracts were washed with brine and dried over anhydrous $Na_2SO_{4(s)}$, filtered and concentrated in vacuo. The residue was purified by silica chromatography (5-95% EtOAc in Hexanes as the gradient eluent) to afford the title compound (assume theoretical yield, 155 mg, 0.557 mmol) in sufficient purity for step 2. MS (apci) m/z=279.1 (M+H).

Step 2: Preparation of (S)-2-methyl-6-(pyrrolidin-3-yloxy)pyridine

To a solution of tert-butyl (S)-3-((6-methylpyridin-2-yl)oxy)pyrrolidine-1-carboxylate (assumed 155 mg, 0.557 mmol) in 2 mL DCM was treated with TFA (2 mL, 26 mmol). The reaction mixture was stirred for 15 min at ambient temperature, and then concentrated in vacuo. The crude residue was diluted with 4:1 DCM:IPA and washed with saturated $NaHCO_{3(aq)}$. The organic extracts were dried over anhydrous $Na_2SO_{4(s)}$, filtered and concentrated in vacuo to afford the title compound (81.6 mg, 70% yield over two steps) in sufficient purity for step 3. MS (apci) m/z=179.1 (M+H).

Step 3: Preparation of (S)-6-(2-hydroxy-2-methylpropoxy)-4-(6-(3-((6-methylpyridin-2-yl)oxy)pyrrolidin-1-yl)pyridin-3-yl)pyrazolo[1,5-a]pyridine-3-carbonitrile To a mixture of 4-(6-fluoropyridin-3-yl)-6-(2-hydroxy-2-methylpropoxy)pyrazolo[1,5-a]pyridine-3-carbonitrile (Intermediate P42; 53.3 mg, 0.163 mmol) and (S)-2-methyl-6-(pyrrolidin-3-yloxy)pyridine (69.9 mg, 0.392 mmol) in DMA (2 mL) was added TEA (111 µL, 0.817 mmol). The reaction mixture was stirred overnight at 80° C. After cooling to ambient temperature, the reaction mixture was diluted with EtOAc washed with water. Then the organic extracts were washed with brine and dried over anhydrous $Na_2SO_{4(s)}$, filtered and concentrated in vacuo. The residue was purified by silica chromatography 1-30% MeOH in EtOAc with 0.1-2% $NH_4OH$ as the gradient eluent) to cleanly provide the title compound (60.8 mg, 76.8% yield) MS (apci) m/z=485.2 (M+H)

Example 209

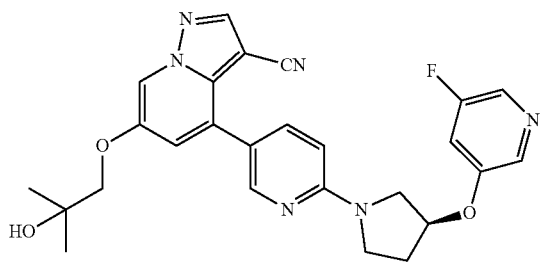 [SMILES: CC(C)(O)COc1cc(-c2ccc(N3CC[C@H](Oc4cncc(F)c4)C3)nc2)c2c(C#N)cnn2c1]

(S)-4-(6-(3-((5-fluoropyridin-3-yl)oxy)pyrrolidin-1-yl)pyridin-3-yl)-6-(2-hydroxy-2-methylpropoxy)pyrazolo[1,5-a]pyridine-3-carbonitrile Step 1: Preparation of tert-butyl (S)-3-((5-fluoropyridin-3-yl)oxy)pyrrolidine-1-carboxylate To a mixture of tert-butyl (R)-3-((methylsulfonyl)oxy)pyrrolidine-1-carboxylate (Intermediate R14; 301.5 mg, 1.136 mmol) and 5-fluoropyridin-3-ol (154.2 mg, 1.364 mmol) in DMF (11 mL) was added potassium carbonate (314.1 mg, 2.273 mmol) and then the reaction mixture was stirred for 16 hours at 80° C. After cooling to ambient temperature, the reaction mixture was diluted with EtOAc washed with water. Then the organic extracts were washed with brine and dried over anhydrous $Na_2SO_{4(s)}$, filtered and concentrated in vacuo. The residue was purified by silica chromatography (5-95% EtOAc in Hexanes as the gradient eluent) to afford the title compound (assume theoretical yield, 320.7 mg, 1.136 mmol) in sufficient purity for step 2. MS (apci) m/z=183.1 (M-Boc).

Step 2: Preparation of (S)-3-fluoro-5-(pyrrolidin-3-yloxy)pyridine

To a solution tert-butyl (S)-3-((5-fluoropyridin-3-yl)oxy)pyrrolidine-1-carboxylate (assumed 320.7 mg, 1.136 mmol) in 2.5 mL DCM was treated with TFA (2.5 mL, 32.7 mmol). The reaction mixture was stirred for 15 min at ambient temperature, and then concentrated in vacuo. The crude residue was diluted with 4:1 DCM:IPA and washed with saturated $NaHCO_{3(aq)}$. The organic extracts were dried over anhydrous $Na_2SO_{4(s)}$, filtered and concentrated in vacuo to afford the title compound (57.2 mg, 41% yield over two steps) in sufficient purity for step 3. MS (apci) m/z=183.1 (M+H).

Step 3: Preparation of (S)-4-(6-(3-((5-fluoropyridin-3-yl)oxy)pyrrolidin-1-yl)pyridin-3-yl)-6-(2-hydroxy-2-methylpropoxy)pyrazolo[1,5-a]pyridine-3-carbonitrile To a mixture of 4-(6-fluoropyridin-3-yl)-6-(2-hydroxy-2-methylpropoxy)pyrazolo[1,5-a]pyridine-3-carbonitrile (Intermediate P42; 32.7 mg, 0.10 mmol) and (S)-3-fluoro-5-(pyrrolidin-3-yloxy)pyridine (48.4 mg, 0.266 mmol) in DMA (2 mL) was added TEA (68 L, 0.501 mmol). The reaction mixture was stirred 16 h at 90° C. After cooling to ambient temperature, the reaction mixture was diluted with EtOAc washed with water. Then the organic extracts were washed with brine and dried over anhydrous $Na_2SO_{4(s)}$, filtered and concentrated in vacuo. The residue was purified by silica chromatography 1-30% MeOH in EtOAc with 0.1-2% $NH_4OH$ as the gradient eluent) to cleanly provide the title compound (23 mg, 47% yield) MS (apci) m/z=489.2 (M+H)

Example 210

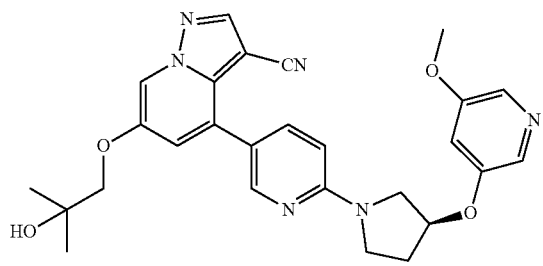 [SMILES: COc1cncc(O[C@H]2CCN(c3ccc(-c4cc(OCC(C)(C)O)cn5ncc(C#N)c45)cn3)C2)c1]

(S)-6-(2-hydroxy-2-methylpropoxy)-4-(6-(3-((5-methoxypyridin-3-yl)oxy)pyrrolidin-1-yl)pyridin-3-yl)pyrazolo[1,5-a]pyridine-3-carbonitrile

Step 1: Preparation of tert-butyl (S)-3-((5-methoxypyridin-3-yl)oxy)pyrrolidine-1-carboxylate To a mixture of tert-butyl (R)-3-((methylsulfonyl)oxy)pyrrolidine-1-carboxylate (Intermediate R14; 301.6 mg, 1.137 mmol) and 5-methoxypyridin-3-ol (170.7 mg, 1.364 mmol) in DMF (11 mL) was added potassium carbonate (314 mg, 2.273 mmol) and then the reaction mixture was stirred for 16 hours at 80° C. After cooling to ambient temperature, the reaction mixture was diluted with EtOAc washed with water. Then the organic extracts were washed with brine and dried over anhydrous $Na_2SO_{4(s)}$, filtered and concentrated in vacuo. The residue was purified by silica chromatography (5-95% EtOAc in Hexanes as the gradient eluent) to afford the title compound (assume theoretical yield, 334.7 mg, 1.137 mmol) in sufficient purity for step 2. MS (apci) m/z=239.1 (M-t-Bu fragment).

Step 2: Preparation of (S)-3-methoxy-5-(pyrrolidin-3-yloxy)pyridine

To a solution of tert-butyl (S)-3-((5-methoxypyridin-3-yl)oxy)pyrrolidine-1-carboxylate (assumed 334.7 mg, 1.137 mmol) in 2.5 mL DCM was treated with TFA (2.5 mL, 32.7 mmol). The reaction mixture was stirred for 15 min at ambient temperature, and then concentrated in vacuo. The crude residue was diluted with 4:1 DCM:IPA and washed with saturated $NaHCO_{3(aq)}$. The organic extracts were dried over anhydrous $Na_2SO_{4(s)}$, filtered and concentrated in vacuo to afford the title compound (59.4 mg, 26.9% yield over two steps) in sufficient purity for step 3. MS (apci) m/z=195.1 (M+H).

Step 3: Preparation of ((S)-6-(2-hydroxy-2-methylpropoxy)-4-(6-(3-((5-methoxypyridin-3-yl)oxy)pyrrolidin-1-yl)pyridin-3-yl)pyrazolo[1,5-a]pyridine-3-carbonitrile To a mixture of 4-(6-fluoropyridin-3-yl)-6-(2-hydroxy-2-methylpropoxy)pyrazolo[1,5-a]pyridine-3-carbonitrile (Intermediate P42; 30 mg, 0.092 mmol) and (S)-3-methoxy-5-(pyrrolidin-3-yloxy)pyridine (59.4 mg, 0.306 mmol) in DMA (2 mL) was added TEA (62 µL, 0.46 mmol). The reaction mixture was stirred 16 h at 90° C. After cooling to ambient temperature, the reaction mixture was diluted with EtOAc washed with water. Then the organic extracts were washed with brine and dried over anhydrous $Na_2SO_{4(s)}$, filtered and concentrated in vacuo. The residue was purified by silica chromatography 1-30% MeOH in EtOAc with 0.1-2% $NH_4OH$ as the gradient eluent) to cleanly provide the title compound (32.6 mg, 71% yield) MS (apci) m/z=501.2 (M+H)

Example 211

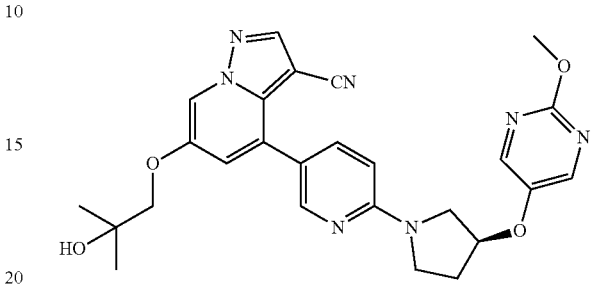

(S)-6-(2-hydroxy-2-methylpropoxy)-4-(6-(3-((2-methoxypyrimidin-5-yl)oxy)pyrrolidin-1-yl)pyridin-3-yl)pyrazolo[1,5-a]pyridine-3-carbonitrile

Step 1: Preparation of tert-butyl (S)-3-((2-methoxypyrimidin-5-yl)oxy)pyrrolidine-1-carboxylate To a mixture of tert-butyl (R)-3-((methylsulfonyl)oxy)pyrrolidine-1-carboxylate (Intermediate R14; 374.0 mg, 1.410 mmol) and 2-methoxypyrimidine-5-ol (213.3 mg, 1.692 mmol) in DMF (14 mL) was added potassium carbonate (390 mg, 2.819 mmol) and then the reaction mixture was stirred for 60 hours at 80° C. After cooling to ambient temperature, the reaction mixture was diluted with EtOAc washed with water. Then the organic extracts were washed with brine and dried over anhydrous $Na_2SO_{4(s)}$, filtered and concentrated in vacuo. The residue was purified by silica chromatography (5-95% EtOAc in Hexanes as the gradient eluent) to afford the title compound (assume theoretical yield, 416.4 mg, 1.410 mmol) in sufficient purity for step 2. MS (apci) m/z=196.1 (M-Boc).

Step 2: Preparation of and (S)-2-methoxy-5-(pyrrolidin-3-yloxy)pyrimidine

To a solution of tert-butyl (S)-3-((2-methoxypyrimidin-5-yl)oxy)pyrrolidine-1-carboxylate (assumed 416.4 mg, 1.410 mmol) in 2 mL DCM was treated with TFA (2 mL, 26 mmol). The reaction mixture was stirred for 15 min at ambient temperature, and then concentrated in vacuo. The crude residue was diluted with 4:1 DCM:IPA and washed with saturated $NaHCO_{3(aq)}$. The organic extracts were dried over anhydrous $Na_2SO_{4(s)}$, filtered and concentrated in vacuo to afford the title compound (61.7 mg, 20% yield over two steps) in sufficient purity for step 3. MS (apci) m/z=196.1 (M+H).

Step 3: Preparation of (S)-6-(2-hydroxy-2-methylpropoxy)-4-(6-(3-((2-methoxypyrimidin-5-yl)oxy)pyrrolidin-1-yl)pyridin-3-yl)pyrazolo[1,5-a]pyridine-3-carbonitrile To a mixture of 4-(6-fluoropyridin-3-yl)-6-(2-hydroxy-2-methylpropoxy)pyrazolo[1,5-a]pyridine-3-carbonitrile (Intermediate P42; 31.7 mg, 0.097 mmol) and (S)-2-methoxy- 5-(pyrrolidin-3-yloxy)pyrimidine (60.7 mg, 0.311 mmol) in DMA (2 mL) was added TEA (79 L, 0.58 mmol). The reaction mixture was stirred 16 h at 80° C. The reaction mixture was stirred at 80° C. for 16 hours. The reaction was heated to 100° C. for 60 hours. The reaction was heated to 150° C. for 2 hours in a microwave reactor. The reaction was heated to 150° C. for 8 hours in a microwave reactor. After cooling to ambient temperature, the reaction mixture was diluted with EtOAc washed with water. Then the organic extracts were washed with brine and dried over anhydrous $Na_2SO_{4(s)}$, filtered and concentrated in vacuo. The reaction was purified by C18 reverse phase chromatography (5-95% ACN in water with 0.1% TFA as the gradient eluent) to afford the title compound as the TFA salt. The TFA salt was treated with saturated $NaHCO_{3(aq)}$ and extracted with 4:1 DCM:IPA. The combined organic extracts were dried over anhydrous $Na_2SO_{4(s)}$, filtered and concentrated in vacuo to afford the title compound (16.6 mg, 34% yield). MS (apci) m/z=502.3 (M+H).

Example 212

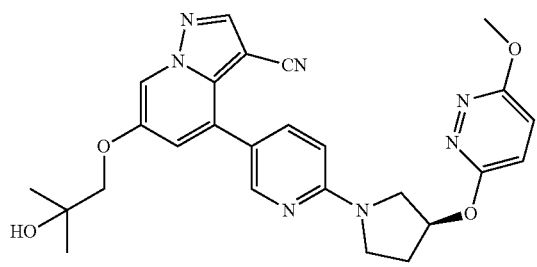 [SMILES: COc1ccc(O[C@H]2CCN(c3ccc(-c4cc(OCC(C)(C)O)cn5ncc(C#N)c45)cn3)C2)nn1]

(S)-6-(2-hydroxy-2-methylpropoxy)-4-(6-(3-((6-methoxypyridazin-3-yl)oxy)pyrrolidin-1-yl)pyridin-3-yl)pyrazolo[1,5-a]pyridine-3-carbonitrile Step 1: Preparation of tert-butyl (S)-3-((6-methoxypyridazin-3-yl)oxy)pyrrolidine-1-carboxylate To a mixture of (S)-1-Boc-3-hydroxypyrrolidine (83.9 mg, 0.448 mmol) 3-Chloro-6-methoxypyridazine (77.7 mg, 0.538 mmol) in DMF (4.5 mL) was added sodium hydride (60% w/w, 35.8 mg, 0.896 mmol) and then the reaction mixture was stirred for 60 hours at 80° C. Additional sodium hydride (60% w/w, 35.8 mg, 0.896 mmol) was added and the reaction mixture was stirred for an additional 16 hours at 80° C. After cooling to ambient temperature, the reaction mixture was diluted with EtOAc and washed with water. Then the organic extracts were washed with brine and dried over anhydrous $Na_2SO_{4(s)}$, filtered and concentrated in vacuo. The residue was purified by silica chromatography (5-95% EtOAc in Hexanes as the gradient eluent) to afford the title compound (assume theoretical yield, 132 mg, 0.448 mmol) in sufficient purity for step 2. MS (apci) m/z=295.1 (M+H).

Step 2: Preparation of (S)-3-methoxy-6-(pyrrolidin-3-yloxy)pyridazine

To a solution of tert-butyl (S)-3-((6-methoxypyridazin-3-yl)oxy)pyrrolidine-1-carboxylate (assumed 132 mg, 0.448 mmol) in 2 mL DCM was treated with TFA (2 mL, 26 mmol). The reaction mixture was stirred for 15 min at ambient temperature, and then concentrated in vacuo. The crude residue was diluted with 4:1 DCM:IPA and washed with saturated $NaHCO_{3(aq)}$. The organic extracts were dried over anhydrous $Na_2SO_{4(s)}$, filtered and concentrated in vacuo to afford the title compound (17.6 mg, 20.1% yield over two steps) in sufficient purity for step 3.

Step 3: Preparation of (S)-6-(2-hydroxy-2-methylpropoxy)-4-(6-(3-((6-methoxypyridazin-3-yl)oxy)pyrrolidin-1-yl)pyridin-3-yl)pyrazolo[15-a]pyridine-3-carbonitrile To a mixture of 4-(6-fluoropyridin-3-yl)-6-(2-hydroxy-2-methylpropoxy)pyrazolo[1,5-a]pyridine-3-carbonitrile (Intermediate P42; 22.4 mg, 0.069 mmol) and (S)-3-methoxy-6-(pyrrolidin-3-yloxy)pyridazine (17.4 mg, 0.892 mmol) in DMA (3 mL) was added TEA (46 L, 0.343 mmol). The reaction mixture was stirred 16 h at 80° C. The reaction mixture was stirred for 60 h at 100° C. The reaction mixture was then stirred for 2 h at 150° C. in a microwave reactor. The reaction was heated for an additional 8 h at 150° C. in a microwave reactor. After cooling to ambient temperature, the reaction mixture was diluted with EtOAc washed with water. Then the organic extracts were washed with brine and dried over anhydrous $Na_2SO_{4(s)}$, filtered and concentrated in vacuo. The reaction was purified by C18 reverse phase chromatography (5-95% ACN in water with 0.1% TFA as the gradient eluent) to afford the title compound as the TFA salt. The TFA salt was treated with saturated $NaHCO_{3(aq)}$ and extracted with 4:1 DCM:IPA. The combined organic extracts were dried over anhydrous $Na_2SO_{4(s)}$, filtered and concentrated in vacuo to afford the title compound (6.3 mg, 18.3% yield). MS (apci) m/z=502.2 (M+H).

Example 213

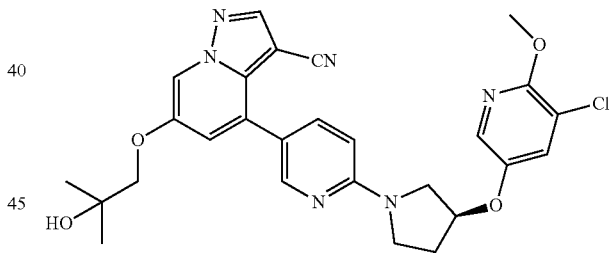

(S)-4-(6-(3-((5-chloro-6-methoxypyridin-3-yl)oxy)pyrrolidin-1-yl)pyridin-3-yl)-6-(2-hydroxy-2-methylpropoxy)pyrazolo[1,5-a]pyridine-3-carbonitrile Step 1: Preparation of tert-butyl (S)-3-((5-chloro-6-methoxypyridin-3-yl)oxy)pyrrolidine-1-carboxylate To a mixture of tert-butyl (R)-3-((methylsulfonyl)oxy)pyrrolidine-1-carboxylate (Intermediate R14; 602.2 mg, 2.27 mmol) and 3-Chloro-5-hydroxy-2-methoxypyridine (301.8 mg, 1.891 mmol) in DMF (22 mL) was added potassium carbonate (522.8 mg, 3.783 mmol) and then the reaction mixture was stirred for 60 hours at 80° C. After cooling to ambient temperature, the reaction mixture was diluted with EtOAc washed with water. Then the organic extracts were washed with brine and dried over anhydrous $Na_2SO_{4(s)}$, filtered and concentrated in vacuo. The residue was purified by silica chromatography (5-95% EtOAc in Hexanes as the gradient eluent) to afford the title compound (assume theoretical yield, 621.7 mg, 1.891 mmol) in sufficient purity for step 2. MS (apci) m/z=229.1 (M-Boc).

Step 2: Preparation of (S)-3-chloro-2-methoxy-5-(pyrrolidin-3-yloxy)pyridine

To a solution tert-butyl (S)-3-((5-chloro-6-methoxypyridin-3-yl)oxy)pyrrolidine-1-carboxylate (assumed 621.7 mg, 1.891 mmol) in 2 mL DCM was treated with TFA (2 mL, 26 mmol). The reaction mixture was stirred for 15 min at ambient temperature, and then concentrated in vacuo. The crude residue was diluted with 4:1 DCM:IPA and washed with saturated $NaHCO_{3(aq)}$. The organic extracts were dried over anhydrous $Na_2SO_{4(s)}$, filtered and concentrated in vacuo to afford the title compound (140.6 mg, 32.5% yield over two steps) in sufficient purity for step 3. MS (apci) m/z=229.10 (M+H).

Step 3: Preparation of (S)-4-(6-(3-((5-chloro-6-methoxypyridin-3-yl)oxy)pyrrolidin-1-yl)pyridin-3-yl)-6-(2-hydroxy-2-methylpropoxy)pyrazolo[1,5-a]pyridine-3-carbonitrile To a mixture of 4-(6-fluoropyridin-3-yl)-6-(2-hydroxy-2-methylpropoxy)pyrazolo[1,5-a]pyridine-3-carbonitrile (Intermediate P42; 26.4 mg, 0.081 mmol) and (S)-3-chloro-2-methoxy-5-(pyrrolidin-3-yloxy)pyridine (64.7 mg, 0.283 mmol) in DMA (1 mL) was added TEA (66 µL, 0.49 mmol). The reaction mixture was stirred 16 h at 80° C. After cooling to ambient temperature, the reaction mixture was diluted with EtOAc washed with water. Then the organic extracts were washed with brine and dried over anhydrous $Na_2SO_4$(s), filtered and concentrated in vacuo. The reaction was purified by C18 reverse phase chromatography (5-95% ACN in water with 0.1% TFA as the gradient eluent) to afford the title compound as the TFA salt. The TFA salt was treated with saturated $NaHCO_{3(aq)}$ and extracted with 4:1 DCM:IPA. The combined organic extracts were dried over anhydrous $Na_2SO_{4(s)}$, filtered and concentrated in vacuo to afford the title compound (27.2 mg, 63% yield). MS (apci) m/z=535.2 (M+H).

Example 214

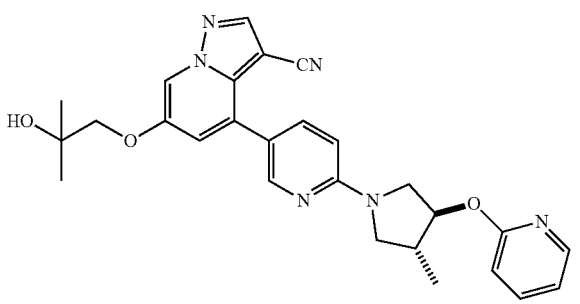 [SMILES: C[C@@H]1CN(c2ccc(-c3cc(OCC(C)(C)O)cn4ncc(C#N)c34)cn2)C[C@H]1Oc1ccccn1]

6-(2-hydroxy-2-methylpropoxy)-4-(6-((trans)-3-methyl-4-(pyridin-2-yloxy)pyrrolidin-1-yl)pyridin-3-yl)pyrazolo[1,5-a]pyridine-3-carbonitrile Step 1: Preparation of tert-butyl (trans)-3-methyl-4-(pyridin-2-yloxy)pyrrolidine-1-carboxylate To a mixture of tert-butyl (trans)-3-hydroxy-4-methylpyrrolidine-1-carboxylate (303.8 mg, 1.509 mmol) and 2-fluoropyridine (259 µL, 3.019 mmol) in DMA (7.5 mL) was added sodium hydride (60% w/w, 120.7 mg, 3.019 mmol). The reaction mixture was stirred for 16 h at 80° C. After cooling to ambient temperature, the reaction mixture was diluted with EtOAc and washed with water. Then the organic extracts were washed with brine and dried over anhydrous $Na_2SO_4$(s), filtered and concentrated in vacuo. The residue was purified by silica chromatography (5-50% EtOAc in hexanes as the gradient eluent) to afford the title compound (assume theoretical yield, 420 mg, 1.509 mmol) in sufficient purity for step 2. MS (apci) m/z=279.1 (M+H).

Step 2: Preparation of 2-(((trans)-4-methylpyrrolidin-3-yl)oxy)pyridine

To a solution of tert-butyl (trans)-3-hydroxy-4-methylpyrrolidine-1-carboxylate (assumed 420 mg, 1.509 mmol) in 3 mL DCM was treated with TFA (3 mL, 39.2 mmol). The reaction mixture was stirred for 15 min at ambient temperature, and then concentrated in vacuo. The crude residue was diluted with 4:1 DCM:IPA and washed with saturated $NaHCO_{3(aq)}$. The organic extracts were dried over anhydrous $Na_2SO_{4(s)}$, filtered and concentrated in vacuo to afford the title compound (178.6 mg, 66% yield over two steps) in sufficient purity for step 3. MS (apci) m/z=179.1 (M+H).

Step 3: Preparation of 6-(2-hydroxy-2-methylpropoxy)-4-(6-((trans)-3-methyl-4-(pyridin-2-yloxy)pyrrolidin-1-yl)pyridin-3-yl)pyrazolo[1,5-a]pyridine-3-carbonitrile To a mixture of 4-(6-fluoropyridin-3-yl)-6-(2-hydroxy-2-methylpropoxy)pyrazolo[1,5-a]pyridine-3-carbonitrile (Intermediate P42; 35 mg, 0.107 mmol) and 2-(((trans)-4-methylpyrrolidin-3-yl)oxy)pyridine (76.5 mg, 0.428 mmol) in DMA (1.1 mL) was added TEA (145 L, 1.07 mmol). The reaction mixture was stirred 16 h at 90° C. After cooling to ambient temperature, the reaction mixture was diluted with water and extracted with EtOAc. The organic extracts were washed with water. Then the organic extracts were washed with brine and dried over anhydrous $Na_2SO_4$(s), filtered and concentrated in vacuo. The reaction was purified by C18 reverse phase chromatography (5-95% ACN in water with 0.1% TFA as the gradient eluent) to afford the title compound as the TFA salt. The TFA salt was treated with saturated $NaHCO_{3(aq)}$ and extracted with 4:1 DCM:IPA. The combined organic extracts were dried over anhydrous $Na_2SO_4$(s), filtered and concentrated in vacuo to afford the title compound (38.2 mg, 73.5% yield). MS (apci) m/z=485.2 (M+H).

Example 215

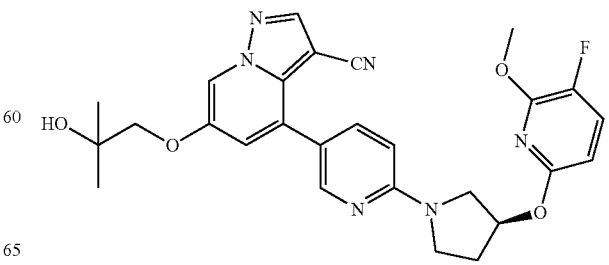

(S)-4-(6-(3-((5-fluoro-6-methoxypyridin-2-yl)oxy) pyrrolidin-1-yl)pyridin-3-yl)-6-(2-hydroxy-2-methylpropoxy)pyrazolo[1,5-a]pyridine-3-carbonitrile Step 1: Preparation of 3,6-difluoro-2-methoxypyridine To a solution of 2,3,6-Trifluoropyridine (1.00 mL, 11.27 mmol) in MeOH (11 mL) was added sodium methoxide (30% solution in MeOH, 2.5 mL), 13.5 mmol). The reaction solution was stirred for 2 h at 70° C. After cooling to ambient temperature, the reaction mixture was diluted with EtOAc and washed with water. Then the organic extracts were washed with brine and dried over anhydrous $Na_2SO_4(s)$, filtered and concentrated in vacuo to afford the title compound (257 mg, 16% yield) in sufficient purity for step 2. $^1$H NMR (400 MHz, DMSO-$d_6$) δ 7.90-7.84 (m, 1H), 6.75-6.72 (m, 1H), 3.92 (s, 3H).

Step 2: Preparation of tert-butyl (S)-3-((5-fluoro-6-methoxypyridin-2-yl)oxy)pyrrolidine-1-carboxylate A solution of (S)-1-Boc-3-hydroxypyrrolidine (255 mg, 1.362 mmol) in 13.6 mL DMF was treated with 3,6-difluoro-2-methoxypyridine (256.9 mg, 1.77 mmol) followed by sodium hydride (60% w/w, 163.4 mg, 4.086 mmol). The reaction mixture was stirred for 16 h at 80° C. After cooling to ambient temperature, the reaction mixture was diluted with water and extracted with EtOAc. The organic extracts were washed with water. Then the organic extracts were washed with brine and dried over anhydrous $Na_2SO_4(s)$, filtered and concentrated in vacuo. The residue was purified by silica chromatography (5-40% EtOAc in Hexanes as the gradient eluent) to afford the title compound (assume theoretical yield, 425 mg, 1.362 mmol) in sufficient purity for step 3. MS (apci) m/z=213.1 (M-Boc).

Step 3: Preparation of (S)-3-fluoro-2-methoxy-6-(pyrrolidin-3-yloxy)pyridine

To a solution of tert-butyl (S)-3-((5-fluoro-6-methoxypyridin-2-yl)oxy)pyrrolidine-1-carboxylate (assumed 425 mg, 1.362 mmol) in 3 mL DCM was treated with TFA (3 mL, 39 mmol). The reaction mixture was stirred for 30 min at ambient temperature, and then concentrated in vacuo. The crude residue was diluted with 4:1 DCM:IPA and washed with saturated $NaHCO_{3(aq)}$. The organic extracts were dried over anhydrous $Na_2SO_{4(s)}$, filtered and concentrated in vacuo to afford the title compound (222.2 mg, 77% yield over two steps) in sufficient purity for step 4. MS (apci) m/z=213.1 (M+H).

Step 4: Preparation of (S)-4-(6-(3-((5-fluoro-6-methoxypyridin-2-yl)oxy)pyrrolidin-1-yl)pyridin-3-yl)-6-(2-hydroxy-2-methylpropoxy)pyrazolo[1,5-a] pyridine-3-carbonitrile To a solution of 4-(6-fluoropyridin-3-yl)-6-(2-hydroxy-2-methylpropoxy)pyrazolo[1,5-a]pyridine-3-carbonitrile (Intermediate P42; 35.2 mg, 0.108 mmol) in DMA (1.1 mL) was added (S)-3-fluoro-2-methoxy-6-(pyrrolidin-3-yloxy) pyridine (91.6 mg, 0.431 mmol) followed by TEA (145 µL, 1.07 mmol). The reaction mixture was stirred for 16 h at 90° C. After cooling to ambient temperature, the reaction mixture was diluted with water and extracted with EtOAc. The organic extracts were washed with water. Then the organic extracts were washed with brine and dried over anhydrous $Na_2SO_4(s)$, filtered and concentrated in vacuo. The reaction was purified by C18 reverse phase chromatography (5-95% ACN in water with 0.1% TFA as the gradient eluent) to afford the title compound as the TFA salt. The TFA salt was treated with saturated $NaHCO_{3(aq)}$ and extracted with 4:1 DCM:IPA. The combined organic extracts were dried over anhydrous Na2SO4(s), filtered and concentrated in vacuo to afford the title compound (44.8 mg, 80.1% yield). MS (apci) m/z=519.2 (M+H).

Example 216

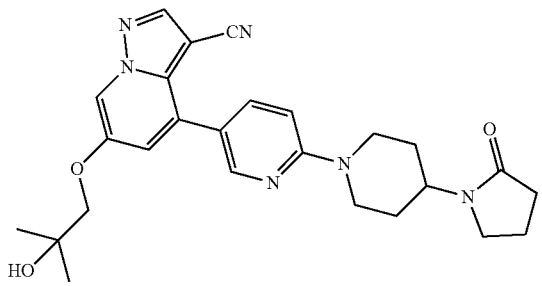 [SMILES: CC(C)(O)COc1cc(-c2ccc(N3CCC(N4CCCC4=O)CC3)nc2)c2c(C#N)cnn2c1]

6-(2-hydroxy-2-methylpropoxy)-4-(6-(4-(2-oxopyrrolidin-1-yl)piperidin-1-yl)pyridin-3-yl)pyrazolo[1,5-a]pyridine-3-carbonitrile To a solution of 4-(6-fluoropyridin-3-yl)-6-(2-hydroxy-2-methylpropoxy)pyrazolo[1,5-a]pyridine-3-carbonitrile (Intermediate P42; 29 mg, 0.09 mmol) and 1-(4-Piperidinyl)-2-pyrrolidinone (30 mg, 0.18 mmol) in DMA (2 mL) was added TEA (61 µL, 0.45 mmol). The reaction mixture was stirred 16 h at 80° C. After cooling to ambient temperature, additional and 1-(4-piperidinyl)-2-pyrrolidinone (30 mg, 0.18 mmol) was added and reaction was stirred 16 h at 80° C. After cooling to ambient temperature, the reaction mixture was diluted with EtOAc and washed with water and brine. The organic extracts were concentrated in vacuo. The residue was purified by C18 reverse phase chromatography (5-95% ACN in water with 0.1% TFA as the gradient eluent) to afford the title compound as the TFA salt. The TFA salt was treated with saturated $NaHCO_{3(aq)}$ and extracted with 4:1 DCM:IPA. The combined organic extracts were dried over anhydrous $Na_2SO_{4(s)}$, filtered and concentrated in vacuo to afford the title compound (14.1 mg, 33% yield). MS (apci) m/z=475.2 (M+H).

Example 217

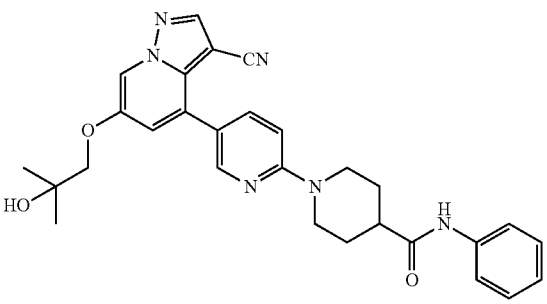 [SMILES: CC(C)(O)COc1cc(-c2ccc(N3CCC(C(=O)Nc4ccccc4)CC3)nc2)c2c(C#N)cnn2c1]

1-(5-(3-cyano-6-(2-hydroxy-2-methylpropoxy)pyrazolo[1,5-a]pyridin-4-yl)pyridin-2-yl)-N-phenylpiperidine-4-carboxamide

Step 1: Preparation of tert-butyl 4-(phenylcarbamoyl)piperidine-1-carboxylate A mixture of Boc-Inp-OH (253 mg, 1.10 mmol), HATU (504 mg, 1.33 mmol), and aniline (111 μL, 1.22 mmol) in DCM (11 mL) was treated with DIEA (385 μL, 2.21 mmol) and then stirred for 12 h at ambient temperature. The reaction mixture was concentrated in vacuo and the residue was purified by silica chromatography (5-95% EtOAc in Hexanes as the gradient eluent) to afford the title compound (assumed theoretical yield, 338 mg) in sufficient purity for step 2. MS (apci) m/z=205.1 (M-Boc).

Step 2: Preparation of N-phenylpiperidine-4-carboxamide

To a solution of tert-butyl 4-(phenylcarbamoyl)piperidine-1-carboxylate (assumed 338 mg, 1.104 mmol) in 2 mL DCM was treated with TFA (2 mL, 26 mmol). The reaction mixture was stirred for 30 min at ambient temperature, and then concentrated in vacuo. The crude residue was diluted with 4:1 DCM:IPA and washed with saturated $NaHCO_{3(aq)}$. The organic extracts were dried over anhydrous $Na_2SO_{4(s)}$, filtered and concentrated in vacuo to afford the title compound (67 mg, 30% yield over two steps) in sufficient purity for step 3. MS (apci) m/z=205.1 (M+H).

Step 3: Preparation of 1-(5-(3-cyano-6-(2-hydroxy-2-methylpropoxy)pyrazolo[1,5-a]pyridin-4-yl)pyridin-2-yl)-N-phenylpiperidine-4-carboxamide To a solution of 4-(6-fluoropyridin-3-yl)-6-(2-hydroxy-2-methylpropoxy)pyrazolo[1,5-a]pyridine-3-carbonitrile (Intermediate P42; 28 mg, 0.09 mmol) and N-phenylpiperidine-4-carboxamide (66 mg, 0.32 mmol) in DMA (0.5 mL) was added TEA (59 μL, 0.43 mmol). The reaction mixture was stirred 16 h at 80° C. After cooling to ambient temperature, additional TEA (59 μL, 0.43 mmol) was added and reaction was stirred 16 h at 90° C. After cooling to ambient temperature, the reaction mixture was diluted with EtOAc and washed with water and brine. The organic extracts were concentrated in vacuo. The residue was purified by C18 reverse phase chromatography (5-95% ACN in water with 0.1% TFA as the gradient eluent) to afford the title compound as the TFA salt. The TFA salt was treated with saturated $NaHCO_{3(aq)}$ and extracted with 4:1 DCM:IPA. The combined organic extracts were dried over anhydrous $Na_2SO_{4(s)}$, filtered and concentrated in vacuo to afford the title compound (21 mg, 47% yield). MS (apci) m/z=511.2 (M+H).

Example 218

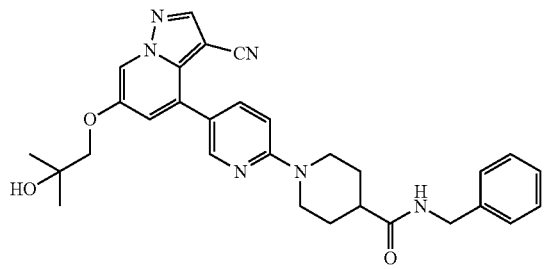 [SMILES: CC(C)(O)COc1cc(-c2ccc(N3CCC(C(=O)NCc4ccccc4)CC3)nc2)c2c(C#N)cnn2c1]

N-benzyl-1-(5-(3-cyano-6-(2-hydroxy-2-methylpropoxy)pyrazolo[1,5-a]pyridin-4-yl)pyridin-2-yl)piperidine-4-carboxamide

Step 1: Preparation of tert-butyl 4-(benzylcarbamoyl)piperidine-1-carboxylate A mixture of Boc-Inp-OH (250 mg, 1.09 mmol), HATU (498 mg, 1.31 mmol), and benzylamine (131 μL, 1.20 mmol) in DCM (11 mL) was treated with DIEA (380 μL, 2.18 mmol) and then stirred for 60 h at ambient temperature. The reaction mixture was concentrated in vacuo and the residue was purified by silica chromatography (5-95% EtOAc in Hexanes as the gradient eluent) to afford the title compound (assumed theoretical yield, 347 mg) in sufficient purity for step 2. MS (apci) m/z=219.1 (M-Boc).

Step 2: Preparation of N-benzylpiperidine-4-carboxamide

To a solution of tert-butyl 4-(benzylcarbamoyl)piperidine-1-carboxylate (assumed 347 mg, 1.09 mmol) in 2 mL DCM was treated with TFA (2 mL, 26 mmol). The reaction mixture was stirred for 30 min at ambient temperature, and then concentrated in vacuo. The crude residue was diluted with 4:1 DCM:IPA and washed with saturated $NaHCO_{3(aq)}$. The organic extracts were dried over anhydrous $Na_2SO_{4(s)}$, filtered and concentrated in vacuo to afford the title compound (33 mg, 14% yield over two steps) in sufficient purity for step 3. MS (apci) m/z=219.2 (M+H).

Step 3: Preparation of N-benzyl-1-(5-(3-cyano-6-(2-hydroxy-2-methylpropoxy)pyrazolo[1,5-a]pyridin-4-yl)pyridin-2-yl)piperidine-4-carboxamide To a solution of 4-(6-fluoropyridin-3-yl)-6-(2-hydroxy-2-methylpropoxy)pyrazolo[1,5-a]pyridine-3-carbonitrile (Intermediate P42; 19 mg, 0.06 mmol) and N-benzylpiperidine-4-carboxamide (33 mg, 0.15 mmol) in DMA (0.3 mL) was added TEA (40 μL, 0.29 mmol). The reaction mixture was stirred 16 h at 80° C. After cooling to ambient temperature, additional TEA (40 μL, 0.29 mmol) was added and reaction was stirred 16 h at 90° C. After cooling to ambient temperature, the reaction mixture was diluted with EtOAc and washed with water and brine. The organic extracts were concentrated in vacuo. The residue was purified by C18 reverse phase chromatography (5-95% ACN in water with 0.1% TFA as the gradient eluent) to afford the title compound as the TFA salt. The TFA salt was treated with saturated $NaHCO_{3(aq)}$ and extracted with 4:1 DCM:IPA. The combined organic extracts were dried over anhydrous $Na_2SO_{4(s)}$, filtered and concentrated in vacuo to afford the title compound (19 mg, 63% yield). MS (apci) m/z=525.2 (M+H).

Example 219

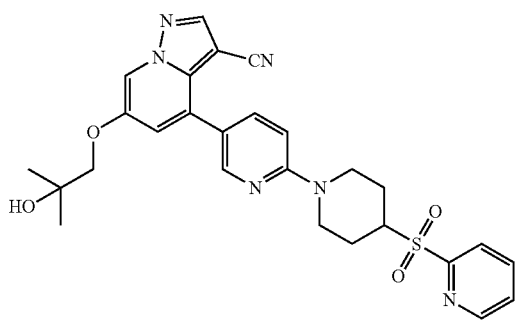 [SMILES: CC(C)(O)COc1cc(-c2ccc(N3CCC(S(=O)(=O)c4ccccn4)CC3)nc2)c2c(C#N)cnn2c1]

6-(2-hydroxy-2-methylpropoxy)-4-(6-(4-(pyridin-2-ylsulfonyl)piperidin-1-yl)pyridin-3-yl)pyrazolo[1,5-a]pyridine-3-carbonitrile

Step 1: Preparation of tert-butyl 4-(pyridin-2-ylthio)piperidine-1-carboxylate To a solution of tert-butyl 4-mercaptopiperidine-1-carboxylate (205 mg, 0.94 mmol) and 2-iodopyridine (263 mg, 1.28 mmol) in DMF (3.8 mL) was added potassium carbonate (521 mg, 3.8 mmol). The reaction mixture was stirred 16 h at 70° C. The reaction was heated 16 h at 90° C. After cooling to ambient temperature, the reaction mixture was diluted with EtOAc and washed with water and brine. The organic extracts were dried over anhydrous $Na_2SO_{4(s)}$, filtered and concentrated in vacuo. The residue was purified using silica chromatography (0-50% EtOAc in Hexanes as the gradient eluent) to afford the title compound (106.2 mg, 361 mmol) in sufficient purity for step 2. MS (apci) m/z=295.2 (M+H).

Step 2: Preparation of tert-butyl 4-(pyridin-2-ylsulfonyl)piperidine-1-carboxylate Tert-butyl 4-(pyridin-2-ylthio)piperidine-1-carboxylate (106 mg, 0.36 mmol) and 3-chlorobenzoperoxoic acid (187 mg, 1.08 mmol) were combined in DCM (3.6 mL) at 0° C. The reaction mixture was warmed to ambient temperature and stirred for 16 h. The reaction mixture was concentrated in vacuo. The residue was diluted with 4:1 DCM:IPA and was washed with saturated $NaHCO_{3(aq)}$. The organic extracts were concentrated in vacuo. The residue was purified by silica chromatography (0-95% EtOAc in Hexanes as the gradient eluent) to afford the title compound (assumed theoretical yield, 118 mg) in sufficient purity for step 3. MS (apci) m/z=227.1 (M-Boc).

Step 3: Preparation of 2-(piperidin-4-ylsulfonyl)pyridine

To a solution of tert-butyl 4-(pyridin-2-ylsulfonyl)piperidine-1-carboxylate (assumed 118 mg, 0.36 mmol) in 2 mL DCM was treated with TFA (2 mL, 26 mmol). The reaction mixture was stirred for 15 min at ambient temperature, and then concentrated in vacuo. The crude residue was diluted with 4:1 DCM:IPA and washed with saturated $NaHCO_{3(aq)}$. The organic extracts were concentrated in vacuo to afford the title compound (47 mg, 57% yield over two steps) in sufficient purity for step 4. MS (apci) m/z=227.1 (M+H).

Step 4: Preparation of 6-(2-hydroxy-2-methylpropoxy)-4-(6-(4-(pyridin-2-yl sulfonyl)piperidin-1-yl)pyridin-3-yl)pyrazolo[1,5-a]pyridine-3-carbonitrile To a solution of 4-(6-fluoropyridin-3-yl)-6-(2-hydroxy-2-methylpropoxy)pyrazolo[1,5-a]pyridine-3-carbonitrile (Intermediate P42; 27 mg, 0.08 mmol) and 2-(piperidin-4-ylsulfonyl)pyridine (57 mg, 0.25 mmol) in DMA (0.5 mL) was added TEA (57 µL, 0.42 mmol). The reaction mixture was stirred 60 h at 80° C. After cooling to ambient temperature, the reaction mixture was diluted with EtOAc and washed with water and brine. The combined organic extracts were dried over anhydrous $Na_2SO_{4(s)}$, filtered and concentrated in vacuo. The residue was purified by silica chromatography (0-100% EtOAc in Hexanes as the gradient eluent) to afford the title compound (20 mg, 46% yield). MS (apci) m/z=533.2 (M+H).

Example 220

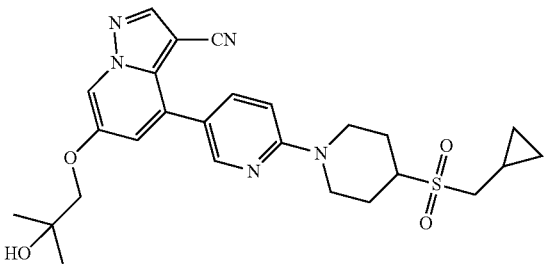 [SMILES: CC(C)(O)COc1cc(-c2ccc(N3CCC(S(=O)(=O)CC4CC4)CC3)nc2)c2c(C#N)cnn2c1]

4-(6-(4-((cyclopropylmethyl)sulfonyl)piperidin-1-yl)pyridin-3-yl)-6-(2-hydroxy-2-methylpropoxy)pyrazolo[1,5-a]pyridine-3-carbonitrile

Step 1: Preparation of tert-butyl 4-((cyclopropylmethyl)thio)piperidine-1-carboxylate To a solution of tert-butyl 4-mercaptopiperidine-1-carboxylate (222 mg, 1.02 mmol) and (Bromomethyl)cyclopropane (184 mg, 1.36 mmol) in DMF (4 mL) was added potassium carbonate (566 mg, 4.09 mmol). The reaction mixture was stirred 60 h at 70° C. After cooling to ambient temperature, the reaction mixture was diluted with EtOAc and washed with water and brine. The organic extracts were dried over anhydrous $Na_2SO_4(s)$, filtered and concentrated in vacuo. The residue was purified using silica chromatography (5-95% EtOAc in Hexanes as the gradient eluent) to afford the title compound (256 mg, 92% yield) in sufficient purity for the next step. $^1H$ NMR (400 MHz, DMSO-$d_6$) δ 3.81-3.77 (m, 2H), 2.92-2.86 (m, 2H), 2.48-2.47 (d, 2H), 1.89-1.85 (m, 2H), 1.38 (s, 9H), 1.33-1.23 (m, 2H), 0.93-0.89 (m, 1H), 0.51-0.47 (m, 2H), 0.19-0.16 (m, 2H).

Step 2: Preparation of tert-butyl 4-((cyclopropylmethyl)sulfonyl)piperidine-1-carboxylate Tert-butyl 4-((cyclopropylmethyl)thio)piperidine-1-carboxylate (256 mg, 0.94 mmol) and 3-chlorobenzoperoxoic acid (187 mg, 1.08 mmol) were combined in DCM (9.5 mL)

at 0° C. The reaction mixture was warmed to ambient temperature and stirred for 16 h. The reaction mixture was concentrated in vacuo. The residue was diluted with 4:1 DCM:IPA and was washed with saturated NaHCO$_{3(aq)}$. The organic extracts were concentrated in vacuo. The residue was purified by silica chromatography (0-95% EtOAc in Hexanes as the gradient eluent) to afford the title compound (assumed theoretical yield, 286 mg) in sufficient purity for step 3. MS (apci) m/z=204.1 (M-Boc).

Step 3: Preparation of 4-((cyclopropylmethyl)sulfonyl)piperidine

To a solution of tert-butyl 4-((cyclopropylmethyl)sulfonyl)piperidine-1-carboxylate (assumed 286 mg, 0.94 mmol) in 2 mL DCM was treated with TFA (2 mL, 26 mmol). The reaction mixture was stirred for 15 min at ambient temperature, and then concentrated in vacuo. The crude residue was diluted with 4:1 DCM:IPA and washed with saturated NaHCO$_{3(aq)}$. The organic extracts were concentrated in vacuo to afford the title compound (60 mg, 31% yield over two steps) in sufficient purity for step 4. MS (apci) m/z=204.1 (M+H).

Step 4: Preparation of 4-(6-(4-((cyclopropylmethyl)sulfonyl)piperidin-1-yl)pyridin-3-yl)-6-(2-hydroxy-2-methylpropoxy)pyrazolo[1,5-a]pyridine-3-carbonitrile To a solution of 4-(6-fluoropyridin-3-yl)-6-(2-hydroxy-2-methylpropoxy)pyrazolo[1,5-a]pyridine-3-carbonitrile (Intermediate P42; 28.1 mg, 0.08 mmol) and of 4-((cyclopropylmethyl)sulfonyl)piperidine (53 mg, 0.26 mmol) in DMA (0.5 mL) was added TEA (44 µL, 0.43 mmol). The reaction mixture was stirred 60 h at 80° C. After cooling to ambient temperature, the reaction mixture was diluted with EtOAc and washed with water and brine. The combined organic extracts were dried over anhydrous Na$_2$SO$_{4(s)}$, filtered and concentrated in vacuo. The residue was purified by silica chromatography (0-100% EtOAc in Hexanes as the gradient eluent). Fractions containing the product were concentrated in vacuo. Residue was purified by silica chromatography (0-95% EtOAc in Hexanes as the gradient eluent) and product-containing fractions were concentrated in vacuo. Residue was purified by C18 reverse phase chromatography (5-95% ACN in water with 0.1% TFA as the gradient eluent) to afford the title compound as the TFA salt. The TFA salt was treated with saturated NaHCO$_{3(aq)}$ and extracted with 4:1 DCM:IPA. The combined organic extracts were dried over anhydrous Na$_2$SO$_{4(s)}$, filtered and concentrated in vacuo to afford the title compound (21 mg, 48% yield). MS (apci) m/z=510.2 (M+H).

Example 221

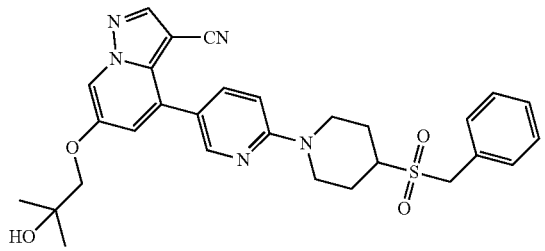 [SMILES: CC(C)(O)COc1cc(-c2ccc(N3CCC(S(=O)(=O)Cc4ccccc4)CC3)nc2)c2c(C#N)cnn2c1]

4-(6-(4-(benzyl sulfonyl)piperidin-1-yl)pyridin-3-yl)-6-(2-hydroxy-2-methylpropoxy)pyrazolo[1,5-a]pyridine-3-carbonitrile Step 1: Preparation of tert-butyl 4-(benzylthio)piperidine-1-carboxylate To a solution of tert-butyl 4-mercaptopiperidine-1-carboxylate (211 mg, 0.97 mmol) and Benzyl bromide (200 mg, 1.17 mmol) in DMF (3.9 mL) was added potassium carbonate (537 mg, 3.89 mmol). The reaction mixture was stirred 60 h at 70° C. After cooling to ambient temperature, the reaction mixture was diluted with EtOAc and washed with water and brine. The organic extracts were concentrated in vacuo. The residue was purified using silica chromatography (1-50% EtOAc in Hexanes as the gradient eluent) to afford the title compound (290 mg, 97% yield) in sufficient purity for step 2. MS (apci) m/z=208.1 (M-Boc).

Step 2: Preparation of tert-butyl 4-(benzylsulfonyl)piperidine-1-carboxylate

Tert-butyl 4-(benzylthio)piperidine-1-carboxylate (290 mg, 0.94 mmol) and 3-chlorobenzoperoxoic acid (489 mg, 1.08 mmol) were combined in DCM (9.5 mL) at 0° C. The reaction mixture was warmed to ambient temperature and stirred for 16 h. The reaction mixture was concentrated in vacuo. The residue was diluted with 4:1 DCM:IPA and was washed with saturated NaHCO$_{3(aq)}$. The organic extracts were concentrated in vacuo. The residue was purified by silica chromatography (0-95% EtOAc in Hexanes as the gradient eluent) to afford the title compound (assumed theoretical yield, 320 mg) in sufficient purity for step 3. MS (apci) m/z=240.1 (M-Boc).

Step 3: Preparation of 4-(benzylsulfonyl)piperidine

To a solution of tert-butyl 4-(benzylsulfonyl)piperidine-1-carboxylate (assumed 320 mg, 0.94 mmol) in 2 mL DCM was treated with TFA (2 mL, 26 mmol). The reaction mixture was stirred for 15 min at ambient temperature, and then concentrated in vacuo. The crude residue was diluted with 4:1 DCM:IPA and washed with saturated NaHCO$_{3(aq)}$. The organic extracts were concentrated in vacuo to afford the title compound (138 mg, 61% yield over two steps) in sufficient purity for step 4. MS (apci) m/z=240.1 (M+H).

Step 4: Preparation of 4-(6-(4-(benzylsulfonyl)piperidin-1-yl)pyridin-3-yl)-6-(2-hydroxy-2-methylpropoxy)pyrazolo[1,5-a]pyridine-3-carbonitrile To a solution of 4-(6-fluoropyridin-3-yl)-6-(2-hydroxy-2-methylpropoxy)pyrazolo[1,5-a]pyridine-3-carbonitrile (Intermediate P42; 24 mg, 0.074 mmol) and of 4-(benzylsulfonyl)piperidine (53 mg, 0.22 mmol) in DMA (0.5 mL) was added TEA (50 µL, 0.37 mmol). The reaction mixture was stirred 76 h at 80° C. After cooling to ambient temperature, the reaction mixture was diluted with EtOAc and washed with water and brine. The combined organic extracts were dried over anhydrous Na$_2$SO$_{4(s)}$, filtered and concentrated in vacuo. The residue was purified by silica chromatography (0-100% EtOAc in Hexanes as the gradient eluent). Fractions containing the product were concentrated in vacuo. Residue was purified by C18 reverse phase chromatography (5-95% ACN in water with 0.1% TFA as the gradient eluent) to afford the title compound as the TFA salt. The TFA salt was treated with saturated NaHCO$_{3(aq)}$ and extracted with 4:1 DCM:IPA. The combined organic extracts were dried over anhydrous Na$_2$SO$_{4(s)}$, filtered and concentrated in vacuo to afford the title compound (23 mg, 57% yield). MS (apci) m/z=546.2 (M+H).

Example 222

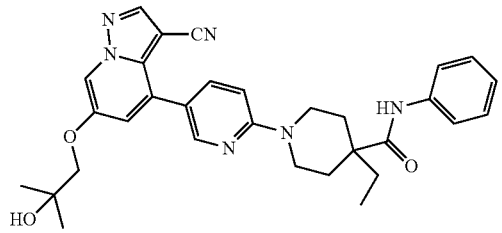 [SMILES: CCC1(C(=O)Nc2ccccc2)CCN(c2ccc(-c3cc(OCC(C)(C)O)cn4ncc(C#N)c34)cn2)CC1]

1-(5-(3-cyano-6-(2-hydroxy-2-methylpropoxy)pyrazolo[1,5-a]pyridin-4-yl)pyridin-2-yl)-4-ethyl-N-phenylpiperidine-4-carboxamide Step 1: Preparation of tert-butyl 4-ethyl-4-(phenylcarbamoyl)piperidine-1-carboxylate A mixture of 1-(tert-butoxycarbonyl)-4-ethylpiperidine-4-carboxylic acid (270 mg, 1.05 mmol), HATU (478 mg, 1.26 mmol), and aniline (105 μL, 1.15 mmol) in DMF (3.9 mL) was treated with DIEA (365 μL, 2.1 mmol) and then stirred for 60 h at 60° C. After cooling to ambient temperature, the reaction mixture was diluted with EtOAc and washed with water and brine. The combined organic extracts were dried over anhydrous Na$_2$SO$_{4(s)}$, filtered and concentrated in vacuo. The residue was purified by silica chromatography (0-100% EtOAc in Hexanes as the gradient eluent) to afford the title compound (assumed theoretical yield, 348 mg) in sufficient purity for step 2. MS (apci) m/z=233.2 (M-Boc).

Step 2: Preparation of 4-ethyl-N-phenylpiperidine-4-carboxamide

To a solution of tert-butyl 4-ethyl-4-(phenylcarbamoyl)piperidine-1-carboxylate (assumed 348 mg, 1.05 mmol) in 2 mL DCM was treated with TFA (2 mL, 26 mmol). The reaction mixture was stirred for 1 h at ambient temperature, and then concentrated in vacuo. The crude residue was diluted with 4:1 DCM:IPA and washed with saturated NaHCO$_{3(aq)}$. The organic extracts were dried over anhydrous Na$_2$SO$_{4(s)}$, filtered and concentrated in vacuo to afford the title compound (162 mg, 67% yield over two steps) in sufficient purity for step 3. MS (apci) m/z=233.1 (M+H).

Step 3: Preparation of 1-(5-(3-cyano-6-(2-hydroxy-2-methylpropoxy)pyrazolo[1,5-a]pyridin-4-yl)pyridin-2-yl)-4-ethyl-N-phenylpiperidine-4-carboxamide To a solution of 4-(6-fluoropyridin-3-yl)-6-(2-hydroxy-2-methylpropoxy)pyrazolo[1,5-a]pyridine-3-carbonitrile (Intermediate P42; 20 mg, 0.06 mmol) and 4-ethyl-N-phenylpiperidine-4-carboxamide (42 mg, 0.18 mmol) in DMA (0.24 mL) was added TEA (41 μL, 0.30 mmol). The reaction mixture was stirred 16 h at 90° C. After cooling to ambient temperature, the reaction mixture was diluted with EtOAc and washed with water and brine. The organic extracts were concentrated in vacuo. The residue was purified by C18 reverse phase chromatography (5-95% ACN in water with 0.1% TFA as the gradient eluent) to afford the title compound as the TFA salt. The TFA salt was treated with saturated NaHCO$_{3(aq)}$ and extracted with 4:1 DCM:IPA. The combined organic extracts were dried over anhydrous Na$_2$SO$_{4(s)}$, filtered and concentrated in vacuo. The residue was repurified using silica chromatography (0-100% EtOAc in Hexanes) to afford the title compound (27 mg, 82% yield). MS (apci) m/z=539.3 (M+H).

Example 223

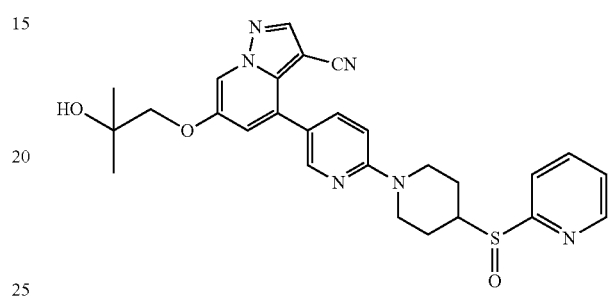

6-(2-hydroxy-2-methylpropoxy)-4-(6-(4-(pyridin-2-ylsulfinyl)piperidin-1-yl)pyridin-3-yl)pyrazolo[1,5-a]pyridine-3-carbonitrile 6-(2-hydroxy-2-methylpropoxy)-4-(6-(4-(pyridin-2-ylthio)piperidin-1-yl)pyridin-3-yl)pyrazolo[1,5-a]pyridine-3-carbonitrile (Intermediate P54, 27 mg, 0.054 mmol) and 3-chloroperoxybenzoic acid (93 mg, 0.54 mmol) were combined in EtOH (270 μL). The reaction was stirred overnight at ambient temperature. The reaction mixture was concentrated in vacuo. The residue was suspended in 60:40 ACN:water containing 2% TFA. The solution was purified directly by C18 reverse phase chromatography (5-95% ACN in water with 0.1% TFA as the gradient eluent) to afford the title compound as the TFA salt. The TFA salt was treated with saturated NaHCO$_{3(aq)}$ and extracted with DCM. The combined organic extracts were washed with brine, then dried over anhydrous Na$_2$SO$_{4(s)}$, filtered and concentrated in vacuo to afford the title compound (13.9 mg, 50% yield). MS (apci) m/z=517.2 (M+H).

Example 224

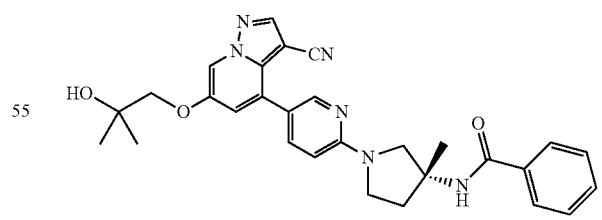

(R)—N-(1-(5-(3-cyano-6-(2-hydroxy-2-methylpropoxy)pyrazolo[1,5-a]pyridin-4-yl)pyridin-2-yl)-3-methylpyrrolidin-3-yl)benzamide A mixture of (R)-4-(6-(3-amino-3-methylpyrrolidin-1-yl)pyridin-3-yl)-6-(2-hydroxy-2-methylpropoxy)pyrazolo[1,5- a]pyridine-3-carbonitrile bis(2,2,2-trifluoroacetate)(Intermediate P49; 40 mg, 0.098 mmol), HATU (75 mg, 0.20 mmol), and benzoic acid (24 mg, 0.20 mmol) in ACN (600 µL) was treated with DIEA (86 µL, 0.49 mmol) and then stirred for 12 h at ambient temperature. The reaction mixture was diluted with 60:40 ACN:water containing 2% TFA. The solution was purified directly by C18 reverse phase chromatography (5-95% ACN in water with 0.1% TFA as the gradient eluent) to afford the title compound as the TFA salt. The TFA salt was treated with saturated NaHCO$_{3(aq)}$ and extracted with EtOAc. The combined organic extracts were washed with brine, then dried over anhydrous MgSO$_{4(s)}$, filtered and concentrated in vacuo to afford the title compound (15 mg, 46% yield). MS (apci) m/z=511.3 (M+H).

The compounds in Table JJ were prepared using a similar method to that described for the synthesis of Example 224, replacing benzoic acid with the appropriate carboxylic acid. Reactions were monitored for completion by LCMS, and reaction durations were adjusted accordingly. Title compounds were cleanly isolated following chromatographic purification using an appropriate gradient eluent (and if necessary converted to the free base).

TABLE JJ

| Ex. # | Structure | Chemical Name | LCMS m/z |
|---|---|---|---|
| 225 | 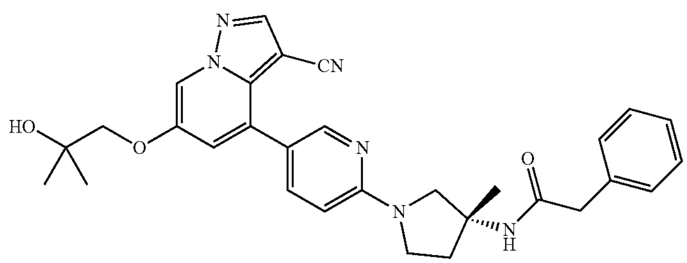 [SMILES: CC(C)(O)COc1cc(-c2ccc(N3CC[C@@](C)(NC(=O)Cc4ccccc4)C3)nc2)c2c(C#N)cnn2c1] | (R)-N-(1-(5-(3-cyano-6-(2-hydroxy-2-methylpropoxy)pyrazolo[1,5-a]pyridin-4-yl)pyridin-2-yl)-3-methylpyrrolidin-3-yl)-2-phenylacetamide | 525.3 (M + H) |
| 226 | 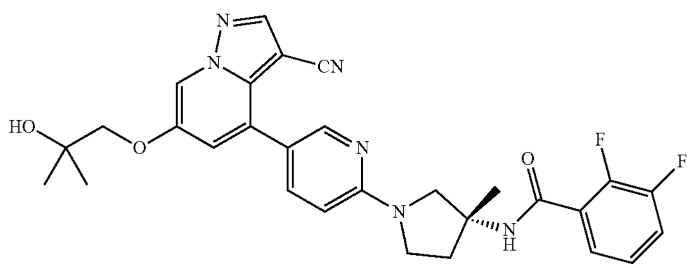 [SMILES: CC(C)(O)COc1cc(-c2ccc(N3CC[C@@](C)(NC(=O)c4cccc(F)c4F)C3)nc2)c2c(C#N)cnn2c1] | (R)-N-(1-(5-(3-cyano-6-(2-hydroxy-2-methylpropoxy)pyrazolo[1,5-a]pyridin-4-yl)pyridin-2-yl)-3-methylpyrrolidin-3-yl)-2,3-difluorobenzamide | 547.3 (M + H) |
| 227 | 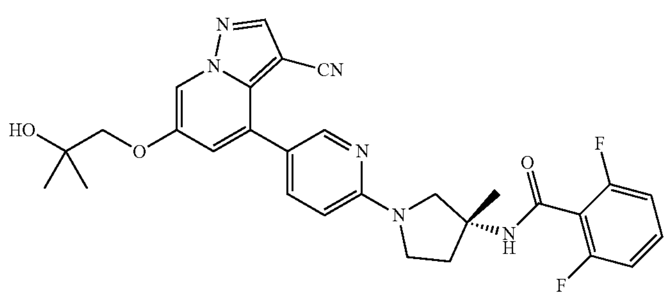 [SMILES: CC(C)(O)COc1cc(-c2ccc(N3CC[C@@](C)(NC(=O)c4c(F)cccc4F)C3)nc2)c2c(C#N)cnn2c1] | (R)-N-(1-(5-(3-cyano-6-(2-hydroxy-2-methylpropoxy)pyrazolo[1,5-a]pyridin-4-yl)pyridin-2-yl)-3-methylpyrrolidin-3-yl)-2,6-difluorobenzamide | 547.3 (M + H) |
| 228 | 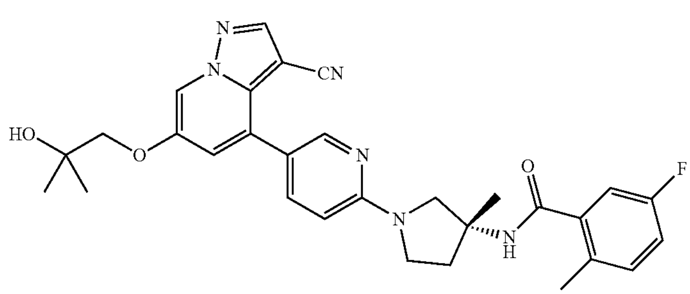 [SMILES: Cc1ccc(F)cc1C(=O)N[C@]1(C)CCN(c2ccc(-c3cc(OCC(C)(C)O)cn4ncc(C#N)c34)cn2)C1] | (R)-N-(1-(5-(3-cyano-6-(2-hydroxy-2-methylpropoxy)pyrazolo[1,5-a]pyridin-4-yl)pyridin-2-yl)-3-methylpyrrolidin-3-yl)-5-fluoro-2-methylbenzamide | 543.3 (M + H) |

TABLE JJ-continued

| Ex. # | Structure | Chemical Name | LCMS m/z |
|---|---|---|---|
| 229 | 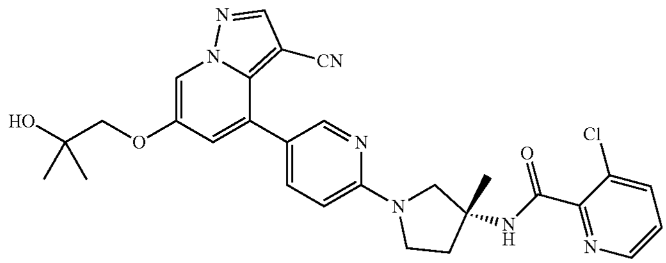 [SMILES: CC(C)(O)COc1cc(-c2ccc(N3CC[C@@](C)(NC(=O)c4ncccc4Cl)C3)nc2)c2c(C#N)cnn2c1] | (R)-3-chloro-N-(1-(5-(3-cyano-6-(2-hydroxy-2-methylpropoxy)pyrazolo[1,5-a]pyridin-4-yl)pyridin-2-yl)-3-methylpyrrolidin-3-yl)-picolinamide | 546.3 (M + H) |
| 230 | 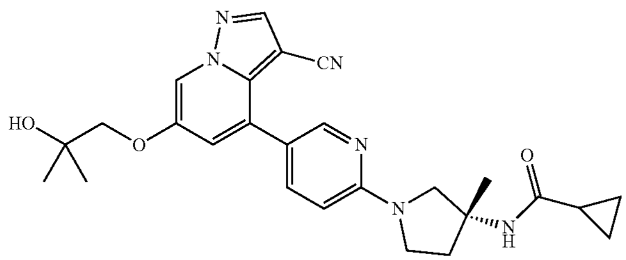 [SMILES: CC(C)(O)COc1cc(-c2ccc(N3CC[C@@](C)(NC(=O)C4CC4)C3)nc2)c2c(C#N)cnn2c1] | (R)-N-(1-(5-(3-cyano-6-(2-hydroxy-2-methylpropoxy)pyrazolo[1,5-a]pyridin-4-yl)pyridin-2-yl)-3-methylpyrrolidin-3-yl)cyclopropanecarboxamide | 475.3 (M + H) |

Example 231

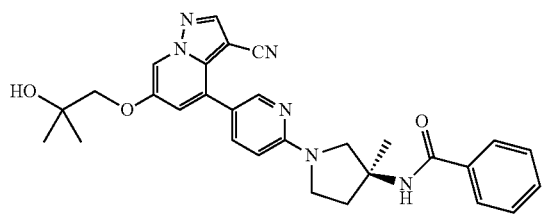 [SMILES: CC(C)(O)COc1cc(-c2ccc(N3CC[C@](C)(NC(=O)c4ccccc4)C3)nc2)c2c(C#N)cnn2c1]

(S)—N-(1-(5-(3-cyano-6-(2-hydroxy-2-methyl-propoxy)pyrazolo[1,5-a]pyridin-4-yl)pyridin-2-yl)-3-methylpyrrolidin-3-yl)benzamide A mixture of (S)-4-(6-(3-amino-3-methylpyrrolidin-1-yl)pyridin-3-yl)-6-(2-hydroxy-2-methylpropoxy)pyrazolo[1,5-a]pyridine-3-carbonitrile bis(2,2,2-trifluoroacetate) (Intermediate P50; 30 mg, 0.047 mmol), HATU (56 mg, 0.15 mmol), and benzoic acid (18 mg, 0.15 mmol) in ACN (600 µL) was treated with DIEA (64 µL, 0.37 mmol) and then stirred for 12 h at ambient temperature. The reaction mixture was diluted with 60:40 ACN:water containing 2% TFA. The solution was purified directly by C18 reverse phase chromatography (5-95% ACN in water with 0.1% TFA as the gradient eluent) to afford the title compound as the TFA salt. The TFA salt was treated with saturated $NaHCO_{3(aq)}$ and extracted with EtOAc. The combined organic extracts were washed with brine, then dried over anhydrous $MgSO_{4(s)}$, filtered and concentrated in vacuo to afford the title compound (12 mg, 51% yield). MS (apci) m/z=511.3 (M+H).

The compounds in Table KK were prepared using a similar method to that described for the synthesis of Example 231, replacing benzoic acid with the appropriate carboxylic acid. Reactions were monitored for completion by LCMS, and reaction durations were adjusted accordingly. Title compounds were cleanly isolated following chromatographic purification using an appropriate gradient eluent (and if necessary converted to the free base).

TABLE KK

| Ex. # | Structure | Chemical Name | LCMS m/z |
|---|---|---|---|
| 232 | 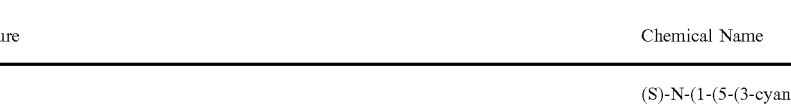 | (S)-N-(1-(5-(3-cyano-6-(2-hydroxy-2-methylpropoxy)pyrazolo[1,5-a]pyridin-4-yl)pyridin-2-yl)-3-methylpyrrolidin-3-yl)-2-phenylacetamide | 525.3 (M + H) |

TABLE KK-continued

| Ex. # | Structure | Chemical Name | LCMS m/z |
|---|---|---|---|
| 233 | 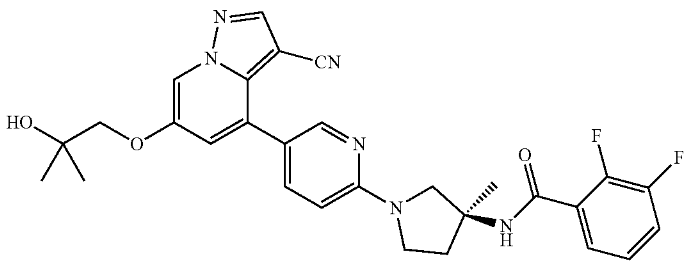 [SMILES: CC(C)(O)COc1cc(-c2ccc(N3CC[C@](C)(NC(=O)c4cccc(F)c4F)C3)nc2)c2c(C#N)cnn2c1] | (S)-N-(1-(5-(3-cyano-6-(2-hydroxy-2-methylpropoxy)pyrazolo[1,5-a]pyridin-4-yl)pyridin-2-yl)-3-methylpyrrolidin-3-yl)-2,3-difluorobenzamide | 547.3 (M + H) |
| 234 | 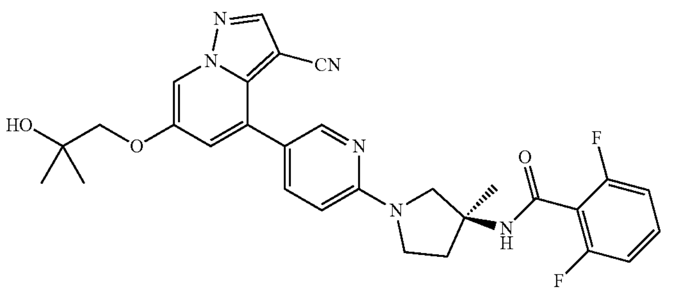 [SMILES: CC(C)(O)COc1cc(-c2ccc(N3CC[C@](C)(NC(=O)c4c(F)cccc4F)C3)nc2)c2c(C#N)cnn2c1] | (S)-N-(1-(5-(3-cyano-6-(2-hydroxy-2-methylpropoxy)pyrazolo[1,5-a]pyridin-4-yl)pyridin-2-yl)-3-methylpyrrolidin-3-yl)-2,6-difluorobenzamide | 547.2 (M + H) |
| 235 | 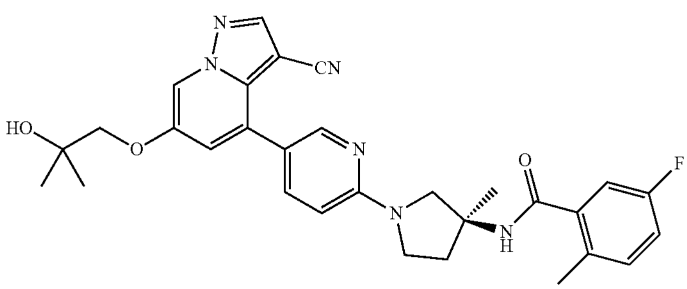 [SMILES: Cc1ccc(F)cc1C(=O)N[C@@]1(C)CCN(c2ccc(-c3cc(OCC(C)(C)O)cn4ncc(C#N)c34)cn2)C1] | (S)-N-(1-(5-(3-cyano-6-(2-hydroxy-2-methylpropoxy)pyrazolo[1,5-a]pyridin-4-yl)pyridin-2-yl)-3-methylpyrrolidin-3-yl)-5-fluoro-2-methylbenzamide | 543.3 (M + H) |
| 236 | 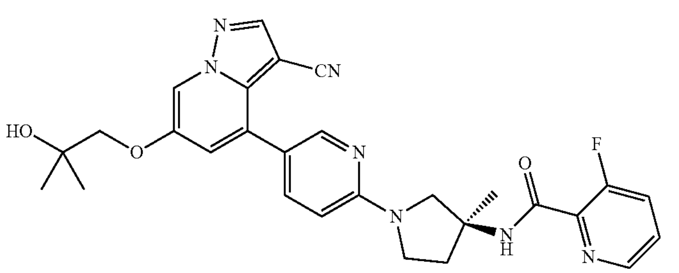 [SMILES: CC(C)(O)COc1cc(-c2ccc(N3CC[C@](C)(NC(=O)c4ncccc4F)C3)nc2)c2c(C#N)cnn2c1] | (S)-N-(1-(5-(3-cyano-6-(2-hydroxy-2-methylpropoxy)pyrazolo[1,5-a]pyridin-4-yl)pyridin-2-yl)-3-methylpyrrolidin-3-yl)-3-fluoropicolinamide | 530.2 (M + H) |
| 237 | 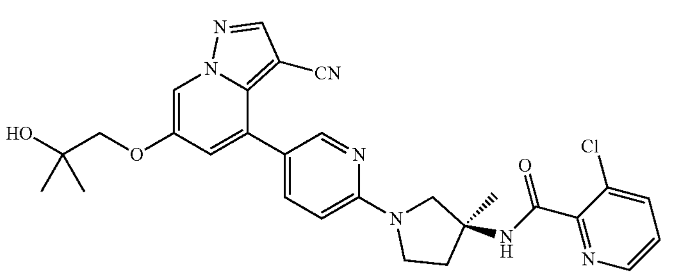 [SMILES: CC(C)(O)COc1cc(-c2ccc(N3CC[C@](C)(NC(=O)c4ncccc4Cl)C3)nc2)c2c(C#N)cnn2c1] | (S)-3-chloro-N-(1-(5-(3-cyano-6-(2-hydroxy-2-methylpropoxy)pyrazolo[1,5-a]pyridin-4-yl)pyridin-2-yl)-3-methylpyrrolidin-3-yl)picolinamide | 546.2 (M + H) |

TABLE KK-continued

| Ex. # | Structure | Chemical Name | LCMS m/z |
|---|---|---|---|
| 238 | 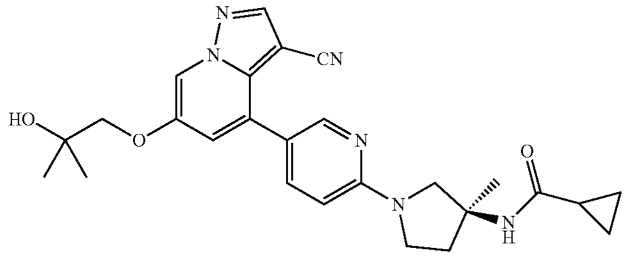 [SMILES: CC(C)(O)COc1cc(-c2ccc(N3CC[C@](C)(NC(=O)C4CC4)C3)nc2)c2c(C#N)cnn2c1] | (S)-N-(1-(5-(3-cyano-6-(2-hydroxy-2-methylpropoxy)pyrazolo[1,5-a]pyridin-4-yl)pyridin-2-yl)-3-methylpyrrolidin-3-yl)cyclopropanecarboxamide | 475.3 (M + H) |
| 239 | 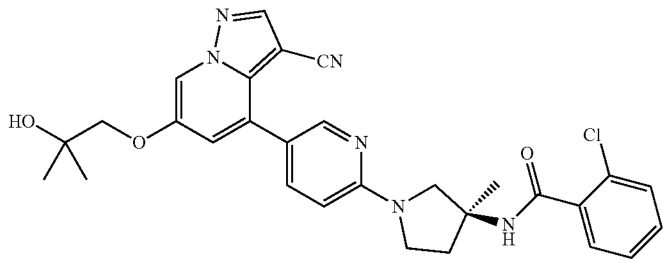 [SMILES: CC(C)(O)COc1cc(-c2ccc(N3CC[C@](C)(NC(=O)c4ccccc4Cl)C3)nc2)c2c(C#N)cnn2c1] | (S)-2-chloro-N-(1-(5-(3-cyano-6-(2-hydroxy-2-methylpropoxy)pyrazolo[1,5-a]pyridin-4-yl)pyridin-2-yl)-3-methylpyrrolidin-3-yl)benzamide | 545.2 (M + H) |
| 240 | 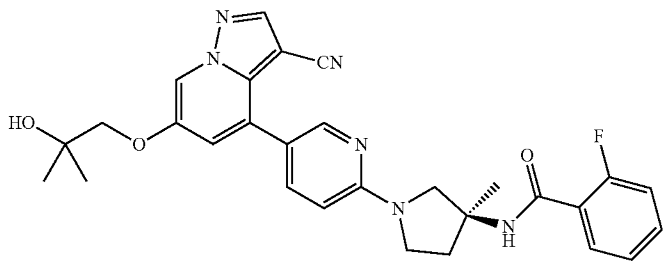 [SMILES: CC(C)(O)COc1cc(-c2ccc(N3CC[C@](C)(NC(=O)c4ccccc4F)C3)nc2)c2c(C#N)cnn2c1] | (S)-N-(1-(5-(3-cyano-6-(2-hydroxy-2-methylpropoxy)pyrazolo[1,5-a]pyridin-4-yl)pyridin-2-yl)-3-methylpyrrolidin-3-yl)-2-fluorobenzamide | 529.3 (M + H) |
| 241 | 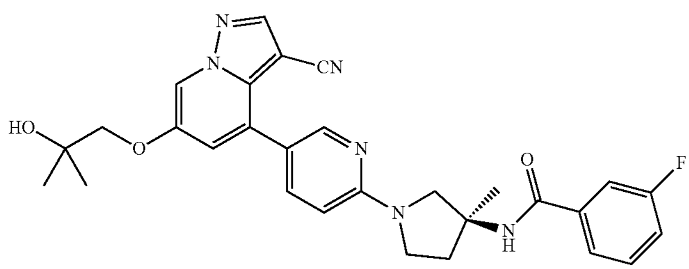 [SMILES: CC(C)(O)COc1cc(-c2ccc(N3CC[C@](C)(NC(=O)c4cccc(F)c4)C3)nc2)c2c(C#N)cnn2c1] | (S)-N-(1-(5-(3-cyano-6-(2-hydroxy-2-methylpropoxy)pyrazolo[1,5-a]pyridin-4-yl)pyridin-2-yl)-3-methylpyrrolidin-3-yl)-3-fluorobenzamide | 529.2 (M + H) |

Example 242

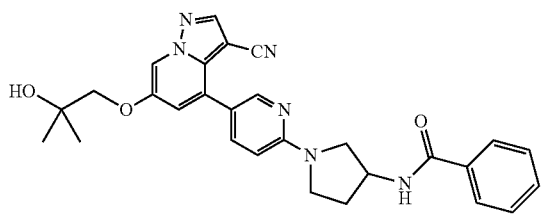 [SMILES: CC(C)(O)COc1cc(-c2ccc(N3CCC(NC(=O)c4ccccc4)C3)nc2)c2c(C#N)cnn2c1]

N-(1-(5-(3-cyano-6-(2-hydroxy-2-methylpropoxy)pyrazolo[1,5-a]pyridin-4-yl)pyridin-2-yl)pyrrolidin-3-yl)benzamide A mixture of 4-(6-(3-aminopyrrolidin-1-yl)pyridin-3-yl)-6-(2-hydroxy-2-methylpropoxy)pyrazolo[1,5-a]pyridine-3-carbonitrile bis(2,2,2-trifluoroacetate) (Intermediate P51; 40 mg, 0.064 mmol), HATU (78 mg, 0.20 mmol), and benzoic acid (25 mg, 0.20 mmol) in ACN (600 µL) was treated with DIEA (89 µL, 0.51 mmol) and then stirred for 12 h at ambient temperature. The reaction mixture was diluted with 60:40 ACN:water containing 2% TFA. The solution was purified directly by C18 reverse phase chromatography (5-95% ACN in water with 0.1% TFA as the gradient eluent) to afford the title compound as the TFA salt. The TFA salt was treated with saturated NaHCO$_{3(aq)}$ and extracted with EtOAc. The combined organic extracts were washed with brine, then dried over anhydrous MgSO$_{4(s)}$, filtered and concentrated in vacuo to afford the title compound (15 mg, 47% yield). MS (apci) m/z=497.2 (M+H).

The compounds in Table LL were prepared using a similar method to that described for the synthesis of Example 242, replacing benzoic acid with the appropriate carboxylic acid. Reactions were monitored for completion by LCMS, and reaction durations were adjusted accordingly. Title compounds were cleanly isolated following chromatographic purification using an appropriate gradient eluent (and if necessary converted to the free base).

TABLE LL

| Ex. # | Structure | Chemical Name | LCMS m/z |
|---|---|---|---|
| 243 | 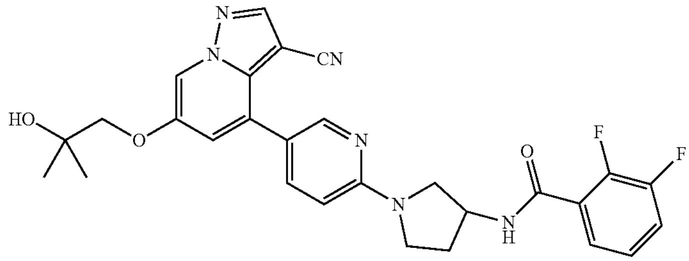 [SMILES: CC(C)(O)COc1cc(-c2ccc(N3CCC(NC(=O)c4cccc(F)c4F)C3)nc2)c2c(C#N)cnn2c1] | N-(1-(5-(3-cyano-6-(2-hydroxy-2-methylpropoxy)pyrazolo[1,5-a]pyridin-4-yl)pyridin-2-yl)pyrrolidin-3-yl)-2,3-difluorobenzamide | 533.2 (M + H) |
| 244 | 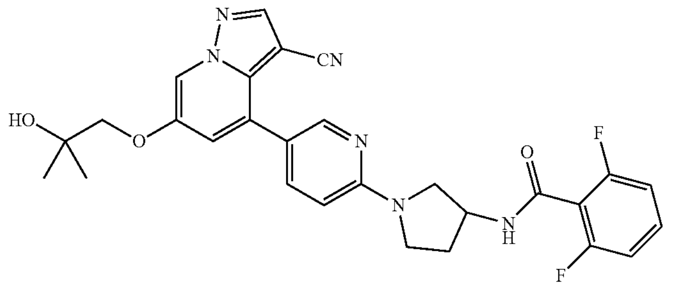 [SMILES: CC(C)(O)COc1cc(-c2ccc(N3CCC(NC(=O)c4c(F)cccc4F)C3)nc2)c2c(C#N)cnn2c1] | N-(1-(5-(3-cyano-6-(2-hydroxy-2-methylpropoxy)pyrazolo[1,5-a]pyridin-4-yl)pyridin-2-yl)pyrrolidin-3-yl)-2,6-difluorobenzamide | 533.2 (M + H) |
| 245 | 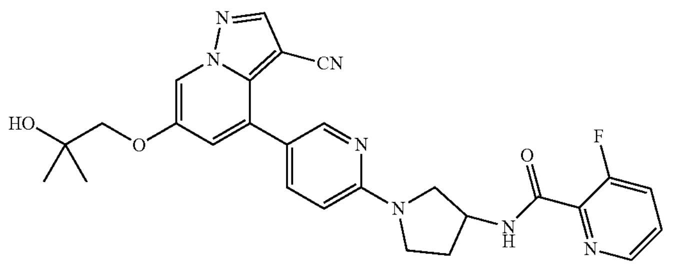 [SMILES: CC(C)(O)COc1cc(-c2ccc(N3CCC(NC(=O)c4ncccc4F)C3)nc2)c2c(C#N)cnn2c1] | N-(1-(5-(3-cyano-6-(2-hydroxy-2-methylpropoxy)pyrazolo[1,5-a]pyridin-4-yl)pyridin-2-yl)pyrrolidin-3-yl)-3-fluoropicolinamide | 516.3 (M + H) |
| 246 | 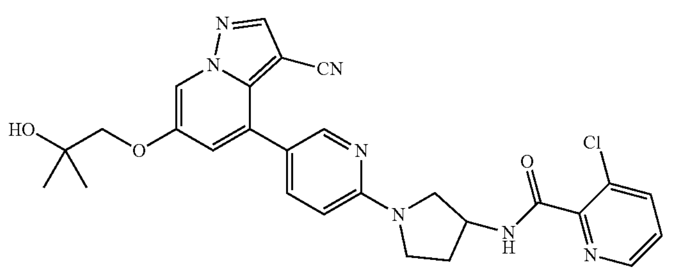 [SMILES: CC(C)(O)COc1cc(-c2ccc(N3CCC(NC(=O)c4ncccc4Cl)C3)nc2)c2c(C#N)cnn2c1] | 3-chloro-N-(1-(5-(3-cyano-6-(2-hydroxy-2-methylpropoxy)pyrazolo[1,5-a]pyridin-4-yl)pyridin-2-yl)pyrrolidin-3-yl)picolinamide | 532.2 (M + H) |

Example 247

6-(2-hydroxy-2-methylpropoxy)-4-(6-(4-(pyrimidin-2-yloxy)piperidin-1-yl)pyridin-3-yl)pyrazolo[1,5-a]pyridine-3-carbonitrile

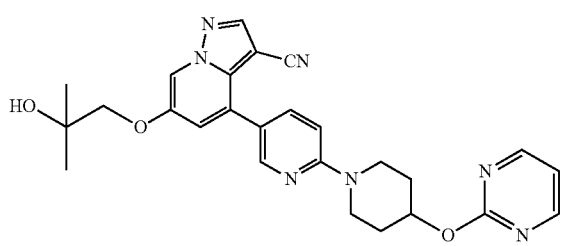 [SMILES: CC(C)(O)COc1cc(-c2ccc(N3CCC(Oc4ncccn4)CC3)nc2)c2c(C#N)cnn2c1]

To a solution of 4-(6-fluoropyridin-3-yl)-6-(2-hydroxy-2-methylpropoxy)pyrazolo[1,5-a]pyridine-3-carbonitrile (Intermediate P42; 40 mg, 0.123 mmol) in DMA (1.2 mL) was added 2-(piperidin-4-yloxy)pyrimidine (242 mg, 0.135 mmol) followed by TEA (33.5 µL, 0.245 mmol). The reaction mixture was sparged with argon and stirred overnight at 90° C. Then additional 2-(piperidin-4-yloxy)pyrimidine (242 mg, 0.135 mmol) and TEA (33.5 µL, 0.245 mmol) and the reaction was stirred for 8 h at 110° C. and then the reaction temperature was lowered to 90° C. where it was stirred at for 60 h. After cooling to ambient temperature, the reaction mixture was diluted with water and extracted with DCM. The organic extracts were washed with water. Then the organic extracts were washed with brine and dried over anhydrous Na$_2$SO$_4$(s), filtered and concentrated in vacuo. The reaction was purified by silica chromatography (40-99% EtOAc in hexanes as the gradient eluent) to afford the title compound (20.8 mg, 35% yield). MS (apci) m/z=486.2 (M+H).

Example 248

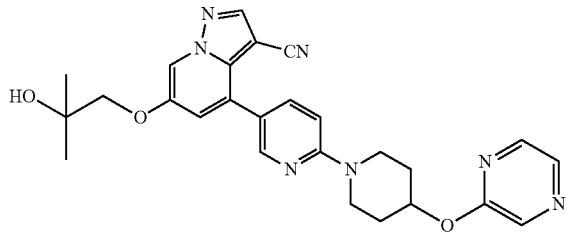 [SMILES: CC(C)(O)COc1cc(-c2ccc(N3CCC(Oc4cnccn4)CC3)nc2)c2c(C#N)cnn2c1]

6-(2-hydroxy-2-methylpropoxy)-4-(6-(4-(pyrazin-2-yloxy)piperidin-1-yl)pyridin-3-yl)pyrazolo[1,5-a]pyridine-3-carbonitrile To a solution of 4-(6-fluoropyridin-3-yl)-6-(2-hydroxy-2-methylpropoxy)pyrazolo[1,5-a]pyridine-3-carbonitrile (Intermediate P42; 25 mg, 0.077 mmol) in DMA (38 mL) was added 2-(piperidin-4-yloxy)pyrazine (13.7 mg, 0.077 mmol) followed by TEA (21 µL, 0.153 mmol). The reaction mixture was sparged with argon and stirred for 60 h at 90° C. After cooling to ambient temperature, the reaction mixture was diluted with DCM the organic extracts were washed with saturated NaHCO$_{3(aq)}$ and then water. Then the organic extracts were washed with brine and dried over anhydrous Na$_2$SO$_4$(s), filtered and concentrated in vacuo. The residue was resuspended in 1 mL DCM and was purified by silica chromatography (40-99% EtOAc in hexanes as the gradient eluent) to afford the title compound (12.3 mg, 33.1% yield). MS (apci) m/z=486.2 (M+H).

Example 249

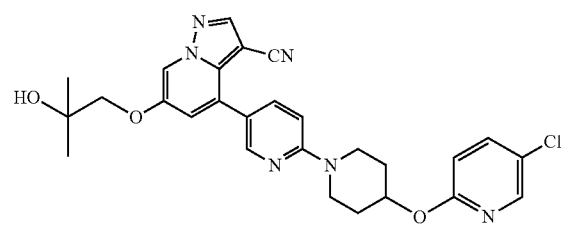 [SMILES: CC(C)(O)COc1cc(-c2ccc(N3CCC(Oc4ccc(Cl)cn4)CC3)nc2)c2c(C#N)cnn2c1]

4-(6-(4-((5-chloropyridin-2-yl)oxy)piperidin-1-yl)pyridin-3-yl)-6-(2-hydroxy-2-methylpropoxy)pyrazolo[1,5-a]pyridine-3-carbonitrile To a solution of 4-(6-fluoropyridin-3-yl)-6-(2-hydroxy-2-methylpropoxy)pyrazolo[1,5-a]pyridine-3-carbonitrile (Intermediate P42; 51.1 mg, 0.157 mmol) in DMA (78 mL) was added 5-chloro-2-(piperidin-4-yloxy)pyridine (40 mg, 0.188 mmol) followed by TEA (43 µL, 0.313 mmol). The reaction mixture was stirred for 48 h at 90° C. After cooling to ambient temperature, the reaction mixture was diluted with DCM the organic extracts were washed with saturated NaHCO$_{3(aq)}$ and then water. Then the organic extracts were washed with brine and dried over anhydrous Na$_2$SO$_4$(s), filtered and concentrated in vacuo. The reaction was purified by silica chromatography (40-75% EtOAc in hexanes as the gradient eluent) to afford the title compound (16.1 mg, 20% yield). MS (apci) m/z=519.2 (M+H).

Example 250

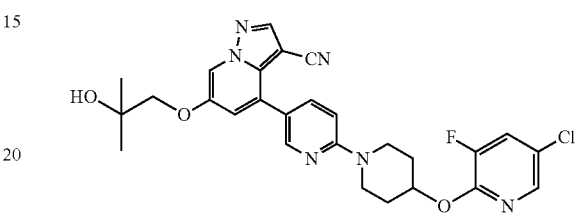

4-(6-(4-((5-chloro-3-fluoropyridin-2-yl)oxy)piperidin-1-yl)pyridin-3-yl)-6-(2-hydroxy-2-methylpropoxy)pyrazolo[1,5-a]pyridine-3-carbonitrile Step 1: Preparation of tert-butyl 4-((5-chloro-3-fluoropyridin-2-yl)oxy)piperidine-1-carboxylate To a solution of tert-butyl-4-hydroxy-1-piperidinecarboxylate (135 mg, 0.67 mmol) in DMF (2.2 mL) was added sodium hydride (60% w/w, 113 mg, 2.825 mmol). The mixture stirred at ambient temperature for 30 minutes and then 5-chloro-2,3-difluoropyridine (100 mg, 0.67 mmol) was added. The reaction mixture was stirred for 60 h at 60° C. After cooling to ambient temperature, the reaction mixture was diluted with DCM and washed with saturated NaHCO$_{3(aq)}$ and then water. Then the organic extracts were washed with brine and dried over anhydrous Na$_2$SO$_4$(s), filtered and concentrated in vacuo to afford the title compound (assume theoretical yield, 222 mg, 0.671 mmol) in sufficient purity for step 2. MS (apci) m/z=213.1 (M-Boc).

Step 2: Preparation of 5-chloro-3-fluoro-2-(piperidin-4-yloxy)pyridine

To a solution of tert-butyl 4-((5-chloro-3-fluoropyridin-2-yl)oxy)piperidine-1-carboxylate (assumed 222 mg, 0.671 mmol) in 3.4 mL DCM was treated with TFA (3.4 mL, 43.6 mmol). The reaction mixture was stirred for 16 h at ambient temperature, and then concentrated in vacuo. The crude residue was resuspended in DCM (1 mL). The solution was purified by silica chromatography 1-10% MeOH in DCM with 0.1-1% NH$_4$OH as the gradient eluent) to provide the title compound (56 mg, 36% yield) in sufficient purity for step 3. MS (apci) m/z=231.1 (M+H).

Step 3: Preparation of 4-(6-(4-((5-chloro-3-fluoropyridin-2-yl)oxy)piperidin-1-yl)pyridin-3-yl)-6-(2-hydroxy-2-methylpropoxy)pyrazolo[1,5-a]pyridine-3-carbonitrile To a mixture of 4-(6-fluoropyridin-3-yl)-6-(2-hydroxy-2-methylpropoxy)pyrazolo[1,5-a]pyridine-3-carbonitrile (Intermediate P42; 25 mg, 0.77 mmol) and 5-chloro-3-fluoro- 2-(piperidin-4-yloxy)pyridine (35 mg, 0.153 mmol) in DMA (0.4 mL) was added TEA (52 µL, 0.383 mmol). The reaction mixture was stirred overnight at 90° C. After cooling to ambient temperature, the reaction mixture was diluted with DCM and washed with saturated NaHCO$_{3(aq)}$ and then water. Then the organic extracts were washed with brine and dried over anhydrous Na$_2$SO$_4$(s), filtered and concentrated in vacuo. The residue was purified by silica chromatography (25-99% EtOAc in hexanes as the gradient eluent) to afford the title compound (8.2 mg, 20% yield). MS (apci) m/z=357.1 (M+H).

Example 251

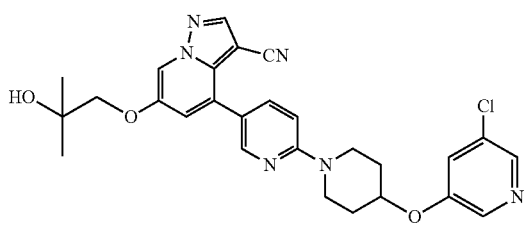

4-(6-(4-((5-chloropyridin-3-yl)oxy)piperidin-1-yl)pyridin-3-yl)-6-(2-hydroxy-2-methylpropoxy)pyrazolo[1,5-a]pyridine-3-carbonitrile Step 1: Preparation of tert-butyl 4-((5-chloropyridin-3-yl)oxy)piperidine-1-carboxylate A solution of 5-Chloro-3-pyridinol (1.018 g, 0.786 mmol) and tert-butyl 4-hydroxypiperidine-1-carboxylate (1.582 mg, 0.786 mmol) in THF was treated with PPh$_3$ (227 mg, 0.864 mmol), then sparged with Ar$_{(g)}$ for 5 min. While stirring at ambient temperature, the mixture was treated slowly with DIAD (186 µL, 0.959 mmol). The resulting reaction mixture was stirred for 5 h at 70° C. and then allowed to cool to ambient temperature. The reaction was diluted with DCM and washed with saturated Na$_2$CO$_{3(aq)}$, water and brine. The combined organic extracts were dried over anhydrous Na$_2$SO$_{4(s)}$, filtered and concentrated in vacuo to afford the title compound (246 mg, assumed quantitative yield). MS (apci) m/z=213.1 (M-Boc).

Step 2: Preparation of 3-chloro-5-(piperidin-4-yloxy)pyridine dihydrochloride

To a solution of tert-butyl 4-((5-chloropyridin-3-yl)oxy)piperidine-1-carboxylate (264 mg, 0.844 mmol) in 4.2 mL DCM was treated with TFA (4.2 mL, 54.5 mmol). The reaction mixture was stirred for 16 h at ambient temperature, and then concentrated in vacuo. The crude residue was resuspended in MeOH and treated with then treated with 4 N HCl in dioxanes (5 mL). The solution was stirred at ambient temperature and concentrated in vacuo to provide the title compound as a dihydrochloride salt, which was used in the next step without further purifications. MS (apci) m/z=213.1 (M+H).

Step 3: Preparation of 4-(6-(4-((5-chloropyridin-3-yl)oxy)piperidin-1-yl)pyridin-3-yl)-6-(2-hydroxy-2-methylpropoxy)pyrazolo[1,5-a]pyridine-3-carbonitrile To a mixture of 4-(6-fluoropyridin-3-yl)-6-(2-hydroxy-2-methylpropoxy)pyrazolo[1,5-a]pyridine-3-carbonitrile (Intermediate P42; 40 mg, 0.123 mmol) and 3-chloro-5-(piperidin-4-yloxy)pyridine dihydrochloride (35 mg, 0.123 mmol) in DMA (0.6 mL) was added TEA (84 µL, 0.613 mmol). The reaction mixture was stirred overnight at 105° C. The reaction was maintained at 90° C. for 60 h. After cooling to ambient temperature, the reaction mixture was diluted with DCM and washed with water. Then the organic extracts were washed with brine and dried over anhydrous Na$_2$SO$_{4(s)}$, filtered and concentrated in vacuo. The residue was suspended in 60:40 ACN:water containing 2% TFA. The solution was purified directly by C18 reverse phase chromatography (5-95% ACN in water with 0.1% TFA as the gradient eluent) to afford the title compound as the TFA salt. The TFA salt was treated with saturated NaHCO$_{3(aq)}$ and extracted with DCM. The combined organic extracts were washed with brine, then dried over anhydrous Na$_2$SO$_{4(s)}$, filtered and concentrated in vacuo to afford the title compound (8.1 mg, 13% yield). MS (apci) m/z=519.20 (M+H).

Example 252

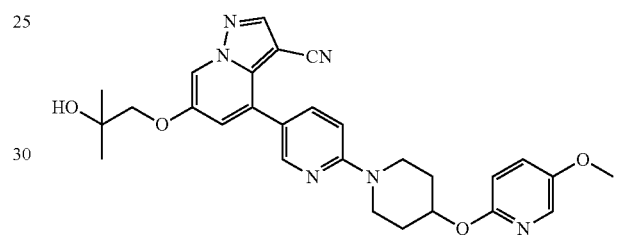

6-(2-hydroxy-2-methylpropoxy)-4-(6-(4-((5-methoxypyridin-2-yl)oxy)piperidin-1-yl)pyridin-3-yl)pyrazolo[1,5-a]pyridine-3-carbonitrile Step 1: Preparation of tert-butyl 4-((5-methoxypyridin-2-yl)oxy)piperidine-1-carboxylate To a solution of tert-butyl 4-hydroxypiperidine-1-carboxylate (158 mg, 0.787 mmol) in DMF (2 mL) was added sodium hydride (60% w/w, 38 mg, 0.944 mmol). The reaction was stirred for 10 min at ambient temperature. Then 2-fluoro-5-methoxypyridine (100 mg, 0.787 mmol) was added and reaction stirred overnight at 60° C. The reaction was heated to 70° C. for an additional overnight. The reaction was cooled to ambient temperature and additional of tert-butyl 4-hydroxypiperidine-1-carboxylate (316 mg, 1.574 mmol) and sodium hydride (60% w/w, 76 mg, 1.888 mmol) was added and reaction was stirred for 60 h at 70° C. The reaction was cooled to ambient temperature and diluted with DCM and washed water and brine. The combined organic extracts were dried over anhydrous Na$_2$SO$_{4(s)}$, filtered and concentrated in vacuo to afford the title compound (243 mg, assumed quantitative yield). MS (apci) m/z=253.1 (M-Bu$^t$).

Step 2: Preparation of 5-methoxy-2-(piperidin-4-yloxy)pyridine dihydrochloride

To a solution of tert-butyl 4-((5-methoxypyridin-2-yl)oxy)piperidine-1-carboxylate (assumed 243 mg, 0.786 mmol) in 2 mL DCM was treated with TFA (2 mL, 26 mmol). The reaction mixture was stirred for 1 h at ambient temperature, and then concentrated in vacuo. The crude residue was resuspended in MeOH and treated with then treated with 4 N HCl in dioxanes (4 mL). The solution was stirred at ambient temperature and concentrated in vacuo to provide the title compound as a dihydrochloride salt (221 mg, 100% yield), which was used in the next step without further purifications.

Step 3: Preparation of 6-(2-hydroxy-2-methylpropoxy)-4-(6-(4-((5-methoxypyridin-2-yl)oxy)piperidin-1-yl)pyridin-3-yl)pyrazolo[1,5-a]pyridine-3-carbonitrile To a mixture of 4-(6-fluoropyridin-3-yl)-6-(2-hydroxy-2-methylpropoxy)pyrazolo[1,5-a]pyridine-3-carbonitrile (Intermediate P42; 25 mg, 0.077 mmol) and 5-methoxy-2-(piperidin-4-yloxy)pyridine dihydrochloride (43 mg, 0.153 mmol) in DMA (0.4 mL) was added TEA (52 µL, 0.383 mmol). The reaction mixture was stirred overnight at 105° C. After cooling to ambient temperature, the reaction mixture was diluted with DCM and washed with saturated NaHCO$_{3(aq)}$, water, and brine. The organic extracts were dried over anhydrous Na$_2$SO$_4$(s), filtered and concentrated in vacuo. The residue was suspended in 60:40 ACN:water containing 2% TFA. The solution was purified directly by C18 reverse phase chromatography (5-95% ACN in water with 0.1% TFA as the gradient eluent) to afford the title compound as the TFA salt. The TFA salt was treated with saturated NaHCO$_{3(aq)}$ and extracted with DCM. The combined organic extracts were washed with brine, then dried over anhydrous Na$_2$SO$_{4(s)}$, filtered and concentrated in vacuo to afford the title compound (4.3 mg, 11% yield). MS (apci) m/z=515.30 (M+H). $^1$H-NMR (CDCl$_3$, 400 MHz) δ 8.34 (m, 1H), 8.20 (s, 1H), 8.14 (d, 1H), 7.81 (d, 1H), 7.69-7.72 (m, 1H), 7.20-7.24 (m, 1H), 7.14 (m, 1H), 6.81 (d, 1H), 6.68 (m, 1H), 5.20-5.26 (m, 1H), 4.03-4.08 (m, 2H), 3.86 (s, 2H), 3.82 (s, 3H), 3.50-3.56 (m, 2H), 2.09-2.14 (m, 2H), 2.04 (s, 1H), 1.82-1.89 (m, 2H), 1.40 (s, 6H).

Example 253

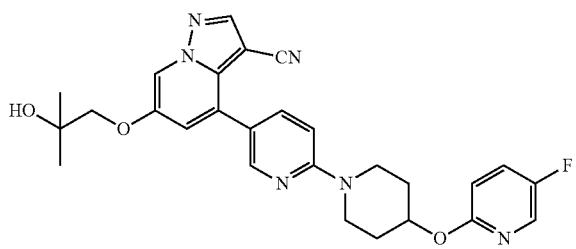 [SMILES: CC(C)(O)COc1cc(-c2ccc(N3CCC(Oc4ccc(F)cn4)CC3)nc2)c2c(C#N)cnn2c1]

4-(6-(4-((5-fluoropyridin-2-yl)oxy)piperidin-1-yl)pyridin-3-yl)-6-(2-hydroxy-2-methylpropoxy)pyrazolo[1,5-a]pyridine-3-carbonitrile Step 1: Preparation of tert-butyl 4-((5-fluoropyridin-2-yl)oxy)piperidine-1-carboxylate To a solution of tert-butyl 4-hydroxypiperidine-1-carboxylate (175 mg, 0.869 mmol) in DMF (2.9 mL) was added sodium hydride (60% w/w, 41.7 mg, 1.043 mmol). The reaction was stirred for 10 min at ambient temperature. 2,5-Difluoropyridine (100 mg, 0.869 mmol) was added and reaction stirred overnight at 60° C. The reaction was heated to 70° C. for an additional overnight. The reaction was cooled to ambient temperature and additional of tert-butyl 4-hydroxypiperidine-1-carboxylate (316 mg, 1.574 mmol) and sodium hydride (60% w/w, 76 mg, 1.888 mmol) was added and reaction was stirred for 4 h at 70° C. The reaction was cooled to ambient temperature and diluted with DCM and washed water and brine. The combined organic extracts were dried over anhydrous Na$_2$SO$_{4(s)}$, filtered and concentrated in vacuo to afford the title compound (257.5 mg, assumed quantitative yield). MS (apci) m/z=197.10 (M-Boc).

Step 2: Preparation of 5-methoxy-2-(piperidin-4-yloxy)pyridine dihydrochloride

To a solution of tert-butyl 4-((5-fluoropyridin-2-yl)oxy)piperidine-1-carboxylate (assumed 257.5 mg, 0.869 mmol) in 2 mL DCM was treated with 4 N HCl in dioxanes (4 mL). The solution was stirred at ambient temperature for 15 min and concentrated in vacuo to provide the title compound as a dihydrochloride salt (202 mg, 100% yield) in sufficient purity for step 3 MS (apci) m/z=197.10 (M+H).

Step 3: Preparation of 4-(6-(4-((5-fluoropyridin-2-yl)oxy)piperidin-1-yl)pyridin-3-yl)-6-(2-hydroxy-2-methylpropoxy)pyrazolo[1,5-a]pyridine-3-carbonitrile To a mixture of 4-(6-fluoropyridin-3-yl)-6-(2-hydroxy-2-methylpropoxy)pyrazolo[1,5-a]pyridine-3-carbonitrile (Intermediate P42; 35 mg, 0.107 mmol) and 5-methoxy-2-(piperidin-4-yloxy)pyridine dihydrochloride (87 mg, 0.322 mmol) in DMA (0.4 mL) was added TEA (117 µL, 0.858 mmol). The reaction mixture was stirred overnight at 105° C. After cooling to ambient temperature, the reaction mixture was diluted with DCM and washed with water and brine. The organic extracts were dried over anhydrous Na$_2$SO$_4$(s), filtered and concentrated in vacuo. The residue was suspended in 60:40 ACN:water containing 2% TFA. The solution was purified directly by C18 reverse phase chromatography (5-95% ACN in water with 0.1% TFA as the gradient eluent) to afford the title compound as the TFA salt. The TFA salt was treated with saturated NaHCO$_{3(aq)}$ and extracted with DCM. The combined organic extracts were washed with brine, then dried over anhydrous Na$_2$SO$_{4(s)}$, filtered and concentrated in vacuo to afford the title compound (7.7 mg, 14% yield). MS (apci) m/z=503.20 (M+H).

Example 254

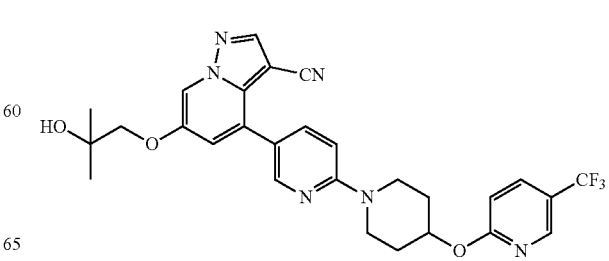

6-(2-hydroxy-2-methylpropoxy)-4-(6-(4-((5-(trifluoromethyl)pyridin-2-yl)oxy)piperidin-1-yl)pyridin-3-yl)pyrazolo[1,5-a]pyridine-3-carbonitrile To a mixture of 4-(6-fluoropyridin-3-yl)-6-(2-hydroxy-2-methylpropoxy)pyrazolo[1,5-a]pyridine-3-carbonitrile (Intermediate P42; 35 mg, 0.107 mmol) and 2-(piperidin-4-yloxy)-5-(trifluoromethyl)pyridine dihydrochloride (79 mg, 0.322 mmol) in DMA (0.4 mL) was added TEA (117 µL, 0.858 mmol). The reaction mixture was stirred overnight at 105° C. After cooling to ambient temperature, the reaction mixture was diluted with DCM and washed with water and brine. The organic extracts were dried over anhydrous $Na_2SO_{4(s)}$, filtered and concentrated in vacuo. The residue was suspended in 60:40 ACN:water containing 2% TFA. The solution was purified directly by C18 reverse phase chromatography (5-95% ACN in water with 0.1% TFA as the gradient eluent) to afford the title compound as the TFA salt. The TFA salt was treated with saturated $NaHCO_{3(aq)}$ and extracted with DCM. The combined organic extracts were washed with brine, then dried over anhydrous $Na_2SO_{4(s)}$, filtered and concentrated in vacuo to afford the title compound (14.6 mg, 25% yield). MS (apci) m/z=553.20 (M+H).

Example 255

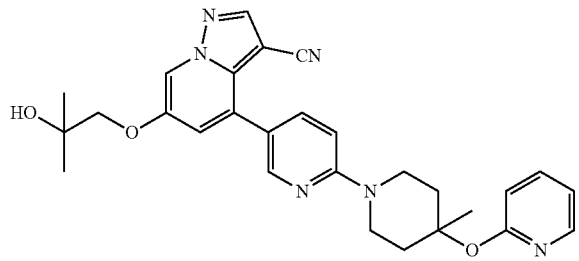 [SMILES: CC(C)(O)COc1cc(-c2ccc(N3CCC(C)(Oc4ccccn4)CC3)nc2)c2c(C#N)cnn2c1]

6-(2-hydroxy-2-methylpropoxy)-4-(6-(4-methyl-4-(pyridin-2-yloxy)piperidin-1-yl)pyridin-3-yl)pyrazolo[1,5-a]pyridine-3-carbonitrile Step 1: Preparation of tert-butyl 4-methyl-4-(pyridin-2-yloxy)piperidine-1-carboxylate To a solution of tert-Butyl 4-hydroxy-4-methylpiperidine-1-carboxylate (266 mg, 1.24 mmol) in DMF (2.6 mL) was added sodium hydride (60% w/w, 91 mg, 2.27 mmol). The reaction was stirred for 5 min at ambient temperature. Then 2-Fluoropyridine (100 mg, 1.03 mmol) was added and reaction stirred overnight at 70° C. The reaction was cooled to ambient temperature and diluted with DCM and washed with saturated $NaHCO_{3(aq)}$, water, and brine. The combined organic extracts were dried over anhydrous $Na_2SO_{4(s)}$, filtered and concentrated in vacuo. The residue was purified by silica chromatography (5-50% EtOAc in hexanes as the gradient eluent) to afford the title compound (assumed quantitative yield, 301 mg) in sufficient purity for step 2. MS (apci) m/z=293.3 (M+H).

Step 2: Preparation of 2-((4-methylpiperidin-4-yl)oxy)pyridine dihydrochloride

To a solution of tert-butyl 4-methyl-4-(pyridin-2-yloxy)piperidine-1-carboxylate (assumed 301 mg, 1.03 mmol) in 2 mL DCM was treated with TFA (2 mL, 26 mmol). The reaction mixture was stirred for 1 h at ambient temperature, and then concentrated in vacuo. The crude residue was resuspended in MeOH and treated with then treated with 4 N HCl in dioxanes (4 mL). The solution was stirred at ambient temperature for 5 min. The reaction was concentrated in vacuo to provide the title compound as a dihydrochloride salt (221 mg, 100% yield) in sufficient purity for step 3. $^1$H NMR (400 MHz, d$^6$-DMSO) δ 8.12 (d, 1H), 7.69 (dd, 1H), 6.97 (dd, 1H), 6.84 (d, 1H), 3.26 (m, 4H), 2.74 (m, 2H), 1.89 (m, 2H), 1.64 (s, 3H).

Step 3: Preparation of 6-(2-hydroxy-2-methylpropoxy)-4-(6-(4-methyl-4-(pyridin-2-yloxy)piperidin-1-yl)pyridin-3-yl)pyrazolo[1,5-a]pyridine-3-carbonitrile To a mixture of 4-(6-fluoropyridin-3-yl)-6-(2-hydroxy-2-methylpropoxy)pyrazolo[1,5a]pyridine-3-carbonitrile (Intermediate P42; 25 mg, 0.077 mmol) and 2-((4-methylpiperidin-4-yl)oxy)pyridine dihydrochloride (44 mg, 0.17 mmol) in DMA (0.3 mL) was added TEA (84 µL, 0.61 mmol). The reaction mixture was stirred overnight at 105° C. After cooling to ambient temperature, the reaction mixture was diluted with DCM and washed with saturated $NaHCO_{3(aq)}$, water, and brine. The organic extracts were dried over anhydrous $Na_2SO_4$(s), filtered and concentrated in vacuo. The residue was suspended in 60:40 ACN:water containing 2% TFA. The solution was purified directly by C18 reverse phase chromatography (5-95% ACN in water with 0.1% TFA as the gradient eluent) to afford the title compound as the TFA salt. The TFA salt was treated with saturated $NaHCO_{3(aq)}$ and extracted with DCM. The combined organic extracts were washed with brine, then dried over anhydrous $Na_2SO_{4(s)}$, filtered and concentrated in vacuo to afford the title compound (5.6 mg, 15% yield). (400 MHz, CDCl3) δ 8.32 (d, 1H), 8.19 (s, 1H), 8.12 (m, 2H), 7.69 (dd, 1H), 7.54 (m, 1H). 7.13 (d, 1H), 6.83 (m, 1H), 6.78 (d, 1H), 6.72 (d, 1H), 4.08 (m, 2H), 3.85 (s, 3H), 3.36 (m, 2H), 2.57 (m, 2H), 1.79 (m, 2H), 1.70 (s, 3H), 1.39 (s, 6H).

Example 256

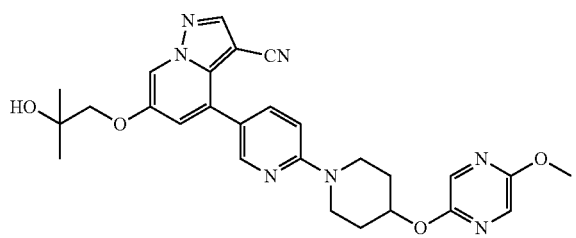 [SMILES: COc1cnc(OC2CCN(c3ccc(-c4cc(OCC(C)(C)O)cn5ncc(C#N)c45)cn3)CC2)cn1]

6-(2-hydroxy-2-methylpropoxy)-4-(6-(4-((5-methoxypyrazin-2-yl)oxy)piperidin-1-yl)pyridin-3-yl)pyrazolo[1,5-a]pyridine-3-carbonitrile Step 1: Preparation of tert-butyl 4-((5-methoxypyrazin-2-yl)oxy)piperidine-1-carboxylate To a solution of tert-butyl 4-hydroxy-4-methylpiperidine-1-carboxylate (278 mg, 1.38 mmol) in DMF (1.7 mL) was added sodium hydride (60% w/w, 61 mg, 1.52 mmol). The reaction was stirred for 5 min at ambient temperature. Then 2-chloro-5-methoxypyrazine (100 mg, 0.692 mmol) was added and reaction stirred overnight at 95° C. The reaction was cooled to ambient temperature and diluted with DCM and washed with saturated NaHCO$_{3(aq)}$, water, and brine. The combined organic extracts were dried over anhydrous Na$_2$SO$_{4(s)}$, filtered and concentrated in vacuo. The residue was purified by silica chromatography (5-40% EtOAc in hexanes as the gradient eluent) to afford the title compound (assumed quantitative yield, 214 mg) in sufficient purity for step 2. MS (apci) m/z=210.1 (M-Boc).

Step 2: Preparation of 2-methoxy-5-(piperidin-4-yloxy)pyrazine dihydrochloride

To a solution of tert-butyl 4-((5-methoxypyrazin-2-yl)oxy)piperidine-1-carboxylate (assumed 214 mg, 0.692 mmol) in 2 mL DCM was treated with TFA (2 mL, 26 mmol). The reaction mixture was stirred for 1 h at ambient temperature, and then concentrated in vacuo. The crude residue was resuspended in MeOH and treated with treated with 4 N HCl in dioxanes (4 mL). The solution was stirred at ambient temperature for 5 min. The reaction was concentrated in vacuo to provide the title compound as a dihydrochloride salt (61.3 mg, 21.7% yield) in sufficient purity for step 3. MS (apci) m/z=210.1 (M+H).

Step 3: Preparation of 6-(2-hydroxy-2-methylpropoxy)-4-(6-(4-((5-methoxypyrazin-2-yl)oxy)piperidin-1-yl)pyridin-3-yl)pyrazolo[1,5-a]pyridine-3-carbonitrile To a mixture of 4-(6-fluoropyridin-3-yl)-6-(2-hydroxy-2-methylpropoxy)pyrazolo[1,5-a]pyridine-3-carbonitrile (Intermediate P42; 32 mg, 0.098 mmol) and 2-methoxy-5-(piperidin-4-yloxy)pyrazine dihydrochloride (61 mg, 0.216 mmol) in DMA (0.3 mL) was added TEA (107 µL, 0.784 mmol). The reaction mixture was stirred overnight at 95° C. After cooling to ambient temperature, the reaction mixture was diluted with DCM and washed with saturated NaHCO$_{3(aq)}$, water, and brine. The organic extracts were dried over anhydrous Na$_2$SO$_4$(s), filtered and concentrated in vacuo. The residue was suspended in 60:40 ACN:water containing 2% TFA. The solution was purified directly by C18 reverse phase chromatography (5-95% ACN in water with 0.1% TFA as the gradient eluent) to afford the title compound as the TFA salt. The TFA salt was treated with saturated NaHCO$_{3(aq)}$ and extracted with DCM. The combined organic extracts were washed with brine, then dried over anhydrous Na$_2$SO$_{4(s)}$, filtered and concentrated in vacuo to afford the title compound (16.7 mg, 33% yield). MS (apci) m/z=516.25 (M+H).

Example 257

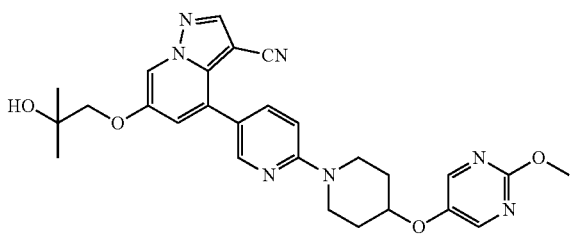 [SMILES: COc1ncc(OC2CCN(c3ccc(-c4cc(OCC(C)(C)O)cn5ncc(C#N)c45)cn3)CC2)cn1]

6-(2-hydroxy-2-methylpropoxy)-4-(6-(4-((2-methoxypyrimidin-5-yl)oxy)piperidin-1-yl)pyridin-3-yl)pyrazolo[1,5-a]pyridine-3-carbonitrile Step 1: Preparation of tert-butyl 4-((2-methoxypyrimidin-5-yl)oxy)piperidine-1-carboxylate To a solution of tert-butyl 4-((methylsulfonyl)oxy)piperidine-1-carboxylate (222 mg, 0.793 mmol) and 2-methoxypyrimidin-5-ol (100 mg, 0.793 mmol) in DMF (2 mL) was added potassium carbonate (219 mg, 1.59 mmol) and then the reaction mixture was stirred overnight at 95° C. After cooling to ambient temperature, the reaction mixture was diluted with DCM and washed with saturated NaHCO$_{3(aq)}$, water, and brine. The organic extracts were dried over anhydrous Na$_2$SO$_4$(s), filtered and concentrated in vacuo to afford the title compound (assumed theoretical yield, 245 mg) in sufficient purity for step 2. MS (apci) m/z=254.1 (M-t-bu).

Step 2: Preparation of 2-methoxy-5-(piperidin-4-yloxy)pyrimidine dihydrochloride To a solution of tert-butyl 4-((2-methoxypyrimidin-5-yl)oxy)piperidine-1-carboxylate (assumed 245 mg, 0.793 mmol) in 2 mL DCM was treated with TFA (2 mL, 26 mmol). The reaction mixture was stirred for 45 min at ambient temperature, and then concentrated in vacuo. The crude residue was treated with 4 N HCl in dioxanes (4 mL). The solution was stirred at ambient temperature for 5 min. The reaction was concentrated in vacuo to provide the title compound as a dihydrochloride salt (166 mg, 74.2% yield) in sufficient purity for step 3. MS (apci) m/z=210.2 (M+H).

Step 3: Preparation of 6-(2-hydroxy-2-methylpropoxy)-4-(6-(4-((2-methoxypyrimidin-5-yl)oxy)piperidin-1-yl)pyridin-3-yl)pyrazolo[1,5-a]pyridine-3-carbonitrile To a mixture of 4-(6-fluoropyridin-3-yl)-6-(2-hydroxy-2-methylpropoxy)pyrazolo[1,5-a]pyridine-3-carbonitrile (Intermediate P42; 31 mg, 0.096 mmol) 2-methoxy-5-(piperidin-4-yloxy)pyrimidine dihydrochloride (81 mg, 0.287 mmol) in DMA (0.3 mL) was added TEA (105 µL, 0.765 mmol). The reaction mixture was stirred overnight at 95° C. After cooling to ambient temperature, the reaction mixture was diluted with DCM and washed with saturated NaHCO$_{3(aq)}$, water, and brine. The organic extracts were dried over anhydrous Na$_2$SO$_4$(s), filtered and concentrated in vacuo. The residue was suspended in 60:40 ACN:water containing 2% TFA. The solution was purified directly by C18 reverse phase chromatography (5-95% ACN in water with 0.1% TFA as the gradient eluent) to afford the title compound as the TFA salt. The TFA salt was treated with saturated NaHCO$_{3(aq)}$ and extracted with DCM. The combined organic extracts were washed with brine, then dried over anhydrous Na$_2$SO$_{4(s)}$, filtered and concentrated in vacuo to afford the title compound (9.6 mg, 20% yield).

Example 258

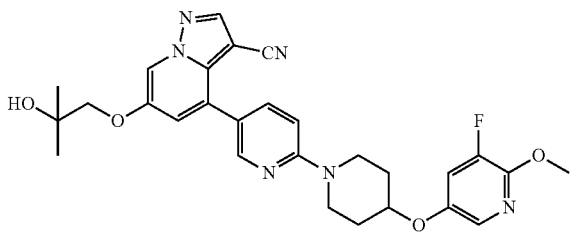 [SMILES: COc1ncc(OC2CCN(c3ccc(-c4cc(OCC(C)(C)O)cn5ncc(C#N)c45)cn3)CC2)cc1F]

4-(6-(4-((5-fluoro-6-methoxypyridin-3-yl)oxy)piperidin-1-yl)pyridin-3-yl)-6-(2-hydroxy-2-methylpropoxy)pyrazolo[1,5-a]pyridine-3-carbonitrile Step 1: Preparation of tert-butyl 4-((5-fluoro-6-methoxypyridin-3-yl)oxy)piperidine-1-carboxylate To a solution of tert-butyl 4-((methyl sulfonyl)oxy)piperidine-1-carboxylate (197 mg, 0.706 mmol) and 5-fluoro-6-methoxypyridin-3-ol (101 mg, 0.706 mmol) in DMF (1.8 mL) was added potassium carbonate (195 mg, 1.41 mmol) and then the reaction mixture was stirred for 60 h at 95° C. After cooling to ambient temperature, the reaction mixture was diluted with saturated NaHCO$_{3(aq)}$ and extracted with EtOAc. The organic extracts were washed with water and brine. The organic extracts were dried over anhydrous Na$_2$SO$_4$(s), filtered and concentrated in vacuo to afford the title compound (assumed theoretical yield, 230 mg) in sufficient purity for step 2. MS (apci) m/z=227.1 (M-Boc).

Step 2: Preparation of 3-fluoro-2-methoxy-5-(piperidin-4-yloxy)pyridine

To a solution of tert-butyl 4-((5-fluoro-6-methoxypyridin-3-yl)oxy)piperidine-1-carboxylate (assumed 230 mg, 0.706 mmol) in 2 mL DCM was treated with TFA (2 mL, 26 mmol). The reaction mixture was stirred for 45 min at ambient temperature, and then concentrated in vacuo. The residue was purified by silica chromatography (1-9% MeOH in DCM with 0.1-0.9% NH$_4$OH as the gradient eluent) to afford the title compound (86 mg, 54% yield over two steps) in sufficient purity for step 3. MS (apci) m/z=227.10 (M+H).

Step 3: Preparation of 4-(6-(4-((5-fluoro-6-methoxypyridin-3-yl)oxy)piperidin-1-yl)pyridin-3-yl)-6-(2-hydroxy-2-methylpropoxy)pyrazolo[1,5-a]pyridine-3-carbonitrile To a solution of 4-(6-fluoropyridin-3-yl)-6-(2-hydroxy-2-methylpropoxy)pyrazolo[1,5-a]pyridine-3-carbonitrile (Intermediate P42; 33 mg, 0.102 mmol) and 3-fluoro-2-methoxy-5-(piperidin-4-yloxy)pyridine (86 mg, 0.380 mmol) in DMA (0.3 mL) was added TEA (97 μL, 0.712 mmol). The reaction mixture was stirred overnight at 105° C. After cooling to ambient temperature, the reaction mixture was diluted with EtOAc and washed with saturated NaHCO$_{3(aq)}$, water, and brine. The organic extracts were dried over anhydrous Na$_2$SO$_4$(s), filtered and concentrated in vacuo. The residue was suspended in 60:40 ACN:water containing 2% TFA. The solution was purified directly by C18 reverse phase chromatography (5-95% ACN in water with 0.1% TFA as the gradient eluent) to afford the title compound as the TFA salt. The TFA salt was treated with saturated NaHCO$_{3(aq)}$ and extracted with DCM. The combined organic extracts were washed with brine, then dried over anhydrous Na$_2$SO$_{4(s)}$, filtered and concentrated in vacuo to afford the title compound (36 mg, 67% yield). MS (apci) m/z=533.20 (M+H).

Example 259

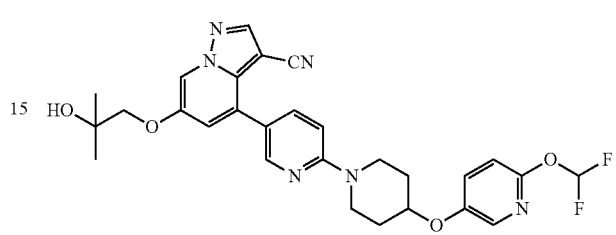

4-(6-(4-((6-(difluoromethoxy)pyridin-3-yl)oxy)piperidin-1-yl)pyridin-3-yl)-6-(2-hydroxy-2-methylpropoxy)pyrazolo[1,5-a]pyridine-3-carbonitrile Step 1: Preparation of tert-butyl 4-((6-(difluoromethoxy)pyridin-3-yl)oxy)piperidine-1-carboxylate To a solution of tert-butyl 4-((methylsulfonyl)oxy)piperidine-1-carboxylate (133 mg, 0.475 mmol) and 6-(difluoromethoxy)pyridin-3-ol (76.5 mg, 0.475 mmol) in DMF (1.2 mL) was added potassium carbonate (197 mg, 1.42 mmol) and then the reaction mixture was stirred overnight at 95° C. After cooling to ambient temperature, the reaction mixture was diluted with saturated NaHCO$_{3(aq)}$ and extracted with EtOAc. The organic extracts were washed with water and brine. The organic extracts were dried over anhydrous Na$_2$SO$_4$(s), filtered and concentrated in vacuo to afford the title compound (assumed theoretical yield, 164 mg) in sufficient purity for step 2. MS (apci) m/z=245.10 (M-Boc).

Step 2: Preparation of 2-(difluoromethoxy)-5-(piperidin-4-yloxy)pyridine

To a solution tert-butyl 4-((6-(difluoromethoxy)pyridin-3-yl)oxy)piperidine-1-carboxylate (assumed 164 mg, 0.706 mmol) in 2 mL DCM was treated with TFA (2 mL, 26 mmol). The reaction mixture was stirred for 45 min at ambient temperature, and then concentrated in vacuo. The residue was purified by silica chromatography (1-9% MeOH in DCM with 0.1-0.9% NH$_4$OH as the gradient eluent) to afford the title compound (61 mg, 53% yield over two steps) in sufficient purity for step 3. MS (apci) m/z=245.10 (M+H).

Step 3: Preparation of 4-(6-(4-((6-(difluoromethoxy)pyridin-3-yl)oxy)piperidin-1-yl)pyridin-3-yl)-6-(2-hydroxy-2-methylpropoxy)pyrazolo[1,5-a]pyridine-3-carbonitrile To a solution of 4-(6-fluoropyridin-3-yl)-6-(2-hydroxy-2-methylpropoxy)pyrazolo[1,5-a]pyridine-3-carbonitrile (Intermediate P42; 31 mg, 0.095 mmol) and 2-(difluoromethoxy)-5-(piperidin-4-yloxy)pyridine (61 mg, 0.25 mmol) in DMA (0.32 mL) was added TEA (65 μL, 0.477 mmol). The reaction mixture was stirred overnight at 95° C.

559

After cooling to ambient temperature, the reaction mixture was diluted with EtOAc and washed with water and brine. The organic extracts were dried over anhydrous $Na_2SO_4(s)$, filtered and concentrated in vacuo. The residue was suspended in 60:40 ACN:water containing 2% TFA. The solution was purified directly by C18 reverse phase chromatography (5-95% ACN in water with 0.1% TFA as the gradient eluent) to afford the title compound as the TFA salt. The TFA salt was treated with saturated $NaHCO_{3(aq)}$ and extracted with DCM. The combined organic extracts were washed with brine, then dried over anhydrous $Na_2SO_{4(s)}$, filtered and concentrated in vacuo to afford the title compound (21 mg, 41% yield). MS (apci) m/z=551.20 (M+H).

Example 260

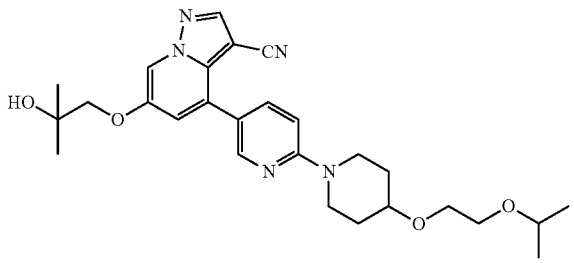 [SMILES: CC(C)OCCOC1CCN(c2ccc(-c3cc(OCC(C)(C)O)cn4ncc(C#N)c34)cn2)CC1]

560

6-(2-hydroxy-2-methylpropoxy)-4-(6-(4-(2-iso-propoxyethoxy)piperidin-1-yl)pyridin-3-yl)pyrazolo[1,5-a]pyridine-3-carbonitrile To a solution of 4-(6-fluoropyridin-3-yl)-6-(2-hydroxy-2-methylpropoxy)pyrazolo[1,5-a]pyridine-3-carbonitrile (Intermediate P42; 35 mg, 0.106 mmol) and 4-[2-(propan-2-yloxy)ethoxy]piperidine HCl (71 mg, 0.319 mmol) in DMA (0.35 mL) was added TEA (102 µL, 0.744 mmol). The reaction mixture was stirred overnight at 95° C. After cooling to ambient temperature, the reaction mixture was diluted with EtOAc and washed with water and brine. The organic extracts were dried over anhydrous $Na_2SO_{4(s)}$, filtered and concentrated in vacuo. The residue was suspended in 60:40 ACN:water containing 2% TFA. The solution was purified directly by C18 reverse phase chromatography (5-95% ACN in water with 0.1% TFA as the gradient eluent) to afford the title compound as the TFA salt. The TFA salt was treated with saturated $NaHCO_{3(aq)}$ and extracted with DCM. The combined organic extracts were washed with brine, then dried over anhydrous $Na_2SO_{4(s)}$, filtered and concentrated in vacuo to afford the title compound (52.5 mg, 66% yield). MS (apci) m/z=494.20 (M+H).

The compounds in Table MM were prepared using a similar method to that described for the synthesis of Example 260, replacing 4-[2-(propan-2-yloxy)ethoxy]piperidine HCl with the appropriate piperidine nucleophile. Reactions were monitored for completion by LCMS, and reaction durations were adjusted accordingly. Title compounds were cleanly isolated following chromatographic purification using an appropriate gradient eluent (and if necessary converted to the free base).

TABLE MM

| Ex. # | Structure | Chemical Name | MS m/z |
|---|---|---|---|
| 261 | 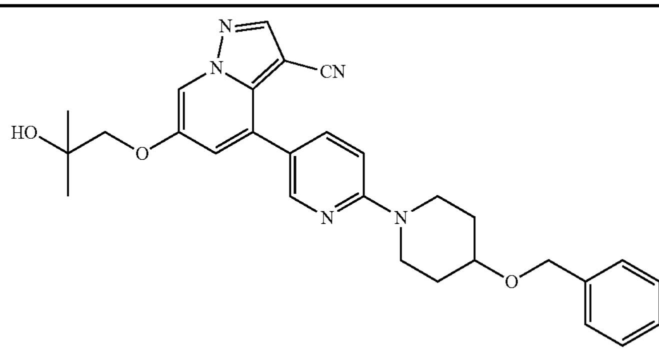 | 4-(6-(4-(benzyloxy)piperidin-1-yl)pyridin-3-yl)-6-(2-hydroxy-2-methylpropoxy)pyrazolo[1,5-a]pyridine-3-carbonitrile | 498.20 (M + H) |
| 262 | 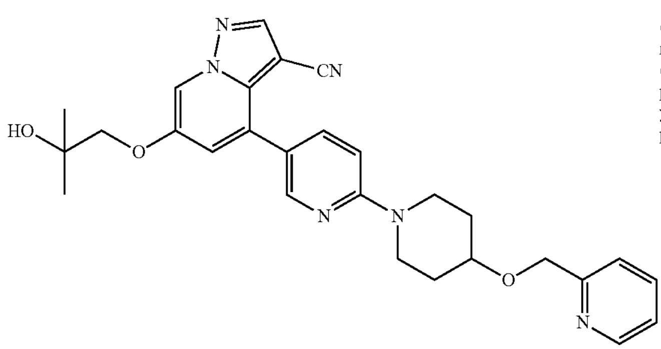 | 6-(2-hydroxy-2-methylpropoxy)-4-(6-(4-(pyridin-2-ylmethoxy)piperidin-1-yl)pyridin-3-yl)pyrazolo[1,5-a]pyridine-3-carbonitrile | 499.20 (M + H) |

| Ex. # | Structure | Chemical Name | MS m/z |
|---|---|---|---|
| 263 | 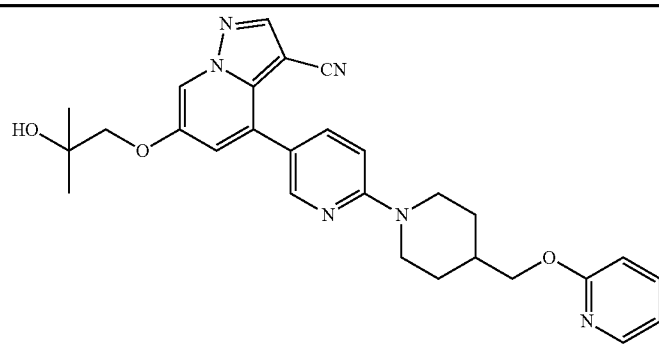 | 6-(2-hydroxy-2-methylpropoxy)-4-(6-(4-((pyridin-2-yloxy)methyl)piperidin-1-yl)pyridin-3-yl)pyrazolo[1,5-a]pyridine-3-carbonitrile | 499.20 (M + H) |

Example 264

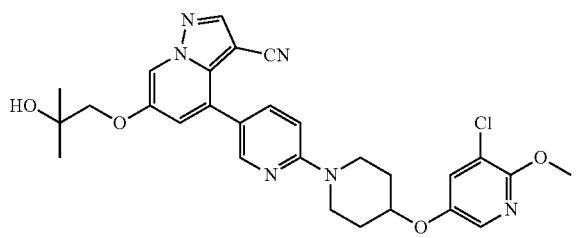 [SMILES: COc1ncc(OC2CCN(c3ccc(-c4cc(OCC(C)(C)O)cn5ncc(C#N)c45)cn3)CC2)cc1Cl]

4-(6-(4-((5-chloro-6-methoxypyridin-3-yl)oxy)piperidin-1-yl)pyridin-3-yl)-6-(2-hydroxy-2-methylpropoxy)pyrazolo[1,5-a]pyridine-3-carbonitrile

Step 1: Preparation of tert-butyl 4-((5-chloro-6-methoxypyridin-3-yl)oxy)piperidine-1-carboxylate To a solution of tert-butyl 4-((methyl sulfonyl)oxy)piperidine-1-carboxylate (186 mg, 0.664 mmol) and 5-chloro-6-methoxypyridin-3-ol (106 mg, 0.664 mmol) in DMF (1.7 mL) was added potassium carbonate (275 mg, 1.99 mmol) and then the reaction mixture was stirred overnight at 105° C. After cooling to ambient temperature, the reaction mixture was diluted with saturated NaHCO$_{3(aq)}$ and extracted with EtOAc. The organic extracts were washed with water and brine. The organic extracts were dried over anhydrous Na$_2$SO$_4$(s), filtered and concentrated in vacuo to afford the title compound (assumed theoretical yield, 228 mg) in sufficient purity for step 2. MS (apci) m/z=243.10 (M-Boc).

Step 2: Preparation 3-chloro-2-methoxy-5-(piperidin-4-yloxy)pyridine

To a solution tert-butyl 4-((5-chloro-6-methoxypyridin-3-yl)oxy)piperidine-1-carboxylate (assumed 228 mg, 0.664 mmol) in 2 mL DCM was treated with TFA (2 mL, 26 mmol). The reaction mixture was stirred for 15 min at ambient temperature, and then concentrated in vacuo. The residue was purified by silica chromatography (1-9% MeOH in DCM with 0.1-0.9% NH$_4$OH as the gradient eluent) to afford the title compound (65 mg, 40% yield over two steps) in sufficient purity for step 3. MS (apci) m/z=243.10 (M+H).

Step 3: Preparation of 4-(6-(4-((5-chloro-6-methoxypyridin-3-yl)oxy)piperidin-1-yl)pyridin-3-yl)-6-(2-hydroxy-2-methylpropoxy)pyrazolo[1,5-a]pyridine-3-carbonitrile To a solution of 4-(6-fluoropyridin-3-yl)-6-(2-hydroxy-2-methylpropoxy)pyrazolo[1,5-a]pyridine-3-carbonitrile (Intermediate P42; 26 mg, 0.079 mmol) and 3-chloro-2-methoxy-5-(piperidin-4-yloxy)pyridine (82 mg, 0.338 mmol) in DMA (0.26 mL) was added TEA (76 µL, 0.553 mmol). The reaction mixture was stirred 1 h at 95° C. After cooling to ambient temperature, the reaction mixture was diluted with 60:40 ACN:water containing 2% TFA. The solution was purified directly by C18 reverse phase chromatography (5-95% ACN in water with 0.1% TFA as the gradient eluent) to afford the title compound as the TFA salt. The TFA salt was treated with saturated NaHCO$_{3(aq)}$ and extracted with DCM. The combined organic extracts were washed with brine, then dried over anhydrous Na$_2$SO$_{4(s)}$, filtered and concentrated in vacuo to afford the title compound (12 mg, 28% yield). MS (apci) m/z=549.15 (M+H).

Example 265

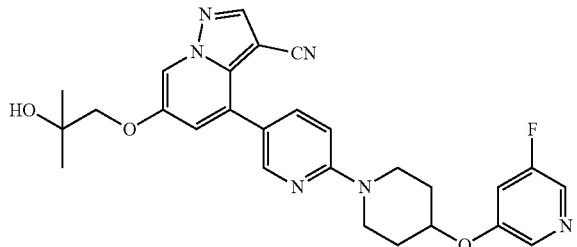

4-(6-(4-((5-fluoropyridin-3-yl)oxy)piperidin-1-yl)pyridin-3-yl)-6-(2-hydroxy-2-methylpropoxy)pyrazolo[1,5-a]pyridine-3-carbonitrile

Step 1: Preparation of tert-butyl 4-((5-fluoropyridin-3-yl)oxy)piperidine-1-carboxylate To a solution of tert-butyl 4-((methylsulfonyl)oxy)piperidine-1-carboxylate (257 mg, 0.920 mmol) and 3-fluoro-5-hydroxypyridine (104 mg, 0.920 mmol) in DMF (2.3 mL)

was added potassium carbonate (381 mg, 2.76 mmol) and then the reaction mixture was stirred overnight at 105° C. After cooling to ambient temperature, the reaction mixture was diluted with saturated NaHCO$_{3(aq)}$ and extracted with EtOAc. The organic extracts were washed with water and brine. The organic extracts were dried over anhydrous Na$_2$SO$_4$(s), filtered and concentrated in vacuo to afford the title compound (assumed theoretical yield, 273 mg) in sufficient purity for step 2. MS (apci) m/z=297.2 (M+H).

Step 2: Preparation
3-fluoro-5-(piperidin-4-yloxy)pyridine

To a solution tert-butyl 4-((5-fluoropyridin-3-yl)oxy)piperidine-1-carboxylate (assumed 273 mg, 0.920 mmol) in 2 mL DCM was treated with TFA (2 mL, 26 mmol). The reaction mixture was stirred for 15 min at ambient temperature, and then concentrated in vacuo. The residue was purified by silica chromatography (1-9% MeOH in DCM with 0.1-0.9% NH4OH as the gradient eluent) to afford the title compound (89 mg, 49% yield over two steps) in sufficient purity for step 3. MS (apci) m/z=197.10 (M+H).

Step 3: Preparation of 4-(6-(4-((5-fluoropyridin-3-yl)oxy)piperidin-1-yl)pyridin-3-yl)-6-(2-hydroxy-2-methylpropoxy)pyrazolo[1,5-a]pyridine-3-carbonitrile To a solution of 4-(6-fluoropyridin-3-yl)-6-(2-hydroxy-2-methylpropoxy)pyrazolo[1,5-a]pyridine-3-carbonitrile (Intermediate P42; 25.5 mg, 0.078 mmol) and 3-fluoro-5-(piperidin-4-yloxy)pyridine (15.3 mg, 0.781 mmol) in DMA (0.26 mL) was added TEA (75 µL, 0.547 mmol). The reaction mixture was stirred 1 h at 95° C. After cooling to ambient temperature, the reaction mixture was diluted with 60:40 ACN:water containing 2% TFA. The solution was purified directly by C18 reverse phase chromatography (5-95% ACN in water with 0.1% TFA as the gradient eluent) to afford the title compound as the TFA salt. The TFA salt was treated with saturated NaHCO$_{3(aq)}$ and extracted with DCM. The combined organic extracts were washed with brine, then dried over anhydrous Na$_2$SO$_{4(s)}$, filtered and concentrated in vacuo to afford the title compound (12 mg, 31% yield). MS (apci) m/z=503.25 (M+H).

Example 266

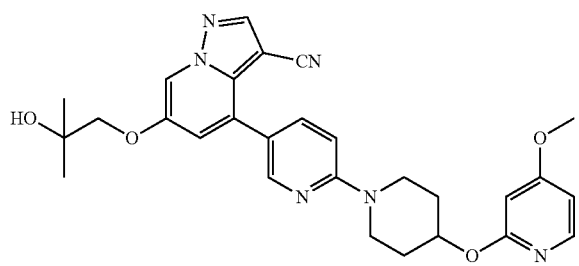 [SMILES: COc1ccnc(OC2CCN(c3ccc(-c4cc(OCC(C)(C)O)cn5ncc(C#N)c45)cn3)CC2)c1]

6-(2-hydroxy-2-methylpropoxy)-4-(6-(4-((4-methoxypyridin-2-yl)oxy)piperidin-1-yl)pyridin-3-yl)pyrazolo[1,5-a]pyridine-3-carbonitrile Step 1: Preparation of tert-butyl 4-((4-methoxypyridin-2-yl)oxy)piperidine-1-carboxylate To a solution of tert-Butyl 4-hydroxy-4-methylpiperidine-1-carboxylate (146 mg, 0.725 mmol) in DMF (2.4 mL) was added sodium hydride (60% w/w, 37.7 mg, 0.943 mmol). The reaction was stirred for 10 min at ambient temperature. Then 2-chloro-4-methoxypyridine (104 mg, 0.725 mmol) was added and reaction stirred 92 h at 95° C. The reaction was cooled to ambient temperature and diluted with water and extracted with EtOAc. Combined organics were washed with saturated NaHCO$_{3(aq)}$, water, and brine. The combined organic extracts were dried over anhydrous Na$_2$SO$_{4(s)}$, filtered and concentrated in vacuo to afford the title compound (assumed quantitative yield, 224 mg) in sufficient purity for step 2. MS (apci) m/z=309.1 (M+H).

Step 2: Preparation of
4-methoxy-2-(piperidin-4-yloxy)pyridine

To a solution tert-butyl 4-((4-methoxypyridin-2-yl)oxy)piperidine-1-carboxylate (assumed 224 mg, 0.725 mmol) in 2 mL DCM was treated with TFA (2 mL, 26 mmol). The reaction mixture was stirred for 20 min at ambient temperature, and then concentrated in vacuo. The crude residue was resuspended in DCM and the solution was purified by silica chromatography (1-9% MeOH in DCM with 0.1-0.9% NH$_4$OH as the gradient eluent) to afford the title compound (54 mg, 36% yield over two steps) in sufficient purity for step 3. MS (apci) m/z=209.1 (M+H).

Step 3: Preparation of 6-(2-hydroxy-2-methylpropoxy)-4-(6-(4-((4-methoxypyridin-2-yl)oxy)piperidin-1-yl)pyridin-3-yl)pyrazolo[1,5-a]pyridine-3-carbonitrile To a mixture of 4-(6-fluoropyridin-3-yl)-6-(2-hydroxy-2-methylpropoxy)pyrazolo[1,5-a]pyridine-3-carbonitrile (Intermediate P42; 25 mg, 0.077 mmol) and 4-methoxy-2-(piperidin-4-yloxy)pyridine (16 mg, 0.077 mmol) in DMA (0.3 mL) was added TEA (73 µL, 0.54 mmol). The reaction mixture was stirred overnight at 95° C. After cooling to ambient temperature, the reaction mixture was diluted with water and extracted with EtOAc. The combined organic extracts were washed with saturated NaHCO$_{3(aq)}$, water, and brine. The organic extracts were dried over anhydrous Na$_2$SO$_4$(s), filtered and concentrated in vacuo. The residue was suspended in 60:40 ACN:water containing 2% TFA. The solution was purified directly by C18 reverse phase chromatography (5-95% ACN in water with 0.1% TFA as the gradient eluent) to afford the title compound as the TFA salt. The TFA salt was treated with saturated NaHCO$_{3(aq)}$ and extracted with DCM. The combined organic extracts were washed with brine, then dried over anhydrous Na$_2$SO$_{4(s)}$, filtered and concentrated in vacuo to afford the title compound (16.7 mg, 33% yield). MS (apci) m/z=515.20 (M+H).

Example 267

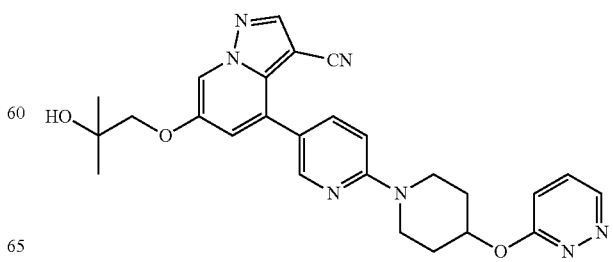

6-(2-hydroxy-2-methylpropoxy)-4-(6-(4-(pyridazin-3-yloxy)piperidin-1-yl)pyridin-3-yl)pyrazolo[1,5-a]pyridine-3-carbonitrile

Step 1: Preparation of tert-butyl 4-(pyridazin-3-yloxy)piperidine-1-carboxylate To a solution of tert-butyl 4-hydroxy-4-methylpiperidine-1-carboxylate (140 mg, 0.696 mmol) in DMF (2.3 mL) was added sodium hydride (60% w/w, 56 mg, 1.39 mmol). The reaction was stirred for 10 min at ambient temperature. Then 3-chloropyridazine (159 mg, 1.39 mmol) was added and reaction stirred 3 h at 95° C. The reaction was cooled to ambient temperature and diluted with water and extracted with EtOAc. Combined organics were washed with saturated NaHCO$_{3(aq)}$, water, and brine. The combined organic extracts were dried over anhydrous Na$_2$SO$_{4(s)}$, filtered and concentrated in vacuo to afford the title compound (assumed quantitative yield, 194 mg) in sufficient purity for step 2. MS (apci) m/z=280.2 (M+H).

Step 2: Preparation of 3-(piperidin-4-yloxy)pyridazine

To a solution of tert-butyl 4-(pyridazin-3-yloxy)piperidine-1-carboxylate (assumed 194 mg, 0.696 mmol) in 2 mL DCM was treated with TFA (2 mL, 26 mmol). The reaction mixture was stirred for 20 min at ambient temperature, and then concentrated in vacuo. The crude residue was resuspended in DCM and the solution was purified by silica chromatography (1-9% MeOH in DCM with 0.1-0.9% NH$_4$OH as the gradient eluent) to afford the title compound (111 mg, 89% yield over two steps) in sufficient purity for the next step. MS (apci) m/z=180.1 (M+H).

Step 3: Preparation of 6-(2-hydroxy-2-methylpropoxy)-4-(6-(4-(pyridazin-3-yloxy)piperidin-1-yl)pyridin-3-yl)pyrazolo[1,5-a]pyridine-3-carbonitrile To a mixture of 4-(6-fluoropyridin-3-yl)-6-(2-hydroxy-2-methylpropoxy)pyrazolo[1,5-a]pyridine-3-carbonitrile (Intermediate P42; 28 mg, 0.086 mmol) and 3-(piperidin-4-yloxy)pyridazine (46 mg, 0.257 mmol) in DMA (0.3 mL) was added TEA (82 µL, 0.601 mmol). The reaction mixture was stirred overnight at 95° C. After cooling to ambient temperature, the reaction mixture was diluted with water and extracted with EtOAc. The combined organic extracts were washed with saturated NaHCO$_{3(aq)}$, water, and brine. The organic extracts were dried over anhydrous Na$_2$SO$_{4(s)}$, filtered and concentrated in vacuo. The residue was suspended in 60:40 ACN:water containing 2% TFA. The solution was purified directly by C18 reverse phase chromatography (5-95% ACN in water with 0.1% TFA as the gradient eluent) to afford the title compound as the TFA salt. The TFA salt was treated with saturated NaHCO$_{3(aq)}$ and extracted with DCM. The combined organic extracts were washed with brine, then dried over anhydrous Na$_2$SO$_{4(s)}$, filtered and concentrated in vacuo to afford the title compound (23.5 mg, 56% yield). MS (apci) m/z=486.20 (M+H).

Example 268

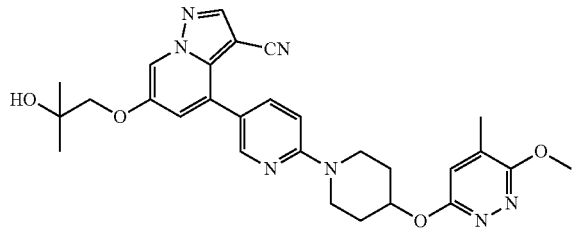 [SMILES: COc1nnc(OC2CCN(c3ccc(-c4cc(OCC(C)(C)O)cn5ncc(C#N)c45)cn3)CC2)cc1C]

6-(2-hydroxy-2-methylpropoxy)-4-(6-(4-((6-methoxy-5-methylpyridazin-3-yl)oxy)piperidin-1-yl)pyridin-3-yl)pyrazolo[1,5-a]pyridine-3-carbonitrile

Step 1: Preparation of tert-butyl 4-((6-methoxy-5-methylpyridazin-3-yl)oxy)piperidine-1-carboxylate To a solution of tert-butyl 4-hydroxy-4-methylpiperidine-1-carboxylate (761 mg, 3.78 mmol) in DMF (7.9 mL) was added sodium hydride (60% w/w, 164 mg, 4.10 mmol). The reaction was stirred for 5 min at ambient temperature. Then 6-chloro-3-methoxy-4-methylpyridazine (500 mg, 3.15 mmol) was added and reaction stirred overnight at 95° C. The reaction was cooled to ambient temperature and diluted with water and extracted with EtOAc. Combined organics were washed with saturated NaHCO$_{3(aq)}$, water, and brine. The combined organic extracts were dried over anhydrous Na$_2$SO$_{4(s)}$, filtered and concentrated in vacuo to afford the title compound (assumed quantitative yield, 1.019 g) in sufficient purity for step 2. MS (apci) m/z=324.1 (M+H).

Step 2: Preparation of 3-methoxy-4-methyl-6-(piperidin-4-yloxy)pyridazine

To a solution of tert-butyl 4-((6-methoxy-5-methylpyridazin-3-yl)oxy)piperidine-1-carboxylate (assumed 1.019 g, 3.15 mmol) in 2 mL DCM was treated with TFA (2 mL, 26 mmol). The reaction mixture was stirred for 20 min at ambient temperature, and then concentrated in vacuo. The crude residue was resuspended in DCM and the solution was purified by silica chromatography (1-9% MeOH in DCM with 0.1-0.9% NH4OH as the gradient eluent) to afford the title compound (70 mg, 10% yield over two steps) in sufficient purity for step 3. MS (apci) m/z=224.15 (M+H).

Step 3: Preparation of 6-(2-hydroxy-2-methylpropoxy)-4-(6-(4-((6-methoxy-5-methylpyridazin-3-yl)oxy)piperidin-1-yl)pyridin-3-yl)pyrazolo[1,5-a]pyridine-3-carbonitrile To a mixture of 4-(6-fluoropyridin-3-yl)-6-(2-hydroxy-2-methylpropoxy)pyrazolo[1,5-a]pyridine-3-carbonitrile (Intermediate P42; 51 mg, 0.156 mmol) and 3-methoxy-4-methyl-6-(piperidin-4-yloxy)pyridazine (70 mg, 0.314 mmol) in DMA (0.8 mL) was added TEA (150 µL, 1.09 mmol). The reaction mixture was stirred 40 h at 95° C. After cooling to ambient temperature, the reaction mixture was diluted with water and extracted with EtOAc. The combined organic extracts were washed with saturated NaHCO$_{3(aq)}$, water, and brine. The organic extracts were dried over anhydrous Na$_2$SO$_4$(s), filtered and concentrated in vacuo. The residue was suspended in 60:40 ACN:water containing 2% TFA. The solution was purified directly by C18 reverse phase chromatography (5-95% ACN in water with 0.1% TFA as the gradient eluent) to afford the title compound as the TFA salt. The TFA salt was treated with saturated NaHCO$_{3(aq)}$ and extracted with DCM. The combined organic extracts were washed with brine, then dried over anhydrous Na$_2$SO$_{4(s)}$, filtered and concentrated in vacuo to afford the title compound (26.5 mg, 32% yield). MS (apci) m/z=530.30 (M+H).

Example 269

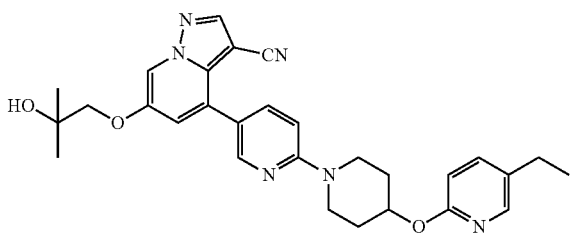 [SMILES: CCc1ccc(OC2CCN(c3ccc(-c4cc(OCC(C)(C)O)cn5ncc(C#N)c45)cn3)CC2)nc1]

4-(6-(4-((5-ethylpyridin-2-yl)oxy)piperidin-1-yl)pyridin-3-yl)-6-(2-hydroxy-2-methylpropoxy)pyrazolo[1,5-a]pyridine-3-carbonitrile Step 1: Preparation of tert-butyl 4-((5-ethylpyridin-2-yl)oxy)piperidine-1-carboxylate To a solution of tert-butyl 4-hydroxy-4-methylpiperidine-1-carboxylate (1.42 g, 7.06 mmol) in DMF (11.8 mL) was added sodium hydride (60% w/w, 311 mg, 7.77 mmol). The reaction was stirred for 15 min at ambient temperature. Then 2-chloro-5-ethylpyridine (1.00 g, 3.15 mmol) was added and reaction stirred 48 h at 90° C. The reaction was cooled to ambient temperature and additional tert-Butyl 4-hydroxy-4-methylpiperidine-1-carboxylate (1.42 g, 7.06 mmol) and sodium hydride (60% w/w, 311 mg, 7.77 mmol) were added. The reaction was stirred for 60 h at 90° C. The reaction was cooled to ambient temperature and additional tert-Butyl 4-hydroxy-4-methylpiperidine-1-carboxylate (1.42 g, 7.06 mmol) and sodium hydride (60% w/w, 311 mg, 7.77 mmol) were added. The reaction was stirred for 4 h at 90° C. The reaction was cooled to ambient temperature and diluted with water and saturated NaHCO$_{3(aq)}$ and extracted with EtOAc. Combined organics were washed with water and brine. The combined organic extracts were dried over anhydrous Na$_2$SO$_{4(s)}$, filtered and concentrated in vacuo. The crude residue was resuspended in DCM and the solution was purified by silica chromatography (5-50% EtOAc in Hexanes as the gradient eluent) to afford the title compound (assumed quantitative yield, 2.163 g) in sufficient purity for step 2. MS (apci) m/z=307.2 (M+H).

Step 2: Preparation of 5-ethyl-2-(piperidin-4-yloxy)pyridine

To a solution of tert-butyl 4-((5-ethylpyridin-2-yl)oxy)piperidine-1-carboxylate (assumed 2.163 g, 7.06 mmol) in 5 mL DCM was treated with TFA (10 mL, 130 mmol). The reaction mixture was stirred for 20 min at ambient temperature, and then concentrated in vacuo. The crude residue was resuspended in DCM and the solution was purified by silica chromatography (1-9% MeOH in DCM with 0.1-0.9% NH$_4$OH as the gradient eluent) to afford the title compound (835 mg, 57% yield over two steps) in sufficient purity for step 3. MS (apci) m/z=207.20 (M+H).

Step 3: Preparation of 4-(6-(4-((5-ethylpyridin-2-yl)oxy)piperidin-1-yl)pyridin-3-yl)-6-(2-hydroxy-2-methylpropoxy)pyrazolo[1,5-a]pyridine-3-carbonitrile To a mixture of 4-(6-fluoropyridin-3-yl)-6-(2-hydroxy-2-methylpropoxy)pyrazolo[1,5-a]pyridine-3-carbonitrile (Intermediate P42; 25 mg, 0.077 mmol) and 5-ethyl-2-(piperidin-4-yloxy)pyridine (55 mg, 0.27 mmol) in DMA (0.8 mL) was added TEA (73 µL, 0.54 mmol). The reaction mixture was stirred 40 h at 95° C. After cooling to ambient temperature, the reaction mixture was diluted with water and extracted with EtOAc. The combined organic extracts were washed with water and brine. The organic extracts were dried over anhydrous Na$_2$SO$_4$(s), filtered and concentrated in vacuo. The residue was suspended in 60:40 ACN:water containing 2% TFA. The solution was purified directly by C18 reverse phase chromatography (5-95% ACN in water with 0.1% TFA as the gradient eluent) to afford the title compound as the TFA salt. The TFA salt was treated with saturated NaHCO$_{3(aq)}$ and extracted with DCM. The combined organic extracts were washed with brine, then dried over anhydrous Na$_2$SO$_{4(s)}$, filtered and concentrated in vacuo to afford the title compound (6.7 mg, 17% yield). MS (apci) m/z=513.30 (M+H).

Example 270

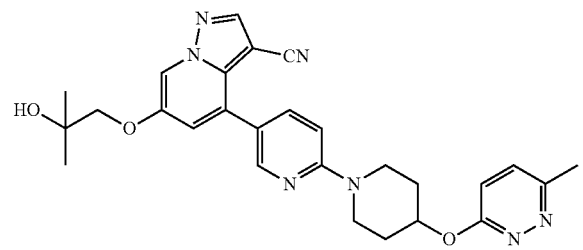 [SMILES: Cc1ccc(OC2CCN(c3ccc(-c4cc(OCC(C)(C)O)cn5ncc(C#N)c45)cn3)CC2)nn1]

6-(2-hydroxy-2-methylpropoxy)-4-(6-(4-((6-methylpyridazin-3-yl)oxy)piperidin-1-yl)pyridin-3-yl)pyrazolo[1,5-a]pyridine-3-carbonitrile Step 1: Preparation of tert-butyl 4-((6-methylpyridazin-3-yl)oxy)piperidine-1-carboxylate To a solution of tert-Butyl 4-hydroxy-4-methylpiperidine-1-carboxylate (313 mg, 1.56 mmol) in DMF (1.94 mL) was added sodium hydride (60% w/w, 68.4 mg, 1.71 mmol). The reaction was stirred for 5 min at ambient temperature. Then 3-chloro-6-methylpyridazine (100 mg, 0.778 mmol) was added and reaction stirred overnight at 95° C. The reaction was cooled to ambient temperature and diluted with saturated NaHCO$_{3(aq)}$ and extracted with EtOAc. Combined organics were washed with water and brine. The combined organic extracts were dried over anhydrous Na$_2$SO$_{4(s)}$, filtered and concentrated in vacuo to afford the title compound (assumed quantitative yield, 228 mg) in sufficient purity for step 2. MS (apci) m/z=294.20 (M+H).

Step 2: 3-methyl-6-(piperidin-4-yloxy)pyridazine

To a solution of tert-butyl 4-((6-methylpyridazin-3-yl)oxy)piperidine-1-carboxylate (assumed 228 mg, 0.778 mmol) in 2 mL DCM was treated with TFA (2 mL, 26 mmol). The reaction mixture was stirred for 1 h at ambient temperature, and then concentrated in vacuo. The crude residue was resuspended in DCM and the solution was purified by silica chromatography (1-9% MeOH in DCM with 0.1-0.9% NH4OH as the gradient eluent) to afford the title compound (104 mg, 69% yield over two steps) in sufficient purity for step 3. MS (apci) m/z=194.1 (M+H).

Step 3: Preparation of 6-(2-hydroxy-2-methylpropoxy)-4-(6-(4-((6-methylpyridazin-3-yl)oxy)piperidin-1-yl)pyridin-3-yl)pyrazolo[1,5-a]pyridine-3-carbonitrile To a mixture of 4-(6-fluoropyridin-3-yl)-6-(2-hydroxy-2-methylpropoxy)pyrazolo[1,5-a]pyridine-3-carbonitrile (Intermediate P42; 32 mg, 0.098 mmol) and 3-methyl-6-(piperidin-4-yloxy)pyridazine (57 mg, 0.29 mmol) in DMA (0.3 mL) was added TEA (67 µL, 0.49 mmol). The reaction mixture was stirred overnight at 95° C. After cooling to ambient temperature, the reaction mixture was diluted with EtOAc and washed with water and brine. The organic extracts were dried over anhydrous Na$_2$SO$_4$(s), filtered and concentrated in vacuo. The residue was suspended in 60:40 ACN:water containing 2% TFA. The solution was purified directly by C18 reverse phase chromatography (5-95% ACN in water with 0.1% TFA as the gradient eluent) to afford the title compound as the TFA salt. The TFA salt was treated with saturated NaHCO$_{3(aq)}$ and extracted with DCM. The combined organic extracts were washed with brine, then dried over anhydrous Na$_2$SO$_{4(s)}$, filtered and concentrated in vacuo to afford the title compound (25 mg, 51% yield). MS (apci) m/z=500.20 (M+H). $^1$H NMR (400 MHz, CDCl$_3$) δ 8.35 (d, 1H), 8.20 (s, 1H), 8.15 (d, 1H), 7.72 (dd, 1H), 7.24 (d, 1H). 7.15 (d, 1H), 6.87 (d, 1H), 6.82 (d, 1H), 5.56 (m, 1H), 4.10 (m, 2H), 3.86 (s, 2H), 3.51 (m, 2H), 2.61 (s, 3H), 2.23 (m, 2H), 1.91 (m, 2H), 1.39 (s, 6H).

Example 271

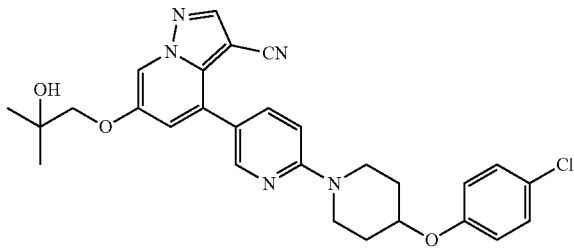 [SMILES: CC(C)(O)COc1cc(-c2ccc(N3CCC(Oc4ccc(Cl)cc4)CC3)nc2)c2c(C#N)cnn2c1]

4-(6-(4-(4-chlorophenoxy)piperidin-1-yl)pyridin-3-yl)-6-(2-hydroxy-2-methylpropoxy)pyrazolo[1,5-a]pyridine-3-carbonitrile To a mixture of 4-(6-fluoropyridin-3-yl)-6-(2-hydroxy-2-methylpropoxy)pyrazolo[1,5-a]pyridine-3-carbonitrile (Intermediate P42; 25.5 mg, 0.078 mmol) and 4-(4-chlorophenoxy)piperidine hydrochloride (38.8 mg, 0.156 mmol) in DMA (0.5 mL) was added TEA (33 µL, 0.234 mmol). The reaction mixture was stirred overnight at 90° C. After cooling to ambient temperature, the reaction mixture was diluted with DCM and washed with water and brine. The organic extracts were dried over anhydrous Na$_2$SO$_4$(s), filtered and concentrated in vacuo. The residue purified by C18 reverse phase chromatography (5-95% ACN in water with 0.1% TFA as the gradient eluent) to afford the title compound as the TFA salt. The TFA salt was treated with saturated Na$_2$CO$_{3(aq)}$ and extracted with DCM. The combined organic extracts were washed with brine, then dried over anhydrous Na$_2$SO$_{4(s)}$, filtered and concentrated in vacuo to afford the title compound (28 mg, 70% yield). MS (apci) m/z=518.1 (M+H).

Example 272

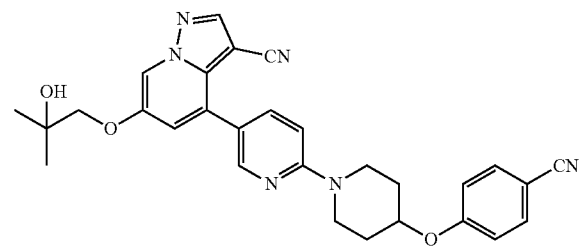 [SMILES: CC(C)(O)COc1cc(-c2ccc(N3CCC(Oc4ccc(C#N)cc4)CC3)nc2)c2c(C#N)cnn2c1]

4-(6-(4-(4-cyanophenoxy)piperidin-1-yl)pyridin-3-yl)-6-(2-hydroxy-2-methylpropoxy)pyrazolo[1,5-a]pyridine-3-carbonitrile The title compound was prepared using a similar method to that described for the synthesis of Example 271, replacing 4-(4-chlorophenoxy)piperidine hydrochloride with 4-(piperidin-4-yloxy)benzonitrile. MS (apci) m/z=509.2 (M+H).

Example 273

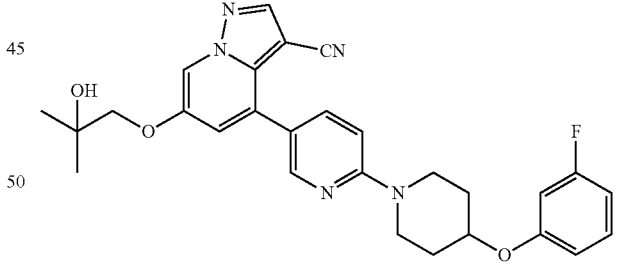

4-(6-(4-(3-fluorophenoxy)piperidin-1-yl)pyridin-3-yl)-6-(2-hydroxy-2-methylpropoxy)pyrazolo[1,5-a]pyridine-3-carbonitrile To a mixture of 4-(6-fluoropyridin-3-yl)-6-(2-hydroxy-2-methylpropoxy)pyrazolo[1,5-a]pyridine-3-carbonitrile (Intermediate P42; 28 mg, 0.085 mmol) and 4-(3-fluorophenoxy)piperidine hydrochloride (39 mg, 0.170 mmol) in DMA (0.6 mL) was added TEA (47 µL, 0.34 mmol). The reaction mixture was stirred overnight at 90° C. After cooling to ambient temperature, the reaction mixture was diluted with DCM and washed with water and brine. The organic extracts were dried over anhydrous Na₂SO₄(s), filtered and concentrated in vacuo. The residue was purified by C18 reverse phase chromatography (5-95% ACN in water with 0.1% TFA as the gradient eluent) to afford the title compound as the TFA salt. The TFA salt was treated with saturated Na₂CO₃(aq) and extracted with DCM. The combined organic extracts were washed with brine, then dried over anhydrous Na₂SO₄(s), filtered and concentrated in vacuo to afford the title compound (25.5 mg, 60% yield). MS (apci) m/z=502.2 (M+H).

Example 274

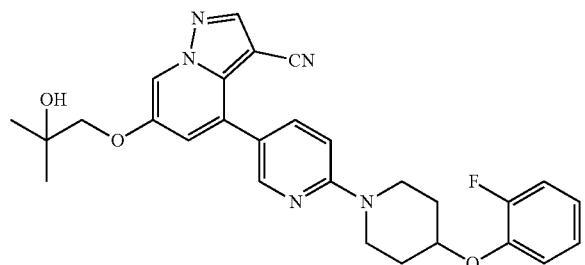

4-(6-(4-(2-fluorophenoxy)piperidin-1-yl)pyridin-3-yl)-6-(2-hydroxy-2-methylpropoxy)pyrazolo[1,5-a]pyridine-3-carbonitrile The title compound was prepared using a similar method to that described for the synthesis of Example 273, replacing 4-(3-fluorophenoxy)piperidine hydrochloride with 4-(2-fluorophenoxy)piperidine. MS (apci) m/z=502.2 (M+H).

Example 275

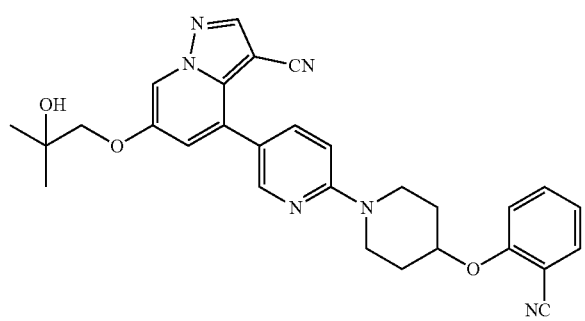 [SMILES: CC(C)(O)COc1cc(-c2ccc(N3CCC(Oc4ccccc4C#N)CC3)nc2)c2c(C#N)cnn2c1]

4-(6-(4-(2-cyanophenoxy)piperidin-1-yl)pyridin-3-yl)-6-(2-hydroxy-2-methylpropoxy)pyrazolo[1,5-a]pyridine-3-carbonitrile To a mixture of 4-(6-fluoropyridin-3-yl)-6-(2-hydroxy-2-methylpropoxy)pyrazolo[1,5-a]pyridine-3-carbonitrile (Intermediate P42; 27 mg, 0.083 mmol) and 2-(piperidin-4-yloxy)benzonitrile (34 mg, 0.166 mmol) in DMA (0.42 mL) was added TEA (70 µL, 0.498 mmol). The reaction mixture was stirred overnight at 95° C. After cooling to ambient temperature, the reaction mixture was diluted with DCM and washed with water and brine. The organic extracts were dried over anhydrous Na₂SO₄(s), filtered and concentrated in vacuo. The residue was purified by C18 reverse phase chromatography (5-95% ACN in water with 0.1% TFA as the gradient eluent) to afford the title compound as the TFA salt. The TFA salt was treated with saturated Na₂CO₃(aq) and extracted with DCM. The combined organic extracts were washed with brine, then dried over anhydrous Na₂SO₄(s), filtered and concentrated in vacuo to afford the title compound (23 mg, 55% yield). MS (apci) m/z=509.2 (M+H).

Example 276

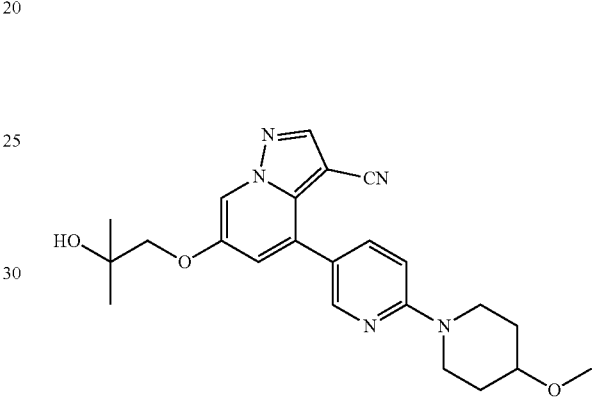

6-(2-hydroxy-2-methylpropoxy)-4-(6-(4-methoxypiperidin-1-yl)pyridin-3-yl)pyrazolo[1,5-a]pyridine-3-carbonitrile To a mixture of 4-(6-fluoropyridin-3-yl)-6-(2-hydroxy-2-methylpropoxy)pyrazolo[1,5-a]pyridine-3-carbonitrile (Intermediate P42; 26.1 mg, 0.08 mmol) in DMA (1 mL) was added 4-methoxy-piperidine (9.7 mg, 0.084 mmol) followed by TEA (54 µL, 0.40 mmol). The reaction mixture was stirred overnight at 90° C. The reaction was cooled to ambient temperature and additional 4-methoxypiperidine (5 mg, 0.04 mmol) was added. After cooling to ambient temperature, the reaction mixture was diluted with water and extracted with EtOAc. Combined organic extracts were washed with water and brine. The organic extracts were dried over anhydrous Na₂SO₄(s), filtered and concentrated in vacuo. The residue was purified by silica chromatography (5-50% Acetone in DCM as the gradient eluent). Fractions containing the product were concentrated in vacuo and repurified by C18 reverse phase chromatography (5-95% ACN in water with 0.1% TFA as the gradient eluent) to afford the title compound as the TFA salt. The TFA salt was treated with saturated Na₂CO₃(aq) and extracted with 4:1 DCM:IPA. The combined organic extracts were washed with brine, then dried over anhydrous Na₂SO₄(s), filtered and concentrated in vacuo to afford the title compound (23 mg, 55% yield). MS (apci) m/z=422.2 (M+H).

Example 277

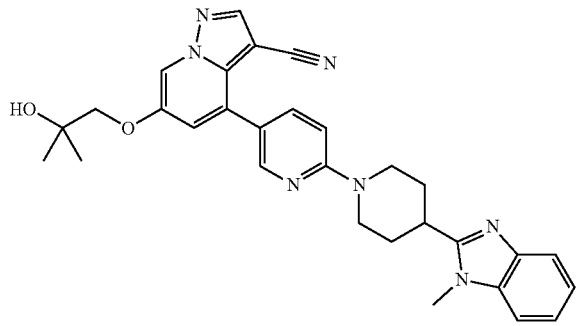 [SMILES: Cn1c(C2CCN(c3ccc(-c4cc(OCC(C)(C)O)cn5ncc(C#N)c45)cn3)CC2)nc2ccccc21]

6-(2-hydroxy-2-methylpropoxy)-4-(6-(4-(1-methyl-1H-benzo[d]imidazol-2-yl)piperidin-1-yl)pyridin-3-yl)pyrazolo[1,5-a]pyridine-3-carbonitrile A mixture of 4-(6-fluoropyridin-3-yl)-6-(2-hydroxy-2-methylpropoxy)pyrazolo[1,5-a]pyridine-3-carbonitrile (Intermediate P42; 50 mg, 0.15 mmol) and 1-methyl-2-(piperidin-4-yl)-1H-benzo[d]imidazole dihydrochloride (66 mg, 0.23 mmol) and DIEA (133 L, 0.77 mmol) were combined in DMSO (306 μL). The reaction mixture was stirred 72 h at 90° C. After cooling to ambient temperature, the reaction mixture was purified directly by C18 reverse phase chromatography (5-45% ACN in water as the gradient eluent) to afford the title compound (38 mg, 47% yield). MS (apci) m/z=522.2 (M+H).

Example 278

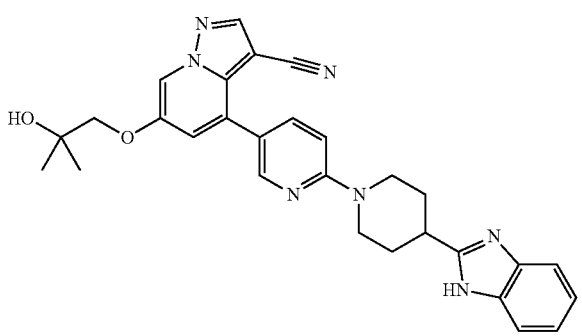 [SMILES: CC(C)(O)COc1cc(-c2ccc(N3CCC(c4nc5ccccc5[nH]4)CC3)nc2)c2c(C#N)cnn2c1]

4-(6-(4-(1H-benzo[d]imidazol-2-yl)piperidin-1-yl)pyridin-3-yl)-6-(2-hydroxy-2-methylpropoxy)pyrazolo[1,5-a]pyridine-3-carbonitrile The title compound was prepared using a similar method to that described for the synthesis of Example 277, replacing 1-methyl-2-(piperidin-4-yl)-1H-benzo[d]imidazole dihydrochloride with 2-(piperidin-4-yl)-1H-benzo[d]imidazole. MS (apci) m/z=508.2 (M+H).

Example 279

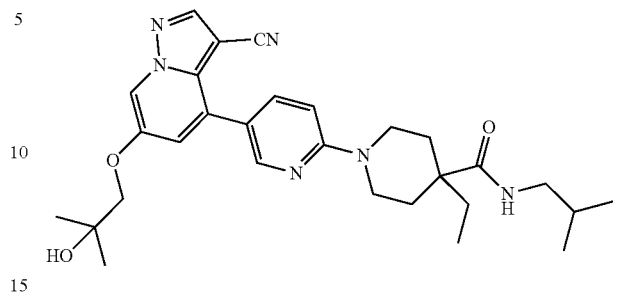

1-(5-(3-cyano-6-(2-hydroxy-2-methylpropoxy)pyrazolo[1,5-a]pyridin-4-yl)pyridin-2-yl)-4-ethyl-N-isobutylpiperidine-4-carb oxamide Step 1: Preparation tert-butyl 4-ethyl-4-(isobutylcarbamoyl)piperidine-1-carboxylate A mixture of 1-(tert-butoxycarbonyl)-4-ethylpiperidine-4-carboxylic acid (260 mg, 1.01 mmol), HATU (461 mg, 1.21 mmol), and 2-methylpropan-1-amine (81 mg, 1.11 mmol) in DMF (4 mL) was treated with DIEA (352 μL, 2.0 mmol) and then stirred for 60 h at 60° C. After cooling to ambient temperature, the reaction mixture was diluted with EtOAc and washed with water and brine. The combined organic extracts were dried over anhydrous $Na_2SO_{4(s)}$, filtered and concentrated in vacuo. The residue was purified by silica chromatography (0-95% EtOAc in Hexanes as the gradient eluent) to afford the title compound (assumed theoretical yield, 316 mg) in sufficient purity for step 2. MS (apci) m/z=256.2 (M-Bu').

Step 2: Preparation of 4-ethyl-N-isobutylpiperidine-4-carboxamide

A solution of tert-butyl 4-ethyl-4-(isobutylcarbamoyl)piperidine-1-carboxylate (assumed 316 mg, 1.01 mmol) in 2 mL DCM was treated with TFA (2 mL, 26 mmol). The reaction mixture was stirred for 1 h at ambient temperature, and then concentrated in vacuo. The crude residue was diluted with 4:1 DCM:IPA and washed with saturated $NaHCO_{3(aq)}$. The organic extracts were dried over anhydrous $Na_2SO_{4(s)}$, filtered and concentrated in vacuo to afford the title compound (101 mg, 84% yield over two steps) in sufficient purity for step 3. MS (apci) m/z=213.2 (M+H).

Step 3: Preparation of 1-(5-(3-cyano-6-(2-hydroxy-2-methylpropoxy)pyrazolo[1,5-a]pyridin-4-yl)pyridin-2-yl)-4-ethyl-N-isobutylpiperidine-4-carboxamide To a solution of 4-(6-fluoropyridin-3-yl)-6-(2-hydroxy-2-methylpropoxy)pyrazolo[1,5-a]pyridine-3-carbonitrile (Intermediate P42; 20 mg, 0.06 mmol) and 4-ethyl-N-phenylpiperidine-4-carboxamide (42 mg, 0.18 mmol) in DMA (0.25 mL) was added TEA (41 μL, 0.30 mmol). The reaction mixture was stirred 14 h at 90° C. After cooling to ambient temperature, the reaction mixture was diluted with EtOAc and washed with water and brine. The organic extracts were dried over anhydrous Na2SO4(s), filtered and concentrated in vacuo. The residue was purified by C18 reverse phase chromatography (5-95% ACN in water with 0.1% TFA as the gradient eluent) to afford the title compound as the TFA salt. The TFA salt was treated with saturated $NaHCO_{3(aq)}$ and extracted with 4:1 DCM:IPA. The combined organic extracts were dried over anhydrous $Na_2SO_{4(s)}$, filtered and concentrated in vacuo. The residue was repurified by silica chromatography (0-30% MeOH in DCM with 0-2% $NH_4OH$ as the gradient eluent) to cleanly provide the title compound (21 mg, 65% yield) MS (apci) m/z=519.3 (M+H).

Example 280

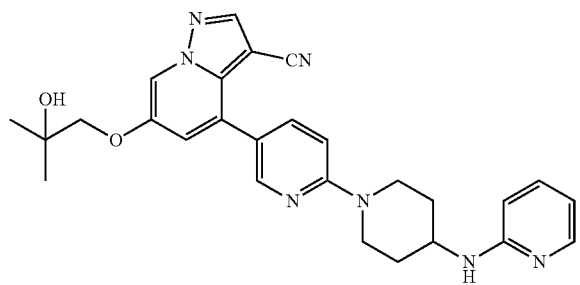 [SMILES: CC(C)(O)COc1cc(-c2ccc(N3CCC(Nc4ccccn4)CC3)nc2)c2c(C#N)cnn2c1]

6-(2-hydroxy-2-methylpropoxy)-4-(6-(4-(pyridin-2-ylamino)piperidin-1-yl)pyridin-3-yl)pyrazolo[1,5-a]pyridine-3-carbonitrile To a solution of 4-(6-fluoropyridin-3-yl)-6-(2-hydroxy-2-methylpropoxy)pyrazolo[1,5-a]pyridine-3-carbonitrile (Intermediate P42; 38 mg, 0.117 mmol)N-(piperidin-4-yl)pyridin-2-amine (42 mg, 0.235 mmol) in DMA (0.78 mL) was added TEA (98 µL, 0.70 mmol). The reaction mixture was stirred overnight at 90° C. After cooling to ambient temperature, the reaction mixture was diluted with DCM and washed with water and brine. The organic extracts were dried over anhydrous $Na_2SO_{4(s)}$, filtered and concentrated in vacuo. The residue was purified by C18 reverse phase chromatography (5-95% ACN in water with 0.1% TFA as the gradient eluent) to afford the title compound as the TFA salt. The TFA salt was treated with saturated $NaHCO_{3(aq)}$ and extracted with 4:1 DCM:IPA. The combined organic extracts were dried over anhydrous $Na_2SO_{4(s)}$, filtered and concentrated in vacuo to cleanly provide the title compound (11 mg, 20% yield) MS (apci) m/z=484.2 (M+H).

Example 281

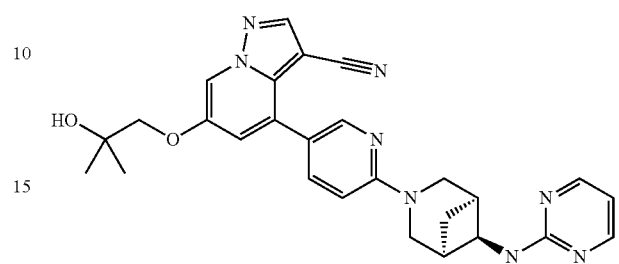

6-(2-hydroxy-2-methylpropoxy)-4-(6-((1R,5S,6r)-6-(pyrimidin-2-ylamino)-3-azabicyclo[3.1.1]heptan-3-yl)pyridin-3-yl)pyrazolo[1,5-a]pyridine-3-carbonitrile To a mixture of 4-(6-((1R,5 S,6r)-6-amino-3-azabicyclo[3.1.1]heptan-3-yl)pyridin-3-yl)-6-(2-hydroxy-2-methylpropoxy)pyrazolo[1,5-a]pyridine-3-carbonitrile dihydrochloride (Intermediate P63; 25 mg, 0.051 mmol) and 2-chloropyrimidine (8.7 mg, 0.076 mmol) in DMSO (102 µL) was added DIEA (44 µL, 0.25 mmol). The reaction mixture was stirred 60 h at 90° C. After cooling to ambient temperature, the reaction was purified directly by C18 reverse phase chromatography (5-40% ACN in water as the gradient eluent) to afford the title compound (9.5 mg, 38% yield) MS (apci) m/z=497.25 (M+H).

The compounds in Table NN were prepared using a similar method to that described for the synthesis of Example 281, replacing 2-chloropyrimidine with the appropriate halogenated heterocycle. Reactions were monitored for completion by LCMS, and reaction durations were adjusted accordingly. Title compounds were cleanly isolated following chromatographic purification using an appropriate gradient eluent (and if necessary converted to the free base).

TABLE NN

| Ex. # | Structure | Chemical Name | MS m/z |
|---|---|---|---|
| 282 | 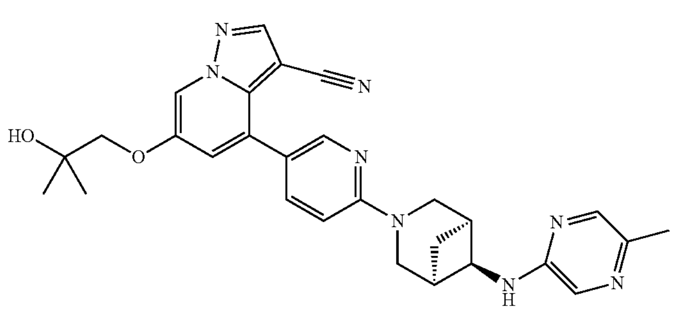 [SMILES: Cc1cnc(N[C@H]2[C@@H]3C[C@H]2CN(c2ccc(-c4cc(OCC(C)(C)O)cn5ncc(C#N)c45)cn2)C3)cn1] | 6-(2-hydroxy-2-methylpropoxy)-4-(6-((1R,5S,6r)-6-((5-methylpyrimidin-2-yl)amino-3-azabicyclo[3.1.1]heptan-3-yl)pyridin-3-yl)pyrazolo[1,5-a]pyridine-3-carbonitrile | 511.2 (M + H) |

TABLE NN-continued

| Ex. # | Structure | Chemical Name | MS m/z |
|---|---|---|---|
| 283 | 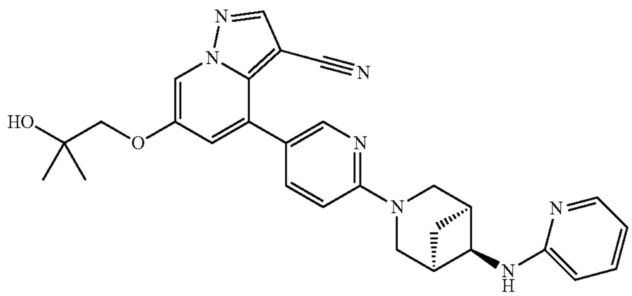 [SMILES: CC(C)(O)COc1cc(-c2ccc(N3C[C@H]4C[C@@H](C3)[C@H]4Nc3ccccn3)nc2)c2c(C#N)cnn2c1] | 6-(2-hydroxy-2-methylpropoxy)-4-(6-((1R,5S,6r)-6-(pyridin-2-ylamino)-3-azabicyclo[3.1.1]heptan-3-yl)pyridin-3-yl)pyrazolo[1,5-a]pyridine-3-carbonitrile | 496.1 (M + H) |
| 284 | 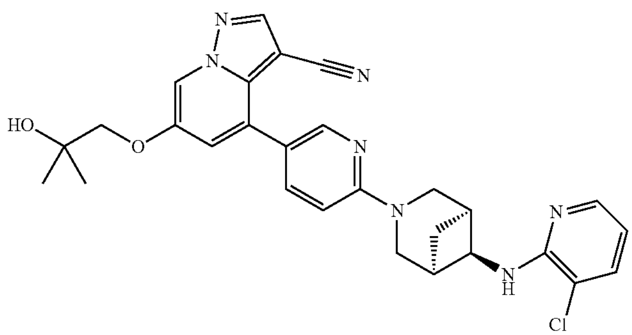 [SMILES: CC(C)(O)COc1cc(-c2ccc(N3C[C@H]4C[C@@H](C3)[C@H]4Nc3ncccc3Cl)nc2)c2c(C#N)cnn2c1] | 4-(6-((1R,5S,6r)-6-((3-chloropyridin-2-yl)amino)-3-azabicyclo[3.1.1]heptan-3-yl)-6-(2-hydroxy-2-methylpropoxy)pyrazolo[1,5-a]pyridine-3-carbonitrile | 530.1 (M + H) |
| 285 | 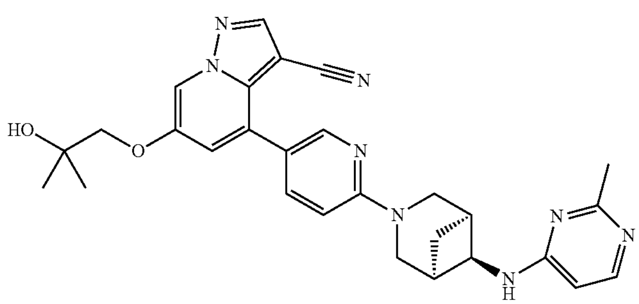 [SMILES: Cc1nccc(N[C@H]2[C@@H]3C[C@H]2CN(c2ccc(-c4cc(OCC(C)(C)O)cn5ncc(C#N)c45)cn2)C3)n1] | 6-(2-hydroxy-2-methylpropoxy)-4-(6-((1R,5S,6r)-6-((2-methylpyrimidin-4-yl)amino)-3-azabicyclo[3.1.1]heptan-3-yl)pyridin-3-yl)pyrazolo[1,5-a]pyridine-3-carbonitrile | 511.2 (M + H) |
| 286 | 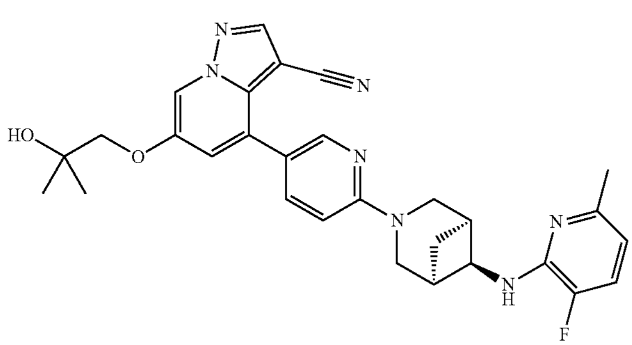 | 4-(6-((1R,5S,6r)-6-((3-fluoro-6-methylpyridin-2-yl)amino)-3-azabicyclo[3.1.1]heptan-3-yl)-6-(2-hydroxy-2-methylpropoxy)pyrazolo[1,5-a]pyridine-3-carbonitrile | 475.2 (M + H) 497.1 (M + Na) |

Example 287

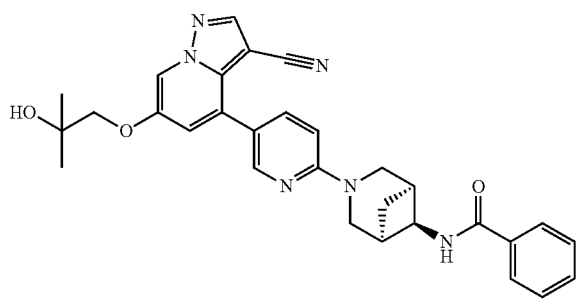

N-((1R,5 S,6r)-3-(5-(3-cyano-6-(2-hydroxy-2-methylpropoxy)pyrazolo[1,5-a]pyridin-4-yl)pyridin-2-yl)-3-azabicyclo[3.1.1]heptan-6-yl)benzamide A mixture of 4-(6-((1R,5 S,6r)-6-amino-3-azabicyclo[3.1.1]heptan-3-yl)pyridin-3-yl)-6-(2-hydroxy-2-methylpropoxy)pyrazolo[1,5-a]pyridine-3-carbonitrile dihydrochloride (Intermediate P63; 25 mg, 0.051 mmol), HATU (21 mg, 0.056 mmol), and benzoic acid (7 mg, 0.061 mmol) in DMSO (254 µL) was treated with DIEA (44 µL, 0.254 mmol) and then stirred for 2 min at ambient temperature. The reaction was purified directly by C18 reverse phase chromatography (5-50% ACN in water as the gradient eluent) to afford the title compound (22.8 mg, 86% yield) MS (apci) m/z=523.2 (M+H), 545.2 (M+Na).

Example 288

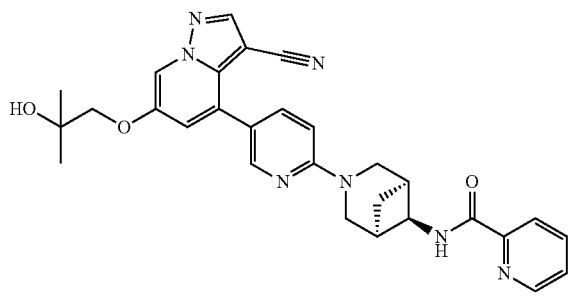 [SMILES: CC(C)(O)COc1cc(-c2ccc(N3C[C@H]4C[C@@H](C3)[C@H]4NC(=O)c3ccccc3)nc2)c2c(C#N)cnn2c1]

N-((1R,5 S,6r)-3-(5-(3-cyano-6-(2-hydroxy-2-methylpropoxy)pyrazolo[1,5-a]pyridin-4-yl)pyridin-2-yl)-3-azabicyclo[3.1.1]heptan-6-yl)picolinamide The title compound was prepared using a similar method to that described for the synthesis of Example 287, replacing benzoic acid with picolinic acid. MS m/z=524.2 (M+H), 546.2 (M+Na)

Example 289

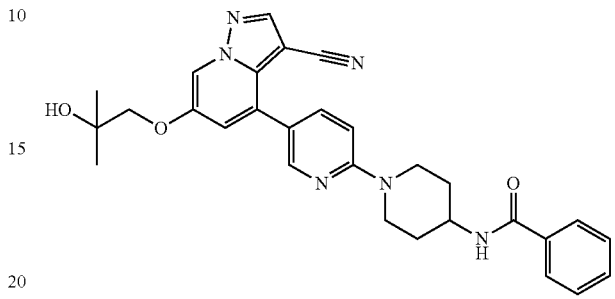

N-(1-(5-(3-cyano-6-(2-hydroxy-2-methylpropoxy)pyrazolo[1,5-a]pyridin-4-yl)pyridin-2-yl)piperidin-4-yl)benzamide A mixture of 4-(6-(4-amino-4-methylpiperidin-1-yl)pyridin-3-yl)-6-(2-hydroxy-2-methylpropoxy)pyrazolo[1,5-a]pyridine-3-carbonitrile (Intermediate P64; 20 mg, 0.049 mmol), HATU (21 mg, 0.054 mmol), and benzoic acid (9 mg, 0.24 mmol) in DCM (0.5 mL) was treated with DIEA (43 µL, 0.054 mmol) and then stirred for 1 h at ambient temperature. The reaction mixture was concentrated in vacuo. The residue was suspended in 60:40 ACN:water containing 2% TFA. The solution was purified directly by C18 reverse phase chromatography (5-95% ACN in water with 0.1% TFA as the gradient eluent) to afford the title compound as the TFA salt. The TFA salt was treated with saturated $NaHCO_{3(aq)}$ and extracted with DCM. The combined organic extracts were washed with brine, then dried over anhydrous $Na_2SO_{4(s)}$, filtered and concentrated in vacuo to afford the title compound (43.7 mg, 49.3% yield). MS (apci) m/z=511.20 (M+H).

The compounds in Table OO were prepared using a similar method to that described for the synthesis of Example 289, replacing benzoic acid with the appropriate carboxylic acid. Reactions were monitored for completion by LCMS, and reaction durations were adjusted accordingly. Title compounds were cleanly isolated following chromatographic purification using an appropriate gradient eluent (and if necessary converted to the free base).

TABLE OO

| Ex. # | Structure | Chemical Name | MS m/z |
|---|---|---|---|
| 290 | 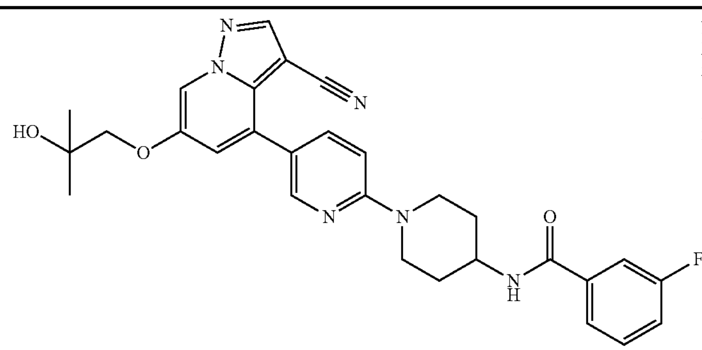 | N-(1-(5-(3-cyano-6-(2-hydroxy-2-methylpropoxy)pyrazolo[1,5-a]pyridin-4-yl)pyridin-2-yl)piperidin-4-yl)-3-fluorobenzamide | 529.20 (M + H) |

TABLE OO-continued

| Ex. # | Structure | Chemical Name | MS m/z |
|---|---|---|---|
| 291 | 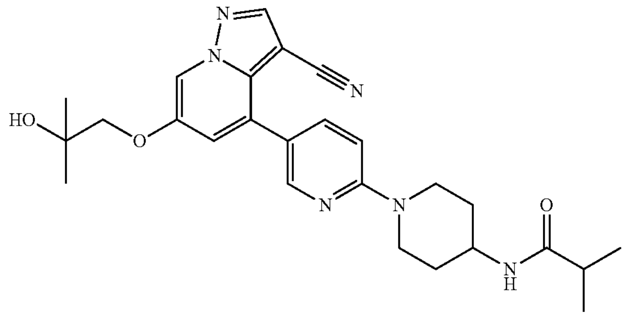 [SMILES: CC(C)C(=O)NC1CCN(c2ccc(-c3cc(OCC(C)(C)O)cn4ncc(C#N)c34)cn2)CC1] | N-(1-(5-(3-cyano-6-(2-hydroxy-2-methylpropoxy)pyrazolo[1,5-a]pyridin-4-yl)pyridin-2-yl)piperidin-4-yl)isobutyramide | 477.20 (M + H) |
| 292 | 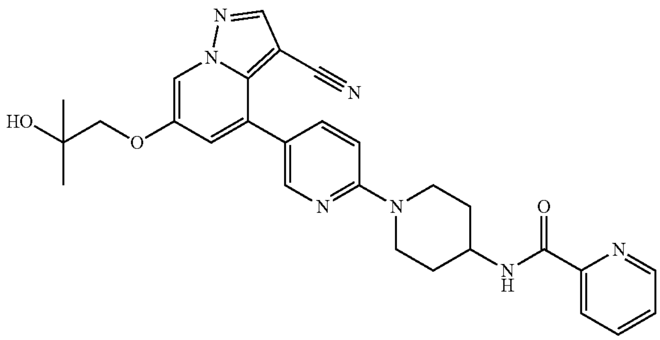 [SMILES: CC(C)(O)COc1cc(-c2ccc(N3CCC(NC(=O)c4ccccn4)CC3)nc2)c2c(C#N)cnn2c1] | N-(1-(5-(3-cyano-6-(2-hydroxy-2-methylpropoxy)pyrazolo[1,5-a]pyridin-4-yl)pyridin-2-yl)piperidin-4-yl)picolinamide | 512.20 (M + H) |
| 293 | 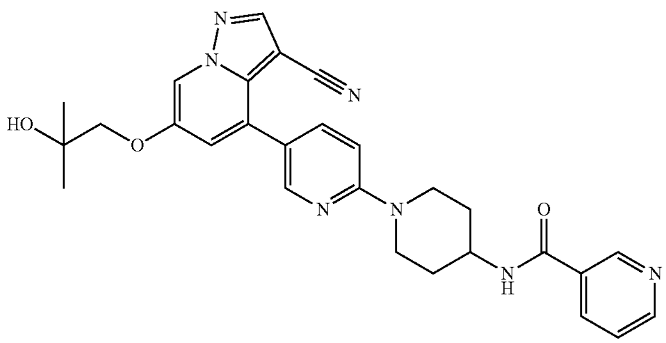 [SMILES: CC(C)(O)COc1cc(-c2ccc(N3CCC(NC(=O)c4cccnc4)CC3)nc2)c2c(C#N)cnn2c1] | N-(1-(5-(3-cyano-6-(2-hydroxy-2-methylpropoxy)pyrazolo[1,5-a]pyridin-4-yl)pyridin-2-yl)piperidin-4-yl)nicotinamide | 512.20 (M + H) |

Example 294

N-(1-(5-(3-cyano-6-(2-hydroxy-2-methylpropoxy)pyrazolo[1,5-a]pyridin-4-yl)pyridin-2-yl)piperidin-4-yl)-4-fluorobenzamide

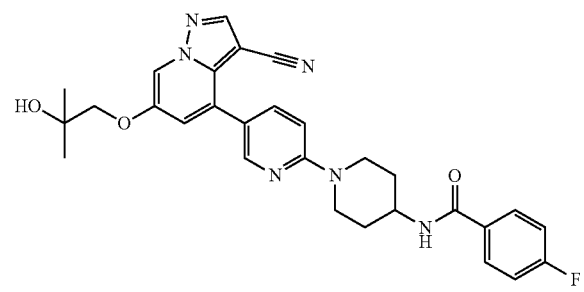 [SMILES: CC(C)(O)COc1cc(-c2ccc(N3CCC(NC(=O)c4ccc(F)cc4)CC3)nc2)c2c(C#N)cnn2c1]

A mixture of 4-(6-(4-amino-4-methylpiperidin-1-yl)pyridin-3-yl)-6-(2-hydroxy-2-methylpropoxy)pyrazolo[1,5-a]pyridine-3-carbonitrile (Intermediate P64; 20 mg, 0.049 mmol), HATU (21 mg, 0.054 mmol), and 4-fluorobenzoic acid (69 mg, 0.049 mmol) in DCM (0.5 mL) was treated with DIEA (43 μL, 0.049 mmol) and then stirred for 2.5 h at ambient temperature. The reaction mixture was concentrated in vacuo. The residue was suspended in 60:40 ACN:water containing 2% TFA. The solution was purified directly by C18 reverse phase chromatography (5-95% ACN in water with 0.1% TFA as the gradient eluent) to afford the title compound as the TFA salt. The TFA salt was treated with saturated $NaHCO_{3(aq)}$ and extracted with DCM. The combined organic extracts were washed with brine, then dried over anhydrous $Na_2SO_{4(s)}$, filtered and concentrated in vacuo to afford the title compound (16 mg, 60% yield). MS (apci) m/z=529.20 (M+H).

Example 295

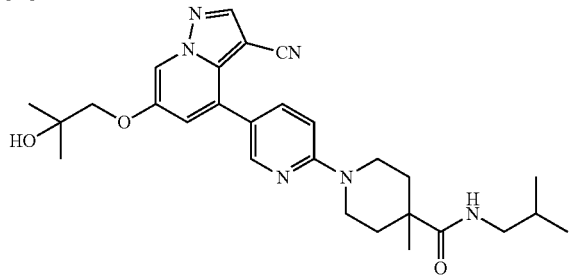

1-(5-(3-cyano-6-(2-hydroxy-2-methylpropoxy)pyrazolo[1,5-a]pyridin-4-yl)pyridin-2-yl)-N-isobutyl-4-methylpiperidine-4-carboxamide A mixture of 1-(5-(3-cyano-6-(2-hydroxy-2-methylpropoxy)pyrazolo[1,5-a]pyridin-4-yl)pyridin-2-yl)-4-methylpiperidine-4-carboxylic acid (Intermediate P65; 30 mg, 0.067 mmol), HATU (31 mg, 0.080 mmol), and isobutylamine (6 mg, 0.08 mmol) in DCM (133 μL) was treated with DIEA (35 μL, 0.2 mmol) and then stirred for 2 h at ambient temperature. The reaction mixture was concentrated in vacuo. The residue was purified directly by C18 reverse phase chromatography (5-95% ACN in water with 1% TFA as the gradient eluent) to afford the title compound as the TFA salt. The TFA salt was treated with saturated NaHCO$_{3(aq)}$ and extracted with DCM. The combined organic extracts were washed with brine, then dried over anhydrous Na$_2$SO$_{4(s)}$, filtered and concentrated in vacuo. The residue was triturated with DCM/Hexanes and concentrated in vacuo to afford the title compound (12 mg, 36% yield). MS (apci) m/z=505.3 (M+H).

Example 296

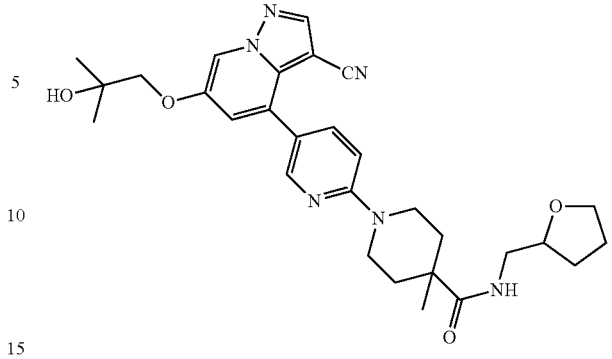

1-(5-(3-cyano-6-(2-hydroxy-2-methylpropoxy)pyrazolo[1,5-a]pyridin-4-yl)pyridin-2-yl)-4-methyl-N-((tetrahydrofuran-2-yl)methyl)piperidine-4-carboxamide A mixture of 1-(5-(3-cyano-6-(2-hydroxy-2-methylpropoxy)pyrazolo[1,5-a]pyridin-4-yl)pyridin-2-yl)-4-methylpiperidine-4-carboxylic acid (Intermediate P65; 30 mg, 0.067 mmol), HATU (30 mg, 0.080 mmol), and (tetrahydrofuran-2-yl)methanamine (7 mg, 0.067 mmol) in DCM (133 μL) was treated with DIEA (35 μL, 0.20 mmol) and then stirred for overnight at ambient temperature. The reaction mixture was concentrated in vacuo. The residue was purified directly by C18 reverse phase chromatography (5-95% ACN in water with 1% TFA as the gradient eluent) to afford the title compound as the TFA salt. The TFA salt was treated with saturated NaHCO$_{3(aq)}$ and extracted with DCM. The combined organic extracts were washed with brine, then dried over anhydrous Na$_2$SO$_{4(s)}$, filtered and concentrated in vacuo. The residue was triturated with DCM/Hexanes and concentrated in vacuo to afford the title compound (24 mg, 67% yield). MS (apci) m/z=533.3 (M+H).

The compounds in Table PP were prepared using a similar method to that described for the synthesis of Example 296, replacing (tetrahydrofuran-2-yl)methanamine with the appropriate amine. Reactions were monitored for completion by LCMS, and reaction durations were adjusted accordingly. Title compounds were cleanly isolated following chromatographic purification using an appropriate gradient eluent (and if necessary converted to the free base).

TABLE PP

| Ex. # | Structure | Chemical Name | MS m/z |
|---|---|---|---|
| 297 | 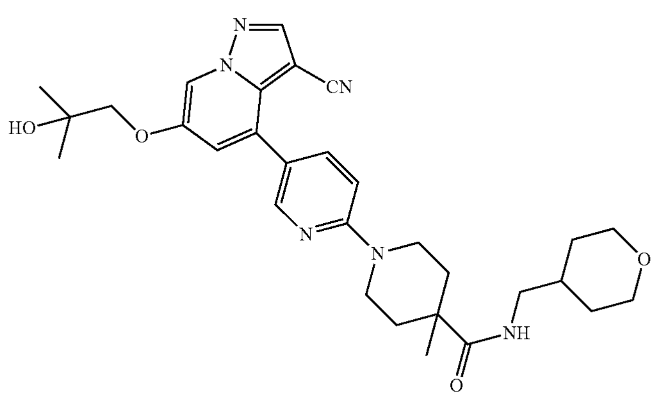 [SMILES: CC(C)(O)COc1cc(-c2ccc(N3CCC(C)(C(=O)NCC4CCOCC4)CC3)nc2)c2c(C#N)cnn2c1] | 1-(5-(3-cyano-6-(2-hydroxy-2-methylpropoxy)pyrazolo[1,5-a]pyridin-4-yl)pyridin-2-yl)-4-methyl-N-((tetrahydro-2H-pyran-4-yl)methyl)piperidine-4-carboxamide | 547.3 (M + H) |

TABLE PP-continued

| Ex. # | Structure | Chemical Name | MS m/z |
|---|---|---|---|
| 298 | 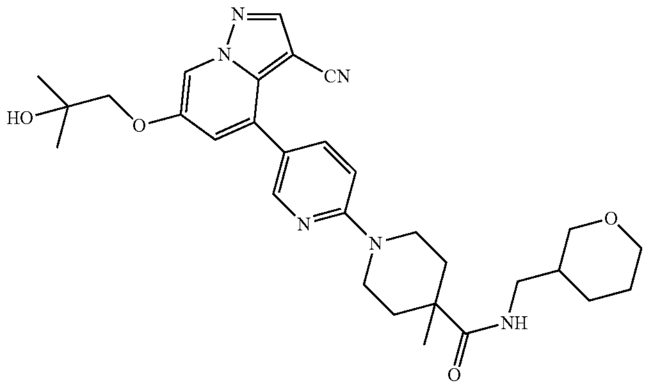 [SMILES: CC(C)(O)COc1cc(-c2ccc(N3CCC(C)(C(=O)NCC4CCCOC4)CC3)nc2)c2c(C#N)cnn2c1] | 1-(5-(3-cyano-6-(2-hydroxy-2-methylpropoxy)pyrazolo[1,5-a]pyridin-4-yl)pyridin-2-yl)-4-methyl-N-((tetrahydro-2H-pyran-3-yl)methyl)piperidine-4-carboxamide | 547.3 (M + H) |

Example 299

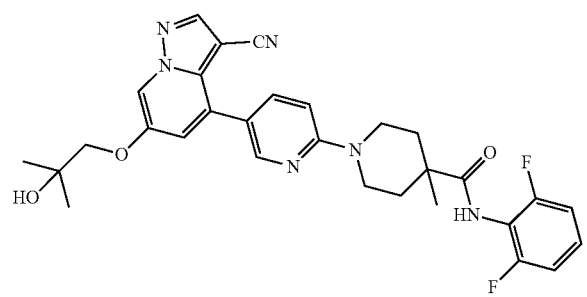 [SMILES: CC(C)(O)COc1cc(-c2ccc(N3CCC(C)(C(=O)Nc4c(F)cccc4F)CC3)nc2)c2c(C#N)cnn2c1]

1-(5-(3-cyano-6-(2-hydroxy-2-methylpropoxy)pyrazolo[1,5-a]pyridin-4-yl)pyridin-2-yl)-N-(2,6-difluorophenyl)-4-methylpiperidine-4-carboxamide

Step 1: Preparation of tert-butyl 4-((2,6-difluorophenyl)carbamoyl)-4-methylpiperidine-1-carboxylate To a solution of 2,6-difluoroaniline (226.2 μL, 2.24 mmol) in toluene (9.0 mL) was treated with trimethylaluminum (1.1 mL, 2.24 mmol) was stirred for 15 min at ambient temperature. Then the solution was treated with ethyl N-Boc-4-methylpiperidine-4-carboxylate (506 mg, 1.86 mmol) and then stirred for 16 h at 70° C. The reaction was cooled to ambient temperature and treated with 0.5 M NaK Tartrate and diluted with EtOAc. The organic solution was washed with water and brine. The organic extracts were dried over anhydrous Na$_2$SO$_{4(s)}$, filtered and concentrated in vacuo. The residue was purified by silica chromatography (5-75% EtOAc in Hexanes as the gradient eluent) to cleanly provide the title compound (211 mg, 32% yield) MS (apci) m/z=343.2 (M−H).

Step 2: Preparation of N-(2,6-difluorophenyl)-4-methylpiperidine-4-carboxamide To a solution of tert-butyl 4-((2,6-difluorophenyl)carbamoyl)-4-methylpiperidine-1-carboxylate (211 mg, 0.60 mmol) in 20 μL DCM was treated with TFA (20 μL, 0.26 mmol). The reaction mixture was stirred for 1 h at ambient temperature, and then concentrated in vacuo vacuo to afford the title compound as the TFA salt. The TFA salt was treated with saturated NaHCO$_{3(aq)}$ and extracted with 4:1 DCM:IPA. The combined organic extracts were dried over anhydrous Na$_2$SO$_{4(s)}$, filtered and concentrated in vacuo. The residue was triturated with DCM/Hexanes and concentrated in vacuo to afford the title compound (107 mg, 71% yield over two steps) in sufficient purity for step 3. MS (apci) m/z=255.1 (M+H).

Step 3: Preparation of 1-(5-(3-cyano-6-(2-hydroxy-2-methylpropoxy)pyrazolo[1,5-a]pyridin-4-yl)pyridin-2-yl)-N-(2,6-difluorophenyl)-4-methylpiperidine-4-carboxamide To a solution of 4-(6-fluoropyridin-3-yl)-6-(2-hydroxy-2-methylpropoxy)pyrazolo[1,5-a]pyridine-3-carbonitrile (Intermediate P42; 46 mg, 0.14 mmol) and N-(2,6-difluorophenyl)-4-methylpiperidine-4-carboxamide (108 mg, 0.46 mmol) in DMSO (0.564 mL) was added DIEA (74 μL, 0.42 mmol). The reaction mixture was stirred overnight at 70° C. After cooling to ambient temperature, the reaction mixture was diluted with 4:1 DCM:IPA and washed with water and brine. The organic extracts were dried over anhydrous Na$_2$SO$_{4(s)}$, filtered and concentrated in vacuo. The residue was purified by C18 reverse phase chromatography (5-95% ACN in water with 0.1% TFA as the gradient eluent) to afford the title compound as the TFA salt. The TFA salt was treated with saturated NaHCO$_{3(aq)}$ and extracted with 4:1 DCM:IPA. The combined organic extracts were dried over anhydrous Na$_2$SO$_{4(s)}$, filtered and concentrated in vacuo. The residue was triturated with DCM/Hexanes and concentrated in vacuo to afford the title compound (50 mg, 63% yield) MS (apci) m/z=561.3 (M+H).

Example 300

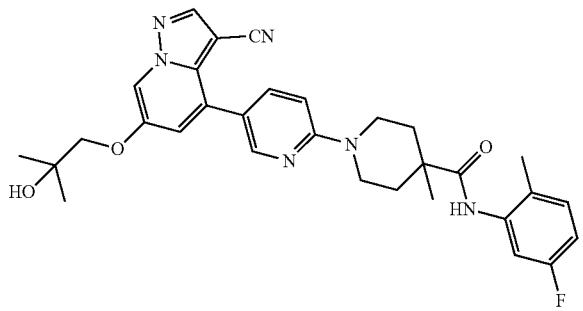 [SMILES: Cc1ccc(F)cc1NC(=O)C1(C)CCN(c2ccc(-c3cc(OCC(C)(C)O)cn4ncc(C#N)c34)cn2)CC1]

1-(5-(3-cyano-6-(2-hydroxy-2-methylpropoxy)pyrazolo[1,5-a]pyridin-4-yl)pyridin-2-yl)-N-(5-fluoro-2-methylphenyl)-4-methylpiperidine-4-carboxamide

Step 1: Preparation of tert-butyl 4-((5-fluoro-2-methylphenyl)carbamoyl)-4-methylpiperidine-1-carboxylate To a solution of 5-fluoro-2-methylaniline (586 mg, 4.68 mmol) in toluene (12.0 mL) was treated with trimethylaluminum (2.3 mL, 4.68 mmol) was stirred for 15 min at ambient temperature. Then the solution was treated with 1-(tert-butyl) 4-ethyl 4-methylpiperidine-1,4-dicarboxylate (635 mg, 2.341 mmol) and then stirred for 16 h at 70° C. The reaction was cooled to ambient temperature and treated with 0.5 M NaK Tartrate and diluted with EtOAc. The organic solution was washed with water and brine. The organic extracts were dried over anhydrous Na$_2$SO$_{4(s)}$, filtered and concentrated in vacuo. The residue was purified by silica chromatography (5-75% EtOAc in Hexanes as the gradient eluent) to cleanly provide the title compound (266 mg, 32% yield) MS (apci) m/z=349.2 (M−H).

Step 2: Preparation of N-(5-fluoro-2-methylphenyl)-4-methylpiperidine-4-carboxamide To a solution of tert-butyl 4-((5-fluoro-2-methylphenyl)carbamoyl)-4-methylpiperidine-1-carboxylate (211 mg, 0.60 mmol) in 25 µL DCM was treated with TFA (25 µL, 0.32 mmol). The reaction mixture was stirred for 1 h at ambient temperature, and then concentrated in vacuo to afford the title compound as the TFA salt. The TFA salt was treated with saturated NaHCO$_{3(aq)}$ and extracted with 4:1 DCM:IPA. The combined organic extracts were dried over anhydrous Na$_2$SO$_{4(s)}$, filtered and concentrated in vacuo. The residue was triturated with DCM/Hexanes and concentrated in vacuo to afford the title compound (127 mg, 64% yield over two steps) in sufficient purity for step 3. MS (apci) m/z=251.1 (M+H).

Step 3: Preparation of 1-(5-(3-cyano-6-(2-hydroxy-2-methylpropoxy)pyrazolo[1,5-a]pyridin-4-yl)pyridin-2-yl)-N-(5-fluoro-2-methylphenyl)-4-methylpiperidine-4-carboxamide To a solution of 4-(6-fluoropyridin-3-yl)-6-(2-hydroxy-2-methylpropoxy)pyrazolo[1,5-a]pyridine-3-carbonitrile (Intermediate P42; 55 mg, 0.17 mmol) and N-(5-fluoro-2-methylphenyl)-4-methylpiperidine-4-carboxamide (127 mg, 0.51 mmol) in DMSO (12 µL) was added DIEA (88 µL, 0.51 mmol). The reaction mixture was stirred overnight at 70° C. After cooling to ambient temperature, the reaction mixture was diluted with 4:1 DCM:IPA and washed with water and brine. The organic extracts were dried over anhydrous Na$_2$SO$_{4(s)}$, filtered and concentrated in vacuo. The residue was purified by C18 reverse phase chromatography (5-95% ACN in water with 0.1% TFA as the gradient eluent) to afford the title compound as the TFA salt. The TFA salt was treated with saturated NaHCO$_{3(aq)}$ and extracted with 4:1 DCM:IPA. The combined organic extracts were dried over anhydrous Na$_2$SO$_{4(s)}$, filtered and concentrated in vacuo. The residue was triturated with DCM/Hexanes and concentrated in vacuo to afford the title compound (48 mg, 51% yield) MS (apci) m/z=557.3 (M+H).

Example 301

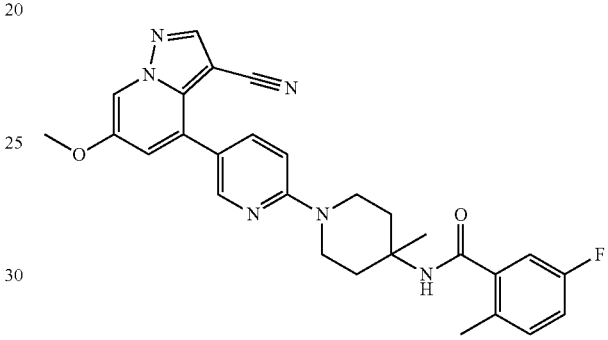

N-(1-(5-(3-cyano-6-methoxypyrazolo[1,5-a]pyridin-4-yl)pyridin-2-yl)-4-methylpiperidin-4-yl)-5-fluoro-2-methylbenzamide To a solution of N-(1-(5-(3-cyano-6-hydroxypyrazolo[1,5-a]pyridin-4-yl)pyridin-2-yl)-4-methylpiperidin-4-yl)-5-fluoro-2-methylbenzamide (P68, 30 mg, 0.619 mmol) in DMF (0.6 mL) was added potassium carbonate (26 mg, 0.186 mmol), followed by iodomethane (6 µL, 0.09 mmol) and was stirred for 1 h at 60° C. The reaction was diluted with EtOAc and washed with water and brine and dried over anhydrous Na$_2$SO$_{4(s)}$, filtered and concentrated in vacuo. The residue was resuspended in DCM (2 mL) and purified using silica chromatography 10-90% EtOAc in Hexanes to afford the title compound (9 mg, 29% yield) MS (apci) m/z=499.2 (M+H).

Example 302

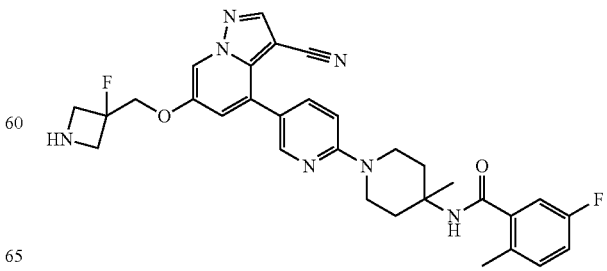

N-(1-(5-(3-cyano-6-((3-fluoroazetidin-3-yl)methoxy)pyrazolo[1,5-a]pyridin-4-yl)pyridin-2-yl)-4-methylpiperidin-4-yl)-5-fluoro-2-methylbenzamide Step 1: Preparation of tert-butyl 3-(((3-cyano-4-(6-(4-(5-fluoro-2-methylbenzamido)-4-methylpiperidin-1-yl)pyridin-3-yl)pyrazolo[1,5-a]pyridin-6-yl)oxy)methyl)-3-fluoroazetidine-1-carboxylate To a mixture of N-(1-(5-(3-cyano-6-hydroxypyrazolo[1,5-a]pyridin-4-yl)pyridin-2-yl)-4-methylpiperidin-4-yl)-5-fluoro-2-methylbenzamide (Intermediate P68; 47 mg, 0.097 mmol) and tert-butyl 3-(bromomethyl)-3-fluoroazetidine-1-carboxylate (39 mg, 0.146 mmol) was added cesium carbonate (126 mg, 0.388 mmol) in DMA (1 mL) and was stirred overnight at 60° C. After cooling to ambient temperature, reaction was diluted with EtOAc and washed with water and dried over anhydrous Na$_2$SO$_{4(s)}$, filtered and concentrated in vacuo. The residue was purified using silica chromatography 25-50% EtOAc in Hexanes to afford the title compound (62 mg, 95% yield) MS (apci) m/z=672.3 (M+H).

Step 2: Preparation of N-(1-(5-(3-cyano-6-((3-fluoroazetidin-3-yl)methoxy)pyrazolo[1,5-a]pyridin-4-yl)pyridin-2-yl)-4-methylpiperidin-4-yl)-5-fluoro-2-methylbenzamide To a solution of tert-butyl 3-(((3-cyano-4-(6-(4-(5-fluoro-2-methylbenzamido)-4-methylpiperidin-1-yl)pyridin-3-yl)pyrazolo[1,5-a]pyridin-6-yl)oxy)methyl)-3-fluoroazetidine-1-carboxylate (62 mg, 0.09 mmol) in DCM (4 mL) was treated with TFA (2 mL, 26 mmol). The reaction mixture was stirred for 2 h at ambient temperature, and then concentrated in vacuo. The residue was purified by C18 reverse phase chromatography (5-95% ACN in water with 0.1% TFA as the gradient eluent). Fractions containing the desired product were combined, diluted with 4:1 DCM:iPrOH and washed sequentially with saturated NaHCO$_{3(aq)}$ and brine. The organic extracts then were dried over anhydrous Na$_2$SO$_{4(s)}$, filtered, and concentrated in vacuo to afford the title compound. (42 mg, 80% yield) MS (apci) m/z=572.3 (M+H).

Example 303

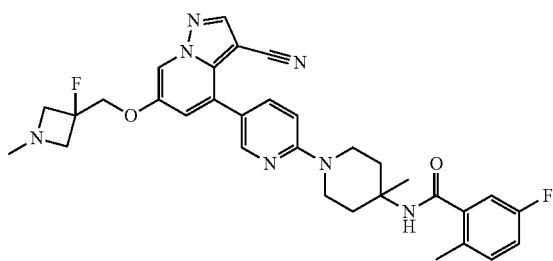 [SMILES: Cc1ccc(F)cc1C(=O)NC1(C)CCN(c2ccc(-c3cc(OCC4(F)CN(C)C4)cn4ncc(C#N)c34)cn2)CC1]

N-(1-(5-(3-cyano-6-((3-fluoro-1-methylazetidin-3-yl)methoxy)pyrazolo[1,5-a]pyridin-4-yl)pyridin-2-yl)-4-methylpiperidin-4-yl)-5-fluoro-2-methylbenzamide A mixture of N-(1-(5-(3-cyano-6-((3-fluoroazetidin-3-yl)methoxy)pyrazolo[1,5-a]pyridin-4-yl)pyridin-2-yl)-4-methylpiperidin-4-yl)-5-fluoro-2-methylbenzamide (Example 302; 30 mg, 0.053 mmol), formaldehyde (20 µL, 0.26 mmol), and NaBH(AcO)$_3$ (56 mg, 0.26 mmol) were dissolved in DMA (2 mL). The reaction mixture was stirred overnight at ambient temperature. The reaction mixture was diluted with EtOAc and washed with water. The combined organic extracts were dried over anhydrous Na$_2$SO$_4$, filtered, and concentrated in vacuo. The residue was purified by C18 reverse phase chromatography (5-95% ACN in water with 0.1% TFA as the gradient eluent). Fractions containing the desired product were combined, diluted with 4:1 DCM:iPrOH and washed sequentially with saturated NaHCO$_{3(aq)}$ and brine. The organic extracts then were dried over anhydrous Na$_2$SO$_{4(s)}$, filtered, and concentrated in vacuo to afford the title compound (27 mg, 87% yield) MS (apci) m/z=586.3 (M+H). $^1$H NMR (400 MHz, CDCl$_3$) δ 8.32-8.30 (m, 1H), 8.19-8.15 (m, 2H), 7.71-7.66 (m, 1H), 7.17-7.13 (m, 2H), 7.06-7.02 (m, 1H), 7.00-6.94 (m, 1H), 6.80-6.77 (m, 1H), 5.50 (br s, 1H), 4.36-4.29 (m, 2H), 4.05-3.92 (m, 2H), 3.75-3.57 (m, 2H), 3.43-3.32 (m, 2H), 3.26-3.13 (m, 2H), 2.43 (s, 3H), 2.39 (s, 3H), 2.33-2.21 (m, 2H), 1.90-1.75 (m, 2H), 1.58 (s, 3H).

Example 304

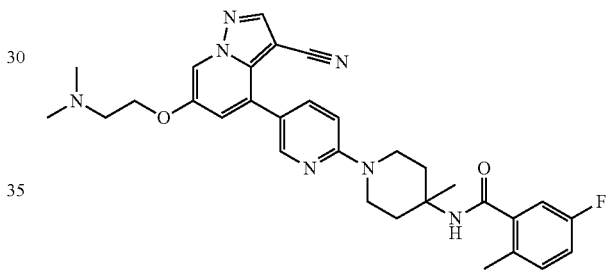

N-(1-(5-(3-cyano-6-(2-(dimethylamino)ethoxy)pyrazolo[1,5-a]pyridin-4-yl)pyridin-2-yl)-4-methylpiperidin-4-yl)-5-fluoro-2-methylbenzamide To a mixture of N-(1-(5-(3-cyano-6-hydroxypyrazolo[1,5-a]pyridin-4-yl)pyridin-2-yl)-4-methylpiperidin-4-yl)-5-fluoro-2-methylbenzamide (Intermediate P68; 39 mg, 0.08 mmol) and 2-bromo-N,N-dimethylethan-1-amine hydrobromide (37 mg, 0.16 mmol) was added cesium carbonate (105 mg, 0.32 mmol) in DMA (1 mL) and was stirred overnight at 60° C. After cooling to ambient temperature, reaction was diluted with EtOAc and washed with water and dried over anhydrous Na$_2$SO$_{4(s)}$, filtered and concentrated in vacuo. The residue was purified using silica chromatography 2-4% MeOH in DCM. Fractions containing the product were concentrated in vacuo. The residue was repurified was purified by C18 reverse phase chromatography (5-95% ACN in water with 0.1% TFA as the gradient eluent). Fractions containing the desired product were combined, diluted with 4:1 DCM:iPrOH and washed sequentially with saturated NaHCO$_{3(aq)}$ and brine. The organic extracts then were dried over anhydrous Na$_2$SO$_{4(s)}$, filtered, and concentrated in vacuo to afford the title compound (8 mg, 18% yield) MS (apci) m/z=556.3 (M+H).

The compounds in Table QQ were prepared using a similar method to that described for the synthesis of Example 304, replacing 2-bromo-N,N-dimethylethan-1- amine hydrobromide with the appropriate alkyl halide. Reactions were monitored for completion by LCMS, and reaction durations were adjusted accordingly. Title compounds were cleanly isolated following chromatographic purification using an appropriate gradient eluent (and if necessary converted to the free base).

mmol) and tert-butyl 3-(bromomethyl)-3-methylazetidine-1-carboxylate (34 mg, 0.13 mmol) was added cesium carbonate (113 mg, 0.347 mmol) in DMA (1 mL) and was stirred overnight at 60° C. After cooling to ambient temperature, reaction was diluted with EtOAc and washed with water and the organic extracts were dried over anhydrous

TABLE QQ

| Ex. # | Structure | Chemical Name | MS m/z |
|---|---|---|---|
| 305 | 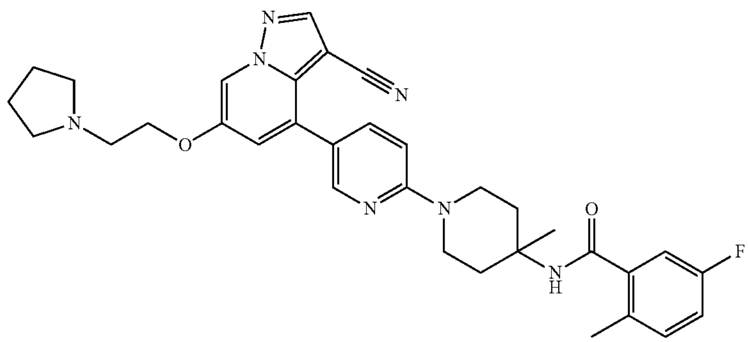 [SMILES: Cc1ccc(F)cc1C(=O)NC1(C)CCN(c2ccc(-c3cc(OCCN4CCCC4)cn4ncc(C#N)c34)cn2)CC1] | N-(1-(5-(3-cyano-6-(2-(pyrrolidin-1-yl)ethoxy)pyrazolo[1,5-a]pyridin-4-yl)pyridin-2-yl)-4-methylpiperidin-4-yl)-5-fluoro-2-methylbenzamide | 582.3 (M + H) |
| 306 | 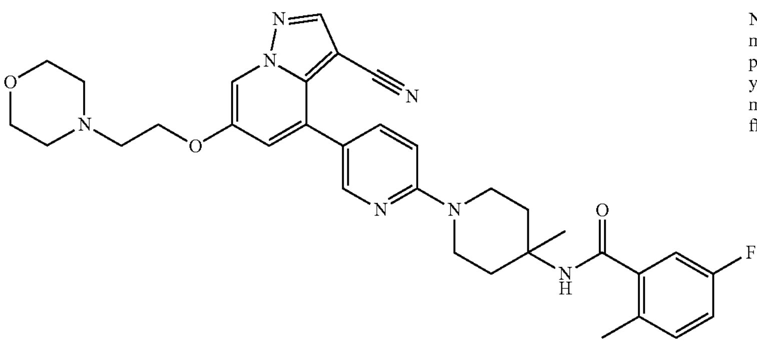 [SMILES: Cc1ccc(F)cc1C(=O)NC1(C)CCN(c2ccc(-c3cc(OCCN4CCOCC4)cn4ncc(C#N)c34)cn2)CC1] | N-(1-(5-(3-cyano-6-(2-morpholinoethoxy)pyrazolo[1,5-a]pyridin-4-yl)pyridin-2-yl)-4-methylpiperidin-4-yl)-5-fluoro-2-methylbenzamide | 598.3 (M + H) |

Example 307

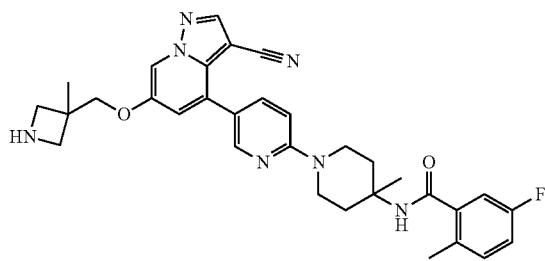 [SMILES: Cc1ccc(F)cc1C(=O)NC1(C)CCN(c2ccc(-c3cc(OCC4(C)CNC4)cn4ncc(C#N)c34)cn2)CC1]

N-(1-(5-(3-cyano-6-((3-methylazetidin-3-yl)methoxy)pyrazolo[1,5-a]pyridin-4-yl)pyridin-2-yl)-4-methylpiperidin-4-yl)-5-fluoro-2-methylbenzamide Step 1: Preparation of tert-butyl 3-(((3-cyano-4-(6-(4-(5-fluoro-2-methylbenzamido)-4-methylpiperidin-1-yl)pyridin-3-yl)pyrazolo[1,5-a]pyridin-6-yl)oxy)methyl)-3-methylazetidine-1-carboxylate To a mixture of N-(1-(5-(3-cyano-6-hydroxypyrazolo[1,5-a]pyridin-4-yl)pyridin-2-yl)-4-methylpiperidin-4-yl)-5-fluoro-2-methylbenzamide (Intermediate P68; 42 mg, 0.087

$Na_2SO_{4(s)}$, filtered and concentrated in vacuo. The residue was purified using silica chromatography 50-100% EtOAc in Hexanes to afford the title compound (21 mg, 36% yield) MS (apci) m/z=668.4 (M+H).

Step 2: Preparation of N-(1-(5-(3-cyano-6-((3-methylazetidin-3-yl)methoxy)pyrazolo[1,5-a]pyridin-4-yl)pyridin-2-yl)-4-methylpiperidin-4-yl)-5-fluoro-2-methylbenzamide To a solution of tert-butyl 3-(((3-cyano-4-(6-(4-(5-fluoro-2-methylbenzamido)-4-methylpiperidin-1-yl)pyridin-3-yl)pyrazolo[1,5-a]pyridin-6-yl)oxy)methyl)-3-methylazetidine-1-carboxylate (21 mg, 0.03 mmol) in DCM (4 mL) was treated with TFA (2 mL, 26 mmol). The reaction mixture was stirred for 2 h at ambient temperature, and then concentrated in vacuo. The residue was purified by C18 reverse phase chromatography (5-95% ACN in water with 0.1% TFA as the gradient eluent). Fractions containing the desired product were combined, diluted with 4:1 DCM:iPrOH and washed sequentially with saturated $NaHCO_{3(aq)}$ and brine. The organic extracts then were dried over anhydrous $Na_2SO_{4(s)}$, filtered, and concentrated in vacuo to afford the title compound. (13 mg, 73% yield) MS (apci) m/z=568.3 (M+H).

Example 308

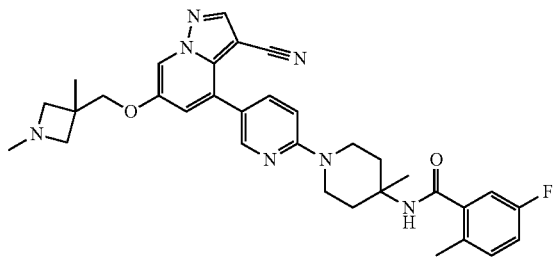 [SMILES: Cc1ccc(F)cc1C(=O)NC1(C)CCN(c2ccc(-c3cc(OCC4(C)CN(C)C4)cn4ncc(C#N)c34)cn2)CC1]

N-(1-(5-(3-cyano-6-((1,3-dimethylazetidin-3-yl)methoxy)pyrazolo[1,5-a]pyridin-4-yl)pyridin-2-yl)-4-methylpiperidin-4-yl)-5-fluoro-2-methylbenzamide A mixture of N-(1-(5-(3-cyano-6-((3-methylazetidin-3-yl)methoxy)pyrazolo[1,5-a]pyridin-4-yl)pyridin-2-yl)-4-methylpiperidin-4-yl)-5-fluoro-2-methylbenzamide (Example 307; 12 mg, 0.021 mmol), formaldehyde (8 μL, 0.106 mmol), and NaBH(AcO)₃ (22 mg, 0.106 mmol) were dissolved in DCM (4 mL). The resulting reaction mixture was allowed to stir overnight at room temperature. The reaction mixture was diluted with EtOAc and washed with water. The combined organic extracts were dried over anhydrous Na₂SO₄, filtered, and concentrated in vacuo. The residue was purified by C18 reverse phase chromatography (5-95% ACN in water with 0.1% TFA as the gradient eluent). Fractions containing the desired product were combined, diluted with 4:1 DCM:iPrOH and washed sequentially with saturated NaHCO₃(aq) and brine. The organic extracts then were dried over anhydrous Na₂SO₄(s), filtered, and concentrated in vacuo to afford the title compound (10 mg, 81% yield) MS (apci) m/z=582.3 (M+H).

Example 309

N-(1-(5-(3-cyano-6-(2-(piperazin-1-yl)ethoxy)pyrazolo[1,5-a]pyridin-4-yl)pyridin-2-yl)-4-methylpiperidin-4-yl)-5-fluoro-2-methylbenzamide Step 1: Preparation of tert-butyl 4-(2-((3-cyano-4-(6-(4-(5-fluoro-2-methylbenzamido)-4-methylpiperidin-1-yl)pyridin-3-yl)pyrazolo[1,5-a]pyridin-6-yl)oxy)ethyl)piperazine-1-carboxylate To a mixture of N-(1-(5-(3-cyano-6-hydroxypyrazolo[1,5-a]pyridin-4-yl)pyridin-2-yl)-4-methylpiperidin-4-yl)-5-fluoro-2-methylbenzamide (Intermediate P68; 55 mg, 0.114 mmol), tert-Butyl 4-(2-chloroethyl)tetrahydro-1(2H)-pyrazine carboxylate (57 mg, 0.227 mmol) was added cesium carbonate (148 mg, 0.454 mmol) in DMA (1 mL) and was stirred overnight at 60° C. After cooling to ambient temperature, reaction was diluted with EtOAc and washed with water and the organic extracts were dried over anhydrous Na₂SO₄(s), filtered and concentrated in vacuo. The residue was purified using silica chromatography (50-100% EtOAc in Hexanes) to afford the title compound (49 mg, 62% yield) MS (apci) m/z=697.4 (M+H).

Step 2: Preparation of N-(1-(5-(3-cyano-6-(2-(piperazin-1-yl)ethoxy)pyrazolo[1,5-a]pyridin-4-yl)pyridin-2-yl)-4-methylpiperidin-4-yl)-5-fluoro-2-methylbenzamide To a solution of tert-butyl 4-(2-((3-cyano-4-(6-(4-(5-fluoro-2-methylbenzamido)-4-methylpiperidin-1-yl)pyridin-3-yl)pyrazolo[1,5-a]pyridin-6-yl)oxy)ethyl)piperazine-1-carboxylate (49 mg, 0.070 mmol) in DCM (4 mL) was treated with TFA (2 mL, 26 mmol). The reaction mixture was stirred for 1 h at ambient temperature, and then concentrated in vacuo. The residue was purified by C18 reverse phase chromatography (5-95% ACN in water with 0.1% TFA as the gradient eluent). Fractions containing the product were concentrated in vacuo. The residue was repurified using silica chromatography (4% MeOH in DCM with 1% TEA as the eluent) to afford the title compound. (33 mg, 79% yield) MS (apci) m/z=597.3 (M+H).

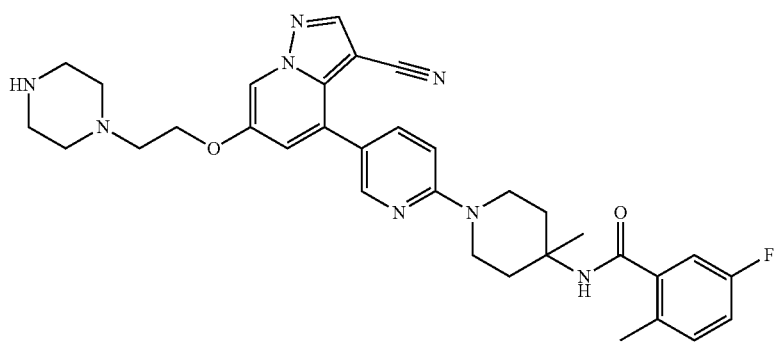 [SMILES: Cc1ccc(F)cc1C(=O)NC1(C)CCN(c2ccc(-c3cc(OCCN4CCNCC4)cn4ncc(C#N)c34)cn2)CC1]

Example 310

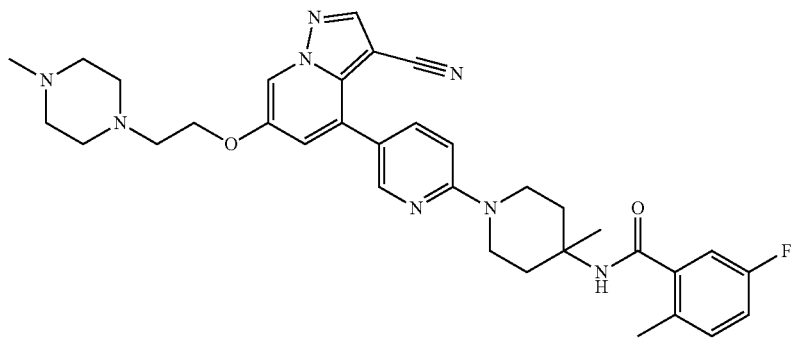 [SMILES: Cc1ccc(F)cc1C(=O)NC1(C)CCN(c2ccc(-c3cc(OCCN4CCN(C)CC4)cn4ncc(C#N)c34)cn2)CC1]

N-(1-(5-(3-cyano-6-(2-(4-methylpiperazin-1-yl)ethoxy)pyrazolo[1,5-a]pyridin-4-yl)pyridin-2-yl)-4-methylpiperidin-4-yl)-5-fluoro-2-methylbenzamide To a solution of N-(1-(5-(3-cyano-6-(2-(piperazin-1-yl)ethoxy)pyrazolo[1,5-a]pyridin-4-yl)pyridin-2-yl)-4-methylpiperidin-4-yl)-5-fluoro-2-methylbenzamide (Example 309; 27 mg, 0.045 mmol) in DCM (0.25 mL) and MeOH (0.25 mL) was added formaldehyde (17 μL, 0.226 mmol) and NaBH(AcO)$_3$ (48 mg, 0.226 mmol) The resulting reaction mixture was allowed to stir overnight at room temperature. The reaction was directly purified by C18 reverse phase chromatography (5-95% ACN in water with 0.1% TFA as the gradient eluent) to afford the title compound as the TFA salt. The TFA salt was treated with saturated NaHCO$_{3(aq)}$ and extracted with 4:1 DCM:IPA. The combined organic extracts were dried over anhydrous Na$_2$SO$_{4(s)}$, filtered and concentrated in vacuo. The residue was triturated with DCM/Hexanes and concentrated in vacuo to afford the title compound (12.5 mg, 45% yield) MS (apci) m/z=611.4 (M+H).

Example 311

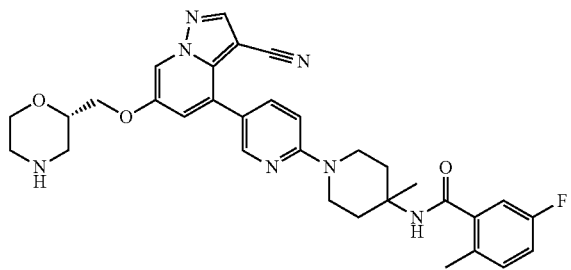 [SMILES: Cc1ccc(F)cc1C(=O)NC1(C)CCN(c2ccc(-c3cc(OC[C@@H]4CNCCO4)cn4ncc(C#N)c34)cn2)CC1]

(S)—N-(1-(5-(3-cyano-6-(morpholin-2-ylmethoxy)pyrazolo[1,5-a]pyridin-4-yl)pyridin-2-yl)-4-methylpiperidin-4-yl)-5-fluoro-2-methylbenzamide Step 1: Preparation of tert-butyl (S)-2-(((3-cyano-4-(6-(4-(5-fluoro-2-methylbenzamido)-4-methylpiperidin-1-yl)pyridin-3-yl)pyrazolo[1,5-a]pyridin-6-yl)oxy)methyl)morpholine-4-carboxylate To N-(1-(5-(3-cyano-6-hydroxypyrazolo[1,5-a]pyridin-4-yl)pyridin-2-yl)-4-methylpiperidin-4-yl)-5-fluoro-2-methylmL). The resulting mixture was sparged with Ar$_{(g)}$ and stirred for 10 min. (S)-tert-butyl 2-(bromomethyl)morpholine-4-carboxylate (26 mg, 0.093 mmol) was added to the reaction mixture. The resulting mixture was sparged with Ar$_{(g)}$ and stirred overnight at 60° C. After cooling to ambient temperature, reaction was diluted with EtOAc and washed with water and brine and the organic extracts were dried over anhydrous Na$_2$SO$_{4(s)}$, filtered and concentrated in vacuo to afford the title compound (42 mg, 99% yield) MS (apci) m/z=684.3 (M+H).

Step 2: Preparation of (S)—N-(1-(5-(3-cyano-6-(morpholin-2-ylmethoxy)pyrazolo[1,5-a]pyridin-4-yl)pyridin-2-yl)-4-methylpiperidin-4-yl)-5-fluoro-2-methylbenzamide To a solution tert-butyl (S)-2-(((3-cyano-4-(6-(4-(5-fluoro-2-methylbenzamido)-4-methylpiperidin-1-yl)pyridin-3-yl)pyrazolo[1,5-a]pyridin-6-yl)oxy)methyl)morpholine-4-carboxylate (42 mg, 0.061 mmol) in DCM (2 mL) was treated with TFA (0.31 mL). The reaction mixture was stirred for 15 min at ambient temperature, and then concentrated in vacuo. The residue was resuspended in DCM (2 mL). The solution was purified by silica chromatography (0.5-10% MeOH in DCM with 0.05-1% NH$_4$OH as the gradient eluent) to afford the title compound (6 mg, 16% yield) MS (apci) m/z=584.3 (M+H).

Example 312

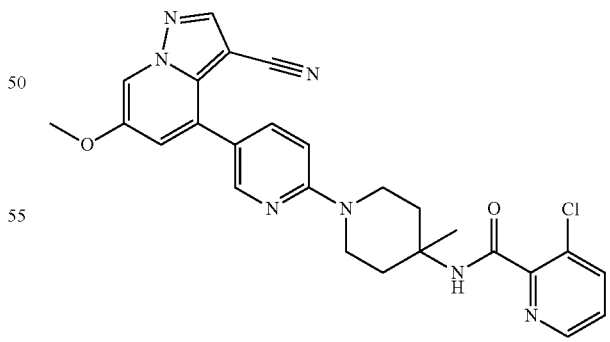

3-chloro-N-(1-(5-(3-cyano-6-methoxypyrazolo[1,5-a]pyridin-4-yl)pyridin-2-yl)-4-methylpiperidin-4-yl)picolinamide To a solution of 3-chloro-N-(1-(5-(3-cyano-6-hydroxypyrazolo[1,5-a]pyridin-4-yl)pyridin-2-yl)-4-methylpiperidin-4-yl)picolinamide (Intermediate P75; 34 mg, 0.070 mmol) in DMF (0.7 mL) was added potassium carbonate (29 mg, 0.209 mmol) and then iodomethane (7 μL, 0.105 mmol) was added to the reaction mixture. The resulting mixture was stirred overnight at 60° C. After cooling to ambient temperature, reaction was diluted with DCM and purified directly using silica chromatography (0.5-10% MeOH in DCM with 0.1-2% NH₄OH as the gradient eluent). Fractions containing the product were concentrated in vacuo. The residue was diluted with EtOAc and washed with water and brine and then dried over anhydrous Na₂SO₄₍s₎, filtered and concentrated in vacuo to afford the title compound (16 mg, 45% yield) MS (apci) m/z=502.2 (M+H).

Example 313

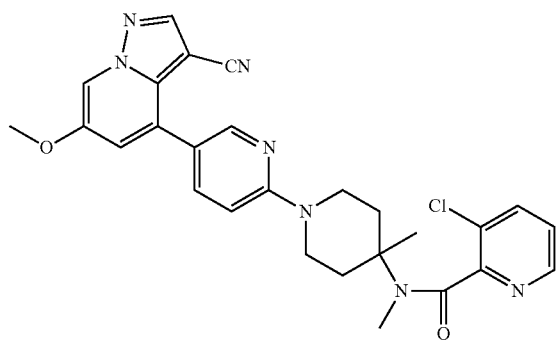 [SMILES: COc1cc(-c2ccc(N3CCC(C)(N(C)C(=O)c4ncccc4Cl)CC3)nc2)c2c(C#N)cnn2c1]

3-chloro-N-(1-(5-(3-cyano-6-methoxypyrazolo[1,5-a]pyridin-4-yl)pyridin-2-yl)-4-methylpiperidin-4-yl)-N-methylpicolinamide To a solution of 3-chloro-N-(1-(5-(3-cyano-6-methoxypyrazolo[1,5-a]pyridin-4-yl)pyridin-2-yl)-4-methylpiperidin-4-yl)picolinamide (Example 312; 10 mg, 0.020 mmol) in ACN (0.3 mL) was added iodomethane (4 μL, 0.06 mmol) followed by sodium hydride (1.4 mg, 0.06 mmol) and then the reaction mixture was stirred for 1 hour at ambient temperature. The reaction was stirred for 1 hour at 85° C. After cooling to ambient temperature, the reaction mixture was directly purified by C18 reverse phase chromatography (5-95% ACN in water with 0.1% TFA as the gradient eluent) to afford the title compound as the TFA salt. The TFA salt was treated with saturated NaHCO₃₍aq₎ and extracted with 4:1 DCM:IPA. The combined organic extracts were dried over anhydrous Na₂SO₄₍s₎, filtered and concentrated in vacuo to afford the title compound (6.5 mg, 63% yield). MS (apci) m/z=516.2 (M+H).

Example 314

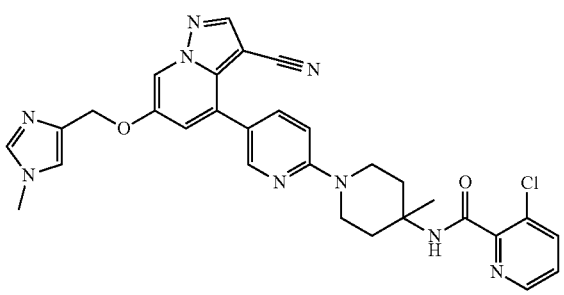 [SMILES: Cn1cnc(COc2cc(-c3ccc(N4CCC(C)(NC(=O)c5ncccc5Cl)CC4)nc3)c3c(C#N)cnn3c2)c1]

3-chloro-N-(1-(5-(3-cyano-6-((1-methyl-1H-imidazol-4-yl)methoxy)pyrazolo[1,5-a]pyridin-4-yl)pyridin-2-yl)-4-methylpiperidin-4-yl)picolinamide To a solution of 3-chloro-N-(1-(5-(3-cyano-6-hydroxypyrazolo[1,5-a]pyridin-4-yl)pyridin-2-yl)-4-methylpiperidin-4-yl)picolinamide (Intermediate P75; 25 mg, 0.051 mmol) in DMF (0.5 mL) was added potassium carbonate (22 mg, 0.159 mmol) then 4-(Chloromethyl)-1-methyl-1H-imidazole (13 mg, 0.102 mmol). The resulting mixture was stirred 2 h at 60° C. After cooling to ambient temperature, reaction was diluted with 60:40 ACN:water. The solution was purified directly by C18 reverse phase chromatography (5-95% ACN in water with 0.1% TFA as the gradient eluent) to afford the title compound as the TFA salt. The TFA salt was dissolved in DCM (10 mL) and MeOH (1 mL) and eluted through a P1-HCO₃ resin. The organic eluent concentrated in vacuo to afford the title compound (14 mg, 45% yield). MS (apci) m/z=582.2 (M+H).

Example 315

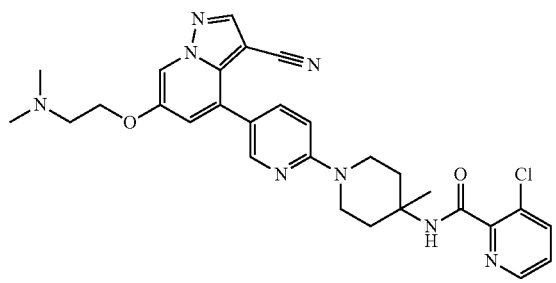 [SMILES: CN(C)CCOc1cc(-c2ccc(N3CCC(C)(NC(=O)c4ncccc4Cl)CC3)nc2)c2c(C#N)cnn2c1]

3-chloro-N-(1-(5-(3-cyano-6-(2-(dimethylamino)ethoxy)pyrazolo[1,5-a]pyridin-4-yl)pyridin-2-yl)-4-methylpiperidin-4-yl)picolinamide To a solution of 3-chloro-N-(1-(5-(3-cyano-6-hydroxypyrazolo[1,5-a]pyridin-4-yl)pyridin-2-yl)-4-methylpiperidin-4-yl)picolinamide (Intermediate P75; 25 mg, 0.051 mmol) in DMA (0.5 mL) was added cesium carbonate (52 mg, 0.159 mmol) then 2-dimethylaminoethyl chloride hydrochloride (15 mg, 0.102 mmol). The resulting mixture was stirred 1 h at 60° C. After cooling to ambient temperature, potassium carbonate was added. The resulting mixture was stirred overnight at 60° C. After cooling to ambient temperature, reaction was diluted with DCM and purified directly by silica chromatography (0.5-10% MeOH in DCM with 0.1-2% NH₄OH as the gradient eluent) to afford the title compound (14 mg, 47% yield). MS (apci) m/z=559.2 (M+H).

Example 316

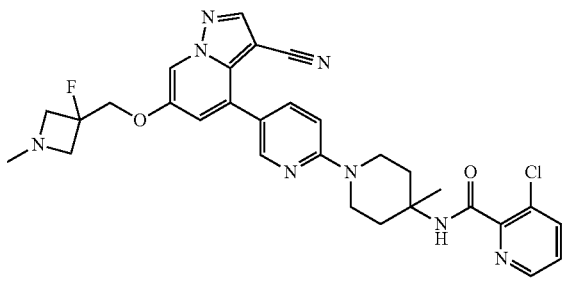 [SMILES: CN1CC(F)(COc2cc(-c3ccc(N4CCC(C)(NC(=O)c5ncccc5Cl)CC4)nc3)c3c(C#N)cnn3c2)C1]

3-chloro-N-(1-(5-(3-cyano-6-((3-fluoro-1-methyl-azetidin-3-yl)methoxy)pyrazolo[1,5-a]pyridin-4-yl)pyridin-2-yl)-4-methylpiperidin-4-yl)picolinamide Step 1: Preparation of tert-butyl 3-(((4-(6-(4-(3-chloropicolinamido)-4-methylpiperidin-1-yl)pyridin-3-yl)-3-cyanopyrazolo[1,5-a]pyridin-6-yl)oxy)methyl)-3-fluoroazetidine-1-carboxylate To a solution of 3-chloro-N-(1-(5-(3-cyano-6-hydroxypyrazolo[1,5-a]pyridin-4-yl)pyridin-2-yl)-4-methylpiperidin-4-yl)picolinamide (Intermediate P75; 37 mg, 0.076 mmol) in DMF (0.76 mL) was added cesium carbonate (27 mg, 0.083 mmol) then tert-butyl 3-(bromomethyl)-3-fluoro-azetidine-1-carboxylate (41 mg, 0.15 mmol). The resulting mixture was stirred 3 h at 60° C. After cooling to ambient temperature, reaction was diluted with EtOAc and washed with water and brine and the organic extracts were dried over anhydrous $Na_2SO_{4(s)}$, filtered and concentrated in vacuo to afford the title compound (Assumed quantitative yield, 51 mg) MS (apci) m/z=675.3 (M+H).

Step 2: Preparation of 3-chloro-N-(1-(5-(3-cyano-6-((3-fluoroazetidin-3-yl)methoxy)pyrazolo[1,5-a]pyridin-4-yl)pyridin-2-yl)-4-methylpiperidin-4-yl)picolinamide To a solution of tert-butyl 3-(((4-(6-(4-(3-chloropicolinamido)-4-methylpiperidin-1-yl)pyridin-3-yl)-3-cyanopyrazolo[1,5-a]pyridin-6-yl)oxy)methyl)-3-fluoroazetidine-1-carboxylate (62 mg, 0.092 mmol) in DCM (0.46 mL) was treated with TFA (0.46 mL, 6 mmol). The reaction mixture was stirred for 15 min at ambient temperature, and then concentrated in vacuo. The residue was resuspended in DCM (3 mL). The solution was passed through two Pl-HCO3 resins and eluted with additional DCM. The eluent was concentrated in vacuo to afford the title compound (30 mg, 57% yield) MS (apci) m/z=575.2 (M+H).

Step 3: Preparation of 3-chloro-N-(1-(5-(3-cyano-6-((3-fluoro-1-methylazetidin-3-yl)methoxy)pyrazolo[1,5-a]pyridin-4-yl)pyridin-2-yl)-4-methylpiperidin-4-yl)picolinamide To a solution of 3-chloro-N-(1-(5-(3-cyano-6-((3-fluoroazetidin-3-yl)methoxy)pyrazolo[1,5-a]pyridin-4-yl)pyridin-2-yl)-4-methylpiperidin-4-yl)picolinamide (35 mg, 0.061 mmol) in DMA (0.61 mL) was added formaldehyde (8 μL, 0.304 mmol) and NaBH(AcO)3 (116 mg, 0.547 mmol) The resulting reaction mixture was allowed to stir overnight at room temperature. The reaction was directly purified by C18 reverse phase chromatography (5-75% ACN in water with 0.1% TFA as the gradient eluent) to afford the title compound as the TFA salt. The TFA salt was diluted with DCM and passed through a Pl-HCO3 resin and eluted with additional DCM. The eluent was concentrated in vacuo. The residue was dissolved in DCM and treated with saturated $NaHCO_{3(aq)}$ and extracted with 4:1 DCM:IPA. The combined organic extracts were dried over anhydrous $Na_2SO_{4(s)}$, filtered and concentrated in vacuo to afford the title compound (7 mg, 19% yield) MS (apci) m/z=589.3 (M+H).

Example 317

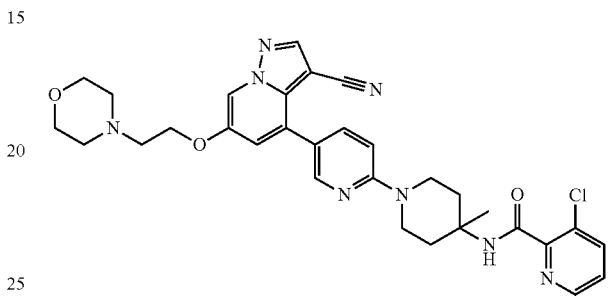

3-chloro-N-(1-(5-(3-cyano-6-(2-morpholinoethoxy)pyrazolo[1,5-a]pyridin-4-yl)pyridin-2-yl)-4-methyl-piperidin-4-yl)picolinamide To a solution of 3-chloro-N-(1-(5-(3-cyano-6-hydroxypyrazolo[1,5-a]pyridin-4-yl)pyridin-2-yl)-4-methylpiperidin-4-yl)picolinamide (Intermediate P75; 36 mg, 0.074 mmol) in DMA (0.74 mL) was added cesium carbonate (26 mg, 0.081 mmol) followed by 4-(2-chloroethyl)morpholine (44 mg, 0.295 mmol) was added to the reaction mixture. The resulting mixture was stirred overnight at 60° C. After cooling to ambient temperature, reaction was diluted with 60:40 ACN:water. The solution was purified directly by C18 reverse phase chromatography (5-95% ACN in water with 0.1% TFA as the gradient eluent) to afford the title compound as the TFA salt. The TFA salt was treated with saturated $NaHCO_{3(aq)}$ and extracted with 4:1 DCM:IPA and then washed with brine. The combined organic extracts were dried over anhydrous $Na_2SO_{4(s)}$, filtered and concentrated in vacuo to afford the title compound (9 mg, 20% yield) MS (apci) m/z=601.3 (M+H).

Example 318

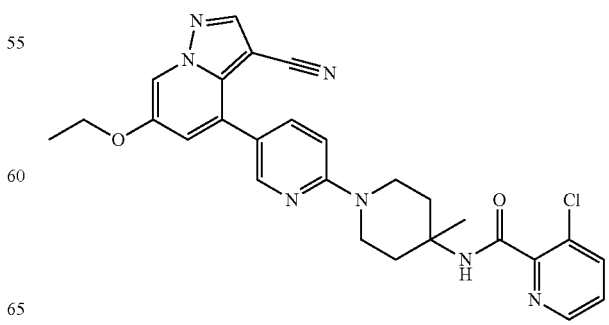

3-chloro-N-(1-(5-(3-cyano-6-ethoxypyrazolo[1,5-a]pyridin-4-yl)pyridin-2-yl)-4-methylpiperidin-4-yl)picolinamide To a solution of 3-chloro-N-(1-(5-(3-cyano-6-hydroxypyrazolo[1,5-a]pyridin-4-yl)pyridin-2-yl)-4-methylpiperidin-4-yl)picolinamide (Intermediate P75; 36 mg, 0.074 mmol) in DMF (0.74 mL) was added potassium carbonate (31 mg, 0.221 mmol) followed by iodoethane (17 mg, 0.111 mmol). The resulting mixture was stirred overnight at 60° C. After cooling to ambient temperature, reaction was diluted with 60:40 ACN:water. The solution was purified directly by C18 reverse phase chromatography (5-95% ACN in water with 0.1% TFA as the gradient eluent) to afford the title compound as the TFA salt. The TFA salt was treated with saturated NaHCO$_{3(aq)}$ and extracted with 4:1 DCM:IPA and then washed with brine. The combined organic extracts were dried over anhydrous Na$_2$SO$_{4(s)}$, filtered and concentrated in vacuo to afford the title compound (19 mg, 50% yield) MS (apci) m/z=516.2 (M+H).

Example 319

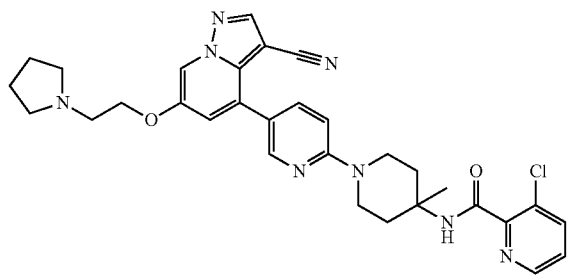 [SMILES: CC1(NC(=O)c2ncccc2Cl)CCN(c2ccc(-c3cc(OCCN4CCCC4)cn4ncc(C#N)c34)cn2)CC1]

3-chloro-N-(1-(5-(3-cyano-6-(2-(pyrrolidin-1-yl)ethoxy)pyrazolo[1,5-a]pyridin-4-yl)pyridin-2-yl)-4-methylpiperidin-4-yl)picolinamide To a solution of 3-chloro-N-(1-(5-(3-cyano-6-hydroxypyrazolo[1,5-a]pyridin-4-yl)pyridin-2-yl)-4-methylpiperidin-4-yl)picolinamide (Intermediate P75; 31 mg, 0.063 mmol) in DMA (0.63 mL) was added potassium carbonate (10 mg, 0.69 mmol) followed by 1-(2-Chloroethyl)-pyrrolidine (25 mg, 0.189 mmol). The resulting mixture was stirred overnight at 60° C. After cooling to ambient temperature, the reaction mixture was diluted with EtOAc and washed with water. The water layer was further extracted using 4:1 DCM:IPA. The organic extracts were separately washed with brine, then combined and dried over anhydrous Na$_2$SO$_4$, filtered, and concentrated in vacuo. The residue was resuspended with 60:40 ACN:water. The solution was purified directly by C18 reverse phase chromatography (5-95% ACN in water with 0.1% TFA as the gradient eluent) to afford the title compound as the TFA salt. The TFA salt was treated with saturated NaHCO$_{3(aq)}$ and extracted with 4:1 DCM:IPA and then washed with brine. The combined organic extracts were dried over anhydrous Na$_2$SO$_{4(s)}$, filtered and concentrated in vacuo to afford the title compound (16 mg, 42% yield) MS (apci) m/z=585.3 (M+H).

Example 320

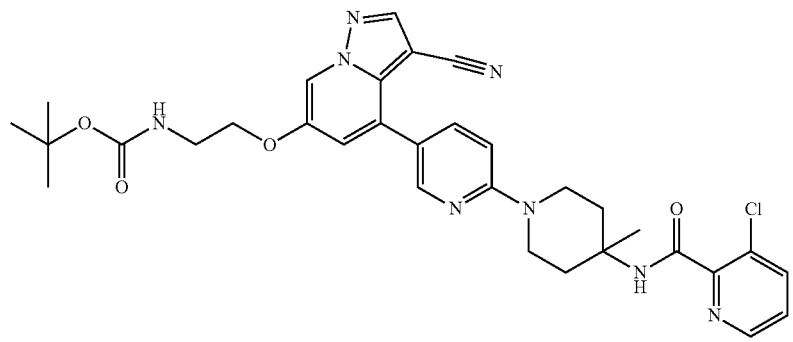 [SMILES: CC1(NC(=O)c2ncccc2Cl)CCN(c2ccc(-c3cc(OCCNC(=O)OC(C)(C)C)cn4ncc(C#N)c34)cn2)CC1]

tert-butyl (2-((4-(6-(4-(3-chloropicolinamido)-4-methylpiperidin-1-yl)pyridin-3-yl)-3-cyanopyrazolo[1,5-a]pyridin-6-yl)oxy)ethyl)carbamate To a mixture of 3-chloro-N-(1-(5-(3-cyano-6-hydroxypyrazolo[1,5-a]pyridin-4-yl)pyridin-2-yl)-4-methylpiperidin-4-yl)picolinamide (Intermediate P75; 150 mg, 0.307 mmol) and potassium carbonate (47 mg, 0.34 mmol) in DMA (3.07 mL) was added 2-(boc-amino)ethyl bromide (138 mg, 0.615 mmol). The resulting mixture was stirred overnight at 60° C. After cooling to ambient temperature, additional 2-(boc-amino)ethyl bromide (69 mg, 0.307 mmol) was added and reaction stirred for 1 h at ambient temperature. Then additional potassium carbonate (42 mg, 0.31 mmol) was added and reaction stirred for two overnights at 60° C. After cooling to ambient temperature, the reaction mixture was diluted with EtOAc and washed with water. The organic extracts were washed with brine, then combined and dried over anhydrous Na$_2$SO$_4$, filtered, and concentrated in vacuo. The residue was purified by silica chromatography (10-90% EtOAc in hexanes as the gradient eluent) to afford the title compound in sufficient purity for the next step. 10 mg of the title compound was repurified using C18 reverse phase chromatography (5-95% ACN in water with 0.1% TFA as the gradient eluent) to afford the title compound as the TFA salt. The TFA salt was treated with saturated NaHCO$_{3(aq)}$ and extracted with 4:1 DCM:IPA and then washed with brine. The combined organic extracts were dried over anhydrous Na$_2$SO$_{4(s)}$, filtered and concentrated in vacuo to afford the title compound. (169 mg, 87% yield) MS (apci) m/z=631.3 (M+H).

Example 321

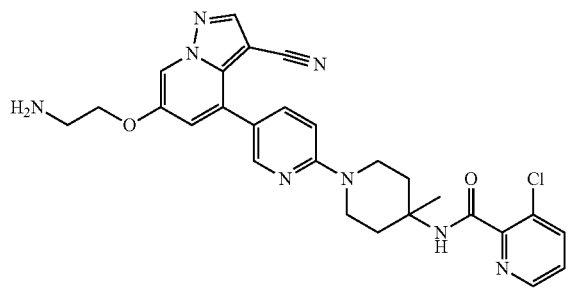 [SMILES: CC1(NC(=O)c2ncccc2Cl)CCN(c2ccc(-c3cc(OCCN)cn4ncc(C#N)c34)cn2)CC1]

N-(1-(5-(6-(2-aminoethoxy)-3-cyanopyrazolo[1,5-a]pyridin-4-yl)pyridin-2-yl)-4-methylpiperidin-4-yl)-3-chloropicolinamide To a solution tert-butyl (2-((4-(6-(4-(3-chloropicolinamido)-4-methylpiperidin-1-yl)pyridin-3-yl)-3-cyanopyrazolo[1,5-a]pyridin-6-yl)oxy)ethyl)carbamate (Example 320, 158 mg, 0.250 mmol) in DCM (2.5 mL) was treated with TFA (2.5 mL, 32 mmol). The reaction mixture was stirred for 10 min at ambient temperature, and then concentrated in vacuo. The residue was treated with saturated NaHCO$_{3(aq)}$ and extracted with 4:1 DCM:IPA and then washed with brine. The combined organic extracts were dried over anhydrous Na$_2$SO$_{4(s)}$, filtered and concentrated in vacuo to afford the title compound (130 mg, 98% yield) MS (apci) m/z=531.2 (M+H)

Example 322

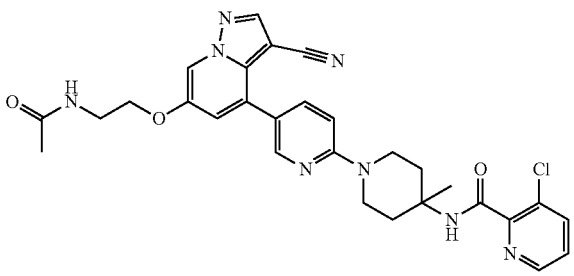 [SMILES: CC(=O)NCCOc1cc(-c2ccc(N3CCC(C)(NC(=O)c4ncccc4Cl)CC3)nc2)c2c(C#N)cnn2c1]

N-(1-(5-(6-(2-acetamidoethoxy)-3-cyanopyrazolo[1,5-a]pyridin-4-yl)pyridin-2-yl)-4-methylpiperidin-4-yl)-3-chloropicolinamide To a solution of N-(1-(5-(6-(2-aminoethoxy)-3-cyanopyrazolo[1,5-a]pyridin-4-yl)pyridin-2-yl)-4-methylpiperidin-4-yl)-3-chloropicolinamide (Example 321; 27 mg, 0.51 mmol) in DCM (0.5 mL) was added acetic anhydride (5 μL, 0.51 mmol) followed by TEA (14 μL, 0.102 mmol). The reaction solution was stirred for 1 h at ambient temperature. The reaction was concentrated in vacuo. The residue was resuspended with 60:40 ACN:water. The solution was purified directly by C18 reverse phase chromatography (5-75% ACN in water with 0.1% TFA as the gradient eluent) to afford the title compound as the TFA salt. The TFA salt was treated with saturated NaHCO$_{3(aq)}$ and extracted with 4:1 DCM:IPA and then washed with brine. The combined organic extracts were dried over anhydrous Na$_2$SO$_{4(s)}$, filtered and concentrated in vacuo to afford the title compound (20 mg, 67% yield) MS (apci) m/z=573.2 (M+H).

Example 323

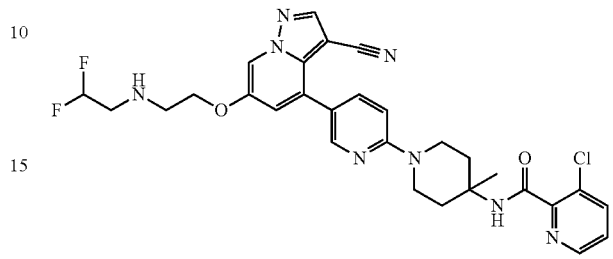

3-chloro-N-(1-(5-(3-cyano-6-(2-((2,2-difluoroethyl)amino)ethoxy)pyrazolo[1,5-a]pyridin-4-yl)pyridin-2-yl)-4-methylpiperidin-4-yl)picolinamide To a solution of N-(1-(5-(6-(2-aminoethoxy)-3-cyanopyrazolo[1,5-a]pyridin-4-yl)pyridin-2-yl)-4-methylpiperidin-4-yl)-3-chloropicolinamide (Example 321, 27 mg, 0.051 mmol) in DMA (0.5 mL) was added potassium carbonate (35 mg, 0.254 mmol). The suspension was sparged with argon and stirred for 10 min at ambient temperature. Then 2,2-difluoroethyl trifluoromethanesulfonate (11 mg, 0.51 mmol). The resulting mixture was sparged with argon and stirred 60 h at 60° C. After cooling to ambient temperature, reaction was diluted with 60:40 ACN:water. The solution was purified directly by C18 reverse phase chromatography (5-95% ACN in water with 0.1% TFA as the gradient eluent) to afford the title compound as the TFA salt. The TFA salt was treated with saturated NaHCO$_{3(aq)}$ and extracted with 4:1 DCM:IPA and then washed with brine. The combined organic extracts were dried over anhydrous Na$_2$SO$_{4(s)}$, filtered and concentrated in vacuo to afford the title compound (4 mg, 13% yield) MS (apci) m/z=595.2 (M+H).

Example 324

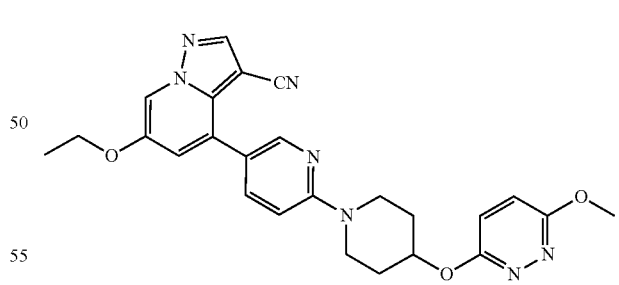

6-ethoxy-4-(6-(4-(((6-methoxypyridazin-3-yl)oxy)piperidin-1-yl)pyridin-3-yl)pyrazolo[1,5-a]pyridine-3-carbonitrile Step 1: Preparation of tert-butyl 4-((6-methoxypyridazin-3-yl)oxy)piperidine-1-carboxylate To a solution of tert-butyl 4-hydroxypiperidine-1-carboxylate (10.0 g, 49.7 mmol) in DMF (82.8 mL) was added sodium hydride (2.19 g, 54.7 mmol). The mixture was stirred at rt for 15 mins, after which 3-chloro-6-methoxypyridazine (7.18 g, 49.7 mmol) was added. The reaction mixture was stirred at 90° C. for 24 h. After cooling to ambient temperature, the reaction mixture was diluted with saturated NaHCO$_{3(aq)}$ and extracted with EtOAc. The combined organic extracts were washed with water and brine, dried over anhydrous Na$_2$SO$_{4(s)}$, and concentrated in vacuo. The residue was purified by silica chromatography (5-50% EtOAc in hexanes as the gradient eluent) to afford the title compound (assumed theoretical yield, 15.4 g, 49.8 mmol) in sufficient purity for Step 2. MS (apci) m/z=310.1 (M+H).

Step 2: Preparation of 3-methoxy-6-(piperidin-4-yloxy)pyridazine

To a solution of tert-butyl 4-((6-methoxypyridazin-3-yl)oxy)piperidine-1-carboxylate (assumed 15.4 g, 49.8 mol) in DCM (16 mL) was added TFA (19.2 mL, 250.9 mmol). The reaction mixture was stirred at rt 15 min, at which time it was concentrated in vacuo. The residue was resuspended in 20 mL DCM and purified by silica chromatography (1-9% MeOH in DCM with 1% NH$_4$OH as the gradient eluent) to afford the title compound (6.0 g, 28.7 mmol, 57.6% yield over two steps) in sufficient purity for Step 3. MS (apci) m/z=210.1 (M+H).

Step 3: Preparation of 6-ethoxy-4-(6-(4-((6-methoxypyridazin-3-yl)oxy)piperidin-1-yl)pyridin-3-yl)pyrazolo[1,5-a]pyridine-3-carbonitrile To a solution of 6-ethoxy-4-(6-fluoropyridin-3-yl)pyrazolo[1,5-a]pyridine-3-carbonitrile (Intermediate P6, 0.012 g, 0.0425 mmol) in DMSO (0.1 mL) was added 3-methoxy-6-(piperidin-4-yloxy)pyridazine (0.0133 g, 0.0638 mmol) and DIEA (37 µL, 0.213 mmol). The reaction mixture was stirred at 110° C. for 24 h. After cooling to ambient temperature, the reaction mixture was diluted with DCM and washed with saturated NH$_4$Cl$_{(aq)}$. The combined aqueous washes were further extracted with DCM, and the combined organic extracts were dried over anhydrous Na$_2$SO$_{4(s)}$ and concentrated in vacuo. The residue was purified by silica chromatography (0-100% EtOAc in hexanes as the gradient eluent) to afford the title compound (6 mg, 0.0127 mmol, 30% yield). MS (apci) m/z=472.2 (M+H).

Example 325

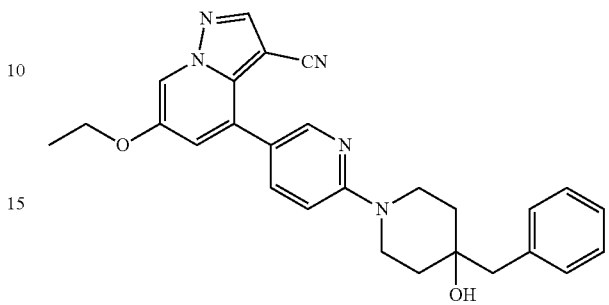

4-(6-(4-benzyl-4-hydroxypiperidin-1-yl)pyridin-3-yl)-6-ethoxypyrazolo[1,5-a]pyridine-3-carbonitrile To a solution of 6-ethoxy-4-(6-fluoropyridin-3-yl)pyrazolo[1,5-a]pyridine-3-carbonitrile (Intermediate P6, 30 mg, 0.106 mmol) in DMA (0.5 mL) was added TEA (0.044 mL, 0.319 mmol) and 4-benzylpiperidin-4-ol (40.7 mg, 0.213 mmol) The reaction mixture was stirred at 90° C. for 24 h. After cooling to ambient temperature, the reaction mixture was diluted with DCM and washed with saturated NH$_4$Cl$_{(aq)}$ then water. The combined aqueous washes were further extracted with DCM, and the combined organic extracts were dried over anhydrous Na$_2$SO$_{4(s)}$ and concentrated in vacuo. The residue was purified by silica chromatography (30-100% EtOAc in hexanes as the gradient eluent) to afford the title compound (39 mg, 0.0860 mmol, 80.9% yield). MS (apci) m/z=454.2 (M+H).

The compounds in Table RR were prepared using a similar method to that described for the synthesis of Example 325, replacing 4-benzylpiperidin-4-ol with the appropriate piperidine nucleophile. Reactions were monitored for completion by LCMS, and reaction durations were adjusted accordingly. Title compounds were cleanly isolated following chromatographic purification using an appropriate gradient eluent (and if necessary converted to the free base).

TABLE RR

| Ex. # | Structure | Chemical Name | MS m/z |
|---|---|---|---|
| 326 | 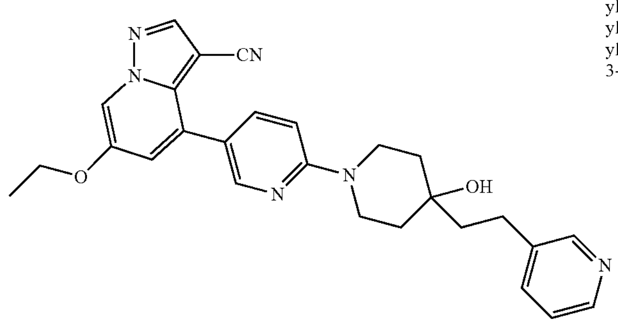 | 6-ethoxy-4-(6-(4-hydroxy-4-(2-(pyridin-3-yl)ethyl)piperidin-1-yl)pyridin-3-yl)pyrazolo[1,5-a]pyridine-3-carbonitrile | 469.15 (M + H) |

TABLE RR-continued

| Ex. # | Structure | Chemical Name | MS m/z |
|---|---|---|---|
| 327 | 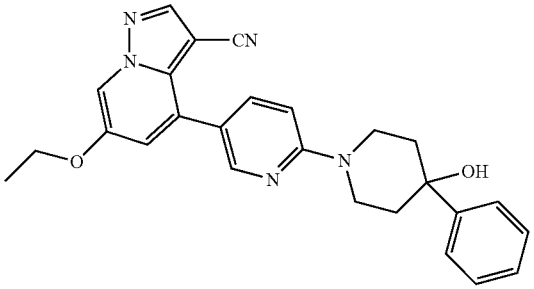 [SMILES: CCOc1cc(-c2ccc(N3CCC(O)(c4ccccc4)CC3)nc2)c2c(C#N)cnn2c1] | 6-ethoxy-4-(6-(4-hydroxy-4-phenylpiperidin-1-yl)pyridin-3-yl)pyrazolo[1,5-a]pyridine-3-carbonitrile | 440.15 (M + H) |
| 328 | 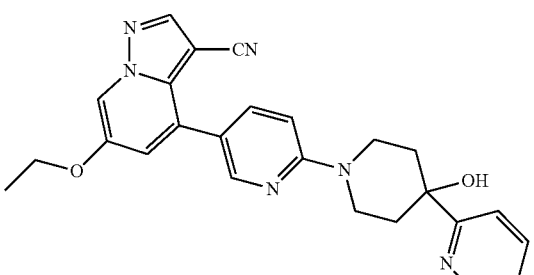 | 6-ethoxy-4-(6-(4-hydroxy-4-(pyridin-2-yl)piperidin-1-yl)pyridin-3-yl)pyrazolo[1,5-a]pyridine-3-carbonitrile | 441.10 (M + H) |
| 329 | 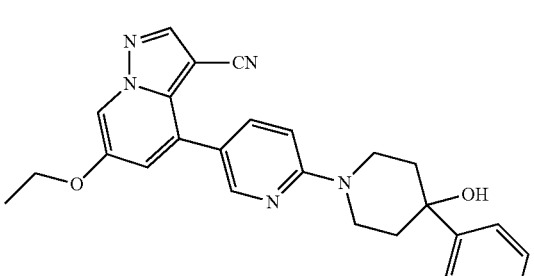 | 6-ethoxy-4-(6-(4-hydroxy-4-(pyridin-3-yl)piperidin-1-yl)pyridin-3-yl)pyrazolo[1,5-a]pyridine-3-carbonitrile | 441.10 (M + H) |
| 330 | 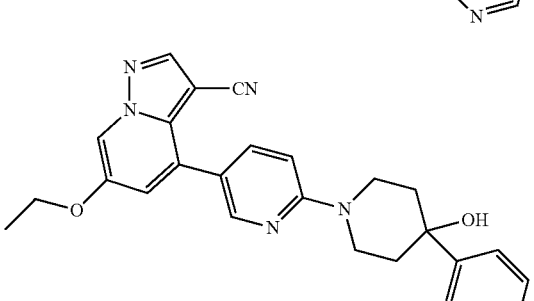 | 6-ethoxy-4-(6-(4-hydroxy-4-(pyridin-4-yl)piperidin-1-yl)pyridin-3-yl)pyrazolo[1,5-a]pyridine-3-carbonitrile | 441.10 (M + H) |

Example 331

6-ethoxy-4-(6-(4-(((6-methylpyridazin-3-yl)oxy)piperidin-1-yl)pyridin-3-yl)pyrazolo[1,5-a]pyridine-3-carbonitrile

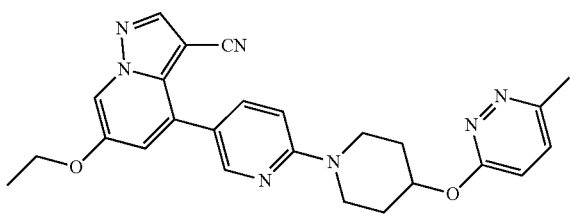 [SMILES: CCOc1cc(-c2ccc(N3CCC(Oc4ccc(C)nn4)CC3)nc2)c2c(C#N)cnn2c1]

To a solution of 6-ethoxy-4-(6-(4-hydroxypiperidin-1-yl)pyridin-3-yl)pyrazolo[1,5-a]pyridine-3-carbonitrile (Intermediate P52, 30 mg, 0.0825 mmol) in 1:1 DCM/THF (0.7 mL) was added 6-methylpyridazin-3-ol (18.2 mg, 0.165 mmol) and triphenylphosphane (43.3 mg, 0.165 mmol). The reaction vessel was sparged with argon, at which time diisopropyl (E)-diazene-1,2-dicarboxylate (0.0235 ml, 0.165 mmol) was added, and the reaction mixture was stirred at rt 24 h. The reaction mixture was diluted with DCM and washed with water. The aqueous fraction was extracted with DCM, and the combined organic extracts were dried over anhydrous Na$_2$SO$_{4(s)}$ and concentrated in vacuo. The residue was purified by silica chromatography (50-100% EtOAc in hexanes as the gradient eluent) to afford the title compound (15 mg, 0.0329 mmol, 39.9% yield). MS (apci) m/z=456.2 (M+H).

Example 332

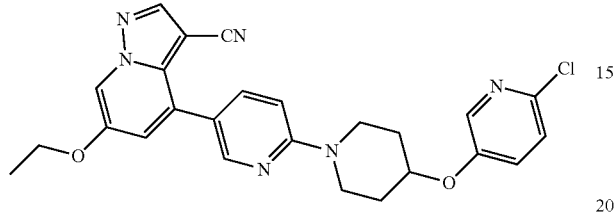

4-(6-(4-((6-chloropyridin-3-yl)oxy)piperidin-1-yl)pyridin-3-yl)-6-ethoxypyrazolo[1,5-a]pyridine-3-carbonitrile The title compound was prepared using a similar method to that described for the synthesis of Example 331, replacing 6-methylpyridazin-3-ol with 6-chloropyridin-3-ol. MS (apci) m/z=475.2 (M+H).

Example 333

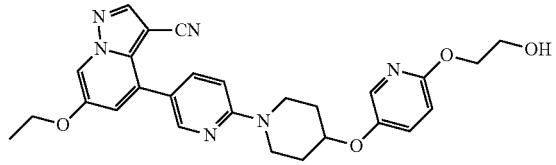 [SMILES: CCOc1cc(-c2ccc(N3CCC(Oc4ccc(OCCO)nc4)CC3)nc2)c2c(C#N)cnn2c1]

6-ethoxy-4-(6-(4-((6-(2-hydroxyethoxy)pyridin-3-yl)oxy)piperidin-1-yl)pyridin-3-yl)pyrazolo[1,5-a]pyridine-3-carbonitrile To a solution of ethane-1,2-diol (9.8 mg, 0.16 mmol) in DMF (0.2 mL) was added sodium hydride (60% w/w, 2.3 mg, 0.095 mmol) and stirred at rt for 5 min, at which time 4-(6-(4-((6-chloropyridin-3-yl)oxy)piperidin-1-yl)pyridin-3-yl)-6-ethoxypyrazolo[1,5-a]pyridine-3-carbonitrile (Example 332, 15 mg, 0.032 mmol) in an additional 0.3 mL of DMF was added. The reaction mixture was stirred at 110° C. for 24 h. After cooling to ambient temperature, the reaction mixture was quenched with saturated NH$_4$Cl and extracted with DCM. The combined organic extracts were dried over anhydrous Na$_2$SO$_{4(s)}$ and concentrated in vacuo. The residue was purified by C-18 reverse phase chromatography (10-90% ACN in water with 0.1% formic acid as the gradient eluent) to afford the title compound (2.2 mg, 0.0044 mmol, 14% yield). MS (apci) m/z=501.25 (M+H).

Example 334

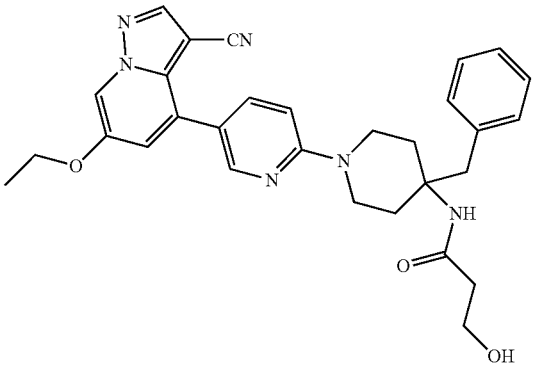 [SMILES: CCOc1cc(-c2ccc(N3CCC(Cc4ccccc4)(NC(=O)CCO)CC3)nc2)c2c(C#N)cnn2c1]

N-(4-benzyl-1-(5-(3-cyano-6-ethoxypyrazolo[1,5-a]pyridin-4-yl)pyridin-2-yl)piperidin-4-yl)-3-hydroxypropanamide To a solution of 4-(6-(4-benzyl-4-hydroxypiperidin-1-yl)pyridin-3-yl)-6-ethoxypyrazolo[1,5-a]pyridine-3-carbonitrile (Intermediate P53, 19.5 mg, 0.0430 mmol) was added 3-hydroxypropanenitrile (0.5 mL, 0.0430 mmol). The mixture was stirred at rt for 5 min, at which time sulfuric acid (98%, 0.0023 mL, 0.0430 mmol) was added dropwise. The reaction mixture was stirred at rt for 24 h. The crude mixture was purified by C-18 reverse phase chromatography (0-70% ACN in water as the gradient eluent) to afford the title compound (6 mg, 0.01 mmol, 27% yield). MS (apci) m/z=547.2 (M+H).

Example 335

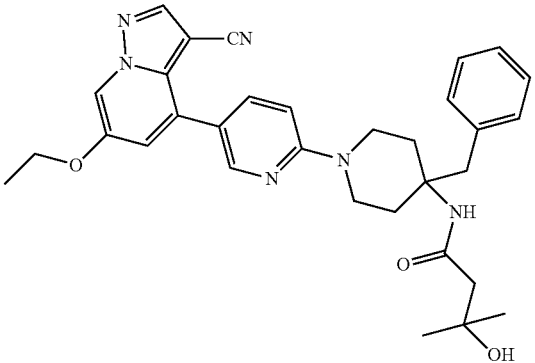 [SMILES: CCOc1cc(-c2ccc(N3CCC(Cc4ccccc4)(NC(=O)CC(C)(C)O)CC3)nc2)c2c(C#N)cnn2c1]

N-(4-benzyl-1-(5-(3-cyano-6-ethoxypyrazolo[1,5-a]pyridin-4-yl)pyridin-2-yl)piperidin-4-yl)-3-hydroxy-3-methylbutanamide The title compound was prepared using a similar method to that described for the synthesis of Example 334, replacing 3-hydroxypropanenitrile with 3-hydroxy-3-methylbutanenitrile. MS (apci) m/z=553.2 (M+H).

Example 336

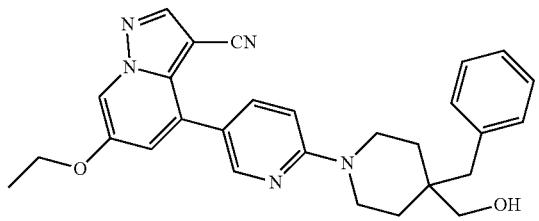 [SMILES: CCOc1cc(-c2ccc(N3CCC(CO)(Cc4ccccc4)CC3)nc2)c2c(C#N)cnn2c1]

4-(6-(4-benzyl-4-(hydroxymethyl)piperidin-1-yl)pyridin-3-yl)-6-ethoxypyrazolo[1,5-a]pyridine-3-carbonitrile To a solution of 6-ethoxy-4-(6-fluoropyridin-3-yl)pyrazolo[1,5-a]pyridine-3-carbonitrile (100.5 mg, 0.3560 mmol) in DMSO (3 ml) was added (4-benzylpiperidin-4-yl)methanol hydrochloride (151.5 mg, 0.6267 mmol) and cesium carbonate (812.0 mg, 2.492 mmol). The reaction mixture was stirred at 60° C. for 24 h. After cooling to ambient temperature, the reaction mixture was diluted with DCM and washed with water and saturated $NH_4Cl_{(aq)}$. The combined aqueous layers were extracted with DCM, then the combined organic extracts were dried over anhydrous $Na_2SO_{4(s)}$ and concentrated in vacuo. The residue was purified by silica chromatography (0-100% EtOAc in hexanes as the gradient eluent) to afford the title compound (118.2 mg, 0.2528 mmol, 71.00% yield). MS (apci) m/z=468.2 (M+H).

Example 337

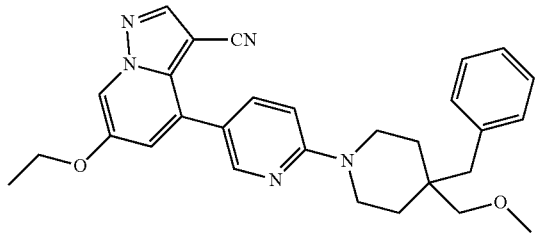 [SMILES: CCOc1cc(-c2ccc(N3CCC(COC)(Cc4ccccc4)CC3)nc2)c2c(C#N)cnn2c1]

4-(6-(4-benzyl-4-(methoxymethyl)piperidin-1-yl)pyridin-3-yl)-6-ethoxypyrazolo[1,5-a]pyridine-3-carbonitrile To a solution of 4-(6-(4-benzyl-4-(hydroxymethyl)piperidin-1-yl)pyridin-3-yl)-6-ethoxypyrazolo[1,5-a]pyridine-3-carbonitrile (Intermediate P55, 9.0 mg, 0.019 mmol) in DMF (0.4 mL) was added sodium hydride (60% w/w, 2.8 mg, 0.070 mmol). This mixture was stirred at rt 1 h, at which time methyl iodide (0.021 ml, 0.34 mmol) was added. The reaction mixture was stirred at rt for 72 h. The reaction mixture was diluted with DCM and washed with water. The combined organic extracts were dried over anhydrous $Na_2SO_{4(s)}$ and concentrated in vacuo. The residue was purified by silica chromatography (0-100% EtOAc in hexanes as the gradient eluent) to afford the title compound (4.0 mg, 0.0083 mmol, 43% yield). MS (apci) m/z=482.25 (M+H).

Example 338

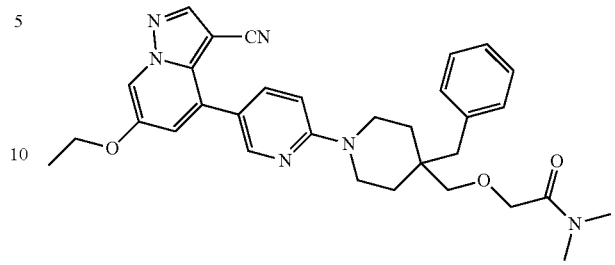

2-((4-benzyl-1-(5-(3-cyano-6-ethoxypyrazolo[1,5-a]pyridin-4-yl)pyridin-2-yl)piperidin-4-yl)methoxy)-N,N-dimethylacetamide The title compound was prepared using a similar method to that described for the synthesis of Example 337, replacing methyl iodide with 2-chloro-N,N-dimethylacetamide. MS (apci) m/z=553.2 (M+H).

Example 339

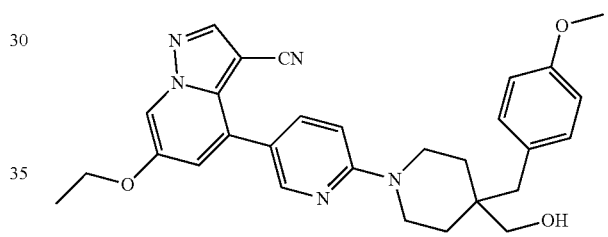

6-ethoxy-4-(6-(4-(hydroxymethyl)-4-(4-methoxybenzyl)piperidin-1-yl)pyridin-3-yl)pyrazolo[1,5-a]pyridine-3-carbonitrile Step 1: Preparation of tert-butyl 4-formyl-4-(4-methoxybenzyl)piperidine-1-carboxylate To a sealed 3-neck flask that had been sparged with $N_2$ was added tert-butyl 4-formylpiperidine-1-carboxylate (201.8 mg, 0.9462 mmol) in THF (2 mL). The mixture was cooled to −78° C. and stirred at this temperature for 10 min, at which time lithium bis(trimethylsilyl)amide (3 mL, 3 mmol) was added dropwise. The reaction mixture was stirred at −78° C. for 40 min then warmed to rt. After 16 h, 1-(bromomethyl)-4-methoxybenzene (0.3 mL, 2.058 mmol) was added, and the reaction mixture was stirred an additional 24 h at rt. The reaction was quenched with water, extracted into EtOAc, and the organic extracts were dried over anhydrous $Na_2SO_{4(s)}$ and concentrated in vacuo to afford the title compound (assumed theoretical yield, 315 mg, 0.946 mmol) in sufficient purity for Step 2. MS (apci) m/z=234.2 (M+H-Boc).

Step 2: Preparation of 4-(4-methoxybenzyl)piperidine-4-carbaldehyde

To a solution of tert-butyl 4-formyl-4-(4-methoxybenzyl)piperidine-1-carboxylate (assumed 315 mg, 0.946 mmol) in DCM (2 mL) was added TFA (2 mL, 26 mmol). The reaction mixture was stirred at rt 30 min then concentrated in vacuo. The residue was diluted in DCM and 10% NH$_4$OH in MeOH and stirred for 15 min. The mixture was concentrated in vacuo to afford the title compound (assumed theoretical yield, 220.8 mg, 0.9462 mmol) in sufficient purity for Step 3. MS (apci) m/z=234.2 (M+H).

Step 3: Preparation of 6-ethoxy-4-(6-(4-formyl-4-(4-methoxybenzyl)piperidin-1-yl)pyridin-3-yl)pyrazolo[1,5-a]pyridine-3-carbonitrile To a solution of 6-ethoxy-4-(6-fluoropyridin-3-yl)pyrazolo[1,5-a]pyridine-3-carbonitrile (Intermediate P6, 40.3 mg, 0.143 mmol) in DMSO (0.5 mL) was added 4-(4-methoxybenzyl)piperidine-4-carbaldehyde (66.6 mg, 0.286 mmol) and cesium carbonate (465 mg, 1.43 mmol). The reaction mixture was stirred at 60° C. for 16 h. After cooling to ambient temperature, the reaction mixture was diluted with water and extracted with DCM. The combined organic extracts were dried over anhydrous Na$_2$SO$_{4(s)}$ and purified by silica chromatography (0-100% EtOAc in hexanes as the gradient eluent) to afford the title compound (assumed theoretical yield, 70.8 mg, 0.143 mmol) in sufficient purity for Step 4. MS (apci) m/z=496.2 (M+H).

Step 4: Preparation of 6-ethoxy-4-(6-(4-(hydroxymethyl)-4-(4-methoxybenzyl)piperidin-1-yl)pyridin-3-yl)pyrazolo[1,5-a]pyridine-3-carbonitrile MeOH (0.5 mL) was added to 6-ethoxy-4-(6-(4-formyl-4-(4-methoxybenzyl)piperidin-1-yl)pyridin-3-yl)pyrazolo[1,5-a]pyridine-3-carbonitrile (assumed 70.8 mg, 0.143 mmol) and stirred at rt 10 min, at which time sodium borohydride (103.5 mg, 2.736 mmol) was added. The reaction mixture was stirred at rt 1.5 h then quenched with water and 2M HCl. The pH of the mixture was adjusted to 12 with 2M NaOH, and the mixture was extracted with 4:1 DCM/IPA. The combined organic extracts were dried over anhydrous Na$_2$SO$_{4(s)}$ and concentrated in vacuo. The residue was purified by C-18 reverse phase chromatography (0-70% ACN in water with 0.1% TFA). The fractions containing the desired product were free-based with saturated NaHCO$_{3(aq)}$ to afford the title compound (1.1 mg, 0.00221 mmol, 1.57% yield over four steps). MS (apci) m/z=498.3 (M+H).

Example 340

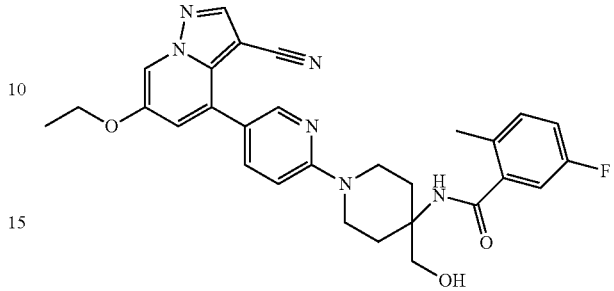

N-(1-(5-(3-cyano-6-ethoxypyrazolo[1,5-a]pyridin-4-yl)pyridin-2-yl)-4-(hydroxymethyl)piperidin-4-yl)-5-fluoro-2-methylbenzamide To a solution of 4-(6-(4-amino-4-(hydroxymethyl)piperidin-1-yl)pyridin-3-yl)-6-ethoxypyrazolo[1,5-a]pyridine-3-carbonitrile (Intermediate P56, 30 mg, 0.0764 mmol) in DCM (0.005 mL) was added 5-fluoro-2-methylbenzoic acid (11.8 mg, 0.0764 mmol), DIEA (13.4 μl, 0.0764 mmol), and HATU (29.1 mg, 0.0764 mmol). The reaction mixture was stirred at rt 24 h then purified by C18 prep HPLC eluting with a 5-95% acetonitrile/water+0.1% TFA gradient then silica chromatography eluting with (0-100% EtOAc in Hexanes then 0-10% MeOH in EtOAc as the gradient eluent) followed by trituration with 1:3 DCM/MTBE to afford the title compound (23.8 mg, 0.045 mmol, 59% yield). MS (apci) m/z=529.2 (M+H).

The compounds in Table SS were prepared using a similar method to that described for the synthesis of Example 340, replacing 5-fluoro-2-methylbenzoic acid with the appropriate carboxylic acid. Reactions were monitored for completion by LCMS, and reaction durations were adjusted accordingly. Title compounds were cleanly isolated following chromatographic purification using an appropriate gradient eluent (and if necessary converted to the free base).

TABLE SS

| Ex. # | Structure | Chemical Name | MS m/z |
|---|---|---|---|
| 341 | 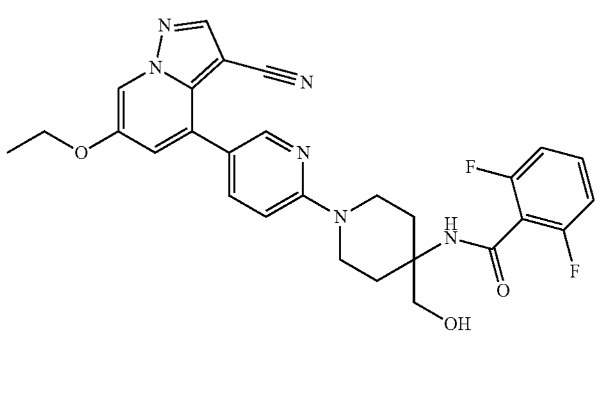 [SMILES: CCOc1cc(-c2ccc(N3CCC(CO)(NC(=O)c4c(F)cccc4F)CC3)nc2)c2c(C#N)cnn2c1] | N-(1-(5-(3-cyano-6-ethoxypyrazolo[1,5-a]pyridin-4-yl)pyridin-2-yl)-4-(hydroxymethyl)piperidin-4-yl)-2,6-difluorobenzamide | 533.20 (M + H) |

TABLE SS-continued

| Ex. # | Structure | Chemical Name | MS m/z |
|---|---|---|---|
| 342 | 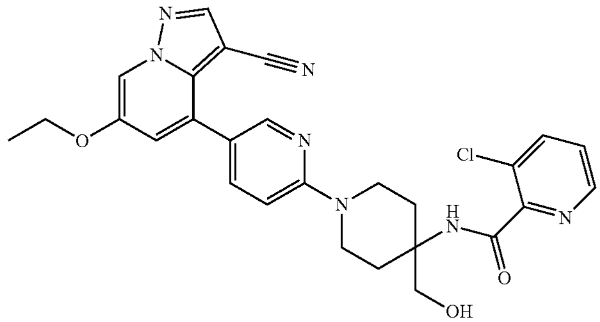 [SMILES: CCOc1cc(-c2ccc(N3CCC(CO)(NC(=O)c4ncccc4Cl)CC3)nc2)c2c(C#N)cnn2c1] | 3-chloro-N-(1-(5-(3-cyano-6-ethoxypyrazolo[1,5-a]pyridin-4-yl)pyridin-2-yl)-4-(hydroxymethyl)piperidin-4-yl)picolinamide | 532.20 (M+) |
| 343 | 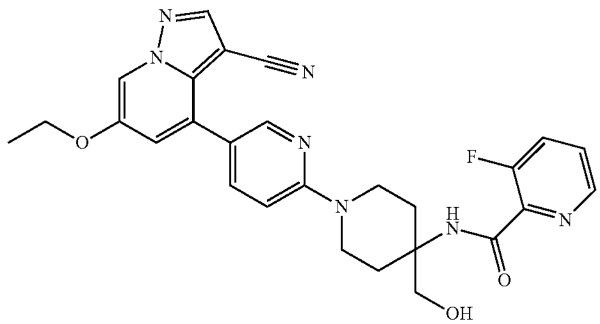 | N-(1-(5-(3-cyano-6-ethoxypyrazolo[1,5-a]pyridin-4-yl)pyridin-2-yl)-4-(hydroxymethyl)piperidin-4-yl)-3-fluoropicolinamide | 516.20 (M + H) |

Example 344

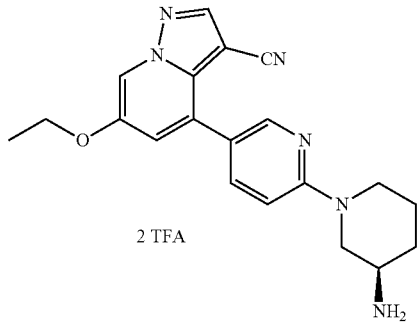 [SMILES: CCOc1cc(-c2ccc(N3CCC[C@@H](N)C3)nc2)c2c(C#N)cnn2c1]

(R)-4-(6-(3-aminopiperidin-1-yl)pyridin-3-yl)-6-ethoxypyrazolo[1,5-a]pyridine-3-carbonitrile bis(2,2,2-trifluoroacetate)

A solution of tert-butyl (R)-(1-(5-(3-cyano-6-ethoxypyrazolo[1,5-a]pyridin-4-yl)pyridin-2-yl)piperidin-3-yl)carbamate (Intermediate P57, 30 mg, 0.0649 mmol) in DCM (0.1 mL) was treated with TFA (0.124 mL). The reaction mixture was stirred at rt for 3 h before it was concentrated in vacuo to yield the title product (12 mg, 31% yield). MS (apci) m/z=363.2 (M+H).

Example 345

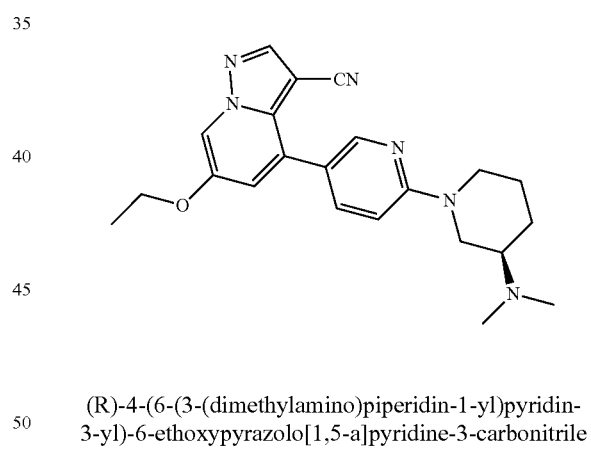

(R)-4-(6-(3-(dimethylamino)piperidin-1-yl)pyridin-3-yl)-6-ethoxypyrazolo[1,5-a]pyridine-3-carbonitrile A solution of tert-butyl (R)-(1-(5-(3-cyano-6-ethoxypyrazolo[1,5-a]pyridin-4-yl)pyridin-2-yl)piperidin-3-yl)carbamate (Intermediate P57, 30 mg, 0.0649 mmol) in formic acid (0.489 mL) was treated with formaldehyde (0.195 mL, 2.59 mmol). The reaction mixture was stirred at 90° C. for 24 h. After cooling to ambient temperature, the reaction mixture was quenched with water and extracted with DCM. The combined organic extracts were dried over anhydrous $Na_2SO_{4(s)}$ and concentrated in vacuo. The residue was purified by C-18 reverse phase chromatography (10-90% ACN in water+0.1% formic acid as the gradient eluent) to afford the title compound (2.0 mg, 0.00512 mmol, 7.90% yield). MS (apci) m/z=391.25 (M+H).

Example 346

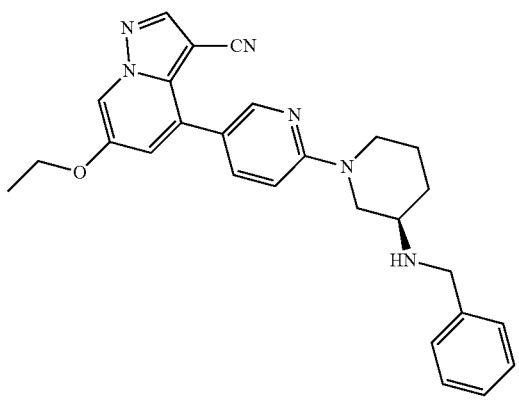 [SMILES: CCOc1cc(-c2ccc(N3CCC[C@@H](NCc4ccccc4)C3)nc2)c2c(C#N)cnn2c1]

(R)-4-(6-(3-(benzylamino)piperidin-1-yl)pyridin-3-yl)-6-ethoxypyrazolo[1,5-a]pyridine-3-carbonitrile To a solution of (R)-4-(6-(3-aminopiperidin-1-yl)pyridin-3-yl)-6-ethoxypyrazolo[1,5-a]pyridine-3-carbonitrile (Example 344, 10 mg, 0.0276 mmol) in DMA (0.4 mL) was added TEA (0.0115 mL, 0.0828 mmol) and (bromomethyl)benzene (0.003 mL, 0.028 mmol). The reaction mixture was stirred at rt for 24 h. The reaction mixture was quenched with saturated $NH_4Cl_{(aq)}$ and extracted into DCM. The combined organic extracts were dried over anhydrous $Na_2SO_{4(s)}$ and concentrated in vacuo. The residue was purified by silica chromatography (0-100% EtOAc in hexanes as the gradient eluent) to afford the title compound (3.9 mg, 31% yield). MS (apci) m/z=453.2 (M+H).

Example 347

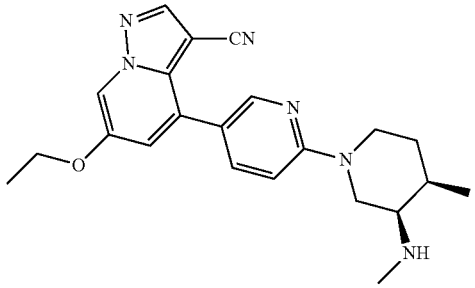 [SMILES: CCOc1cc(-c2ccc(N3CC[C@@H](C)[C@@H](NC)C3)nc2)c2c(C#N)cnn2c1]

6-ethoxy-4-(6-((3R,4R)-4-methyl-3-(methylamino)piperidin-1-yl)pyridin-3-yl)pyrazolo[1,5-a]pyridine-3-carbonitrile Step 1: Preparation of tert-butyl ((3R,4R)-1-(5-(3-cyano-6-ethoxypyrazolo[1,5-a]pyridin-4-yl)pyridin-2-yl)-4-methylpiperidin-3-yl)(methyl)carbamate To a solution of 6-ethoxy-4-(6-fluoropyridin-3-yl)pyrazolo[1,5-a]pyridine-3-carbonitrile (Intermediate P6, 60 mg, 0.213 mmol) in DMSO (0.4 mL) was added potassium carbonate (147 mg, 1.06 mmol) and tert-butyl methyl((3R,4R)-4-methylpiperidin-3-yl)carbamate (146 mg, 0.638 mmol). The reaction mixture was stirred at 110° C. for 24 h. After cooling to ambient temperature, the reaction mixture was quenched with saturated $NH_4Cl_{(aq)}$ and extracted into DCM. The combined organic extracts were dried over anhydrous $Na_2SO_{4(s)}$ and concentrated in vacuo. The residue was purified by silica chromatography (0-100% EtOAc in hexanes as the gradient eluent) to afford the title compound (72.5 mg, 0.148 mmol, 69.5% yield) in sufficient purity for step 2. MS (apci) m/z=491.3 (M+H).

Step 2: Preparation of 6-ethoxy-4-(6-((3R,4R)-4-methyl-3-(methylamino)piperidin-1-yl)pyridin-3-yl)pyrazolo[1,5-a]pyridine-3-carbonitrile To a solution of tert-butyl ((3R,4R)-1-(5-(3-cyano-6-ethoxypyrazolo[1,5-a]pyridin-4-yl)pyridin-2-yl)-4-methylpiperidin-3-yl)(methyl)carbamate (0.020 g, 0.0408 mmol) in DCM (0.2 mL) was added 5M HCl in IPA (0.204 mL, 1.02 mmol). The reaction mixture was stirred at rt for 24 h, at which time it was quenched in water and adjusted to pH 10 by addition of 2M $NaOH_{(aq)}$. The solution was extracted with DCM, and the combined organic extracts were concentrated in vacuo to afford the title compound (0.0145 g, 0.0371 mmol, 91.1% yield). MS (apci) m/z=391.2 (M+H).

Example 348

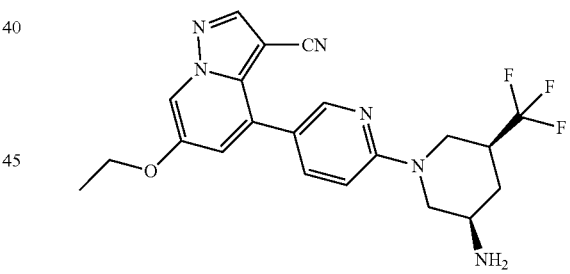

4-(6-((3R,5S)-3-amino-5-(trifluoromethyl)piperidin-1-yl)pyridin-3-yl)-6-ethoxypyrazolo[1,5-a]pyridine-3-carbonitrile A solution of tert-butyl ((3R,5S)-1-(5-(3-cyano-6-ethoxypyrazolo[1,5-a]pyridin-4-yl)pyridin-2-yl)-5-(trifluoromethyl)piperidin-3-yl)carbamate (Intermediate P62, 0.020 g, 0.038 mmol) in DCM (0.2 mL) was treated with 5M HCl in IPA (0.19 mL, 1.1 mmol). The reaction was stirred at rt 6 h. The reaction mixture was concentrated in vacuo, and the residue was purified by silica chromatography (0-30% [9:1 MeOH/$NH_4OH$] in EtOAc) to afford the title compound (0.0073 g, 0.017 mmol, 45% yield). MS (apci) m/z=431.2 (M+H).

Example 349

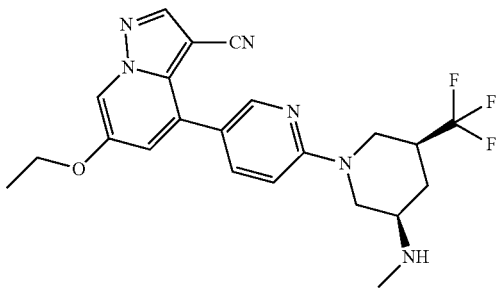 [SMILES: CCOc1cc(-c2ccc(N3C[C@H](NC)C[C@H](C(F)(F)F)C3)nc2)c2c(C#N)cnn2c1]

6-ethoxy-4-(6-((3R,5 S)-3-(methylamino)-5-(trifluoromethyl)piperidin-1-yl)pyridin-3-yl)pyrazolo[1,5-a]pyridine-3-carbonitrile

Step 1: Preparation of tert-butyl ((3R,5 S)-1-(5-(3-cyano-6-ethoxypyrazolo[1,5-a]pyridin-4-yl)pyridin-2-yl)-5-(trifluoromethyl)piperidin-3-yl)(methyl)carbamate A solution of tert-butyl ((3R,5S)-1-(5-(3-cyano-6-ethoxypyrazolo[1,5-a]pyridin-4-yl)pyridin-2-yl)-5-(trifluoromethyl)piperidin-3-yl)carbamate (Intermediate P62, 0.020 g, 0.038 mmol) in DMA (0.5 mL) was cooled to 0° C. then treated with sodium hydride (60% w/w, 0.0090 g, 0.11 mmol). The reaction mixture was warmed to rt and stirred for 20 min, at which time iodomethane (0.016 g, 0.11 mmol) was added and the reaction mixture stirred at rt an additional 24 h. The reaction mixture was quenched with saturated $NH_4Cl_{(aq)}$ and extracted into DCM. The combined organic extracts were dried over anhydrous $Na_2SO_{4(s)}$ and concentrated in vacuo. The residue was purified by silica chromatography (0-100% EtOAc in hexanes as the gradient eluent) to afford the title compound (0.010 g, 0.018 mmol, 49% yield) in sufficient purity for step 2. MS (apci) m/z=545.25 (M+H).

Step 2: Preparation of 6-ethoxy-4-(6-((3R,5 S)-3-(methylamino)-5-(trifluoromethyl)piperidin-1-yl)pyridin-3-yl)pyrazolo[1,5-a]pyridine-3-carbonitrile A solution of tert-butyl ((3R,5S)-1-(5-(3-cyano-6-ethoxypyrazolo[1,5-a]pyridin-4-yl)pyridin-2-yl)-5-(trifluoromethyl)piperidin-3-yl)(methyl)carbamate (0.010 g, 0.018 mmol) in DCM (0.2 mL) was treated with 5M HCl in IPA (0.2 ml, 0.018 mmol). The reaction was stirred at rt 6 h. The reaction mixture was concentrated in vacuo, and the residue was purified by silica chromatography (0-30% [9:1 MeOH/$NH_4OH$] in EtOAc) to afford the title compound (0.0045 g, 0.010 mmol, 55% yield). MS (apci) m/z=445.2 (M+H).

Example 350

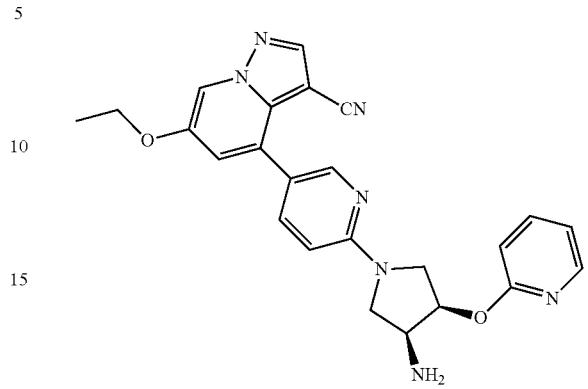

4-(6-((3S,4R)-3-amino-4-(pyridin-2-yloxy)pyrrolidin-1-yl)pyridin-3-yl)-6-ethoxypyrazolo[1,5-a]pyridine-3-carbonitrile

Step 1: Preparation of 4-(6-((3S,4R)-3-azido-4-(pyridin-2-yloxy)pyrrolidin-1-yl)pyridin-3-yl)-6-ethoxypyrazolo[1,5-a]pyridine-3-carbonitrile To a solution of 4-(6-((3S,4S)-3-azido-4-hydroxypyrrolidin-1-yl)pyridin-3-yl)-6-ethoxypyrazolo[1,5-a]pyridine-3-carbonitrile (Intermediate P58, 0.050 g, 0.128 mmol) in 1:1 DCM/THF (0.7 mL) was added pyridin-2-ol (0.0244 g, 0.256 mmol) and triphenylphosphane (0.0672 g, 0.256 mmol). The reaction mixture was sparged with argon, diisopropyl (E)-diazene-1,2-dicarboxylate (0.0350 mL, 0.256 mmol) was added. The reaction mixture was stirred at rt for 24 h. It was quenched with water and extracted into DCM. The combined organic extracts were dried over anhydrous $Na_2SO_{4(s)}$ and concentrated in vacuo. The residue was purified by silica chromatography (20-100% EtOAc in hexanes as the gradient eluent) to afford the title compound (0.014 g, 0.0299 mmol, 23.4% yield) in sufficient purity for step 2. MS (apci) m/z=468.1 (M+H).

Step 2: Preparation of 4-(6-((3S,4R)-3-amino-4-(pyridin-2-yloxy)pyrrolidin-1-yl)pyridin-3-yl)-6-ethoxypyrazolo[1,5-a]pyridine-3-carbonitrile To a solution of 4-(6-((3S,4R)-3-azido-4-(pyridin-2-yloxy)pyrrolidin-1-yl)pyridin-3-yl)-6-ethoxypyrazolo[1,5-a]pyridine-3-carbonitrile (0.013 g, 0.028 mmol) in 1:1 MeOH/EtOAc (2 mL) was added 10% palladium on carbon (0.33 mg, 0.0028 mmol). The reaction mixture was sparged with $H_2$ and stirred at rt for 24 h. The solids were removed by filtration, and the filtrate was concentrated in vacuo. The residue was purified by silica chromatography (0-40% [9:1 MeOH/$NH_4OH$] in EtOAc as the gradient eluent) to afford the title compound (7 mg, 56% yield). MS (apci) m/z=442.2 (M+H).

Example 351

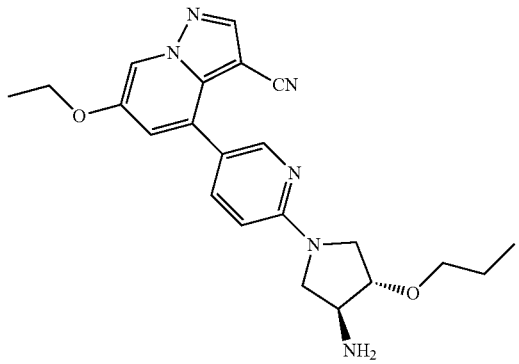 [SMILES: CCCO[C@H]1CN(c2ccc(-c3cc(OCC)cn4ncc(C#N)c34)cn2)C[C@@H]1N]

4-(6-((3S,4S)-3-amino-4-propoxypyrrolidin-1-yl)
pyridin-3-yl)-6-ethoxypyrazolo[1,5-a]pyridine-3-
carbonitrile

Step 1: Preparation of 4-(6-((3S,4S)-3-azido-4-propoxypyrrolidin-1-yl)pyridin-3-yl)-6-ethoxypyrazolo[1,5-a]pyridine-3-carbonitrile To a solution of 4-(6-((3S,4S)-3-azido-4-hydroxypyrrolidin-1-yl)pyridin-3-yl)-6-ethoxypyrazolo[1,5-a]pyridine-3-carbonitrile (Intermediate P58, 0.027 g, 0.069 mmol) in DMA (0.5 mL) was added potassium carbonate (0.029 g, 0.21 mmol) and 1-iodopropane (0.021 ml, 0.21 mmol). The reaction mixture was stirred at 85° C. for 48 h. After cooling to ambient temperature, the reaction was quenched with water and extracted into DCM. The combined organic extracts were dried over anhydrous $Na_2SO_{4(s)}$ and concentrated in vacuo. The residue was purified by silica chromatography (0-100% EtOAc in hexanes as the gradient eluent) to afford the title compound (assumed theoretical yield, 0.030 g, 0.069 mmol) in sufficient purity for step 2. MS (apci) m/z=433.2 (M+H).

Step 2: Preparation of 4-(6-((3S,4S)-3-amino-4-propoxypyrrolidin-l-yl)pyridin-3-yl)-6-ethoxypyrazolo[1,5-a]pyridine-3-carbonitrile To a solution of 4-(6-((3S,4S)-3-azido-4-propoxypyrrolidin-1-yl)pyridin-3-yl)-6-ethoxypyrazolo[1,5-a]pyridine-3-carbonitrile (0.022 g, 0.051 mmol) in EtOAc (5 mL) was added 10% palladium on carbon (0.012 g, 0.010 mmol). The reaction mixture was sparged with $H_2$ and stirred at rt for 24 h. The solids were removed by filtration, and the filtrate was concentrated in vacuo. The residue was purified by silica chromatography (0-40% [9:1 $MeOH/NH_4OH$] in EtOAc as the gradient eluent) to afford the title compound (0.0026 g, 0.0064 mmol, 13% yield over two steps). MS (apci) m/z=407.2 (M+H).

Example 352

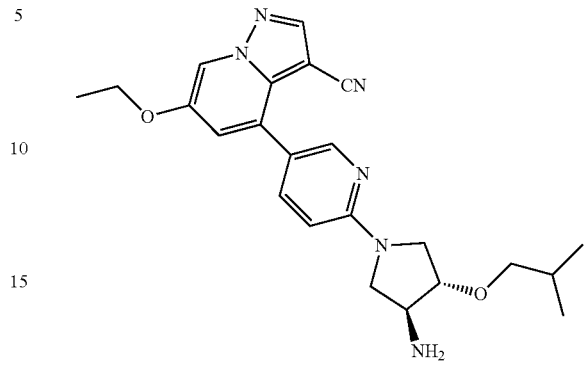

4-(6-((3S,4S)-3-amino-4-isobutoxypyrrolidin-1-yl)
pyridin-3-yl)-6-ethoxypyrazolo[1,5-a]pyridine-3-
carbonitrile

Step 1: Preparation of 4-(6-((3S,4S)-3-azido-4-isobutoxypyrrolidin-1-yl)pyridin-3-yl)-6-ethoxypyrazolo[1,5-a]pyridine-3-carbonitrile To a solution of 4-(6-((3S,4S)-3-azido-4-hydroxypyrrolidin-1-yl)pyridin-3-yl)-6-ethoxypyrazolo[1,5-a]pyridine-3-carbonitrile (Intermediate P58, 0.027 g, 0.069 mmol) in DMA (0.5 mL) was added potassium carbonate (0.029 g, 0.21 mmol) and 1-bromo-2-methylpropane (0.024 ml, 0.21 mmol). The reaction mixture was stirred at 85° C. for 120 h. It was quenched with saturated $NH_4Cl_{(aq)}$ and extracted into DCM. The combined organic extracts were dried over anhydrous $Na_2SO_{4(s)}$ and concentrated in vacuo. The residue was purified by silica chromatography (0-100% EtOAc in hexanes as the gradient eluent) to afford the title compound (assumed theoretical yield, 0.031 g, 0.069 mmol) in sufficient purity for step 2. MS (apci) m/z=447.1 (M+H).

Step 2: Preparation of 4-(6-((3S,4S)-3-amino-4-isobutoxypyrrolidin-1-yl)pyridin-3-yl)-6-ethoxypyrazolo[1,5-a]pyridine-3-carbonitrile To a solution of 4-(6-((3S,4S)-3-azido-4-isobutoxypyrrolidin-1-yl)pyridin-3-yl)-6-ethoxypyrazolo[1,5-a]pyridine-3-carbonitrile (0.015 g, 0.034 mmol) in EtOAc (5 mL) was added 10% palladium on carbon (0.012 g, 0.010 mmol). The reaction mixture was sparged with $H_2$ and stirred at rt for 24 h. The solids were removed by filtration, and the filtrate was concentrated in vacuo. The residue was purified by silica chromatography (0-40% [9:1 $MeOH/NH_4OH$] in EtOAc as the gradient eluent) to afford the title compound (0.0033 g, 0.0078 mmol, 23% yield over two steps). MS (apci) m/z=421.25 (M+H).

Example 353

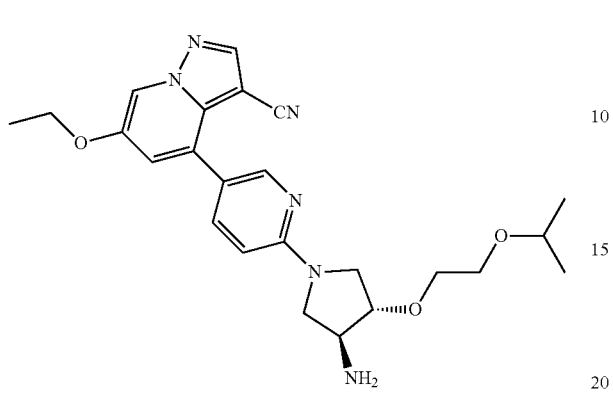

4-(6-((3S,4S)-3-amino-4-(2-isopropoxyethoxy)pyrrolidin-1-yl)pyridin-3-yl)-6-ethoxypyrazolo[1,5-a]pyridine-3-carbonitrile

Step 1: Preparation of 4-(6-((3S,4S)-3-azido-4-(2-isopropoxyethoxy)pyrrolidin-1-yl)pyridin-3-yl)-6-ethoxypyrazolo[1,5-a]pyridine-3-carbonitrile To a solution of 4-(6-((3S,4S)-3-azido-4-hydroxypyrrolidin-1-yl)pyridin-3-yl)-6-ethoxypyrazolo[1,5-a]pyridine-3-carbonitrile (Intermediate P58, 0.040 g, 0.10 mmol) in DMA (0.7 mL) was added cesium carbonate (0.17 g, 0.51 mmol) and 2-(2-bromoethoxy)propane (0.086 g, 0.51 mmol). The reaction mixture was stirred at 90° C. for 96 h. It was quenched with saturated $NH_4Cl_{(aq)}$ and extracted into DCM. The combined organic extracts were dried over anhydrous $Na_2SO_{4(s)}$ and concentrated in vacuo. The residue was purified by silica chromatography (0-100% EtOAc in hexanes as the gradient eluent) to afford the title compound (assumed theoretical yield, 0.048 g, 0.10 mmol) in sufficient purity for step 2.

Step 2: Preparation of 4-(6-((3S,4S)-3-amino-4-(2-isopropoxyethoxy)pyrrolidin-1-yl)pyridin-3-yl)-6-ethoxypyrazolo[1,5-a]pyridine-3-carbonitrile To a solution of 4-(6-((3S,4S)-3-azido-4-(2-isopropoxyethoxy)pyrrolidin-1-yl)pyridin-3-yl)-6-ethoxypyrazolo[1,5-a]pyridine-3-carbonitrile (0.048 g, 0.010 mmol) in EtOAc (2 mL) was added 10% palladium on carbon (0.010 g, 0.010 mmol). The reaction mixture was sparged with $H_2$ and stirred at rt for 24 h. The solids were removed by filtration, and the filtrate was concentrated in vacuo. The residue was purified by silica chromatography (0-40% [9:1 MeOH/NH$_4$OH] in EtOAc as the gradient eluent) to afford the title compound (8 mg, 0.017 mmol, 16% yield over two steps). MS (apci) m/z=452.3 (M+H).

Example 354

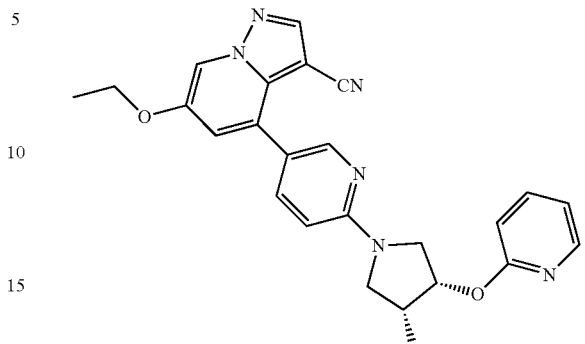

4-(6-((3R,4S)-3-amino-4-(pyridin-2-yloxy)pyrrolidin-1-yl)pyridin-3-yl)-6-ethoxypyrazolo[1,5-a]pyridine-3-carbonitrile

Step 1: Preparation of 4-(6-((3R,4S)-3-azido-4-(pyridin-2-yloxy)pyrrolidin-1-yl)pyridin-3-yl)-6-ethoxypyrazolo[1,5-a]pyridine-3-carbonitrile To a solution of 4-(6-((3R,4R)-3-azido-4-hydroxypyrrolidin-1-yl)pyridin-3-yl)-6-ethoxypyrazolo[1,5-a]pyridine-3-carbonitrile (Intermediate P59, 0.050 g, 0.128 mmol) in 1:1 DCM/THF (0.7 mL) was added pyridin-2-ol (0.0244 g, 0.256 mmol) and triphenylphosphane (0.0672 g, 0.256 mmol). The reaction mixture was sparged with argon, diisopropyl (E)-diazene-1,2-dicarboxylate (0.0350 mL, 0.256 mmol) was added. The reaction mixture was stirred at rt for 24 h. It was quenched with water and extracted into DCM. The combined organic extracts were dried over anhydrous $Na_2SO_{4(s)}$ and concentrated in vacuo. The residue was purified by silica chromatography (20-100% EtOAc in hexanes as the gradient eluent) to afford the title compound (0.025 g, 0.0535 mmol, 41.8% yield) in sufficient purity for step 2. MS (apci) m/z=468.1 (M+H).

Step 2: Preparation of 4-(6-((3R,4S)-3-amino-4-(pyridin-2-yloxy)pyrrolidin-1-yl)pyridin-3-yl)-6-ethoxypyrazolo[1,5-a]pyridine-3-carbonitrile To a solution of 4-(6-((3R,4S)-3-azido-4-(pyridin-2-yloxy)pyrrolidin-1-yl)pyridin-3-yl)-6-ethoxypyrazolo[1,5-a]pyridine-3-carbonitrile (0.022 g, 0.0471 mmol) in 1:1 MeOH/EtOAc (2 mL) was added 10% palladium on carbon (0.56 mg, 0.0047 mmol). The reaction mixture was sparged with $H_2$ and stirred at rt for 24 h. The solids were removed by vacuum filtration, and the filtrate was concentrated in vacuo. The residue was purified by silica chromatography (0-40% [9:1 MeOH/NH$_4$OH] in EtOAc as the gradient eluent) to afford the title compound (13 mg, 0.0297 mmol, 63.1% yield). MS (apci) m/z=442.2 (M+H).

Example 355

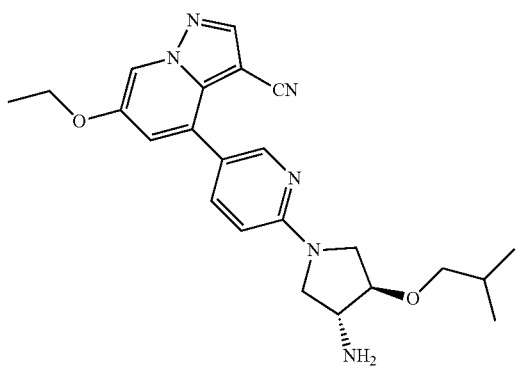 [SMILES: CCOc1cc(-c2ccc(N3C[C@@H](N)[C@H](OCC(C)C)C3)nc2)c2c(C#N)cnn2c1]

4-(6-((3R,4R)-3-amino-4-isobutoxypyrrolidin-1-yl)pyridin-3-yl)-6-ethoxypyrazolo[1,5-a]pyridine-3-carbonitrile

Step 1: Preparation of 4-(6-((3R,4R)-3-azido-4-isobutoxypyrrolidin-1-yl)pyridin-3-yl)-6-ethoxypyrazolo[1,5-a]pyridine-3-carbonitrile To a solution of 4-(6-((3R,4R)-3-azido-4-hydroxypyrrolidin-1-yl)pyridin-3-yl)-6-ethoxypyrazolo[1,5-a]pyridine-3-carbonitrile (Intermediate P59, 0.025 g, 0.064 mmol) in DMA (0.5 mL) was added potassium carbonate (0.027 g, 0.19 mmol) and 1-bromo-2-methylpropane (0.022 ml, 0.19 mmol). The reaction mixture was stirred at 85° C. for 120 h. It was quenched with saturated $NH_4Cl_{(aq)}$ and extracted into DCM. The combined organic extracts were dried over anhydrous $Na_2SO_{4(s)}$ and concentrated in vacuo. The residue was purified by silica chromatography (0-100% EtOAc in hexanes as the gradient eluent) to afford the title compound (assumed theoretical yield, 0.029 g, 0.064 mmol) in sufficient purity for step 2. MS (apci) m/z=447.2 (M+H).

Step 2: Preparation of 4-(6-((3R,4R)-3-amino-4-isobutoxypyrrolidin-1-yl)pyridin-3-yl)-6-ethoxypyrazolo[1,5-a]pyridine-3-carbonitrile To a solution of 4-(6-((3R,4R)-3-azido-4-isobutoxypyrrolidin-1-yl)pyridin-3-yl)-6-ethoxypyrazolo[1,5-a]pyridine-3-carbonitrile (0.014 g, 0.032 mmol) in EtOAc (5 mL) was added 10% palladium on carbon (0.012 g, 0.010 mmol). The reaction mixture was sparged with $H_2$ and stirred at rt for 24 h. The solids were removed by filtration, and the filtrate was concentrated in vacuo. The residue was purified by silica chromatography (0-40% [9:1 MeOH/$NH_4OH$] in EtOAc as the gradient eluent) to afford the title compound (1 mg, 0.0024 mmol, 7.3% yield over two steps). MS (apci) m/z=421.3 (M+H).

Example 356

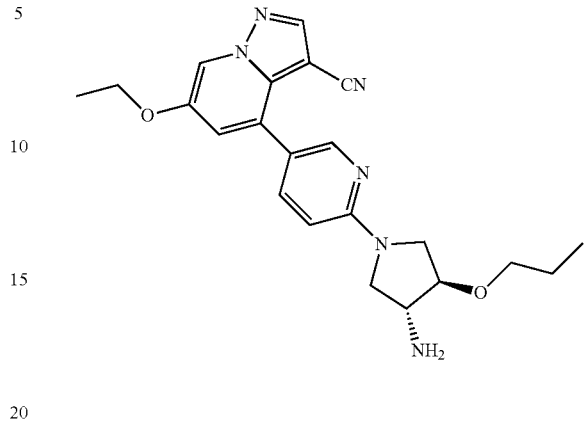

4-(6-((3R,4R)-3-amino-4-propoxypyrrolidin-1-yl)pyridin-3-yl)-6-ethoxypyrazolo[1,5-a]pyridine-3-carbonitrile

Step 1: Preparation of 4-(6-((3R,4R)-3-azido-4-propoxypyrrolidin-1-yl)pyridin-3-yl)-6-ethoxypyrazolo[1,5-a]pyridine-3-carbonitrile To a solution of 4-(6-((3R,4R)-3-azido-4-hydroxypyrrolidin-1-yl)pyridin-3-yl)-6-ethoxypyrazolo[1,5-a]pyridine-3-carbonitrile (Intermediate P59, 0.025 g, 0.064 mmol) in DMA (0.5 mL) was added potassium carbonate (0.027 g, 0.19 mmol) and 1-iodopropane (0.019 mL, 0.19 mmol). The reaction mixture was stirred at 85° C. for 48 h. After cooling to ambient temperature, the reaction was quenched with water and extracted into DCM. The combined organic extracts were dried over anhydrous $Na_2SO_{4(s)}$ and concentrated in vacuo. The residue was purified by silica chromatography (0-100% EtOAc in hexanes as the gradient eluent) to afford the title compound (assumed theoretical yield, 0.028 g, 0.064 mmol) in sufficient purity for step 2. MS (apci) m/z=433.2 (M+H).

Step 2: Preparation of 4-(6-((3R,4R)-3-amino-4-propoxypyrrolidin-1-yl)pyridin-3-yl)-6-ethoxypyrazolo[1,5-a]pyridine-3-carbonitrile To a solution of 4-(6-((3R,4R)-3-azido-4-propoxypyrrolidin-1-yl)pyridin-3-yl)-6-ethoxypyrazolo[1,5-a]pyridine-3-carbonitrile (0.017 g, 0.039 mmol) in EtOAc (5 mL) was added 10% palladium on carbon (0.0093 g, 0.0079 mmol). The reaction mixture was sparged with $H_2$ and stirred at rt for 24 h. The solids were removed by vacuum filtration, and the filtrate was concentrated in vacuo. The residue was purified by silica chromatography (0-40% [9:1 MeOH/$NH_4OH$] in EtOAc as the gradient eluent) to afford the title compound (0.0026 g, 0.0064 mmol, 16% yield over two steps). MS (apci) m/z=407.2 (M+H).

Example 357

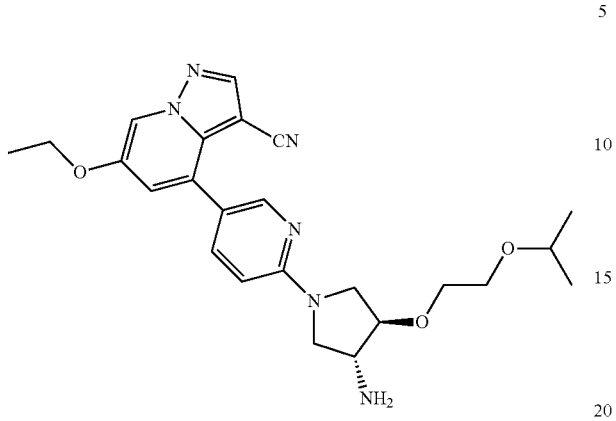

4-(6-((3R,4R)-3-amino-4-(2-isopropoxyethoxy)pyrrolidin-1-yl)pyridin-3-yl)-6-ethoxypyrazolo[1,5-a]pyridine-3-carbonitrile

Step 1: Preparation of 4-(6-((3R,4R)-3-azido-4-(2-isopropoxyethoxy)pyrrolidin-1-yl)pyridin-3-yl)-6-ethoxypyrazolo[1,5-a]pyridine-3-carbonitrile To a solution of 4-(6-((3R,4R)-3-azido-4-hydroxypyrrolidin-1-yl)pyridin-3-yl)-6-ethoxypyrazolo[1,5-a]pyridine-3-carbonitrile (Intermediate P59, 0.025 g, 0.064 mmol) in DMA (0.5 mL) was added cesium carbonate (0.10 g, 0.32 mmol) and 2-(2-bromoethoxy)propane (0.053 g, 0.32 mmol). The reaction mixture was stirred at 90° C. for 96 h. It was quenched with saturated $NH_4Cl_{(aq)}$ and extracted into DCM. The combined organic extracts were dried over anhydrous $Na_2SO_{4(s)}$ and concentrated in vacuo. The residue was purified by silica chromatography (0-100% EtOAc in hexanes as the gradient eluent) to afford the title compound (assumed theoretical yield, 0.031 g, 0.064 mmol) in sufficient purity for step 2.

Step 2: Preparation of 4-(6-((3R,4R)-3-amino-4-(2-isopropoxyethoxy)pyrrolidin-1-yl)pyridin-3-yl)-6-ethoxypyrazolo[1,5-a]pyridine-3-carbonitrile To a solution of 4-(6-((3R,4R)-3-azido-4-(2-isopropoxyethoxy)pyrrolidin-1-yl)pyridin-3-yl)-6-ethoxypyrazolo[1,5-a]pyridine-3-carbonitrile (0.031 g, 0.064 mmol) in EtOAc (2 mL) was added 10% palladium on carbon (0.010 g, 0.010 mmol). The reaction mixture was sparged with $H_2$ and stirred at rt for 24 h. The solids were removed by filtration, and the filtrate was concentrated in vacuo. The residue was purified by silica chromatography (0-40% [9:1 MeOH/$NH_4OH$] in EtOAc as the gradient eluent) to afford the title compound (0.0043 g, 0.0095 mmol, 15% yield over two steps). MS (apci) m/z=452.3 (M+H).

Example 358

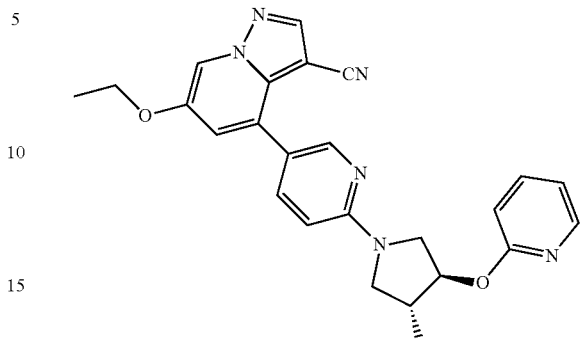

4-(6-((3R,4R)-3-amino-4-(pyridin-2-yloxy)pyrrolidin-1-yl)pyridin-3-yl)-6-ethoxypyrazolo[1,5-a]pyridine-3-carbonitrile

Step 1: Preparation of tert-butyl ((3R,4R)-1-(5-(3-cyano-6-ethoxypyrazolo[1,5-a]pyridin-4-yl)pyridin-2-yl)-4-(pyridin-2-yloxy)pyrrolidin-3-yl)carbamate To a solution of tert-butyl ((3R,4S)-1-(5-(3-cyano-6-ethoxypyrazolo[1,5-a]pyridin-4-yl)pyridin-2-yl)-4-hydroxypyrrolidin-3-yl)carbamate (Intermediate P60, 0.030 g, 0.0646 mmol) in 1:1 DCM/THF (0.75 mL) was added pyridin-2-ol (0.0123 g, 0.129 mmol) and triphenylphosphane (0.0339 g, 0.129 mmol). The reaction mixture was sparged with argon, and diisopropyl (E)-diazene-1,2-dicarboxylate (0.0176 mL, 0.129 mmol) was added. The reaction mixture was stirred at rt for 24 h. It was quenched with water and extracted into DCM. The combined organic extracts were dried over anhydrous $Na_2SO_{4(s)}$ and concentrated in vacuo. The residue was purified by silica chromatography (20-100% EtOAc in hexanes as the gradient eluent) to afford the title compound (assumed theoretical yield, 0.035 g, 0.0646 mmol) in sufficient purity for step 2.

Step 2: Preparation of 4-(6-((3R,4R)-3-amino-4-(pyridin-2-yloxy)pyrrolidin-1-yl)pyridin-3-yl)-6-ethoxypyrazolo[1,5-a]pyridine-3-carbonitrile A solution of tert-butyl ((3R,4R)-1-(5-(3-cyano-6-ethoxypyrazolo[1,5-a]pyridin-4-yl)pyridin-2-yl)-4-(pyridin-2-yloxy)pyrrolidin-3-yl)carbamate (0.035 g, 0.0646 mmol) in DCM (2 mL) was treated with 6M HCl in IPA (2 mL) and stirred at rt for 24 h. The reaction mixture was concentrated in vacuo, and the residue was taken up in water. 2M NaOH was added and extracted with DCM. The combined organic extracts were passed through a phase separator frit then purified by silica chromatography (0-40% [9:1 MeOH/$NH_4OH$] in EtOAc as the gradient eluent) to afford the title compound (0.0073 g, 0.0165 mmol, 25.6% yield over two steps). MS (apci) m/z=442.2 (M+H).

Example 359

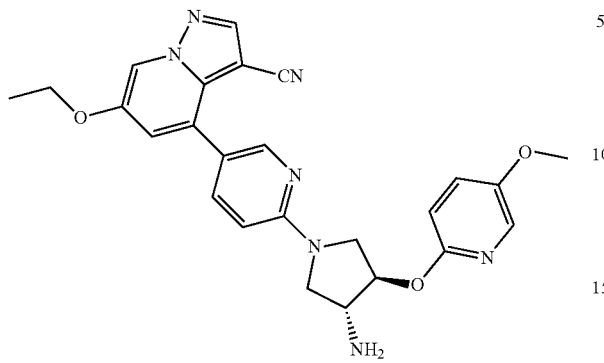

4-(6-((3R,4R)-3-amino-4-((6-methoxypyridin-3-yl)oxy)pyrrolidin-1-yl)pyridin-3-yl)-6-ethoxypyrazolo[1,5-a]pyridine-3-carbonitrile

Step 1: Preparation of tert-butyl ((3R,4R)-1-(5-(3-cyano-6-ethoxypyrazolo[1,5-a]pyridin-4-yl)pyridin-2-yl)-4-(pyridin-2-yloxy)pyrrolidin-3-yl)carbamate To a solution of tert-butyl ((3R,4S)-1-(5-(3-cyano-6-ethoxypyrazolo[1,5-a]pyridin-4-yl)pyridin-2-yl)-4-hydroxypyrrolidin-3-yl)carbamate (Intermediate P60, 0.030 g, 0.0646 mmol) in 1:1 DCM/THF (0.75 mL) was added 5-methoxypyridin-2-ol (0.0162 g, 0.129 mmol) and triphenylphosphane (0.0339 g, 0.129 mmol). The reaction mixture was sparged with argon, and diisopropyl (E)-diazene-1,2-dicarboxylate (0.0176 mL, 0.129 mmol) was added. The reaction mixture was stirred at rt for 24 h. It was quenched with water and extracted into DCM. The combined organic extracts were dried over anhydrous $Na_2SO_{4(s)}$ and concentrated in vacuo. The residue was purified by silica chromatography (20-100% EtOAc in hexanes as the gradient eluent) to afford the title compound (assumed theoretical yield, 0.037 g, 0.0646 mmol) in sufficient purity for step 2.

Step 2: Preparation of 4-(6-((3R,4R)-3-amino-4-((6-methoxypyridin-3-yl)oxy)pyrrolidin-1-yl)pyridin-3-yl)-6-ethoxypyrazolo[1,5-a]pyridine-3-carbonitrile A solution of tert-butyl ((3R,4R)-1-(5-(3-cyano-6-ethoxypyrazolo[1,5-a]pyridin-4-yl)pyridin-2-yl)-4-(pyridin-2-yloxy)pyrrolidin-3-yl)carbamate (0.037 g, 0.0646) in DCM (2 mL) was treated with 6M HCl in IPA (2 mL) and stirred at rt for 24 h. The reaction mixture was concentrated in vacuo, and the residue was taken up in water. 2M NaOH was added and extracted with DCM. The combined organic extracts were passed through a phase separator frit then purified by silica chromatography (0-40% [9:1 MeOH/$NH_4OH$] in EtOAc as the gradient eluent) to afford the title compound (0.0065 g, 0.0138 mmol, 21.3% yield over two steps). MS (apci) m/z=472.2 (M+H).

Example 360

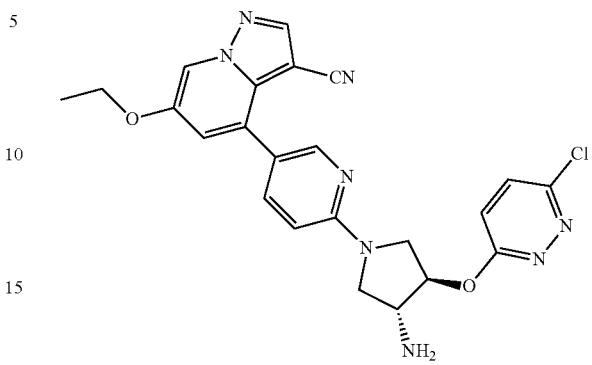

4-(6-((3R,4R)-3-amino-4-((6-chloropyridazin-3-yl)oxy)pyrrolidin-1-yl)pyridin-3-yl)-6-ethoxypyrazolo[1,5-a]pyridine-3-carbonitrile

Step 1: Preparation of tert-butyl ((3R,4R)-4-((6-chloropyridazin-3-yl)oxy)-1-(5-(3-cyano-6-ethoxypyrazolo[1,5-a]pyridin-4-yl)pyridin-2-yl)pyrrolidin-3-yl)carbamate To a solution of tert-butyl ((3R,4S)-1-(5-(3-cyano-6-ethoxypyrazolo[1,5-a]pyridin-4-yl)pyridin-2-yl)-4-hydroxypyrrolidin-3-yl)carbamate (Intermediate P60, 0.030 g, 0.0646 mmol) in 1:1 DCM/THF (0.7 mL) was added 6-chloropyridazin-3-ol (0.0169 g, 0.129 mmol) and triphenylphosphane (0.0339 g, 0.129 mmol). The reaction mixture was sparged with argon, and diisopropyl (E)-diazene-1,2-dicarboxylate (0.0176 mL, 0.129 mmol) was added. The reaction mixture was stirred at rt for 24 h. It was quenched with water and extracted into DCM. The combined organic extracts were dried over anhydrous $Na_2SO_{4(s)}$ and concentrated in vacuo. The residue was purified by silica chromatography (20-100% EtOAc in hexanes as the gradient eluent) to afford the title compound (assumed theoretical yield, 0.031 g, 0.0646 mmol) in sufficient purity for step 2.

Step 2: Preparation of 4-(6-((3R,4R)-3-amino-4-((6-chloropyridazin-3-yl)oxy)pyrrolidin-1-yl)pyridin-3-yl)-6-ethoxypyrazolo[1,5-a]pyridine-3-carbonitrile A solution of tert-butyl ((3R,4R)-4-((6-chloropyridazin-3-yl)oxy)-1-(5-(3-cyano-6-ethoxypyrazolo[1,5-a]pyridin-4-yl)pyridin-2-yl)pyrrolidin-3-yl)carbamate (0.031 g, 0.0646) in DCM (2 mL) was treated with 6M HCl in IPA (2 mL) and stirred at rt for 24 h. The reaction mixture was concentrated in vacuo, and the residue was taken up in water. 2M NaOH was added and extracted with DCM. The combined organic extracts were passed through a phase separator frit then purified by silica chromatography (0-40% [9:1 MeOH/$NH_4OH$] in EtOAc as the gradient eluent) to afford the title compound (0.013 g, 0.0273 mmol, 42.2% yield over two steps). MS (apci) m/z=477.1 (M+H).

Example 361

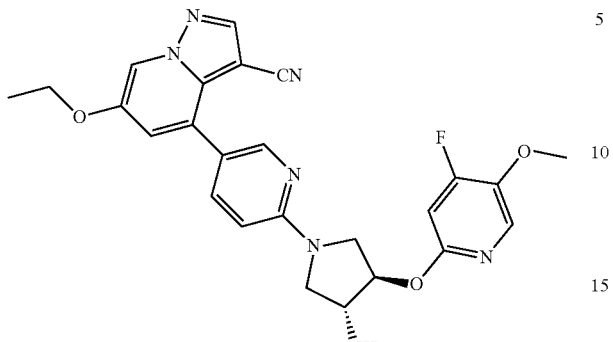

4-(6-((3R,4R)-3-amino-4-((5-fluoro-6-methoxypyridin-3-yl)oxy)pyrrolidin-1-yl)pyridin-3-yl)-6-ethoxypyrazolo[1,5-a]pyridine-3-carbonitrile

Step 1: Preparation of tert-butyl ((3R,4R)-1-(5-(3-cyano-6-ethoxypyrazolo[1,5-a]pyridin-4-yl)pyridin-2-yl)-4-((5-fluoro-6-methoxypyridin-3-yl)oxy)pyrrolidin-3-yl)carbamate To a solution of tert-butyl ((3R,4S)-1-(5-(3-cyano-6-ethoxypyrazolo[1,5-a]pyridin-4-yl)pyridin-2-yl)-4-hydroxypyrrolidin-3-yl)carbamate (Intermediate P60, 0.030 g, 0.0646 mmol) in 1:1 DCM/THF (0.7 mL) was added 5-fluoro-6-methoxypyridin-3-ol (0.0185 g, 0.129 mmol) and triphenylphosphane (0.0339 g, 0.129 mmol). The reaction mixture was sparged with argon, and diisopropyl (E)-diazene-1,2-dicarboxylate (0.0176 mL, 0.129 mmol) was added. The reaction mixture was stirred at rt for 24 h. It was quenched with water and extracted into DCM. The combined organic extracts were dried over anhydrous $Na_2SO_{4(s)}$ and concentrated in vacuo. The residue was purified by silica chromatography (20-100% EtOAc in hexanes as the gradient eluent) to afford the title compound (assumed theoretical yield, 0.038 g, 0.0646 mmol) in sufficient purity for step 2.

Step 2: Preparation of 4-(6-((3R,4R)-3-amino-4-((5-fluoro-6-methoxypyridin-3-yl)oxy)pyrrolidin-1-yl)pyridin-3-yl)-6-ethoxypyrazolo[1,5-a]pyridine-3-carbonitrile A solution of tert-butyl ((3R,4R)-1-(5-(3-cyano-6-ethoxypyrazolo[1,5-a]pyridin-4-yl)pyridin-2-yl)-4-((5-fluoro-6-methoxypyridin-3-yl)oxy)pyrrolidin-3-yl)carbamate (0.038 g, 0.0646) in DCM (2 mL) was treated with 6M HCl in IPA (2 mL) and stirred at rt for 24 h. The reaction mixture was concentrated in vacuo, and the residue was taken up in water. 2M NaOH was added and extracted with DCM. The combined organic extracts were passed through a phase separator frit then purified by silica chromatography (0-40% [9:1 MeOH/NH$_4$OH] in EtOAc as the gradient eluent) to afford the title compound (0.0014 g, 0.00286 mmol, 4.43% yield over two steps). MS (apci) m/z=490.2 (M+H).

Example 362

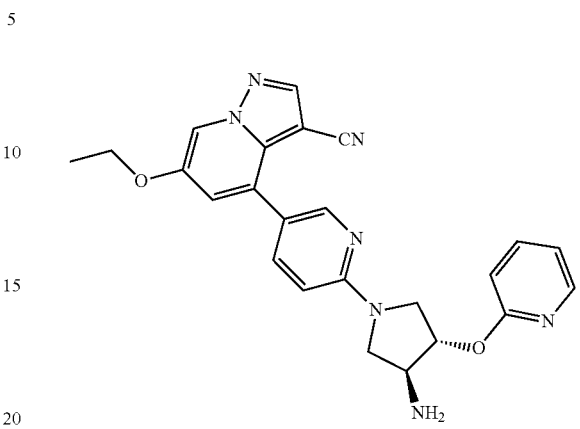

4-(6-((3S,4S)-3-amino-4-(pyridin-2-yloxy)pyrrolidin-1-yl)pyridin-3-yl)-6-ethoxypyrazolo[1,5-a]pyridine-3-carbonitrile

Step 1: Preparation of tert-butyl ((3S,4S)-1-(5-(3-cyano-6-ethoxypyrazolo[1,5-a]pyridin-4-yl)pyridin-2-yl)-4-(pyridin-2-yloxy)pyrrolidin-3-yl)carbamate To a solution of tert-butyl ((3S,4R)-1-(5-(3-cyano-6-ethoxypyrazolo[1,5-a]pyridin-4-yl)pyridin-2-yl)-4-hydroxypyrrolidin-3-yl)carbamate (Intermediate P61, 0.030 g, 0.0646 mmol) in 1:1 DCM/THF (0.75 mL) was added pyridin-2-ol (0.0123 g, 0.129 mmol) and triphenylphosphane (0.0339 g, 0.129 mmol). The reaction mixture was sparged with argon, and diisopropyl (E)-diazene-1,2-dicarboxylate (0.0176 mL, 0.129 mmol) was added. The reaction mixture was stirred at rt for 24 h. It was quenched with water and extracted into DCM. The combined organic extracts were dried over anhydrous $Na_2SO_{4(s)}$ and concentrated in vacuo. The residue was purified by silica chromatography (20-100% EtOAc in hexanes as the gradient eluent) to afford the title compound (assumed theoretical yield, 0.035 g, 0.0646 mmol) in sufficient purity for step 2. MS (apci) m/z=542.3 (M+H).

Step 2: Preparation of 4-(6-((3S,4S)-3-amino-4-(pyridin-2-yloxy)pyrrolidin-1-yl)pyridin-3-yl)-6-ethoxypyrazolo[1,5-a]pyridine-3-carbonitrile A solution of tert-butyl ((3S,4 S)-1-(5-(3-cyano-6-ethoxypyrazolo[1,5-a]pyridin-4-yl)pyridin-2-yl)-4-(pyridin-2-yloxy)pyrrolidin-3-yl)carbamate (0.035 g, 0.0646 mmol) in DCM (2 mL) was treated with 6M HCl in IPA (2 mL) and stirred at rt for 24 h. The reaction mixture was concentrated in vacuo, and the residue was taken up in water. 2M NaOH was added and extracted with DCM. The combined organic extracts were passed through a phase separator frit then purified by silica chromatography (0-40% [9:1 MeOH/NH$_4$OH] in EtOAc as the gradient eluent) to afford the title compound (0.0101 g, 0.0229 mmol, 35.4% yield over two steps). MS (apci) m/z=442.2 (M+H).

Example 363

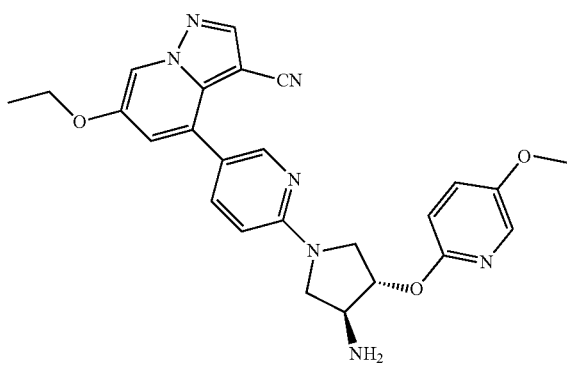 [SMILES: CCOc1cc(-c2ccc(N3C[C@H](Oc4ccc(OC)cn4)[C@@H](N)C3)nc2)c2c(C#N)cnn2c1]

4-(6-((3S,4S)-3-amino-4-((6-methoxypyridin-3-yl)oxy)pyrrolidin-1-yl)pyridin-3-yl)-6-ethoxypyrazolo[1,5-a]pyridine-3-carbonitrile Step 1: Preparation of tert-butyl ((3S,4S)-1-(5-(3-cyano-6-ethoxypyrazolo[1,5-a]pyridin-4-yl)pyridin-2-yl)-4-(pyridin-2-yloxy)pyrrolidin-3-yl)carbamate To a solution of tert-butyl ((3S,4R)-1-(5-(3-cyano-6-ethoxypyrazolo[1,5-a]pyridin-4-yl)pyridin-2-yl)-4-hydroxypyrrolidin-3-yl)carbamate (Intermediate P61, 0.030 g, 0.0646 mmol) in 1:1 DCM/THF (0.75 mL) was added 5-methoxypyridin-2-ol (0.0162 g, 0.129 mmol) and triphenylphosphane (0.0339 g, 0.129 mmol). The reaction mixture was sparged with argon, and diisopropyl (E)-diazene-1,2-dicarboxylate (0.0176 mL, 0.129 mmol) was added. The reaction mixture was stirred at rt for 48 h. It was quenched with water and extracted into DCM. The combined organic extracts were dried over anhydrous $Na_2SO_{4(s)}$ and concentrated in vacuo. The residue was purified by silica chromatography (20-100% EtOAc in hexanes as the gradient eluent) to afford the title compound (assumed theoretical yield, 0.037 g, 0.0646 mmol) in sufficient purity for step 2. MS (apci) m/z=572.3 (M+H).

Step 2: Preparation of 4-(6-((3S,4S)-3-amino-4-((6-methoxypyridin-3-yl)oxy)pyrrolidin-1-yl)pyridin-3-yl)-6-ethoxypyrazolo[1,5-a]pyridine-3-carbonitrile A solution of tert-butyl ((3S,4S)-1-(5-(3-cyano-6-ethoxypyrazolo[1,5-a]pyridin-4-yl)pyridin-2-yl)-4-(pyridin-2-yloxy)pyrrolidin-3-yl)carbamate (0.037 g, 0.0646) in DCM (2 mL) was treated with 6M HCl in IPA (2 mL) and stirred at rt for 24 h. The reaction mixture was concentrated in vacuo, and the residue was taken up in water. 2M NaOH was added and extracted with DCM. The combined organic extracts were passed through a phase separator frit then purified by silica chromatography (0-40% [9:1 MeOH/$NH_4OH$] in EtOAc as the gradient eluent) to afford the title compound (0.0112 g, 0.0238 mmol, 36.8% yield over two steps). MS (apci) m/z=472.2 (M+H).

Example 364

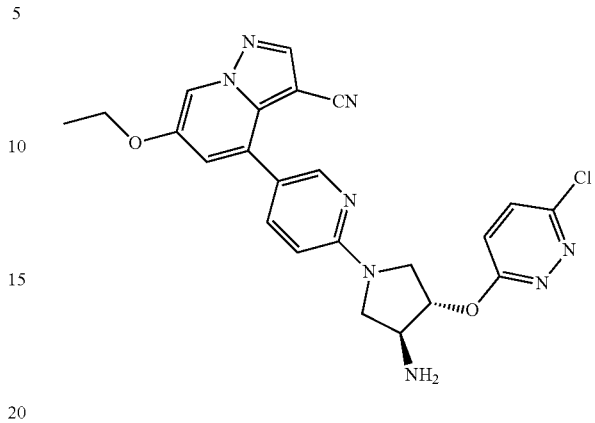

4-(6-((3S,4 S)-3-amino-4-((6-chloropyridazin-3-yl)oxy)pyrrolidin-1-yl)pyridin-3-yl)-6-ethoxypyrazolo[1,5-a]pyridine-3-carbonitrile Step 1: Preparation of tert-butyl ((3S,4S)-4-((6-chloropyridazin-3-yl)oxy)-1-(5-(3-cyano-6-ethoxypyrazolo[1,5-a]pyridin-4-yl)pyridin-2-yl)pyrrolidin-3-yl)carbamate To a solution of tert-butyl ((3S,4R)-1-(5-(3-cyano-6-ethoxypyrazolo[1,5-a]pyridin-4-yl)pyridin-2-yl)-4-hydroxypyrrolidin-3-yl)carbamate (Intermediate P61, 0.030 g, 0.0646 mmol) in 1:1 DCM/THF (0.7 mL) was added 6-chloropyridazin-3-ol (0.0169 g, 0.129 mmol) and triphenylphosphine (0.0339 g, 0.129 mmol). The reaction mixture was sparged with argon, and diisopropyl (E)-diazene-1,2-dicarboxylate (0.0176 mL, 0.129 mmol) was added. The reaction mixture was stirred at rt for 24 h. It was quenched with water and extracted into DCM. The combined organic extracts were dried over anhydrous $Na_2SO_{4(s)}$ and concentrated in vacuo. The residue was purified by silica chromatography (20-100% EtOAc in hexanes as the gradient eluent) to afford the title compound (assumed theoretical yield, 0.031 g, 0.0646 mmol) in sufficient purity for step 2. MS (apci) m/z=577.2 (M+H).

Step 2: Preparation of 4-(6-((3S,4S)-3-amino-4-((6-chloropyridazin-3-yl)oxy)pyrrolidin-1-yl)pyridin-3-yl)-6-ethoxypyrazolo[1,5-a]pyridine-3-carbonitrile A solution of tert-butyl ((3S,4S)-4-((6-chloropyridazin-3-yl)oxy)-1-(5-(3-cyano-6-ethoxypyrazolo[1,5-a]pyridin-4-yl)pyridin-2-yl)pyrrolidin-3-yl)carbamate (0.031 g, 0.0646) in DCM (2 mL) was treated with 6M HCl in IPA (2 mL) and stirred at rt for 24 h. The reaction mixture was concentrated in vacuo, and the residue was taken up in water. 2M NaOH was added and extracted with DCM. The combined organic extracts were passed through a phase separator frit then purified by silica chromatography (0-40% [9:1 MeOH/$NH_4OH$] in EtOAc as the gradient eluent) to afford the title compound (0.0096 g, 0.0201 mmol, 31.2% yield over two steps). MS (apci) m/z=477.2 (M+H).

Example 365

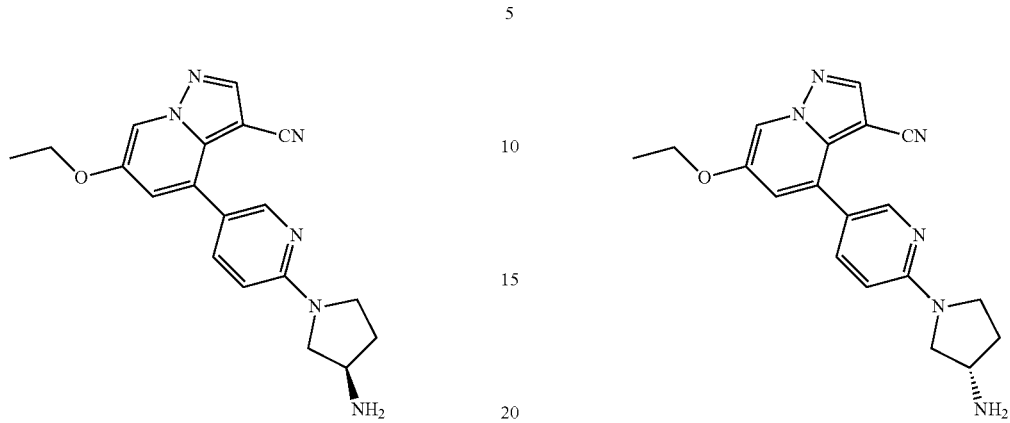

(R)-4-(6-(3-aminopyrrolidin-1-yl)pyridin-3-yl)-6-ethoxypyrazolo[1,5-a]pyridine-3-carbonitrile

Step 1: Preparation of tert-butyl (R)-(1-(5-(3-cyano-6-ethoxypyrazolo[1,5-a]pyridin-4-yl)pyridin-2-yl)pyrrolidin-3-yl)carbamate To a solution of 6-ethoxy-4-(6-fluoropyridin-3-yl)pyrazolo[1,5-a]pyridine-3-carbonitrile (Intermediate P6, 0.025 g, 0.0886 mmol) in DMSO (0.5 mL) was added N-ethyl-N-isopropylpropan-2-amine (0.0771 ml, 0.443 mmol) and tert-butyl (R)-pyrrolidin-3-ylcarbamate (0.0330 g, 0.177 mmol). The reaction mixture was stirred 100° C. for 24 h. After cooling to ambient temperature, the reaction mixture was quenched with saturated $NH_4Cl_{(aq)}$ and extracted into DCM. The combined organic extracts were dried over anhydrous $Na_2SO_{4(s)}$ and concentrated in vacuo. The residue was purified by silica chromatography (40-100% EtOAc in hexanes as the gradient eluent) to afford the title compound (assumed theoretical yield, 0.040 g, 0.0886 mmol) in sufficient purity for step 2. MS (apci) m/z=449.2 (M+H).

Step 2: Preparation of (R)-4-(6-(3-aminopyrrolidin-1-yl)pyridin-3-yl)-6-ethoxypyrazolo[1,5-a]pyridine-3-carbonitrile A solution of tert-butyl (R)-(1-(5-(3-cyano-6-ethoxypyrazolo[1,5-a]pyridin-4-yl)pyridin-2-yl)pyrrolidin-3-yl)carbamate (0.040 g, 0.0886 mmol) in DCM (1.5 mL) was treated with 5M HCl in IPA (1.5 mL) and stirred at rt for 2 h. The reaction mixture was concentrated in vacuo, and the residue was taken up in DCM. 2M NaOH was added and extracted with DCM. The combined organic extracts were passed through a phase separator frit then concentrated in vacuo to afford the title compound (0.0227 g, 0.0652 mmol, 73.6% yield over two steps). MS (apci) m/z=349.2 (M+H).

Example 366

(S)-4-(6-(3-aminopyrrolidin-1-yl)pyridin-3-yl)-6-ethoxypyrazolo[1,5-a]pyridine-3-carbonitrile

Step 1: Preparation of tert-butyl (S)-(1-(5-(3-cyano-6-ethoxypyrazolo[1,5-a]pyridin-4-yl)pyridin-2-yl)pyrrolidin-3-yl)carbamate To a solution of 6-ethoxy-4-(6-fluoropyridin-3-yl)pyrazolo[1,5-a]pyridine-3-carbonitrile (Intermediate P6, 0.025 g, 0.0886 mmol) in DMSO (0.5 mL) was added N-ethyl-N-isopropylpropan-2-amine (0.0771 ml, 0.443 mmol) and tert-butyl (S)-pyrrolidin-3-ylcarbamate (0.0396 g, 0.213 mmol). The reaction mixture was stirred 100° C. for 24 h. After cooling to ambient temperature, the reaction mixture was quenched with saturated $NH_4Cl_{(aq)}$ and extracted into DCM. The combined organic extracts were dried over anhydrous $Na_2SO_{4(s)}$ and concentrated in vacuo. The residue was purified by silica chromatography (40-100% EtOAc in hexanes as the gradient eluent) to afford the title compound (assumed theoretical yield, 0.040 g, 0.0886 mmol) in sufficient purity for step 2. MS (apci) m/z=449.2 (M+H).

Step 2: Preparation of (S)-4-(6-(3-aminopyrrolidin-1-yl)pyridin-3-yl)-6-ethoxypyrazolo[1,5-a]pyridine-3-carbonitrile A solution of tert-butyl (S)-(1-(5-(3-cyano-6-ethoxypyrazolo[1,5-a]pyridin-4-yl)pyridin-2-yl)pyrrolidin-3-yl)carbamate (0.040 g, 0.0886 mmol) in DCM (1.5 mL) was treated with 5M HCl in IPA (1.5 mL) and stirred at rt for 2 h. The reaction mixture was concentrated in vacuo, and the residue was taken up in DCM. 2M NaOH was added and extracted with DCM. The combined organic extracts were passed through a phase separator frit then concentrated in vacuo to afford the title compound (0.0236 g, 0.0677 mmol, 63.7% yield over two steps). MS (apci) m/z=349.1 (M+H).

Example 367

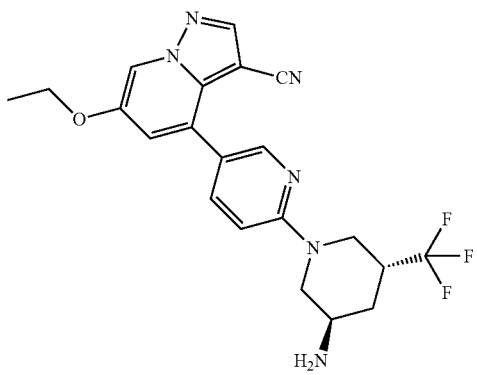 [SMILES: CCOc1cc(-c2ccc(N3C[C@H](N)C[C@@H](C(F)(F)F)C3)nc2)c2c(C#N)cnn2c1]

4-(6-((3R,5R)-3-amino-5-(trifluoromethyl)piperidin-1-yl)pyridin-3-yl)-6-ethoxypyrazolo[1,5-a]pyridine-3-carbonitrile To a solution of 6-ethoxy-4-(6-fluoropyridin-3-yl)pyrazolo[1,5-a]pyridine-3-carbonitrile (Intermediate P6, 0.050 g, 0.18 mmol) in DMSO (0.35 mL) was added cesium carbonate (0.23 g, 0.71 mmol) and tert-butyl ((3R,5R)-5-(trifluoromethyl)piperidin-3-yl)carbamate (0.052 g, 0.19 mmol). The reaction mixture was stirred 105° C. for 24 h. After cooling to ambient temperature, the reaction mixture was quenched with saturated $NH_4Cl_{(aq)}$ and extracted into DCM. The combined organic extracts were dried over anhydrous $Na_2SO_{4(s)}$ and concentrated in vacuo. The residue was purified by silica chromatography (0-40% [9:1 MeOH/$NH_4OH$] in EtOAc as the gradient eluent) followed by purification by preparative HPLC (5-95% ACN in water [+0.1% TFA] as the gradient eluent). The final product fractions were washed with 2M NaOH and extracted with DCM. The combined organic extracts were passed through a phase separator frit and concentrated in vacuo to afford the title compound (0.0085 g, 0.020 mmol, 11% yield). MS (apci) m/z=431.2 (M+H).

Example 368

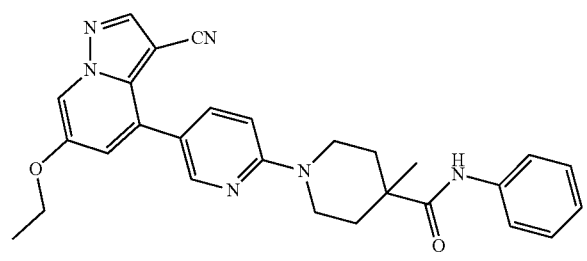 [SMILES: CCOc1cc(-c2ccc(N3CCC(C)(C(=O)Nc4ccccc4)CC3)nc2)c2c(C#N)cnn2c1]

1-(5-(3-cyano-6-ethoxypyrazolo[1,5-a]pyridin-4-yl)pyridin-2-yl)-4-methyl-N-phenylpiperidine-4-carboxamide Step 1: Preparation of tert-butyl 4-methyl-4-(phenylcarbamoyl)piperidine-1-carboxylate A solution of 1-Boc-4-methyl-piperidine-4-carboxylic acid (717.3 mg, 2.948 mmol) and HATU (1345 mg, 3.538 mmol) in DCM (30 mL) was treated with DIEA (1.027 mL, 5.896 mmol) and aniline (0.2958 mL, 3.243 mmol). The reaction mixture was stirred at rt for 60 h, then concentrated in vacuo. The residue was purified by silica chromatography (5-70% EtOAc in hexanes as the gradient eluent) to afford the title compound (assumed theoretical yield, 938.6 mg, 2.948 mmol) in sufficient purity for step 2. MS (apci) m/z=219.2 (M+H-Boc).

Step 2: Preparation of 4-methyl-N-phenylpiperidine-4-carboxamide

A solution of tert-butyl 4-methyl-4-(phenylcarbamoyl)piperidine-1-carboxylate (938.6 mg, 2.948 mmol) in DCM (2 mL) was treated with TFA (2 mL, 26 mmol) and stirred at rt for 16 h. The reaction mixture was concentrated in vacuo. The residue was diluted with saturated $NaHCO_{3(aq)}$ and extracted with 4:1 DCM/IPA. The combined organic extracts were dried over anhydrous $Na_2SO_{4(s)}$ and concentrated in vacuo to afford the title compound (240.9 mg, 1.104 mmol, 37% yield over two steps) in sufficient purity for step 3. MS (apci) m/z=219.2 (M+H).

Step 3: Preparation of 1-(5-(3-cyano-6-ethoxypyrazolo[1,5-a]pyridin-4-yl)pyridin-2-yl)-4-methyl-N-phenylpiperidine-4-carboxamide To a solution of 6-ethoxy-4-(6-fluoropyridin-3-yl)pyrazolo[1,5-a]pyridine-3-carbonitrile (Intermediate P6, 0.030 g, 0.108 mmol) in DMA (0.5 mL) was added TEA (0.073 mL, 0.538 mmol) and 4-methyl-N-phenylpiperidine-4-carboxamide (0.0705 g, 0.323 mmol). The reaction mixture was stirred 80° C. for 20 h. After cooling to ambient temperature, the reaction mixture was quenched with water and extracted into EtOAc. The combined organic extracts were washed with water and saturated $NaCl_{(aq)}$, then dried over anhydrous $Na_2SO_{4(s)}$ and concentrated in vacuo. The residue was purified by C-18 reverse phase chromatography (5-95% ACN in water [+0.1% TFA] as the gradient eluent). The fractions containing the desired product were washed with saturated $NaHCO_{3(aq)}$ and extracted with 4:1 DCM/IPA. The combined organic extracts were dried over anhydrous $Na_2SO_{4(s)}$ and concentrated in vacuo to afford the title compound (0.0227 g, 0.0472 mmol, 44% yield). MS (apci) m/z=481.2 (M+H).

Example 369

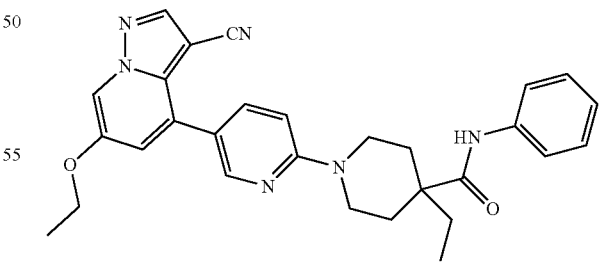

1-(5-(3-cyano-6-ethoxypyrazolo[1,5-a]pyridin-4-yl)pyridin-2-yl)-4-ethyl-N-phenylpiperidine-4-carboxamide To a solution of 6-ethoxy-4-(6-fluoropyridin-3-yl)pyrazolo[1,5-a]pyridine-3-carbonitrile (Intermediate P6, 20.8 mg, 0.0737 mmol) in DMA (0.3 mL) was added TEA (0.0502 mL, 0.368 mmol) and 4-ethyl-N-phenylpiperidine-4-carboxamide (Intermediate R15, 51.4 mg, 0.221 mmol). The reaction mixture was stirred 90° C. for 16 h. After cooling to ambient temperature, the reaction mixture was quenched with water and extracted into EtOAc. The combined organic extracts were washed with water and saturated NaCl$_{(aq)}$, then dried over anhydrous Na$_2$SO$_{4(s)}$ and concentrated in vacuo. The residue was purified by C-18 reverse phase chromatography (5-95% ACN in water [+0.1% TFA] as the gradient eluent). The fractions containing the desired product were washed with saturated NaHCO$_{3(aq)}$ and extracted with 4:1 DCM/IPA. The combined organic extracts were dried over anhydrous Na$_2$SO$_{4(s)}$ and concentrated in vacuo. The residue was purified by silica chromatography (0-100% EtOAc in hexanes as the gradient eluent) to afford the title compound (36.4 mg, 0.0166 mmol, 22.5% yield). MS (apci) m/z=495.3 (M+H).

Example 370

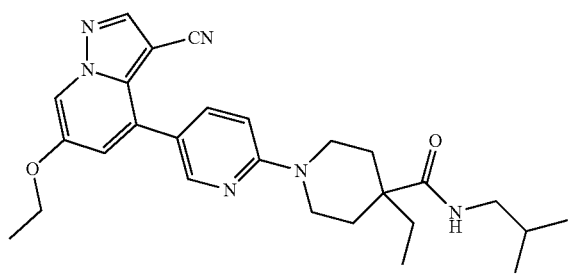 [SMILES: CCOc1cc(-c2ccc(N3CCC(CC)(C(=O)NCC(C)C)CC3)nc2)c2c(C#N)cnn2c1]

1-(5-(3-cyano-6-ethoxypyrazolo[1,5-a]pyridin-4-yl)pyridin-2-yl)-4-ethyl-N-isobutylpiperidine-4-carboxamide To a solution of 6-ethoxy-4-(6-fluoropyridin-3-yl)pyrazolo[1,5-a]pyridine-3-carbonitrile (Intermediate P6, 21.4 mg, 0.0758 mmol) in DMA (0.25 mL) was added TEA (0.0517 mL, 0.379 mmol) and 4-ethyl-N-isobutylpiperidine-4-carboxamide (Intermediate R16, 48.3 mg, 0.227 mmol). The reaction mixture was stirred 90° C. for 14 h. After cooling to ambient temperature, the reaction mixture was quenched with water and extracted into EtOAc. The combined organic extracts were washed with water and saturated NaCl$_{(aq)}$, then dried over anhydrous Na$_2$SO$_{4(s)}$ and concentrated in vacuo. The residue was purified by C-18 reverse phase chromatography (5-95% ACN in water [+0.1% TFA] as the gradient eluent). The fractions containing the desired product were washed with saturated NaHCO$_{3(aq)}$ and extracted with 4:1 DCM/IPA. The combined organic extracts were dried over anhydrous Na$_2$SO$_{4(s)}$ and concentrated in vacuo. The residue was purified by silica chromatography (0-30% MeOH [+2% NH$_4$OH] in DCM as the gradient eluent) to afford the title compound (25.6 mg, 0.0539 mmol, 71.1% yield). MS (apci) m/z=475.3 (M+H).

Example 371

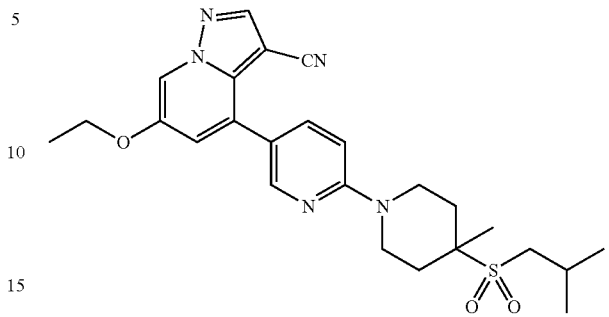

6-ethoxy-4-(6-(4-(isobutylsulfonyl)-4-methylpiperidin-1-yl)pyridin-3-yl)pyrazolo[1,5-a]pyridine-3-carbonitrile Step 1: Preparation of 6-benzyl-1-oxa-6-azaspiro[2.5]octane A solution of sodium hydride (60% w/w, 4.07 g, 102 mmol) in DMSO (200 mL) was treated with trimethylsulfoxonium iodide (22.4 g, 102 mmol) portionwise at rt over the course of 30 min. This mixture was stirred at rt 1 h then treated with 1-benzyl-4-piperidone (14.0 mL, 78.2 mmol). The reaction mixture was stirred at 60° C. for 16 h. After cooling to ambient temperature, the reaction mixture was quenched with water and extracted into EtOAc. The combined organic extracts were washed with water and saturated NaCl$_{(aq)}$, then dried over anhydrous Na$_2$SO$_{4(s)}$ and concentrated in vacuo. The residue was purified by silica chromatography (5-95% EtOAc [+2% TEA] in DCM as the gradient eluent) to afford the title compound (6.5 g, 32.0 mmol, 40.9% yield) in sufficient purity for step 2.

Step 2: Preparation of 6-benzyl-1-thia-6-azaspiro[2.5]octane

To a solution of 6-benzyl-1-oxa-6-azaspiro[2.5]octane (6.50 g, 32.0 mmol) in MeOH (130 mL) was added thiourea (2.68 g, 35.2 mmol). The reaction mixture was stirred at 40° C. for 16 h. After cooling to ambient temperature, the reaction mixture was diluted with EtOAc and washed with water and saturated NaCl$_{(aq)}$. The organic extracts were dried over anhydrous Na$_2$SO$_{4(s)}$ and concentrated in vacuo. The residue was purified by silica chromatography (5-75% EtOAc [+2% TEA] in DCM as the gradient eluent) to afford the title compound (4.84 g, 22.1 mmol, 69% yield) in sufficient purity for step 3.

Step 3: Preparation of 1-benzyl-4-methylpiperidine-4-thiol

A solution of 6-benzyl-1-thia-6-azaspiro[2.5]octane (4.84 g, 22.1 mmol) in THF (110 mL) was sparged with N$_2$ and cooled to 0° C. To this solution was added lithium aluminum hydride (33.1 mL, 33.1 mmol), and the mixture was stirred at 0° C. for 1 h. The reaction mixture was treated with dropwise addition of water and 1M NaOH. The reaction mixture was extracted with DCM, and the combined organic extracts were washed with water then dried over anhydrous Na$_2$SO$_{4(s)}$ and concentrated in vacuo to afford the title compound (2.22 g, 10.0 mmol, 45.5% yield) in sufficient purity for step 4.

Step 4: Preparation of 1-benzyl-4-(isobutylthio)-4-methylpiperidine

A solution of 1-benzyl-4-methylpiperidine-4-thiol (1.36 g, 6.144 mmol) in DMF (20 mL) was treated with potassium carbonate (2.547 g, 18.43 mmol) and 1-bromo-2-methylpropane (0.8017 mL, 7.373 mmol). The reaction mixture was stirred at 60° C. for 16 h. After cooling to ambient temperature, the reaction mixture was diluted with EtOAc and washed with water and saturated NaCl$_{(aq)}$. The organic extracts were dried over anhydrous Na$_2$SO$_{4(s)}$ and concentrated in vacuo. The residue was purified by silica chromatography (5-95% EtOAc [+2% TEA] in DCM as the gradient eluent). The fractions containing the desired product were combined and concentrated in vacuo, and the residue was purified by C-18 reverse phase chromatography (5-95% ACN in water [+0.1% TFA] as the gradient eluent). The fractions containing the desired product were combined and washed with saturated NaHCO$_{3(aq)}$ and extracted into 4:1 DCM/IPA. The combined organic extracts were dried over anhydrous Na$_2$SO$_{4(s)}$ and concentrated in vacuo to afford the title compound (281.3 mg, 1.014 mmol, 16.5% yield) in sufficient purity for step 5.

Step 5: Preparation of 1-benzyl-4-(isobutylsulfonyl)-4-methylpiperidine

A solution of 1-benzyl-4-(isobutylthio)-4-methylpiperidine (10.138 mL, 1.014 mmol) in DCM (10 mL) was treated with 3-chloroperoxybenzoic acid (681.6 mg, 3.041 mmol). The reaction mixture was stirred at rt for 16 h. The reaction mixture was diluted with DCM and washed with 10% Na$_2$CO$_{3(aq)}$. The organic extract was dried over anhydrous Na$_2$SO$_{4(s)}$ and concentrated in vacuo. The residue was purified by C-18 reverse phase chromatography (5-95% ACN in water [+0.1% TFA] as the gradient eluent). The fractions containing the desired product were combined and washed with saturated NaHCO$_{3(aq)}$ and extracted into 4:1 DCM/IPA. The combined organic extracts were dried over anhydrous Na$_2$SO$_{4(s)}$ and concentrated in vacuo to afford the title compound (206 mg, 0.6657 mmol, 66.5% yield) in sufficient purity for step 6.

Step 6: Preparation of 4-(isobutylsulfonyl)-4-methylpiperidine

A solution of 1-benzyl-4-(isobutylsulfonyl)-4-methylpiperidine (206.0 mg, 0.666 mmol) in EtOH (6.7 mL) was treated with palladium on carbon (5%, 70.8 mg, 0.0333 mmol). The reaction mixture was sparged with N$_2$ then H$_2$, and was stirred at rt under an H$_2$ atmosphere for 16 h. The solids were removed by vacuum filtration, and the filtrate was concentrated in vacuo to afford the title compound (144.6 mg, 0.659 mmol, 99% yield) in sufficient purity for step 7.

Step 7: Preparation of 6-ethoxy-4-(6-(4-(isobutylsulfonyl)-4-methylpiperidin-1-yl)pyridin-3-yl)pyrazolo[1,5-a]pyridine-3-carbonitrile To a solution of 6-ethoxy-4-(6-fluoropyridin-3-yl)pyrazolo[1,5-a]pyridine-3-carbonitrile (Intermediate P6, 118.2 mg, 0.4187 mmol) in DMSO (4.2 mL) was added 4-(isobutylsulfonyl)-4-methylpiperidine (137.8 mg, 0.6281 mmol) and DIEA (0.1459 mL, 0.8375 mmol). The reaction mixture was stirred at 90° C. for 16 h. After cooling to ambient temperature, the reaction mixture was diluted with EtOAc and washed with water and saturated NaCl$_{(aq)}$. The organic extracts were dried over anhydrous Na$_2$SO$_{4(s)}$ and concentrated in vacuo. The residue was purified by C-18 reverse phase chromatography (5-95% ACN in water [+0.1% TFA] as the gradient eluent). The fractions containing the desired product were combined and washed with saturated NaHCO$_{3(aq)}$ and extracted into 4:1 DCM/IPA. The combined organic extracts were dried over anhydrous Na$_2$SO$_{4(s)}$ and concentrated in vacuo to afford the title compound (72.5 mg, 0.1505 mmol, 36% yield). MS (apci) m/z=482.2 (M+H).

Example 372

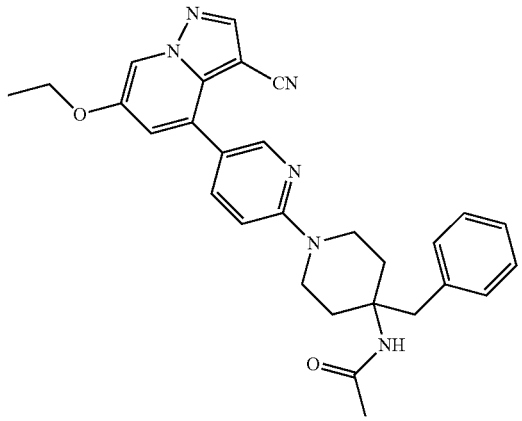 [SMILES: CCOc1cc(-c2ccc(N3CCC(Cc4ccccc4)(NC(C)=O)CC3)nc2)c2c(C#N)cnn2c1]

N-(4-benzyl-1-(5-(3-cyano-6-ethoxypyrazolo[1,5-a]pyridin-4-yl)pyridin-2-yl)piperidin-4-yl)acetamide

Step 1: Preparation of N-(4-benzylpiperidin-4-yl)acetamide

A solution of 4-benzylpiperidin-4-ol (0.100 g, 0.523 mmol) in ACN (0.5 mL) was cooled to 0° C. and then treated with dropwise addition of sulfuric acid (98%, 0.418 mL, 7.84 mmol). The reaction mixture was warmed to rt and stirred at the same temperature for 24 h. The reaction mixture was cooled to 0° C. and treated with slow addition of 2M NaOH until basic. The solution was extracted with DCM, and the combined organic extracts were passed through a phase separation frit then concentrated in vacuo to afford the title compound (0.102 g, 0.439 mmol, 84% yield) in sufficient purity for step 2. MS (apci) m/z=233.2 (M+H).

Step 2: Preparation of N-(4-benzyl-1-(-5-(3-cyano-6-ethoxypyrazolo[1,5-a]pyridin-4-yl)pyridin-2-yl)piperidin-4-yl)acetamide To a solution of 6-ethoxy-4-(6-fluoropyridin-3-yl)pyrazolo[1,5-a]pyridine-3-carbonitrile (Intermediate P6, 0.060 g, 0.213 mmol) in DMSO (1 mL) was added DIEA (0.184 mL, 1.06 mmol) and N-(4-benzylpiperidin-4-yl)acetamide (0.0988 g, 0.425 mmol). The reaction mixture was stirred at 100° C. for 24 h. After cooling to ambient temperature, the reaction mixture was quenched with saturated NH$_4$Cl$_{(aq)}$ and extracted into DCM. The combined organic extracts were dried over anhydrous Na$_2$SO$_{4(s)}$ and concentrated in vacuo. The residue was purified by silica chromatography (0-100% EtOAc in hexanes as the gradient eluent) to afford the title compound (0.072 g, 0.146 mmol, 68.5% yield). MS (apci) m/z=495.2 (M+H).

Example 373

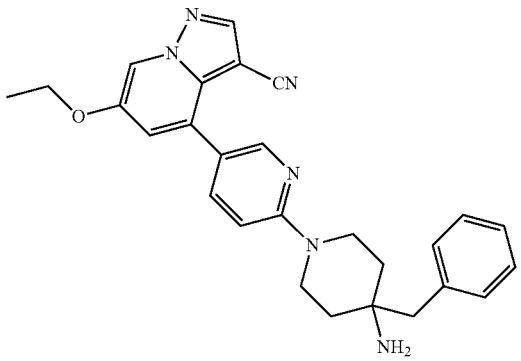 [SMILES: CCOc1cc(-c2ccc(N3CCC(N)(Cc4ccccc4)CC3)nc2)c2c(C#N)cnn2c1]

4-(6-(4-amino-4-benzylpiperidin-1-yl)pyridin-3-yl)-6-ethoxypyrazolo[1,5-a]pyridine-3-carbonitrile To a solution of N-(4-benzyl-1-(5-(3-cyano-6-ethoxy-pyrazolo[1,5-a]pyridin-4-yl)pyridin-2-yl)piperidin-4-yl)acetamide (Example 372, 0.020 g, 0.040 mmol) in 1:1 THF/DCM (0.7 mL) was added titanium(IV) propan-2-olate (0.048 mL, 0.16 mmol) and diphenylsilane (0.030 g, 0.16 mmol). The reaction mixture was stirred at rt for 24 h then quenched with water. The mixture was extracted with DCM, and the combined organic extracts were dried over anhydrous Na$_2$SO$_{4(s)}$ and concentrated in vacuo. The residue was purified by preparative HPLC (5-95% ACN in water [+0.1% TFA] as the gradient eluent). The fractions containing the desired product were combined and washed with 2M NaOH and extracted into DCM. The combined organic extracts were passed through a phase separation frit then concentrated in vacuo to afford the title compound (0.0030 g, 0.0066 mmol, 16% yield). MS (apci) m/z=453.3 (M+H).

Example 374

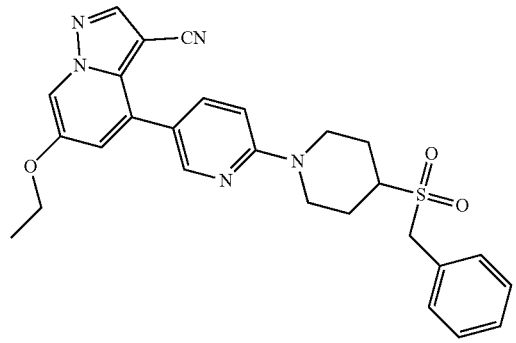 [SMILES: CCOc1cc(-c2ccc(N3CCC(S(=O)(=O)Cc4ccccc4)CC3)nc2)c2c(C#N)cnn2c1]

4-(6-(4-(benzylsulfonyl)piperidin-1-yl)pyridin-3-yl)-6-ethoxypyrazolo[1,5-a]pyridine-3-carbonitrile To a solution of 6-ethoxy-4-(6-fluoropyridin-3-yl)pyrazolo[1,5-a]pyridine-3-carbonitrile (Intermediate P6, 21.3 mg, 0.0755 mmol) in DMA (0.35 mL) was added TEA (0.0526 mL, 0.377 mmol) and 4-(benzylsulfonyl)piperidine (52.4 mg, 0.219 mmol). The reaction mixture was stirred at 90° C. for 16 h. After cooling to ambient temperature, the reaction mixture was diluted with EtOAc and washed successively with water and saturated NaCl$_{(aq)}$. The combined organic extracts were dried over anhydrous Na$_2$SO$_{4(s)}$ and concentrated in vacuo. The residue was purified by C-18 reverse phase chromatography (5-95% ACN in water [+0.1% TFA] as the gradient eluent). The fractions containing the desired product were combined and washed with saturated NaHCO$_{3(aq)}$ and extracted into 4:1 DCM/IPA. The combined organic extracts were dried over anhydrous Na$_2$SO$_{4(s)}$ and concentrated in vacuo. The residue was purified by silica chromatography (0-100% EtOAc in hexanes as the gradient eluent) to afford the title compound (13 mg, 0.0255 mmol, 34% yield). MS (apci) m/z=502.2 (M+H).

Example 375

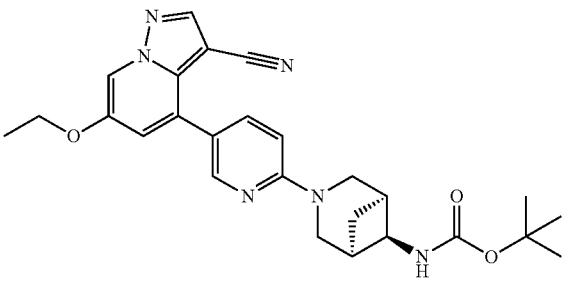 [SMILES: CCOc1cc(-c2ccc(N3C[C@H]4C[C@@H](C3)[C@H]4NC(=O)OC(C)(C)C)nc2)c2c(C#N)cnn2c1]

tert-butyl ((1R,5 S,6r)-3-(5-(3-cyano-6-ethoxypyrazolo[1,5-a]pyridin-4-yl)pyridin-2-yl)-3-azabicyclo[3.1.1]heptan-6-yl)carbamate To a solution of 6-ethoxy-4-(6-fluoropyridin-3-yl)pyrazolo[1,5-a]pyridine-3-carbonitrile (Intermediate P6, 80 mg, 0.283 mmol) in DMSO (0.567 mL) was added tert-butyl ((1R,5 S,6r)-3-azabicyclo[3.1.1]heptan-6-yl)carbamate (72.2 mg, 0.340 mmol) and DIEA (0.148 mL, 0.850 mmol). The reaction mixture was stirred at 90° C. for 17 h. After cooling to ambient temperature, the reaction mixture was diluted with water and stirred for 1 h. The resultant precipitate was isolated by vacuum filtration and rinsed on the filter successively with water and heptane to afford the title compound (130 mg, 0.266 mmol, 94% yield). MS (apci) m/z=475.2 (M+H).

Example 376

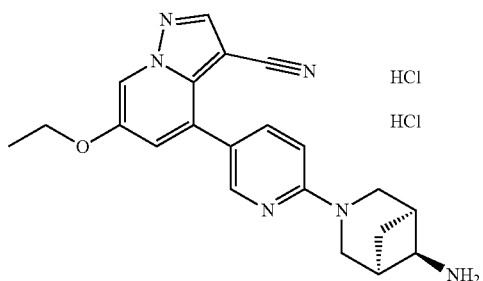

4-(6-((1R,5 S,6r)-6-amino-3-azabicyclo[3.1.1]hep-
tan-3-yl)pyridin-3-yl)-6-ethoxypyrazolo[1,5-a]pyri-
dine-3-carbonitrile dihydrochloride To a solution of tert-butyl ((1R,5S,6r)-3-(5-(3-cyano-6-ethoxypyrazolo[1,5-a]pyridin-4-yl)pyridin-2-yl)-3-azabicyclo[3.1.1]heptan-6-yl)carbamate (Example 375, 130 mg, 0.274 mmol) in MeOH (0.548 mL) was added HCl (37% w/w, 0.457 mL, 5.48 mmol) dropwise at rt. The reaction slurry was stirred at rt for 3 h. The slurry was vacuum filtered, and the isolated solid was rinsed on the filter with MeOH and MTBE to afford the title compound (114 mg, 0.252 mmol, 92% yield). MS (apci) m/z=375.2 (M+H).

Example 377

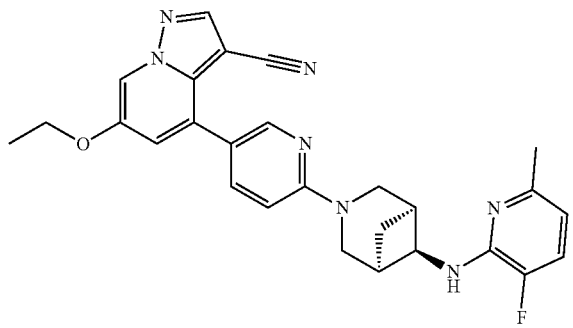 [SMILES: CCOc1cc(-c2ccc(N3C[C@H]4C[C@@H](C3)[C@H]4Nc3nc(C)ccc3F)nc2)c2c(C#N)cnn2c1]

6-ethoxy-4-(6-((1R,5 S,6r)-6-((3-fluoro-6-methyl-
pyridin-2-yl)amino)-3-azabicyclo[3.1.1]heptan-3-yl)
pyridin-3-yl)pyrazolo[1,5-a]pyridine-3-carbonitrile To a mixture of 4-(6-((1R,5 S,6r)-6-amino-3-azabicyclo[3.1.1]heptan-3-yl)pyridin-3-yl)-6-ethoxypyrazolo[1,5-a]pyridine-3-carbonitrile dihydrochloride (Example 376, 25 mg, 0.056 mmol) and 2,3-difluoro-6-methylpyridine (11 mg, 0.084 mmol) in DMSO (0.112 mL) was added DIEA (0.049 mL, 0.28 mmol). The reaction mixture was stirred at 110° C. for 24 h then 150° C. for an additional 24 h. After cooling to ambient temperature, the reaction mixture was directly purified by C-18 reverse phase chromatography (5-95% ACN in water as the gradient eluent) to afford the title compound (7.7 mg, 0.015 mmol, 28%). MS (apci) m/z=484.2 (M+H).

Example 378

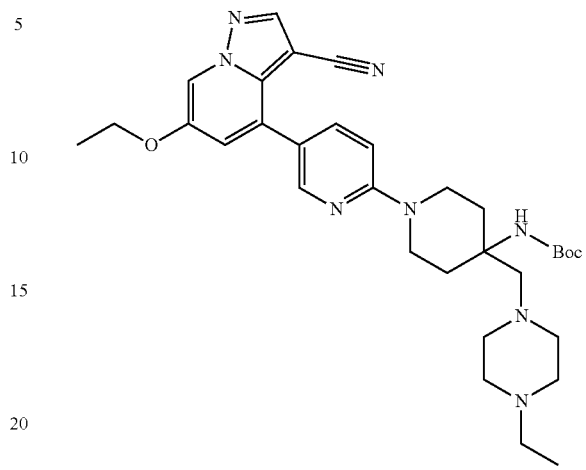

tert-butyl (1-(5-(3-cyano-6-ethoxypyrazolo[1,5-a]
pyridin-4-yl)pyridin-2-yl)-4-((4-ethylpiperazin-1-yl)
methyl)piperidin-4-yl)carbamate To a solution of tert-butyl (1-(5-(3-cyano-6-ethoxypyrazolo[1,5-a]pyridin-4-yl)pyridin-2-yl)-4-formylpiperidin-4-yl)carbamate (Intermediate P71, 0.225 g, 0.459 mmol), in DCE (2.29 mL) was added 1-ethylpiperazine (0.157 g, 1.38 mmol). The mixture was stirred at rt for 30 min, then sodium triacetoxyborohydride (0.146 g, 0.688 mmol) was added. The reaction mixture was stirred at rt an additional 16 h. The crude reaction mixture was directly purified by silica chromatography (1-10% MeOH in DCM with 0.1-1% NH₄OH as the gradient eluent) to afford the title compound (0.149 mg, 0.253 mmol, 55% yield). MS (apci) m/z=589.4 (M+H).

Example 379

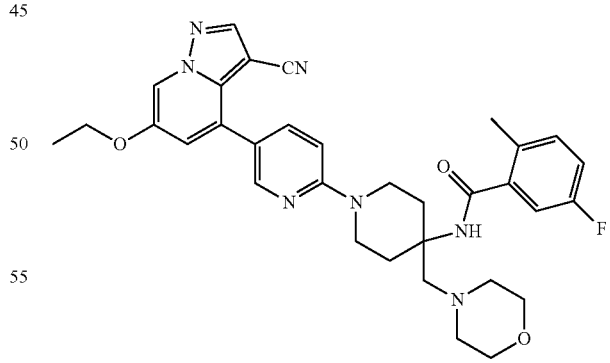

N-(1-(5-(3-cyano-6-ethoxypyrazolo[1,5-a]pyridin-4-
yl)pyridin-2-yl)-4-(morpholinomethyl)piperidin-4-
yl)-5-fluoro-2-methylbenzamide To a solution of N-(1-(5-(3-cyano-6-ethoxypyrazolo[1,5-a]pyridin-4-yl)pyridin-2-yl)-4-formylpiperidin-4-yl)-5- fluoro-2-methylbenzamide (Intermediate P70, 0.0196 g, 0.03722 mmol) in DCE (0.1861 mL) was added morpholine (0.009661 mL, 0.1117 mmol) and sodium triacetoxyborohydride (0.01183 g, 0.05583 mmol). The reaction mixture was stirred at rt for 16 h. The crude reaction mixture was directly purified by silica chromatography (0-100% EtOAc in Hexanes then 0-10% MeOH in $CHCl_3$ as the gradient eluent) to afford the title compound (0.0172 g, 0.02878 mmol, 77% yield). MS (apci) m/z=598.3 (M+H).

The compounds in Table TT were prepared using a similar method to that described for the synthesis of Example 379, replacing morpholine with the appropriate amine. Reactions were monitored for completion by LCMS, and reaction durations were adjusted accordingly. Title compounds were cleanly isolated following chromatographic purification using an appropriate gradient eluent (and if necessary converted to the free base).

TABLE TT

| Ex. # | Structure | Chemical Name | MS m/z |
|---|---|---|---|
| 380 | 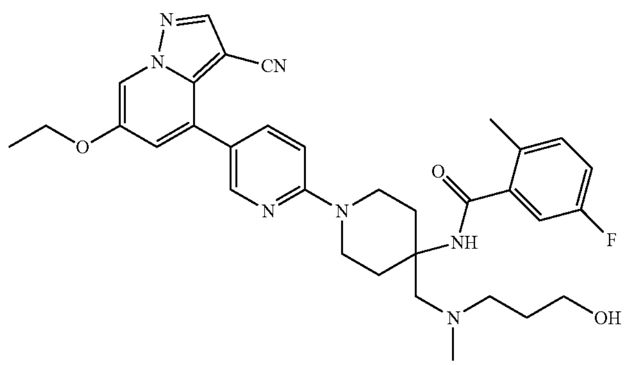 [SMILES: CCOc1cc(-c2ccc(N3CCC(CN(C)CCCO)(NC(=O)c4cc(F)ccc4C)CC3)nc2)c2c(C#N)cnn2c1] | N-(1-(5-(3-cyano-6-ethoxypyrazolo[1,5-a]pyridin-4-yl)pyridin-2-yl)-4-(((3-hydroxypropyl)(methyl)amino)methyl)piperidin-4-yl)-5-fluoro-2-methylbenzamide | 600.30 (M + H) |
| 381 | 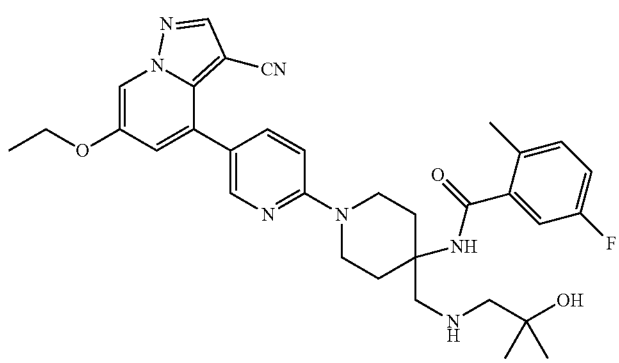 [SMILES: CCOc1cc(-c2ccc(N3CCC(CNCC(C)(C)O)(NC(=O)c4cc(F)ccc4C)CC3)nc2)c2c(C#N)cnn2c1] | N-(1-(5-(3-cyano-6-ethoxypyrazolo[1,5-a]pyridin-4-yl)pyridin-2-yl)-4-(((2-hydroxy-2-methylpropyl)amino)methyl)piperidin-4-yl)-5-fluoro-2-methylbenzamide | 600.30 (M + H) |
| 382 | 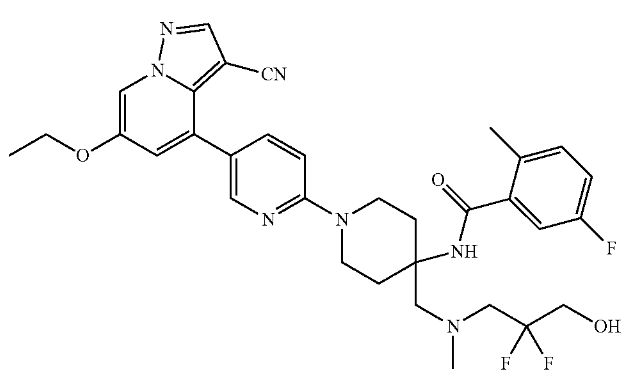 [SMILES: CCOc1cc(-c2ccc(N3CCC(CN(C)CC(F)(F)CO)(NC(=O)c4cc(F)ccc4C)CC3)nc2)c2c(C#N)cnn2c1] | N-(1-(5-(3-cyano-6-ethoxypyrazolo[1,5-a]pyridin-4-yl)pyridin-2-yl)-4-(((2,2-difluoro-3-hydroxypropyl)(methyl)amino)methyl)piperidin-4-yl)-5-fluoro-2-methylbenzamide | 636.40 (M + H) |

Example 383

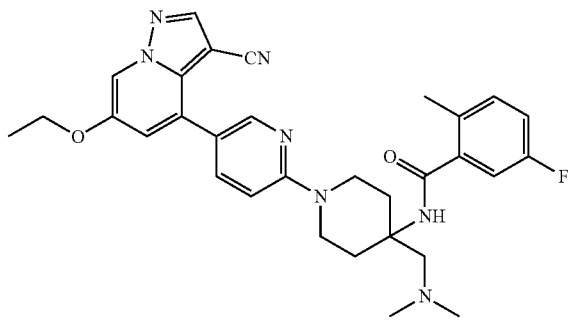 [SMILES: CCOc1cc(-c2ccc(N3CCC(CN(C)C)(NC(=O)c4cc(F)ccc4C)CC3)nc2)c2c(C#N)cnn2c1]

N-(1-(5-(3-cyano-6-ethoxypyrazolo[1,5-a]pyridin-4-yl)pyridin-2-yl)-4-((dimethylamino)methyl)piperidin-4-yl)-5-fluoro-2-methylbenzamide To a solution of 4-(6-(4-amino-4-((dimethylamino)methyl)piperidin-1-yl)pyridin-3-yl)-6-ethoxypyrazolo[1,5-a]pyridine-3-carbonitrile (Intermediate P72, 7 mg, 0.017 mmol) in DMF (0.334 mL) was added 5-fluoro-2-methylbenzoic acid (5.1 mg, 0.033 mmol), HATU (13 mg, 0.033 mmol), and DIEA (0.015 mL, 0.083 mmol). The reaction mixture was stirred at rt for 1 h. The crude reaction mixture was directly purified by silica chromatography (0-100% EtOAc in Hexanes then 1-10% MeOH in EtOAc with 0.1-1% NH$_4$OH as the gradient eluent) to afford the title compound (5 mg, 0.0090 mmol, 54% yield). MS (apci) m/z=556.2 (M+H).

Example 384

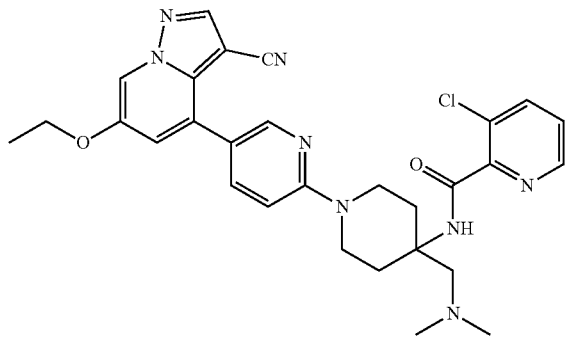 [SMILES: CCOc1cc(-c2ccc(N3CCC(CN(C)C)(NC(=O)c4ncccc4Cl)CC3)nc2)c2c(C#N)cnn2c1]

3-chloro-N-(1-(5-(3-cyano-6-ethoxypyrazolo[1,5-a]pyridin-4-yl)pyridin-2-yl)-4-((dimethylamino)methyl)piperidin-4-yl)picolinamide To a mixture of 4-(6-(4-amino-4-((dimethylamino)methyl)piperidin-1-yl)pyridin-3-yl)-6-ethoxypyrazolo[1,5-a]pyridine-3-carbonitrile (Intermediate P72, 0.050 g, 0.119 mmol) in DMSO (0.795 mL) was added 3-chloropicolinic acid (0.0282 g, 0.179 mmol) followed by Hunig's base (0.0934 mL, 0.536 mmol) and HATU (0.0906 g, 0.238 mmol). The reaction mixture was stirred at rt for 16 h. The reaction mixture was diluted with EtOAc and washed with water. The organic extract was washed with saturated NaCl$_{(aq)}$, dried over anhydrous Na$_2$SO$_{4(s)}$, and concentrated in vacuo. The residue was purified by preparative HPLC (5-95% ACN in water [+0.1% TFA] as the gradient eluent). The fractions containing the desired product were combined and washed with saturated NaHCO$_{3(aq)}$ and extracted into DCM. The combined organic extracts were washed with saturated NaCl$_{(aq)}$, dried over anhydrous Na$_2$SO$_{4(s)}$, and concentrated in vacuo to afford the title compound (0.0108 g, 0.0193 mmol, 16.2% yield). MS (apci) m/z=559.3 (M+H).

Example 385

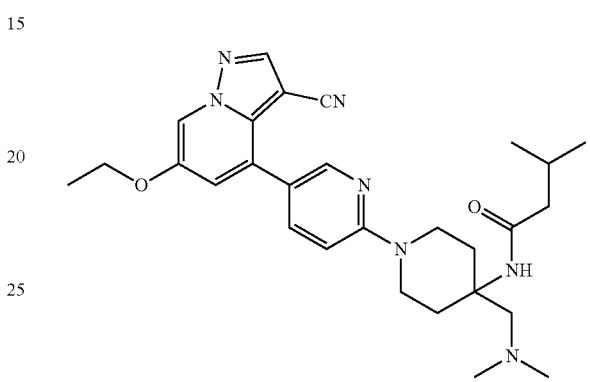

N-(1-(5-(3-cyano-6-ethoxypyrazolo[1,5-a]pyridin-4-yl)pyridin-2-yl)-4-((dimethylamino)methyl)piperidin-4-yl)-3-methylbutanamide To a solution of 4-(6-(4-amino-4-((dimethylamino)methyl)piperidin-1-yl)pyridin-3-yl)-6-ethoxypyrazolo[1,5-a]pyridine-3-carbonitrile (Intermediate P72, 40 mg, 0.095 mmol) in DCM (0.953 mL) was added and isovaleryl chloride (11 mg, 0.095 mmol) and TEA (0.027 mL, 0.19 mmol). The reaction mixture was stirred at rt 3 h. The reaction mixture was diluted with 4:1 DCM:IPA and washed successively with saturated NaHCO$_{3(aq)}$, water, and saturated NaCl$_{(aq)}$. The organic extract was dried over anhydrous Na$_2$SO$_{4(s)}$, filtered, and concentrated in vacuo to afford the title compound (48 mg, 0.095 mmol, 100% yield). MS (apci) m/z=504.3 (M+H).

Example 386

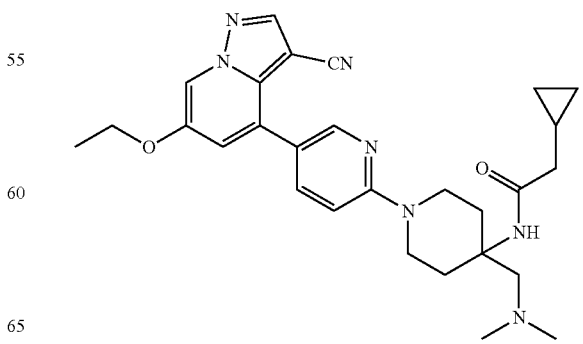

651

N-(1-(5-(3-cyano-6-ethoxypyrazolo[1,5-a]pyridin-4-yl)pyridin-2-yl)-4-((dimethylamino)methyl)piperidin-4-yl)-2-cyclopropylacetamide The compound was prepared using a similar method to that described for the synthesis of Example 385, replacing isovaleryl chloride with the 2-cyclopropylacetyl chloride. LCMS m/z=502.3 (M+H).

Example 387

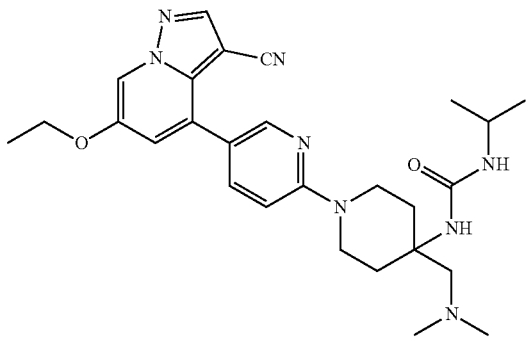 [SMILES: CCOc1cc(-c2ccc(N3CCC(CN(C)C)(NC(=O)NC(C)C)CC3)nc2)c2c(C#N)cnn2c1]

1-(1-(5-(3-cyano-6-ethoxypyrazolo[1,5-a]pyridin-4-yl)pyridin-2-yl)-4-((dimethylamino)methyl)piperidin-4-yl)-3-isopropylurea To a solution of 4-(6-(4-amino-4-((dimethylamino)methyl)piperidin-1-yl)pyridin-3-yl)-6-ethoxypyrazolo[1,5-a]pyridine-3-carbonitrile (Intermediate P72, 30 mg, 0.072 mmol) and DIEA (125 µL, 0.715 mmol) in DMA (1.43 mL) was added 4-nitrophenyl chloroformate (17 mg, 0.086 mmol). The reaction mixture was stirred for 1 h at ambient temperature. Propan-2-amine (31 µL, 0.358 mmol) was added to the reaction mixture. The reaction mixture was stirred overnight at 80° C. The reaction mixture was cooled to ambient temperature and concentrated in vacuo. The residue was purified by C18 reverse phase chromatography (5-95% ACN in water with 0.1% TFA as the gradient eluent) to afford the title compound as the TFA salt. The TFA salt was treated with saturated NaHCO$_{3(aq)}$ and extracted with 4:1 DCM:IPA. The combined organic extracts were washed with brine, then dried over anhydrous Na$_2$SO$_{4(s)}$, filtered and concentrated in vacuo to afford the title compound (4 mg, 11% yield). MS (apci) m/z=505.3 (M+H).

Example 388

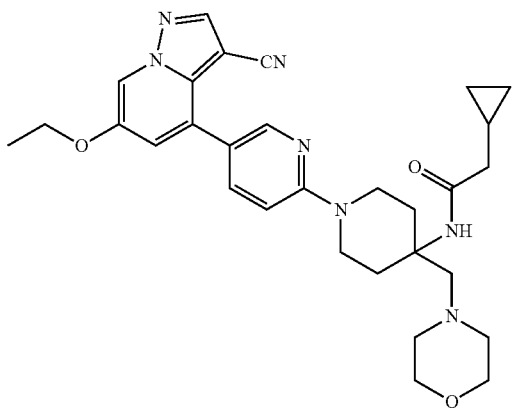 [SMILES: CCOc1cc(-c2ccc(N3CCC(CN4CCOCC4)(NC(=O)CC4CC4)CC3)nc2)c2c(C#N)cnn2c1]

652

N-(1-(5-(3-cyano-6-ethoxypyrazolo[1,5-a]pyridin-4-yl)pyridin-2-yl)-4-(morpholinomethyl)piperidin-4-yl)-2-cyclopropylacetamide To a solution of 4-(6-(4-amino-4-(morpholinomethyl)piperidin-1-yl)pyridin-3-yl)-6-ethoxypyrazolo[1,5-a]pyridine-3-carbonitrile (Intermediate P73, 30 mg, 0.065 mmol) in DCM (0.650 mL) was added TEA (0.018 mL, 0.13 mmol) and cyclopropylacetyl chloride (9.2 mg, 0.078 mmol). The reaction mixture was stirred at rt for 16 h. The reaction mixture was diluted with 4:1 DCM:IPA and washed successively with saturated NaHCO$_{3(aq)}$, water, and saturated NaCl$_{(aq)}$. The organic extract was dried over anhydrous Na$_2$SO$_{4(s)}$, filtered, and concentrated in vacuo to afford the title compound (35 mg, 0.064 mmol, 99% yield). MS (apci) m/z=544.3 (M+H).

Example 389

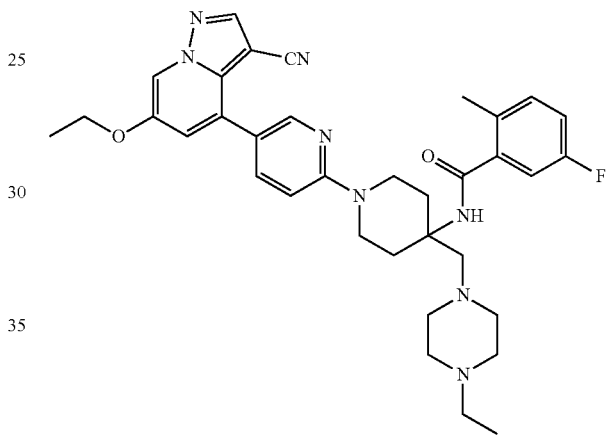

N-(1-(5-(3-cyano-6-ethoxypyrazolo[1,5-a]pyridin-4-yl)pyridin-2-yl)-4-((4-ethylpiperazin-1-yl)methyl)piperidin-4-yl)-5-fluoro-2-methylbenzamide To a solution of 4-(6-(4-amino-4-((4-ethylpiperazin-1-yl)methyl)piperidin-1-yl)pyridin-3-yl)-6-ethoxypyrazolo[1,5-a]pyridine-3-carbonitrile dihydrochloride (Intermediate P74. 20 mg, 0.0356 mmol) in DMF (0.356 mL) was added 5-fluoro-2-methylbenzoic acid (6.86 mg, 0.0445 mmol), DIEA (0.0311 mL, 0.178 mmol), and HATU (16.9 mg, 0.0445 mmol). The reaction mixture was stirred at rt for 5 min. The crude reaction mixture was directly purified by silica chromatography (0-100% EtOAc in Hexanes then 1-10% MeOH in EtOAc with 0.1-1% NH$_4$OH as the gradient eluent) to afford the title compound (7 mg, 0.0112 mmol, 31.5% yield). MS (apci) m/z=625.4 (M+H).

The compounds in Table UU were prepared using a similar method to that described for the synthesis of Example 389, replacing 5-fluoro-2-methylbenzoic acid with the appropriate carboxylic acid. Reactions were monitored for completion by LCMS, and reaction durations were adjusted accordingly. Title compounds were cleanly isolated following chromatographic purification using an appropriate gradient eluent (and if necessary converted to the free base).

TABLE UU

| Ex. # | Structure | Chemical Name | MS (apci) m/z |
|---|---|---|---|
| 390 | 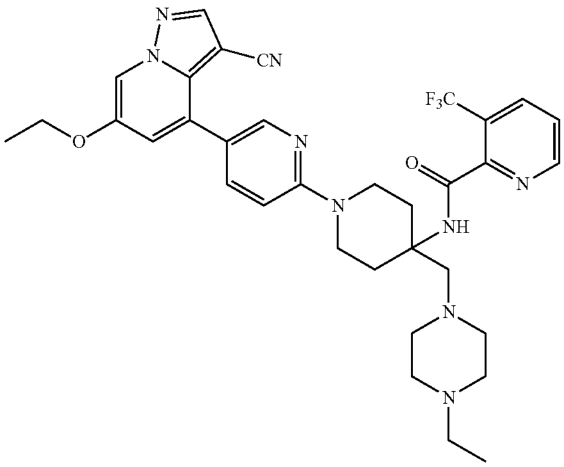 [SMILES: CCOc1cc(-c2ccc(N3CCC(CN4CCN(CC)CC4)(NC(=O)c4ncccc4C(F)(F)F)CC3)nc2)c2c(C#N)cnn2c1] | N-(1-(5-(3-cyano-6-ethoxypyrazolo[1,5-a]pyridin-4-yl)pyridin-2-yl)-4-((4-ethylpiperazin-1-yl)methyl)piperidin-4-yl)-3-(trifluoromethyl)picolinamide | 662.20 (M + H) |

Example 391

Example 392

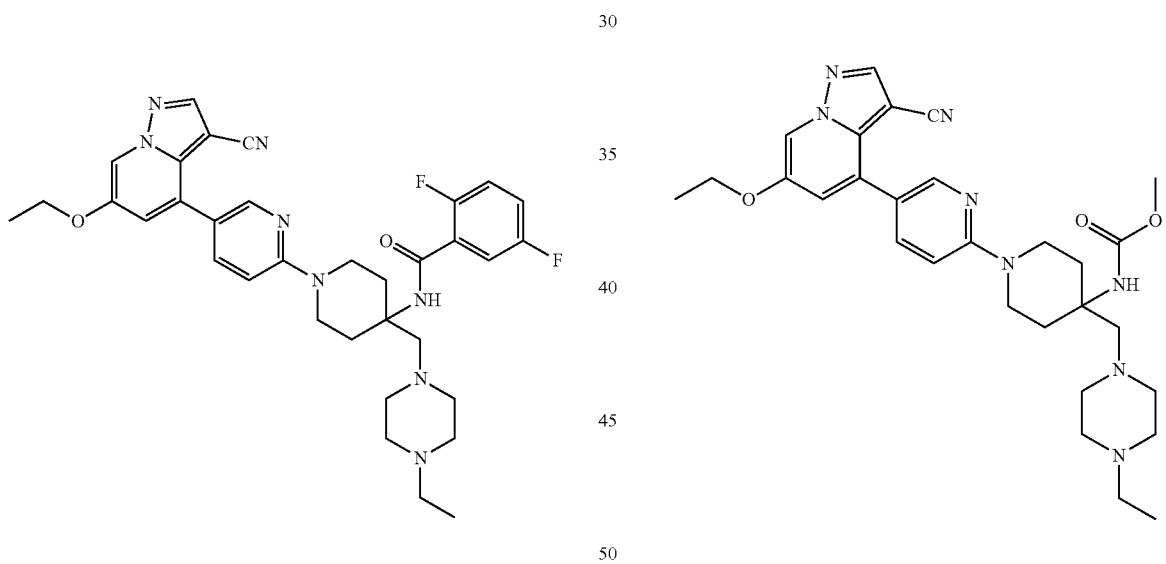

N-(1-(5-(3-cyano-6-ethoxypyrazolo[1,5-a]pyridin-4-yl)pyridin-2-yl)-4-((4-ethylpiperazin-1-yl)methyl)piperidin-4-yl)-2,5-difluorobenzamide methyl (1-(5-(3-cyano-6-ethoxypyrazolo[1,5-a]pyridin-4-yl)pyridin-2-yl)-4-((4-ethylpiperazin-1-yl)methyl)piperidin-4-yl)carbamate To a solution of 4-(6-(4-amino-4-(hydroxymethyl)piperidin-1-yl)pyridin-3-yl)-6-ethoxypyrazolo[1,5-a]pyridine-3-carbonitrile (Intermediate P74, 0.0238 g, 0.0606 mmol) in DMSO (0.606 mL) was added DIEA (0.0530 ml, 0.303 mmol), 2,6-difluorobenzoic acid (0.0192 g, 0.121 mmol), HATU (0.0461 g, 0.121 mmol). The reaction mixture was stirred at rt for 16 h. The crude reaction mixture was directly purified by silica chromatography (1-10% MeOH in DCM with 0.1-1% NH$_4$OH as the gradient eluent) to afford the title compound (29 mg, 0.023 mmol, 49.5% yield). MS (apci) m/z=629.4 (M+H).

To a solution of 4-(6-(4-amino-4-(hydroxymethyl)piperidin-1-yl)pyridin-3-yl)-6-ethoxypyrazolo[1,5-a]pyridine-3-carbonitrile (Intermediate P74, 0.0238 g, 0.0606 mmol) in DCM (0.48 mL) was added DIEA (13 μL, 0.072 mmol) followed by methyl chloroformate (5 μL, 0.058 mmol). The reaction mixture was stirred for 1 h at ambient temperature. The crude reaction mixture was filtered and the filtrate was directly purified by silica chromatography (1-10% MeOH in DCM with 0.1-1% NH$_4$OH as the gradient eluent) to afford the title compound (1.9 mg, 7% yield). MS (apci) m/z=547.3 (M+H).

Example 393

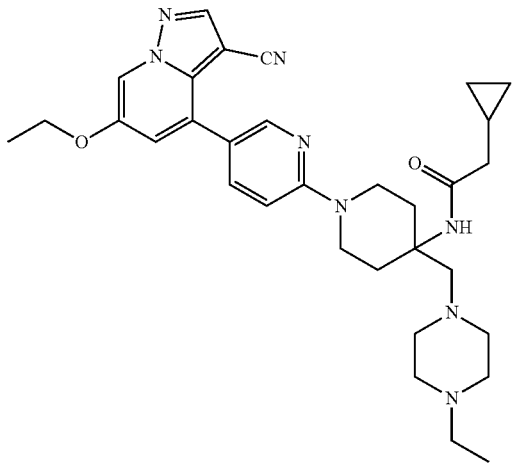 [SMILES: CCOc1cc(-c2ccc(N3CCC(CN4CCN(CC)CC4)(NC(=O)CC4CC4)CC3)nc2)c2c(C#N)cnn2c1]

N-(1-(5-(3-cyano-6-ethoxypyrazolo[1,5-a]pyridin-4-yl)pyridin-2-yl)-4-((4-ethylpiperazin-1-yl)methyl)piperidin-4-yl)-2-cyclopropylacetamide To a solution of 4-(6-(4-amino-4-((4-ethylpiperazin-1-yl)methyl)piperidin-1-yl)pyridin-3-yl)-6-ethoxypyrazolo[1,5-a]pyridine-3-carbonitrile (Intermediate P74, 50 mg, 0.10 mmol) in DMA (1.023 mL) was added cyclopropylacetyl chloride (15 mg, 0.12 mmol) and TEA (0.029 mL, 0.20 mmol). The reaction mixture was stirred at rt for 3 h. The reaction mixture was diluted with 4:1 DCM:IPA and washed successively with saturated NaHCO$_{3(aq)}$, water, and saturated NaCl$_{(aq)}$. The organic extract was dried over anhydrous Na$_2$SO$_{4(s)}$, filtered, and concentrated in vacuo to afford the title compound (45 mg, 0.079 mmol, 77% yield). MS (apci) m/z=571.4 (M+H).

Example 394

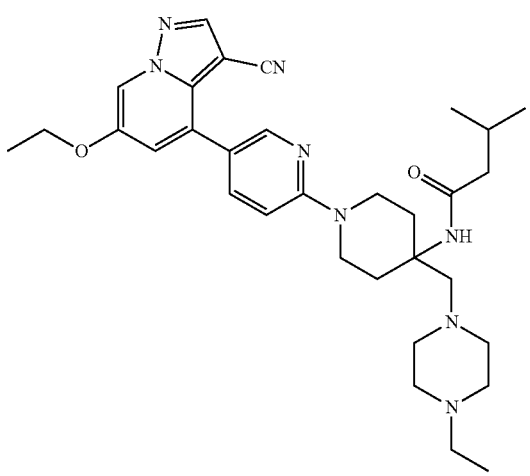 [SMILES: CCOc1cc(-c2ccc(N3CCC(CN4CCN(CC)CC4)(NC(=O)CC(C)C)CC3)nc2)c2c(C#N)cnn2c1]

N-(1-(5-(3-cyano-6-ethoxypyrazolo[1,5-a]pyridin-4-yl)pyridin-2-yl)-4-((4-ethylpiperazin-1-yl)methyl)piperidin-4-yl)-3-methylbutanamide The compound was prepared using a similar method to that described for the synthesis of Example 393, replacing 2-cyclopropylacetyl chloride with 3-methylbutanoyl chloride. MS (apci) m/z=573.4 (M+H).

Example 395

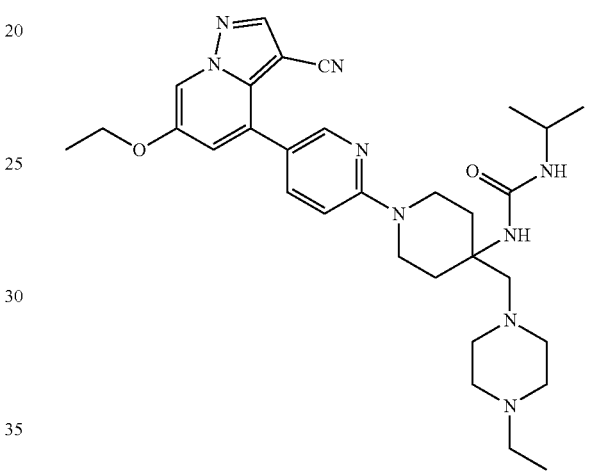

1-(1-(5-(3-cyano-6-ethoxypyrazolo[1,5-a]pyridin-4-yl)pyridin-2-yl)-4-((4-ethylpiperazin-1-yl)methyl)piperidin-4-yl)-3-isopropylurea To a solution of 4-(6-(4-amino-4-((4-ethylpiperazin-1-yl)methyl)piperidin-1-yl)pyridin-3-yl)-6-ethoxypyrazolo[1,5-a]pyridine-3-carbonitrile (Intermediate P74, 30 mg, 0.061 mmol) and DIEA (107 µL, 0.614 mmol) in DMA (1.228 mL) was added 4-nitrophenyl chloroformate (15 mg, 0.074 mmol). The reaction mixture was stirred for 1 h at ambient temperature before propan-2-amine (26.3 µl, 0.307 mmol). was introduced. The reaction mixture was stirred for 2 h at 80° C. The reaction mixture was cooled to ambient temperature and concentrated in vacuo. The residue was purified by C18 reverse phase chromatography (5-95% ACN in water with 0.1% TFA as the gradient eluent) to afford the title compound as the TFA salt. The TFA salt was treated with saturated NaHCO$_{3(aq)}$ and extracted with 4:1 DCM:IPA. The combined organic extracts were washed with brine, then dried over anhydrous Na$_2$SO$_{4(s)}$, filtered and concentrated in vacuo to afford the title compound (27 mg, 77% yield). MS (apci) m/z=574.4 (M+H).

Example 396

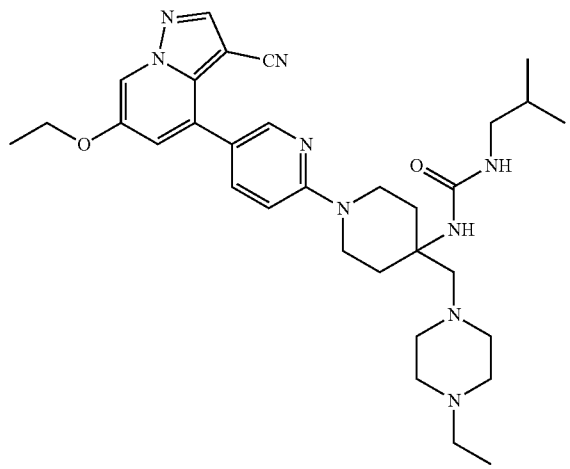 [SMILES: CCOc1cc(-c2ccc(N3CCC(CN4CCN(CC)CC4)(NC(=O)NCC(C)C)CC3)nc2)c2c(C#N)cnn2c1]

1-(1-(5-(3-cyano-6-ethoxypyrazolo[1,5-a]pyridin-4-yl)pyridin-2-yl)-4-((4-ethylpiperazin-1-yl)methyl)piperidin-4-yl)-3-isobutylurea The title compound was prepared using a similar method to that described for the synthesis of Example 395, replacing propan-2-amine with 2-methylpropan-1-amine. MS (apci) m/z=588.4 (M+H).

Example 397

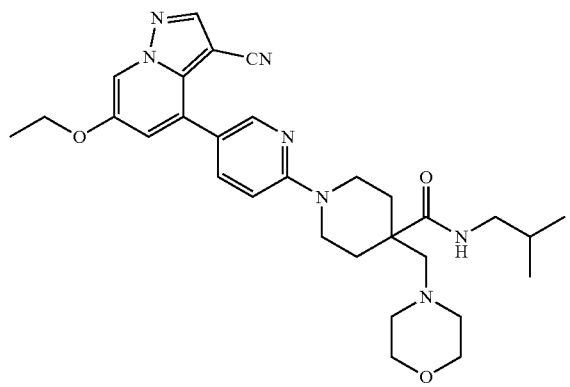 [SMILES: CCOc1cc(-c2ccc(N3CCC(CN4CCOCC4)(C(=O)NCC(C)C)CC3)nc2)c2c(C#N)cnn2c1]

1-(5-(3-cyano-6-ethoxypyrazolo[1,5-a]pyridin-4-yl)pyridin-2-yl)-N-isobutyl-4-(morpholinomethyl)piperidine-4-carboxamide To a solution of 1-(5-(3-cyano-6-ethoxypyrazolo[1,5-a]pyridin-4-yl)pyridin-2-yl)-4-formyl-N-isobutylpiperidine-4-carboxamide (Intermediate P76, 101.6 mg, 0.2141 mmol) in DCM (1.0 mL) was added morpholine (0.0942 mL, 1.070 mmol) and sodium triacetoxyborohydride (226.9 mg, 1.070 mmol). The reaction mixture was stirred at rt for 16 h. The reaction mixture was concentrated in vacuo, and the resultant crude residue was directly purified by C-18 reverse phase chromatography (5-95% ACN in water [+0.1% TFA] as the gradient eluent). The fractions containing the desired product were diluted with 4:1 DCM:IPA and washed with saturated NaHCO$_{3(aq)}$. The organic extract was dried over anhydrous Na$_2$SO$_{4(s)}$, filtered, and concentrated in vacuo. The residue was purified by silica chromatography (1-30% MeOH [+2% NH$_4$OH] in DCM as the gradient eluent) afford the title compound (71.1 mg, 0.1303 mmol, 60.86% yield). MS (apci) m/z=546.4 (M+H).

Example 398

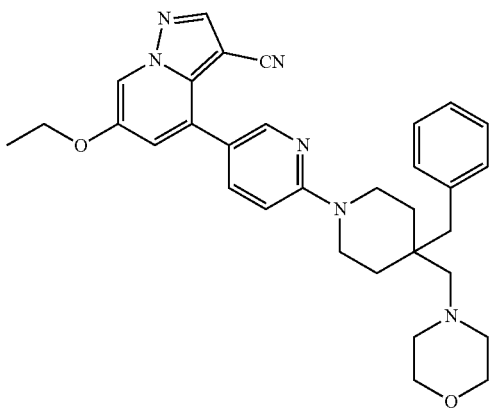 [SMILES: CCOc1cc(-c2ccc(N3CCC(Cc4ccccc4)(CN4CCOCC4)CC3)nc2)c2c(C#N)cnn2c1]

4-(6-(4-benzyl-4-(morpholinomethyl)piperidin-1-yl)pyridin-3-yl)-6-ethoxypyrazolo[1,5-a]pyridine-3-carbonitrile To a solution of 4-(6-(4-benzyl-4-formylpiperidin-1-yl)pyridin-3-yl)-6-ethoxypyrazolo[1,5-a]pyridine-3-carbonitrile (Intermediate P77, 10.4 mg, 0.0223 mmol) in DCE (0.75 mL) was added morpholine (9.1 mg, 0.104 mmol). The mixture was stirred at rt for 1 hr then was treated with sodium triacetoxyborohydride (34.0 mg, 0.160 mmol). The reaction mixture was stirred at rt for 96 h. The reaction mixture was diluted with DCM and washed with water. The organic extract was dried over anhydrous Na$_2$SO$_{4(s)}$ and purified by silica chromatography (0-100% EtOAc in hexanes as the gradient eluent to afford the title compound (1.6 mg, 0.00295 mmol, 13.2% yield). MS (apci) m/z=537.3 (M+H).

Example 399

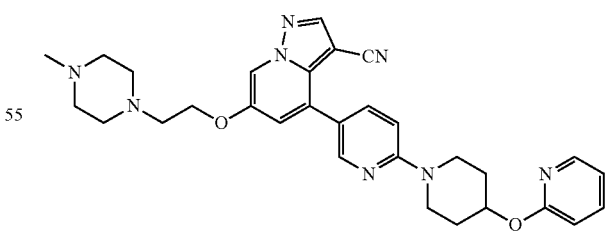

6-(2-(4-methylpiperazin-1-yl)ethoxy)-4-(6-(4-(pyridin-2-yloxy)piperidin-1-yl)pyridin-3-yl)pyrazolo[1,5-a]pyridine-3-carbonitrile A solution of triphenylphosphane (31.7966 mg, 0.121 mmol) in 1:1 DCM:THF (0.6 mL) was cooled to 0° C. and treated with diisopropyl azodicarboxylate (0.023 mL, 0.121 mmol) and stirred at 0° C. for 15 min. The reaction mixture was treated with 6-hydroxy-4-(6-(4-(pyridin-2-yloxy)piperidin-1-yl)pyridin-3-yl)pyrazolo[1,5-a]pyridine-3-carbonitrile (Intermediate P78, 25.0 mg, 0.0606 mmol) in a 1:1 DCM:THF (0.6 mL) and 1-(N-hydroxyethyl)-4-methyl piperazine (13.1 mg, 0.0909 mmol). The reaction mixture was allowed to warm to rt and was stirred at this temperature for 30 min. The reaction mixture was concentrated in vacuo, and the resultant crude residue was directly purified by C-18 reverse phase chromatography (5-95% ACN in water [+0.1% TFA] as the gradient eluent). The fractions containing the desired product were diluted with 4:1 DCM:IPA and washed with saturated NaHCO$_{3(aq)}$. The organic extract was dried over anhydrous Na$_2$SO$_{4(s)}$, filtered, and concentrated in vacuo to afford the title compound (31.5 mg, 0.0526 mmol, 86.8% yield). MS (apci) m/z=539.2 (M+H).

The compounds in Table VV were prepared using a similar method to that described for the synthesis of Example 399, replacing 1-(N-hydroxyethyl)-4-methyl piperazine with the appropriate alcohol. Reactions were monitored for completion by LCMS, and reaction durations were adjusted accordingly. Title compounds were cleanly isolated following chromatographic purification using an appropriate gradient eluent (and if necessary converted to the free base).

TABLE VV

| Ex. # | Structure | Chemical Name | MS m/z |
|---|---|---|---|
| 400 | 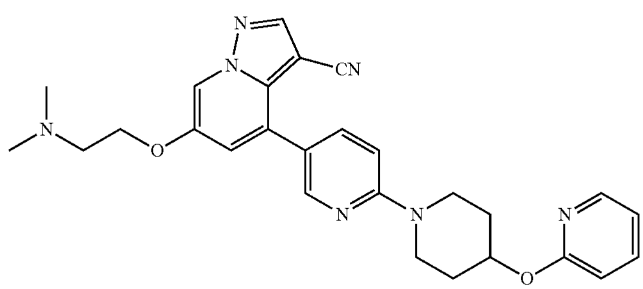 [SMILES: CN(C)CCOc1cc(-c2ccc(N3CCC(Oc4ccccn4)CC3)nc2)c2c(C#N)cnn2c1] | 6-(2-(dimethylamino)ethoxy)-4-(6-(4-(pyridin-2-yloxy)piperidin-1-yl)pyridin-3-yl)pyrazolo[1,5-a]pyridine-3-carbonitrile | 484.20 (M + H) |
| 401 | 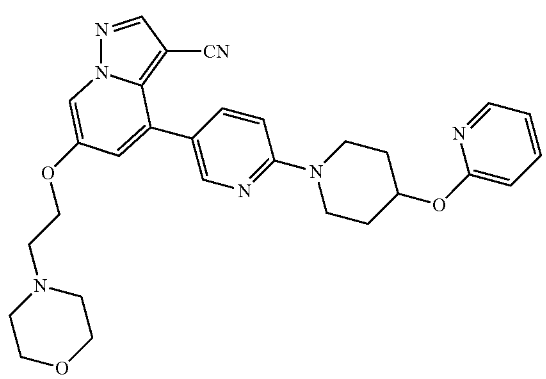 [SMILES: N#Cc1cnn2cc(OCCN3CCOCC3)cc(-c3ccc(N4CCC(Oc5ccccn5)CC4)nc3)c12] | 6-(2-morpholinoethoxy)-4-(6-(4-(pyridin-2-yloxy)piperidin-1-yl)pyridin-3-yl)pyrazolo[1,5-a]pyridine-3-carbonitrile | 526.20 (M + H) |
| 402 | 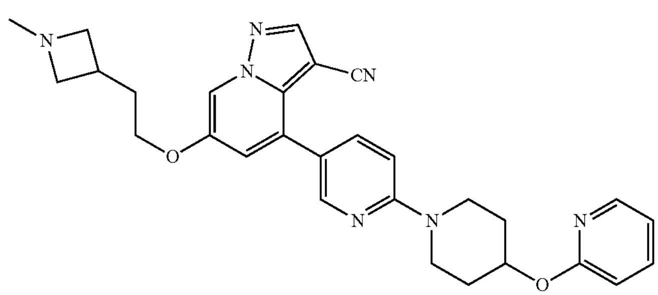 [SMILES: CN1CC(CCOc2cc(-c3ccc(N4CCC(Oc5ccccn5)CC4)nc3)c3c(C#N)cnn3c2)C1] | 6-(2-(1-methylazetidin-3-yl)ethoxy)-4-(6-(4-(pyridin-2-yloxy)piperidin-1-yl)pyridin-3-yl)pyrazolo[1,5-a]pyridine-3-carbonitrile | 510.20 (M + H) |

TABLE VV-continued

| Ex. # | Structure | Chemical Name | MS m/z |
|---|---|---|---|
| 403 | 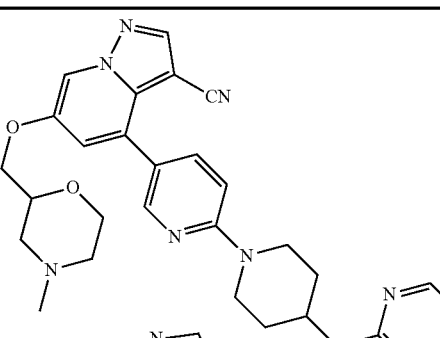 | 6-((4-methylmorpholin-2-yl)methoxy)-4-(6-(4-(pyridin-2-yloxy)piperidin-1-yl)pyridin-3-yl)pyrazolo[1,5-a]pyridine-3-carbonitrile | 526.20 (M + H) |
| 404 | 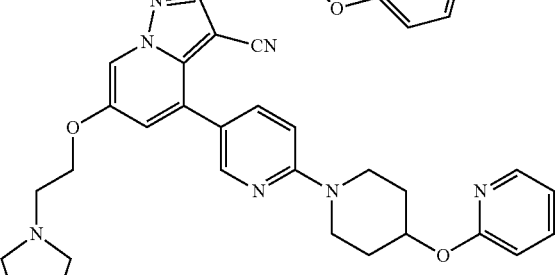 | 4-(6-(4-(pyridin-2-yloxy)piperidin-1-yl)pyridin-3-yl)-6-(2-(pyrrolidin-1-yl)ethoxy)pyrazolo[1,5-a]pyridine-3-carbonitrile | 510.30 (M + H) |

Example 405

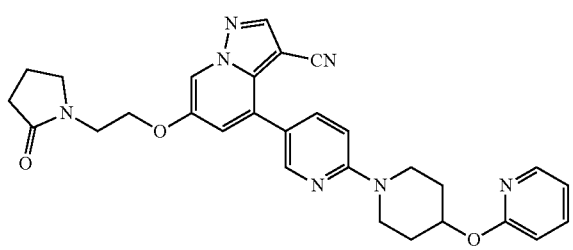 [SMILES: N#Cc1cnn2cc(OCCN3CCCC3=O)cc(-c3ccc(N4CCC(Oc5ccccn5)CC4)nc3)c12]

6-(2-(2-oxopyrrolidin-1-yl)ethoxy)-4-(6-(4-(pyridin-2-yloxy)piperidin-1-yl)pyridin-3-yl)pyrazolo[1,5-a]pyridine-3-carbonitrile To a solution of 6-hydroxy-4-(6-(4-(pyridin-2-yloxy)piperidin-1-yl)pyridin-3-yl)pyrazolo[1,5-a]pyridine-3-carbonitrile (Intermediate P78, 0.010 g, 0.0242 mmol) in DMF (0.8 mL) was added 1-(2-chloroethyl)pyrrolidin-2-one (7.16 mg, 0.0485 mmol), potassium carbonate (6.7 mg, 0.0485 mmol), and sodium bromide (3.24 mg, 0.0315 mmol). The reaction mixture was stirred at 100° C. for 72 h. After cooling to ambient temperature, the crude reaction mixture purified by C-18 reverse phase chromatography (0-70% ACN in water as the gradient eluent) to afford the title compound (8 mg, 0.0153 mmol, 63% yield). MS (apci) m/z=524.2 (M+H).

The compounds in Table WW were prepared using a similar method to that described for the synthesis of Example 405, replacing 1-(2-chloroethyl)pyrrolidin-2-one with the appropriate alkyl halide. Reactions were monitored for completion by LCMS, and reaction durations were adjusted accordingly. Title compounds were cleanly isolated following chromatographic purification using an appropriate gradient eluent (and if necessary converted to the free base).

TABLE WW

| Ex. # | Structure | Chemical Name | MS m/z |
|---|---|---|---|
| 406 | 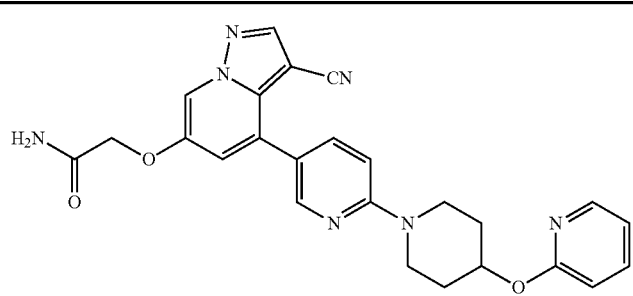 | 2-((3-cyano-4-(6-(4-(pyridin-2-yloxy)piperidin-1-yl)pyridin-3-yl)pyrazolo[1,5-a]pyridin-6-yl)oxy)acetamide | 470.10 (M + H) |

TABLE WW-continued

| Ex. # | Structure | Chemical Name | MS m/z |
|---|---|---|---|
| 407 | 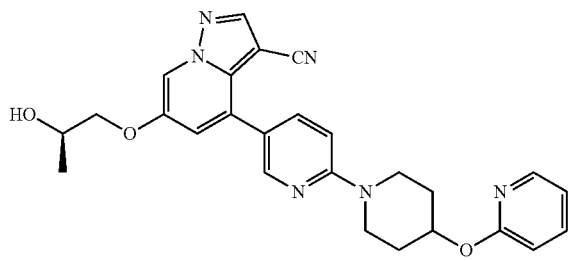 | 2-((3-cyano-4-(6-(4-(pyridin-2-yloxy)piperidin-1-yl)pyridin-3-yl)pyrazolo[1,5-a]pyridin-6-yl)oxy)-N-methylacetamide | 484.10 (M + H) |
| 408 | 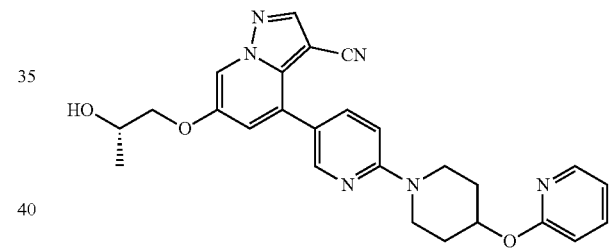 | 2-((3-cyano-4-(6-(4-(pyridin-2-yloxy)piperidin-1-yl)pyridin-3-yl)pyrazolo[1,5-a]pyridin-6-yl)oxy)-N,N-dimethylacetamide | 498.15 (M + H) |

Example 409

(R)-6-(2-hydroxypropoxy)-4-(6-(4-(pyridin-2-yloxy)piperidin-1-yl)pyridin-3-yl)pyrazolo[1,5-a]pyridine-3-carbonitrile To a solution of 6-hydroxy-4-(6-(4-(pyridin-2-yloxy)piperidin-1-yl)pyridin-3-yl)pyrazolo[1,5-a]pyridine-3-carbonitrile (Intermediate P78, 1.023 mL, 0.0512 mmol) in DMF (1.0 mL) was added aqueous sodium hydroxide (1M, 0.0563 mL, 0.0563 mmol). The mixture was stirred at rt for 5 min, at which time R-(+)-propylene oxide (35.8 μL, 0.512 mmol) was added. The reaction mixture was stirred at 80° C. for 16 h. After cooling to ambient temperature, the reaction mixture was diluted with EtOAc then washed successively with water and saturated NaCl$_{(aq)}$. The organic extract was dried over anhydrous Na$_2$SO$_{4(s)}$, filtered, and concentrated in vacuo. The residue was purified by C-18 reverse phase chromatography (5-95% ACN in water [+0.1% TFA] as the gradient eluent). The fractions containing the desired product were diluted with 4:1 DCM/IPA and washed with saturated NaHCO$_{3(aq)}$. The organic extract was dried over anhydrous Na$_2$SO$_{4(s)}$, filtered, and concentrated in vacuo to afford the title compound (8.5 mg, 0.0181 mmol, 35.3% yield). MS (apci) m/z=471.2 (M+H).

Example 410

(S)-6-(2-hydroxypropoxy)-4-(6-(4-(pyridin-2-yloxy)piperidin-1-yl)pyridin-3-yl)pyrazolo[1,5-a]pyridine-3-carbonitrile The title compound was prepared using a similar method to that described for the synthesis of Example 409, replacing R-(+)-propylene oxide with S-(−)-propylene oxide. MS (apci) m/z=471.2 (M+H).

Example 411

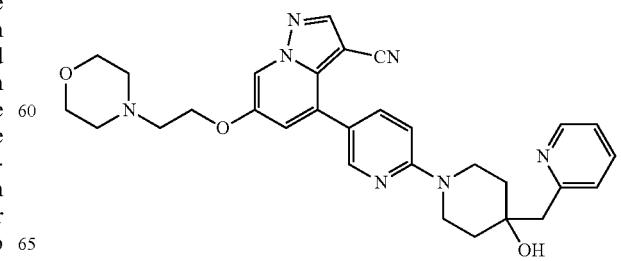

4-(6-(4-hydroxy-4-(pyridin-2-ylmethyl)piperidin-1-yl)pyridin-3-yl)-6-(2-morpholinoethoxy)pyrazolo[1,5-a]pyridine-3-carbonitrile To a solution of 4-(6-fluoropyridin-3-yl)-6-(2-morpholinoethoxy)pyrazolo[1,5-a]pyridine-3-carbonitrile (Intermediate P79, 19.7 mg, 0.05362 mmol) in DMSO (1 mL) was added 4-(pyridin-2-ylmethyl)piperidin-4-ol hydrochloride (39.3 mg, 0.1718 mmol) and cesium carbonate (157.2 mg, 0.4826 mmol). The reaction mixture was stirred at 60° C. for 16 h. After cooling to ambient temperature, the reaction mixture was diluted with DCM and washed successively with water and saturated $NH_4Cl_{(aq)}$. The aqueous fraction was extracted with DCM, and the combined organic extracts were dried over anhydrous $Na_2SO_{4(s)}$. The mixture was purified by silica chromatography (0-100% MeOH in DCM as the gradient eluent) to afford the title compound (16.9 mg, 0.02505 mmol, 46.72% yield). MS (apci) m/z=540.2 (M+H).

The compounds in Table XX were prepared using a similar method to that described for the synthesis of Example 411, replacing 4-(pyridin-2-ylmethyl)piperidin-4-ol hydrochloride with the appropriate amine. Reactions were monitored for completion by LCMS, and reaction durations were adjusted accordingly. Title compounds were cleanly isolated following chromatographic purification using an appropriate gradient eluent (and if necessary converted to the free base).

Example 414

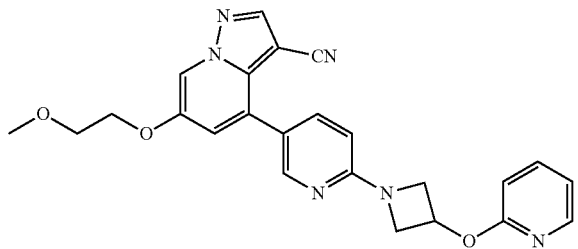

6-(2-methoxyethoxy)-4-(6-(3-(pyridin-2-yloxy)azetidin-1-yl)pyridin-3-yl)pyrazolo[1,5-a]pyridine-3-carbonitrile Step 1: Preparation of 6-hydroxy-4-(6-(3-(pyridin-2-yloxy)azetidin-1-yl)pyridin-3-yl)pyrazolo[1,5-a]pyridine-3-carbonitrile To a solution of 4-(6-fluoropyridin-3-yl)-6-hydroxypyrazolo[1,5-a]pyridine-3-carbonitrile (Intermediate P66, 0.250 g, 0.9834 mmol) in DMA (2.458 mL) was added 2-(azetidin-3-yloxy)pyridine (0.452 g, 3.010 mmol) and TEA (0.9413

TABLE XX

| Ex. # | Structure | Chemical Name | MS m/z |
|---|---|---|---|
| 412 | 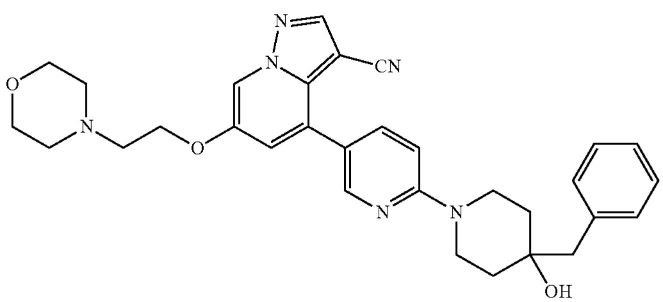 [SMILES: N#Cc1cnn2cc(OCCN3CCOCC3)cc(-c3ccc(N4CCC(O)(Cc5ccccc5)CC4)nc3)c12] | 4-(6-(4-benzyl-4-hydroxypiperidin-1-yl)pyridin-3-yl)-6-(2-morpholinoethoxy)pyrazolo[1,5-a]pyridine-3-carbonitrile | 539.20 (M + H) |
| 413 | | 6-(2-morpholinoethoxy)-4-(6-(3-(pyridin-2-yloxy)azetidin-1-yl)pyridin-3-yl)pyrazolo[1,5-a]pyridine-3-carbonitrile | 498.20 (M + H) | mL, 6.884 mmol). The reaction mixture was stirred at 95° C. for 72 h. After cooling to ambient temperature, the reaction mixture was quenched with saturated NaHCO$_{3(aq)}$ and extracted with EtOAc. The combined organic extracts were washed successively with water and saturated NaCl$_{(aq)}$ then dried over anhydrous Na$_2$SO$_{4(s)}$, filtered, and concentrated in vacuo. The residue was purified by silica chromatography (1-9% MeOH in DCM as the gradient eluent) to afford the title compound (0.1557 g, 0.4050 mmol, 41.19% yield) in sufficient purity for step 2. MS (apci) m/z=385.1 (M+H).

Step 2: Preparation of 6-(2-methoxyethoxy)-4-(6-(3-(pyridin-2-yloxy)azetidin-1-yl)pyridin-3-yl)pyrazolo[1,5-a]pyridine-3-carbonitrile To a solution of 6-hydroxy-4-(6-(3-(pyridin-2-yloxy)azetidin-1-yl)pyridin-3-yl)pyrazolo[1,5-a]pyridine-3-carbonitrile (0.030 g, 0.07804 mmol) in DMF (0.3902 mL) was added potassium carbonate (0.02157 g, 0.1561 mmol) and 2-bromoethyl methyl ether (0.01467 mL, 0.1561 mmol). The reaction mixture was stirred at 95° C. for 16 h. After cooling to ambient temperature, the reaction mixture was quenched with saturated NaHCO$_{3(aq)}$ and extracted with EtOAc. The combined organic extracts were washed successively with water and saturated NaCl$_{(aq)}$ then dried over anhydrous Na$_2$SO$_{4(s)}$, filtered, and concentrated in vacuo. The residue was purified by preparative HPLC (5-95% ACN in water [+0.1% TFA] as the gradient eluent). The fractions containing the desired product were washed with saturated NaHCO$_{3(aq)}$ and extracted with DCM. The combined organic extracts were washed successively with water and saturated NaCl$_{(aq)}$ then dried over anhydrous Na$_2$SO$_{4(s)}$, filtered, and concentrated in vacuo to afford the title compound (0.0108 g, 0.02441 mmol, 31.27% yield). MS (apci) m/z=443.2 (M+H).

Example 415

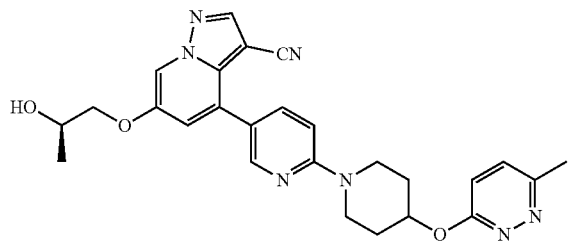 [SMILES: Cc1ccc(OC2CCN(c3ccc(-c4cc(OC[C@@H](C)O)cn5ncc(C#N)c45)cn3)CC2)nn1]

(R)-6-(2-hydroxypropoxy)-4-(6-(4-((6-methylpyridazin-3-yl)oxy)piperidin-1-yl)pyridin-3-yl)pyrazolo[1,5-a]pyridine-3-carbonitrile To a solution of (R)-4-(6-fluoropyridin-3-yl)-6-(2-hydroxypropoxy)pyrazolo[1,5-a]pyridine-3-carbonitrile (Intermediate P80, 0.020 g, 0.0640 mmol) in DMA (0.640 mL) was added 3-methyl-6-(piperidin-4-yloxy)pyridazine (0.039 g, 0.202 mmol) and TEA (0.0613 ml, 0.448 mmol). The reaction mixture was stirred at 90° C. for 48 h. After cooling to ambient temperature, the reaction mixture was quenched with water and extracted with EtOAc. The combined organic extracts were washed successively with water and saturated NaCl$_{(aq)}$ then dried over anhydrous Na$_2$SO$_{4(s)}$, filtered, and concentrated in vacuo. The residue was purified by preparative HPLC (5-95% ACN in water [+0.1% TFA] as the gradient eluent). The fractions containing the desired product were washed with saturated NaHCO$_{3(aq)}$ and extracted with DCM. The combined organic extracts were washed successively with water and saturated NaCl$_{(aq)}$ then dried over anhydrous Na$_2$SO$_{4(s)}$, filtered, and concentrated in vacuo to afford the title compound (11 mg, 0.022 mmol, 34% yield). MS (apci) m/z=486.2 (M+H).

Example 416

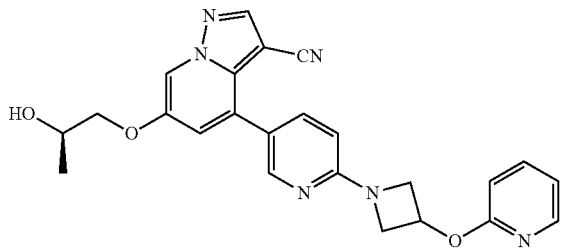 [SMILES: C[C@@H](O)COc1cc(-c2ccc(N3CC(Oc4ccccn4)C3)nc2)c2c(C#N)cnn2c1]

(R)-6-(2-hydroxypropoxy)-4-(6-(3-(pyridin-2-yloxy)azetidin-1-yl)pyridin-3-yl)pyrazolo[1,5-a]pyridine-3-carbonitrile The compound was prepared using a similar method to that described for the synthesis of Example 415, replacing 3-methyl-6-(piperidin-4-yloxy)pyridazine with 2-(azetidin-3-yloxy)pyridine. MS (apci) m/z=443.1 (M+H).

Example 417

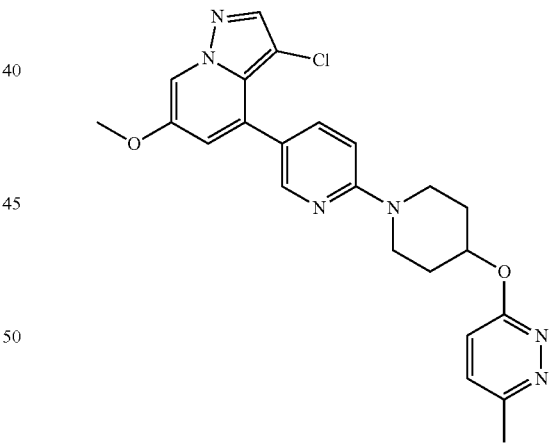

3-chloro-6-methoxy-4-(6-(4-((6-methylpyridazin-3-yl)oxy)piperidin-1-yl)pyridin-3-yl)pyrazolo[1,5-a]pyridine Step 1: Preparation of 4-(6-fluoropyridin-3-yl)-6-methoxypyrazolo[1,5-a]pyridine To a mixture of 4-bromo-6-methoxypyrazolo[1,5-a]pyridine (10.0 g, 44.04 mmol) in 1,4-dioxane (88.08 mL) was added 2-fluoro-5-(4,4,5,5-tetramethyl-1,3,2-dioxaborolan-2-yl)pyridine (11.79 g, 52.85 mmol), tetrakis(triphenylphosphine)palladium(O) (1.018 g, 0.8808 mmol) and aqueous sodium carbonate (2M, 46.24 mL, 92.49 mmol). The reaction mixture was stirred at 90° C. for 16 h. After cooling to ambient temperature, the reaction mixture was poured onto water and stirred for 4 h. The resultant precipitate was isolated by vacuum filtration then taken up in MTBE and stirred an additional 30 min. The precipitate was isolated by vacuum filtration to afford the title compound (4.616 g, 18.98 mmol, 43.09% yield) in sufficient yield for step 2. MS (apci) m/z=244.0 (M+H).

Step 2: Preparation of 3-chloro-4-(6-fluoropyridin-3-yl)-6-methoxypyrazolo[1,5-a]pyridine A solution of 4-(6-fluoropyridin-3-yl)-6-methoxypyrazolo[1,5-a]pyridine (1.00 g, 4.11 mmol) in DCM (27.4 mL) was treated with NCS (0.549 g, 4.11 mmol). The reaction mixture was stirred at rt for 16 h. The mixture was poured into 2M NaOH and extracted with 10% IPA in DCM in a PS frit. The organic extract was concentrated in vacuo, and the residue was triturated with Et$_2$O. The solid was isolated on a glass frit to afford the title compound (0.98 g, 3.53 mmol, 85.8% yield) in sufficient purity for step 3. MS (apci) m/z=278.0 (M+H).

Step 3: Preparation of 3-chloro-6-methoxy-4-(6-(4-((6-methylpyridazin-3-yl)oxy)piperidin-1-yl)pyridin-3-yl)pyrazolo[1,5-a]pyridine To a solution of 3-chloro-4-(6-fluoropyridin-3-yl)-6-methoxypyrazolo[1,5-a]pyridine (30 mg, 0.11 mmol) in DMSO (0.2 mL) was added 3-methyl-6-(piperidin-4-yloxy)pyridazine (31 mg, 0.16 mmol) and cesium carbonate (176 mg, 0.54 mmol). The reaction mixture was stirred at 90° C. for 16 h. After cooling to ambient temperature, the mixture was poured into 2M NaOH and extracted with 10% IPA in DCM in a PS frit. The organic extract was concentrated in vacuo, and the residue was purified by silica chromatography (0-100% EtOAc in hexanes as the gradient eluent) to afford the title compound (14 mg, 0.031 mmol, 29% yield). MS (apci) m/z=451.2 (M+H).

Example 418

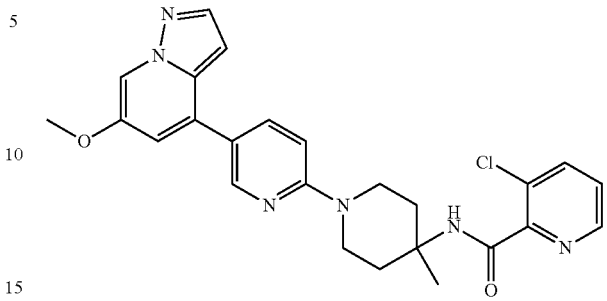

3-chloro-N-(1-(5-(6-methoxypyrazolo[1,5-a]pyridin-4-yl)pyridin-2-yl)-4-methylpiperidin-4-yl)picolinamide To a mixture of 1-(5-(6-methoxypyrazolo[1,5-a]pyridin-4-yl)pyridin-2-yl)-4-methylpiperidin-4-amine (0.057 g, 0.169 mmol) in DMSO (1.13 mL) was added 3-chloropicolinic acid (0.0399 g, 0.253 mmol), DIEA (0.132 mL, 0.760 mmol), and HATU (0.128 g, 0.338 mmol). The reaction mixture was stirred at rt for 16 h. The reaction mixture was diluted with EtOAc and washed successively with water and saturated NaCl$_{(aq)}$. The organic extract was dried over anhydrous Na$_2$SO$_{4(s)}$, and concentrated in vacuo. The residue was purified by preparative HPLC (5-95% ACN in water [+0.1% TFA] as the gradient eluent). The fractions containing the desired product were diluted with DCM and washed successively with saturated NaHCO$_{3(aq)}$ and saturated NaCl$_{(aq)}$. The organic extract was dried over anhydrous Na$_2$SO$_{4(s)}$, filtered, and concentrated in vacuo to afford the title compound (0.0501 g, 0.105 mmol, 62.2% yield). MS (apci) m/z=477.2 (M+H).

The compounds in Table YY were prepared using a similar method to that described for the synthesis of Example 418, replacing 3-chloropicolinic acid with the appropriate carboxylic acid. Reactions were monitored for completion by LCMS, and reaction durations were adjusted accordingly. Title compounds were cleanly isolated following chromatographic purification using an appropriate gradient eluent (and if necessary converted to the free base).

TABLE YY

| Ex. # | Structure | Chemical Name | MS (apci) m/z |
|---|---|---|---|
| 419 | 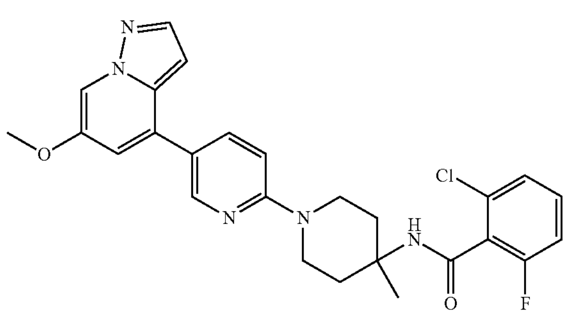 [SMILES: COc1cc(-c2ccc(N3CCC(C)(NC(=O)c4c(F)cccc4Cl)CC3)nc2)c2ccnn2c1] | 2-chloro-6-fluoro-N-(1-(5-(6-methoxypyrazolo[1,5-a]pyridin-4-yl)pyridin-2-yl)-4-methylpiperidin-4-yl)benzamide | 494.20 (M + H) |

TABLE YY-continued

| Ex. # | Structure | Chemical Name | MS (apci) m/z |
|---|---|---|---|
| 420 | 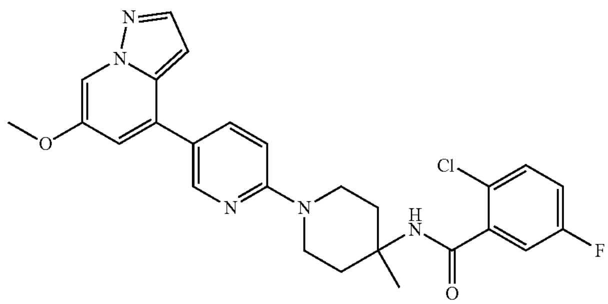 [SMILES: COc1cc(-c2ccc(N3CCC(C)(NC(=O)c4cc(F)ccc4Cl)CC3)nc2)c2ccnn2c1] | 2-chloro-5-fluoro-N-(1-(5-(6-methoxypyrazolo[1,5-a]pyridin-4-yl)pyridin-2-yl)-4-methylpiperidin-4-yl)benzamide | 494.20 (M + H) |

Example 421

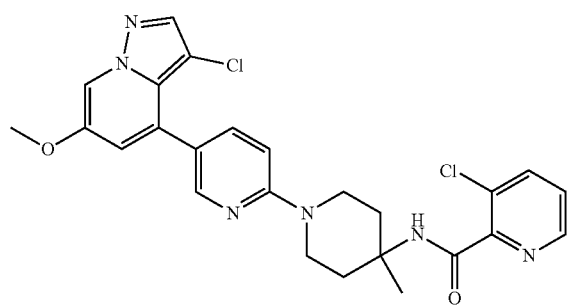 [SMILES: COc1cc(-c2ccc(N3CCC(C)(NC(=O)c4ncccc4Cl)CC3)nc2)c2c(Cl)cnn2c1]

3-chloro-N-(1-(5-(3-chloro-6-methoxypyrazolo[1,5-a]pyridin-4-yl)pyridin-2-yl)-4-methylpiperidin-4-yl)picolinamide To a mixture of 1-(5-(3-chloro-6-methoxypyrazolo[1,5-a]pyridin-4-yl)pyridin-2-yl)-4-methylpiperidin-4-amine (0.057 g, 0.153 mmol) in DMSO (1.02 mL) was added 3-chloropicolinic acid (0.0362 g, 0.230 mmol), DIEA (0.120 mL, 0.690 mmol), and HATU (0.117 g, 0.307 mmol). The reaction mixture was stirred at rt for 16 h. The reaction mixture was diluted with EtOAc and washed successively with water and saturated NaCl$_{(aq)}$. The organic extract was dried over anhydrous Na$_2$SO$_{4(s)}$, and concentrated in vacuo. The residue was purified by silica chromatography (10-99% EtOAc in hexanes as the gradient eluent) to afford the title compound (0.0415 g, 0.0811 mmol, 52.9% yield). MS (apci) m/z=511.2 (M+).

The compounds in Table ZZ were prepared using a similar method to that described for the synthesis of Example 421, replacing 3-chloropicolinic acid with the appropriate carboxylic acid. Reactions were monitored for completion by LCMS, and reaction durations were adjusted accordingly. Title compounds were cleanly isolated following chromatographic purification using an appropriate gradient eluent (and if necessary converted to the free base).

TABLE ZZ

| Ex. # | Structure | Chemical Name | MS m/z |
|---|---|---|---|
| 422 | 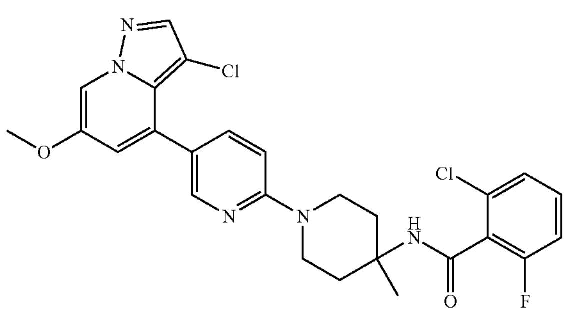 [SMILES: COc1cc(-c2ccc(N3CCC(C)(NC(=O)c4c(F)cccc4Cl)CC3)nc2)c2c(Cl)cnn2c1] | 2-chloro-N-(1-(5-(3-chloro-6-methoxypyrazolo[1,5-a]pyridin-4-yl)pyridin-2-yl)-4-methylpiperidin-4-yl)-6-fluorobenzamide | 528.20 (M$^+$) |

TABLE ZZ-continued

| Ex. # | Structure | Chemical Name | MS m/z |
|---|---|---|---|
| 423 | 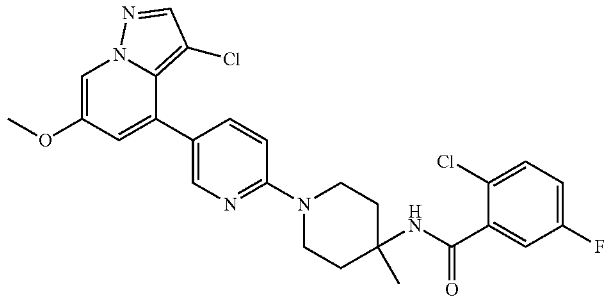 [SMILES: COc1cc(-c2ccc(N3CCC(C)(NC(=O)c4cc(F)ccc4Cl)CC3)nc2)c2c(Cl)cnn2c1] | 2-chloro-N-(1-(5-(3-chloro-6-methoxypyrazolo[1,5-a]pyridin-4-yl)pyridin-2-yl)-4-methylpiperidin-4-yl)-5-fluorobenzamide | 528.20 (M+) |

Example 424

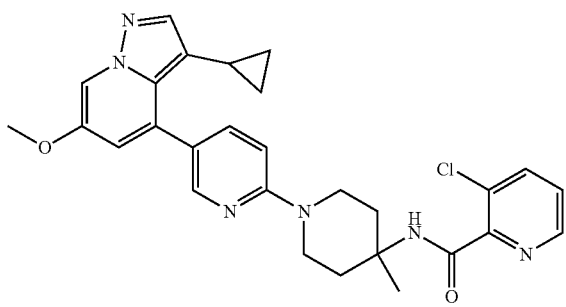 [SMILES: COc1cc(-c2ccc(N3CCC(C)(NC(=O)c4ncccc4Cl)CC3)nc2)c2c(C3CC3)cnn2c1]

3-chloro-N-(1-(5-(3-cyclopropyl-6-methoxypyrazolo[1,5-a]pyridin-4-yl)pyridin-2-yl)-4-methylpiperidin-4-yl)picolinamide Step 1: Preparation of tert-butyl (1-(5-(3-bromo-6-methoxypyrazolo[1,5-a]pyridin-4-yl)pyridin-2-yl)-4-methylpiperidin-4-yl)carbamate To a solution of tert-butyl (1-(5-(6-methoxypyrazolo[1,5-a]pyridin-4-yl)pyridin-2-yl)-4-methylpiperidin-4-yl)carbamate (Intermediate P81, 0.806 g, 1.84 mmol) in DCM (12.3 mL) was added NBS (0.328 g, 1.84 mmol). The reaction mixture was stirred at rt for 16 h. The reaction mixture was diluted with EtOAc and washed successively with water and saturated $NaCl_{(aq)}$. The organic extract was dried over anhydrous $Na_2SO_{4(s)}$, and concentrated in vacuo. The residue was purified by silica chromatography (10-90% EtOAc in hexanes as the gradient eluent) to afford the title compound (0.839 g, 1.62 mmol, 88% yield) in sufficient purity for step 2. MS (apci) m/z=518.1 (M+H+1).

Step 2: Preparation of tert-butyl (1-(5-(3-cyclopropyl-6-methoxypyrazolo[1,5-a]pyridin-4-yl)pyridin-2-yl)-4-methylpiperidin-4-yl)carbamate To a mixture of tert-butyl (1-(5-(3-bromo-6-methoxypyrazolo[1,5-a]pyridin-4-yl)pyridin-2-yl)-4-methylpiperidin-4-yl)carbamate (0.250 g, 0.484 mmol) in a biphasic mixture of toluene (2.42 mL) and water (0.4 mL) was added cyclopropylboronic acid (0.0832 g, 0.968 mmol), potassium phosphate (0.308 g, 1.45 mmol), palladium(II) acetate (0.0109 g, 0.0484 mmol) and tricyclopentylphosphine (0.0272 g, 0.0968 mmol). The reaction mixture was stirred at 90° C. for 16 h. After cooling to ambient temperature, the reaction mixture was diluted with EtOAc and washed successively with water and saturated $NaCl_{(aq)}$. The organic extract was dried over anhydrous $Na_2SO_{4(s)}$, and concentrated in vacuo. The residue was purified by silica chromatography (10-90% EtOAc in hexanes as the gradient eluent) to afford the title compound (0.061 g, 0.128 mmol, 26% yield) in sufficient purity for step 3. MS (apci) m/z=478.3 (M+H).

Step 3: Preparation of 1-(5-(3-cyclopropyl-6-methoxypyrazolo[1,5-a]pyridin-4-yl)pyridin-2-yl)-4-methylpiperidin-4-amine A solution of tert-butyl (1-(5-(3-cyclopropyl-6-methoxypyrazolo[1,5-a]pyridin-4-yl)pyridin-2-yl)-4-methylpiperidin-4-yl)carbamate (0.060 g, 0.13 mmol) in DCM (12 mL) was treated with TFA (12 mL). The reaction mixture was stirred at rt for 1 h. The reaction mixture was diluted with DCM and washed with saturated $NaHCO_{3(aq)}$. The organic extract was dried over anhydrous $Na_2SO_{4(s)}$, and concentrated in vacuo to afford the title compound (0.047 g, 0.12 mmol, 99% yield) in sufficient purity for step 4. MS (apci) m/z=378.2 (M+H).

Step 4: Preparation of 3-chloro-N-(1-(5-(3-cyclopropyl-6-methoxypyrazolo[1,5-a]pyridin-4-yl)pyridin-2-yl)-4-methylpiperidin-4-yl)picolinamide To a mixture of 1-(5-(3-cyclopropyl-6-methoxypyrazolo[1,5-a]pyridin-4-yl)pyridin-2-yl)-4-methylpiperidin-4-amine (0.047 g, 0.125 mmol) in DMSO (0.830 mL) was added 3-chloropicolinic acid (0.0294 g, 0.187 mmol), DIEA (0.0976 mL, 0.560 mmol), and HATU (0.0947 g, 0.249 mmol). The reaction mixture was stirred at rt for 16 h. The reaction mixture was diluted with EtOAc and washed successively with water and saturated $NaCl_{(aq)}$. The organic extract was dried over anhydrous $Na_2SO_{4(s)}$, and concentrated in vacuo. The residue was purified by preparative HPLC (5-95% ACN in water [+0.1% TFA] as the gradient eluent). The fractions containing the desired product were diluted with DCM and washed successively with saturated $NaHCO_{3(aq)}$ and saturated $NaCl_{(aq)}$. The organic extract was dried over anhydrous $Na_2SO_{4(s)}$, filtered, and concentrated in vacuo to afford the title compound (0.0441 g, 0.0853 mmol, 68.5% yield). MS (apci) m/z=517.2 (M+).

Example 425

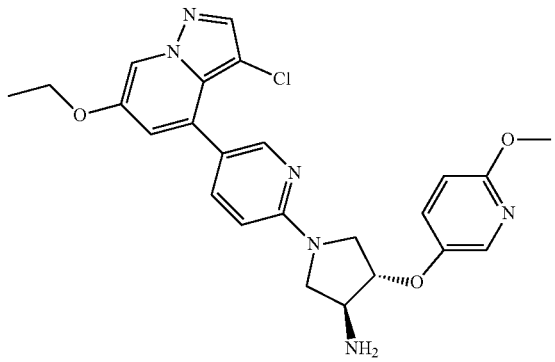 [SMILES: CCOc1cc(-c2ccc(N3C[C@H](Oc4ccc(OC)nc4)[C@@H](N)C3)nc2)c2c(Cl)cnn2c1]

(3S,4S)-1-(5-(3-chloro-6-ethoxypyrazolo[1,5-a]pyridin-4-yl)pyridin-2-yl)-4-((6-methoxypyridin-3-yl)oxy)pyrrolidin-3-amine Step 1: Preparation of 4-bromo-3-chloro-6-ethoxypyrazolo[1,5-a]pyridine To a solution of 4-bromo-3-chloropyrazolo[1,5-a]pyridin-6-ol (Intermediate P84, 2.5 g, 10.1 mmol) in DMA (150 mL) was added potassium carbonate (14.0 g, 101 mmol) and iodoethane (2.45 mL, 30.3 mmol). The reaction mixture was stirred at 65° C. for 16 h. After cooling to ambient temperature, the reaction mixture was quenched with water and extracted with EtOAc. The combined organic extracts were dried over anhydrous $Na_2SO_{4(s)}$, and concentrated in vacuo to afford the title compound (2.00 g, 7.26 mmol, 72% yield) in sufficient purity for step 2. MS (apci) m/z=277.0 (M+H).

Step 2: Preparation of 3-chloro-6-ethoxy-4-(6-fluoropyridin-3-yl)pyrazolo[1,5-a]pyridine To a solution of 4-bromo-3-chloro-6-ethoxypyrazolo[1,5-a]pyridine (1.0 g, 3.6 mmol) in 1,4-dioxane (18 mL) was added 2-fluoro-5-(4,4,5,5-tetramethyl-1,3,2-dioxaborolan-2-yl)pyridine (1.1 g, 4.7 mmol), tetrakis(triphenylphosphine)palladium (0) (0.21 g, 0.18 mmol), and aqueous sodium carbonate (2M, 9.1 mL, 18 mmol). The reaction mixture was sparged with $N_2$ and stirred at 90° C. for 4 h. After cooling to ambient temperature, the reaction mixture was quenched with water and sonicated for 5 min. The resultant precipitate was isolated by vacuum filtration and washed on the filter with $Et_2O$ to afford the title compound (0.4 g, 1.4 mmol, 38% yield) in sufficient purity for step 3. MS (apci) m/z=292.1 (M+H).

Step 3: Preparation of tert-butyl ((3S,4R)-1-(5-(3-chloro-6-ethoxypyrazolo[1,5-a]pyridin-4-yl)pyridin-2-yl)-4-hydroxypyrrolidin-3-yl)carbamate To a solution of 3-chloro-6-ethoxy-4-(6-fluoropyridin-3-yl)pyrazolo[1,5-a]pyridine (0.100 g, 0.343 mmol) in DMSO (1 mL) was added DIEA (0.296 mL, 1.71 mmol) and tert-butyl ((3S,4R)-4-hydroxypyrrolidin-3-yl)carbamate (0.139 g, 0.686 mmol). The reaction mixture was stirred at 95° C. for 16 h. After cooling to ambient temperature, the reaction mixture was quenched with water and cooled to 0° C. The resultant precipitate was isolated by vacuum filtration then taken up in 1:1 MTBE/pentane. The slurry was sonicated for 20 min, and the solids were isolated by vacuum filtration to afford the title compound (0.148 g, 0.312 mmol, 91.1% yield) in sufficient purity for step 4. MS (apci) m/z=474.15 (M+H).

Step 4: Preparation of (3S,4S)-1-(5-(3-chloro-6-ethoxypyrazolo[1,5-a]pyridin-4-yl)pyridin-2-yl)-4-((6-methoxypyridin-3-yl)oxy)pyrrolidin-3-amine To a solution of tert-butyl ((3S,4R)-1-(5-(3-chloro-6-ethoxypyrazolo[1,5-a]pyridin-4-yl)pyridin-2-yl)-4-hydroxypyrrolidin-3-yl)carbamate (0.040 g, 0.0844 mmol) in 1:1 THF/DCM (0.8 mL) was added 6-methoxypyridin-3-ol (0.0211 g, 0.169 mmol) and triphenylphosphane (0.0443 g, 0.169 mmol). The reaction mixture was sparged with argon and stirred at rt for 16 h. The reaction mixture was quenched with saturated $NH_4Cl_{(aq)}$ and extracted with DCM. The combined organic extracts were dried using a PS frit, concentrated in vacuo, and purified by silica chromatography (0-100% EtOAc in hexanes as the gradient eluent). The fractions containing the desired product were concentrated in vacuo, and the residue was taken up in 6M HCl in IPA and stirred for 2 h. The mixture was concentrated in vacuo, taken up in water and 2M NaOH, then extracted with DCM. The combined organic extracts were dried using a PS frit, concentrated in vacuo, and purified by silica chromatography (0-35% [9:1 MeOH/$NH_4$OH] in EtOAc as the gradient eluent to afford the title compound (0.004 g, 0.00832 mmol, 9.85% yield). MS (apci) m/z=481.2 (M+H).

Example 426

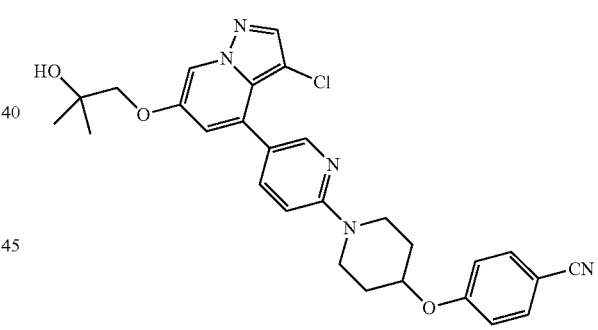

4-((1-(5-(3-chloro-6-(2-hydroxy-2-methylpropoxy)pyrazolo[1,5-a]pyridin-4-yl)pyridin-2-yl)piperidin-4-yl)oxy)benzonitrile To a solution of 1-((3-chloro-4-(6-fluoropyridin-3-yl)pyrazolo[1,5-a]pyridin-6-yl)oxy)-2-methylpropan-2-ol (Intermediate P85, 0.026 g, 0.077 mmol) in DMA (0.5 mL) was added TEA (0.024 g, 0.23 mmol) and 4-(piperidin-4-yloxy)benzonitrile (0.023 g, 0.12 mmol). The reaction mixture was stirred at 105° C. for 16 h. After cooling to ambient temperature, the reaction mixture was quenched with water and extracted with DCM. The combined organic extracts were dried over anhydrous $Na_2SO_{4(s)}$, concentrated in vacuo, and purified by silica chromatography (0-100% EtOAc in hexanes as the gradient eluent) to afford the title compound (0.012 g, 0.023 mmol, 30% yield). MS (apci) m/z=518.2 (M+H).

The compounds in Table AAA were prepared using a similar method to that described for the synthesis of Example 426, replacing 4-(piperidin-4-yloxy)benzonitrile with the appropriate amine reagent. Reactions were monitored for completion by LCMS, and reaction durations were adjusted accordingly. Title compounds were cleanly isolated following chromatographic purification using an appropriate gradient eluent (and if necessary converted to the free base).

TABLE AAA

| Ex. # | Structure | Chemical Name | MS m/z |
|---|---|---|---|
| 427 | 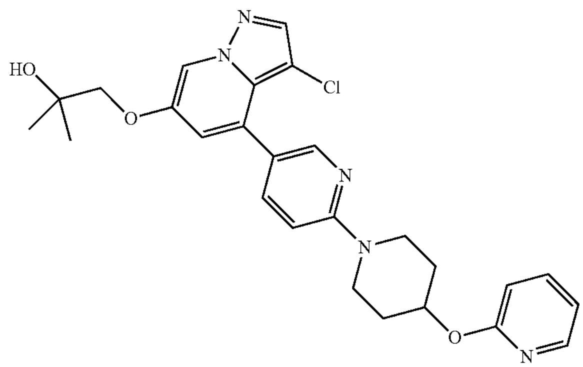 [SMILES: CC(C)(O)COc1cc(-c2ccc(N3CCC(Oc4ccccn4)CC3)nc2)c2c(Cl)cnn2c1] | 1-((3-chloro-4-(6-(4-(pyridin-2-yloxy)piperidin-1-yl)pyridin-3-yl)pyrazolo[1,5-a]pyridin-6-yl)oxy)-2-methylpropan-2-ol | 494.20 (M + H) |
| 428 | 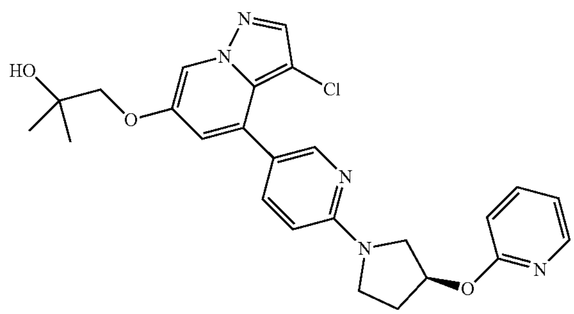 [SMILES: CC(C)(O)COc1cc(-c2ccc(N3CC[C@H](Oc4ccccn4)C3)nc2)c2c(Cl)cnn2c1] | (S)-1-((3-chloro-4-(6-(3-(pyridin-2-yloxy)pyrrolidin-1-yl)pyridin-3-yl)pyrazolo[1,5-a]pyridin-6-yl)oxy)-2-methylpropan-2-ol | 480.20 (M + H) |
| 429 | 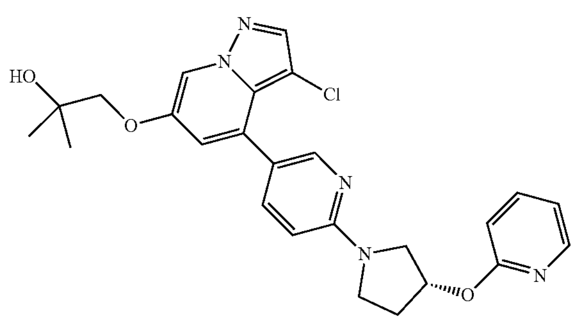 [SMILES: CC(C)(O)COc1cc(-c2ccc(N3CC[C@@H](Oc4ccccn4)C3)nc2)c2c(Cl)cnn2c1] | (R)-1-((3-chloro-4-(6-(3-(pyridin-2-yloxy)pyrrolidin-1-yl)pyridin-3-yl)pyrazolo[1,5-a]pyridin-6-yl)oxy)-2-methylpropan-2-ol | 480.20 (M + H) |
| 430 | 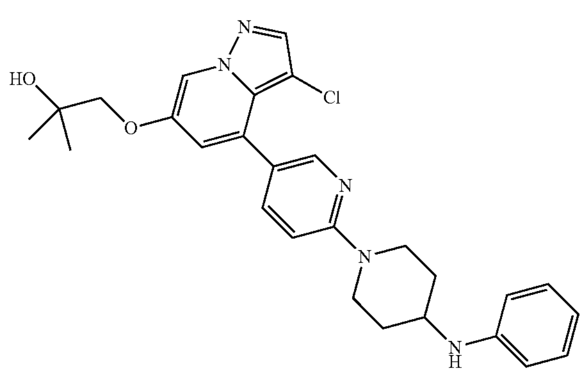 [SMILES: CC(C)(O)COc1cc(-c2ccc(N3CCC(Nc4ccccc4)CC3)nc2)c2c(Cl)cnn2c1] | 1-((3-chloro-4-(6-(4-(phenylamino)piperidin-1-yl)pyridin-3-yl)pyrazolo[1,5-a]pyridin-6-yl)oxy)-2-methylpropan-2-ol | 492.20 (M + H) |

TABLE AAA-continued

| Ex. # Structure | Chemical Name | MS m/z |
|---|---|---|
| 431 | 1-((3-chloro-4-(6-(4-((6-methoxypyridin-3-yl)oxy)piperidin-1-yl)pyridin-3-yl)pyrazolo[1,5-a]pyridin-6-yl)oxy)-2-methylpropan-2-ol | 524.20 (M + H) |

Example 432

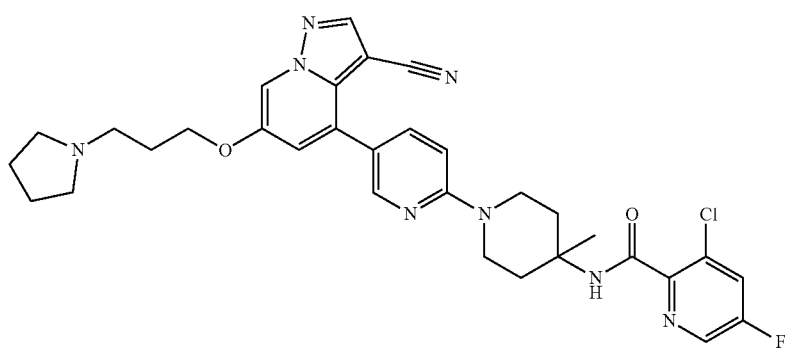 [SMILES: CC1(NC(=O)c2ncc(F)cc2Cl)CCN(c2ccc(-c3cc(OCCCN4CCCC4)cn4ncc(C#N)c34)cn2)CC1]

3-chloro-N-(1-(5-(3-cyano-6-(3-(pyrrolidin-1-yl)propoxy)pyrazolo[1,5-a]pyridin-4-yl)pyridin-2-yl)-4-methylpiperidin-4-yl)-5-fluoropicolinamide To a solution of 3-chloro-N-(1-(5-(3-cyano-6-hydroxypyrazolo[1,5-a]pyridin-4-yl)pyridin-2-yl)-4-methylpiperidin-4-yl)-5-fluoropicolinamide (Intermediate P86, 0.035 g, 0.0692 mmol) in DMA (0.692 mL) was added potassium carbonate (0.0478 g, 0.346 mmol). The reaction mixture was sparged with argon, then 1-(3-chloropropyl)-pyrrolidine (0.0204 g, 0.138 mmol) was added, and the reaction mixture was stirred at 60° C. for 5 h. After cooling to ambient temperature, the reaction mixture was directly purified by preparative HPLC (5-75% ACN in water [+2% TFA] as the gradient eluent). The fractions containing the desired product were diluted with 4:1 DCM/IPA and washed successively with saturated $NaHCO_{3(aq)}$ and saturated $NaCl_{(aq)}$. The organic extract was dried over anhydrous $Na_2SO_{4(s)}$, filtered, and concentrated in vacuo to afford the title compound (0.0186 g, 0.0301 mmol, 43.6% yield). MS (apci) m/z=617.3 (M+H).

The compounds in Table BBB were prepared using a similar method to that described for the synthesis of Example 432, replacing 1-(3-chloropropyl)-pyrrolidine with the appropriate alkyl halide. Reactions were monitored for completion by LCMS, and reaction durations were adjusted accordingly. Title compounds were cleanly isolated following chromatographic purification using an appropriate gradient eluent (and if necessary converted to the free base).

TABLE BBB

| Ex. # | Structure | Chemical Name | MS m/z |
|---|---|---|---|
| 433 | 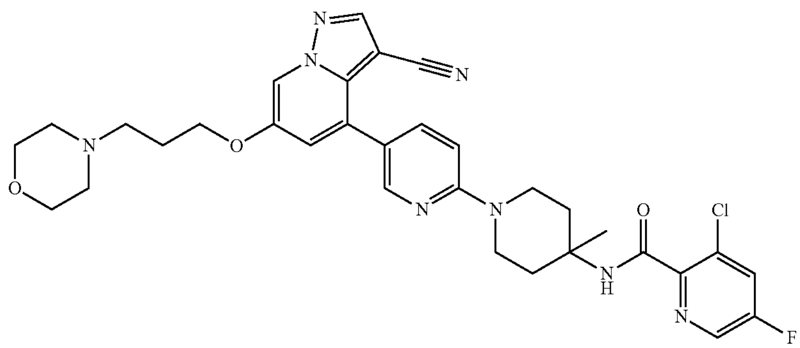 [SMILES: CC1(NC(=O)c2ncc(F)cc2Cl)CCN(c2ccc(-c3cc(OCCCN4CCOCC4)cn4ncc(C#N)c34)cn2)CC1] | 3-chloro-N-(1-(5-(3-cyano-6-(3-morpholinopropoxy)pyrazolo[1,5-a]pyridin-4-yl)pyridin-2-yl)-4-methylpiperidin-4-yl)-5-fluoropicolinamide | 633.30 (M + H) |
| 434 | 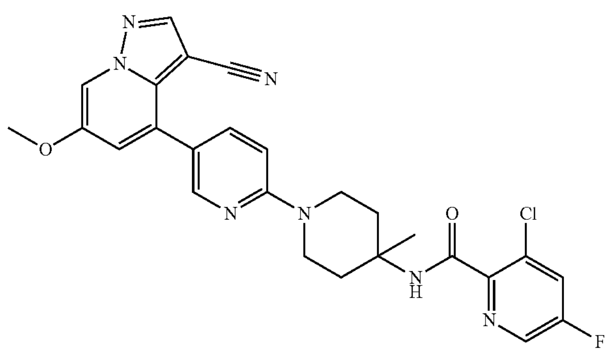 [SMILES: COc1cc(-c2ccc(N3CCC(C)(NC(=O)c4ncc(F)cc4Cl)CC3)nc2)c2c(C#N)cnn2c1] | 3-chloro-N-(1-(5-(3-cyano-6-methoxypyrazolo[1,5-a]pyridin-4-yl)pyridin-2-yl)-4-methylpiperidin-4-yl)-5-fluoropicolinamide | 520.2 (M + H) |
| 435 | 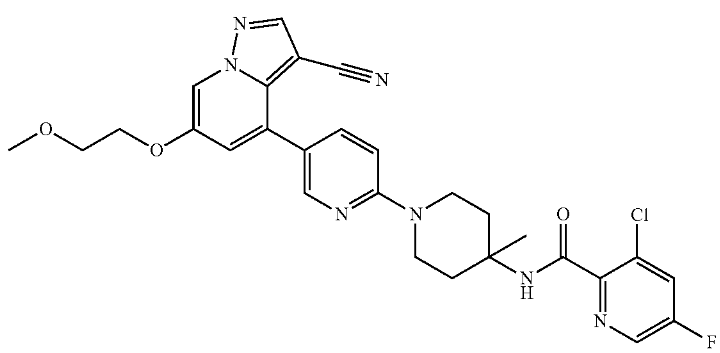 [SMILES: COCCOc1cc(-c2ccc(N3CCC(C)(NC(=O)c4ncc(F)cc4Cl)CC3)nc2)c2c(C#N)cnn2c1] | 3-chloro-N-(1-(5-(3-cyano-6-(2-methoxyethoxy)pyrazolo[1,5-a]pyridin-4-yl)pyridin-2-yl)-4-methylpiperidin-4-yl)-5-fluoropicolinamide | 564.20 (M + H) |
| 436 | 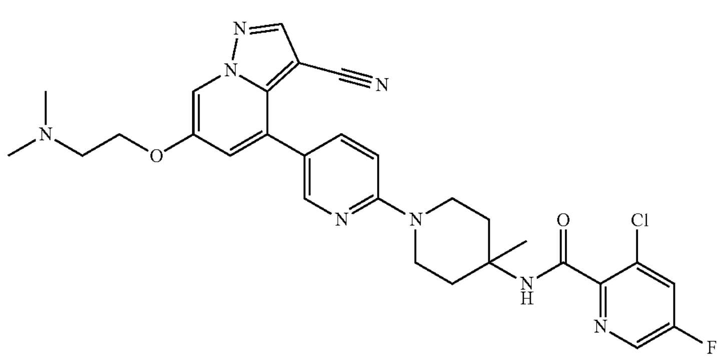 [SMILES: CN(C)CCOc1cc(-c2ccc(N3CCC(C)(NC(=O)c4ncc(F)cc4Cl)CC3)nc2)c2c(C#N)cnn2c1] | 3-chloro-N-(1-(5-(3-cyano-6-(2-(dimethylamino)ethoxy)pyrazolo[1,5-a]pyridin-4-yl)pyridin-2-yl)-4-methylpiperidin-4-yl)-5-fluoropicolinamide | 577.20 (M + H) |

Example 437

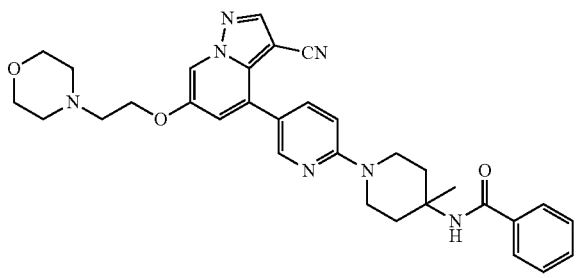 [SMILES: CC1(NC(=O)c2ccccc2)CCN(c2ccc(-c3cc(OCCN4CCOCC4)cn4ncc(C#N)c34)cn2)CC1]

N-(1-(5-(3-cyano-6-(2-morpholinoethoxy)pyrazolo[1,5-a]pyridin-4-yl)pyridin-2-yl)-4-methylpiperidin-4-yl)benzamide To a solution of N-(1-(5-(3-cyano-6-hydroxypyrazolo[1,5-a]pyridin-4-yl)pyridin-2-yl)-4-methylpiperidin-4-yl)benzamide (Intermediate P87, 30.3 mg, 0.0670 mmol) in DMA (0.7 mL) was added 4-(2-chloroethyl)morpholine hydrochloride (24.9 mg, 0.134 mmol) and cesium carbonate (109 mg, 0.335 mmol). The reaction mixture was stirred at 60° C. for 16 h. After cooling to ambient temperature, the reaction mixture was diluted with EtOAc and washed successively with water and saturated NaCl$_{(aq)}$, dried over anhydrous Na$_2$SO$_{4(s)}$, filtered, and concentrated in vacuo. The residue was purified by C-18 reverse phase chromatography (5-95% ACN in water [+0.1% TFA] as the gradient eluent). The fractions containing the desired product were diluted with 4:1 DCM/IPA and washed with saturated NaHCO$_{3(aq)}$. The organic extract was dried over anhydrous Na$_2$SO$_{4(s)}$, filtered, and concentrated in vacuo to afford the title compound (22.3 mg, 0.0394 mmol, 58.9% yield). MS (apci) m/z=566.3 (M+H).

The compounds in Table CCC were prepared using a similar method to that described for the synthesis of Example 437, replacing 4-(2-chloroethyl)morpholine hydrochloride with the appropriate alkyl halide. Reactions were monitored for completion by LCMS, and reaction durations were adjusted accordingly. Title compounds were cleanly isolated following chromatographic purification using an appropriate gradient eluent (and if necessary converted to the free base).

TABLE CCC

| Ex. # | Structure | Chemical Name | MS m/z |
|---|---|---|---|
| 438 | 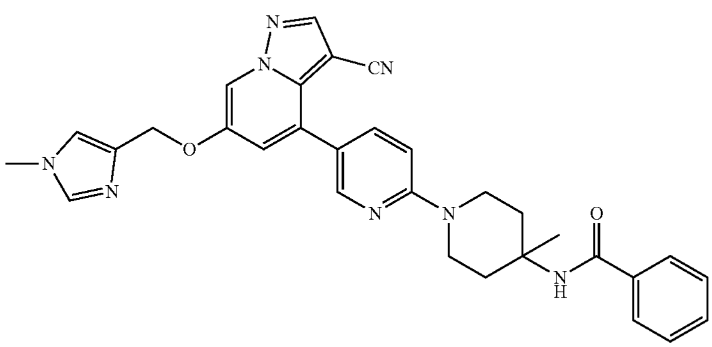 [SMILES: Cn1cnc(COc2cc(-c3ccc(N4CCC(C)(NC(=O)c5ccccc5)CC4)nc3)c3c(C#N)cnn3c2)c1] | N-(1-(5-(3-cyano-6-((1-methyl-1H-imidazol-4-yl)methoxy)pyrazolo[1,5-a]pyridin-4-yl)pyridin-2-yl)-4-methylpiperidin-4-yl)benzamide | 547.30 (M + H) |
| 439 | 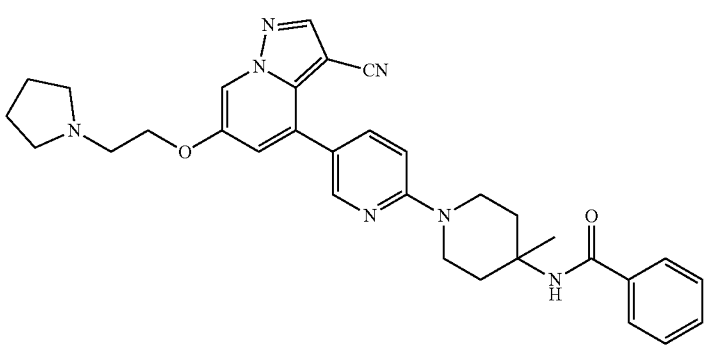 [SMILES: CC1(NC(=O)c2ccccc2)CCN(c2ccc(-c3cc(OCCN4CCCC4)cn4ncc(C#N)c34)cn2)CC1] | N-(1-(5-(3-cyano-6-(2-(pyrrolidin-1-yl)ethoxy)pyrazolo[1,5-a]pyridin-4-yl)pyridin-2-yl)-4-methylpiperidin-4-yl)benzamide | 550.30 (M + H) |

TABLE CCC-continued

| Ex. # | Structure | Chemical Name | MS m/z |
|---|---|---|---|
| 440 | 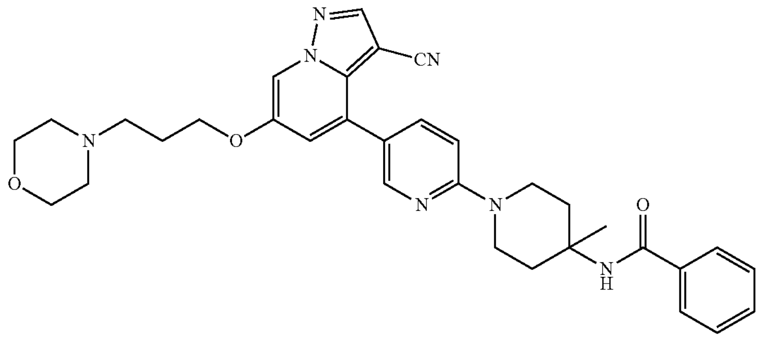 [SMILES: CC1(NC(=O)c2ccccc2)CCN(c2ccc(-c3cc(OCCCN4CCOCC4)cn4ncc(C#N)c34)cn2)CC1] | N-(1-(5-(3-cyano-6-(3-morpholinopropoxy)pyrazolo[1,5-a]pyridin-4-yl)pyridin-2-yl)-4-methylpiperidin-4-yl)benzamide | 580.30 (M + H) |

Example 441

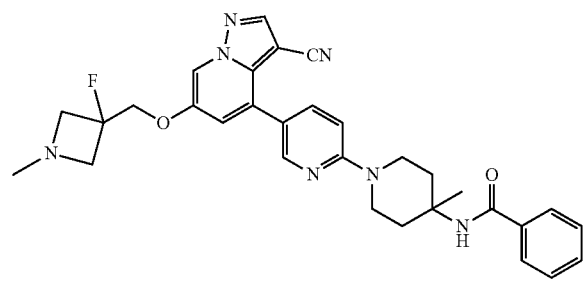 [SMILES: CN1CC(F)(COc2cc(-c3ccc(N4CCC(C)(NC(=O)c5ccccc5)CC4)nc3)c3c(C#N)cnn3c2)C1]

N-(1-(5-(3-cyano-6-((3-fluoro-1-methylazetidin-3-yl)methoxy)pyrazolo[1,5-a]pyridin-4-yl)pyridin-2-yl)-4-methylpiperidin-4-yl)benzamide Step 1: Preparation of tert-butyl 3-(((4-(6-(4-benzamido-4-methylpiperidin-1-yl)pyridin-3-yl)-3-cyanopyrazolo[1,5-a]pyridin-6-yl)oxy)methyl)-3-fluoroazetidine-1-carboxylate To a solution of N-(1-(5-(3-cyano-6-hydroxypyrazolo[1,5-a]pyridin-4-yl)pyridin-2-yl)-4-methylpiperidin-4-yl)benzamide (Intermediate P87, 44.8 mg, 0.0990 mmol) in DMA (1 mL) was added tert-butyl 3-(bromomethyl)-3-fluoroazetidine-1-carboxylate (53.1 mg, 0.198 mmol) and cesium carbonate (161 mg, 0.495 mmol). The reaction mixture was stirred at 60° C. for 16 h. After cooling to ambient temperature, the reaction mixture was diluted with EtOAc and washed successively with water and brine. The organic extract was dried over anhydrous Na$_2$SO$_{4(s)}$, filtered, and concentrated in vacuo to afford the title compound (assumed theoretical yield, 63 mg, 0.099 mmol) in sufficient purity for step 2. MS (apci) m/z=640.25 (M+H).

Step 2: Preparation of N-(1-(5-(3-cyano-6-((3-fluoroazetidin-3-yl)methoxy)pyrazolo[1,5-a]pyridin-4-yl)pyridin-2-yl)-4-methylpiperidin-4-yl)benzamide A solution of tert-butyl 3-(((4-(6-(4-benzamido-4-methylpiperidin-1-yl)pyridin-3-yl)-3-cyanopyrazolo[1,5-a]pyridin-6-yl)oxy)methyl)-3-fluoroazetidine-1-carboxylate in DCM (0.5 mL) was treated with TFA (0.5 mL, 6.5 mmol). The reaction mixture was stirred at rt for 30 min then concentrated in vacuo. The resultant crude residue was directly purified by C-18 reverse phase chromatography (5-95% ACN in water [+0.1% TFA] as the gradient eluent). The fractions containing the desired product were diluted with 4:1 DCM/IPA and washed with saturated NaHCO$_{3(aq)}$. The organic extract was dried over anhydrous Na$_2$SO$_{4(s)}$, filtered, and concentrated in vacuo to afford the title compound (29.5 mg, 0.055 mmol, 55.2% yield over two steps). MS (apci) m/z=540.3 (M+H).

Step 3: Preparation of N-(1-(5-(3-cyano-6-((3-fluoro-1-methylazetidin-3-yl)methoxy)pyrazolo[1,5-a]pyridin-4-yl)pyridin-2-yl)-4-methylpiperidin-4-yl)benzamide To a solution of N-(1-(5-(3-cyano-6-((3-fluoroazetidin-3-yl)methoxy)pyrazolo[1,5-a]pyridin-4-yl)pyridin-2-yl)-4-methylpiperidin-4-yl)benzamide (29.5 mg, 0.055 mmol) in 1:1 DCM:MeOH (1.1 mL) was added formaldehyde (21 µL, 0.273 mmol) was added, followed by NaBH(AcO)$_3$ (58 mg, 0.273 mmol) The resulting reaction mixture was allowed to stir 30 min at ambient temperature. The reaction was concentrated in vacuo. The residue was purified directly by C18 reverse phase chromatography (5-95% ACN in water with 0.1% TFA as the gradient eluent) to afford the title compound as the TFA salt. The TFA salt was treated with saturated NaHCO$_{3(aq)}$ and extracted with 4:1 DCM:IPA. The combined organic extracts were dried over anhydrous Na$_2$SO$_{4(s)}$, filtered and concentrated in vacuo to afford the title compound (24 mg, 78% yield). MS (apci) m/z=554.3 (M+H).

Example 442

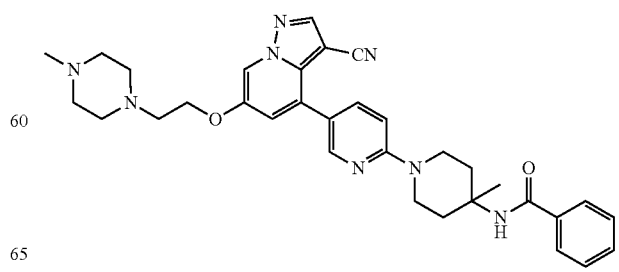

687

N-(1-(5-(3-cyano-6-(2-(4-methylpiperazin-1-yl)ethoxy)pyrazolo[1,5-a]pyridin-4-yl)pyridin-2-yl)-4-methylpiperidin-4-yl)benzamide To a solution of N-(1-(5-(3-cyano-6-(2-(piperazin-1-yl)ethoxy)pyrazolo[1,5-a]pyridin-4-yl)pyridin-2-yl)-4-methylpiperidin-4-yl)benzamide (Intermediate P88, 32.7 mg, 0.0579 mmol) in 1:1 DCM/MeOH (1 mL) was added formaldehyde (0.0218 mL, 0.290 mmol) and sodium triacetoxyborohydride (61.4 mg, 0.290 mmol). The reaction mixture was stirred at rt for 16 h then concentrated in vacuo. The residue was directly purified by C-18 reverse phase chromatography (5-95% ACN in water [+0.1% TFA] as the gradient eluent). The fractions containing the desired product were diluted with 4:1 DCM/IPA and washed with saturated $NaHCO_{3(aq)}$. The organic extract was dried over anhydrous $Na_2SO_{4(s)}$, filtered, and concentrated in vacuo to afford the title compound (21.4 mg, 0.0370 mmol, 63.9% yield). MS (apci) m/z=579.4 (M+H).

Example 443

688

N-(1-(5-(6-(2-(4-acetylpiperazin-1-yl)ethoxy)-3-cyanopyrazolo[1,5-a]pyridin-4-yl)pyridin-2-yl)-4-methylpiperidin-4-yl)benzamide To a solution of N-(1-(5-(3-cyano-6-(2-(piperazin-1-yl)ethoxy)pyrazolo[1,5-a]pyridin-4-yl)pyridin-2-yl)-4-methylpiperidin-4-yl)benzamide (Intermediate P88, 46.4 mg, 0.0822 mmol) in DCM (1 mL) was added TEA (0.0557 mL, 0.411 mmol) then acetyl chloride (0.164 mL, 0.164 mmol). The reaction mixture was stirred at rt for 16 h then concentrated in vacuo. The residue was directly purified by C-18 reverse phase chromatography (5-95% ACN in water [+0.1% TFA] as the gradient eluent). The fractions containing the desired product were diluted with 4:1 DCM/IPA and washed with saturated $NaHCO_{3(aq)}$. The organic extract was dried over anhydrous $Na_2SO_{4(s)}$, filtered, and concentrated in vacuo. The residue was purified by silica chromatography (1-30% [MeOH+2% $NH_4OH$] in DCM as the gradient eluent) to afford the title compound (24.7 mg, 0.0407 mmol, 49.5% yield). MS (apci) m/z=607.4 (M+H).

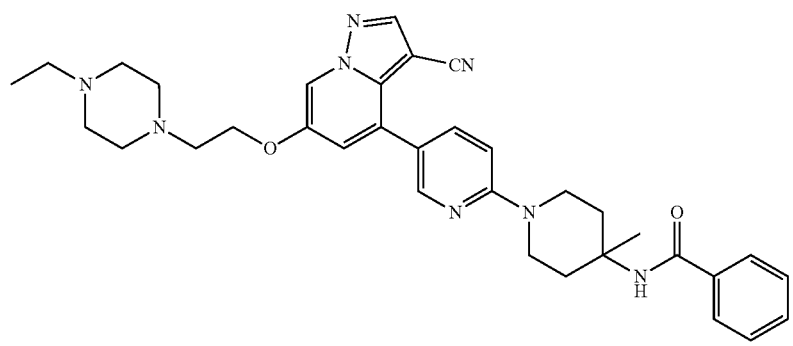 [SMILES: CCN1CCN(CCOc2cc(-c3ccc(N4CCC(C)(NC(=O)c5ccccc5)CC4)nc3)c3c(C#N)cnn3c2)CC1]

N-(1-(5-(3-cyano-6-(2-(4-ethylpiperazin-1-yl)ethoxy)pyrazolo[1,5-a]pyridin-4-yl)pyridin-2-yl)-4-methylpiperidin-4-yl)benzamide The compound was prepared using a similar method to that described for the synthesis of Example 442, replacing formaldehyde with acetaldehyde. MS (apci) m/z=593.4 (M+H).

Example 444

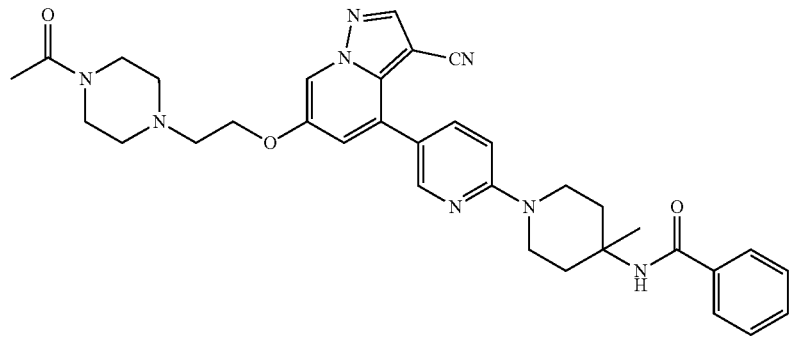 [SMILES: CC(=O)N1CCN(CCOc2cc(-c3ccc(N4CCC(C)(NC(=O)c5ccccc5)CC4)nc3)c3c(C#N)cnn3c2)CC1]

Example 445

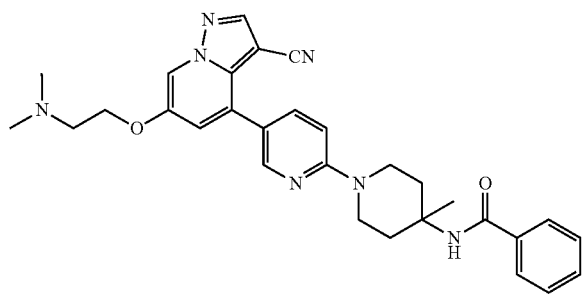 [SMILES: CN(C)CCOc1cc(-c2ccc(N3CCC(C)(NC(=O)c4ccccc4)CC3)nc2)c2c(C#N)cnn2c1]

N-(1-(5-(3-cyano-6-(2-(dimethylamino)ethoxy)pyrazolo[1,5-a]pyridin-4-yl)pyridin-2-yl)-4-methylpiperidin-4-yl)benzamide Step 1: Preparation of tert-butyl (2-((4-(6-(4-benzamido-4-methylpiperidin-1-yl)pyridin-3-yl)-3-cyanopyrazolo[1,5-a]pyridin-6-yl)oxy)ethyl)carbamate To a solution of N-(1-(5-(3-cyano-6-hydroxypyrazolo[1,5-a]pyridin-4-yl)pyridin-2-yl)-4-methylpiperidin-4-yl)benzamide (Intermediate P87, 64.2 mg, 0.142 mmol) in DMA (1.5 mL) was added 2-(Boc-amino)ethyl bromide (63.6 mg, 0.284 mmol) and cesium carbonate (231 mg, 0.709 mmol). The reaction mixture was stirred at 60° C. for 16 h. After cooling to ambient temperature, the reaction mixture was diluted with EtOAc and washed successively with water and saturated NaCl$_{(aq)}$, dried over anhydrous Na$_2$SO$_{4(s)}$, filtered, and concentrated in vacuo to afford the title compound (assumed theoretical yield, 84.6 mg, 0.142 mmol) in sufficient purity for step 2. MS (apci) m/z=596.3 (M+H).

Step 2: Preparation of N-(1-(5-(6-(2-aminoethoxy)-3-cyanopyrazolo[1,5-a]pyridin-4-yl)pyridin-2-yl)-4-methylpiperidin-4-yl)benzamide A solution of tert-butyl (2-((4-(6-(4-benzamido-4-methylpiperidin-1-yl)pyridin-3-yl)-3-cyanopyrazolo[1,5-a]pyridin-6-yl)oxy)ethyl)carbamate (84.6 mg, 0.142 mmol) in DCM (0.75 mL) was treated with TFA (0.75 mL, 9.8 mmol). The reaction mixture was stirred at rt for 30 min then concentrated in vacuo. The residue was directly purified by C-18 reverse phase chromatography (5-95% ACN in water [+0.1% TFA] as the gradient eluent). The fractions containing the desired product were diluted with 4:1 DCM/IPA and washed with saturated NaHCO$_{3(aq)}$. The organic extract was dried over anhydrous Na$_2$SO$_{4(s)}$, filtered, and concentrated in vacuo to afford the title compound (17.9 mg, 0.0361 mmol, 25.5% yield over two steps). MS (apci) m/z=496.2 (M+H).

Step 3: Preparation of N-(1-(5-(3-cyano-6-((3-fluoro-1-methylazetidin-3-yl)methoxy)pyrazolo[1,5-a]pyridin-4-yl)pyridin-2-yl)-4-methylpiperidin-4-yl)benzamide To a solution of N-(1-(5-(6-(2-aminoethoxy)-3-cyanopyrazolo[1,5-a]pyridin-4-yl)pyridin-2-yl)-4-methylpiperidin-4-yl)benzamide (18 mg, 0.036 mmol) in 1:1 DCM:MeOH (0.5 mL) was added formaldehyde (27 µL, 0.36 mmol) was added, followed by NaBH(AcO)$_3$ (77 mg, 0.36 mmol) The resulting reaction mixture was allowed to stir 16 h at ambient temperature. The reaction was concentrated in vacuo. The residue was purified directly by C18 reverse phase chromatography (5-95% ACN in water with 0.1% TFA as the gradient eluent) to afford the title compound as the TFA salt. The TFA salt was treated with saturated NaHCO$_{3(aq)}$ and extracted with 4:1 DCM:IPA. The combined organic extracts were dried over anhydrous Na$_2$SO$_{4(s)}$, filtered and concentrated in vacuo to afford the title compound (9 mg, 49% yield). MS (apci) m/z=524.3 (M+H).

Example 446

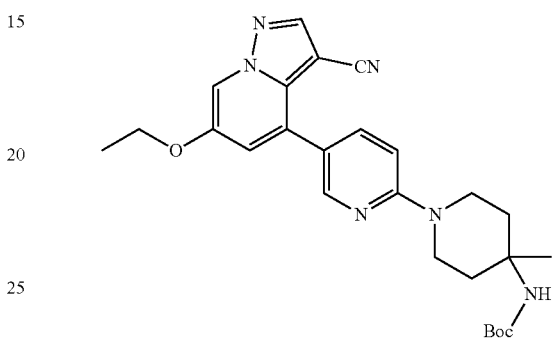

tert-butyl (1-(5-(3-cyano-6-ethoxypyrazolo[1,5-a]pyridin-4-yl)pyridin-2-yl)-4-methylpiperidin-4-yl)carbamate To a solution of 6-ethoxy-4-(6-fluoropyridin-3-yl)pyrazolo[1,5-a]pyridine-3-carbonitrile (Intermediate P6, 106.2 mg, 0.3762 mmol) in DMSO (1 mL) was added tert-butyl (4-methylpiperidin-4-yl)carbamate (201.6 mg, 0.9406 mmol) and cesium carbonate (858.1 mg, 2.634 mmol). The reaction mixture was stirred at 60° C. for 16 h. After cooling to ambient temperature, the reaction mixture was diluted with water and extracted into DCM. The combined organic extracts were dried over anhydrous Na$_2$SO$_{4(s)}$ and purified by silica chromatography (0-100% EtOAc in hexanes as the gradient eluent) to afford the title compound (159.2 mg, 0.3274 mmol, 87.01% yield). MS (apci) m/z=477.2 (M+H).

Example 447

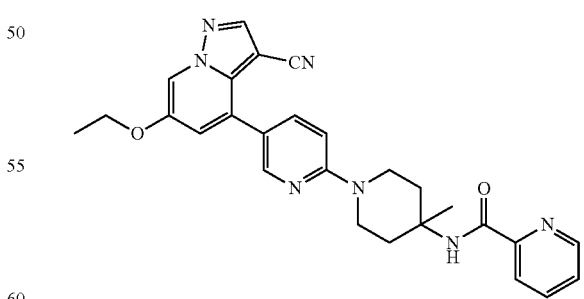

N-(1-(5-(3-cyano-6-ethoxypyrazolo[1,5-a]pyridin-4-yl)pyridin-2-yl)-4-methylpiperidin-4-yl)picolinamide To a solution of 4-(6-(4-amino-4-methylpiperidin-1-yl)pyridin-3-yl)-6-ethoxypyrazolo[1,5-a]pyridine-3-carbonitrile (Intermediate P89, 25.6 mg, 0.0680 mmol) in DCM (0.136 mL) was added 2-picolinic acid (10.9 mg, 0.0884 mmol), HATU (31.0 mg, 0.0816 mmol), and DIEA (0.0474 mL, 0.272 mmol). The reaction mixture was stirred at rt for 72 h. After cooling to ambient temperature, the reaction mixture was washed with water and concentrated in vacuo. The residue was purified by silica chromatography (50-100% EtOAc in hexanes then 0-10% MeOH in EtOAc as the gradient eluent) to afford the title compound (23 mg, 0.0473 mmol, 70% yield). MS (apci) m/z=482.2 (M+H).

Example 448

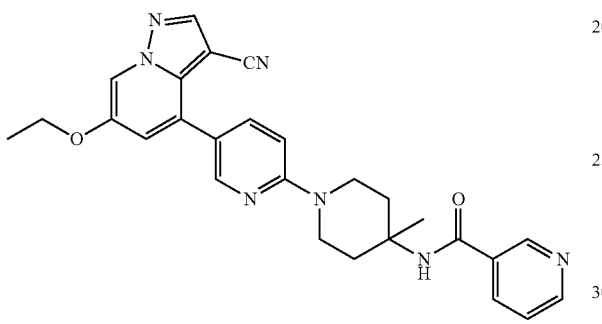

N-(1-(5-(3-cyano-6-ethoxypyrazolo[1,5-a]pyridin-4-yl)pyridin-2-yl)-4-methylpiperidin-4-yl)nicotinamide The title compound was prepared using a similar method to that described for the synthesis of Example 447, replacing 2-picolinic acid with nicotinic acid. MS (apci) m/z=482.2 (M+H).

Example 449

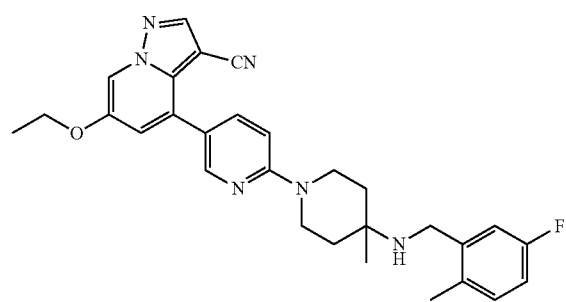 [SMILES: CCOc1cc(-c2ccc(N3CCC(C)(NCc4cc(F)ccc4C)CC3)nc2)c2c(C#N)cnn2c1]

6-ethoxy-4-(6-(4-(((5-fluoro-2-methylbenzyl)amino)-4-methylpiperidin-1-yl)pyridin-3-yl)pyrazolo[1,5-a]pyridine-3-carbonitrile To a solution of 4-(6-(4-amino-4-methylpiperidin-1-yl)pyridin-3-yl)-6-ethoxypyrazolo[1,5-a]pyridine-3-carbonitrile hydrochloride (Intermediate P89, 26 mg, 0.0630 mmol) in DMF (0.315 mL) was added TEA (0.018 mL, 0.126 mmol) and stirred for 5 min, at which time 5-fluoro-2-methylbenzaldehyde (13.0 mg, 0.0944 mmol) and sodium triacetoxyborohydride (66.7 mg, 0.315 mmol) was added. The reaction mixture was stirred at rt then purified by silica chromatography (0-100% EtOAc in hexanes as the gradient eluent) to afford the title compound (20 mg, 0.0401 mmol, 63.7% yield). MS (apci) m/z=499.2 (M+H).

Example 450

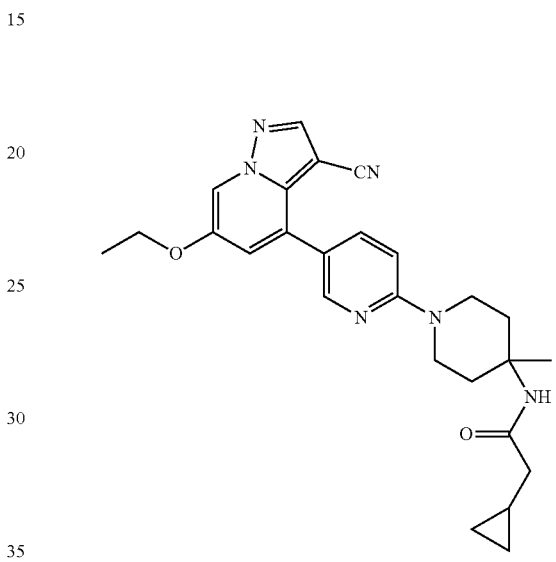

N-(1-(5-(3-cyano-6-ethoxypyrazolo[1,5-a]pyridin-4-yl)pyridin-2-yl)-4-methylpiperidin-4-yl)-2-cyclopropylacetamide To a solution of 4-(6-(4-amino-4-methylpiperidin-1-yl)pyridin-3-yl)-6-ethoxypyrazolo[1,5-a]pyridine-3-carbonitrile (Intermediate P89, 4.3 mg, 0.0114 mmol) in DCM (0.5 mL) was added DIEA (2.95 mg, 0.0228 mmol) and 2-cyclopropylacetyl chloride (1.63 mg, 0.0137 mmol). The reaction mixture was stirred at rt for 2 h then diluted with 4:1 DCM/IPA. The mixture was washed successively with 2M HCl, water, and saturated NaHCO$_{3(aq)}$. The organic extract was dried over anhydrous Na$_2$SO$_{4(s)}$, filtered, concentrated in vacuo, and purified by silica chromatography (0-100% EtOAc in hexanes as the gradient eluent) to afford the title compound (2.3 mg, 0.00502 mmol, 43.9% yield). MS (apci) m/z=459.2 (M+H).

The compounds in Table DDD were prepared using a similar method to that described for the synthesis of Example 450, replacing 2-cyclopropylacetyl chloride with the appropriate acyl chloride or chloroformate. Reactions were monitored for completion by LCMS, and reaction durations were adjusted accordingly. Title compounds were cleanly isolated following chromatographic purification using an appropriate gradient eluent (and if necessary converted to the free base).

TABLE DDD

| Ex. # | Structure | Chemical Name | MS m/z |
|---|---|---|---|
| 451 | 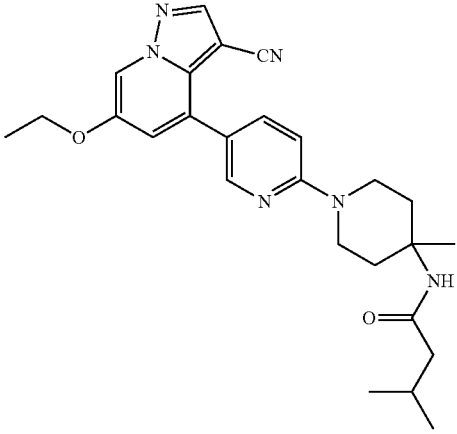 [SMILES: CCOc1cc(-c2ccc(N3CCC(C)(NC(=O)OC(C)C)CC3)nc2)c2c(C#N)cnn2c1] | N-(1-(5-(3-cyano-6-ethoxypyrazolo[1,5-a]pyridin-4-yl)pyridin-2-yl)-4-methylpiperidin-4-yl)-3-methylbutanamide | 461.20 (M + H) |
| 452 | 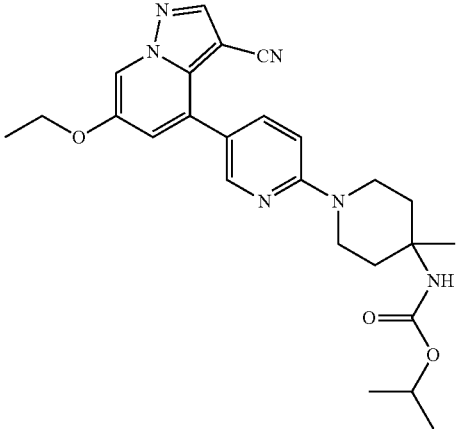 | isopropyl (1-(5-(3-cyano-6-ethoxypyrazolo[1,5-a]pyridin-4-yl)pyridin-2-yl)-4-methylpiperidin-4-yl)carbamate | 463.20 (M + H) |

Example 453

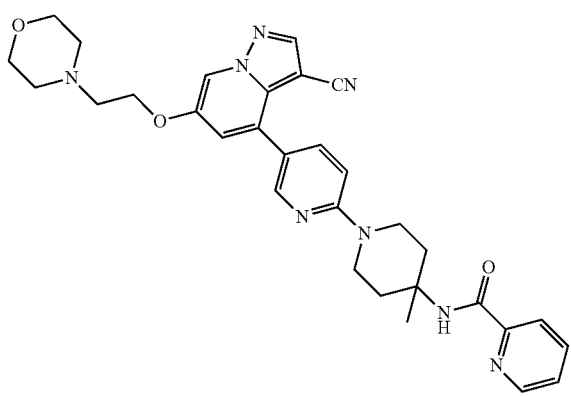 [SMILES: CC1(NC(=O)c2ccccn2)CCN(c2ccc(-c3cc(OCCN4CCOCC4)cn4ncc(C#N)c34)cn2)CC1]

N-(1-(5-(3-cyano-6-(2-morpholinoethoxy)pyrazolo[1,5-a]pyridin-4-yl)pyridin-2-yl)-4-methylpiperidin-4-yl)picolinamide To a solution of N-(1-(5-(3-cyano-6-hydroxypyrazolo[1,5-a]pyridin-4-yl)pyridin-2-yl)-4-methylpiperidin-4-yl)picolinamide (Intermediate P90, 40 mg, 0.0882 mmol) in DMA (0.882 mL) was added 4-(2-chloroethyl)morpholine hydrochloride (32.8 mg, 0.176 mmol) and cesium carbonate (144 mg, 0.441 mmol). The reaction mixture was stirred at 60° C. for 16 h. After cooling to ambient temperature, the reaction mixture was diluted with 4:1 DCM/IPA and washed successively with water and saturated $NaCl_{(aq)}$. The organic extract was dried over anhydrous $Na_2SO_{4(s)}$, filtered, concentrated in vacuo, and purified by C-18 reverse phase chromatography (5-95% ACN in water [+0.1% TFA] as the gradient eluent). The fractions containing the desired product were diluted with 4:1 DCM/IPA and washed with saturated $NaHCO_{3(aq)}$ and saturated $NaCl_{(aq)}$. The organic extract was dried over anhydrous $Na_2SO_{4(s)}$, filtered, and concentrated in vacuo to afford the title compound (15.0 mg, 0.0265 mmol, 30.0% yield). MS (apci) m/z=567.3 (M+H).

The compounds in Table EEE were prepared using a similar method to that described for the synthesis of Example 453, replacing 4-(2-chloroethyl)morpholine hydrochloride with the appropriate alkyl halide. Reactions were monitored for completion by LCMS, and reaction durations were adjusted accordingly. Title compounds were cleanly isolated following chromatographic purification using an appropriate gradient eluent (and if necessary converted to the free base).

TABLE EEE

| Ex. # | Structure | Chemical Name | MS m/z |
|---|---|---|---|
| 454 | 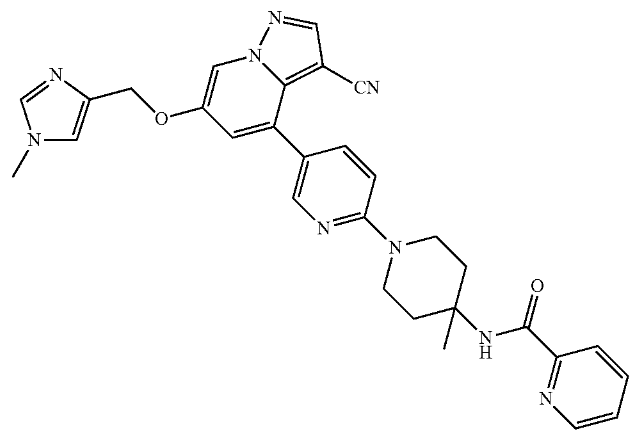 [SMILES: Cn1cnc(COc2cc(-c3ccc(N4CCC(C)(NC(=O)c5ccccn5)CC4)nc3)c3c(C#N)cnn3c2)c1] | N-(1-(5-(3-cyano-6-((1-methyl-1H-imidazol-4-yl)methoxy)pyrazolo[1,5-a]pyridin-4-yl)pyridin-2-yl)-4-methylpiperidin-4-yl)picolinamide | 548.30 (M + H) |
| 455 | 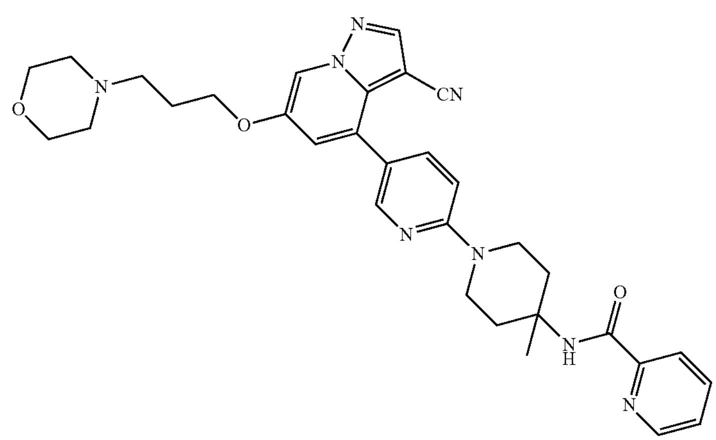 [SMILES: CC1(NC(=O)c2ccccn2)CCN(c2ccc(-c3cc(OCCCN4CCOCC4)cn4ncc(C#N)c34)cn2)CC1] | N-(1-(5-(3-cyano-6-(3-morpholinopropoxy)pyrazolo[1,5-a]pyridin-4-yl)pyridin-2-yl)-4-methylpiperidin-4-yl)picolinamide | 581.30 (M + H) |
| 456 | 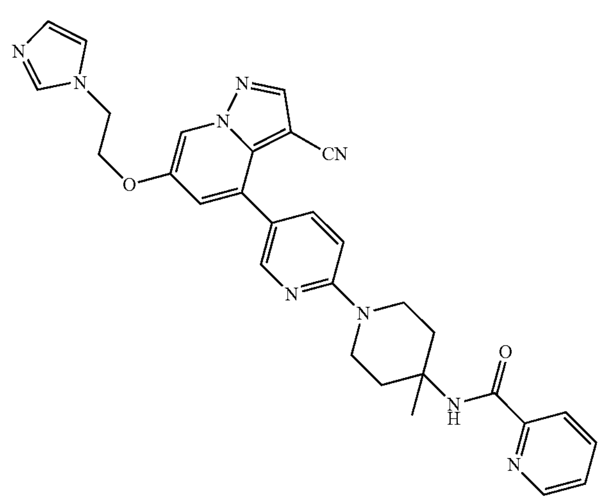 [SMILES: CC1(NC(=O)c2ccccn2)CCN(c2ccc(-c3cc(OCCn4ccnc4)cn4ncc(C#N)c34)cn2)CC1] | N-(1-(5-(6-(2-(1H-imidazol-1-yl)ethoxy)-3-cyanopyrazolo[1,5-a]pyridin-4-yl)pyridin-2-yl)-4-methylpiperidin-4-yl)picolinamide | 548.30 (M + H) |

TABLE EEE-continued

| Ex. # | Structure | Chemical Name | MS m/z |
|---|---|---|---|
| 457 | 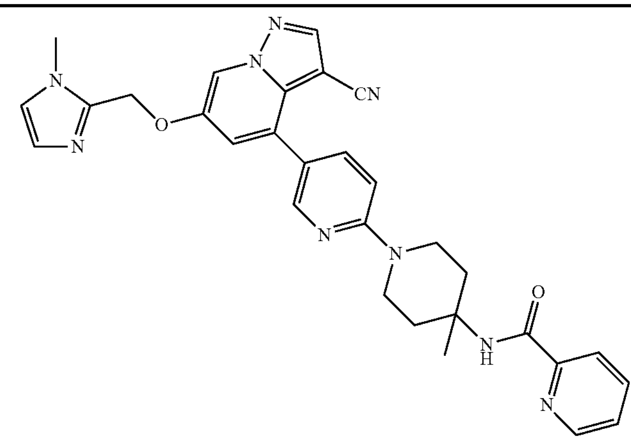 | N-(1-(5-(3-cyano-6-((1-methyl-1H-imidazol-2-yl)methoxy)pyrazolo[1,5-a]pyridin-4-yl)pyridin-2-yl)-4-methylpiperidin-4-yl)picolinamide | 548.30 (M + H) |
| 458 | 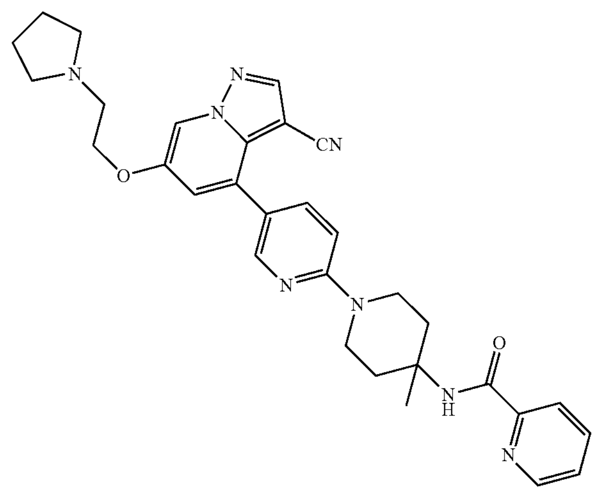 [SMILES: CC1(NC(=O)c2ccccn2)CCN(c2ccc(-c3cc(OCCN4CCCC4)cn4ncc(C#N)c34)cn2)CC1] | N-(1-(5-(3-cyano-6-(2-(pyrrolidin-1-yl)ethoxy)pyrazolo[1,5-a]pyridin-4-yl)pyridin-2-yl)-4-methylpiperidin-4-yl)picolinamide | 551.30 (M + H) |

Example 459

N-(1-(5-(6-(azetidin-3-ylmethoxy)-3-cyanopyrazolo[1,5-a]pyridin-4-yl)pyridin-2-yl)-4-methylpiperidin-4-yl)picolinamide Step 1: Preparation of tert-butyl 3-(((3-cyano-4-(6-(4-methyl-4-(picolinamido)piperidin-1-yl)pyridin-3-yl)pyrazolo[1,5-a]pyridin-6-yl)oxy)methyl)azetidine-1-carboxylate

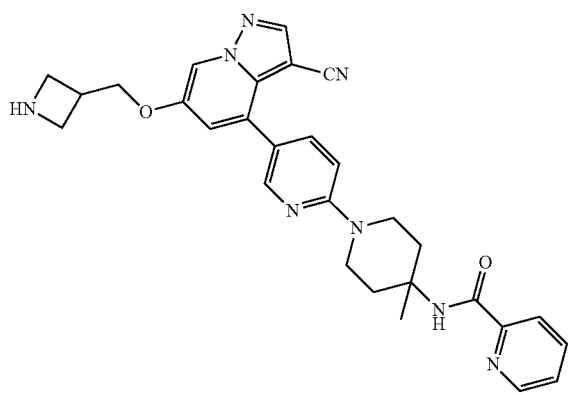 [SMILES: CC1(NC(=O)c2ccccn2)CCN(c2ccc(-c3cc(OCC4CNC4)cn4ncc(C#N)c34)cn2)CC1]

To a solution of N-(1-(5-(3-cyano-6-hydroxypyrazolo[1,5-a]pyridin-4-yl)pyridin-2-yl)-4-methylpiperidin-4-yl)picolinamide (Intermediate P90, 40 mg, 0.088 mmol) in DMA (0.882 mL) was added 3-bromomethyl-azetidine-1-carboxylic acid tert-butyl ester (22 mg, 0.088 mmol) and cesium carbonate (144 mg, 0.44 mmol). The reaction mixture was stirred at 60° C. for 16 h. After cooling to ambient temperature the reaction mixture was diluted with 4:1 DCM/IPA and washed successively with water and saturated $NaCl_{(aq)}$. The organic extract was dried over anhydrous $Na_2SO_{4(s)}$, filtered, concentrated in vacuo, and purified by C-18 reverse phase chromatography (5-95% ACN in water [+0.1% TFA] as the gradient eluent). The fractions containing the desired product were diluted with 4:1 DCM/IPA and washed with saturated $NaHCO_{3(aq)}$ and saturated $NaCl_{(aq)}$. The organic extract was dried over anhydrous $Na_2SO_{4(s)}$, filtered, and concentrated in vacuo to afford the title compound (15.0 mg, 0.0265 mmol, 30.0% yield) in sufficient purity for step 2. MS (apci) m/z=623.3 (M+H).

Step 2: Preparation of N-(1-(5-(6-(azetidin-3-yl-methoxy)-3-cyanopyrazolo[1,5-a]pyridin-4-yl)pyridin-2-yl)-4-methylpiperidin-4-yl)picolinamide A solution of tert-butyl 3-(((3-cyano-4-(6-(4-methyl-4-(picolinamido)piperidin-1-yl)pyridin-3-yl)pyrazolo[1,5-a]pyridin-6-yl)oxy)methyl)azetidine-1-carboxylate (55 mg, 0.088 mmol) in 1:1 (v/v) mixture of DCM:TFA (883 μL) was stirred at rt for 16 h. The reaction mixture was diluted with 4:1 DCM/IPA and washed successively with saturated NaHCO$_{3(aq)}$ and brine. The organic extract was dried over anhydrous Na$_2$SO$_{4(s)}$, filtered, and concentrated in vacuo to afford the title compound (46 mg, 0.088 mmol, 100% yield). MS (apci) m/z=523.3 (M+H).

Example 460

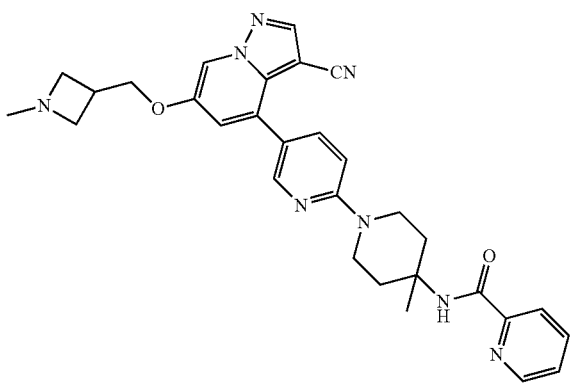 [SMILES: CN1CC(COc2cc(-c3ccc(N4CCC(C)(NC(=O)c5ccccn5)CC4)nc3)c3c(C#N)cnn3c2)C1]

N-(1-(5-(3-cyano-6-((1-methylazetidin-3-yl)methoxy)pyrazolo[1,5-a]pyridin-4-yl)pyridin-2-yl)-4-methylpiperidin-4-yl)picolinamide To a solution of N-(1-(5-(6-(azetidin-3-ylmethoxy)-3-cyanopyrazolo[1,5-a]pyridin-4-yl)pyridin-2-yl)-4-methylpiperidin-4-yl)picolinamide (Example 459, 46 mg, 0.088 mmol) in DCM (1.760 mL) was added formaldehyde (0.066 mL, 0.88 mmol) and sodium triacetoxyborohydride (93 mg, 0.44 mmol). The reaction mixture was stirred at rt for 1 h then concentrated in vacuo. The resultant crude residue was directly purified by C-18 reverse phase chromatography (5-95% ACN in water [+0.1% TFA] as the gradient eluent). The fractions containing the desired product were diluted with 4:1 DCM/IPA and washed with saturated NaHCO$_{3(aq)}$ and saturated NaCl$_{(aq)}$. The organic extract was dried over anhydrous Na$_2$SO$_{4(s)}$, filtered, and concentrated in vacuo to afford the title compound (9.4 mg, 0.017 mmol, 20% yield) in sufficient purity for step 2. MS (apci) m/z=537.3 (M+H).

Example 461

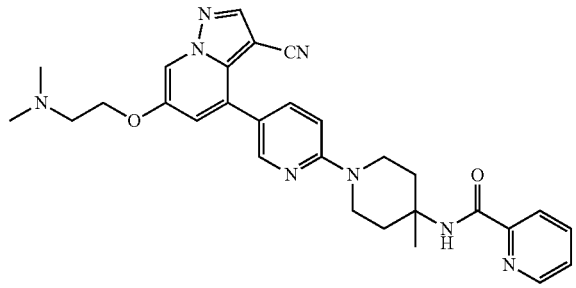 [SMILES: CN(C)CCOc1cc(-c2ccc(N3CCC(C)(NC(=O)c4ccccn4)CC3)nc2)c2c(C#N)cnn2c1]

N-(1-(5-(3-cyano-6-(2-(dimethylamino)ethoxy)pyrazolo[1,5-a]pyridin-4-yl)pyridin-2-yl)-4-methylpiperidin-4-yl)picolinamide Step 1: Preparation of tert-butyl (2-((3-cyano-4-(6-(4-methyl-4-(picolinamido)piperidin-1-yl)pyridin-3-yl)pyrazolo[1,5-a]pyridin-6-yl)oxy)ethyl)carbamate To a solution of N-(1-(5-(3-cyano-6-hydroxypyrazolo[1,5-a]pyridin-4-yl)pyridin-2-yl)-4-methylpiperidin-4-yl)picolinamide (Intermediate P90, 40 mg, 0.088 mmol) in DMA (0.882 mL) was added 2-(Boc-amino)ethyl bromide (20 mg, 0.088 mmol) and cesium carbonate (144 mg, 0.44 mmol). The reaction mixture was stirred at 70° C. for 3 h. After cooling to ambient temperature, the reaction mixture was diluted with 4:1 DCM/IPA and washed successively with water and saturated NaCl$_{(aq)}$. The organic extract was dried over anhydrous Na$_2$SO$_{4(s)}$, filtered, concentrated in vacuo, and purified by C-18 reverse phase chromatography (5-95% ACN in water [+0.1% TFA] as the gradient eluent). The fractions containing the desired product were diluted with 4:1 DCM/IPA and washed with saturated NaHCO$_{3(aq)}$ and saturated NaCl$_{(aq)}$. The organic extract was dried over anhydrous Na$_2$SO$_{4(s)}$, filtered, and concentrated in vacuo to afford the title compound (assumed theoretical yield, 53 mg, 0.088 mmol) in sufficient purity for step 2. MS (apci) m/z=597.3 (M+H).

Step 2: Preparation of N-(1-(5-(6-(2-aminoethoxy)-3-cyanopyrazolo[1,5-a]pyridin-4-yl)pyridin-2-yl)-4-methylpiperidin-4-yl)picolinamide A solution of tert-butyl (2-((3-cyano-4-(6-(4-methyl-4-(picolinamido)piperidin-1-yl)pyridin-3-yl)pyrazolo[1,5-a]pyridin-6-yl)oxy)ethyl)carbamate (53 mg, 0.089 mmol) in 1:1 (v/v) mixture of DCM:TFA (0.89 mL) was stirred at rt for 16 h. The reaction mixture was diluted with 4:1 DCM/IPA and washed successively with saturated NaHCO$_{3(aq)}$ and brine. The organic extract was dried over anhydrous Na$_2$SO$_{4(s)}$, filtered, and concentrated in vacuo to afford the title compound (34 mg, 0.068 mmol, 77% yield over two steps) in sufficient purity for step 3. MS (apci) m/z=497.2 (M+H).

Step 3: Preparation of N-(1-(5-(3-cyano-6-(2-(dimethylamino)ethoxy)pyrazolo[1,5-a]pyridin-4-yl)pyridin-2-yl)-4-methylpiperidin-4-yl)picolinamide To a solution of N-(1-(5-(6-(2-aminoethoxy)-3-cyanopyrazolo[1,5-a]pyridin-4-yl)pyridin-2-yl)-4-methylpiperidin- 4-yl)picolinamide (34 mg, 0.0685 mmol) in DCM (1.369 mL) was added formaldehyde (0.051 mL, 0.685 mmol) and sodium triacetoxyborohydride (72.6 mg, 0.342 mmol). The reaction mixture was stirred at rt for 1 h then concentrated in vacuo. The resultant crude residue was directly purified by C-18 reverse phase chromatography (5-95% ACN in water [+0.1% TFA] as the gradient eluent). The fractions containing the desired product were diluted with 4:1 DCM/IPA and washed with saturated NaHCO$_{3(aq)}$ and saturated NaCl$_{(aq)}$. The organic extract was dried over anhydrous Na$_2$SO$_{4(s)}$, filtered, and concentrated in vacuo. The resultant film was triturated with DCM/hexanes and concentrated in vacuo to afford the title compound (10.5 mg, 0.0198 mmol, 29% yield). MS (apci) m/z=525.3 (M+H).

Example 462

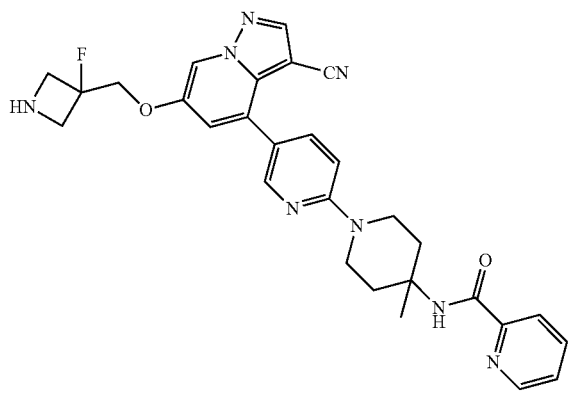 [SMILES: CC1(NC(=O)c2ccccn2)CCN(c2ccc(-c3cc(OCC4(F)CNC4)cn4ncc(C#N)c34)cn2)CC1]

N-(1-(5-(3-cyano-6-((3-fluoroazetidin-3-yl)methoxy)pyrazolo[1,5-a]pyridin-4-yl)pyridin-2-yl)-4-methyl-piperidin-4-yl)picolinamide Step 1: Preparation of tert-butyl 3-(((3-cyano-4-(6-(4-methyl-4-(picolinamido)piperidin-1-yl)pyridin-3-yl)pyrazolo[1,5-a]pyridin-6-yl)oxy)methyl)-3-fluoroazetidine-1-carboxylate To a solution of N-(1-(5-(3-cyano-6-hydroxypyrazolo[1,5-a]pyridin-4-yl)pyridin-2-yl)-4-methylpiperidin-4-yl)picolinamide (Intermediate P90, 40 mg, 0.088 mmol) in DMA (0.882 mL) was added 1-boc-3-bromomethyl-azetidine (24 mg, 0.088 mmol) and cesium carbonate (144 mg, 0.44 mmol). The reaction mixture was stirred at 60° C. for 16 h. After cooling to ambient temperature, the reaction mixture was diluted with 4:1 DCM/IPA and washed successively with water and saturated NaCl$_{(aq)}$. The organic extract was dried over anhydrous Na$_2$SO$_{4(s)}$, filtered, concentrated in vacuo, and purified by C-18 reverse phase chromatography (5-95% ACN in water [+0.1% TFA] as the gradient eluent). The fractions containing the desired product were diluted with 4:1 DCM/IPA and washed with saturated NaHCO$_{3(aq)}$ and saturated NaCl$_{(aq)}$. The organic extract was dried over anhydrous Na$_2$SO$_{4(s)}$, filtered, and concentrated in vacuo to afford the title compound (54 mg, 0.084 mmol, 96% yield) in sufficient purity for step 2. MS (apci) m/z=641.3 (M+H).

Step 2: Preparation of N-(1-(5-(3-cyano-6-((3-fluoroazetidin-3-yl)methoxy)pyrazolo[1,5-a]pyridin-4-yl)pyridin-2-yl)-4-methylpiperidin-4-yl)picolinamide A solution of tert-butyl 3-(((3-cyano-4-(6-(4-methyl-4-(picolinamido)piperidin-1-yl)pyridin-3-yl)pyrazolo[1,5-a]pyridin-6-yl)oxy)methyl)-3-fluoroazetidine-1-carboxylate (54 mg, 0.084 mmol) in 1:1 (v/v) mixture of DCM:TFA (0.84 mL) was stirred at rt for 1 h. The reaction mixture was diluted with 4:1 DCM/IPA and washed successively with saturated NaHCO$_{3(aq)}$ and brine. The organic extract was dried over anhydrous Na$_2$SO$_{4(s)}$, filtered, and concentrated in vacuo. The residue was purified by C-18 reverse phase chromatography (5-95% ACN in water [+0.1% TFA] as the gradient eluent). The fractions containing the desired product were diluted with 4:1 DCM/IPA and washed with saturated NaHCO$_{3(aq)}$ and saturated NaCl$_{(aq)}$. The organic extract was dried over anhydrous Na$_2$SO$_{4(s)}$, filtered, and concentrated in vacuo to afford the title compound (5.0 mg, 11% yield). MS (apci) m/z=541.2 (M+H).

Example 463

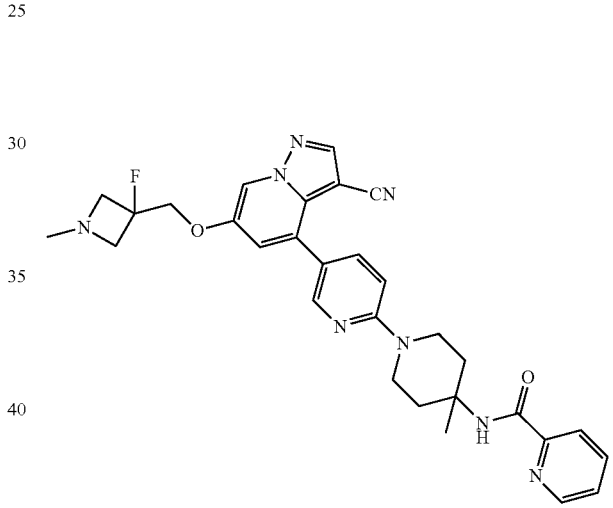

N-(1-(5-(3-cyano-6-((3-fluoro-1-methylazetidin-3-yl)methoxy)pyrazolo[1,5-a]pyridin-4-yl)pyridin-2-yl)-4-methylpiperidin-4-yl)picolinamide To a solution of N-(1-(5-(3-cyano-6-((3-fluoroazetidin-3-yl)methoxy)pyrazolo[1,5-a]pyridin-4-yl)pyridin-2-yl)-4-methylpiperidin-4-yl)picolinamide (Example 462, 35 mg, 0.065 mmol) in DCM (1.295 mL) was added formaldehyde (0.048 mL, 0.65 mmol) and sodium triacetoxyborohydride (69 mg, 0.32 mmol). The reaction mixture was stirred at rt for 1 h. The reaction mixture was concentrated in vacuo, and the resultant crude residue was directly purified by C-18 reverse phase chromatography (5-95% ACN in water [+0.1% TFA] as the gradient eluent). The fractions containing the desired product were diluted with 4:1 DCM/IPA and washed with saturated NaHCO$_{3(aq)}$ and saturated NaCl$_{(aq)}$. The organic extract was dried over anhydrous Na$_2$SO$_{4(s)}$, filtered, and concentrated in vacuo to afford the title compound (19 mg, 0.034 mmol, 53% yield). MS (apci) m/z=555.3 (M+H).

Example 464

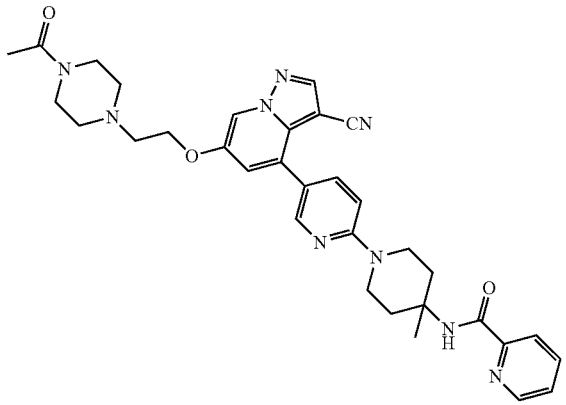 [SMILES: CC(=O)N1CCN(CCOc2cc(-c3ccc(N4CCC(C)(NC(=O)c5ccccn5)CC4)nc3)c3c(C#N)cnn3c2)CC1]

N-(1-(5-(6-(2-(4-acetylpiperazin-1-yl)ethoxy)-3-cyanopyrazolo[1,5-a]pyridin-4-yl)pyridin-2-yl)-4-methylpiperidin-4-yl)picolinamide To a solution of N-(1-(5-(3-cyano-6-(2-(piperazin-1-yl)ethoxy)pyrazolo[1,5-a]pyridin-4-yl)pyridin-2-yl)-4-methylpiperidin-4-yl)picolinamide (Intermediate P91, 35 mg, 0.0619 mmol) in DCM (0.619 mL) was added TEA (0.00862 mL, 0.0619 mmol) and acetyl chloride (0.124 mL, 0.124 mmol). The reaction mixture was stirred at rt for 1 h. The reaction mixture was diluted with 4:1 DCM/IPA and washed successively with water and brine. The organic extract was dried over anhydrous Na$_2$SO$_{4(s)}$, filtered, and concentrated in vacuo. The residue was purified by C-18 reverse phase chromatography (5-95% ACN in water [+0.1% TFA] as the gradient eluent). The fractions containing the desired product were diluted with 4:1 DCM/IPA and washed with saturated NaHCO$_{3(aq)}$ and saturated NaCl$_{(aq)}$. The organic extract was dried over anhydrous Na$_2$SO$_{4(s)}$, filtered, and concentrated in vacuo to afford the title compound (27.7 mg, 0.0456 mmol, 73.7% yield). MS (apci) m/z=608.3 (M+H).

Example 465

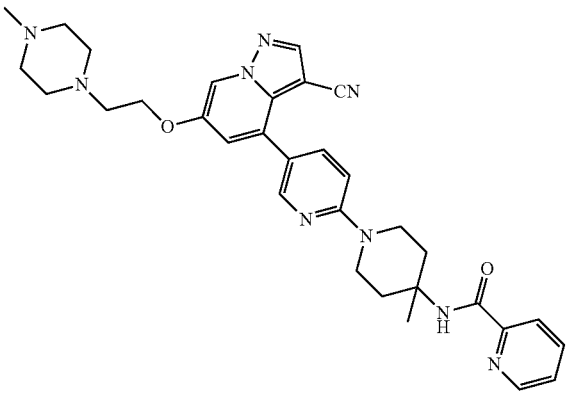 [SMILES: CN1CCN(CCOc2cc(-c3ccc(N4CCC(C)(NC(=O)c5ccccn5)CC4)nc3)c3c(C#N)cnn3c2)CC1]

N-(1-(5-(3-cyano-6-(2-(4-methylpiperazin-1-yl)ethoxy)pyrazolo[1,5-a]pyridin-4-yl)pyridin-2-yl)-4-methylpiperidin-4-yl)picolinamide To a solution of N-(1-(5-(3-cyano-6-(2-(piperazin-1-yl)ethoxy)pyrazolo[1,5-a]pyridin-4-yl)pyridin-2-yl)-4-methylpiperidin-4-yl)picolinamide (Intermediate P91, 40 mg, 0.0707 mmol) in DCM (1.414 mL) was added formaldehyde (0.0526 mL, 0.707 mmol) and sodium triacetoxyborohydride (74.9 mg, 0.354 mmol). The reaction mixture was stirred at rt for 1 h. The reaction mixture was concentrated in vacuo, and the resultant crude residue was directly purified by C-18 reverse phase chromatography (5-95% ACN in water [+0.1% TFA] as the gradient eluent). The fractions containing the desired product were diluted with 4:1 DCM/IPA and washed with saturated NaHCO$_3$ (acs and saturated NaCl$_{(aq)}$. The organic extract was dried over anhydrous Na$_2$SO$_{4(s)}$, filtered, and concentrated in vacuo. The residue was purified by silica chromatography (0-10% MeOH in DCM as the gradient eluent) to afford the title compound (15.4 mg, 37.6% yield). MS (apci) m/z=580.3 (M+H).

Example 466

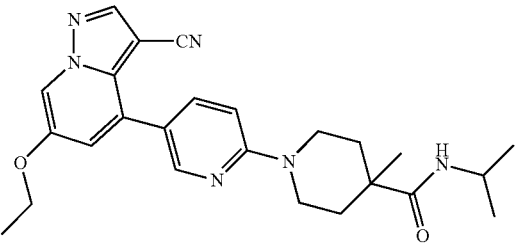 [SMILES: CCOc1cc(-c2ccc(N3CCC(C)(C(=O)NC(C)C)CC3)nc2)c2c(C#N)cnn2c1]

1-(5-(3-cyano-6-ethoxypyrazolo[1,5-a]pyridin-4-yl)pyridin-2-yl)-N-isopropyl-4-methylpiperidine-4-carboxamide To a solution of 1-(5-(3-cyano-6-ethoxypyrazolo[1,5-a]pyridin-4-yl)pyridin-2-yl)-4-methylpiperidine-4-carboxylic acid (Intermediate P92, 38.2 mg, 0.0942 mmol) in DCM (0.942 mL) was added HATU (43.0 mg, 0.113 mmol), DIEA (0.033 mL, 0.188 mmol), and propan-2-amine (0.009 mL, 0.104 mmol). The reaction mixture was stirred at rt for 16 h. The reaction mixture was concentrated in vacuo, and the resultant crude residue was directly purified by C-18 reverse phase chromatography (5-95% ACN in water [+2% TFA] as the gradient eluent). The fractions containing the desired product were diluted with 4:1 DCM/IPA and washed with saturated NaHCO$_{3(aq)}$. The organic extract was dried over anhydrous Na$_2$SO$_{4(s)}$, filtered, and concentrated in vacuo to afford the title compound (32.4 mg, 0.0726 mmol, 77% yield). MS (apci) m/z=447.2 (M+H).

The compounds in Table FFF were prepared using a similar method to that described for the synthesis of Example 466, replacing propan-2-amine with the appropriate amine coupling partner. Reactions were monitored for completion by LCMS, and reaction durations were adjusted accordingly. Title compounds were cleanly isolated following chromatographic purification using an appropriate gradient eluent (and if necessary converted to the free base).

TABLE FFF

| Ex. # | Structure | Chemical Name | MS m/z |
|---|---|---|---|
| 467 | 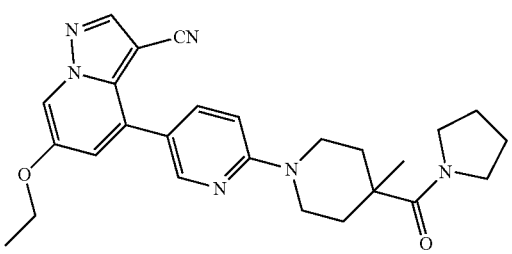 [SMILES: CCOc1cc(-c2ccc(N3CCC(C)(C(=O)N4CCCC4)CC3)nc2)c2c(C#N)cnn2c1] | 6-ethoxy-4-(6-(4-methyl-4-(pyrrolidine-1-carbonyl)piperidin-1-yl)pyridin-3-yl)pyrazolo[1,5-a]pyridine-3-carbonitrile | 459.25 (M + H) |
| 468 | 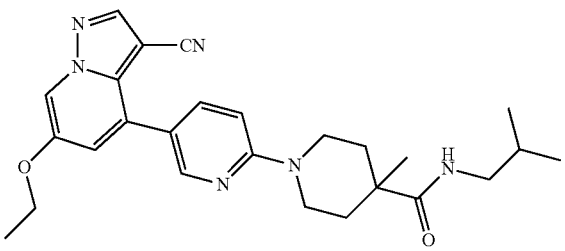 [SMILES: CCOc1cc(-c2ccc(N3CCC(C)(C(=O)NCC(C)C)CC3)nc2)c2c(C#N)cnn2c1] | 1-(5-(3-cyano-6-ethoxypyrazolo[1,5-a]pyridin-4-yl)pyridin-2-yl)-N-isobutyl-4-methylpiperidine-4-carboxamide | 461.25 (M + H) |
| 469 | 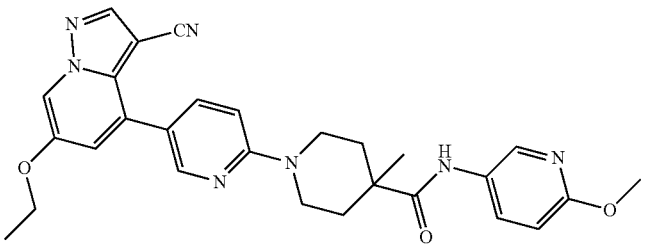 [SMILES: CCOc1cc(-c2ccc(N3CCC(C)(C(=O)Nc4ccc(OC)nc4)CC3)nc2)c2c(C#N)cnn2c1] | 1-(5-(3-cyano-6-ethoxypyrazolo[1,5-a]pyridin-4-yl)pyridin-2-yl)-N-(6-methoxypyridin-3-yl)-4-methylpiperidine-4-carboxamide | 512.20 (M + H) |
| 470 | 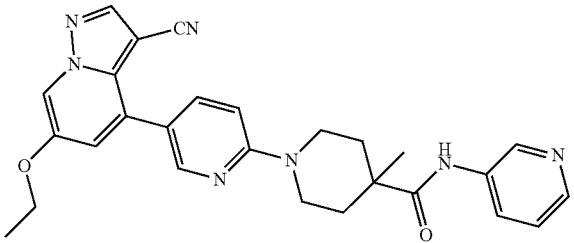 [SMILES: CCOc1cc(-c2ccc(N3CCC(C)(C(=O)Nc4cccnc4)CC3)nc2)c2c(C#N)cnn2c1] | 1-(5-(3-cyano-6-ethoxypyrazolo[1,5-a]pyridin-4-yl)pyridin-2-yl)-4-methyl-N-(pyridin-3-yl)piperidine-4-carboxamide | 482.20 (M + H) |
| 471 | 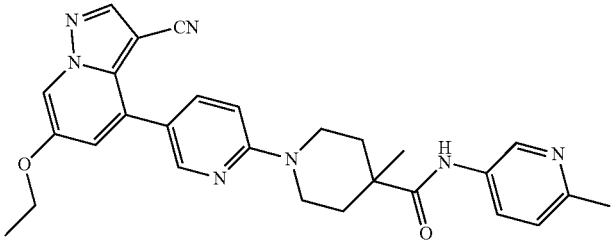 [SMILES: CCOc1cc(-c2ccc(N3CCC(C)(C(=O)Nc4ccc(C)nc4)CC3)nc2)c2c(C#N)cnn2c1] | 1-(5-(3-cyano-6-ethoxypyrazolo[1,5-a]pyridin-4-yl)pyridin-2-yl)-4-methyl-N-(6-methylpyridin-3-yl)piperidine-4-carboxamide | 496.20 (M + H) |
| 472 | 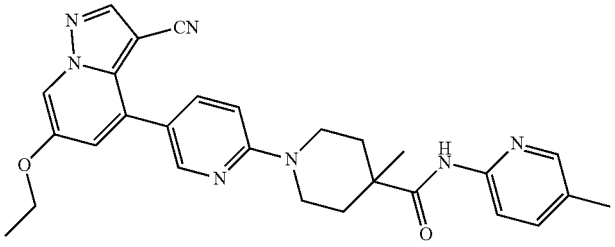 [SMILES: CCOc1cc(-c2ccc(N3CCC(C)(C(=O)Nc4ccc(C)cn4)CC3)nc2)c2c(C#N)cnn2c1] | 1-(5-(3-cyano-6-ethoxypyrazolo[1,5-a]pyridin-4-yl)pyridin-2-yl)-4-methyl-N-(5-methylpyridin-2-yl)piperidine-4-carboxamide | 496.20 (M + H) |

TABLE FFF-continued

| Ex. # | Structure | Chemical Name | MS m/z |
|---|---|---|---|
| 473 | 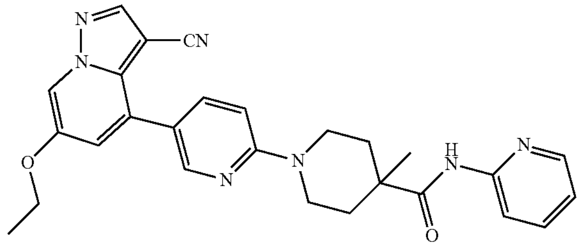 [SMILES: CCOc1cc(-c2ccc(N3CCC(C)(C(=O)Nc4ccccn4)CC3)nc2)c2c(C#N)cnn2c1] | 1-(5-(3-cyano-6-ethoxypyrazolo[1,5-a]pyridin-4-yl)pyridin-2-yl)-4-methyl-N-(pyridin-2-yl)piperidine-4-carboxamide | 482.20 (M + H) |
| 474 | 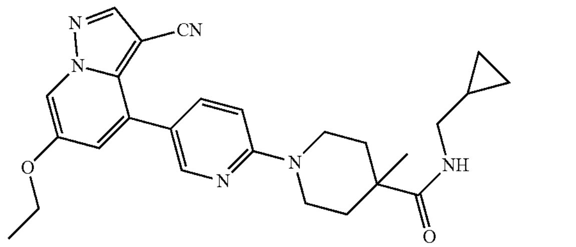 [SMILES: CCOc1cc(-c2ccc(N3CCC(C)(C(=O)NCC4CC4)CC3)nc2)c2c(C#N)cnn2c1] | 1-(5-(3-cyano-6-ethoxypyrazolo[1,5-a]pyridin-4-yl)pyridin-2-yl)-N-(cyclopropylmethyl)-4-methylpiperidine-4-carboxamide | 459.20 (M + H) |
| 475 | 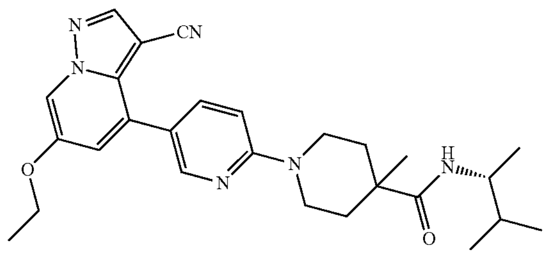 [SMILES: CCOc1cc(-c2ccc(N3CCC(C)(C(=O)N[C@H](C)C(C)C)CC3)nc2)c2c(C#N)cnn2c1] | (R)-1-(5-(3-cyano-6-ethoxypyrazolo[1,5-a]pyridin-4-yl)pyridin-2-yl)-4-methyl-N-(3-methylbutan-2-yl)piperidine-4-carboxamide | 475.30 (M + H) |
| 476 | 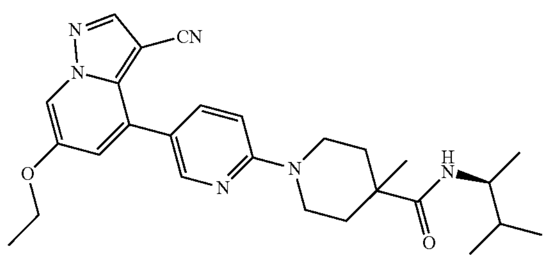 [SMILES: CCOc1cc(-c2ccc(N3CCC(C)(C(=O)N[C@@H](C)C(C)C)CC3)nc2)c2c(C#N)cnn2c1] | (S)-1-(5-(3-cyano-6-ethoxypyrazolo[1,5-a]pyridin-4-yl)pyridin-2-yl)-4-methyl-N-(3-methylbutan-2-yl)piperidine-4-carboxamide | 475.30 (M + H) |
| 477 | 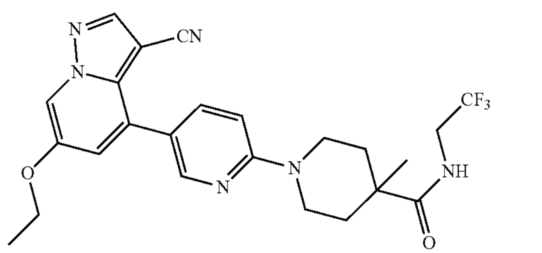 [SMILES: CCOc1cc(-c2ccc(N3CCC(C)(C(=O)NCC(F)(F)F)CC3)nc2)c2c(C#N)cnn2c1] | 1-(5-(3-cyano-6-ethoxypyrazolo[1,5-a]pyridin-4-yl)pyridin-2-yl)-4-methyl-N-(2,2,2-trifluoroethyl)piperidine-4-carboxamide | 487.20 (M + H) |
| 478 | 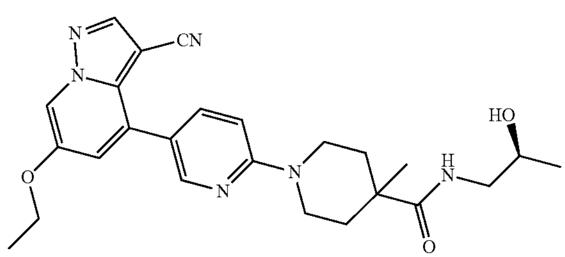 [SMILES: CCOc1cc(-c2ccc(N3CCC(C)(C(=O)NC[C@H](C)O)CC3)nc2)c2c(C#N)cnn2c1] | (S)-1-(5-(3-cyano-6-ethoxypyrazolo[1,5-a]pyridin-4-yl)pyridin-2-yl)-N-(2-hydroxypropyl)-4-methylpiperidine-4-carboxamide | 463.20 (M + H) |

Example 479

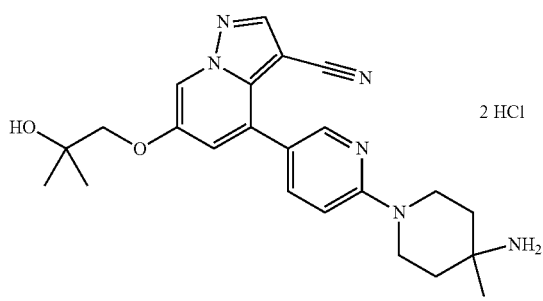 [SMILES: CC(C)(O)COc1cc(-c2ccc(N3CCC(C)(N)CC3)nc2)c2c(C#N)cnn2c1]

4-(6-(4-amino-4-methylpiperidin-1-yl)pyridin-3-yl)-6-(2-hydroxy-2-methylpropoxy)pyrazolo[1,5-a]pyridine-3-carbonitrile dihydrochloride Step 1: Preparation of tert-butyl (1-(5-(3-cyano-6-(2-hydroxy-2-methylpropoxy)pyrazolo[1,5-a]pyridin-4-yl)pyridin-2-yl)-4-methylpiperidin-4-yl)carbamate A solution of 4-(6-fluoropyridin-3-yl)-6-(2-hydroxy-2-methylpropoxy)pyrazolo[1,5-a]pyridine-3-carbonitrile (Intermediate P42; 2.535 g, 7.768 mmol) in DMSO (6.1 mL) was treated sequentially with tert-butyl (4-methylpiperidin-4-yl)carbamate (1.998 mg, 9.322 mmol) and DIEA (4.06 mL, 23.3 mmol). The resulting mixture stirred overnight at 90° C. After cooling to ambient temperature, the reaction mixture was poured into 80 mL water and diluted with 80 mL heptane and stirred for 1 hour. The suspension was filtered and the solids were rinsed with 25 mL water then 25 mL heptane. The isolated solids were dried under vacuum for 18 hours to afford the title compound (4.04 g, 99.9% yield) in sufficient purity for step 2. MS (apci) m/z=521.3 (M+H)

Step 2: Preparation of 4-(6-(4-amino-4-methylpiperidin-1-yl)pyridin-3-yl)-6-(2-hydroxy-2-methylpropoxy)pyrazolo[1,5-a]pyridine-3-carbonitrile dihydrochloride A solution of tert-butyl (1-(5-(3-cyano-6-(2-hydroxy-2-methylpropoxy)pyrazolo[1,5-a]pyridin-4-yl)pyridin-2-yl)-4-methylpiperidin-4-yl)carbamate (4.04 g, 7.76 mmol) in DCM (20 mL) was cooled to 0° C. The reaction was treated with TFA (5.98 mL) and allowed to warm to RT. After stirring for 30 min at ambient the reaction mixture was concentrated in vacuo. The residue was dissolved in MeOH (20 mL) and cooled to 0° C. and then treated with Hydrochloric acid, 5 to 6N solution in 2-propanol (15.5 mL, 77.5 mmol) and stirred for 15 min at 0° C. The reaction was diluted with 20 mL MTBE, filtered, and solids were rinsed with 20 mL 1:1 MTBE: MeOH. The isolated solids were dried under vacuum to cleanly provide the title compound (3.37 g, 88% yield). MS (apci) m/z=421.2 (M+H).

Example 480

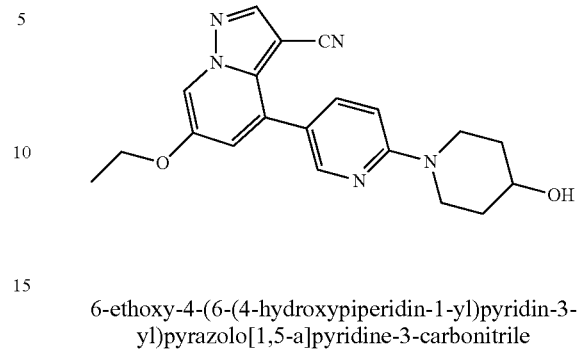

6-ethoxy-4-(6-(4-hydroxypiperidin-1-yl)pyridin-3-yl)pyrazolo[1,5-a]pyridine-3-carbonitrile To a solution of 6-ethoxy-4-(6-fluoropyridin-3-yl)pyrazolo[1,5-a]pyridine-3-carbonitrile (Intermediate P6, 0.500 g, 1.77 mmol) in DMSO (3.5 mL) was added TEA (0.741 mL, 5.31 mmol) and piperidin-4-ol (269 mg, 2.66 mmol). The reaction mixture was stirred at 70° C. for 5 h. After cooling to ambient temperature, the reaction mixture was poured into ice water. The resultant solids were isolated by vacuum filtration to afford the title compound (501 mg, 1.38 mmol, 77.8% yield). MS (apci) m/z=364.2 (M+H).

Example 481

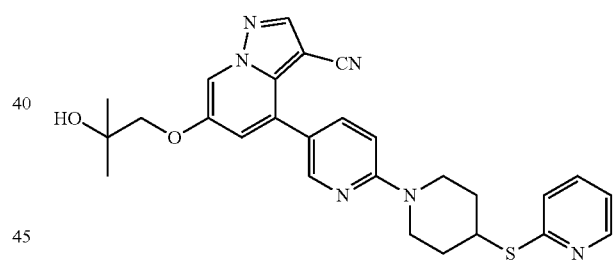

6-(2-hydroxy-2-methylpropoxy)-4-(6-(4-(pyridin-2-ylthio)piperidin-1-yl)pyridin-3-yl)pyrazolo[1,5-a]pyridine-3-carbonitrile To a solution of 4-(6-fluoropyridin-3-yl)-6-(2-hydroxy-2-methylpropoxy)pyrazolo[1,5-a]pyridine-3-carbonitrile (Intermediate P42; 210 mg, 0.64 mmol) and 2-(piperidin-4-ylsulfanyl)pyridine (357 mg, 1.84 mmol) in DMA (1.6 mL) was added TEA (628 µL, 4.50 mmol). The reaction mixture was stirred overnight at 95° C. After cooling to ambient temperature, the reaction mixture was diluted water and extracted with EtOAc. The organic extracts were washed with water and brine. The organic extracts were dried over anhydrous $Na_2SO_{4(s)}$, filtered and concentrated in vacuo. The residue was purified by silica chromatography (10-90% EtOAc in Hexanes to afford the title compound (20 mg, 61% yield). MS (apci) m/z=501.2 (M+H).

Example 482

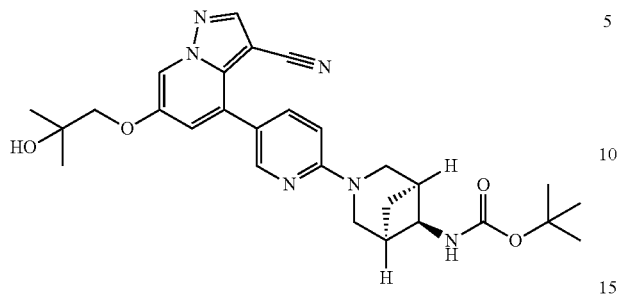

Step 1: Preparation of tert-butyl ((1R,5S,6r)-3-(5-(3-cyano-6-(2-hydroxy-2-methylpropoxy)pyrazolo[1,5-a]pyridin-4-yl)pyridin-2-yl)-3-azabicyclo[3.1.1]heptan-6-yl)carbamate To a solution of 4-(6-fluoropyridin-3-yl)-6-(2-hydroxy-2-methylpropoxy)pyrazolo[1,5-a]pyridine-3-carbonitrile (Intermediate P42; 200 mg, 0.57 mmol) and tert-butyl ((1R,5S,6r)-3-azabicyclo[3.1.1]heptan-6-yl)carbamate (169 mg, 0.80 mmol) in DMSO (0.57 mL) was added DIEA (298 µL, 1.71 mmol). The reaction mixture was stirred overnight under a $N_{2(g)}$ atmosphere at 90° C. After cooling to ambient temperature, the reaction mixture was diluted with water (5.7 mL). The suspension was filtered and the solids were rinsed with water (3×5 mL) then MTBE (3×5 mL). The isolated solids were dried under vacuum while the MTBE filtrate was concentrated in vacuo. The filtrate residue was purified by C18 reverse phase chromatography (5-50% ACN in water). The precipitate solids and chromatography product were combined and concentrated in vacuo to cleanly provide the title compound (292 mg, 98% yield) in sufficient purity for step 2. MS (apci) m/z=519.20 (M+H).

Example 483

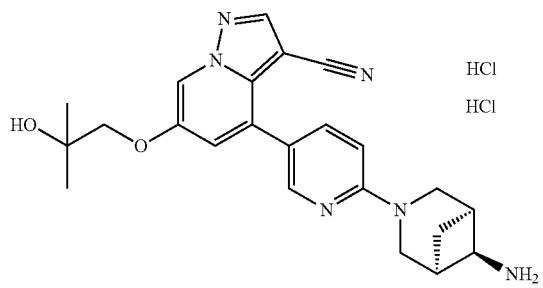 [SMILES: CC(C)(O)COc1cc(-c2ccc(N3C[C@H]4C[C@@H](C3)[C@H]4N)nc2)c2c(C#N)cnn2c1 ; Cl ; Cl]

4-(6-((1R,5 S,6r)-6-amino-3-azabicyclo[3.1.1]heptan-3-yl)pyridin-3-yl)-6-(2-hydroxy-2-methylpropoxy)pyrazolo[1,5-a]pyridine-3-carbonitrile dihydrochloride To a solution of tert-butyl ((1R,5S,6r)-3-(5-(3-cyano-6-(2-hydroxy-2-methylpropoxy)pyrazolo[1,5-a]pyridin-4-yl)pyridin-2-yl)-3-azabicyclo[3.1.1]heptan-6-yl)carbamate (Example 507A; 148 mg, 0.29 mmol) in MeOH (571 µL) was added HCl (conc.) (476 µL, 5.71 mmol) dropwise. The reaction was stirred for 2 h at ambient temperature. The reaction was diluted with EtOAc (1 mL) and was stirred at ambient temperature for 10 minutes. MTBE (1 mL) was added and a suspension formed. The suspension was filtered and solids were rinsed with 10% MeOH in MTBE (3×1 mL) to cleanly provide the title compound (114 mg, 81% yield). MS (apci) m/z=419.15 (M+H).

Example 484

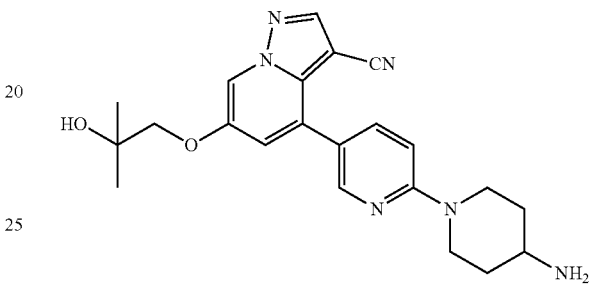

4-(6-(4-aminopiperidin-1-yl)pyridin-3-yl)-6-(2-hydroxy-2-methylpropoxy)pyrazolo[1,5-a]pyridine-3-carbonitrile Step 1: Preparation of tert-butyl (1-(5-(3-cyano-6-(2-hydroxy-2-methylpropoxy)pyrazolo[1,5-a]pyridin-4-yl)pyridin-2-yl)piperidin-4-yl)carbamate To a solution of 4-(6-fluoropyridin-3-yl)-6-(2-hydroxy-2-methylpropoxy)pyrazolo[1,5-a]pyridine-3-carbonitrile (Intermediate P42; 205 mg, 0.628 mmol) and tert-butyl piperidin-4-ylcarbamate (252 mg, 1.26 mmol) in DMA (2.09 mL) was added DIEA (549 µL, 3.14 mmol). The reaction was stirred 2 h at 95° C. After cooling to ambient temperature, the reaction mixture was diluted with water and extracted with EtOAc. The organic extracts were washed with water and brine. The organic extracts were dried over anhydrous $Na_2SO_{4(s)}$, filtered and concentrated in vacuo to afford the title compound (assumed quantitative yield, 319 mg) in sufficient purity for step 2. MS (apci) m/z=507.20 (M+H)

Step 2: Preparation of 4-(6-(4-aminopiperidin-1-yl)pyridin-3-yl)-6-(2-hydroxy-2-methylpropoxy)pyrazolo[1,5-a]pyridine-3-carbonitrile To a solution of tert-butyl (1-(5-(3-cyano-6-(2-hydroxy-2-methylpropoxy)pyrazolo[1,5-a]pyridin-4-yl)pyridin-2-yl)piperidin-4-yl)carbamate (319 mg, 0.63 mmol) in DCM (3.15 mL) was added TFA (3.14 mL, 40.9 mmol). The reaction was stirred for 30 min at ambient temperature. The reaction was concentrated in vacuo. The residue was resuspended in DCM and purified using silica chromatography (1-9% MeOH in DCM with 0.1-0.9% NH₄OH as the gradient eluent) to cleanly provide the title compound (37 mg, 53% yield) MS (apci) m/z=407.2 (M+H).

Example 485

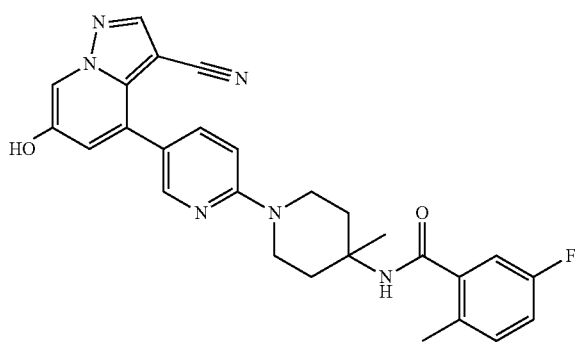 [SMILES: Cc1ccc(F)cc1C(=O)NC1(C)CCN(c2ccc(-c3cc(O)cn4ncc(C#N)c34)cn2)CC1]

N-(1-(5-(3-cyano-6-hydroxypyrazolo[1,5-a]pyridin-4-yl)pyridin-2-yl)-4-methylpiperidin-4-yl)-5-fluoro-2-methylbenzamide To a solution of 4-(6-(4-amino-4-methylpiperidin-1-yl)pyridin-3-yl)-6-hydroxypyrazolo[1,5-a]pyridine-3-carbonitrile dihydrochloride (Intermediate P67; 503 mg, 1.19 mmol), 5-fluoro-2-methylbenzoic acid (552 mg, 3.58 mmol), and HATU (1.36 g, 3.58 mmol) in DMSO (5 mL) was added DIEA (1.7 mL, 9.55 mmol). The reaction was stirred 16 h at ambient temperature. The reaction mixture was diluted with THF (4 mL) and treated with NaOH (5.97 mL, 11.9 mmol) and stirred for 4 h at ambient temperature. The reaction was concentrated in vacuo. The residue was diluted with EtOAc and washed with water. The pH was adjusted to pH 5 with AcOH and then extracted with EtOAc. The organic extracts were washed with brine. The organic extracts were dried over anhydrous $Na_2SO_{4(s)}$, filtered and concentrated in vacuo. The residue was purified using silica chromatography (50-100% Hexanes to EtOAc) to afford the title compound (534 mg, 92% yield) in sufficient purity for step 2. MS (apci) m/z=485.2 (M+H).

Example 486

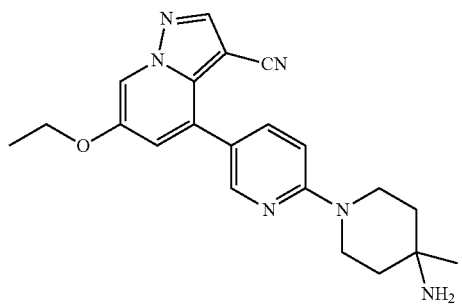 [SMILES: CCOc1cc(-c2ccc(N3CCC(C)(N)CC3)nc2)c2c(C#N)cnn2c1]

4-(6-(4-amino-4-methylpiperidin-1-yl)pyridin-3-yl)-6-ethoxypyrazolo[1,5-a]pyridine-3-carbonitrile A solution of tert-butyl (1-(5-(3-cyano-6-ethoxypyrazolo[1,5-a]pyridin-4-yl)pyridin-2-yl)-4-methylpiperidin-4-yl)carbamate (Example 446, 100 mg, 0.210 mmol) in DCM (2 mL) was treated with TFA (2 mL). The reaction mixture was stirred at rt for 1 h. The crude reaction mixture was directly purified by silica chromatography (5-50% [MeOH+2% NH$_4$OH] in DCM as the gradient eluent) to afford the title compound (20 mg, 0.0531 mmol, 25.3% yield). MS (apci) m/z=377.2 (M+H).

Example 487

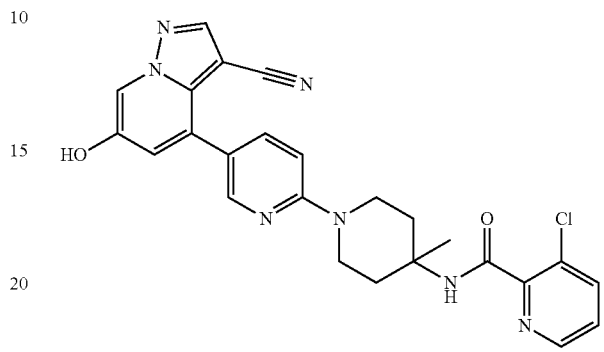

3-chloro-N-(1-(5-(3-cyano-6-hydroxypyrazolo[1,5-a]pyridin-4-yl)pyridin-2-yl)-4-methylpiperidin-4-yl)picolinamide To a solution of 4-(6-(4-amino-4-methylpiperidin-1-yl)pyridin-3-yl)-6-hydroxypyrazolo[1,5-a]pyridine-3-carbonitrile dihydrochloride (Intermediate P67; 256 mg, 0.608 mmol), 3-Chloropicolinic acid (287 mg, 1.82 mmol), and HATU (294 mg, 1.82 mmol) in DMSO (3 mL) was added DIEA (0.74 mL, 4.25 mmol). The reaction was stirred overnight at ambient temperature. The reaction mixture was diluted with EtOAc (10 mL) and washed with water (10 mL) and 4:1AcOH:water (10 mL) and then extracted with EtOAc. The organic extracts were washed with 4:1 AcOH:Water and then brine. The organic extracts were dried over anhydrous $Na_2SO_{4(s)}$, filtered and concentrated in vacuo. The residue was diluted with THF (4 mL) and 2M NaOH (6 mL). The solution was concentrated in vacuo. The residue was resuspended in DCM (2 mL) and purified by C18 reverse phase chromatography (5-95% ACN in water with 0.1% TFA as the gradient eluent) to afford the title compound as the TFA salt. The TFA salt was resuspended in DCM and passed through a Pl-HCO$_3$ resin to elute the free-based product. The organic eluents were concentrated in vacuo and recrystallized using DCM/Hexanes to afford the title compound (226 mg, 76% yield). MS (apci) m/z=488.2 (M+H).

Example 488

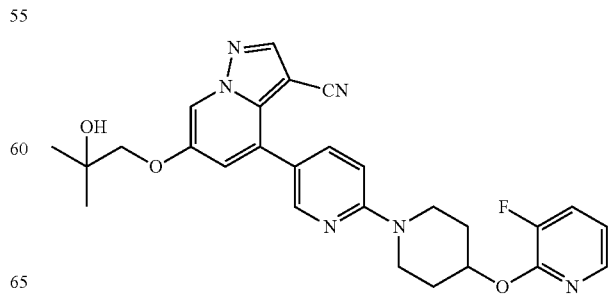

4-(6-(4-((3-fluoropyridin-2-yl)oxy)piperidin-1-yl) pyridin-3-yl)-6-(2-hydroxy-2-methylpropoxy)pyrazolo[1,5-a]pyridine-3-carbonitrile

Step 1: Preparation of tert-butyl 4-((3-fluoropyridin-2-yl)oxy)piperidine-1-carboxylate To a solution of tert-Butyl 4-hydroxy-4-methylpiperidine-1-carboxylate (175 mg, 0.869 mmol) in DMF (2.2 mL) was added sodium hydride (60% w/w, 41.7 mg, 1.04 mmol). The reaction was stirred for 10 min at ambient temperature. 2,3-Difluoropyridine (100 mg, 0.869 mmol) was added and reaction stirred overnight at 60° C. The reaction was cooled to ambient temperature and diluted with DCM and washed with saturated $NaHCO_{3(aq)}$, water, and brine. The combined organic extracts were dried over anhydrous $Na_2SO_{4(s)}$, filtered and concentrated in vacuo to afford the title compound (assumed quantitative yield, 258 mg) in sufficient purity for step 2. MS (apci) m/z=197.2 (M-Boc).

Step 2: Preparation of 3-fluoro-2-(piperidin-4-yloxy)pyridine hydrochloride To a solution of tert-butyl 4-((3-fluoropyridin-2-yl)oxy) piperidine-1-carboxylate (assumed 258 mg, 0.869 mmol) in 4.3 mL DCM was treated with TFA (4.3 mL, 55.8 mmol). The reaction mixture was stirred for 1 h at ambient temperature, and then concentrated in vacuo. The crude residue was resuspended in MeOH and treated with treated with 4 N HCl in dioxanes (4 mL). The solution was stirred at ambient temperature for 15 min. The reaction was concentrated in vacuo to provide the title compound as a dihydrochloride salt, which was used in the next step without further purifications. MS (apci) m/z=197.1 (M+H).

Step 3: Preparation of 4-(6-(4-((3-fluoropyridin-2-yl)oxy)piperidin-1-yl)pyridin-3-yl)-6-(2-hydroxy-2-methylpropoxy)pyrazolo[1,5-a]pyridine-3-carbonitrile To a mixture of 4-(6-fluoropyridin-3-yl)-6-(2-hydroxy-2-methylpropoxy)pyrazolo[1,5-a]pyridine-3-carbonitrile (Intermediate P42; 40 mg, 0.123 mmol) and 3-fluoro-2-(piperidin-4-yloxy)pyridine dihydrochloride (66 mg, 0.245 mmol) in DMA (0.817 mL) was added TEA (103 μL, 0.735 mmol). The reaction mixture was stirred overnight at 95° C. After cooling to ambient temperature, the reaction mixture was diluted with DCM and washed with water and brine. The organic extracts were dried over anhydrous $Na_2SO_{4(s)}$, filtered and concentrated in vacuo. The residue was purified by C18 reverse phase chromatography (5-95% ACN in water with 0.1% TFA as the gradient eluent) to afford the title compound as the TFA salt. The TFA salt was treated with saturated $Na_2CO_{3(aq)}$ and extracted with DCM. The combined organic extracts were washed with brine, then dried over anhydrous $Na_2SO_{4(s)}$, filtered and concentrated in vacuo to afford the title compound (17 mg, 28% yield). MS (apci) m/z=503.2 (M+H).

Example 489

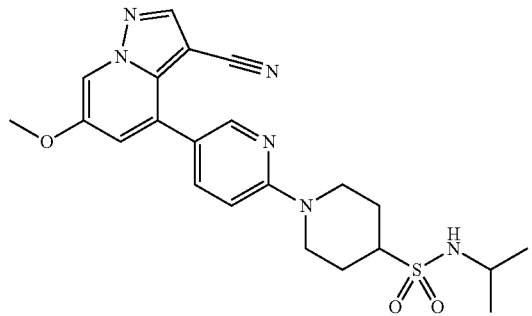 [SMILES: COc1cc(-c2ccc(N3CCC(S(=O)(=O)NC(C)C)CC3)nc2)c2c(C#N)cnn2c1]

1-(5-(3-cyano-6-methoxypyrazolo[1,5-a]pyridin-4-yl)pyridin-2-yl)-N-isopropylpiperidine-4-sulfonamide A mixture of 4-(6-fluoropyridin-3-yl)-6-methoxypyrazolo [1,5-a]pyridine-3-carbonitrile (Intermediate P93; 31.8 mg, 0.119 mmol), N-isopropylpiperidine-4-sulfonamide (Intermediate R18; 45 mg, 0.218 mmol) and DIEA (62.1 μL, 0.356 mmol) in DMSO (500 L) was stirred for 2 d at 90° C. After cooling to ambient temperature, the mixture was diluted with water, cooled to 0° C., and the resultant suspension was filtered. The solids were rinsed with water, and purified by silica chromatography (using 30-100% Hexanes/ EtOAc as the gradient eluent) to afford the title compound (11.5 mg, 21% yield). MS (apci) m/z=455.15 (M+H).

Example 490

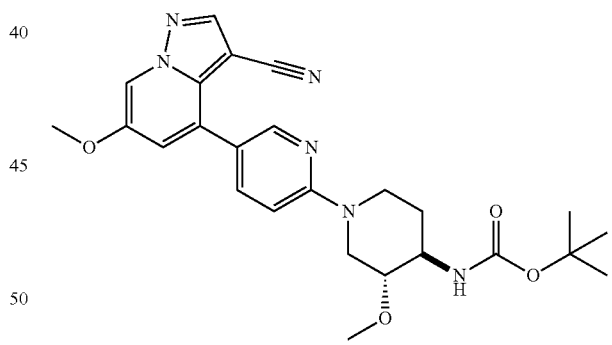

trans-tert-butyl 1-(5-(3-cyano-6-methoxypyrazolo[1,5-a]pyridin-4-yl)pyridin-2-yl)-3-methoxypiperidin-4-yl)carbamate A mixture of 4-(6-fluoropyridin-3-yl)-6-methoxypyrazolo [1,5-a]pyridine-3-carbonitrile (Intermediate P93; 201.7 mg, 0.7519 mmol), tert-butyl (3-methoxypiperidin-4-yl)carbamate (mixture of trans isomers) (259.8 mg, 1.128 mmol) and DIEA (394.0 μL, 2.256 mmol) in DMSO (3 mL) was stirred overnight at 90° C. After cooling to ambient temperature, the mixture was diluted with water, and cooled to 0° C. The resultant suspension was filtered, and the solids were rinsed with cold water (3x), and purified by silica chromatography (using 30-70% Hexanes/EtOAc as the gradient eluent) to afford the title compound (299.8 mg, 83% yield). MS (apci) m/z=479.2 (M+H).

Example 491

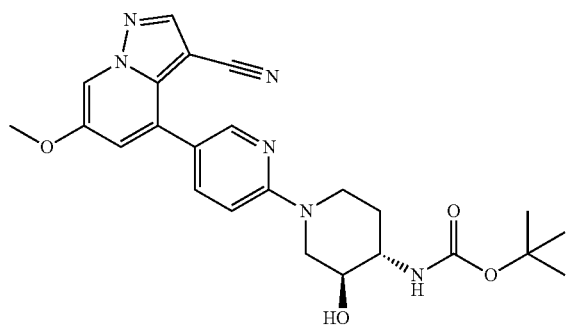 [SMILES: COc1cc(-c2ccc(N3CC[C@H](NC(=O)OC(C)(C)C)[C@@H](O)C3)nc2)c2c(C#N)cnn2c1]

tert-butyl ((3S,4S)-1-(5-(3-cyano-6-methoxypyrazolo[1,5-a]pyridin-4-yl)pyridin-2-yl)-3-hydroxypiperidin-4-yl)carbamate A solution of 4-(6-fluoropyridin-3-yl)-6-methoxypyrazolo[1,5-a]pyridine-3-carbonitrile (Intermediate P93; 158.5 mg, 0.5909 mmol), and tert-butyl ((3S,4S)-3-hydroxypiperidin-4-yl)carbamate (216.3 mg, 1.000 mmol) in DMSO (2 mL) was treated with DIEA (516.0 µL, 2.954 mmol), then stirred overnight at 100° C. After cooling to ambient temperature, the mixture was diluted with water, and the resultant suspension was filtered. The solids were rinsed with water (3×), then dried in vacuo to cleanly afford the title compound (335.8 mg, quantitative yield). MS (apci) m/z=465.2 (M+H).

Example 492

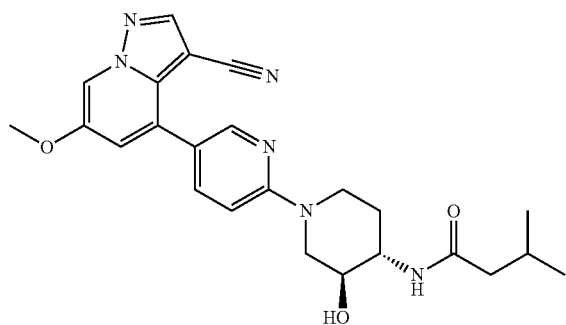 [SMILES: COc1cc(-c2ccc(N3CC[C@H](NC(=O)CC(C)C)[C@@H](O)C3)nc2)c2c(C#N)cnn2c1]

N-((3S,4S)-1-(5-(3-cyano-6-methoxypyrazolo[1,5-a]pyridin-4-yl)pyridin-2-yl)-3-hydroxypiperidin-4-yl)-3-methylbutanamide A solution of 4-(6-((3S,4S)-4-amino-3-hydroxypiperidin-1-yl)pyridin-3-yl)-6-methoxypyrazolo[1,5-a]pyridine-3-carbonitrile dihydrochloride (Intermediate P94; 50 mg, 0.11 mmol) and DIEA (120 µL, 0.69 mmol) in DCM (2 mL) was cooled to 0° C., then treated with isovaleryl chloride (33 µL, 0.27 mmol). The resulting mixture was stirred for 10 min at 0° C., and then for 2 h at ambient temperature. The reaction mixture was purified by silica chromatography (using 20-100% EtOAc in Hexanes as the gradient eluent), then again by C18 reverse phase chromatography (using 20-80% ACN in water with 0.1% TFA as the gradient eluent) to cleanly provide the title compound as the TFA salt. The TFA salt was partitioned between saturated $NaHCO_{3(aq)}$ and 4:1 DCM:iPrOH, and passed through a PS Frit. The organic extracts were concentrated in vacuo to cleanly afford the title compound (2.0 mg, 3% yield). MS (apci) m/z=449.2 (M+H).

Example 493

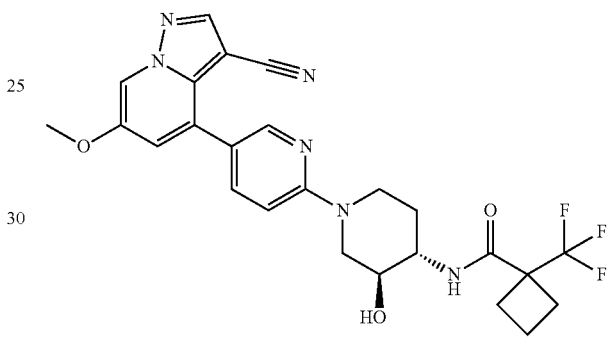

N-((3S,4S)-1-(5-(3-cyano-6-methoxypyrazolo[1,5-a]pyridin-4-yl)pyridin-2-yl)-3-hydroxypiperidin-4-yl)-1-(trifluoromethyl)cyclobutane-1-carboxamide A solution of 4-(6-((3S,4S)-4-amino-3-hydroxypiperidin-1-yl)pyridin-3-yl)-6-methoxypyrazolo[1,5-a]pyridine-3-carbonitrile dihydrochloride (Intermediate P94; 50 mg, 0.11 mmol) and DIEA (120 µL, 0.686 mmol) in DCM (2 mL) was treated sequentially with 1-(trifluoromethyl)cyclobutane-1-carboxylic acid (46.1 mg, 0.274 mmol) and HATU (104 mg, 0.274 mmol), then stirred for 1.5 h at ambient temperature. The resulting mixture was purified directly by silica chromatography (using 20-100% EtOAc in Hexanes as the gradient eluent) to cleanly provide the title compound (18.4 mg, 26% yield). MS (apci) m/z=515.2 (M+H).

The compounds in Table GGG were prepared using a similar method to that described in the synthesis of N-((3S,4S)-1-(5-(3-cyano-6-methoxypyrazolo[1,5-a]pyridin-4-yl)pyridin-2-yl)-3-hydroxypiperidin-4-yl)-1-(trifluoromethyl)cyclobutane-1-carboxamide (Example 493) replacing 1-(trifluoromethyl)cyclobutane-1-carboxylic acid with the appropriate carboxylic acid. Reactions were monitored for completion by LCMS, and reaction durations were adjusted accordingly. The title compounds were isolated following a chromatographic purification utilizing an appropriate gradient eluent.

TABLE GGG

| Ex # | Structure | Chemical Name | MS (apci) m/z |
|---|---|---|---|
| 494 | 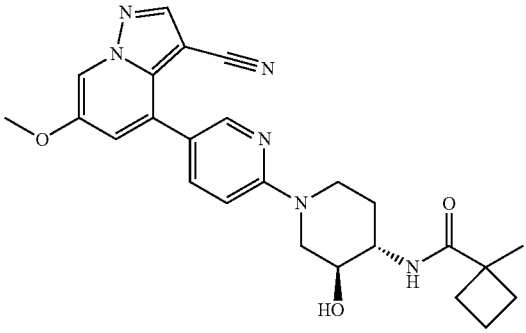 | N-((3S,4S)-1-(5-(3-cyano-6-methoxypyrazolo[1,5-a]pyridin-4-yl)pyridin-2-yl)-3-hydroxypiperidin-4-yl)-1-methylcyclobutane-1-carboxamide | 461.3 (M + H) |
| 495 | 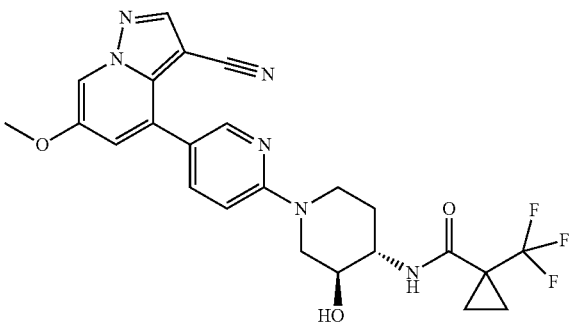 [SMILES: COc1cc(-c2ccc(N3CC[C@H](NC(=O)C4(C(F)(F)F)CC4)[C@@H](O)C3)nc2)c2c(C#N)cnn2c1] | N-((3S,4S)-1-(5-(3-cyano-6-methoxypyrazolo[1,5-a]pyridin-4-yl)pyridin-2-yl)-3-hydroxypiperidin-4-yl)-1-(trifluoromethyl)cyclopropane-1-carboxamide | 501.2 (M + H) |
| 496 | 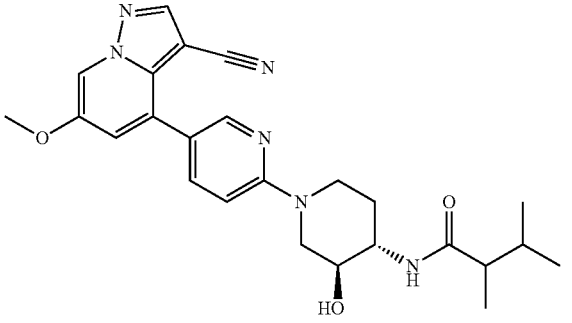 [SMILES: COc1cc(-c2ccc(N3CC[C@H](NC(=O)C(C)C(C)C)[C@@H](O)C3)nc2)c2c(C#N)cnn2c1] | N-((3S,4S)-1-(5-(3-cyano-6-methoxypyrazolo[1,5-a]pyridin-4-yl)pyridin-2-yl)-3-hydroxypiperidin-4-yl)-2,3-dimethylbutanamide | 463.2 (M + H) |

Example 497

Isopropyl (1-(5-(3-cyano-6-methoxypyrazolo[1,5-a]pyridin-4-yl)pyridin-2-yl)-4-methylpiperidin-4-yl)carbamate

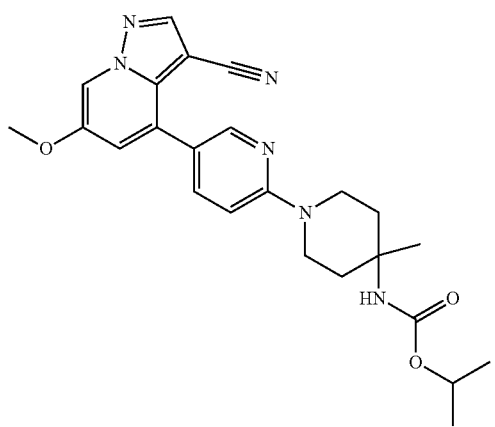 [SMILES: COc1cc(-c2ccc(N3CCC(C)(NC(=O)OC(C)C)CC3)nc2)c2c(C#N)cnn2c1]

A mixture of 4-(6-fluoropyridin-3-yl)-6-methoxypyrazolo[1,5-a]pyridine-3-carbonitrile (Intermediate P93; 26.5 mg, 0.0988 mmol), isopropyl (4-methylpiperidin-4-yl)carbamate hydrochloride (Intermediate R19, part B; 72.3 mg, 0.305 mmol) and $Cs_2CO_{3(s)}$ (322 mg, 0.988 mmol) in DMSO (1.5 mL) was stirred overnight at 100° C. The reaction mixture was cooled to ambient temperature. The incomplete reaction mixture was treated with additional isopropyl (4-methylpiperidin-4-yl)carbamate hydrochloride (72.3 mg, 0.305 mmol) and a few drops of DIEA. After stirring for 6 d at ambient temperature, the reaction mixture was diluted with water and extracted with additional DCM (4×). The combined DCM extracts were dried over anhydrous $Na_2SO_{4(s)}$, filtered and concentrated in vacuo. The resulting crude residue was purified by silica chromatography (using 0-100% Hexanes/EtOAc as the gradient eluent) to cleanly afford the title compound (5.1 mg, 12% yield). MS (apci) m/z=449.2 (M+H).

Example 498

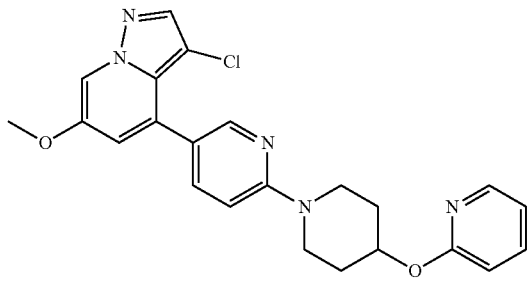 [SMILES: COc1cc(-c2ccc(N3CCC(Oc4ccccn4)CC3)nc2)c2c(Cl)cnn2c1]

3-chloro-6-methoxy-4-(6-(4-(pyridin-2-yloxy)piperidin-1-yl)pyridin-3-yl)pyrazolo[1,5-a]pyridine In a pressure vessel, a mixture of 3-chloro-4-(6-fluoropyridin-3-yl)-6-methoxypyrazolo[1,5-a]pyridine (Example 417, Step 2; 30 mg, 0.11 mmol), 2-(piperidin-4-yloxy)pyridine (29 mg, 0.16 mmol) and $Cs_2CO_{3(s)}$ (176 mg, 0.54 mmol) in DMSO (200 μL) was stirred overnight at 90° C. After cooling to ambient temperature, the reaction mixture was poured into 2N $NaOH_{(aq)}$ (2 mL), and extracted with 10% iPrOH in DCM (2×3 mL) in a PS Frit. The combined organic extracts were concentrated in vacuo. The resulting crude residue was purified by silica chromatography (using 0-100% EtOAc/Hexanes as the gradient eluent) to cleanly afford the title compound (22 mg, 47% yield). MS (apci) m/z=436.1 (M+H).

Example 499

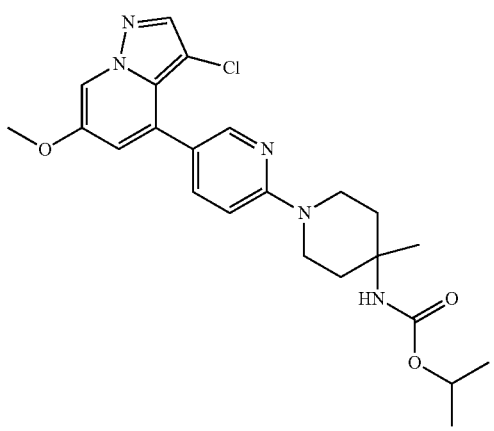 [SMILES: COc1cc(-c2ccc(N3CCC(C)(NC(=O)OC(C)C)CC3)nc2)c2c(Cl)cnn2c1]

isopropyl (1-(5-(3-chloro-6-methoxypyrazolo[1,5-a]pyridin-4-yl)pyridin-2-yl)-4-methylpiperidin-4-yl)carbamate A mixture of 3-chloro-4-(6-fluoropyridin-3-yl)-6-methoxypyrazolo[1,5-a]pyridine (Example 417, Step 2; 26.5 mg, 0.0954 mmol), isopropyl (4-methylpiperidin-4-yl)carbamate hydrochloride (Intermediate R19; 70.9 mg, 0.299 mmol) and $Cs_2CO_{3(s)}$ (311 mg, 0.954 mmol) in DMSO (3 mL) was stirred overnight at 100° C. The reaction mixture was cooled to ambient temperature. The incomplete reaction mixture was treated with additional isopropyl (4-methylpiperidin-4-yl)carbamate hydrochloride (Intermediate R19, part B; 70.9 mg, 0.299 mmol) and a few drops of DIEA. After stirring for 6 d at ambient temperature, the reaction mixture was partitioned between water and DCM then extracted with additional DCM (3×). The DCM extracts were combined, dried over anhydrous $Na_2SO_{4(s)}$, filtered and concentrated in vacuo. The resulting crude residue was purified by silica chromatography (using 0-100% Hexanes/EtOAc as the gradient eluent) to cleanly afford the title compound (1.8 mg, 3% yield). MS (apci) m/z=458.15 (M+H).

Example 500

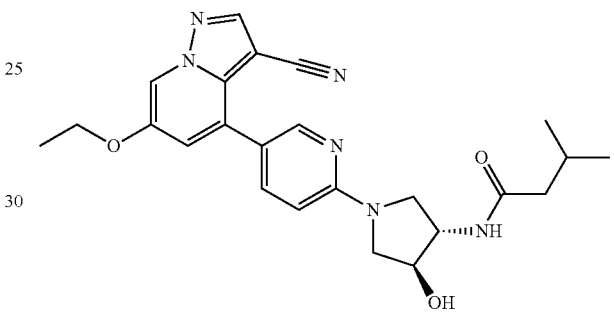

N-((3S,4S)-1-(5-(3-cyano-6-ethoxypyrazolo[1,5-a]pyridin-4-yl)pyridin-2-yl)-4-hydroxypyrrolidin-3-yl)-3-methylbutanamide A solution of 6-ethoxy-4-(6-fluoropyridin-3-yl)pyrazolo[1,5-a]pyridine-3-carbonitrile (Intermediate P6, 176.2 mg, 0.6242 mmol), and N-((3S,4S)-4-hydroxypyrrolidin-3-yl)-3-methylbutanamide hydrochloride (Intermediate R21; 270 mg, 1.212 mmol) in DMSO (1.5 mL) was treated with DIEA (545.1 μL, 3.121 mmol). The reaction mixture was stirred overnight at 90° C., then cooled to ambient temperature, and diluted with water. The resultant suspension was filtered, and the solids were rinsed with water (3×), then dried in vacuo. The crude solids were purified by C18 reverse phase chromatography (using 5-95% ACN in water with 0.1% TFA as the gradient eluent) to afford the title compound as the TFA salt. The TFA salt was suspended in MeOH, eluted through a basic resin (Stratospheres MP-HCO3) to cleanly afford the title compound (5.5 mg, 77% yield). MS (apci) m/z=449.2 (M+H).

The compounds in Table HHH were prepared using a similar method to that described for the preparation, isolation and purification of N-((3S,4S)-1-(5-(3-cyano-6-ethoxypyrazolo[1,5-a]pyridin-4-yl)pyridin-2-yl)-4-hydroxypyrrolidin-3-yl)-3-methylbutanamide (Example 500), replacing the N-((3S,4S)-4-hydroxypyrrolidin-3-yl)-3-methylbutanamide hydrochloride with the appropriate commercial pyrrolidine. Reactions were monitored for completion by LCMS. And reaction durations were adjusted accordingly.

TABLE HHH

| Ex # | Structure | Chemical Name | MS (apci) m/z |
|---|---|---|---|
| 501 | 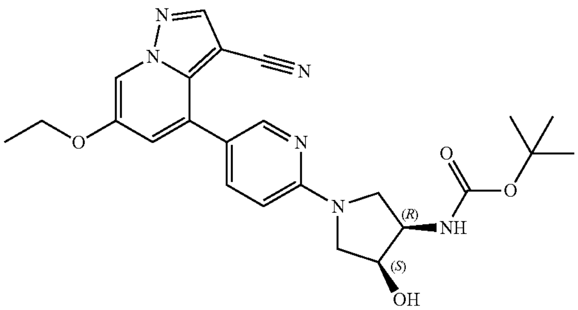 | tert-butyl ((3R,4S)-1-(5-(3-cyano-6-ethoxypyrazolo[1,5-a]pyridin-4-yl)pyridin-2-yl)-4-hydroxypyrrolidin-3-yl)carbamate | 465.2 (M + H) |
| 502 | 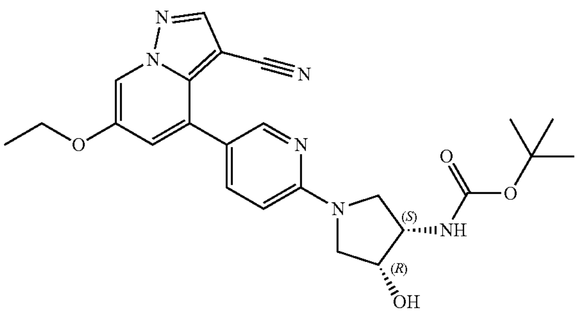 | tert-butyl ((3S,4R)-1-(5-(3-cyano-6-ethoxypyrazolo[1,5-a]pyridin-4-yl)pyridin-hydroxypyrrolidin-3-yl)carbamate | 465.2 (M + H) |

Example 503

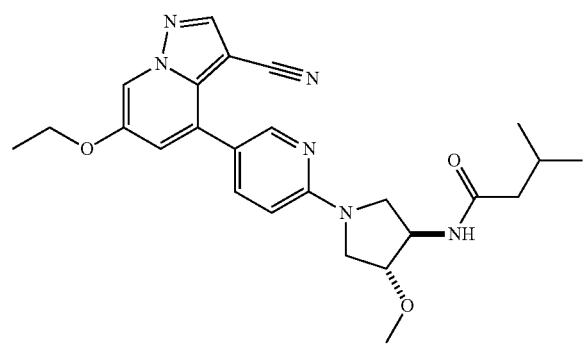 [SMILES: CCOc1cc(-c2ccc(N3C[C@@H](NC(=O)CC(C)C)[C@H](OC)C3)nc2)c2c(C#N)cnn2c1]

N-(1-(5-(3-cyano-6-ethoxypyrazolo[1,5-a]pyridin-4-yl)pyridin-2-yl)-((trans)-4-methoxypyrrolidin-3-yl)-3-methylbutanamide Step 1: Preparation of 4-(6-((trans)-3-amino-4-methoxypyrrolidin-1-yl)pyridin-3-yl)-6-ethoxypyrazolo[1,5-a]pyridine-3-carbonitrile A solution of 6-ethoxy-4-(6-fluoropyridin-3-yl)pyrazolo[1,5-a]pyridine-3-carbonitrile (Intermediate P6, 252.1 mg, 0.8931 mmol) in DMSO (4.5 mL) was treated with tert-butyl ((3R,4R)-4-methoxypyrrolidin-3-yl)carbamate (386.3 mg, 1.786 mmol) and DIEA (311.1 µL, 1.786 mmol). The reaction mixture was stirred for 1 h at 90° C. After cooling to ambient temperature, the reaction mixture was diluted with EtOAc, washed with water (3×) and brine (1×). The organic extracts were dried over Na$_2$SO$_{4(s)}$, then filtered, and concentrated in vacuo. The crude residue was dissolved in 1:1 DCM:TFA (4.5 mL), stirred for 30 min at ambient temperature, and subsequently concentrated in vacuo. The residue was purified by C18 reverse phase chromatography (5-95% ACN in water with 0.1% TFA). Fractions containing the desired compound were combined, and partitioned between 4:1 DCM:iPrOH and saturated NaHCO$_{3(aq)}$. The organic extracts were dried over anhydrous Na$_2$SO$_{4(s)}$, filtered, and concentrated in vacuo to afford the title compound (125.8 mg, 37% yield). MS (apci) m/z=379.2 (M+H).

Step 2: Preparation of N-((trans)-1-(5-(3-cyano-6-ethoxypyrazolo[1,5-a]pyridin-4-yl)pyridin-2-yl)-4-methoxypyrrolidin-3-yl)-3-methylbutanamide A solution of 4-(6-((trans)-3-amino-4-methoxypyrrolidin-1-yl)pyridin-3-yl)-6-ethoxypyrazolo[1,5-a]pyridine-3-carbonitrile (46.0 mg, 0.122 mmol) in DCM (1.2 mL) was treated with isovaleryl chloride (29.6 µL, 0.243 mmol) and TEA (84.7 µL, 0.608 mmol), then stirred for 16 h at ambient temperature. The reaction mixture was directly purified by silica chromatography (using 5-60% DCM-Acetone as the gradient eluent) to cleanly provide the title compound (45.6 mg, 81% yield). MS (apci) m/z=463.3 (M+H).

Example 504

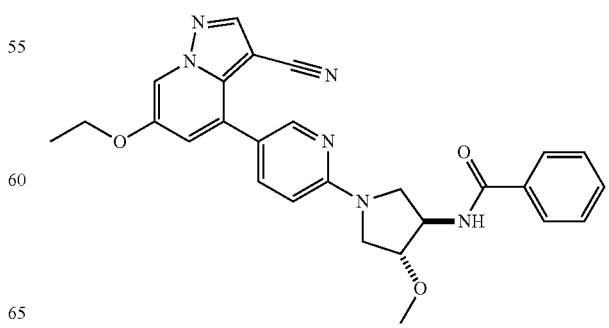

N-((trans)-1-(5-(3-cyano-6-ethoxypyrazolo[1,5-a]pyridin-4-yl)pyridin-2-yl)-4-methoxypyrrolidin-3-yl)benzamide A solution of 4-(6-((trans)-3-amino-4-methoxypyrrolidin-1-yl)pyridin-3-yl)-6-ethoxypyrazolo[1,5-a]pyridine-3-carbonitrile (Example 503, step 1: 46.5 mg, 0.1229 mmol) in DCM (1.2 mL) was treated with benzoyl chloride (28.53 µL, 0.2457 mmol) and TEA (85.63 µL, 0.6144 mmol), then stirred for 16 h at ambient temperature. The reaction mixture was directly purified by silica chromatography (using 5-60% DCM-Acetone as the gradient eluent) to cleanly provide the title compound (45.6 mg, 81% yield). MS (apci) m/z=483.3 (M+H).

Example 505

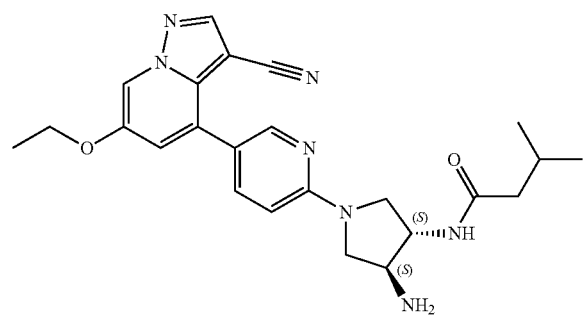

N-((3S,4S)-4-amino-1-(5-(3-cyano-6-ethoxypyrazolo[1,5-a]pyridin-4-yl)pyridin-2-yl)pyrrolidin-3-yl)-3-methylbutanamide

Step 1: Preparation of tert-butyl ((3S,4S)-4-azido-1-(5-(3-cyano-6-ethoxypyrazolo[1,5-a]pyridin-4-yl)pyridin-2-yl)pyrrolidin-3-yl)carbamate A mixture of tert-butyl ((3S,4R)-1-(5-(3-cyano-6-ethoxypyrazolo[1,5-a]pyridin-4-yl)pyridin-2-yl)-4-hydroxypyrrolidin-3-yl)carbamate (Intermediate P61, 49.1 mg, 0.106 mmol), DIAD (41.1 µL, 0.211 mmol), diphenyl phosphorazidate (58.2 mg, 0.211 mmol) and PPh$_3$ (55.4 mg, 0.211 mmol) in THF (1 mL) was stirred overnight at ambient temperature. The reaction mixture was concentrated in vacuo, and purified by silica chromatography (using 0-70% EtOAc in Hexanes as the gradient eluent) to cleanly afford the title compound (51 mg, 99% yield). MS (apci) m/z=448.2 (M+H).

Step 2: Preparation of 4-(6-((3S,4S)-3-amino-4-azidopyrrolidin-1-yl)pyridin-3-yl)-6-ethoxypyrazolo[1,5-a]pyridine-3-carbonitrile dihydrochloride A solution of tert-butyl ((3S,4 S)-4-azido-1-(5-(3-cyano-6-ethoxypyrazolo[1,5-a]pyridin-4-yl)pyridin-2-yl)pyrrolidin-3-yl)carbamate (51 mg, 0.10 mmol) in dioxane (1.0 mL) was treated with conc. HCl$_{(aq)}$ (6.3 µL, 0.21 mmol). The resulting mixture was stirred overnight at ambient temperature before concentrating the mixture in vacuo to afford the title compound (48 mg, 100% yield). MS (apci) m/z=390.15 (M+H).

Step 3: Preparation of N-((3S,4S)-4-azido-1-(5-(3-cyano-6-ethoxypyrazolo[1,5-a]pyridin-4-yl)pyridin-2-yl)pyrrolidin-3-yl)-3-methylbutanamide A 0° C. solution of 4-(6-((3S,4S)-3-amino-4-azidopyrrolidin-1-yl)pyridin-3-yl)-6-ethoxypyrazolo[1,5-a]pyridine-3-carbonitrile dihydrochloride (48 mg, 0.104 mmol) and DIEA (90.7 µL, 0.519 mmol) in DCM (1 mL) was treated dropwise with isovaleryl chloride (15.2 µL, 0.125 mmol). The cooling bath was removed, and resulting mixture was stirred overnight at ambient temperature. The reaction mixture was diluted with DCM, and washed with water. The organic extracts were directly purified by silica chromatography (using 20-80% EtOAc in Hexanes as the gradient eluent) to cleanly provide the title compound (40.1 mg, 82% yield). MS (apci) m/z=474.2 (M+H).

Step 4: Preparation of N-((3S,4S)-4-amino-1-(5-(3-cyano-6-ethoxypyrazolo[1,5-a]pyridin-4-yl)pyridin-2-yl)pyrrolidin-3-yl)-3-methylbutanamide A solution of N-((3S,4S)-4-azido-1-(5-(3-cyano-6-ethoxypyrazolo[1,5-a]pyridin-4-yl)pyridin-2-yl)pyrrolidin-3-yl)-3-methylbutanamide (40.1 mg, 0.0847 mmol) and PPh$_3$ (44.4 mg, 0.169 mmol) in THF (1 mL) was stirred at for 30 min at ambient temperature. The resulting mixture was diluted with water (0.1 mL, 0.0847 mmol), then stirred for 2 h at ambient temperature. Subsequently, additional water (0.1 mL, 0.0847 mmol) was introduced, and the reaction mixture was stirred overnight at ambient temperature. As the reaction remained incomplete, additional water (0.1 mL, 0.0847 mmol) was introduced, and the mixture was stirred overnight at 55° C. After cooling to ambient temperature, the mixture was concentrated in vacuo. The residue was purified by C18 reverse phase chromatography (using 5-95% water-ACN with 0.1% TFA as the gradient eluent) to afford the title compound as the TFA salt. The TFA salt was suspended in MeOH and filtered through a basic resin (Stratospheres MP-HCO$_3$). The filtrate was concentrated in vacuo to cleanly afford the title compound (5.5 mg, 14% yield). MS (apci) m/z=448.2 (M+H).

Example 506

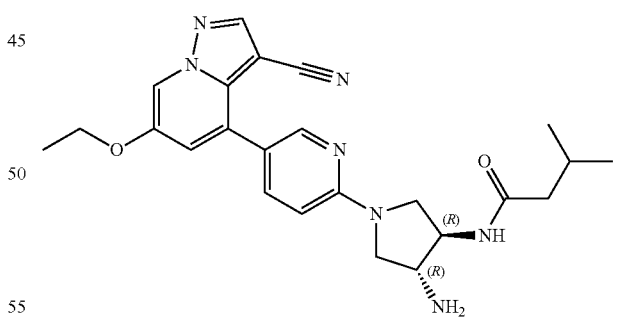

N-((3R,4R)-4-amino-1-(5-(3-cyano-6-ethoxypyrazolo[1,5-a]pyridin-4-yl)pyridin-2-yl)pyrrolidin-3-yl)-3-methylbutanamide

Step 1: Preparation of tert-butyl ((3R,4R)-4-azido-1-(5-(3-cyano-6-ethoxypyrazolo[1,5-a]pyridin-4-yl)pyridin-2-yl)pyrrolidin-3-yl)carbamate A mixture of tert-butyl ((3R,4S)-1-(5-(3-cyano-6-ethoxypyrazolo[1,5-a]pyridin-4-yl)pyridin-2-yl)-4-hydroxypyrrolidin-3-yl)carbamate (Intermediate P60, 52.9 mg, 0.114 mmol), DIAD (44.3 μL, 0.228 mmol), diphenyl phosphorazidate (62.7 mg, 0.228 mmol) and PPh₃ (59.7 mg, 0.228 mmol) in THF (1 mL) was stirred overnight at ambient temperature. The reaction mixture was concentrated in vacuo, and purified by silica chromatography (using 0-70% EtOAc in Hexanes as the gradient eluent) to cleanly afford the title compound (55 mg, 99% yield). MS (apci) m/z=490.2 (M+H).

Step 2: Preparation of 4-(6-((3R,4R)-3-amino-4-azidopyrrolidin-1-yl)pyridin-3-yl)-6-ethoxypyrazolo[1,5-a]pyridine-3-carbonitrile dihydrochloride A solution of tert-butyl ((3R,4R)-4-azido-1-(5-(3-cyano-6-ethoxypyrazolo[1,5-a]pyridin-4-yl)pyridin-2-yl)pyrrolidin-3-yl)carbamate (55 mg, 0.11 mmol) in dioxane (1.0 mL) was treated with 12 M HCl$_{(aq)}$ (6.8 μL, 0.22 mmol). The resulting mixture was stirred overnight at ambient temperature before concentrating the mixture in vacuo to afford the title compound (52 mg, 100% yield). MS (apci) m/z=390.1 (M+H).

Step 3: Preparation of N-((3R,4R)-4-azido-1-(5-(3-cyano-6-ethoxypyrazolo[1,5-a]pyridin-4-yl)pyridin-2-yl)pyrrolidin-3-yl)-3-methylbutanamide A cold (0° C.) solution of 4-(6-((3R,4R)-3-amino-4-azidopyrrolidin-1-yl)pyridin-3-yl)-6-ethoxypyrazolo[1,5-a]pyridine-3-carbonitrile dihydrochloride (52 mg, 0.112 mmol) and DIEA (98.2 μL, 0.562 mmol) in DCM (1 mL) was treated dropwise with isovaleryl chloride (16.5 μL, 0.135 mmol). The cooling bath was removed, and resulting mixture was stirred overnight at ambient temperature. The reaction mixture was diluted with DCM, and washed with water. The organic extracts were directly purified by silica chromatography (using 20-80% EtOAc in Hexanes as the gradient eluent) to cleanly provide the title compound (55.3 mg, quantitative yield). MS (apci) m/z=474.2 (M+H).

Step 4: Preparation of N-((3R,4R)-4-amino-1-(5-(3-cyano-6-ethoxypyrazolo[1,5-a]pyridin-4-yl)pyridin-2-yl)pyrrolidin-3-yl)-3-methylbutanamide A solution of N-((3R,4R)-4-azido-1-(5-(3-cyano-6-ethoxypyrazolo[1,5-a]pyridin-4-yl)pyridin-2-yl)pyrrolidin-3-yl)-3-methylbutanamide (55.3 mg, 0.117 mmol) and PPh₃ (61.3 mg, 0.234 mmol) in THF (9.57 μL) was stirred at for 30 min at ambient temperature. The resulting mixture was diluted with water (2.10 μL, 0.117 mmol), then stirred for 2 h at ambient temperature. As the reaction remained incomplete, additional water (2.10 μL, 0.117 mmol) was introduced, and the mixture was stirred for 5 d at 55° C. After cooling to ambient temperature, the mixture was concentrated in vacuo. The residue was purified by C18 reverse phase chromatography (using 5-95% water-ACN with 0.1% TFA as the gradient eluent) to afford the title compound as the TFA salt. The TFA salt was suspended in MeOH and filtered through a basic resin (Stratospheres MP-HCO3). The filtrate was concentrated in vacuo to cleanly afford the title compound (5.2 mg, 10% yield). MS (apci) m/z=448.2 (M+H).

Example 507

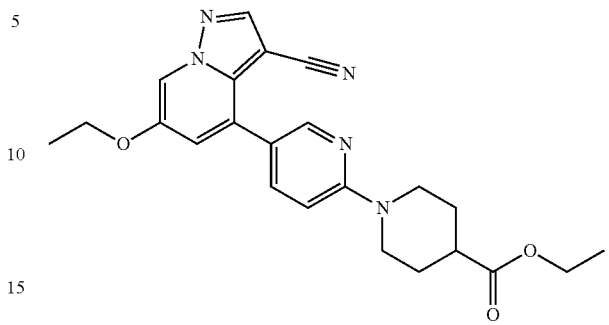

ethyl 1-(5-(3-cyano-6-ethoxypyrazolo[1,5-a]pyridin-4-yl)pyridin-2-yl)piperidine-4-carboxylate A mixture of 6-ethoxy-4-(6-fluoropyridin-3-yl)pyrazolo[1,5-a]pyridine-3-carbonitrile (Intermediate P6, 103.4 mg, 0.3663 mmol), ethyl piperidine-4-carboxylate hydrochloride (Intermediate R22; 242.3 mg, 1.251 mmol) and TEA (510.6 μL, 3.663 mmol) in DMSO (3 mL) was stirred for 6 d at 60° C. The reaction mixture was cooled to ambient temperature, and partitioned between water and DCM. The resulting biphasic mixture was extracted with DCM (3×) and then with 4:1 DCM/iPrOH. The combined organic extracts were dried over anhydrous Na₂SO₄$_{(s)}$, filtered and concentrated in vacuo. The resulting crude residue was purified by silica chromatography (using 0-25% DCM/MeOH as the gradient eluent) to cleanly afford the title compound (66.3 mg, 41% yield). MS (apci) m/z=420.2 (M+H).

Example 508

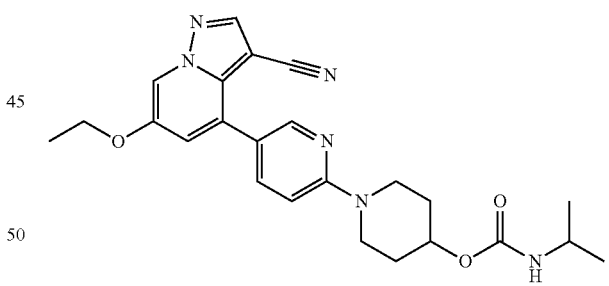

1-(5-(3-cyano-6-ethoxypyrazolo[1,5-a]pyridin-4-yl)pyridin-2-yl)piperidin-4-yl isopropylcarbamate A solution of 2-isocyanatopropane (50.5 mg, 0.593 mmol) in DCM (1 mL) and 12 M HCl$_{(aq)}$ (0.1 mL, 0.0825 mmol) was added to 6-ethoxy-4-(6-(4-hydroxypiperidin-1-yl)pyridin-3-yl)pyrazolo[1,5-a]pyridine-3-carbonitrile (Intermediate P52, 30 mg, 0.0825 mmol). After stirring overnight at ambient temperature, the reaction mixture was purified directly by silica chromatography (using 20-80% Hexanes/EtOAc as the gradient eluent) to cleanly provide the title compound (6.0 mg, 16% yield). MS (apci) m/z=449.2 (M+H).

Example 509

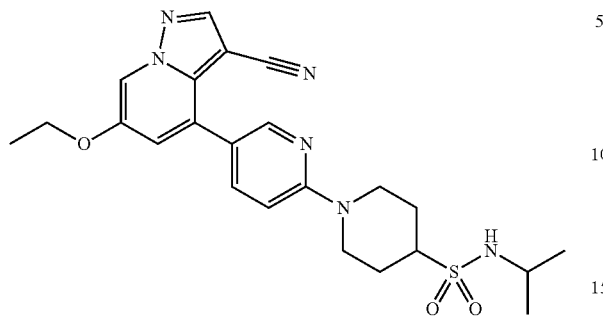

1-(5-(3-cyano-6-ethoxypyrazolo[1,5-a]pyridin-4-yl)
pyridin-2-yl)-N-isopropylpiperidine-4-sulfonamide A mixture of 6-ethoxy-4-(6-fluoropyridin-3-yl)pyrazolo[1,5-a]pyridine-3-carbonitrile (Intermediate P6, 32.1 mg, 0.114 mmol), N-isopropylpiperidine-4-sulfonamide (Intermediate R18; 45 mg, 0.218 mmol) and DIEA (59.6 μL, 0.341 mmol) in DMSO (500 L) was stirred for 2 d at 90° C. After cooling to ambient temperature, the mixture was diluted with water, cooled to 0° C., and the resultant suspension was filtered. The solids were rinsed with water, and purified by silica chromatography (using 30-100% Hexanes/EtOAc as the gradient eluent) to afford the title compound (9.8 mg, 16% yield). MS (apci) m/z=469.2 (M+H).

Example 510

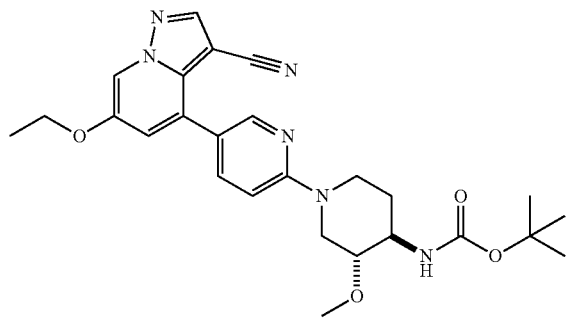 [SMILES: CCOc1cc(-c2ccc(N3CC[C@@H](NC(=O)OC(C)(C)C)[C@H](OC)C3)nc2)c2c(C#N)cnn2c1]

trans-tert-butyl (1-(5-(3-cyano-6-ethoxypyrazolo[1,5-a]pyridin-4-yl)pyridin-2-yl)-((3-methoxypiperidin-4-yl)carbamate A mixture of 6-ethoxy-4-(6-fluoropyridin-3-yl)pyrazolo[1,5-a]pyridine-3-carbonitrile (Intermediate P6, 106.1 mg, 0.3759 mmol), tert-butyl (3-methoxypiperidin-4-yl)carbamate (mixture of trans isomers) (173.1 mg, 0.7517 mmol), and $Cs_2CO_{3(s)}$ (612.3 mg, 1.879 mmol) in DMSO (2.0 mL) was stirred for 4 d at 60° C. The reaction mixture was cooled to ambient temperature, and diluted with water. The resulting suspension was filtered, and the solids were rinsed with water. The crude solid was purified by silica chromatography (using 20-60% Hexanes/EtOAc as the gradient eluent) to cleanly afford the title compound (154 mg, 83% yield). MS (apci) m/z=493.2 (M+H).

Example 511

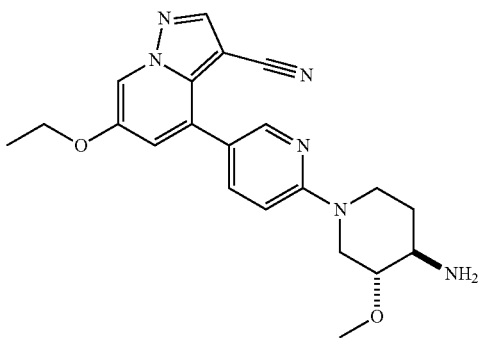 [SMILES: CCOc1cc(-c2ccc(N3CC[C@@H](N)[C@H](OC)C3)nc2)c2c(C#N)cnn2c1]

trans-4-(6-((3R,4R)-4-amino-3-methoxypiperidin-1-yl)pyridin-3-yl)-6-ethoxypyrazolo[1,5-a]pyridine-3-carbonitrile A solution of tert-butyl (1-(5-(3-cyano-6-ethoxypyrazolo[1,5-a]pyridin-4-yl)pyridin-2-yl)-3-methoxypiperidin-4-yl)carbamate (Example 510; 181 mg, 0.367 mmol) was suspended in DCM (3 mL) and treated with TFA (1.5 mL, 19 mmol). The resulting mixture was stirred for 1 h at ambient temperature before concentrating the mixture in vacuo. The crude residue was partitioned between DCM and saturated $NaHCO_{3(aq)}$ then extracted with 4:1 DCM:iPrOH (3×), then with EtOAc. The combined organic extracts were dried over anhydrous $Na_2SO_{4(s)}$, filtered and concentrated in vacuo to afford the title compound (45.4 mg, 32% yield). MS (apci) m/z=393.2 (M+H).

Example 512

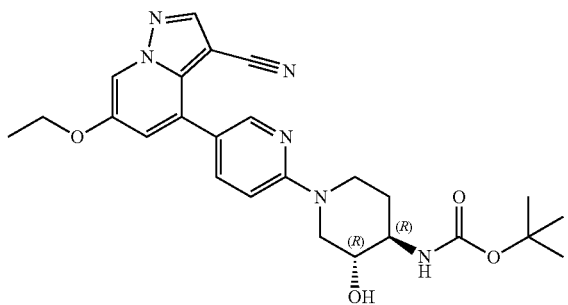

tert-butyl ((3R,4R)-1-(5-(3-cyano-6-ethoxypyrazolo[1,5-a]pyridin-4-yl)pyridin-2-yl)-3-hydroxypiperidin-4-yl)carbamate A solution of 6-ethoxy-4-(6-fluoropyridin-3-yl)pyrazolo[1,5-a]pyridine-3-carbonitrile (Intermediate P6, 177.8 mg, 0.6299 mmol) and tert-butyl ((3R,4R)-3-hydroxypiperidin-4-yl)carbamate (199 mg, 0.9201 mmol) in DMSO (1.5 mL) was treated with DIEA (55.01 µL, 3.149 mmol), and stirred for 2 d at 90° C. After cooling to ambient temperature, the mixture was diluted with water, and the resultant suspension was filtered. The solids were rinsed with water (3×), then dried in vacuo to afford the title compound (255.2 mg, 81% yield). MS (apci) m/z=479.2 (M+H).

The compounds in Table III were prepared using a similar method to that described for the preparation, isolation and purification of tert-butyl ((3R,4R)-1-(5-(3-cyano-6-ethoxypyrazolo[1,5-a]pyridin-4-yl)pyridin-2-yl)-3-hydroxypiperidin-4-yl)carbamate (Example 512), replacing the tert-butyl ((3R,4R)-3-hydroxypiperidin-4-yl)carbamate with the appropriate commercial piperidine. Reactions were conducted at 90-95° C., and monitored for completion by LCMS. And reaction durations were adjusted accordingly.

TABLE III

| Ex # | Structure | Chemical Name | MS (apci) m/z |
|---|---|---|---|
| 513 | 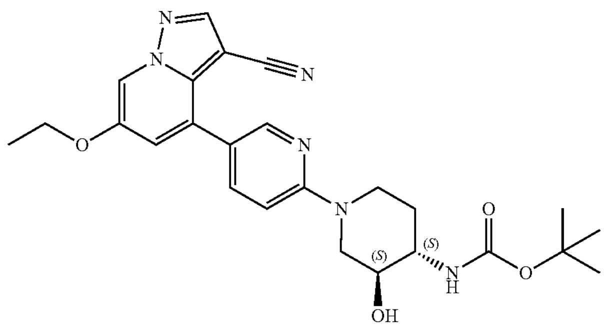 | tert-butyl ((3S,4S)-1-(5-(3-cyano-6-ethoxypyrazolo[1,5-a]pyridin-4-yl)pyridin-hydroxypiperidin-4-yl)carbamate | 479.2 (M + H) |
| 514 | 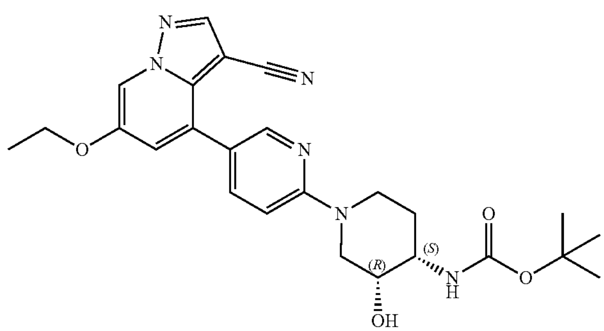 | tert-butyl ((3R,4S)-1-(5-(3-cyano-6-ethoxypyrazolo[1,5-a]pyridin-4-yl)pyridin-2-yl)-3-hydroxypiperidin-4-yl)carbamate | 479.2 (M + H) |
| 515 | 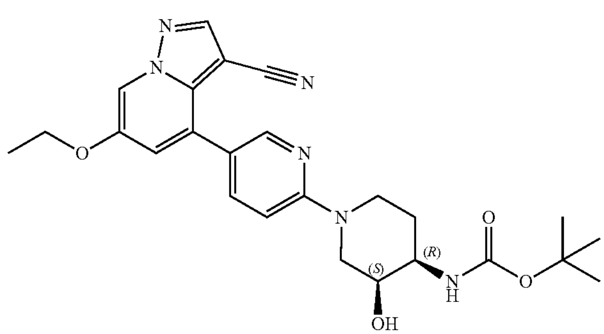 | tert-butyl ((3S,4R)-1-(5-(3-cyano-6-ethoxypyrazolo[1,5-a]pyridin-4-yl)pyridin-2-yl)-3-hydroxypiperidin-4-yl)carbamate | 479.2 (M + H) |

Example 516

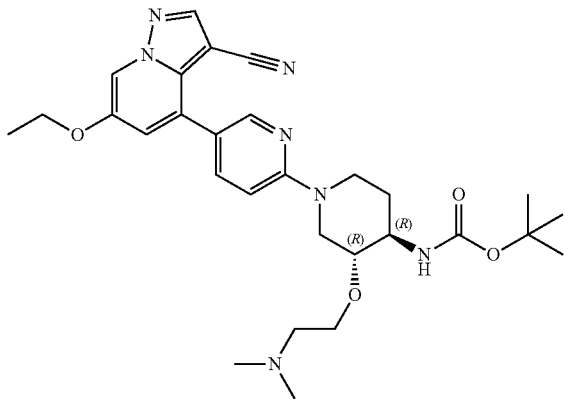

tert-butyl ((3R,4R)-1-(5-(3-cyano-6-ethoxypyrazolo
[1,5-a]pyridin-4-yl)pyridin-2-yl)-3-(2-(dimethyl
amino)ethoxy)piperidin-4-yl)carbamate A solution of tert-butyl ((3R,4R)-1-(5-(3-cyano-6-ethoxy-pyrazolo[1,5-a]pyridin-4-yl)pyridin-2-yl)-3-hydroxypiperidin-4-yl)carbamate (Example 512; 51.8 mg, 0.108 mmol) and 2-bromo-N,N-dimethylethan-1-amine hydrobromide (25.2 mg, 0.108 mmol) in DCM (1 mL) was treated with DIEA (189 μL, 1.08 mmol). After stirring overnight at ambient temperature, 5 mg of NaH was introduced. The reaction was stirred for 3 d at ambient temperature before additional 2-bromo-N,N-dimethylethan-1-amine hydrobromide (25.2 mg, 0.108 mmol) and DIEA (189 μL, 1.08 mmol) in 1 mL DCM was added. The resulting mixture was stirred overnight at ambient temperature. The reaction mixture was diluted with DCM and washed with water. The organic extracts were purified by C18 reverse phase chromatography (5-95% ACN in water with 0.1% TFA) to cleanly provide the title compound as the TFA salt. The TFA salt was suspended in MeOH, eluted through a basic resin (Stratospheres MP-HCO$_3$) to cleanly afford the title compound (2.7 mg, 5% yield). MS (apci) m/z=550.2 (M+H).

Example 517

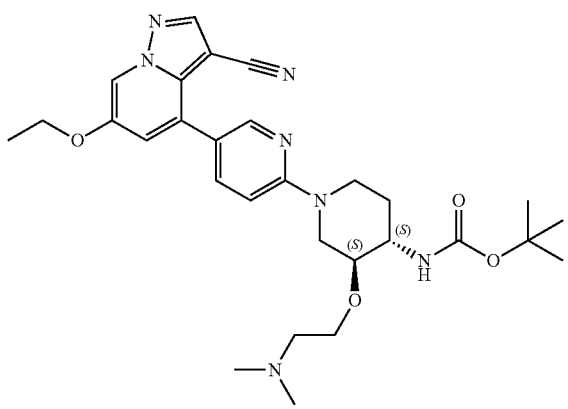

tert-butyl ((3S,4S)-1-(5-(3-cyano-6-ethoxypyrazolo
[1,5-a]pyridin-4-yl)pyridin-2-yl)-3-(2-(dimethyl
amino)ethoxy)piperidin-4-yl)carbamate The title compound was prepared, worked up and purified using a similar procedure to that described for tert-butyl ((3R,4R)-1-(5-(3-cyano-6-ethoxypyrazolo[1,5-a]pyridin-4-yl)pyridin-2-yl)-3-(2-(dimethylamino)ethoxy)piperidin-4-yl)carbamate (Example 516), replacing tert-butyl ((3R,4R)-1-(5-(3-cyano-6-ethoxypyrazolo[1,5-a]pyridin-4-yl)pyridin-2-yl)-3-hydroxypiperidin-4-yl)carbamate (Example 512) with tert-butyl ((3S,4S)-1-(5-(3-cyano-6-ethoxypyrazolo[1,5-a]pyridin-4-yl)pyridin-2-yl)-3-hydroxypiperidin-4-yl)carbamate (Example 513). MS (apci) m/z=550.3 (M+H).

Example 518

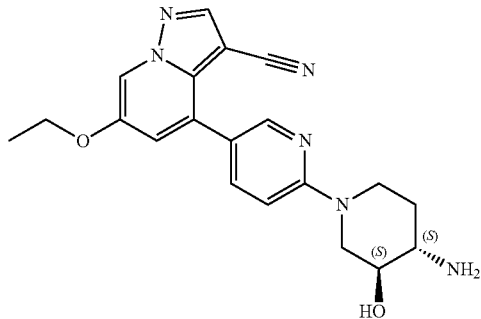

4-(6-((3S,4S)-4-amino-3-hydroxypiperidin-1-yl)
pyridin-3-yl)-6-ethoxypyrazolo[1,5-a]pyridine-3-
carbonitrile A solution of tert-butyl ((3S,4S)-1-(5-(3-cyano-6-ethoxy-pyrazolo[1,5-a]pyridin-4-yl)pyridin-2-yl)-3-hydroxypiperidin-4-yl)carbamate (Example 513; 174.3 mg, 0.36 mmol) in dioxane (2.0 mL) was treated with 12 M HCl$_{(aq)}$ (22.13 μL, 0.7284 mmol). The resulting mixture was stirred for 1 h at ambient temperature before concentrating the mixture in vacuo. The crude residue was dissolve in MeOH and eluted through a basic resin (Stratospheres MP-HCO$_3$), to cleanly afford the title compound (137 mg, 96% yield). MS (apci) m/z=379.15 (M+H).

Example 519

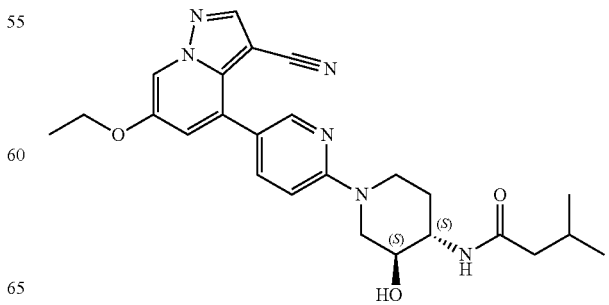

N-((3S,4S)-1-(5-(3-cyano-6-ethoxypyrazolo[1,5-a]pyridin-4-yl)pyridin-2-yl)-3-hydroxypiperidin-4-yl)-3-methylbutanamide A solution of 4-(6-((3S,4S)-4-amino-3-hydroxypiperidin-1-yl)pyridin-3-yl)-6-ethoxypyrazolo[1,5-a]pyridine-3-carbonitrile (Example 518; 50 mg, 0.132 mmol) and DIEA (115 μL, 0.661 mmol) in DCM (2 mL) was stirred for 20 min at 0° C. The cold solution was treated dropwise with isovaleryl chloride (32.2 μL, 0.264 mmol). The resulting mixture was stirred overnight at ambient temperature. The reaction mixture was directly purified by silica chromatography (using 20-80% EtOAc in Hexanes as the gradient eluent) to cleanly provide the title compound (30.9 mg, 51% yield). MS (apci) m/z=463.25 (M+H).

Example 520

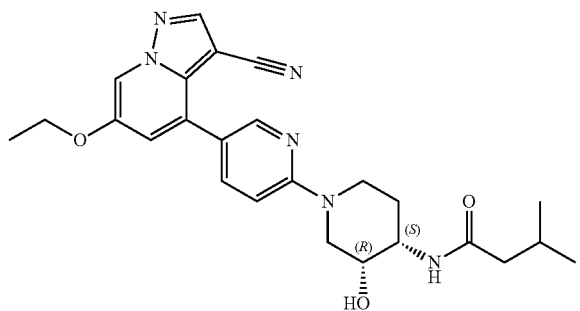

N-((3R,4S)-1-(5-(3-cyano-6-ethoxypyrazolo[1,5-a]pyridin-4-yl)pyridin-2-yl)-3-hydroxypiperidin-4-yl)-3-methylbutanamide Step 1: Preparation of 4-(6-((3R,4S)-4-amino-3-hydroxypiperidin-1-yl)pyridin-3-yl)-6-ethoxypyrazolo[1,5-a]pyridine-3-carbonitrile dihydrochloride A solution tert-butyl ((3R,4 S)-1-(5-(3-cyano-6-ethoxypyrazolo[1,5-a]pyridin-4-yl)pyridin-2-yl)-3-hydroxypiperidin-4-yl)carbamate (Example 514; 293.5 mg, 0.6133 mmol) in dioxane (2.0 mL) was treated with 12 M HCl$_{(aq)}$ (100.7 μL, 1.227 mmol). The resulting mixture was stirred overnight at ambient temperature, then concentrated in vacuo to cleanly afford the title compound (276 mg, 100% yield). MS (apci) m/z=379.2 (M+H).

Step 2: Preparation of N-((3R,4S)-1-(5-(3-cyano-6-ethoxypyrazolo[1,5-a]pyridin-4-yl)pyridin-2-yl)-3-hydroxypiperidin-4-yl)-3-methylbutanamide A solution of 4-(6-((3R,4 S)-4-amino-3-hydroxypiperidin-1-yl)pyridin-3-yl)-6-ethoxypyrazolo[1,5-a]pyridine-3-carbonitrile dihydrochloride (112 mg, 0.2481 mmol) in DCM (2 mL) was treated with DIEA (433.4 μL, 2.481 mmol), and then stirred for 5 min at 0° C. The cold solution was treated dropwise with isovaleryl chloride (60.51 μL, 0.4963 mmol). The cooling bath was removed, and the resulting mixture was stirred for 1 h at ambient temperature. The reaction mixture was directly purified by silica chromatography (using 20-100% EtOAc in Hexanes as the gradient eluent) to cleanly provide the title compound (115.7 mg, quantitative yield). MS (apci) m/z=463.2 (M+H).

Example 521

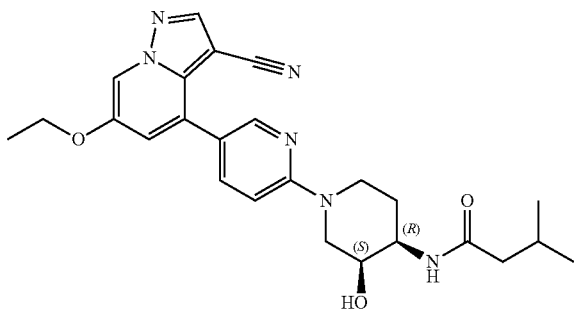

N-((3S,4R)-1-(5-(3-cyano-6-ethoxypyrazolo[1,5-a]pyridin-4-yl)pyridin-2-yl)-3-hydroxypiperidin-4-yl)-3-methylbutanamide Step 1: Preparation of 4-(6-((3S,4R)-4-amino-3-hydroxypiperidin-1-yl)pyridin-3-yl)-6-ethoxypyrazolo[1,5-a]pyridine-3-carbonitrile dihydrochloride A solution of tert-butyl ((3S,4R)-1-(5-(3-cyano-6-ethoxypyrazolo[1,5-a]pyridin-4-yl)pyridin-2-yl)-3-hydroxypiperidin-4-yl)carbamate (Example 515; 341.5 mg, 0.7136 mmol) in dioxane (2.0 mL) was treated with 12 M HCl$_{(aq)}$ (117.2 μL, 1.427 mmol). The resulting mixture was stirred overnight at ambient temperature, then concentrated in vacuo to cleanly afford the title compound (322 mg, 100% yield). MS (apci) m/z=379.2 (M+H).

Step 2: Preparation of N-((3S,4R)-1-(5-(3-cyano-6-ethoxypyrazolo[1,5-a]pyridin-4-yl)pyridin-2-yl)-3-hydroxypiperidin-4-yl)-3-methylbutanamide A solution of 4-(6-((3S,4R)-4-amino-3-hydroxypiperidin-1-yl)pyridin-3-yl)-6-ethoxypyrazolo[1,5-a]pyridine-3-carbonitrile dihydrochloride (160.4 mg, 0.3554 mmol) in DCM (2 mL) was treated with DIEA (620.7 μL, 3.554 mmol), and then stirred for 5 min at 0° C. The cold solution was treated dropwise with isovaleryl chloride (86.65 μL, 0.7108 mmol). The cooling bath was removed, and the resulting mixture was stirred for 1 h at ambient temperature. The reaction mixture was directly purified by silica chromatography (using 30-100% EtOAc in Hexanes as the gradient eluent) to cleanly provide the title compound (63.4 mg, 39% yield). MS (apci) m/z=463.2 (M+H).

Example 522

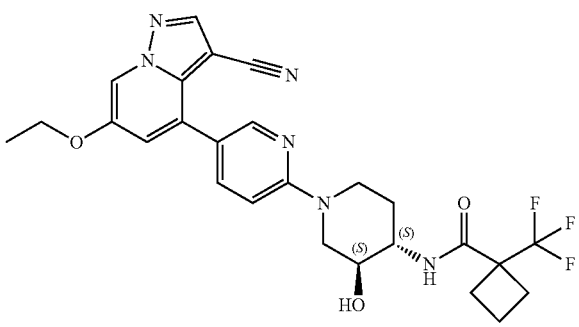

N-((3S,4S)-1-(5-(3-cyano-6-ethoxypyrazolo[1,5-a]pyridin-4-yl)pyridin-2-yl)-3-hydroxypiperidin-4-yl)-1-(trifluoromethyl)cyclobutane-1-carboxamide Step 1: Preparation of 4-(6-((3S,4S)-4-amino-3-hydroxypiperidin-1-yl)pyridin-3-yl)-6-ethoxypyrazolo[1,5-a]pyridine-3-carbonitrile dihydrochloride A solution of tert-butyl ((3S,4S)-1-(5-(3-cyano-6-ethoxypyrazolo[1,5-a]pyridin-4-yl)pyridin-2-yl)-3-hydroxypiperidin-4-yl)carbamate (Example 513; 845.1 mg, 1.766 mmol) in dioxane (3.0 mL) was treated with 12 M HCl$_{(aq)}$ (290.0 µL, 3.532 mmol). The resulting mixture was stirred overnight at ambient temperature then concentrated in vacuo to cleanly afford the title compound (797 mg, 100% yield). MS (apci) m/z=379.3 (M+H).

Step 2: Preparation of N-((3S,4S)-1-(5-(3-cyano-6-ethoxypyrazolo[1,5-a]pyridin-4-yl)pyridin-2-yl)-3-hydroxypiperidin-4-yl)-1-(trifluoromethyl)cyclobutane-1-carboxamide A solution of 4-(6-((3S,4S)-4-amino-3-hydroxypiperidin-1-yl)pyridin-3-yl)-6-ethoxypyrazolo[1,5-a]pyridine-3-carbonitrile dihydrochloride (61.6 mg, 0.136 mmol) and 1-(trifluoromethyl)cyclobutane-1-carboxylic acid (45.9 mg, 0.273 mmol) in DCM (1 mL) was treated sequentially with DIEA (119 µL, 0.682 mmol) and HATU (104 mg, 0.273 mmol), then stirred for 1 h at ambient temperature. The resulting mixture was purified directly by silica chromatography (using 20-100% EtOAc in Hexanes as the gradient eluent) to cleanly provide the title compound (45.5 mg, 63% yield). MS (apci) m/z=529.25 (M+H).

The compounds in Table JJJ were prepared using a similar method to that described in Step 2 in the synthesis of N-((3S,4S)-1-(5-(3-cyano-6-ethoxypyrazolo[1,5-a]pyridin-4-yl)pyridin-2-yl)-3-hydroxypiperidin-4-yl)-1-(trifluoromethyl)cyclobutane-1-carboxamide (Example 522), replacing 1-(trifluoromethyl)cyclobutane-1-carboxylic acid with the appropriate carboxylic acid. Reactions were monitored for completion by LCMS, and reaction durations were adjusted accordingly. The title compounds were isolated following a chromatographic purification utilizing an appropriate gradient eluent. Where noted (*) an aqueous work up, consisting of dilution of the reaction mixture with DCM and water wash preceded the chromatographic purification.

TABLE JJJ

| Ex # | Structure | Chemical Name | MS (apci) m/z |
|---|---|---|---|
| 523* | 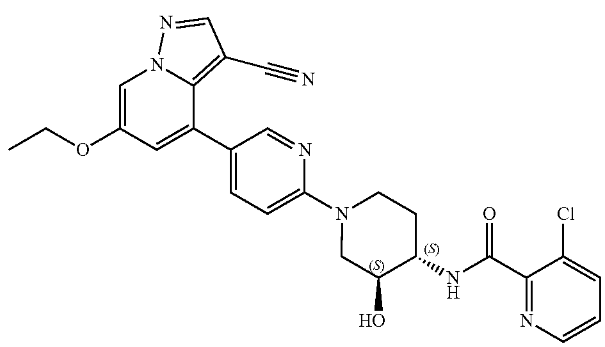 | 3-chloro-N-((3S,4S)-1-(5-(3-cyano-6-ethoxypyrazolo[1,5-a]pyridin-4-yl)pyridin-2-yl)-3-hydroxypiperidin-4-yl)picolinamide | 518.15 (M + H) |
| 524 | 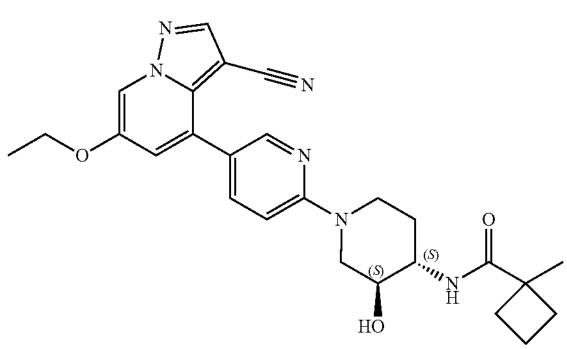 | N-((3S,4S)-1-(5-(3-cyano-6-ethoxypyrazolo[1,5-a]pyridin-4-yl)pyridin-2-yl)-3-hydroxypiperidin-4-yl)-1-methylcyclobutane-1-carboxamide | 475.3 (M + H) |

TABLE JJJ-continued

| Ex # | Structure | Chemical Name | MS (apci) m/z |
|---|---|---|---|
| 525 | 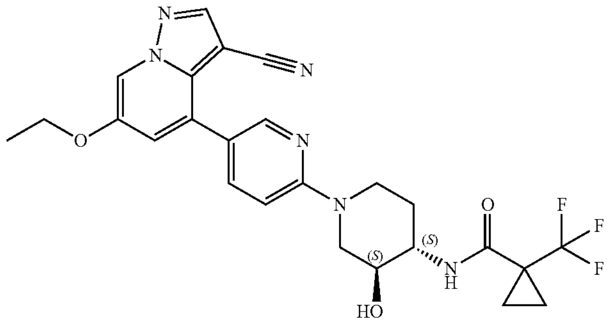 | N-((3S,4S)-1-(5-(3-cyano-6-ethoxypyrazolo[1,5-a]pyridin-4-yl)pyridin-2-yl)-3-hydroxypiperidin-4-yl)-1-(trifluoromethyl)cyclopropane-1-carboxamide | 515.2 (M + H) |
| 526 | 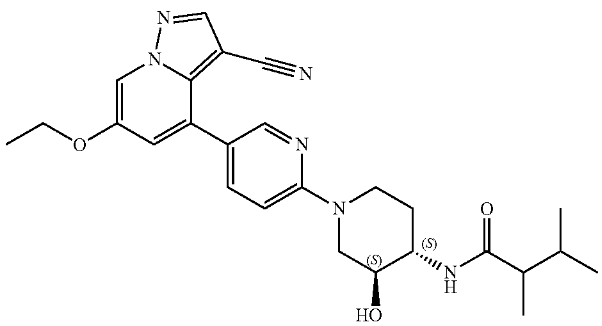 | N-((3S,4S)-1-(5-(3-cyano-6-ethoxypyrazolo[1,5-a]pyridin-4-yl)pyridin-2-yl)-3-hydroxypiperidin-4-yl)-2,3-dimethylbutanamide | 477.3 (M + H) |

Example 527

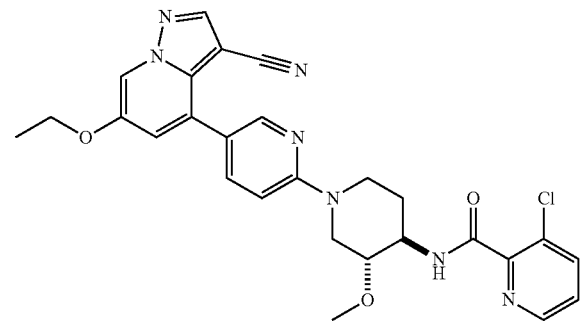 [SMILES: CCOc1cc(-c2ccc(N3CC[C@@H](NC(=O)c4ncccc4Cl)[C@H](OC)C3)nc2)c2c(C#N)cnn2c1]

trans-3-chloro-N-(( )-1-(5-(3-cyano-6-ethoxypyrazolo[1,5-a]pyridin-4-yl)pyridin-2-yl)-3-methoxypiperidin-4-yl)picolinamide A solution of trans-4-(6-(O-4-amino-3-methoxypiperidin-1-yl)pyridin-3-yl)-6-ethoxypyrazolo[1,5-a]pyridine-3-carbonitrile (Example 511; 26.5 mg, 0.0675 mmol) in DMSO (500 μL) was treated sequentially with 3-chloropicolinic acid (21.3 mg, 0.135 mmol), DIEA (59.0 μL, 0.338 mmol) and HATU (51.3 mg, 0.135 mmol). The mixture was stirred 2.5 h at ambient temperature then diluted with DCM, and washed with water. The organic extracts were purified directly by silica chromatography (using 30-100% EtOAc in Hexanes as the gradient eluent) to cleanly provide the title compound (21.5 mg, 60% yield). MS (apci) m/z=532.2 (M+H).

Example 528

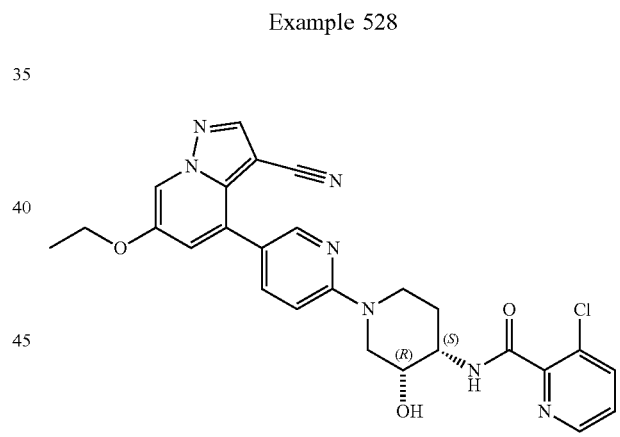

3-chloro-N-((3R,4S)-1-(5-(3-cyano-6-ethoxypyrazolo[1,5-a]pyridin-4-yl)pyridin-2-yl)-3-hydroxypiperidin-4-yl)picolinamide A solution of 4-(6-((3R,4S)-4-amino-3-hydroxypiperidin-1-yl)pyridin-3-yl)-6-ethoxypyrazolo[1,5-a]pyridine-3-carbonitrile dihydrochloride (Example 520, Step 1; 164 mg, 0.3634 mmol) in DCM (2 mL) was treated sequentially with DIEA (634.6 μL, 3.634 mmol), 3-chloropicolinic acid (229.0 mg, 1.453 mmol) and HATU (276.3 mg, 0.7267 mmol). The resulting mixture was stirred for 3 h at ambient temperature, and washed with water. The organic extracts were purified directly by silica chromatography (using 30-100% EtOAc in Hexanes as the gradient eluent) to cleanly provide the title compound (241.1 mg, quantitative yield). MS (apci) m/z=518.1 (M+H).

Example 529

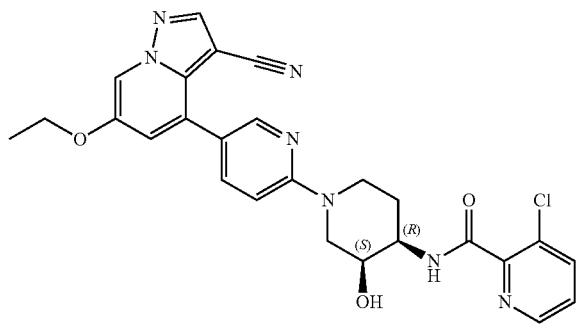

3-chloro-N-((3S,4R)-1-(5-(3-cyano-6-ethoxypyrazolo[1,5-a]pyridin-4-yl)pyridin-2-yl)-3-hydroxypiperidin-4-yl)picolinamide A solution of 4-(6-((3S,4R)-4-amino-3-hydroxypiperidin-1-yl)pyridin-3-yl)-6-ethoxypyrazolo[1,5-a]pyridine-3-carbonitrile dihydrochloride (Example 521, Step 1; 161.6 mg, 0.3580 mmol) in DCM (2 mL) was treated sequentially with DIEA (625.3 µL, 3.580 mmol), 3-chloropicolinic acid (225.6 mg, 1.432 mmol) and HATU (272.3 mg, 0.7161 mmol). The resulting mixture was stirred for 3 h at ambient temperature, and washed with water. The organic extracts were purified directly by silica chromatography (using 30-100% EtOAc in Hexanes as the gradient eluent) to cleanly provide the title compound (241.1 mg, quantitative yield). MS (apci) m/z=518.1 (M+H).

Example 530

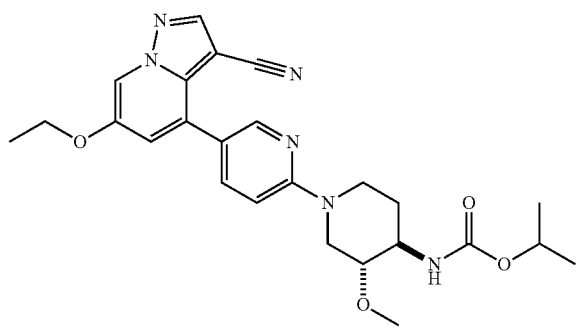 [SMILES: CCOc1cc(-c2ccc(N3CC[C@@H](NC(=O)OC(C)C)[C@H](OC)C3)nc2)c2c(C#N)cnn2c1]

Trans-isopropyl (1-(5-(3-cyano-6-ethoxypyrazolo[1,5-a]pyridin-4-yl)pyridin-2-yl)-3-methoxypiperidin-4-yl)carbamate A solution of trans-4-(6-(4-amino-3-methoxypiperidin-1-yl)pyridin-3-yl)-6-ethoxypyrazolo[1,5-a]pyridine-3-carbonitrile (Example 511; 50 mg, 0.13 mmol) and DIEA (4.45 µL, 0.0255 mmol) in DCM (500 µL) was treated with isopropyl carbonochloridate (2.34 mg, 0.0191 mmol). The resulting mixture was stirred overnight at ambient temperature, and then directly purified by silica chromatography (using 20-80% Hexanes/EtOAc as the gradient eluent) to cleanly provide the title compound (6.3 mg, quantitative yield). MS (apci) m/z=479.15 (M+H).

Example 531

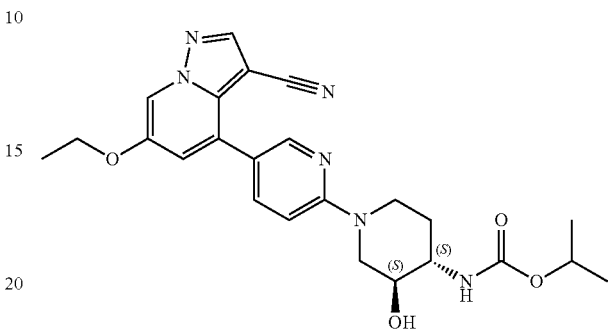

isopropyl ((3S,4S)-1-(5-(3-cyano-6-ethoxypyrazolo[1,5-a]pyridin-4-yl)pyridin-2-yl)-3-hydroxypiperidin-4-yl)carbamate A solution of 4-(6-((3S,4S)-4-amino-3-hydroxypiperidin-1-yl)pyridin-3-yl)-6-ethoxypyrazolo[1,5-a]pyridine-3-carbonitrile (Example 518; 50 mg, 0.13 mmol) and DIEA (120 µL, 0.69 mmol) in DCM (2 mL) was stirred for 20 min at 0° C. The cold solution was treated with isopropyl chloroformate (33 µL, 0.26 mmol), and the resulting mixture was stirred for 3 d at ambient temperature. The reaction mixture was directly purified by silica chromatography (using 20-90% EtOAc in Hexanes as the gradient eluent) to cleanly provide the title compound (60 mg, 98% yield). MS (apci) m/z=465.2 (M+H).

Example 532

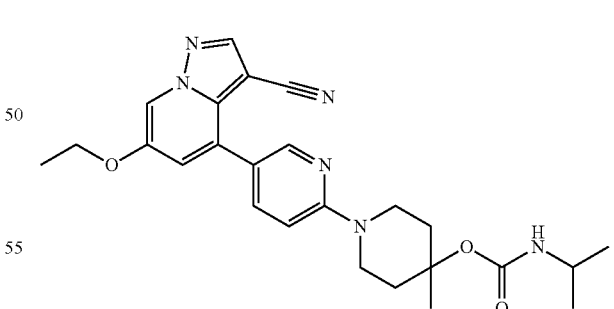

1-(5-(3-cyano-6-ethoxypyrazolo[1,5-a]pyridin-4-yl)pyridin-2-yl)-4-methylpiperidin-4-yl isopropylcarbamate A mixture of 6-ethoxy-4-(6-fluoropyridin-3-yl)pyrazolo[1,5-a]pyridine-3-carbonitrile (Intermediate P6, 26.4 mg, 0.0935 mmol), 4-methylpiperidin-4-yl isopropylcarbamate hydrochloride (Intermediate R24; 50 mg, 0.211 mmol) and Cs₂CO₃₍s₎ (400 mg, 1.23 mmol) in DMSO (1.0 mL) was stirred overnight at 60° C. The reaction mixture was cooled to ambient temperature. The reaction mixture was partitioned between DCM and water, then extracted with DCM (3×). The combined organic extracts were dried over Na₂SO₄₍s₎, then filtered, and concentrated in vacuo. The crude residue was purified first by silica chromatography (using 0-100% Hexanes/EtOAc as the gradient eluent), then by C18 reverse phase chromatography (using 0-70% water/ACN with 0.1% TFA as the gradient eluent) to afford the title compound as the TFA salt. The TFA salt was partitioned between DCM and saturated NaHCO₃₍aq₎, and the biphasic mixture was extracted with DCM (2×). The combined organic extracts were dried over anhydrous Na₂SO₄₍s₎, filtered, and concentrated in vacuo to cleanly afford the title compound (2.7 mg, 6% yield). MS (apci) m/z=463.2 (M+H).

Example 533

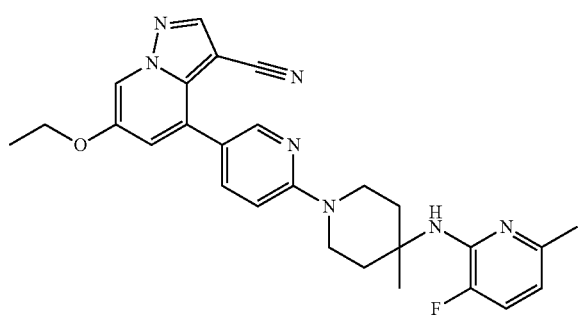 [SMILES: CCOc1cc(-c2ccc(N3CCC(C)(Nc4nc(C)ccc4F)CC3)nc2)c2c(C#N)cnn2c1]

6-ethoxy-4-(6-(4-((3-fluoro-6-methylpyridin-2-yl)amino)-4-methylpiperidin-1-yl)pyridin-3-yl)pyrazolo[1,5-a]pyridine-3-carbonitrile A mixture of 4-(6-(4-amino-4-methylpiperidin-1-yl)pyridin-3-yl)-6-ethoxypyrazolo[1,5-a]pyridine-3-carbonitrile (Intermediate P89, 16.1 mg, 0.0428 mmol), 2,3-difluoro-6-methylpyridine (28.7 mg, 0.222 mmol) and Cs₂CO₃₍s₎ (139.3 mg, 0.4277 mmol) in DMSO (1.0 mL) was stirred for 4 d at 60° C. Subsequently, additional 2,3-difluoro-6-methylpyridine (28.7 mg, 0.222 mmol) was introduced, and the reaction mixture was stirred overnight at 100° C. As the reaction had still not progressed sufficiently, the mixture was cooled to ambient temperature and DIEA (a few drops) was added. The resulting mixture was stirred for 7 d at ambient temperature. The reaction mixture was partitioned between DCM and water, then extracted with DCM (3×). The combined organic extracts were dried over Na₂SO₄₍s₎, then filtered, and concentrated in vacuo. The crude residue was purified by silica chromatography (using 0-100% Hexanes/EtOAc as the gradient eluent) to cleanly afford the title compound (2.1 mg, 10% yield). MS (apci) m/z=486.2 (M+H).

Example 534

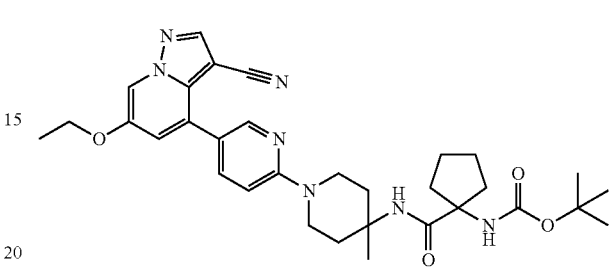

tert-butyl (1-((1-(5-(3-cyano-6-ethoxypyrazolo[1,5-a]pyridin-4-yl)pyridin-2-yl)-4-methylpiperidin-4-yl)carbamoyl)cyclopentyl)carbamate A solution of 1-((tert-butoxycarbonyl)amino)cyclopentane-1-carboxylic acid (24 mg, 0.11 mmol) in DMA (445 μL) was treated sequentially with HATU (41 mg, 0.11 mmol), 4-(6-(4-amino-4-methylpiperidin-1-yl)pyridin-3-yl)-6-ethoxypyrazolo[1,5-a]pyridine-3-carbonitrile dihydrochloride (Intermediate P95; 40 mg, 0.089 mmol) and DIEA (78 μL, 0.45 mmol). The resulting mixture was stirred for 16 h at ambient temperature, and then vacuum filtered. The solids were washed sequentially with DMA (3×0.2 mL) and heptane (3×0.5 mL) then dried in vacuo. The filtrate was concentrated in vacuo, and purified by C18 reverse phase chromatography (using 5-60% ACN in water as the gradient eluent). The solids from the filtration were combined with the pure fractions from the chromatography to cleanly afford the title compound (50 mg, 96% yield). MS (apci) m/z=588.3 (M+H); 610.2 (M+Na).

The compounds in Table KKK were prepared using a similar method to that described in the synthesis of tert-butyl (1-((1-(5-(3-cyano-6-ethoxypyrazolo[1,5-a]pyridin-4-yl)pyridin-2-yl)-4-methylpiperidin-4-yl)carbamoyl)cyclopentyl)carbamate (Example 534), replacing 1-((tert-butoxycarbonyl)amino)cyclopentane-1-carboxylic acid with the appropriate carboxylic acid. Reactions were monitored for completion by LCMS, and reaction durations were adjusted accordingly. Reactions that produced suspensions were worked up/purified following a method similar to that used in the synthesis of Example 534 substituting an appropriate gradient eluent for the chromatographic purification of the filtrate. For reactions that produced solutions, the reaction mixtures were directly subjected to chromatographic purification using an appropriate gradient eluent. Either method allowed for the clean isolation of the title compounds shown.

TABLE KKK

| Ex # | Structure | Chemical Name | MS (apci) m/z |
|---|---|---|---|
| 535 | 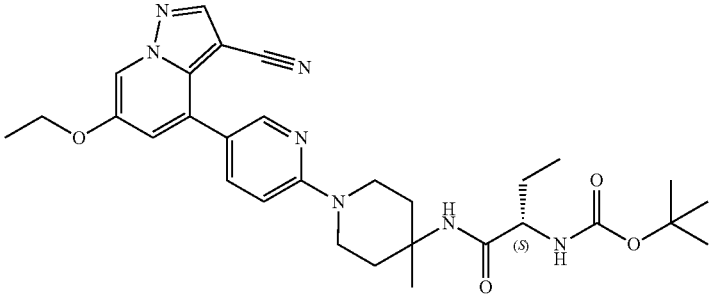 | tert-butyl (S)-(1-((1-(5-(3-cyano-6-ethoxypyrazolo[1,5-a]pyridin-4-yl)pyridin-2-yl)-4-methylpiperidin-4-yl)amino)-1-oxobutan-2-yl)carbamate | 562.3 (M + H), 584.3 (M + Na) |
| 536 | 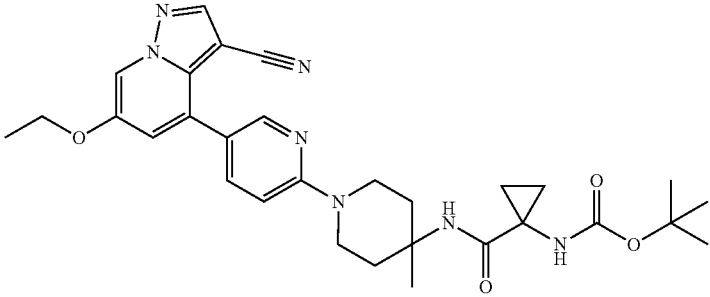 [SMILES: CCOc1cc(-c2ccc(N3CCC(C)(NC(=O)C4(NC(=O)OC(C)(C)C)CC4)CC3)nc2)c2c(C#N)cnn2c1] | tert-butyl (1-((1-(5-(3-cyano-6-ethoxypyrazolo[1,5-a]pyridin-4-yl)pyridin-2-yl)-4-methylpiperidin-4-yl)carbamoyl)cyclopropyl)carbamate | 560.2 (M + H), 582.3 (M + Na) |
| 537 | 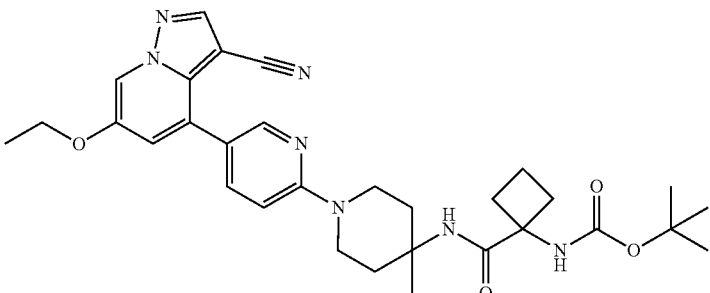 | tert-butyl (1-((1-(5-(3-cyano-6-ethoxypyrazolo[1,5-a]pyridin-4-yl)pyridin-2-yl)-4-methylpiperidin-4-yl)carbamoyl)cyclobutyl)carbamate | 574.3 (M + H), 596.2 (M + Na) |
| 538 | 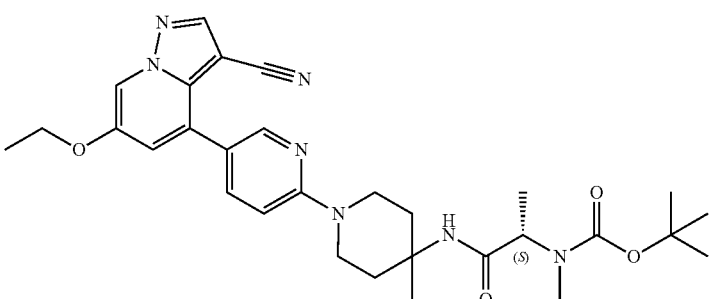 | tert-butyl (S)-(1-((1-(5-(3-cyano-6-ethoxypyrazolo[1,5-a]pyridin-4-yl)pyridin-2-yl)-4-methylpiperidin-4-yl)amino)-1-oxopropan-2-yl)(methyl)carbamate | 562.3 (M + H), 584.2 (M + Na) |
| 539 | 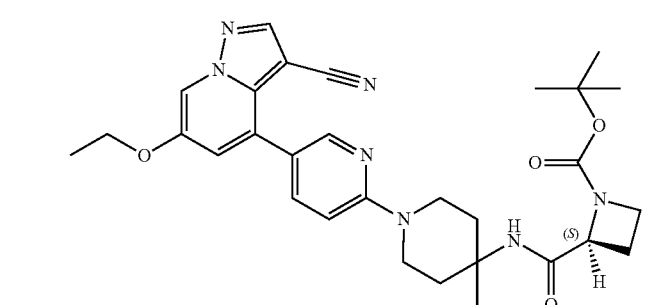 | tert-butyl (S)-2-((1-(5-(3-cyano-6-ethoxypyrazolo[1,5-a]pyridin-4-yl)pyridin-2-yl)-4-methylpiperidin-4-yl)carbamoyl)azetidine-1-carboxylate | 560.2 (M + H) |

TABLE KKK-continued

| Ex # | Structure | Chemical Name | MS (apci) m/z |
|---|---|---|---|
| 540 | 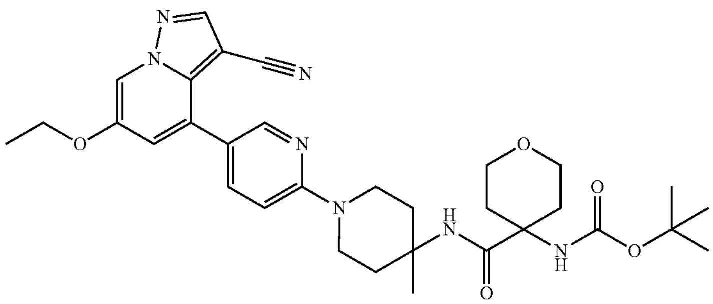 [SMILES: CCOc1cc(-c2ccc(N3CCC(C)(NC(=O)C4(NC(=O)OC(C)(C)C)CCOCC4)CC3)nc2)c2c(C#N)cnn2c1] | tert-butyl (4-((1-(5-(3-cyano-6-ethoxypyrazolo[1,5-a]pyridin-4-yl)pyridin-2-yl)-4-methylpiperidin-4-yl)carbamoyl)tetrahydro-2H-pyran-4-yl)carbamate | 604.3 (M + H), 626.2 (M + Na) |
| 541 | 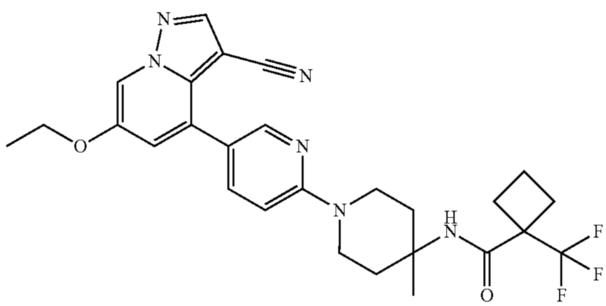 [SMILES: CCOc1cc(-c2ccc(N3CCC(C)(NC(=O)C4(C(F)(F)F)CCC4)CC3)nc2)c2c(C#N)cnn2c1] | N-(1-(5-(3-cyano-6-ethoxypyrazolo[1,5-a]pyridin-4-yl)pyridin-2-yl)-4-methylpiperidin-4-yl)-1-(trifluoromethyl)cyclobutane-1-carboxamide | 527.2 (M + H), 549.2 (M + Na) |
| 542 | 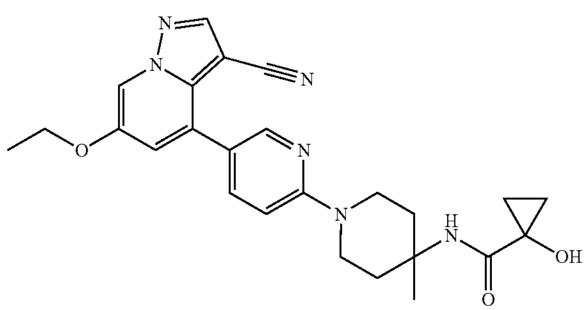 [SMILES: CCOc1cc(-c2ccc(N3CCC(C)(NC(=O)C4(O)CC4)CC3)nc2)c2c(C#N)cnn2c1] | N-(1-(5-(3-cyano-6-ethoxypyrazolo[1,5-a]pyridin-4-yl)pyridin-2-yl)-4-methylpiperidin-4-yl)-1-hydroxycyclopropane-1-carboxamide | 461.2 (M + H), 483.2 (M + Na) |
| 543 | 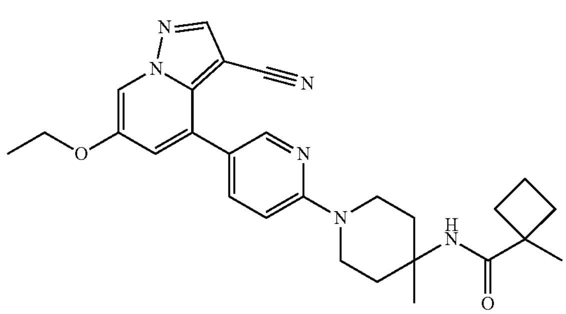 [SMILES: CCOc1cc(-c2ccc(N3CCC(C)(NC(=O)C4(C)CCC4)CC3)nc2)c2c(C#N)cnn2c1] | N-(1-(5-(3-cyano-6-ethoxypyrazolo[1,5-a]pyridin-4-yl)pyridin-2-yl)-4-methylpiperidin-4-yl)-1-methylcyclobutane-1-carboxamide | 473.3 (M + H), 495.2 (M + Na) |

Example 544

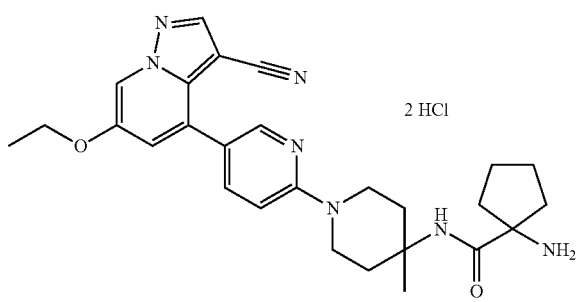 [SMILES: CCOc1cc(-c2ccc(N3CCC(C)(NC(=O)C4(N)CCCC4)CC3)nc2)c2c(C#N)cnn2c1]

1-amino-N-(1-(5-(3-cyano-6-ethoxypyrazolo[1,5-a]pyridin-4-yl)pyridin-2-yl)-4-methylpiperidin-4-yl)cyclopentane-1-carboxamide dihydrochloride A solution of tert-butyl (1-((1-(5-(3-cyano-6-ethoxypyrazolo[1,5-a]pyridin-4-yl)pyridin-2-yl)-4-methylpiperidin-4-yl)carbamoyl)cyclopentyl)carbamate (Example 534; 45 mg, 0.077 mmol) in DCM (766 μL) was treated with 5-6 N HCl in iPrOH (306 μL, 1.5 mmol), and stirred overnight at ambient temperature. The resulting slurry was diluted with MTBE (1 mL) and vacuum filtered. The solids were rinsed with MTBE (3×1 mL), and dried in vacuo to cleanly afford the title compound (26 mg, 60% yield). MS (apci) m/z=488.3 (M+H); 510.2 (M+Na).

Example 545

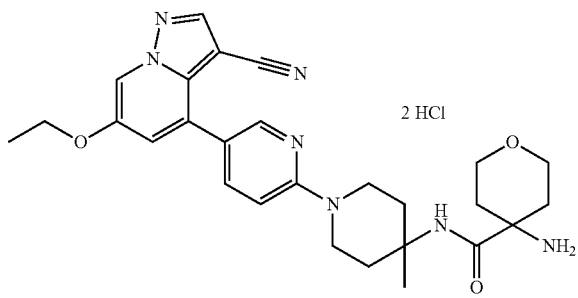 [SMILES: CCOc1cc(-c2ccc(N3CCC(C)(NC(=O)C4(N)CCOCC4)CC3)nc2)c2c(C#N)cnn2c1]

4-amino-N-(1-(5-(3-cyano-6-ethoxypyrazolo[1,5-a]pyridin-4-yl)pyridin-2-yl)-4-methylpiperidin-4-yl)tetrahydro-2H-pyran-4-carboxamide dihydrochloride A solution of tert-butyl (4-((1-(5-(3-cyano-6-ethoxypyrazolo[1,5-a]pyridin-4-yl)pyridin-2-yl)-4-methylpiperidin-4-yl)carbamoyl)tetrahydro-2H-pyran-4-yl)carbamate (Example 540; 30 mg, 0.050 mmol) in DCM (497 μL) was treated with 5-6 N HCl in iPrOH (199 μL, 0.99 mmol), and stirred overnight at ambient temperature. The resulting slurry was diluted with MTBE (1 mL) and vacuum filtered. The solids were rinsed with MTBE (3×1 mL), and dried in vacuo to cleanly afford the title compound (28 mg, 98% yield). MS (apci) m/z=504.3 (M+H); 526.2 (M+Na).

Example 546

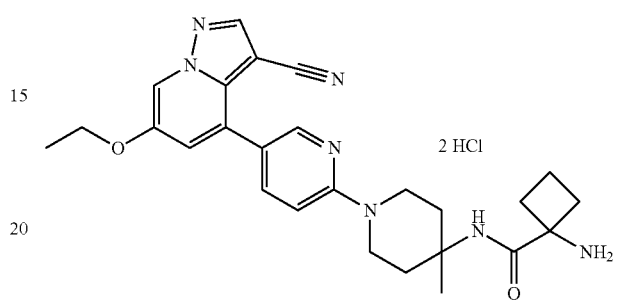

1-amino-N-(1-(5-(3-cyano-6-ethoxypyrazolo[1,5-a]pyridin-4-yl)pyridin-2-yl)-4-methylpiperidin-4-yl)cyclobutane-1-carboxamide dihydrochloride A solution of tert-butyl (1-((1-(5-(3-cyano-6-ethoxypyrazolo[1,5-a]pyridin-4-yl)pyridin-2-yl)-4-methylpiperidin-4-yl)carbamoyl)cyclobutyl)carbamate (Example 537; 25 mg, 0.044 mmol) in DCM (436 μL) was treated with 5-6 N HCl in iPrOH (174 μL, 0.87 mmol), then stirred for 3 h at ambient temperature. The resulting mixture was concentrated in vacuo to cleanly afford the title compound (24 mg, 99% yield). MS (apci) m/z=474.2 (M+H); 496.2 (M+Na).

The compounds in Table LLL were prepared using a similar method to that described in the synthesis of 1-amino-N-(1-(5-(3-cyano-6-ethoxypyrazolo[1,5-a]pyridin-4-yl)pyridin-2-yl)-4-methylpiperidin-4-yl)cyclobutane-1-carboxamide dihydrochloride (Example 546), replacing tert-butyl (1-((1-(5-(3-cyano-6-ethoxypyrazolo[1,5-a]pyridin-4-yl)pyridin-2-yl)-4-methylpiperidin-4-yl)carbamoyl)cyclobutyl)carbamate (Example 537) with the appropriate Boc-Protected amino from Table KKK.

TABLE LLL

| Ex # | Structure | Chemical Name | MS (apci) m/z |
|---|---|---|---|
| 547 | ![structure] | ((S)-2-amino-N-(1-(5-(3-cyano-6-ethoxypyrazolo[1,5-a]pyridin-4-yl)pyridin-2-yl)-4-methylpiperidin-4-yl)butanamide dihydrochloride | 462.2 (M + H), 484.3 (M + Na) |

TABLE LLL-continued

| Ex # | Structure | Chemical Name | MS (apci) m/z |
|---|---|---|---|
| 548 | 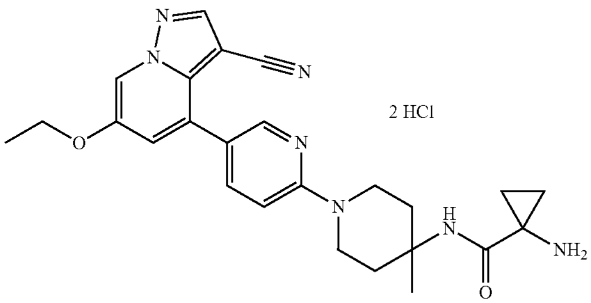 [SMILES: CCOc1cc(-c2ccc(N3CCC(C)(NC(=O)C4(N)CC4)CC3)nc2)c2c(C#N)cnn2c1] | 1-amino-N-(1-(5-(3-cyano-6-ethoxypyrazolo[1,5-a]pyridin-4-yl)pyridin-2-yl)-4-methylpiperidin-4-yl)cyclopropane-1-carboxamide dihydrochloride | 460.2 (M + H), 482.2 (M + Na) |
| 549 | 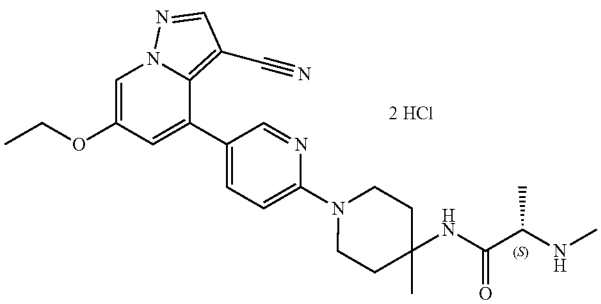 | (S)-N-(1-(5-(3-cyano-6-ethoxypyrazolo[1,5-a]pyridin-4-yl)pyridin-2-yl)-4-methylpiperidin-4-yl)-2-(methylamino)propanamide dihydrochloride | 462.2 (M + H) |

Example 550

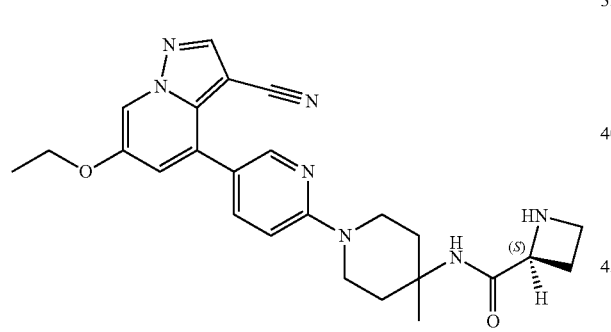

(S)—N-(1-(5-(3-cyano-6-ethoxypyrazolo[1,5-a]pyridin-4-yl)pyridin-2-yl)-4-methylpiperidin-4-yl)azetidine-2-carboxamide A solution of tert-butyl (S)-2-((1-(5-(3-cyano-6-ethoxypyrazolo[1,5-a]pyridin-4-yl)pyridin-2-yl)-4-methylpiperidin-4-yl)carbamoyl)azetidine-1-carboxylate (Example 539; 40 mg, 0.071 mmol) in DCM (357 μL) was treated with TFA (55 μL, 0.71 mmol). The resulting mixture was stirred overnight at ambient temperature then concentrated in vacuo. The residue was dissolved in MeOH (0.5 mL), and eluted through a basic resin (StratoSpheres Pl-HCO3), rinsing with additional MeOH (3×0.5 mL). The combined MeOH filtrates were concentrated in vacuo to cleanly afford the title compound as white solid. MS (apci) m/z=460.2 (M+H); 482.2 (M+Na).

Example 551

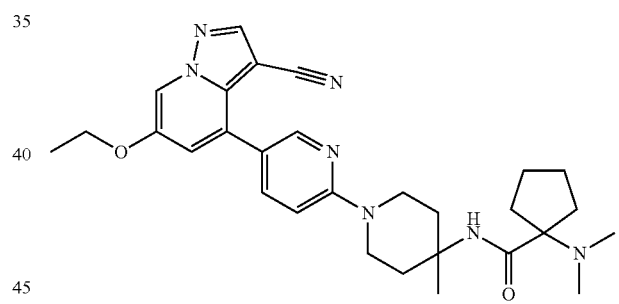

N-(1-(5-(3-cyano-6-ethoxypyrazolo[1,5-a]pyridin-4-yl)pyridin-2-yl)-4-methylpiperidin-4-yl)-1-(dimethylamino)cyclopentane-1-carboxamide A solution of 1-amino-N-(1-(5-(3-cyano-6-ethoxypyrazolo[1,5-a]pyridin-4-yl)pyridin-2-yl)-4-methylpiperidin-4-yl)cyclopentane-1-carboxamide dihydrochloride (Example 544; 24 mg, 0.0428 mmol) and formaldehyde (37 wt. % in water with 5-15% MeOH stabilizer; 31.9 μL, 0.428 mmol) in DCM (428 μL) was treated with NaBH(AcO)$_3$ (45.4 mg, 0.214 mmol), and stirred overnight at room temperature. The resulting mixture was directly purified by C18 reverse phase chromatography (using 5-75% ACN in water as the gradient eluent) to afford the title compound (21 mg, 94% yield). MS (apci) m/z=516.2 (M+H); 538.2 (M+Na).

The compounds in Table MMM were prepared using a similar method to that described in the synthesis of N-(1-(5-(3-cyano-6-ethoxypyrazolo[1,5-a]pyridin-4-yl)pyridin-2-yl)-4-methylpiperidin-4-yl)-1-(dimethylamino)cyclopentane-1-carboxamide (Example 551), replacing 1-amino-N-(1-(5-(3-cyano-6-ethoxypyrazolo[1,5-a]pyridin-4-yl)pyridin-2-yl)-4-methylpiperidin-4-yl)cyclopentane-1-carboxamide dihydrochloride (Example 544) with the listed amine. Reactions were monitored for completion by LCMS, and reaction durations were adjusted accordingly. Title compounds were isolated following chromatographic purification using an appropriate gradient eluent.

cyclopropylmethyl (1-(5-(3-cyano-6-ethoxypyrazolo[1,5-a]pyridin-4-yl)pyridin-2-yl)-4-methylpiperidin-4-yl)carbamate A solution of 4-(6-(4-amino-4-methylpiperidin-1-yl)pyridin-3-yl)-6-ethoxypyrazolo[1,5-a]pyridine-3-carbonitrile (Intermediate P89, 15.9 mg, 0.0422 mmol) and DIEA (14.6 µL, 0.0845 mmol) in DCM (500 µL) was treated with

TABLE MMM

| Ex # | Starting Amine Ex # | Structure | Chemical Name | MS (apci) m/z |
|---|---|---|---|---|
| 552 | 546 | 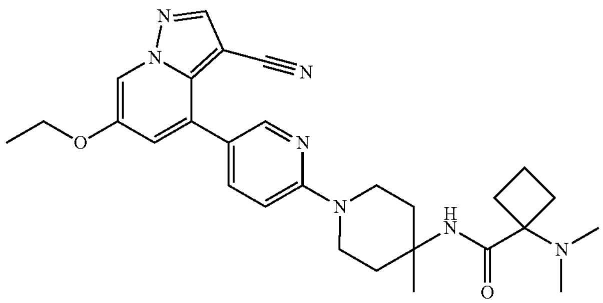 [SMILES: CCOc1cc(-c2ccc(N3CCC(C)(NC(=O)C4(N(C)C)CCC4)CC3)nc2)c2c(C#N)cnn2c1] | N-(1-(5-(3-cyano-6-ethoxypyrazolo[1,5-a]pyridin-4-yl)pyridin-2-yl)-4-methylpiperidin-4-yl)-1-(dimethylamino)cyclobutane-1-carboxamide | 502.2 (M + H), 524.2 (M + Na) |
| 553 | 550 | 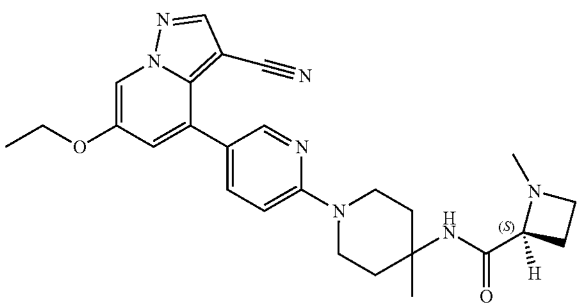 | (S)-N-(1-(5-(3-cyano-6-ethoxypyrazolo[1,5-a]pyridin-4-yl)pyridin-2-yl)-4-methylpiperidin-4-yl)-1-methylazetidine-2-carboxamide | 474.2 (M + H), 496.2 (M + Na) |
| 554 | 545 | 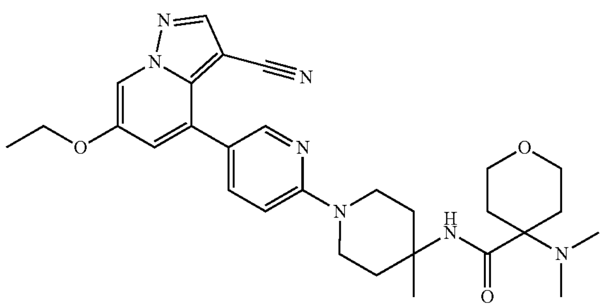 [SMILES: CCOc1cc(-c2ccc(N3CCC(C)(NC(=O)C4(N(C)C)CCOCC4)CC3)nc2)c2c(C#N)cnn2c1] | N-(1-(5-(3-cyano-6-ethoxypyrazolo[1,5-a]pyridin-4-yl)pyridin-2-yl)-4-methylpiperidin-4-yl)-4-(dimethylamino)tetrahydro-2H-pyran-4-carboxamide | 532.3 (M + H), 554.3 (M + Na) |

Example 555

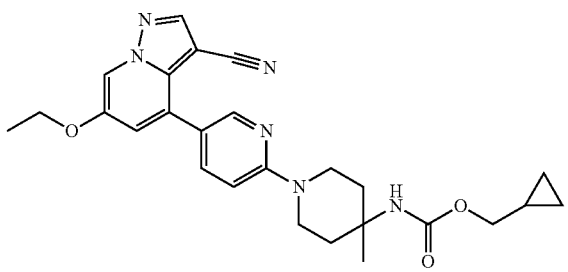 [SMILES: CCOc1cc(-c2ccc(N3CCC(C)(NC(=O)OCC4CC4)CC3)nc2)c2c(C#N)cnn2c1]

cyclopropylmethyl carbonochloridate (6.82 mg, 0.0507 mmol). The resulting mixture was stirred overnight at ambient temperature, and then directly purified by silica chromatography (using 20-80% Hexanes/EtOAc as the gradient eluent) to cleanly provide the title compound (13.4 mg, 66% yield). MS (apci) m/z=475.2 (M+H).

The compounds in Table NNN were prepared using a similar method to that described in the synthesis of cyclopropylmethyl (1-(5-(3-cyano-6-ethoxypyrazolo[1,5-a]pyridin-4-yl)pyridin-2-yl)-4-methylpiperidin-4-yl)carbamate (Example 555), replacing cyclopropylmethyl carbonochloridate with the appropriate carbonochloridate. Where noted (*) the carbonochloridate is prepared in the reagents section, otherwise commercial reagents were utilized. Reactions were monitored for completion by LCMS, and reaction durations were adjusted accordingly. Title compounds were isolated following chromatographic purification using an appropriate gradient eluent.

TABLE NNN

| Ex # | Structure | Chemical Name | MS (apci) m/z |
|---|---|---|---|
| 556 | 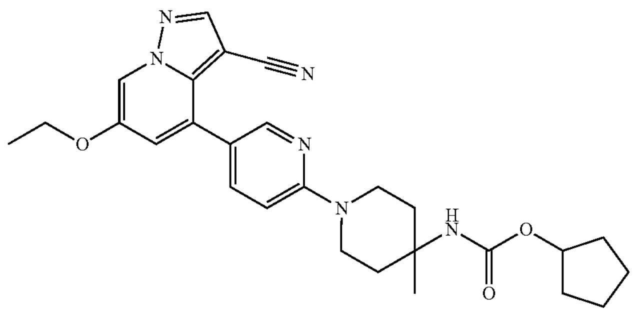 [SMILES: CCOc1cc(-c2ccc(N3CCC(C)(NC(=O)OC4CCCC4)CC3)nc2)c2c(C#N)cnn2c1] | cyclopentyl (1-(5-(3-cyano-6-ethoxypyrazolo[1,5-a]pyridin-4-yl)pyridin-2-yl)-4-methylpiperidin-4-yl)carbamate | 489.25 (M + H) |
| 557 | 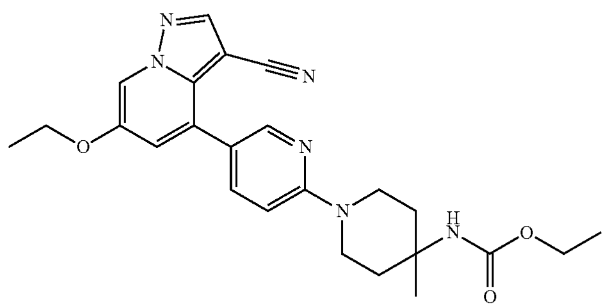 [SMILES: CCOC(=O)NC1(C)CCN(c2ccc(-c3cc(OCC)cn4ncc(C#N)c34)cn2)CC1] | ethyl (1-(5-(3-cyano-6-ethoxypyrazolo[1,5-a]pyridin-4-yl)pyridin-2-yl)-4-methylpiperidin-4-yl)carbamate | 449.2 (M + H) |
| 558 | 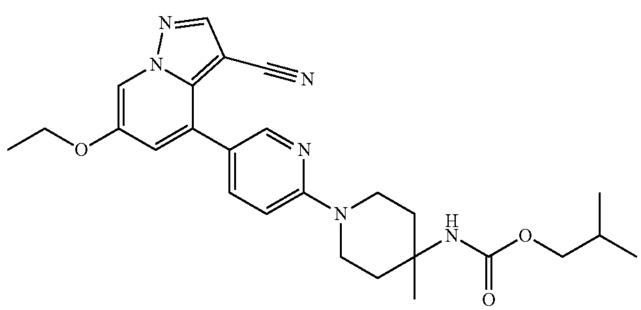 [SMILES: CCOc1cc(-c2ccc(N3CCC(C)(NC(=O)OCC(C)C)CC3)nc2)c2c(C#N)cnn2c1] | isobutyl (1-(5-(3-cyano-6-ethoxypyrazolo[1,5-a]pyridin-4-yl)pyridin-2-yl)-4-methylpiperidin-4-yl)carbamate | 477.2 (M + H) |
| 559* | 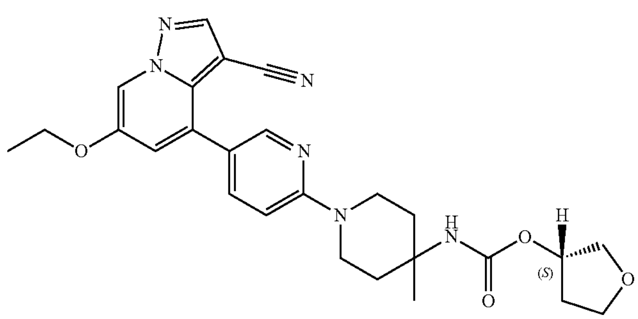 | (S)-tetrahydrofuran-3-yl (1-(5-(3-cyano-6-ethoxypyrazolo[1,5-a]pyridin-4-yl)pyridin-2-yl)-4-methylpiperidin-4-yl)carbamate | 491.2 (M + H) |
| 560* | 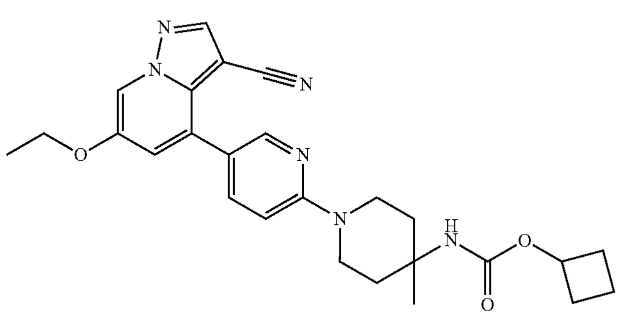 [SMILES: CCOc1cc(-c2ccc(N3CCC(C)(NC(=O)OC4CCC4)CC3)nc2)c2c(C#N)cnn2c1] | cyclobutyl (1-(5-(3-cyano-6-ethoxypyrazolo[1,5-a]pyridin-4-yl)pyridin-2-yl)-4-methylpiperidin-4-yl)carbamate | 475.2 (M + H) |

Example 561

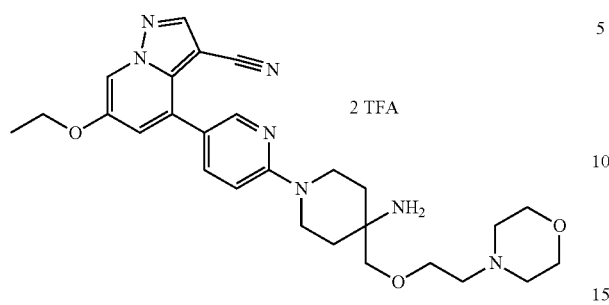

4-(6-(4-amino-4-((2-morpholinoethoxy)methyl)piperidin-1-yl)pyridin-3-yl)-6-ethoxypyrazolo[1,5-a]pyridine-3-carbonitrile bis(2,2,2-trifluoroacetate)

A suspension of 4-(6-(4-amino-4-(hydroxymethyl)piperidin-1-yl)pyridin-3-yl)-6-ethoxypyrazolo[1,5-a]pyridine-3-carbonitrile (Intermediate P56, 40 mg, 0.10 mmol) in DMF (2 mL) was treated sequentially with NaH (60 wt. % in mineral oil; 41 mg, 1.0 mmol) and 4-(2-chloroethyl)morpholine (76 mg, 0.51 mmol). After stirring for 4 h at 50° C., the reaction mixture was cooled to ambient temperature, and quenched with water (2 mL). The quenched mixture was concentrated to dryness in vacuo. The residue was purified by C18 reverse phase chromatography (5-95% ACN in water with 0.1% TFA) to afford the title compound (40 mg, 55% yield). MS (apci) m/z=506.3 (M+H).

Example 562

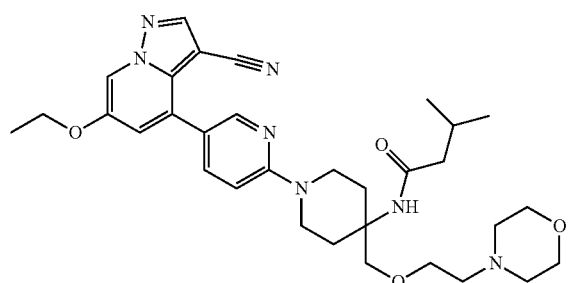

N-(1-(5-(3-cyano-6-ethoxypyrazolo[1,5-a]pyridin-4-yl)pyridin-2-yl)-4-((2-morpholinoethoxy)methyl)piperidin-4-yl)-3-methylbutanamide A solution of 4-(6-(4-amino-4-((2-morpholinoethoxy)methyl)piperidin-1-yl)pyridin-3-yl)-6-ethoxypyrazolo[1,5-a]pyridine-3-carbonitrile (Example 561; 25 mg, 0.030 mmol) in DCM (1.0 mL) was treated sequentially with TEA (8.3 μL, 0.059 mmol) and isovaleryl chloride (4.3 μL, 0.036 mmol), then stirred for 30 min at ambient temperature. The reaction mixture was concentrated in vacuo, and the resulting residue was purified by silica chromatography (0-7% MeOH in DCM) to cleanly afford the title compound (1.7 mg, 10% yield). MS (apci) m/z=590.3 (M+H).

Example 563

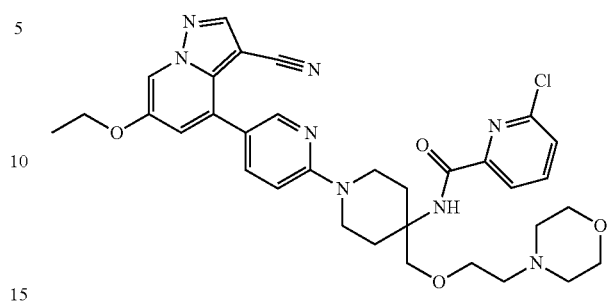

6-chloro-N-(1-(5-(3-cyano-6-ethoxypyrazolo[1,5-a]pyridin-4-yl)pyridin-2-yl)-4-((2-morpholinoethoxy)methyl)piperidin-4-yl)picolinamide A suspension of 4-(6-(4-amino-4-((2-morpholinoethoxy)methyl)piperidin-1-yl)pyridin-3-yl)-6-ethoxypyrazolo[1,5-a]pyridine-3-carbonitrile) (Example 561; 25 mg, 0.049 mmol) in DMF (1 mL) was treated sequentially with DIEA (35 μL, 0.20 mmol), 6-chloropicolinic acid (16 mg, 0.099 mmol) and HATU (38 mg, 0.099 mmol). The resulting mixture was stirred for 15 h at ambient temperature. The mixture was diluted with EtOAc (20 mL), and washed sequentially with saturated $NaHCO_{3(aq)}$, and water. The combined organic extracts were concentrated in vacuo. The organic extracts were purified directly by silica chromatography (0-7% MeOH in DCM) to cleanly afford the title compound (21 mg, 66% yield). MS (apci) m/z=645.2 (M+H).

Example 564

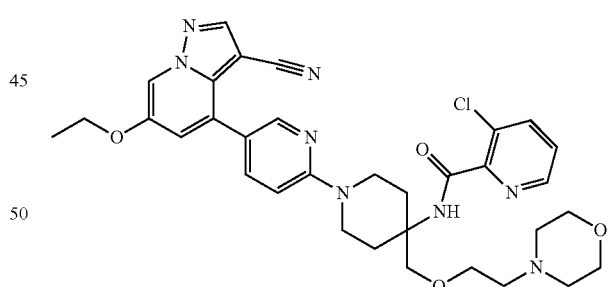

3-chloro-N-(1-(5-(3-cyano-6-ethoxypyrazolo[1,5-a]pyridin-4-yl)pyridin-2-yl)-4-((2-morpholinoethoxy)methyl)piperidin-4-yl)picolinamide The title compound (12 mg, 52% yield) was prepared and worked up using a similar procedure to that described for 6-chloro-N-(1-(5-(3-cyano-6-ethoxypyrazolo[1,5-a]pyridin-4-yl)pyridin-2-yl)-4-((2-morpholinoethoxy)methyl)piperidin-4-yl)picolinamide (Example 563), replacing 6-chloropicolinic acid with 3-chloropicolinic acid. MS (apci) m/z=645.2 (M+H).

Example 565

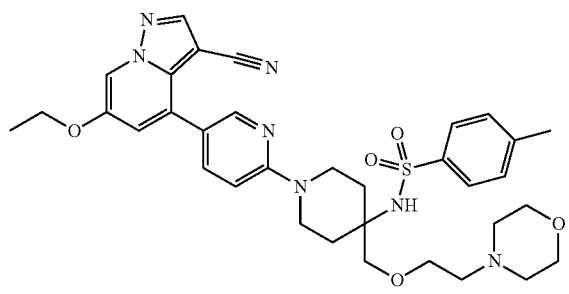 [SMILES: CCOc1cc(-c2ccc(N3CCC(COCCN4CCOCC4)(NS(=O)(=O)c4ccc(C)cc4)CC3)nc2)c2c(C#N)cnn2c1]

N-(1-(5-(3-cyano-6-ethoxypyrazolo[1,5-a]pyridin-4-yl)pyridin-2-yl)-4-((2-morpholinoethoxy)methyl)piperidin-4-yl)-4-methylbenzenesulfonamide Under an inert atmosphere (N$_{2(g)}$), a suspension of 6-ethoxy-4-(6-(1-tosyl-1,6-diazaspiro[2.5]octan-6-yl)pyridin-3-yl)pyrazolo[1,5-a]pyridine-3-carbonitrile (Intermediate R51; 40 mg, 0.076 mmol), 2-morpholinoethan-1-ol (30 mg, 0.23 mmol) and 18-Crown-6 (40 mg, 0.15 mmol) in DMA (1.5 mL) was cooled to −10° C., then treated with a 1 M solution of KOtBu in THF (150 µL, 1.0 mmol). The reaction mixture was stirred for 30 min at −10° C., then allowed to stir for an additional 1 h at temperatures between −10° C.-0° C. The reaction mixture was quenched with saturated NH$_4$Cl$_{(aq)}$, and diluted with water (2 mL). The resulting suspension was filtered. The solids were rinsed with water (20 mL), then dried in vacuo to afford the title compound (38 mg, 76% yield). MS (apci) m/z=660.3 (M+H).

Example 566

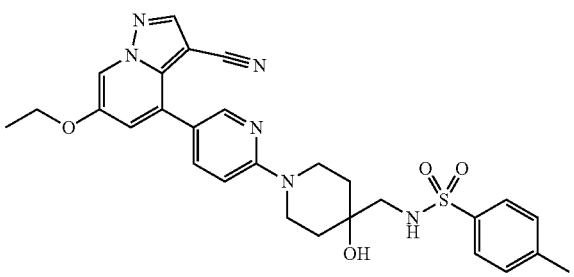 [SMILES: CCOc1cc(-c2ccc(N3CCC(O)(CNS(=O)(=O)c4ccc(C)cc4)CC3)nc2)c2c(C#N)cnn2c1]

N-((1-(5-(3-cyano-6-ethoxypyrazolo[1,5-a]pyridin-4-yl)pyridin-2-yl)-4-hydroxypiperidin-4-yl)methyl)-4-methylbenzenesulfonamide A solution of 6-ethoxy-4-(6-(1-tosyl-1,6-diazaspiro[2.5]octan-6-yl)pyridin-3-yl)pyrazolo[1,5-a]pyridine-3-carbonitrile (Intermediate R51; 26 mg, 0.049 mmol) in dioxane (2 mL) and 2 M H$_2$SO$_{4(aq)}$ (1 mL, 2.00 mmol) was stirred for 15 h at ambient temperature. The reaction mixture was quenched with 2 M K$_2$CO$_{3(aq)}$ (5 mL) and extracted with EtOAc. The organic extracts were dried over anhydrous Na$_2$SO$_{4(s)}$, filtered, concentrated in vacuo. The residue was triturated with MTBE, and filtered. The solids collected were purified by silica chromatography (using 0-70% EtOAc in Hexanes as the gradient eluent) to cleanly afford the title compound (17 mg, 63% yield). MS (apci) m/z=547.2 (M+H).

Example 567

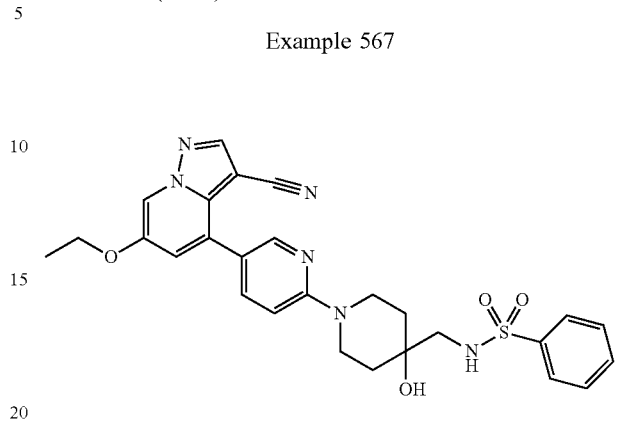

N-((1-(5-(3-cyano-6-ethoxypyrazolo[1,5-a]pyridin-4-yl)pyridin-2-yl)-4-hydroxypiperidin-4-yl)methyl)benzenesulfonamide A solution of 6-ethoxy-4-(6-(1-(phenylsulfonyl)-1,6-diazaspiro[2.5]octan-6-yl)pyridin-3-yl)pyrazolo[1,5-a]pyridine-3-carbonitrile (Intermediate R52; 10.5 mg, 0.0204 mmol) in dioxane (2 mL) and 2 M H$_2$SO$_{4(aq)}$ (0.5 mL, 1.00 mmol) was stirred for 1 h at ambient temperature. The reaction mixture was quenched with 2 M Na$_2$CO$_{3(aq)}$ (5 mL), and diluted with water. The resulting suspension was extracted with DCM. The organic extracts were concentrated in vacuo, and the residue was purified by silica chromatography (using 0-100% EtOAc in Hexanes as the gradient eluent) to cleanly afford the title compound (1.8 mg, 17% yield). MS (apci) m/z=533.2 (M+H).

Example 568

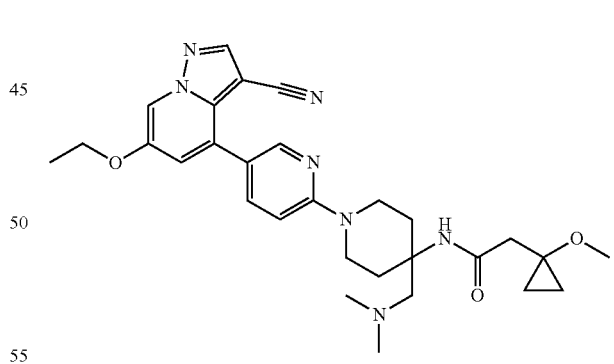

N-(1-(5-(3-cyano-6-ethoxypyrazolo[1,5-a]pyridin-4-yl)pyridin-2-yl)-4-((dimethylamino)methyl)piperidin-4-yl)-2-(1-methoxycyclopropyl)acetamide Step 1. Preparation of ethyl 2-cyclopropylideneacetate A solution of ((1-ethoxycyclopropyl)oxy)trimethylsilane (2.30 mL, 11.5 mmol) in toluene (29 mL) was treated with (carboethoxymethylene)triphenylphosphorane (4.20 g, 12.0 mmol) and benzoic acid (1.54 g, 12.6 mmol), then stirred at 90° C. for 2 hrs. After cooled to RT, the reaction mixture was directly purified by silica chromatography (0 to 50% EtOAc in hexanes) to yield the title product (1.1 g, 75%).

Step 2. Preparation of 2-(1-methoxycyclopropyl)acetic acid

To a solution of ethyl 2-cyclopropylideneacetate (0.50 g, 3.96 mmol) in MeOH (10 mL) was added trimethylphosphine (0.0205 mL, 0.198 mmol). The reaction was sealed and heated at 45° C. for 3 d. After removal of most solvent under vacuum, the residue was taken up in MeOH and treated with NaOH (2 N, aq; 3.96 mL) at RT for overnight. The reaction mixture was concentrated first, then diluted with water (5 mL) and washed with washed with EtOAc (2×). After phase-separation, the aqueous layer was acidified to pH~2 and then extracted with EtOAc (2×). The combined organics were dried ($Na_2SO_4$), filtered and concentrated to yield the title product (0.2 g, 39%).

Step 3. Preparation of N-(1-(5-(3-cyano-6-ethoxy-pyrazolo[1,5-a]pyridin-4-yl)pyridin-2-yl)-4-((dimethylamino)methyl)piperidin-4-yl)-2-(1-methoxycyclopropyl)acetamide A mixture of 4-(6-(4-amino-4-((dimethylamino)methyl)piperidin-1-yl)pyridin-3-yl)-6-ethoxypyrazolo[1,5-a]pyridine-3-carbonitrile (Intermediate P72, 32.2 mg, 0.0768 mmol), 2-(1-methoxycyclopropyl)acetic acid (10 mg, 0.077 mmol) and HATU (73.0 mg, 0.192 mmol) in DCM (154 µL) was treated with DIEA (134 µL, 0.768 mmol), then stirred overnight at ambient temperature. The resulting mixture was concentrated in vacuo, and the residue was purified by C18 reverse phase chromatography (using 5-95% water:ACN with 0.1% TFA as the gradient eluent). Fractions containing the desired compound were combined, diluted with 4:1 DCM:iPrOH, and extracted sequentially with saturated $NaHCO_{3(aq)}$ and brine. The organic extracts were dried over anhydrous $Na_2SO_{4(s)}$, filtered, and concentrated in vacuo to afford the title compound (26 mg, 64% yield). MS (apci) m/z=532.3 (M+H).

Example 569

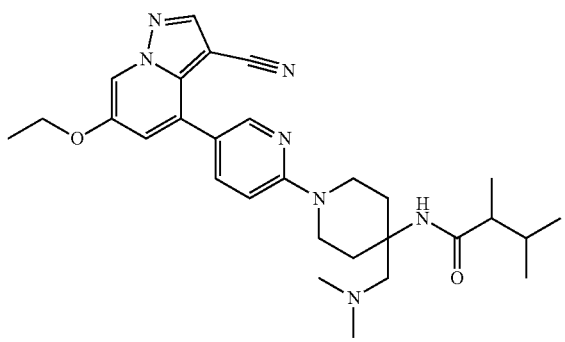 [SMILES: CCOc1cc(-c2ccc(N3CCC(CN(C)C)(NC(=O)C(C)C(C)C)CC3)nc2)c2c(C#N)cnn2c1]

N-(1-(5-(3-cyano-6-ethoxypyrazolo[1,5-a]pyridin-4-yl)pyridin-2-yl)-4-((dimethylamino)methyl)piperidin-4-yl)-2,3-dimethylbutanamide The title compound (21 mg, 43% yield) was prepared and worked up using a similar procedure to that described for N-(1-(5-(3-cyano-6-ethoxypyrazolo[1,5-a]pyridin-4-yl)pyridin-2-yl)-4-((dimethylamino)methyl)piperidin-4-yl)-2-(1-methoxycyclopropyl)acetamide (Example 568), replacing 2-(1-methoxycyclopropyl)acetic acid with 2,3-dimethylbutanoic acid. MS (apci) m/z=518.3 (M+H).

Example 570

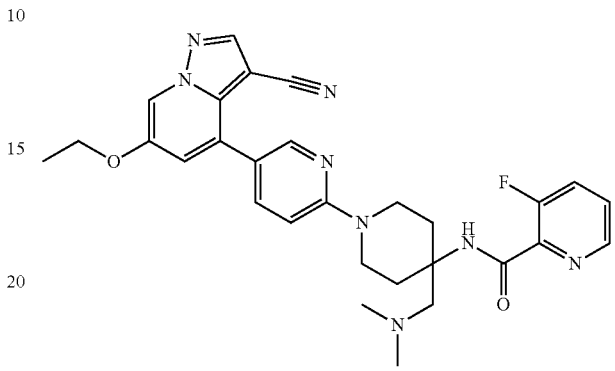

N-(1-(5-(3-cyano-6-ethoxypyrazolo[1,5-a]pyridin-4-yl)pyridin-2-yl)-4-((dimethylamino)methyl)piperidin-4-yl)-3-fluoropicolinamide A solution of 4-(6-(4-amino-4-((dimethylamino)methyl)piperidin-1-yl)pyridin-3-yl)-6-ethoxypyrazolo[1,5-a]pyridine-3-carbonitrile (Intermediate P72, 50 mg, 0.119 mmol) in DMSO (795 µL) was treated sequentially with 3-fluoropicolinic acid (0.0252 g, 0.179 mmol), DIEA (93.4 µL, 0.536 mmol) and HATU (90.6 mg, 0.238 mmol). The resulting mixture was stirred overnight at ambient temperature, and then partitioned between EtOAc and water. The organic extracts were washed with brine, dried over anhydrous $Na_2SO_{4(s)}$, filtered, and concentrated in vacuo. The crude residue was purified by C18 reverse phase chromatography (using 5-95% water:ACN with 0.1% TFA as the gradient eluent) to afford the title compound as the TFA salt. The TFA salt was dissolved in DCM, and extracted sequentially with saturated $NaHCO_{3(aq)}$ and brine. The organic extracts were dried over anhydrous $Na_2SO_{4(s)}$, filtered, and concentrated in vacuo to afford the title compound (40.1 mg, 62% yield). MS (apci) m/z=543.3 (M+H).

Example 571

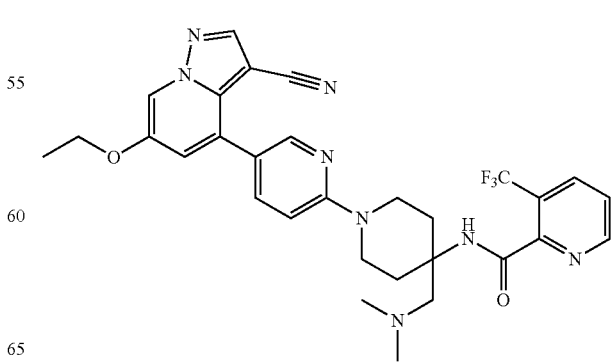

763

N-(1-(5-(3-cyano-6-ethoxypyrazolo[1,5-a]pyridin-4-yl)pyridin-2-yl)-4-((dimethylamino)methyl)piperidin-4-yl)-3-(trifluoromethyl)picolinamide The title compound (24 mg, 34% yield) was prepared, worked up and purified using a similar procedure to that described for N-(1-(5-(3-cyano-6-ethoxypyrazolo[1,5-a]pyridin-4-yl)pyridin-2-yl)-4-((dimethylamino)methyl)piperidin-4-yl)-3-fluoropicolinamide (Example 570), replacing 3-fluoropicolinic acid with 3-(trifluoromethyl)picolinic acid. MS (apci) m/z=593.3 (M+H).

Example 572

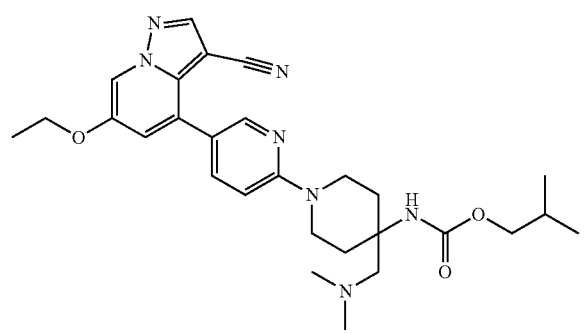 [SMILES: CCOc1cc(-c2ccc(N3CCC(CN(C)C)(NC(=O)OCC(C)C)CC3)nc2)c2c(C#N)cnn2c1]

isobutyl (1-(5-(3-cyano-6-ethoxypyrazolo[1,5-a]pyridin-4-yl)pyridin-2-yl)-4-((dimethylamino)methyl)piperidin-4-yl)carbamate A solution of 4-(6-(4-amino-4-((dimethylamino)methyl)piperidin-1-yl)pyridin-3-yl)-6-ethoxypyrazolo[1,5-a]pyridine-3-carbonitrile (Intermediate P72, 30 mg, 0.072 mmol) and TEA (20 µL, 0.14 mmol) in DCM (715 µL) was treated with isobutyl chloroformate (9.4 µL, 0.072 mmol), and the resulting mixture was stirred for 6 d at ambient temperature. The reaction mixture was concentrated in vacuo, and the residue was purified by C18 reverse phase chromatography (using 5-95% water:ACN with 0.1% TFA as the gradient eluent). Fractions containing the desired product were combined, diluted with 4:1 DCM:iPrOH, then extracted sequentially with saturated NaHCO$_{3(aq)}$ and brine. The organic extracts were dried over anhydrous Na$_2$SO$_{4(s)}$, filtered, and concentrated in vacuo to afford the title compound (30 mg, 81% yield). MS (apci) m/z=520.3 (M+H).

Example 573

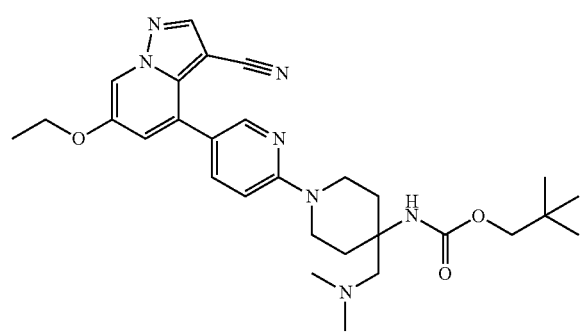 [SMILES: CCOc1cc(-c2ccc(N3CCC(CN(C)C)(NC(=O)OCC(C)(C)C)CC3)nc2)c2c(C#N)cnn2c1]

764 neopentyl (1-(5-(3-cyano-6-ethoxypyrazolo[1,5-a]pyridin-4-yl)pyridin-2-yl)-4-((dimethylamino)methyl)piperidin-4-yl)carbamate The title compound (18 mg, 44% yield) was prepared, worked up and purified using a similar procedure to that described for isobutyl (1-(5-(3-cyano-6-ethoxypyrazolo[1,5-a]pyridin-4-yl)pyridin-2-yl)-4-((dimethylamino)methyl)piperidin-4-yl)carbamate (Example 572), replacing isobutyl chloroformate with neopentyl chloroformate. MS (apci) m/z=534.4 (M+H).

Example 574

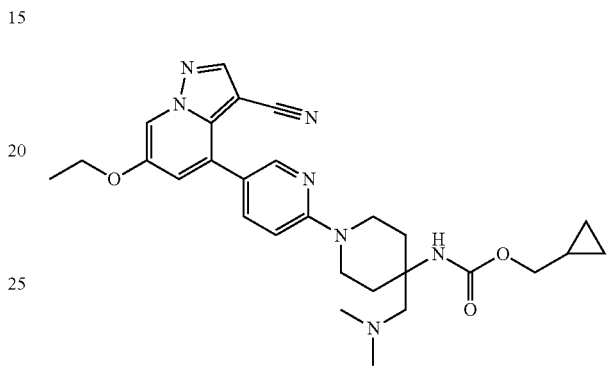

cyclopropylmethyl (1-(5-(3-cyano-6-ethoxypyrazolo[1,5-a]pyridin-4-yl)pyridin-2-yl)-4-((dimethylamino)methyl)piperidin-4-yl)carbamate The title compound (21 mg, 57% yield) was prepared, worked up and purified using a similar procedure to that described for isobutyl (1-(5-(3-cyano-6-ethoxypyrazolo[1,5-a]pyridin-4-yl)pyridin-2-yl)-4-((dimethylamino)methyl)piperidin-4-yl)carbamate (Example 572), replacing isobutyl chloroformate (1 equivalent) with cyclopropylmethyl chloroformate (1.2 equivalents). MS (apci) m/z=518.3 (M+H).

Example 575

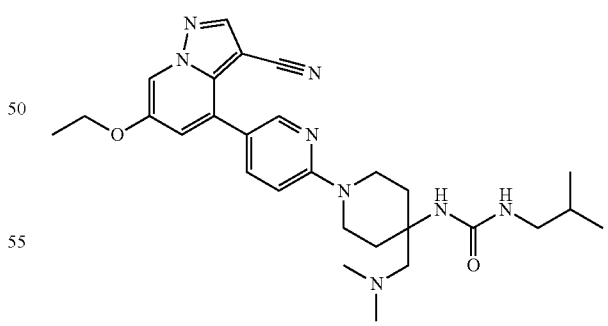

1-(1-(5-(3-cyano-6-ethoxypyrazolo[1,5-a]pyridin-4-yl)pyridin-2-yl)-4-((dimethylamino)methyl)piperidin-4-yl)-3-isobutylurea A solution of 4-(6-(4-amino-4-((dimethylamino)methyl)piperidin-1-yl)pyridin-3-yl)-6-ethoxypyrazolo[1,5-a]pyridine-3-carbonitrile (Intermediate P72, 30 mg, 0.072 mmol)

and DIEA (125 µL, 0.715 mmol) in DMA (1.4 mL) was treated with 4-nitrophenyl chloroformate (17.3 mg, 0.0858 mmol). The resulting mixture was stirred for 1 h at ambient temperature, before adding isobutylamine (35.5 µL, 0.358 mmol). The resulting mixture was stirred overnight at 80° C. After cooling to ambient temperature, the reaction mixture was concentrated in vacuo, and the residue was purified by C18 reverse phase chromatography (using 5-95% water: ACN with 0.1% TFA as the gradient eluent). Fractions containing the desired product were combined, diluted with 4:1 DCM:iPrOH, then extracted sequentially with saturated NaHCO$_{3(aq)}$ (1×) and brine (2×). The organic extracts were dried over anhydrous Na$_2$SO$_{4(s)}$, filtered, and concentrated in vacuo to afford the title compound (35 mg, 94% yield). MS (apci) m/z=519.3 (M+H).

Example 576

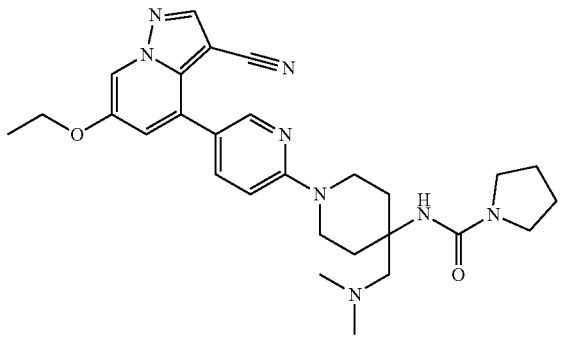 [SMILES: CCOc1cc(-c2ccc(N3CCC(CN(C)C)(NC(=O)N4CCCC4)CC3)nc2)c2c(C#N)cnn2c1]

N-(1-(5-(3-cyano-6-ethoxypyrazolo[1,5-a]pyridin-4-yl)pyridin-2-yl)-4-((dimethylamino)methyl)piperidin-4-yl)pyrrolidine-1-carboxamide The title compound (25 mg, 68% yield) was prepared using a similar procedure to that described for 1-(1-(5-(3-cyano-6-ethoxypyrazolo[1,5-a]pyridin-4-yl)pyridin-2-yl)-4-((dimethylamino)methyl)piperidin-4-yl)-3-isobutylurea (Example 575), replacing isobutylamine (5 equivalents) with pyrrolidine (1 equivalent). The cooled reaction mixture was diluted with water then extracted with EtOAc. The EtOAc extracts were washed sequentially with water and brine, then dried over anhydrous Na$_2$SO$_{4(s)}$, filtered, and concentrated in vacuo, prior to employing similar purification/free basing steps as those used in Example 575. MS (apci) m/z=517.3 (M+H).

Example 577

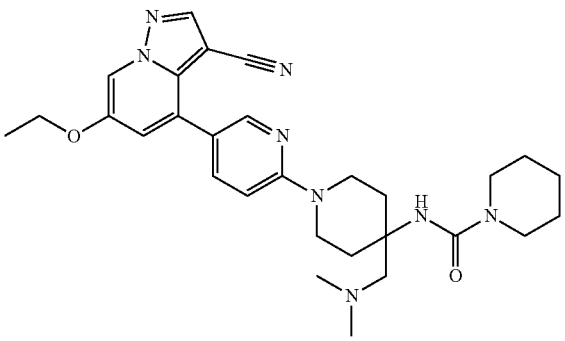 [SMILES: CCOc1cc(-c2ccc(N3CCC(CN(C)C)(NC(=O)N4CCCCC4)CC3)nc2)c2c(C#N)cnn2c1]

N-(1-(5-(3-cyano-6-ethoxypyrazolo[1,5-a]pyridin-4-yl)pyridin-2-yl)-4-((dimethylamino)methyl)piperidin-4-yl)piperidine-1-carboxamide The title compound (25 mg, 68% yield) was prepared using a similar procedure to that described for 1-(1-(5-(3-cyano-6-ethoxypyrazolo[1,5-a]pyridin-4-yl)pyridin-2-yl)-4-((dimethylamino)methyl)piperidin-4-yl)-3-isobutylurea (Example 575), replacing isobutylamine (5 equivalents) with piperidine (1 equivalent). For the work up, the cooled reaction mixture was diluted with water then extracted with EtOAc. The EtOAc extracts were washed sequentially with water and brine then dried over anhydrous Na$_2$SO$_{4(s)}$, filtered, and concentrated in vacuo, prior to employing similar purification/free basing steps as those used in Example 575. MS (apci) m/z=531.3 (M+H).

Example 578

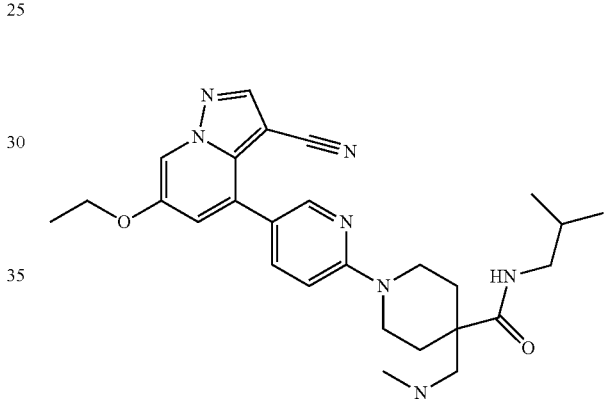

1-(5-(3-cyano-6-ethoxypyrazolo[1,5-a]pyridin-4-yl)pyridin-2-yl)-4-((dimethylamino)methyl)-N-isobutylpiperidine-4-carboxamide A solution of dimethylamine hydrochloride (41.7 mg, 0.511 mmol) in DCM (1.0 ml) was treated with triethylamine (69.3 µL, 0.511 mmol) and stirred for 5 min at ambient temperature before introducing 1-(5-(3-cyano-6-ethoxypyrazolo[1,5-a]pyridin-4-yl)pyridin-2-yl)-4-formyl-N-isobutylpiperidine-4-carboxamide (Intermediate P76, 48.5 mg, 0.102 mmol). The resulting mixture was treated with NaBH(AcO)$_3$ (108 mg, 0.511 mmol), stirred overnight at room temperature, and then concentrated in vacuo. The crude residue was purified by C18 reverse phase chromatography (using 5-95% water-ACN with 0.1% TFA as the gradient eluent). Fractions containing the desired product were diluted with 4:1 DCM:iPrOH, and extracted with saturated NaHCO$_{3(aq)}$. The organic extracts were dried over anhydrous Na$_2$SO$_{4(s)}$, filtered, and concentrated in vacuo to cleanly afford the title compound (23.1 mg, 45% yield). MS (apci) m/z=504.3 (M+H).

Example 579

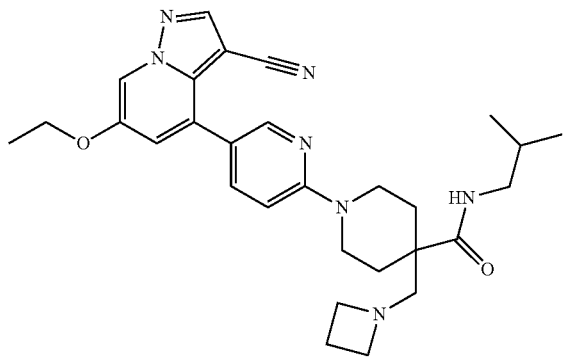 [SMILES: CCOc1cc(-c2ccc(N3CCC(CN4CCC4)(C(=O)NCC(C)C)CC3)nc2)c2c(C#N)cnn2c1]

4-(azetidin-1-ylmethyl)-1-(5-(3-cyano-6-ethoxypyra-zolo[1,5-a]pyridin-4-yl)pyridin-2-yl)-N-isobutylpip-eridine-4-carboxamide A solution of 1-(5-(3-cyano-6-ethoxypyrazolo[1,5-a]pyridin-4-yl)pyridin-2-yl)-4-formyl-N-isobutylpiperidine-4-carboxamide (Intermediate P76, 58.6 mg, 0.123 mmol) in DCM (1.2 mL) was treated sequentially with azetidine (41.6 µL, 0.617 mmol) and NaBH(AcO)$_3$ (131 mg, 0.617 mmol), and stirred for 16 h at ambient temperature. The reaction mixture was concentrated in vacuo. The crude residue was purified directly by C18 reverse phase chromatography (using 5-95% water:ACN with 0.1% TFA as the gradient eluent). Fractions containing the desired product were partitioned between 4:1 DCM:iPrOH and saturated NaHCO$_{3(aq)}$. The organic extracts were dried over anhydrous Na$_2$SO$_{4(s)}$, filtered, and concentrated in vacuo to afford the title compound (42.8 mg, 57% yield). MS (apci) m/z=516.4 (M+H).

Example 580

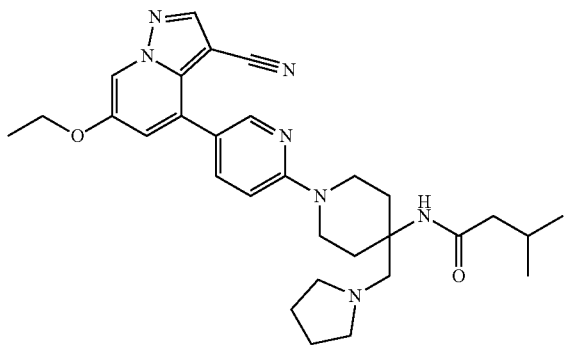 [SMILES: CCOc1cc(-c2ccc(N3CCC(CN4CCCC4)(NC(=O)CC(C)C)CC3)nc2)c2c(C#N)cnn2c1]

N-(1-(5-(3-cyano-6-ethoxypyrazolo[1,5-a]pyridin-4-yl)pyridin-2-yl)-4-(pyrrolidin-1-ylmethyl)piperidin-4-yl)-3-methylbutanamide A solution of 4-(6-(4-amino-4-(pyrrolidin-1-ylmethyl)piperidin-1-yl)pyridin-3-yl)-6-ethoxypyrazolo[1,5-a]pyridine-3-carbonitrile (Intermediate P97; 30 mg, 0.065 mmol) and TEA (19 µL, 0.13 mmol) in DCM (673 µL) was treated with isovaleryl chloride (8.2 µL, 0.067 mmol), and then stirred overnight at ambient temperature. The reaction mixture was purified directly by C18 reverse phase chromatography (using 5-95% water:ACN with 0.1% TFA as the gradient eluent). Fractions containing the desired product were combined, diluted with 4:1 DCM:iPrOH, then extracted sequentially with saturated NaHCO$_{3(aq)}$ (1×) and brine (2×). The organic extracts were dried over anhydrous Na$_2$SO$_{4(s)}$, filtered, and concentrated in vacuo to afford the title compound (23 mg, 64% yield). MS (apci) m/z=530.4 (M+H).

Example 581

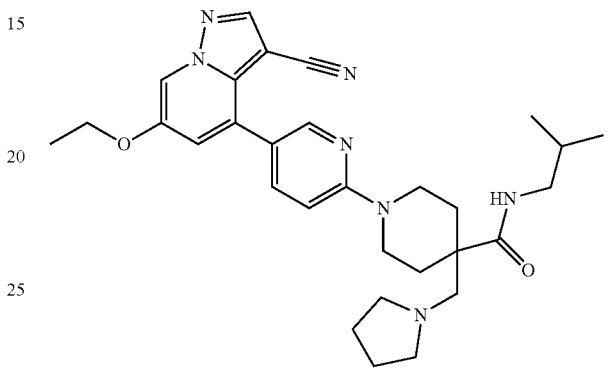

1-(5-(3-cyano-6-ethoxypyrazolo[1,5-a]pyridin-4-yl)pyridin-2-yl)-N-isobutyl-4-(pyrrolidin-1-ylmethyl)piperidine-4-carboxamide A solution of 1-(5-(3-cyano-6-ethoxypyrazolo[1,5-a]pyridin-4-yl)pyridin-2-yl)-4-formyl-N-isobutylpiperidine-4-carboxamide (Intermediate P76, 54.6 mg, 0.115 mmol) in DCM (1.2 mL) was treated sequentially with pyrrolidine (48.0 µL, 0.575 mmol) and NaBH(AcO)$_3$ (122 mg, 0.575 mmol), and stirred for 16 h at ambient temperature. The reaction mixture was concentrated in vacuo. The crude residue was purified directly by C18 reverse phase chromatography (using 5-95% water:ACN with 0.1% TFA as the gradient eluent). Fractions containing the desired product were partitioned between 4:1 DCM:iPrOH, and saturated NaHCO$_{3(aq)}$. The organic extracts were dried over anhydrous Na$_2$SO$_{4(s)}$, filtered, and concentrated in vacuo to afford the title compound (44.4 mg, 73% yield). MS (apci) m/z=530.2 (M+H).

Example 582

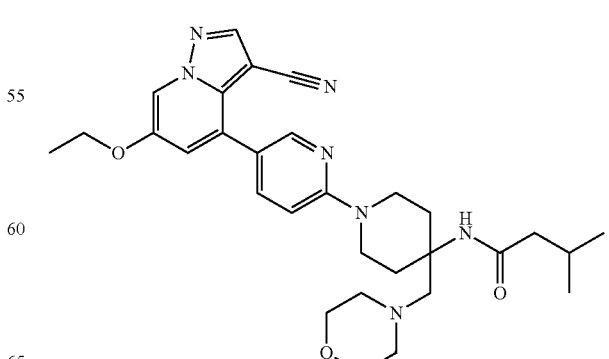

N-(1-(5-(3-cyano-6-ethoxypyrazolo[1,5-a]pyridin-4-yl)pyridin-2-yl)-4-(morpholinomethyl)piperidin-4-yl)-3-methylbutanamide A solution of 4-(6-(4-amino-4-(morpholinomethyl)piperidin-1-yl)pyridin-3-yl)-6-ethoxypyrazolo[1,5-a]pyridine-3-carbonitrile (Intermediate P73, 30 mg, 0.065 mmol) and TEA (18 µL, 0.13 mmol) in DCM (650 µL) was treated with isovaleryl chloride (7.9 µL, 0.065 mmol), and then stirred overnight at ambient temperature. The mixture was treated with additional isovaleryl chloride (7.9 µL, 0.065 mmol), and stirred for an additional 3 h. The resulting mixture was diluted with 4:1 DCM:iPrOH, and then extracted with saturated $NaHCO_{3(aq)}$, water (1×) and brine (2×). The organic extracts were dried over anhydrous $Na_2SO_{4(s)}$, filtered and concentrated in vacuo to cleanly afford the title compound (35 mg, 99% yield). MS (apci) m/z=546.3 (M+H).

Example 583

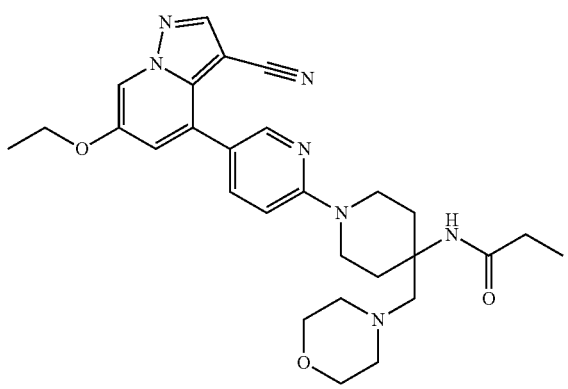 [SMILES: CCOc1cc(-c2ccc(N3CCC(CN4CCOCC4)(NC(=O)CC)CC3)nc2)c2c(C#N)cnn2c1]

N-(1-(5-(3-cyano-6-ethoxypyrazolo[1,5-a]pyridin-4-yl)pyridin-2-yl)-4-(morpholinomethyl)piperidin-4-yl)propionamide A solution of 4-(6-(4-amino-4-(morpholinomethyl)piperidin-1-yl)pyridin-3-yl)-6-ethoxypyrazolo[1,5-a]pyridine-3-carbonitrile (Intermediate P73, 40 mg, 0.087 mmol) and TEA (24 µL, 0.17 mmol) in DCM (867 µL) was treated with propionyl chloride (8.0 mg, 0.087 mmol), and then stirred overnight at ambient temperature. The mixture was concentrated in vacuo and the residue was purified by C18 reverse phase chromatography (5-95% water:ACN with 0.1% TFA). Fractions containing the desired product were combined, diluted with 4:1 DCM:iPrOH, and then extracted with saturated $NaHCO_{3(aq)}$, water (1×) and brine (2×). The organic extracts were dried over anhydrous $Na_2SO_{4(s)}$, filtered and concentrated in vacuo to cleanly afford the title compound (31 mg, 69% yield). MS (apci) m/z=518.3 (M+H).

Example 584

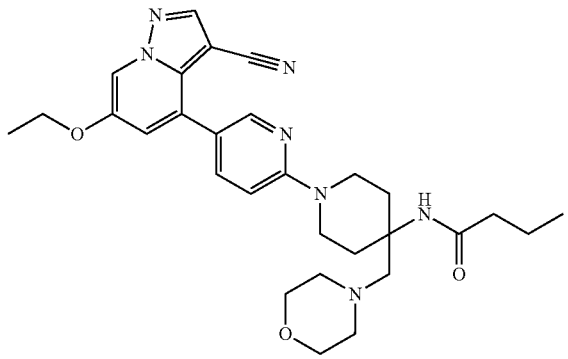

N-(1-(5-(3-cyano-6-ethoxypyrazolo[1,5-a]pyridin-4-yl)pyridin-2-yl)-4-(morpholinomethyl)piperidin-4-yl)butyramide The title compound (29 mg, 63% yield) was prepared, worked up and purified using a similar procedure to that described for N-(1-(5-(3-cyano-6-ethoxypyrazolo[1,5-a]pyridin-4-yl)pyridin-2-yl)-4-(morpholinomethyl)piperidin-4-yl)propionamide (Example 583), replacing propionyl chloride with butyryl chloride. MS (apci) m/z=532.4 (M+H).

Example 585

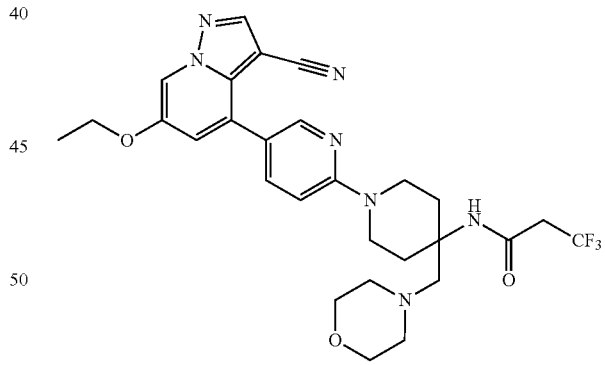

N-(1-(5-(3-cyano-6-ethoxypyrazolo[1,5-a]pyridin-4-yl)pyridin-2-yl)-4-(morpholinomethyl)piperidin-4-yl)-3,3,3-trifluoropropanamide The title compound (29 mg, 47% yield) was prepared, worked up and purified using a similar procedure to that described for N-(1-(5-(3-cyano-6-ethoxypyrazolo[1,5-a]pyridin-4-yl)pyridin-2-yl)-4-(morpholinomethyl)piperidin-4-yl)propionamide (Example 583), replacing propionyl chloride with 3,3,3-trifluoropropionyl chloride. MS (apci) m/z=572.3 (M+H).

Example 586

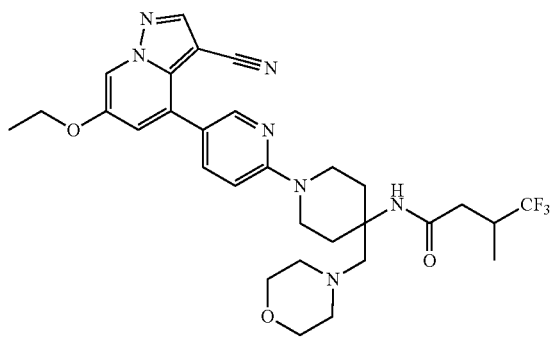 [SMILES: CCOc1cc(-c2ccc(N3CCC(CN4CCOCC4)(NC(=O)CC(C)C(F)(F)F)CC3)nc2)c2c(C#N)cnn2c1]

N-(1-(5-(3-cyano-6-ethoxypyrazolo[1,5-a]pyridin-4-yl)pyridin-2-yl)-4-(morpholinomethyl)piperidin-4-yl)-4,4,4-trifluoro-3-methylbutanamide A mixture of 4-(6-(4-amino-4-(morpholinomethyl)piperidin-1-yl)pyridin-3-yl)-6-ethoxypyrazolo[1,5-a]pyridine-3-carbonitrile (Intermediate P73, 30 mg, 0.065 mmol), 3-trifluoromethylbutyric acid (10 mg, 0.065 mmol) and HATU (62 mg, 0.16 mmol) in DCM (130 μL) was treated with DIEA (114 μL, 0.65 mmol), then stirred for 3 d at ambient temperature. The resulting mixture was concentrated in vacuo, and the residue was purified by C18 reverse phase chromatography (using 5-95% water:ACN with 0.1% TFA as the gradient eluent). Fractions containing the desired compound were combined, diluted with 4:1 DCM:iPrOH, and extracted sequentially with saturated $NaHCO_{3(aq)}$ and brine. The organic extracts were dried over anhydrous $Na_2SO_{4(s)}$, filtered, and concentrated in vacuo to afford the title compound (31 mg, 80% yield). MS (apci) m/z=600.3 (M+H).

The compounds in Table 000 were prepared using a similar method to that described in the synthesis of N-(1-(5-(3-cyano-6-ethoxypyrazolo[1,5-a]pyridin-4-yl)pyridin-2-yl)-4-(morpholinomethyl)piperidin-4-yl)-4,4,4-trifluoro-3-methylbutanamide (Example 586), replacing 3-trifluoromethylbutyric acid with the appropriate carboxylic acid. Where noted (*) the carboxylic acid is prepared in the reagents section, otherwise commercial reagents were utilized. Reactions were monitored for completion by LCMS, and reaction durations were adjusted accordingly. Title compounds were isolated following chromatographic purification using an appropriate gradient eluent. When chromatographic conditions resulted in the isolation of the TFA salt of the title compound, chromatography was followed by a basic work up as in Example 586.

TABLE OOO

| Ex # | Structure | Chemical Name | MS (apci) m/z |
|---|---|---|---|
| 587 | 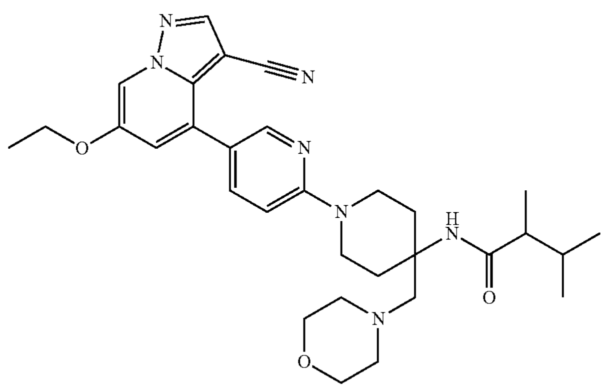 [SMILES: CCOc1cc(-c2ccc(N3CCC(CN4CCOCC4)(NC(=O)C(C)C(C)C)CC3)nc2)c2c(C#N)cnn2c1] | N-(1-(5-(3-cyano-6-ethoxypyrazolo[1,5-a]pyridin-4-yl)pyridin-2-yl)-4-(morpholinomethyl)piperidin-4-yl)-2,3-dimethylbutanamide | 560.3 (M + H) |
| 588 | 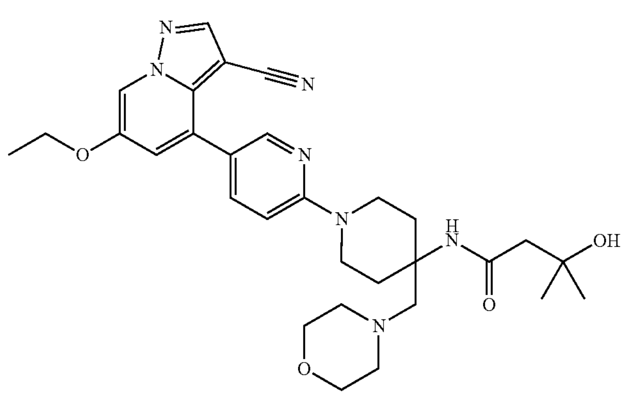 [SMILES: CCOc1cc(-c2ccc(N3CCC(CN4CCOCC4)(NC(=O)CC(C)(C)O)CC3)nc2)c2c(C#N)cnn2c1] | N-(1-(5-(3-cyano-6-ethoxypyrazolo[1,5-a]pyridin-4-yl)pyridin-2-yl)-4-(morpholinomethyl)piperidin-4-yl)-3-hydroxy-3-methylbutanamide | 562.3 (M + H) |

TABLE OOO-continued

| Ex # | Structure | Chemical Name | MS (apci) m/z |
|---|---|---|---|
| 589 | 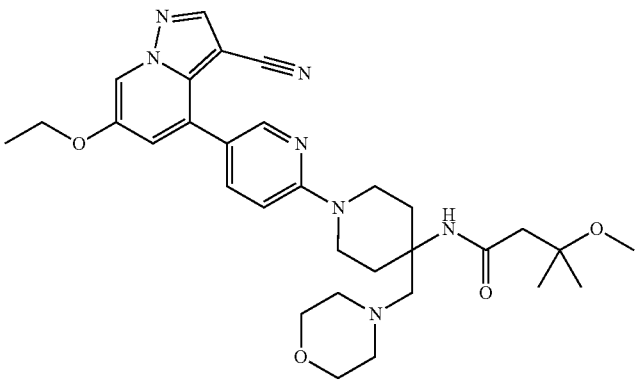 [SMILES: CCOc1cc(-c2ccc(N3CCC(CN4CCOCC4)(NC(=O)CC(C)(C)OC)CC3)nc2)c2c(C#N)cnn2c1] | N-(1-(5-(3-cyano-6-ethoxypyrazolo[1,5-a]pyridin-4-yl)pyridin-2-yl)-4-(morpholinomethyl)piperidin-4-yl)-3-methoxy-3-methylbutanamide | 576.4 (M + H) |
| 590 | 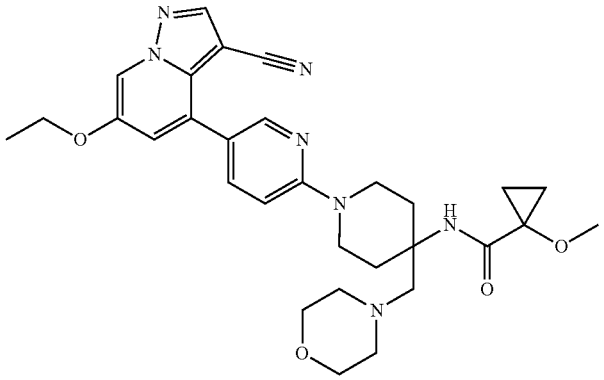 [SMILES: CCOc1cc(-c2ccc(N3CCC(CN4CCOCC4)(NC(=O)C4(OC)CC4)CC3)nc2)c2c(C#N)cnn2c1] | N-(1-(5-(3-cyano-6-ethoxypyrazolo[1,5-a]pyridin-4-yl)pyridin-2-yl)-4-(morpholinomethyl)piperidin-4-yl)-1-methoxycyclopropane-1-carboxamide | 560.3 (M + H) |

Example 591

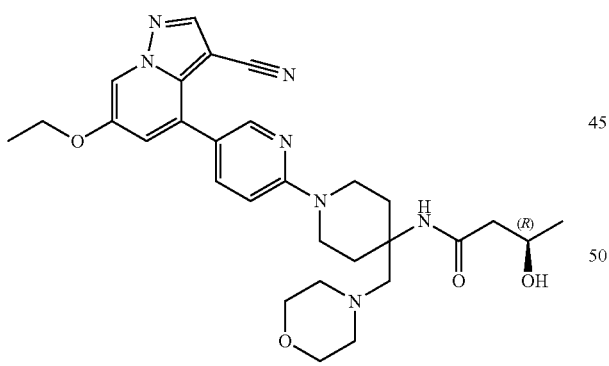

(R)—N-(1-(5-(3-cyano-6-ethoxypyrazolo[1,5-a]pyridin-4-yl)pyridin-2-yl)-4-(morpholinomethyl)piperidin-4-yl)-3-hydroxybutanamide A mixture of 4-(6-(4-amino-4-(morpholinomethyl)piperidin-1-yl)pyridin-3-yl)-6-ethoxypyrazolo[1,5-a]pyridine-3-carbonitrile (Intermediate P73, 30 mg, 0.065 mmol), (R)-3-hydroxybutyric acid (6.8 mg, 0.065 mmol) and HATU (25 mg, 0.065 mmol) in DCM (650 µL) was treated with DIEA (11 µL, 0.065 mmol), then stirred for 3 d at ambient temperature. The resulting mixture was concentrated in vacuo, and the residue was purified by C18 reverse phase chromatography (using 5-95% water:ACN with 0.1% TFA as the gradient eluent). Fractions containing the desired compound were combined, diluted with 4:1 DCM:iPrOH, and extracted sequentially with saturated $NaHCO_{3(aq)}$ and brine. The organic extracts were dried over anhydrous $Na_2SO_{4(s)}$, filtered, and concentrated in vacuo to afford the title compound (17 mg, 48% yield). MS (apci) m/z=548.3 (M+H).

Example 592

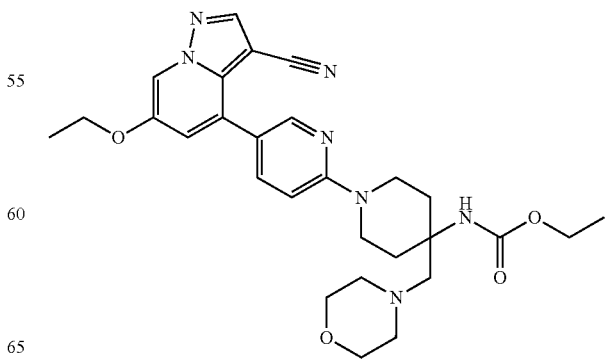

Ethyl (1-(5-(3-cyano-6-ethoxypyrazolo[1,5-a]pyridin-4-yl)pyridin-2-yl)-4-(morpholinomethyl)piperidin-4-yl)carbamate A solution of 4-(6-(4-amino-4-(morpholinomethyl)piperidin-1-yl)pyridin-3-yl)-6-ethoxypyrazolo[1,5-a]pyridine-3-carbonitrile (Intermediate P73, 25 mg, 0.054 mmol) and DIEA (18.9 µL, 0.108 mmol) in DCM (500 µL) was treated with ethyl carbonochloridate (7.05 mg, 0.0650 mmol). The resulting mixture was stirred overnight at ambient temperature, and then directly purified by silica chromatography (using 40-100% Hexanes/EtOAc as the gradient eluent) to cleanly provide the title compound (20.5 mg, 70% yield). MS (apci) m/z=534.2 (M+H).

Example 593

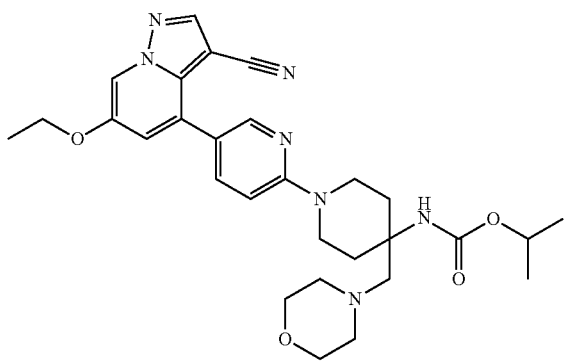

Isopropyl (1-(5-(3-cyano-6-ethoxypyrazolo[1,5-a]pyridin-4-yl)pyridin-2-yl)-4-(morpholinomethyl)piperidin-4-yl)carbamate The title compound (22 mg, 64% yield) was prepared, worked up and purified using a similar procedure to that described for ethyl (1-(5-(3-cyano-6-ethoxypyrazolo[1,5-a]pyridin-4-yl)pyridin-2-yl)-4-(morpholinomethyl)piperidin-4-yl)carbamate (Example 592), replacing ethyl carbonochloridate with isopropyl carbonochloridate. MS (apci) m/z=548.2 (M+H).

Example 594

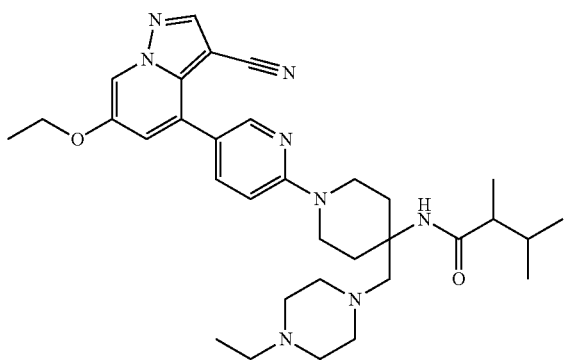

N-(1-(5-(3-cyano-6-ethoxypyrazolo[1,5-a]pyridin-4-yl)pyridin-2-yl)-4-((4-ethylpiperazin-1-yl)methyl)piperidin-4-yl)-2,3-dimethylbutanamide A mixture of 4-(6-(4-amino-4-((4-ethylpiperazin-1-yl)methyl)piperidin-1-yl)pyridin-3-yl)-6-ethoxypyrazolo[1,5-a]pyridine-3-carbonitrile (Intermediate P74, 40 mg, 0.082 mmol), 2,3-dimethylbutanoic acid (9.5 mg, 0.082 mmol) and HATU (78 mg, 0.20 mmol) in DCM (164 µL) was treated with DIEA (143 µL, 0.820 mmol). The resulting mixture was stirred overnight at ambient temperature, and then concentrated in vacuo. The crude residue was purified by C18 reverse phase chromatography (5-95% ACN:water with 0.1% TFA). Fractions containing the desired product were combined, diluted with 4:1 DCM:iPrOH, then sequentially extracted with saturated $NaHCO_{3(aq)}$, water and brine. The organic extracts were dried over anhydrous $Na_2SO_{4(s)}$, filtered, and concentrated in vacuo to cleanly afford the title compound (18 mg, 37% yield). MS (apci) m/z=587.4 (M+H).

Example 595

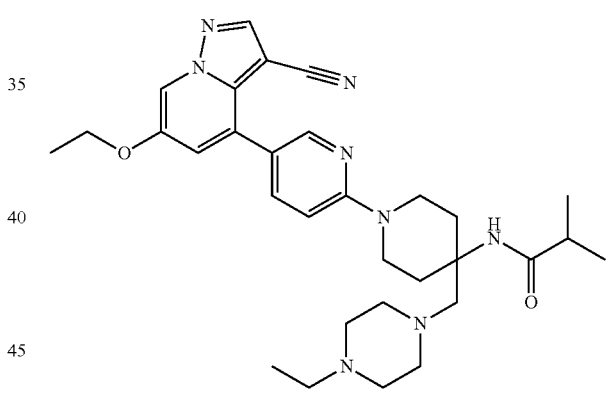

N-(1-(5-(3-cyano-6-ethoxypyrazolo[1,5-a]pyridin-4-yl)pyridin-2-yl)-4-((4-ethylpiperazin-1-yl)methyl)piperidin-4-yl)isobutyramide A solution of 4-(6-(4-amino-4-((4-ethylpiperazin-1-yl)methyl)piperidin-1-yl)pyridin-3-yl)-6-ethoxypyrazolo[1,5-a]pyridine-3-carbonitrile dihydrochloride (Intermediate P98; 9.5 mg, 0.0169 mmol), isobutyric acid (1.86 mg, 0.0211 mmol) and DIEA (14.8 µL, 0.0846 mmol) in DMF (169 µL) was treated with HATU (8.04 mg, 0.0211 mmol). The resulting mixture was stirred for 5 min at ambient temperature, and then purified by silica chromatography (using 0-10% [MeOH with 1% $NH_4OH$] in EtOAc as the gradient eluent). The purified residue was triturated with MTBE then concentrated in vacuo to cleanly afford the title compound (9 mg, 95% yield). MS (apci) m/z=559.3 (M+H).

Example 596

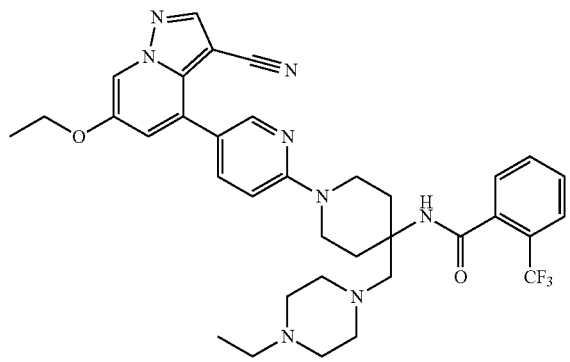 [SMILES: CCOc1cc(-c2ccc(N3CCC(CN4CCN(CC)CC4)(NC(=O)c4ccccc4C(F)(F)F)CC3)nc2)c2c(C#N)cnn2c1]

N-(1-(5-(3-cyano-6-ethoxypyrazolo[1,5-a]pyridin-4-yl)pyridin-2-yl)-4-((4-ethylpiperazin-1-yl)methyl)piperidin-4-yl)-2-(trifluoromethyl)benzamide The title compound can be prepared in a similar fashion as described for N-(1-(5-(3-cyano-6-ethoxypyrazolo[1,5-a]pyridin-4-yl)pyridin-2-yl)-4-((4-ethylpiperazin-1-yl)methyl)piperidin-4-yl)isobutyramide (Example 595), replacing isobutyric acid with 2-(trifluoromethyl)benzoic acid.

Example 597

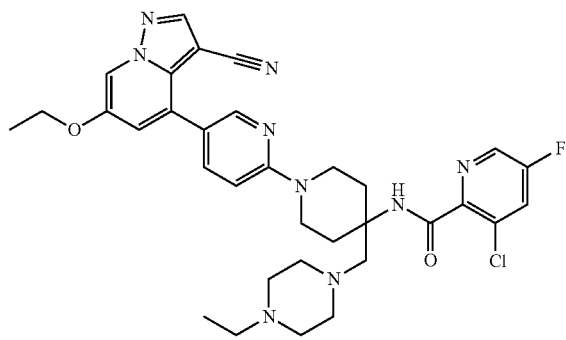 [SMILES: CCOc1cc(-c2ccc(N3CCC(CN4CCN(CC)CC4)(NC(=O)c4ncc(F)cc4Cl)CC3)nc2)c2c(C#N)cnn2c1]

3-chloro-N-(1-(5-(3-cyano-6-ethoxypyrazolo[1,5-a]pyridin-4-yl)pyridin-2-yl)-4-((4-ethylpiperazin-1-yl)methyl)piperidin-4-yl)-5-fluoropicolinamide A solution of 4-(6-(4-amino-4-((4-ethylpiperazin-1-yl)methyl)piperidin-1-yl)pyridin-3-yl)-6-ethoxypyrazolo[1,5-a]pyridine-3-carbonitrile (Intermediate P74, 23.5 mg, 0.0481 mmol) in DMSO (481 µL) was treated with DIEA (42.0 µL, 0.240 mmol), 3-chloro-5-fluoropicolinic acid (16.9 mg, 0.0962 mmol) and HATU (36.6 mg, 0.0962 mmol). The resulting mixture was stirred overnight at ambient temperature, and then purified directly by silica chromatography (using 0-10% [MeOH with 1% NH$_4$OH] in DCM as the gradient eluent) to cleanly afford the title compound (20.6 mg, 66% yield). MS (apci) m/z=646.3 (M+H).

Example 598

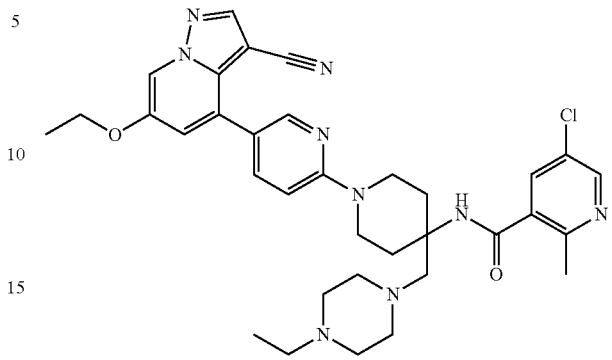

5-chloro-N-(1-(5-(3-cyano-6-ethoxypyrazolo[1,5-a]pyridin-4-yl)pyridin-2-yl)-4-((4-ethylpiperazin-1-yl)methyl)piperidin-4-yl)-2-methylnicotinamide The title compound (17.2 mg, 56% yield) was prepared, worked up and purified using a similar procedure to that described for 3-chloro-N-(1-(5-(3-cyano-6-ethoxypyrazolo[1,5-a]pyridin-4-yl)pyridin-2-yl)-4-((4-ethylpiperazin-1-yl)methyl)piperidin-4-yl)-5-fluoropicolinamide (Example 597), replacing 3-chloro-5-fluoropicolinic acid (2 equivalents) with 5-chloro-2-methyl-3-pyridinecarboxylic acid (1 equivalent). MS (apci) m/z=642.4 (M+H).

Example 599

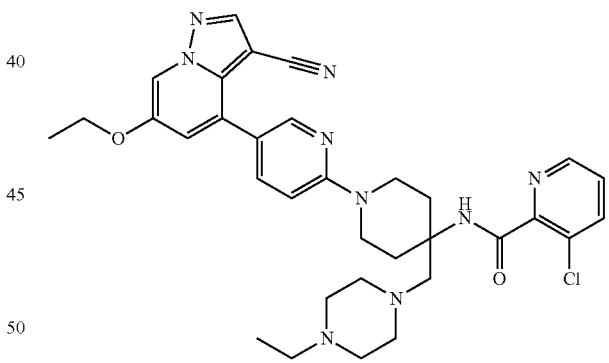

3-chloro-N-(1-(5-(3-cyano-6-ethoxypyrazolo[1,5-a]pyridin-4-yl)pyridin-2-yl)-4-((4-ethylpiperazin-1-yl)methyl)piperidin-4-yl)picolinamide A solution of 4-(6-(4-amino-4-((4-ethylpiperazin-1-yl)methyl)piperidin-1-yl)pyridin-3-yl)-6-ethoxypyrazolo[1,5-a]pyridine-3-carbonitrile dihydrochloride (Intermediate P98; 31.9 mg, 0.0568 mmol) in DMF (169 µL) was treated with DIEA (9.2 µL, 0.0568 mmol), 3-chloropicolinic acid (26.9 mg, 0.170 mmol) and HATU (43.2 mg, 0.114 mmol). The resulting mixture was stirred for 30 min at ambient temperature, and then purified directly by silica chromatography (using 10-25% [MeOH with 1% NH$_4$OH] in DCM as

Example 600

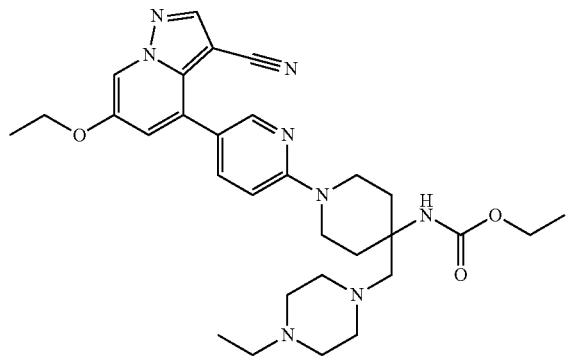 [SMILES: CCOC(=O)NC1(CN2CCN(CC)CC2)CCN(c2ccc(-c3cc(OCC)cn4ncc(C#N)c34)cn2)CC1]

ethyl (1-(5-(3-cyano-6-ethoxypyrazolo[1,5-a]pyridin-4-yl)pyridin-2-yl)-4-((4-ethylpiperazin-1-yl)methyl)piperidin-4-yl)carbamate The title compound (13.7 mg, 51% yield) was prepared, worked up and purified using a similar procedure to that described for methyl (1-(5-(3-cyano-6-ethoxypyrazolo[1,5-a]pyridin-4-yl)pyridin-2-yl)-4-((4-ethylpiperazin-1-yl)methyl)piperidin-4-yl)carbamate (Example 392), with the following exceptions, methyl chloroformate was replaced with ethyl chloroformate, and the reaction was allowed to stir only 1 h before filtering. MS (apci) m/z=561.3 (M+H).

Example 601

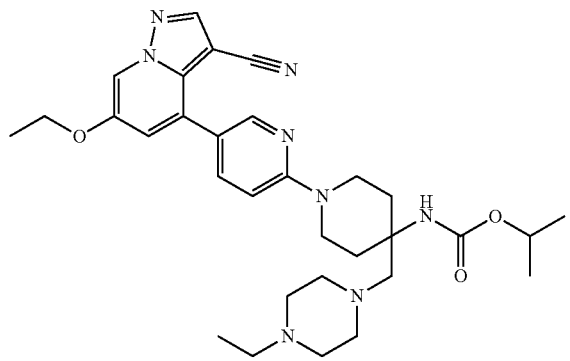

Isopropyl (1-(5-(3-cyano-6-ethoxypyrazolo[1,5-a]pyridin-4-yl)pyridin-2-yl)-4-((4-ethylpiperazin-1-yl)methyl)piperidin-4-yl)carbamate The title compound (8.5 mg, 30% yield) was prepared, worked up and purified using a similar procedure to that described for methyl (1-(5-(3-cyano-6-ethoxypyrazolo[1,5-a]pyridin-4-yl)pyridin-2-yl)-4-((4-ethylpiperazin-1-yl)methyl)piperidin-4-yl)carbamate (Example 392), with the following exceptions, methyl chloroformate was replaced with isopropyl chloroformate, and the reaction was allowed to stir overnight before filtering. MS (apci) m/z=574.4 (M+H).

Example 602

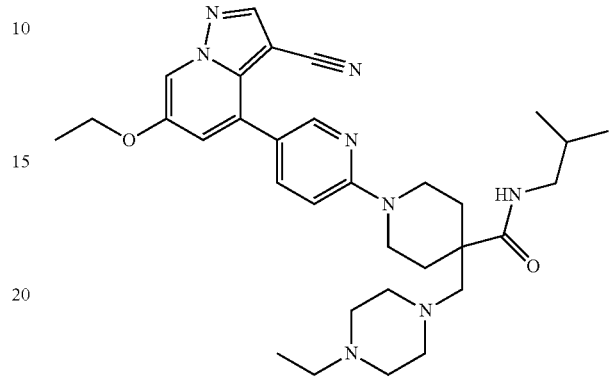

1-(5-(3-cyano-6-ethoxypyrazolo[1,5-a]pyridin-4-yl)pyridin-2-yl)-4-((4-ethylpiperazin-1-yl)methyl)-N-isobutylpiperidine-4-carboxamide A solution of 1-(5-(3-cyano-6-ethoxypyrazolo[1,5-a]pyridin-4-yl)pyridin-2-yl)-4-formyl-N-isobutylpiperidine-4-carboxamide (Intermediate P76, 51.8 mg, 0.109 mmol) in DCM (1.0 mL) was treated sequentially with 1-ethylpiperazine (69.3 μL, 0.546 mmol) and NaBH(AcO)$_3$ (116 mg, 0.546 mmol), and stirred for 16 h at ambient temperature. The reaction mixture was concentrated in vacuo. The crude residue was purified directly by C18 reverse phase chromatography (using 5-95% water:ACN with 0.1% TFA as the gradient eluent). Fractions containing the desired product were partitioned between 4:1 DCM:iPrOH and saturated NaHCO$_{3(aq)}$. The organic extracts were dried over anhydrous Na$_2$SO$_{4(s)}$, filtered, and concentrated in vacuo to afford the title compound (32.3 mg, 52% yield). MS (apci) m/z=573.4 (M+H).

Example 603

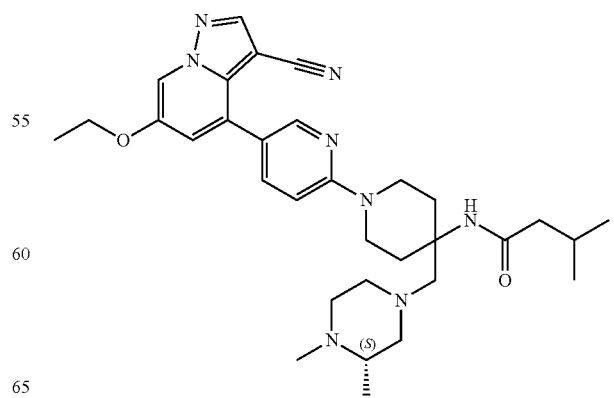

(S)—N-(1-(5-(3-cyano-6-ethoxypyrazolo[1,5-a]pyridin-4-yl)pyridin-2-yl)-4-((3,4-dimethylpiperazin-1-yl)methyl)piperidin-4-yl)-3-methylbutanamide A solution of N-(1-(5-(3-cyano-6-ethoxypyrazolo[1,5-a]pyridin-4-yl)pyridin-2-yl)-4-formylpiperidin-4-yl)-3-methylbutanamide (Intermediate P102; 500 mg, 1.189 mmol) in DCM (5 mL) was treated with (S)-1,2-dimethylpiperazine (Intermediate R28; 42.6 mg, 0.373 mmol), and stirred for 2 h at ambient temperature. The resulting mixture was treated with NaBH(AcO)₃ (63.2 mg, 0.298 mmol), and stirred overnight at ambient temperature. The reaction mixture was diluted with DCM and extracted with saturated NaHCO₃₍ₐq₎. The organic extracts were purified directly by silica chromatography (using 0-20% [MeOH with 1% NH₄OH] in DCM as the gradient eluent) to cleanly afford the title compound (5.4 mg, 12% yield). MS (apci) m/z=573.3 (M+H).

Example 604

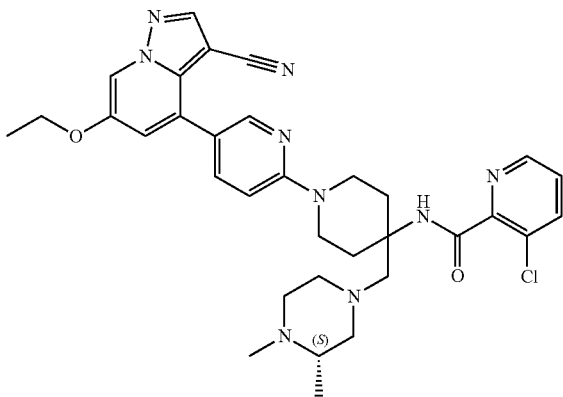

(S)-3-chloro-N-(1-(5-(3-cyano-6-ethoxypyrazolo[1,5-a]pyridin-4-yl)pyridin-2-yl)-4-((3,4-dimethylpiperazin-1-yl)methyl)piperidin-4-yl)picolinamide A solution of (S)-4-(6-(4-amino-4-((3,4-dimethylpiperazin-1-yl)methyl)piperidin-1-yl)pyridin-3-yl)-6-ethoxypyrazolo[1,5-a]pyridine-3-carbonitrile (Intermediate P155; 37.0 mg, 0.0757 mmol) in DCM (2 mL) was treated with DIEA (132 µL, 0.757 mmol), 3-chloropicolinic acid (35.8 mg, 0.227 mmol) and HATU (57.6 mg, 0.151 mmol). The resulting mixture was stirred overnight at ambient temperature, and then purified directly by silica chromatography (using 0-20% [MeOH with 1% NH₄OH] in DCM as the gradient eluent). Fractions containing the desired product were concentrated, and the resultant residue was taken up with saturated NaHCO₃₍ₐq₎ and extracted into EtOAc. The organic extracts were dried over Na₂SO₄₍s₎, filtered, and concentrated in vacuo to afford the title compound (14.6 mg, 29% yield). MS (apci) m/z=628.2 (M+H).

Example 605

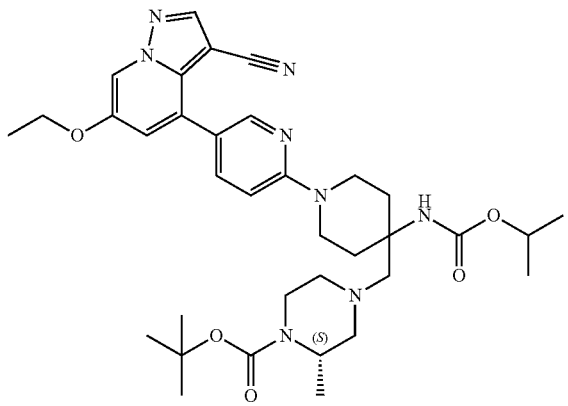

tert-butyl (S)-4-((1-(5-(3-cyano-6-ethoxypyrazolo[1,5-a]pyridin-4-yl)pyridin-2-yl)-4-((isopropoxycarbonyl)amino)piperidin-4-yl)methyl)-2-methylpiperazine-1-carboxylate A solution of isopropyl (1-(5-(3-cyano-6-ethoxypyrazolo[1,5-a]pyridin-4-yl)pyridin-2-yl)-4-formylpiperidin-4-yl)carbamate (Intermediate P105; 47.8 mg, 0.100 mmol) in DCE (3 mL) was treated with tert-butyl (S)-2-methylpiperazine-1-carboxylate (100 mg, 0.502 mmol), and stirred for 45 min at ambient temperature. The resulting mixture was treated with NaBH(AcO)₃ (128 mg, 0.602 mmol), and stirred for 1.5 h at ambient temperature. The reaction mixture was diluted with DCM, and extracted with water. The organic extracts were purified directly by silica chromatography (first using 0-25% MeOH in DCM as the gradient eluent, then using 0-40% [MeOH with 1% NH₄OH] in EtOAc) to afford the title compound (44.5 mg, 63% yield). MS (apci) m/z=661.3 (M+H).

Example 606

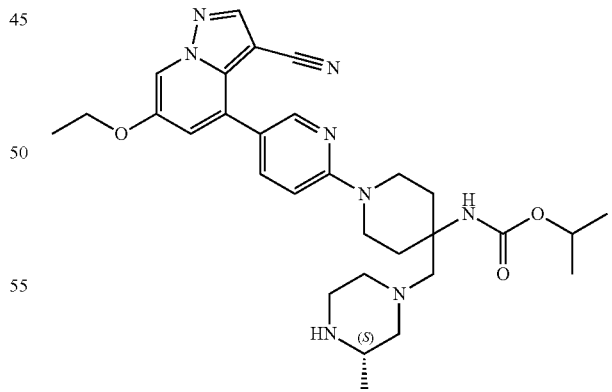

isopropyl (S)-(1-(5-(3-cyano-6-ethoxypyrazolo[1,5-a]pyridin-4-yl)pyridin-2-yl)-4-((3-methylpiperazin-1-yl)methyl)piperidin-4-yl)carbamate A solution of tert-butyl (S)-4-((1-(5-(3-cyano-6-ethoxypyrazolo[1,5-a]pyridin-4-yl)pyridin-2-yl)-4-((isopropoxycarbonyl)amino)piperidin-4-yl)methyl)-2-methylpiperazine-1-carboxylate (Example 605; 23.1 mg, 0.0350 mmol) in dioxane (500 μL) was treated with 12 M HCl$_{(aq)}$ (5.74 μL, 0.0699 mmol). The resulting mixture was stirred for 1 h at ambient temperature, then concentrated in vacuo. The crude residue was dissolved in 4:1 DCM:iPrOH, then extracted with saturated NaHCO$_{3(aq)}$. The organic extracts were dried over anhydrous Na$_2$SO$_{4(s)}$, filtered, and concentrated in vacuo to cleanly afford the title compound (21.5 mg, quantitative yield). MS (apci) m/z=561.3 (M+H).

Example 607

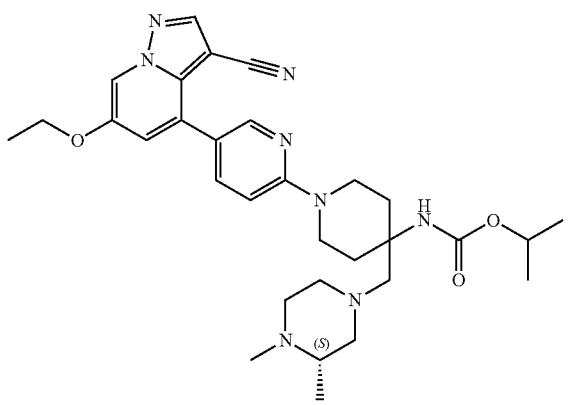

isopropyl (S)-(1-(5-(3-cyano-6-ethoxypyrazolo[1,5-a]pyridin-4-yl)pyridin-2-yl)-4-((3,4-dimethylpiperazin-1-yl)methyl)piperidin-4-yl)carbamate A solution of isopropyl (S)-(1-(5-(3-cyano-6-ethoxypyrazolo[1,5-a]pyridin-4-yl)pyridin-2-yl)-4-((3-methylpiperazin-1-yl)methyl)piperidin-4-yl)carbamate (Example 606; 12.5 mg, 0.02229 mmol) in DCE (1.0 mL) was treated with formaldehyde (37 wt. % in water with 5-15% MeOH stabilizer; 9.046 mg, 0.1115 mmol), and stirred for 45 min at ambient temperature. The resulting mixture was treated with NaBH(AcO)$_3$ (28.35 mg, 0.1338 mmol), stirred for 2 h at ambient temperature, and then concentrated in vacuo. The crude residue was suspended in 4:1 DCM:iPrOH and then filtered. The filtrate was concentrated in vacuo to cleanly provide the title compound (8.7 mg, 64% yield). MS (apci) m/z=575.3 (M+H).

Example 608

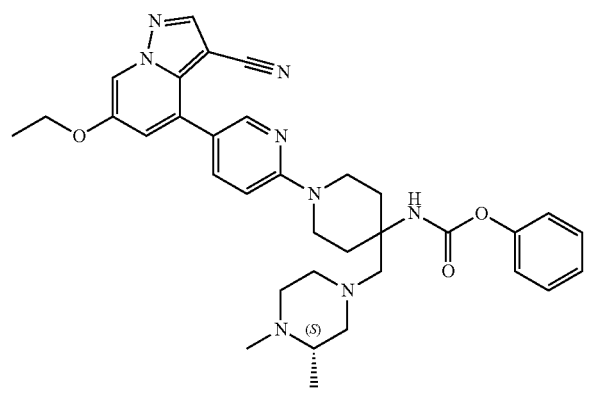

Phenyl (S)-(1-(5-(3-cyano-6-ethoxypyrazolo[1,5-a]pyridin-4-yl)pyridin-2-yl)-4-((3,4-dimethylpiperazin-1-yl)methyl)piperidin-4-yl)carbamate A solution of (S)-4-(6-(4-amino-4-((3,4-dimethylpiperazin-1-yl)methyl)piperidin-1-yl)pyridin-3-yl)-6-ethoxypyrazolo[1,5-a]pyridine-3-carbonitrile (Intermediate P155; 33.1 mg, 0.0677 mmol) in DCM (2 mL) was treated with DIEA (47.3 μL, 0.271 mmol) and phenyl carbonochloridate (12.8 μL, 0.102 mmol). The resulting mixture was stirred overnight at ambient temperature, then diluted with DCM. The DCM solution was extracted with saturated NaHCO$_{3(aq)}$. The organic extracts were purified by silica chromatography (using 0-20% [MeOH with 1% NH$_4$OH] in DCM as the gradient eluent) to cleanly provide the title compound (1.4 mg, 3% yield). MS (apci) m/z=609.3 (M+H).

Example 609

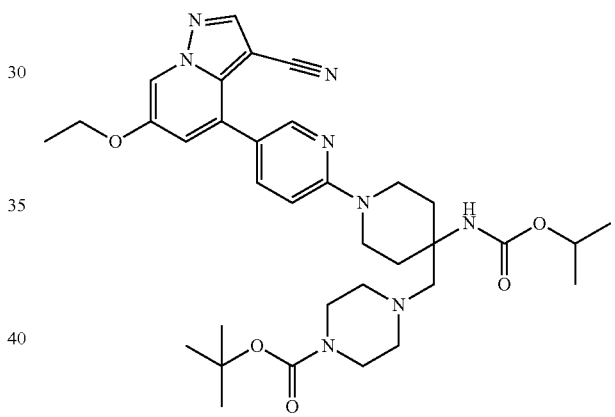

Tert-butyl 4-((1-(5-(3-cyano-6-ethoxypyrazolo[1,5-a]pyridin-4-yl)pyridin-2-yl)-4-((isopropoxycarbonyl)amino)piperidin-4-yl)methyl)piperazine-1-carboxylate A solution of isopropyl (1-(5-(3-cyano-6-ethoxypyrazolo[1,5-a]pyridin-4-yl)pyridin-2-yl)-4-formylpiperidin-4-yl)carbamate (Intermediate P105; 38.9 mg, 0.0816 mmol) in DCE (1.5 mL) was treated with tert-butyl piperazine-1-carboxylate (76.0 mg, 0.408 mmol), and stirred for 45 min at ambient temperature. The resulting mixture was treated with NaBH(AcO)$_3$ (104 mg, 0.490 mmol) and stirred for 1.5 h at ambient temperature. The reaction mixture was diluted with DCM and extracted with water. The organic extracts were purified directly by silica chromatography (using 0-100% EtOAc in hexanes as the gradient eluent) to cleanly afford the title compound (19.7 mg, 37% yield). MS (apci) m/z=647.3 (M+H).

Example 610

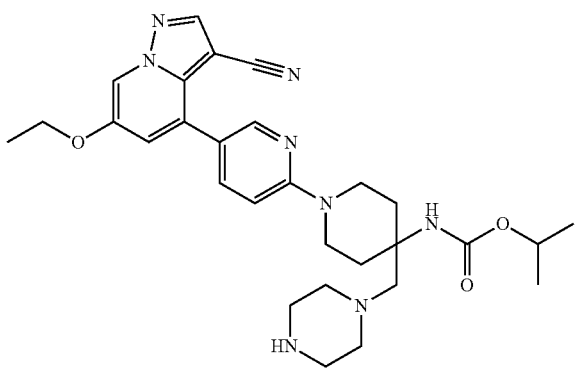 [SMILES: CCOc1cc(-c2ccc(N3CCC(CN4CCNCC4)(NC(=O)OC(C)C)CC3)nc2)c2c(C#N)cnn2c1]

isopropyl (1-(5-(3-cyano-6-ethoxypyrazolo[1,5-a]
pyridin-4-yl)pyridin-2-yl)-4-(piperazin-1-ylmethyl)
piperidin-4-yl)carbamate A solution of tert-butyl 4-((1-(5-(3-cyano-6-ethoxypyrazolo[1,5-a]pyridin-4-yl)pyridin-2-yl)-4-((isopropoxycarbonyl)amino)piperidin-4-yl)methyl)piperazine-1-carboxylate (Example 609; 14.5 mg, 0.0224 mmol) in dioxane (500 μL) was treated with 12 M HCl$_{(aq)}$ (3.68 μL, 0.0448 mmol). The resulting mixture was stirred for 1 h at ambient temperature then concentrated in vacuo. The crude residue was dissolved in 4:1 DCM:iPrOH, then extracted with saturated NaHCO$_{3(aq)}$. The organic extracts were dried over anhydrous Na$_2$SO$_{4(s)}$, filtered, and concentrated in vacuo to cleanly afford the title compound (8.5 mg, 69% yield). MS (apci) m/z=547.25 (M+H).

Example 611

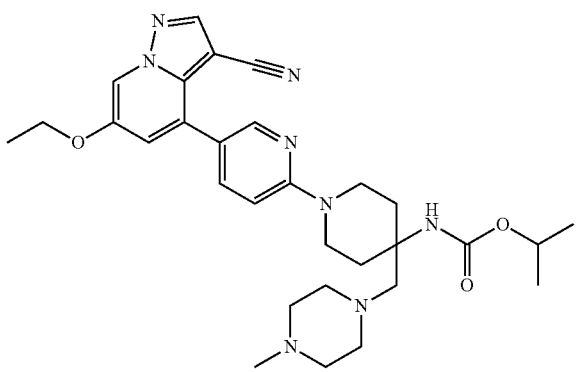 [SMILES: CCOc1cc(-c2ccc(N3CCC(CN4CCN(C)CC4)(NC(=O)OC(C)C)CC3)nc2)c2c(C#N)cnn2c1]

Isopropyl (1-(5-(3-cyano-6-ethoxypyrazolo[1,5-a]
pyridin-4-yl)pyridin-2-yl)-4-((4-methylpiperazin-1-
yl)methyl)piperidin-4-yl)carbamate A solution of isopropyl (1-(5-(3-cyano-6-ethoxypyrazolo[1,5-a]pyridin-4-yl)pyridin-2-yl)-4-(piperazin-1-ylmethyl)piperidin-4-yl)carbamate (Example 610; 5.7 mg, 0.010 mmol) in DCE (1.0 mL) was treated with formaldehyde (37 wt. % in water with 5-15% MeOH stabilizer; 4.231 mg, 0.05213 mmol), and stirred for 45 min at ambient temperature. The resulting mixture was treated with NaBH(AcO)$_3$ (13.26 mg, 0.06256 mmol), stirred for 2 h at ambient temperature, and then concentrated in vacuo. The crude residue was dissolved in DCM, then extracted sequentially with water and saturated NaHCO$_{3(aq)}$. After back extracting the aqueous extracts with DCM, the organic extracts were combined, dried over anhydrous Na$_2$SO$_{4(s)}$, and filtered. The filtrate was directly purified silica chromatography (using 0-30% [MeOH with 1% NH$_4$OH] in DCM as the gradient eluent) to cleanly provide the title compound (2.1 mg, 36% yield). MS (apci) m/z=561.3 (M+H).

Example 612

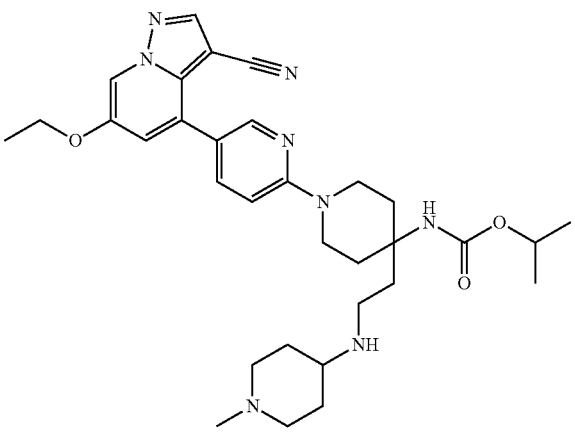 [SMILES: CCOc1cc(-c2ccc(N3CCC(CCNC4CCN(C)CC4)(NC(=O)OC(C)C)CC3)nc2)c2c(C#N)cnn2c1]

isopropyl (1-(5-(3-cyano-6-ethoxypyrazolo[1,5-a]
pyridin-4-yl)pyridin-2-yl)-4-(2-((1-methylpiperidin-
4-yl)amino)ethyl)piperidin-4-yl)carbamate A solution of isopropyl (1-(5-(3-cyano-6-ethoxypyrazolo[1,5-a]pyridin-4-yl)pyridin-2-yl)-4-formylpiperidin-4-yl)carbamate (Intermediate P105; 35.5 mg, 0.0745 mmol) in DCE (1.0 mL) was treated with 1-methylpiperidin-4-amine (42.5 mg, 0.372 mmol), and stirred for 45 min at ambient temperature. The resulting mixture was treated with NaBH(AcO)$_3$ (94.7 mg, 0.447 mmol), and stirred overnight at ambient temperature. The reaction mixture was diluted with DCM, and extracted sequentially with water and saturated NaHCO$_{3(aq)}$. After back extracting the aqueous extracts with DCM, the organic extracts were combined, dried over anhydrous Na$_2$SO$_{4(s)}$, and filtered. The filtrate was purified directly by silica chromatography (using 0-50% [MeOH with 1% NH$_4$OH] in DCM as the gradient eluent) to cleanly afford the title compound (2.3 mg, 5% yield). MS (apci) m/z=575.3 (M+H).

Example 613

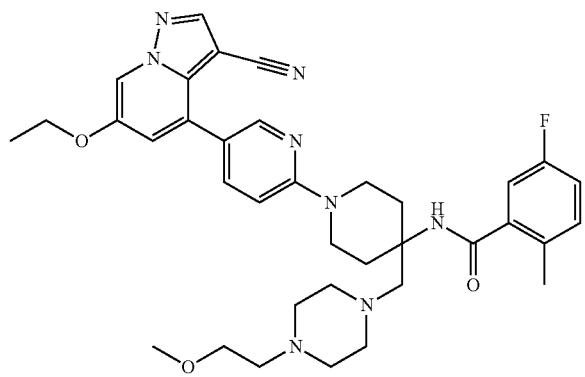 [SMILES: CCOc1cc(-c2ccc(N3CCC(CN4CCN(CCOC)CC4)(NC(=O)c4cc(F)ccc4C)CC3)nc2)c2c(C#N)cnn2c1]

N-(1-(5-(3-cyano-6-ethoxypyrazolo[1,5-a]pyridin-4-yl)pyridin-2-yl)-4-((4-(2-methoxyethyl)piperazin-1-yl)methyl)piperidin-4-yl)-5-fluoro-2-methylbenzamide A solution of N-(1-(5-(3-cyano-6-ethoxypyrazolo[1,5-a]pyridin-4-yl)pyridin-2-yl)-4-formylpiperidin-4-yl)-5-fluoro-2-methylbenzamide (Intermediate P70, 33.6 mg, 0.0638 mmol) and 1-(2-methoxyethyl)piperazine (28.5 µL, 0.191 mmol) in DCM (319 µL) was stirred for 30 min at ambient temperature. The resulting mixture was treated with NaBH(AcO)$_3$ (20.3 mg, 0.0957 mmol), and stirred overnight at room temperature. The resulting mixture was directly purified by silica chromatography (using 0-10% [9:1 DCM:MeOH with 1% NH$_4$OH] in DCM as the gradient eluent) to afford the title compound (30.3 mg, 73% yield). MS (apci) m/z=655.4 (M+H).

Example 614

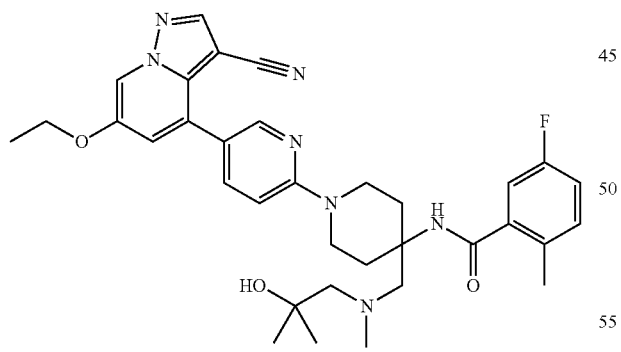

N-(1-(5-(3-cyano-6-ethoxypyrazolo[1,5-a]pyridin-4-yl)pyridin-2-yl)-4-(((2-hydroxy-2-methylpropyl)(methyl)amino)methyl)piperidin-4-yl)-5-fluoro-2-methylbenzamide A solution of N-(1-(5-(3-cyano-6-ethoxypyrazolo[1,5-a]pyridin-4-yl)pyridin-2-yl)-4-(((2-hydroxy-2-methylpropyl)amino)methyl)piperidin-4-yl)-5-fluoro-2-methylbenzamide (Example 381; 30.6 mg, 0.0510 mmol) and formaldehyde (37 wt. % in water with 5-15% MeOH stabilizer; 19.2 µL, 0.255 mmol) in DCE (255 µL) was stirred for 30 min at ambient temperature. The resulting mixture was treated with NaBH(AcO)$_3$ (108 mg, 0.510 mmol), and stirred overnight at room temperature. The resulting mixture was directly purified by silica chromatography (using 0-10% [9:1 DCM:MeOH with 1% NH$_4$OH] in DCM as the gradient eluent) to afford the title compound (26.5 mg, 85% yield). MS (apci) m/z=614.4 (M+H).

Example 615

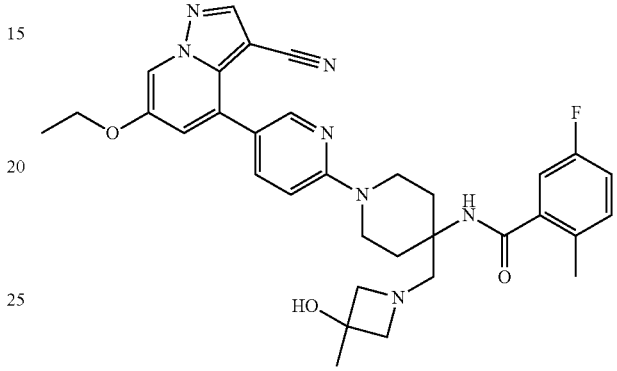

N-(1-(5-(3-cyano-6-ethoxypyrazolo[1,5-a]pyridin-4-yl)pyridin-2-yl)-4-((3-hydroxy-3-methylazetidin-1-yl)methyl)piperidin-4-yl)-5-fluoro-2-methylbenzamide A solution of N-(1-(5-(3-cyano-6-ethoxypyrazolo[1,5-a]pyridin-4-yl)pyridin-2-yl)-4-formylpiperidin-4-yl)-5-fluoro-2-methylbenzamide (Intermediate P70, 44.3 mg, 0.0841 mmol), 3-hydroxy-3-methylazetidine hydrochloride (31.2 mg, 0.252 mmol) and DIEA (44.1 µL, 0.252 mmol) in DCM (421 µL) was stirred for 30 min at ambient temperature. The resulting mixture was treated with NaBH(AcO)$_3$ (26.7 mg, 0.126 mmol), and stirred overnight at room temperature. The resulting mixture was directly purified by silica chromatography (using 0-10% [9:1 DCM:MeOH with 1% NH$_4$OH] in DCM as the gradient eluent) to afford the title compound (42.2 mg, 84% yield). MS (apci) m/z=598.3 (M+H).

Example 616

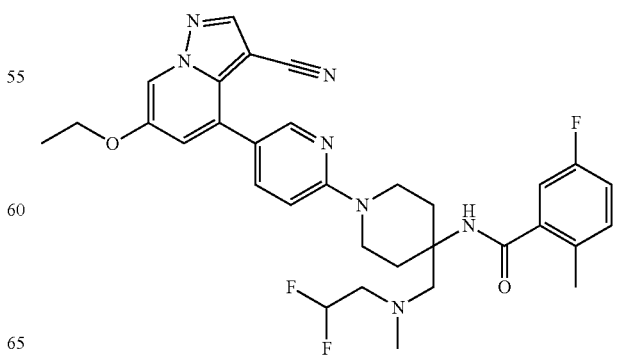

789

N-(1-(5-(3-cyano-6-ethoxypyrazolo[1,5-a]pyridin-4-yl)pyridin-2-yl)-4-(((2,2-difluoroethyl)(methyl)amino)methyl)piperidin-4-yl)-5-fluoro-2-methylbenzamide

The title compound (17.5 mg, 35% yield) was prepared, worked up and purified using a similar procedure to that described for N-(1-(5-(3-cyano-6-ethoxypyrazolo[1,5-a]pyridin-4-yl)pyridin-2-yl)-4-((3-hydroxy-3-methylazetidin-1-yl)methyl)piperidin-4-yl)-5-fluoro-2-methylbenzamide (Example 615), replacing 3-hydroxy-3-methylazetidine hydrochloride with 2,2-difluoro-N-methylethanamine hydrochloride. MS (apci) m/z=606.3 (M+H).

Example 617

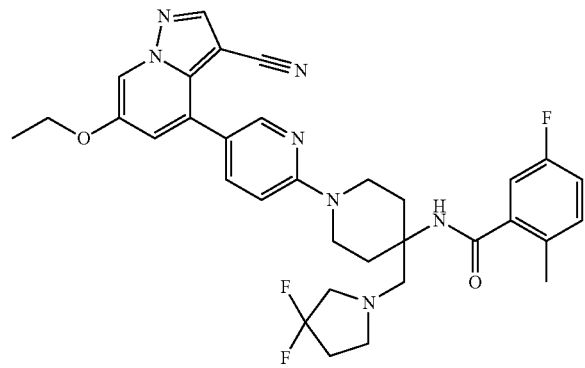 [SMILES: CCOc1cc(-c2ccc(N3CCC(CN4CCC(F)(F)C4)(NC(=O)c4cc(F)ccc4C)CC3)nc2)c2c(C#N)cnn2c1]

N-(1-(5-(3-cyano-6-ethoxypyrazolo[1,5-a]pyridin-4-yl)pyridin-2-yl)-4-((3,3-difluoropyrrolidin-1-yl)methyl)piperidin-4-yl)-5-fluoro-2-methylbenzamide

The title compound (45.4 mg, 84% yield) was prepared, worked up and purified using a similar procedure to that described for N-(1-(5-(3-cyano-6-ethoxypyrazolo[1,5-a]pyridin-4-yl)pyridin-2-yl)-4-((3-hydroxy-3-methylazetidin-1-yl)methyl)piperidin-4-yl)-5-fluoro-2-methylbenzamide (Example 615), replacing 3-hydroxy-3-methylazetidine hydrochloride with 3,3-difluoropyrrolidine hydrochloride. MS (apci) m/z=618.3 (M+H).

Example 618

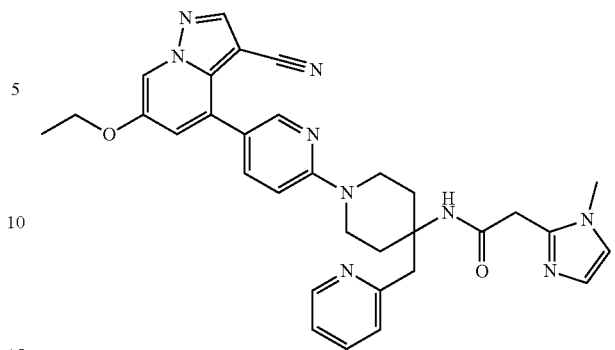

N-(1-(5-(3-cyano-6-ethoxypyrazolo[1,5-a]pyridin-4-yl)pyridin-2-yl)-4-(pyridin-2-ylmethyl)piperidin-4-yl)-2-(1-methyl-1H-imidazol-2-yl)acetamide

A solution of 2-(1-methyl-1H-imidazol-2-yl)-N-(4-(pyridin-2-ylmethyl)piperidin-4-yl)acetamide bis(2,2,2-trifluoroacetate) (Intermediate R33; 92.9 mg, 0.172 mmol), 6-ethoxy-4-(6-fluoropyridin-3-yl)pyrazolo[1,5-a]pyridine-3-carbonitrile (Intermediate P6, 44 mg, 0.156 mmol) and $K_2CO_{3(s)}$ (108 mg, 0.779 mmol) in DMSO (1039 µL) was stirred overnight at 90° C. After cooling to ambient temperature, the mixture was filtered, and the filtrate was purified directly by C18 reverse phase chromatography (using 5-95% ACN/water with 0.1% TFA as the gradient eluent) to afford the title compound as the TFA salt. The TFA salt was suspended in MeOH (5 mL), eluted through a basic resin (Stratospheres Pl-HCO3) to cleanly afford the title compound (34.9 mg, 39% yield). MS (apci) m/z=576.3 (M+H).

The compounds in Table PPP were prepared, worked up, purified and free based using a similar method to that described in the synthesis of N-(1-(5-(3-cyano-6-ethoxypyrazolo[1,5-a]pyridin-4-yl)pyridin-2-yl)-4-(pyridin-2-ylmethyl)piperidin-4-yl)-2-(1-methyl-1H-imidazol-2-yl)acetamide (Example 618), replacing 2-(1-methyl-1H-imidazol-2-yl)-N-(4-(pyridin-2-ylmethyl)piperidin-4-yl)acetamide bis(2,2,2-trifluoroacetate) (Intermediate R33) with the appropriate amine (1.0-1.5 equivalents). Reactions were monitored for completion by LCMS, and reaction durations were adjusted accordingly.

TABLE PPP

| Ex # | Structure | Chemical Name | MS (apci) m/z |
|---|---|---|---|
| 619 | 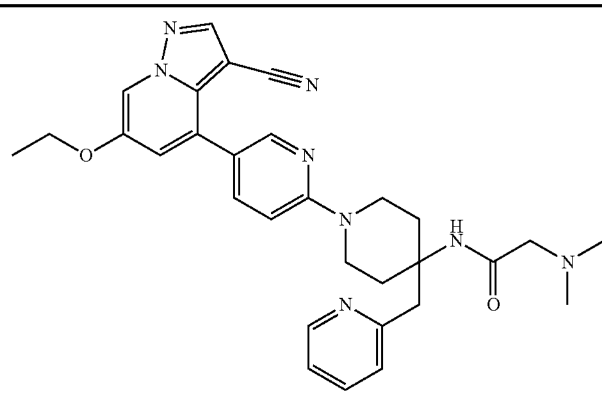 | N-(1-(5-(3-cyano-6-ethoxypyrazolo[1,5-a]pyridin-4-yl)pyridin-2-yl)-4-(pyridin-2-ylmethyl)piperidin-4-yl)-2-(dimethylamino)acetamide | 539.3 (M + H) |

TABLE PPP-continued

| Ex # | Structure | Chemical Name | MS (apci) m/z |
|---|---|---|---|
| 620 | 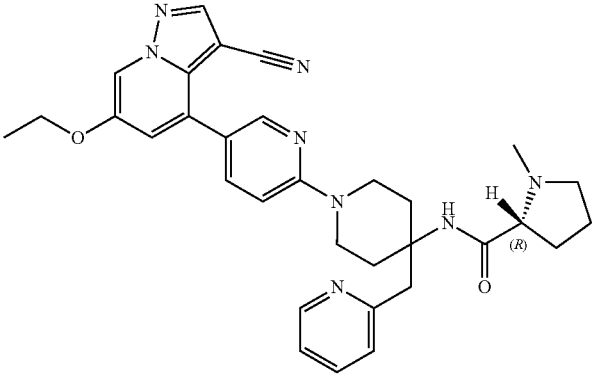 | (R)-N-(1-(5-(3-cyano-6-ethoxypyrazolo[1,5-a]pyridin-4-yl)pyridin-2-yl)-4-(pyridin-2-ylmethyl)piperidin-4-yl)-1-methylpyrrolidine-2-carboxamide | 565.3 (M + H) |
| 621 | 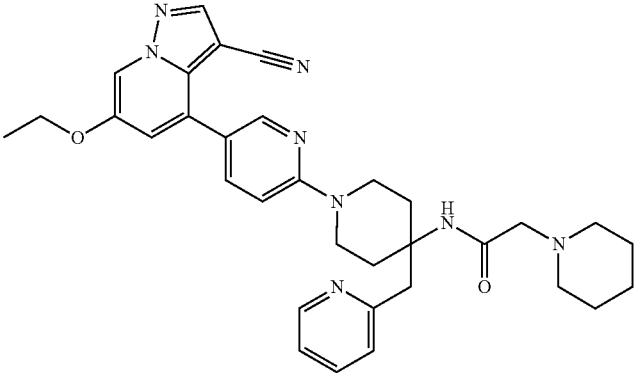 [SMILES: CCOc1cc(-c2ccc(N3CCC(Cc4ccccn4)(NC(=O)CN4CCCCC4)CC3)nc2)c2c(C#N)cnn2c1] | N-(1-(5-(3-cyano-6-ethoxypyrazolo[1,5-a]pyridin-4-yl)pyridin-2-yl)-4-(pyridin-2-ylmethyl)piperidin-4-yl)-2-(piperidin-1-yl)acetamide | 579.4 (M + H) |
| 622 | 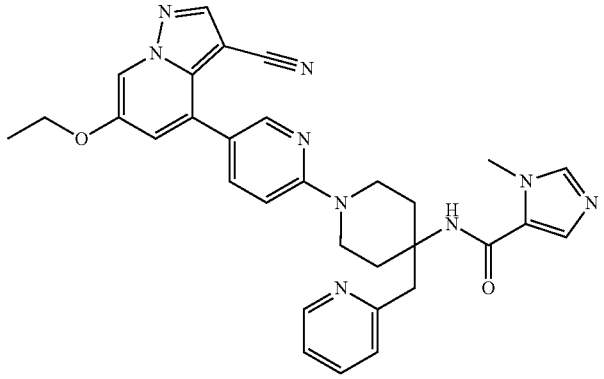 [SMILES: CCOc1cc(-c2ccc(N3CCC(Cc4ccccn4)(NC(=O)c4cncn4C)CC3)nc2)c2c(C#N)cnn2c1] | N-(1-(5-(3-cyano-6-ethoxypyrazolo[1,5-a]pyridin-4-yl)pyridin-2-yl)-4-(pyridin-2-ylmethyl)piperidin-4-yl)-1-methyl-1H-imidazole-5-carboxamide | 562.3 (M + H) |
| 623 | 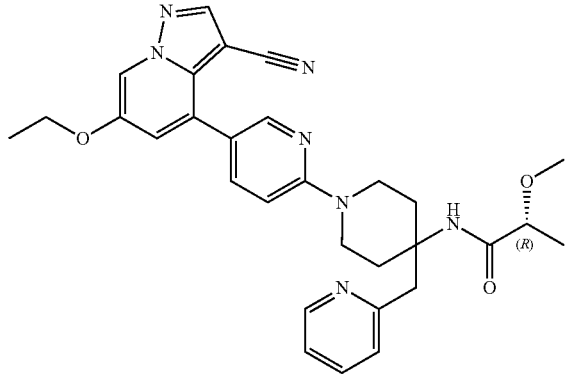 | (R)-N-(1-(5-(3-cyano-6-ethoxypyrazolo[1,5-a]pyridin-4-yl)pyridin-2-yl)-4-(pyridin-2-ylmethyl)piperidin-4-yl)-2-methoxypropanamide | 540.2 (M + H) |

TABLE PPP-continued

| Ex # | Structure | Chemical Name | MS (apci) m/z |
|---|---|---|---|
| 624 | 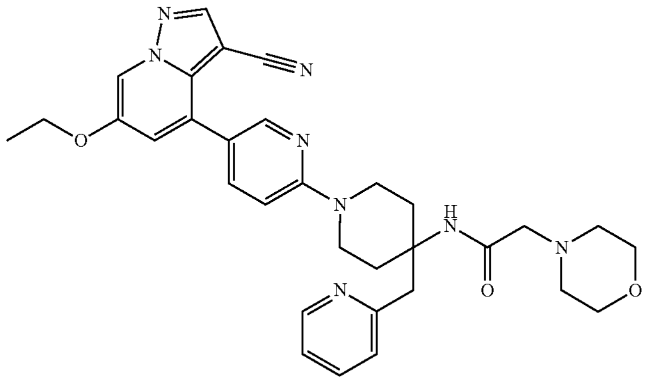 [SMILES: CCOc1cc(-c2ccc(N3CCC(Cc4ccccn4)(NC(=O)CN4CCOCC4)CC3)nc2)c2c(C#N)cnn2c1] | N-(1-(5-(3-cyano-6-ethoxypyrazolo[1,5-a]pyridin-4-yl)pyridin-2-yl)-4-(pyridin-2-ylmethyl)piperidin-4-yl)-2-morpholinoacetamide | 581.3 (M + H) |

Example 625

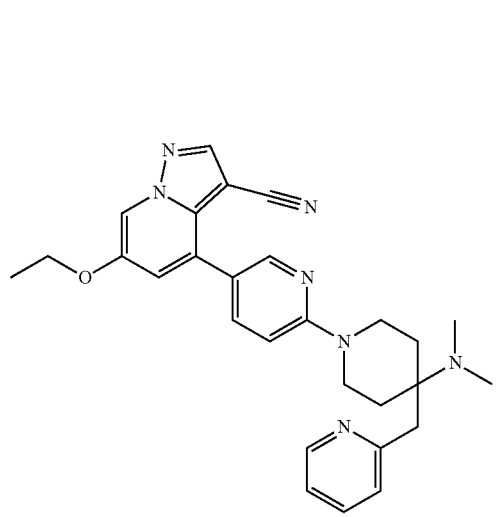 [SMILES: CCOc1cc(-c2ccc(N3CCC(Cc4ccccn4)(N(C)C)CC3)nc2)c2c(C#N)cnn2c1]

4-(6-(4-(dimethylamino)-4-(pyridin-2-ylmethyl)piperidin-1-yl)pyridin-3-yl)-6-ethoxypyrazolo[1,5-a]pyridine-3-carbonitrile A solution of N,N-dimethyl-4-(pyridin-2-ylmethyl)piperidin-4-amine bis(2,2,2-trifluoroacetate) (Intermediate R29; 71 mg, 0.16 mmol), 6-ethoxy-4-(6-fluoropyridin-3-yl)pyrazolo[1,5-a]pyridine-3-carbonitrile (Intermediate P6, 30 mg, 0.11 mmol) and $K_2CO_{3(s)}$ (73 mg, 0.53 mmol) in DMSO (1063 µL) was stirred for 1 h at 100° C. After cooling to ambient temperature, the mixture was filtered, and the filtrate was purified directly by C18 reverse phase chromatography (using 5-95% ACN/water with 0.1% TFA as the gradient eluent) to afford the title compound as the TFA salt. The TFA salt was suspended in MeOH (5 mL), eluted through a basic resin (Stratospheres Pl-HCO3) to cleanly afford the title compound (15 mg, 29% yield). MS (apci) m/z=482.3 (M+H).

Example 626

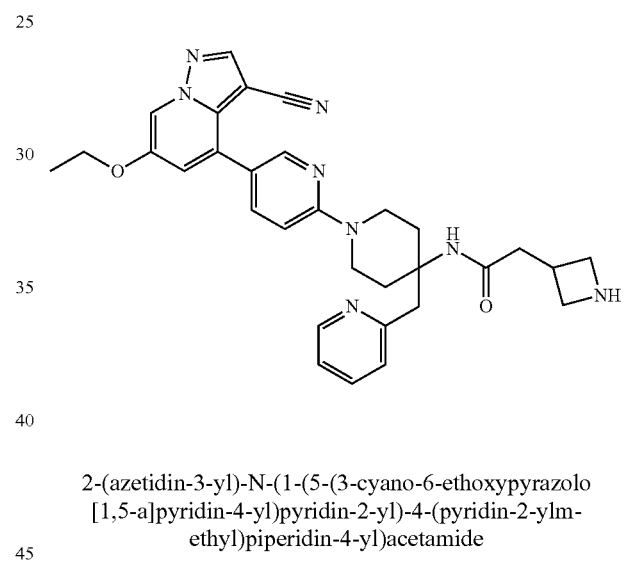

2-(azetidin-3-yl)-N-(1-(5-(3-cyano-6-ethoxypyrazolo[1,5-a]pyridin-4-yl)pyridin-2-yl)-4-(pyridin-2-ylmethyl)piperidin-4-yl)acetamide Step 1: Preparation of tert-butyl 3-(2-((1-(5-(3-cyano-6-ethoxypyrazolo[1,5-a]pyridin-4-yl)pyridin-2-yl)-4-(pyridin-2-ylmethyl)piperidin-4-yl)amino)-2-oxoethyl)azetidine-1-carboxylate A solution of 4-(6-(4-amino-4-(pyridin-2-ylmethyl)piperidin-1-yl)pyridin-3-yl)-6-ethoxypyrazolo[1,5-a]pyridine-3-carbonitrile (Intermediate P106; 41 mg, 0.09 mmol) and 2-(1-(tert-butoxycarbonyl)azetidin-3-yl)acetic acid (21 mg, 0.1 mmol) in DCM (0.5 mL) was treated sequentially with DIEA (32 µL, 0.18 mmol) and HATU (41 mg, 0.11 mmol). The resulting mixture was stirred overnight at ambient temperature then diluted with water and extracted with DCM (3×20 mL). The combined organic extracts were dried over anhydrous $Na_2SO_{4(s)}$, filtered and concentrated in vacuo. The crude residue was purified by silica chromatography (using 0-50% [20% MeOH in DCM] in DCM as the gradient eluent) to cleanly afford the title compound (59 mg, 100% yield). MS (apci) m/z=651 (M+H).

Step 2: Preparation of 2-(azetidin-3-yl)-N-(1-(5-(3-cyano-6-ethoxypyrazolo[1,5-a]pyridin-4-yl)pyridin-2-yl)-4-(pyridin-2-ylmethyl)piperidin-4-yl)acetamide A solution of tert-butyl 3-(2-((1-(5-(3-cyano-6-ethoxypyrazolo[1,5-a]pyridin-4-yl)pyridin-2-yl)-4-(pyridin-2-ylmethyl)piperidin-4-yl)amino)-2-oxoethyl)azetidine-1-carboxylate (59 mg, 0.091 mmol) in DCM (3.00 mL) was treated with TFA (3.00 mL, 39.2 mmol). The resulting mixture was stirred for 1.5 h at ambient temperature. The mixture was diluted with saturated NaHCO$_{3(aq)}$ (3 mL) and extracted with DCM (3×5 mL). The combined organic extracts were concentrated in vacuo. The residue was purified by silica chromatography (using 0-50% [20% MeOH/DCM] in DCM followed by 0-50% MeOH in (20% MeOH/DCM) as the gradient eluent) to cleanly afford the title compound (10 mg, 20% yield). MS (apci) m/z=551.2 (M+H).

Example 627

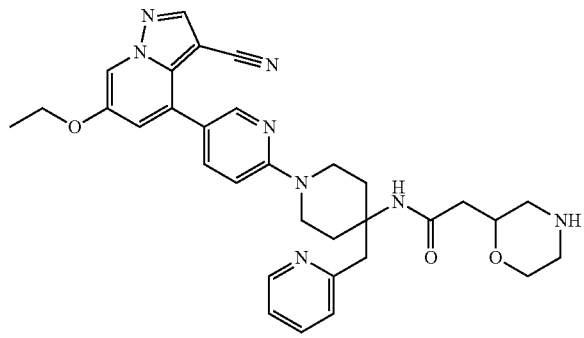 [SMILES: CCOc1cc(-c2ccc(N3CCC(Cc4ccccn4)(NC(=O)CC4CNCCO4)CC3)nc2)c2c(C#N)cnn2c1]

N-(1-(5-(3-cyano-6-ethoxypyrazolo[1,5-a]pyridin-4-yl)pyridin-2-yl)-4-(pyridin-2-ylmethyl)piperidin-4-yl)-2-(morpholin-2-yl)acetamide Step 1: Preparation of tert-butyl 2-(2-((1-(5-(3-cyano-6-ethoxypyrazolo[1,5-a]pyridin-4-yl)pyridin-2-yl)-4-(pyridin-2-ylmethyl)piperidin-4-yl)amino)-2-oxoethyl)morpholine-4-carboxylate A solution of 4-(6-(4-amino-4-(pyridin-2-ylmethyl)piperidin-1-yl)pyridin-3-yl)-6-ethoxypyrazolo[1,5-a]pyridine-3-carbonitrile (Intermediate P106; 32 mg, 0.07 mmol) and 2-(4-(tert-butoxycarbonyl)morpholin-2-yl)acetic acid (19 mg, 0.08 mmol) in DCM (0.35 mL) was treated sequentially with DIEA (25 μL, 0.14 mmol) and HATU (32 mg, 0.085 mmol). The resulting mixture was stirred overnight at ambient temperature, then diluted with water and extracted with DCM (3×15 mL). The combined organic extracts were dried over anhydrous Na$_2$SO$_{4(s)}$, filtered and concentrated in vacuo. The crude residue was purified by silica chromatography (using 0-50% [20% MeOH in DCM] in DCM as the gradient eluent) to cleanly afford the title compound (48 mg, 100% yield). MS (apci) m/z=681 (M+H).

Step 2: Preparation of N-(1-(5-(3-cyano-6-ethoxypyrazolo[1,5-a]pyridin-4-yl)pyridin-2-yl)-4-(pyridin-2-ylmethyl)piperidin-4-yl)-2-(morpholin-2-yl)acetamide A solution of tert-butyl 2-(2-((1-(5-(3-cyano-6-ethoxypyrazolo[1,5-a]pyridin-4-yl)pyridin-2-yl)-4-(pyridin-2-ylmethyl)piperidin-4-yl)amino)-2-oxoethyl)morpholine-4-carboxylate (Step 1; 48 mg, 0.071 mmol) in DCM (300 μL) was treated with TFA (300 μL, 3.92 mmol). The resulting mixture was stirred for 80 min at ambient temperature. The resulting mixture was diluted with saturated NaHCO$_{3(aq)}$, and extracted with DCM (3×10 mL). The combined organic extracts were dried over anhydrous Na$_2$SO$_{4(s)}$, filtered and concentrated in vacuo. The crude residue was purified by silica chromatography (using 0-50% MeOH in [20% MeOH/DCM] as the gradient eluent) to cleanly afford the title compound (8 mg, 20% yield). MS (apci) m/z=581.25 (M+H).

Example 628

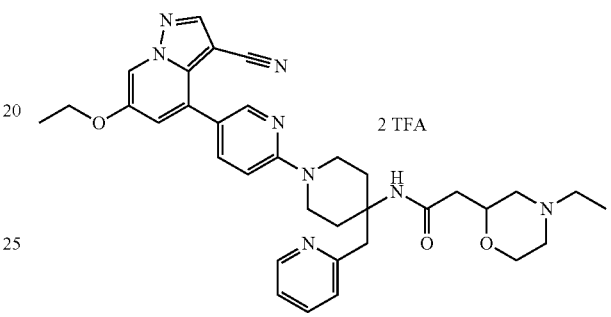

N-(1-(5-(3-cyano-6-ethoxypyrazolo[1,5-a]pyridin-4-yl)pyridin-2-yl)-4-(pyridin-2-ylmethyl)piperidin-4-yl)-2-(4-ethylmorpholin-2-yl)acetamide bis(2,2,2-trifluoroacetate)

A solution of N-(1-(5-(3-cyano-6-ethoxypyrazolo[1,5-a]pyridin-4-yl)pyridin-2-yl)-4-(pyridin-2-ylmethyl)piperidin-4-yl)-2-(morpholin-2-yl)acetamide (Example 627; 6 mg, 0.01 mmol) in DCM (100 μL) was treated sequentially with acetaldehyde (2 μL, 0.03 mmol) and NaBH(AcO)$_3$ (11 mg, 0.052 mmol), and stirred for 2 d and 19 h at room temperature. The resulting mixture was diluted with water (10 mL) and extracted with DCM (3×10 mL). The combined organic extracts were dried over anhydrous Na$_2$SO$_{4(s)}$, filtered and concentrated in vacuo. The crude residue was purified by C18 reverse phase chromatography (5-95% ACN:water with 0.1% TFA) to afford the title compound (0.831 mg, 13% yield). MS (apci) m/z=609.3 (M+H).

Example 629

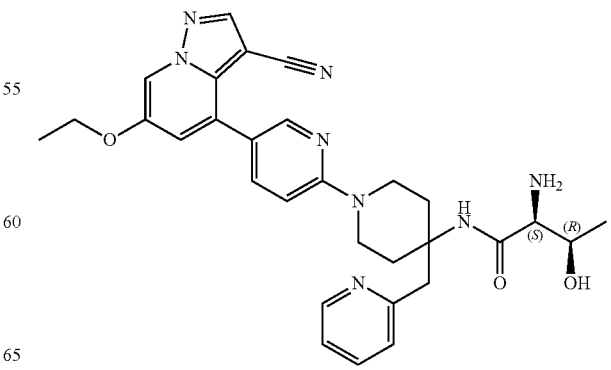

(2S,3R)-2-amino-N-(1-(5-(3-cyano-6-ethoxypyra-
zolo[1,5-a]pyridin-4-yl)pyridin-2-yl)-4-(pyridin-2-
ylmethyl)piperidin-4-yl)-3-hydroxybutanamide Step 1: Preparation of (9H-fluoren-9-yl)methyl
((2S,3R)-1-((1-(5-(3-cyano-6-ethoxypyrazolo[1,5-a]
pyridin-4-yl)pyridin-2-yl)-4-(pyridin-2-ylmethyl)
piperidin-4-yl)amino)-3-hydroxy-1-oxobutan-2-yl)
carbamate A solution of 4-(6-(4-amino-4-(pyridin-2-ylmethyl)pip-
eridin-1-yl)pyridin-3-yl)-6-ethoxypyrazolo[1,5-a]pyridine-
3-carbonitrile (Intermediate P106; 7.8 mg, 0.0172 mmol) in
DCM (0.35 mL) was treated sequentially with HATU (7.85
mg, 0.0206 mmol), DIEA (3.00 µL, 0.0172 mmol) and
(((9H-fluoren-9-yl)methoxy)carbonyl)-L-threonine (5.87
mg, 0.0172 mmol). The resulting mixture was stirred for 3
d at ambient temperature, then concentrated in vacuo to
afford crude title compound (0.0172 mmol; assumed quan-
titative yield) which was carried directly into step 2. MS
(apci) m/z=777.3 (M+H).

Step 2: Preparation of (2S,3R)-2-amino-N-(1-(5-(3-
cyano-6-ethoxypyrazolo[1,5-a]pyridin-4-yl)pyridin-
2-yl)-4-(pyridin-2-ylmethyl)piperidin-4-yl)-3-hy-
droxybutanamide A solution of (9H-fluoren-9-yl)methyl ((2S,3R)-1-((1-(5-
(3-cyano-6-ethoxypyrazolo[1,5-a]pyridin-4-yl)pyridin-2-
yl)-4-(pyridin-2-ylmethyl)piperidin-4-yl)amino)-3-hy-
droxy-1-oxobutan-2-yl)carbamate (0.0172 mmol) in 1:1 v/v
morpholine DCM (1 mL) was stirred for 3 h at ambient
temperature, then concentrated and purified by reverse-
phase chromatography (5 to 95% acetonitrile/water with
0.2% TFA) to yield the title product after freebasing with
HCO₃ Stratosphere resin (5 mg, 52% yield). MS (apci)
m/z=555.7 (M+H).

Example 630

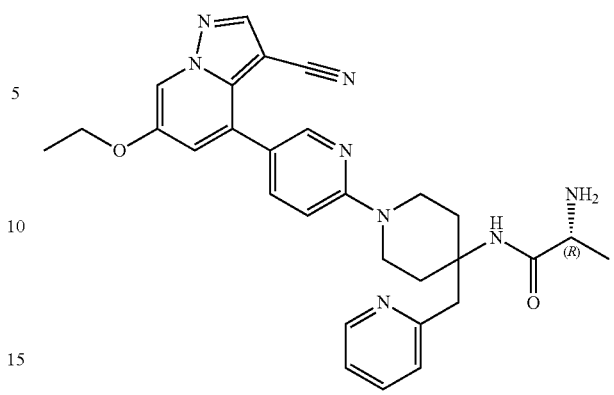

(R)-2-amino-N-(1-(5-(3-cyano-6-ethoxypyrazolo[1,
5-a]pyridin-4-yl)pyridin-2-yl)-4-(pyridin-2-ylm-
ethyl)piperidin-4-yl)propanamide A solution of (9H-fluoren-9-yl)methyl (R)-(1-oxo-1-((4-
(pyridin-2-ylmethyl)piperidin-4-yl)amino)propan-2-yl)car-
bamate bis(2,2,2-trifluoroacetate) (Intermediate R39; 130
mg, 0.182 mmol) in DMF (0.3 mL) was treated with
Cs₂CO₃(s) (270 mg, 0.829 mmol) and 6-ethoxy-4-(6-fluoro-
pyridin-3-yl)pyrazolo[1,5-a]pyridine-3-carbonitrile (Inter-
mediate P6, 46.8 mg, 0.166 mmol). The resulting mixture
was stirred overnight at 90° C. After cooling to ambient
temperature, the mixture was purified directly by C18
reverse phase chromatography (using 5-95% ACN/water
with 0.1% TFA as the gradient eluent) to afford the title
compound as the TFA salt. The TFA salt was suspended in
MeOH (5 mL), eluted through a basic resin (Stratospheres
Pl-HCO3) to cleanly afford the title compound (30.2 mg,
35% yield). MS (apci) m/z=525.2 (M+H).

The compounds in Table QQQ were prepared, worked up,
purified and free based using a similar method to that
described in the synthesis of (R)-2-amino-N-(1-(5-(3-cyano-
6-ethoxypyrazolo[1,5-a]pyridin-4-yl)pyridin-2-yl)-4-(pyri-
din-2-ylmethyl)piperidin-4-yl)propanamide (Example 630),
replacing (9H-fluoren-9-yl)methyl (R)-(1-oxo-1-((4-(pyri-
din-2-ylmethyl)piperidin-4-yl)amino)propan-2-yl)carbam-
ate bis(2,2,2-trifluoroacetate) (Intermediate R39) with the
appropriate amine (1.0-1.5 equivalents). Reactions were
monitored for completion by LCMS, and reaction durations
were adjusted accordingly.

TABLE QQQ

| Ex # | Structure | Chemical Name | MS (apci) m/z |
|---|---|---|---|
| 631 | 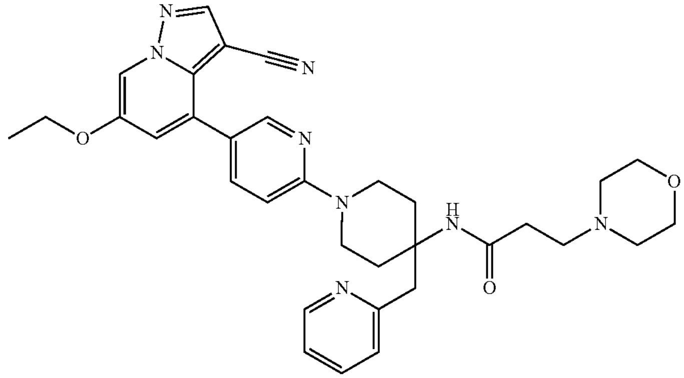 [SMILES: CCOc1cc(-c2ccc(N3CCC(Cc4ccccn4)(NC(=O)CCN4CCOCC4)CC3)nc2)c2c(C#N)cnn2c1] | N-(1-(5-(3-cyano-6-ethoxypyrazolo[1,5-a]pyridin-4-yl)pyridin-2-yl)-4-(pyridin-2-ylmethyl)piperidin-4-yl)-3-morpholinopropanamide | 595.3 (M + H) |

TABLE QQQ-continued

| Ex # | Structure | Chemical Name | MS (apci) m/z |
|---|---|---|---|
| 632 | 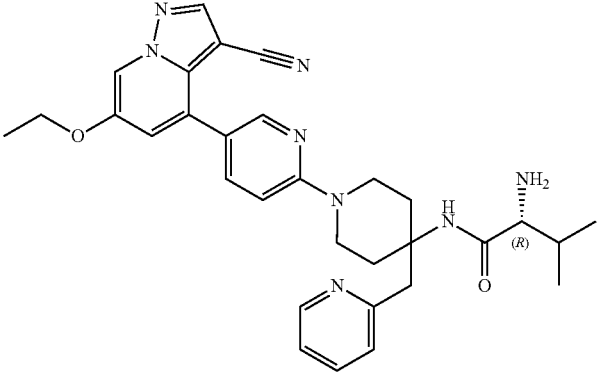 | (R)-2-amino-N-(1-(5-(3-cyano-6-ethoxypyrazolo[1,5-a]pyridin-4-yl)pyridin-2-yl)-4-(pyridin-2-ylmethyl)piperidin-4-yl)-3-methylbutanamide | 553.3 (M + H) |
| 633 | 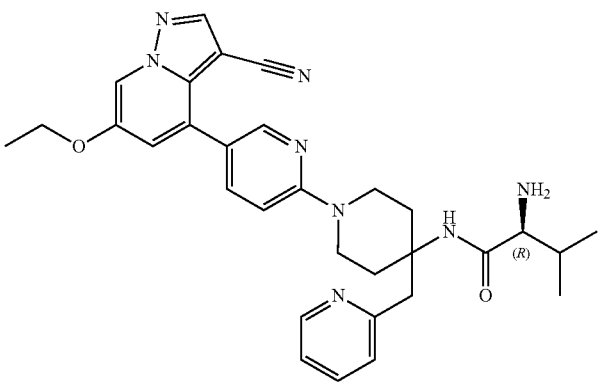 | (S)-2-amino-N-(1-(5-(3-cyano-6-ethoxypyrazolo[1,5-a]pyridin-4-yl)pyridin-2-yl)-4-(pyridin-2-ylmethyl)piperidin-4-yl)-3-methylbutanamide | 553.3 (M + H) |

Example 634

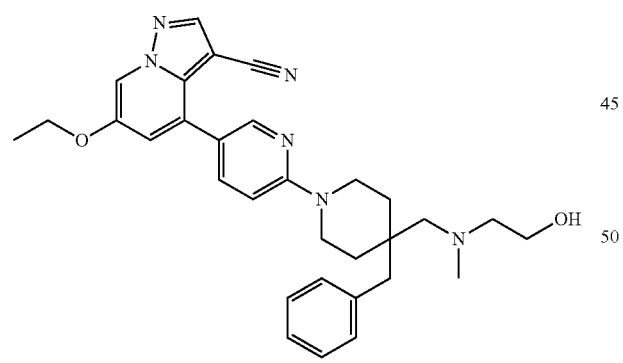

4-(6-(4-benzyl-4-(((2-hydroxyethyl)(methyl)amino)methyl)piperidin-1-yl)pyridin-3-yl)-6-ethoxypyrazolo[1,5-a]pyridine-3-carbonitrile A solution of 4-(6-(4-benzyl-4-formylpiperidin-1-yl)pyridin-3-yl)-6-ethoxypyrazolo[1,5-a]pyridine-3-carbonitrile (Intermediate P77, 10 mg, 0.0215 mmol) and 2-(methylamino)ethan-1-ol (13.0 mg, 0.173 mmol) in DCE (750 µL) was stirred for 1 h at ambient temperature, then treated with NaBH(AcO)₃ (105.9 mg, 0.4997 mmol). The resulting mixture was stirred for 4 d at ambient temperature, before introducing additional 2-(methylamino)ethan-1-ol (13.0 mg, 0.173 mmol) and NaBH(AcO)₃ (105.9 mg, 0.4997 mmol). The resulting mixture was stirred overnight at ambient temperature before diluting with DCM, and extracting with water (3×). The combined organic extracts were dried over anhydrous Na₂SO₄₍ₛ₎, and filtered. The filtrate was purified directly by silica chromatography (using 0-100% Hexanes/EtOAc as the gradient eluent) to afford the title compound (1.8 mg, 16% yield). MS (apci) m/z=525.25 (M+H).

Example 635

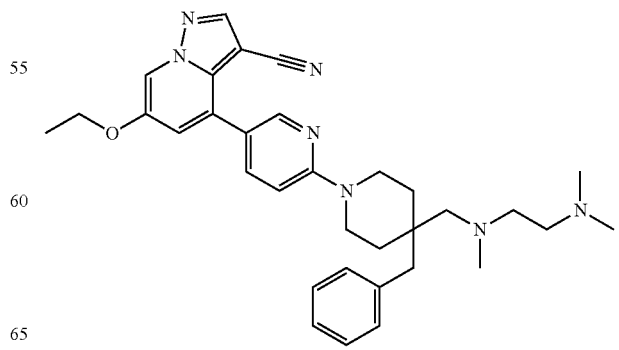

4-(6-(4-benzyl-4-(((2-(dimethylamino)ethyl)(methyl) amino)methyl)piperidin-1-yl)pyridin-3-yl)-6-ethoxy-pyrazolo[1,5-a]pyridine-3-carbonitrile A solution of 4-(6-(4-benzyl-4-formylpiperidin-1-yl)pyridin-3-yl)-6-ethoxypyrazolo[1,5-a]pyridine-3-carbonitrile (Intermediate P77, 10.5 mg, 0.0226 mmol) and $N^1,N^1,N^2$-trimethylethane-1,2-diamine (24.1 mg, 0.236 mmol) in DCE (750 μL) was stirred for 1 h at ambient temperature then treated with NaBH(AcO)$_3$ (75 mg, 0.354 mmol). The resulting mixture was stirred overnight at ambient temperature. The resulting mixture was diluted with water, and extracted with DCM. The combined organic extracts were dried over anhydrous Na$_2$SO$_{4(s)}$, and filtered. The filtrate was purified directly by silica chromatography (using 0-50% DCM/MeOH as the gradient eluent) to afford the title compound (6.0 mg, 48% yield). MS (apci) m/z=552.3 (M+H).

Example 636

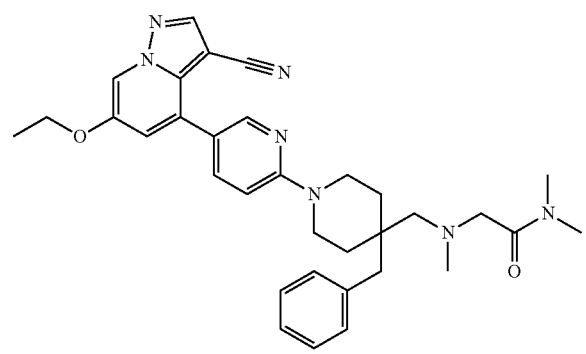 [SMILES: CCOc1cc(-c2ccc(N3CCC(Cc4ccccc4)(CN(C)CC(=O)N(C)C)CC3)nc2)c2c(C#N)cnn2c1]

2-(((4-benzyl-1-(5-(3-cyano-6-ethoxypyrazolo[1,5-a]pyridin-4-yl)pyridin-2-yl)piperidin-4-yl)methyl) (methyl)amino)-N,N-dimethylacetamide A solution of 4-(6-(4-benzyl-4-formylpiperidin-1-yl)pyridin-3-yl)-6-ethoxypyrazolo[1,5-a]pyridine-3-carbonitrile (Intermediate P77, 11.4 mg, 0.0245 mmol) and N,N-dimethyl-2-(methylamino)acetamide (28.4 mg, 0.245 mmol) in DCE (750 μL) was stirred for 2 h at ambient temperature then treated with NaBH(AcO)$_3$ (104 mg, 0.490 mmol). The resulting mixture was stirred overnight at ambient temperature. The resulting mixture was diluted with water, and extracted with DCM. The combined organic extracts were dried over anhydrous Na$_2$SO$_{4(s)}$, and filtered. The filtrate was purified directly by silica chromatography (using 0-100% Hexanes/EtOAc as the gradient eluent) to afford the title compound (2.3 mg, 17% yield). MS (apci) m/z=566.25 (M+H).

Example 637

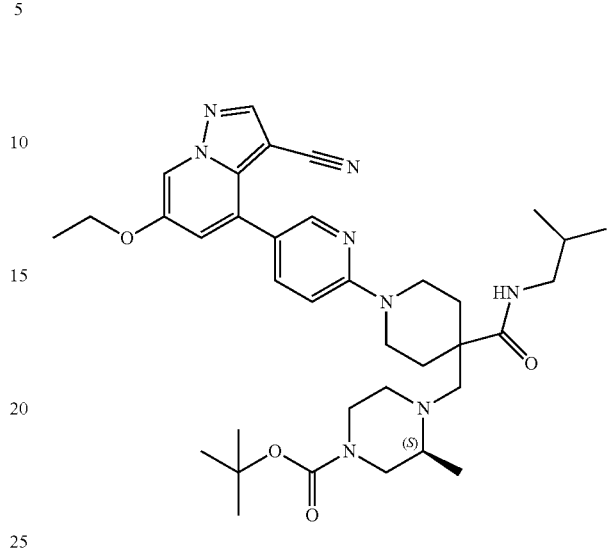

tert-butyl (S)-4-((1-(5-(3-cyano-6-ethoxypyrazolo[1, 5-a]pyridin-4-yl)pyridin-2-yl)-4-(isobutylcarbamoyl) piperidin-4-yl)methyl)-3-methylpiperazine-1-carboxylate A solution of 1-(5-(3-cyano-6-ethoxypyrazolo[1,5-a]pyridin-4-yl)pyridin-2-yl)-4-formyl-N-isobutylpiperidine-4-carboxamide (Intermediate P76, 45.6 mg, 0.0961 mmol) and tert-butyl (S)-3-methylpiperazine-1-carboxylate (96.22 mg, 0.4804 mmol) in DCE (1 mL) was stirred for 30 min at ambient temperature before adding NaBH(AcO)$_3$ (122.2 mg, 0.5765 mmol). The resulting mixture was stirred for 5 d at ambient temperature, then diluted with DCM, and washed with water. The organic extracts were purified directly by silica chromatography (using 20-80% Hexanes/EtOAc as the gradient eluent) to cleanly provide the title compound (37.9 mg, 57% yield). MS (apci) m/z=659.3 (M+H).

The compounds in Table RRR were prepared using a similar method to that described in the synthesis of tert-butyl (S)-4-((1-(5-(3-cyano-6-ethoxypyrazolo[1,5-a]pyridin-4-yl)pyridin-2-yl)-4-(isobutylcarbamoyl)piperidin-4-yl)methyl)-3-methylpiperazine-1-carboxylate (Example 637), replacing 1 tert-butyl (S)-3-methylpiperazine-1-carboxylate with the appropriate amine and using 4-6 equivalents of NaBH(AcO)$_3$. Reactions were monitored for completion by LCMS, as such reaction durations, both prior to and after NaBH(AcO)$_3$ addition, were adjusted accordingly. Title compounds were isolated following a similar aqueous work up with water or brine, followed by a chromatographic purification using an appropriate gradient eluent.

TABLE RRR

| Ex # | Structure | Chemical Name | MS (apci) m/z |
|---|---|---|---|
| 638 | 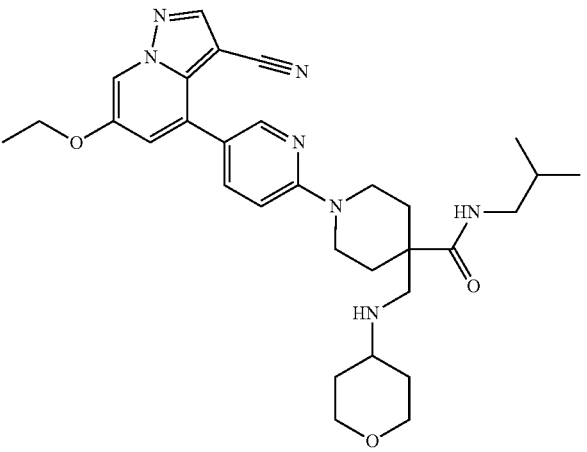 [SMILES: CCOc1cc(-c2ccc(N3CCC(CNC4CCOCC4)(C(=O)NCC(C)C)CC3)nc2)c2c(C#N)cnn2c1] | 1-(5-(3-cyano-6-ethoxypyrazolo[1,5-a]pyridin-4-yl)pyridin-2-yl)-N-isobutyl-4-(((tetrahydro-2H-pyran-4-yl)amino)methyl)piperidine-4-carboxamide | 560.3 (M + H) |
| 639 | 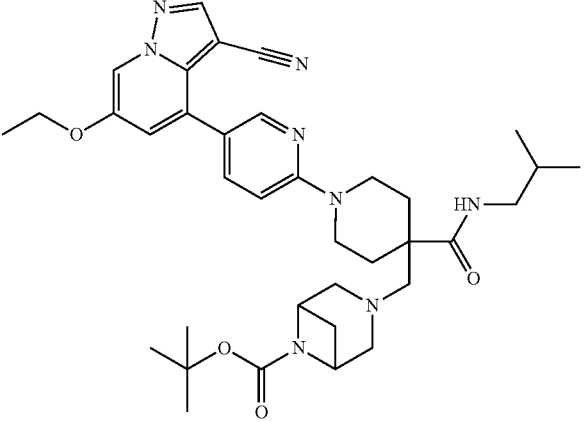 [SMILES: CCOc1cc(-c2ccc(N3CCC(CN4CC5CC(C4)N5C(=O)OC(C)(C)C)(C(=O)NCC(C)C)CC3)nc2)c2c(C#N)cnn2c1] | tert-butyl 3-((1-(5-(3-cyano-6-ethoxypyrazolo[1,5-a]pyridin-4-yl)pyridin-2-yl)-4-(isobutylcarbamoyl)piperidin-4-yl)methyl)-3,6-diazabicyclo[3.1.1]heptane-6-carboxylate | 657.3 (M + H) |
| 640 | 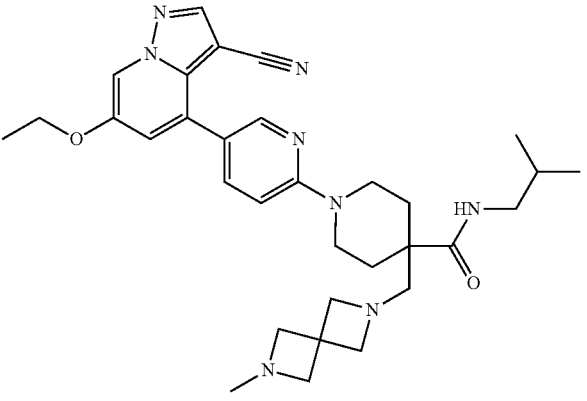 [SMILES: CCOc1cc(-c2ccc(N3CCC(CN4CC5(CN(C)C5)C4)(C(=O)NCC(C)C)CC3)nc2)c2c(C#N)cnn2c1] | 1-(5-(3-cyano-6-ethoxypyrazolo[1,5-a]pyridin-4-yl)pyridin-2-yl)-N-isobutyl-4-((6-methyl-2,6-diazaspiro[3.3]heptan-2-yl)methyl)piperidine-4-carboxamide | 571.3 (M + H) |

Example 641

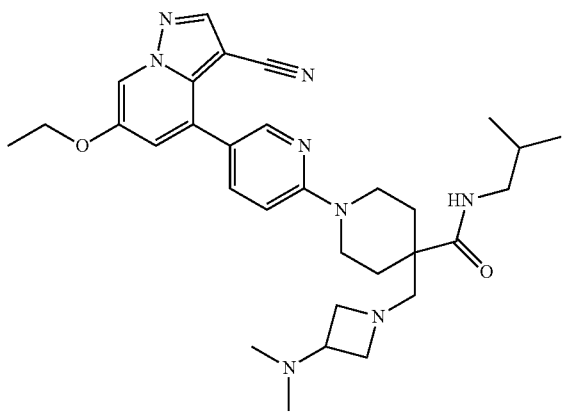 [SMILES: CCOc1cc(-c2ccc(N3CCC(CN4CC(N(C)C)C4)(C(=O)NCC(C)C)CC3)nc2)c2c(C#N)cnn2c1]

1-(5-(3-cyano-6-ethoxypyrazolo[1,5-a]pyridin-4-yl)pyridin-2-yl)-4-((3-(dimethylamino)azetidin-1-yl)methyl)-N-isobutylpiperidine-4-carboxamide A solution of 1-(5-(3-cyano-6-ethoxypyrazolo[1,5-a]pyridin-4-yl)pyridin-2-yl)-4-formyl-N-isobutylpiperidine-4-carboxamide (Intermediate P76, 40 mg, 0.084 mmol) and N,N-dimethylazetidin-3-amine hydrochloride (42 mg, 0.42 mmol) in DCM (169 μL) was stirred for 30 min at ambient temperature. The resulting mixture was treated with NaBH(AcO)$_3$ (89 mg, 0.42 mmol), and stirred overnight at ambient temperature. The reaction mixture was concentrated in vacuo. The crude residue was purified directly by C18 reverse phase chromatography (using 5-95% water:ACN with 0.1% TFA as the gradient eluent). Fractions containing the desired product were diluted with 4:1 DCM:iPrOH, and extracted sequentially with saturated NaHCO$_{3(aq)}$ (1×), and brine (2×). The organic extracts were dried over anhydrous Na$_2$SO$_{4(s)}$, filtered, and concentrated in vacuo to afford the title compound (23 mg, 49% yield). MS (apci) m/z=559.4 (M+H).

The compounds in Table SSS were prepared using a similar method to that described in the synthesis of 1-(5-(3-cyano-6-ethoxypyrazolo[1,5-a]pyridin-4-yl)pyridin-2-yl)-4-((3-(dimethylamino)azetidin-1-yl)methyl)-N-isobutylpiperidine-4-carboxamide (Example 641), replacing N,N-dimethylazetidin-3-amine hydrochloride with 2-5 equivalents of the appropriate amine and 5-6 equivalents of NaBH(AcO)$_3$. Reactions were monitored for completion by LCMS, as such reaction durations, both prior to and after the NaBH(AcO)$_3$ addition, were adjusted accordingly. Title compounds were isolated following a chromatographic purification using an appropriate gradient eluent. For examples in which an acid modifier (e.g. 0.1% TFA) was employed in the chromatographic purification conditions, a basic work up (e.g. an aqueous work up as described for Example 641; or use of a basic resin) was used to isolate the title compound.

TABLE SSS

| Ex # | Structure | Chemical Name | MS (apci) m/z |
|---|---|---|---|
| 642 | 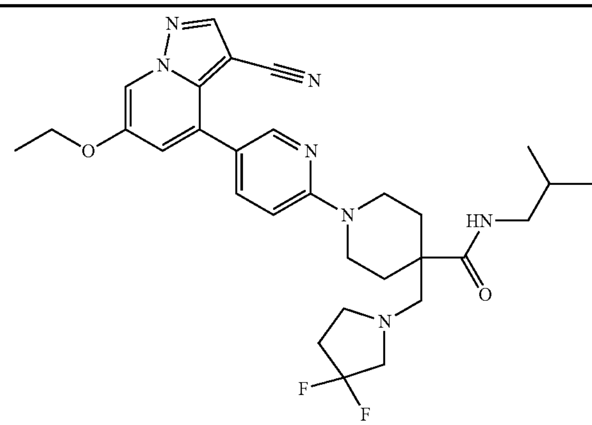 | 1-(5-(3-cyano-6-ethoxypyrazolo[1,5-a]pyridin-4-yl)pyridin-2-yl)-4-((3,3-difluoropyrrolidin-1-yl)methyl)-N-isobutylpiperidine-4-carboxamide | 566.3 (M + H) |
| 643 | 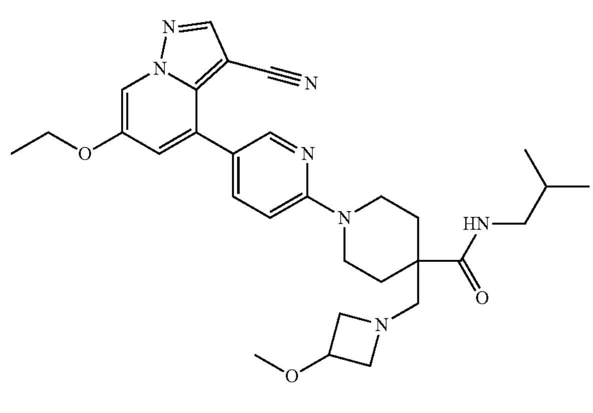 [SMILES: CCOc1cc(-c2ccc(N3CCC(CN4CC(OC)C4)(C(=O)NCC(C)C)CC3)nc2)c2c(C#N)cnn2c1] | 1-(5-(3-cyano-6-ethoxypyrazolo[1,5-a]pyridin-4-yl)pyridin-2-yl)-N-isobutyl-4-((3-methoxyazetidin-1-yl)methyl)piperidine-4-carboxamide | 546.3 (M + H) |

TABLE SSS-continued

| Ex # | Structure | Chemical Name | MS (apci) m/z |
|---|---|---|---|
| 644 | 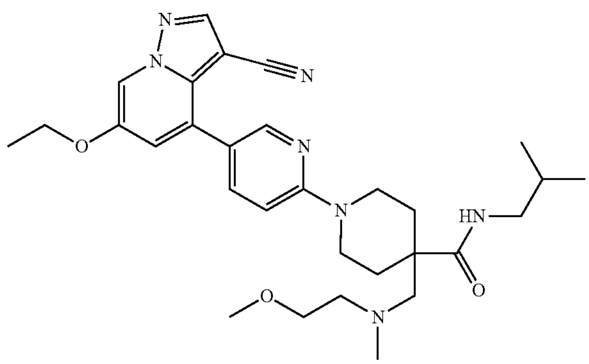 [SMILES: CCOc1cc(-c2ccc(N3CCC(CN(C)CCOC)(C(=O)NCC(C)C)CC3)nc2)c2c(C#N)cnn2c1] | 1-(5-(3-cyano-6-ethoxypyrazolo[1,5-a]pyridin-4-yl)pyridin-2-yl)-N-isobutyl-4-(((2-methoxyethyl)(methyl)amino)methyl)piperidine-4-carboxamide | 548.4 (M + H) |
| 645 | 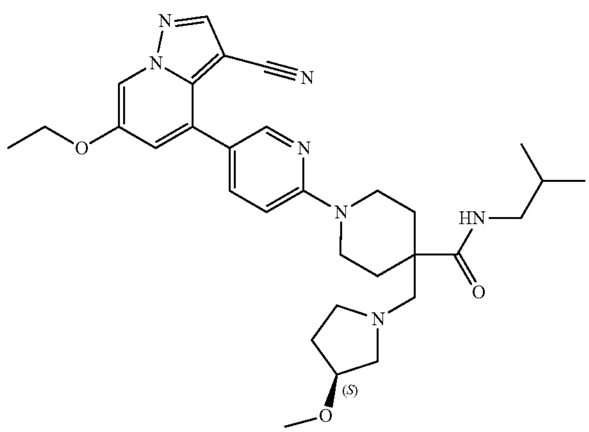 | (S)-1-(5-(3-cyano-6-ethoxypyrazolo[1,5-a]pyridin-4-yl)pyridin-2-yl)-N-isobutyl-4-((3-methoxypyrrolidin-1-yl)methyl)piperidine-4-carboxamide | 560.4 (M + H) |
| 646 | 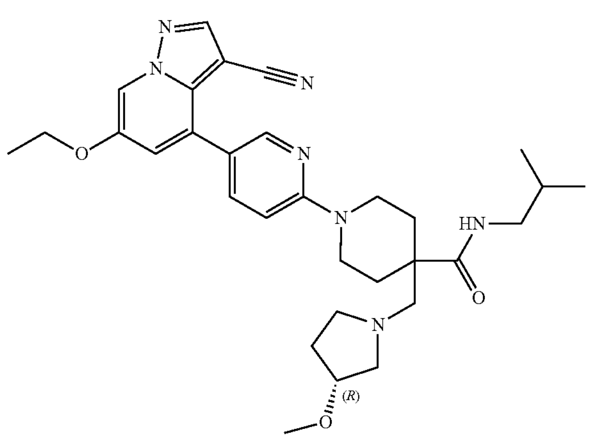 | (R)-1-(5-(3-cyano-6-ethoxypyrazolo[1,5-a]pyridin-4-yl)pyridin-2-yl)-N-isobutyl-4-((3-methoxypyrrolidin-1-yl)methyl)piperidine-4-carboxamide | 560.4 (M + H) |

TABLE SSS-continued

| Ex # | Structure | Chemical Name | MS (apci) m/z |
|---|---|---|---|
| 647 | 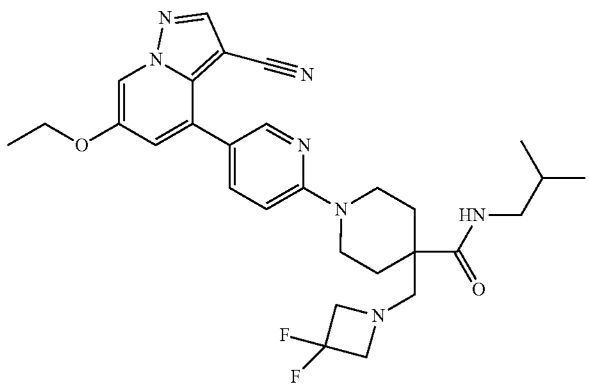 [SMILES: CCOc1cc(-c2ccc(N3CCC(CN4CC(F)(F)C4)(C(=O)NCC(C)C)CC3)nc2)c2c(C#N)cnn2c1] | 1-(5-(3-cyano-6-ethoxypyrazolo[1,5-a]pyridin-4-yl)pyridin-difluoroazetidin-1-yl)methyl)-N-isobutylpiperidine-4-carboxamide | 552.25, M + H |
| 648 | 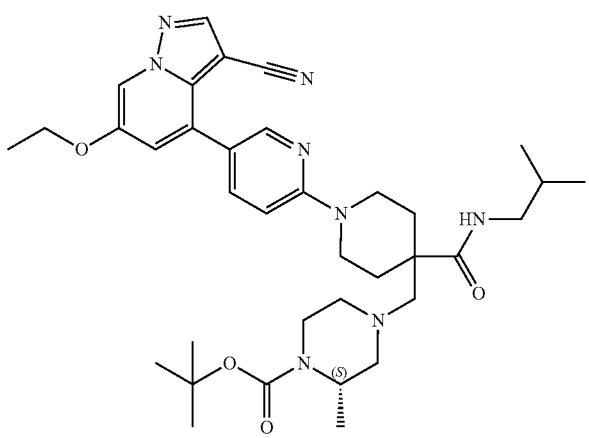 | tert-butyl (S)-4-((1-(5-(3-cyano-6-ethoxypyrazolo[1,5-a]pyridin-4-yl)pyridin-2-yl)-4-(isobutylcarbamoyl)piperidin-4-yl)methyl)-2-methylpiperazine-1-carboxylate | 659.35, M + H |
| 649 | 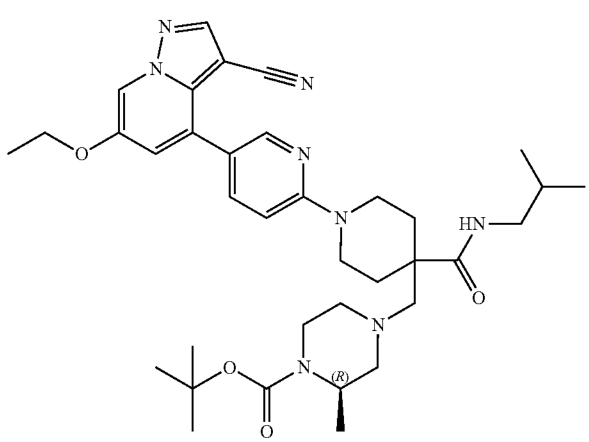 | tert-butyl (R)-4-((1-(5-(3-cyano-6-ethoxypyrazolo[1,5-a]pyridin-4-yl)pyridin-2-yl)-4-(isobutylcarbamoyl)piperidin-4-yl)methyl)-2-methylpiperazine-1-carboxylate | 659.3, M + H |

TABLE SSS-continued

| Ex # | Structure | Chemical Name | MS (apci) m/z |
|---|---|---|---|
| 650 | 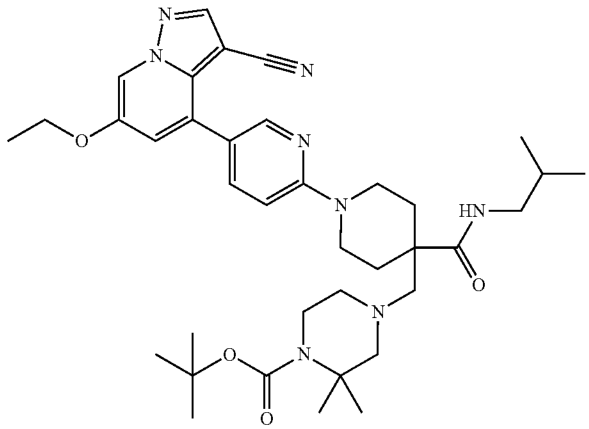 [SMILES: CCOc1cc(-c2ccc(N3CCC(CN4CCN(C(=O)OC(C)(C)C)C(C)(C)C4)(C(=O)NCC(C)C)CC3)nc2)c2c(C#N)cnn2c1] | tert-butyl 4-((1-(5-(3-cyano-6-ethoxypyrazolo[1,5-a]pyridin-4-yl)pyridin-2-yl)-4-(isobutylcarbamoyl)piperidin-4-yl)methyl)-2,2-dimethylpiperazine-1-carboxylate | 673.3, M + H |

Example 651

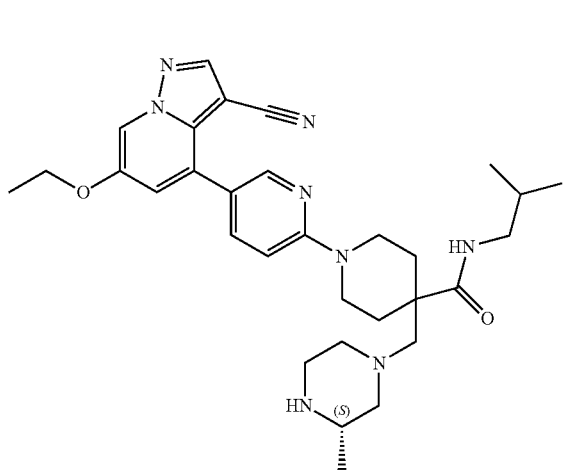

(S)-1-(5-(3-cyano-6-ethoxypyrazolo[1,5-a]pyridin-4-yl)pyridin-2-yl)-N-isobutyl-4-((3-methylpiperazin-1-yl)methyl)piperidine-4-carboxamide A solution of tert-butyl (S)-4-((1-(5-(3-cyano-6-ethoxypyrazolo[1,5-a]pyridin-4-yl)pyridin-2-yl)-4-(isobutylcarbamoyl)piperidin-4-yl)methyl)-2-methylpiperazine-1-carboxylate (Example 648; 27 mg, 0.0410 mmol) in DCM (1.5 mL) was treated with TFA (1.5 mL, 19 mmol). The resulting mixture was stirred at ambient temperature until LCMS indicated complete consumption of starting Boc-protected compound, then concentrated in vacuo. The residue was diluted with EtOAc, and extracted with saturated NaHCO$_{3(aq)}$ (2×). After back extracting the aqueous extracts with EtOAc, the organic extracts were combined, dried over anhydrous Na$_2$SO$_{4(s)}$, filtered, and concentrated in vacuo to cleanly afford the title compound (21.5 mg, 94% yield). MS (apci) m/z=559.3 (M+H).

Example 652

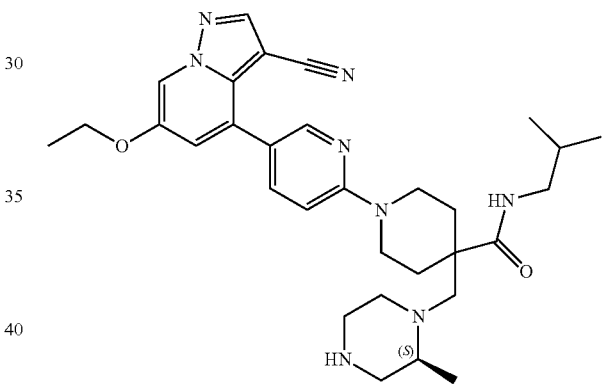

(S)-1-(5-(3-cyano-6-ethoxypyrazolo[1,5-a]pyridin-4-yl)pyridin-2-yl)-N-isobutyl-4-((2-methylpiperazin-1-yl)methyl)piperidine-4-carboxamide A solution of tert-butyl (S)-4-((1-(5-(3-cyano-6-ethoxypyrazolo[1,5-a]pyridin-4-yl)pyridin-2-yl)-4-(isobutylcarbamoyl)piperidin-4-yl)methyl)-3-methylpiperazine-1-carboxylate (Example 637; 35 mg, 0.053 mmol) in DCM (3.0 mL) was treated with TFA (1.5 mL, 19 mmol). The resulting mixture was stirred for 4 d at ambient temperature, then concentrated in vacuo. The residue was diluted with 4:1 DCM/iPrOH, and extracted with saturated NaHCO$_{3(aq)}$. The organic extracts were combined, dried over anhydrous Na$_2$SO$_{4(s)}$, filtered, and concentrated in vacuo. The crude residue was purified by C18 reverse phase chromatography (using 0-70% ACN in water with 0.1% TFA as the gradient eluent). Fractions containing the desired product were diluted with 4:1 DCM:iPrOH, and extracted with saturated NaHCO$_{3(aq)}$. After back extracting the aqueous extracts with 4:1 DCM:iPrOH, the organic extracts were combined, dried over anhydrous Na$_2$SO$_{4(s)}$, filtered, and concentrated in

Example 653

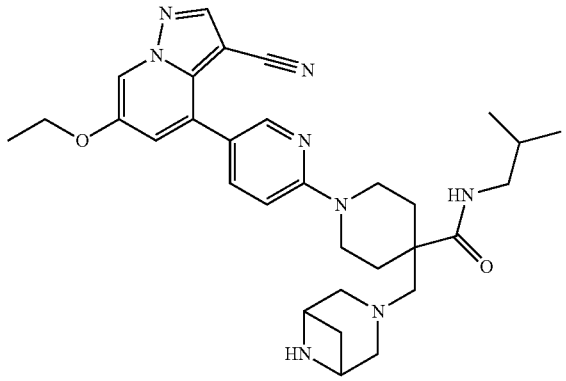 [SMILES: CCOc1cc(-c2ccc(N3CCC(CN4CC5CC(C4)N5)(C(=O)NCC(C)C)CC3)nc2)c2c(C#N)cnn2c1]

4-((3,6-diazabicyclo[3.1.1]heptan-3-yl)methyl)-1-(5-(3-cyano-6-ethoxypyrazolo[1,5-a]pyridin-4-yl)pyridin-2-yl)-N-isobutylpiperidine-4-carboxamide A solution of tert-butyl 3-((1-(5-(3-cyano-6-ethoxypyrazolo[1,5-a]pyridin-4-yl)pyridin-2-yl)-4-(isobutylcarbamoyl)piperidin-4-yl)methyl)-3,6-diazabicyclo[3.1.1]heptane-6-carboxylate (Example 639; 15.7 mg, 0.0239 mmol) in DCM (2 mL) was treated with TFA (1.0 mL, 13 mmol). The resulting mixture was stirred for 30 min at ambient temperature, then concentrated in vacuo. The residue was diluted with 4:1 DCM:iPrOH, and extracted with saturated NaHCO$_{3(aq)}$ (2×). After back extracting the aqueous extracts with 4:1 DCM:iPrOH, the organic extracts were combined, dried over anhydrous Na$_2$SO$_{4(s)}$, filtered, and concentrated in vacuo to cleanly afford the title compound (13.9 mg, 100% yield). MS (apci) m/z=557.3 (M+H).

Example 654

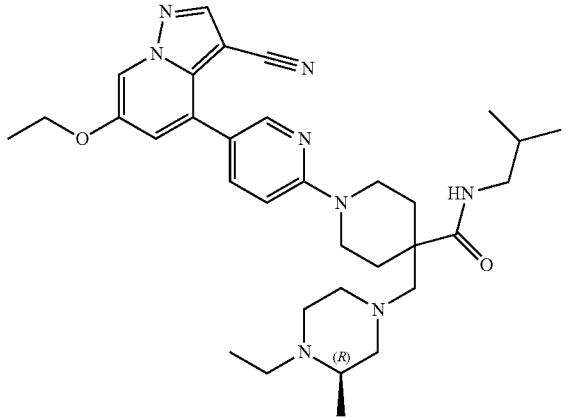

vacuo to afford the title compound to cleanly afford the title compound (3.3 mg, 9% yield). MS (apci) m/z=559.3 (M+H).

(R)-1-(5-(3-cyano-6-ethoxypyrazolo[1,5-a]pyridin-4-yl)pyridin-2-yl)-4-((4-ethyl-3-methylpiperazin-1-yl)methyl)-N-isobutylpiperidine-4-carboxamide Step 1: Preparation of (R)-1-(5-(3-cyano-6-ethoxypyrazolo[1,5-a]pyridin-4-yl)pyridin-2-yl)-N-isobutyl-4-((3-methylpiperazin-1-yl)methyl)piperidine-4-carboxamide bis(2,2,2-trifluoroacetate)

A mixture of tert-butyl (R)-4-((1-(5-(3-cyano-6-ethoxypyrazolo[1,5-a]pyridin-4-yl)pyridin-2-yl)-4-(isobutylcarbamoyl)piperidin-4-yl)methyl)-2-methylpiperazine-1-carboxylate (Example 649; 6.3 mg, 0.0096 mmol) in DCM (0.5 mL) was treated with TFA (0.1 mL, 1.3 mmol). The resulting mixture was stirred for 1 h at ambient temperature before concentrating the mixture in vacuo to afford the title compound (5.3 mg, quantitative yield). MS (apci) m/z=559.3 (M+H).

Step 2: Preparation of (R)-1-(5-(3-cyano-6-ethoxypyrazolo[1,5-a]pyridin-4-yl)pyridin-2-yl)-N-isobutyl-4-((3-methylpiperazin-1-yl)methyl)piperidine-4-carboxamide A solution of (R)-1-(5-(3-cyano-6-ethoxypyrazolo[1,5-a]pyridin-4-yl)pyridin-2-yl)-N-isobutyl-4-((3-methylpiperazin-1-yl)methyl)piperidine-4-carboxamide (5.3 mg, 0.00949 mmol) in DCM (0.61 µL) was treated with acetaldehyde (0.550 µL, 0.0190 mmol) and NaBH(AcO)$_3$ (4.02 mg, 0.0190 mmol), and stirred overnight at room temperature. The resulting mixture was diluted with 4:1 DCM:iPrOH, and extracted with saturated NaHCO$_{3(aq)}$, and filtered through PS frit. The organic filtrate was concentrated in vacuo to cleanly afford the title compound (4.4 mg, 79% yield). MS (apci) m/z=587.3 (M+H).

Example 655

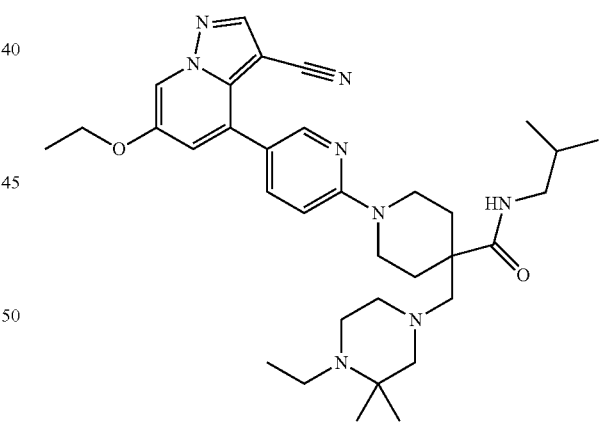

1-(5-(3-cyano-6-ethoxypyrazolo[1,5-a]pyridin-4-yl)pyridin-2-yl)-4-((4-ethyl-3,3-dimethylpiperazin-1-yl)methyl)-N-isobutylpiperidine-4-carboxamide Step 1: Preparation of 1-(5-(3-cyano-6-ethoxypyrazolo[1,5-a]pyridin-4-yl)pyridin-2-yl)-4-((3,3-dimethylpiperazin-1-yl)methyl)-N-isobutylpiperidine-4-carboxamide bis(2,2,2-trifluoroacetate)

A mixture of tert-butyl tert-butyl 4-((1-(5-(3-cyano-6-ethoxypyrazolo[1,5-a]pyridin-4-yl)pyridin-2-yl)-4-(isobutylcarbamoyl)piperidin-4-yl)methyl)-2,2-dimethylpiperazine-1-carboxylate (Example 650; 7.7 mg, 0.011 mmol) in DCM (0.5 mL) was treated with TFA (0.1 mL, 1.3 mmol). The resulting mixture was stirred for 1 h at ambient temperature before concentrating the mixture in vacuo to afford the title compound (6.6 mg, quantitative yield). MS (apci) m/z=573.4 (M+H).

Step 2: Preparation of 1-(5-(3-cyano-6-ethoxypyrazolo[1,5-a]pyridin-4-yl)pyridin-2-yl)-4-((4-ethyl-3,3-dimethylpiperazin-1-yl)methyl)-N-isobutylpiperidine-4-carboxamide A solution of 1-(5-(3-cyano-6-ethoxypyrazolo[1,5-a]pyridin-4-yl)pyridin-2-yl)-4-((3,3-dimethylpiperazin-1-yl)methyl)-N-isobutylpiperidine-4-carboxamide (6.6 mg, 0.0115 mmol) in DCM (0.73 µL) was treated with acetaldehyde (0.668 µL, 0.0230 mmol) and NaBH(AcO)$_3$ (4.88 mg, 0.0230 mmol), and stirred overnight at room temperature. The resulting mixture was purified directly by silica chromatography (using 0-100% DCM/[10% MeOH/1% NH$_4$OH in DCM] as the gradient eluent) to cleanly afford the title compound (3.8 mg, 55% yield). MS (apci) m/z=601.3 (M+H).

Example 656

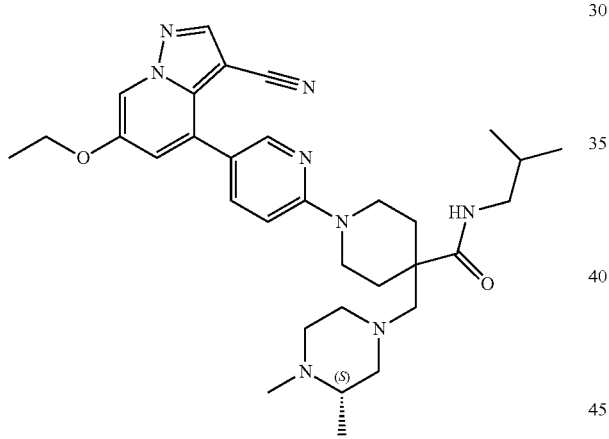

(S)-1-(5-(3-cyano-6-ethoxypyrazolo[1,5-a]pyridin-4-yl)pyridin-2-yl)-4-((3,4-dimethylpiperazin-1-yl)methyl)-N-isobutylpiperidine-4-carboxamide A solution of (S)-1-(5-(3-cyano-6-ethoxypyrazolo[1,5-a]pyridin-4-yl)pyridin-2-yl)-N-isobutyl-4-((3-methylpiperazin-1-yl)methyl)piperidine-4-carboxamide (Example 651; 23.6 mg, 0.04224 mmol) in DCE (1000 µL) was treated with formaldehyde (37 wt. % in water with 5-15% MeOH stabilizer; 17.14 mg, 0.2112 mmol), then stirred for 45 min at ambient temperature before adding NaBH(AcO)$_3$ (53.71 mg, 0.2534 mmol). The resulting mixture was stirred for 3 d at room temperature. The reaction mixture was diluted with acetone, and concentrated in vacuo. The residue was dissolved in DCM, and washed with water. The organic extracts were purified directly by silica chromatography (using 0-100% [10% MeOH+1% NH4OH] in DCM as the gradient eluent) to cleanly afford the title compound (16.2 mg, 67% yield). MS (apci) m/z=575.3 (M+H).

Example 657

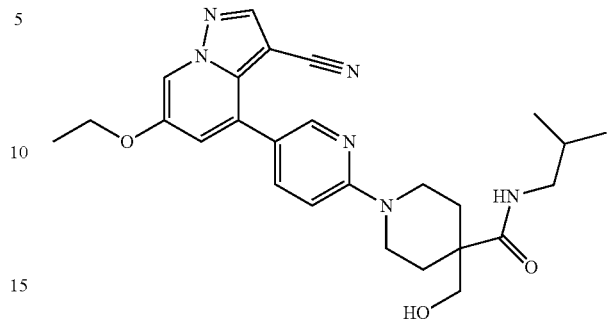

1-(5-(3-cyano-6-ethoxypyrazolo[1,5-a]pyridin-4-yl)pyridin-2-yl)-4-(hydroxymethyl)-N-isobutylpiperidine-4-carboxamide A solution of 1-(5-(3-cyano-6-ethoxypyrazolo[1,5-a]pyridin-4-yl)pyridin-2-yl)-4-formyl-N-isobutylpiperidine-4-carboxamide (Intermediate P76, 62.8 mg, 0.132 mmol) in 1:1 DCM:MeOH (1.3 mL) was treated with NaBH$_4$ (98%; 50.1 mg, 1.32 mmol), stirred overnight at room temperature, and then concentrated in vacuo. The residue was diluted with 4:1 DCM:iPrOH, and extracted with saturated NaHCO$_{3(aq)}$. The organic extracts were dried over anhydrous Na$_2$SO$_{4(s)}$, filtered, and concentrated in vacuo to cleanly afford the title compound (44.4 mg, 70% yield). MS (apci) m/z=477.3 (M+H).

Example 658

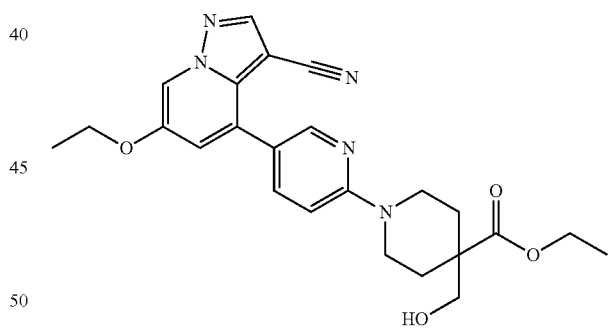

Ethyl 1-(5-(3-cyano-6-ethoxypyrazolo[1,5-a]pyridin-4-yl)pyridin-2-yl)-4-(hydroxymethyl)piperidine-4-carboxylate A slurry of 6-ethoxy-4-(6-fluoropyridin-3-yl)pyrazolo[1,5-a]pyridine-3-carbonitrile (Intermediate P6, 76 mg, 0.269 mmol), ethyl 4-(hydroxymethyl)piperidine-4-carboxylate hydrochloride (Intermediate R42; 84.1 mg, 0.323 mmol), and DIEA (141 µL, 0.808 mmol) in DMSO (538 µL) was stirred for 2 d at 90° C. After cooling to ambient temperature, the mixture was purified directly by C18 reverse phase chromatography (using 5-50% ACN/water as the gradient eluent). This allowed for the clean separation and isolation of the title compound (35.2 mg, 29% yield; MS (apci)

m/z=450.2 (M+H)) and another product 1-(5-(3-cyano-6-ethoxypyrazolo[1,5-a]pyridin-4-yl)pyridin-2-yl)-4-(hydroxymethyl)piperidine-4-carboxylic acid (Intermediate P156; 7.4 mg, 7% yield):

Example 659

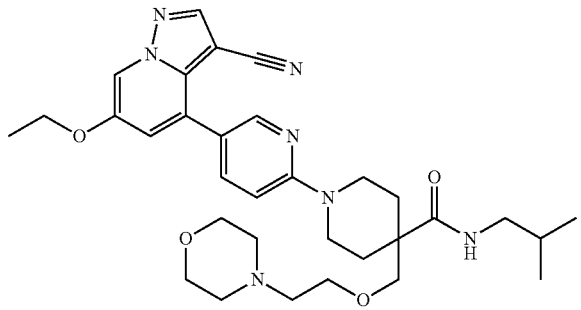 [SMILES: CCOc1cc(-c2ccc(N3CCC(COCCN4CCOCC4)(C(=O)NCC(C)C)CC3)nc2)c2c(C#N)cnn2c1]

1-(5-(3-cyano-6-ethoxypyrazolo[1,5-a]pyridin-4-yl)pyridin-2-yl)-N-isobutyl-4-((2-morpholinoethoxy)methyl)piperidine-4-carboxamide A solution of 1-(5-(3-cyano-6-ethoxypyrazolo[1,5-a]pyridin-4-yl)pyridin-2-yl)-4-((2-morpholinoethoxy)methyl)piperidine-4-carboxylic acid dihydrochloride (Intermediate P107; 25 mg, 0.044 mmol), DIEA (32.6 µL, 0.187 mmol), HATU (35.6 mg, 0.0935 mmol) and isobutylamine (13.9 µL, 0.140 mmol) in DMF (1.0 mL) was stirred for 5 h at ambient temperature. The mixture was concentrated in vacuo, and purified directly by C18 reverse phase chromatography (5 to 95% acetonitrile in water) to cleanly afford the title compound (6 mg, 22% yield). MS (apci) m/z=590.3 (M+H).

Example 660

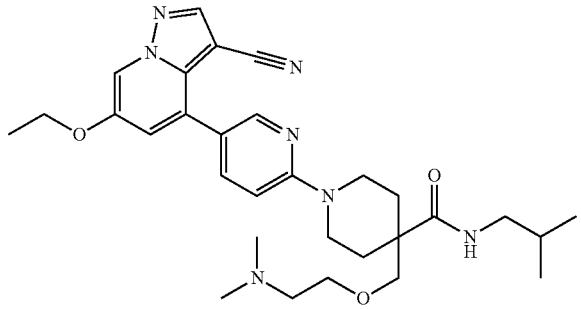 [SMILES: CCOc1cc(-c2ccc(N3CCC(COCCN(C)C)(C(=O)NCC(C)C)CC3)nc2)c2c(C#N)cnn2c1]

1-(5-(3-cyano-6-ethoxypyrazolo[1,5-a]pyridin-4-yl)pyridin-2-yl)-4-((2-(dimethylamino)ethoxy)methyl)-N-isobutylpiperidine-4-carboxamide A solution of 1-(5-(3-cyano-6-ethoxypyrazolo[1,5-a]pyridin-4-yl)pyridin-2-yl)-4-((2-(dimethylamino)ethoxy)methyl)piperidine-4-carboxylic acid dihydrochloride (Intermediate P109; 22 mg, 0.0447 mmol), DIEA (31.1 µL, 0.179 mmol), HATU (34.0 mg, 0.0893 mmol) and isobutylamine (13.4 µL, 0.134 mmol) in DMF (1.0 mL) was stirred for 15 h at ambient temperature. The mixture was concentrated in vacuo, and purified directly by C18 reverse phase chromatography (5 to 95% acetonitrile in water) to cleanly afford the title compound (4 mg, 16% yield). MS (apci) m/z=548.3 (M+H).

Example 661

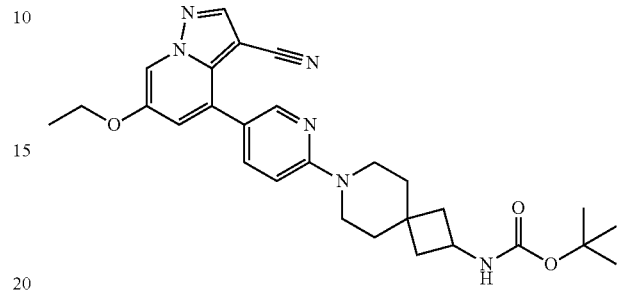

Tert-butyl (7-(5-(3-cyano-6-ethoxypyrazolo[1,5-a]pyridin-4-yl)pyridin-2-yl)-7-azaspiro[3.5]nonan-2-yl)carbamate A slurry of 6-ethoxy-4-(6-fluoropyridin-3-yl)pyrazolo[1,5-a]pyridine-3-carbonitrile (Intermediate P6, 100 mg, 0.354 mmol), tert-butyl (7-azaspiro[3.5]nonan-2-yl)carbamate (102 mg, 0.425 mmol), and DIEA (185 µL, 1.06 mmol) in DMSO (1417 µL) was stirred for 18 h at 90° C. After cooling to ambient temperature, the mixture was poured into water (12 mL) while stirring. The resulting suspension was vacuum filtered, and the solids were rinsed sequentially with water (3×15 mL) and heptane (3×5 mL), then dried in vacuo to cleanly afford the title compound (175 mg, 98% yield). MS (apci) m/z=503.2 (M+H).

Example 662

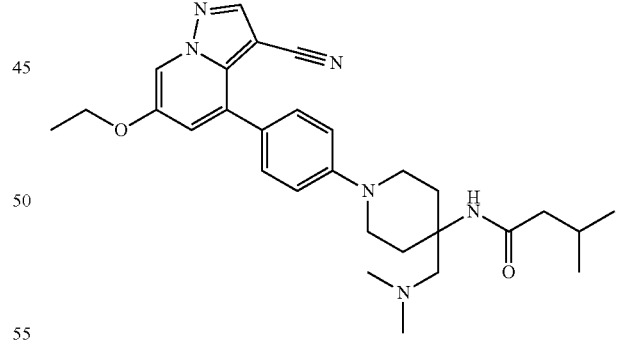

N-(1-(4-(3-cyano-6-ethoxypyrazolo[1,5-a]pyridin-4-yl)phenyl)-4-((dimethylamino)methyl)piperidin-4-yl)-3-methylbutanamide A solution of 4-(4-(4-amino-4-((dimethylamino)methyl)piperidin-1-yl)phenyl)-6-ethoxypyrazolo[1,5-a]pyridine-3-carbonitrile (Intermediate P114; 35.7 mg, 0.0853 mmol) in DCM (6.6 µL) was treated with TEA (59.4 µL, 0.426 mmol) and isovaleryl chloride (20.8 µL, 0.171 mmol). The resulting mixture was stirred for 30 min at ambient temperature, and Example 663

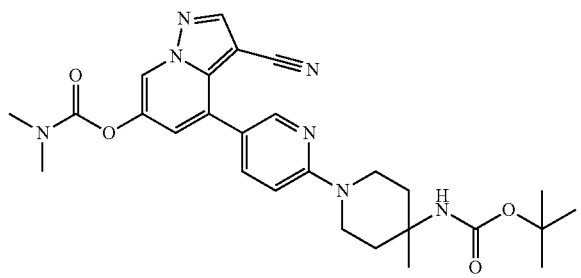 [SMILES: CN(C)C(=O)Oc1cc(-c2ccc(N3CCC(C)(NC(=O)OC(C)(C)C)CC3)nc2)c2c(C#N)cnn2c1]

4-(6-(4-((tert-butoxycarbonyl)amino)-4-methylpiperidin-1-yl)pyridin-3-yl)-3-cyanopyrazolo[1,5-a]pyridin-6-yl dimethylcarbamate A slurry of 3-cyano-4-(6-fluoropyridin-3-yl)pyrazolo[1,5-a]pyridin-6-yl dimethylcarbamate (Intermediate P115; 69.4 mg, 0.213 mmol), tert-butyl (4-methylpiperidin-4-yl)carbamate (114 mg, 0.533 mmol) and DIEA (186 µL, 1.07 mmol) in DMSO (3 mL) was stirred for 2 h at 90° C. After cooling to ambient temperature, the mixture was diluted with water and extracted with EtOAc (3×). The combined organic extracts were washed sequentially with water (2×) and brine. The aqueous extracts were combined, neutralized (pH 6-7) with the addition 6 M HCl$_{(aq)}$, and then extracted with EtOAc (2×). The organic extracts from the neutralization were combined, and concentrated in vacuo. The crude residue was purified by silica chromatography (using 30-90% Hexanes/EtOAc as the gradient eluent), resulting in the clean isolation of 4-(6-(4-((tert-butoxycarbonyl)amino)-4-methylpiperidin-1-yl)pyridin-3-yl)-3-cyanopyrazolo[1,5-a]pyridin-6-yl dimethylcarbamate (45.3 mg), along with mixed fractions containing both 4-(6-(4-((tert-butoxycarbonyl)amino)-4-methylpiperidin-1-yl)pyridin-3-yl)-3-cyanopyrazolo[1,5-a]pyridin-6-yl dimethylcarbamate and the desired tert-butyl (1-(5-(3-cyano-6-hydroxypyrazolo[1,5-a]pyridin-4-yl)pyridin-2-yl)-4-methylpiperidin-4-yl)carbamate. The mixed fractions were combined and concentrated in vacuo. The residue was dissolved in DCM (500 µL), and treated with DIEA (100 µL, 0.57 mmol) and dimethylcarbamyl chloride (52 µL, 0.57 mmol). The resulting mixture was stirred for a total of 5 d, supplementing with additional dimethylcarbamyl chloride (52 µL, 0.57 mmol) after the initial 24 h. The resulting mixture was washed sequentially with water and 2 M NaOH$_{(aq)}$. The organic extracts were purified directly by silica chromatography (using 50-90% Hexanes/EtOAc as the gradient eluent) to cleanly afford the title compound (74.8 mg, 66% yield). MS (apci) m/z=520.2 (M+H).

Example 664

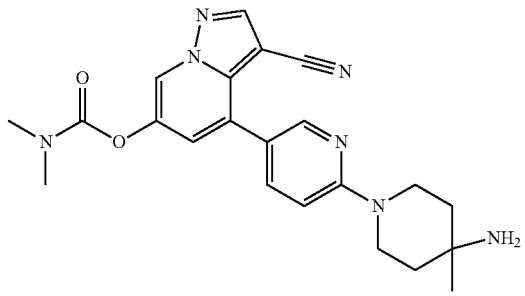 [SMILES: CN(C)C(=O)Oc1cc(-c2ccc(N3CCC(C)(N)CC3)nc2)c2c(C#N)cnn2c1]

4-(6-(4-amino-4-methylpiperidin-1-yl)pyridin-3-yl)-3-cyanopyrazolo[1,5-a]pyridin-6-yl dimethylcarbamate A solution of 4-(6-(4-((tert-butoxycarbonyl)amino)-4-methylpiperidin-1-yl)pyridin-3-yl)-3-cyanopyrazolo[1,5-a]pyridin-6-yl dimethylcarbamate (Example 663; 70 mg, 0.135 mmol) in DCM (3 mL) was treated with TFA 1.5 mL, 19 mmol). The resulting mixture was stirred for 30 min at ambient temperature before concentrating in vacuo. The residue was diluted with DCM, and washed with saturated NaHCO$_{3(aq)}$. After back extracting the aqueous extracts with 4:1 DCM:iPrOH, the organic extracts were combined, dried over anhydrous Na$_2$SO$_{4(s)}$, filtered, and concentrated in vacuo to cleanly afford the title compound (25.2 mg, 45% yield). MS (apci) m/z=420.2 (M+H).

Example 665

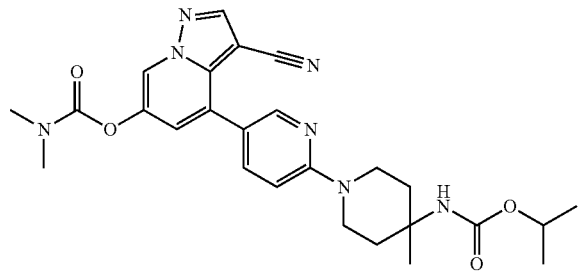 [SMILES: CC(C)OC(=O)NC1(C)CCN(c2ccc(-c3cc(OC(=O)N(C)C)cn4ncc(C#N)c34)cn2)CC1]

3-cyano-4-(6-(4-((isopropoxycarbonyl)amino)-4-methylpiperidin-1-yl)pyridin-3-yl)pyrazolo[1,5-a]pyridin-6-yl dimethylcarbamate A mixture of 4-(6-(4-amino-4-methylpiperidin-1-yl)pyridin-3-yl)-3-cyanopyrazolo[1,5-a]pyridin-6-yl dimethylcarbamate (Example 664; 13.6 mg, 0.0324 mmol) and DIEA (22.6 µL, 0.130 mmol) in DCM (500 µL) was treated with isopropyl carbonochloridate (4.77 mg, 0.0389 mmol). The resulting mixture was stirred for 1 h at ambient temperature, and was purified directly by silica chromatography (using 0-100% Hexanes/EtOAc as the gradient eluent) to cleanly afford the title compound (11.5 mg, 69% yield). MS (apci) m/z=506.2 (M+H).

Example 666

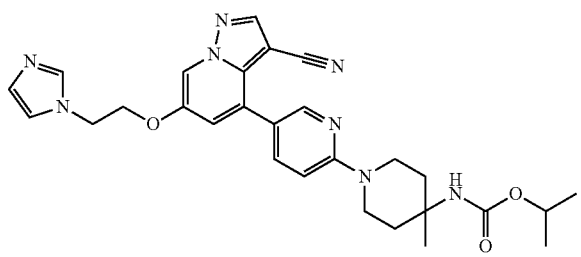 [SMILES: CC(C)OC(=O)NC1(C)CCN(c2ccc(-c3cc(OCCn4ccnc4)cn4ncc(C#N)c34)cn2)CC1]

isopropyl (1-(5-(6-(2-(1H-imidazol-1-yl)ethoxy)-3-cyanopyrazolo[1,5-a]pyridin-4-yl)pyridin-2-yl)-4-methylpiperidin-4-yl)carbamate A mixture of 6-(2-(1H-imidazol-1-yl)ethoxy)-4-(6-fluoropyridin-3-yl)pyrazolo[1,5-a]pyridine-3-carbonitrile (Intermediate P116; 12 mg, 0.034 mmol), isopropyl (4-methylpiperidin-4-yl)carbamate hydrochloride (Intermediate R19, part B; 16 mg, 0.069 mmol) and $Cs_2CO_{3(s)}$ (112 mg, 0.34 mmol) in DMSO (1.5 mL) was stirred overnight at 100° C. Subsequently, additional isopropyl (4-methylpiperidin-4-yl)carbamate hydrochloride (Intermediate R19, part B; 16 mg, 0.069 mmol) was introduced, and the resulting mixture was stirred overnight at 100° C. After cooling to ambient temperature, the reaction mixture was diluted with water, and washed sequentially with DCM (4×) and 4:1 DCM:iPrOH. The combined organic extracts were dried over anhydrous $Na_2SO_{4(s)}$, and filtered. The filtrate was purified directly by silica chromatography (using 0-50% DCM/MeOH with 1% $NH_4OH$ as the gradient eluent). Fractions containing the desired compound were combined, concentrated in vacuo, then partitioned between water and DCM. The organic extracts were separated, and concentrated in vacuo to cleanly afford the title compound (7.2 mg, 34% yield). MS (apci) m/z=529.2 (M+H).

Example 667

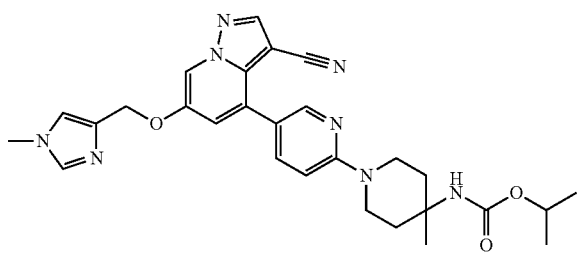 [SMILES: CC(C)OC(=O)NC1(C)CCN(c2ccc(-c3cc(OCc4cn(C)cn4)cn4ncc(C#N)c34)cn2)CC1]

Isopropyl (1-(5-(3-cyano-6-((1-methyl-1H-imidazol-4-yl)methoxy)pyrazolo[1,5-a]pyridin-4-yl)pyridin-2-yl)-4-methylpiperidin-4-yl)carbamate A solution of 4-(6-fluoropyridin-3-yl)-6-((1-methyl-1H-imidazol-4-yl)methoxy)pyrazolo[1,5-a]pyridine-3-carbonitrile (Intermediate P117; 26.0 mg, 0.0746 mmol) in DMA (1.0 mL) was treated with isopropyl (4-methylpiperidin-4-yl)carbamate hydrochloride (Intermediate R19; 35.34 mg, 0.1493 mmol) and TEA (104.1 µL, 0.7464 mmol) was stirred for 60 h at 60° C. After cooling to ambient temperature, the reaction mixture purified directly by C18 reverse phase chromatography (using 0-50% water/ACN with 0.1% TFA as the gradient eluent). Fractions containing the desired product were combined, concentrated in vacuo to remove the ACN, then partitioned between saturated $NaHCO_{3(aq)}$ and 4:1 DCM:iPrOH. The organic extracts were concentrated in vacuo to afford the title compound (8.7 mg, 18% yield). MS (apci) m/z=529.2 (M+H).

Example 668

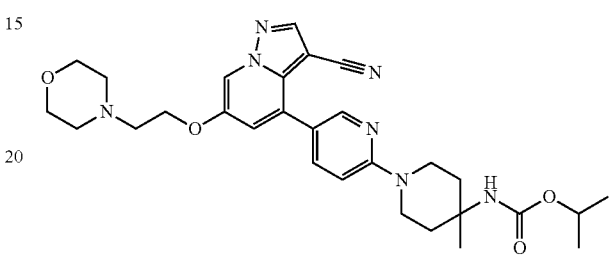

isopropyl (1-(5-(3-cyano-6-(2-morpholinoethoxy)pyrazolo[1,5-a]pyridin-4-yl)pyridin-2-yl)-4-methylpiperidin-4-yl)carbamate A mixture of 4-(6-fluoropyridin-3-yl)-6-(2-morpholinoethoxy)pyrazolo[1,5-a]pyridine-3-carbonitrile (Intermediate P79, 22.1 mg, 0.0602 mmol), isopropyl (4-methylpiperidin-4-yl)carbamate hydrochloride (Intermediate R19; 28.5 mg, 0.120 mmol) and $Cs_2CO_{3(s)}$ (196 mg, 0.602 mmol) in DMSO (1.5 mL) was stirred overnight at 100° C. Subsequently, additional isopropyl (4-methylpiperidin-4-yl)carbamate hydrochloride (Intermediate R19; 28.5 mg, 0.120 mmol) was introduced, and the resulting mixture was stirred overnight at 100° C. After cooling to ambient temperature, the reaction mixture was diluted with water, and washed sequentially with DCM (4×) and 4:1 DCM:iPrOH. The combined organic extracts were dried over anhydrous $Na_2SO_{4(s)}$, and filtered. The filtrate was purified directly by silica chromatography (using 0-50% water/ACN with 0.1% TFA as the gradient eluent). Fractions containing the desired product were combined, concentrated in vacuo to remove the ACN, then partitioned between saturated $NaHCO_{3(aq)}$ and 4:1 DCM:iPrOH. The organic extracts were concentrated in vacuo to afford the title compound (2.7 mg, 8% yield). MS (apci) m/z=548.2 (M+H).

Example 669

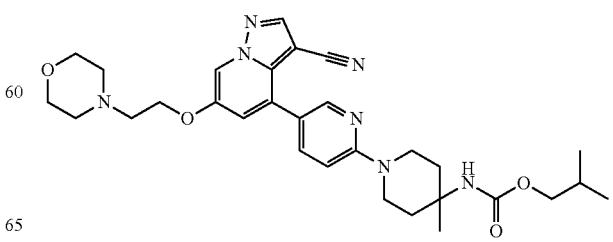

823 isobutyl (1-(5-(3-cyano-6-(2-morpholinoethoxy) pyrazolo[1,5-a]pyridin-4-yl)pyridin-2-yl)-4-methyl-piperidin-4-yl)carbamate A solution of 4-(6-(4-amino-4-methylpiperidin-1-yl)pyridin-3-yl)-6-(2-morpholinoethoxy)pyrazolo[1,5-a]pyridine-3-carbonitrile bis(2,2,2-trifluoroacetate) (Intermediate P119; 41 mg, 0.060 mmol) in DCM (500 µL) was treated sequentially with DIEA (30.9 µL, 0.178 mmol) and isobutyl chloroformate (13.9 µL, 0.107 mmol). The resulting mixture was stirred for 24 h at ambient temperature. The reaction mixture was diluted with 4:1 DCM:iPrOH, and extracted sequentially with water and brine. After back extracting the aqueous extracts with 4:1 DCM:iPrOH, the organic extracts were combined, dried over anhydrous Na$_2$SO$_{4(s)}$, then concentrated in vacuo. The residue was purified by C18 reverse phase chromatography (using 5-95% water:ACN with 0.1% TFA as the gradient eluent) to afford the title compound as the TFA salt. The TFA salt was suspended in MeOH (5 mL), and eluted through a basic resin (Stratospheres Pl-HCO3) to cleanly afford the title compound (11.2 mg, 33% yield). MS (apci) m/z=562.3 (M+H).

Example 670

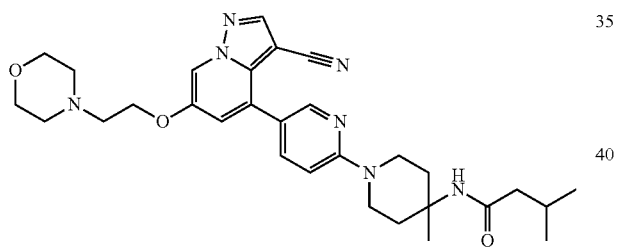

N-(1-(5-(3-cyano-6-(2-morpholinoethoxy)pyrazolo [1,5-a]pyridin-4-yl)pyridin-2-yl)-4-methylpiperidin-4-yl)-3-methylbutanamide A solution of 4-(6-(4-amino-4-methylpiperidin-1-yl)pyridin-3-yl)-6-(2-morpholinoethoxy)pyrazolo[1,5-a]pyridine-3-carbonitrile bis(2,2,2-trifluoroacetate) (Intermediate P119; 40 mg, 0.058 mmol) in DCM (578 µL) was treated sequentially with DIEA (30.2 µL, 0.173 mmol), HATU (39.5 mg, 0.104 mmol) and isovaleric acid (10.5 µL, 0.0953 mmol). The resulting mixture was stirred overnight at ambient temperature, then purified directly by C18 reverse phase chromatography (using 5-95% ACN/water with 0.1% TFA as the gradient eluent) to afford the TFA salt of the title compound. The TFA salt was dissolved in MeOH (1 mL), and eluted through a basic resin (Stratospheres Pl-HCO3) to cleanly afford the title compound (19 mg, 60% yield). MS (apci) m/z=546.2 (M+H).

824

Example 671

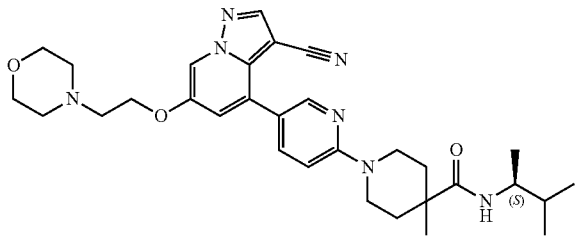

(S)-1-(5-(3-cyano-6-(2-morpholinoethoxy)pyrazolo [1,5-a]pyridin-4-yl)pyridin-2-yl)-4-methyl-N-(3-methylbutan-2-yl)piperidine-4-carboxamide A solution of 1-(5-(3-cyano-6-(2-morpholinoethoxy) pyrazolo[1,5-a]pyridin-4-yl)pyridin-2-yl)-4-methylpiperidine-4-carboxylic acid (Intermediate P121; 40 mg, 0.0815 mmol) in DCM (544 µL) was treated sequentially with DIEA (28.4 µL, 0.163 mmol), HATU (37.2 mg, 0.0978 mmol) and (S)-(+)-3-methyl-2-butylamine (9.48 µL, 0.0815 mmol). The resulting mixture was stirred for 16 h at ambient temperature, then concentrated in vacuo. The crude residue was purified by silica chromatography (using 5-95% ACN/water with 0.1% TFA as the gradient eluent) to afford the TFA salt of the title compound. The TFA salt was dissolved in MeOH (5 mL), and eluted through a basic resin (Stratospheres Pl-HCO3) to cleanly afford the title compound (21 mg, 46% yield). MS (apci) m/z=560.4 (M+H).

Example 672

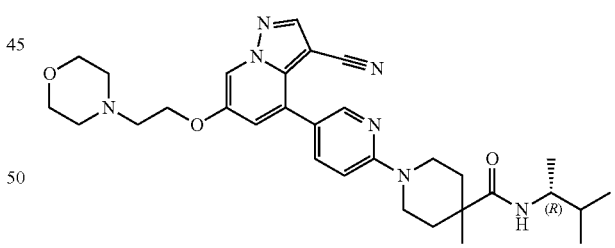

(R)-1-(5-(3-cyano-6-(2-morpholinoethoxy)pyrazolo [1,5-a]pyridin-4-yl)pyridin-2-yl)-4-methyl-N-(3-methylbutan-2-yl)piperidine-4-carboxamide The title compound (22.5 mg, 47% yield) was prepared and purified using a similar procedure to that described for (S)-1-(5-(3-cyano-6-(2-morpholinoethoxy)pyrazolo[1,5-a] pyridin-4-yl)pyridin-2-yl)-4-methyl-N-(3-methylbutan-2-yl)piperidine-4-carboxamide (Example 671), replacing (S)-(+)-3-methyl-2-butylamine (1 equiv) with (R)-(−)-3-methyl-2-butylamine (1.1 equiv). MS (apci) m/z=560.4 (M+H).

Example 673

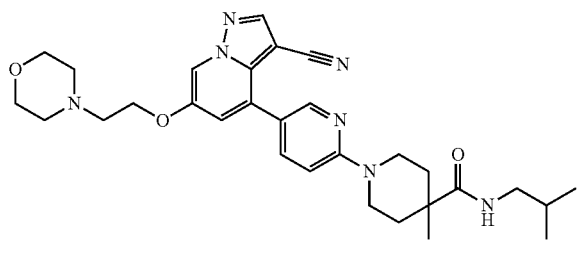 [SMILES: CC(C)CNC(=O)C1(C)CCN(c2ccc(-c3cc(OCCN4CCOCC4)cn4ncc(C#N)c34)cn2)CC1]

1-(5-(3-cyano-6-(2-morpholinoethoxy)pyrazolo[1,5-a]pyridin-4-yl)pyridin-2-yl)-N-isobutyl-4-methylpiperidine-4-carboxamide The title compound (26.7 mg, 60% yield) was prepared and purified using a similar procedure to that described for (S)-1-(5-(3-cyano-6-(2-morpholinoethoxy)pyrazolo[1,5-a]pyridin-4-yl)pyridin-2-yl)-4-methyl-N-(3-methylbutan-2-yl)piperidine-4-carboxamide (Example 671), replacing (S)-(+)-3-methyl-2-butylamine with isobutylamine. MS (apci) m/z=546.3 (M+H).

Example 674

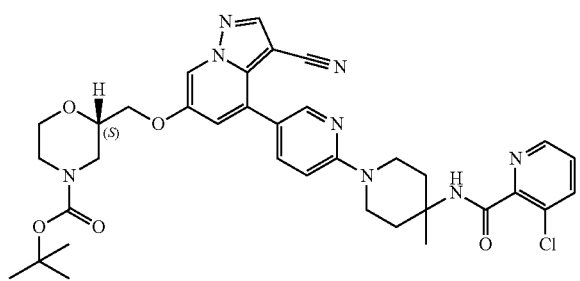

tert-butyl (S)-2-(((4-(6-(4-(3-chloropicolinamido)-4-methylpiperidin-1-yl)pyridin-3-yl)-3-cyanopyrazolo[1,5-a]pyridin-6-yl)oxy)methyl)morpholine-4-carboxylate A solution of 3-chloro-N-(1-(5-(3-cyano-6-hydroxypyrazolo[1,5-a]pyridin-4-yl)pyridin-2-yl)-4-methylpiperidin-4-yl)picolinamide (Intermediate P75, 100 mg, 0.205 mmol) and Cs$_2$CO$_{3(s)}$ (134 mg, 0.410 mmol) in DMF (1366 μL) was treated with tert-butyl (S)-2-(bromomethyl)morpholine-4-carboxylate (57.4 mg 0.205 mmol) was stirred overnight at 60° C. After cooling to ambient temperature, the reaction mixture was diluted with water (10 mL), and extracted with EtOAc (4×10 mL). The combined organic extracts were washed sequentially with water (3×10 mL) and brine (10 mL). The organic extracts were dried over anhydrous Na$_2$SO$_{4(s)}$, filtered and concentrated in vacuo. The residue was purified twice by silica chromatography (first using 0-100% [10% MeOH with 1% NH$_4$OH in DCM]/DCM, and again using a stepped gradient of 0-100% EtOAc/Hexanes followed by 0-10% EtOAc/MeOH as the gradient eluent) to afford the title compound (130 mg, 84% yield). MS (apci) m/z=687.2 (M+H).

Example 675

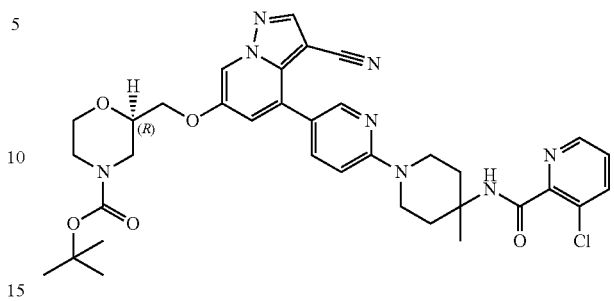

tert-butyl (R)-2-(((4-(6-(4-(3-chloropicolinamido)-4-methylpiperidin-1-yl)pyridin-3-yl)-3-cyanopyrazolo[1,5-a]pyridin-6-yl)oxy)methyl)morpholine-4-carboxylate The title compound (110 mg, 78% yield) was prepared, worked up and purified using a similar procedure to that described for tert-butyl (S)-2-(((4-(6-(4-(3-chloropicolinamido)-4-methylpiperidin-1-yl)pyridin-3-yl)-3-cyanopyrazolo[1,5-a]pyridin-6-yl)oxy)methyl)morpholine-4-carboxylate (Example 674), replacing tert-butyl (S)-2-(bromomethyl)morpholine-4-carboxylate with tert-butyl (R)-2-(bromomethyl)morpholine-4-carboxylate. MS (apci) m/z=687.2 (M+H).

Example 676

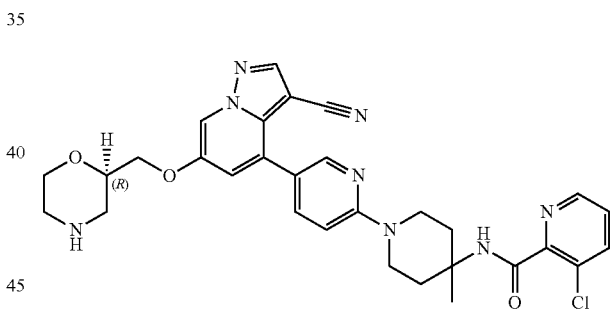

(R)-3-chloro-N-(1-(5-(3-cyano-6-(morpholin-2-ylmethoxy)pyrazolo[1,5-a]pyridin-4-yl)pyridin-2-yl)-4-methylpiperidin-4-yl)picolinamide A solution of tert-butyl (R)-2-(((4-(6-(4-(3-chloropicolinamido)-4-methylpiperidin-1-yl)pyridin-3-yl)-3-cyanopyrazolo[1,5-a]pyridin-6-yl)oxy)methyl)morpholine-4-carboxylate (Example 675; 110 mg, 0.160 mmol) in DCM (10.2 μL) and TFA (12.2 μL, 0.160 mmol) was stirred for 1 h at ambient temperature. The reaction mixture was concentrated in vacuo, and the residue was dissolved in MeOH (3 mL). A portion of the methanolic solution (2 mL) was concentrated in vacuo to afford the TFA salt of the title compound, (R)-3-chloro-N-(1-(5-(3-cyano-6-(morpholin-2-ylmethoxy)pyrazolo[1,5-a]pyridin-4-yl)pyridin-2-yl)-4-methylpiperidin-4-yl)picolinamide bis(2,2,2-trifluoroacetate) (63 mg, 48% yield; MS (apci) m/z=587.2 (M+H)). The remaining portion of the methanolic solution (1 mL) was purified by C18 reverse phase chromatography (using 5-95% ACN in water with 0.2% TFA as the gradient eluent). Fractions containing the desired compound were combined, then sequentially, concentrated in vacuo, dissolved in MeOH (5 mL), and eluted through a basic resin (Stratospheres MP-HCO3) to cleanly afford the title compound (9.3 mg, 10% yield). MS (apci) m/z=587.2 (M+H).

Example 677

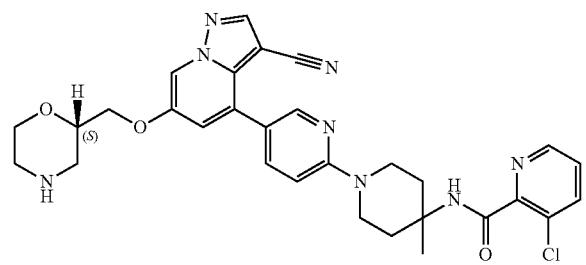

(S)-3-chloro-N-(1-(5-(3-cyano-6-(morpholin-2-ylmethoxy)pyrazolo[1,5-a]pyridin-4-yl)pyridin-2-yl)-4-methylpiperidin-4-yl)picolinamide The title compound (8.2 mg, 7% yield), along with the TFA salt of the title compound (S)-3-chloro-N-(1-(5-(3-cyano-6-(morpholin-2-ylmethoxy)pyrazolo[1,5-a]pyridin-4-yl)pyridin-2-yl)-4-methylpiperidin-4-yl)picolinamide bis (2,2,2-trifluoroacetate) (78 mg, 51% yield) were prepared, separated and purified using a similar procedure to that described for (R)-3-chloro-N-(1-(5-(3-cyano-6-(morpholin-2-ylmethoxy)pyrazolo[1,5-a]pyridin-4-yl)pyridin-2-yl)-4-methylpiperidin-4-yl)picolinamide (Example 676), replacing tert-butyl (R)-2-(((4-(6-(4-(3-chloropicolinamido)-4-methylpiperidin-1-yl)pyridin-3-yl)-3-cyanopyrazolo[1,5-a]pyridin-6-yl)oxy)methyl)morpholine-4-carboxylate (Example 675; with tert-butyl (S)-2-(((4-(6-(4-(3-chloropicolinamido)-4-methylpiperidin-1-yl)pyridin-3-yl)-3-cyanopyrazolo[1,5-a]pyridin-6-yl)oxy)methyl)morpholine-4-carboxylate (Example 674). MS (apci) m/z=587.2 (M+H).

Example 678

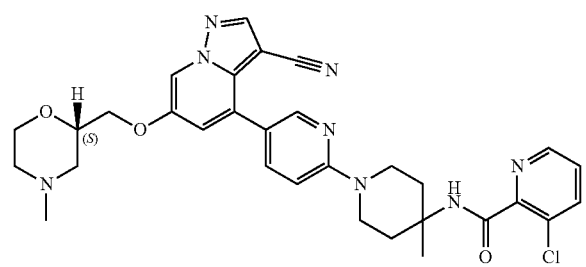

(S)-3-chloro-N-(1-(5-(3-cyano-6-((4-methylmorpholin-2-yl)methoxy)pyrazolo[1,5-a]pyridin-4-yl)pyridin-2-yl)-4-methylpiperidin-4-yl)picolinamide A solution of (S)-3-chloro-N-(1-(5-(3-cyano-6-(morpholin-2-ylmethoxy)pyrazolo[1,5-a]pyridin-4-yl)pyridin-2-yl)-4-methylpiperidin-4-yl)picolinamide bis(2,2,2-trifluoroacetate) (Example 677, TFA salt; 78 mg, 0.0957 mmol) in DCM (957 µL) was treated with formaldehyde (35 wt. % in water with 5-15% MeOH stabilizer; 38 µL, 0.478), and NaBH(AcO)3 (203 mg, 0.957 mmol), and stirred for 1 h at room temperature. The reaction mixture was purified directly by C18 reverse phase chromatography (using 5-95% ACN in water with 0.2% TFA as the gradient eluent). Fractions containing the desired compound were combined, then sequentially, concentrated in vacuo, dissolved in MeOH (5 mL), and eluted through a basic resin (Stratospheres MP-HCO3) to cleanly afford the title compound (31 mg, 54% yield). MS (apci) m/z=601.2 (M+H).

Example 679

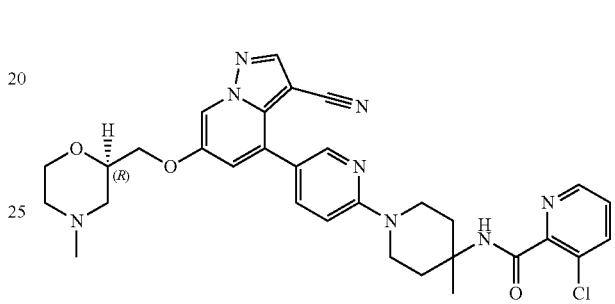

(R)-3-chloro-N-(1-(5-(3-cyano-6-((4-methylmorpholin-2-yl)methoxy)pyrazolo[1,5-a]pyridin-4-yl)pyridin-2-yl)-4-methylpiperidin-4-yl)picolinamide The title compound (21 mg, 45% yield) was prepared and purified using a similar procedure to that described for (S)-3-chloro-N-(1-(5-(3-cyano-6-((4-methylmorpholin-2-yl)methoxy)pyrazolo[1,5-a]pyridin-4-yl)pyridin-2-yl)-4-methylpiperidin-4-yl)picolinamide (Example 678), replacing (S)-3-chloro-N-(1-(5-(3-cyano-6-(morpholin-2-ylmethoxy)pyrazolo[1,5-a]pyridin-4-yl)pyridin-2-yl)-4-methylpiperidin-4-yl)picolinamide bis(2,2,2-trifluoroacetate) (Example 677) with (R)-3-chloro-N-(1-(5-(3-cyano-6-(morpholin-2-ylmethoxy)pyrazolo[1,5-a]pyridin-4-yl)pyridin-2-yl)-4-methylpiperidin-4-yl)picolinamide bis(2,2,2-trifluoroacetate) (Example 676). MS (apci) m/z=601.2 (M+H).

Example 680

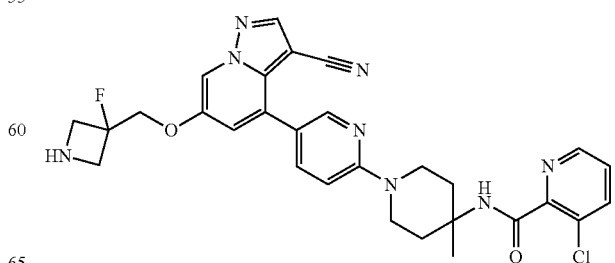

3-chloro-N-(1-(5-(3-cyano-6-((3-fluoroazetidin-3-yl)methoxy)pyrazolo[1,5-a]pyridin-4-yl)pyridin-2-yl)-4-methylpiperidin-4-yl)picolinamide Step 1: Preparation of tert-butyl 3-(((4-(6-(4-(3-chloropicolinamido)-4-methylpiperidin-1-yl)pyridin-3-yl)-3-cyanopyrazolo[1,5-a]pyridin-6-yl)oxy)methyl)-3-fluoroazetidine-1-carboxylate A mixture of 3-chloro-N-(1-(5-(3-cyano-6-hydroxypyrazolo[1,5-a]pyridin-4-yl)pyridin-2-yl)-4-methylpiperidin-4-yl)picolinamide (Intermediate P75, 200 mg, 0.410 mmol), tert-butyl 3-(bromomethyl)-3-fluoroazetidine-1-carboxylate (220 mg, 0.820 mmol) and Cs$_2$CO$_{3(s)}$ (160 mg, 0.492 mmol) in DMA (4099 μL) was stirred overnight at 60° C. Subsequently, additional Cs$_2$CO$_{3(s)}$ (160 mg, 0.492 mmol) was introduced, and the reaction mixture was stirred overnight again at 60° C. After cooling to ambient temperature, the reaction mixture was partitioned between 4:1 DCM:IPA and water through a PS Frit rinsing with 4:1 DCM:IPA (3×). The combined organic extracts were concentrated in vacuo, and purified by silica chromatography (using a stepped gradient of 0-100% EtOAc/Hexanes as the gradient eluent) to afford the title compound contaminated with DMA (277 mg, quantitative yield assumed). MS (apci) m/z=675.3 (M+H).

Step 2: Preparation of 3-chloro-N-(1-(5-(3-cyano-6-((3-fluoroazetidin-3-yl)methoxy)pyrazolo[1,5-a]pyridin-2-yl)-4-methylpiperidin-4-yl)picolinamide A solution of tert-butyl 3-(((4-(6-(4-(3-chloropicolinamido)-4-methylpiperidin-1-yl)pyridin-3-yl)-3-cyanopyrazolo[1,5-a]pyridin-6-yl)oxy)methyl)-3-fluoroazetidine-1-carboxylate (277 mg, 0.410 mmol) in DMA (~0.5 mL; a solution that carried through the column) was treated with TFA (1106 μL, 14.4 mmol) and stirred for 60 h at ambient temperature. The reaction mixture was diluted with DCM and brine, then neutralized to pH 7 with 2 N NaOH$_{(aq)}$. The resulting biphasic mixture was passed through a PS Frit, and the organics were concentrated in vacuo. The crude residue was purified by silica chromatography (using 0-15% MeOH in EtOAc with 0.2% NH$_4$OH as the gradient eluent) to cleanly afford the title compound (79 mg, 34% yield, over 2 steps). MS (apci) m/z=575.2 (M+H).

Example 681

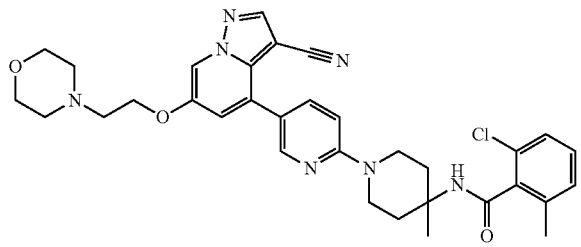 [SMILES: Cc1cccc(Cl)c1C(=O)NC1(C)CCN(c2ccc(-c3cc(OCCN4CCOCC4)cn4ncc(C#N)c34)cn2)CC1]

2-chloro-N-(1-(6-(3-cyano-6-(2-morpholinoethoxy)pyrazolo[1,5-a]pyridin-4-yl)pyridin-3-yl)-4-methylpiperidin-4-yl)-6-methylbenzamide A solution of 4-(5-(4-amino-4-methylpiperidin-1-yl)pyridin-2-yl)-6-(2-morpholinoethoxy)pyrazolo[1,5-a]pyridine-3-carbonitrile dihydrochloride (Intermediate P124; 4.8 mg, 0.010 mmol) in DCM (0.2 mL) was treated sequentially with 2-chloro-6-methylbenzoic acid (3.5 mg, 0.021 mmol), DIEA (27 μL, 0.16 mmol), HATU (7.9 mg, 0.021 mmol). The resulting mixture was stirred for 17 h at ambient temperature, before diluting with water (10 mL) and extracting with DCM (2×10 mL). The combined organic extracts were dried over anhydrous MgSO$_{4(s)}$, filtered and concentrated in vacuo. The crude residue was purified by C18 reverse phase chromatography (using 5-95% ACN in water with 0.2% TFA as the gradient eluent) to afford the TFA salt of the title compound. The TFA salt was dissolved in MeOH (1 mL), and eluted through a basic resin (Stratospheres SPE MP-HCO3) to cleanly afford the title compound (3.5 mg, 55% yield). MS (apci) m/z=614.2 (M+H).

Example 682

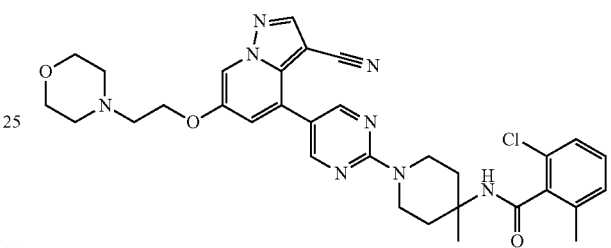

2-chloro-N-(1-(5-(3-cyano-6-(2-morpholinoethoxy)pyrazolo[1,5-a]pyridin-4-yl)pyrimidin-2-yl)-4-methylpiperidin-4-yl)-6-methylbenzamide A solution of 4-(2-(4-amino-4-methylpiperidin-1-yl)pyrimidin-5-yl)-6-(2-morpholinoethoxy)pyrazolo[1,5-a]pyridine-3-carbonitrile bis(2,2,2-trifluoroacetate) (Intermediate P131; 22.7 mg, 0.0329 mmol) in DCM (579 μL) was treated with 2-chloro-6-methylbenzoic acid (25.1 mg, 0.147 mmol), DIEA (15 μL, 0.087 mmol) and HATU (13 mg, 0.035 mmol). The resulting mixture was stirred for 3 h at ambient temperature, was concentrated in vacuo. The residue was purified directly by silica chromatography (0-100% EtOAc in Hexanes followed by 0-10% MeOH in DCM). Persistent impurities required a second silica chromatography (0-10% MeOH in DCM with 0-0.1% NH$_4$OH) to cleanly afford the title compound (2.8 mg, 9% yield). MS (apci) m/z=615.2 (M+H).

Example 683

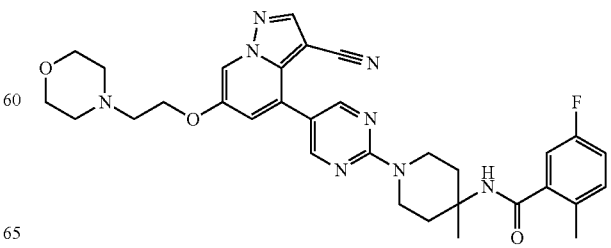

N-(1-(5-(3-cyano-6-(2-morpholinoethoxy)pyrazolo[1,5-a]pyridin-4-yl)pyrimidin-2-yl)-4-methylpiperidin-4-yl)-5-fluoro-2-methylbenzamide The title compound (12.34 mg, 42% yield) was prepared and purified using a similar procedure to that described for N-(1-(5-(3-cyano-6-(2-morpholinoethoxy)pyrazolo[1,5-a]pyridin-4-yl)pyrazin-2-yl)-4-methylpiperidin-4-yl)-5-fluoro-2-methylbenzamide (Example 682), replacing 2-chloro-6-methylbenzoic acid with 5-fluoro-2-methylbenzoic acid. MS (apci) m/z=599.3 (M+H).

Example 684

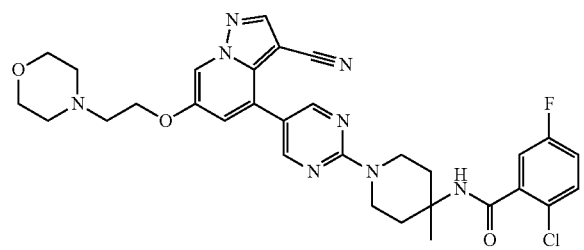 [SMILES: CC1(NC(=O)c2cc(F)ccc2Cl)CCN(c2ncc(-c3cc(OCCN4CCOCC4)cn4ncc(C#N)c34)cn2)CC1]

2-chloro-N-(1-(5-(3-cyano-6-(2-morpholinoethoxy)pyrazolo[1,5-a]pyridin-4-yl)pyrimidin-2-yl)-4-methylpiperidin-4-yl)-5-fluorobenzamide The title compound (14 mg, 46% yield) was prepared and purified using a similar procedure to that described for N-(1-(5-(3-cyano-6-(2-morpholinoethoxy)pyrazolo[1,5-a]pyridin-4-yl)pyrazin-2-yl)-4-methylpiperidin-4-yl)-5-fluoro-2-methylbenzamide (Example 682), except 2-chloro-6-methylbenzoic acid was replaced with 2-chloro-5-fluorobenzoic acid and the reaction was allowed to stir overnight at ambient temperature before the work up and purification required only a single silica chromatographic separation (using 0-100% EtOAc in Hex then 0-10% MeOH in EtOAc as the gradient eluent). MS (apci) m/z=619.2 (M+H).

Example 685

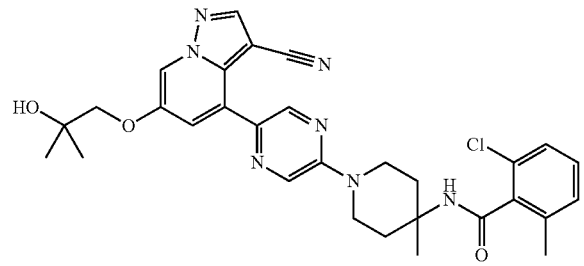 [SMILES: Cc1cccc(Cl)c1C(=O)NC1(C)CCN(c2cnc(-c3cc(OCC(C)(C)O)cn4ncc(C#N)c34)cn2)CC1]

2-chloro-N-(1-(5-(3-cyano-6-(2-hydroxy-2-methylpropoxy)pyrazolo[1,5-a]pyridin-4-yl)pyrazin-2-yl)-4-methylpiperidin-4-yl)-6-methylbenzamide In a sealed vessel, a solution of 4-bromo-6-(2-hydroxy-2-methylpropoxy)pyrazolo[1,5-a]pyridine-3-carbonitrile (Intermediate P41, 18 mg, 0.058 mmol) in dioxane (0.5 mL) was treated sequentially with water (0.15 mL), $Cs_2CO_{3(s)}$ (57 mg, 0.17 mmol), and 2-chloro-6-methyl-N-(4-methyl-1-(5-(4,4,5,5-tetramethyl-1,3,2-dioxaborolan-2-yl)pyrazin-2-yl)piperidin-4-yl)benzamide (Intermediate P125; 38 mg, 0.058 mmol). The resulting mixture was sparged with $N_{2(g)}$ for 5 min then treated with X-phos (11 mg, 0.023 mmol) and $Pd_2(dba)_3$ (5.3 mg, 0.0058 mmol). After sparging with $N_{2(g)}$ for 5 min, the vessel was sealed, and the resulting mixture was stirred for 17 h at 80° C. After cooling to ambient temperature, the resulting suspension was diluted with water (10 mL) and extracted with DCM (2×10 mL). The combined organic extracts were dried over anhydrous $MgSO_{4(s)}$, filtered and concentrated in vacuo. The crude residue was purified by C18 reverse phase chromatography (using 5-95% ACN in water with 0.1% TFA as the gradient eluent) to afford the TFA salt of the title compound. The TFA salt was dissolved in MeOH (1 mL), and eluted through a basic resin (Stratospheres SPE MP-HCO3) to cleanly afford the title compound (3.6 mg, 11% yield). MS (apci) m/z=574.2 (M+H); 596.2 (M+Na).

Example 686

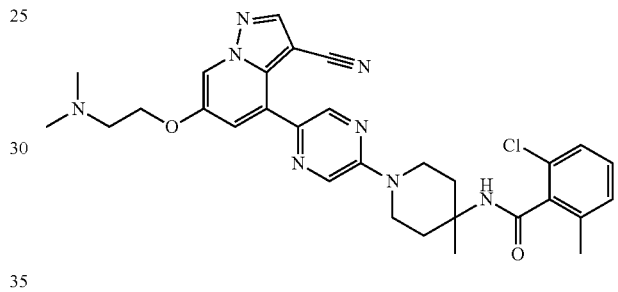

2-chloro-N-(1-(5-(3-cyano-6-(2-(dimethylamino)ethoxy)pyrazolo[1,5-a]pyridin-4-yl)pyrazin-2-yl)-4-methylpiperidin-4-yl)-6-methylbenzamide A solution of N-(1-(5-(6-(2-aminoethoxy)-3-cyanopyrazolo[1,5-a]pyridin-4-yl)pyrazin-2-yl)-4-methylpiperidin-4-yl)-2-chloro-6-methylbenzamide bis(2,2,2-trifluoroacetate) (Intermediate P152; 80 mg, 0.103 mmol) in DCM (66 μL) was treated with formaldehyde (37% aq, 19.3 μL, 0.517 mmol) and NaBH(AcO)$_3$ (110 mg, 0.517 mmol), then stirred overnight at ambient temperature. The resulting mixture was partitioned between 4:1 DCM:iPrOH and saturated NaHCO$_{3(aq)}$, and eluted through a PS Frit. The organic filtrate was concentrated in vacuo to cleanly afford the title compound (12.6 mg, 21% yield). MS (apci) m/z=573.3 (M+H).

Example 687

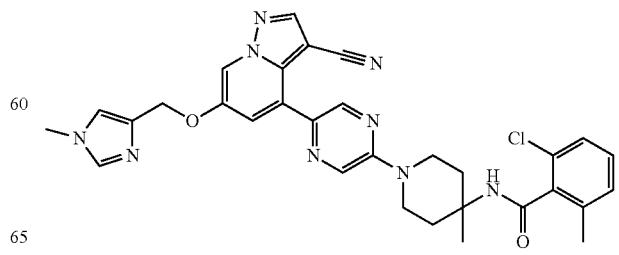

2-chloro-N-(1-(5-(3-cyano-6-((1-methyl-1H-imidazol-4-yl)methoxy)pyrazolo[1,5-a]pyridin-4-yl)pyrazin-2-yl)-4-methylpiperidin-4-yl)-6-methylbenzamide In a pressure tube, a mixture of 6-((1-methyl-1H-imidazol-4-yl)methoxy)-4-(4,4,5,5-tetramethyl-1,3,2-dioxaborolan-2-yl)pyrazolo[1,5-a]pyridine-3-carbonitrile (Intermediate P145; 54 mg, 0.142 mmol), 2-chloro-N-(1-(5-chloropyrazin-2-yl)-4-methylpiperidin-4-yl)-6-methylbenzamide (Intermediate R48; 54.0 mg, 0.142 mmol), 2 M $K_3PO_{4(aq)}$ (214 μL, 0.427 mmol), X-phos (13.6 mg, 0.0285 mmol) and $Pd_2(dba)_3$ (6.52 mg, 0.00712 mmol) in dioxane (1.0 mL) was sparged with $Ar_{(g)}$ for 10 min, and then the vessel was sealed. The reaction mixture was stirred overnight at 80° C. After cooling to ambient temperature, the reaction mixture was diluted with DCM, and extracted sequentially with water (3×) and brine (1×). The organic extracts were purified directly by silica chromatography (0-100% EtOAc/Hexanes), and then by C18 reverse phase chromatography (5-95% ACN in water with 0.1% TFA) to cleanly provide the title compound (12.5 mg, 14.7% yield). MS (apci) m/z=596.2 (M+H).

Example 688

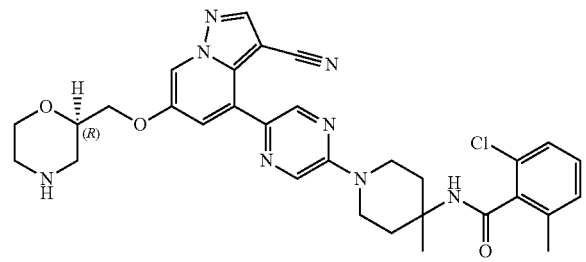

(R)-2-chloro-N-(1-(5-(3-cyano-6-(morpholin-2-ylmethoxy)pyrazolo[1,5-a]pyridin-4-yl)pyrazin-2-yl)-4-methylpiperidin-4-yl)-6-methylbenzamide A solution of tert-butyl (R)-2-(((4-(5-(4-(2-chloro-6-methylbenzamido)-4-methylpiperidin-1-yl)pyrazin-2-yl)-3-cyanopyrazolo[1,5-a]pyridin-6-yl)oxy)methyl)morpholine-4-carboxylate (Intermediate P148; 40.3 mg, 0.0575 mmol) in DCM (1 mL) and TFA (500 μL, 6.53 mmol) was stirred for 2 h at ambient temperature. Reaction was then concentrated down and purified by silica chromatography (using 0-100% [10% MeOH in DCM WITH 1% $NH_4OH$]/DCM as the gradient eluent) to cleanly afford the title compound (21.3 mg, 10% yield). MS (apci) m/z=601.2 (M+H).

Example 689

(R)-2-chloro-N-(1-(5-(3-cyano-6-((4-ethylmorpholin-2-yl)methoxy)pyrazolo[1,5-a]pyridin-4-yl)pyrazin-2-yl)-4-methylpiperidin-4-yl)-6-methylbenzamide A solution of (R)-2-chloro-N-(1-(5-(3-cyano-6-(morpholin-2-ylmethoxy)pyrazolo[1,5-a]pyridin-4-yl)pyrazin-2-yl)-4-methylpiperidin-4-yl)-6-methylbenzamide (Example 688; 12 mg, 0.02 mmol) in DCM (100 μL) was treated with acetaldehyde (1 μL, 0.02 mmol) and $NaBH(AcO)_3$ (4 mg, 0.02 mmol), and stirred for 20 h at ambient temperature. The resulting mixture was concentrated in vacuo, and the residue was purified by C18 reverse phase chromatography (using 5-95% water-ACN with 0.1% TFA as the gradient eluent) to afford the TFA salt of the title compound. The TFA salt was partitioned between 4:1 DCM:iPrOH and saturated $NaHCO_{3(aq)}$. The organic extracts were separated, dried over anhydrous $Na_2SO_{4(s)}$, filtered and concentrated in vacuo to cleanly afford the title compound (2.25 mg, 18% yield). MS (apci) m/z=629.2 (M+H).

Example 690

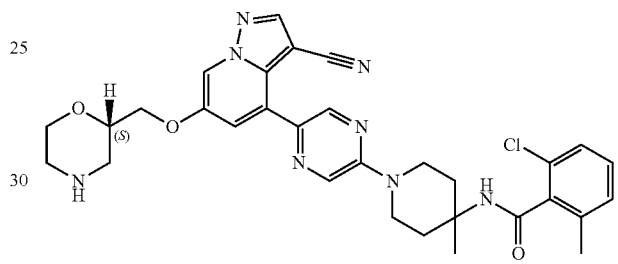

(S)-2-chloro-N-(1-(5-(3-cyano-6-(morpholin-2-ylmethoxy)pyrazolo[1,5-a]pyridin-4-yl)pyrazin-2-yl)-4-methylpiperidin-4-yl)-6-methylbenzamide The title compound (26.2 mg, quantitative yield) was prepared and purified using a similar procedure to that described for (R)-2-chloro-N-(1-(5-(3-cyano-6-(morpholin-2-ylmethoxy)pyrazolo[1,5-a]pyridin-4-yl)pyrazin-2-yl)-4-methylpiperidin-4-yl)-6-methylbenzamide (Example 688), replacing tert-butyl (R)-2-(((4-(5-(4-(2-chloro-6-methylbenzamido)-4-methylpiperidin-1-yl)pyrazin-2-yl)-3-cyanopyrazolo[1,5-a]pyridin-6-yl)oxy)methyl)morpholine-4-carboxylate (Intermediate P148; 0.0575 mmol) with of tert-butyl (S)-2-(((4-(5-(4-(2-chloro-6-methylbenzamido)-4-methylpiperidin-1-yl)pyrazin-2-yl)-3-cyanopyrazolo[1,5-a]pyridin-6-yl)oxy)methyl)morpholine-4-carboxylate (Intermediate P150; 0.164 mmol) and using 1 mL TFA. MS (apci) m/z=601.2 (M+H).

Example 691

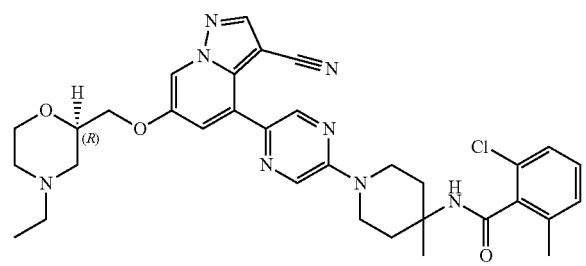

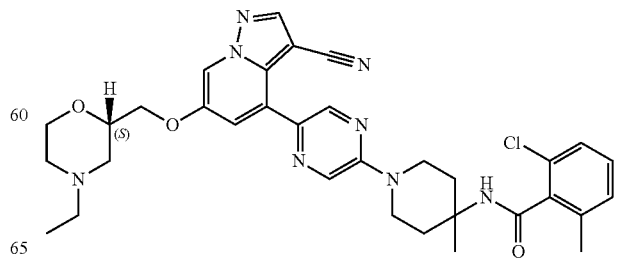

835

(S)-2-chloro-N-(1-(5-(3-cyano-6-((4-ethylmorpholin-2-yl)methoxy)pyrazolo[1,5-a]pyridin-4-yl)pyrazin-2-yl)-4-methylpiperidin-4-yl)-6-methylbenzamide A solution of (S)-2-chloro-N-(1-(5-(3-cyano-6-(morpholin-2-ylmethoxy)pyrazolo[1,5-a]pyridin-4-yl)pyrazin-2-yl)-4-methylpiperidin-4-yl)-6-methylbenzamide (Example 690; 19.5 mg, 0.0324 mmol) in DCM (200 µL) was treated with acetaldehyde (1.88 µL, 0.0649 mmol) and NaBH(AcO)$_3$ (13.8 mg, 0.0649 mmol), and stirred overnight at ambient temperature. The resulting mixture was partitioned between 4:1 DCM:iPrOH and saturated NaHCO$_{3(aq)}$, and eluted through a PS Frit. The combined organic filtrates were concentrated in vacuo to cleanly afford the title compound (9.4 mg, 46% yield). MS (apci) m/z=629.3 (M+H).

Example 692

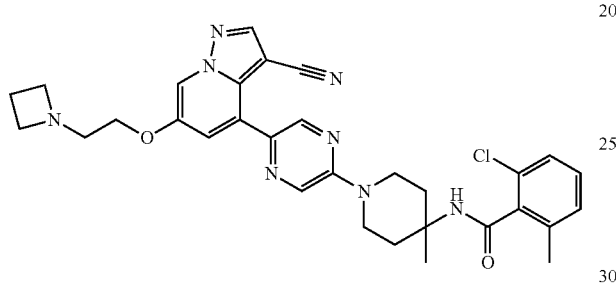

N-(1-(5-(6-(2-(azetidin-1-yl)ethoxy)-3-cyanopyrazolo[1,5-a]pyridin-4-yl)pyrazin-2-yl)-4-methylpiperidin-4-yl)-2-chloro-6-methylbenzamide In a pressure tube, a mixture of 6-(2-(azetidin-1-yl)ethoxy)-4-bromopyrazolo[1,5-a]pyridine-3-carbonitrile (Intermediate P126; 26.4 mg, 0.0822 mmol), 2-chloro-6-methyl-N-(4-methyl-1-(5-(4,4,5,5-tetramethyl-1,3,2-dioxaborolan-2-yl)pyrazin-2-yl)piperidin-4-yl)benzamide (Intermediate R49; 53 mg, 0.0822 mmol), Pd(PPh$_3$)$_4$ (2.85 mg, 0.00247 mmol) and 2 M Na$_2$CO$_{3(aq)}$ (247 µL, 0.493 mmol) in dioxane (2 mL) was sparged with Ar$_{(g)}$. The vessel was sealed, and the mixture was stirred for 2 h at 80° C. After cooling to ambient temperature, the reaction mixture was diluted with water (10 mL) and extracted with 4:1 DCM:iPrOH (5×10 mL). The combined organic extracts were concentrated in vacuo, and the residue was purified by silica chromatography (using 0-10% MeOH in DCM as the gradient eluent) to cleanly afford the title compound (17 mg, 35% yield). MS (apci), m/z=585.3 (M+H).

Example 693

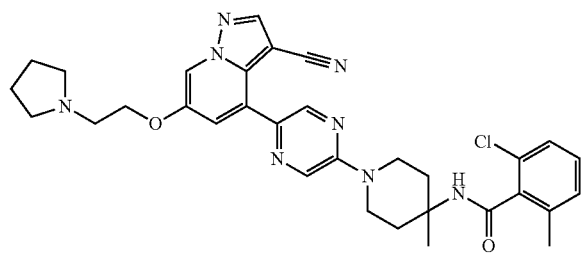 [SMILES: Cc1cccc(Cl)c1C(=O)NC1(C)CCN(c2cnc(-c3cc(OCCN4CCCC4)cn4ncc(C#N)c34)cn2)CC1]

836

2-chloro-N-(1-(5-(3-cyano-6-(2-(pyrrolidin-1-yl)ethoxy)pyrazolo[1,5-a]pyridin-4-yl)pyrazin-2-yl)-4-methylpiperidin-4-yl)-6-methylbenzamide In a pressure tube, a mixture of 6-(2-(pyrrolidin-1-yl)ethoxy)-4-(4,4,5,5-tetramethyl-1,3,2-dioxaborolan-2-yl)pyrazolo[1,5-a]pyridine-3-carbonitrile (Intermediate P143; 68 mg, 0.178 mmol), 2-chloro-N-(1-(5-chloropyrazin-2-yl)-4-methylpiperidin-4-yl)-6-methylbenzamide (Intermediate R48; 67.5 mg, 0.178 mmol), 2 M K$_3$PO$_{4(aq)}$ (267 µL, 0.534 mmol), X-phos (17.0 mg, 0.0356 mmol) and Pd$_2$(dba)$_3$ (8.14 mg, 0.00889 mmol) in dioxane (889 µL) was sparged with Ar$_{(g)}$ for 3 min, and then the vessel was sealed. The reaction mixture was stirred overnight at 80° C. After cooling to ambient temperature, the reaction mixture was diluted with water, and extracted with DCM (4×). The combined organic extracts were washed with brine (1×), dried over anhydrous Na$_2$SO$_{4(s)}$, filtered, and concentrated in vacuo. The residue was purified by silica chromatography (using 0-20% MeOH in DCM as the gradient eluent) to cleanly afford the title compound (2.04 mg, 2% yield). MS (apci), m/z=599.2 (M+H).

Example 694

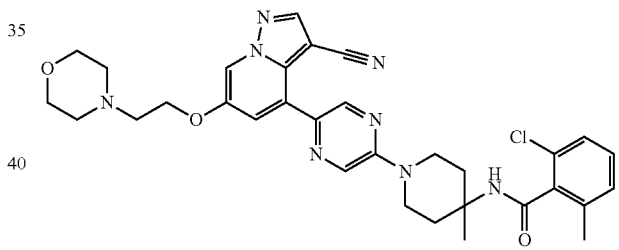

2-chloro-N-(1-(5-(3-cyano-6-(2-morpholinoethoxy)pyrazolo[1,5-a]pyridin-4-yl)pyrazin-2-yl)-4-methylpiperidin-4-yl)-6-methylbenzamide A solution of 4-(5-(4-amino-4-methylpiperidin-1-yl)pyrazin-2-yl)-6-(2-morpholinoethoxy)pyrazolo[1,5-a]pyridine-3-carbonitrile bis(2,2,2-trifluoroacetate) (Intermediate P129; 20 mg, 0.0290 mmol), HATU (13.2 mg, 0.0348 mmol) and 2-chloro-6-methylbenzoic acid (5.43 mg, 0.0319 mmol) in DCM (579 µL) was treated with DIEA (15.2 µL, 0.0869 mmol). The resulting mixture was stirred overnight at ambient temperature, before introducing additional HATU (3.4 mg, 0.015 mmol) and DIEA (5 µL, 0.029 mmol). The resulting mixture was stirred for 60 h at ambient temperature. The reaction mixture was purified directly by silica chromatography (using 0-10% MeOH in EtOAc with 0.2% NH$_4$OH as the gradient eluent) to cleanly afford the title compound (2.87 mg, 16% yield). MS (apci) m/z=615.4 (M+H).

Example 695

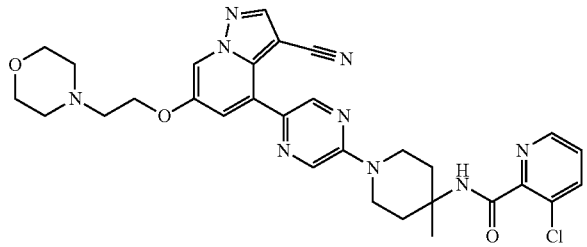 [SMILES: CC1(NC(=O)c2ncccc2Cl)CCN(c2cnc(-c3cc(OCCN4CCOCC4)cn4ncc(C#N)c34)cn2)CC1]

3-chloro-N-(1-(5-(3-cyano-6-(2-morpholinoethoxy)pyrazolo[1,5-a]pyridin-4-yl)pyrazin-2-yl)-4-methylpiperidin-4-yl)picolinamide A solution of 4-(5-(4-amino-4-methylpiperidin-1-yl)pyrazin-2-yl)-6-(2-morpholinoethoxy)pyrazolo[1,5-a]pyridine-3-carbonitrile bis(2,2,2-trifluoroacetate) (Intermediate P129; 20 mg, 0.0290 mmol), HATU (13 mg, 0.035 mmol) and 3-chloropicolinic acid (5.0 mg, 0.032 mmol) in DCM (579 μL) was treated with DIEA (15 μL, 0.087 mmol). The resulting mixture was stirred overnight at ambient temperature, was purified directly by silica chromatography (using 0-10% MeOH in EtOAc with 0.2% NH$_4$OH as the gradient eluent) to cleanly afford the title compound (4 mg, 22% yield). MS (apci) m/z=602.3 (M+H).

Example 696

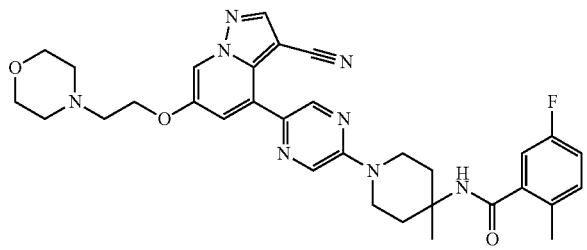 [SMILES: Cc1ccc(F)cc1C(=O)NC1(C)CCN(c2cnc(-c3cc(OCCN4CCOCC4)cn4ncc(C#N)c34)cn2)CC1]

N-(1-(5-(3-cyano-6-(2-morpholinoethoxy)pyrazolo[1,5-a]pyridin-4-yl)pyrazin-2-yl)-4-methylpiperidin-4-yl)-5-fluoro-2-methylbenzamide A solution of 4-(5-(4-amino-4-methylpiperidin-1-yl)pyrazin-2-yl)-6-(2-morpholinoethoxy)pyrazolo[1,5-a]pyridine-3-carbonitrile bis(2,2,2-trifluoroacetate) (Intermediate P129; 20 mg, 0.0290 mmol), HATU (13 mg, 0.035 mmol) and 5-fluoro-2-methylbenzoic acid (4.9 mg, 0.032 mmol) in DCM (579 μL) was treated with DIEA (15 μL, 0.087 mmol). The resulting mixture was stirred overnight at ambient temperature, was purified directly by silica chromatography (using 0-10% MeOH in EtOAc with 0.2% NH$_4$OH as the gradient eluent) to cleanly afford the title compound (4 mg, 22% yield). MS (apci) m/z=599.3 (M+H).

Example 697

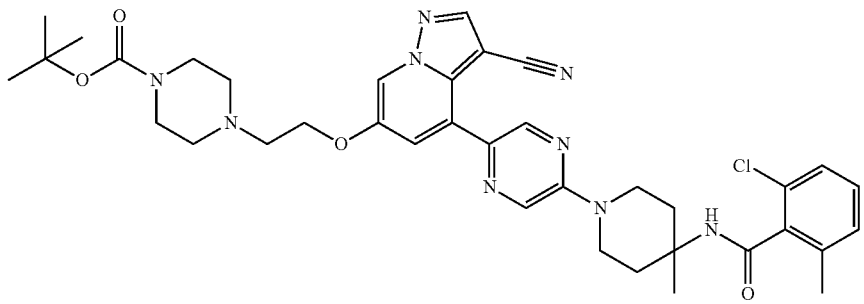 [SMILES: Cc1cccc(Cl)c1C(=O)NC1(C)CCN(c2cnc(-c3cc(OCCN4CCN(C(=O)OC(C)(C)C)CC4)cn4ncc(C#N)c34)cn2)CC1]

tert-butyl 4-(2-((4-(5-(4-(2-chloro-6-methylbenzamido)-4-methylpiperidin-1-yl)pyrazin-2-yl)-3-cyanopyrazolo[1,5-a]pyridin-6-yl)oxy)ethyl)piperazine-1-carboxylate In a pressure tube, a mixture of tert-butyl 4-(2-((3-cyano-4-(4,4,5,5-tetramethyl-1,3,2-dioxaborolan-2-yl)pyrazolo[1,5-a]pyridin-6-yl)oxy)ethyl)piperazine-1-carboxylate (Intermediate P141; 50 mg, 0.10 mmol), 2-chloro-N-(1-(5-chloropyrazin-2-yl)-4-methylpiperidin-4-yl)-6-methylbenzamide (Intermediate R48; 38 mg, 0.10 mmol), 2 M K$_3$PO$_{4(aq)}$ (151 μL, 0.30 mmol), X-phos (9.6 mg, 0.02 mmol) and Pd$_2$(dba)$_3$ (4.6 mg, 0.0050 mmol) in dioxane (503 μL) was sparged with Ar$_{(g)}$ for 3 min, and then the vessel was sealed. The reaction mixture was stirred for 4 h at 80° C. After cooling to ambient temperature, the reaction mixture was diluted with water, and extracted with DCM (4×). The combined organic extracts were washed with brine (1×), dried over anhydrous Na$_2$SO$_{4(s)}$, filtered, and concentrated in vacuo. The residue was purified twice by silica chromatography (using 0-100% EtOAc in Hexanes then with 0-20% MeOH in DCM as the gradient eluent) to cleanly afford the title compound (2.04 mg, 2% yield). MS (apci), m/z=714.3 (M+H).

Example 698

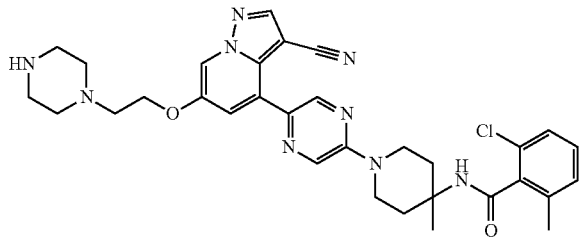 [SMILES: Cc1cccc(Cl)c1C(=O)NC1(C)CCN(c2cnc(-c3cc(OCCN4CCNCC4)cn4ncc(C#N)c34)cn2)CC1]

2-chloro-N-(1-(5-(3-cyano-6-(2-(piperazin-1-yl)ethoxy)pyrazolo[1,5-a]pyridin-4-yl)pyrazin-2-yl)-4-methylpiperidin-4-yl)-6-methylbenzamide A solution of tert-butyl 4-(2-((4-(5-(4-(2-chloro-6-methylbenzamido)-4-methylpiperidin-1-yl)pyrazin-2-yl)-3-cyanopyrazolo[1,5-a]pyridin-6-yl)oxy)ethyl)piperazine-1-carboxylate (Example 697; 26 mg, 0.036 mmol) in DCM (1 mL) and TFA (1 mL, 13 mmol) was stirred for 45 min at ambient temperature. The reaction mixture was treated with saturated NaHCO$_{3(aq)}$ (20 mL), extracted with 4:1 DCM:iPrOH (3×) and eluted through a PS Frit. The organics were concentrated in vacuo, and the residue was purified by silica chromatography (using 0-100% DCM in Hexanes then 0-10% MeOH in DCM with 0.1% NH$_4$OH as the gradient eluent) to cleanly afford the title compound (7 mg, 31% yield). MS (apci) m/z=614.2 (M+H).

Example 699

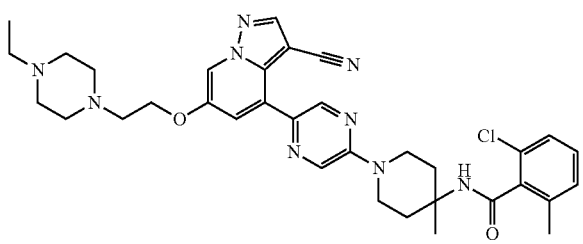 [SMILES: CCN1CCN(CCOc2cc(-c3cnc(N4CCC(C)(NC(=O)c5c(C)cccc5Cl)CC4)cn3)c3c(C#N)cnn3c2)CC1]

2-chloro-N-(1-(5-(3-cyano-6-(2-(4-ethylpiperazin-1-yl)ethoxy)pyrazolo[1,5-a]pyridin-4-yl)pyrazin-2-yl)-4-methylpiperidin-4-yl)-6-methylbenzamide A solution of 2-chloro-N-(1-(5-(3-cyano-6-(2-(piperazin-1-yl)ethoxy)pyrazolo[1,5-a]pyridin-4-yl)pyrazin-2-yl)-4-methylpiperidin-4-yl)-6-methylbenzamide (Example 698; 6 mg, 0.01 mmol) in DCM (488 μL) was treated with acetaldehyde (2.74 μL, 0.0488 mmol) and NaBH(AcO)$_3$ (20.7 mg, 0.10 mmol), then stirred for 2 d at ambient temperature. The resulting mixture was purified directly by silica chromatography (using 0-20% MeOH in DCM with 0.1% NH$_4$OH as the gradient eluent) to cleanly afford the title compound (1.33 mg, 20% yield). MS (apci) m/z=642.3 (M+H).

Example 700

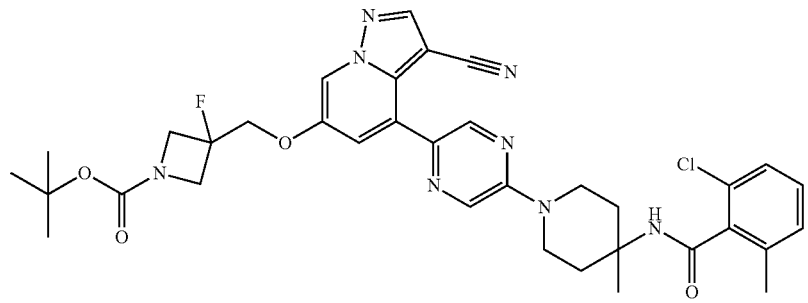 [SMILES: Cc1cccc(Cl)c1C(=O)NC1(C)CCN(c2cnc(-c3cc(OCC4(F)CN(C(=O)OC(C)(C)C)C4)cn4ncc(C#N)c34)cn2)CC1]

tert-butyl 3-(((4-(5-(4-(2-chloro-6-methylbenzamido)-4-methylpiperidin-1-yl)pyrazin-2-yl)-3-cyanopyrazolo[1,5-a]pyridin-6-yl)oxy)methyl)-3-fluoroazetidine-1-carboxylate In a pressure tube, a mixture tert-butyl 3-(((3-cyano-4-(4,4,5,5-tetramethyl-1,3,2-dioxaborolan-2-yl)pyrazolo[1,5-a]pyridin-6-yl)oxy)methyl)-3-fluoroazetidine-1-carboxylate (Intermediate P144; 125 mg, 0.264 mmol), 2-chloro-N-(1-(5-chloropyrazin-2-yl)-4-methylpiperidin-4-yl)-6-methylbenzamide (Intermediate R48; 50 mg, 0.132 mmol), 2 M K$_3$PO$_{4(aq)}$ (198 μL, 0.395 mmol), X-phos (12.6 mg, 0.0264 mmol) and Pd$_2$(dba)$_3$ (6.04 mg, 0.00659 mmol) in dioxane (659 μL) was sparged with Ar$_{(g)}$ for 10 min, and then the vessel was sealed. The reaction mixture was stirred overnight at 80° C. After cooling to ambient temperature, the reaction mixture was diluted with DCM, and extracted with water (3×) and brine (1×). The organic extracts were concentrated in vacuo. The residue was purified by silica chromatography (using 0-100% EtOAc in Hexanes as the gradient eluent) to cleanly afford the title compound (28.2 mg, 31% yield). MS (apci), m/z=689.3 (M+H).

Example 701

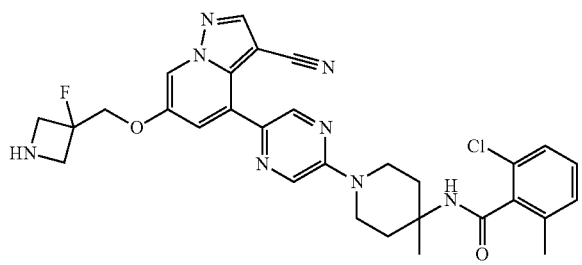 [SMILES: Cc1cccc(Cl)c1C(=O)NC1(C)CCN(c2cnc(-c3cc(OCC4(F)CNC4)cn4ncc(C#N)c34)cn2)CC1]

2-chloro-N-(1-(5-(3-cyano-6-((3-fluoroazetidin-3-yl)methoxy)pyrazolo[1,5-a]pyridin-4-yl)pyrazin-2-yl)-4-methylpiperidin-4-yl)-6-methylbenzamide A solution tert-butyl 3-(((4-(5-(4-(2-chloro-6-methylbenzamido)-4-methylpiperidin-1-yl)pyrazin-2-yl)-3-cyanopyrazolo[1,5-a]pyridin-6-yl)oxy)methyl)-3-fluoroazetidine-1-carboxylate (Example 700; 27 mg, 0.039 mmol) in DCM (1 mL) and TFA (0.2 mL, 2.6 mmol) was stirred overnight at ambient temperature. The reaction mixture was concentrated in vacuo, and the residue was purified by silica chromatography (using 0-100% DCM/10% MeOH/1% NH$_4$OH as the gradient eluent) to cleanly afford the title compound (19 mg, 82% yield). MS (apci) m/z=589.2 (M+H).

Example 702

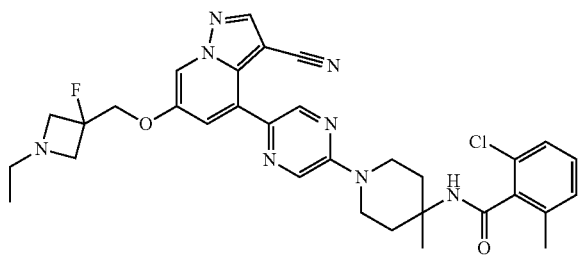 [SMILES: CCN1CC(F)(COc2cc(-c3cnc(N4CCC(C)(NC(=O)c5c(C)cccc5Cl)CC4)cn3)c3c(C#N)cnn3c2)C1]

2-chloro-N-(1-(5-(3-cyano-6-((1-ethyl-3-fluoroazetidin-3-yl)methoxy)pyrazolo[1,5-a]pyridin-4-yl)pyrazin-2-yl)-4-methylpiperidin-4-yl)-6-methylbenzamide A solution of 2-chloro-N-(1-(5-(3-cyano-6-((3-fluoroazetidin-3-yl)methoxy)pyrazolo[1,5-a]pyridin-4-yl)pyrazin-2-yl)-4-methylpiperidin-4-yl)-6-methylbenzamide (Example 701; 16 mg, 0.0270 mmol) in DCM (0.15 mL) was treated with acetaldehyde (7.6 µL, 0.136 mmol) and NaBH(AcO)$_3$ (29 mg, 0.136 mmol), then stirred for 15 h at ambient temperature. The resulting mixture was concentrated in vacuo. The residue was purified by C18 reverse phase chromatography (5-95% acetonitrile in water with 0.1% TFA) to cleanly afford the title compound (10 mg, 60% yield). MS (apci) m/z=617.2 (M+H).

Example 703

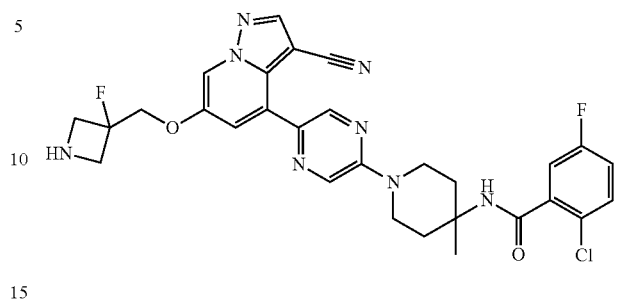

2-chloro-N-(1-(5-(3-cyano-6-((3-fluoroazetidin-3-yl)methoxy)pyrazolo[1,5-a]pyridin-4-yl)pyrazin-2-yl)-4-methylpiperidin-4-yl)-5-fluorobenzamide A solution of tert-butyl 3-(((4-(5-(4-(2-chloro-5-fluorobenzamido)-4-methylpiperidin-1-yl)pyrazin-2-yl)-3-cyanopyrazolo[1,5-a]pyridin-6-yl)oxy)methyl)-3-fluoroazetidine-1-carboxylate (Intermediate P154; 3 mg, 0.0043 mmol) in DCM (0.25 mL) and TFA (0.05 mL, 0.65 mmol) was stirred overnight at ambient temperature. The reaction mixture was diluted with DCM, treated with saturated NaHCO$_{3(aq)}$, and the biphasic mixture was extracted with DCM (3×). The combined organic extracts were washed with brine, dried over anhydrous Na$_2$SO$_{4(s)}$, filtered and concentrated in vacuo to afford the title compound (1.79 mg, 70% yield). MS (apci) m/z=593.2 (M+H).

Example 704

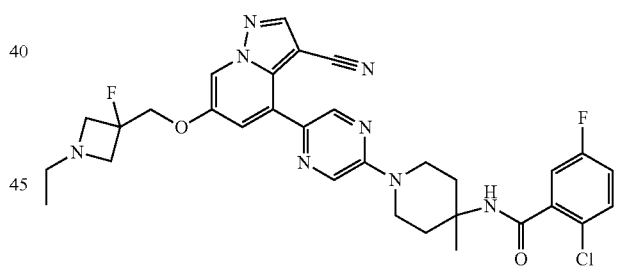

2-chloro-N-(1-(5-(3-cyano-6-((1-ethyl-3-fluoroazetidin-3-yl)methoxy)pyrazolo[1,5-a]pyridin-4-yl)pyrazin-2-yl)-4-methylpiperidin-4-yl)-5-fluorobenzamide A solution of 2-chloro-N-(1-(5-(3-cyano-6-((3-fluoroazetidin-3-yl)methoxy)pyrazolo[1,5-a]pyridin-4-yl)pyrazin-2-yl)-4-methylpiperidin-4-yl)-5-fluorobenzamide (Example 703; 16 mg, 0.0270 mmol) in DCM (1.72 mL) was treated with acetaldehyde (7.57 µL, 0.135 mmol) and NaBH(AcO)$_3$ (57.2 mg, 0.270 mmol), then stirred for 1 h at ambient temperature. The resulting mixture was purified directly by silica chromatography (using 0-20% MeOH in DCM with 0.1% NH$_4$OH as the gradient eluent) to cleanly afford the title compound (2 mg, 12% yield). MS (apci) m/z=521.2 (M+H).

Example 705

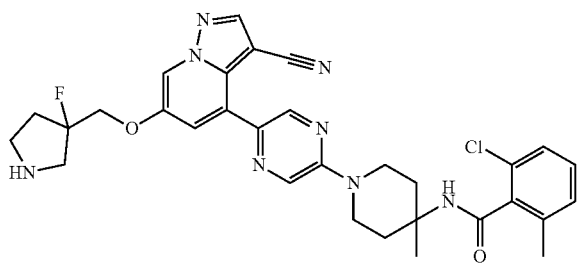 [SMILES: Cc1cccc(Cl)c1C(=O)NC1(C)CCN(c2cnc(-c3cc(OCC4(F)CCNC4)cn4ncc(C#N)c34)cn2)CC1]

2-chloro-N-(1-(5-(3-cyano-6-((3-fluoropyrrolidin-3-yl)methoxy)pyrazolo[1,5-a]pyridin-4-yl)pyrazin-2-yl)-4-methylpiperidin-4-yl)-6-methylbenzamide A solution of tert-butyl 3-(((4-(5-(4-(2-chloro-6-methylbenzamido)-4-methylpiperidin-1-yl)pyrazin-2-yl)-3-cyanopyrazolo[1,5-a]pyridin-6-yl)oxy)methyl)-3-fluoropyrrolidine-1-carboxylate (Intermediate P149; 15 mg, 0.019 mmol) in DCM (1 mL) and TFA (1 mL, 13 mmol) was stirred overnight at ambient temperature. The reaction mixture was concentrated in vacuo, and the residue was purified directly by silica chromatography (using 0-100% DCM in Hexanes then 0-10% MeOH in DCM with 0.1% NH4OH as the gradient eluent to cleanly afford the title compound (7 mg, 60% yield). MS (apci) m/z=603.2 (M+H).

Example 706

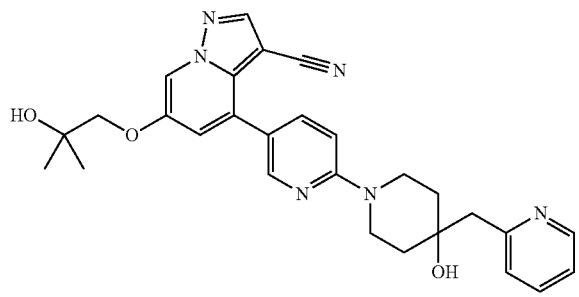 [SMILES: CC(C)(O)COc1cc(-c2ccc(N3CCC(O)(Cc4ccccn4)CC3)nc2)c2c(C#N)cnn2c1]

6-(2-hydroxy-2-methylpropoxy)-4-(6-(4-hydroxy-4-(pyridin-2-ylmethyl)piperidin-1-yl)pyridin-3-yl)pyrazolo[1,5-a]pyridine-3-carbonitrile To a suspension of 4-(6-fluoropyridin-3-yl)-6-(2-hydroxy-2-methylpropoxy)pyrazolo[1,5-a]pyridine-3-carbonitrile (Intermediate P42, 90 mg, 0.276 mmol) in DMSO (2 mL) was added DIEA (193 µL, 1.10 mmol), followed by the addition of 4-(pyridin-2-ylmethyl)piperidin-4-ol hydrochloride (69 mg, 0.303 mmol). The reaction mixture was stirred at 90° C. for 60 h, then purified directly by C18 reverse phase chromatography (using 5-95% acetonitrile in water with 0.1% TFA as the gradient eluent). Fractions containing the desired product were combined, partially concentrated in vacuo to remove the ACN, then partitioned between saturated NaHCO$_{3(aq)}$ and DCM. The biphasic mixture was extracted with additional DCM (2×). The combined organic extracts were dried over anhydrous MgSO$_{4(s)}$, filtered and concentrated in vacuo. The residue was sonicated in Et$_2$O (2 mL) and then concentrated in vacuo to afford the title compound (48 mg, 35% yield). MS (apci) m/z=499.2 (M+H).

Example 707

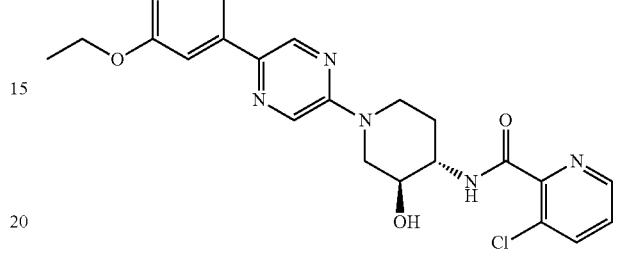

3-chloro-N-((3S,4S)-1-(5-(3-cyano-6-ethoxypyrazolo[1,5-a]pyridin-4-yl)pyrazin-2-yl)-3-hydroxypiperidin-4-yl)picolinamide Step 1: Preparation of tert-butyl ((3S,4S)-1-(5-(3-cyano-6-ethoxypyrazolo[1,5-a]pyridin-4-yl)pyrazin-2-yl)-3-hydroxypiperidin-4-yl)carbamate To a mixture of 6-ethoxy-4-(4,4,5,5-tetramethyl-1,3,2-dioxaborolan-2-yl)pyrazolo[1,5-a]pyridine-3-carbonitrile (Intermediate P110, 296 mg, 0.782 mmol) and tert-butyl ((3S,4S)-1-(5-chloropyrazin-2-yl)-3-hydroxypiperidin-4-yl)carbamate (Intermediate R53, 181 mg, 0.55 mmol) in dioxane (2.7 mL) was added XPhos (52 mg, 0.11 mmol), Pd$_2$(dba)$_3$ (25 mg, 0.028 mmol), and K$_3$PO$_4$ (2 M aq., 0.82 mL). The reaction was sparged with Argon for one minute before heating to 85° C. and stirring overnight. After cooling to RT, the reaction was diluted with water (15 mL) and extracted with DCM (3×15 mL). The combined organic extracts were washed with brine (15 mL), dried over anhydrous Na$_2$SO$_{4(s)}$, filtered, and concentrated in vacuo. The crude material was purified by silica chromatography (0-15% MeOH/DCM) to afford the title compound (147 mg, 56% yield). MS (apci) m/z=480.2 (M+H).

Step 2: Preparation of 4-(5-((3S,4S)-4-amino-3-hydroxypiperidin-1-yl)pyrazin-2-yl)-6-ethoxypyrazolo[1,5-a]pyridine-3-carbonitrile A solution of tert-butyl ((3S,4S)-1-(5-(3-cyano-6-ethoxypyrazolo[1,5-a]pyridin-4-yl)pyrazin-2-yl)-3-hydroxypiperidin-4-yl)carbamate (147 mg, 0.31 mmol) in DCM (3 mL) and TFA (2 mL) was stirred for 30 minutes at RT. The solution was concentrated in vacuo, then diluted with saturated NaHCO$_3$ (10 mL) and extracted with DCM (3×10 mL). The combined organic extracts were dried over anhydrous Na$_2$SO$_{4(s)}$, filtered, and concentrated in vacuo to afford the title compound (58 mg, 50% yield). MS (apci) m/z=380.2 (M+H).

Step 3: Preparation of 3-chloro-N-((3S,4S)-1-(5-(3-cyano-6-ethoxypyrazolo[1,5-a]pyridin-4-yl)pyrazin-2-yl)-3-hydroxypiperidin-4-yl)picolinamide To a solution of 4-(5-((3S,4S)-4-amino-3-hydroxypiperidin-1-yl)pyrazin-2-yl)-6-ethoxypyrazolo[1,5-a]pyridine-3- carbonitrile (21.2 mg, 0.056 mmol) in DMSO (0.6 mL) was added 3-chloropicolinic acid (8.8 mg, 0.056 mmol) and DIEA (0.1 mL, 0.56 mmol), followed by the addition of HATU (23.4 mg, 0.061 mmol). After stirring for 80 minutes at RT, the reaction mixture was diluted with saturated NaHCO$_3$ (5 mL) and extracted with DCM (3×5 mL). The combined organic extracts were washed with brine (5 mL), dried over anhydrous Na$_2$SO$_{4(s)}$, filtered, and concentrated in vacuo to afford the title compound (29 mg, 99% yield). MS (apci) m/z=519.1 (M+H).

The compounds in Table ZZZ were prepared using a similar method as described in Example 707 Step 3, replacing 3-chloropicolinic acid with the appropriate carboxylic acid.

TABLE ZZZ

| Ex. # | Structure | Chemical Name | LCMS m/z |
|---|---|---|---|
| 708 | 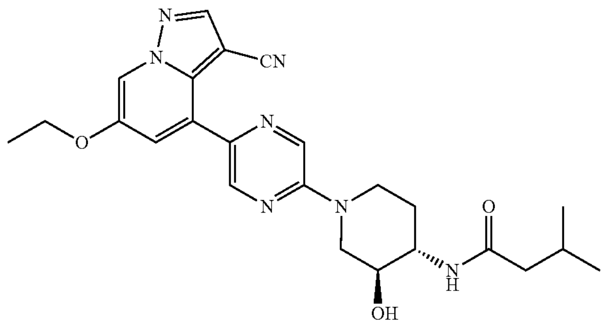 [SMILES: CCOc1cc(-c2cnc(N3CC[C@H](NC(=O)CC(C)C)[C@@H](O)C3)cn2)c2c(C#N)cnn2c1] | N-((3S,4S)-1-(5-(3-cyano-6-ethoxypyrazolo[1,5-a]pyridin-4-yl)pyrazin-2-yl)-3-hydroxypiperidin-4-yl)-3-methylbutanamide | 464.2 (M + H) |
| 709 | 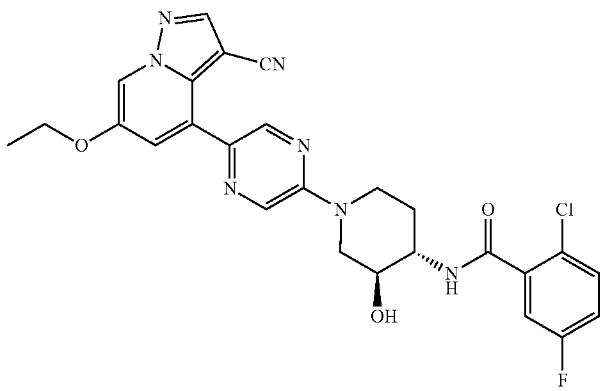 [SMILES: CCOc1cc(-c2cnc(N3CC[C@H](NC(=O)c4cc(F)ccc4Cl)[C@@H](O)C3)cn2)c2c(C#N)cnn2c1] | 2-chloro-N-((3S,4S)-1-(5-(3-cyano-6-ethoxypyrazolo[1,5-a]pyridin-4-yl)pyrazin-2-yl)-3-hydroxypiperidin-4-yl)-5-fluorobenzamide | 536.1 (M + H) |
| 710 | 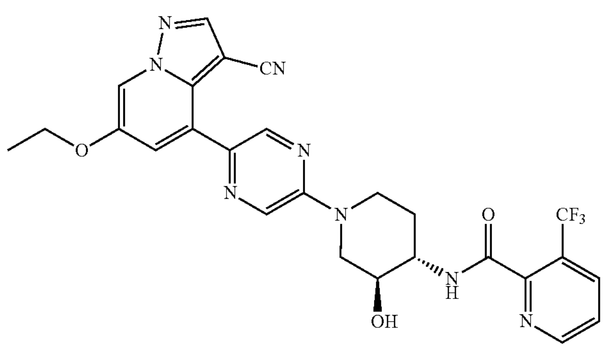 [SMILES: CCOc1cc(-c2cnc(N3CC[C@H](NC(=O)c4ncccc4C(F)(F)F)[C@@H](O)C3)cn2)c2c(C#N)cnn2c1] | N-((3S,4S)-1-(5-(3-cyano-6-ethoxypyrazolo[1,5-a]pyridin-4-yl)pyrazin-2-yl)-3-hydroxypiperidin-4-yl)-3-(trifluoromethyl)picolinamide | 553.1 (M + H) |
| 711 | 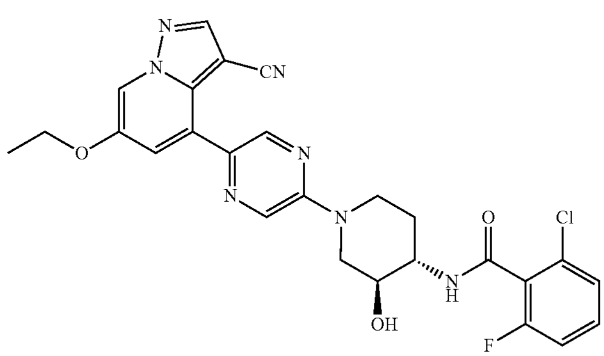 [SMILES: CCOc1cc(-c2cnc(N3CC[C@H](NC(=O)c4c(F)cccc4Cl)[C@@H](O)C3)cn2)c2c(C#N)cnn2c1] | 2-chloro-N-((3S,4S)-1-(5-(3-cyano-6-ethoxypyrazolo[1,5-a]pyridin-4-yl)pyrazin-2-yl)-3-hydroxypiperidin-4-yl)-6-fluorobenzamide | 536.1 (M + H) |

| Ex. # | Structure | Chemical Name | LCMS m/z |
|---|---|---|---|
| 712 | 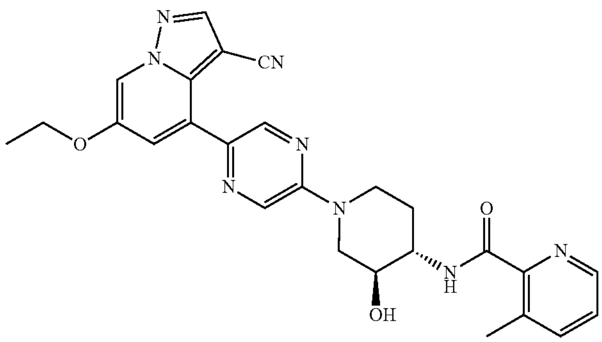 [SMILES: CCOc1cc(-c2cnc(N3CC[C@H](NC(=O)c4ncccc4C)[C@@H](O)C3)cn2)c2c(C#N)cnn2c1] | N-((3S,4S)-1-(5-(3-cyano-6-ethoxypyrazolo[1,5-a]pyridin-4-yl)pyrazin-2-yl)-3-hydroxypiperidin-4-yl)-3-methylpicolinamide | 499.2, 521.2 (M + H, M + Na) |

Example 713

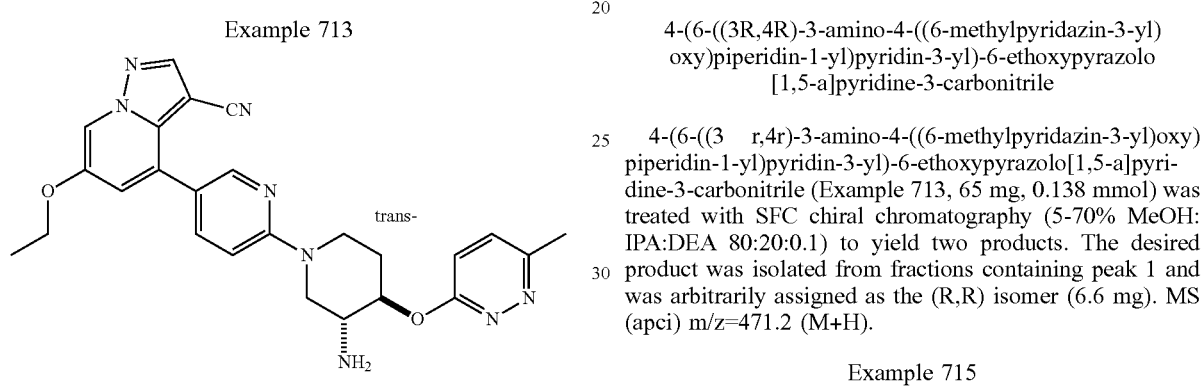

4-(6-((3 r,4r)-3-amino-4-((6-methylpyridazin-3-yl)oxy)piperidin-1-yl)pyridin-3-yl)-6-ethoxypyrazolo[1,5-a]pyridine-3-carbonitrile A mixture of tert-butyl ((3r,4r)-1-(5-(3-cyano-6-ethoxypyrazolo[1,5-a]pyridin-4-yl)pyridin-2-yl)-4-hydroxypiperidin-3-yl)carbamate (Intermediate P158, 0.025 g, 0.052 mmol), 3-chloro-6-methylpyridazine (0.010 g, 0.078 mmol) and NaH (0.0042 g, 0.10 mmol) in DMF (0.26 mL) was heated to 90° C. overnight. The mixture was then concentrated down and purified by preparative HPLC (5-95% ACN in water with 1% TFA). The mixture was then worked up with DCM and sat. NaHCO₃. The organic layers were washed with brine, dried with Na₂SO₄ and concentrated to yield the title product (6.4 mg, 26% yield). MS (apci) m/z=471.2 (M+H).

Example 714

4-(6-((3R,4R)-3-amino-4-((6-methylpyridazin-3-yl)oxy)piperidin-1-yl)pyridin-3-yl)-6-ethoxypyrazolo[1,5-a]pyridine-3-carbonitrile 4-(6-((3 r,4r)-3-amino-4-((6-methylpyridazin-3-yl)oxy)piperidin-1-yl)pyridin-3-yl)-6-ethoxypyrazolo[1,5-a]pyridine-3-carbonitrile (Example 713, 65 mg, 0.138 mmol) was treated with SFC chiral chromatography (5-70% MeOH:IPA:DEA 80:20:0.1) to yield two products. The desired product was isolated from fractions containing peak 1 and was arbitrarily assigned as the (R,R) isomer (6.6 mg). MS (apci) m/z=471.2 (M+H).

Example 715

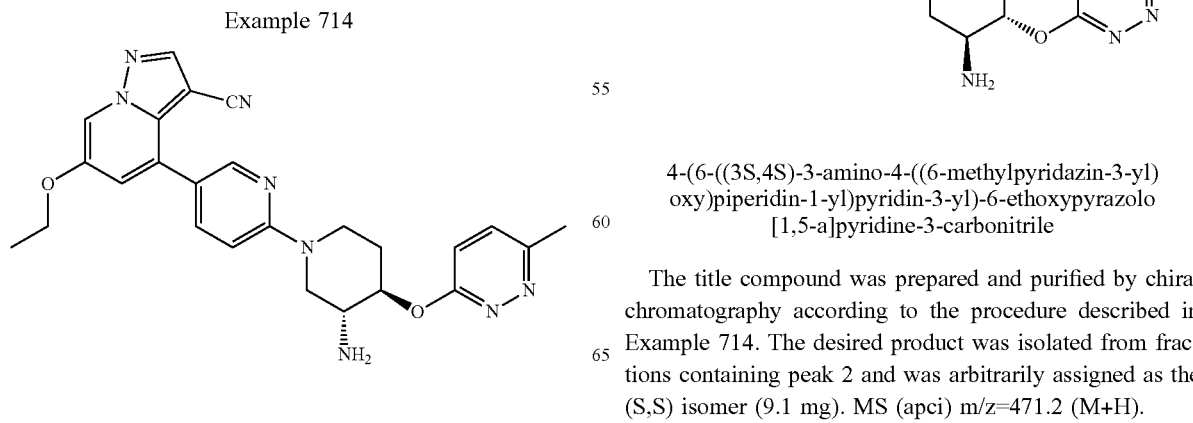

4-(6-((3S,4S)-3-amino-4-((6-methylpyridazin-3-yl)oxy)piperidin-1-yl)pyridin-3-yl)-6-ethoxypyrazolo[1,5-a]pyridine-3-carbonitrile The title compound was prepared and purified by chiral chromatography according to the procedure described in Example 714. The desired product was isolated from fractions containing peak 2 and was arbitrarily assigned as the (S,S) isomer (9.1 mg). MS (apci) m/z=471.2 (M+H).

Example 716

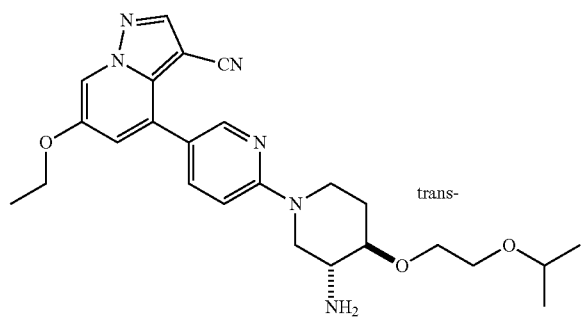 [SMILES: CCOc1cc(-c2ccc(N3CC[C@@H](OCCOC(C)C)[C@H](N)C3)nc2)c2c(C#N)cnn2c1]

4-(6-((3r,4r)-3-amino-4-(2-isopropoxyethoxy)piperidin-1-yl)pyridin-3-yl)-6-ethoxypyrazolo[1,5-a]pyridine-3-carbonitrile A mixture of tert-butyl ((3r,4r)-1-(5-(3-cyano-6-ethoxypyrazolo[1,5-a]pyridin-4-yl)pyridin-2-yl)-4-hydroxypiperidin-3-yl)carbamate (Intermediate P158, 0.035 g, 0.073 mmol), 2-(2-bromoethoxy)propane (0.012 g, 0.073 mmol) and NaH (0.0035 g, 0.088 mmol) in DMF (0.49 mL) was heated to 90° C. overnight. The mixture was concentrated and purified by preparative HPLC (5-95% ACN in water with 1% TFA). The fractions containing the product were concentrated and partitioned between DCM and sat. NaHCO₃. After phase-separation and aqueous extractions with DCM, the combined organic extracts were washed with brine, dried with Na₂SO₄, and concentrated to yield the title product (2.9 mg, 8.5% yield). MS (apci) m/z=465.3 (M+H).

Example 717

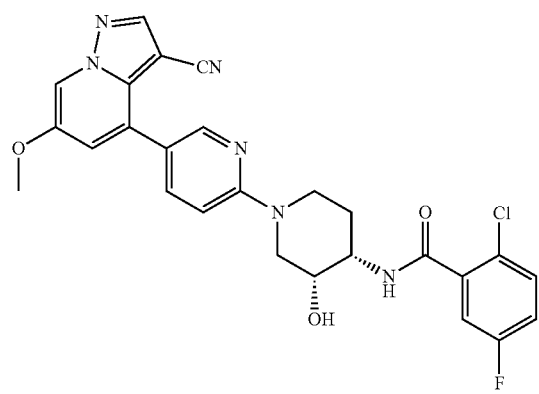 [SMILES: COc1cc(-c2ccc(N3CC[C@H](NC(=O)c4cc(F)ccc4Cl)[C@H](O)C3)nc2)c2c(C#N)cnn2c1]

2-chloro-N-((3R,4S)-1-(5-(3-cyano-6-methoxypyrazolo[1,5-a]pyridin-4-yl)pyridin-2-yl)-3-hydroxypiperidin-4-yl)-5-fluorobenzamide A mixture of 4-(6-((3R,4S)-4-amino-3-hydroxypiperidin-1-yl)pyridin-3-yl)-6-methoxypyrazolo[1,5-a]pyridine-3-carbonitrile (Intermediate P159, 0.025 g, 0.0686 mmol), 2-chloro-5-fluorobenzoic acid (0.0180 g, 0.103 mmol), HATU (0.0522 g, 0.137 mmol) and Hunig's base (0.0358 ml, 0.206 mmol) in DMSO (0.686 mL) was stirred at RT overnight. The mixture was worked up with DCM and water. The organic layer was washed with brine, dried with Na₂SO₄, filtered and concentrated. The crude material was purified by preparative HPLC (5-95% ACN in water with 1% TFA). The combined fractions containing the product were worked up with DCM and sat. NaHCO₃. The combined organic extracts were washed with brine, dried (Na₂SO₄), filtered and concentrated to yield the title product (0.0198 g, 55.4% yield). MS (apci) m/z=521.1 (M+H).

Example 718

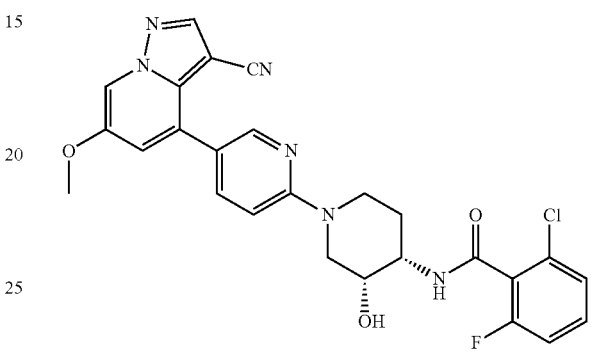

2-chloro-N-((3R,4S)-1-(5-(3-cyano-6-methoxypyrazolo[1,5-a]pyridin-4-yl)pyridin-2-yl)-3-hydroxypiperidin-4-yl)-6-fluorobenzamide The title product was prepared according to the procedure described in Example 717, replacing 2-chloro-5-fluorobenzoic acid with 2-chloro-6-fluorobenzoic acid. MS (apci) m/z=521.1 (M+H).

Example 719

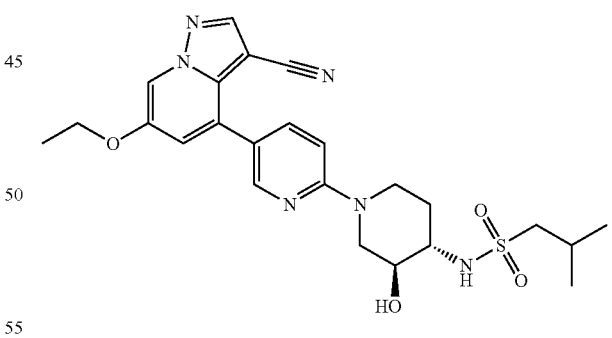

N-((3S,4S)-1-(5-(3-cyano-6-ethoxypyrazolo[1,5-a]pyridin-4-yl)pyridin-2-yl)-3-hydroxypiperidin-4-yl)-2-methylpropane-1-sulfonamide A solution of 4-(6-((3S,4S)-4-amino-3-hydroxypiperidin-1-yl)pyridin-3-yl)-6-ethoxypyrazolo[1,5-a]pyridine-3-carbonitrile dihydrochloride (Example 522, Step 1; 30.6 mg, 0.0678 mmol) and 2-methylpropane-1-sulfonyl chloride (15.9 mg, 0.102 mmol) in DCM (1 mL) was treated with DIEA (0.118 mL, 0.678 mmol) and stirred at RT for 1 h. The reaction mixture was treated with silica chromatography (30-100% EtOAc in hexanes) to yield the title product (12.3 mg, 36.4% yield). MS (apci) m/z=499.2, 521.2 (M+H, M+Na).

Example 720

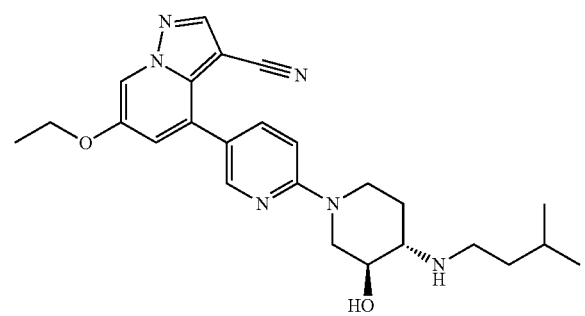 [SMILES: CCOc1cc(-c2ccc(N3CC[C@H](NCCC(C)C)[C@@H](O)C3)nc2)c2c(C#N)cnn2c1]

6-ethoxy-4-(6-((3S,4S)-3-hydroxy-4-(isopentylamino)piperidin-1-yl)pyridin-3-yl)pyrazolo[1,5-a]pyridine-3-carbonitrile The title product was prepared according to the procedure described in Example 719, replacing 2-methylpropane-1-sulfonyl chloride with 1-bromo-3-methylbutane. The crude material was first treated with silica chromatography (0-25% MeOH in DCM), followed by preparative HPLC (15-85% ACN in water with 0.1% TFA). The combined fractions containing the product were partitioned between sat. NaHCO₃ and 4:1 DCM/IPA, and the combined organic extracts were passed thru a PS-Separator frit and concentrated to yield the title product as white solid (2.7 mg, 8% yield) MS (apci) m/z=449.3 (M+H).

Example 721

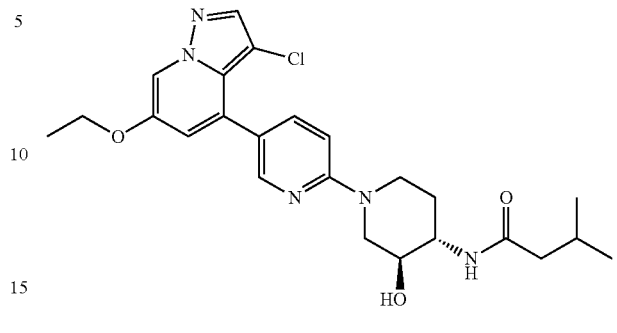

N-((3S,4S)-1-(5-(3-chloro-6-ethoxypyrazolo[1,5-a]pyridin-4-yl)pyridin-2-yl)-3-hydroxypiperidin-4-yl)-3-methylbutanamide A solution of (3S,4S)-4-amino-1-(5-(3-chloro-6-ethoxypyrazolo[1,5-a]pyridin-4-yl)pyridin-2-yl)piperidin-3-ol dihydrochloride (Intermediate P161; 50 mg, 0.109 mmol) in DCM (1 mL, 0.109 mmol) was treated with DIEA (0.190 mL, 1.09 mmol) and 3-methylbutanoyl chloride (19.6 mg, 0.163 mmol). The reaction mixture was stirred at rt for 1 h, then purified by silica chromatography (20-100% EtOAc in hexanes) to yield the title product as white solid (14.6 mg, 28% yield). MS (apci) m/z=472.2 (M+H).

The compounds in Table X1 were prepared using a similar method to that described in Step 2 in the synthesis of N-((3S,4S)-1-(5-(3-cyano-6-ethoxypyrazolo[1,5-a]pyridin-4-yl)pyridin-2-yl)-3-hydroxypiperidin-4-yl)-1-(trifluoromethyl)cyclobutane-1-carboxamide (Example 522), replacing 1-(trifluoromethyl)cyclobutane-1-carboxylic acid with the appropriate carboxylic acid. Reactions were monitored for completion by LCMS, and reaction durations were adjusted accordingly. The title compounds were isolated following a chromatographic purification utilizing an appropriate gradient eluent.

TABLE X1

| Ex # | Structure | Chemical Name | MS (apci) m/z |
|---|---|---|---|
| 722 | 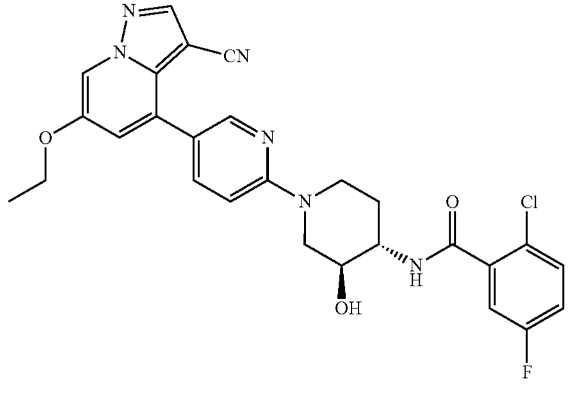 [SMILES: CCOc1cc(-c2ccc(N3CC[C@H](NC(=O)c4cc(F)ccc4Cl)[C@@H](O)C3)nc2)c2c(C#N)cnn2c1] | 2-chloro-N-((3S,4S)-1-(5-(3-cyano-6-ethoxypyrazolo[1,5-a]pyridin-4-yl)pyridin-2-yl)-3-hydroxypiperidin-4-yl)-5-fluorobenzamide | 535.2 (M + H) |

TABLE X1-continued

| Ex # | Structure | Chemical Name | MS (apci) m/z |
|---|---|---|---|
| 723 | 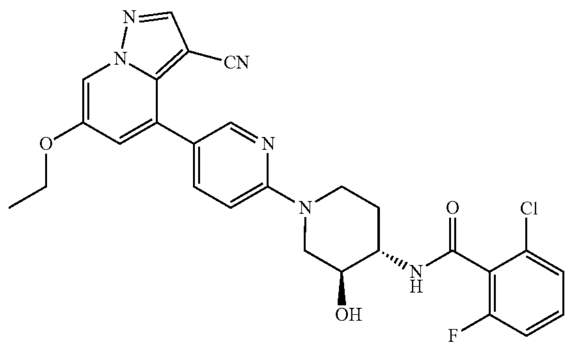 [SMILES: CCOc1cc(-c2ccc(N3CC[C@H](NC(=O)c4c(F)cccc4Cl)[C@@H](O)C3)nc2)c2c(C#N)cnn2c1] | 2-chloro-N-((3S,4S)-1-(5-(3-cyano-6-ethoxypyrazolo[1,5-a]pyridin-4-yl)pyridin-2-yl)-3-hydroxypiperidin-4-yl)-6-fluorobenzamide | 535.1 (M + H) |
| 724 | 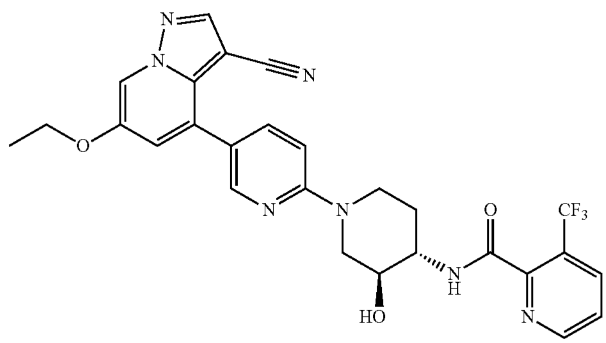 [SMILES: CCOc1cc(-c2ccc(N3CC[C@H](NC(=O)c4ncccc4C(F)(F)F)[C@@H](O)C3)nc2)c2c(C#N)cnn2c1] | N-((3S,4S)-1-(5-(3-cyano-6-ethoxypyrazolo[1,5-a]pyridin-4-yl)pyridin-2-yl)-3-hydroxypiperidin-4-yl)-3-(trifluoromethyl)picolinamide | 552.1 (M + H) |
| 725 | 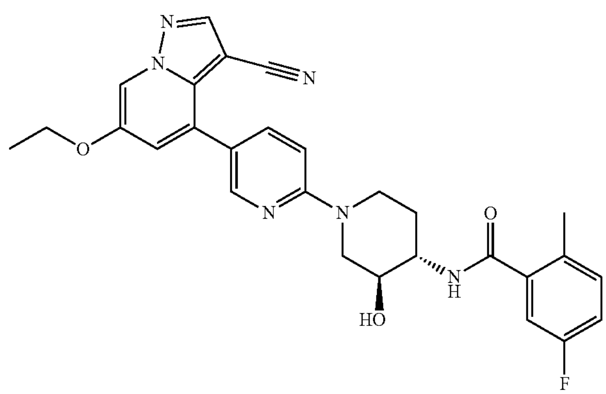 [SMILES: CCOc1cc(-c2ccc(N3CC[C@H](NC(=O)c4cc(F)ccc4C)[C@@H](O)C3)nc2)c2c(C#N)cnn2c1] | N-((3S,4S)-1-(5-(3-cyano-6-ethoxypyrazolo[1,5-a]pyridin-4-yl)pyridin-2-yl)-3-hydroxypiperidin-4-yl)-5-fluoro-2-methylbenzamide | 515.2, 557.2 (M + H, M + Na) |
| 726 | 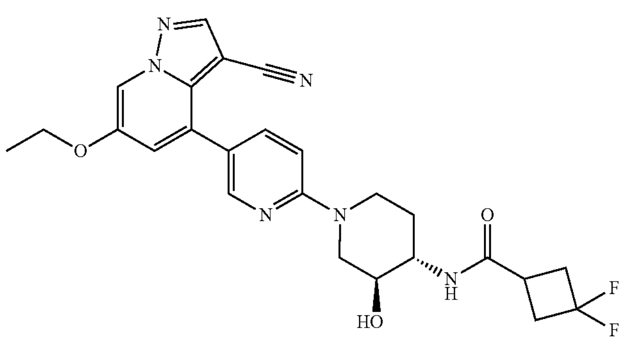 [SMILES: CCOc1cc(-c2ccc(N3CC[C@H](NC(=O)C4CC(F)(F)C4)[C@@H](O)C3)nc2)c2c(C#N)cnn2c1] | N-((3S,4S)-1-(5-(3-cyano-6-ethoxypyrazolo[1,5-a]pyridin-4-yl)pyridin-2-yl)-3-hydroxypiperidin-4-yl)-3,3-difluorocyclobutane-1-carboxamide | 497.2 (M + H) |

| Ex # | Structure | Chemical Name | MS (apci) m/z |
|---|---|---|---|
| 727 | 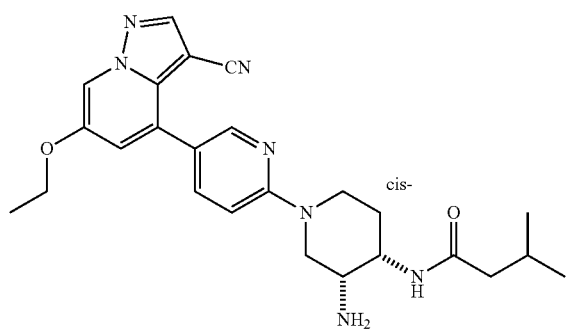 | N-((3S,4S)-1-(5-(3-cyano-6-ethoxypyrazolo[1,5-a]pyridin-4-yl)pyridin-2-yl)-3-hydroxypiperidin-4-yl)-4,4,4-trifluorobutanamide | 503.1 (M + H) |

Example 728

N-((3r,4s)-3-amino-1-(5-(3-cyano-6-ethoxypyrazolo[1,5-a]pyridin-4-yl)pyridin-2-yl)piperidin-4-yl)-3-methylbutanamide Step 1: Preparation of (3r,4r)-3-((tert-butoxycarbonyl)amino)-1-(5-(3-cyano-6-ethoxypyrazolo[1,5-a]pyridin-4-yl)pyridin-2-yl)piperidin-4-yl methanesulfonate A mixture of tert-butyl ((3r,4r)-1-(5-(3-cyano-6-ethoxypyrazolo[1,5-a]pyridin-4-yl)pyridin-2-yl)-4-hydroxypiperidin-3-yl)carbamate (Intermediate P158, 0.0234 g, 0.0489 mmol), methanesulfonyl chloride (0.00454 ml, 0.0587 mmol) and Hunig's base (0.0128 ml, 0.0733 mmol) in DCM (0.489 mL) was stirred at RT overnight. The mixture was worked up with DCM and water. The organic layers were washed with brine, dried with Na₂SO₄ and concentrated to yield the title compound (0.025 g, 91.9% yield). MS (apci) m/z=557.2 (M+H).

Step 2: Preparation of tert-butyl ((3r,4s)-4-azido-1-(5-(3-cyano-6-ethoxypyrazolo[1,5-a]pyridin-4-yl)pyridin-2-yl)piperidin-3-yl)carbamate (3r,4r)-3-((tert-butoxycarbonyl)amino)-1-(5-(3-cyano-6-ethoxypyrazolo[1,5-a]pyridin-4-yl)pyridin-2-yl)piperidin-4-yl methanesulfonate (0.025 g, 0.045 mmol) and NaN₃ (0.0035 g, 0.054 mmol) in DMF (0.45 mL) was heated to 90° C. overnight. The mixture was worked up with DCM and water. The organic layers were combined, washed with brine, dried over Na₂SO₄, and concentrated to yield the title compound (0.021 g, 93% yield). MS (apci) m/z=504.2 (M+H).

Step 3: Preparation of tert-butyl ((3r,4s)-4-amino-1-(5-(3-cyano-6-ethoxypyrazolo[1,5-a]pyridin-4-yl)pyridin-2-yl)piperidin-3-yl)carbamate Tert-butyl ((3r,4s)-4-azido-1-(5-(3-cyano-6-ethoxypyrazolo[1,5-a]pyridin-4-yl)pyridin-2-yl)piperidin-3-yl)carbamate (0.021 g, 0.042 mmol) and Pd/C was stirred in MeOH under H₂ balloon for 4 hours. The mixture was then filtered and concentrated down to yield the title compound (0.017 g, 85% yield). MS (apci) m/z=478.2 (M+H).

Step 4: Preparation of N-((3r,4r)-3-amino-1-(5-(3-cyano-6-ethoxypyrazolo[1,5-a]pyridin-4-yl)pyridin-2-yl)piperidin-4-yl)-3-methylbutanamide A mixture of tert-butyl ((3 r,4s)-4-amino-1-(5-(3-cyano-6-ethoxypyrazolo[1,5-a]pyridin-4-yl)pyridin-2-yl)piperidin-3-yl)carbamate (0.017 g, 0.0356 mmol), 3-methylbutanoic acid (0.00545 g, 0.0534 mmol), HATU (0.0271 g, 0.0712 mmol) and Hunig's base (0.00806 mL, 0.0463 mmol) in DMSO (0.356 mL) was stirred RT overnight. The mixture was worked up with DCM and water. The organic layers were combined, washed with brine, dried over Na₂SO₄ and concentrated, and then stirred in DCM (1 mL) and TFA (1 mL) for 1 h. The mixture was concentrated and then purified by preparative HPLC (5-95% ACN in water with 1% TFA). The fractions containing the product were combined and worked up with DCM and sat. NaHCO₃. The combined organic extracts were washed with brine, dried (Na₂SO₄), filtered and concentrated to yield the title product (0.0066 g, 40% yield). MS (apci) m/z=462.2 (M+H).

Example 729

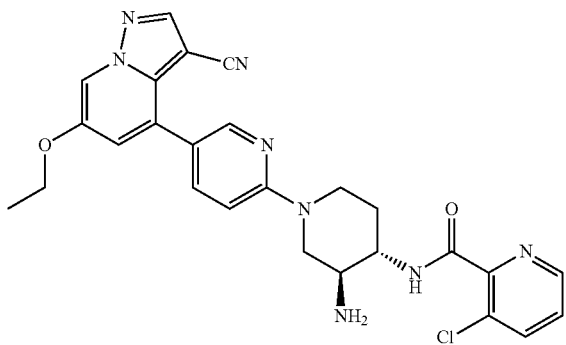 [SMILES: CCOc1cc(-c2ccc(N3CC[C@H](NC(=O)c4ncccc4Cl)[C@@H](N)C3)nc2)c2c(C#N)cnn2c1]

N-((3S,4S)-3-amino-1-(5-(3-cyano-6-ethoxypyrazolo[1,5-a]pyridin-4-yl)pyridin-2-yl)piperidin-4-yl)-3-chloropicolinamide A mixture of tert-butyl ((3S,4S)-4-amino-1-(5-(3-cyano-6-ethoxypyrazolo[1,5-a]pyridin-4-yl)pyridin-2-yl)piperidin-3-yl)carbamate (Intermediate P162; 0.026 g, 0.0544 mmol), 3-chloropicolinic acid (0.00944 g, 0.0599 mmol), HATU (0.0414 g, 0.109 mmol) and Hunig's base (0.0123 ml, 0.0708 mmol) in DMSO (0.544 mL) was stirred at room temp overnight. The mixture was worked up with DCM and water. The organic layer was washed with brine, dried with $Na_2SO_4$, filtered and concentrated. The concentrated material was stirred in DCM (1 mL) and TFA (1 mL) for 1 h, then concentrated and purified by preparative HPLC (5-95% acetonitrile in water with 1% TFA). The fractions containing the product were combined and partitioned between DCM and saturated $NaHCO_3$ The combined organic extracts were washed with brine, dried ($Na_2SO_4$), filtered and concentrated to yield the title product (0.008 g, 28.4% yield). MS (apci) m/z=517.2 (M+H).

The compounds in Table X2 were prepared using a similar method to that described in Example 729, replacing 3-chloropicolinic acid with the appropriate carboxylic acid. Reactions were monitored for completion by LCMS, and reaction durations were adjusted accordingly. The title compounds were isolated following a chromatographic purification utilizing an appropriate gradient eluent.

TABLE X2

| Ex # | Structure | Chemical Name | MS (apci) m/z |
| --- | --- | --- | --- |
| 730 | 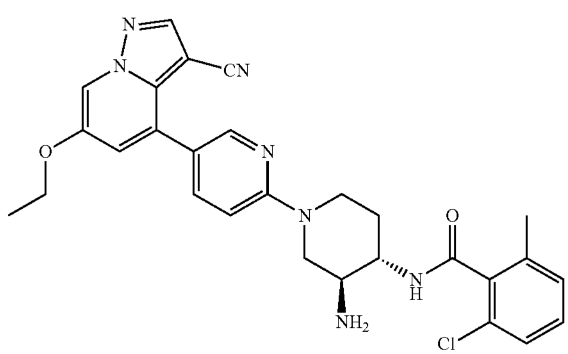 [SMILES: CCOc1cc(-c2ccc(N3CC[C@H](NC(=O)c4c(C)cccc4Cl)[C@@H](N)C3)nc2)c2c(C#N)cnn2c1] | N-((3S,4S)-3-amino-1-(5-(3-cyano-6-ethoxypyrazolo[1,5-a]pyridin-4-yl)pyridin-2-yl)piperidin-4-yl)-2-chloro-6-methylbenzamide | 530.2 (M + H) |
| 731 | 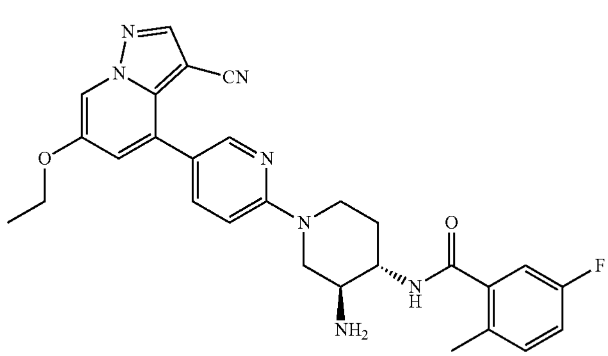 [SMILES: CCOc1cc(-c2ccc(N3CC[C@H](NC(=O)c4cc(F)ccc4C)[C@@H](N)C3)nc2)c2c(C#N)cnn2c1] | N-((3S,4S)-3-amino-1-(5-(3-cyano-6-ethoxypyrazolo[1,5-a]pyridin-4-yl)pyridin-2-yl)piperidin-4-yl)-5-fluoro-2-methylbenzamide | 514.2 (M + H) |

Example 732

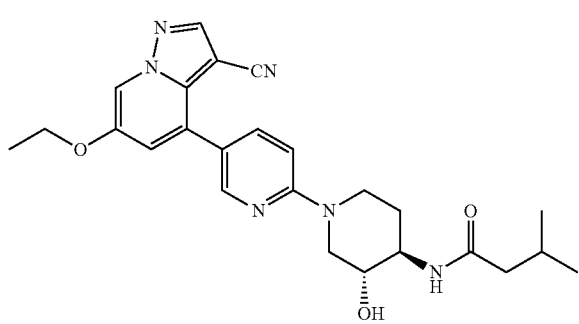 [SMILES: CCOc1cc(-c2ccc(N3CC[C@@H](NC(=O)CC(C)C)[C@H](O)C3)nc2)c2c(C#N)cnn2c1]

N-((3R,4R)-1-(5-(3-cyano-6-ethoxypyrazolo[1,5-a]pyridin-4-yl)pyridin-2-yl)-3-hydroxypiperidin-4-yl)-3-methylbutanamide Step 1: Preparation of 4-(6-((3R,4R)-4-amino-3-hydroxypiperidin-1-yl)pyridin-3-yl)-6-ethoxypyrazolo[1,5-a]pyridine-3-carbonitrile To a solution of tert-butyl ((3R,4R)-1-(5-(3-cyano-6-ethoxypyrazolo[1,5-a]pyridin-4-yl)pyridin-2-yl)-3-hydroxypiperidin-4-yl)carbamate (Example 512; 110 mg, 0.23 mmol) in DCM (2 mL) was added TFA (1 mL). After 90 min stirring, the reaction was concentrated, taken up in minimal amount of MeOH and passed thru a Pl-HCO3 resin plug. Removal of solvent under reduced pressure yielded the title compound, which was directly used in the next step without further purifications, assuming quantitative yield. MS (apci) m/z=379.2 (M+H).

Step 2: Preparation of N-((3R,4R)-1-(5-(3-cyano-6-ethoxypyrazolo[1,5-a]pyridin-4-yl)pyridin-2-yl)-3-hydroxypiperidin-4-yl)-3-methylbutanamide A mixture of 4-(6-((3R,4R)-4-amino-3-hydroxypiperidin-1-yl)pyridin-3-yl)-6-ethoxypyrazolo[1,5-a]pyridine-3-carbonitrile (24 mg, 0.0634 mmol), 3-methylbutanoic acid (0.01 mL, 0.063 mmol), DCM (0.6 mL), DIEA (0.066 mL, 0.38 mmol) and HATU (29 mg, 0.076 mmol) was stirred at RT overnight. The reaction mixture was partitioned between DCM and water (10 mL each). The organic layer was concentrated and purified by preparative HPLC (5-95% acetonitrile in water with 1% TFA) to yield the title product (2 mg, 6% yield). MS (apci) m/z=463.2 (M+H).

Example 733

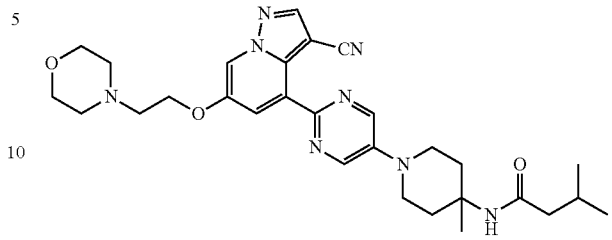

N-(1-(2-(3-cyano-6-(2-morpholinoethoxy)pyrazolo[1,5-a]pyridin-4-yl)pyrimidin-5-yl)-4-methylpiperidin-4-yl)-3-methylbutanamide To a solution of 4-(5-(4-amino-4-methylpiperidin-1-yl)pyrimidin-2-yl)-6-(2-morpholinoethoxy)pyrazolo[1,5-a]pyridine-3-carbonitrile (P163, 4 mg, 0.00865 mmol) in DCM (0.3 mL) was added 3-methylbutanoic acid (0.001 mL, 0.013 mmol), N-ethyl-N-isopropylpropan-2-amine (0.009 mL, 0.052 mmol) and HATU (4.3 mg, 0.0112 mmol). After stirred at RT overnight, the reaction was partitioned between DCM and saturated NaHCO₃. After phase-separation, the aqueous was extracted with DCM (3×10 mL). The organic extracts were combined and concentrated. The crude material was purified by preparative HPLC (5-95% acetonitrile in water with 1% TFA) to yield the title product (1.7 mg, 36%). MS (apci) m/z=547.3 (M+H).

Example 734

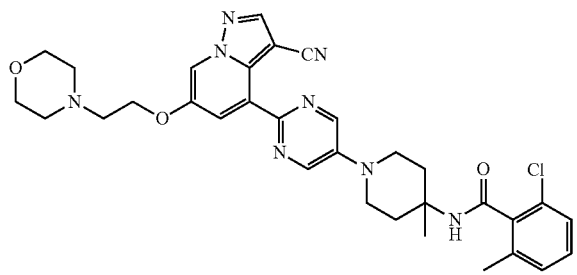 [SMILES: Cc1cccc(Cl)c1C(=O)NC1(C)CCN(c2cnc(-c3cc(OCCN4CCOCC4)cn4ncc(C#N)c34)nc2)CC1]

2-chloro-N-(1-(2-(3-cyano-6-(2-morpholinoethoxy)pyrazolo[1,5-a]pyridin-4-yl)pyrimidin-5-yl)-4-methylpiperidin-4-yl)-6-methylbenzamide The title compound was prepared using a similar method to that described in Example 733, replacing 3-methylbutanoic acid with the 2-chloro-6-methylbenzoic acid. MS (apci) m/z=615.2 (M+H).

The compounds in Table X3 were prepared using a similar method as described in Example 88, replacing 3,6-dimethylpicolinic acid with the appropriate carboxylic acid.

TABLE X3

| Ex. # | Structure | Chemical Name | LCMS m/z |
|---|---|---|---|
| 735 | 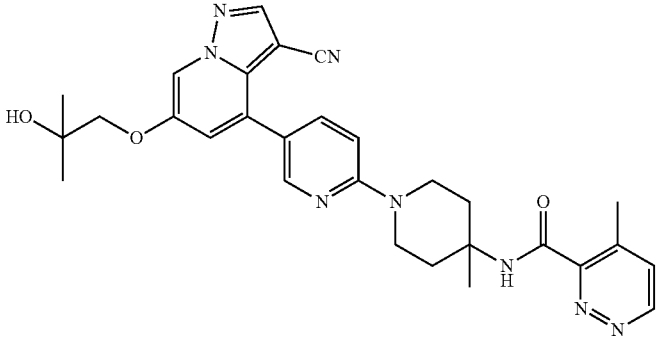 [SMILES: Cc1ccnnc1C(=O)NC1(C)CCN(c2ccc(-c3cc(OCC(C)(C)O)cn4ncc(C#N)c34)cn2)CC1] | N-(1-(5-(3-cyano-6-(2-hydroxy-2-methylpropoxy)pyrazolo[1,5-a]pyridin-4-yl)pyridin-2-yl)-4-methylpiperidin-4-yl)-4-methylpyridazine-3-carboxamide | 541.2 (M + H) |
| 736 | 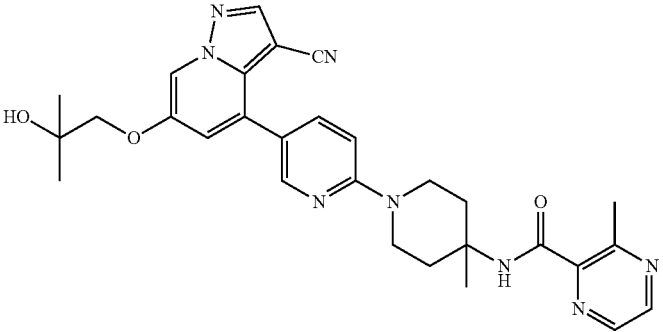 [SMILES: Cc1nccnc1C(=O)NC1(C)CCN(c2ccc(-c3cc(OCC(C)(C)O)cn4ncc(C#N)c34)cn2)CC1] | N-(1-(5-(3-cyano-6-(2-hydroxy-2-methylpropoxy)pyrazolo[1,5-a]pyridin-4-yl)pyridin-2-yl)-4-methylpiperidin-4-yl)-3-methylpyrazine-2-carboxamide | 541.2 (M + H) |
| 737 | 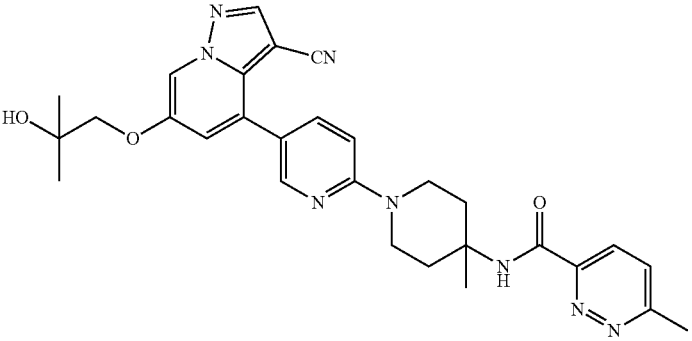 [SMILES: Cc1ccc(C(=O)NC2(C)CCN(c3ccc(-c4cc(OCC(C)(C)O)cn5ncc(C#N)c45)cn3)CC2)nn1] | N-(1-(5-(3-cyano-6-(2-hydroxy-2-methylpropoxy)pyrazolo[1,5-a]pyridin-4-yl)pyridin-2-yl)-4-methylpiperidin-4-yl)-6-methylpyridazine-3-carboxamide | 541.2 (M + H) |
| 738 | 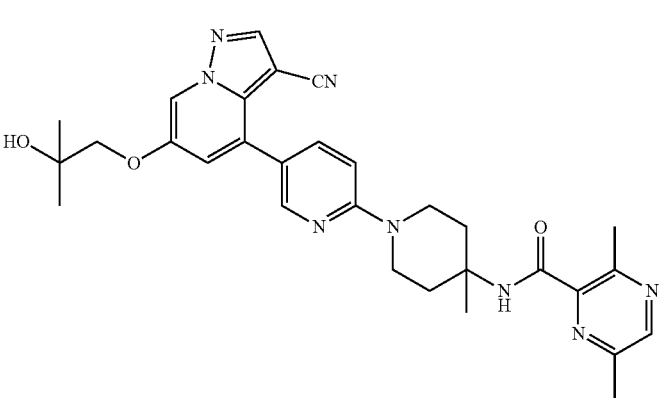 [SMILES: Cc1cnc(C)c(C(=O)NC2(C)CCN(c3ccc(-c4cc(OCC(C)(C)O)cn5ncc(C#N)c45)cn3)CC2)n1] | N-(1-(5-(3-cyano-6-(2-hydroxy-2-methylpropoxy)pyrazolo[1,5-a]pyridin-4-yl)pyridin-2-yl)-4-methylpiperidin-4-yl)-3,6-dimethylpyrazine-2-carboxamide | 555.3 (M + H) |

Example 739

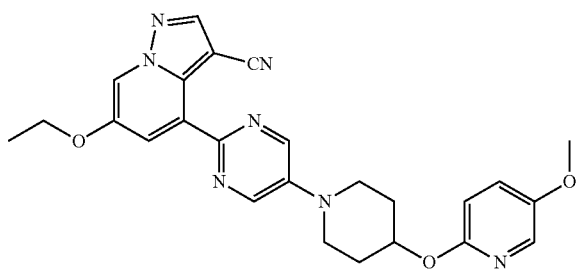 [SMILES: CCOc1cc(-c2ncc(N3CCC(Oc4ccc(OC)cn4)CC3)cn2)c2c(C#N)cnn2c1]

6-ethoxy-4-(5-(4-((5-methoxypyridin-2-yl)oxy)piperidin-1-yl)pyrimidin-2-yl)pyrazolo[1,5-a]pyridine-3-carbonitrile Step 1: Preparation of 4-(5-bromopyrimidin-2-yl)-6-ethoxypyrazolo[1,5-a]pyridine-3-carbonitrile To (3-cyano-6-(2-morpholinoethoxy)pyrazolo[1,5-a]pyridin-4-yl)boronic acid (Intermediate P110, 190 mg, 0.61 mmol) and 5-bromo-2-iodopyrimidine (225 mg, 0.789 mmol) in dioxane (2 mL) was added XPhos (58 mg, 0.121 mmol), $Pd_2(dba)_3$ (3.3 mg, 0.03 mmol) and $K_3PO_4$ (2 M aq, 0.9 mL, 1.8 mmol). The reaction mixture was sparged with argon and heated at 85° C. overnight. After cooling to RT, the reaction was partitioned in 1:1 DCM:water (30 mL). After phase-separation, the aqueous was extracted with DCM (2×15 mL). The combined organic extracts were dried ($Na_2SO_4$), filtered and concentrated. The crude material was purified by silica chromatography (0-60% EtOAc/hexanes) to afford the title compound (30 mg, 14%).

Step 2: Preparation of 6-ethoxy-4-(5-(4-((5-methoxypyridin-2-yl)oxy)piperidin-1-yl)pyrimidin-2-yl)pyrazolo[1,5-a]pyridine-3-carbonitrile A mixture of 4-(5-bromopyrimidin-2-yl)-6-ethoxypyrazolo[1,5-a]pyridine-3-carbonitrile (30 mg, 0.087 mmol), 5-methoxy-2-(piperidin-4-yloxy)pyridine (37 mg, 0.18 mmol), $Cs_2CO_3$ (57 mg, 0.17 mmol), XPhos (4 mg, 0.0087 mmol) and $Pd_2(dba)_3$ (4 mg, 0.0044 mmol) in dioxane (0.44 mL) was sparged with argon, and stirred at 90° C. overnight. After cooling to RT, the reaction was partitioned in 1:1 DCM:water (20 mL). After phase-separation, the aqueous was extracted with DCM (2×10 mL). The combined organic extracts were dried ($Na_2SO_4$), filtered and concentrated. The crude material was purified by preparative TLC (10% MeOH in DCM) to afford the title product (1.4 mg, 3%). MS (apci) m/z=472.2 (M+H).

The compounds in Table X4 were prepared using a similar method as described in Example 706, replacing 4-(pyridin-2-ylmethyl)piperidin-4-ol hydrochloride with the appropriate piperidine intermediate.

TABLE X4

| Ex. # | Structure | Chemical Name | LCMS m/z | Intermediate |
|---|---|---|---|---|
| 740 | 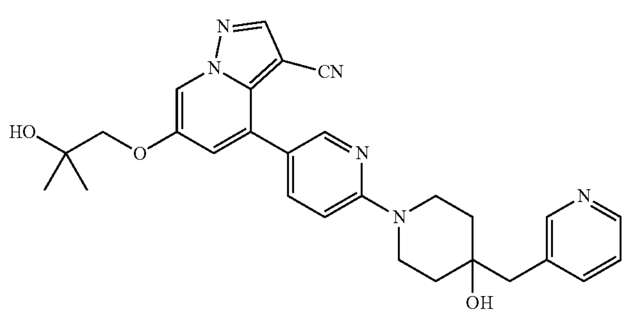 [SMILES: CC(C)(O)COc1cc(-c2ccc(N3CCC(O)(Cc4cccnc4)CC3)nc2)c2c(C#N)cnn2c1] | 6-(2-hydroxy-2-methylpropoxy)-4-(6-(4-hydroxy-4-(pyridin-3-ylmethyl)piperidin-1-yl)pyridin-3-yl)pyrazolo[1,5-a]pyridine-3-carbonitrile | 499.2 (M + H) | 4-(pyridin-3-ylmethyl)piperidihydrochloride (commercially available) |
| 741 | 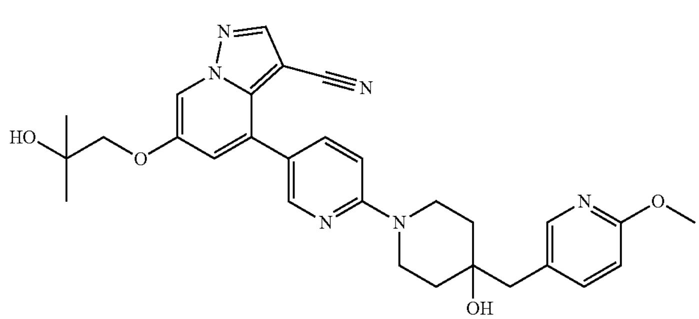 [SMILES: COc1ccc(CC2(O)CCN(c3ccc(-c4cc(OCC(C)(C)O)cn5ncc(C#N)c45)cn3)CC2)cn1] | 6-(2-hydroxy-2-methylpropoxy)-4-(6-(4-hydroxy-4-((6-methoxypyridin-3-yl)methyl)piperidin-1-yl)pyridin-3-yl)pyrazolo[1,5-a]pyridine-3-carbonitrile | 529.2 (M + H) | R66 |

TABLE X4-continued

| Ex. # | Structure | Chemical Name | LCMS m/z | Intermediate |
|---|---|---|---|---|
| 742 | 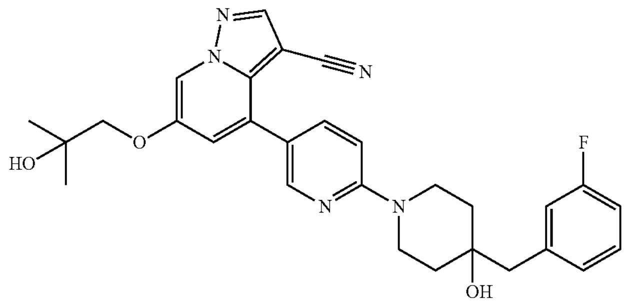 [SMILES: CC(C)(O)COc1cc(-c2ccc(N3CCC(O)(Cc4cccc(F)c4)CC3)nc2)c2c(C#N)cnn2c1] | 4-(6-(4-(3-fluorobenzyl)-4-hydroxypiperidin-1-yl)pyridin-3-yl)-6-(2-hydroxy-2-methylpropoxy)pyrazolo[1,5-a]pyridine-3-carbonitrile | 516.2 (M + H) | R67 |
| 743 | 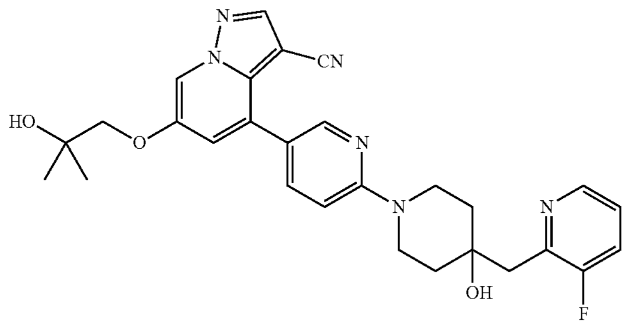 [SMILES: CC(C)(O)COc1cc(-c2ccc(N3CCC(O)(Cc4ncccc4F)CC3)nc2)c2c(C#N)cnn2c1] | 4-(6-(4-((3-fluoropyridin-2-yl)methyl)-4-hydroxypiperidin-1-yl)pyridin-3-yl)-6-(2-hydroxy-2-methylpropoxy)pyrazolo[1,5-a]pyridine-3-carbonitrile | 517.2 (M + H) | R68 |
| 744 | 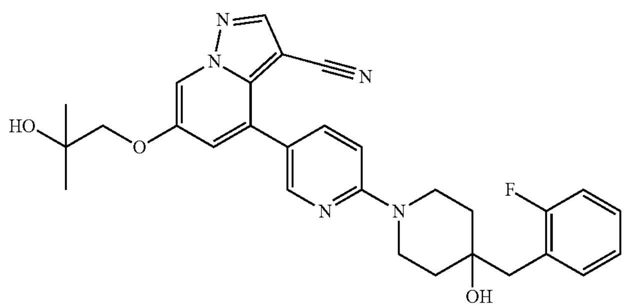 [SMILES: CC(C)(O)COc1cc(-c2ccc(N3CCC(O)(Cc4ccccc4F)CC3)nc2)c2c(C#N)cnn2c1] | 4-(6-(4-(2-fluorobenzyl)-4-hydroxypiperidin-1-yl)pyridin-3-yl)-6-(2-hydroxy-2-methylpropoxy)pyrazolo[1,5-a]pyridine-3-carbonitrile | 516.3 (M + H) | R55 |
| 745 | 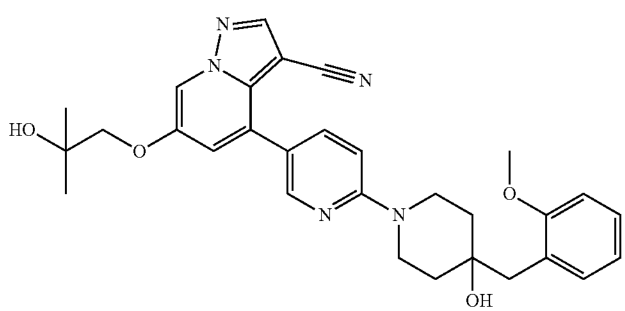 [SMILES: COc1ccccc1CC1(O)CCN(c2ccc(-c3cc(OCC(C)(C)O)cn4ncc(C#N)c34)cn2)CC1] | 6-(2-hydroxy-2-methylpropoxy)-4-(6-(4-hydroxy-4-(2-methoxybenzyl)piperidin-1-yl)pyridin-3-yl)pyrazolo[1,5-a]pyridine-3-carbonitrile | 528.3 (M + H) | R56 |
| 746 | 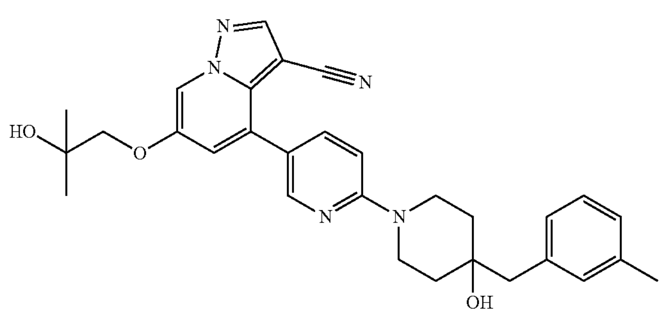 [SMILES: Cc1cccc(CC2(O)CCN(c3ccc(-c4cc(OCC(C)(C)O)cn5ncc(C#N)c45)cn3)CC2)c1] | 6-(2-hydroxy-2-methylpropoxy)-4-(6-(4-hydroxy-4-(3-methylbenzyl)piperidin-1-yl)pyridin-3-yl)pyrazolo[1,5-a]pyridine-3-carbonitrile | 512.3 (M + H) | R62 |

TABLE X4-continued

| Ex. # | Structure | Chemical Name | LCMS m/z | Intermediate |
|---|---|---|---|---|
| 747 | 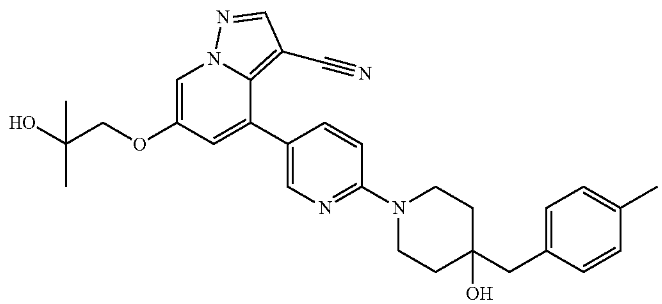 [SMILES: Cc1ccc(CC2(O)CCN(c3ccc(-c4cc(OCC(C)(C)O)cn5ncc(C#N)c45)cn3)CC2)cc1] | 6-(2-hydroxy-2-methylpropoxy)-4-(6-(4-hydroxy-4-(4-methylbenzyl)piperidin-1-yl)pyridin-3-yl)pyrazolo[1,5-a]pyridine-3-carbonitrile | 512.2 (M + H) | R63 |
| 748 | 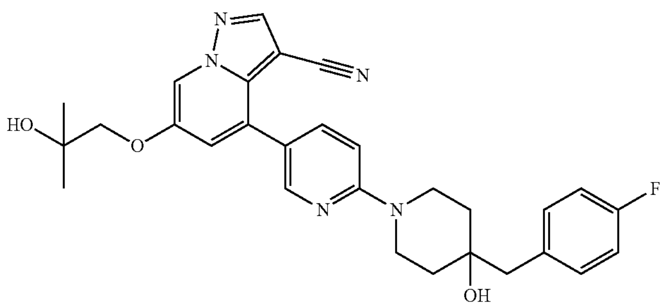 [SMILES: CC(C)(O)COc1cc(-c2ccc(N3CCC(O)(Cc4ccc(F)cc4)CC3)nc2)c2c(C#N)cnn2c1] | 4-(6-(4-(4-fluorobenzyl)-4-hydroxypiperidin-1-yl)pyridin-3-yl)-6-(2-hydroxy-2-methylpropoxy)pyrazolo[1,5-a]pyridine-3-carbonitrile | 516.2 (M + H) | R57 |
| 749 | 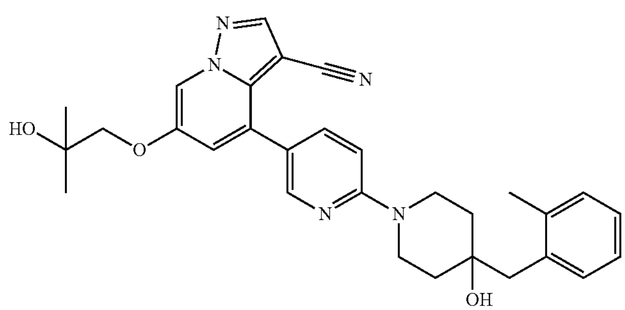 [SMILES: Cc1ccccc1CC1(O)CCN(c2ccc(-c3cc(OCC(C)(C)O)cn4ncc(C#N)c34)cn2)CC1] | 6-(2-hydroxy-2-methylpropoxy)-4-(6-(4-hydroxy-4-(2-methylbenzyl)piperidin-1-yl)pyridin-3-yl)pyrazolo[1,5-a]pyridine-3-carbonitrile | 512.3 (M + H) | R64 |
| 750 | 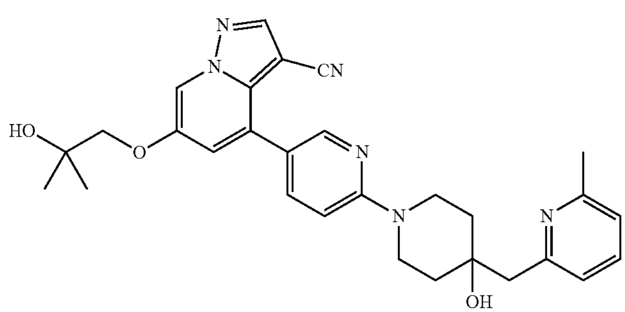 [SMILES: Cc1cccc(CC2(O)CCN(c3ccc(-c4cc(OCC(C)(C)O)cn5ncc(C#N)c45)cn3)CC2)n1] | 6-(2-hydroxy-2-methylpropoxy)-4-(6-(4-hydroxy-4-((6-methylpyridin-2-yl)methyl)piperidin-1-yl)pyridin-3-yl)pyrazolo[1,5-a]pyridine-3-carbonitrile | 513.2 (M + H) | R58 |
| 751 | 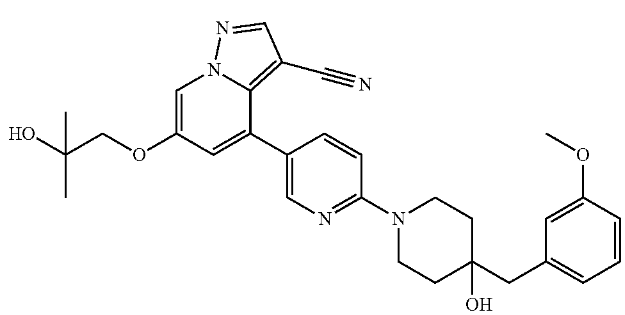 [SMILES: COc1cccc(CC2(O)CCN(c3ccc(-c4cc(OCC(C)(C)O)cn5ncc(C#N)c45)cn3)CC2)c1] | 6-(2-hydroxy-2-methylpropoxy)-4-(6-(4-hydroxy-4-(3-methoxybenzyl)piperidin-1-yl)pyridin-3-yl)pyrazolo[1,5-a]pyridine-3-carbonitrile | 528.3 (M + H) | R59 |

TABLE X4-continued

| Ex. # | Structure | Chemical Name | LCMS m/z | Intermediate |
|---|---|---|---|---|
| 752 | 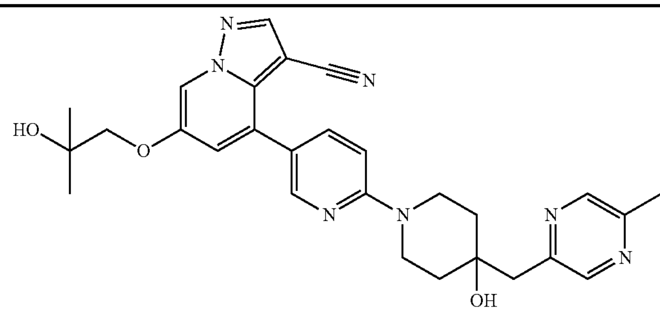 | 6-(2-hydroxy-2-methylpropoxy)-4-(6-(4-hydroxy-4-((5-methylpyrazin-2-yl)methyl)piperidin-1-yl)pyridin-3-yl)pyrazolo[1,5-a]pyridine-3-carbonitrile | 514.3 (M + H) | R65 |
| 753 | 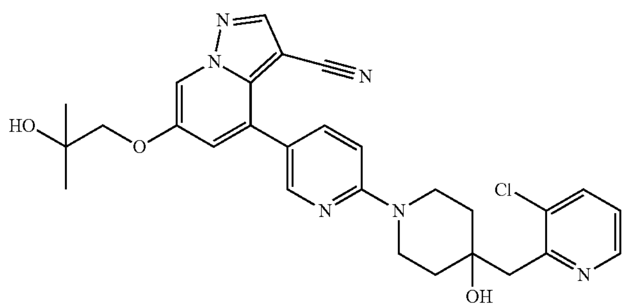 [SMILES: CC(C)(O)COc1cc(-c2ccc(N3CCC(O)(Cc4ncccc4Cl)CC3)nc2)c2c(C#N)cnn2c1] | 4-(6-(4-((3-chloropyridin-2-yl)methyl)-4-hydroxypiperidin-1-yl)pyridin-3-yl)-6-(2-hydroxy-2-methylpropoxy)pyrazolo[1,5-a]pyridine-3-carbonitrile | 533.2 (M + H) | R60 |
| 754 | 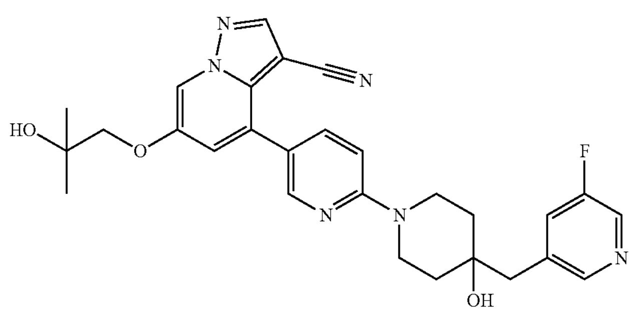 [SMILES: CC(C)(O)COc1cc(-c2ccc(N3CCC(O)(Cc4cncc(F)c4)CC3)nc2)c2c(C#N)cnn2c1] | 4-(6-(4-((5-fluoropyridin-3-yl)methyl)-4-hydroxypiperidin-1-yl)pyridin-3-yl)-6-(2-hydroxy-2-methylpropoxy)pyrazolo[1,5-a]pyridine-3-carbonitrile | 517.3 (M + H) | R61 |

The compounds in Table X5 were prepared using a similar method as described in Example 325, replacing 4-benzylpiperidin-4-ol with the appropriate piperidine intermediate.

TABLE X5

| Ex. # | Structure | Chemical Name | MS m/z | Intermediate |
|---|---|---|---|---|
| 755 | 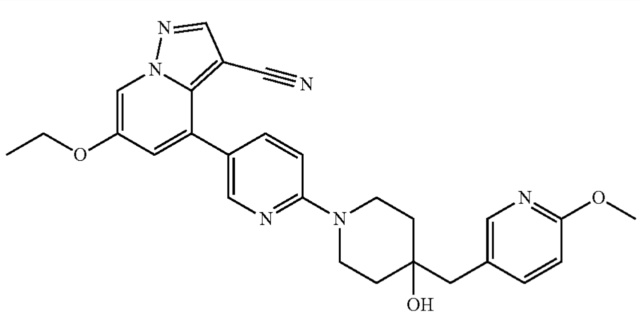 [SMILES: CCOc1cc(-c2ccc(N3CCC(O)(Cc4ccc(OC)nc4)CC3)nc2)c2c(C#N)cnn2c1] | 6-ethoxy-4-(6-(4-hydroxy-4-((6-methoxypyridin-3-yl)methyl)piperidin-1-yl)pyridin-3-yl)pyrazolo[1,5-a]pyridine-3-carbonitrile | 485.2 (M + H) | R66 |

TABLE X5-continued

| Ex. # | Structure | Chemical Name | MS m/z | Intermediate |
|---|---|---|---|---|
| 756 | 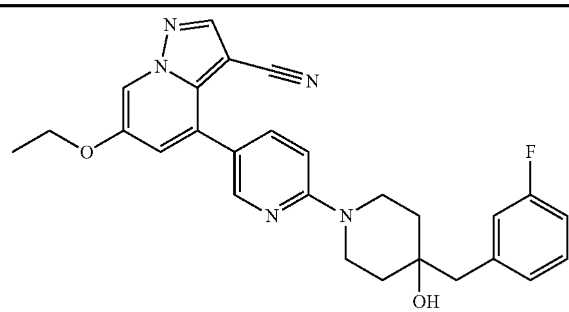 | 6-ethoxy-4-(6-(4-(3-fluorobenzyl)-4-hydroxypiperidin-1-yl)pyridin-3-yl)pyrazolo[1,5-a]pyridine-3-carbonitrile | 472.2 (M + H) | R67 |

The compounds in Table X6 were prepared according to the procedure described in Example 415, reacting either Intermediate P80 (Method A) or Intermediate P165 (Method B) with an appropriate piperidine intermediate.

TABLE X6

| Ex. # | Structure | Chemical Name | MS m/z | Intermediate (Method) |
|---|---|---|---|---|
| 757 | 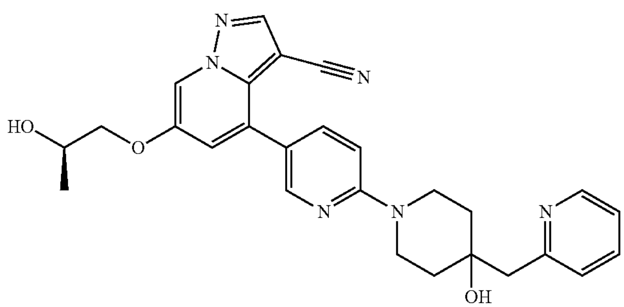 | (R)-4-(6-(4-hydroxy-4-(pyridin-2-ylmethyl)piperidin-1-yl)pyridin-3-yl)-6-(2-hydroxypropoxy)pyrazolo[1,5-a]pyridine-3-carbonitrile | 485.3 (M + H) | 4-(pyridin-2-ylmethyl)piperidin-4-ol hydrochloride (Commercially available) (Method A) |
| 758 | 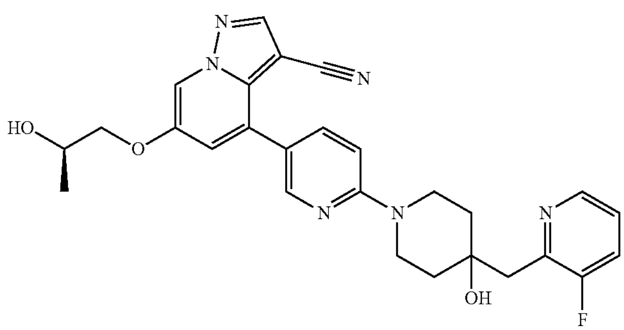 | (R)-4-(6-(4-((3-fluoropyridin-2-yl)methyl)-4-hydroxypiperidin-1-yl)pyridin-3-yl)-6-(2-hydroxypropoxy)pyrazolo[1,5-a]pyridine-3-carbonitrile | 503.2 (M + H) | R68 (Method A) |
| 759 | 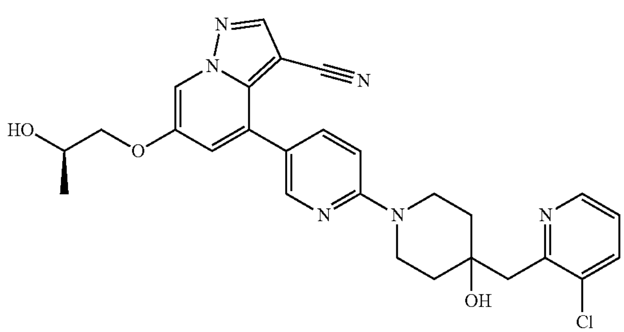 | (R)-4-(6-(4-((3-chloropyridin-2-yl)methyl)-4-hydroxypiperidin-1-yl)pyridin-3-yl)-6-(2-hydroxypropoxy)pyrazolo[1,5-a]pyridine-3-carbonitrile | 519.1 (M + H) | R60 (Method A) |

TABLE X6-continued

| Ex. # | Structure | Chemical Name | MS m/z | Intermediate (Method) |
|---|---|---|---|---|
| 760 | 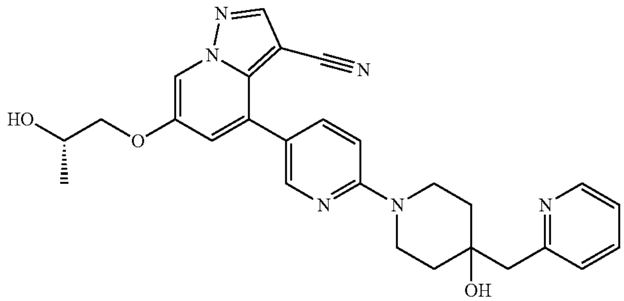 [SMILES: C[C@H](O)COc1cc(-c2ccc(N3CCC(O)(Cc4ccccn4)CC3)nc2)c2c(C#N)cnn2c1] | (S)-4-(6-(4-hydroxy-4-(pyridin-2-ylmethyl)piperidin-1-yl)pyridin-3-yl)-6-(2-hydroxypropoxy)pyrazolo[1,5-a]pyridine-3-carbonitrile | 485.2 (M + H) | 4-(pyridin-2-ylmethyl)piperidin-4-ol hydrochloride (Commercially available) (Method B) |
| 761 | 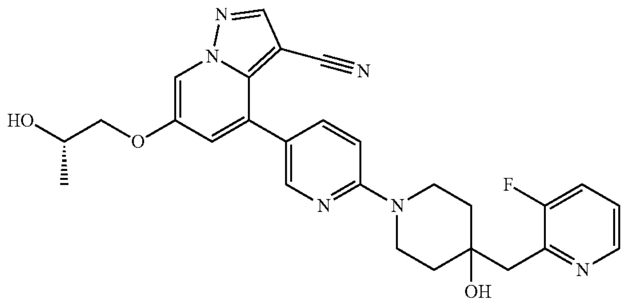 [SMILES: C[C@H](O)COc1cc(-c2ccc(N3CCC(O)(Cc4ncccc4F)CC3)nc2)c2c(C#N)cnn2c1] | (S)-4-(6-(4-((3-fluoropyridin-2-yl)methyl)-4-hydroxypiperidin-1-yl)pyridin-3-yl)-6-(2-hydroxypropoxy)pyrazolo[1,5-a]pyridine-3-carbonitrile | 503.2 (M + H) | R68 (Method B) |
| 762 | 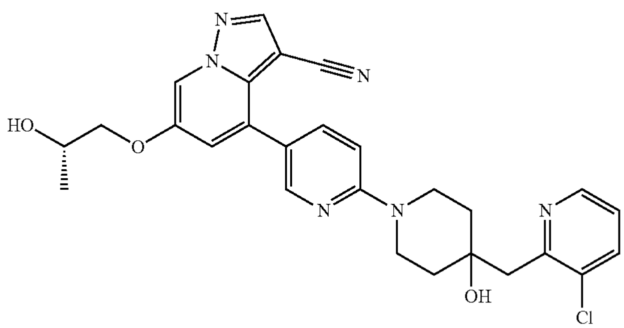 [SMILES: C[C@H](O)COc1cc(-c2ccc(N3CCC(O)(Cc4ncccc4Cl)CC3)nc2)c2c(C#N)cnn2c1] | (S)-4-(6-(4-((3-chloropyridin-2-yl)methyl)-4-hydroxypiperidin-1-yl)pyridin-3-yl)-6-(2-hydroxypropoxy)pyrazolo[1,5-a]pyridine-3-carbonitrile | 519.2 (M + H) | R60 (Method B) |

Example 763

4-(5-(4-((3-chloropyridin-2-yl)methyl)-4-hydroxypiperidin-1-yl)pyrazin-2-yl)-6-(2-hydroxy-2-methylpropoxy)pyrazolo[1,5-a]pyridine-3-carbonitrile A pressure vessel was charged with 6-(2-hydroxy-2-methylpropoxy)-4-(4,4,5,5-tetramethyl-1,3,2-dioxaborolan-2-yl)pyrazolo[1,5-a]pyridine-3-carbonitrile (P166 76.0 mg, 0.213 mmol), 1-(5-chloropyrazin-2-yl)-4-((3-chloropyridin-2-yl)methyl)piperidin-4-ol (R69, 65.6 mg, 0.193 mmol), and K$_3$PO$_4$ (123 mg, 0.580 mmol), followed by 1,4-dioxane (1.5 mL) and water (0.2 mL). The reaction mixture was sparged with N$_2$ for 10 min before Pd$_2$(dba)$_3$ (8.85 mg, 0.00967 mmol) and XPhos (18.4 mg, 0.0387 mmol) were introduced. The reaction was sparged with N$_2$ for an additional 3 min before it was sealed and heated to 100° C. for 3 d to reach ~79% conversion (LCMS). After cooling to RT, the reaction was diluted with 60/40 ACN:H$_2$O with 2% TFA and filtered through a Pall Acrodisc to remove solids. The filtrate was concentrated and purified by preparative HPLC (40-60% ACN/H$_2$O with 0.1% TFA). The combined fractions containing the product were concentrated, and the residue was taken up in MeOH and filtered through MP-HCO$_3$ resin. The filtrate was concentrated to yield the title product as yellow powder (2.0 mg, 1.9%). MS (apci) m/z=534.2 (M+H).

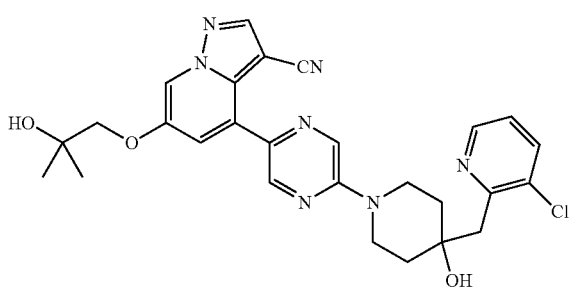 [SMILES: CC(C)(O)COc1cc(-c2cnc(N3CCC(O)(Cc4ncccc4Cl)CC3)cn2)c2c(C#N)cnn2c1]

Example 764

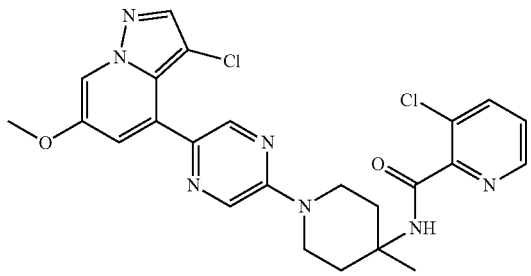 [SMILES: COc1cc(-c2cnc(N3CCC(C)(NC(=O)c4ncccc4Cl)CC3)cn2)c2c(Cl)cnn2c1]

3-chloro-N-(1-(5-(3-chloro-6-methoxypyrazolo[1,5-a]pyridin-4-yl)pyrazin-2-yl)-4-methylpiperidin-4-yl)picolinamide To a mixture of 3-chloropicolinic acid (23 mg, 0.14 mmol) and HATU (37 mg, 0.097 mmol) in DCM (2.4 mL) was added DIEA (84 μL, 0.48 mmol). After 30-min stirring at RT, 1-(5-(3-chloro-6-methoxypyrazolo[1,5-a]pyridin-4-yl)pyrazin-2-yl)-4-methylpiperidin-4-amine (Intermediate P175, 29 mg, 0.078 mmol) was added in one portion. The reaction was stirred for 3 h at ambient temperature, then partitioned in sat. NH₄Cl and DCM. After phase-separation, the organic layer was concentrated and purified by silica chromatography (0-100% EtOAc in hexanes) to afford the title product (20 mg, 50%). MS (apci) m/z=512.2 (M+H).

Example 765

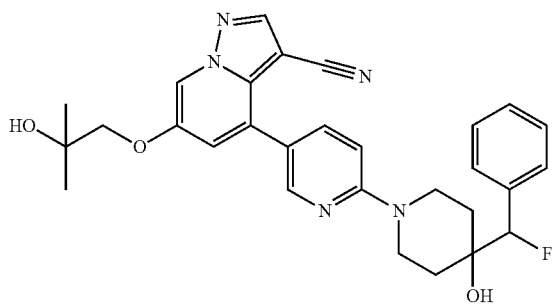 [SMILES: CC(C)(O)COc1cc(-c2ccc(N3CCC(O)(C(F)c4ccccc4)CC3)nc2)c2c(C#N)cnn2c1]

4-(6-(4-(fluoro(phenyl)methyl)-4-hydroxypiperidin-1-yl)pyridin-3-yl)-6-(2-hydroxy-2-methylpropoxy)pyrazolo[1,5-a]pyridine-3-carbonitrile To a solution of 1-chloromethyl-4-fluoro-1,4-diazoniabicyclo[2.2.2]octane bis(tetrafluoroborate) (115 mg, 0.325 mmol) and V203 (2.87 mg, 0.0192 mmol) in CH₃CN (2 mL) was added 4-(6-(4-benzyl-4-hydroxypiperidin-1-yl)pyridin-3-yl)-6-(2-hydroxy-2-methylpropoxy)pyrazolo[1,5-a]pyridine-3-carbonitrile (Example 27, 95.3 mg, 0.192 mmol). The reaction mixture was frozen at −78° C., and purged of air. The mixture was slowly warmed up to RT and stirred overnight. After diluting the reaction with H₂O, the mixture was extracted with EtOAc (3×). The combined organic extracts were concentrated and purified by preparative HPLC (20-80% ACN in H₂O with 0.1% TFA). The combined fractions containing the product were concentrated, dissolved in minimal amount of MeOH, and passed through PL-HCO3 resin. The filtrate was concentrated to afford the title product as a pale yellow solid (4.2 mg, 4%). MS (apci) m/z=516.2 (M+H).

Example 766

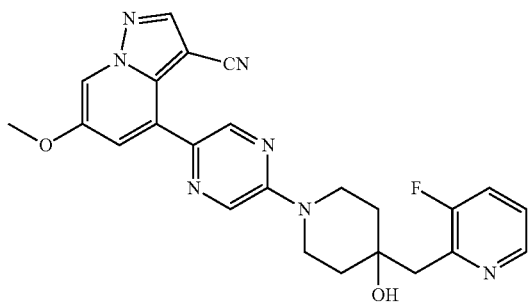 [SMILES: COc1cc(-c2cnc(N3CCC(O)(Cc4ncccc4F)CC3)cn2)c2c(C#N)cnn2c1]

4-(5-(4-((3-fluoropyridin-2-yl)methyl)-4-hydroxypiperidin-1-yl)pyrazin-2-yl)-6-methoxypyrazolo[1,5-a]pyridine-3-carbonitrile To 6-methoxy-4-(4,4,5,5-tetramethyl-1,3,2-dioxaborolan-2-yl)pyrazolo[1,5-a]pyridine-3-carbonitrile (Intermediate P168, 126 mg, 0.211 mmol) and 1-(5-chloropyrazin-2-yl)-4-((3-fluoropyridin-2-yl)methyl)piperidin-4-ol (Intermediate R70, 68 mg, 0.211 mmol) in dioxane (1.5 mL) were added XPhos (20 mg, 0.04 mmol), Pd₂(dba)₃ (10 mg, 0.011 mmol) and K₃PO₄ (2 M aq, 0.3 mL, 0.3 mmol). The mixture was sparged with Ar and heated to 90° C. for 17 h. After cooling to RT, the reaction was partitioned in 1:1 DCM/water (30 mL). After phase-separation, the organic layer was washed with water and brine and concentrated. The crude material was purified by preparative HPLC (5 to 95% acetonitrile in water with 1% TFA) to afford the title product (3.4 mg, 2.8%). MS (apci) m/z=460.2 (M+H).

The compounds in Table X7 were prepared according to the procedure described in Example 766, coupling the appropriate boronate and halide intermediates.

TABLE X7

| Ex. # | Structure | Chemical Name | LCMS m/z | Reactant Intermediates |
|---|---|---|---|---|
| 767 | 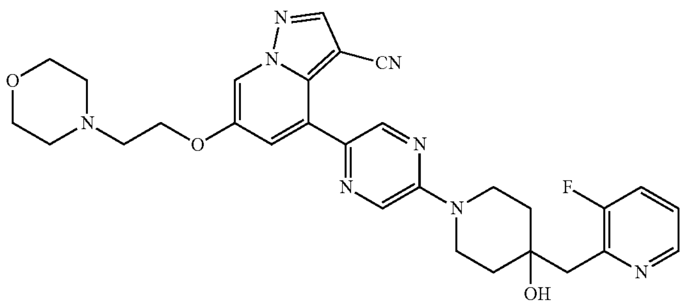 [SMILES: N#Cc1cnn2cc(OCCN3CCOCC3)cc(-c3cnc(N4CCC(O)(Cc5ncccc5F)CC4)cn3)c12] | 4-(5-(4-((3-fluoropyridin-2-yl)methyl)-4-hydroxypiperidin-1-yl)pyrazin-2-yl)-6-(2-morpholinoethoxy)pyrazolo[1,5-a]pyridine-3-carbonitrile | 559.2 (M + H) | P12 and R70 |
| 768 | 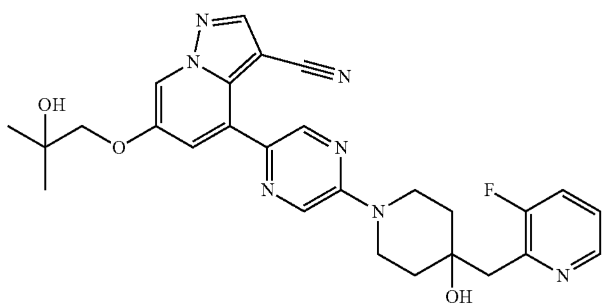 [SMILES: CC(C)(O)COc1cc(-c2cnc(N3CCC(O)(Cc4ncccc4F)CC3)cn2)c2c(C#N)cnn2c1] | 4-(5-(4-((3-fluoropyridin-2-yl)methyl)-4-hydroxypiperidin-1-yl)pyrazin-2-yl)-6-(2-hydroxy-2-methylpropoxy)pyrazolo[1,5-a]pyridine-3-carbonitrile | 518.2 (M + H) | P166 and R70 |
| 769 | 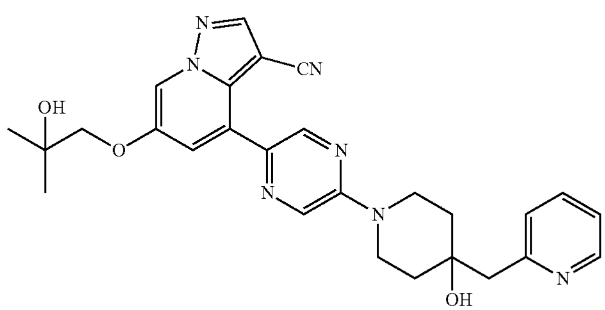 [SMILES: CC(C)(O)COc1cc(-c2cnc(N3CCC(O)(Cc4ccccn4)CC3)cn2)c2c(C#N)cnn2c1] | 6-(2-hydroxy-2-methylpropoxy)-4-(5-(4-hydroxy-4-(pyridin-2-ylmethyl)piperidin-1-yl)pyrazin-2-yl)pyrazolo[1,5-a]pyridine-3-carbonitrile | 500.2 (M + H) | P166 and R71 |

Example 770

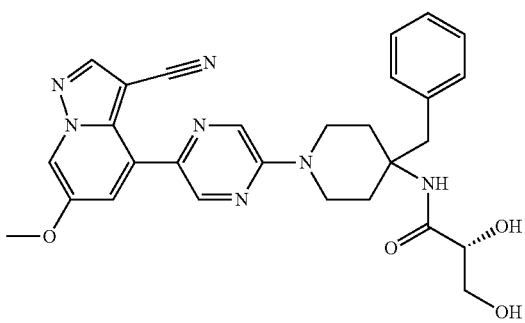 [SMILES: COc1cc(-c2cnc(N3CCC(Cc4ccccc4)(NC(=O)[C@H](O)CO)CC3)cn2)c2c(C#N)cnn2c1]

(R)—N-(4-benzyl-1-(5-(3-cyano-6-methoxypyrazolo[1,5-a]pyridin-4-yl)pyrazin-2-yl)piperidin-4-yl)-2,3-dihydroxypropanamide Step 1: Preparation of 4-(5-(4-amino-4-benzylpiperidin-1-yl)pyrazin-2-yl)-6-methoxypyrazolo[1,5-a]pyridine-3-carbonitrile The title compound (62.7 mg, 53%) was prepared in the same method as described in Example 766, replacing 1-(5-chloropyrazin-2-yl)-4-((3-fluoropyridin-2-yl)methyl)piperidin-4-ol with 4-benzyl-1-(5-chloropyrazin-2-yl)piperidin-4-amine (Intermediate R72). LCMS m/z=440.2 (M+H).

Step 2: Preparation of (R)—N-(4-benzyl-1-(5-(3-cyano-6-methoxypyrazolo[1,5-a]pyridin-4-yl)pyrazin-2-yl)piperidin-4-yl)-2,3-dihydroxypropanamide To a mixture of D-glyceric acid hemicalcium salt (5.79 mg, 0.0396 mmol) and HATU in DMA was added N-ethyl- N-isopropylpropan-2-amine (9.19 µl, 0.0528 mmol). After stirring at RT for 1 h, 4-(5-(4-amino-4-benzylpiperidin-1-yl)pyrazin-2-yl)-6-methoxypyrazolo[1,5-a]pyridine-3-carbonitrile (11.6 mg, 0.0264 mmol) was introduced and the reaction was heated at 60° C. overnight. After cooling to RT, the reaction was diluted with DCM, washed with water (3×) and brine (1×), then concentrated and purified by preparative HPLC (5-95% MeCN/H$_2$O/0.2% TFA). The combined fractions containing the product were concentrated, then taken up in sat. NaHCO$_3$ and 4:1 DCM/IPA. The organic layer was separated and concentrated to yield the title product (4 mg, 27%). MS (apci) m/z=528.2 (M+H).

Example 771

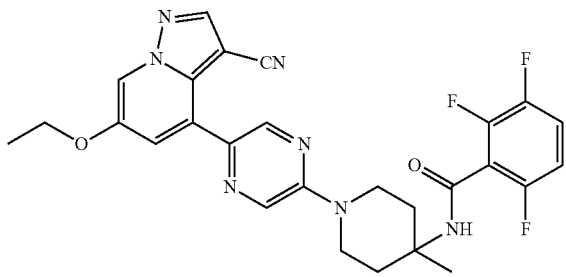 [SMILES: CCOc1cc(-c2cnc(N3CCC(C)(NC(=O)c4c(F)ccc(F)c4F)CC3)cn2)c2c(C#N)cnn2c1]

N-(1-(5-(3-cyano-6-ethoxypyrazolo[1,5-a]pyridin-4-yl)pyrazin-2-yl)-4-methylpiperidin-4-yl)-2,3,6-trifluorobenzamide To a mixture of 2,3,6-trifluorobenzoic acid (22 mg, 0.12 mmol) and HATU (31 mg, 0.083 mmol) in DCM (2.1 mL) was added DIEA (72 µl, 0.41 mmol) and stirred for 30 min at RT, followed by addition of 4-(5-(4-amino-4-methylpiperidin-1-yl)pyrazin-2-yl)-6-ethoxypyrazolo[1,5-a]pyridine-3-carbonitrile bis(2,2,2-trifluoroacetate) (Intermediate P172; 25 mg, 0.041 mmol) in one portion. After stirred for another 2 h, the reaction was diluted with sat. NH$_4$Cl (2 mL) and passed through a Phase Separator frit. The organic filtrate was purified by silica chromatography (0-100% EtOAc in hexanes) to afford the title compound (17 mg, 77%). MS (apci) m/z=536.1 (M+H).

The compounds in Table X8 were prepared using a similar method as described in Example 771, replacing 2,3,6-trifluorobenzoic acid with the appropriate carboxylic acid.

TABLE X8

| Ex. # | Structure | Chemical Name | LCMS m/z |
|---|---|---|---|
| 772 | 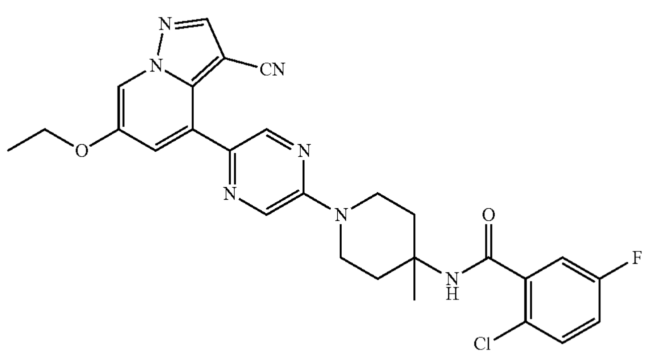 [SMILES: CCOc1cc(-c2cnc(N3CCC(C)(NC(=O)c4cc(F)ccc4Cl)CC3)cn2)c2c(C#N)cnn2c1] | 2-chloro-N-(1-(5-(3-cyano-6-ethoxypyrazolo[1,5-a]pyridin-4-yl)pyrazin-2-yl)-4-methylpiperidin-4-yl)-5-fluorobenzamide | 534.2 (M + H) |
| 773 | 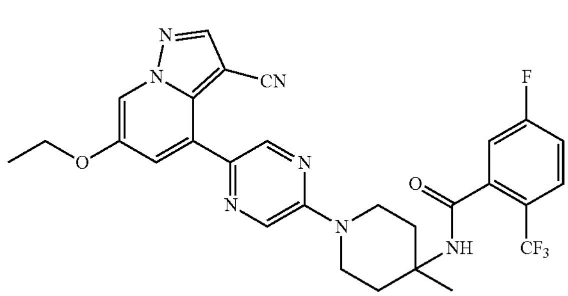 [SMILES: CCOc1cc(-c2cnc(N3CCC(C)(NC(=O)c4cc(F)ccc4C(F)(F)F)CC3)cn2)c2c(C#N)cnn2c1] | N-(1-(5-(3-cyano-6-ethoxypyrazolo[1,5-a]pyridin-4-yl)pyrazin-2-yl)-4-methylpiperidin-4-yl)-5-fluoro-2-(trifluoromethyl)benzamide | 568.2 (M + H) |

TABLE X8-continued

| Ex. # | Structure | Chemical Name | LCMS m/z |
|---|---|---|---|
| 774 | 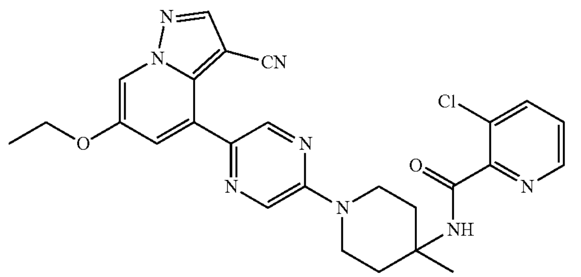 [SMILES: CCOc1cc(-c2cnc(N3CCC(C)(NC(=O)c4ncccc4Cl)CC3)cn2)c2c(C#N)cnn2c1] | 3-chloro-N-(1-(5-(3-cyano-6-ethoxypyrazolo[1,5-a]pyridin-4-yl)pyrazin-2-yl)-4-methylpiperidin-4-yl)picolinamide | 517.1 (M + H) |
| 775 | 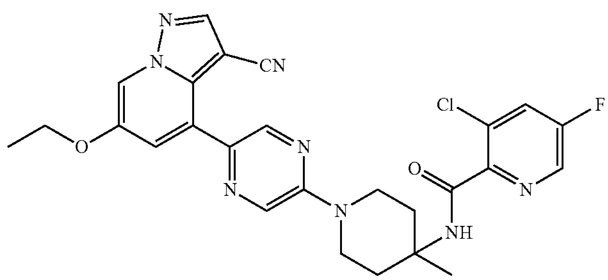 [SMILES: CCOc1cc(-c2cnc(N3CCC(C)(NC(=O)c4ncc(F)cc4Cl)CC3)cn2)c2c(C#N)cnn2c1] | 3-chloro-N-(1-(5-(3-cyano-6-ethoxypyrazolo[1,5-a]pyridin-4-yl)pyrazin-2-yl)-4-methylpiperidin-4-yl)-5-fluoropicolinamide | 535.1 (M + H) |
| 776 | 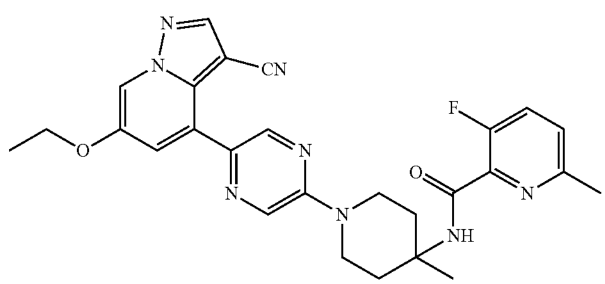 [SMILES: CCOc1cc(-c2cnc(N3CCC(C)(NC(=O)c4nc(C)ccc4F)CC3)cn2)c2c(C#N)cnn2c1] | N-(1-(5-(3-cyano-6-ethoxypyrazolo[1,5-a]pyridin-4-yl)pyrazin-2-yl)-4-methylpiperidin-4-yl)-3-fluoro-6-methylpicolinamide | 515.2 (M + H) |
| 777 | 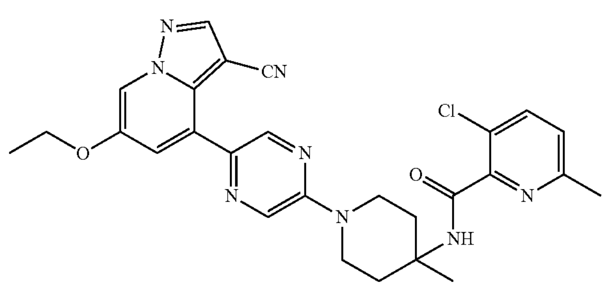 [SMILES: CCOc1cc(-c2cnc(N3CCC(C)(NC(=O)c4nc(C)ccc4Cl)CC3)cn2)c2c(C#N)cnn2c1] | 3-chloro-N-(1-(5-(3-cyano-6-ethoxypyrazolo[1,5-a]pyridin-4-yl)pyrazin-2-yl)-4-methylpiperidin-4-yl)-6-methylpicolinamide | 531.2, 553.2 (M + H, M + Na) |
| 778 | 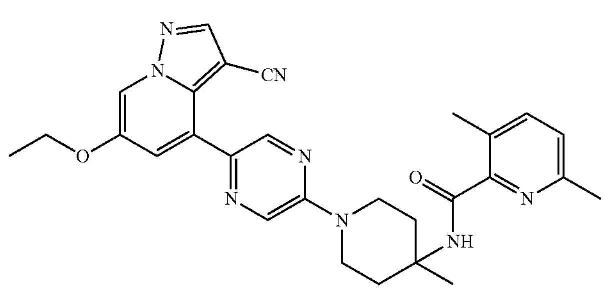 [SMILES: CCOc1cc(-c2cnc(N3CCC(C)(NC(=O)c4nc(C)ccc4C)CC3)cn2)c2c(C#N)cnn2c1] | N-(1-(5-(3-cyano-6-ethoxypyrazolo[1,5-a]pyridin-4-yl)pyrazin-2-yl)-4-methylpiperidin-4-yl)-3,6-dimethylpicolinamide | 511.2 (M + H) |

Example 779

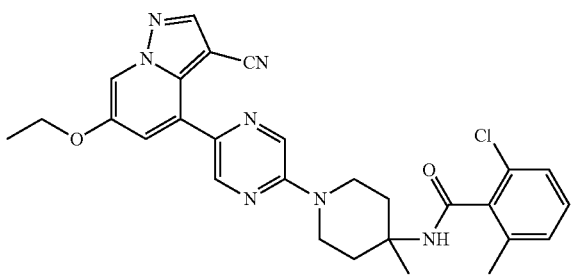 [SMILES: CCOc1cc(-c2cnc(N3CCC(C)(NC(=O)c4c(C)cccc4Cl)CC3)cn2)c2c(C#N)cnn2c1]

2-chloro-N-(1-(5-(3-cyano-6-ethoxypyrazolo[1,5-a]
pyridin-4-yl)pyrazin-2-yl)-4-methylpiperidin-4-yl)-
6-methylbenzamide In a 15-mL pressure tube was charged 4-bromo-6-ethoxy-
pyrazolo[1,5-a]pyridine-3-carbonitrile (Intermediate P5; 15 mg, 0.056 mmol) and dioxane (0.5 mL) to form a suspension, followed by addition of water (0.15 mL), $Cs_2CO_3$ (55 mg, 0.17 mmol) and 2-chloro-6-methyl-N-(4-methyl-1-(5-(4,4,5,5-tetramethyl-1,3,2-dioxaborolan-2-yl)pyrazin-2-yl)piperidin-4-yl)benzamide (Intermediate R49; 37 mg, 0.056 mmol). The mixture was sparged with $N_2$ for 5 min before XPHOS (11 mg, 0.023 mmol) and $Pd_2dba_3$ (5.2 mg, 0.0056 mmol) were added, followed by an additional 5 min of sparging with $N_2$ before the reaction was sealed and heated at 80° C. for 17 h. Once cooled to RT, the reaction was diluted with water (10 mL) and extracted with DCM (2×10 mL). The combined organic phases were dried ($MgSO_4$), filtered, and concentrated. The crude material was purified first by preparative HPLC (5-95% MeCN/$H_2O$ with 0.2% TFA), followed by silica chromatography (0-100% acetone/hexanes) to afford the title product (2.1 mg, 7%). MS (apci) m/z=530.2 (M+H).

The compounds in Table X9 were prepared according to the procedure described in Example 779, replacing 4-bromo-6-ethoxypyrazolo[1,5-a]pyridine-3-carbonitrile with the appropriate bromide intermediate.

TABLE X9

| Ex. # | Structure | Chemical Name | LCMS m/z | Bromide Intermediate |
|---|---|---|---|---|
| 780* | 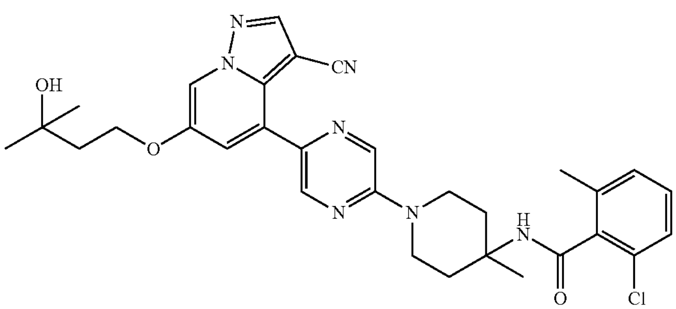 [SMILES: Cc1cccc(Cl)c1C(=O)NC1(C)CCN(c2cnc(-c3cc(OCCC(C)(C)O)cn4ncc(C#N)c34)cn2)CC1] | 2-chloro-N-(1-(5-(3-cyano-6-(3-hydroxy-3-methylbutoxy)pyrazolo[1,5-a]pyridin-4-yl)pyrazin-2-yl)-4-methylpiperidin-4-yl)-6-methylbenzamide | 588.2 (M + H) | P169 |
| 781 | 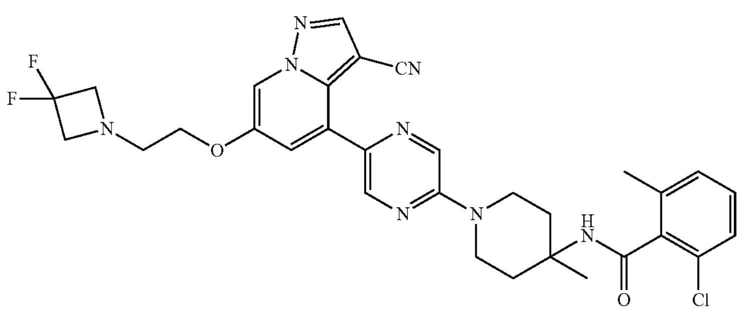 [SMILES: Cc1cccc(Cl)c1C(=O)NC1(C)CCN(c2cnc(-c3cc(OCCN4CC(F)(F)C4)cn4ncc(C#N)c34)cn2)CC1] | 2-chloro-N-(1-(5-(3-cyano-6-(2-(3,3-difluoroazetidin-1-yl)ethoxy)pyrazolo[1,5-a]pyridin-4-yl)pyrazin-2-yl)-4-methylpiperidin-4-yl)-6-methylbenzamide | 621.2 (M + H) | P170 |
| 782 | 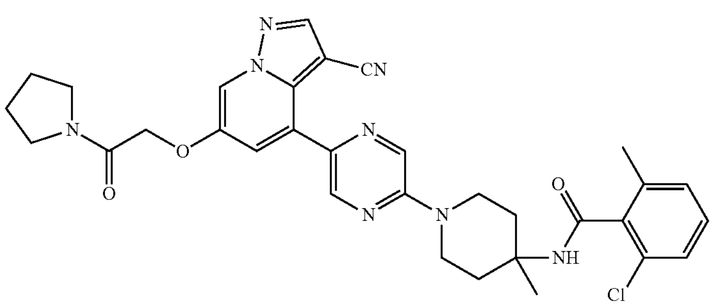 [SMILES: Cc1cccc(Cl)c1C(=O)NC1(C)CCN(c2cnc(-c3cc(OCC(=O)N4CCCC4)cn4ncc(C#N)c34)cn2)CC1] | 2-chloro-N-(1-(5-(3-cyano-6-(2-oxo-2-(pyrrolidin-1-yl)ethoxy)pyrazolo[1,5-a]pyridin-4-yl)pyrazin-2-yl)-4-methylpiperidin-4-yl)-6-methylbenzamide | 613.2 (M + H) | P171 |

TABLE X9-continued

| Ex. # | Structure | Chemical Name | LCMS m/z | Bromide Intermediate |
|---|---|---|---|---|
| 783 | 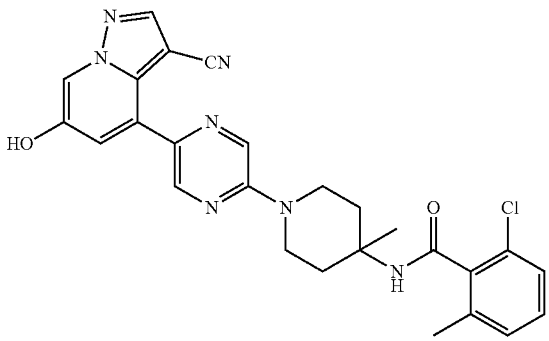 [SMILES: Cc1cccc(Cl)c1C(=O)NC1(C)CCN(c2cnc(-c3cc(O)cn4ncc(C#N)c34)cn2)CC1] | 2-chloro-N-(1-(5-(3-cyano-6-hydroxypyrazolo[1,5-a]pyridin-4-yl)pyrazin-2-yl)-4-methylpiperidin-4-yl)-6-methylbenzamide | 502.1 (M + H) | P1 |

*Note: TBS protective group was removed during preparative HPLC purification (5-95% ACN in water with 0.1% TFA).

Example 784

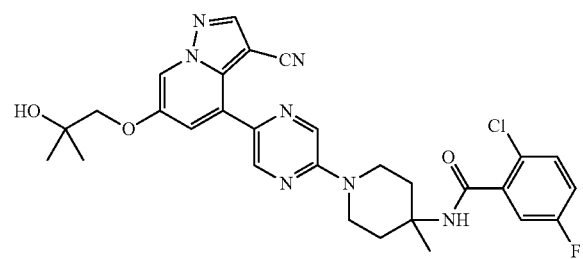 [SMILES: CC(C)(O)COc1cc(-c2cnc(N3CCC(C)(NC(=O)c4cc(F)ccc4Cl)CC3)cn2)c2c(C#N)cnn2c1]

2-chloro-N-(1-(5-(3-cyano-6-(2-hydroxy-2-methylpropoxy)pyrazolo[1,5-a]pyridin-4-yl)pyrazin-2-yl)-4-methylpiperidin-4-yl)-5-fluorobenzamide To a suspension of 4-(5-(4-amino-4-methylpiperidin-1-yl)pyrazin-2-yl)-6-(2-hydroxy-2-methylpropoxy)pyrazolo[1,5-a]pyridine-3-carbonitrile dihydrochloride (Intermediate P173; 10 mg, 0.020 mmol) in DCM (0.2 mL) were added 2-chloro-5-fluorobenzoic acid (4.2 mg, 0.024 mmol), DIEA (14 µl, 0.081 mmol) and HATU (12 mg, 0.030 mmol). The reaction was stirred at RT for 2 d, then diluted with H₂O (10 mL), extracted with DCM (3×10 mL), and the combined organic phases were concentrated. The crude material was purified by preparative HPLC (5-95% MeCN/H₂O with 0.1% TFA). The combined fractions containing the product were diluted with sat. NaHCO₃ (10 mL) and extracted with DCM (3×10 mL). The combined organic phases were washed with brine (15 mL), dried (MgSO₄), filtered, and concentrated to afford the title product (1.2 mg, 10%). MS (apci) m/z=578.2 (M+H).

The compounds in Table X10 were prepared using a similar method as described in Example 784, replacing 2-chloro-5-fluorobenzoic acid with the appropriate carboxylic acid.

TABLE X10

| Ex. # | Structure | Chemical Name | LCMS m/z |
|---|---|---|---|
| 785 | 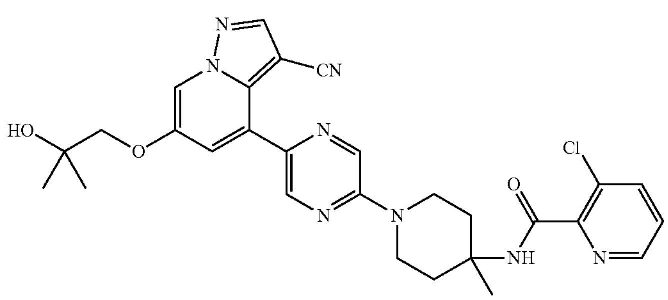 [SMILES: CC(C)(O)COc1cc(-c2cnc(N3CCC(C)(NC(=O)c4ncccc4Cl)CC3)cn2)c2c(C#N)cnn2c1] | 3-chloro-N-(1-(5-(3-cyano-6-(2-hydroxy-2-methylpropoxy)pyrazolo[1,5-a]pyridin-4-yl)pyrazin-2-yl)-4-methylpiperidin-4-yl)picolinamide | 561.2, 583.2 (M + H, M + Na) |

TABLE X10-continued

| Ex. # | Structure | Chemical Name | LCMS m/z |
|---|---|---|---|
| 786 | 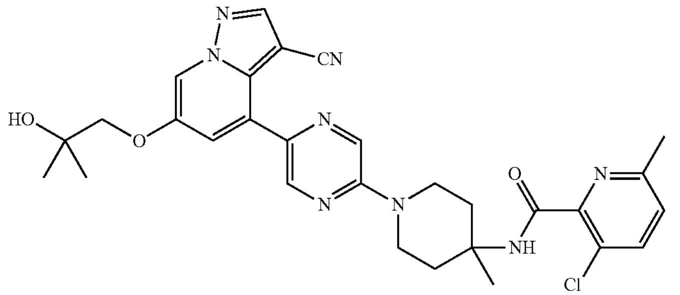 [SMILES: Cc1ccc(Cl)c(C(=O)NC2(C)CCN(c3cnc(-c4cc(OCC(C)(C)O)cn5ncc(C#N)c45)cn3)CC2)n1] | 3-chloro-N-(1-(5-(3-cyano-6-(2-hydroxy-2-methylpropoxy)pyrazolo[1,5-a]pyridin-4-yl)pyrazin-2-yl)-4-methylpiperidin-4-yl)-6-methylpicolinamide | 575.2, 597.2 (M + H, M + Na) |
| 787 | 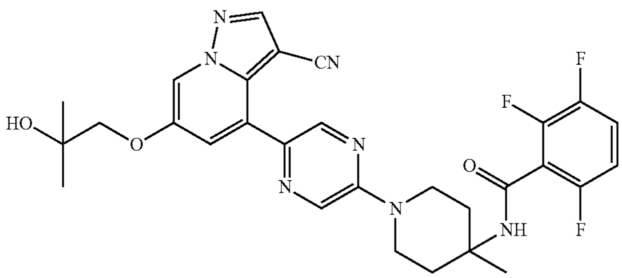 [SMILES: CC(C)(O)COc1cc(-c2cnc(N3CCC(C)(NC(=O)c4c(F)ccc(F)c4F)CC3)cn2)c2c(C#N)cnn2c1] | N-(1-(5-(3-cyano-6-(2-hydroxy-2-methylpropoxy)pyrazolo[1,5-a]pyridin-4-yl)pyrazin-2-yl)-4-methylpiperidin-4-yl)-2,3,6-trifluorobenzamide | 580.2 (M + H) |
| 788 | 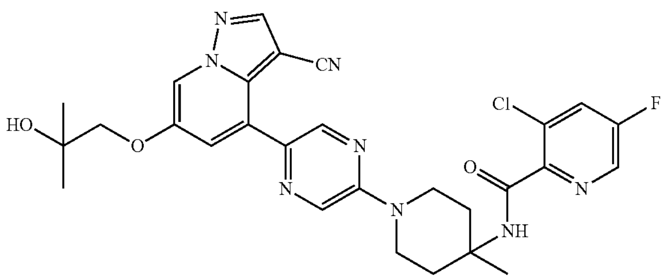 [SMILES: CC(C)(O)COc1cc(-c2cnc(N3CCC(C)(NC(=O)c4ncc(F)cc4Cl)CC3)cn2)c2c(C#N)cnn2c1] | 3-chloro-N-(1-(5-(3-cyano-6-(2-hydroxy-2-methylpropoxy)pyrazolo[1,5-a]pyridin-4-yl)pyrazin-2-yl)-4-methylpiperidin-4-yl)-5-fluoropicolinamide | 579.2 (M + H) |
| 789 | 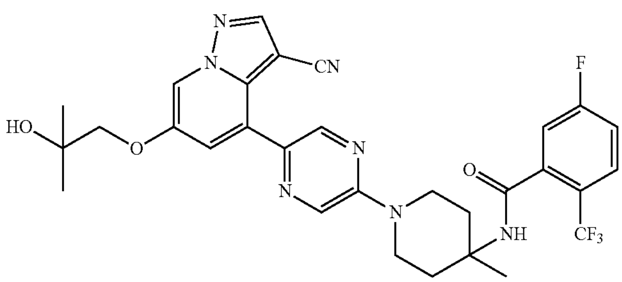 [SMILES: CC(C)(O)COc1cc(-c2cnc(N3CCC(C)(NC(=O)c4cc(F)ccc4C(F)(F)F)CC3)cn2)c2c(C#N)cnn2c1] | N-(1-(5-(3-cyano-6-(2-hydroxy-2-methylpropoxy)pyrazolo[1,5-a]pyridin-4-yl)pyrazin-2-yl)-4-methylpiperidin-4-yl)-5-fluoro-2-(trifluoromethyl)benzamide | 612.2, 634.2 (M + H, M + Na) |

Example 790

3-chloro-N-(1-(5-(3-cyano-6-((3-fluoroazetidin-3-yl)methoxy)pyrazolo[1,5-a]pyridin-4-yl)pyrazin-2-yl)-4-methylpiperidin-4-yl)picolinamide

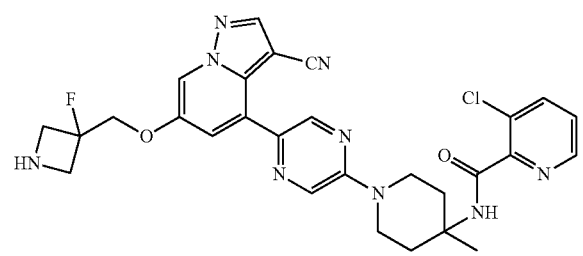 [SMILES: CC1(NC(=O)c2ncccc2Cl)CCN(c2cnc(-c3cc(OCC4(F)CNC4)cn4ncc(C#N)c34)cn2)CC1]

Step 1: Preparation of tert-butyl 3-(((4-(5-(4-(3-chloropicolinamido)-4-methylpiperidin-1-yl)pyrazin-2-yl)-3-cyanopyrazolo[1,5-a]pyridin-6-yl)oxy)methyl)-3-fluoroazetidine-1-carboxylate A mixture of 3-chloropicolinic acid (24 mg, 0.15 mmol) and HATU (38 mg, 0.10 mmol) in DCM (2.5 mL) was treated with DIEA (88 µL, 0.50 mmol), then stirred for 30 min at RT before tert-butyl 3-(((4-(5-(4-amino-4-methylpiperidin-1-yl)pyrazin-2-yl)-3-cyanopyrazolo[1,5-a]pyridin-6-yl)oxy)methyl)-3-fluoroazetidine-1-carboxylate (Intermediate P153; 27 mg, 0.050 mmol) was added in one portion.

After overnight stirring, the reaction was diluted with sat. NH₄Cl₍ₐq₎ (2 mL) and passed through a Phase Separator frit. The filtrate was purified by silica chromatography (0-100% EtOAc in hexanes) to afford the title compound (34 mg, quantitative yield). LCMS m/z=676.2 (M+H).

Step 2: Preparation of (R)—N-(4-benzyl-1-(5-(3-cyano-6-methoxypyrazolo[1,5-a]pyridin-4-yl)pyrazin-2-yl)piperidin-4-yl)-2,3-dihydroxypropanamide A solution of tert-butyl 3-(((4-(5-(4-(3-chloropicolinamido)-4-methylpiperidin-1-yl)pyrazin-2-yl)-3-cyanopyrazolo[1,5-a]pyridin-6-yl)oxy)methyl)-3-fluoroazetidine-1-carboxylate (34 mg, 0.050 mmol) in DCM (2 mL) was treated with TFA (2 mL). The reaction was stirred for 20 min at ambient temperature before it was concentrated in vacuo and purified by silica chromatography (0-10% MeOH in DCM with 0.1% NH₄OH) to afford the title product (12 mg, 41%). MS (apci) m/z=576.2 (M+H).

Example 791

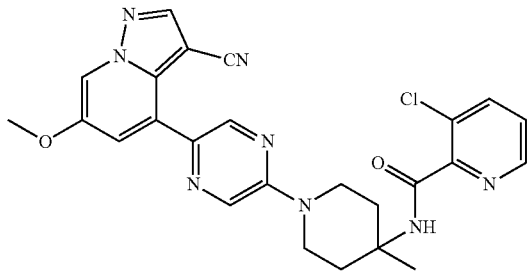 [SMILES: COc1cc(-c2cnc(N3CCC(C)(NC(=O)c4ncccc4Cl)CC3)cn2)c2c(C#N)cnn2c1]

3-chloro-N-(1-(5-(3-cyano-6-methoxypyrazolo[1,5-a]pyridin-4-yl)pyrazin-2-yl)-4-methylpiperidin-4-yl)picolinamide To a mixture of 3-chloropicolinic acid (15 mg, 0.096 mmol) and HATU (24 mg, 0.064 mmol) in DCM (1.6 mL) was added DIEA (56 µl, 0.32 mmol), then stirred for 30 min before 4-(5-(4-amino-4-methylpiperidin-1-yl)pyrazin-2-yl)-6-methoxypyrazolo[1,5-a]pyridine-3-carbonitrile bis(2,2,2-trifluoroacetate) (Intermediate P174; 20 mg, 0.032 mmol) was added in one portion. The reaction was stirred for 1 h at RT, then diluted with sat. NH₄Cl₍ₐq₎ (2 mL) and passed through a Phase Separator frit. The organic filtrate was purified by silica chromatography (0-100% EtOAc in hexanes) to yield the title product as solid (14 mg, 87%). MS (apci) m/z=503.2 (M+H).

The compounds in Table X11 were prepared using a similar method as described in Example 791, replacing 3-chloropicolinic acid with the appropriate carboxylic acid.

TABLE X11

| Ex. # | Structure | Chemical Name | LCMS m/z |
|---|---|---|---|
| 792 | 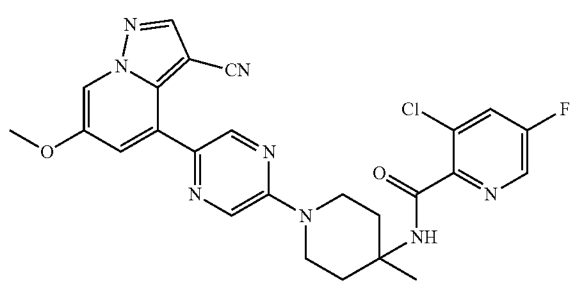 [SMILES: COc1cc(-c2cnc(N3CCC(C)(NC(=O)c4ncc(F)cc4Cl)CC3)cn2)c2c(C#N)cnn2c1] | 3-chloro-N-(1-(5-(3-cyano-6-methoxypyrazolo[1,5-a]pyridin-4-yl)pyrazin-2-yl)-4-methylpiperidin-4-yl)-5-fluoropicolinamide | 521.1 (M + H) |
| 793 | 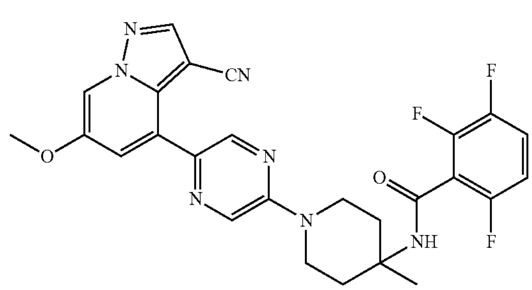 [SMILES: COc1cc(-c2cnc(N3CCC(C)(NC(=O)c4c(F)ccc(F)c4F)CC3)cn2)c2c(C#N)cnn2c1] | N-(1-(5-(3-cyano-6-methoxypyrazolo[1,5-a]pyridin-4-yl)pyrazin-2-yl)-4-methylpiperidin-4-yl)-2,3,6-trifluorobenzamide | 522.1 (M + H) |

TABLE X11-continued

| Ex. # | Structure | Chemical Name | LCMS m/z |
|---|---|---|---|
| 794 | 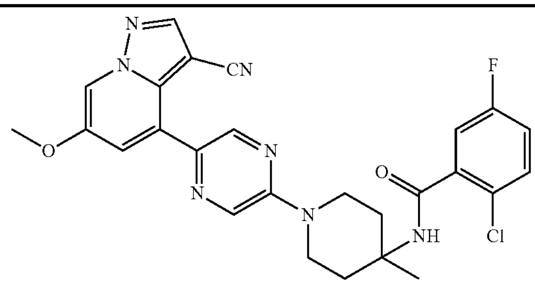 | 2-chloro-N-(1-(5-(3-cyano-6-methoxypyrazolo[1,5-a]pyridin-4-yl)pyrazin-2-yl)-4-methylpiperidin-4-yl)-5-fluorobenzamide | 520.1 (M + H) |
| 795 | 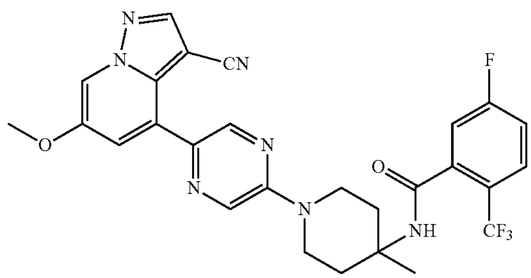 [SMILES: COc1cc(-c2cnc(N3CCC(C)(NC(=O)c4cc(F)ccc4C(F)(F)F)CC3)cn2)c2c(C#N)cnn2c1] | N-(1-(5-(3-cyano-6-methoxypyrazolo[1,5-a]pyridin-4-yl)pyrazin-2-yl)-4-methylpiperidin-4-yl)-5-fluoro-2-(trifluoromethyl)benzamide | 554.2 (M + H) |
| 796 | 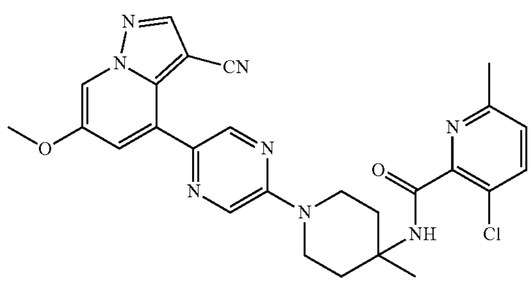 [SMILES: COc1cc(-c2cnc(N3CCC(C)(NC(=O)c4nc(C)ccc4Cl)CC3)cn2)c2c(C#N)cnn2c1] | 3-chloro-N-(1-(5-(3-cyano-6-methoxypyrazolo[1,5-a]pyridin-4-yl)pyrazin-2-yl)-4-methylpiperidin-4-yl)-6-methylpicolinamide | 517.2 (M + H) |

Example 797

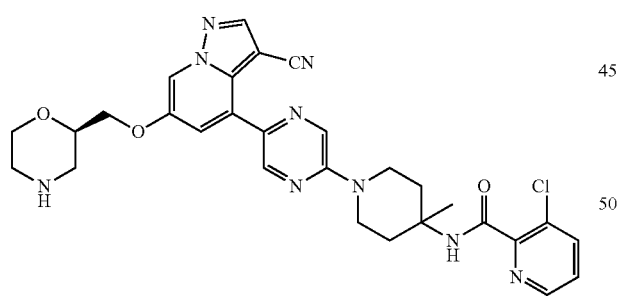

(R)-3-chloro-N-(1-(5-(3-cyano-6-(morpholin-2-ylmethoxy)pyrazolo[1,5-a]pyridin-4-yl)pyrazin-2-yl)-4-methylpiperidin-4-yl)picolinamide Step 1: Preparation of tert-butyl (R)-2-(((4-(5-(4-(3-chloropicolinamido)-4-methylpiperidin-1-yl)pyrazin-2-yl)-3-cyanopyrazolo[1,5-a]pyridin-6-yl)oxy)methyl)morpholine-4-carboxylate The title compound (30 mg, 67%) was prepared according to the procedure described in Example 791, replacing 4-(5-(4-amino-4-methylpiperidin-1-yl)pyrazin-2-yl)-6-methoxypyrazolo[1,5-a]pyridine-3-carbonitrile bis(2,2,2-trifluoroacetate) with tert-butyl (R)-2-(((4-(5-(4-amino-4-methylpiperidin-1-yl)pyrazin-2-yl)-3-cyanopyrazolo[1,5-a]pyridin-6-yl)oxy)methyl)morpholine-4-carboxylate (Intermediate P176). LCMS m/z=688.2 (M+H).

Step 2: Preparation of (R)-3-chloro-N-(1-(5-(3-cyano-6-(morpholin-2-ylmethoxy)pyrazolo[1,5-a]pyridin-4-yl)pyrazin-2-yl)-4-methylpiperidin-4-yl)picolinamide To a solution of tert-butyl (R)-2-(((4-(5-(4-(3-chloropicolinamido)-4-methylpiperidin-1-yl)pyrazin-2-yl)-3-cyanopyrazolo[1,5-a]pyridin-6-yl)oxy)methyl)morpholine-4-carboxylate (30.2 mg, 0.044 mmol) in DCM (2 mL) was added TFA (1 mL), then stirred for 2 h at RT and then concentrated and redissolved in 4:1 DCM/IPA. The mixture was washed with sat. NaHCO₃, dried (Na₂SO₄), filtered and concentrated to yield the title product (21.5 mg, 83% yield). MS (apci) m/z=588.3 (M+H).

The compounds in Table X12 were prepared using a similar method as described in Example 797, replacing 3-chloropicolinic acid with the appropriate carboxylic acid in Step 1.

TABLE X12

| Ex. # | Structure | Chemical Name | LCMS m/z |
|---|---|---|---|
| 798 | 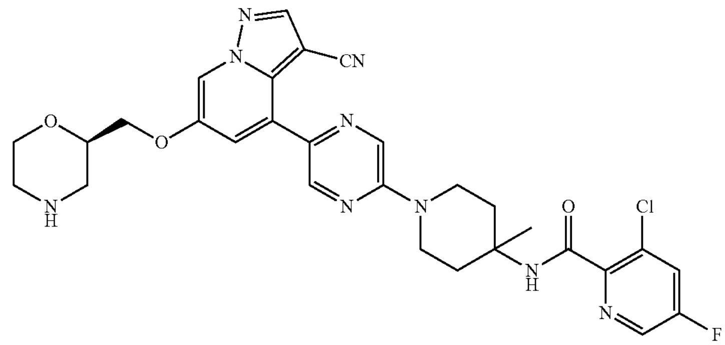 [SMILES: CC1(NC(=O)c2ncc(F)cc2Cl)CCN(c2cnc(-c3cc(OC[C@H]4CNCCO4)cn4ncc(C#N)c34)cn2)CC1] | (R)-3-chloro-N-(1-(5-(3-cyano-6-(morpholin-2-ylmethoxy)pyrazolo[1,5-a]pyridin-4-yl)pyrazin-2-yl)-4-methylpiperidin-4-yl)-5-fluoropicolinamide | 606.2 (M + H) |
| 799 | 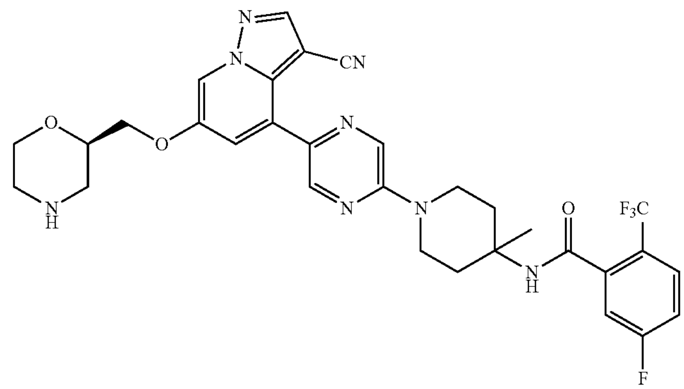 [SMILES: CC1(NC(=O)c2cc(F)ccc2C(F)(F)F)CCN(c2cnc(-c3cc(OC[C@H]4CNCCO4)cn4ncc(C#N)c34)cn2)CC1] | (R)-N-(1-(5-(3-cyano-6-(morpholin-2-ylmethoxy)pyrazolo[1,5-a]pyridin-4-yl)pyrazin-2-yl)-4-methylpiperidin-4-yl)-5-fluoro-2-(trifluoromethyl)benzamide | 639.2 (M + H) |

Example 800

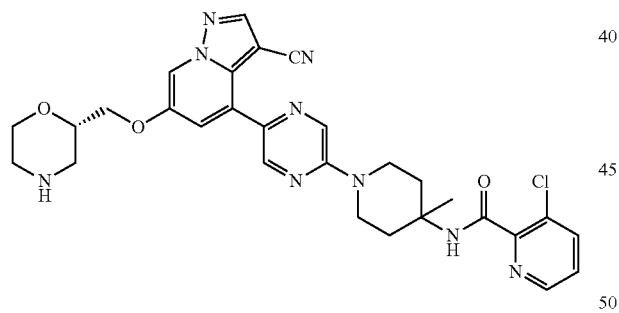

(S)-3-chloro-N-(1-(5-(3-cyano-6-(morpholin-2-ylmethoxy)pyrazolo[1,5-a]pyridin-4-yl)pyrazin-2-yl)-4-methylpiperidin-4-yl)picolinamide The title compound (50 mg, 74%) was prepared according to the procedure described in Example 797, replacing tert-butyl (R)-2-(((4-(5-(4-amino-4-methylpiperidin-1-yl)pyrazin-2-yl)-3-cyanopyrazolo[1,5-a]pyridin-6-yl)oxy)methyl)morpholine-4-carboxylate with tert-butyl (S)-2-(((4-(5-(4-amino-4-methylpiperidin-1-yl)pyrazin-2-yl)-3-cyanopyrazolo[1,5-a]pyridin-6-yl)oxy)methyl)morpholine-4-carboxylate (Intermediate 177). LCMS m/z=688.2 (M+H).

Example 801

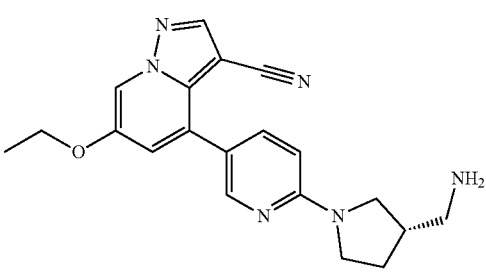 [SMILES: CCOc1cc(-c2ccc(N3CC[C@@H](CN)C3)nc2)c2c(C#N)cnn2c1]

(S)-4-(6-(3-(aminomethyl)pyrrolidin-1-yl)pyridin-3-yl)-6-ethoxypyrazolo[1,5-a]pyridine-3-carbonitrile Step 1: Preparation of tert-butyl (S)-((1-(5-(3-cyano-6-ethoxypyrazolo[1,5-a]pyridin-4-yl)pyridin-2-yl)pyrrolidin-3-yl)methyl)carbamate A solution of 6-ethoxy-4-(6-fluoropyridin-3-yl)pyrazolo[1,5-a]pyridine-3-carbonitrile (Intermediate P6, 50.7 mg, 0.180 mmol) and tert-butyl (R)-(pyrrolidin-3-ylmethyl)carbamate (54.0 mg, 0.269 mmol) in DMSO (1.5 mL) was treated with DIEA (0.157 mL, 0.898 mmol) and stirred at 115° C. overnight. After cooling to RT, the reaction was diluted with H₂O and filtered. The solid was rinsed with water, and then dried under vacuum to afford the title product as a light tan solid (83 mg, 99% yield). LCMS m/z=463.2 (M+H).

Step 2: Preparation of (S)-4-(6-(3-(aminomethyl)pyrrolidin-1-yl)pyridin-3-yl)-6-ethoxypyrazolo[1,5-a]pyridine-3-carbonitrile A solution of tert-butyl (S)-((1-(5-(3-cyano-6-ethoxypyrazolo[1,5-a]pyridin-4-yl)pyridin-2-yl)pyrrolidin-3-yl)methyl)carbamate (83 mg, 0.18 mmol) in 1,4-dioxane (1.5 mL) was treated with conc. HCl (0.029 mL, 0.36 mmol) and stirred at RT overnight. The reaction was concentrated, then taken up in 4:1 DCM/IPA and free-based with sat. NaHCO₃. The organic layer was passed through a Phase-Separator frit and concentrated to yield the title product as solid (8.9 mg, 13%). MS (apci) m/z=363.2 (M+H).

Example 802

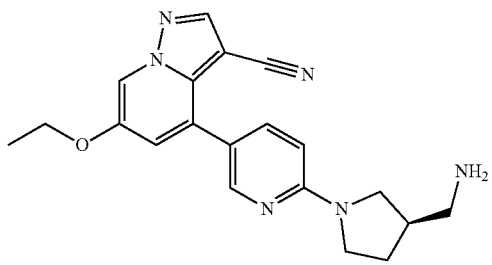 [SMILES: CCOc1cc(-c2ccc(N3CC[C@H](CN)C3)nc2)c2c(C#N)cnn2c1]

(R)-4-(6-(3-(aminomethyl)pyrrolidin-1-yl)pyridin-3-yl)-6-ethoxypyrazolo[1,5-a]pyridine-3-carbonitrile The title compound (12 mg, 18%) was prepared according to the procedure described in Example 801, replacing tert-butyl (R)-(pyrrolidin-3-ylmethyl)carbamate with tert-butyl (S)-(pyrrolidin-3-ylmethyl)carbamate in Step 1. LCMS m/z=363.2 (M+H).

Example 803

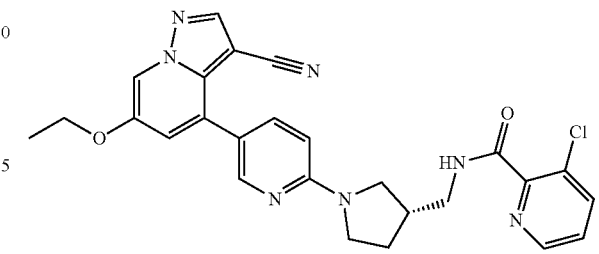

(S)-3-chloro-N-((1-(5-(3-cyano-6-ethoxypyrazolo[1,5-a]pyridin-4-yl)pyridin-2-yl)pyrrolidin-3-yl)methyl)picolinamide The title compound (32.6 mg, 71%) was prepared according to the procedure described in Example 791, replacing 4-(5-(4-amino-4-methylpiperidin-1-yl)pyrazin-2-yl)-6-methoxypyrazolo[1,5-a]pyridine-3-carbonitrile bis(2,2,2-trifluoroacetate) with (S)-4-(6-(3-(aminomethyl)pyrrolidin-1-yl)pyridin-3-yl)-6-ethoxypyrazolo[1,5-a]pyridine-3-carbonitrile (Example 801). LCMS m/z=502.2 (M+H).

The compounds in Table X13 were prepared according to the procedure described in Example 803, coupling the appropriate amine intermediate the corresponding carboxylic acid.

TABLE X13

| Ex. # | Structure | Chemical Name | LCMS m/z | Amine intermediate |
|---|---|---|---|---|
| 804 | ![structure] | (S)-N-((1-(5-(3-cyano-6-ethoxypyrazolo[1,5-a]pyridin-4-yl)pyridin-2-yl)pyrrolidin-3-yl)methyl)-3-methylbutanamide | 447.3 (M + H) | Example 801 |
| 805 | ![structure] | (R)-N-((1-(5-(3-cyano-6-ethoxypyrazolo[1,5-a]pyridin-4-yl)pyridin-2-yl)pyrrolidin-3-yl)methyl)-3-methylbutanamide | 447.3 (M + H) | Example 802 |

TABLE X13-continued

| Ex. # | Structure | Chemical Name | LCMS m/z | Amine intermediate |
|---|---|---|---|---|
| 806 | 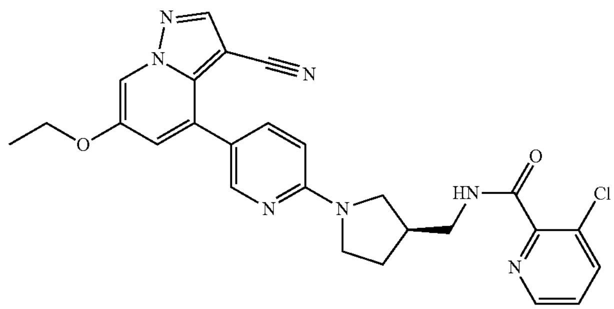 [SMILES: CCOc1cc(-c2ccc(N3CC[C@H](CNC(=O)c4ncccc4Cl)C3)nc2)c2c(C#N)cnn2c1] | (R)-3-chloro-N-((1-(5-(3-cyano-6-ethoxypyrazolo[1,5-a]pyridin-4-yl)pyridin-2-yl)pyrrolidin-3-yl)methyl)picolinamide | 502.1 (M + H) | Example 802 |

Example 807

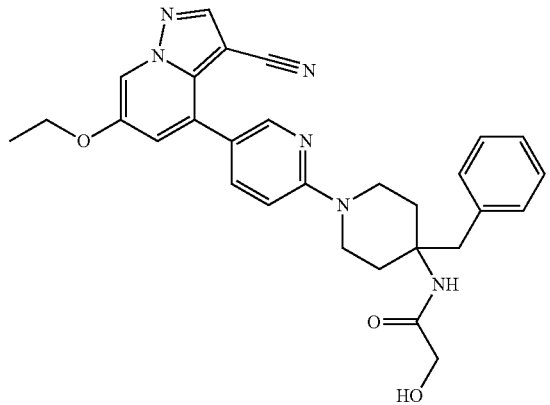 [SMILES: CCOc1cc(-c2ccc(N3CCC(Cc4ccccc4)(NC(=O)CO)CC3)nc2)c2c(C#N)cnn2c1]

N-(4-benzyl-1-(5-(3-cyano-6-ethoxypyrazolo[1,5-a]pyridin-4-yl)pyridin-2-yl)piperidin-4-yl)-2-hydroxyacetamide Step 1: Preparation of 4-(6-(4-amino-4-benzylpiperidin-1-yl)pyridin-3-yl)-6-ethoxypyrazolo[1,5-a]pyridine-3-carbonitrile A solution of tert-butyl 4-amino-4-benzylpiperidine-1-carboxylate (220 mg, 0.758 mmol) in DCM (1.5 mL) was treated with TFA (0.5 mL), stirred at RT for 1 h then concentrated. The residue was re-dissolved in DMA (3.8 mL), followed by addition of 6-ethoxy-4-(6-fluoropyridin-3-yl)pyrazolo[1,5-a]pyridine-3-carbonitrile (Intermediate P6, 214 mg, 0.758 mmol) and $K_2CO_3$ (524 mg, 3.79 mmol). The mixture was stirred at 60° C. for 24 h before it was cooled to RT and diluted with water. The aqueous mixture was extracted with EtOAc, and the combined organic extractions was concentrated and purified by silica chromatography (0-100% DCM/10% MeOH/1% $^NH_4OH$) to yield the title compound (261 mg, 76%). LCMS m/z=453.2 (M+H).

Step 2: Preparation of N-(4-benzyl-1-(5-(3-cyano-6-ethoxypyrazolo[1,5-a]pyridin-4-yl)pyridin-2-yl)piperidin-4-yl)-2-hydroxyacetamide To a solution of 4-(6-(4-amino-4-benzylpiperidin-1-yl)pyridin-3-yl)-6-ethoxypyrazolo[1,5-a]pyridine-3-carbonitrile (30 mg, 0.0663 mmol) in DCM (0.66 mL) was added 2-hydroxyacetic acid (5.55 mg, 0.0729 mmol), N-ethyl-N-isopropylpropan-2-amine (23.1 µl, 0.133 mmol), and HATU (30.2 mg, 0.0795 mmol), then stirred at RT overnight. The reaction mixture was directly treated with reverse phase chromatography (5-95% MeCN/$H_2O$/0.2% TFA). The combined fractions containing the product were partitioned between 4:1 DCM/IPA and sat. $NaHCO_3$. After phase-separation the organic layer was concentrated to yield the title product as solid (7.2 mg, 21%). MS (apci) m/z=511.2 (M+H).

The compounds in Table X14 were prepared using a similar method as described in Step 2 of Example 807, replacing 2-hydroxyacetic acid with the appropriate carboxylic acid.

TABLE X14
| Ex. # | Structure | Chemical Name | LCMS m/z |
|---|---|---|---|
| 808 | 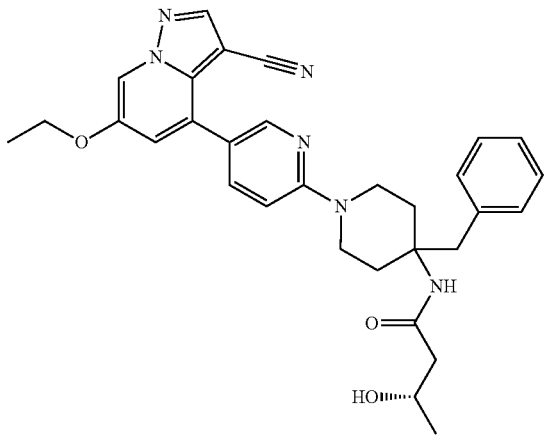 [SMILES: CCOc1cc(-c2ccc(N3CCC(Cc4ccccc4)(NC(=O)C[C@H](C)O)CC3)nc2)c2c(C#N)cnn2c1] | (S)-N-(4-benzyl-1-(5-(3-cyano-6-ethoxypyrazolo[1,5-a]pyridin-4-yl)pyridin-2-yl)piperidin-4-yl)-3-hydroxybutanamide | 539.2 (M + H) |
| 809 | 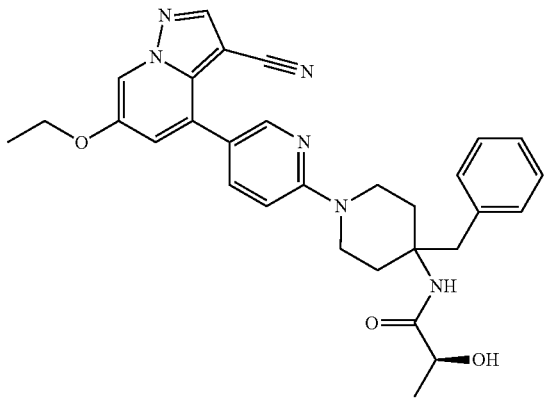 [SMILES: CCOc1cc(-c2ccc(N3CCC(Cc4ccccc4)(NC(=O)[C@H](C)O)CC3)nc2)c2c(C#N)cnn2c1] | (S)-N-(4-benzyl-1-(5-(3-cyano-6-ethoxypyrazolo[1,5-a]pyridin-4-yl)pyridin-2-yl)piperidin-4-yl)-2-hydroxypropanamide | 525.3 (M + H) |
| 810 | 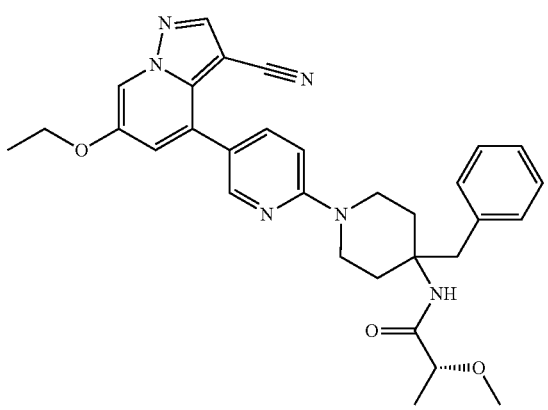 [SMILES: CCOc1cc(-c2ccc(N3CCC(Cc4ccccc4)(NC(=O)[C@@H](C)OC)CC3)nc2)c2c(C#N)cnn2c1] | (R)-N-(4-benzyl-1-(5-(3-cyano-6-ethoxypyrazolo[1,5-a]pyridin-4-yl)pyridin-2-yl)piperidin-4-yl)-2-methoxypropanamide | 539.3 (M + H) |

TABLE X14-continued

| Ex. # | Structure | Chemical Name | LCMS m/z |
|---|---|---|---|
| 811 | 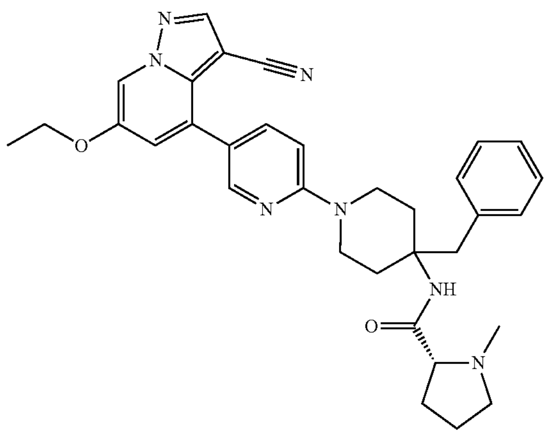 [SMILES: CCOc1cc(-c2ccc(N3CCC(Cc4ccccc4)(NC(=O)[C@H]4CCCN4C)CC3)nc2)c2c(C#N)cnn2c1] | (R)-N-(4-benzyl-1-(5-(3-cyano-6-ethoxypyrazolo[1,5-a]pyridin-4-yl)pyridin-2-yl)piperidin-4-yl)-1-methylpyrrolidine-2-carboxamide | 564.3 (M + H) |
| 812 | 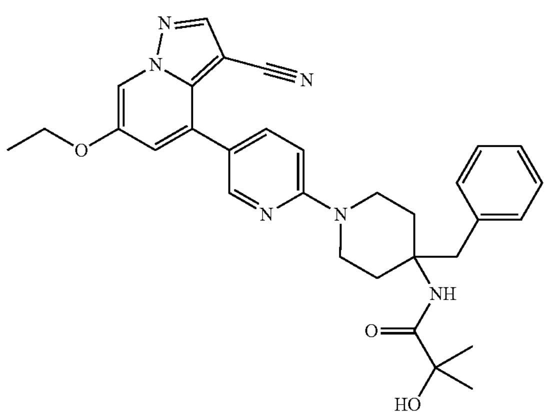 [SMILES: CCOc1cc(-c2ccc(N3CCC(Cc4ccccc4)(NC(=O)C(C)(C)O)CC3)nc2)c2c(C#N)cnn2c1] | N-(4-benzyl-1-(5-(3-cyano-6-ethoxypyrazolo[1,5-a]pyridin-4-yl)pyridin-2-yl)piperidin-4-yl)-2-hydroxy-2-methylpropanamide | 539.2 (M + H) |
| 813 | 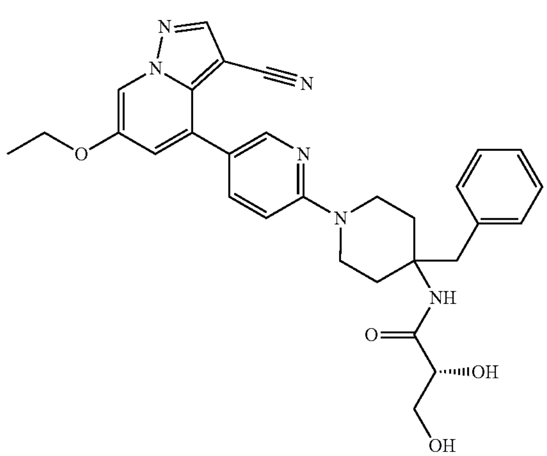 [SMILES: CCOc1cc(-c2ccc(N3CCC(Cc4ccccc4)(NC(=O)[C@H](O)CO)CC3)nc2)c2c(C#N)cnn2c1] | (R)-N-(4-benzyl-1-(5-(3-cyano-6-ethoxypyrazolo[1,5-a]pyridin-4-yl)pyridin-2-yl)piperidin-4-yl)-2,3-dihydroxypropanamide | 541.2 (M + H) |

TABLE X14-continued

| Ex. # | Structure | Chemical Name | LCMS m/z |
|---|---|---|---|
| 814 | 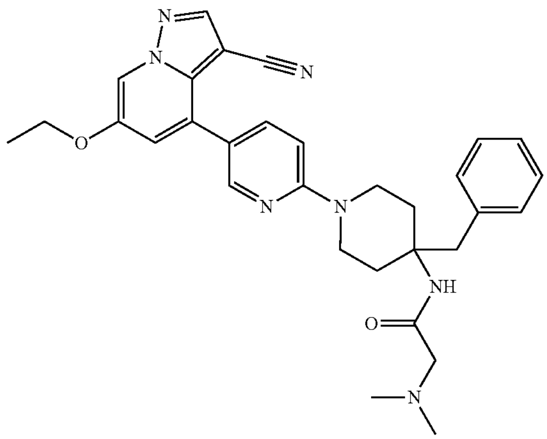 [SMILES: CCOc1cc(-c2ccc(N3CCC(Cc4ccccc4)(NC(=O)CN(C)C)CC3)nc2)c2c(C#N)cnn2c1] | N-(4-benzyl-1-(5-(3-cyano-6-ethoxypyrazolo[1,5-a]pyridin-4-yl)pyridin-2-yl)piperidin-4-yl)-2-(dimethylamino)acetamide | 538.2 (M + H) |

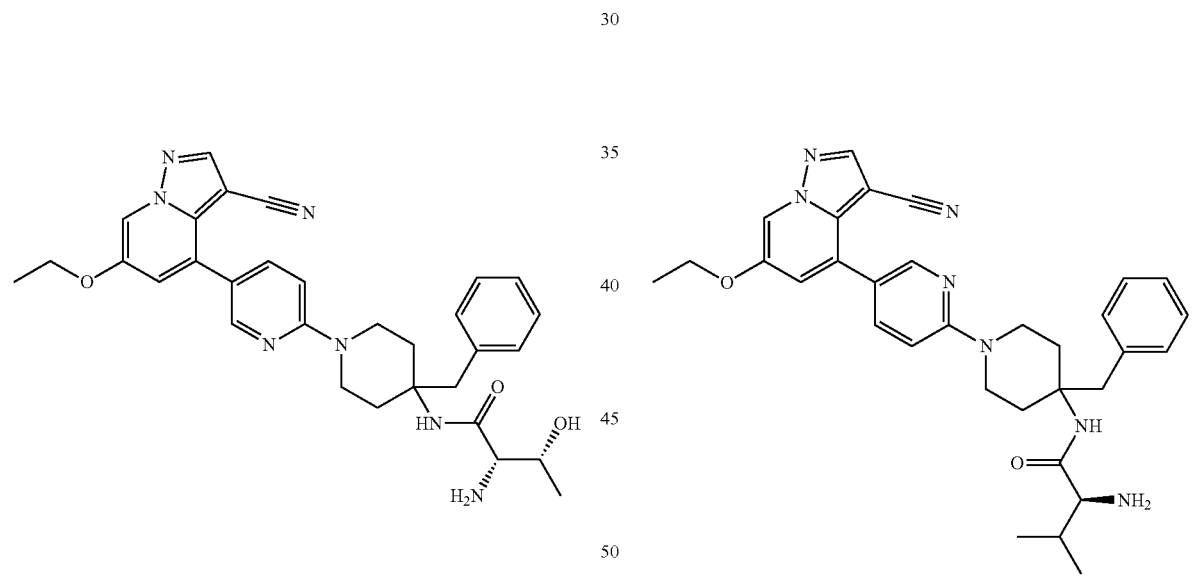

Example 815

(2S,3R)-2-amino-N-(4-benzyl-1-(5-(3-cyano-6-ethoxypyrazolo[1,5-a]pyridin-4-yl)pyridin-2-yl)piperidin-4-yl)-3-hydroxybutanamide The title compound was prepared using a similar method as described in Step 2 of Example 807, replacing 2-hydroxyacetic acid with an N-Fmoc-protected acid (((9H-fluoren-9-yl)methoxy)carbonyl)-L-threonine. The N-protected crude product was treated with 1:1 morpholine:DCM to remove the protective group, then concentrated and purified according to the procedure described in Example 807 to afford the final product as solid (13.8 mg, 28%). MS (apci) m/z=554.3 (M+H).

Example 816

(S)-2-amino-N-(4-benzyl-1-(5-(3-cyano-6-ethoxypyrazolo[1,5-a]pyridin-4-yl)pyridin-2-yl)piperidin-4-yl)-3-methylbutanamide The title compound (3 mg, 8%) was prepared using a similar method as described in Example 815, replacing (((9H-fluoren-9-yl)methoxy)carbonyl)-L-threonine with (((9H-fluoren-9-yl)methoxy)carbonyl)-L-valine. MS (apci) m/z=552.3 (M+H).

Example 817

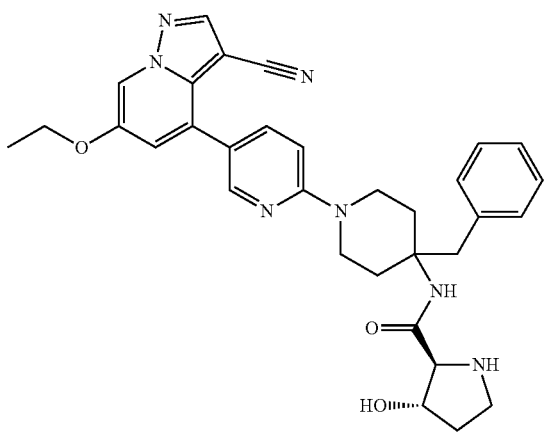 [SMILES: CCOc1cc(-c2ccc(N3CCC(Cc4ccccc4)(NC(=O)[C@H]4NCC[C@@H]4O)CC3)nc2)c2c(C#N)cnn2c1]

(2S,3 S)—N-(4-benzyl-1-(5-(3-cyano-6-ethoxypyra-zolo[1,5-a]pyridin-4-yl)pyridin-2-yl)piperidin-4-yl)-3-hydroxypyrrolidine-2-carboxamide The title compound was prepared using a similar method as described in Step 2 of Example 807, replacing 2-hydroxyacetic acid with an N-Boc-protected acid (2S,3S)-1-(tert-butoxycarbonyl)-3-hydroxypyrrolidine-2-carboxylic acid. The N-protected product was isolated after a silica chromatography (0-100% EtOAc in hexanes). The isolated product was dissolved in 1:1 DCM:TFA at 0° C., then allowed to slowly warm up to RT over 24 h. After removal of solvent, The crude material was treated with a second silica chromatography (0-100% 1:9 MeOH:DCM with 1% NH$_4$OH in DCM) to afford the title product as solid (33 mg, 36%). MS (apci) m/z=566.2 (M+H).

Example 818

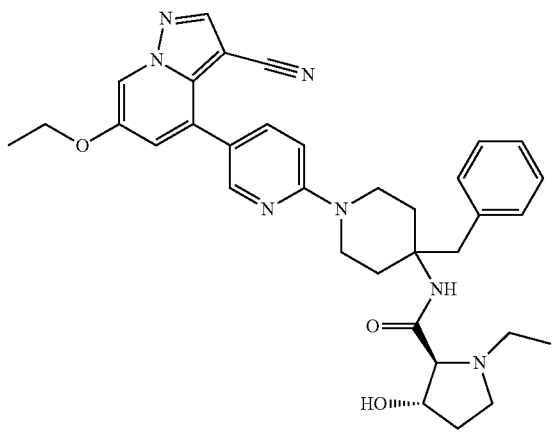 [SMILES: CCOc1cc(-c2ccc(N3CCC(Cc4ccccc4)(NC(=O)[C@@H]4[C@@H](O)CCN4CC)CC3)nc2)c2c(C#N)cnn2c1]

(2S,3 S)—N-(4-benzyl-1-(5-(3-cyano-6-ethoxypyra-zolo[1,5-a]pyridin-4-yl)pyridin-2-yl)piperidin-4-yl)-1-ethyl-3-hydroxypyrrolidine-2-carboxamide A solution of (2S,3 S)—N-(4-benzyl-1-(5-(3-cyano-6-ethoxypyrazolo[1,5-a]pyridin-4-yl)pyridin-2-yl)piperidin-4-yl)-3-hydroxypyrrolidine-2-carboxamide (Example 817, 15 mg, 0.0265 mmol) in DCM (0.13 mL) was treated with sodium triacetoxyhydroborate (11.2 mg, 0.0530 mmol) and acetaldehyde (0.769 µL, 0.0265 mmol), then stirred at RT overnight. The reaction mixture was diluted with 4:1 DCM/IPA and washed with sat. NaHCO$_3$ (aq). After phase separation, the organic layer was concentrated to yield the title product (11 mg, 72%). MS (apci) m/z=594.3 (M+H).

Example 819

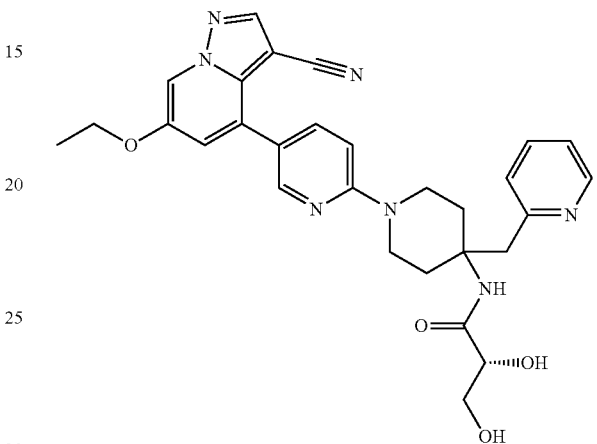

(R)—N-(1-(5-(3-cyano-6-ethoxypyrazolo[1,5-a]pyridin-4-yl)pyridin-2-yl)-4-(pyridin-2-ylmethyl)piperidin-4-yl)-2,3-dihydroxypropanamide The title product (21.6 mg, 18%) was prepared using a similar method as described in Step 1 of Example 626, replacing 2-(1-(tert-butoxycarbonyl)azetidin-3-yl)acetic acid with D(+)-glyceric acid hemicalcium salt. MS (apci) m/z=542.2 (M+H).

| Abbreviations: | |
|---|---|
| 18-Crown-6 | 1,4,7,10,13,16-hexaoxacyclooctadecane |
| ACN | Acetonitrile |
| AcOH | Acetic Acid |
| (±)-BINAP | 2,2'-Bis(diphenylphosphino)-1,1'-binaphthalene |
| Bis(pinacolato) diboron | 4,4,4',4',5,5,5',5'-octamethyl-2,2'-bi(1,3,2-dioxaborolane) |
| Boc | tert-butyl carboxylate group |
| Boc-anhydride | di-tert-butyl dicarbonate |
| Boc—Inp—OH | 1-Boc-piperidine-4-carboxylic acid; or Boc-isonipecotic acid |
| n-BuLi | n-butyllithium or 1-butyllithium |
| s-BuOH | Sec-Butanol or 2-Butanol |
| t-BuOH | tert-Butanol or 2-Methylpropan-2-ol |
| Celite ® | Diatomaceous earth; SiO$_2$ |
| CuI | Copper (I) iodide |
| Cu(OAc)$_2$ | Copper (II) diacetate |
| d | day, days |
| DCE | 1,2-Dichloroethane |
| DCM | Dichloromethane |
| DIAD | Diisopropyl azodicarboxylate |
| DIEA | N,N-Diisopropylethylamine |
| DI water | Deionized water |
| dioxane | 1,4-dioxane |
| DMA | N,N-Dimethylacetamide |
| DMAP | 4-Dimethylaminopyridine |
| DME | 1,2-Dimethoxyethane |
| DMF | N,N-Dimethylformamide |

Abbreviations:

| | |
|---|---|
| DMSO | Dimethylsulfoxide |
| DMP | Dess-MartinPeriodinane; 1,1,1-Tris(acetyloxy)-1,1-dihydro-1,2-benziodoxol-3-(1H)-one |
| EDC—HCl | 1-Ethyl-3-(3-dimethylaminopropyl)carbodiimide hydrochloride |
| Et$_2$O | Diethyl Ether |
| EtOAc | Ethyl Acetate |
| EtOH | Ethanol |
| eq | equivalent |
| GF/F paper | GF/F glass microfiber filter paper |
| h | hour, hours |
| HATU | 1-[Bis(dimethylamino)methylene]-1H-1,2,3-triazolo[4,5-b]pyridinium 3-oxide hexafluorophosphate or 2-(7-Aza-1H-benzotriazole-1-yl)-1,1,3,3-tetramethyluronium hexafluorophosphate |
| HBTU | 3-[Bis(dimethylamino)methyliumyl]-3H-benzotriazol-1-oxide hexafluorophosphate or 2-(1H-benzotriazole-1-yl)-1,1,3,3-tetramethyluronium hexafluorophosphate |
| HOAc | Acetic Acid |
| isobutyl chloroformate | isobutyl carbonochloridate |
| isovaleryl chloride | 3-methylbutanoyl chloride |
| iPrOH | Isopropanol |
| i-PrMgCl | Isopropyl magnesium chloride |
| KOAc | Potassium Acetate |
| KOtBu | Potassium tert-Butoxide |
| K$_2$HPO$_4$ | Potassium Phosphate, Dibasic |
| LCMS | Liquid chromatography-mass spectrometry |
| LiHMDS | Lithium Hexamethyldisilazide; or Lithium bis(trimethylsilyl)amide |
| MeOH | Methanol |
| Me$_4$N(AcO)$_3$BH | Tetramethylammonium Triacetoxyborohydride |
| min | minute, minutes |
| MSH | o-(mesitylsulfonyl)hydroxylamine |
| MTBE | Methyl tert-Butyl Ether |
| NCS | N-Chlorosuccinimide |
| NBS | N-Bromosuccinimide |
| NIS | N-Iodosuccinimide |
| NaBH(AcO)$_3$ | Sodium Triacetoxyborohydride |
| NH$_4$OAc | Ammonium Acetate |
| P1-HCO$_3$ resin | Stratospheres MP-HCO3 |
| 10% Pd/C | Palladium 10 wt. % (dry basis), active carbon, wet, Degussa |
| Pd(PPh$_3$)$_4$ | Tetrakis(triphenylphosphine)palladium (0) |
| Pd$_2$(dba)$_3$ | tris(dibenzylideneacetone)dipalladium (0) |
| PdCl$_2$(dppf)•CH$_2$Cl$_2$ | 1,1'-Bis(diphenylphosphino)ferrocene-palladium(II)dichloride dichloromethane complex |
| Pd$_2$(dba)$_3$•CHCl$_3$ | tris(dibenzylideneacetone)dipalladium (0) chloroform complex |
| PdCl$_2$(PPh$_3$)$_2$ | Palladium(II)bis(triphenylphosphine) dichloride, |
| PPh$_3$ | Triphenylphosphine |
| PPTS | Pyridinium p-toluenesulfonate |
| PS frit | Biotage ® "Isolute ® Phase Separators" |
| PS paper | Whatman ® silicone treated Phase Separators filter paper |
| PVDF (0.45 µm) disc | polyvinylidene difluoride membrane with a 0.45-micron pore size |
| rt | Room temperature |
| TBAF | Tetra-n-butylammonium fluoride |
| TEA | Triethylamine |
| TFA | Trifluoroacetic acid |
| THF | tetrahydrofuran |
| Triphosgene | (bis(trichloromethyl) carbonate |
| Tf—O—Tf | trifluoromethanesulfonic anhydride |
| TsCl | 4-Toluenesulfonyl chloride |
| X-Phos | dicyclohexyl(2',4',6'-triisopropyl-[1,1'-biphenyl]-2- yl)phosphine |

---

What is claimed is:

1. A compound of the Formula I:

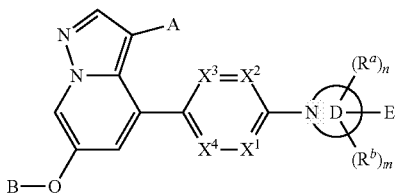

I and pharmaceutically acceptable salts and solvates thereof, wherein:

$X^1$, $X^2$, $X^3$ and $X^4$ are independently CH or N, wherein zero, one or two of $X^1$, $X^2$, $X^3$ and $X^4$ is N;

A is CN;

B is:

(b) C1-C6 alkyl optionally substituted with 1-3 fluoros, (c) hydroxyC2-C6 alkyl- wherein the alkyl portion is optionally substituted with a C3-C6 cycloalkylidene ring, or (i) (hetCyc$^a$)C1-C3 alkyl-;

hetCyc$^a$ is a 4-6 membered heterocyclic ring having 1-2 ring heteroatoms independently selected from N and 0 and optionally substituted with one or more substituents independently selected from OH, C1-C6 alkyl (optionally substituted with 1-3 fluoros), hydroxyC1-C6 alkyl, halogen, (C1-C6 alkyl)C(=O)—, C1-C6 alkoxy, oxo, and (C1-C6 alkoxy)C(=O)—;

Ring D is a saturated monocyclic 4-7 membered heterocyclic ring having one ring heteroatom which is nitrogen;

each $R^a$ is independently C1-C6 alkyl (optionally substituted with 1-3 fluoros);

$R^b$ is (a) hydroxy;

n is 0 or 1;

m is 0 or 1;

E is:

(e) hetAr$^2$C1-C6 alkyl-, (h) hetAr$^2$—O—, (k) $R^3$C(=O)NR$^g$— where $R^g$ is H or C1-C6 alkyl, (l) Ar$^j$C(=O)NR$^g$— where $R^g$ is H or C1-C6 alkyl, or (m) hetAr$^2$C(=O)NR$^g$(CH$_2$)$_p$— where p is 0 or 1 and $R^g$ is H or C1-C6 alkyl;

Ar$^1$ is phenyl optionally substituted with one or more substituents independently selected from the group consisting of halogen, CN, C1-C6 alkyl (optionally substituted with 1-3 fluoros), C1-C6 alkoxy (optionally substituted with 1-3 fluoros), (C1-C6 alkoxy)C1-C6 alkyl- (optionally substituted with 1-3 fluoros), C3-C6 cycloalkyl, hydroxyC1-C6 alkyl, (C1-C6 alkyl)SO$_2$—, R$^e$R$^f$N— and (R$^e$R$^f$N)C1-C6 alkyl- where each R$^e$ and R$^f$ is independently H or C1-C6 alkyl;

hetAr$^2$ is a 5-6 membered heteroaryl ring having 1-3 ring heteroatoms independently selected from N, O and S, or a 9-10 membered bicyclic heteroaryl having 1-2 ring nitrogen atoms, wherein hetAr$^2$ is optionally substituted with one or more substituents independently selected from the group consisting of halogen, CN, C1-C6 alkyl (optionally substituted with 1-3 fluoros), C1-C6 alkoxy (optionally substituted with 1-3 fluoros), (C1-C6 alkoxy)C1-C6 alkyl- (optionally substituted with 1-3 fluoros) and hydroxyC1-C6 alkoxy-;

$R^3$ is C1-C6 alkyl (optionally substituted with 1-3 fluoros), hydroxyC1-C6 alkyl-, C1-C6 alkoxy, C3-C6 cycloalkyl, (C3-C6 cycloalkyl)CH$_2$—, (C3-C6 cycloalkyl)O—, (C3-C6 cycloalkyl)CH$_2$O—, hetCyc$^7$O—, Ph-O—, or (C1-C6 alkoxy)C1-C6 alkyl-; wherein each of said C3-C6 cycloalkyl moieties is optionally substituted with C1-C6 alkyl (optionally substituted with 1-3 fluoros), C1-C6 alkoxy, OH, or R'R"N— where R' and R" are independently hydrogen or C1-C6 alkyl; and hetCyc$^7$ is a 5-7 membered heterocyclic ring having 1-3 ring heteroatoms independently selected from N, O and S.

2. A compound according to claim 1, wherein Ring D is

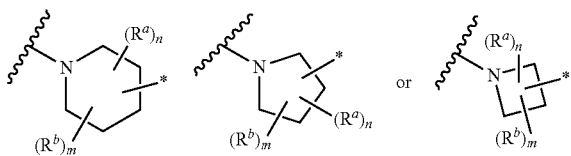

wherein the wavy line indicates the point of attachment of Ring D to the ring comprising $X^1$, $X^2$, $X^3$ and $X^4$, and the asterisk indicates the point of attachment of Ring D to the E group.

3. A compound according to claim 2, wherein D is

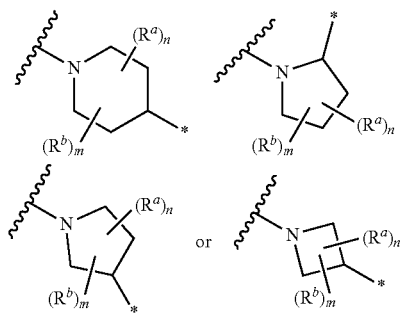

wherein the wavy line indicates the point of attachment of Ring D to the ring comprising $X^1$, $X^2$, $X^3$ and $X^4$, and the asterisk indicates the point of attachment of Ring D to the E group.

4. A compound according to claim 3, wherein D is

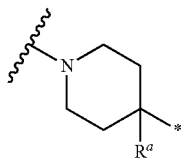

wherein the wavy line indicates the point of attachment of Ring D to the ring comprising $X^1$, $X^2$, $X^3$ and $X^4$, and the asterisk indicates the point of attachment of Ring D to the E group.

5. A compound according to claim 3, wherein D is

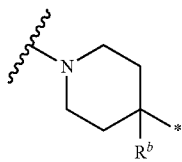

wherein the wavy line indicates the point of attachment of Ring D to the ring comprising $X^1$, $X^2$, $X^3$ and $X^4$, and the asterisk indicates the point of attachment to the E group.

6. A compound according to claim 3, wherein E is:
(e) hetAr$^2$C1-C6 alkyl-,
(h) hetAr$^2$—O—,
(l) Ar$^1$C(=O)NR$^g$— where R$^g$ is H or C1-C6 alkyl, or
(m) hetAr$^2$C(=O)NR$^g$(CH$_2$)$_p$— where p is 0 or 1 and R$^g$ is H or C1-C6 alkyl.

7. A compound according to claim 3, wherein B is C1-C6 alkyl optionally substituted with 1-3 fluoros, or hydroxyC2-C6 alkyl wherein the alkyl portion is optionally substituted with a C3-C6 cycloalkylidene ring.

8. A compound according to claim 3, wherein $X^1$ is N, and $X^2$, $X^3$ and $X^4$ are CH.

9. A compound according to claim 1, wherein the compound of Formula I is selected from the group consisting of:
N-(1-(5-(3-cyano-6-(2-hydroxy-2-methylpropoxy)pyrazolo[1,5-a]pyridin-4-yl)pyridin-2-yl)-4-methylpiperidin-4-yl)benzamide;
6-ethoxy-4-(6-(4-hydroxy-4-(pyridin-2-ylmethyl)piperidin-1-yl)pyridin-3-yl)pyrazolo[1,5-a]pyridine-3-carbonitrile;
6-(2-hydroxy-2-methylpropoxy)-4-(6-(3-(pyridin-2-yloxy)azetidin-1-yl)pyridin-3-yl)pyrazolo[1,5-a]pyridine-3-carbonitrile;
6-(2-hydroxy-2-methylpropoxy)-4-(6-(4-((6-methoxypyridazin-3-yl)oxy)piperidin-1-yl)pyridin-3-yl)pyrazolo[1,5-a]pyridine-3-carbonitrile;
(S)-6-(2-hydroxy-2-methylpropoxy)-4-(6-(3-(pyridin-2-yloxy)pyrrolidin-1-yl)pyridin-3-yl)pyrazolo[1,5-a]pyridine-3-carbonitrile;
N-(1-(5-(3-cyano-6-((3-fluoro-1-methylazetidin-3-yl)methoxy)pyrazolo[1,5-a]pyridin-4-yl)pyridin-2-yl)-4-methylpiperidin-4-yl)-5-fluoro-2-methylbenzamide;
3-chloro-N-(1-(5-(3-cyano-6-((3-fluoro-1-methylazetidin-3-yl)methoxy)pyrazolo[1,5-a]pyridin-4-yl)pyridin-2-yl)-4-methylpiperidin-4-yl)picolinamide;
N-((3 S,4 S)-1-(5-(3-cyano-6-ethoxypyrazolo[1,5-a]pyridin-4-yl)pyridin-2-yl)-3-hydroxypiperidin-4-yl)-3-methylbutanamide;
6-(2-hydroxy-2-methylpropoxy)-4-(6-(4-hydroxy-4-(pyridin-2-ylmethyl)piperidin-1-yl)pyridin-3-yl)pyrazolo[1,5-a]pyridine-3-carbonitrile; and
3-chloro-N-((3 S,4 S)-1-(5-(3-cyano-6-ethoxypyrazolo[1,5-a]pyridin-4-yl)pyrazin-2-yl)-3-hydroxypiperidin-4-yl)picolinamide;
or a pharmaceutically acceptable salt thereof.

10. A compound according to claim 1, wherein the compound of Formula I is
N-(1-(5-(3-cyano-6-(2-hydroxy-2-methylpropoxy)pyrazolo[1,5-a]pyridin-4-yl)pyridin-2-yl)-4-methylpiperidin-4-yl)benzamide, or a pharmaceutically acceptable salt thereof.

11. A compound according to claim 1, wherein the compound of Formula I is
6-ethoxy-4-(6-(4-hydroxy-4-(pyridin-2-ylmethyl)piperidin-1-yl)pyridin-3-yl)pyrazolo[1,5-a]pyridine-3-carbonitrile, or a pharmaceutically acceptable salt thereof.

12. A compound according to claim 1, wherein the compound of Formula I is
6-(2-hydroxy-2-methylpropoxy)-4-(6-(3-(pyridin-2-yloxy)azetidin-1-yl)pyridin-3-yl)pyrazolo[1,5-a]pyridine-3-carbonitrile, or a pharmaceutically acceptable salt thereof.

13. A compound according to claim 1, wherein the compound of Formula I is
6-(2-hydroxy-2-methylpropoxy)-4-(6-(4-((6-methoxypyridazin-3-yl)oxy)piperidin-1-yl)pyridin-3-yl)pyrazolo[1,5-a]pyridine-3-carbonitrile, or a pharmaceutically acceptable salt thereof.

14. A compound according to claim 1, wherein the compound of Formula I is (S)-6-(2-hydroxy-2-methylpropoxy)-4-(6-(3-(pyridin-2-yloxy)pyrrolidin-1-yl)pyridin-3-yl)pyrazolo[1,5-a]pyridine-3-carbonitrile, or a pharmaceutically acceptable salt thereof.

15. A compound according to claim 1, wherein the compound of Formula I is
N-(1-(5-(3-cyano-6-((3-fluoro-1-methylazetidin-3-yl)methoxy)pyrazolo[1,5-a]pyridin-4-yl)pyridin-2-yl)-4-methylpiperidin-4-yl)-5-fluoro-2-methylbenzamide, or a pharmaceutically acceptable salt thereof.

16. A compound according to claim 1, wherein the compound of Formula I is
3-chloro-N-(1-(5-(3-cyano-6-((3-fluoro-1-methylazetidin-3-yl)methoxy)pyrazolo[1,5-a]pyridin-4-yl)pyridin-2-yl)-4-methylpiperidin-4-yl)picolinamide, or a pharmaceutically acceptable salt thereof.

17. A compound according to claim 1, wherein the compound of Formula I is
N-((3 S,4S)-1-(5-(3-cyano-6-ethoxypyrazolo[1,5-a]pyridin-4-yl)pyridin-2-yl)-3-hydroxypiperidin-4-yl)-3-methylbutanamide, or a pharmaceutically acceptable salt thereof.

18. A compound according to claim 1, wherein the compound of Formula I is
6-(2-hydroxy-2-methylpropoxy)-4-(6-(4-hydroxy-4-(pyridin-2-ylmethyl)piperidin-1-yl)pyridin-3-yl)pyrazolo[1,5-a]pyridine-3-carbonitrile, or a pharmaceutically acceptable salt thereof.

19. A compound according to claim 1, wherein the compound of Formula I is
3-chloro-N-((3 S,4 S)-1-(5-(3-cyano-6-ethoxypyrazolo[1,5-a]pyridin-4-yl)pyrazin-2-yl)-3-hydroxypiperidin-4-yl)picolinamide, or a pharmaceutically acceptable salt thereof.

20. A pharmaceutical composition, comprising a compound according to claim 1, or a pharmaceutically acceptable salt or solvate thereof, in admixture with a pharmaceutically acceptable diluent or carrier.

21. A pharmaceutical composition according to claim 20, wherein the compound of Formula I is
N-(1-(5-(3-cyano-6-(2-hydroxy-2-methylpropoxy)pyrazolo[1,5-a]pyridin-4-yl)pyridin-2-yl)-4-methylpiperidin-4-yl)benzamide, or a pharmaceutically acceptable salt thereof.

22. A pharmaceutical composition according to claim 20, wherein the compound of Formula I is
6-ethoxy-4-(6-(4-hydroxy-4-(pyridin-2-ylmethyl)piperidin-1-yl)pyridin-3-yl)pyrazolo[1,5-a]pyridine-3-carbonitrile, or a pharmaceutically acceptable salt thereof.

23. A pharmaceutical composition according to claim 20, wherein the compound of Formula I is
6-(2-hydroxy-2-methylpropoxy)-4-(6-(3-(pyridin-2-yloxy)azetidin-1-yl)pyridin-3-yl)pyrazolo[1,5-a]pyridine-3-carbonitrile, or a pharmaceutically acceptable salt thereof.

24. A pharmaceutical composition according to claim 20, wherein the compound of Formula I is
6-(2-hydroxy-2-methylpropoxy)-4-(6-(4-(((6-methoxypyridazin-3-yl)oxy)piperidin-1-yl)pyridin-3-yl)pyrazolo [1,5-a]pyridine-3-carbonitrile, or a pharmaceutically acceptable salt thereof.

25. A pharmaceutical composition according to claim 20, wherein the compound of Formula I is
(S)-6-(2-hydroxy-2-methylpropoxy)-4-(6-(3-(pyridin-2-yloxy)pyrrolidin-1-yl)pyridin-3-yl)pyrazolo [1,5-a]pyridine-3-carbonitrile, or a pharmaceutically acceptable salt thereof.

26. A pharmaceutical composition according to claim 20, wherein the compound of Formula I is
N-(1-(5-(3-cyano-6-((3-fluoro-1-methylazetidin-3-yl)methoxy)pyrazolo[1,5-a]pyridin-4-yl)pyridin-2-yl)-4-methylpiperidin-4-yl)-5-fluoro-2-methylbenzamide, or a pharmaceutically acceptable salt thereof.

27. A pharmaceutical composition according to claim 20, wherein the compound of Formula I is
3-chloro-N-(1-(5-(3-cyano-6-((3-fluoro-1-methylazetidin-3-yl)methoxy)pyrazolo[1,5-a]pyridin-4-yl)pyridin-2-yl)-4-methylpiperidin-4-yl)picolinamide, or a pharmaceutically acceptable salt thereof.

28. A pharmaceutical composition according to claim 20, wherein the compound of Formula I is
N-((3S,4S)-1-(5-(3-cyano-6-ethoxypyrazolo[1,5-a]pyridin-4-yl)pyridin-2-yl)-3-hydroxypiperidin-4-yl)-3-methylbutanamide, or a pharmaceutically acceptable salt thereof.

29. A pharmaceutical composition according to claim 20, wherein the compound of Formula I is
6-(2-hydroxy-2-methylpropoxy)-4-(6-(4-hydroxy-4-(pyridin-2-ylmethyl)piperidin-1-yl)pyridin-3-yl)pyrazolo[1,5-a]pyridine-3-carbonitrile, or a pharmaceutically acceptable salt thereof.

30. A pharmaceutical composition according to claim 20, wherein the compound of Formula I is
3-chloro-N-((3 S,4 S)-1-(5-(3-cyano-6-ethoxypyrazolo[1,5-a]pyridin-4-yl)pyrazin-2-yl)-3-hydroxypiperidin-4-yl)picolinamide, or a pharmaceutically acceptable salt thereof.

* * * * *

SEQUENCE LISTING

```
<160> NUMBER OF SEQ ID NOS: 1

<210> SEQ ID NO 1
<211> LENGTH: 1114
<212> TYPE: PRT
<213> ORGANISM: Homo sapiens

<400> SEQUENCE: 1

Met Ala Lys Ala Thr Ser Gly Ala Ala Gly Leu Arg Leu Leu Leu Leu
1               5                   10                  15

Leu Leu Leu Pro Leu Leu Gly Lys Val Ala Leu Gly Leu Tyr Phe Ser
                20                  25                  30

Arg Asp Ala Tyr Trp Glu Lys Leu Tyr Val Asp Gln Ala Ala Gly Thr
            35                  40                  45

Pro Leu Leu Tyr Val His Ala Leu Arg Asp Ala Pro Glu Glu Val Pro
        50                  55                  60

Ser Phe Arg Leu Gly Gln His Leu Tyr Gly Thr Tyr Arg Thr Arg Leu
65                  70                  75                  80

His Glu Asn Asn Trp Ile Cys Ile Gln Glu Asp Thr Gly Leu Leu Tyr
                85                  90                  95

Leu Asn Arg Ser Leu Asp His Ser Ser Trp Glu Lys Leu Ser Val Arg
            100                 105                 110

Asn Arg Gly Phe Pro Leu Leu Thr Val Tyr Leu Lys Val Phe Leu Ser
        115                 120                 125

Pro Thr Ser Leu Arg Glu Gly Glu Cys Gln Trp Pro Gly Cys Ala Arg
130                 135                 140
```

-continued

```
Val Tyr Phe Ser Phe Phe Asn Thr Ser Phe Pro Ala Cys Ser Ser Leu
145                 150                 155                 160

Lys Pro Arg Glu Leu Cys Phe Pro Glu Thr Arg Pro Ser Phe Arg Ile
            165                 170                 175

Arg Glu Asn Arg Pro Pro Gly Thr Phe His Gln Phe Arg Leu Leu Pro
        180                 185                 190

Val Gln Phe Leu Cys Pro Asn Ile Ser Val Ala Tyr Arg Leu Leu Glu
            195                 200                 205

Gly Glu Gly Leu Pro Phe Arg Cys Ala Pro Asp Ser Leu Glu Val Ser
        210                 215                 220

Thr Arg Trp Ala Leu Asp Arg Glu Gln Arg Lys Tyr Glu Leu Val
225                 230                 235                 240

Ala Val Cys Thr Val His Ala Gly Ala Arg Glu Glu Val Met Val
                245                 250                 255

Pro Phe Pro Val Thr Val Tyr Asp Glu Asp Asp Ser Ala Pro Thr Phe
            260                 265                 270

Pro Ala Gly Val Asp Thr Ala Ser Ala Val Val Glu Phe Lys Arg Lys
        275                 280                 285

Glu Asp Thr Val Val Ala Thr Leu Arg Val Phe Asp Ala Asp Val Val
290                 295                 300

Pro Ala Ser Gly Glu Leu Val Arg Arg Tyr Thr Ser Thr Leu Leu Pro
305                 310                 315                 320

Gly Asp Thr Trp Ala Gln Gln Thr Phe Arg Val Glu His Trp Pro Asn
                325                 330                 335

Glu Thr Ser Val Gln Ala Asn Gly Ser Phe Val Arg Ala Thr Val His
            340                 345                 350

Asp Tyr Arg Leu Val Leu Asn Arg Asn Leu Ser Ile Ser Glu Asn Arg
        355                 360                 365

Thr Met Gln Leu Ala Val Leu Val Asn Asp Ser Asp Phe Gln Gly Pro
        370                 375                 380

Gly Ala Gly Val Leu Leu Leu His Phe Asn Val Ser Val Leu Pro Val
385                 390                 395                 400

Ser Leu His Leu Pro Ser Thr Tyr Ser Leu Ser Val Ser Arg Arg Ala
                405                 410                 415

Arg Arg Phe Ala Gln Ile Gly Lys Val Cys Val Glu Asn Cys Gln Ala
            420                 425                 430

Phe Ser Gly Ile Asn Val Gln Tyr Lys Leu His Ser Ser Gly Ala Asn
        435                 440                 445

Cys Ser Thr Leu Gly Val Val Thr Ser Ala Glu Asp Thr Ser Gly Ile
    450                 455                 460

Leu Phe Val Asn Asp Thr Lys Ala Leu Arg Arg Pro Lys Cys Ala Glu
465                 470                 475                 480

Leu His Tyr Met Val Val Ala Thr Asp Gln Gln Thr Ser Arg Gln Ala
                485                 490                 495

Gln Ala Gln Leu Leu Val Thr Val Glu Gly Ser Tyr Val Ala Glu Glu
            500                 505                 510

Ala Gly Cys Pro Leu Ser Cys Ala Val Ser Lys Arg Arg Leu Glu Cys
        515                 520                 525

Glu Glu Cys Gly Gly Leu Gly Ser Pro Thr Gly Arg Cys Glu Trp Arg
530                 535                 540

Gln Gly Asp Gly Lys Gly Ile Thr Arg Asn Phe Ser Thr Cys Ser Pro
545                 550                 555                 560
```

```
Ser Thr Lys Thr Cys Pro Asp Gly His Cys Asp Val Val Glu Thr Gln
            565                 570                 575
Asp Ile Asn Ile Cys Pro Gln Asp Cys Leu Arg Gly Ser Ile Val Gly
            580                 585                 590
Gly His Glu Pro Gly Glu Pro Arg Gly Ile Lys Ala Gly Tyr Gly Thr
            595                 600                 605
Cys Asn Cys Phe Pro Glu Glu Lys Cys Phe Cys Glu Pro Glu Asp
            610                 615                 620
Ile Gln Asp Pro Leu Cys Asp Glu Leu Cys Arg Thr Val Ile Ala Ala
625                 630                 635                 640
Ala Val Leu Phe Ser Phe Ile Val Ser Val Leu Ser Ala Phe Cys
            645                 650                 655
Ile His Cys Tyr His Lys Phe Ala His Lys Pro Pro Ile Ser Ser Ala
            660                 665                 670
Glu Met Thr Phe Arg Arg Pro Ala Gln Ala Phe Pro Val Ser Tyr Ser
            675                 680                 685
Ser Ser Gly Ala Arg Arg Pro Ser Leu Asp Ser Met Glu Asn Gln Val
            690                 695                 700
Ser Val Asp Ala Phe Lys Ile Leu Glu Asp Pro Lys Trp Glu Phe Pro
705                 710                 715                 720
Arg Lys Asn Leu Val Leu Gly Lys Thr Leu Gly Glu Gly Glu Phe Gly
            725                 730                 735
Lys Val Val Lys Ala Thr Ala Phe His Leu Lys Gly Arg Ala Gly Tyr
            740                 745                 750
Thr Thr Val Ala Val Lys Met Leu Lys Glu Asn Ala Ser Pro Ser Glu
            755                 760                 765
Leu Arg Asp Leu Leu Ser Glu Phe Asn Val Leu Lys Gln Val Asn His
            770                 775                 780
Pro His Val Ile Lys Leu Tyr Gly Ala Cys Ser Gln Asp Gly Pro Leu
785                 790                 795                 800
Leu Leu Ile Val Glu Tyr Ala Lys Tyr Gly Ser Leu Arg Gly Phe Leu
            805                 810                 815
Arg Glu Ser Arg Lys Val Gly Pro Gly Tyr Leu Gly Ser Gly Gly Ser
            820                 825                 830
Arg Asn Ser Ser Ser Leu Asp His Pro Asp Glu Arg Ala Leu Thr Met
            835                 840                 845
Gly Asp Leu Ile Ser Phe Ala Trp Gln Ile Ser Gln Gly Met Gln Tyr
850                 855                 860
Leu Ala Glu Met Lys Leu Val His Arg Asp Leu Ala Ala Arg Asn Ile
865                 870                 875                 880
Leu Val Ala Glu Gly Arg Lys Met Lys Ile Ser Asp Phe Gly Leu Ser
            885                 890                 895
Arg Asp Val Tyr Glu Glu Asp Ser Tyr Val Lys Arg Ser Gln Gly Arg
            900                 905                 910
Ile Pro Val Lys Trp Met Ala Ile Glu Ser Leu Phe Asp His Ile Tyr
            915                 920                 925
Thr Thr Gln Ser Asp Val Trp Ser Phe Gly Val Leu Leu Trp Glu Ile
            930                 935                 940
Val Thr Leu Gly Gly Asn Pro Tyr Pro Gly Ile Pro Pro Glu Arg Leu
945                 950                 955                 960
Phe Asn Leu Leu Lys Thr Gly His Arg Met Glu Arg Pro Asp Asn Cys
            965                 970                 975
Ser Glu Glu Met Tyr Arg Leu Met Leu Gln Cys Trp Lys Gln Glu Pro
```

-continued

```
            980                 985                 990
Asp Lys Arg Pro Val Phe Ala Asp Ile Ser Lys Asp Leu Glu Lys Met
        995                 1000                1005

Met Val Lys Arg Arg Asp Tyr Leu Asp Leu Ala Ala Ser Thr Pro
    1010                1015                1020

Ser Asp Ser Leu Ile Tyr Asp Asp Gly Leu Ser Glu Glu Glu Thr
    1025                1030                1035

Pro Leu Val Asp Cys Asn Asn Ala Pro Leu Pro Arg Ala Leu Pro
    1040                1045                1050

Ser Thr Trp Ile Glu Asn Lys Leu Tyr Gly Met Ser Asp Pro Asn
    1055                1060                1065

Trp Pro Gly Glu Ser Pro Val Pro Leu Thr Arg Ala Asp Gly Thr
    1070                1075                1080

Asn Thr Gly Phe Pro Arg Tyr Pro Asn Asp Ser Val Tyr Ala Asn
    1085                1090                1095

Trp Met Leu Ser Pro Ser Ala Ala Lys Leu Met Asp Thr Phe Asp
    1100                1105                1110

Ser
```